US011596639B2

(12) United States Patent
Lee et al.

(10) Patent No.: US 11,596,639 B2
(45) Date of Patent: Mar. 7, 2023

(54) SUBSTITUTED INDOLE MCL-1 INHIBITORS

(71) Applicant: Vanderbilt University, Nashville, TN (US)

(72) Inventors: Taekyu Lee, Brentwood, TN (US); James C. Tarr, Franklin, TN (US); KyuOk Jeon, Nashville, TN (US); James M. Salovich, Nashville, TN (US); Subrata Shaw, Nashville, TN (US); Nagarathanam Veerasamy, Nashville, TN (US); Kwangho Kim, Nashville, TN (US); Plamen P. Christov, Mount Juliet, TN (US); Edward T. Olejniczak, Nashville, TN (US); Bin Zhao, Brentwood, TN (US); Stephen W. Fesik, Nashville, TN (US); Zhiguo Bian, Lake Bluff, IL (US)

(73) Assignee: Vanderbilt University, Nashville, TN (US)

( * ) Notice: Subject to any disclaimer, the term of this patent is extended or adjusted under 35 U.S.C. 154(b) by 1133 days.

(21) Appl. No.: 16/081,709

(22) PCT Filed: Mar. 3, 2017

(86) PCT No.: PCT/US2017/020699
§ 371 (c)(1),
(2) Date: Aug. 31, 2018

(87) PCT Pub. No.: WO2017/152076
PCT Pub. Date: Sep. 8, 2017

(65) Prior Publication Data
US 2021/0283138 A1 Sep. 16, 2021

Related U.S. Application Data

(60) Provisional application No. 62/304,124, filed on Mar. 4, 2016, provisional application No. 62/402,903, filed on Sep. 30, 2016.

(51) Int. Cl.
*A61P 35/00* (2006.01)
*A61K 45/06* (2006.01)
*C07D 487/04* (2006.01)
*A61K 31/551* (2006.01)
*A61K 31/4985* (2006.01)
*A61K 31/506* (2006.01)
*A61K 31/5377* (2006.01)
*A61K 31/538* (2006.01)
*C07D 401/14* (2006.01)
*C07D 403/04* (2006.01)
*C07D 403/14* (2006.01)
*C07D 519/00* (2006.01)

(52) U.S. Cl.
CPC ........ *A61K 31/551* (2013.01); *A61K 31/4985* (2013.01); *A61K 31/506* (2013.01); *A61K 31/538* (2013.01); *A61K 31/5377* (2013.01); *A61K 45/06* (2013.01); *A61P 35/00* (2018.01); *C07D 401/14* (2013.01); *C07D 403/04* (2013.01); *C07D 403/14* (2013.01); *C07D 487/04* (2013.01); *C07D 519/00* (2013.01)

(58) Field of Classification Search
CPC .. C07D 401/14; C07D 403/04; C07D 403/14; C07D 487/04; C07D 519/00
See application file for complete search history.

(56) References Cited

U.S. PATENT DOCUMENTS

| | | | |
|---|---|---|---|
| 4,703,053 A | 10/1987 | Connor et al. | |
| 4,980,368 A | 12/1990 | Thielke et al. | |
| 4,994,477 A | 2/1991 | Kempf et al. | |
| 5,324,725 A | 6/1994 | Jasserand et al. | |
| 5,436,264 A | 7/1995 | Pfister et al. | |
| 6,500,853 B1 | 12/2002 | Seehra et al. | |
| 6,787,651 B2 | 9/2004 | Stolle et al. | |
| 10,533,010 B2 | 1/2020 | Lee et al. | |
| 2003/0109533 A1 | 6/2003 | Lavielle et al. | |
| 2005/0124675 A1 | 6/2005 | Hsieh et al. | |
| 2009/0054402 A1 | 2/2009 | Wang et al. | |
| 2009/0270497 A1 | 10/2009 | Buggy | |
| 2010/0009986 A1 | 1/2010 | Zemolka et al. | |
| 2010/0009991 A1 | 1/2010 | Terasaka et al. | |
| 2011/0263599 A1 | 10/2011 | Song et al. | |
| 2012/0172285 A1 | 7/2012 | Walensky et al. | |
| 2014/0005386 A1 | 1/2014 | Doemling | |
| 2014/0322229 A1 | 10/2014 | Wang et al. | |
| 2015/0336925 A1 | 11/2015 | Lee et al. | |

FOREIGN PATENT DOCUMENTS

| | | |
|---|---|---|
| EP | 639573 | 2/1995 |
| EP | 2161266 | 3/2010 |
| JP | S62181252 A | 8/1987 |
| JP | 3739432 | 1/2006 |
| JP | 2013537191 A | 9/2013 |
| JP | 2014533734 A | 12/2014 |
| WO | 9742188 | 11/1997 |
| WO | 9810778 | 3/1998 |
| WO | 9842710 | 10/1998 |
| WO | 9842710 A1 | 10/1998 |
| WO | 2006034391 A2 | 3/2006 |
| WO | 2007112322 | 10/2007 |
| WO | 2010123507 | 10/2010 |
| WO | 2011157668 | 12/2011 |
| WO | 2013112878 | 8/2013 |
| WO | 2014047427 | 3/2014 |
| WO | 2015031608 | 3/2015 |
| WO | 2015148854 A1 | 10/2015 |

OTHER PUBLICATIONS

Cancer and Metastasis Reviews (1998), 17(1), 91-106.*
(Continued)

*Primary Examiner* — Alicia L Otton
(74) *Attorney, Agent, or Firm* — Michael Best & Friedrich LLP

(57) ABSTRACT

The present disclosure provides for compounds that inhibit the activity of an anti-apoptotic Bcl-2 family member Myeloid cell leukemia-1 (Mcl-1) protein. The present disclosure also provides for pharmaceutical compositions as well as methods for using compounds for treatment of diseases and conditions (e.g., cancer) characterized by the over-expression or dysregulation of Mcl-1 protein.

20 Claims, No Drawings

(56) References Cited

OTHER PUBLICATIONS

Science (1999), vol. 286, 531-537.*
Cancer [online], [retrieved on Jul. 6, 2007], Retrieved from the internet, URL http://www.nlm.nih.gov/medlineplus/cancer.html>.*
European Patent Office action for Application No. 17760914.6 dated Nov. 25, 2021 (3 pages).
Mexican Institute of Industrial Property office action for Application No. MX/a/2018/010678 dated Nov. 3, 2021 (13 pages including English summary).
Eurasian Patent Office Action for Application No. 201891988/28, with English Translation, dated Jun. 5, 2019, 9 pages.
Intellectual Property Office of the Phillipines Bureau of Patents Substantive Examination Report for Application No. 1/2018/501877 dated Oct. 1, 2020 (51 pages).
Australian Patent Office Examination Report No. 1 for Application No. 2017228385 dated Oct. 16, 2020 (64 pages).
Mexican Patent Office Action for Application No. MX/a/2018/010678 dated Sep. 25, 2020 (52 pages including English translation).
Chilean Patent Office Examination Report for Application No. 201802516 dated Nov. 2, 2020 (13 pages including statement of relevance).
Chan et al., "Document No. 150:563639," retrieved from STN; May 22, 2009.
Friberg, "Discovery of Potent Myeloid Cell Leukemia 1 (Mcl 1) Inhibitors Using Fragment Based Methods and Structure Based Design," manuscript (2014) pp. 1-38, National Institutes of Health.
Hung et al., "Document No. 152:66468, Caplus," retrieved from STN; Oct. 28, 2009.
Jansen et al., "Document No. 140:111233, Caplus," retrieved from STN; Oct. 22, 2009.
Wahyuningsih, et al. Document No. 147:235137, retrieved from STN; entered in STN on Jun. 11, 2007.
Medline Plus, "Cancer" retrieved from http://www.nlm.nih.gov/medlineplus/cancer.html on Jul. 6, 2007.
Golub et al., "Molecular classification of cancer: class discovery and class prediction by gene expression monitoring," Science (1999), vol. 286, 531-537.
Lala et al., "Role of nitric oxide in tumor progression: lessons from experimental tumors," Cancer and Metastasis Reviews (1998), 17(1), 91-106.
PCT/US2013/060881 International Search Report and Written Opinion dated May 5, 2014 (11 pages).
PCT/US2014/053148 International Search Report and Written Opinion dated Jan. 27, 2015 (12 pages).
PCT/US2014/053148 International Preliminary Report on Patentability dated Mar. 1, 2016 (2 pages).
PCT/US2015/022841 International Search Report and Written Opinion dated Jun. 29, 2015 (12 pages).
PCT/US2017/020699 International Search Report and Written Opinion dated May 23, 2017 (9 pages).
Shultz et al. "Optimization of the in vitro cardiac safety of hydroxamate-based histone deacetylase inhibitors." Journal of medicinal chemistry. Jun. 17, 2011;54(13):4752-72.
Tabatabaeian et al., "Solvent-free, ruthenium-catalyzed, regioselective ring-opening of epoxides, an efficient route to various 3-alkylated indoles." Tetrahedron Letters. Feb. 25, 2008;49(9):1450-4.
Kalaus et al., "Synthesis of vinca alkaloids and related compounds. 63. A new synthetic pathway for preparing alkaloids and related compounds with the aspidosperma skeleton. Total syntheses of (.+−.)-vincadifformine, tabersonine, and (.+−.)-oxotabersonine." The Journal of Organic Chemistry. Mar. 1993,58(6):1434-42.
Vago et al., "Synthesis of vinca alkaloids and related compounds 95. Attempted build-up of the aspidospermidine skeleton by [4+2] cycloaddition. Some unexpected reactions, and formation of a new ring system." Heterocycles. May 1, 2001;55(5):873-80.
Shaw et al., "Optimization of potent and selective tricyclic indole diazepinone myeloid cell leukemia-1 inhibitors using structure-based design." Journal of medicinal chemistry. Jan. 11, 2018;61(6):2410-21.
Japanese Patent Office Action for Application No. 2017502932 dated Dec. 6, 2018, with translation, 15 pages.
European Patent Office Examination Report for Application No. 17760914.6 dated Jul. 1, 2020 (4 pages).
Intellectual Property Office of India Examination Report for Application No. 201817035157 dated Jun. 29, 2020 (7 pages including English translation).
State of Israel Ministry of Justice Patent Office Notification of Defects in Patent Application No. 261231 dated Jun. 4, 2020 (29 pages including English translation).
Australian Patent Office Examination Report No. 2 for Application No. 2015235944 dated May 7, 2020 (10 pages).
European Patent Office Examination Report for Application No. 17760914.6 dated Apr. 6, 2021 (4 pages).
Mexican Patent Office Action for Application No. MX/a/2018/010678 dated Apr. 20, 2021 (10 pages including English summary).
Brazilian Patent Office Search Report and Written Opinion for Application No. BR112018067775-2 dated Aug. 12, 2021 (7 pages including English translation).
Korean Intellectual Property Office Notice of Preliminary Rejection for Application No. 10-2018-7028435 dated Jul. 27, 2021 (11 pages including English translation).
National Intellectual Property Adminitration People's Republic of China First Office Action for Application No. 201780027686.5 dated Jul. 23, 2021 (19 pages including English translation).
Chilean Patent Office Examination Report for Application No. 201802516 dated Nov. 13, 2019 (17 pages including partial English translation).
Japanese Patent Office Action for Application No. 2018-546464 dated Feb. 21, 2021 (12 pages including English translation).
Australian Patent Office Examination Report No. 2 for Application No. 2017228385 dated Apr. 7, 2021 (3 pages).
European Patent Office Extended Search Report for Application No. 17760914.6 dated Jul. 11, 2019 (5 pages).
Australian Patent Office Action for Application No. 2015235944, dated Aug. 28, 2019, 6 pages.
Philippine Patent Office Action for application 1/2018/501877, dated Sep. 23, 2022 (5 pages).

* cited by examiner

SUBSTITUTED INDOLE MCL-1 INHIBITORS

RELATED APPLICATIONS

This patent application is the U.S. national stage entry, under 35 U.S.C. § 371, of international application number PCT/US2017/020699, filed Mar. 3, 2017, which claims the benefit of U.S. provisional application Ser. No. 62/304,124, filed Mar. 4, 2016, and U.S. provisional application Ser. No. 62/402,903, filed Sep. 30, 2016, the entire contents of each being incorporated herein by reference in their entirety.

STATEMENT REGARDING FEDERALLY SPONSORED RESEARCH

This invention was made with government support under Award DP1OD006933/DP1CA174419, awarded by the National Institutes of Health; under Contract No. HHSN261200800001E, awarded by the NCI Experimental Therapeutics (NExT) Program; and under Grant No. P50CA098131, awarded by the NCI SPORE grant in breast cancer. The government has certain rights in the invention.

TECHNICAL FIELD

The present disclosure pertains to compounds that inhibit the activity of an anti-apoptotic Bcl-2 family member Myeloid cell leukemia-1 (Mcl-1) protein, compositions containing the compounds, and methods of treating cancer involving over-expressed or dysregulated Mcl-1 protein.

BACKGROUND

Abnormal regulation of apoptosis is now recognized to play an important role in the development of cancer. The apoptosis pathway can be initiated by various extracellular and intracellular stresses, including growth factor deprivation, DNA damage, oncogene induction, and cytotoxic drugs (Danial, N. N. and Korsmeyer, S J. *Cell* (2004) 116, 205-219). The death signal leads to the oligomerization of the pro-apoptotic proteins Bax and Bak. Upon activation, they permeabilize the mitochondrial outer membrane and release apoptogenic factors into the cytoplasm. This process is tightly regulated by both pro-apoptotic (Bax, Bak, Bad, Bid, Bim, Bmf, NOXA, PUMA) and anti-apoptotic (Bcl-2, Bcl-xL, Bcl-w, Bcl2-A1, Mcl-1) members of the Bcl-2 family of proteins. Recent data suggests that the anti-apoptotic Bcl-2 proteins function to protect the cell from apoptotic insults, primarily by preventing disruption of mitochondrial outer membrane integrity by binding to the pro-apoptotic proteins as described in Adams, J. M. and Cory S. *Oncogene* (2007) 26, 1324-1337; Willis, S. N. et al. *Science* (2007) 315, 856-859. Because tumor cells are under stress, alterations in their apoptotic signaling pathways are believed to be crucial for survival. Recent data implicates down-regulated apoptosis in the onset of cancer. Research has shown, for example, that anti-apoptotic proteins, are over-expressed in many cancer cell types as described in Beroukhim, R et al. *Nature* (2010) 463, 899-905; Zhang J. Y., *Nature Reviews Drug Discovery*, (2002) 1, 101; Kirkin, V. et al. *Biochimica et Biophysica Acta* (2004) 1644, 229-249; and Amundson, S. A. et al. *Cancer Research* (2000) 60, 6101-6110. This dysregulation results in the survival of cells that would otherwise have undergone apoptosis such as cancer cells. This suggests that neutralizing the function of anti-apoptotic Bcl-2 proteins may offer an effective strategy for the elimination of cancer cells. In addition, resistance to chemotherapy which is a major cause of treatment failure and poor prognosis in many cancers can be caused by the upregulation of anti-apoptotic Bcl-2 family proteins.

An important anti-apoptotic member of the Bcl-2 family is Myeloid cell leukemia-1 (Mcl-1). Mcl-1 is one of the most frequently amplified anti-apoptotic genes in human cancers including prostate, lung, pancreatic, breast, ovarian, and cervical cancers, as well as melanoma. B-cell chronic lymphocytic leukemia (B-CLL), acute myeloid leukemia (AML) and acute lymphoblastic leukemia (ALL) (Beroukhim et al. *Nature* (2010) 46, 899-905). Moreover, its overexpression is implicated as a resistance factor for multiple therapies including widely prescribed microtubule-targeted agents for breast cancers, such as paclitaxel and vincristine as well as Gemcitabine, a first-line treatment option for pancreatic cancer (Wei et al. *Cancer Chemother Pharmacol* (2008) 62, 1055-1064 and Wertz et al. *Nature* (2011) 471, 110-114). These data suggest that Mcl-1 is an important target for a wide variety of cancers.

In many cancer cell types, the cancer cell's survival is attributed to the dysregulation of the apoptotic pathway caused by the over-expression of one or more anti-apoptotic Bcl-2 protein family members. Because of the important role for Bcl-2 family of proteins in regulating apoptosis in both cancerous and non-cancerous cells, and the inter-cell variability of Bcl-2 family protein expression, it could be advantageous to have a small molecule inhibitor that selectively targets and preferably binds to one type or a subset of anti-apoptotic Bcl-2 protein(s). A selective compound also may confer certain advantages in the clinical setting, by providing flexibility to select a dosing regimen to reduce on-target toxic effects in normal cells.

Because Mcl-1 protein is an important Bcl-2 family member associated with a number of diseases, there is a need for compounds which bind to and inhibit the activity of Mcl-1 protein.

SUMMARY

In some embodiments, the present disclosure provides compounds, and pharmaceutically acceptable compositions thereof, that are effective as inhibitors of Mcl-1.

Compounds of the present disclosure, and pharmaceutically acceptable compositions thereof, are useful for treating a variety of diseases, disorders or conditions, associated with MCl-1. Such diseases, disorders, or conditions include those described herein.

Compounds provided by this disclosure are also useful for the study of Mcl-1 in biological and pathological phenomena and the comparative evaluation of new Mcl-1 inhibitors in vitro or in vivo.

DETAILED DESCRIPTION

1. General Description of Compounds of the Disclosure

In one aspect, the present disclosure provides inhibitors of Mcl-1. In some embodiments, such compounds include those of formula (I):

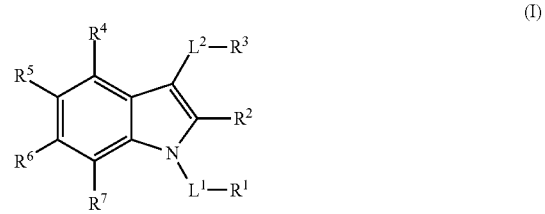

or a pharmaceutically acceptable salt thereof, wherein: $L^1$ is selected from a covalent bond or an optionally substituted bivalent straight or branched $C_{1-6}$ hydrocarbon chain wherein one or more methylene units are optionally and independently replaced with -Cy-; -Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur; $L^2$ is an optionally substituted bivalent straight or branched $C_{3-6}$ hydrocarbon chain wherein one or two methylene units of $L^2$ are optionally and independently replaced with —O—, —S—, or —N(R')—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur; each R' is independently selected from hydrogen or optionally substituted $C_{1-4}$ alkyl; $R^1$ is selected from hydrogen, halogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)$R^x$, —S(O)$_2$OH, —S(O)$R^y$, or —S(O)$_2R^y$; $R^2$ is selected from —C(O)-$L^3$-$R^z$, —C(O)N(R)-$L^3$-$R^z$, —C(O)N(R)—C(R)$_2$-$L^3$-$R^z$, —C(O)O-$L^3$-$R^z$ or —C(O)S-$L^3$-$R^z$; $L^3$ is selected from a covalent bond or an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—; $R^z$ is selected from hydrogen, -Cy-R, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R, —S(O)$_2$OH, or —S(O)$_2R^y$, or is selected from:

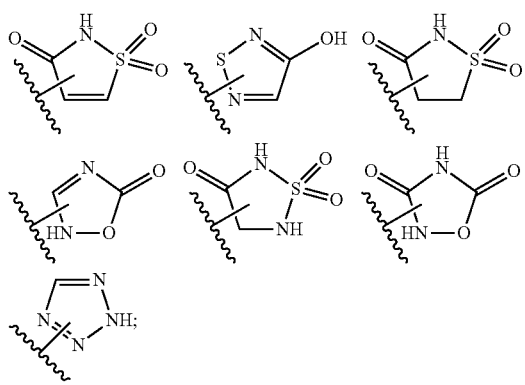

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R; $R^y$ is selected from —N(R)C(O)CF$_3$, —N(R)C(O)R, or —N(R)C(O)N(R)$_2$; each R is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, an 8-10 membered bicyclic heteroaryl ring having 1-5 heteroatoms independently selected from nitrogen, oxygen or sulfur, or a 12-15 membered tricyclic heteroaryl ring having 1-5 heteroatoms independently selected from nitrogen, oxygen or sulfur; $R^3$ is an optionally substituted ring selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; each of $R^4$, $R^5$, and $R^6$ is independently selected from R, halogen, —CN, —NO$_2$, —C(O)OR', —OR', —SR', —C(O)N(R')$_2$, —N(R')$_2$, —S(O)$_2$N(R')$_2$, —N(R')S(O)$_2$CF$_3$, —C(O)R', —N(R')C(O)R', —S(O)R', —S(O)$_2$R', —N(R')C(O)OR', and —N(R')S(O)$_2$R'; $R^7$ is selected from hydrogen, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally $R^1$ and $R^2$, $R^1$ and $R^7$, $R^4$ and $R^5$, $R^5$ and $R^6$ and/or $R^6$ and $R^7$ are taken together with their intervening atoms to form an optionally substituted ring selected from a 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In other embodiments are compounds of formula (I), or a pharmaceutically acceptable salt, thereof, wherein $L^1$ is selected from a covalent bond or an optionally substituted bivalent straight or branched $C_{1-6}$ hydrocarbon chain wherein one or more methylene units are optionally and independently replaced with -Cy-; -Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur; $L^2$ is an optionally substituted bivalent straight or branched $C_{3-6}$ hydrocarbon chain wherein one or two methylene units of $L^2$ are optionally and independently replaced with —O—, —S—, or —N(R')—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur; each R' is independently selected from hydrogen or optionally substituted $C_{1-4}$ alkyl; $R^1$ is selected from hydrogen, halogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, —S(O)R$^y$, or —S(O)$_2$R$^y$; $R^2$ is selected from —C(O)-L$^3$-R$^z$, —C(O)N(R)-L$^3$-R$^z$, —C(O)N(R)—C(R)$_2$-L$^3$-R$^z$, —C(O)O-L$^3$-R$^z$ or —C(O)S-L$^3$-R$^z$; $L^3$ is selected from a covalent bond or an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—; $R^z$ is selected from hydrogen, -Cy-R, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^y$, or is selected from:

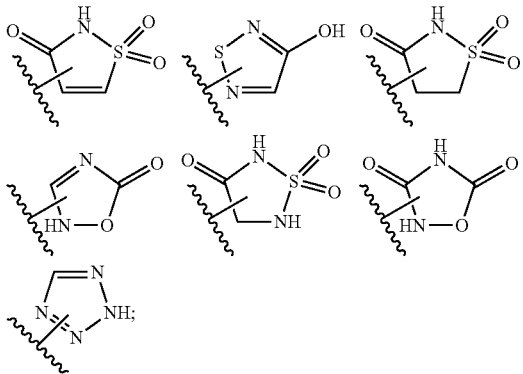

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R; $R^y$ is selected from —N(R)C(O)CF$_3$, —N(R)C(O)R, or —N(R)C(O)N(R)$_2$; each R is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; $R^3$ is an optionally substituted ring selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; each of $R^4$, $R^5$, and $R^6$ is independently selected from R, halogen, —CN, —NO$_2$, —C(O)OR', —OR', —SR', —C(O)N(R')$_2$, —N(R')$_2$, —S(O)$_2$N(R)$_2$, —N(R')S(O)$_2$CF$_3$, —C(O)R'. —N(R')C(O)R', —S(O)R', —S(O)$_2$R', —N(R')C(O)OR', and —N(R')S(O)$_2$R'; $R^7$ is selected from hydrogen, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally $R^1$ and $R^2$, $R^1$ and $R^7$, $R^4$ and $R^5$, $R^5$ and $R^6$ and/or $R^6$ and $R^7$ are taken together with their intervening atoms to form an optionally substituted ring selected from a 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

2. Compounds and Definitions

Compounds of this disclosure include those described generally above, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic or polycyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C3-C6 hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a C1-4 straight or branched alkyl group. Exemplary lower alkyl groups are methyl, ethyl, propyl, isopropyl, butyl, isobutyl, and tert-butyl.

The term "lower haloalkyl" refers to a C1-4 straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen; or a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

As used herein, the term "bivalent C1-8 (or C1-6) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —($CH_2$)n-, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system which includes, but not limited to, phenyl, naphthyl, anthracyl and the like, which may be optionally substituted. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, or 5 to 15 ring atoms, preferably 5, 6, or 9 ring atoms; having 6, 10, or 14 n electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, 3,4-dihydro-1H-[1,4]oxazino[4,3-a]indole, 3,4-dihydro-1H-[1,4]oxazino[4,3-a]indol-1-one, 1,2,3,4-tetrahydropyrazino[1,2-a]indole, and 3,4-dihydropyrazino[1,2-a]indol-1(2H)-one. A heteroaryl group may be mono-, bicyclic, or tricyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ_2$; —N(R$^\circ$)C(S)NR$^\circ_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O)(CH$_2$)$_{0-4}$SR—; —(CH$_2$)$_{0-4}$SC(O)R$^\circ$; —(CH$_2$)$_{0-4}$C(O)NR$^\circ_2$; —(CH$_2$)$_{0-4}$C(O)N(R$^\circ$)S(O)$_2$R$^\circ$; —C(S)NR$^\circ_2$; —C(S)SR$^\circ$; —SC(S)SR$^\circ$, —(CH$_2$)$_{0-4}$OC(O)NR$^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)R$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ_2$; —S(O)$_2$N(R$^\circ$)C(O)R$^\circ$; —(CH$_2$)$_{0-4}$S(O)R$^\circ$; —N(R$^\circ$)S(O)$_2$NR$^\circ_2$; —N(R$^\circ$)S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; —SiR$^\circ_3$; —(C1-4 straight or branched alkylene)O—N(R$^\circ$)$_2$; or —(C1-4 straight or branched alkylene)C(O)O—N(R$^\circ$)$_2$, wherein each R$^\circ$ may be substituted as defined below and is independently hydrogen, an optionally substituted group selected from C$_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur, —CH$_2$Ph, —O(CH$_2$)$_{0-1}$Ph, or —CH$_2$-(5-6 membered heteroaryl ring), or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$, —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR, —(CH$_2$)$_{0-2}$SR$^\bullet$, —(CH$_2$)$_{0-2}$S(O)R$^\bullet$, —(CH$_2$)$_{0-2}$S(O)$_2$R$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)R$^\bullet$, or —SSR$^\bullet$ wherein each R$^\bullet$ is unsubstituted or where preceded by "halo" is substituted with one or more halogens, and is independently selected from an C$_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur. —CH$_2$Ph, or —O(CH$_2$)$_{0-1}$Ph. Suitable divalent substituents on a saturated carbon atom of R$^\circ$ include =O and =S.

Suitable divalent substituents on a suitable carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)R$^\bullet$, —C(O)OH, —C(O)OR$^\bullet$, —C(O)NR$^\bullet_2$, —SR$^\bullet$, —S(O)R$^\bullet$, —S(O)$_2$R$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)

$R^{\dagger}$, —S(O)$_2$R$^{\dagger}$, —S(O)$_2$NR$^{\dagger}$$_2$, —C(S)NR$^{\dagger}$$_2$, —C(NH)NR$^{\dagger}$$_2$, —C(NR$^{\dagger}$)NR$^{\dagger}$$_2$, or —N(R$^{\dagger}$)S(O)$_2$R$^{\dagger}$; wherein each R$^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^{\dagger}$ are independently halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —C(O)NR$^{\bullet}$$_2$, —SR$^{\bullet}$, —S(O)R$^{\bullet}$, —S(O)$_2$R$^{\bullet}$, —NH$_2$, —NHR$^{\bullet}$, —NR$^{\bullet}$$_2$, or —NO$_2$, wherein each R$^{\bullet}$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N+(C1-4alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this disclosure. Such compounds are useful, for example, as analytical tools, as probes in biological assays, or as therapeutic agents in accordance with the present disclosure.

3. Description of Exemplary Embodiments

In one aspect, disclosed is a compound of formula (I):

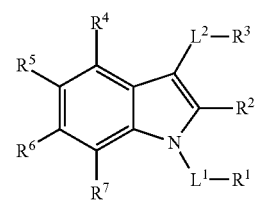

(I)

or a pharmaceutically acceptable salt thereof, wherein $R^1$, $R^2$, $R^3$, $R^4$, $R^5$, $R^6$, $R^7$, $L^1$, and $L^2$ are as defined above.

In certain embodiments, $R^2$ is selected from —C(O)-L$^3$-R$^z$, —C(O)N(R)-L$^3$-R$^z$, —C(O)N(R)—C(R)$_2$-L$^3$-R$^z$, or —C(O)S-L$^3$-R$^z$.

In certain embodiments, $L^2$ is selected from:

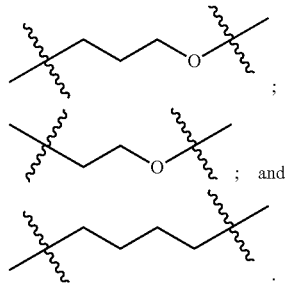

In certain embodiments, $L^2$ is

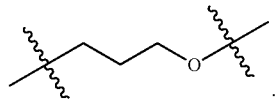 [SMILES: *CCCO*]

In certain embodiments, $R^4$ is hydrogen; $R^5$ is hydrogen; and $R^6$ is halogen, $C_1$-$C_6$-haloalkyl, or cyclopropyl.

In certain embodiments, $R^6$ is chloro.

In certain embodiments, the compound of formula (I) has formula (I-a) or (I-b):

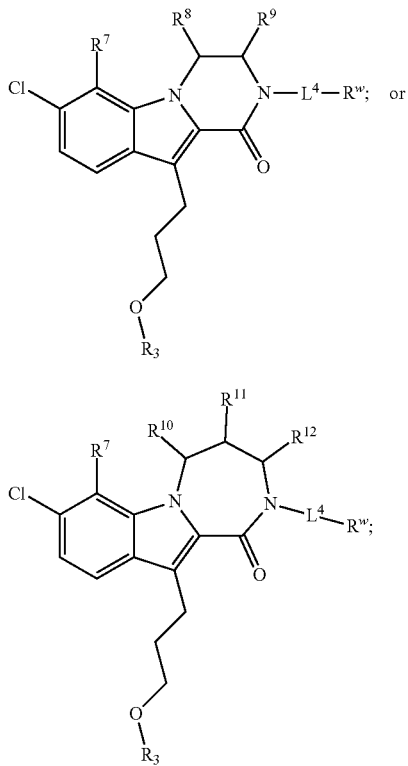

or a pharmaceutically acceptable salt thereof, wherein: $L^4$ is independently selected from a covalent bond or an optionally substituted bivalent straight or branched $C_{1-8}$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—; -Cy'- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, 3-8 membered saturated or partially unsaturated heterocyclylene having 1-4 heteroatoms independently selected from nitrogen, oxygen, or sulfur, an 8-10 membered bicyclic arylene or heteroarylene having 1-4 heteroatoms independently selected from nitrogen, oxygen, or sulfur, or an 8-10 membered saturated or partially unsaturated heterocyclylene having 1-4 heteroatoms independently selected from nitrogen, oxygen, or sulfur; $R^w$ is selected from hydrogen, -Cy'—R, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)OR, —C(O)R$^x$, —S(O)$_2$OH, or —S(O)$_2$R$^y$, or is selected from:

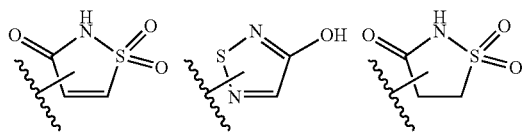

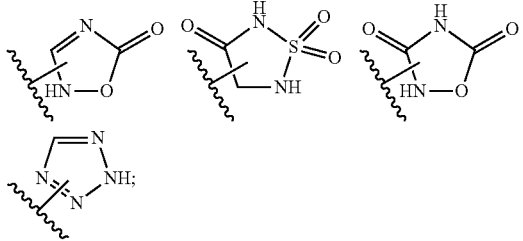

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R; $R^y$ is selected from —N(R)C(O)CF$_3$, —N(R)C(O)R, or —N(R)C(O)N(R)$_2$; each R is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; each of $R^5$, $R^6$, $R^8$, $R^9$, $R^{10}$, $R^{11}$, and $R^{12}$ is independently selected from R, halogen, —CN, —NO$_2$, —C(O)OR', —OR—, —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'; each R' is independently selected from hydrogen or optionally substituted $C_{1-4}$ alkyl; and $R^7$ is selected from hydrogen, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In certain embodiments, of formula (I-a) or (I-b), or a pharmaceutically acceptable salt thereof, $L^4$ is independently selected from a covalent bond or an optionally substituted bivalent straight or branched $C_{1-8}$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—; -Cy'- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, 3-8 membered saturated or partially unsaturated heterocyclylene having 1-4 heteroatoms independently selected from nitrogen, oxygen, or sulfur, an 8-10 membered bicyclic arylene or heteroarylene having 1-4 heteroatoms independently selected from nitrogen, oxygen, or sulfur, or an 8-10 membered saturated or partially unsaturated heterocyclylene having 1-4 heteroatoms independently selected from nitrogen, oxygen, or sulfur; R* is selected from hydrogen, R, -Cy¹—R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)OR, —C(O)R$^x$, —S(O)$_2$OH, or —S(O)$_2$R$^y$, or is selected from:

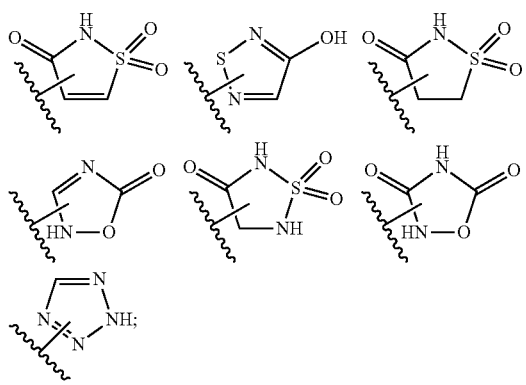

R$^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R; R$^y$ is selected from —N(R)C(O)CF$_3$, —N(R)C(O)R, or —N(R)C(O)N(R)$_2$; each R is independently selected from hydrogen or an optionally substituted group selected from C$_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, an 8-10 membered bicyclic heteroaryl ring having 1-5 heteroatoms independently selected from nitrogen, oxygen or sulfur, or a 12-15 membered tricyclic heteroaryl ring having 1-5 heteroatoms independently selected from nitrogen, oxygen or sulfur; each of R$^5$, R$^6$, R$^8$, R$^9$, R$^{10}$, R$^{11}$, and R$^{12}$ is independently selected from R, halogen, —CN, —NO$_2$, —C(O)OR', —OR', —SR', —C(O)N(R')$_2$, —N(R')$_2$, —S(O)$_2$N(R')$_2$, —N(R')S(O)$_2$CF$_3$, —C(O)R', —N(R')C(O)R', —S(O)R', —S(O)$_2$R', —N(R')C(O)OR', and —N(R')S(O)$_2$R'; each R' is independently selected from hydrogen or optionally substituted C$_{1-4}$ alkyl; and R$^7$ is selected from hydrogen, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R, or an optionally substituted group selected from C$_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In certain embodiments, the compound of formula (I) has formula:

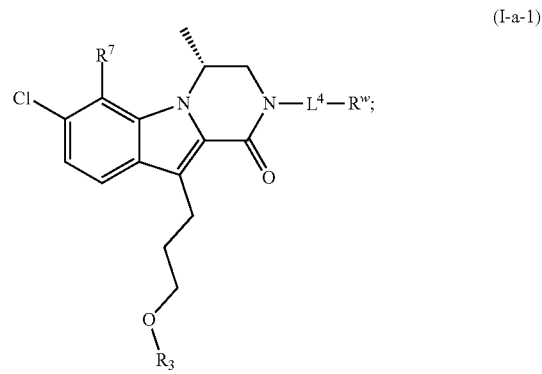

(I-a-1)

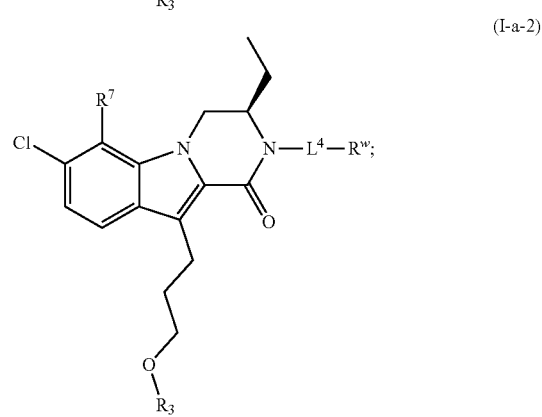

(I-a-2)

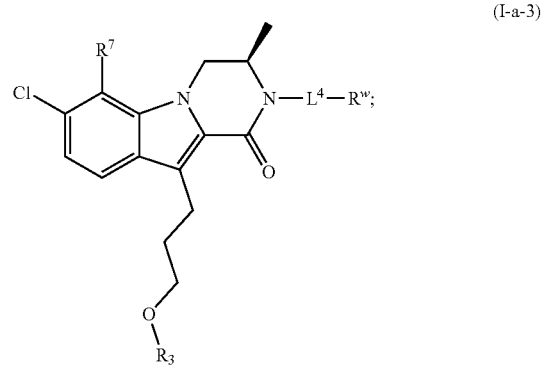

(I-a-3)

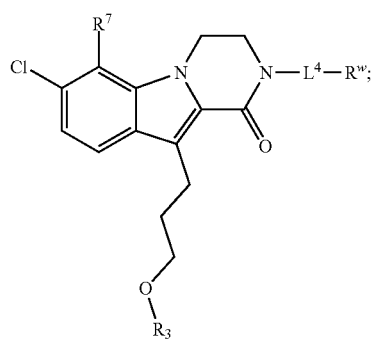
(I-a-4)
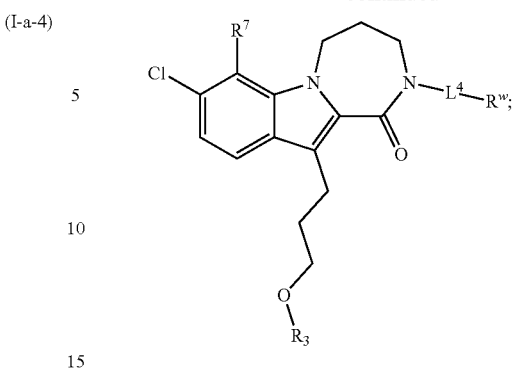
(I-b-1)
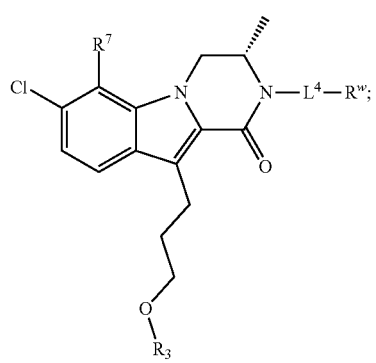
(I-a-5)
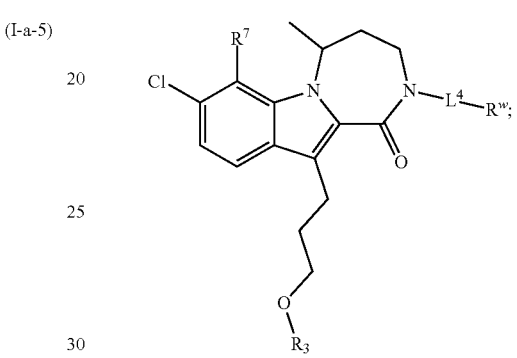
(I-b-2)
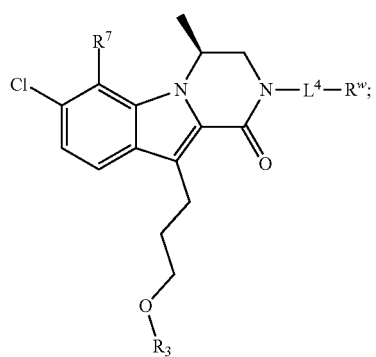
(I-a-6)
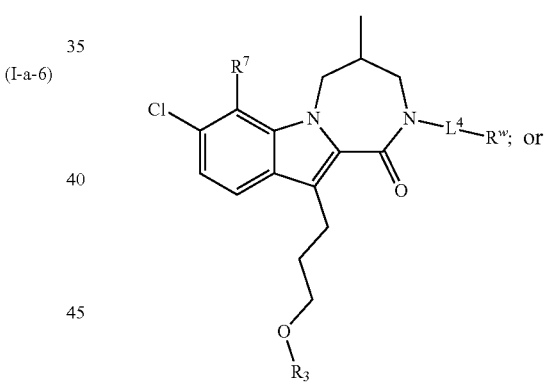
(I-b-3) or
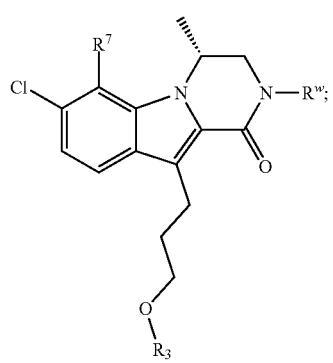
(I-a-7)
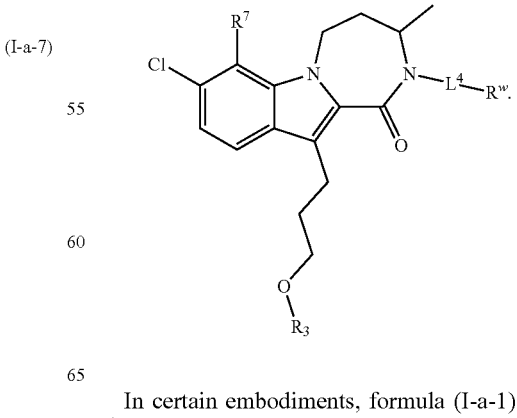
(I-b-4)
In certain embodiments, formula (I-a-1) is formula (I-a-7).

In certain embodiments, R³ is selected from:

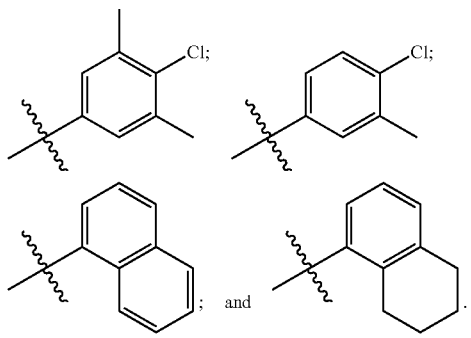

In certain embodiments, R³ is selected from

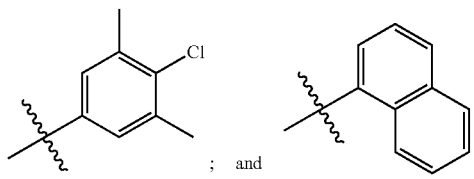

In certain embodiments, R⁷ is an optionally substituted group selected from phenyl and a 5-6 membered heteroaryl ring having 1-4 heteroatoms independently selected from nitrogen. Exemplary optional substituents include, but are not limited to, halogen, oxo (=O), =S, cyano, nitro, fluoroalkyl, alkoxy fluoroalkyl, fluoroalkoxy, alkyl, alkenyl, alkynyl, haloalkyl, haloalkoxy, heteroalkyl, cycloalkyl, cycloalkenyl, aryl, heteroaryl, heterocyclyl, cycloalkylalkyl, cycloalkenylalkyl, heteroarylalkyl, arylalkyl, heterocyclylalkyl, hydroxy, hydroxyalkyl, alkoxy, alkylthio, alkoxyalkyl, alkylene, aryloxy, arylthio, phenoxy, benzyloxy, amino, alkylamino, dialkylamino, acylamino, aminoalkyl, arylamino, diarylamino, sulfonylamino, sulfinylamino, sulfonyl, alkylsulfonyl, arylsulfonyl, aminosulfonyl, sulfinyl, —COOH, ketone, alkoxycarbonyl, aryloxycarbonyl, amide, carbamate, acyl, boronic acid, and boronic ester.

In certain embodiments, R⁷ is

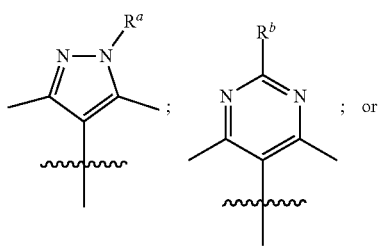

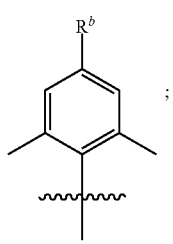

and R^a and R^b are each independently hydrogen, hydroxy, alkyl, heteroalkyl, heterocyclyl, or heterocyclylalkyl, wherein said alkyl, heteroalkyl, heterocyclyl, and heterocyclylalkyl are independently substituted by 0, 1, 2, 3, 4, or 5 substituents independently selected from the group consisting of halogen, oxo (=O), =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocyclyl, cycloalkylalkyl, cycloalkenylalkyl, heteroarylalkyl, arylalkyl, heterocyclylalkyl, hydroxy, hydroxyalkyl, alkoxy, alkylthio, alkoxyalkyl, alkylene, aryloxy, arylthio, phenoxy, benzyloxy, amino, alkylamino, dialkylamino, acylamino, aminoalkyl, arylamino, diarylamino, sulfonylamino, sulfinylamino, sulfonyl, alkylsulfonyl, arylsulfonyl, aminosulfonyl, sulfinyl, —COOH, ketone, alkoxycarbonyl, aryloxycarbonyl, amide, carbamate, acyl, boronic acid, and boronic ester.

In certain embodiments, R^a and R^b are selected from:

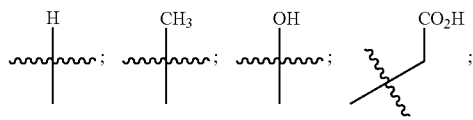

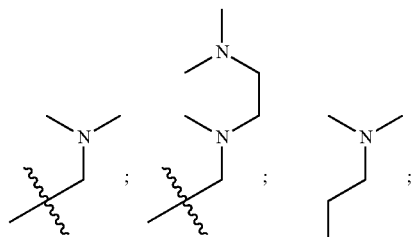

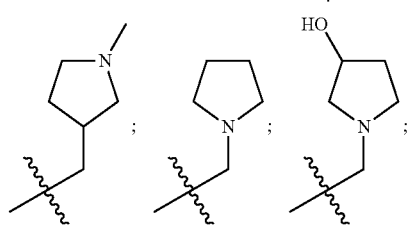

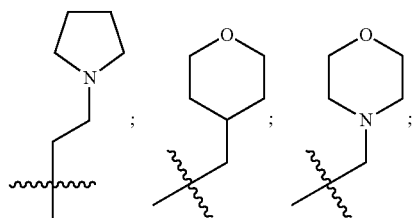

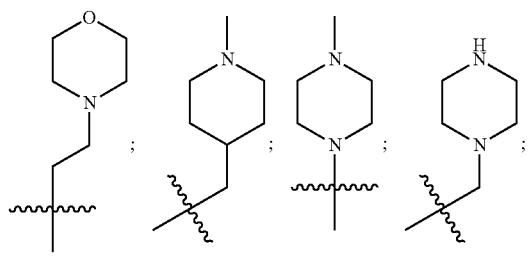

-continued
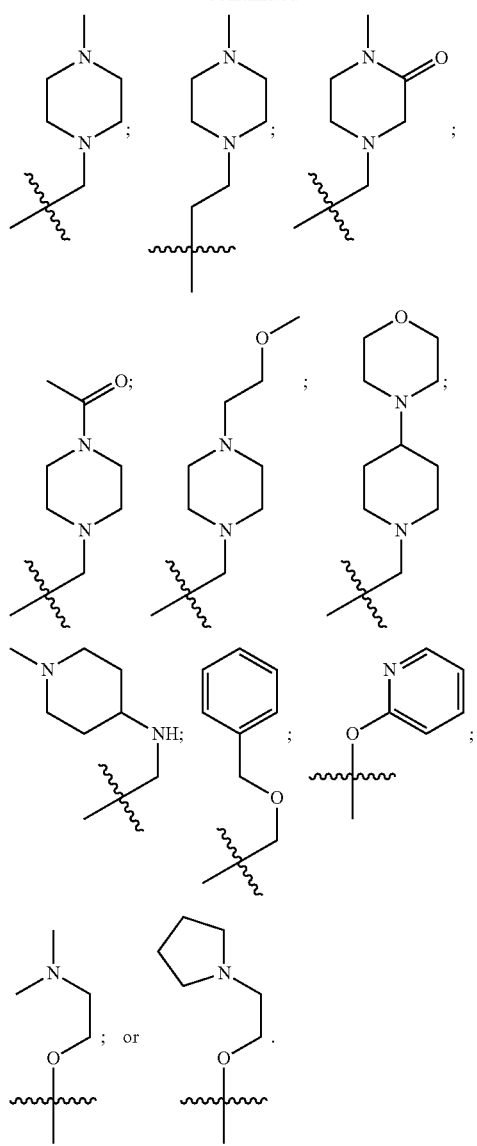
In certain embodiments, R⁷ is selected from:
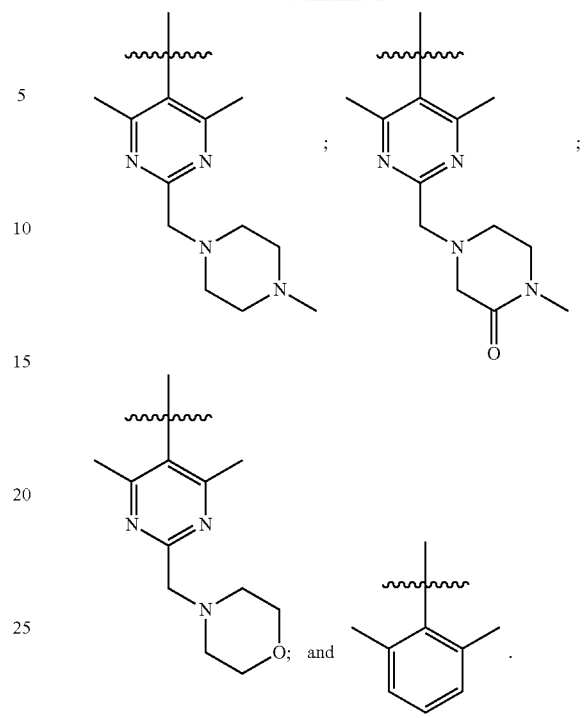
In certain embodiments, R⁷ is selected from:
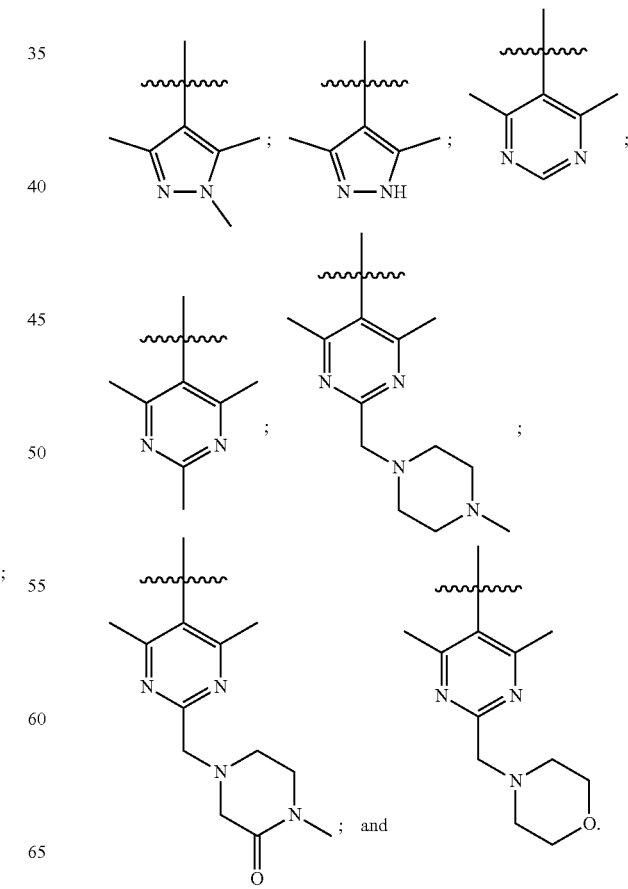

In certain embodiments, $R^7$ is selected from:

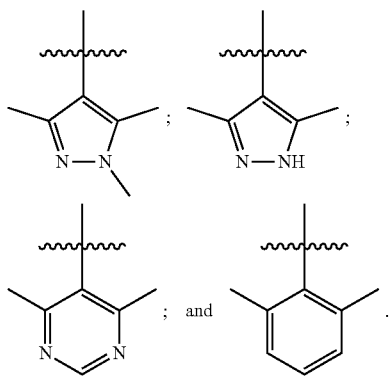

In certain embodiments, $R^7$ is

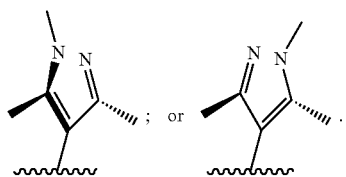

In certain embodiments, $L^4$-$R^w$ is an optionally substituted 8-10 membered bicyclic saturated, partially unsaturated or aryl ring, an optionally substituted 8-10 membered bicyclic saturated or partially unsaturated heterocyclic ring having 1-5 heteroatoms independently selected from nitrogen, oxygen, or sulfur, or an optionally substituted 8-10 membered bicyclic heteroaryl ring having 1-5 heteroatoms independently selected from nitrogen, oxygen, or sulfur.

In other embodiments, $L^4$-$R^w$ is an optionally substituted 8-10 membered bicyclic saturated, partially unsaturated or aryl ring, an optionally substituted 8-10 membered bicyclic saturated or partially unsaturated heterocyclic ring having 1-5 heteroatoms independently selected from nitrogen, oxygen, or sulfur, an optionally substituted 8-10 membered bicyclic heteroaryl ring having 1-5 heteroatoms independently selected from nitrogen, oxygen, or sulfur, an optionally substituted 1,2,3,4-tetrahydropyrazino[1,2-a]indole, or an optionally substituted 3,4-dihydro-1H-[1,4]oxazino[4,3-a]indole.

In certain embodiments, $L^4$-$R^w$ is

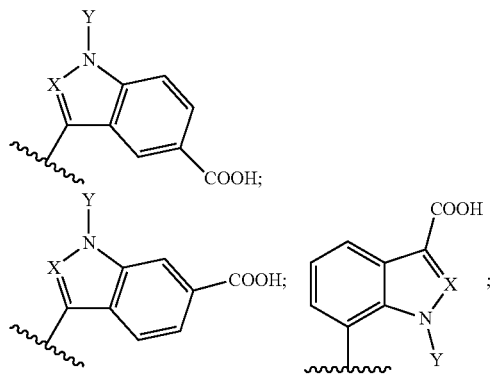

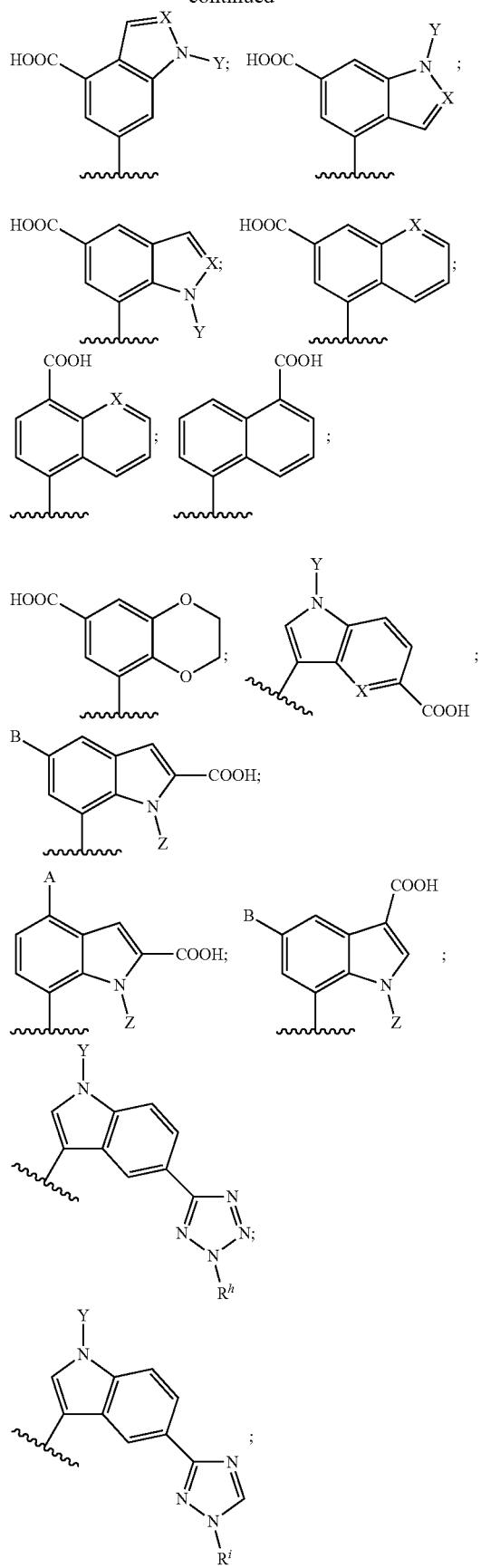

-continued

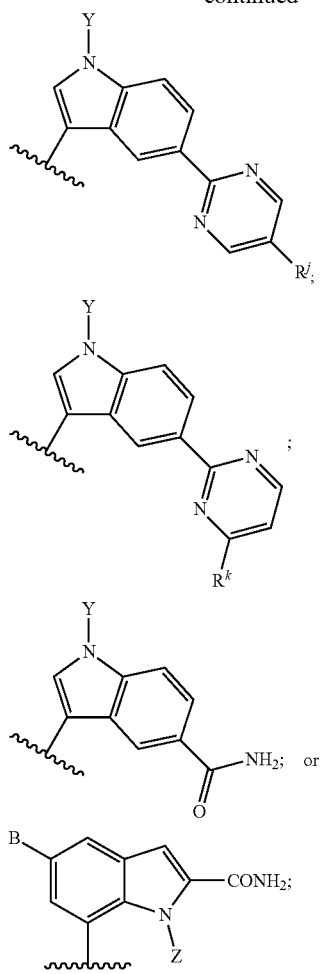

wherein
A and B are each independently hydrogen, halogen, $C_1$-$C_4$-alkyl, $C_1$-$C_4$-haloalkyl, $C_1$-$C_4$-alkoxy, $C_1$-$C_4$-haloalkoxy, halogen, —$OR^c$, —$CH_2OR^d$,

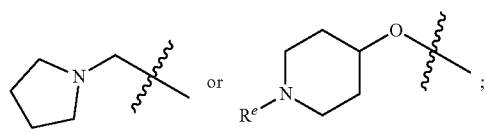

X is C(H), C($C_1$-$C_4$-alkyl), C($C_1$-$C_4$-haloalkyl) or N;
Y is hydrogen, $C_1$-$C_4$-alkyl,

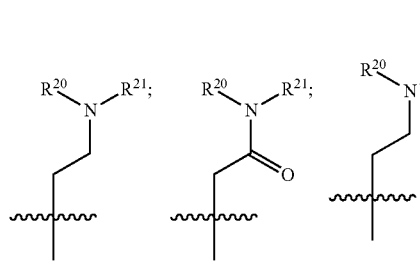

-continued

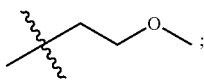

Z is

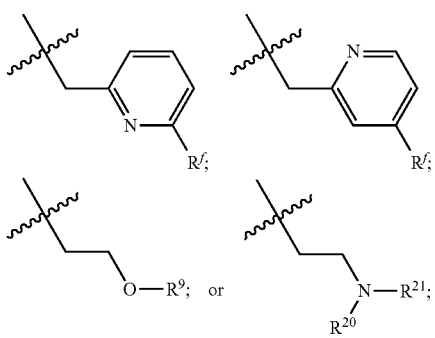

$R^{20}$ and $R^{21}$ are each independently hydrogen or $C_1$-$C_4$-alkyl, or $R^{20}$ and $R^{21}$ together with the nitrogen to which they are attached can form an optionally substituted 4-8 membered heterocyclic ring;
$R^c$ is $C_1$-$C_4$-alkyl, $C_2$-$C_4$-alkenyl,

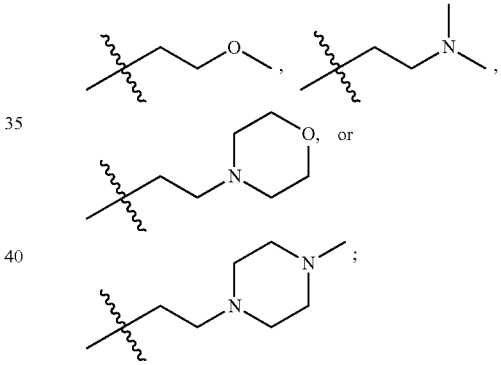

$R^d$ is $C_1$-$C_4$-alkyl; $R^e$ is $C_1$-$C_4$-alkyl; $R^f$ is $C_1$-$C_4$-alkyl, $C_2$-$C_4$-alkenyl, or cyano; $R^g$ is $C_1$-$C_4$-alkyl; $R^h$ is $C_1$-$C_4$-alkyl; $R^i$ is $C_1$-$C_4$-alkyl,

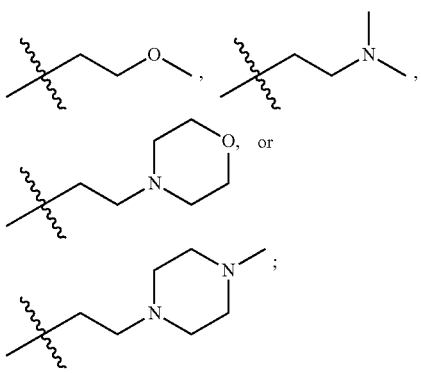

$R^j$ is $C_1$-$C_4$-alkyl or $C_1$-$C_4$-alkoxy; and $R^k$ is $C_1$-$C_4$-alkyl.

In certain embodiments, $L^4$-$R^w$ is
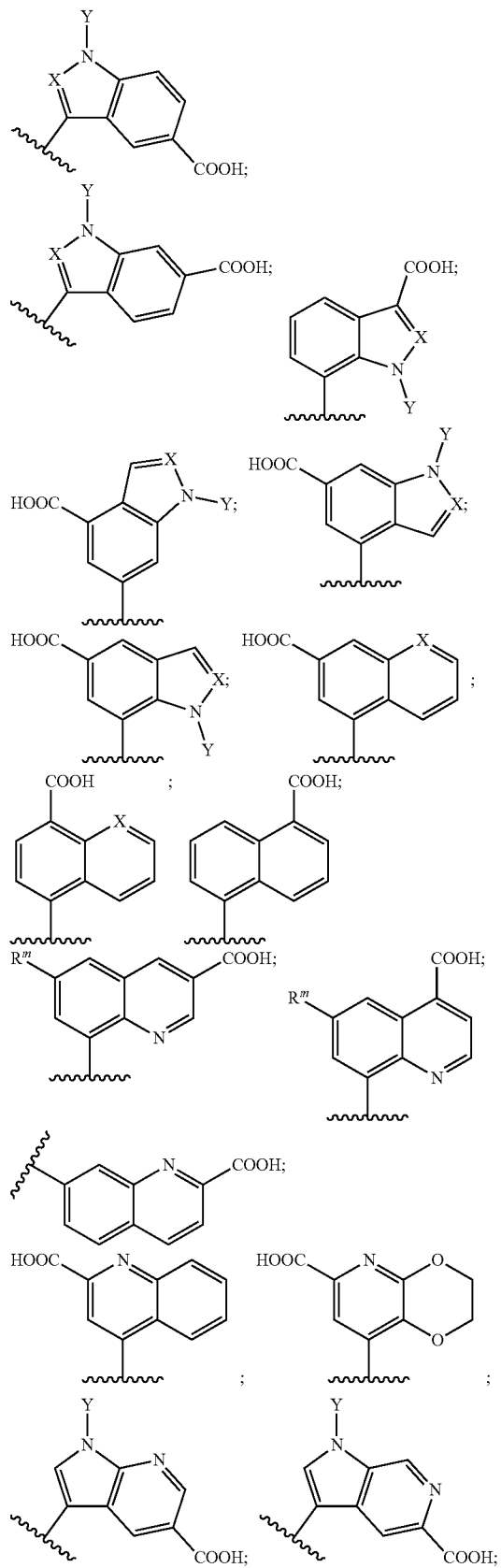
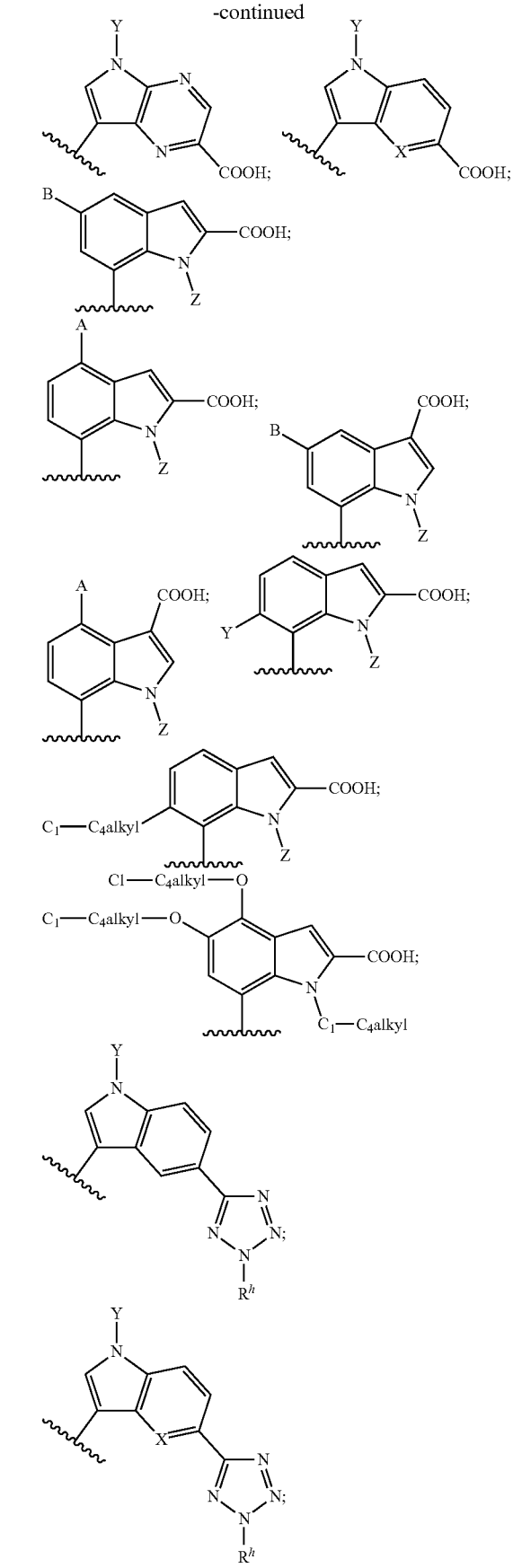

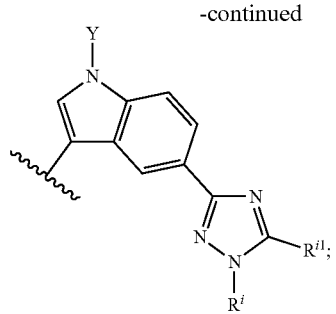
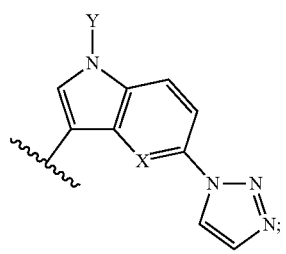
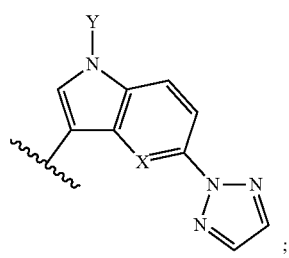
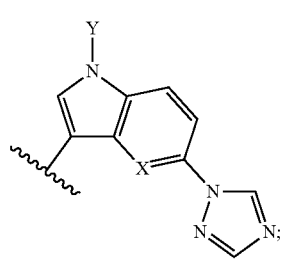
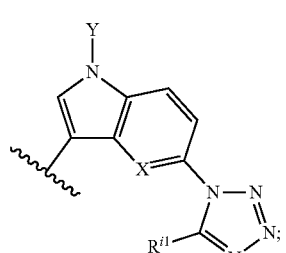
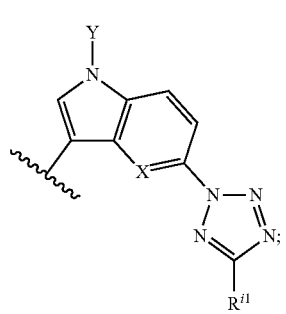
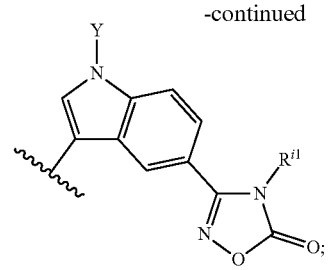
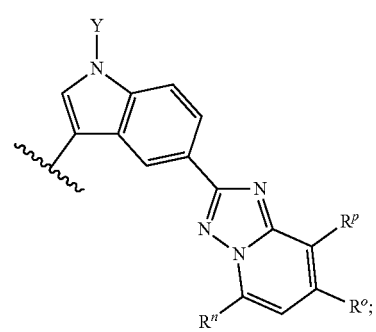
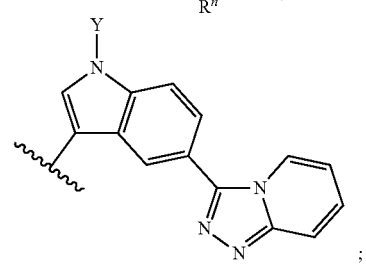
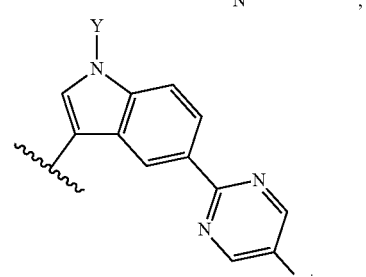
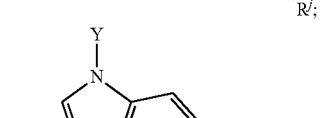
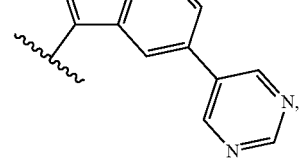
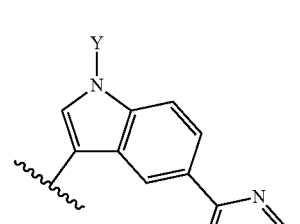
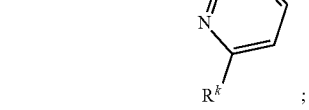

-continued

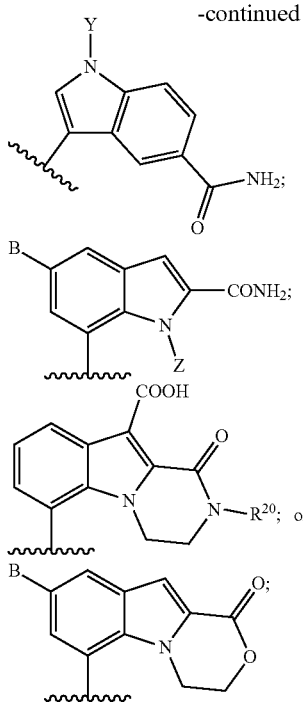

wherein

A and B are each independently hydrogen, halogen, $C_1$-$C_4$-alkyl, $C_1$-$C_4$-haloalkyl, $C_1$-$C_4$-alkoxy, $C_1$-$C_4$-haloalkoxy, halogen, —$OR^c$, —$CH_2OR^c$, $CH_2CH_2OC_1$-$C_4$alkyl, —$NHC(O)R^i$, —$N(C_1$-$C_4$alkyl)$C(O)R^i$, —$NR^cR^c$, $CH_2N(R^c)_2$, $CH_2CH_2N(R^c)_2$, COOH,

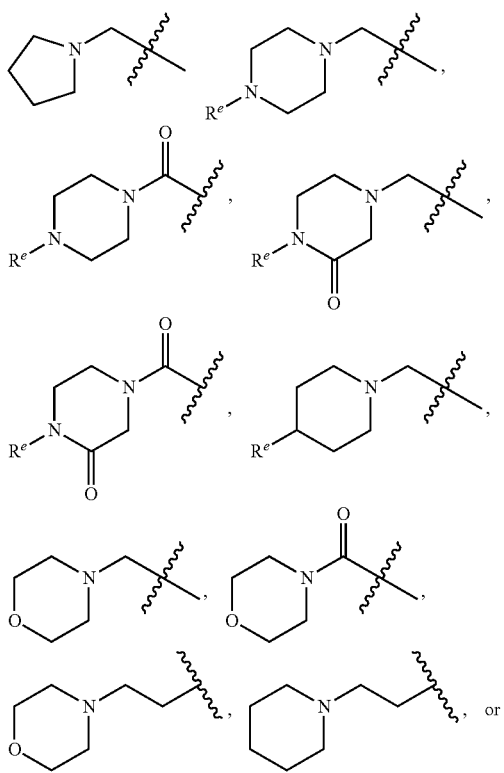

-continued

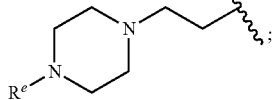

X is C(H), C($C_1$-$C_4$-alkyl), C($C_1$-$C_4$-haloalkyl) or N;
Y is hydrogen, $C_1$-$C_4$-alkyl,

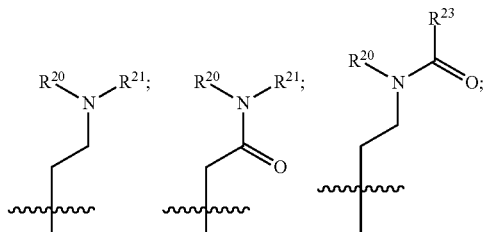

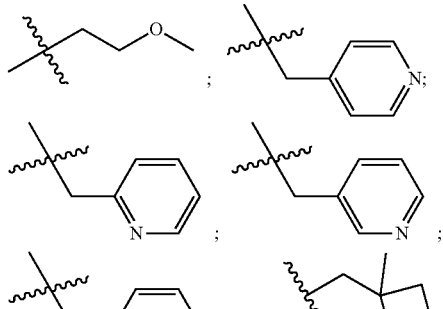

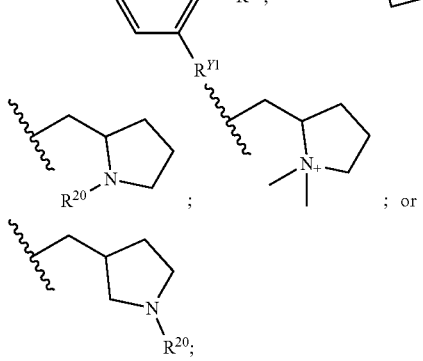

$R^{Y1}$, at each occurrence, is independently a halogen;
Z is $C_1$-$C_4$-alkyl

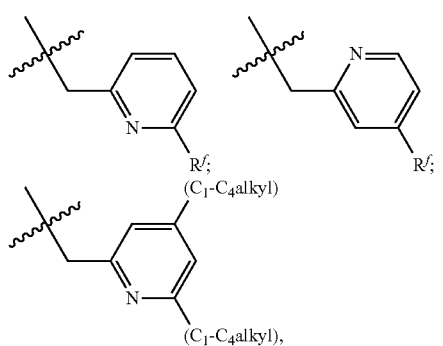

-continued

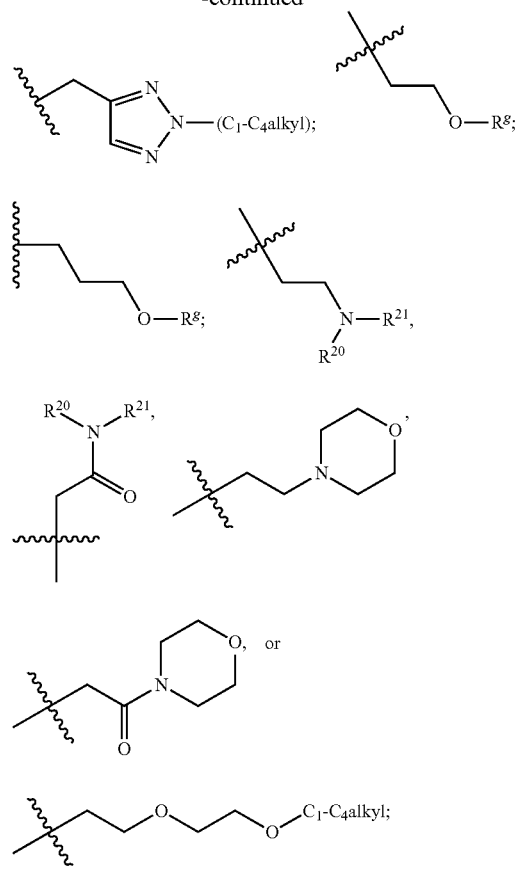

R[20] and R[21] are each independently hydrogen or $C_1$-$C_4$-alkyl, or R[20] and R[21] together with the nitrogen to which they are attached can form an optionally substituted 4-8 membered heterocyclic ring;

R[c], at each occurrence, is independently hydrogen, $C_1$-$C_4$-alkyl, $C_2$-$C_4$-alkenyl,

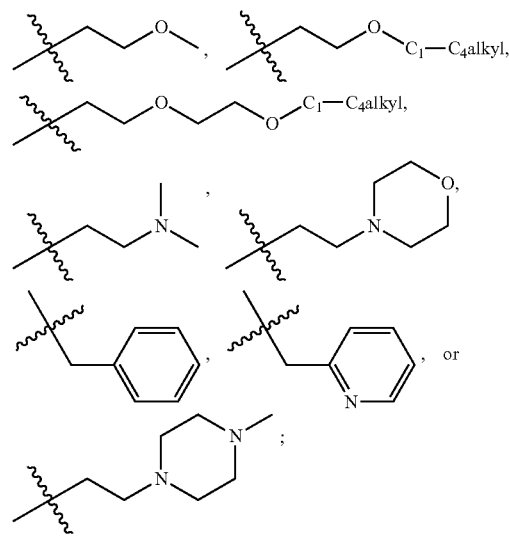

R[d] is $C_1$-$C_4$-alkyl,

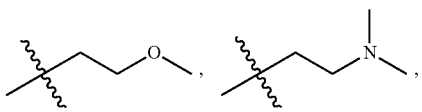

R[e] is $C_1$-$C_4$-alkyl, —O$C_1$-$C_4$-alkyl,

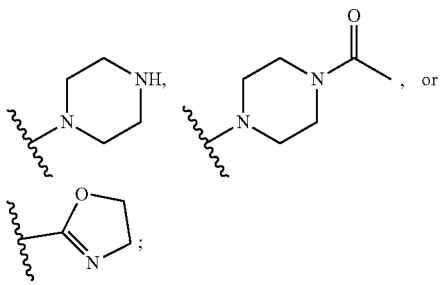

C(O)$C_1$-$C_4$alkyl, or

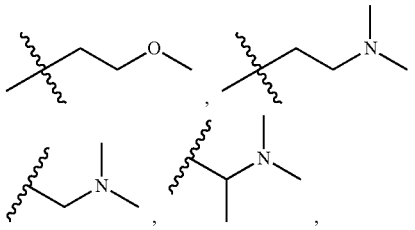

where R[e1] is halogen;

R[f] is hydrogen, $C_1$-$C_4$-alkyl, $C_2$-$C_4$-alkenyl, cyano,

R[g] is hydrogen or $C_1$-$C_4$-alkyl;
R[h] is hydrogen or $C_1$-$C_4$-alkyl;
R[i] is hydrogen, $C_1$-$C_4$-alkyl,

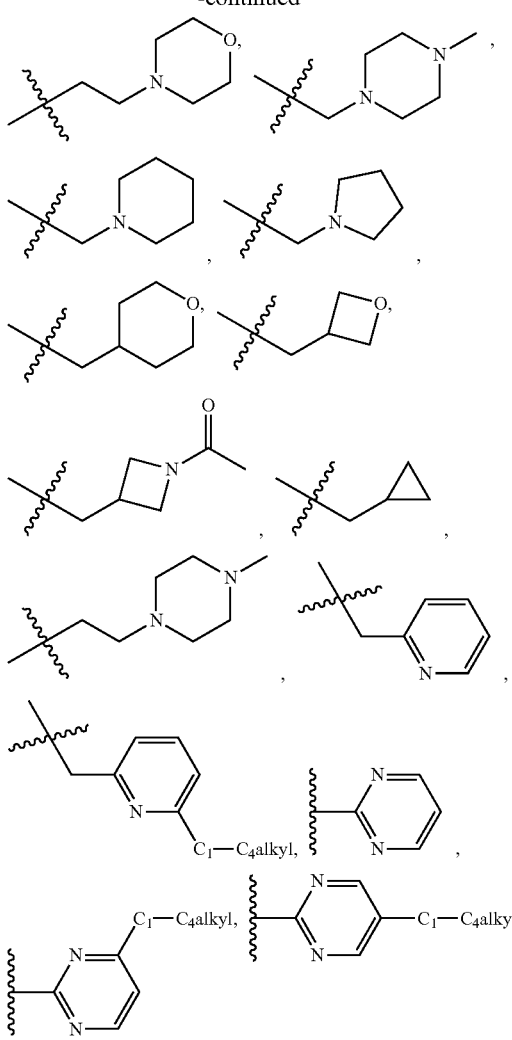

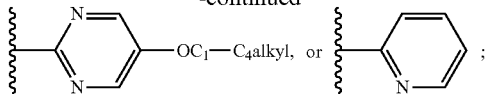

$R^{i1}$ is hydrogen, $C_1$-$C_4$-alkyl, $CH_2$—O—$C_1$-$C_4$alkyl;
$R^j$ is hydrogen, $C_1$-$C_4$-alkyl or $C_1$-$C_4$-alkoxy;
$R^k$ is $C_1$-$C_4$-alkyl;
$R^m$ is hydrogen or $C_1$-$C_4$alkyl;
$R^n$ is hydrogen or $C_1$-$C_4$alkyl;
$R^o$ is hydrogen or $C_1$-$C_4$alkyl; and
$R^p$ is hydrogen, $C_1$-$C_4$alkyl, $CH_2OC_1$-$C_4$alkyl, or

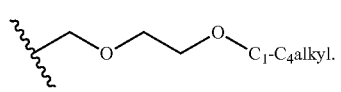

In certain embodiments, the optionally substituted 4-8 membered heterocyclic ring formed by $R^{20}$ and $R^{21}$ together with the nitrogen to which they are attached is selected from the group consisting of

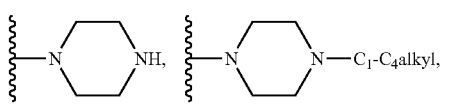

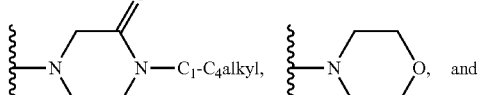

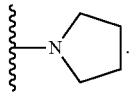

In certain embodiments, the compound of formula (I) is selected from the group consisting of the compounds in Table 1, or a pharmaceutically acceptable salt thereof.

TABLE 1

Exemplary compounds.

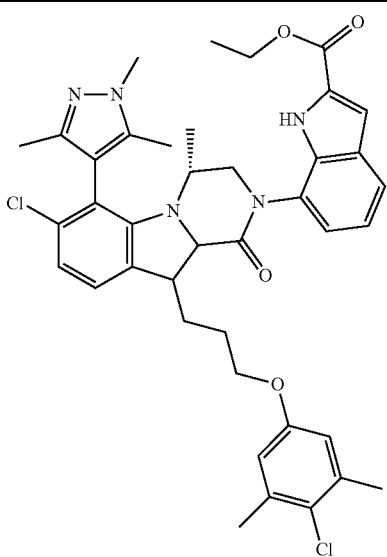

I-1

TABLE 1-continued
Exemplary compounds.
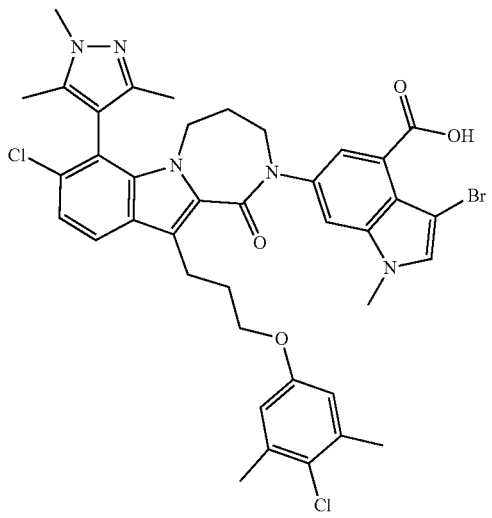 [SMILES: Cc1cc(OCCCc2c3n(c4c(-c5c(C)nn(C)c5C)c(Cl)ccc24)CCCN(c2cc(C(=O)O)c4c(Br)cn(C)c4c2)C3=O)cc(C)c1Cl]
I-2
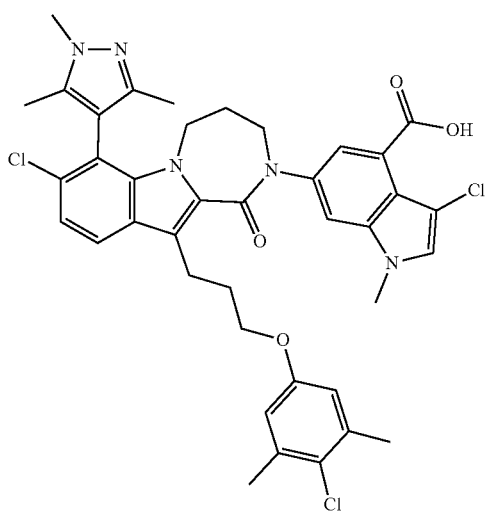 [SMILES: Cc1cc(OCCCc2c3n(c4c(-c5c(C)nn(C)c5C)c(Cl)ccc24)CCCN(c2cc(C(=O)O)c4c(Cl)cn(C)c4c2)C3=O)cc(C)c1Cl]
I-3
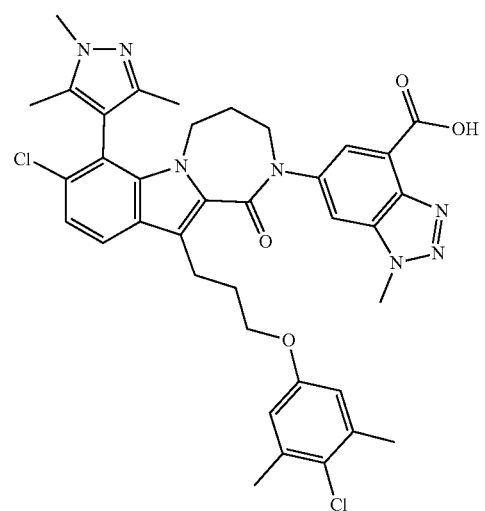 [SMILES: Cc1cc(OCCCc2c3n(c4c(-c5c(C)nn(C)c5C)c(Cl)ccc24)CCCN(c2cc(C(=O)O)c4nnn(C)c4c2)C3=O)cc(C)c1Cl]
I-4

TABLE 1-continued
Exemplary compounds.
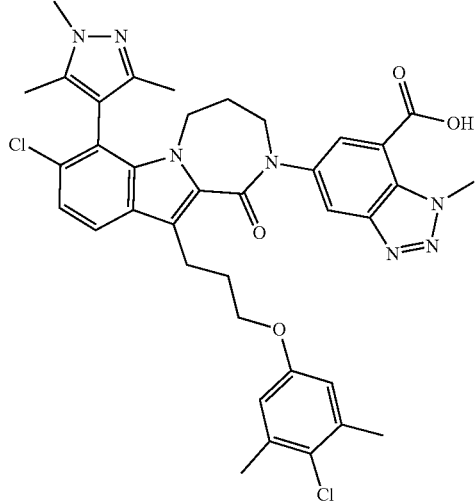 [SMILES: Cc1cc(OCCCc2c3n(c4c(-c5c(C)nn(C)c5C)c(Cl)ccc24)CCCN(c2cc(C(=O)O)c4c(c2)nnn4C)C3=O)cc(C)c1Cl]
I-5
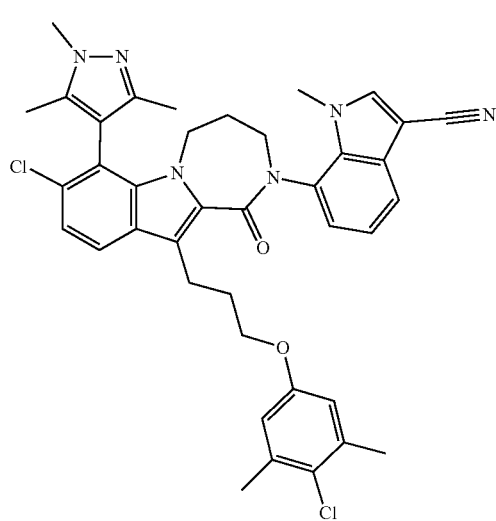 [SMILES: Cc1cc(OCCCc2c3n(c4c(-c5c(C)nn(C)c5C)c(Cl)ccc24)CCCN(c2cccc4c(C#N)cn(C)c24)C3=O)cc(C)c1Cl]
I-6
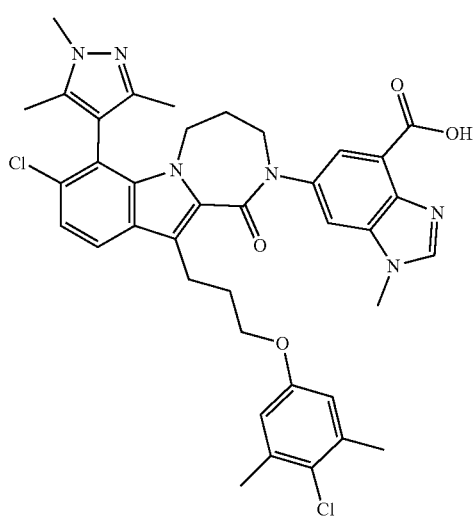 [SMILES: Cc1cc(OCCCc2c3n(c4c(-c5c(C)nn(C)c5C)c(Cl)ccc24)CCCN(c2cc(C(=O)O)c4ncn(C)c4c2)C3=O)cc(C)c1Cl]
I-7

TABLE 1-continued
Exemplary compounds.
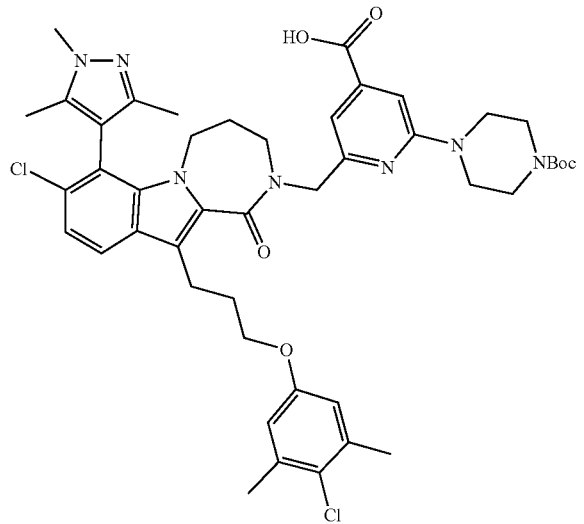 [SMILES: Cc1cc(OCCCc2c3n(c4c(-c5c(C)nn(C)c5C)c(Cl)ccc24)CCCN(Cc2cc(C(=O)O)cc(N4CCN(C(=O)OC(C)(C)C)CC4)n2)C3=O)cc(C)c1Cl]
I-8
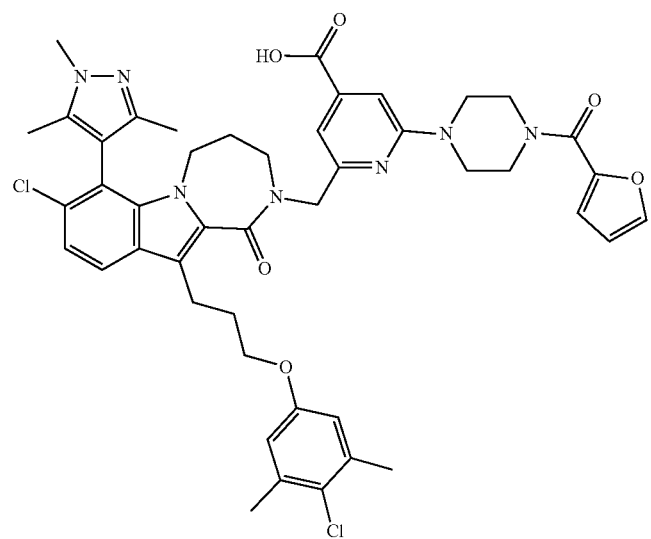 [SMILES: Cc1cc(OCCCc2c3n(c4c(-c5c(C)nn(C)c5C)c(Cl)ccc24)CCCN(Cc2cc(C(=O)O)cc(N4CCN(C(=O)c5ccco5)CC4)n2)C3=O)cc(C)c1Cl]
I-9
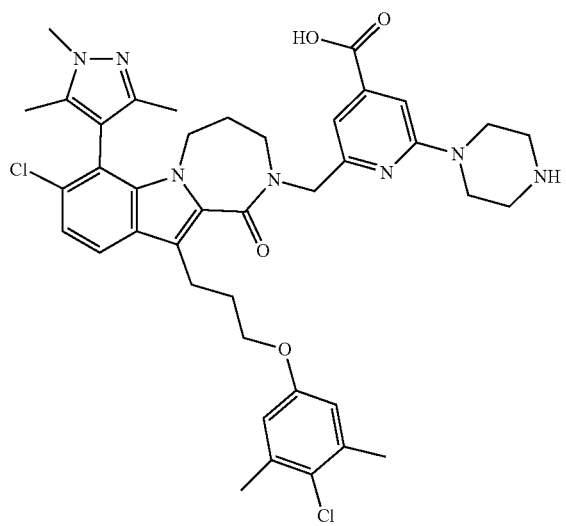 [SMILES: Cc1cc(OCCCc2c3n(c4c(-c5c(C)nn(C)c5C)c(Cl)ccc24)CCCN(Cc2cc(C(=O)O)cc(N4CCNCC4)n2)C3=O)cc(C)c1Cl]
I-10

TABLE 1-continued
Exemplary compounds.
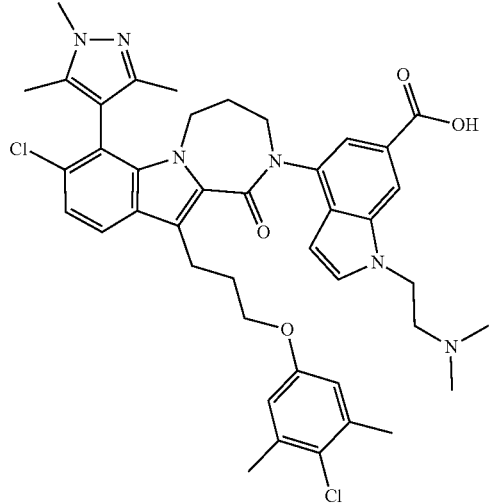
I-11
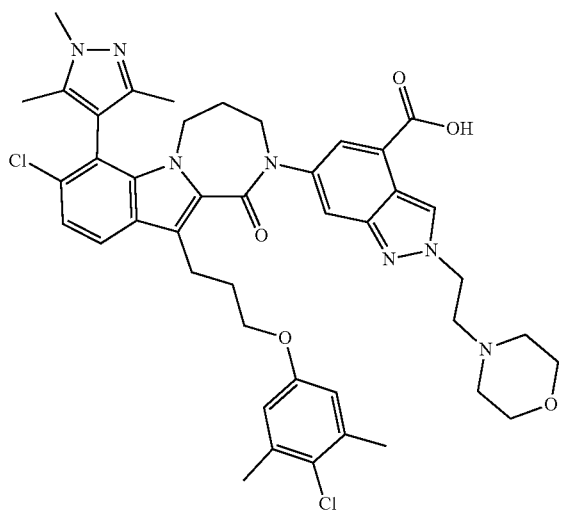 [SMILES: Cc1cc(OCCCc2c3n(c4c(-c5c(C)nn(C)c5C)c(Cl)ccc24)CCCN(c2cc(C(=O)O)c4cn(CCN5CCOCC5)nc4c2)C3=O)cc(C)c1Cl]
I-12
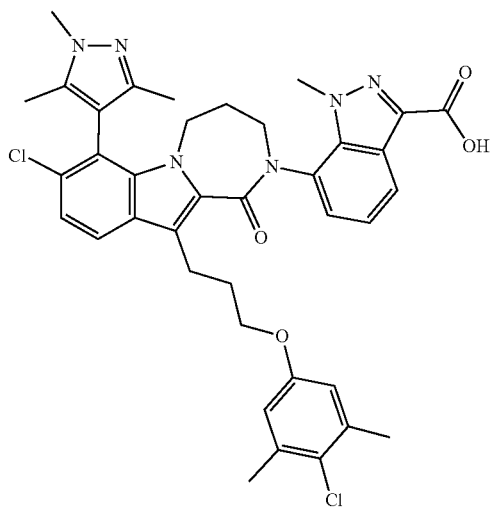 [SMILES: Cc1cc(OCCCc2c3n(c4c(-c5c(C)nn(C)c5C)c(Cl)ccc24)CCCN(c2cccc4c(C(=O)O)nn(C)c24)C3=O)cc(C)c1Cl]
I-13

TABLE 1-continued
Exemplary compounds.
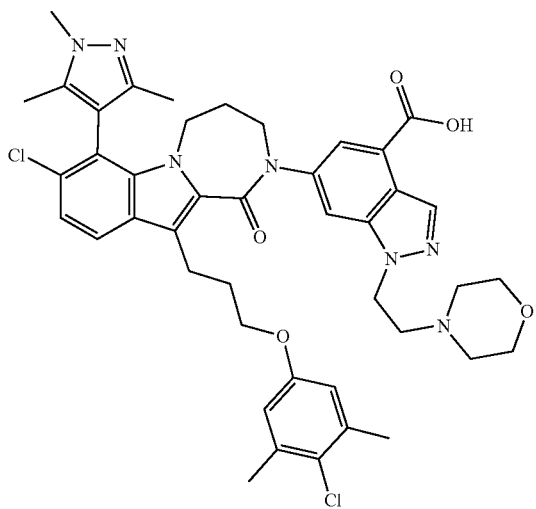 [SMILES: Cc1cc(OCCCc2c3n(c4c(-c5c(C)nn(C)c5C)c(Cl)ccc24)CCCN(c2cc(C(=O)O)c4cnn(CCN5CCOCC5)c4c2)C3=O)cc(C)c1Cl]
I-14
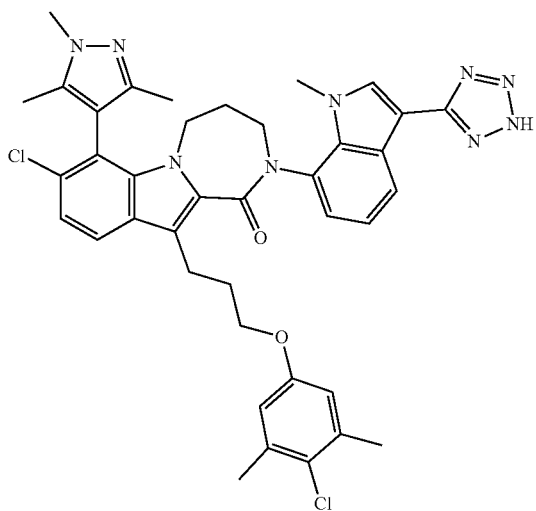 [SMILES: Cc1cc(OCCCc2c3n(c4c(-c5c(C)nn(C)c5C)c(Cl)ccc24)CCCN(c2cccc4c(-c5nn[nH]n5)cn(C)c24)C3=O)cc(C)c1Cl]
I-15
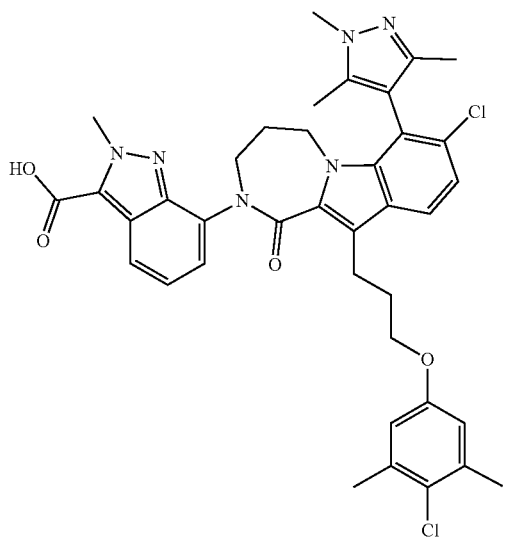 [SMILES: Cc1cc(OCCCc2c3n(c4c(-c5c(C)nn(C)c5C)c(Cl)ccc24)CCCN(c2cccc4c(C(=O)O)n(C)nc24)C3=O)cc(C)c1Cl]
I-16

TABLE 1-continued
Exemplary compounds.
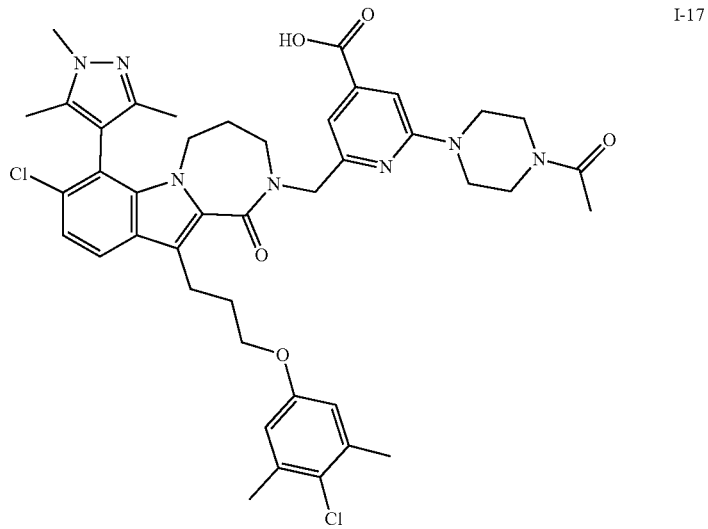
I-17
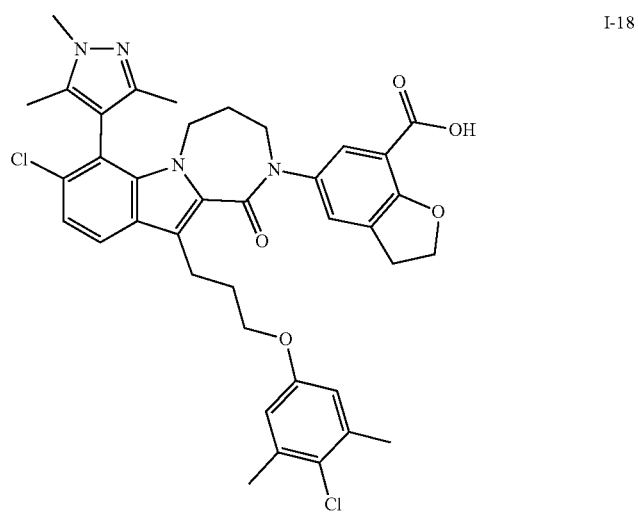
I-18
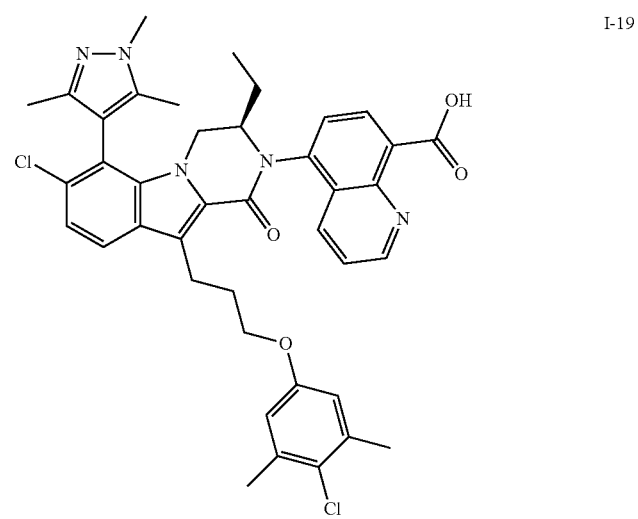
I-19

TABLE 1-continued
Exemplary compounds.
I-20
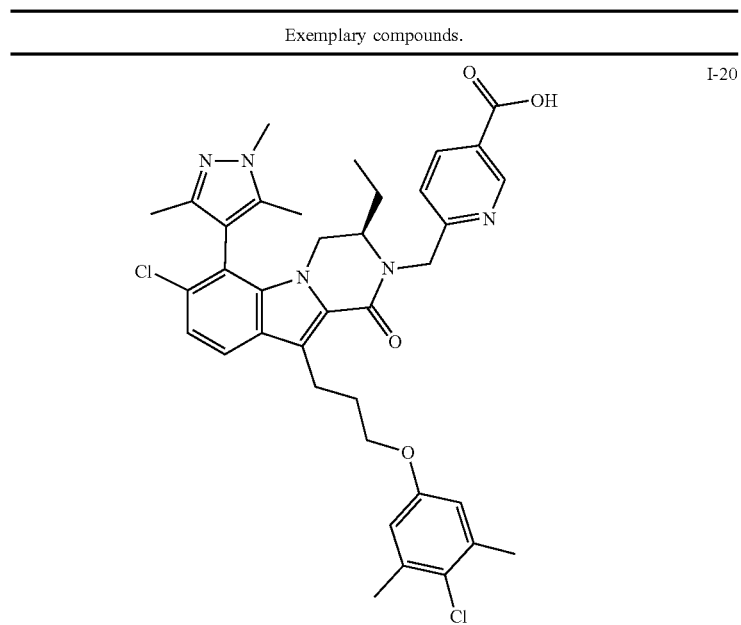
I-21
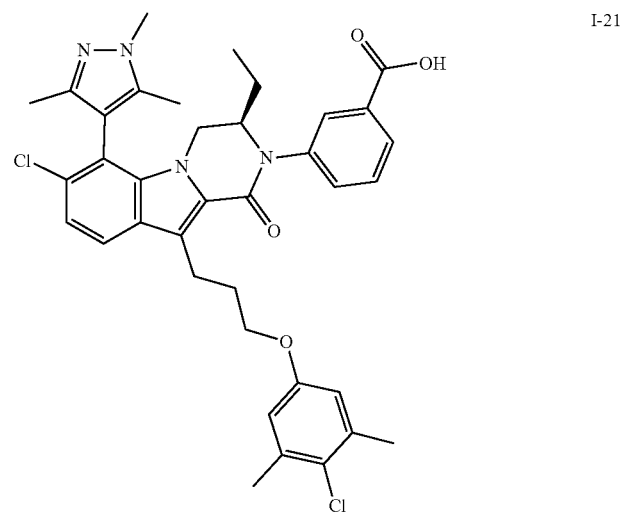
I-22
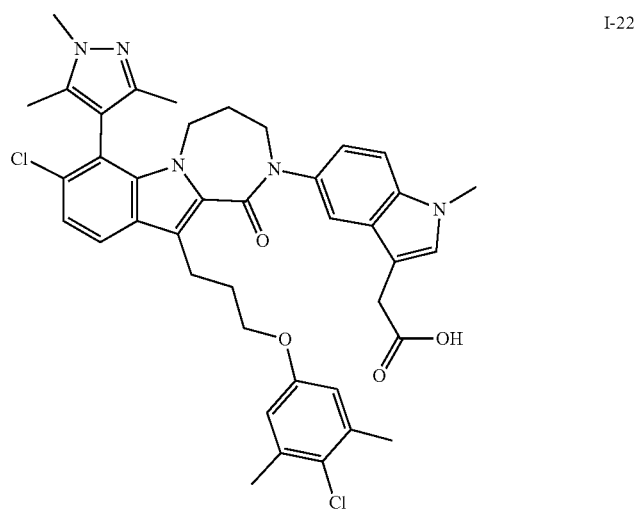

TABLE 1-continued
Exemplary compounds.
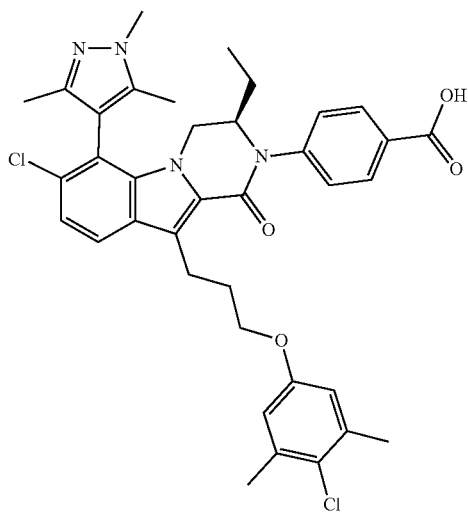 [SMILES: CC[C@@H]1Cn2c(c(CCCOc3cc(C)c(Cl)c(C)c3)c3ccc(Cl)c(-c4c(C)nn(C)c4C)c32)C(=O)N1c1ccc(C(=O)O)cc1]
I-23
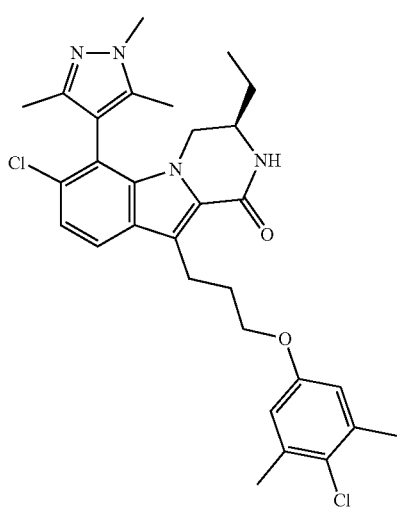
I-24
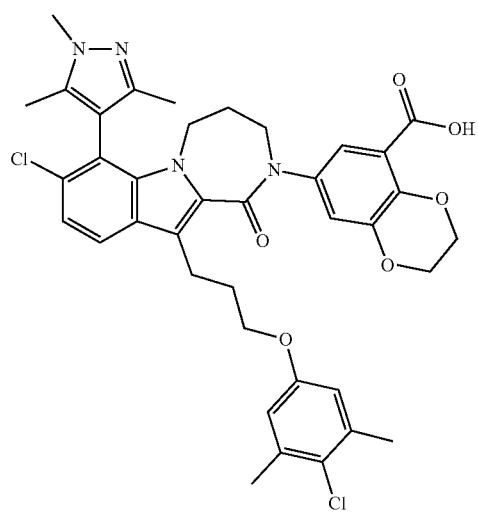 [SMILES: Cc1cc(OCCCc2c3n(c4c(-c5c(C)nn(C)c5C)c(Cl)ccc24)CCCN(c2cc4c(c(C(=O)O)c2)OCCO4)C3=O)cc(C)c1Cl]
I-25

TABLE 1-continued
Exemplary compounds.
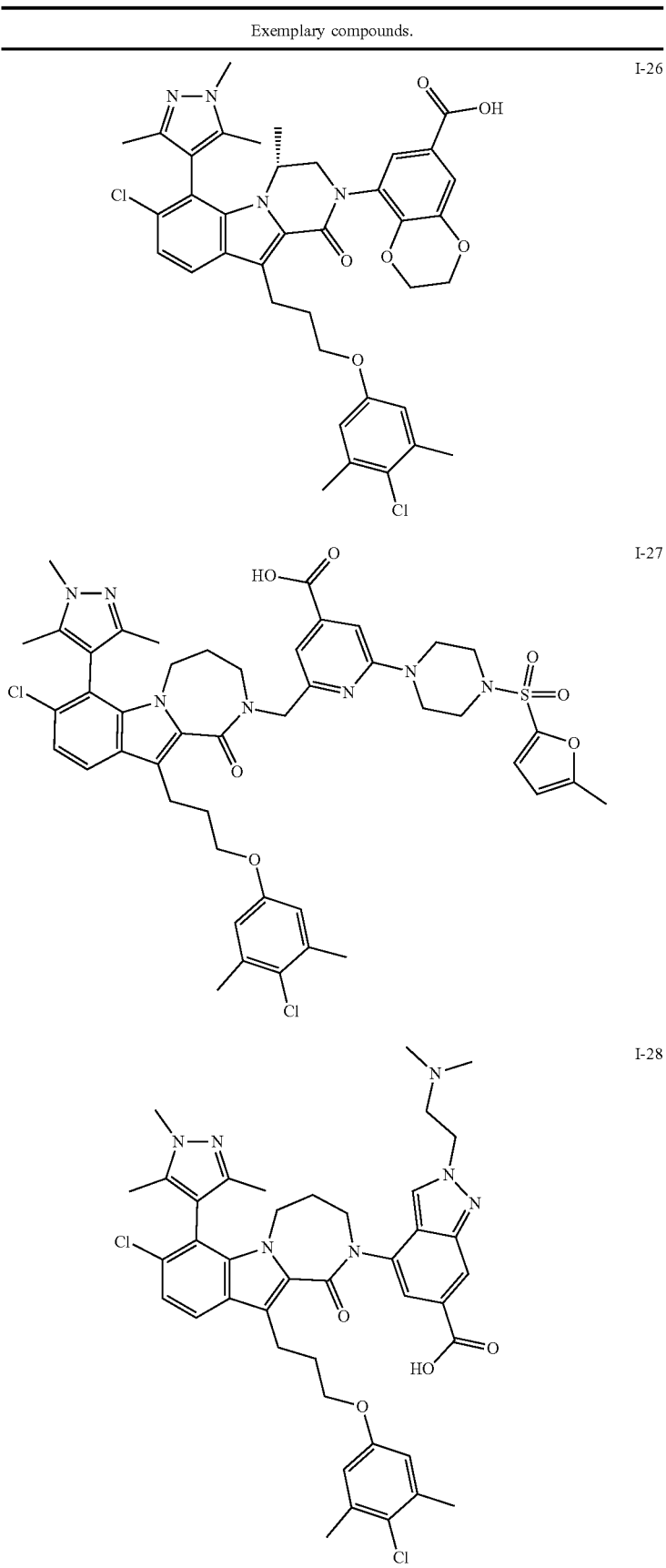

TABLE 1-continued

Exemplary compounds.

I-29

I-30

I-31

TABLE 1-continued
Exemplary compounds.
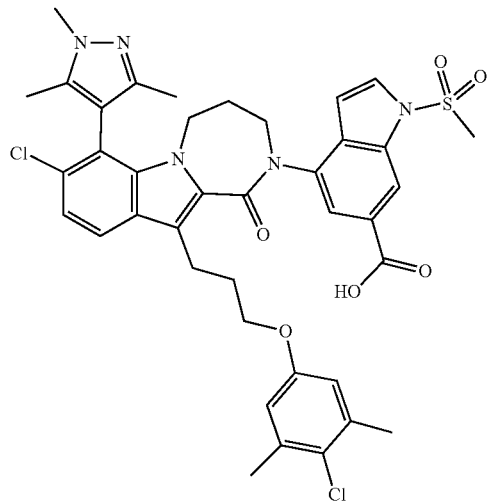 [SMILES: Cc1cc(OCCCc2c3n(c4c(-c5c(C)nn(C)c5C)c(Cl)ccc24)CCCN(c2cc(C(=O)O)cc4c2ccn4S(C)(=O)=O)C3=O)cc(C)c1Cl]
I-32
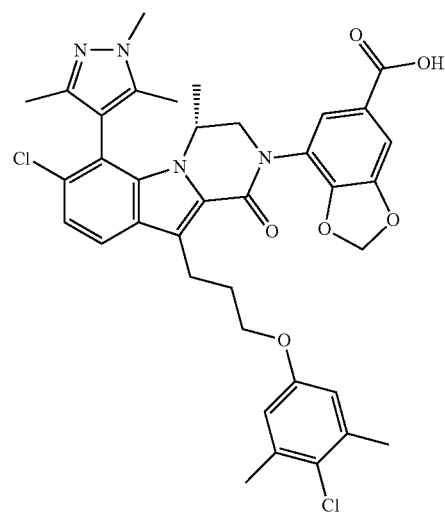 [SMILES: Cc1cc(OCCCc2c3n(c4c(-c5c(C)nn(C)c5C)c(Cl)ccc24)[C@H](C)CN(c2cc(C(=O)O)cc4c2OCO4)C3=O)cc(C)c1Cl]
I-33
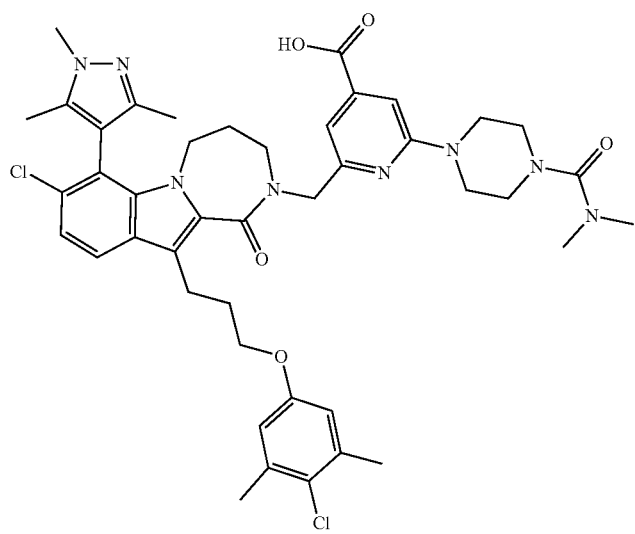 [SMILES: Cc1cc(OCCCc2c3n(c4c(-c5c(C)nn(C)c5C)c(Cl)ccc24)CCCN(Cc2cc(C(=O)O)cc(N4CCN(C(=O)N(C)C)CC4)n2)C3=O)cc(C)c1Cl]
I-34

TABLE 1-continued
Exemplary compounds.
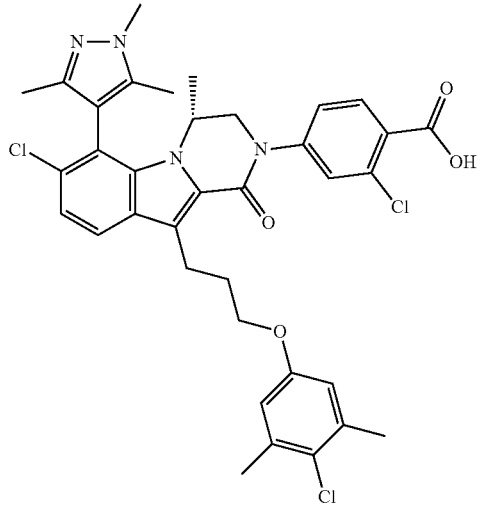 [SMILES: Cc1cc(OCCCc2c3n(c4c(-c5c(C)nn(C)c5C)c(Cl)ccc24)[C@H](C)CN(c2ccc(C(=O)O)c(Cl)c2)C3=O)cc(C)c1Cl]
I-35
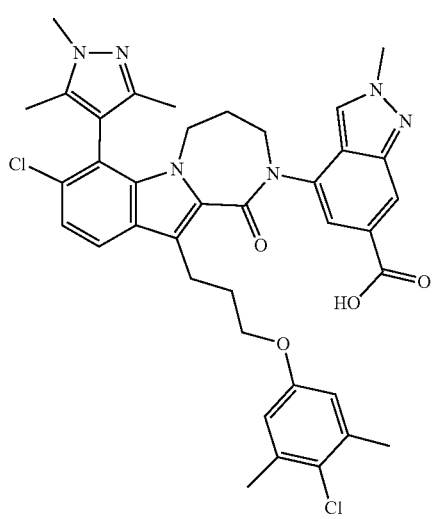 [SMILES: Cc1cc(OCCCc2c3n(c4c(-c5c(C)nn(C)c5C)c(Cl)ccc24)CCCN(c2cc(C(=O)O)cc4nn(C)cc24)C3=O)cc(C)c1Cl]
I-36
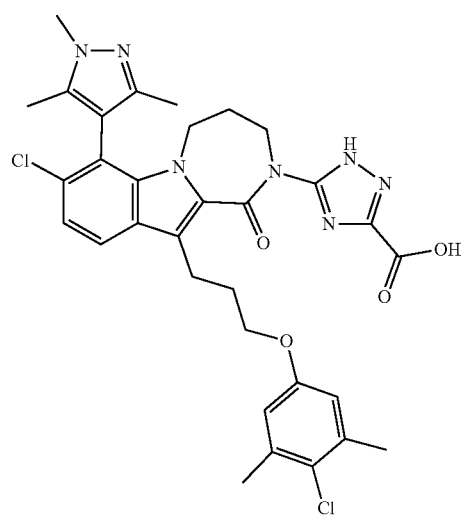 [SMILES: Cc1cc(OCCCc2c3n(c4c(-c5c(C)nn(C)c5C)c(Cl)ccc24)CCCN(c2nc(C(=O)O)n[nH]2)C3=O)cc(C)c1Cl]
I-37

TABLE 1-continued
Exemplary compounds.
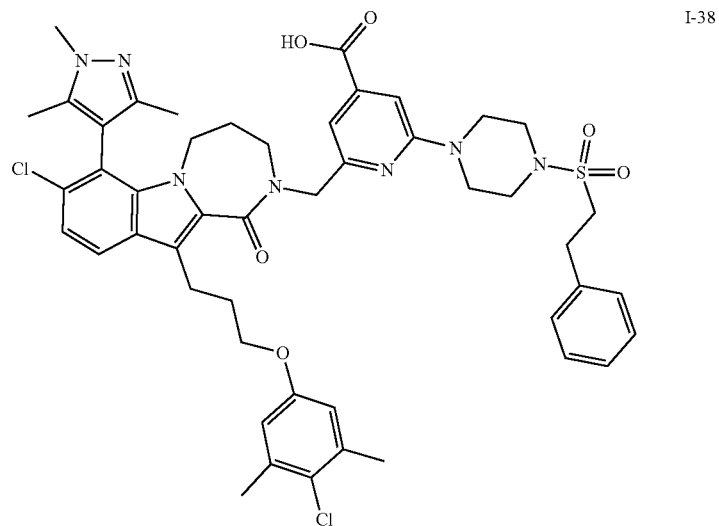
I-38
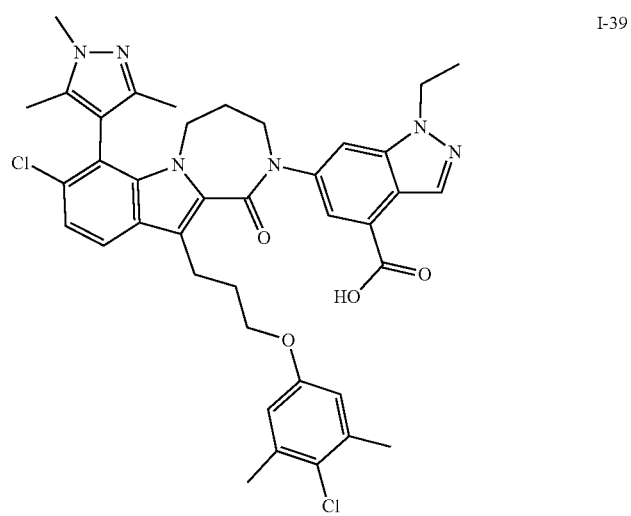
I-39
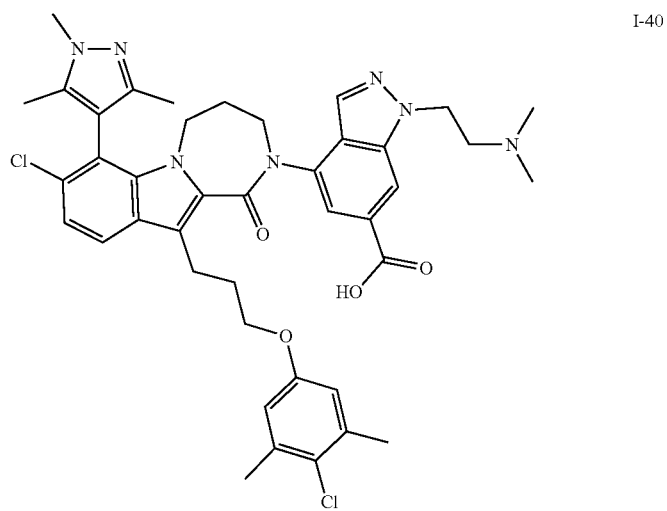
I-40

TABLE 1-continued
Exemplary compounds.
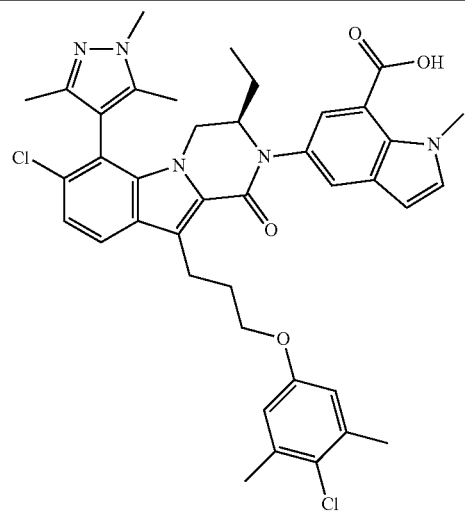
I-41
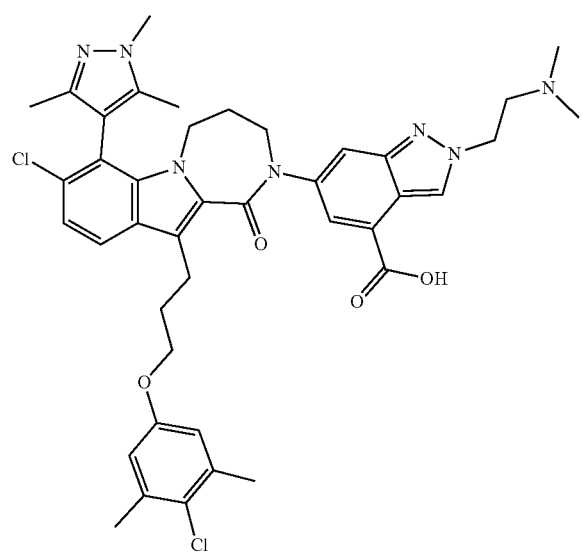 [SMILES: Cc1cc(OCCCc2c3n(c4c(-c5c(C)nn(C)c5C)c(Cl)ccc24)CCCN(c2cc(C(=O)O)c4cn(CCN(C)C)nc4c2)C3=O)cc(C)c1Cl]
I-42
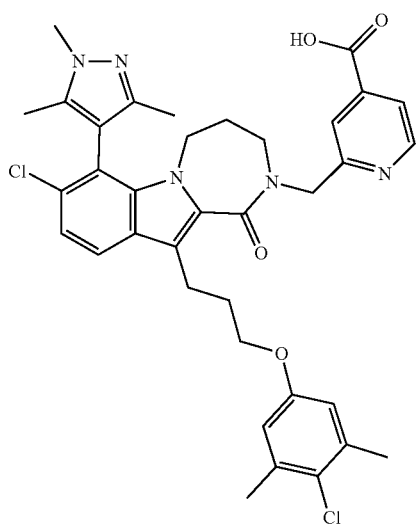 [SMILES: Cc1cc(OCCCc2c3n(c4c(-c5c(C)nn(C)c5C)c(Cl)ccc24)CCCN(Cc2cc(C(=O)O)ccn2)C3=O)cc(C)c1Cl]
I-43

TABLE 1-continued
Exemplary compounds.
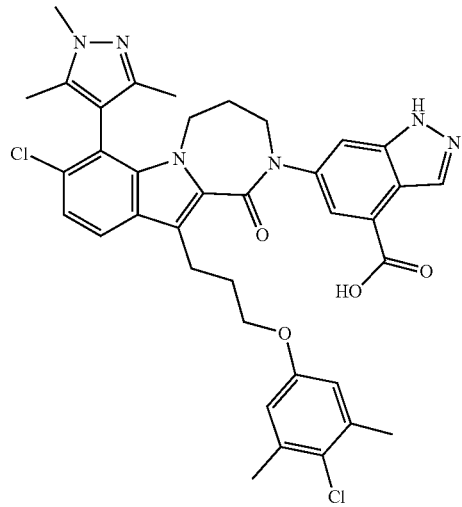 [SMILES: Cc1cc(OCCCc2c3n(c4c(-c5c(C)nn(C)c5C)c(Cl)ccc24)CCCN(c2cc(C(=O)O)c4cn[nH]c4c2)C3=O)cc(C)c1Cl]
I-44
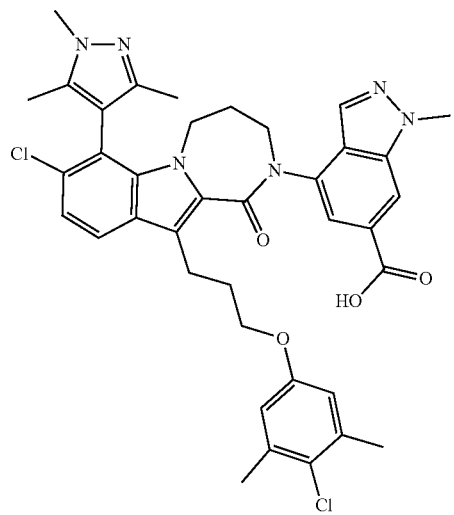 [SMILES: Cc1cc(OCCCc2c3n(c4c(-c5c(C)nn(C)c5C)c(Cl)ccc24)CCCN(c2cc(C(=O)O)cc4c2cnn4C)C3=O)cc(C)c1Cl]
I-45
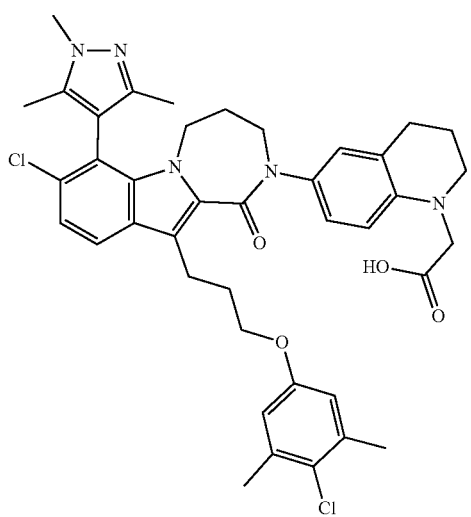 [SMILES: Cc1cc(OCCCc2c3n(c4c(-c5c(C)nn(C)c5C)c(Cl)ccc24)CCCN(c2ccc4c(c2)CCCN4CC(=O)O)C3=O)cc(C)c1Cl]
I-46

TABLE 1-continued
Exemplary compounds.
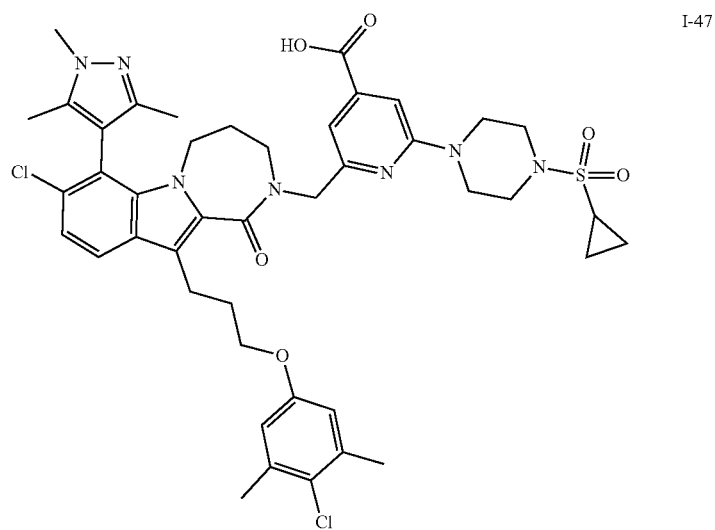
I-47
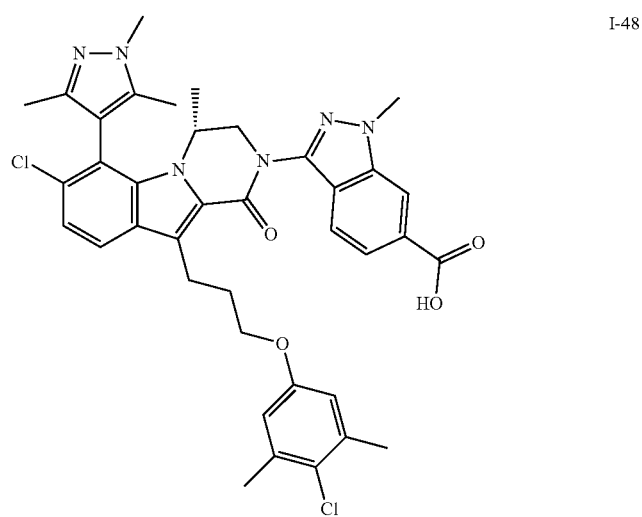
I-48
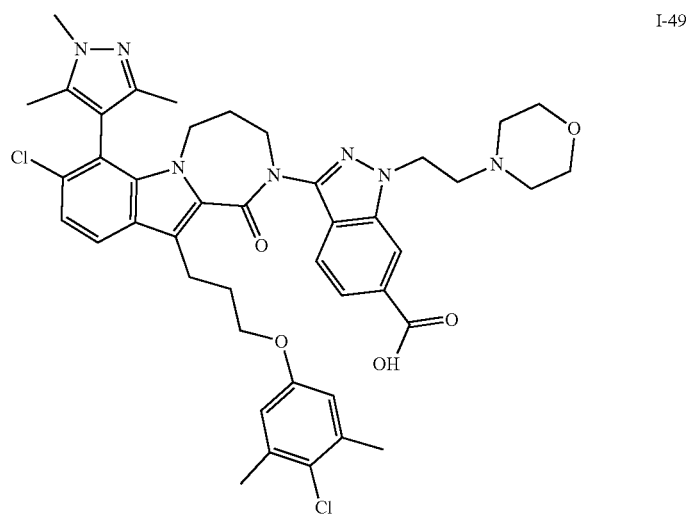
I-49

TABLE 1-continued
Exemplary compounds.
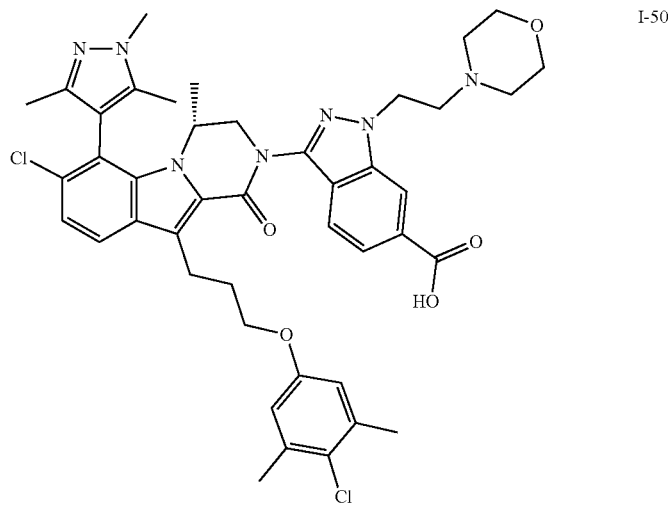
I-50
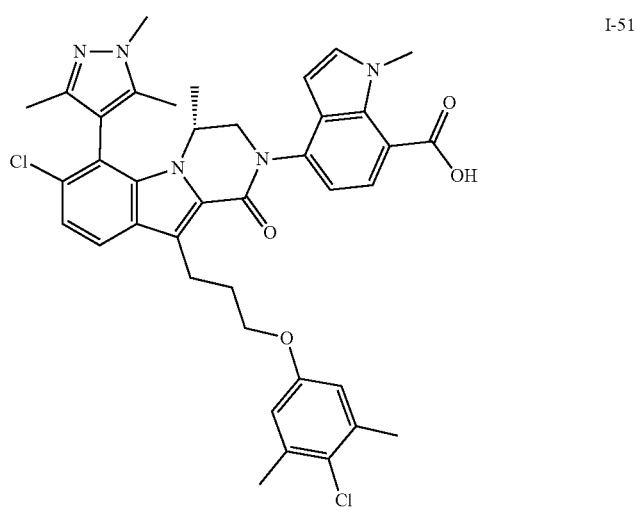
I-51
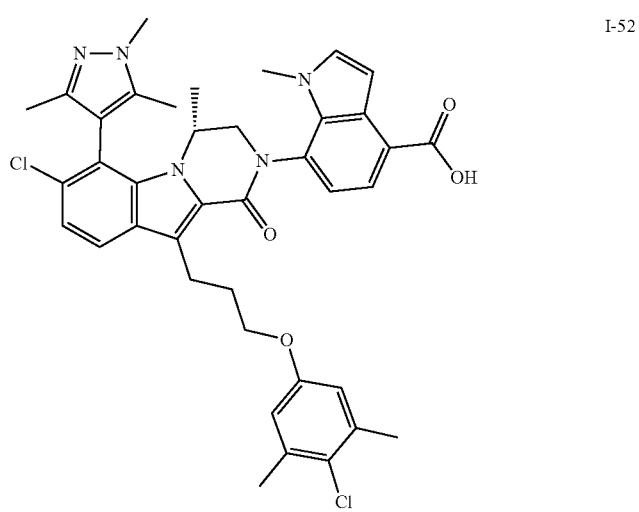
I-52

TABLE 1-continued
Exemplary compounds.
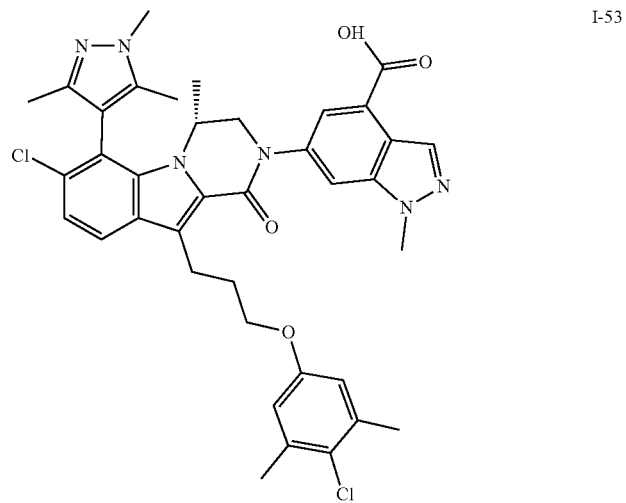
I-53
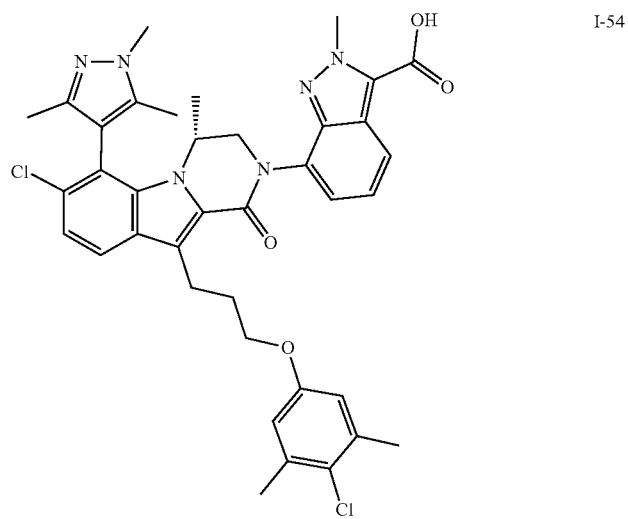
I-54
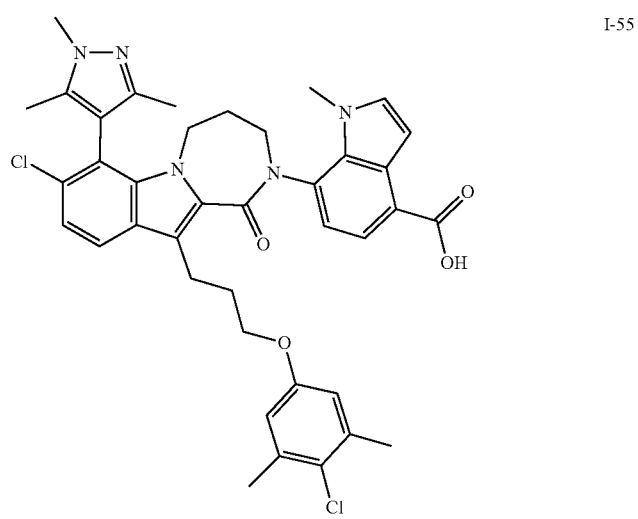
I-55

TABLE 1-continued
Exemplary compounds.
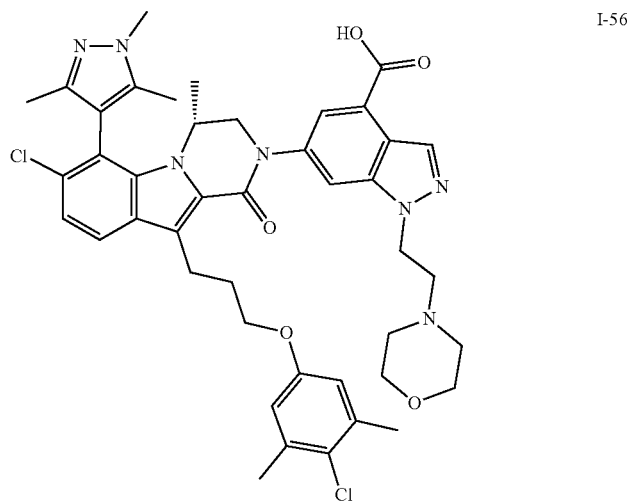
I-56
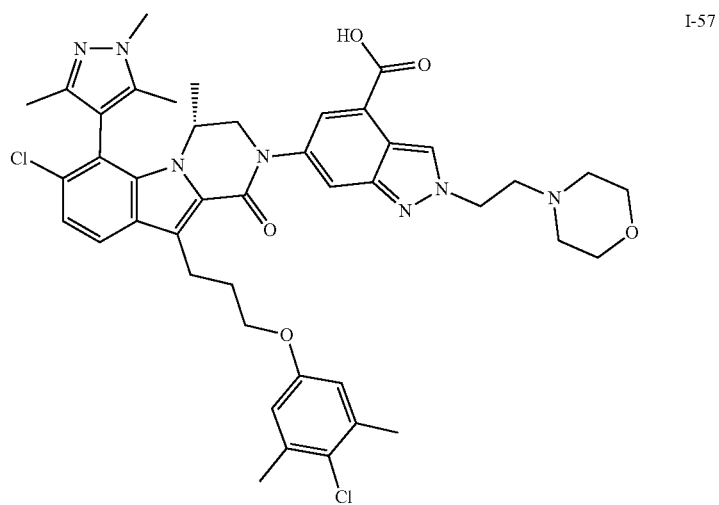
I-57
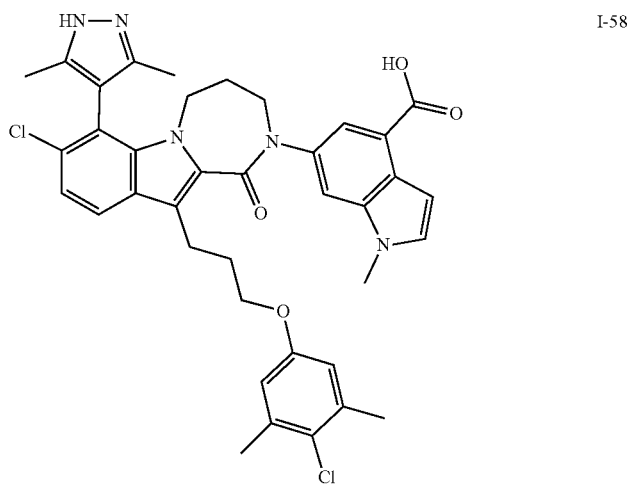
I-58

TABLE 1-continued
Exemplary compounds.
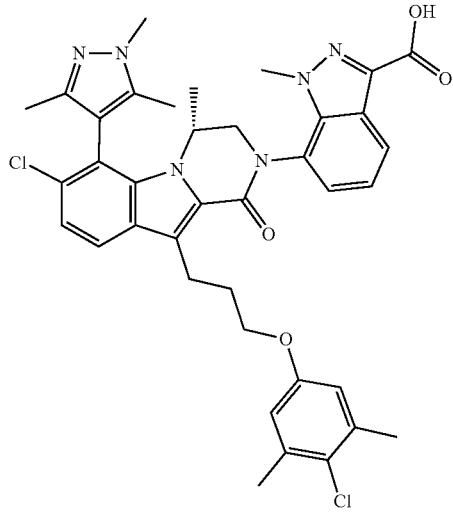 [SMILES: Cc1cc(OCCCc2c3n(c4c(-c5c(C)nn(C)c5C)c(Cl)ccc24)[C@H](C)CN(c2cccc4c(C(=O)O)nn(C)c24)C3=O)cc(C)c1Cl]
I-59
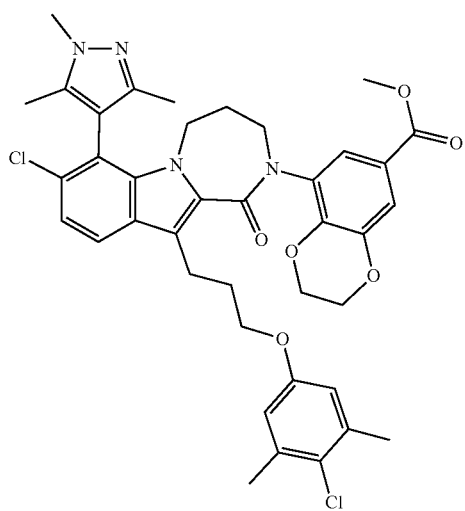 [SMILES: COC(=O)c1cc2c(c(N3CCCn4c(c(CCCOc5cc(C)c(Cl)c(C)c5)c5ccc(Cl)c(-c6c(C)nn(C)c6C)c54)C3=O)c1)OCCO2]
I-60
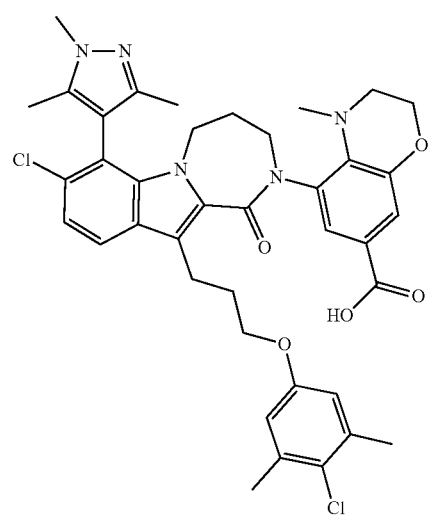 [SMILES: Cc1cc(OCCCc2c3n(c4c(-c5c(C)nn(C)c5C)c(Cl)ccc24)CCCN(c2cc(C(=O)O)cc4c2N(C)CCO4)C3=O)cc(C)c1Cl]
I-61

TABLE 1-continued

Exemplary compounds.

I-62

I-63

I-64

TABLE 1-continued
Exemplary compounds.
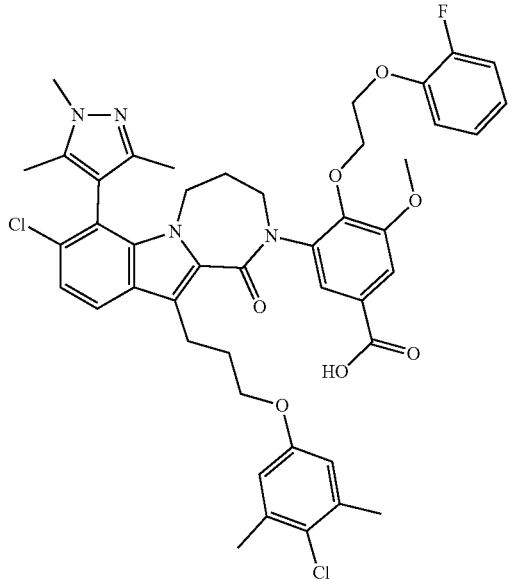 [SMILES: COc1cc(C(=O)O)cc(N2CCCn3c(c(CCCOc4cc(C)c(Cl)c(C)c4)c4ccc(Cl)c(-c5c(C)nn(C)c5C)c43)C2=O)c1OCCOc1ccccc1F]
I-65
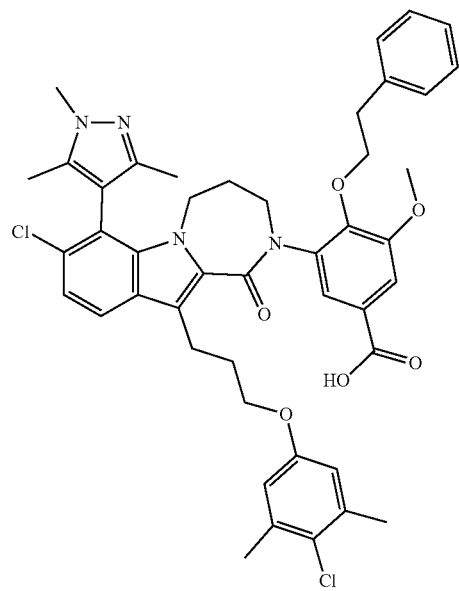 [SMILES: COc1cc(C(=O)O)cc(N2CCCn3c(c(CCCOc4cc(C)c(Cl)c(C)c4)c4ccc(Cl)c(-c5c(C)nn(C)c5C)c43)C2=O)c1OCCc1ccccc1]
I-66

TABLE 1-continued
Exemplary compounds.
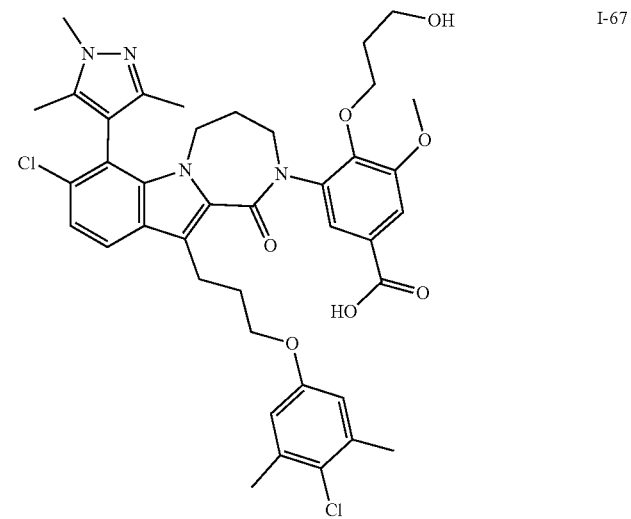
I-67
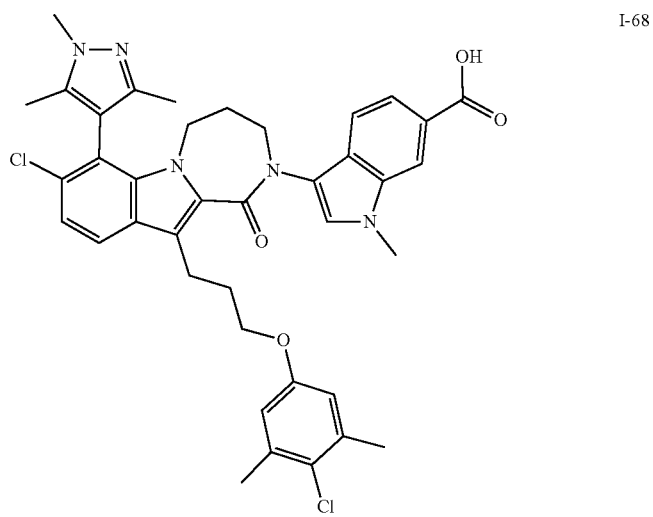
I-68
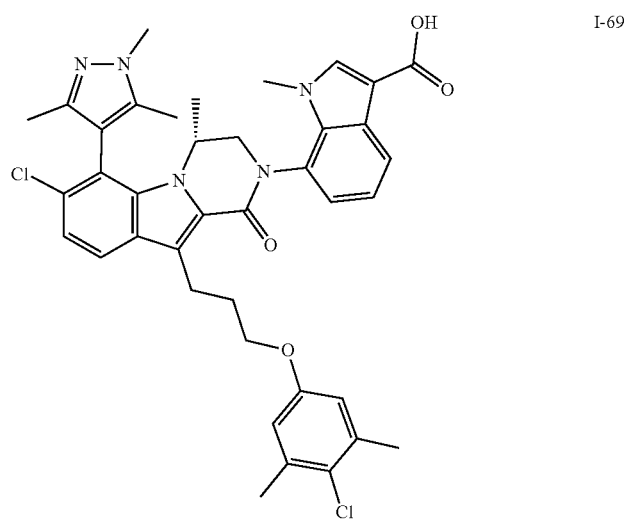
I-69

TABLE 1-continued
Exemplary compounds.
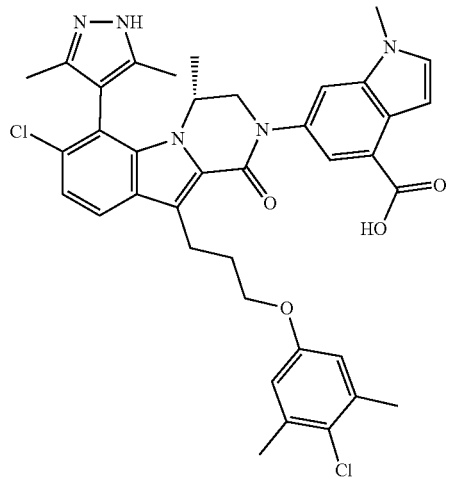 [SMILES: Cc1cc(OCCCc2c3n(c4c(-c5c(C)n[nH]c5C)c(Cl)ccc24)[C@H](C)CN(c2cc(C(=O)O)c4ccn(C)c4c2)C3=O)cc(C)c1Cl]
I-70
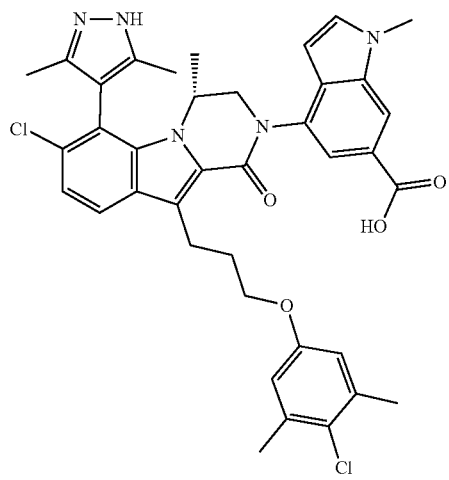 [SMILES: Cc1cc(OCCCc2c3n(c4c(-c5c(C)n[nH]c5C)c(Cl)ccc24)[C@H](C)CN(c2cc(C(=O)O)cc4c2ccn4C)C3=O)cc(C)c1Cl]
I-71
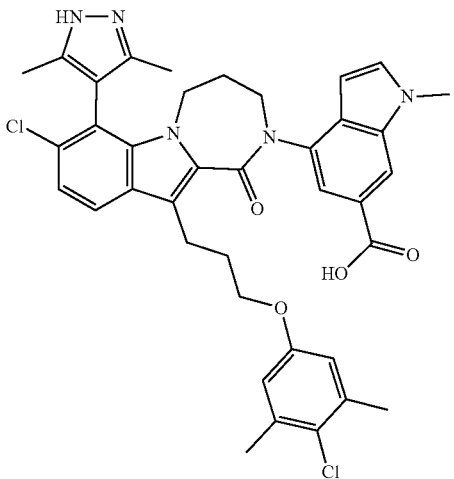 [SMILES: Cc1cc(OCCCc2c3n(c4c(-c5c(C)n[nH]c5C)c(Cl)ccc24)CCCN(c2cc(C(=O)O)cc4c2ccn4C)C3=O)cc(C)c1Cl]
I-72

TABLE 1-continued
Exemplary compounds.
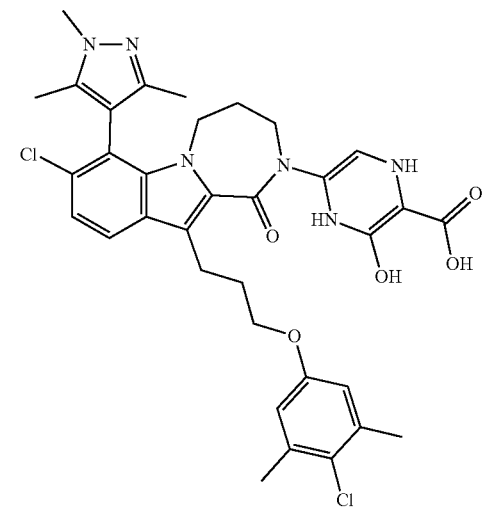 [SMILES: Cc1cc(OCCCc2c3n(c4c(-c5c(C)nn(C)c5C)c(Cl)ccc24)CCCN(C2=CNC(C(=O)O)=C(O)N2)C3=O)cc(C)c1Cl]
I-73
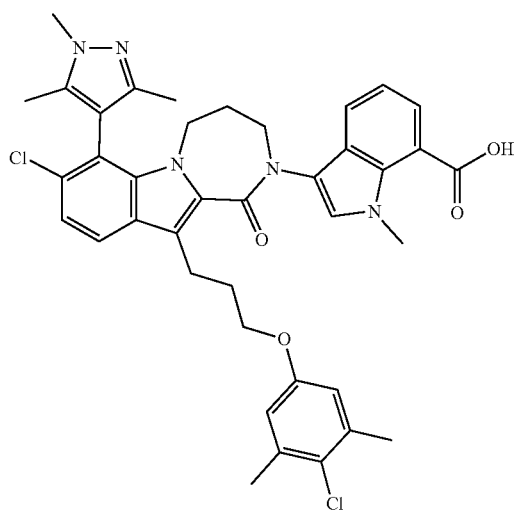 [SMILES: Cc1cc(OCCCc2c3n(c4c(-c5c(C)nn(C)c5C)c(Cl)ccc24)CCCN(c2cn(C)c4c(C(=O)O)cccc24)C3=O)cc(C)c1Cl]
I-74
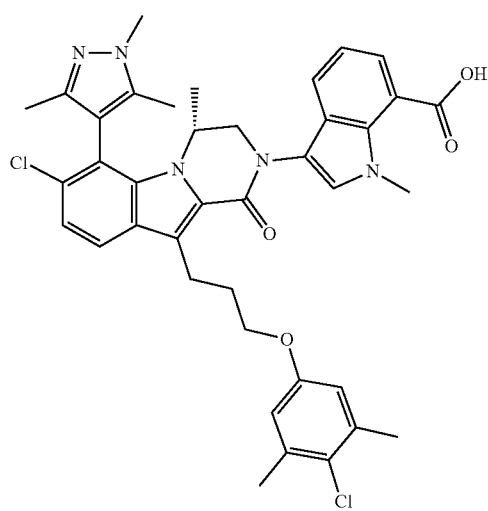 [SMILES: Cc1cc(OCCCc2c3n(c4c(-c5c(C)nn(C)c5C)c(Cl)ccc24)[C@H](C)CN(c2cn(C)c4c(C(=O)O)cccc24)C3=O)cc(C)c1Cl]
I-75

TABLE 1-continued
Exemplary compounds.
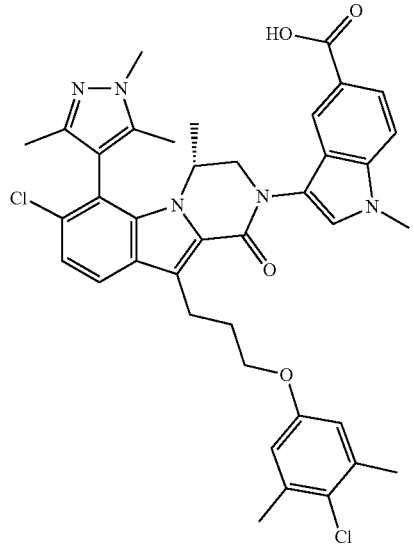 [SMILES: Cc1cc(OCCCc2c3n(c4c(-c5c(C)nn(C)c5C)c(Cl)ccc24)[C@H](C)CN(c2cn(C)c4ccc(C(=O)O)cc24)C3=O)cc(C)c1Cl]
I-76
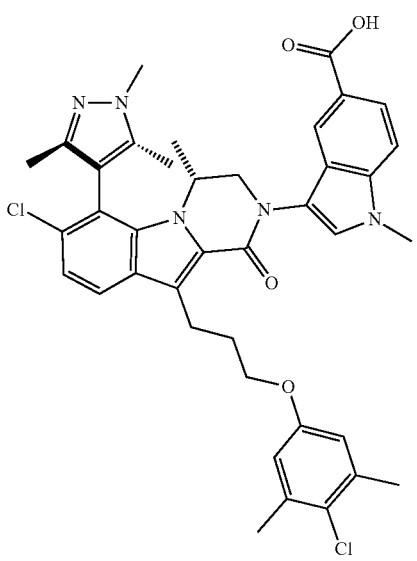
I-77

TABLE 1-continued
Exemplary compounds.
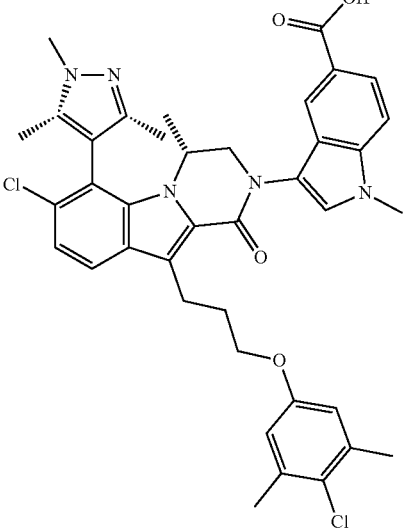
I-78
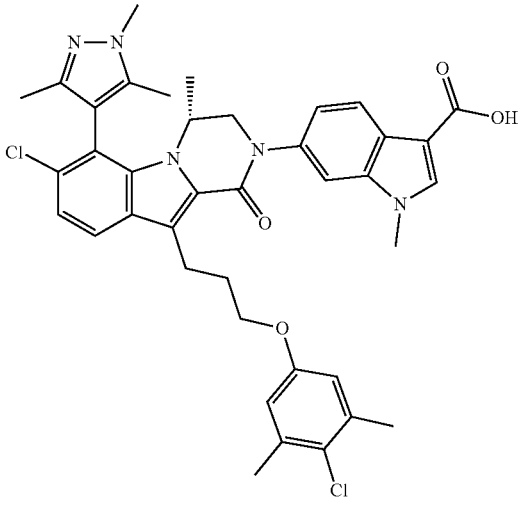 [SMILES: Cc1cc(OCCCc2c3n(c4c(-c5c(C)nn(C)c5C)c(Cl)ccc24)[C@H](C)CN(c2ccc4c(C(=O)O)cn(C)c4c2)C3=O)cc(C)c1Cl]
I-79
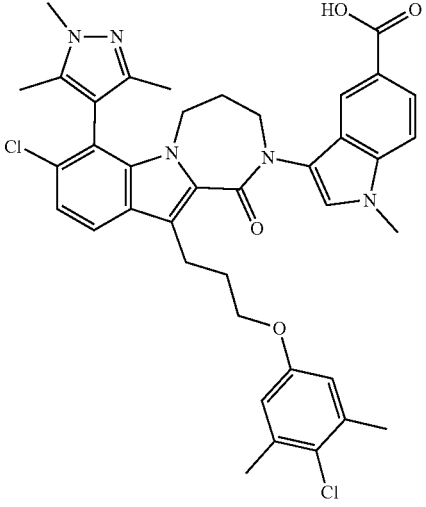 [SMILES: Cc1cc(OCCCc2c3n(c4c(-c5c(C)nn(C)c5C)c(Cl)ccc24)CCCN(c2cn(C)c4ccc(C(=O)O)cc24)C3=O)cc(C)c1Cl]
I-80

TABLE 1-continued
Exemplary compounds.
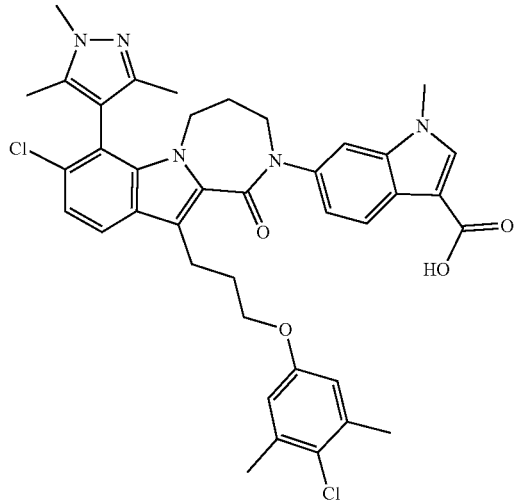 [SMILES: Cc1cc(OCCCc2c3n(c4c(-c5c(C)nn(C)c5C)c(Cl)ccc24)CCCN(c2ccc4c(C(=O)O)cn(C)c4c2)C3=O)cc(C)c1Cl]
I-81
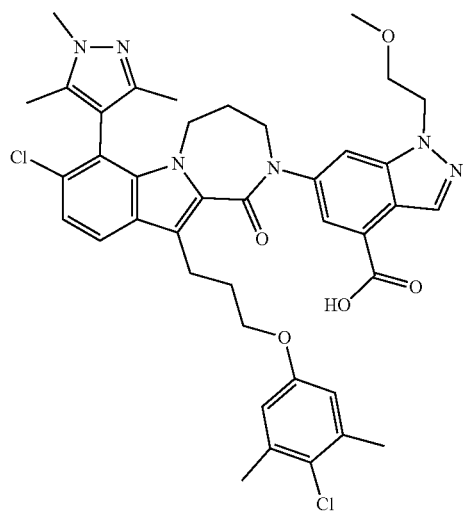 [SMILES: COCCn1ncc2c(C(=O)O)cc(N3CCCn4c(c(CCCOc5cc(C)c(Cl)c(C)c5)c5ccc(Cl)c(-c6c(C)nn(C)c6C)c54)C3=O)cc21]
I-82
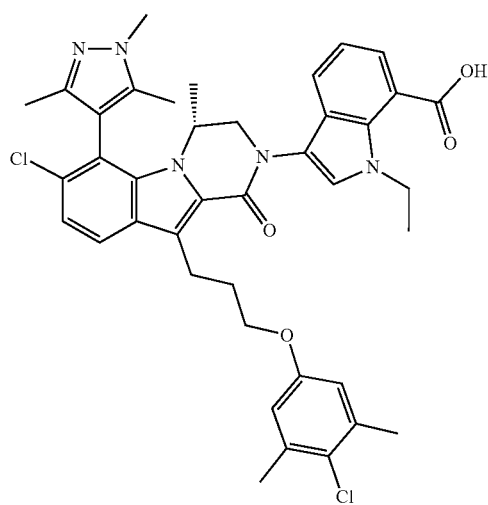 [SMILES: CCn1cc(N2C[C@@H](C)n3c(c(CCCOc4cc(C)c(Cl)c(C)c4)c4ccc(Cl)c(-c5c(C)nn(C)c5C)c43)C2=O)c2cccc(C(=O)O)c21]
I-83

TABLE 1-continued
Exemplary compounds.
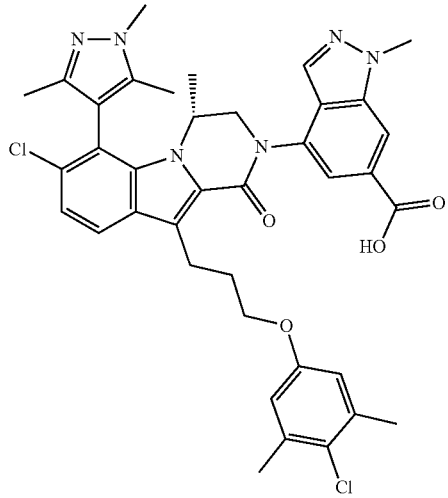 [SMILES: Cc1cc(OCCCc2c3n(c4c(-c5c(C)nn(C)c5C)c(Cl)ccc24)[C@H](C)CN(c2cc(C(=O)O)cc4c2cnn4C)C3=O)cc(C)c1Cl]
I-84
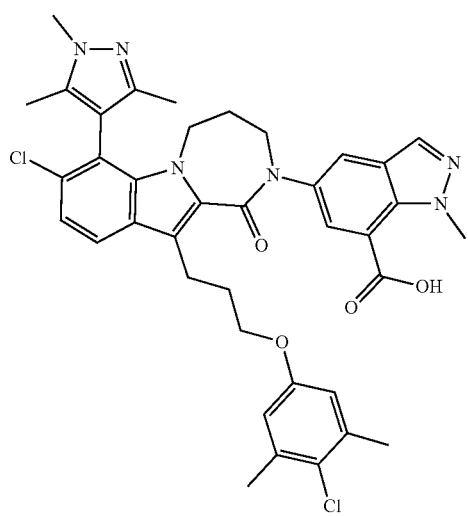 [SMILES: Cc1cc(OCCCc2c3n(c4c(-c5c(C)nn(C)c5C)c(Cl)ccc24)CCCN(c2cc(C(=O)O)c4c(cnn4C)c2)C3=O)cc(C)c1Cl]
I-85
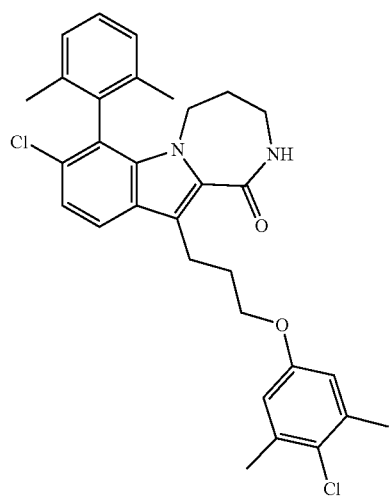 [SMILES: Cc1cc(OCCCc2c3n(c4c(-c5c(C)cccc5C)c(Cl)ccc24)CCCNC3=O)cc(C)c1Cl]
I-86

TABLE 1-continued
Exemplary compounds.
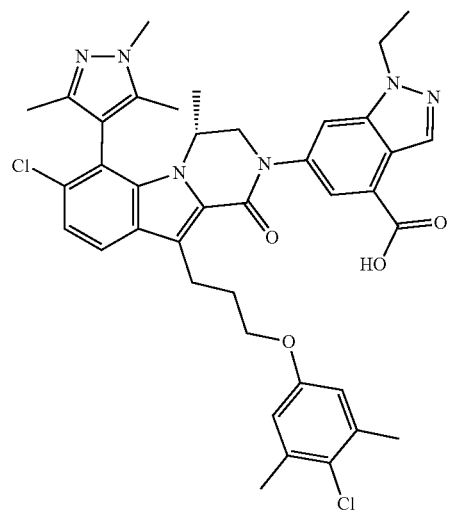 [SMILES: CCn1ncc2c(C(=O)O)cc(N3C[C@@H](C)n4c(c(CCCOc5cc(C)c(Cl)c(C)c5)c5ccc(Cl)c(-c6c(C)nn(C)c6C)c54)C3=O)cc21]
I-87
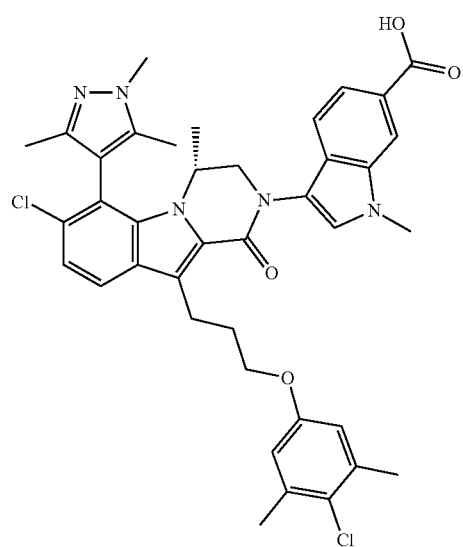 [SMILES: Cc1cc(OCCCc2c3n(c4c(-c5c(C)nn(C)c5C)c(Cl)ccc24)[C@H](C)CN(c2cn(C)c4cc(C(=O)O)ccc24)C3=O)cc(C)c1Cl]
I-88
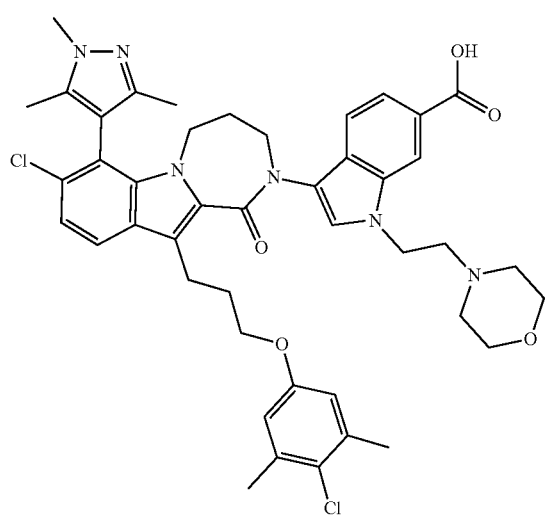 [SMILES: Cc1cc(OCCCc2c3n(c4c(-c5c(C)nn(C)c5C)c(Cl)ccc24)CCCN(c2cn(CCN4CCOCC4)c4cc(C(=O)O)ccc24)C3=O)cc(C)c1Cl]
I-89

TABLE 1-continued
Exemplary compounds.
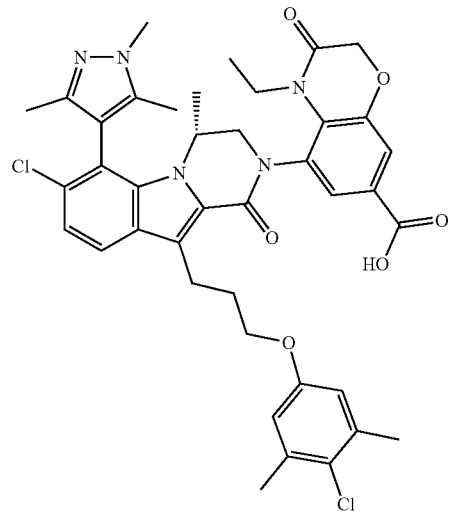 [SMILES: CCN1C(=O)COc2cc(C(=O)O)cc(N3C[C@@H](C)n4c(c(CCCOc5cc(C)c(Cl)c(C)c5)c5ccc(Cl)c(-c6c(C)nn(C)c6C)c54)C3=O)c21]
I-90
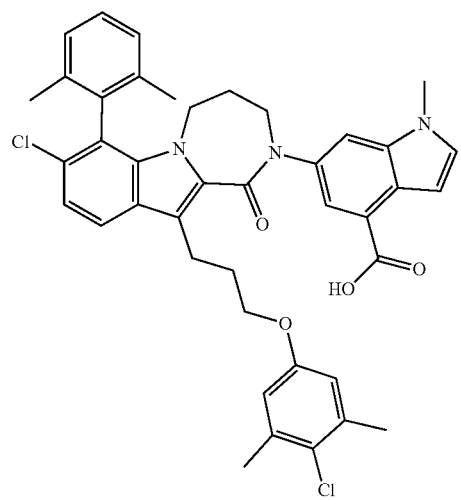 [SMILES: Cc1cc(OCCCc2c3n(c4c(-c5c(C)cccc5C)c(Cl)ccc24)CCCN(c2cc(C(=O)O)c4ccn(C)c4c2)C3=O)cc(C)c1Cl]
I-91
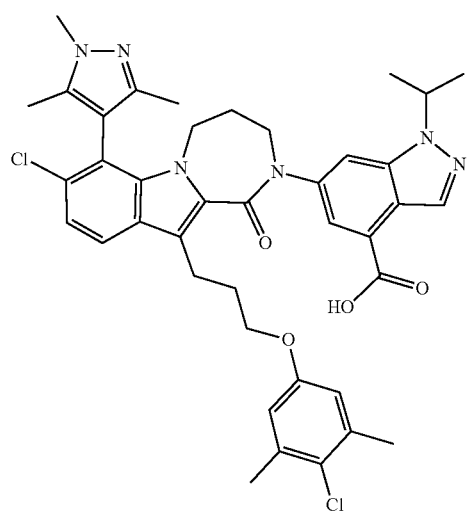 [SMILES: Cc1cc(OCCCc2c3n(c4c(-c5c(C)nn(C)c5C)c(Cl)ccc24)CCCN(c2cc(C(=O)O)c4cnn(C(C)C)c4c2)C3=O)cc(C)c1Cl]
I-92

TABLE 1-continued
Exemplary compounds.
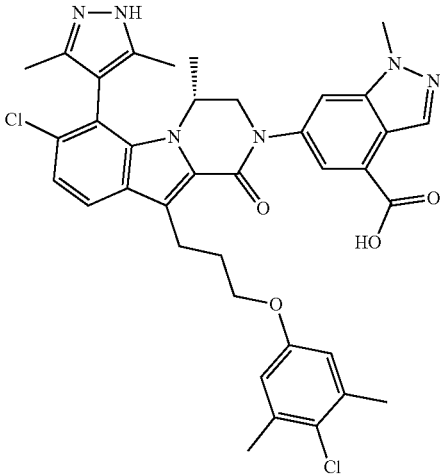 [SMILES: Cc1cc(OCCCc2c3n(c4c(-c5c(C)n[nH]c5C)c(Cl)ccc24)[C@H](C)CN(c2cc(C(=O)O)c4cnn(C)c4c2)C3=O)cc(C)c1Cl]
I-93
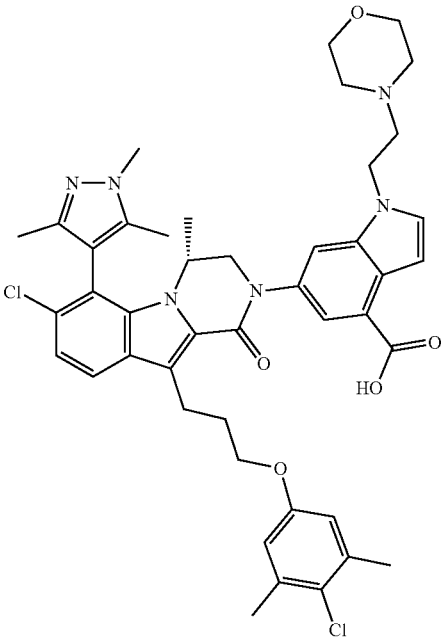 [SMILES: Cc1cc(OCCCc2c3n(c4c(-c5c(C)nn(C)c5C)c(Cl)ccc24)[C@H](C)CN(c2cc(C(=O)O)c4ccn(CCN5CCOCC5)c4c2)C3=O)cc(C)c1Cl]
I-94
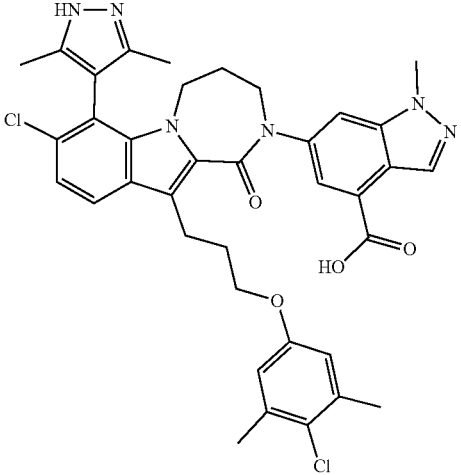 [SMILES: Cc1cc(OCCCc2c3n(c4c(-c5c(C)n[nH]c5C)c(Cl)ccc24)CCCN(c2cc(C(=O)O)c4cnn(C)c4c2)C3=O)cc(C)c1Cl]
I-95

TABLE 1-continued
Exemplary compounds.
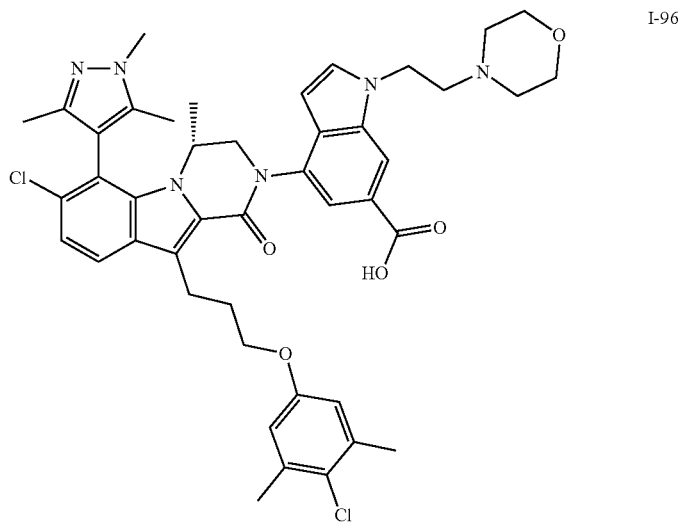
I-96
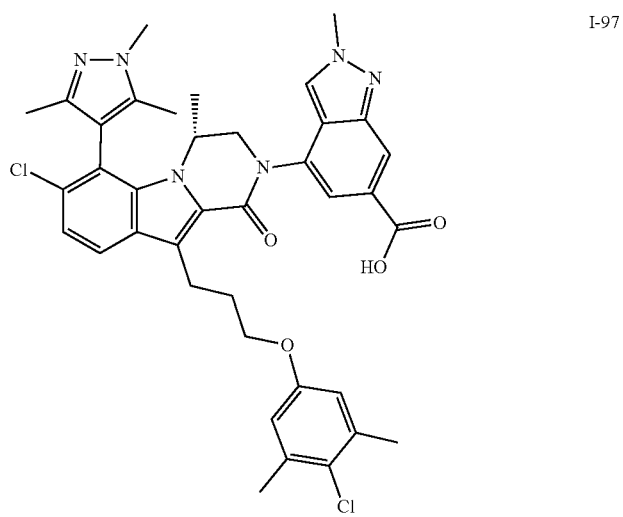
I-97
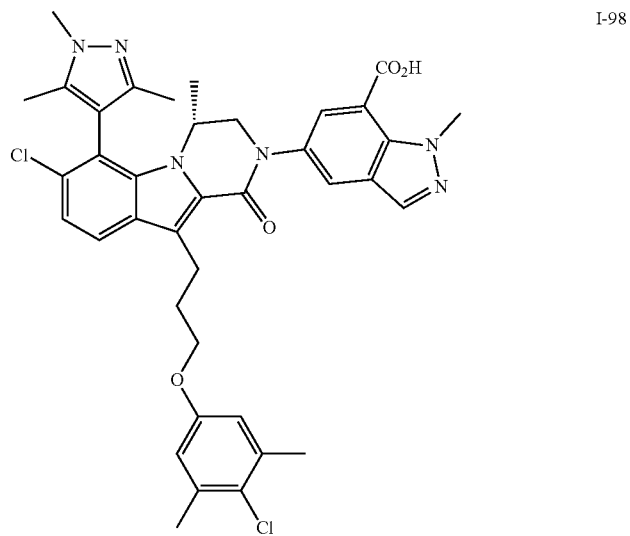
I-98

TABLE 1-continued
Exemplary compounds.
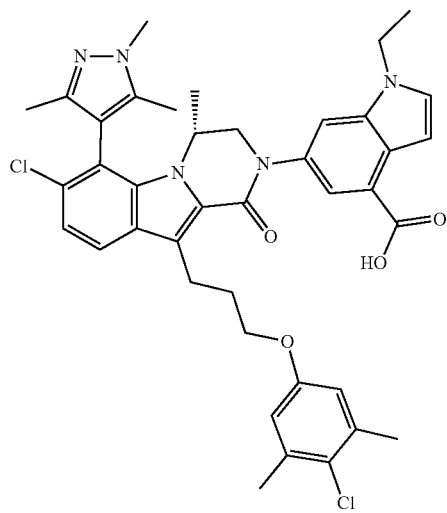 [SMILES: CCn1ccc2c(C(=O)O)cc(N3C[C@@H](C)n4c(c(CCCOc5cc(C)c(Cl)c(C)c5)c5ccc(Cl)c(-c6c(C)nn(C)c6C)c54)C3=O)cc21]
I-99
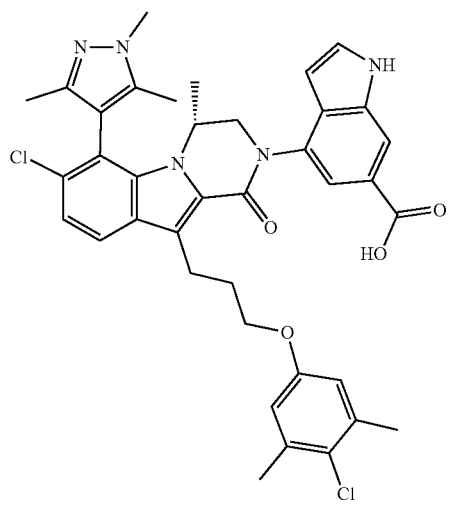 [SMILES: Cc1cc(OCCCc2c3n(c4c(-c5c(C)nn(C)c5C)c(Cl)ccc24)[C@H](C)CN(c2cc(C(=O)O)cc4[nH]ccc24)C3=O)cc(C)c1Cl]
I-100
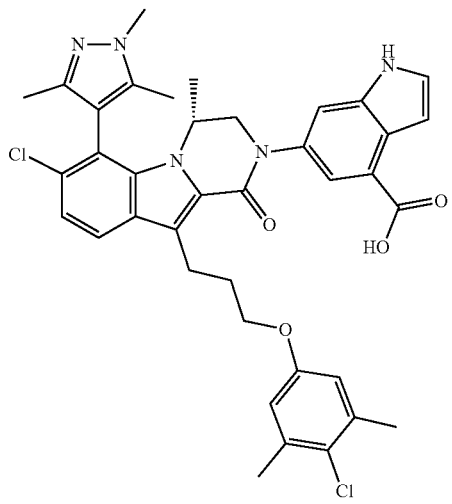 [SMILES: Cc1cc(OCCCc2c3n(c4c(-c5c(C)nn(C)c5C)c(Cl)ccc24)[C@H](C)CN(c2cc(C(=O)O)c4cc[nH]c4c2)C3=O)cc(C)c1Cl]
I-101

TABLE 1-continued
Exemplary compounds.
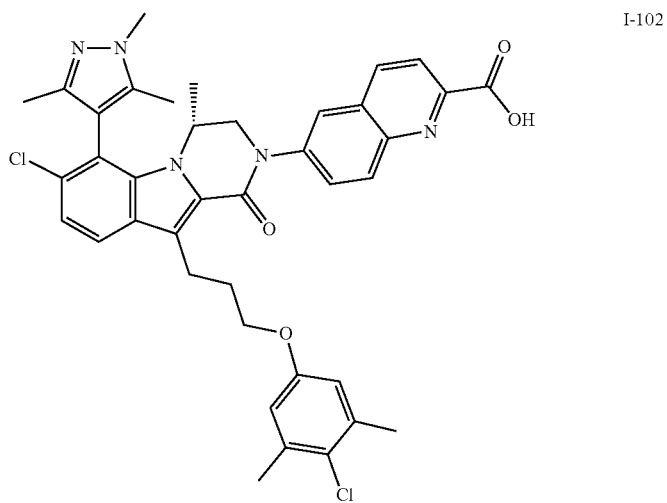
I-102
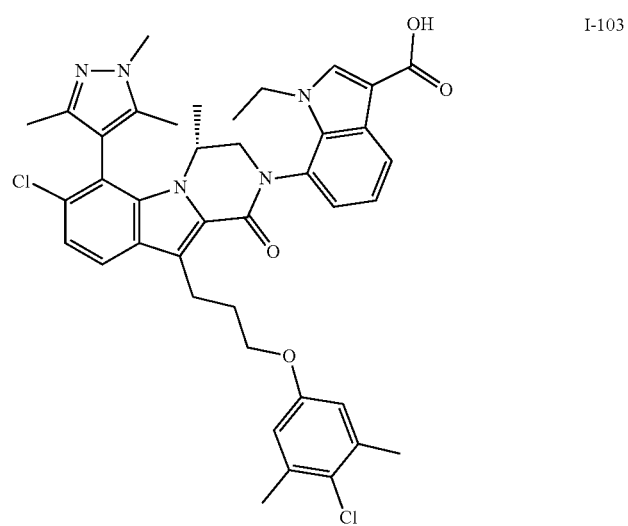
I-103
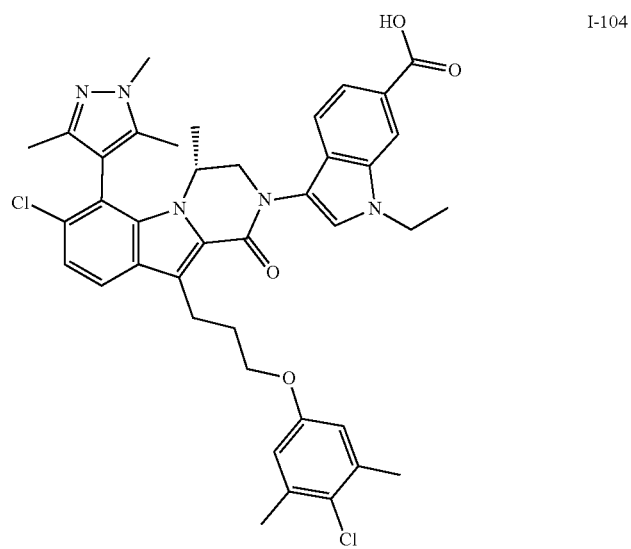
I-104

TABLE 1-continued
Exemplary compounds.
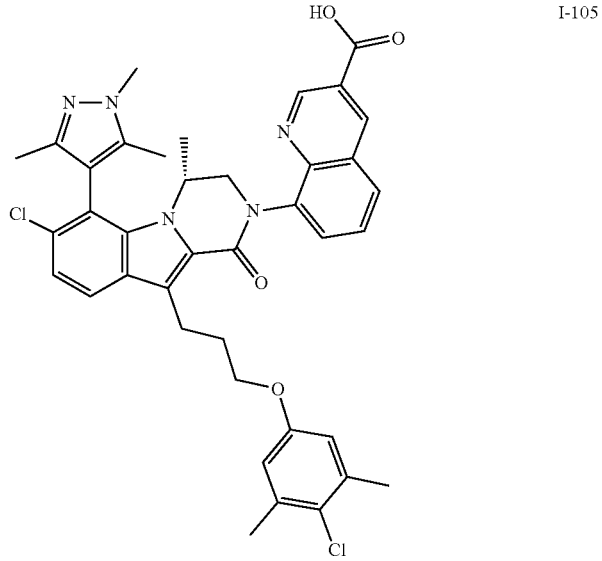
I-105
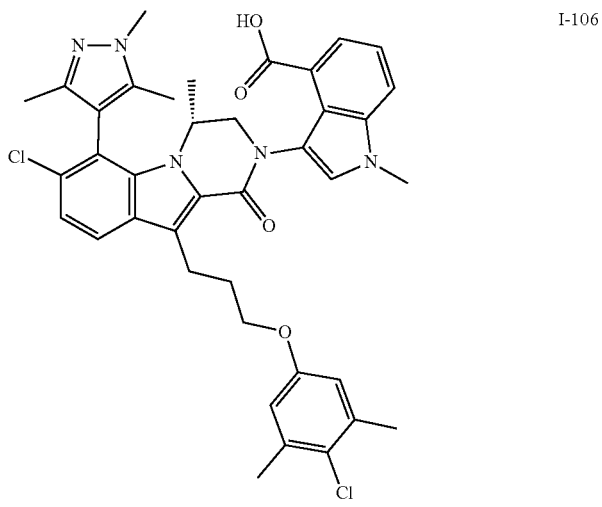
I-106
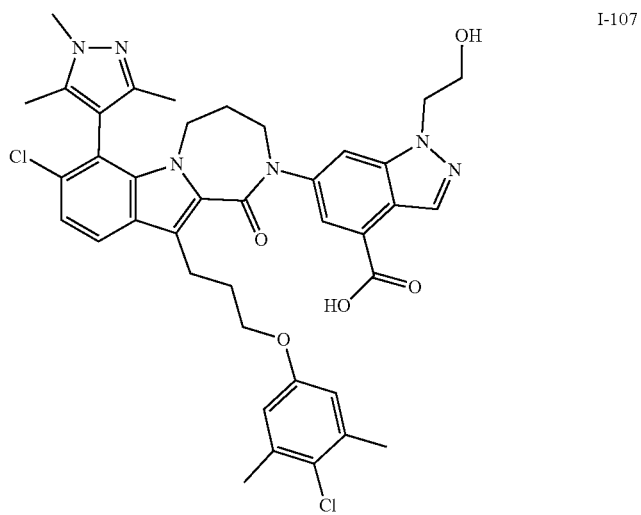
I-107

TABLE 1-continued
Exemplary compounds.
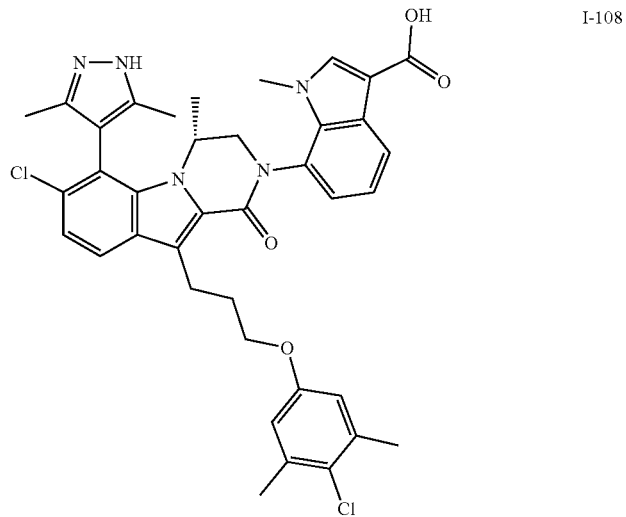
I-108
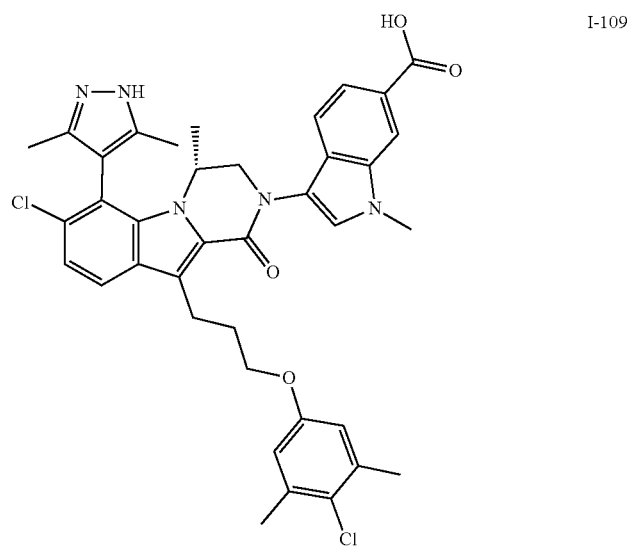
I-109
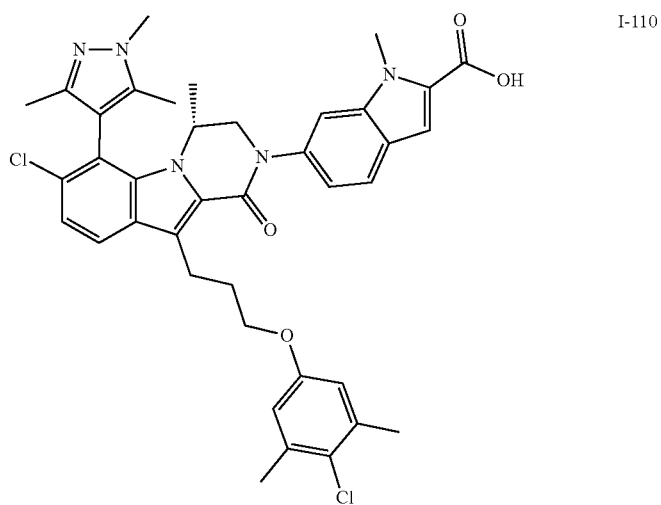
I-110

TABLE 1-continued
Exemplary compounds.
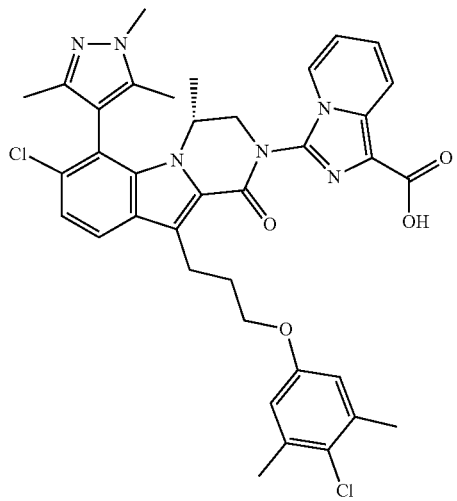 [SMILES: Cc1cc(OCCCc2c3n(c4c(-c5c(C)nn(C)c5C)c(Cl)ccc24)[C@H](C)CN(c2nc(C(=O)O)c4ccccn24)C3=O)cc(C)c1Cl]
I-111
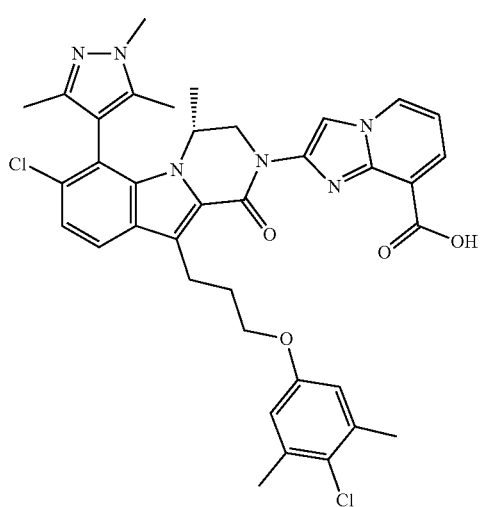 [SMILES: Cc1cc(OCCCc2c3n(c4c(-c5c(C)nn(C)c5C)c(Cl)ccc24)[C@H](C)CN(c2cn4cccc(C(=O)O)c4n2)C3=O)cc(C)c1Cl]
I-112
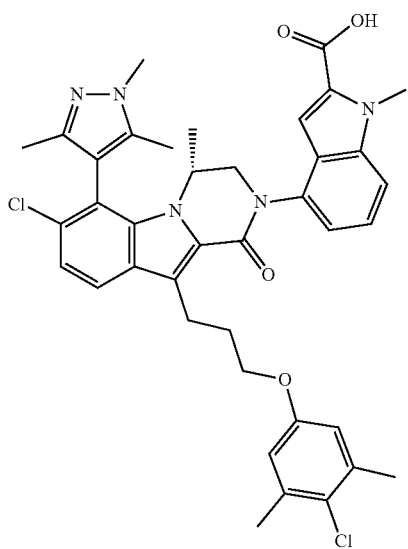
I-113

TABLE 1-continued
Exemplary compounds.
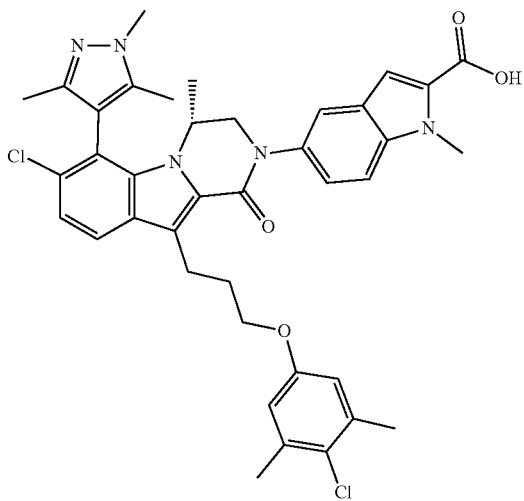 [SMILES: Cc1cc(OCCCc2c3n(c4c(-c5c(C)nn(C)c5C)c(Cl)ccc24)[C@H](C)CN(c2ccc4c(c2)cc(C(=O)O)n4C)C3=O)cc(C)c1Cl]
I-114
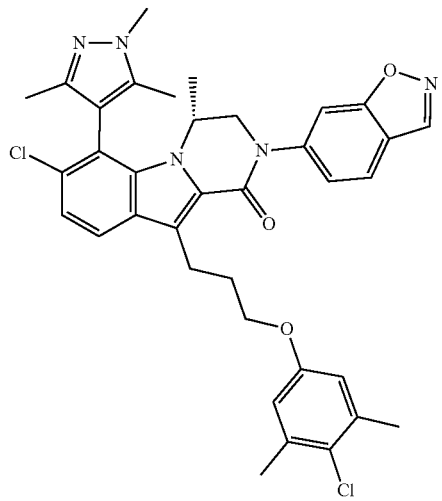 [SMILES: Cc1cc(OCCCc2c3n(c4c(-c5c(C)nn(C)c5C)c(Cl)ccc24)[C@H](C)CN(c2ccc4cnoc4c2)C3=O)cc(C)c1Cl]
I-115
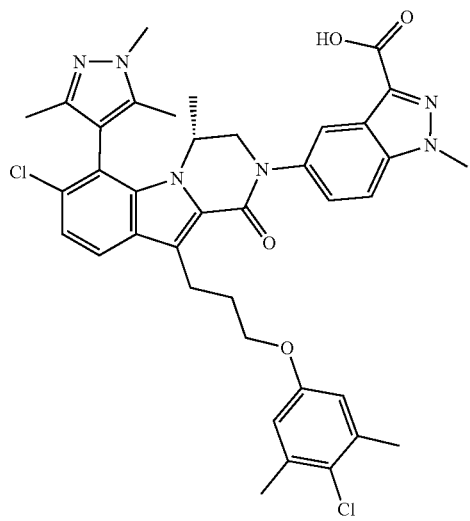 [SMILES: Cc1cc(OCCCc2c3n(c4c(-c5c(C)nn(C)c5C)c(Cl)ccc24)[C@H](C)CN(c2ccc4c(c2)c(C(=O)O)nn4C)C3=O)cc(C)c1Cl]
I-116

TABLE 1-continued
Exemplary compounds.
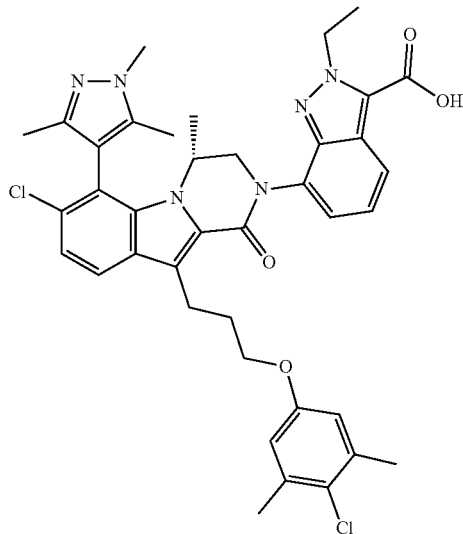 [SMILES: CCn1nc2c(N3C[C@@H](C)n4c(c(CCCOc5cc(C)c(Cl)c(C)c5)c5ccc(Cl)c(-c6c(C)nn(C)c6C)c54)C3=O)cccc2c1C(=O)O]
I-117
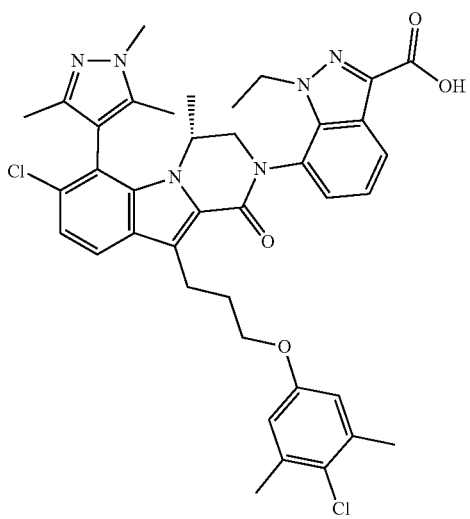 [SMILES: CCn1nc(C(=O)O)c2cccc(N3C[C@@H](C)n4c(c(CCCOc5cc(C)c(Cl)c(C)c5)c5ccc(Cl)c(-c6c(C)nn(C)c6C)c54)C3=O)c21]
I-118
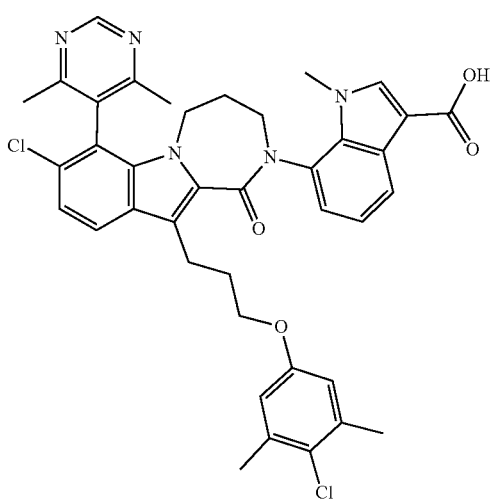 [SMILES: Cc1cc(OCCCc2c3n(c4c(-c5c(C)ncnc5C)c(Cl)ccc24)CCCN(c2cccc4c(C(=O)O)cn(C)c24)C3=O)cc(C)c1Cl]
I-119

TABLE 1-continued
Exemplary compounds.
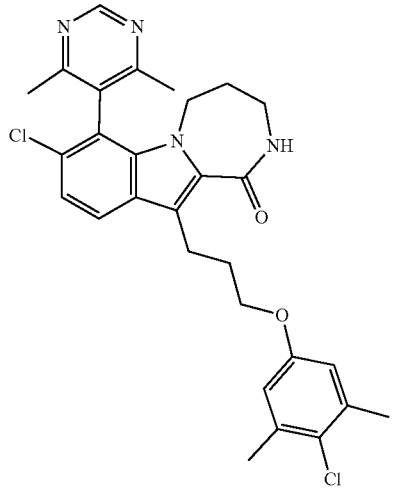 [SMILES: Cc1cc(OCCCc2c3n(c4c(-c5c(C)ncnc5C)c(Cl)ccc24)CCCNC3=O)cc(C)c1Cl]
I-120
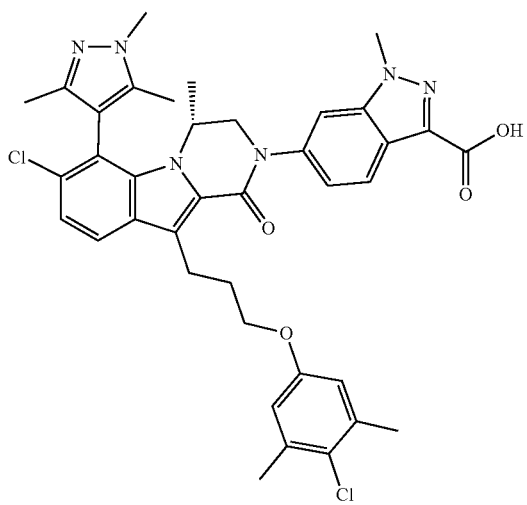 [SMILES: Cc1cc(OCCCc2c3n(c4c(-c5c(C)nn(C)c5C)c(Cl)ccc24)[C@H](C)CN(c2ccc4c(C(=O)O)nn(C)c4c2)C3=O)cc(C)c1Cl]
I-121
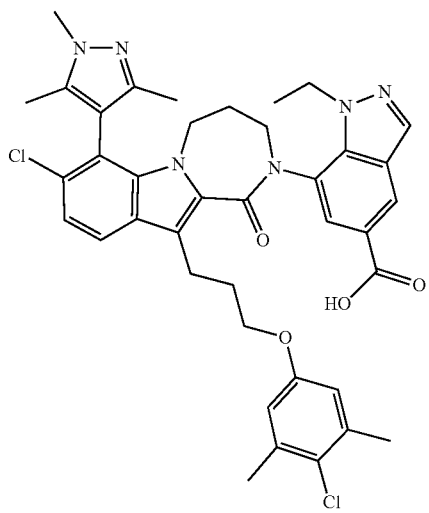 [SMILES: CCn1ncc2cc(C(=O)O)cc(N3CCCn4c(c(CCCOc5cc(C)c(Cl)c(C)c5)c5ccc(Cl)c(-c6c(C)nn(C)c6C)c54)C3=O)c21]
I-122

TABLE 1-continued
Exemplary compounds.
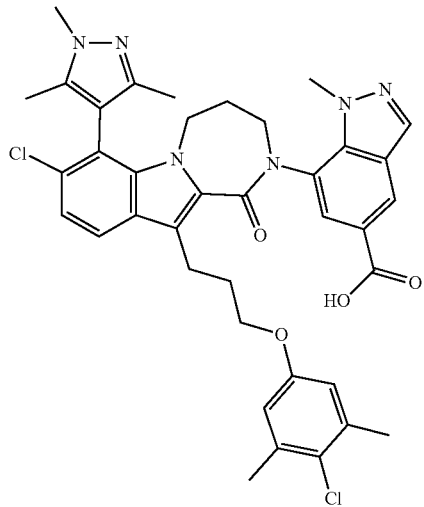 [SMILES: Cc1cc(OCCCc2c3n(c4c(-c5c(C)nn(C)c5C)c(Cl)ccc24)CCCN(c2cc(C(=O)O)cc4cnn(C)c24)C3=O)cc(C)c1Cl]
I-123
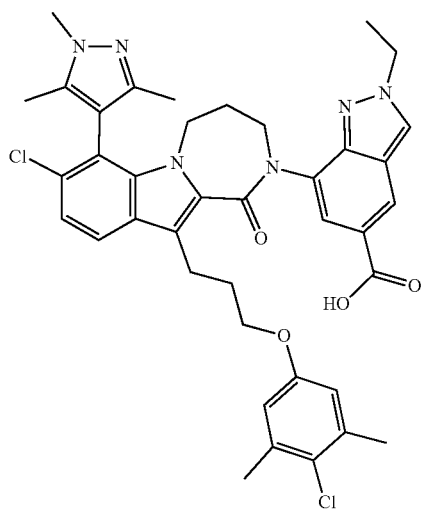 [SMILES: CCn1cc2cc(C(=O)O)cc(N3CCCn4c(c(CCCOc5cc(C)c(Cl)c(C)c5)c5ccc(Cl)c(-c6c(C)nn(C)c6C)c54)C3=O)c2n1]
I-124
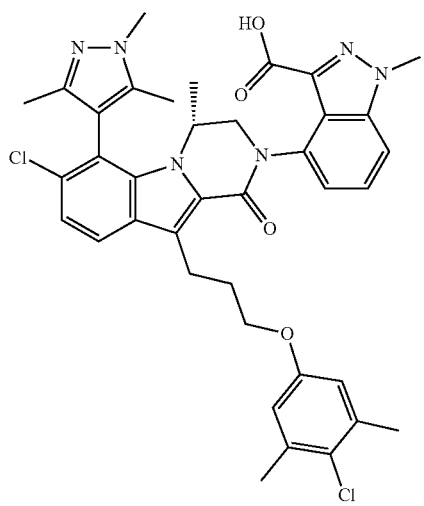 [SMILES: Cc1cc(OCCCc2c3n(c4c(-c5c(C)nn(C)c5C)c(Cl)ccc24)[C@H](C)CN(c2cccc4c2c(C(=O)O)nn4C)C3=O)cc(C)c1Cl]
I-125

TABLE 1-continued
Exemplary compounds.
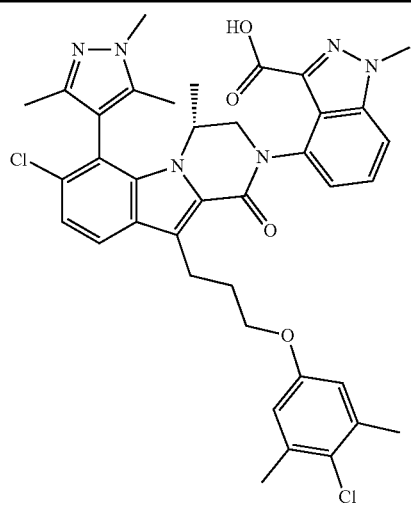
I-126
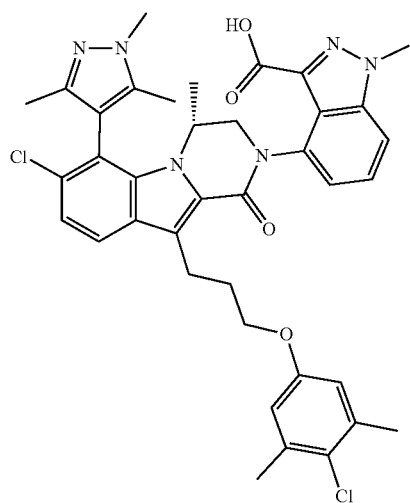 [SMILES: Cc1cc(OCCCc2c3n(c4c(-c5c(C)nn(C)c5C)c(Cl)ccc24)[C@H](C)CN(c2cccc4c2c(C(=O)O)nn4C)C3=O)cc(C)c1Cl]
I-127
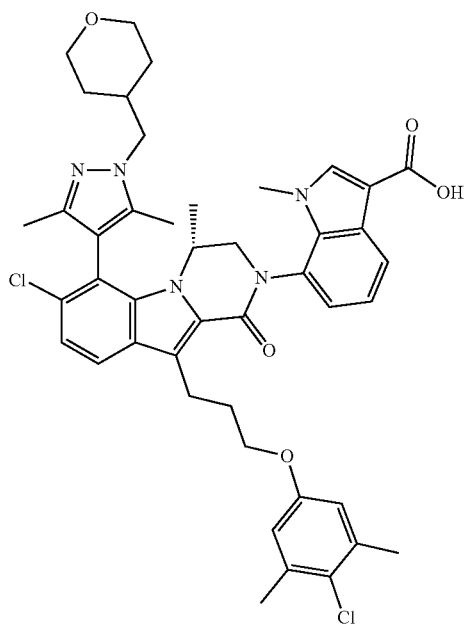 [SMILES: Cc1cc(OCCCc2c3n(c4c(-c5c(C)nn(CC6CCOCC6)c5C)c(Cl)ccc24)[C@H](C)CN(c2cccc4c(C(=O)O)cn(C)c24)C3=O)cc(C)c1Cl]
I-128

TABLE 1-continued
Exemplary compounds.
I-129
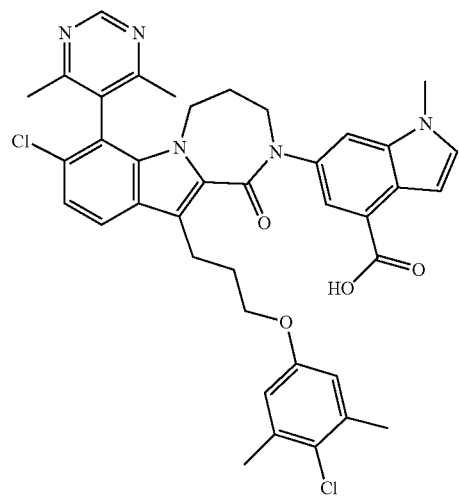 [SMILES: Cc1cc(OCCCc2c3n(c4c(-c5c(C)ncnc5C)c(Cl)ccc24)CCCN(c2cc(C(=O)O)c4ccn(C)c4c2)C3=O)cc(C)c1Cl]
I-130
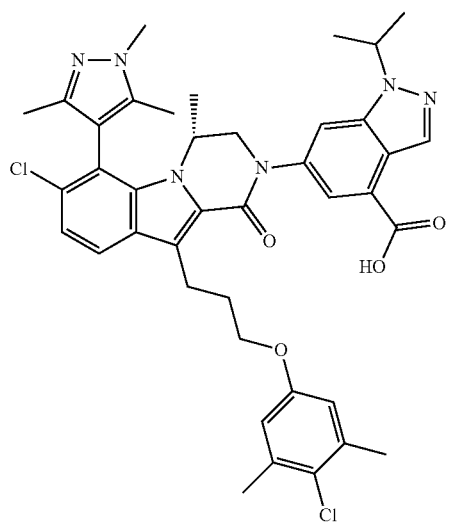 [SMILES: Cc1cc(OCCCc2c3n(c4c(-c5c(C)nn(C)c5C)c(Cl)ccc24)[C@H](C)CN(c2cc(C(=O)O)c4cnn(C(C)C)c4c2)C3=O)cc(C)c1Cl]
I-131

TABLE 1-continued
Exemplary compounds.
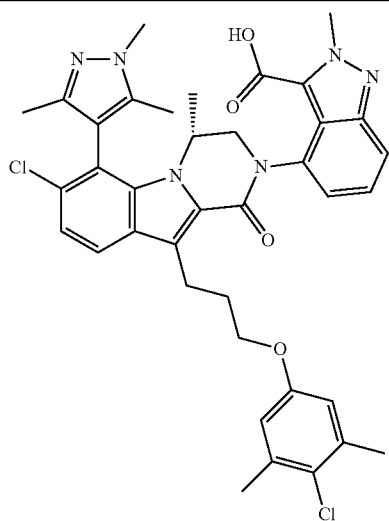
I-132
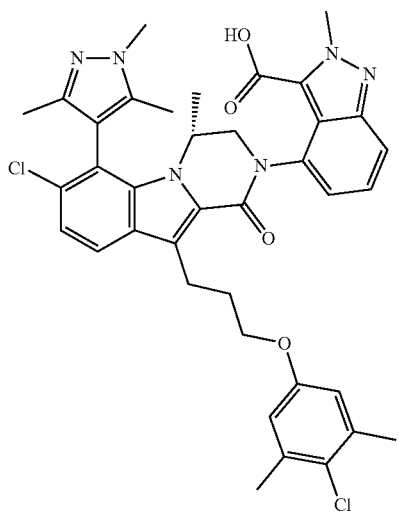 [SMILES: Cc1cc(OCCCc2c3n(c4c(-c5c(C)nn(C)c5C)c(Cl)ccc24)[C@H](C)CN(c2cccc4nn(C)c(C(=O)O)c24)C3=O)cc(C)c1Cl]
I-133
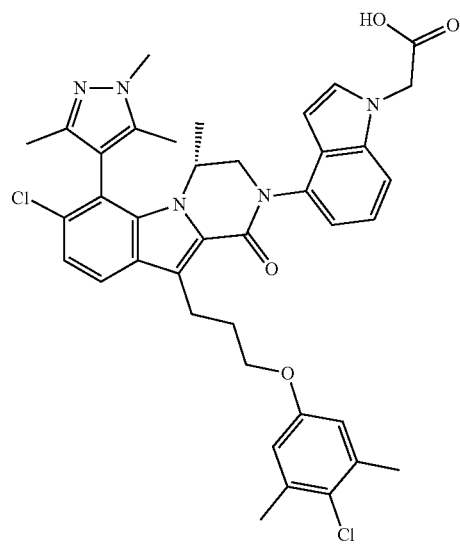 [SMILES: Cc1cc(OCCCc2c3n(c4c(-c5c(C)nn(C)c5C)c(Cl)ccc24)[C@H](C)CN(c2cccc4c2ccn4CC(=O)O)C3=O)cc(C)c1Cl]
I-134

TABLE 1-continued
Exemplary compounds.
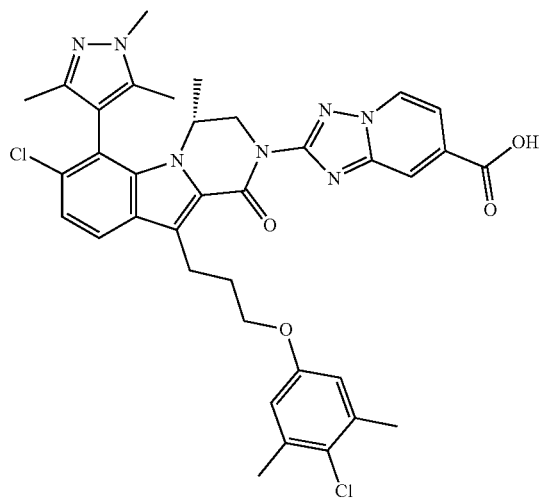 [SMILES: Cc1cc(OCCCc2c3n(c4c(-c5c(C)nn(C)c5C)c(Cl)ccc24)[C@H](C)CN(c2nc4cc(C(=O)O)ccn4n2)C3=O)cc(C)c1Cl]
I-135
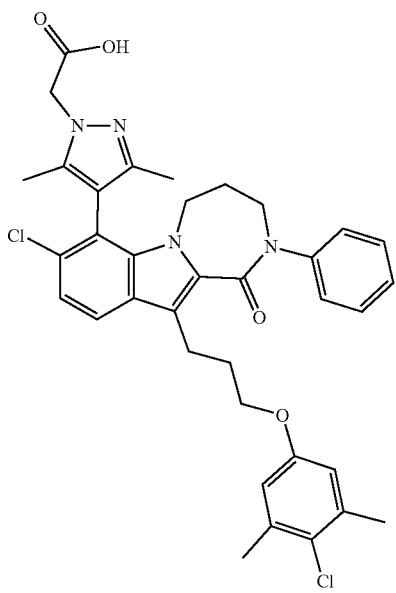 [SMILES: Cc1cc(OCCCc2c3n(c4c(-c5c(C)nn(CC(=O)O)c5C)c(Cl)ccc24)CCCN(c2ccccc2)C3=O)cc(C)c1Cl]
I-136

TABLE 1-continued
Exemplary compounds.
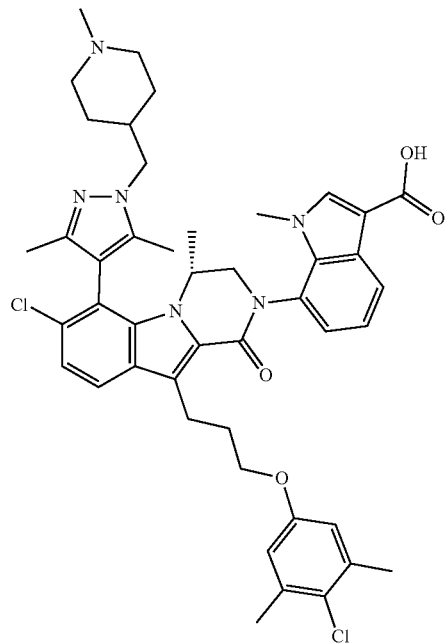 [SMILES: Cc1cc(OCCCc2c3n(c4c(-c5c(C)nn(CC6CCN(C)CC6)c5C)c(Cl)ccc24)[C@H](C)CN(c2cccc4c(C(=O)O)cn(C)c24)C3=O)cc(C)c1Cl]
I-137
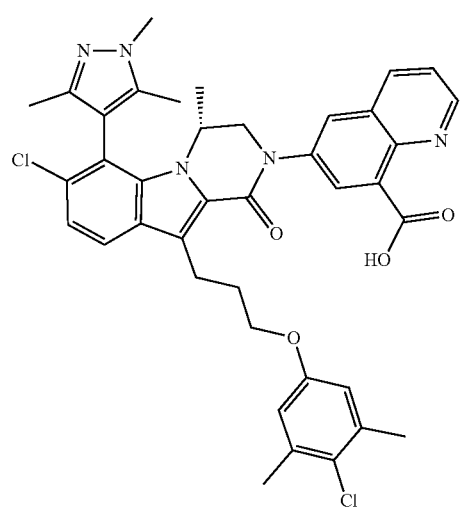 [SMILES: Cc1cc(OCCCc2c3n(c4c(-c5c(C)nn(C)c5C)c(Cl)ccc24)[C@H](C)CN(c2cc(C(=O)O)c4ncccc4c2)C3=O)cc(C)c1Cl]
I-138

TABLE 1-continued
Exemplary compounds.
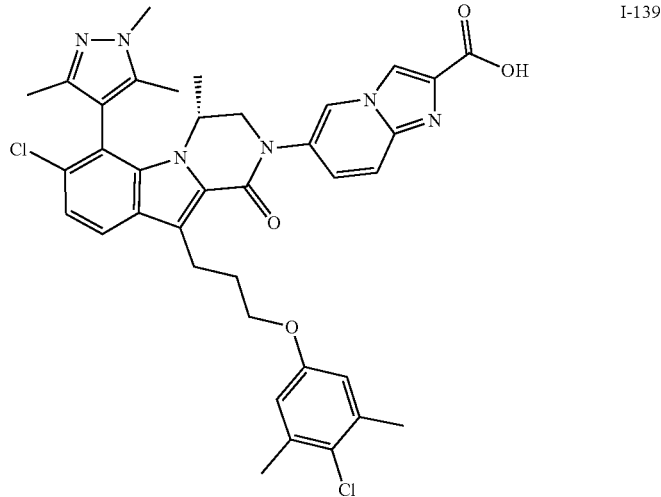
I-139
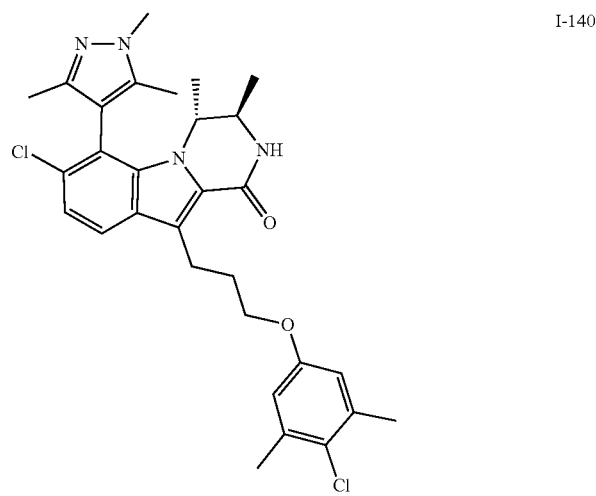
I-140
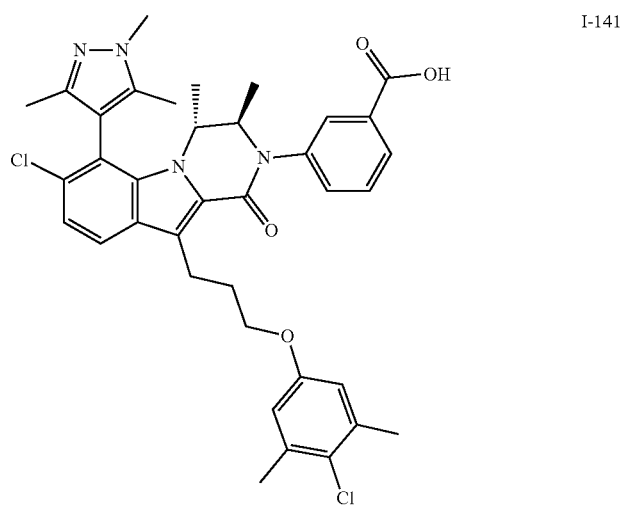
I-141

TABLE 1-continued
Exemplary compounds.
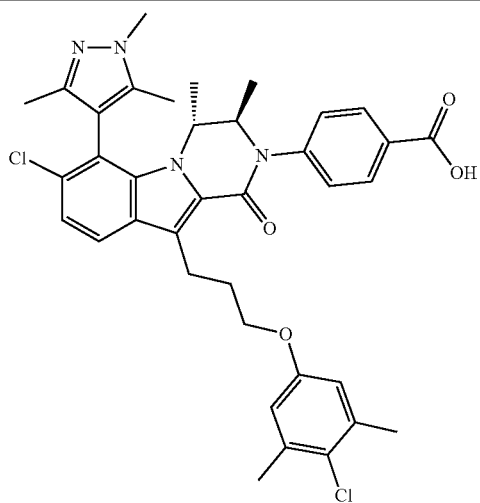
I-142
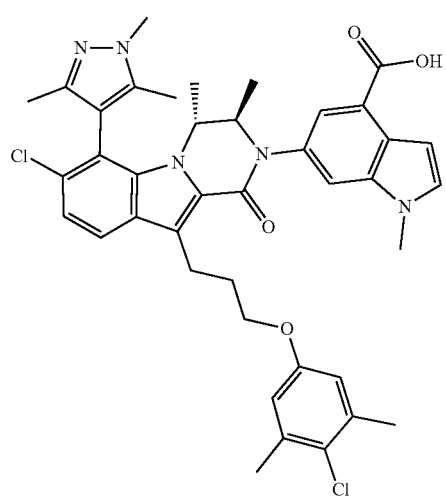 [SMILES: Cc1cc(OCCCc2c3n(c4c(-c5c(C)nn(C)c5C)c(Cl)ccc24)[C@H](C)[C@@H](C)N(c2cc(C(=O)O)c4ccn(C)c4c2)C3=O)cc(C)c1Cl]
I-143
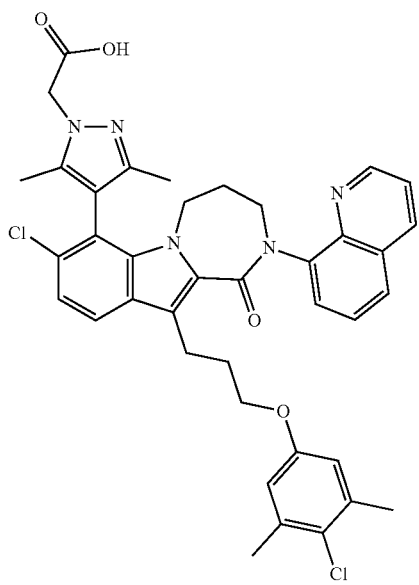 [SMILES: Cc1cc(OCCCc2c3n(c4c(-c5c(C)nn(CC(=O)O)c5C)c(Cl)ccc24)CCCN(c2cccc4cccnc24)C3=O)cc(C)c1Cl]
I-144

TABLE 1-continued
Exemplary compounds.
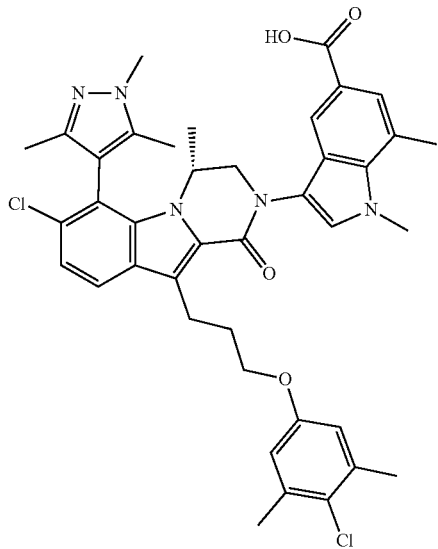 [SMILES: Cc1cc(OCCCc2c3n(c4c(-c5c(C)nn(C)c5C)c(Cl)ccc24)[C@H](C)CN(c2cn(C)c4c(C)cc(C(=O)O)cc24)C3=O)cc(C)c1Cl]
I-145
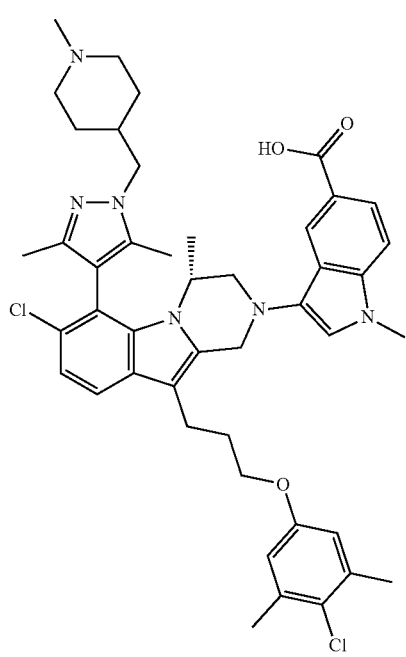
I-146

TABLE 1-continued
Exemplary compounds.
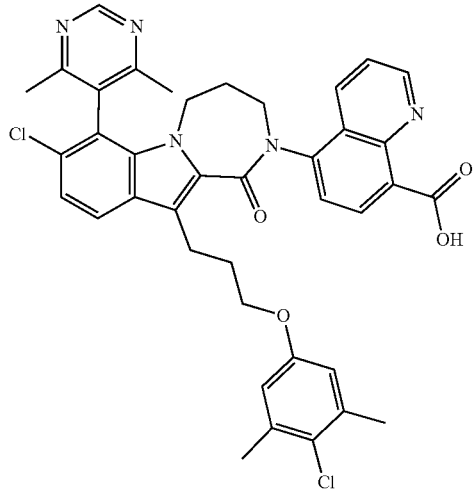 [SMILES: Cc1cc(OCCCc2c3n(c4c(-c5c(C)ncnc5C)c(Cl)ccc24)CCCN(c2ccc(C(=O)O)c4ncccc24)C3=O)cc(C)c1Cl]
I-147
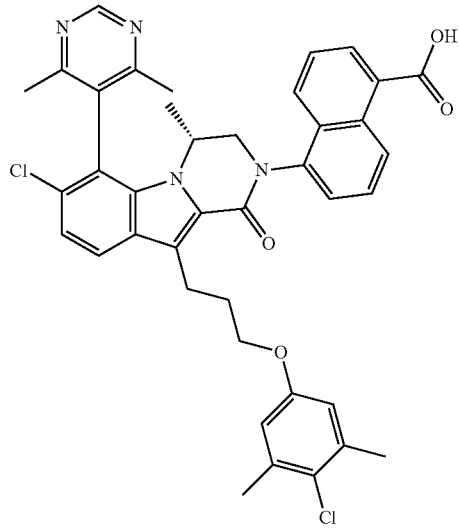 [SMILES: Cc1cc(OCCCc2c3n(c4c(-c5c(C)ncnc5C)c(Cl)ccc24)[C@H](C)CN(c2cccc4c(C(=O)O)cccc24)C3=O)cc(C)c1Cl]
I-148
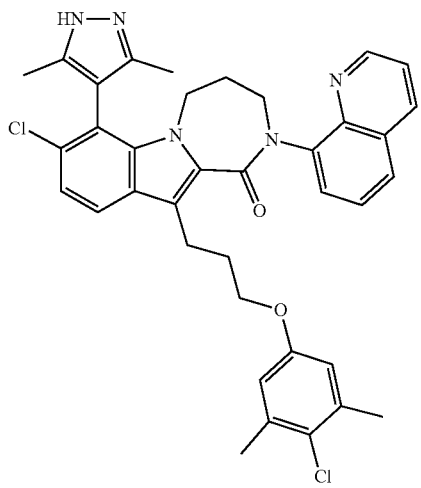 [SMILES: Cc1cc(OCCCc2c3n(c4c(-c5c(C)n[nH]c5C)c(Cl)ccc24)CCCN(c2cccc4cccnc24)C3=O)cc(C)c1Cl]
I-150

TABLE 1-continued
Exemplary compounds.
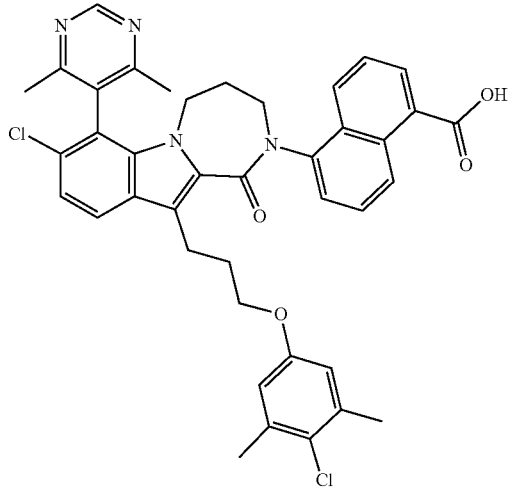 [SMILES: Cc1cc(OCCCc2c3n(c4c(-c5c(C)ncnc5C)c(Cl)ccc24)CCCN(c2cccc4c(C(=O)O)cccc24)C3=O)cc(C)c1Cl]
I-151
I-152
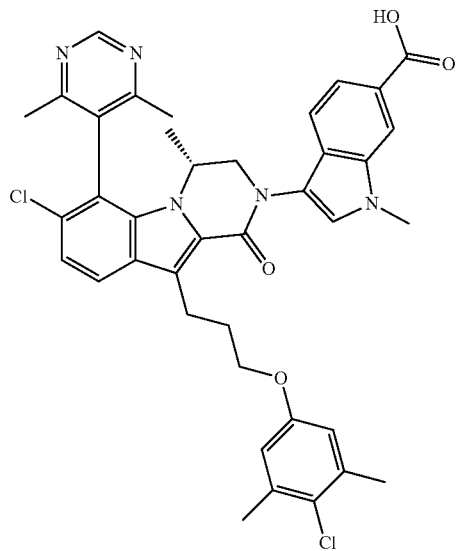 [SMILES: Cc1cc(OCCCc2c3n(c4c(-c5c(C)ncnc5C)c(Cl)ccc24)[C@H](C)CN(c2cn(C)c4cc(C(=O)O)ccc24)C3=O)cc(C)c1Cl]
I-153

TABLE 1-continued
Exemplary compounds.
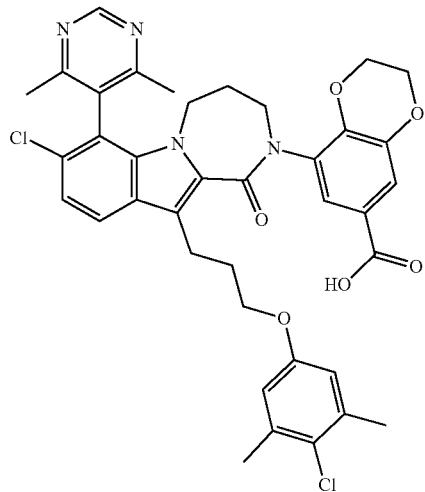 [SMILES: Cc1cc(OCCCc2c3n(c4c(-c5c(C)ncnc5C)c(Cl)ccc24)CCCN(c2cc(C(=O)O)cc4c2OCCO4)C3=O)cc(C)c1Cl]
I-154
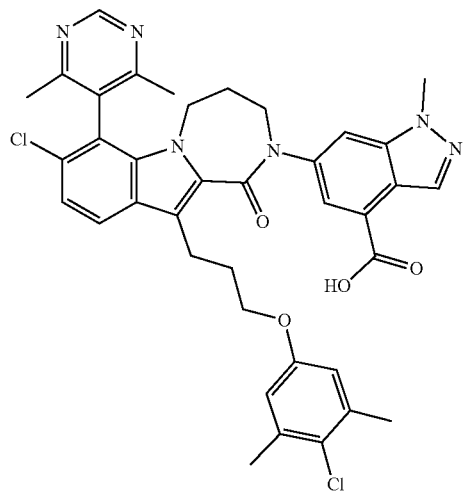 [SMILES: Cc1cc(OCCCc2c3n(c4c(-c5c(C)ncnc5C)c(Cl)ccc24)CCCN(c2cc(C(=O)O)c4cnn(C)c4c2)C3=O)cc(C)c1Cl]
I-155
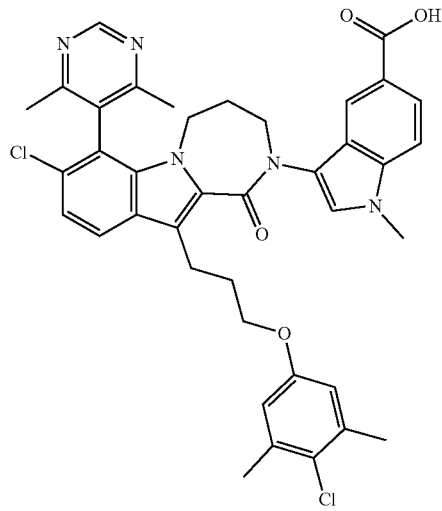 [SMILES: Cc1cc(OCCCc2c3n(c4c(-c5c(C)ncnc5C)c(Cl)ccc24)CCCN(c2cn(C)c4ccc(C(=O)O)cc24)C3=O)cc(C)c1Cl]
I-156

TABLE 1-continued
Exemplary compounds.
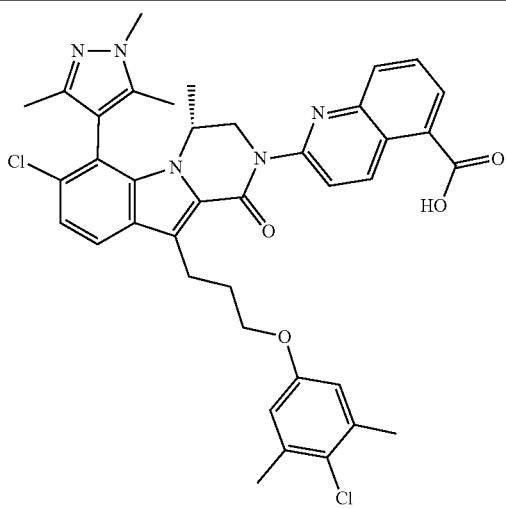
I-157
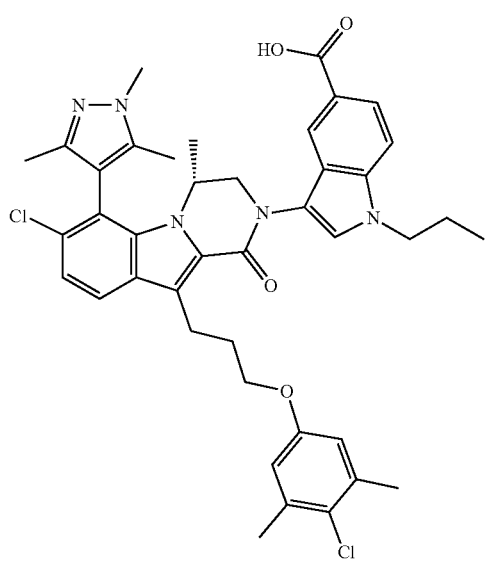 [SMILES: CCCn1cc(N2C[C@@H](C)n3c(c(CCCOc4cc(C)c(Cl)c(C)c4)c4ccc(Cl)c(-c5c(C)nn(C)c5C)c43)C2=O)c2cc(C(=O)O)ccc21]
I-158
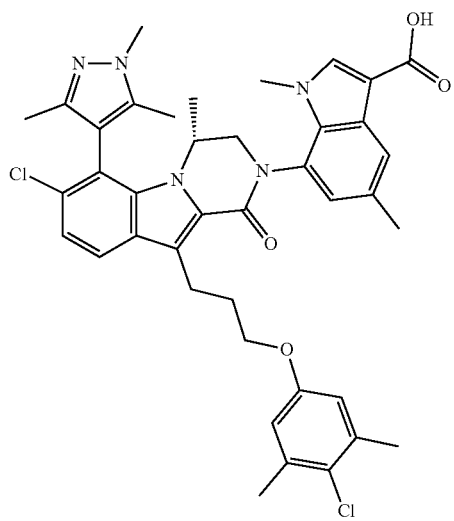 [SMILES: Cc1cc(N2C[C@@H](C)n3c(c(CCCOc4cc(C)c(Cl)c(C)c4)c4ccc(Cl)c(-c5c(C)nn(C)c5C)c43)C2=O)c2c(c1)c(C(=O)O)cn2C]
I-159

TABLE 1-continued
Exemplary compounds.
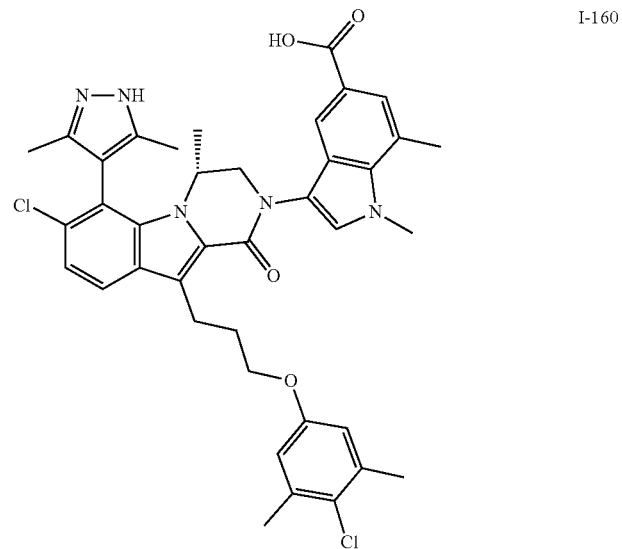
I-160
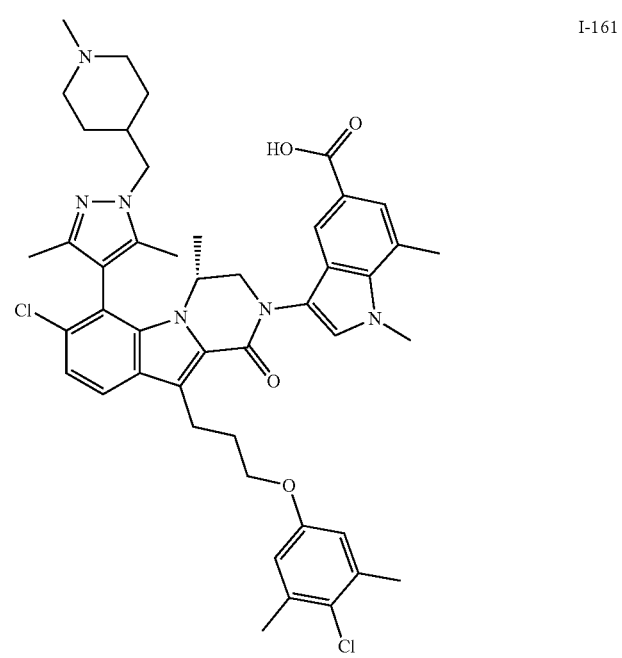
I-161

TABLE 1-continued
Exemplary compounds.
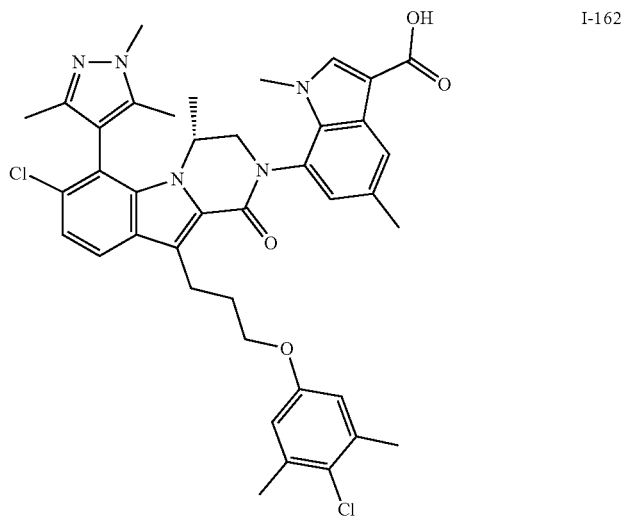
I-162
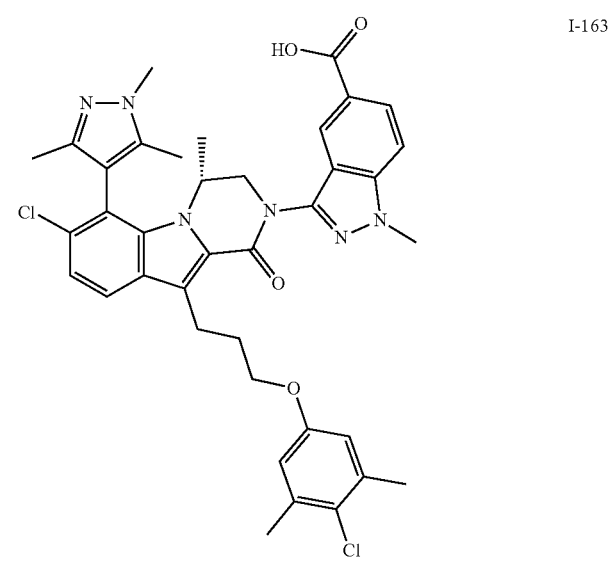
I-163
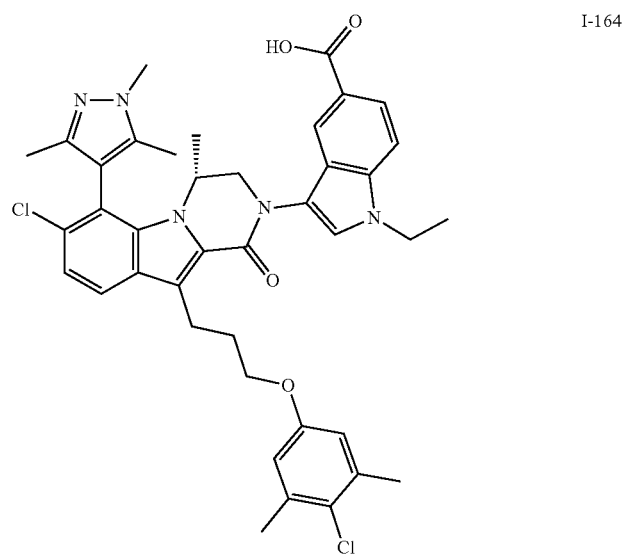
I-164

TABLE 1-continued
Exemplary compounds.
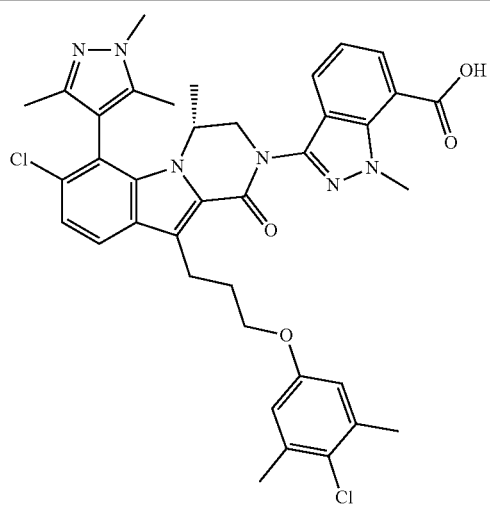 [SMILES: Cc1cc(OCCCc2c3n(c4c(-c5c(C)nn(C)c5C)c(Cl)ccc24)[C@H](C)CN(c2nn(C)c4c(C(=O)O)cccc24)C3=O)cc(C)c1Cl]
I-165
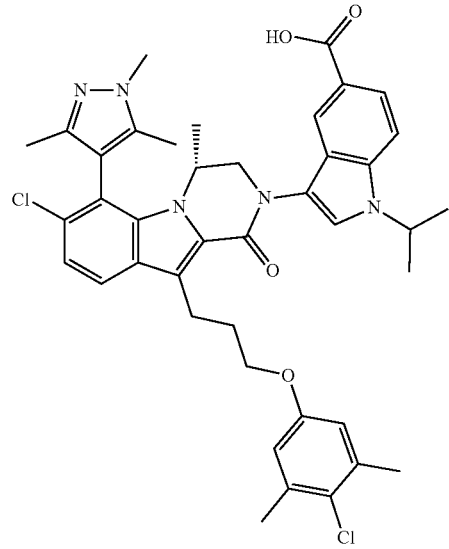 [SMILES: Cc1cc(OCCCc2c3n(c4c(-c5c(C)nn(C)c5C)c(Cl)ccc24)[C@H](C)CN(c2cn(C(C)C)c4ccc(C(=O)O)cc24)C3=O)cc(C)c1Cl]
I-166
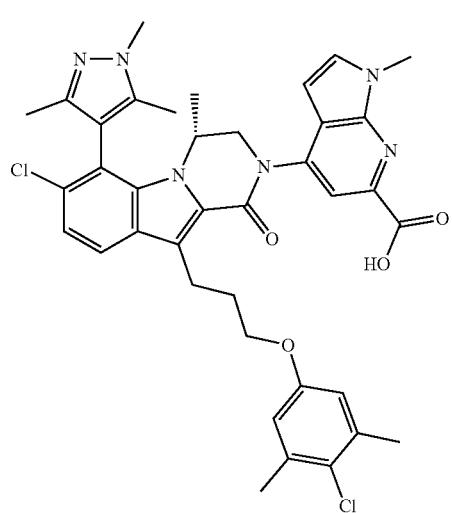 [SMILES: Cc1cc(OCCCc2c3n(c4c(-c5c(C)nn(C)c5C)c(Cl)ccc24)[C@H](C)CN(c2cc(C(=O)O)nc4c2ccn4C)C3=O)cc(C)c1Cl]
I-167

TABLE 1-continued
Exemplary compounds.
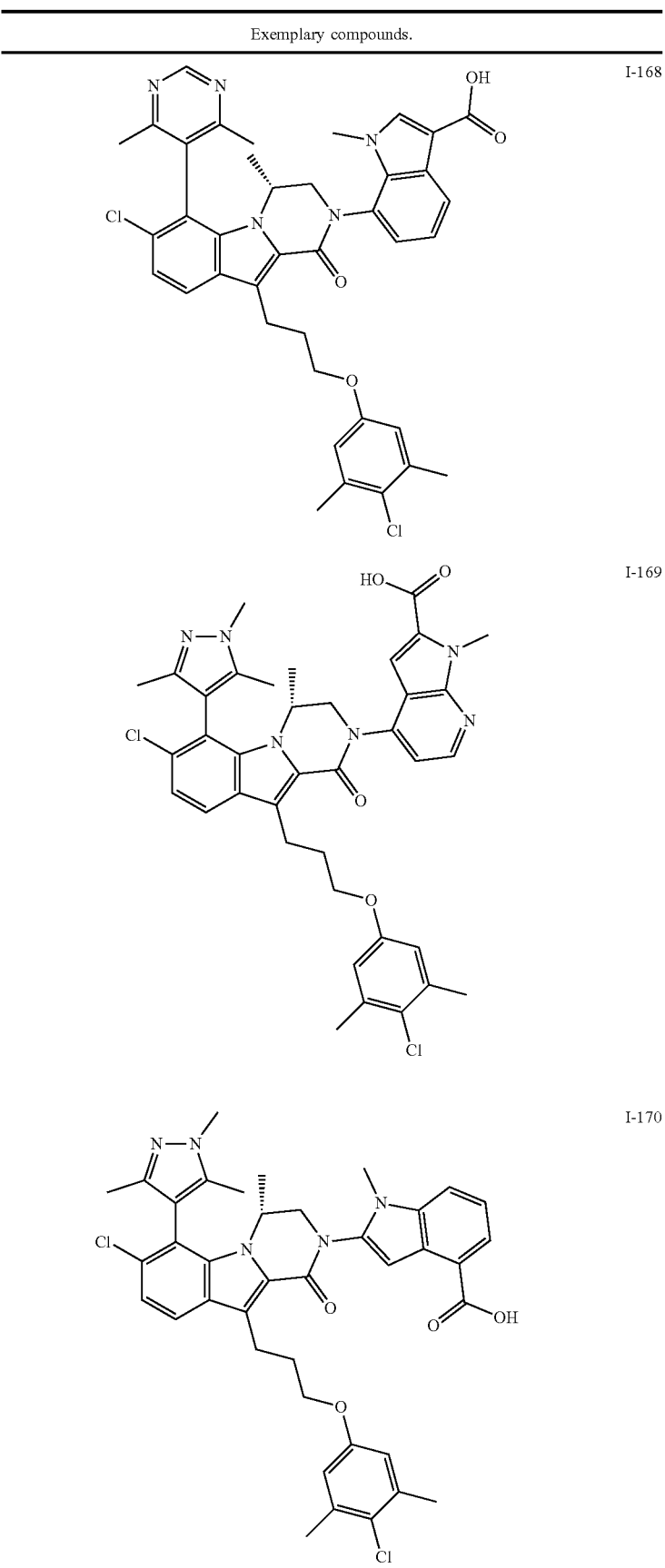
I-168
I-169
I-170

TABLE 1-continued
Exemplary compounds.
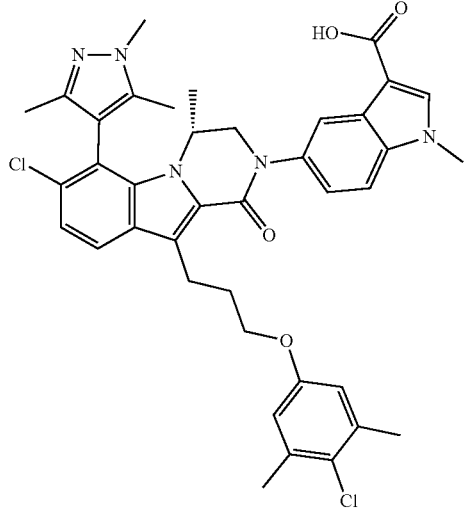 [SMILES: Cc1cc(OCCCc2c3n(c4c(-c5c(C)nn(C)c5C)c(Cl)ccc24)[C@H](C)CN(c2ccc4c(c2)c(C(=O)O)cn4C)C3=O)cc(C)c1Cl]
I-171
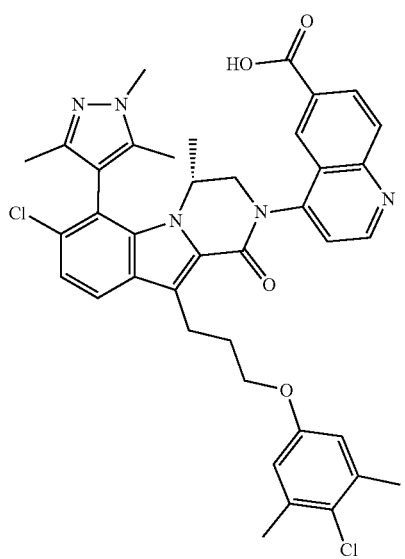 [SMILES: Cc1cc(OCCCc2c3n(c4c(-c5c(C)nn(C)c5C)c(Cl)ccc24)[C@H](C)CN(c2ccnc4ccc(C(=O)O)cc24)C3=O)cc(C)c1Cl]
I-172
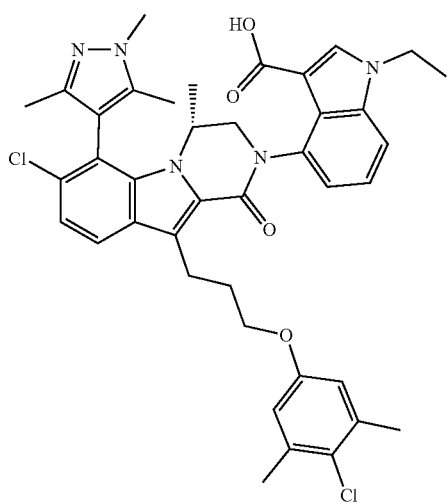 [SMILES: CCn1cc(C(=O)O)c2c(N3C[C@@H](C)n4c(c(CCCOc5cc(C)c(Cl)c(C)c5)c5ccc(Cl)c(-c6c(C)nn(C)c6C)c54)C3=O)cccc21]
I-173

TABLE 1-continued
Exemplary compounds.
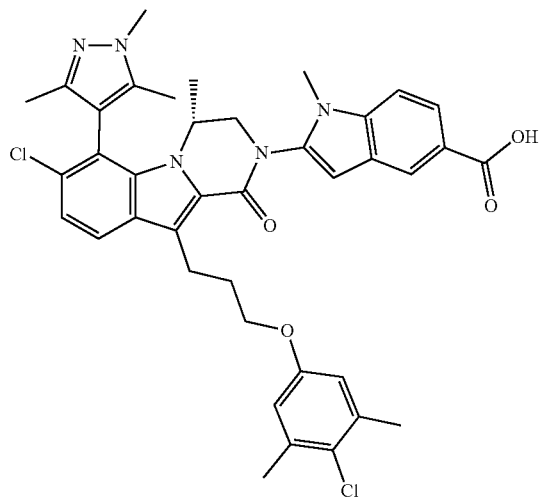 [SMILES: Cc1cc(OCCCc2c3n(c4c(-c5c(C)nn(C)c5C)c(Cl)ccc24)[C@H](C)CN(c2cc4cc(C(=O)O)ccc4n2C)C3=O)cc(C)c1Cl]
I-174
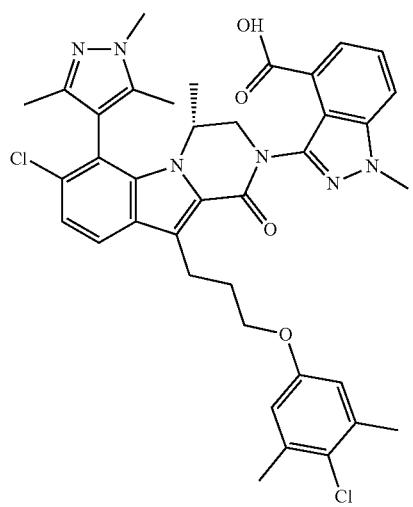
I-175
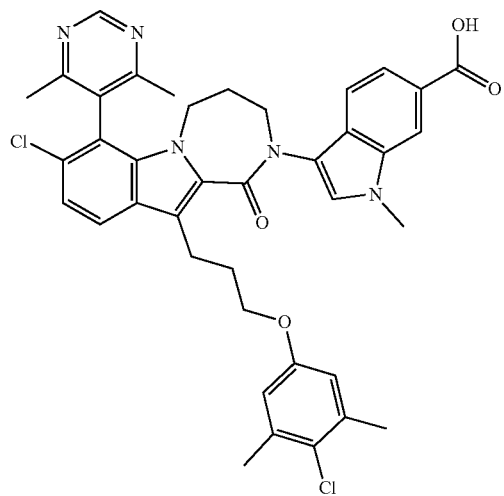 [SMILES: Cc1cc(OCCCc2c3n(c4c(-c5c(C)ncnc5C)c(Cl)ccc24)CCCN(c2cn(C)c4cc(C(=O)O)ccc24)C3=O)cc(C)c1Cl]
I-176

TABLE 1-continued
Exemplary compounds.
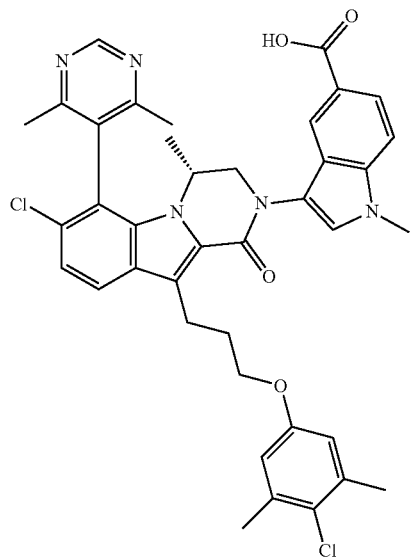
I-177
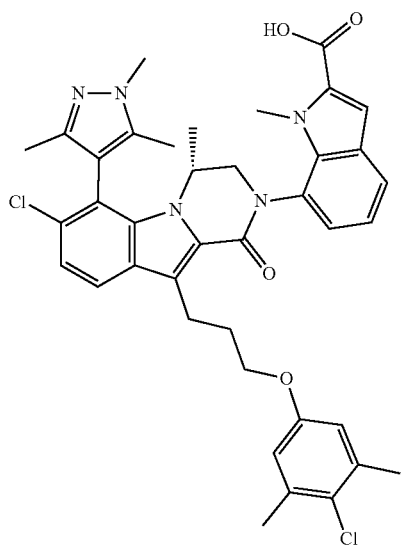 [SMILES: Cc1cc(OCCCc2c3n(c4c(-c5c(C)nn(C)c5C)c(Cl)ccc24)[C@H](C)CN(c2cccc4cc(C(=O)O)n(C)c24)C3=O)cc(C)c1Cl]
I-178
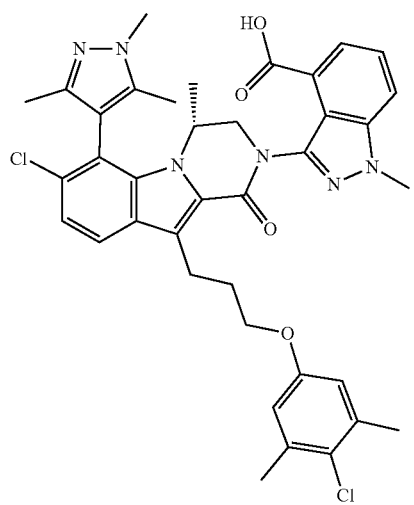 [SMILES: Cc1cc(OCCCc2c3n(c4c(-c5c(C)nn(C)c5C)c(Cl)ccc24)[C@H](C)CN(c2nn(C)c4cccc(C(=O)O)c24)C3=O)cc(C)c1Cl]
I-179

TABLE 1-continued
Exemplary compounds.
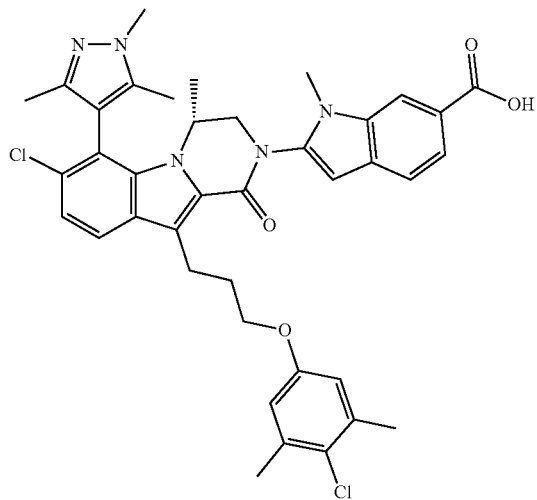 [SMILES: Cc1cc(OCCCc2c3n(c4c(-c5c(C)nn(C)c5C)c(Cl)ccc24)[C@H](C)CN(c2cc4ccc(C(=O)O)cc4n2C)C3=O)cc(C)c1Cl]
I-180
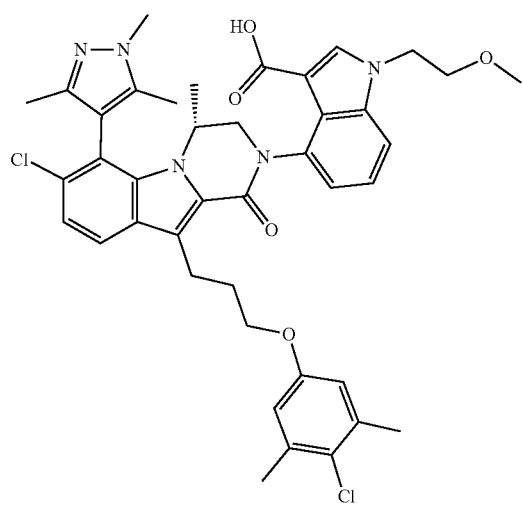 [SMILES: COCCn1cc(C(=O)O)c2c(N3C[C@@H](C)n4c(c(CCCOc5cc(C)c(Cl)c(C)c5)c5ccc(Cl)c(-c6c(C)nn(C)c6C)c54)C3=O)cccc21]
I-181
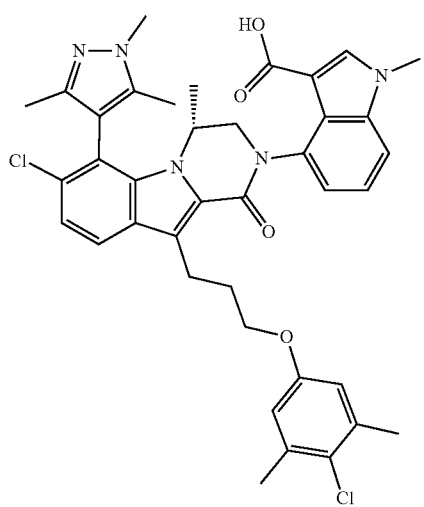 [SMILES: Cc1cc(OCCCc2c3n(c4c(-c5c(C)nn(C)c5C)c(Cl)ccc24)[C@H](C)CN(c2cccc4c2c(C(=O)O)cn4C)C3=O)cc(C)c1Cl]
I-182

TABLE 1-continued
Exemplary compounds.
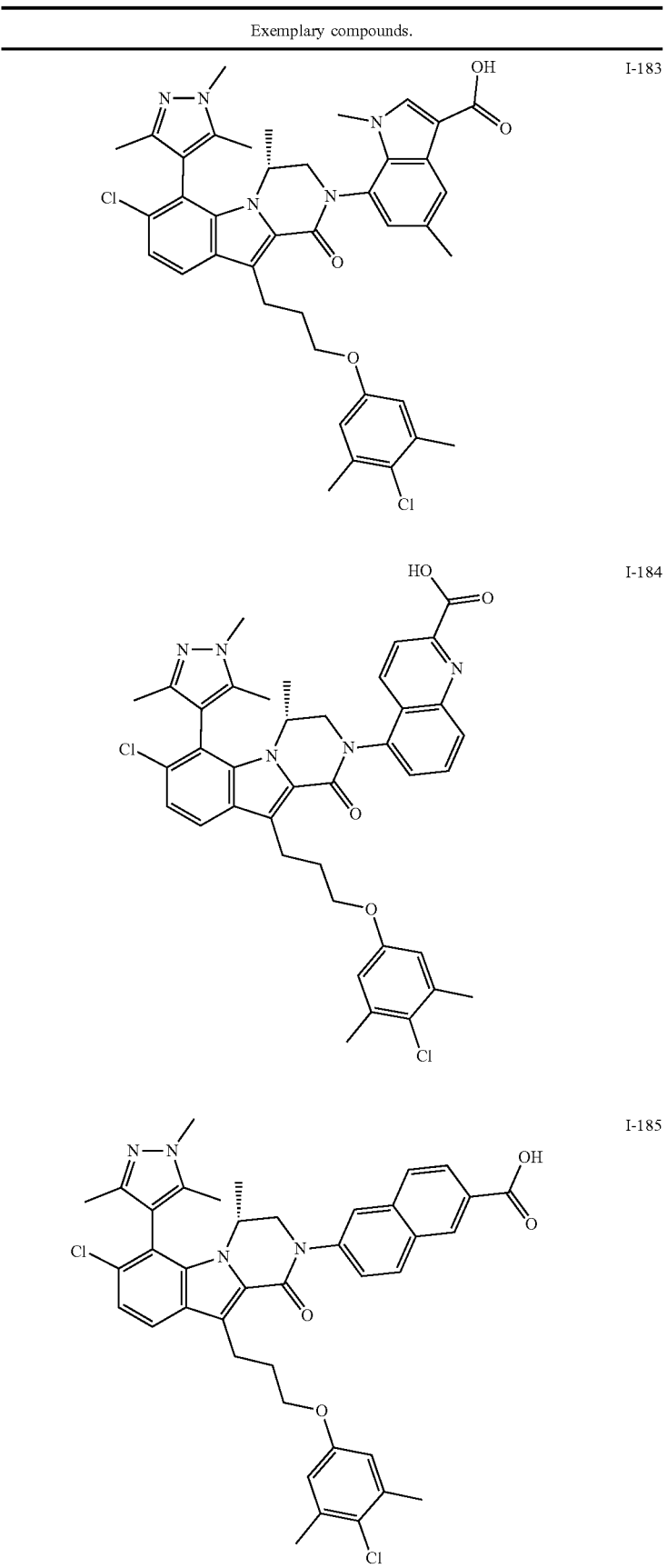
I-183
I-184
I-185

TABLE 1-continued

Exemplary compounds.

I-186

I-187

I-188

TABLE 1-continued
Exemplary compounds.
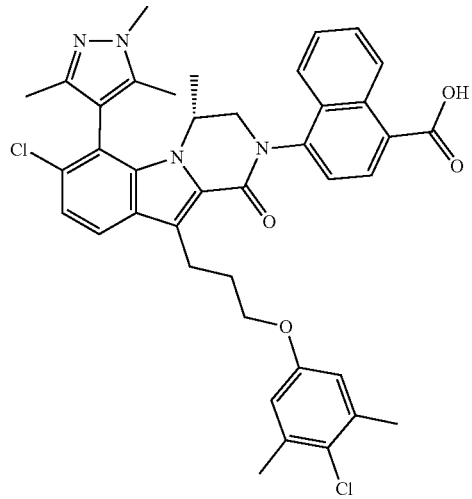 [SMILES: Cc1cc(OCCCc2c3n(c4c(-c5c(C)nn(C)c5C)c(Cl)ccc24)[C@H](C)CN(c2ccc(C(=O)O)c4ccccc24)C3=O)cc(C)c1Cl]
I-189
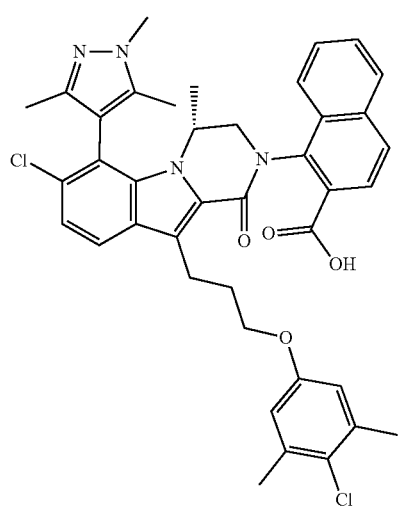 [SMILES: Cc1cc(OCCCc2c3n(c4c(-c5c(C)nn(C)c5C)c(Cl)ccc24)[C@H](C)CN(c2c(C(=O)O)ccc4ccccc24)C3=O)cc(C)c1Cl]
I-190
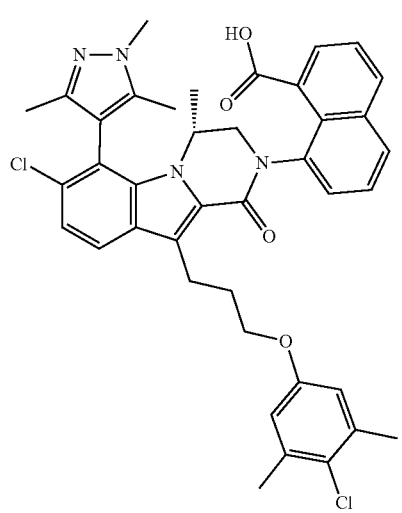 [SMILES: Cc1cc(OCCCc2c3n(c4c(-c5c(C)nn(C)c5C)c(Cl)ccc24)[C@H](C)CN(c2cccc4cccc(C(=O)O)c24)C3=O)cc(C)c1Cl]
I-191

TABLE 1-continued
Exemplary compounds.
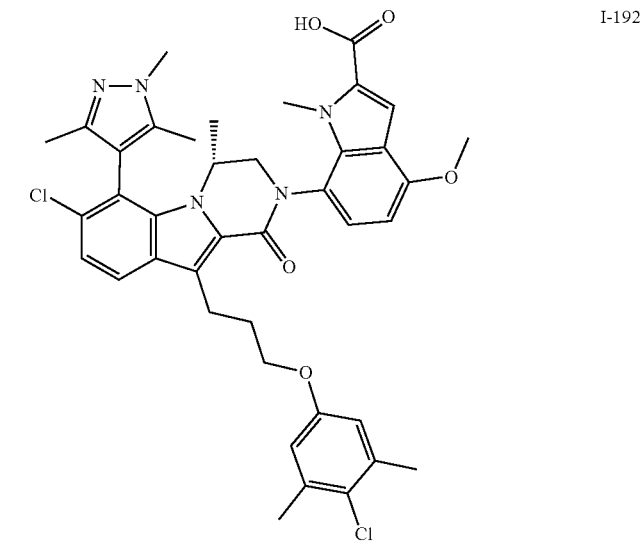
I-192
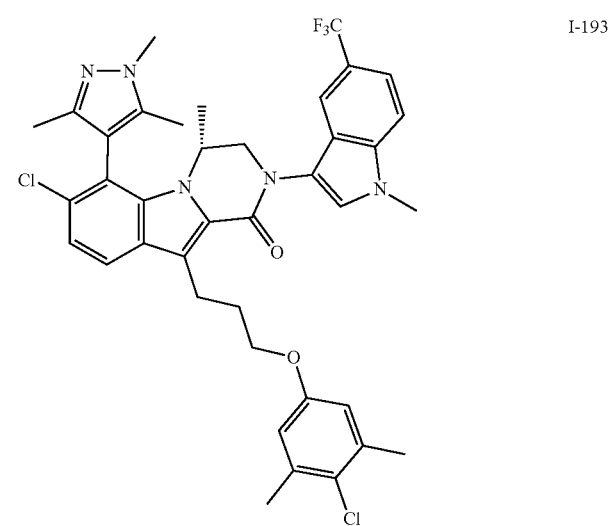
I-193
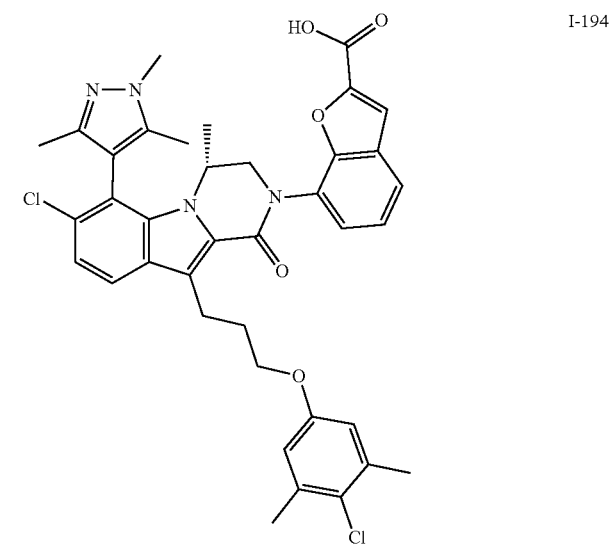
I-194

TABLE 1-continued
Exemplary compounds.
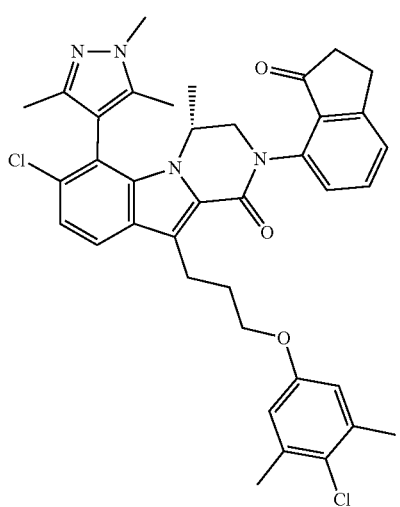 [SMILES: Cc1cc(OCCCc2c3n(c4c(-c5c(C)nn(C)c5C)c(Cl)ccc24)[C@H](C)CN(c2cccc4c2C(=O)CC4)C3=O)cc(C)c1Cl]
I-195
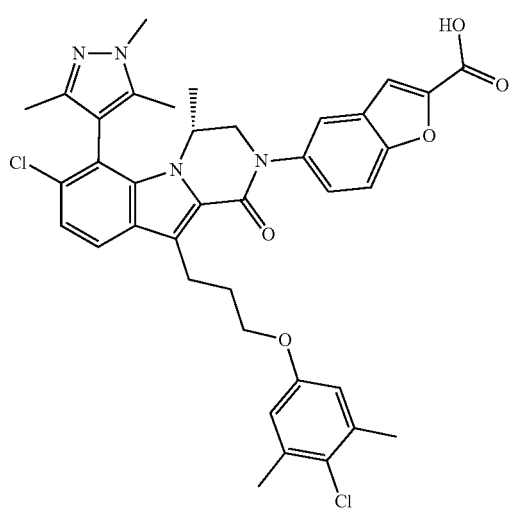 [SMILES: Cc1cc(OCCCc2c3n(c4c(-c5c(C)nn(C)c5C)c(Cl)ccc24)[C@H](C)CN(c2ccc4oc(C(=O)O)cc4c2)C3=O)cc(C)c1Cl]
I-196
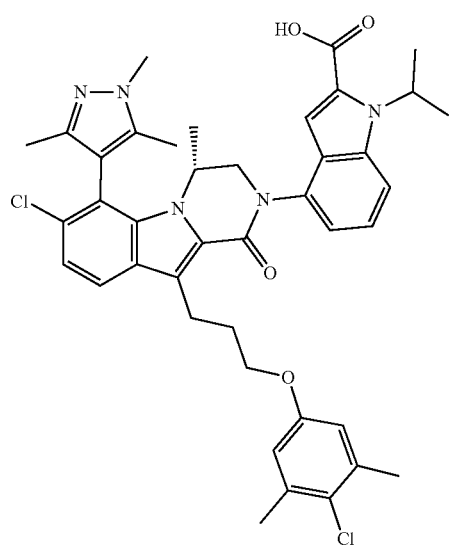 [SMILES: Cc1cc(OCCCc2c3n(c4c(-c5c(C)nn(C)c5C)c(Cl)ccc24)[C@H](C)CN(c2cccc4c2cc(C(=O)O)n4C(C)C)C3=O)cc(C)c1Cl]
I-197

TABLE 1-continued
Exemplary compounds.
I-198
I-199
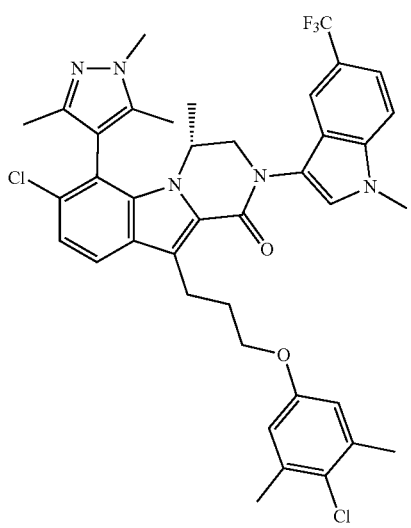
I-200

TABLE 1-continued
Exemplary compounds.
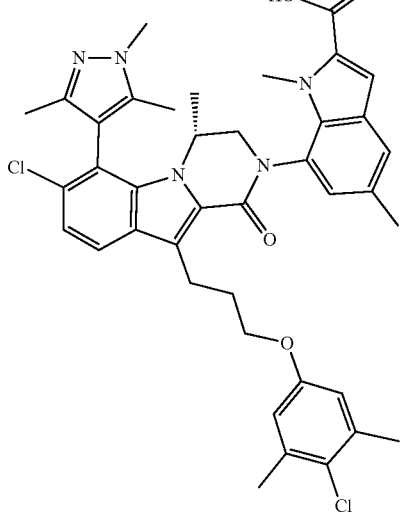
I-201
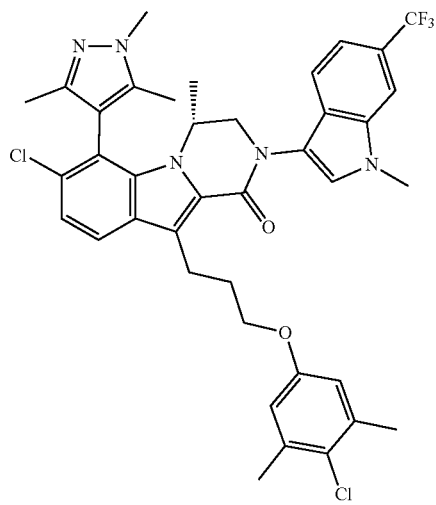 [SMILES: Cc1cc(OCCCc2c3n(c4c(-c5c(C)nn(C)c5C)c(Cl)ccc24)[C@H](C)CN(c2cn(C)c4cc(C(F)(F)F)ccc24)C3=O)cc(C)c1Cl]
I-202
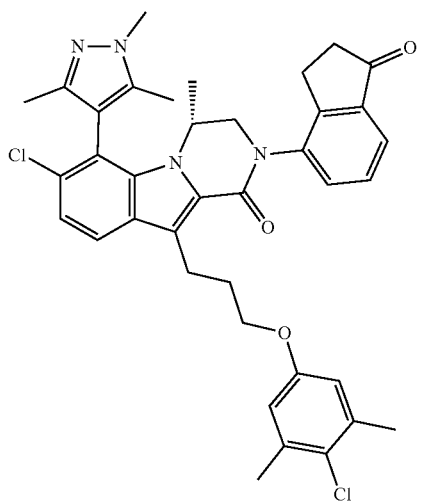 [SMILES: Cc1cc(OCCCc2c3n(c4c(-c5c(C)nn(C)c5C)c(Cl)ccc24)[C@H](C)CN(c2cccc4c2CCC4=O)C3=O)cc(C)c1Cl]
I-203

TABLE 1-continued
Exemplary compounds.
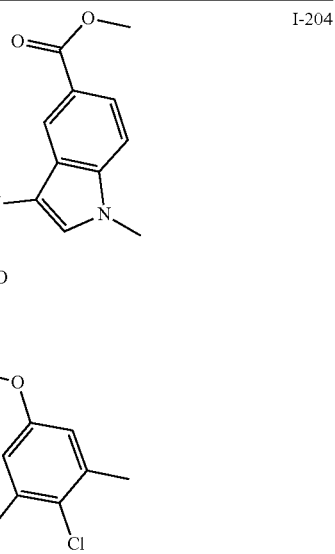
I-204
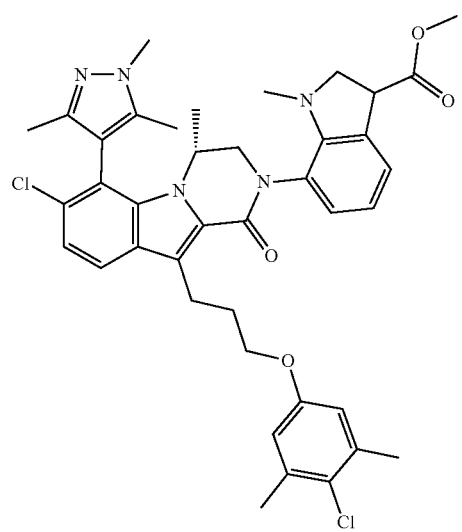 [SMILES: COC(=O)C1CN(C)c2c1cccc2N1C[C@@H](C)n2c(c(CCCOc3cc(C)c(Cl)c(C)c3)c3ccc(Cl)c(-c4c(C)nn(C)c4C)c32)C1=O]
I-205
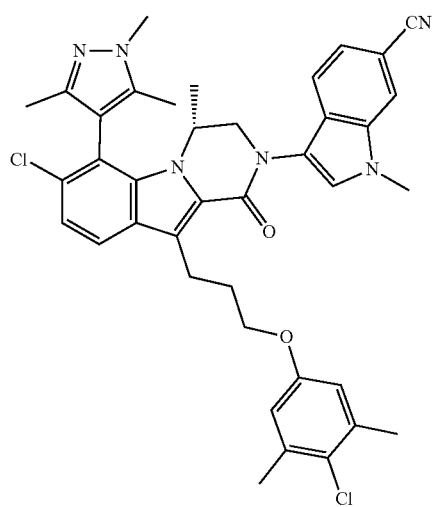 [SMILES: Cc1cc(OCCCc2c3n(c4c(-c5c(C)nn(C)c5C)c(Cl)ccc24)[C@H](C)CN(c2cn(C)c4cc(C#N)ccc24)C3=O)cc(C)c1Cl]
I-206

TABLE 1-continued
Exemplary compounds.
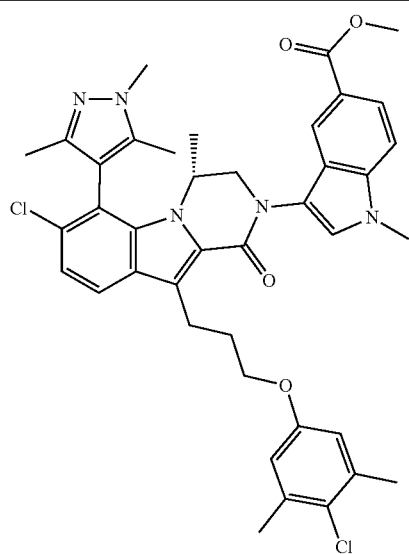
I-207
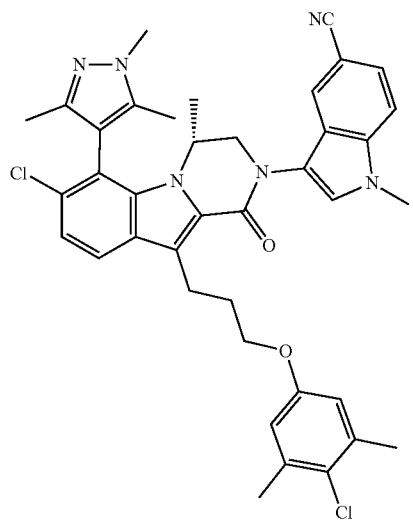 [SMILES: Cc1cc(OCCCc2c3n(c4c(-c5c(C)nn(C)c5C)c(Cl)ccc24)[C@H](C)CN(c2cn(C)c4ccc(C#N)cc24)C3=O)cc(C)c1Cl]
I-208
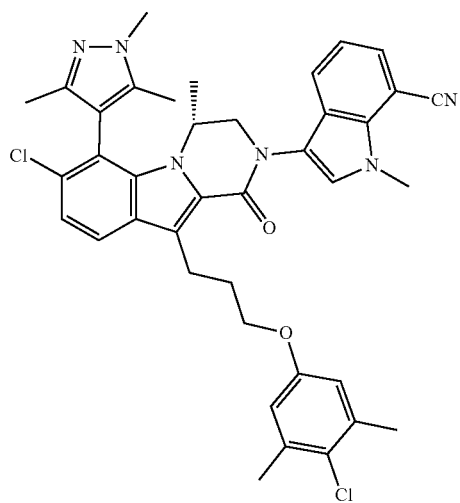 [SMILES: Cc1cc(OCCCc2c3n(c4c(-c5c(C)nn(C)c5C)c(Cl)ccc24)[C@H](C)CN(c2cn(C)c4c(C#N)cccc24)C3=O)cc(C)c1Cl]
I-209

TABLE 1-continued
Exemplary compounds.
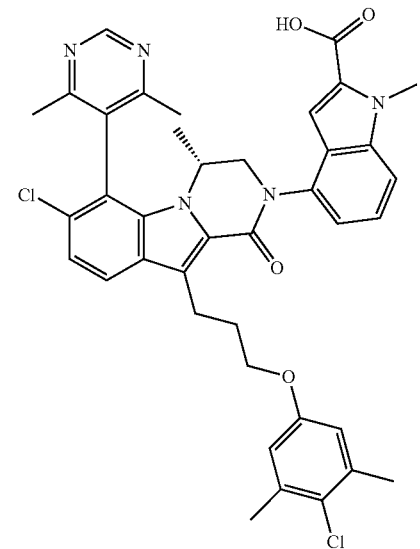 [SMILES: Cc1cc(OCCCc2c3n(c4c(-c5c(C)ncnc5C)c(Cl)ccc24)[C@H](C)CN(c2cccc4c2cc(C(=O)O)n4C)C3=O)cc(C)c1Cl]
I-210
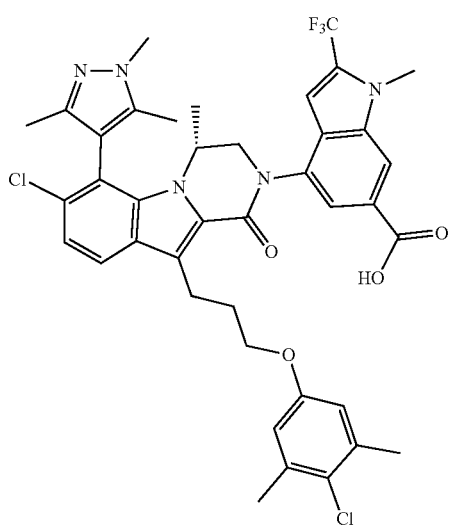 [SMILES: Cc1cc(OCCCc2c3n(c4c(-c5c(C)nn(C)c5C)c(Cl)ccc24)[C@H](C)CN(c2cc(C(=O)O)cc4c2cc(C(F)(F)F)n4C)C3=O)cc(C)c1Cl]
I-211
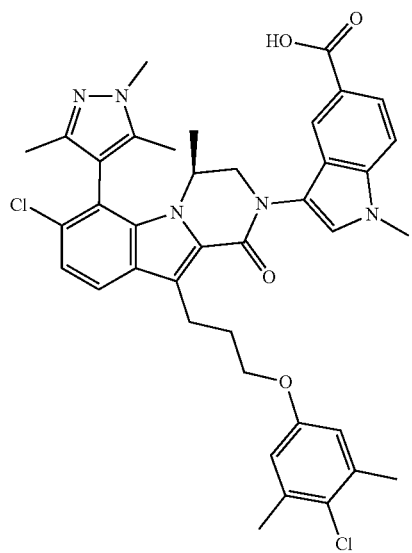 [SMILES: Cc1cc(OCCCc2c3n(c4c(-c5c(C)nn(C)c5C)c(Cl)ccc24)[C@@H](C)CN(c2cn(C)c4ccc(C(=O)O)cc24)C3=O)cc(C)c1Cl]
I-212

TABLE 1-continued
Exemplary compounds.
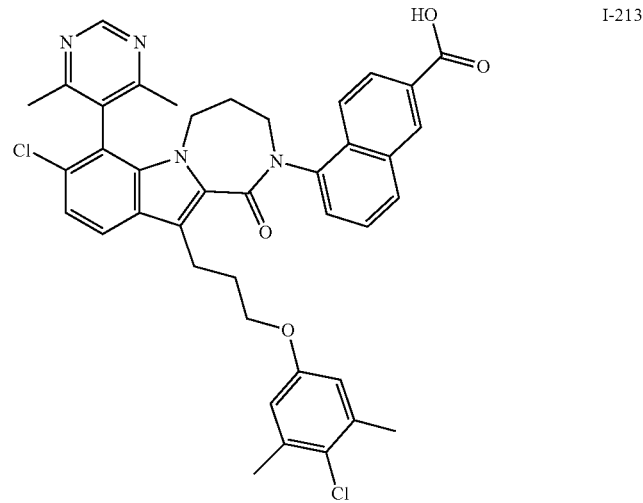
I-213
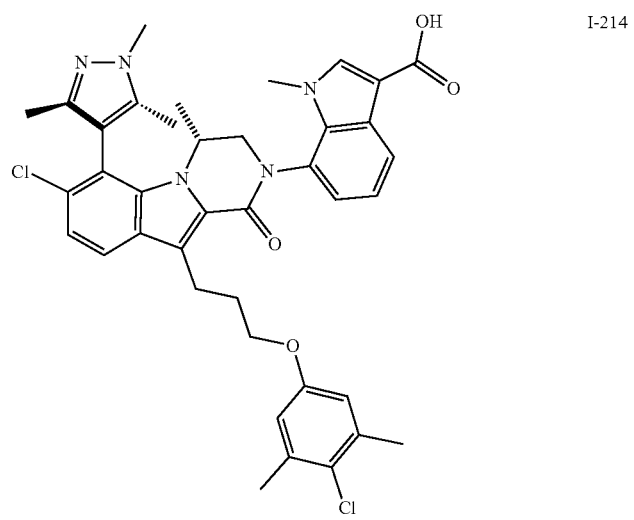
I-214
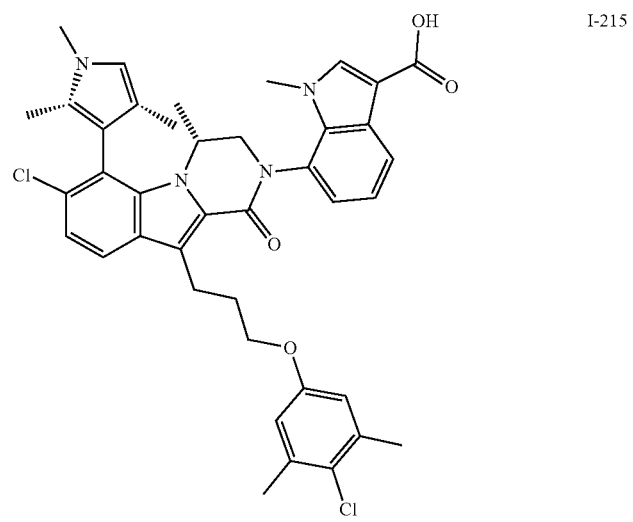
I-215

TABLE 1-continued
Exemplary compounds.
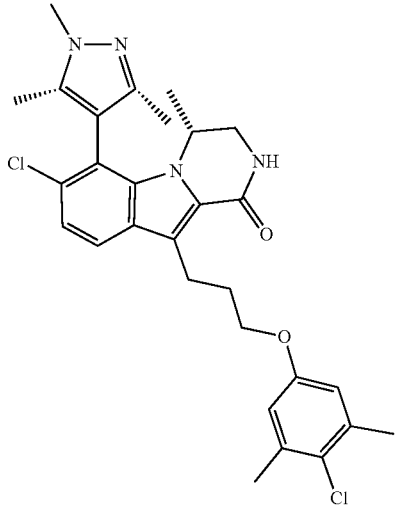
I-216
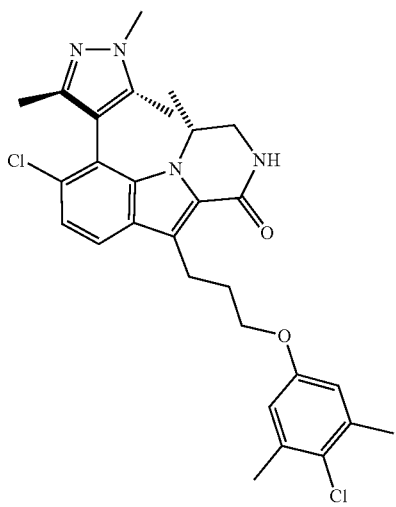
I-217
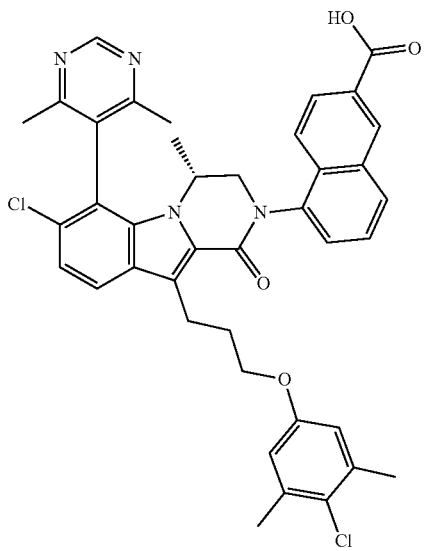 [SMILES: Cc1cc(OCCCc2c3n(c4c(-c5c(C)ncnc5C)c(Cl)ccc24)[C@H](C)CN(c2cccc4cc(C(=O)O)ccc24)C3=O)cc(C)c1Cl]
I-218

TABLE 1-continued
Exemplary compounds.
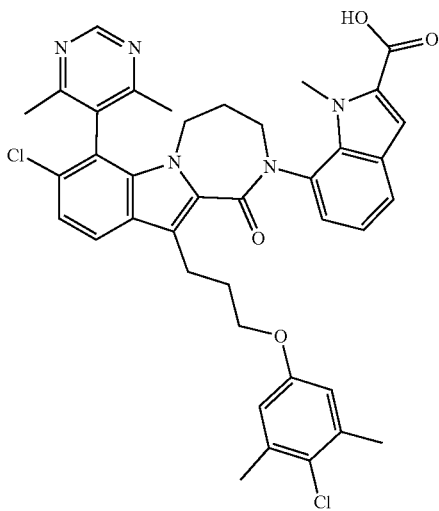 [SMILES: Cc1cc(OCCCc2c3n(c4c(-c5c(C)ncnc5C)c(Cl)ccc24)CCCN(c2cccc4cc(C(=O)O)n(C)c24)C3=O)cc(C)c1Cl]
I-219
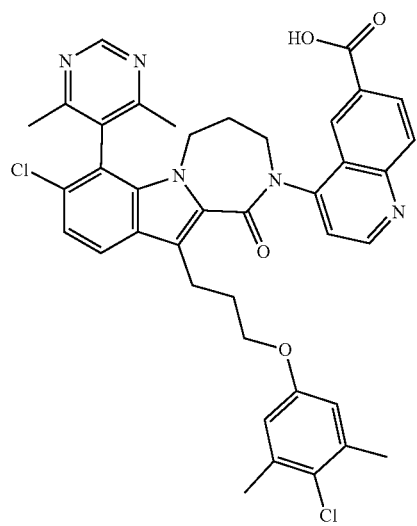 [SMILES: Cc1cc(OCCCc2c3n(c4c(-c5c(C)ncnc5C)c(Cl)ccc24)CCCN(c2ccnc4ccc(C(=O)O)cc24)C3=O)cc(C)c1Cl]
I-220
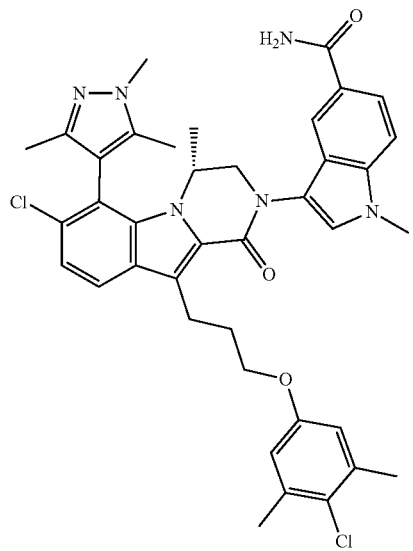 [SMILES: Cc1cc(OCCCc2c3n(c4c(-c5c(C)nn(C)c5C)c(Cl)ccc24)[C@H](C)CN(c2cn(C)c4ccc(C(N)=O)cc24)C3=O)cc(C)c1Cl]
I-221

TABLE 1-continued
Exemplary compounds.
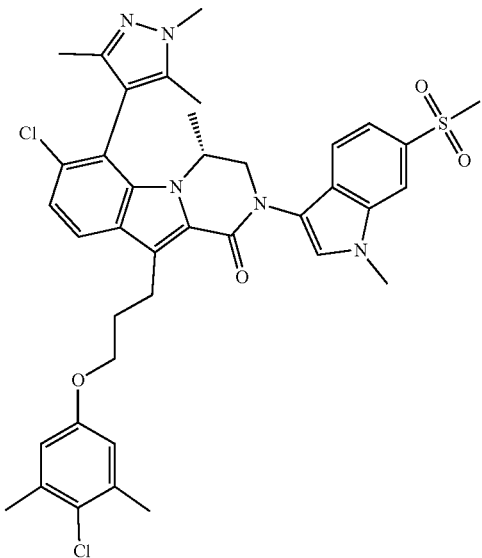
I-222
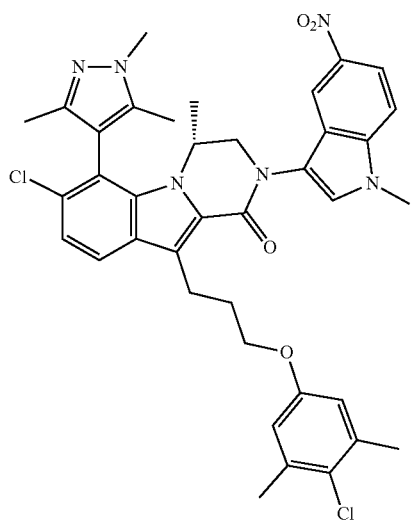 [SMILES: Cc1cc(OCCCc2c3n(c4c(-c5c(C)nn(C)c5C)c(Cl)ccc24)[C@H](C)CN(c2cn(C)c4ccc([N+](=O)[O-])cc24)C3=O)cc(C)c1Cl]
I-223
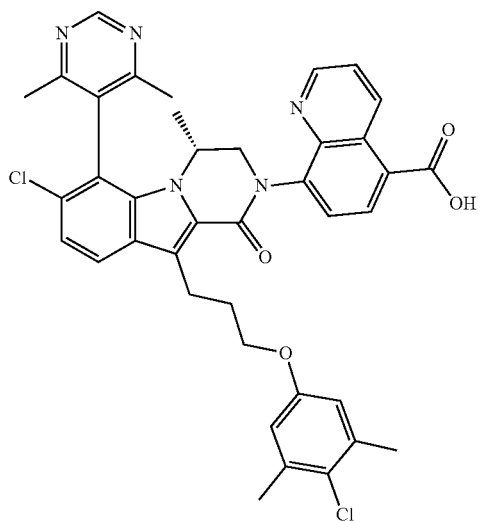 [SMILES: Cc1cc(OCCCc2c3n(c4c(-c5c(C)ncnc5C)c(Cl)ccc24)[C@H](C)CN(c2ccc(C(=O)O)c4cccnc24)C3=O)cc(C)c1Cl]
I-224

TABLE 1-continued
Exemplary compounds.

I-225
I-226
I-227

TABLE 1-continued
Exemplary compounds.
I-228
I-229

TABLE 1-continued
Exemplary compounds.
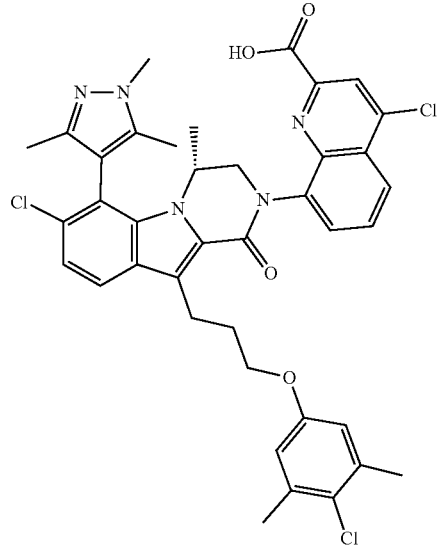 [SMILES: Cc1cc(OCCCc2c3n(c4c(-c5c(C)nn(C)c5C)c(Cl)ccc24)[C@H](C)CN(c2cccc4c(Cl)cc(C(=O)O)nc24)C3=O)cc(C)c1Cl]
I-230
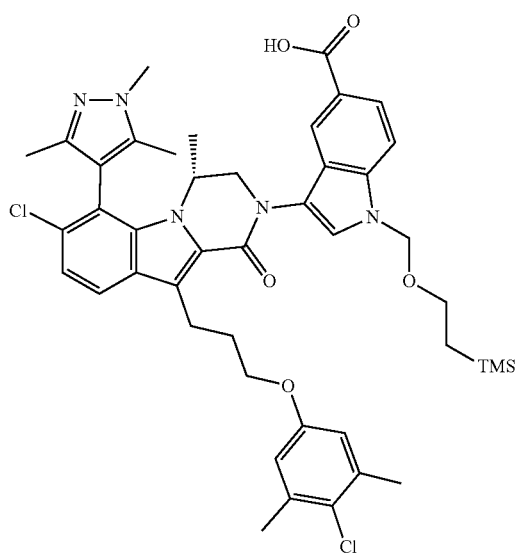 [SMILES: Cc1cc(OCCCc2c3n(c4c(-c5c(C)nn(C)c5C)c(Cl)ccc24)[C@H](C)CN(c2cn(COCC[Si](C)(C)C)c4ccc(C(=O)O)cc24)C3=O)cc(C)c1Cl]
I-231

TABLE 1-continued
Exemplary compounds.
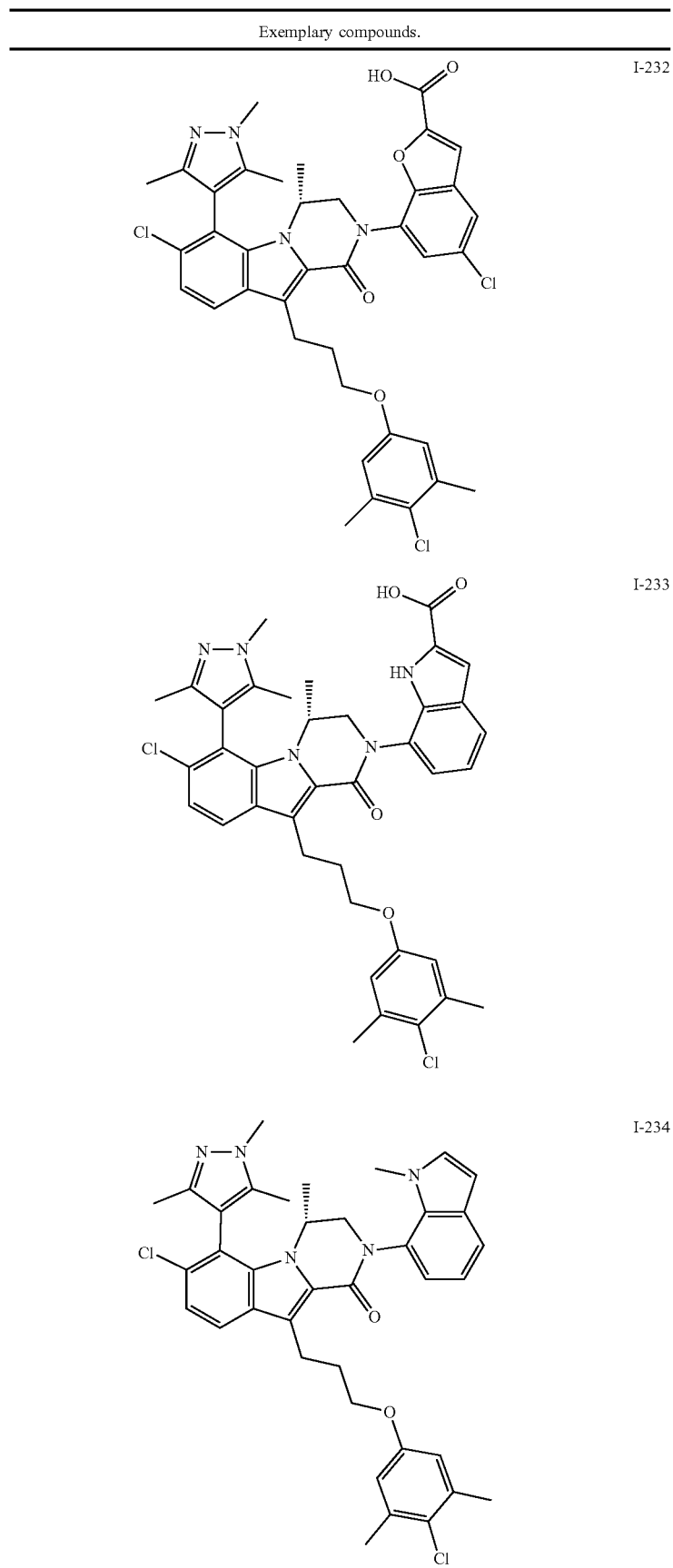
I-232
I-233
I-234

TABLE 1-continued
Exemplary compounds.
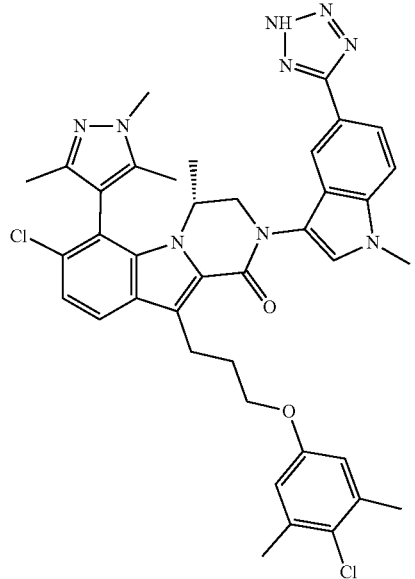 [SMILES: Cc1cc(OCCCc2c3n(c4c(-c5c(C)nn(C)c5C)c(Cl)ccc24)[C@H](C)CN(c2cn(C)c4ccc(-c5nn[nH]n5)cc24)C3=O)cc(C)c1Cl]
I-235
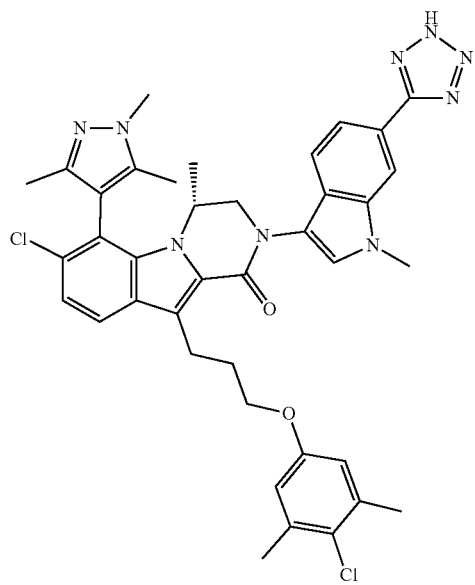 [SMILES: Cc1cc(OCCCc2c3n(c4c(-c5c(C)nn(C)c5C)c(Cl)ccc24)[C@H](C)CN(c2cn(C)c4cc(-c5nn[nH]n5)ccc24)C3=O)cc(C)c1Cl]
I-236

TABLE 1-continued
Exemplary compounds.
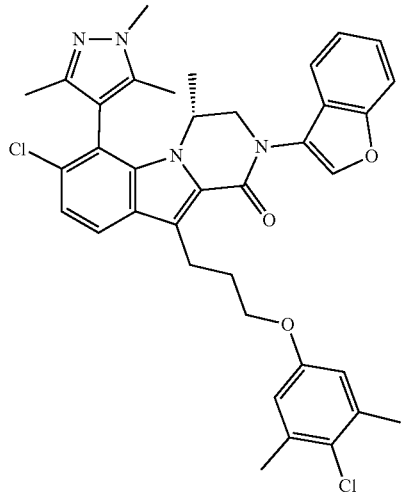 [SMILES: Cc1cc(OCCCc2c3n(c4c(-c5c(C)nn(C)c5C)c(Cl)ccc24)[C@H](C)CN(c2coc4ccccc24)C3=O)cc(C)c1Cl]
I-237
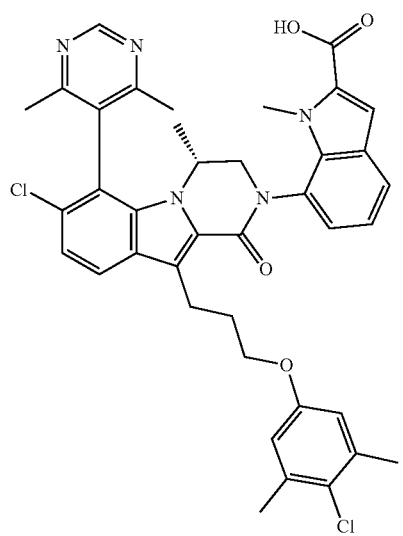 [SMILES: Cc1cc(OCCCc2c3n(c4c(-c5c(C)ncnc5C)c(Cl)ccc24)[C@H](C)CN(c2cccc4cc(C(=O)O)n(C)c24)C3=O)cc(C)c1Cl]
I-238
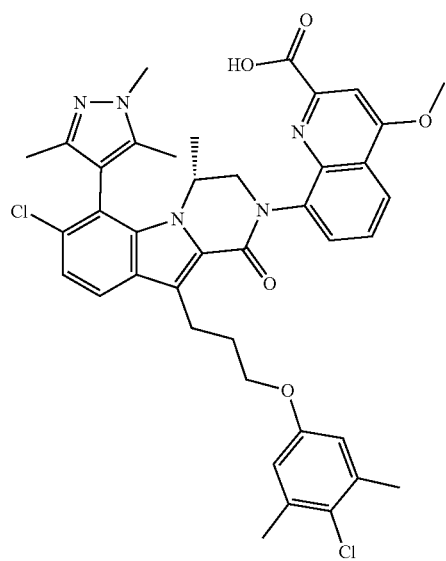 [SMILES: COc1cc(C(=O)O)nc2c(N3C[C@@H](C)n4c(c(CCCOc5cc(C)c(Cl)c(C)c5)c5ccc(Cl)c(-c6c(C)nn(C)c6C)c54)C3=O)cccc12]
I-239

TABLE 1-continued
Exemplary compounds.
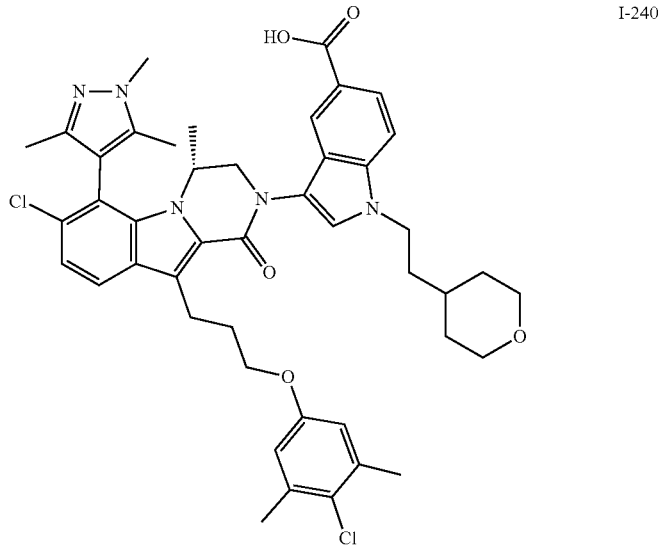
I-240
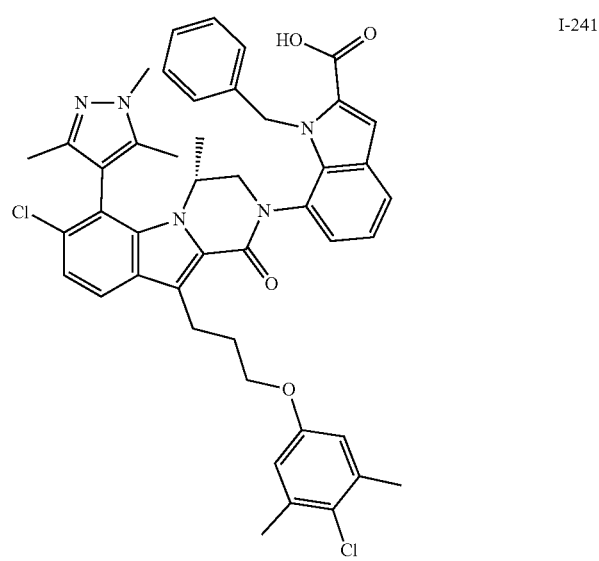
I-241

TABLE 1-continued
Exemplary compounds.
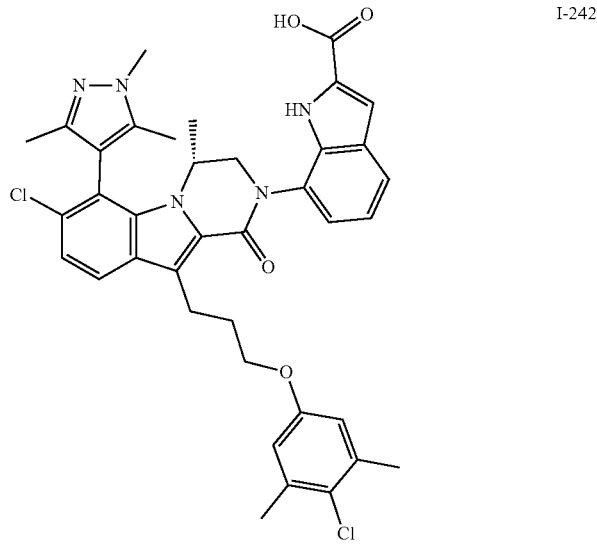
I-242
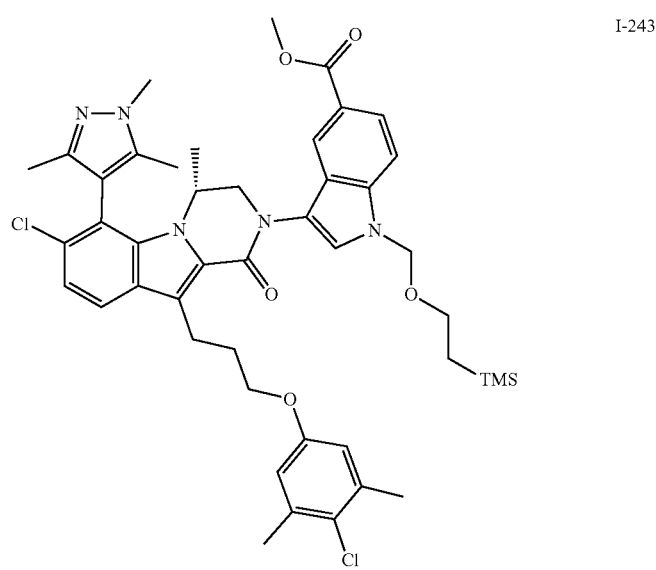
I-243

TABLE 1-continued
Exemplary compounds.
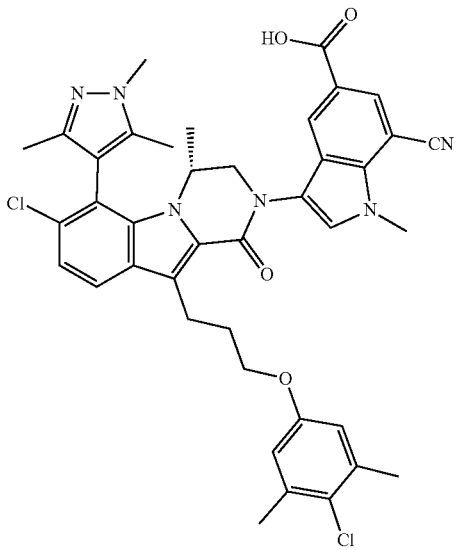 [SMILES: Cc1cc(OCCCc2c3n(c4c(-c5c(C)nn(C)c5C)c(Cl)ccc24)[C@H](C)CN(c2cn(C)c4c(C#N)cc(C(=O)O)cc24)C3=O)cc(C)c1Cl]
I-244
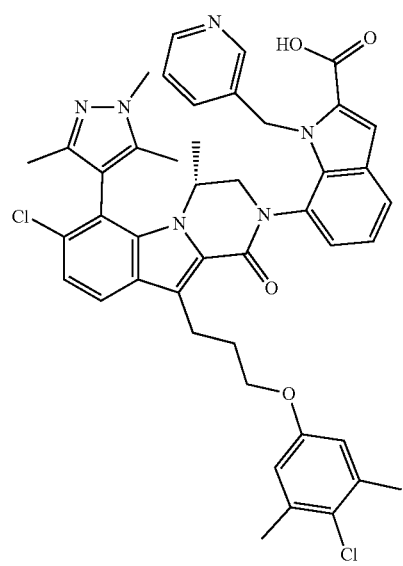 [SMILES: Cc1cc(OCCCc2c3n(c4c(-c5c(C)nn(C)c5C)c(Cl)ccc24)[C@H](C)CN(c2cccc4cc(C(=O)O)n(Cc5cccnc5)c24)C3=O)cc(C)c1Cl]
I-245
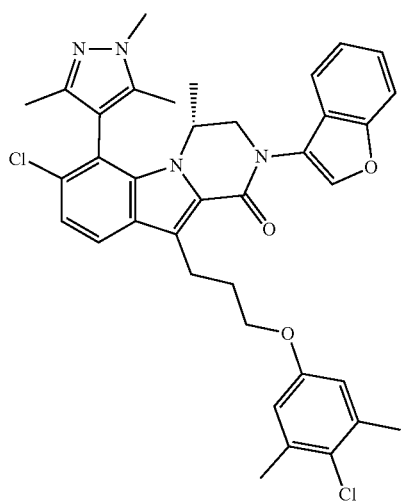 [SMILES: Cc1cc(OCCCc2c3n(c4c(-c5c(C)nn(C)c5C)c(Cl)ccc24)[C@H](C)CN(c2coc4ccccc24)C3=O)cc(C)c1Cl]
I-246

TABLE 1-continued
Exemplary compounds.
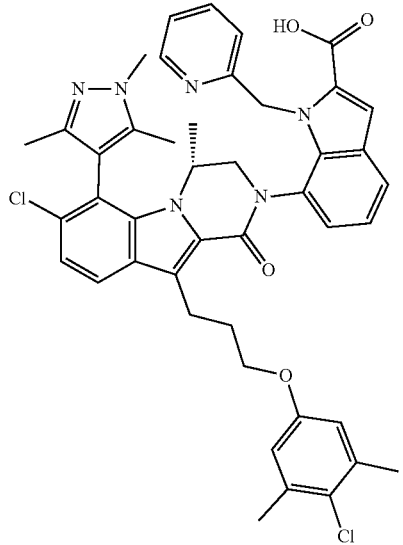 [SMILES: Cc1cc(OCCCc2c3n(c4c(-c5c(C)nn(C)c5C)c(Cl)ccc24)[C@H](C)CN(c2cccc4cc(C(=O)O)n(Cc5ccccn5)c24)C3=O)cc(C)c1Cl]
I-247
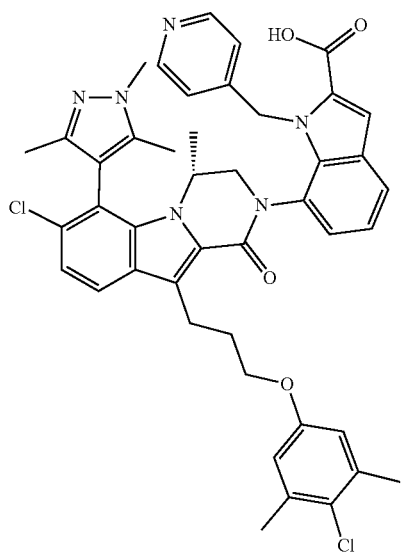 [SMILES: Cc1cc(OCCCc2c3n(c4c(-c5c(C)nn(C)c5C)c(Cl)ccc24)[C@H](C)CN(c2cccc4cc(C(=O)O)n(Cc5ccncc5)c24)C3=O)cc(C)c1Cl]
I-248

TABLE 1-continued
Exemplary compounds.
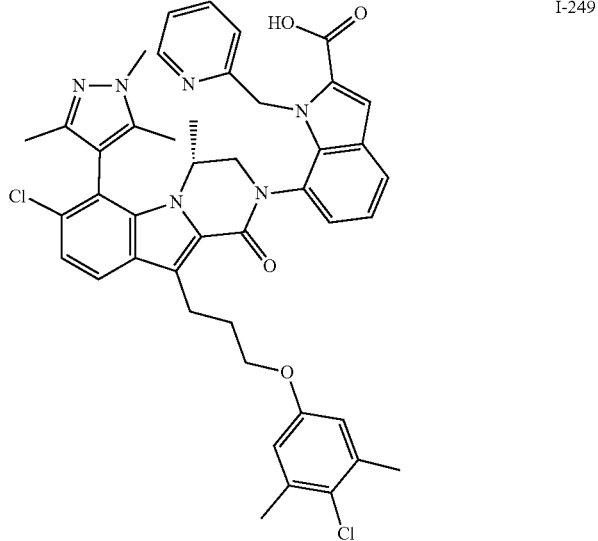
I-249
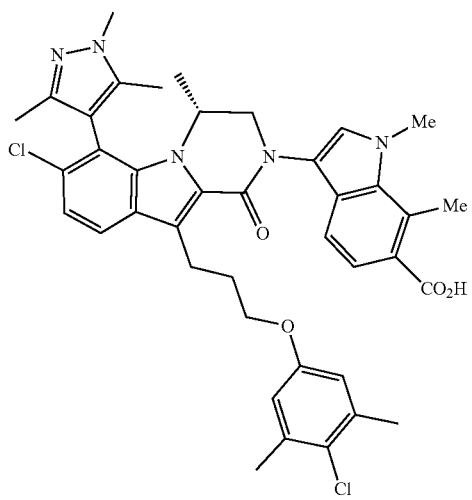 [SMILES: Cc1cc(OCCCc2c3n(c4c(-c5c(C)nn(C)c5C)c(Cl)ccc24)[C@H](C)CN(c2cn(C)c4c(C)c(C(=O)O)ccc24)C3=O)cc(C)c1Cl]
I-250
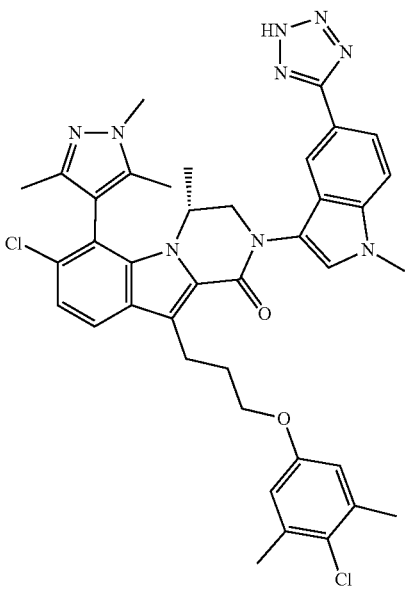 [SMILES: Cc1cc(OCCCc2c3n(c4c(-c5c(C)nn(C)c5C)c(Cl)ccc24)[C@H](C)CN(c2cn(C)c4ccc(-c5nn[nH]n5)cc24)C3=O)cc(C)c1Cl]
I-251

TABLE 1-continued
Exemplary compounds.
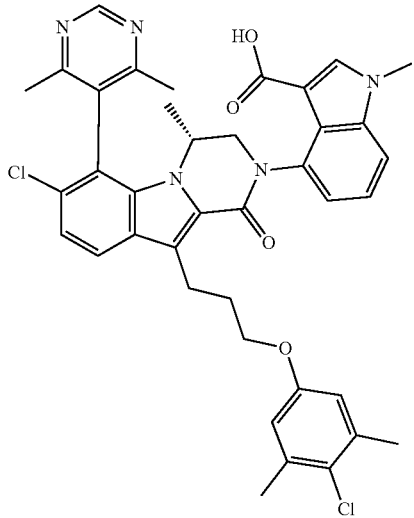 [SMILES: Cc1cc(OCCCc2c3n(c4c(-c5c(C)ncnc5C)c(Cl)ccc24)[C@H](C)CN(c2cccc4c2c(C(=O)O)cn4C)C3=O)cc(C)c1Cl]
I-252
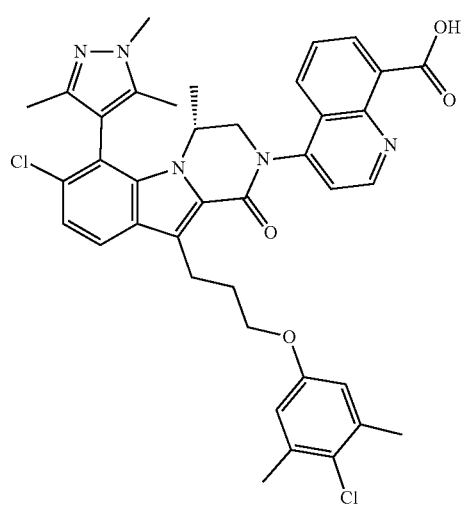 [SMILES: Cc1cc(OCCCc2c3n(c4c(-c5c(C)nn(C)c5C)c(Cl)ccc24)[C@H](C)CN(c2ccnc4c(C(=O)O)cccc24)C3=O)cc(C)c1Cl]
I-253
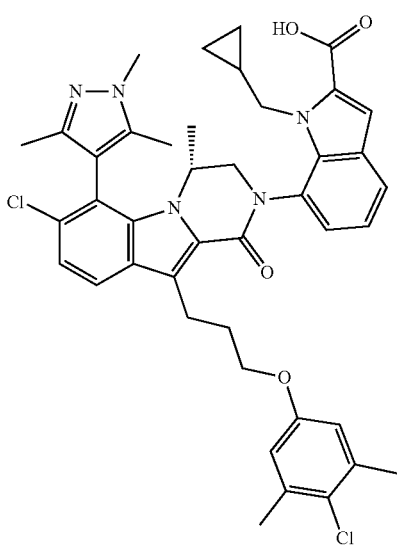
I-254

US 11,596,639 B2
TABLE 1-continued
Exemplary compounds.
I-255
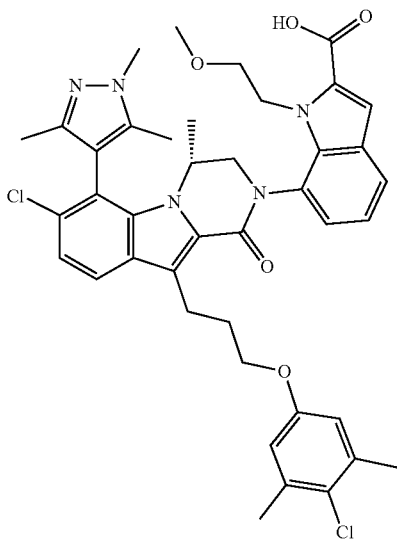
I-256
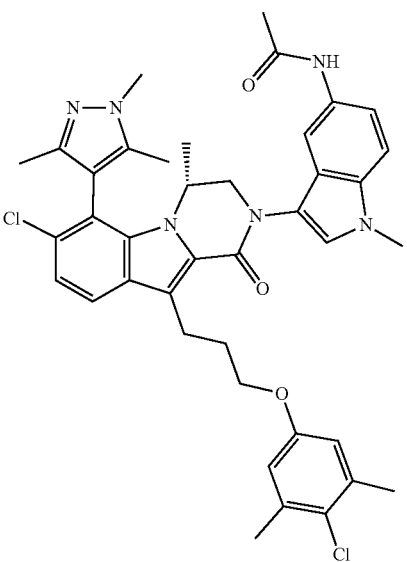 [SMILES: CC(=O)Nc1ccc2c(c1)c(N1C[C@@H](C)n3c(c(CCCOc4cc(C)c(Cl)c(C)c4)c4ccc(Cl)c(-c5c(C)nn(C)c5C)c43)C1=O)cn2C]
I-257

TABLE 1-continued
Exemplary compounds.
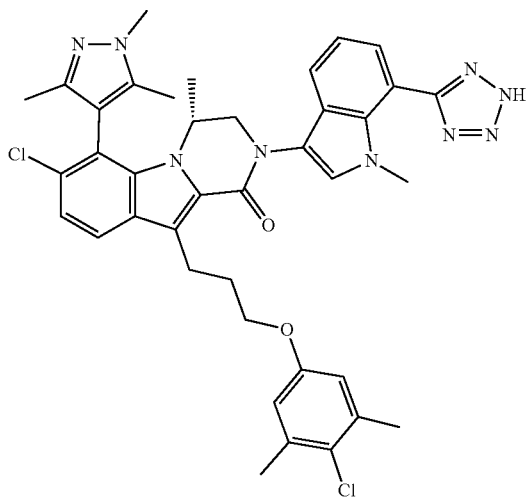 [SMILES: Cc1cc(OCCCc2c3n(c4c(-c5c(C)nn(C)c5C)c(Cl)ccc24)[C@H](C)CN(c2cn(C)c4c(-c5nn[nH]n5)cccc24)C3=O)cc(C)c1Cl]
I-258
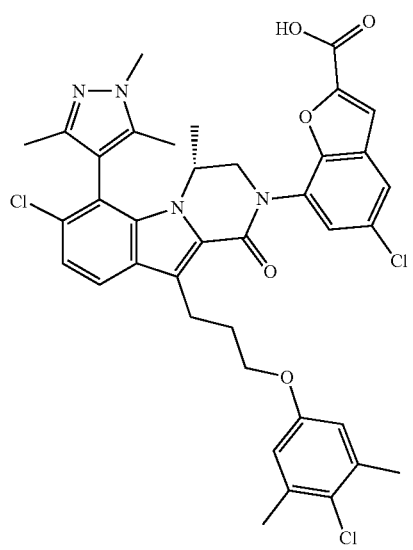
I-259
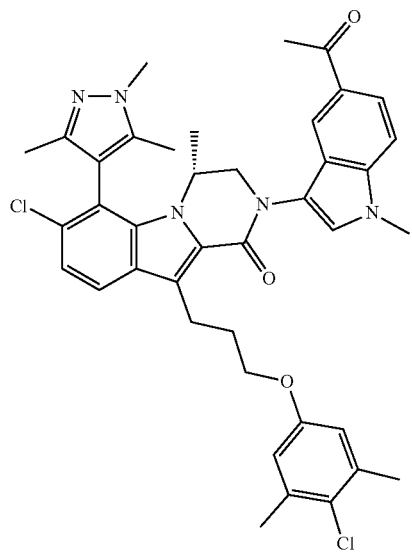 [SMILES: CC(=O)c1ccc2c(c1)c(N1C[C@@H](C)n3c(c(CCCOc4cc(C)c(Cl)c(C)c4)c4ccc(Cl)c(-c5c(C)nn(C)c5C)c43)C1=O)cn2C]
I-260

TABLE 1-continued
Exemplary compounds.
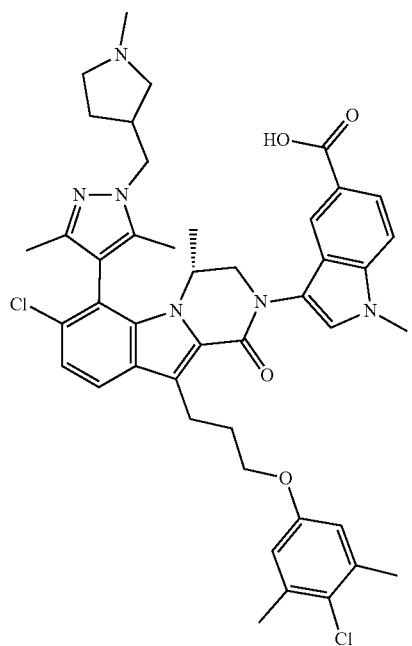 [SMILES: Cc1cc(OCCCc2c3n(c4c(-c5c(C)nn(CC6CCN(C)C6)c5C)c(Cl)ccc24)[C@H](C)CN(c2cn(C)c4ccc(C(=O)O)cc24)C3=O)cc(C)c1Cl]
I-261
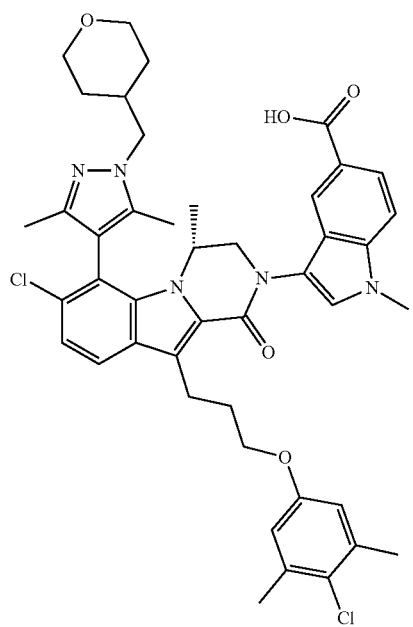 [SMILES: Cc1cc(OCCCc2c3n(c4c(-c5c(C)nn(CC6CCOCC6)c5C)c(Cl)ccc24)[C@H](C)CN(c2cn(C)c4ccc(C(=O)O)cc24)C3=O)cc(C)c1Cl]
I-262

TABLE 1-continued
Exemplary compounds.
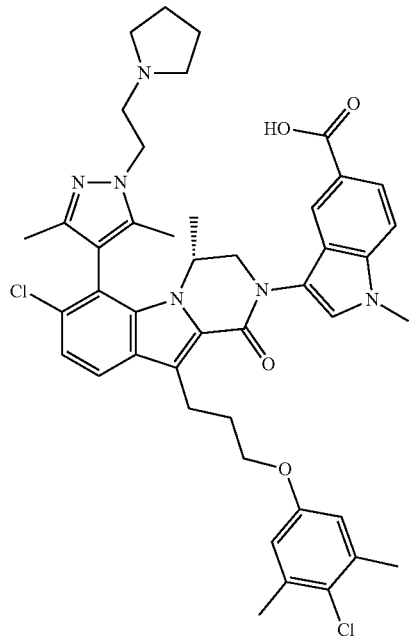 [SMILES: Cc1cc(OCCCc2c3n(c4c(-c5c(C)nn(CCN6CCCC6)c5C)c(Cl)ccc24)[C@H](C)CN(c2cn(C)c4ccc(C(=O)O)cc24)C3=O)cc(C)c1Cl]
I-263
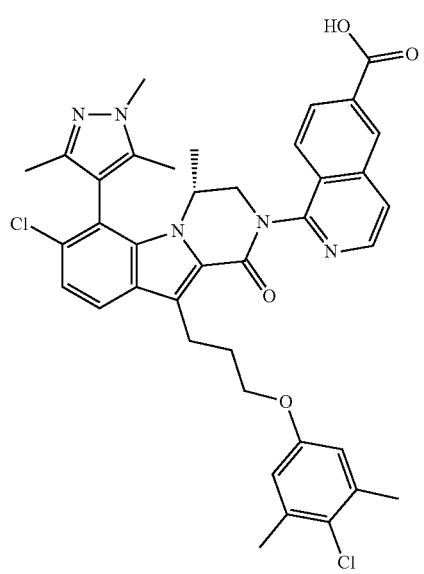 [SMILES: Cc1cc(OCCCc2c3n(c4c(-c5c(C)nn(C)c5C)c(Cl)ccc24)[C@H](C)CN(c2nccc4cc(C(=O)O)ccc24)C3=O)cc(C)c1Cl]
I-264

TABLE 1-continued
Exemplary compounds.
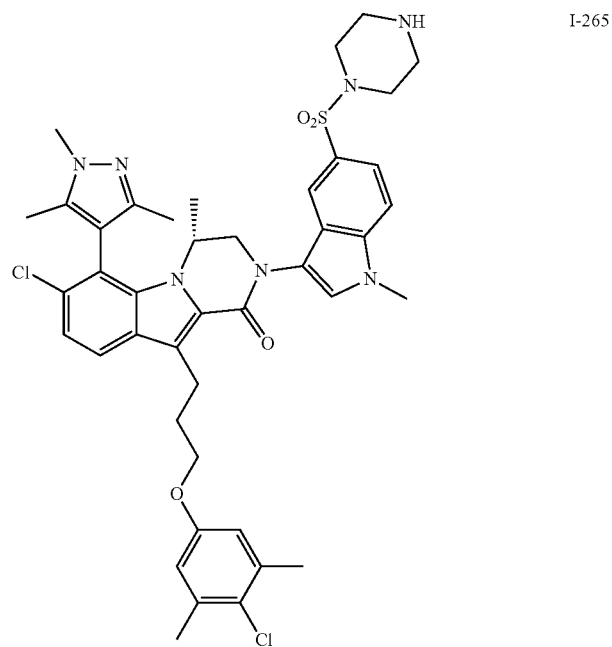
I-265
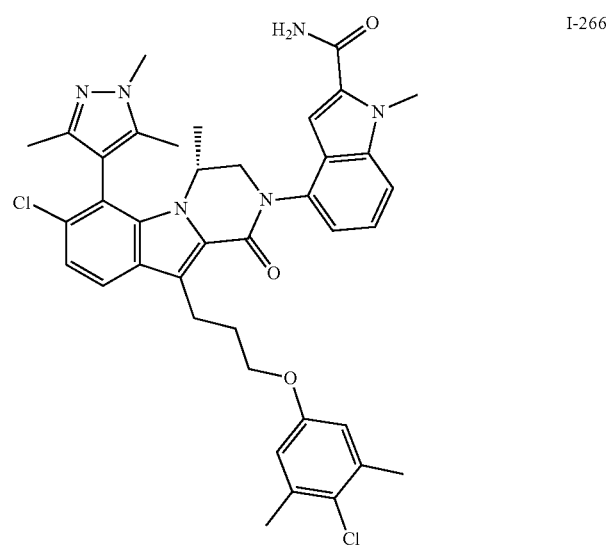
I-266

TABLE 1-continued
Exemplary compounds.
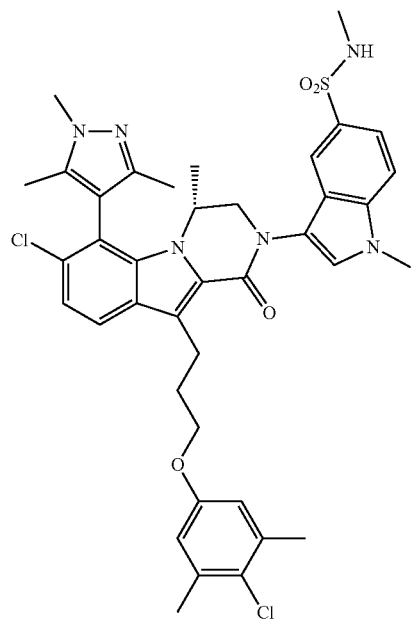
I-267
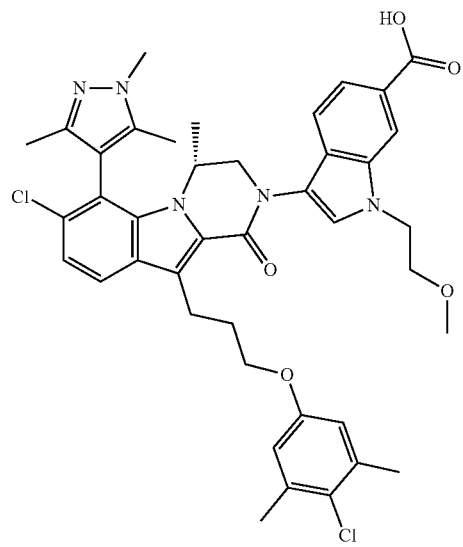 [SMILES: COCCn1cc(N2C[C@@H](C)n3c(c(CCCOc4cc(C)c(Cl)c(C)c4)c4ccc(Cl)c(-c5c(C)nn(C)c5C)c43)C2=O)c2ccc(C(=O)O)cc21]
I-268

TABLE 1-continued
Exemplary compounds.
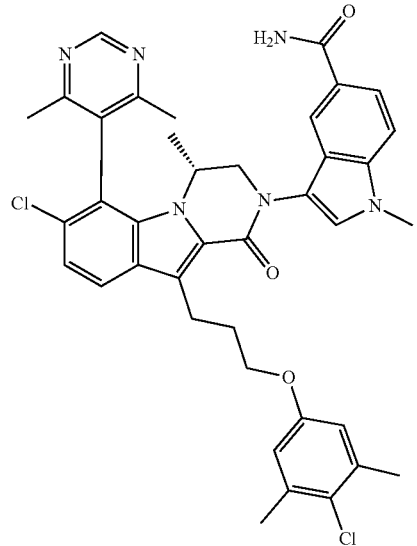 [SMILES: Cc1cc(OCCCc2c3n(c4c(-c5c(C)ncnc5C)c(Cl)ccc24)[C@H](C)CN(c2cn(C)c4ccc(C(N)=O)cc24)C3=O)cc(C)c1Cl]
I-269
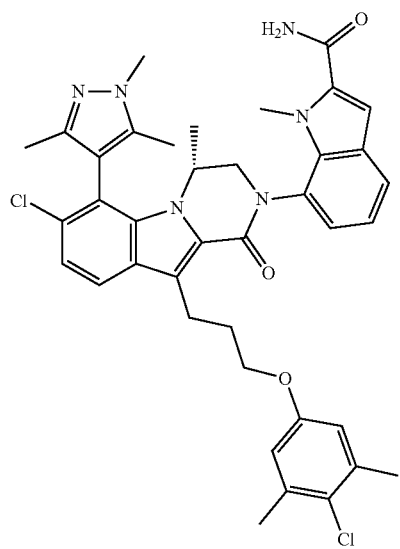 [SMILES: Cc1cc(OCCCc2c3n(c4c(-c5c(C)nn(C)c5C)c(Cl)ccc24)[C@H](C)CN(c2cccc4cc(C(N)=O)n(C)c24)C3=O)cc(C)c1Cl]
I-270

TABLE 1-continued
Exemplary compounds.
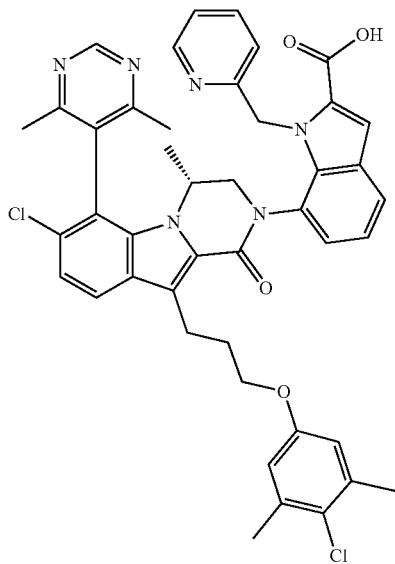
I-271
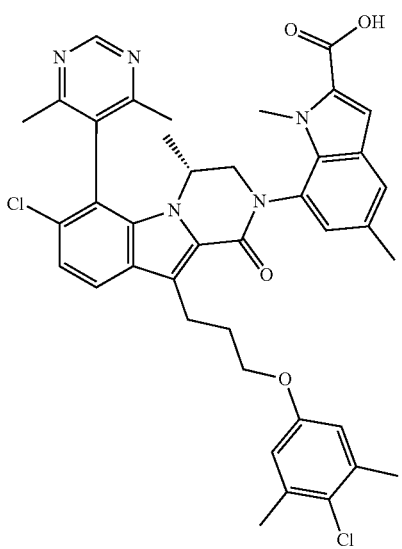 [SMILES: Cc1cc(N2C[C@@H](C)n3c(c(CCCOc4cc(C)c(Cl)c(C)c4)c4ccc(Cl)c(-c5c(C)ncnc5C)c43)C2=O)c2c(c1)cc(C(=O)O)n2C]
I-272
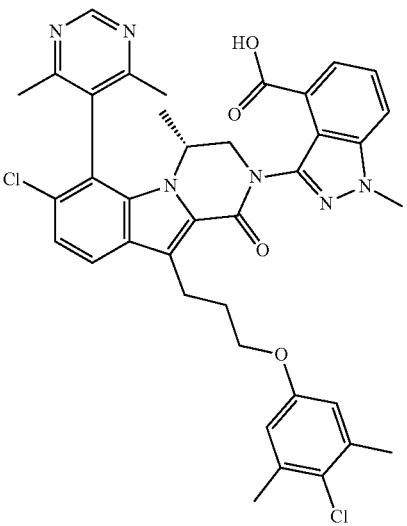 [SMILES: Cc1cc(OCCCc2c3n(c4c(-c5c(C)ncnc5C)c(Cl)ccc24)[C@H](C)CN(c2nn(C)c4cccc(C(=O)O)c24)C3=O)cc(C)c1Cl]
I-273

TABLE 1-continued
Exemplary compounds.
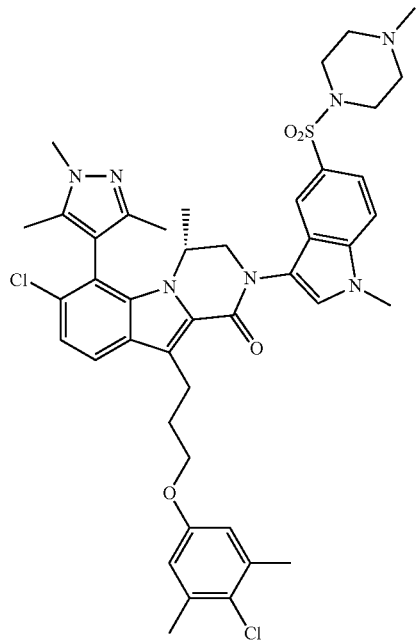
I-274
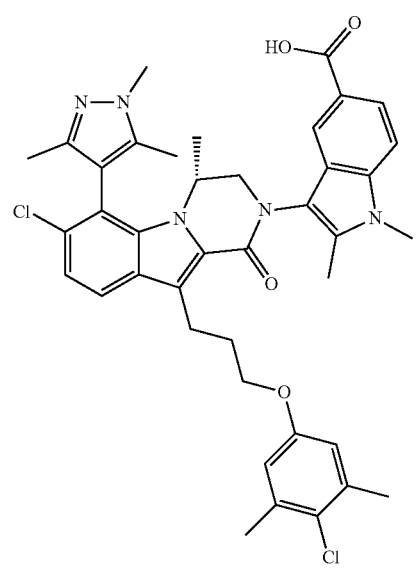 [SMILES: Cc1cc(OCCCc2c3n(c4c(-c5c(C)nn(C)c5C)c(Cl)ccc24)[C@H](C)CN(c2c(C)n(C)c4ccc(C(=O)O)cc24)C3=O)cc(C)c1Cl]
I-275

TABLE 1-continued
Exemplary compounds.
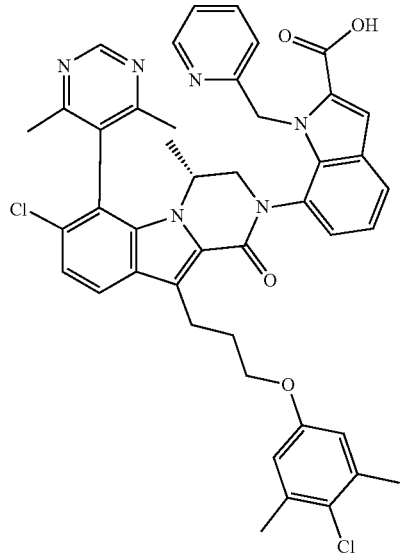 [SMILES: Cc1cc(OCCCc2c3n(c4c(-c5c(C)ncnc5C)c(Cl)ccc24)[C@H](C)CN(c2cccc4cc(C(=O)O)n(Cc5ccccn5)c24)C3=O)cc(C)c1Cl]
I-276
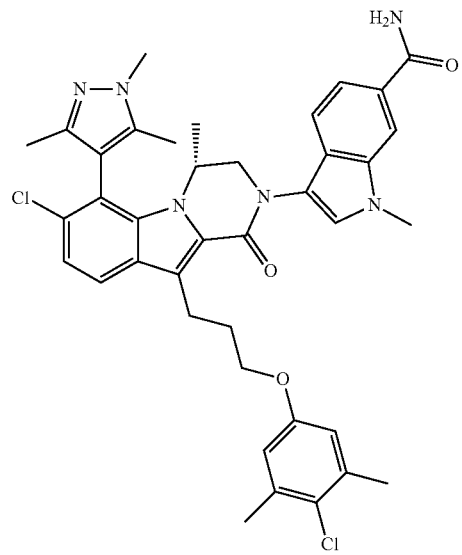 [SMILES: Cc1cc(OCCCc2c3n(c4c(-c5c(C)nn(C)c5C)c(Cl)ccc24)[C@H](C)CN(c2cn(C)c4cc(C(N)=O)ccc24)C3=O)cc(C)c1Cl]
I-277

TABLE 1-continued
Exemplary compounds.
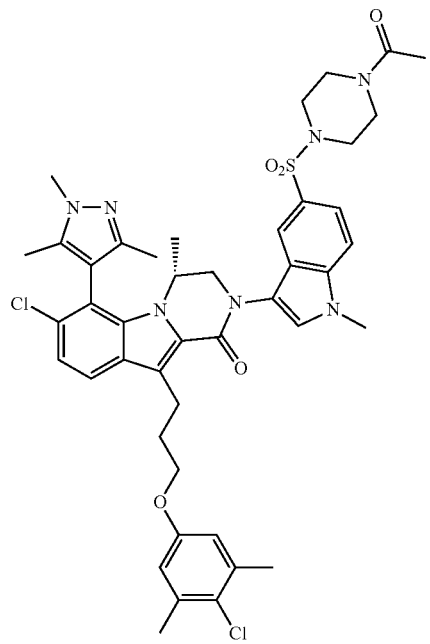 [SMILES: CC(=O)N1CCN(S(=O)(=O)c2ccc3c(c2)c(N2C[C@@H](C)n4c(c(CCCOc5cc(C)c(Cl)c(C)c5)c5ccc(Cl)c(-c6c(C)nn(C)c6C)c54)C2=O)cn3C)CC1]
I-278
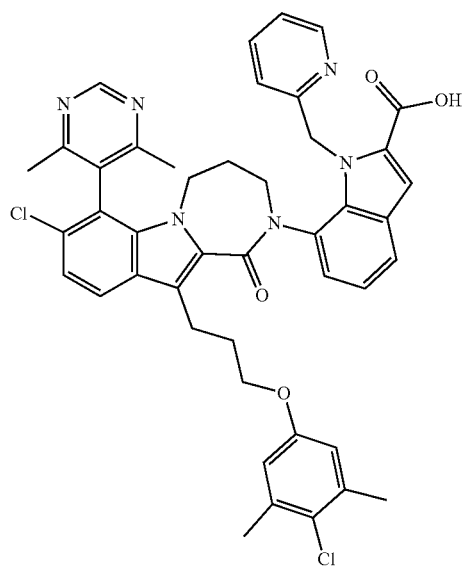 [SMILES: Cc1cc(OCCCc2c3n(c4c(-c5c(C)ncnc5C)c(Cl)ccc24)CCCN(c2cccc4cc(C(=O)O)n(Cc5ccccn5)c24)C3=O)cc(C)c1Cl]
I-279

TABLE 1-continued
Exemplary compounds.
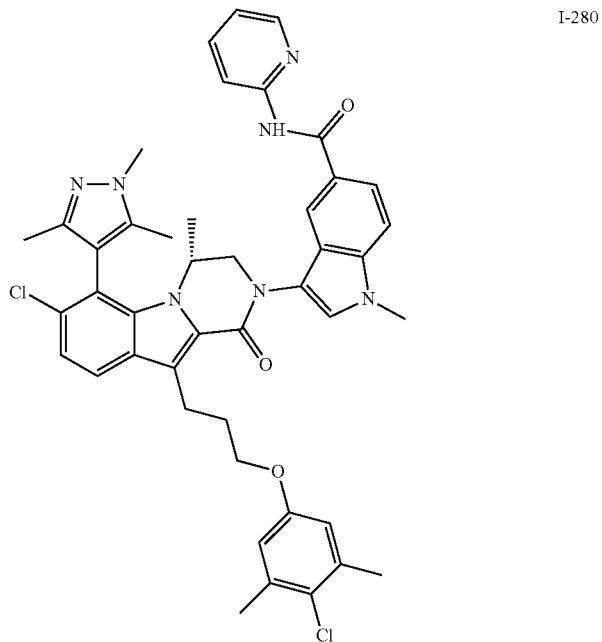
I-280
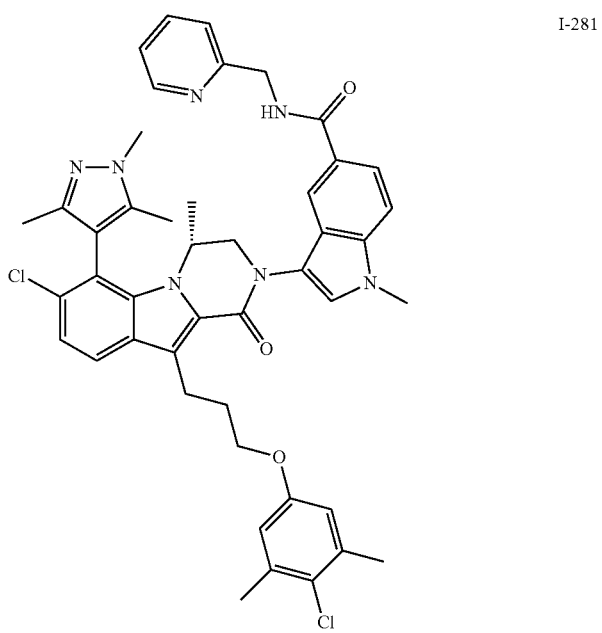
I-281

TABLE 1-continued
Exemplary compounds.
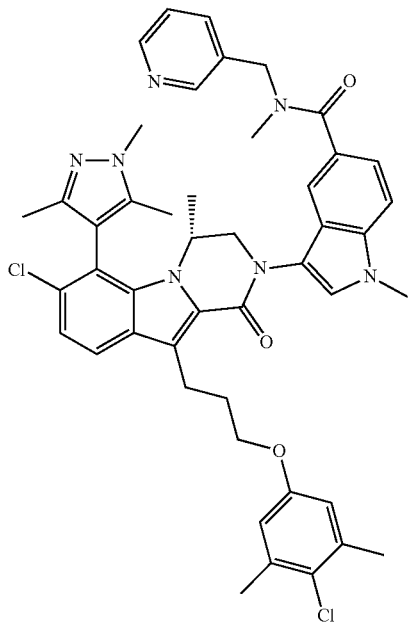 [SMILES: Cc1cc(OCCCc2c3n(c4c(-c5c(C)nn(C)c5C)c(Cl)ccc24)[C@H](C)CN(c2cn(C)c4ccc(C(=O)N(C)Cc5cccnc5)cc24)C3=O)cc(C)c1Cl]
I-282
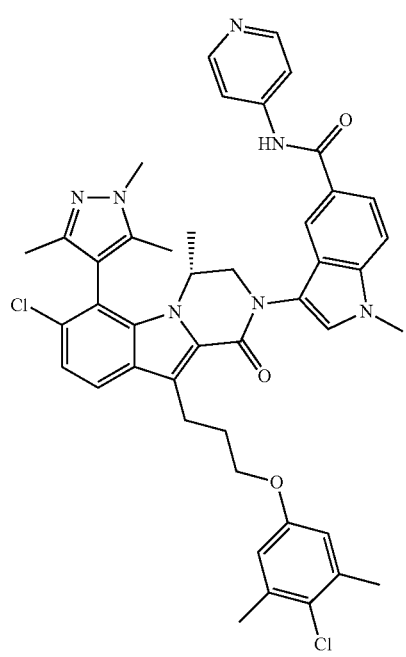 [SMILES: Cc1cc(OCCCc2c3n(c4c(-c5c(C)nn(C)c5C)c(Cl)ccc24)[C@H](C)CN(c2cn(C)c4ccc(C(=O)Nc5ccncc5)cc24)C3=O)cc(C)c1Cl]
I-283

TABLE 1-continued
Exemplary compounds.
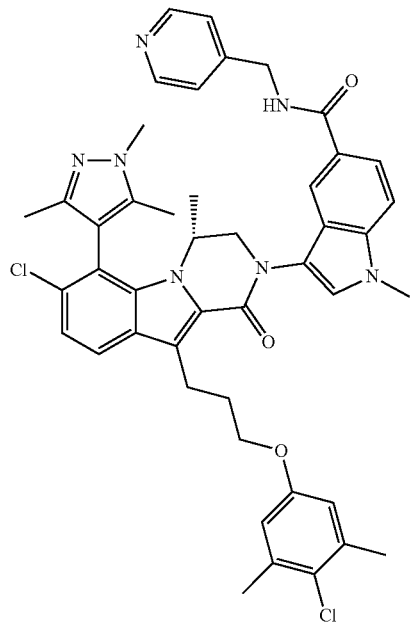 [SMILES: Cc1cc(OCCCc2c3n(c4c(-c5c(C)nn(C)c5C)c(Cl)ccc24)[C@H](C)CN(c2cn(C)c4ccc(C(=O)NCc5ccncc5)cc24)C3=O)cc(C)c1Cl]
I-284
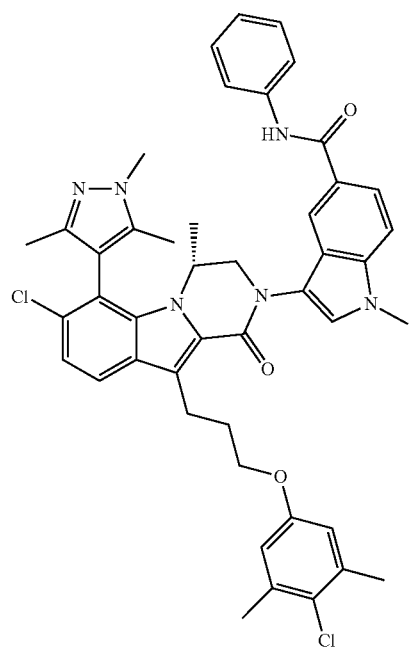 [SMILES: Cc1cc(OCCCc2c3n(c4c(-c5c(C)nn(C)c5C)c(Cl)ccc24)[C@H](C)CN(c2cn(C)c4ccc(C(=O)Nc5ccccc5)cc24)C3=O)cc(C)c1Cl]
I-285

TABLE 1-continued
Exemplary compounds.
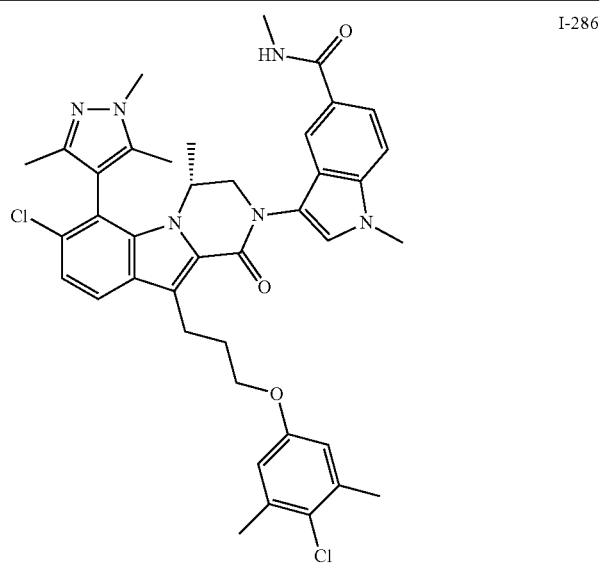
I-286
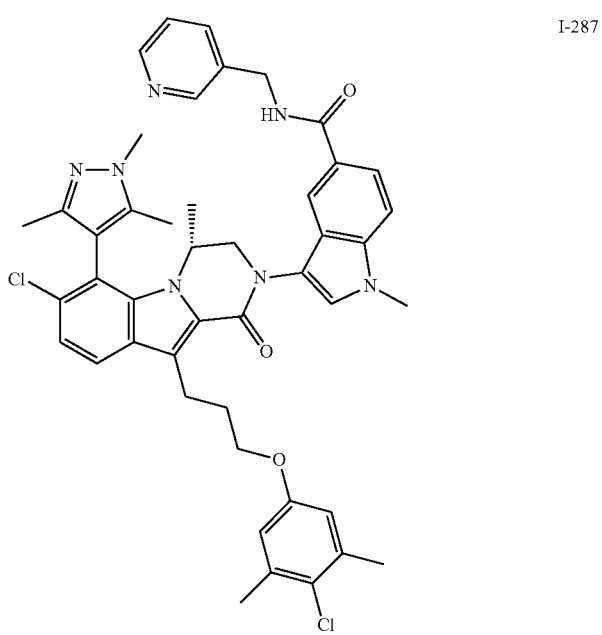
I-287

TABLE 1-continued
Exemplary compounds.
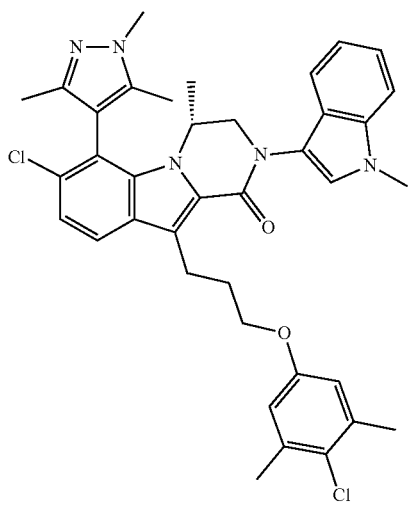
I-288
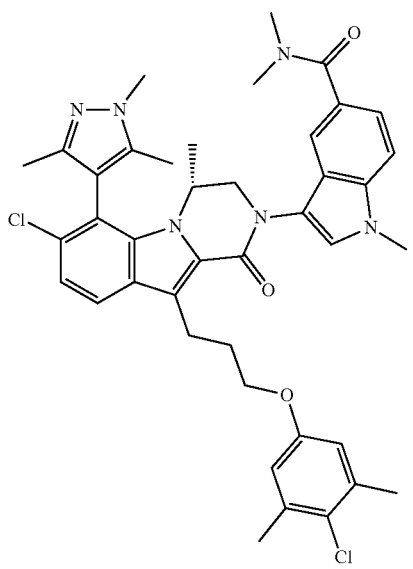 [SMILES: Cc1cc(OCCCc2c3n(c4c(-c5c(C)nn(C)c5C)c(Cl)ccc24)[C@H](C)CN(c2cn(C)c4ccc(C(=O)N(C)C)cc24)C3=O)cc(C)c1Cl]
I-289
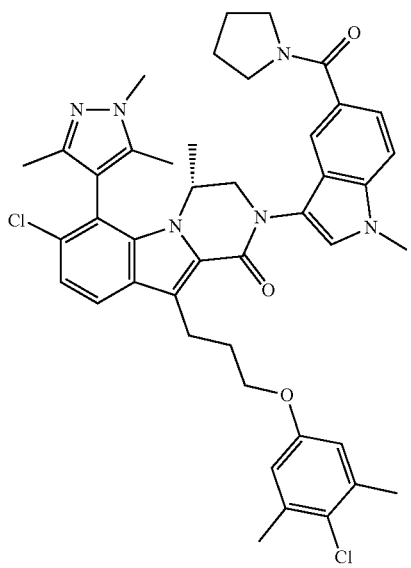 [SMILES: Cc1cc(OCCCc2c3n(c4c(-c5c(C)nn(C)c5C)c(Cl)ccc24)[C@H](C)CN(c2cn(C)c4ccc(C(=O)N5CCCC5)cc24)C3=O)cc(C)c1Cl]
I-290

TABLE 1-continued
Exemplary compounds.
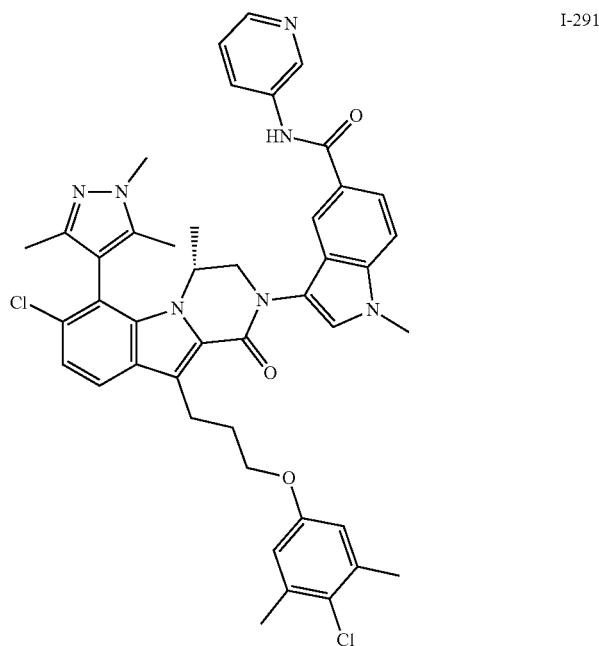
I-291
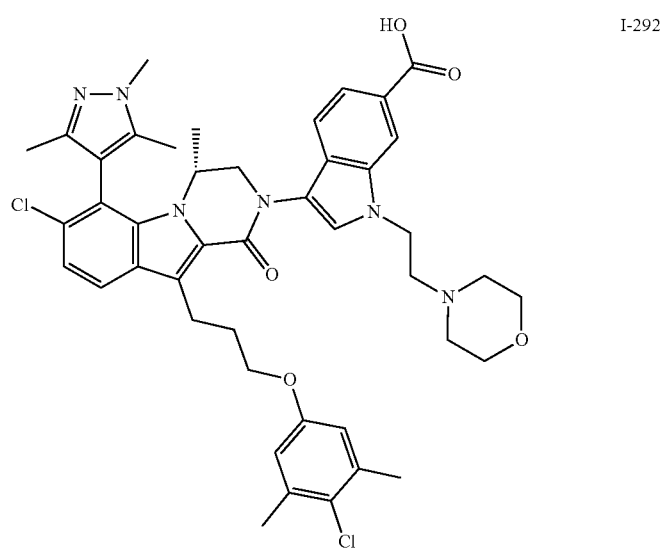
I-292

TABLE 1-continued
Exemplary compounds.
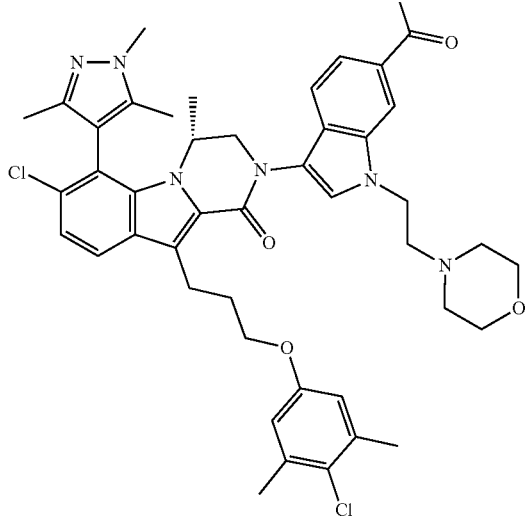
I-293
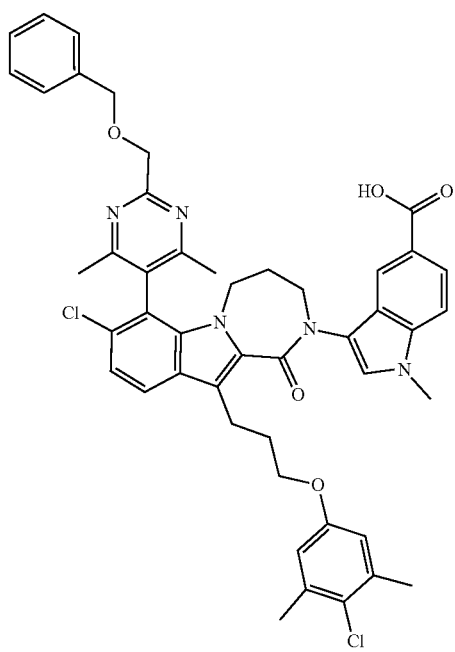 [SMILES: Cc1cc(OCCCc2c3n(c4c(-c5c(C)nc(COCc6ccccc6)nc5C)c(Cl)ccc24)CCCN(c2cn(C)c4ccc(C(=O)O)cc24)C3=O)cc(C)c1Cl]
I-294

TABLE 1-continued
Exemplary compounds.
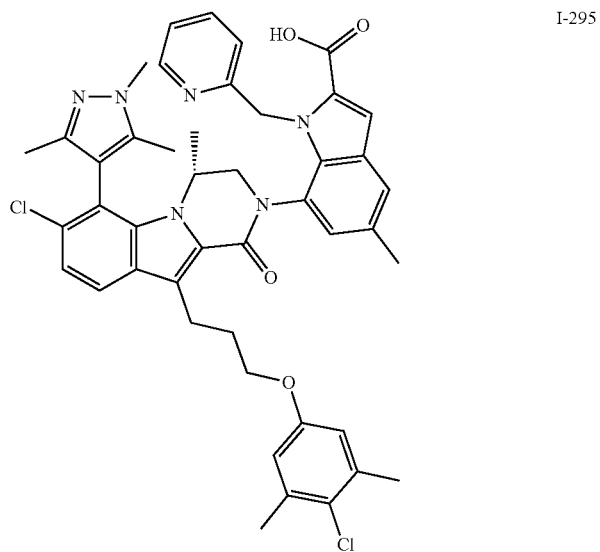
I-295
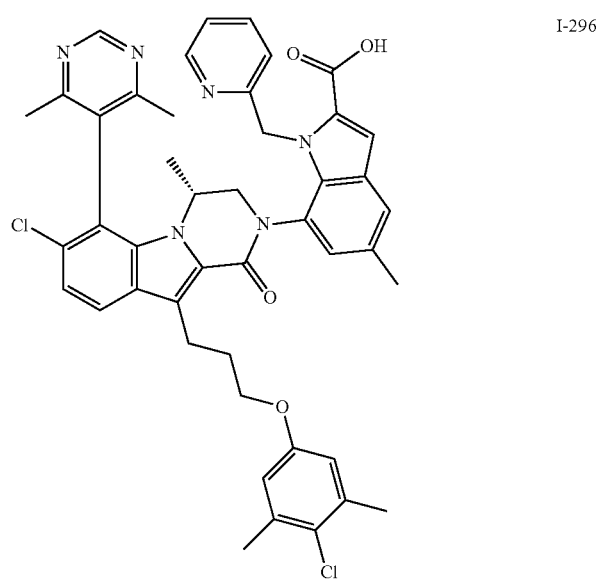
I-296

TABLE 1-continued
Exemplary compounds.
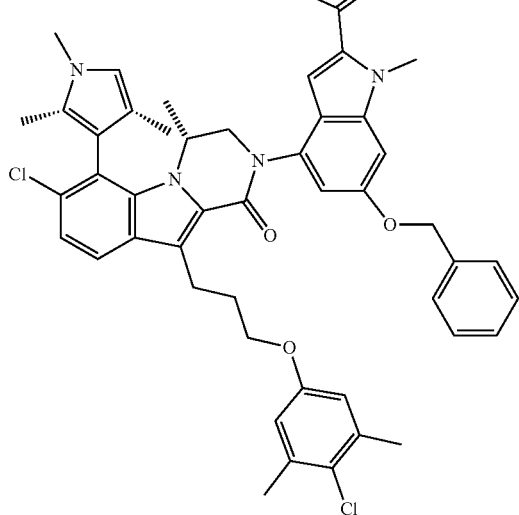
I-297
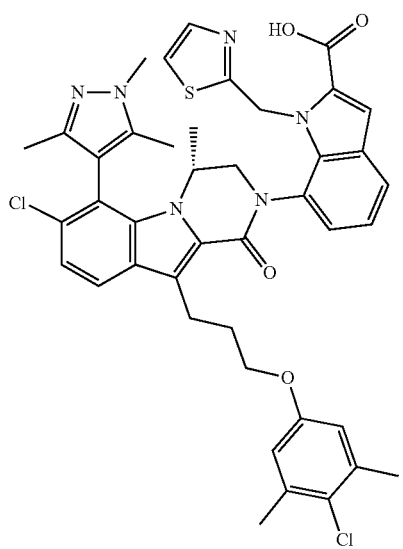 [SMILES: Cc1cc(OCCCc2c3n(c4c(-c5c(C)nn(C)c5C)c(Cl)ccc24)[C@H](C)CN(c2cccc4cc(C(=O)O)n(Cc5nccs5)c24)C3=O)cc(C)c1Cl]
I-298
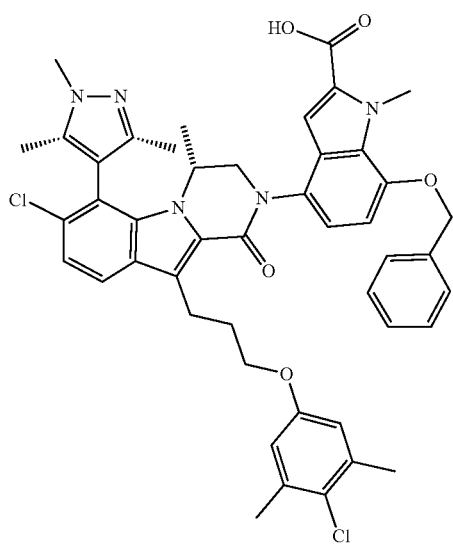
I-299

TABLE 1-continued
Exemplary compounds.
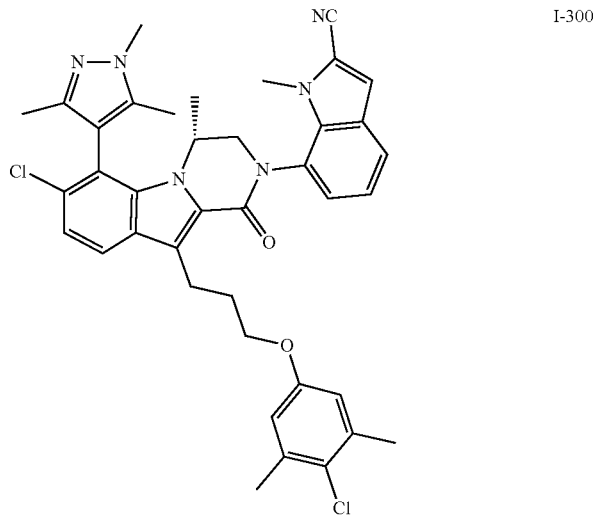
I-300
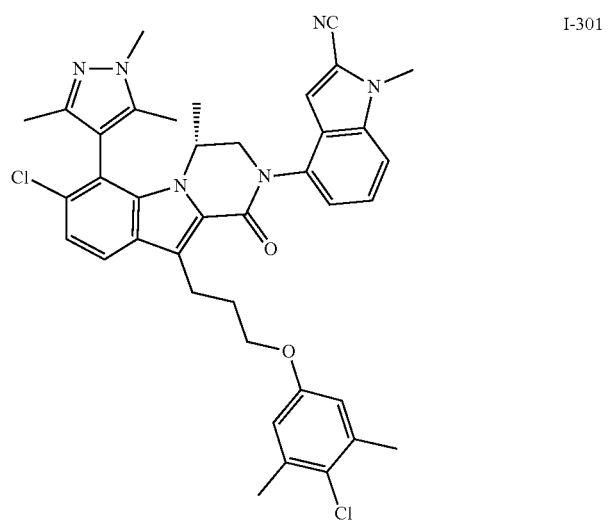
I-301
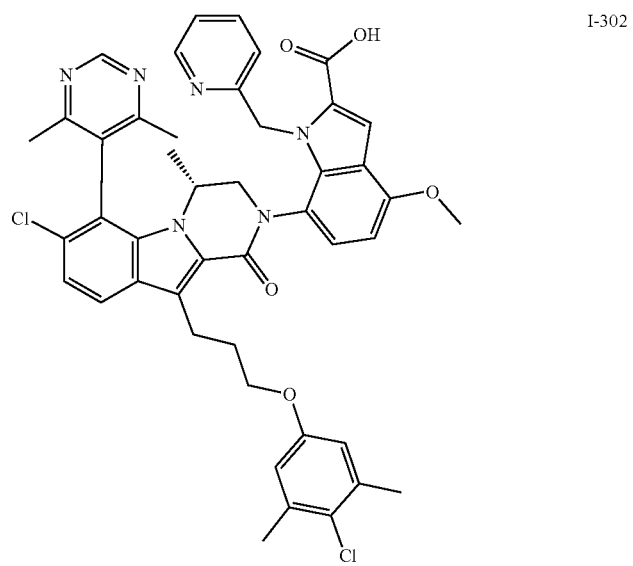
I-302

TABLE 1-continued
Exemplary compounds.
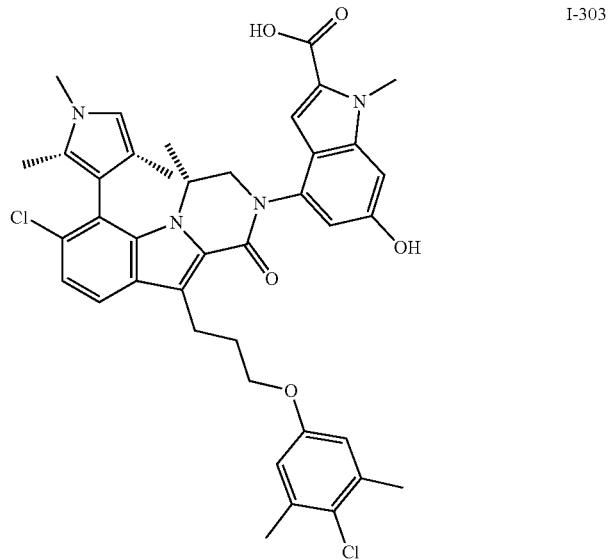
I-303
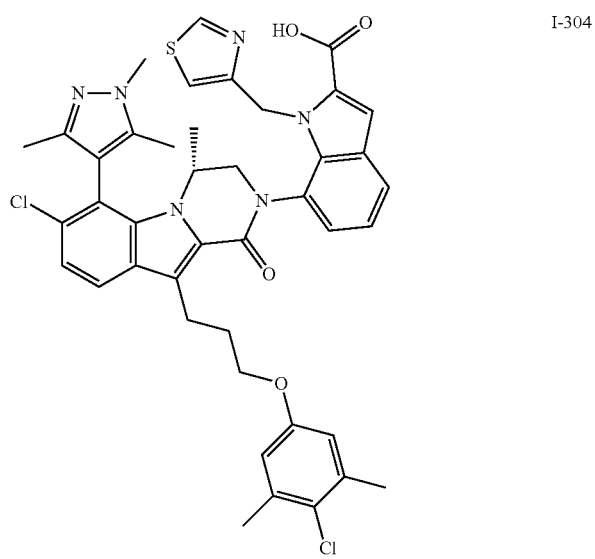
I-304

TABLE 1-continued
Exemplary compounds.
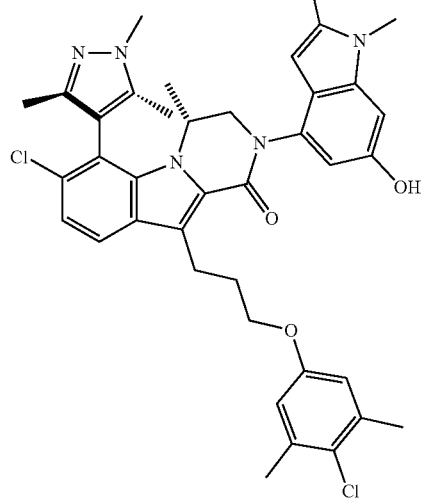
I-305
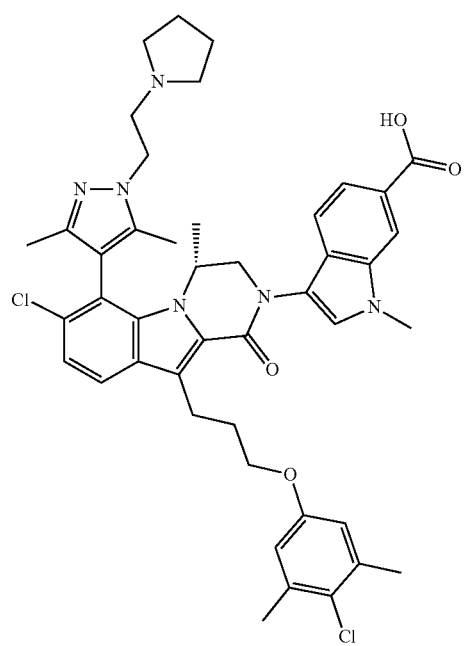 [SMILES: Cc1cc(OCCCc2c3n(c4c(-c5c(C)nn(CCN6CCCC6)c5C)c(Cl)ccc24)[C@H](C)CN(c2cn(C)c4cc(C(=O)O)ccc24)C3=O)cc(C)c1Cl]
I-306

TABLE 1-continued
Exemplary compounds.
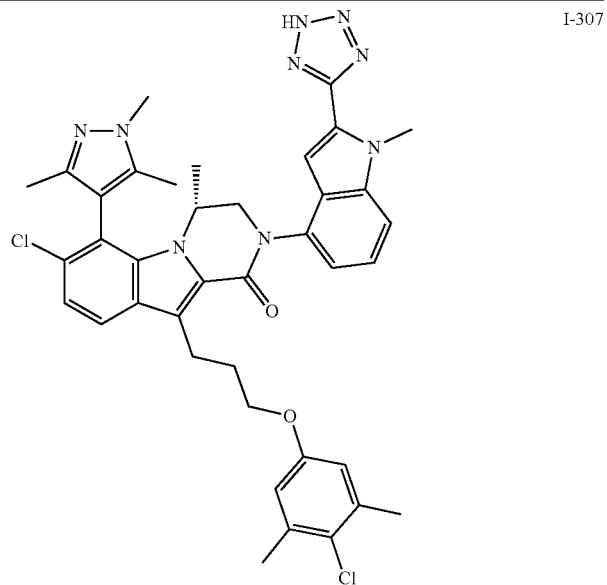
I-307
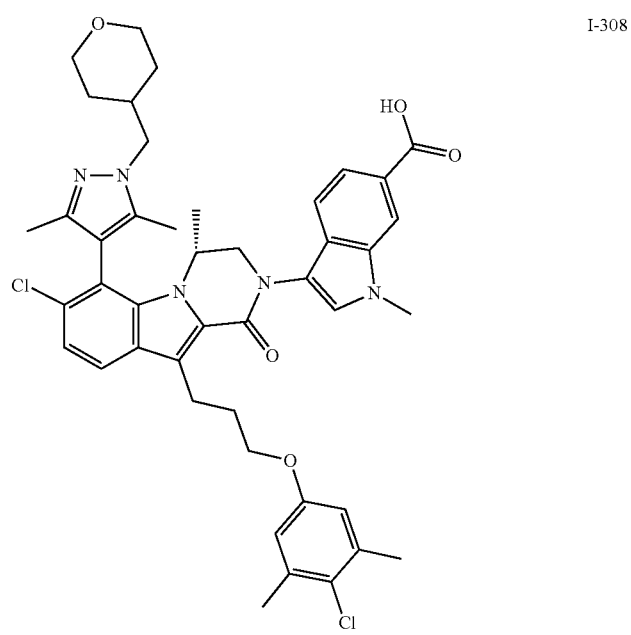
I-308

TABLE 1-continued
Exemplary compounds.
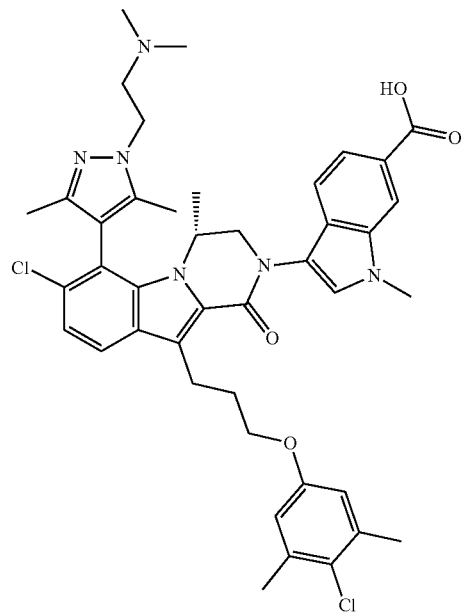 [SMILES: Cc1cc(OCCCc2c3n(c4c(-c5c(C)nn(CCN(C)C)c5C)c(Cl)ccc24)[C@H](C)CN(c2cn(C)c4cc(C(=O)O)ccc24)C3=O)cc(C)c1Cl]
I-309
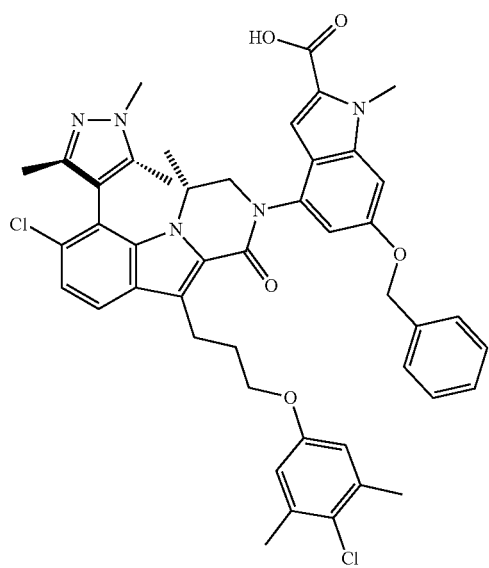
I-310

TABLE 1-continued
Exemplary compounds.
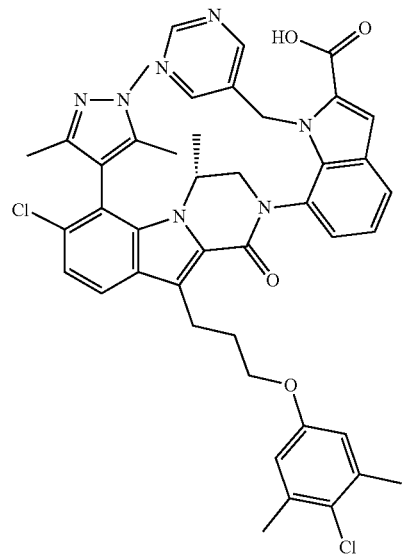 [SMILES: Cc1cc(OCCCc2c3n(c4c(-c5c(C)nn(C)c5C)c(Cl)ccc24)[C@H](C)CN(c2cccc4cc(C(=O)O)n(Cc5cncnc5)c24)C3=O)cc(C)c1Cl]
I-311
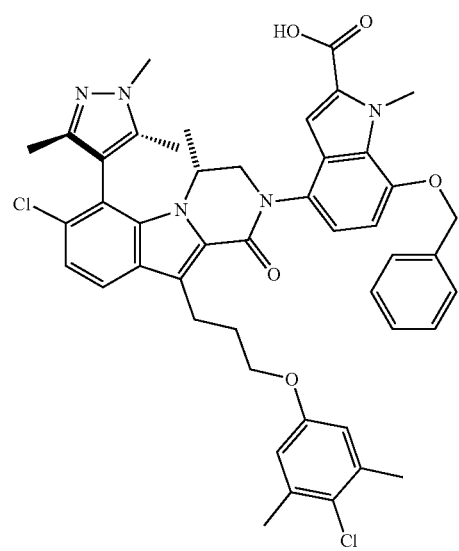
I-312

TABLE 1-continued
Exemplary compounds.
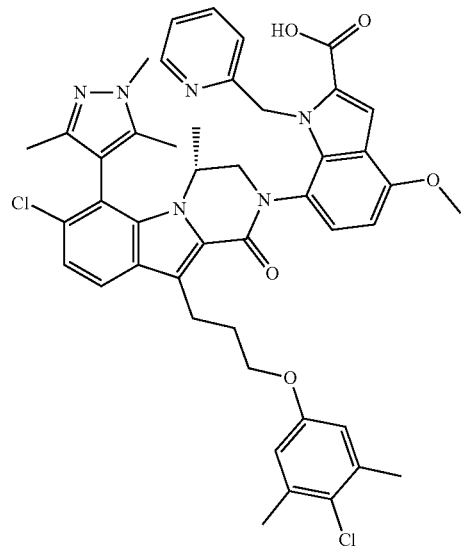 [SMILES: COc1ccc(N2C[C@@H](C)n3c(c(CCCOc4cc(C)c(Cl)c(C)c4)c4ccc(Cl)c(-c5c(C)nn(C)c5C)c43)C2=O)c2c1cc(C(=O)O)n2Cc1ccccn1]
I-313
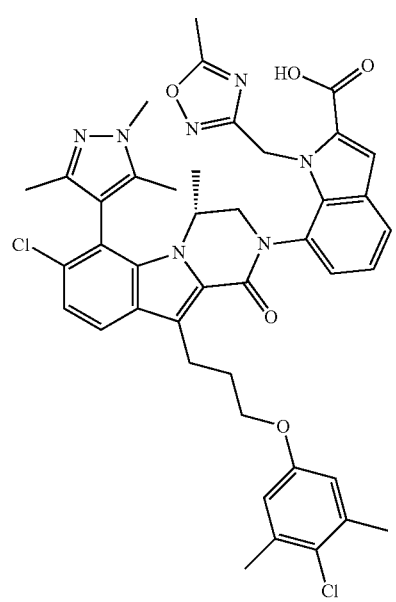 [SMILES: Cc1nc(Cn2c(C(=O)O)cc3cccc(N4C[C@@H](C)n5c(c(CCCOc6cc(C)c(Cl)c(C)c6)c6ccc(Cl)c(-c7c(C)nn(C)c7C)c65)C4=O)c32)no1]
I-314

TABLE 1-continued
Exemplary compounds.
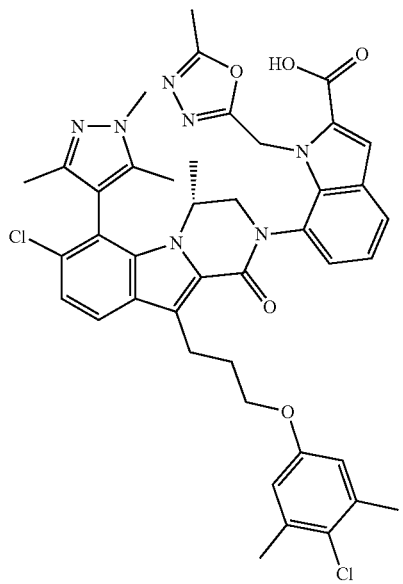 [SMILES: Cc1nnc(Cn2c(C(=O)O)cc3cccc(N4C[C@@H](C)n5c(c(CCCOc6cc(C)c(Cl)c(C)c6)c6ccc(Cl)c(-c7c(C)nn(C)c7C)c65)C4=O)c32)o1]
I-315
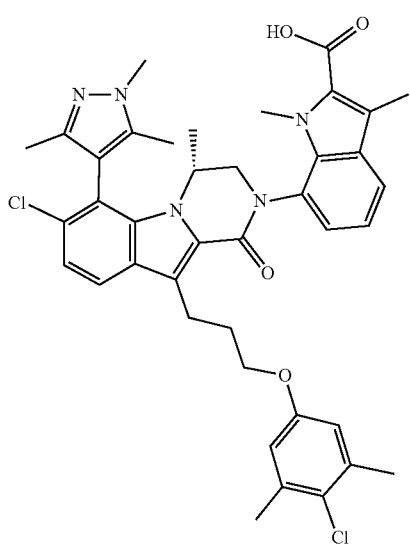 [SMILES: Cc1cc(OCCCc2c3n(c4c(-c5c(C)nn(C)c5C)c(Cl)ccc24)[C@H](C)CN(c2cccc4c(C)c(C(=O)O)n(C)c24)C3=O)cc(C)c1Cl]
I-316

TABLE 1-continued
Exemplary compounds.
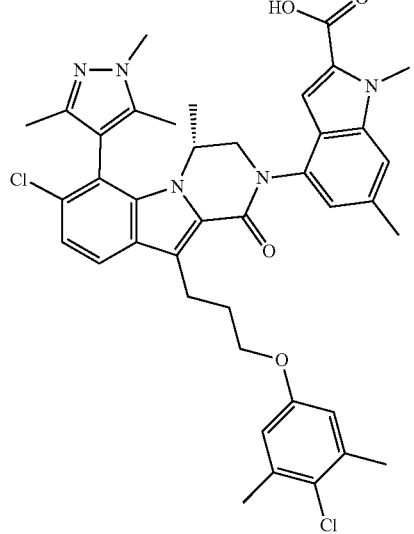
I-317
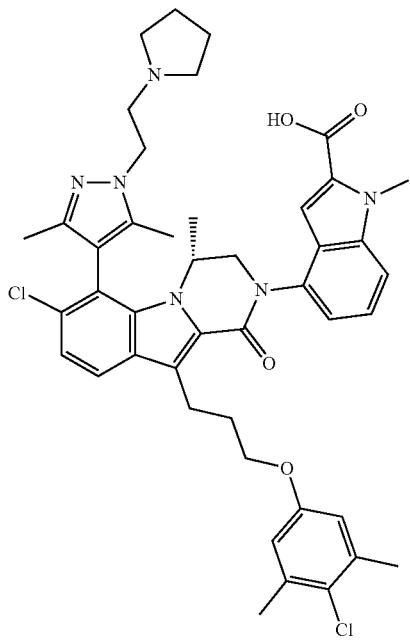 [SMILES: Cc1cc(OCCCc2c3n(c4c(-c5c(C)nn(CCN6CCCC6)c5C)c(Cl)ccc24)[C@H](C)CN(c2cccc4c2cc(C(=O)O)n4C)C3=O)cc(C)c1Cl]
I-318

TABLE 1-continued
Exemplary compounds.
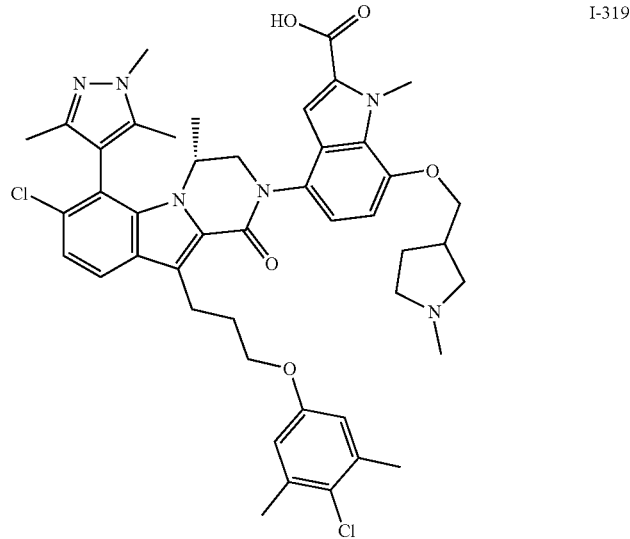
I-319
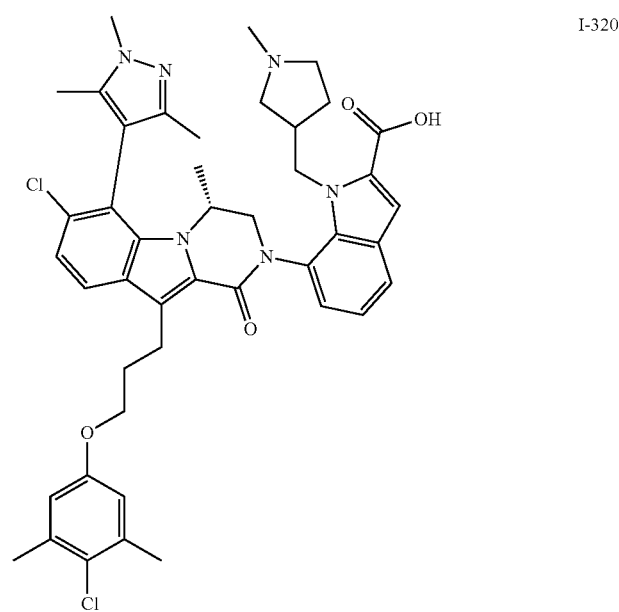
I-320

TABLE 1-continued

Exemplary compounds.

I-321

I-322

I-323

TABLE 1-continued
Exemplary compounds.
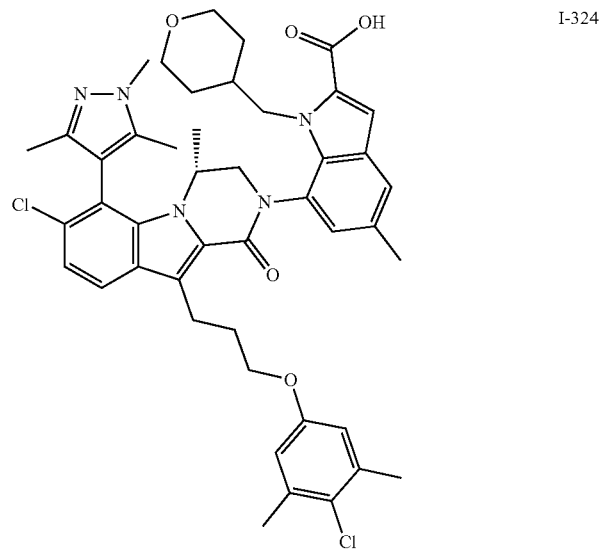
I-324
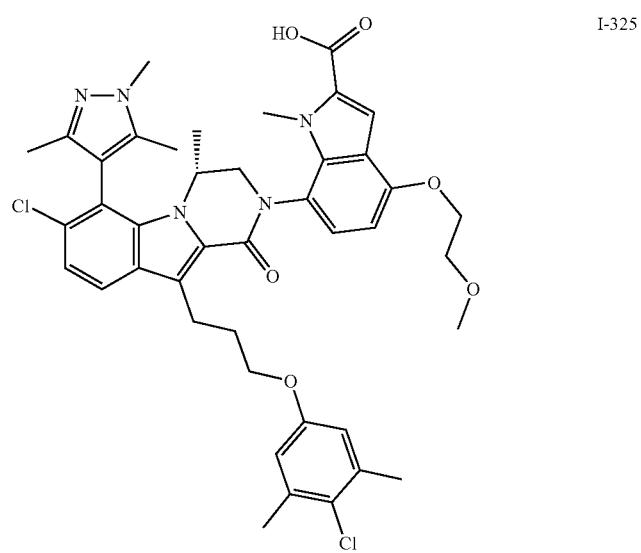
I-325

TABLE 1-continued

Exemplary compounds.

I-326

I-327

I-328

TABLE 1-continued
Exemplary compounds.
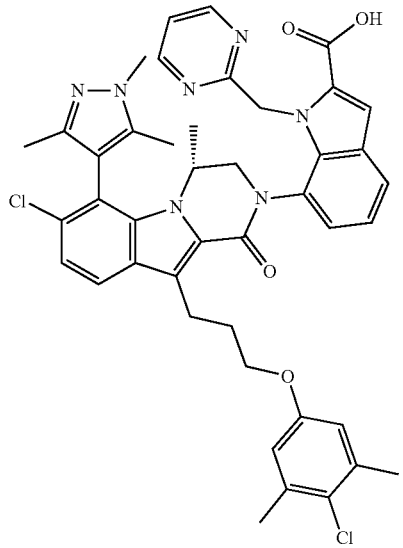 [SMILES: Cc1cc(OCCCc2c3n(c4c(-c5c(C)nn(C)c5C)c(Cl)ccc24)[C@H](C)CN(c2cccc4cc(C(=O)O)n(Cc5ncccn5)c24)C3=O)cc(C)c1Cl]
I-329
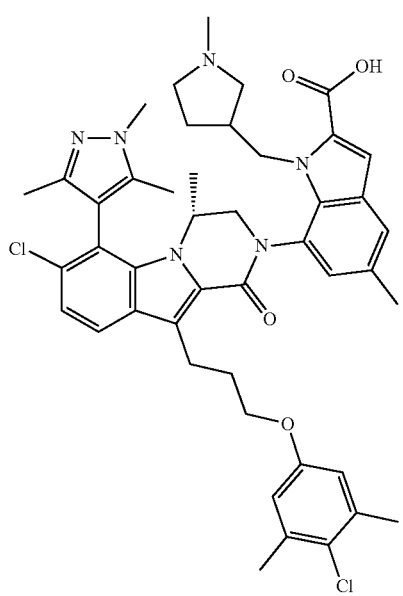 [SMILES: Cc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(=O)O)n2CC1CCN(C)C1]
I-330

TABLE 1-continued
Exemplary compounds.
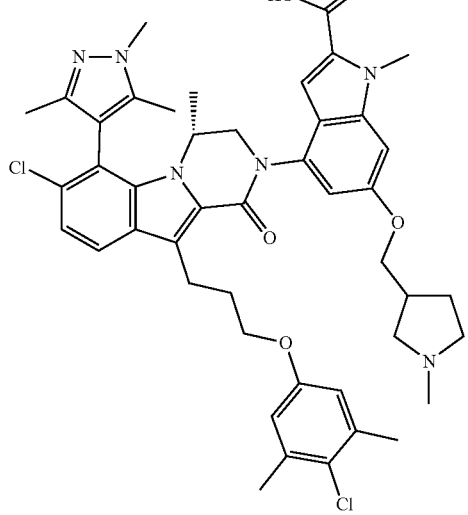
I-331
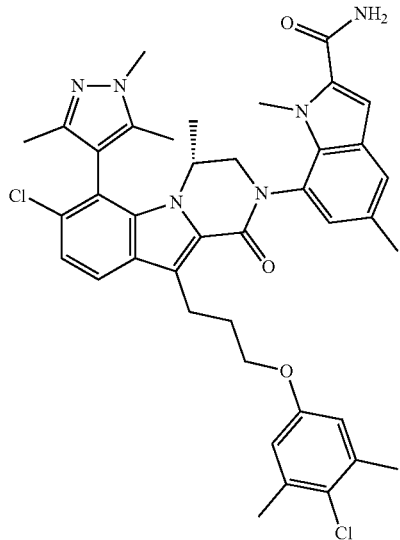 [SMILES: Cc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(N)=O)n2C]
I-332
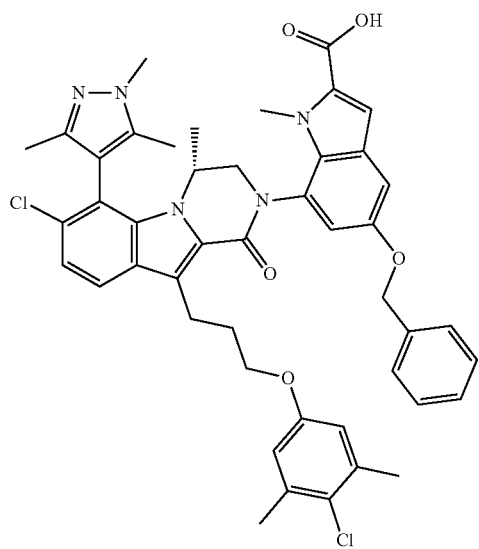 [SMILES: Cc1cc(OCCCc2c3n(c4c(-c5c(C)nn(C)c5C)c(Cl)ccc24)[C@H](C)CN(c2cc(OCc4ccccc4)cc4cc(C(=O)O)n(C)c24)C3=O)cc(C)c1Cl]
I-333

TABLE 1-continued
Exemplary compounds.
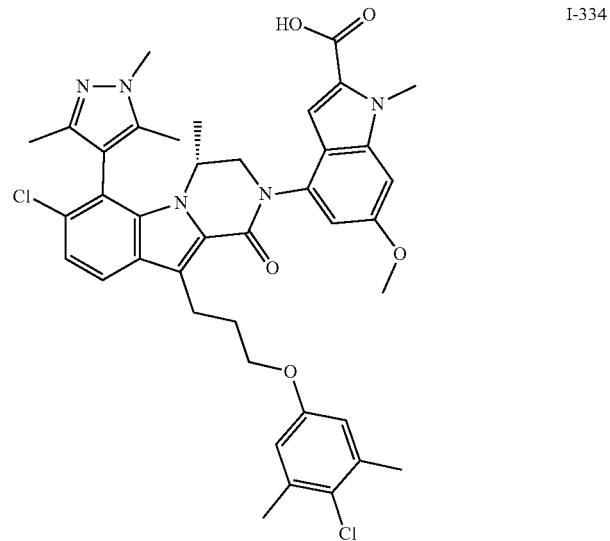
I-334
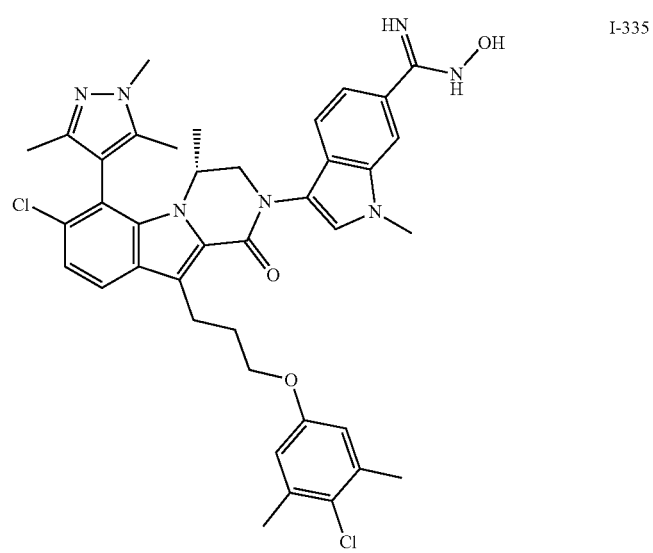
I-335

TABLE 1-continued
Exemplary compounds.
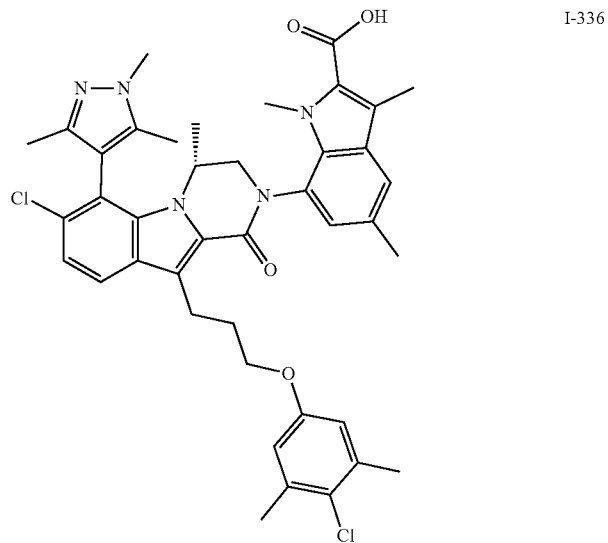
I-336
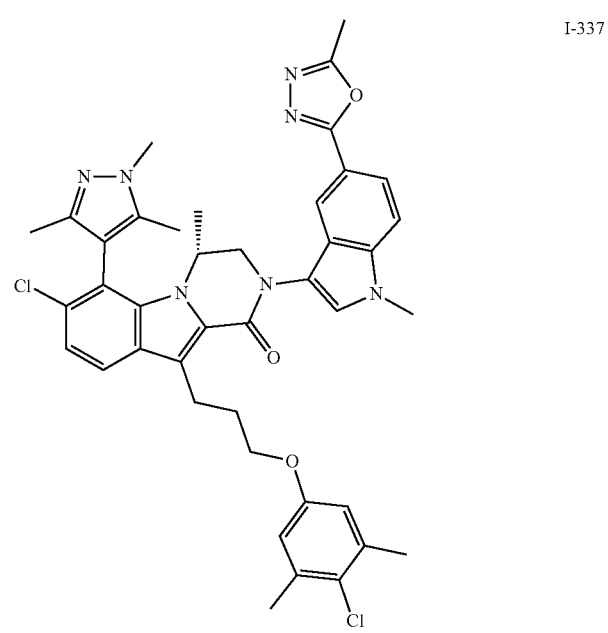
I-337

TABLE 1-continued
Exemplary compounds.
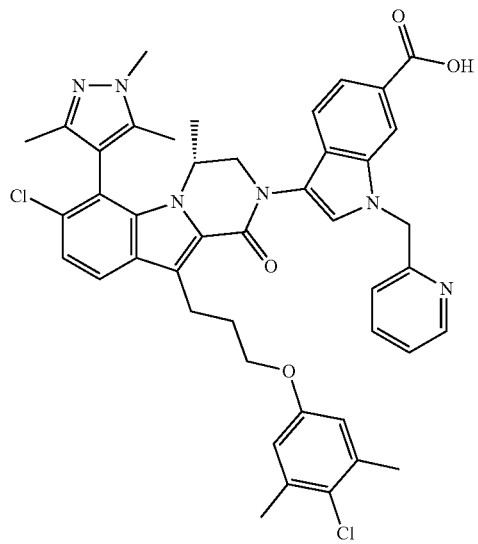 [SMILES: Cc1cc(OCCCc2c3n(c4c(-c5c(C)nn(C)c5C)c(Cl)ccc24)[C@H](C)CN(c2cn(Cc4ccccn4)c4cc(C(=O)O)ccc24)C3=O)cc(C)c1Cl]
I-338
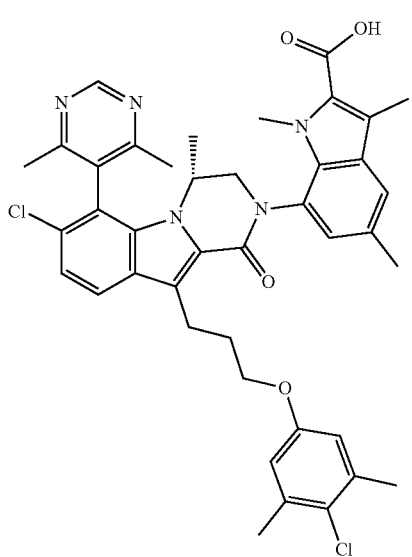 [SMILES: Cc1cc(N2C[C@@H](C)n3c(c(CCCOc4cc(C)c(Cl)c(C)c4)c4ccc(Cl)c(-c5c(C)ncnc5C)c43)C2=O)c2c(c1)c(C)c(C(=O)O)n2C]
I-339
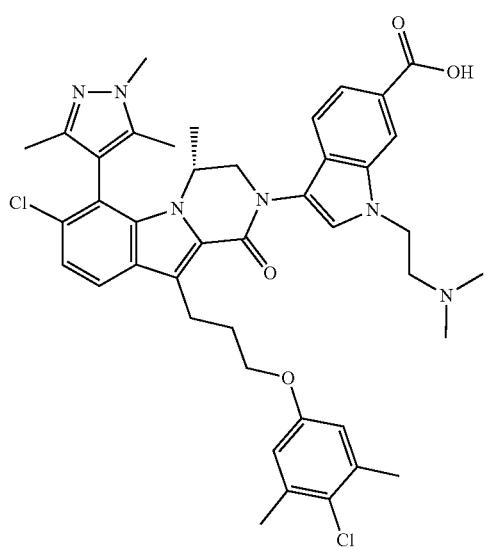 [SMILES: Cc1cc(OCCCc2c3n(c4c(-c5c(C)nn(C)c5C)c(Cl)ccc24)[C@H](C)CN(c2cn(CCN(C)C)c4cc(C(=O)O)ccc24)C3=O)cc(C)c1Cl]
I-340

TABLE 1-continued
Exemplary compounds.
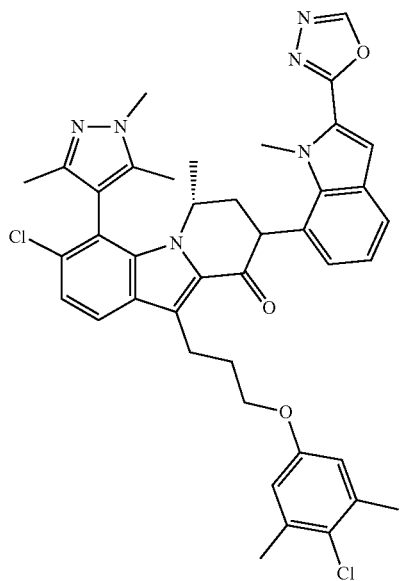 [SMILES: Cc1cc(OCCCc2c3n(c4c(-c5c(C)nn(C)c5C)c(Cl)ccc24)[C@H](C)CC(c2cccc4cc(-c5nnco5)n(C)c24)C3=O)cc(C)c1Cl]
I-341
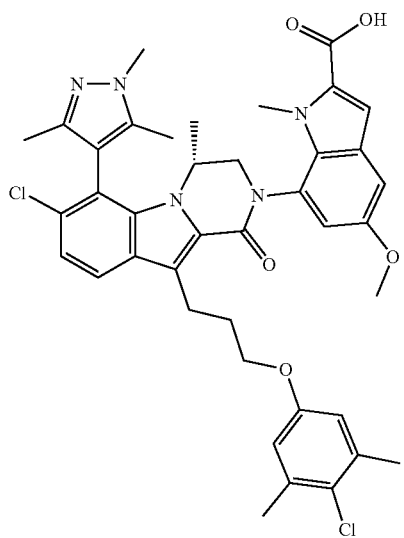 [SMILES: COc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(=O)O)n2C]
I-342

TABLE 1-continued
Exemplary compounds.
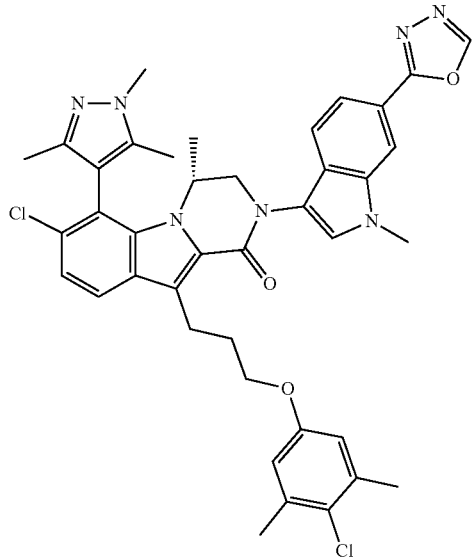 [SMILES: Cc1cc(OCCCc2c3n(c4c(-c5c(C)nn(C)c5C)c(Cl)ccc24)[C@H](C)CN(c2cn(C)c4cc(-c5nnco5)ccc24)C3=O)cc(C)c1Cl]
I-343
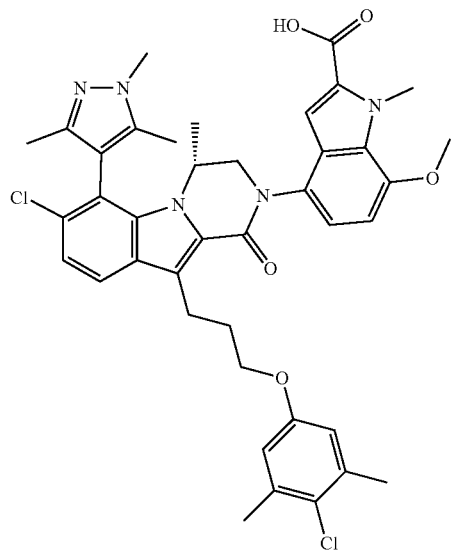 [SMILES: COc1ccc(N2C[C@@H](C)n3c(c(CCCOc4cc(C)c(Cl)c(C)c4)c4ccc(Cl)c(-c5c(C)nn(C)c5C)c43)C2=O)c2cc(C(=O)O)n(C)c12]
I-344

TABLE 1-continued
Exemplary compounds.
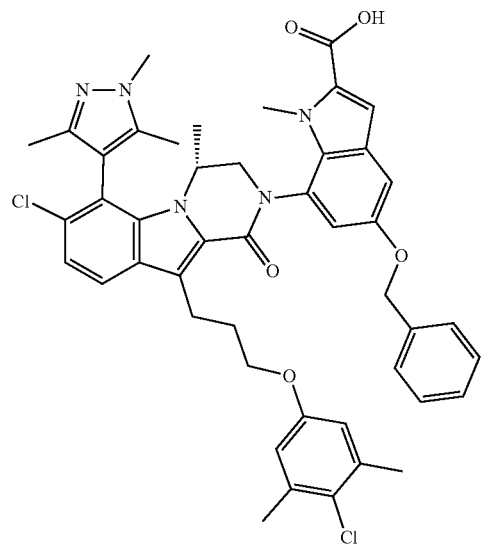 [SMILES: Cc1cc(OCCCc2c3n(c4c(-c5c(C)nn(C)c5C)c(Cl)ccc24)[C@H](C)CN(c2cc(OCc4ccccc4)cc4cc(C(=O)O)n(C)c24)C3=O)cc(C)c1Cl]
I-345
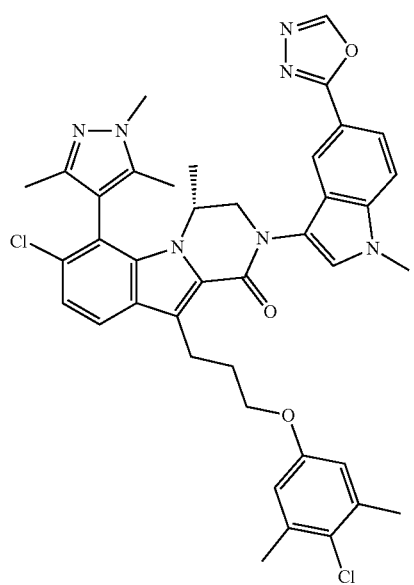 [SMILES: Cc1cc(OCCCc2c3n(c4c(-c5c(C)nn(C)c5C)c(Cl)ccc24)[C@H](C)CN(c2cn(C)c4ccc(-c5nnco5)cc24)C3=O)cc(C)c1Cl]
I-346

TABLE 1-continued
Exemplary compounds.
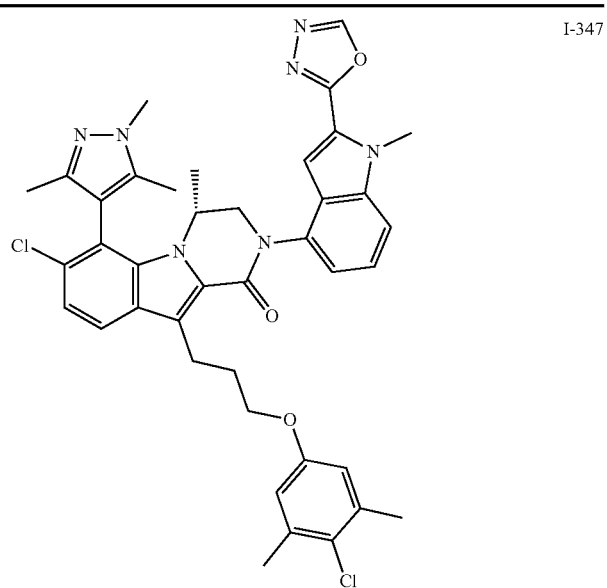
I-347
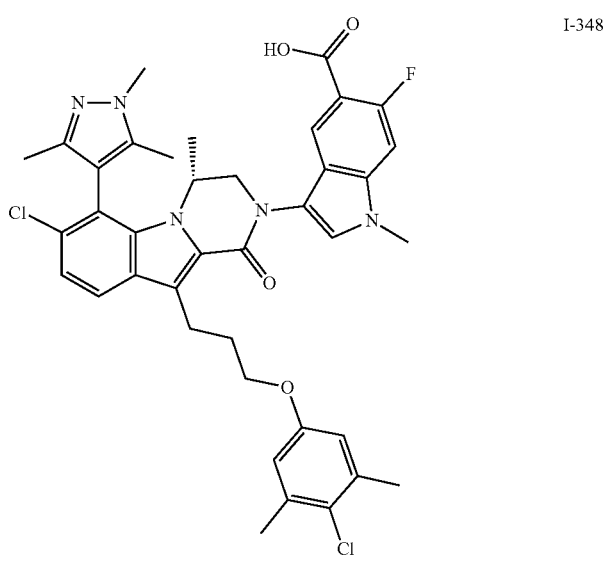
I-348

TABLE 1-continued
Exemplary compounds.
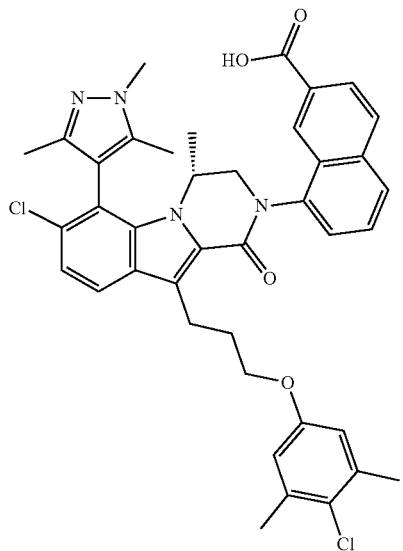 [SMILES: Cc1cc(OCCCc2c3n(c4c(-c5c(C)nn(C)c5C)c(Cl)ccc24)[C@H](C)CN(c2cccc4ccc(C(=O)O)cc24)C3=O)cc(C)c1Cl]
I-349
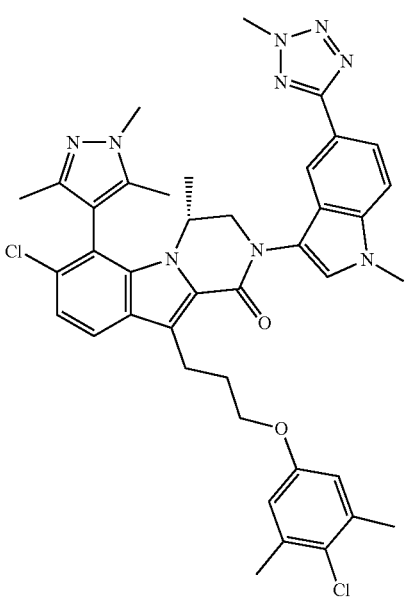 [SMILES: Cc1cc(OCCCc2c3n(c4c(-c5c(C)nn(C)c5C)c(Cl)ccc24)[C@H](C)CN(c2cn(C)c4ccc(-c5nnn(C)n5)cc24)C3=O)cc(C)c1Cl]
I-350

TABLE 1-continued

Exemplary compounds.

I-351

I-352

I-353

TABLE 1-continued
Exemplary compounds.
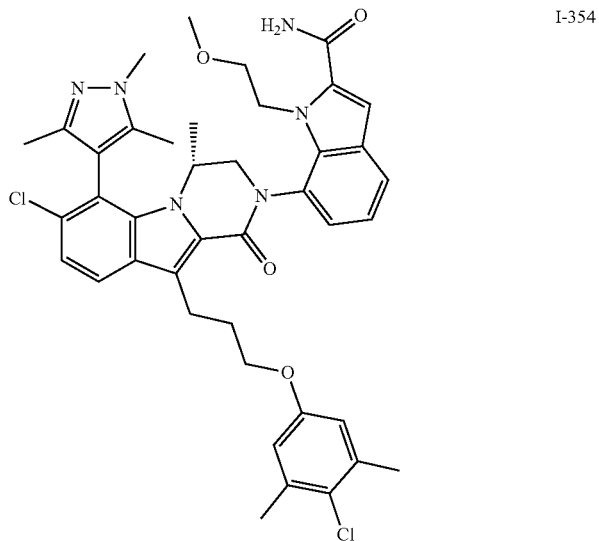
I-354
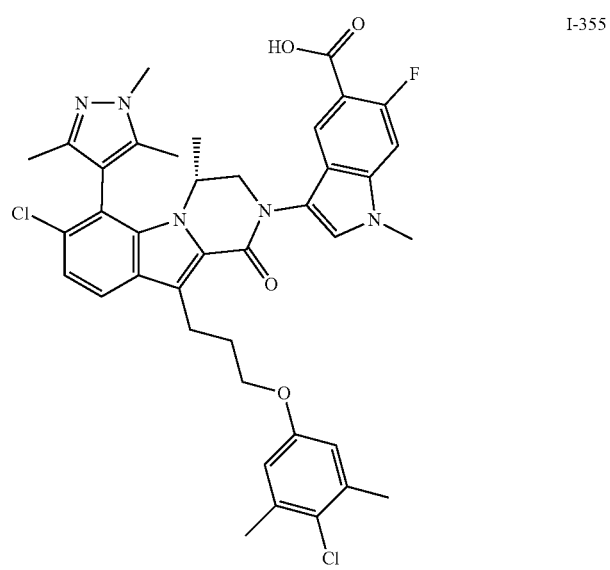
I-355

TABLE 1-continued
Exemplary compounds.
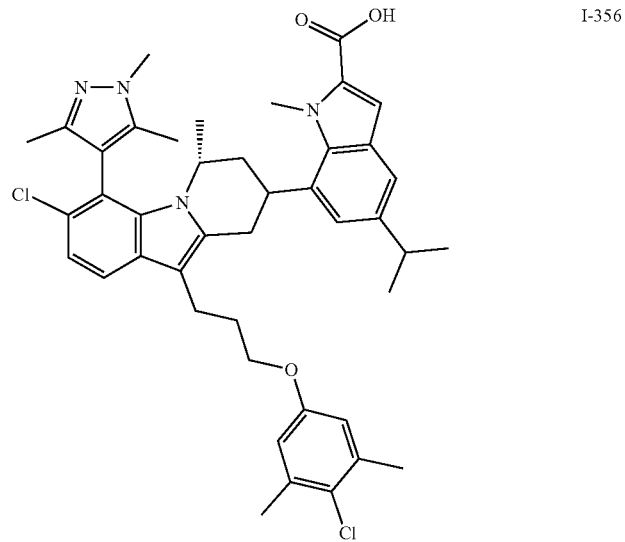
I-356
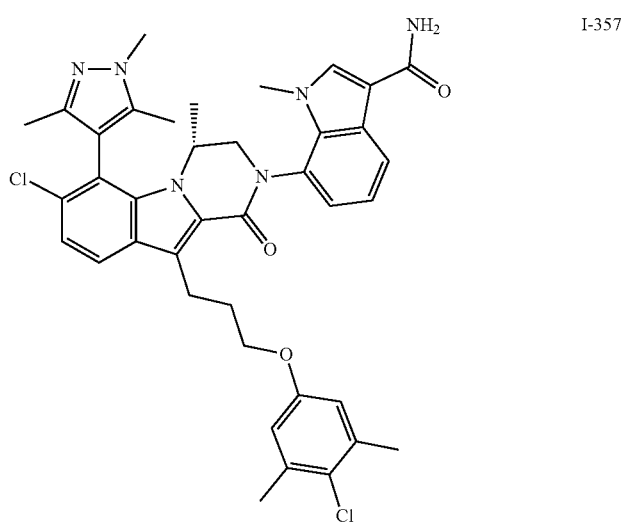
I-357

TABLE 1-continued
Exemplary compounds.
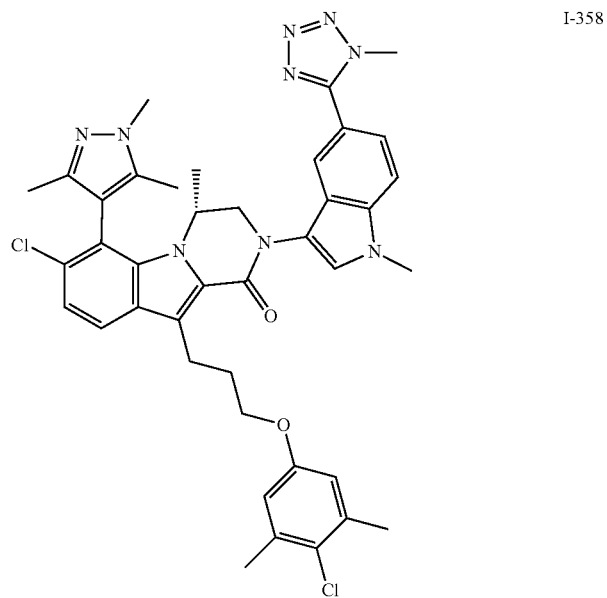
I-358
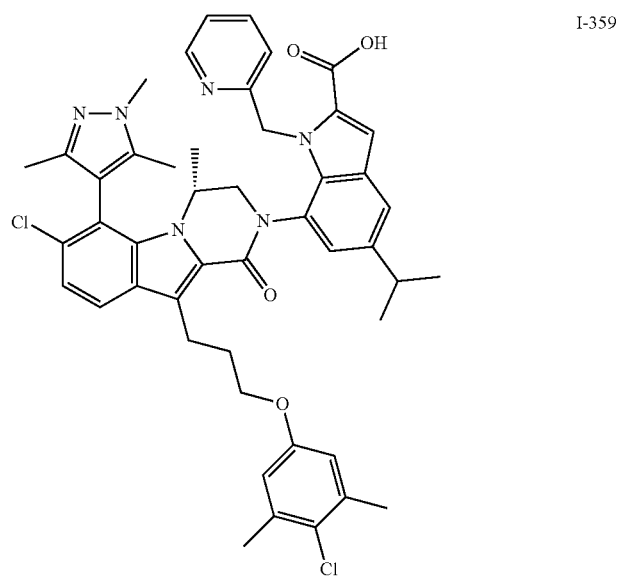
I-359

TABLE 1-continued
Exemplary compounds.
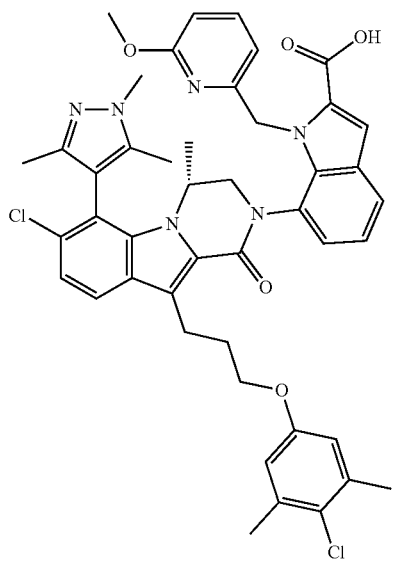
I-360
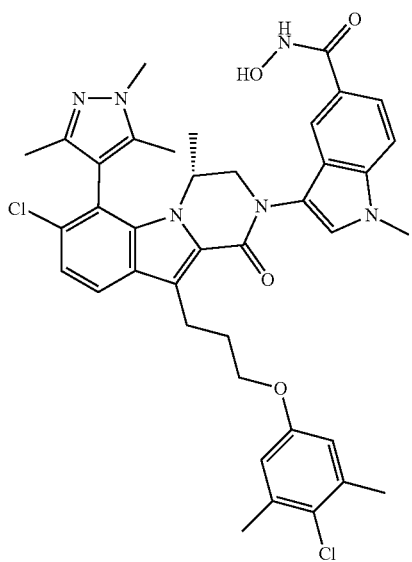 [SMILES: Cc1cc(OCCCc2c3n(c4c(-c5c(C)nn(C)c5C)c(Cl)ccc24)[C@H](C)CN(c2cn(C)c4ccc(C(=O)NO)cc24)C3=O)cc(C)c1Cl]
I-361
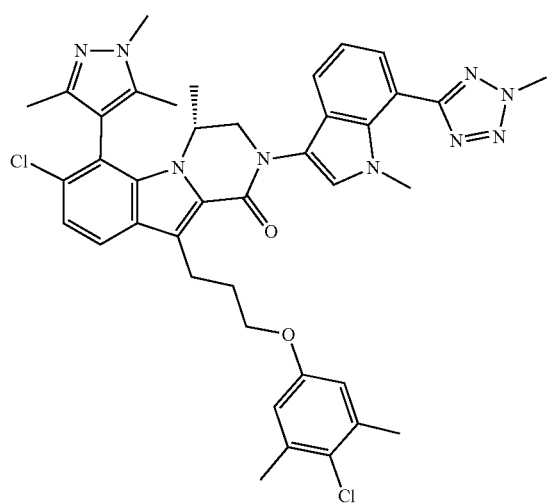 [SMILES: Cc1cc(OCCCc2c3n(c4c(-c5c(C)nn(C)c5C)c(Cl)ccc24)[C@H](C)CN(c2cn(C)c4c(-c5nnn(C)n5)cccc24)C3=O)cc(C)c1Cl]
I-362

TABLE 1-continued
Exemplary compounds.
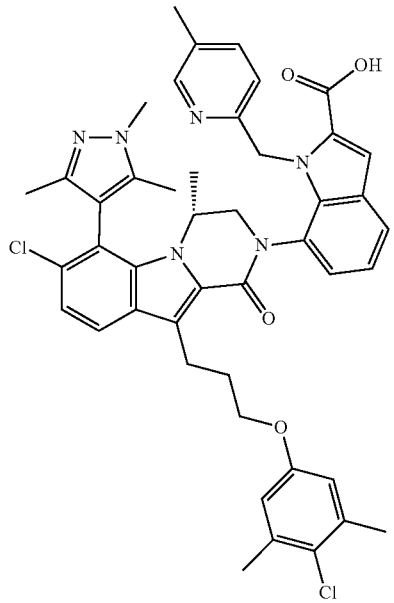 [SMILES: Cc1ccc(Cn2c(C(=O)O)cc3cccc(N4C[C@@H](C)n5c(c(CCCOc6cc(C)c(Cl)c(C)c6)c6ccc(Cl)c(-c7c(C)nn(C)c7C)c65)C4=O)c32)nc1]
I-363
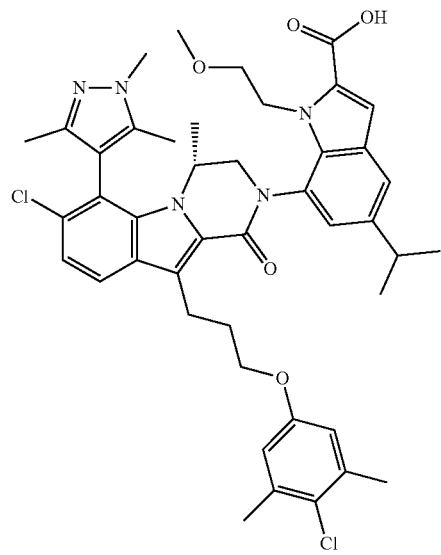 [SMILES: COCCn1c(C(=O)O)cc2cc(C(C)C)cc(N3C[C@@H](C)n4c(c(CCCOc5cc(C)c(Cl)c(C)c5)c5ccc(Cl)c(-c6c(C)nn(C)c6C)c54)C3=O)c21]
I-364

TABLE 1-continued
Exemplary compounds.
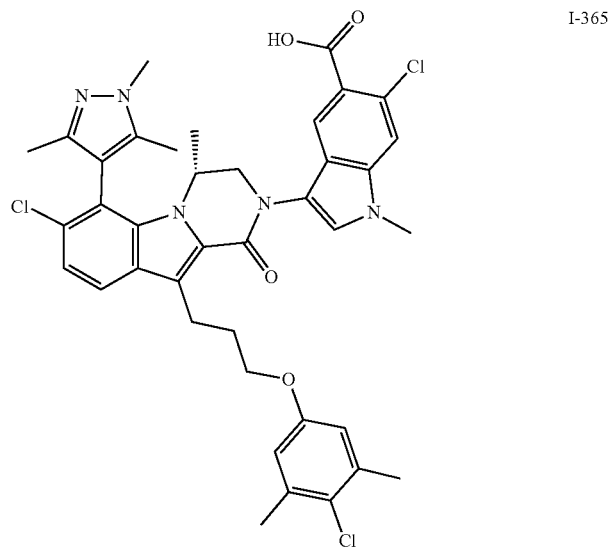
I-365
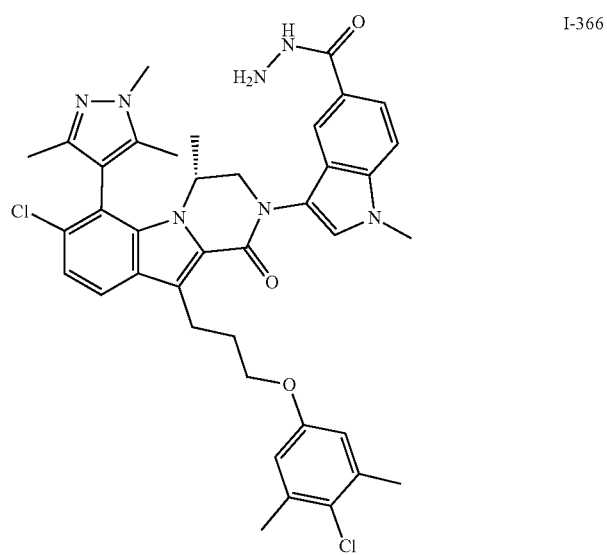
I-366

TABLE 1-continued
Exemplary compounds.
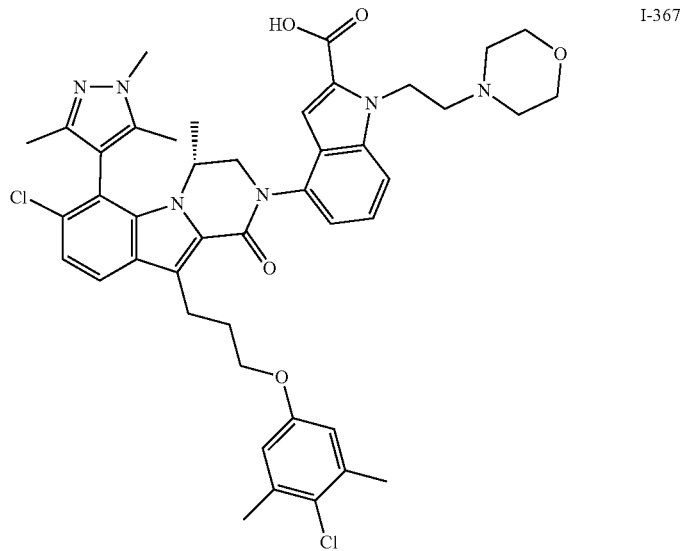
I-367
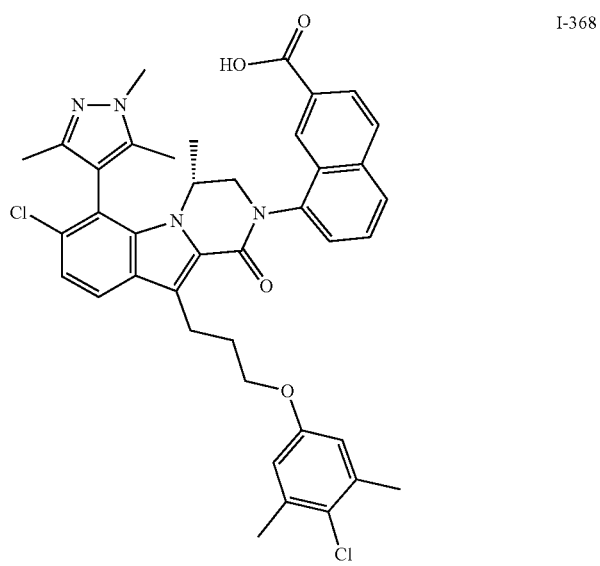
I-368

TABLE 1-continued
Exemplary compounds.
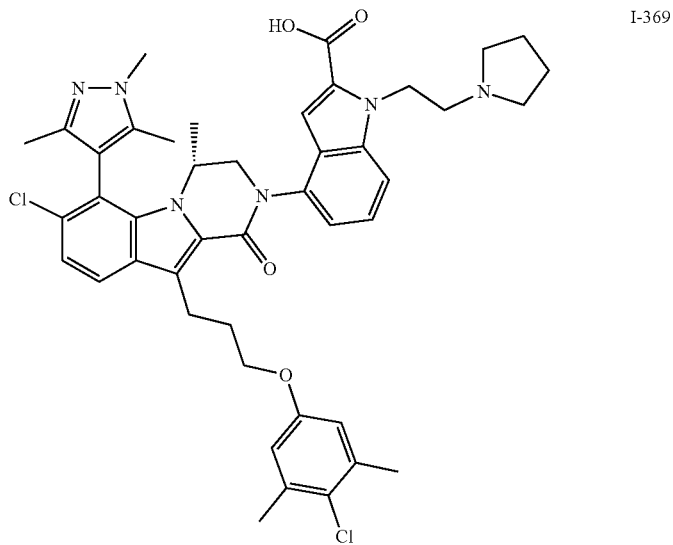
I-369
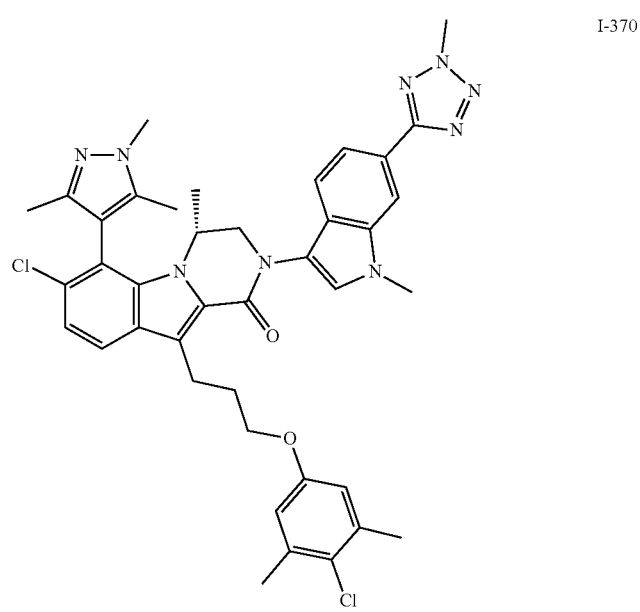
I-370

TABLE 1-continued
Exemplary compounds.
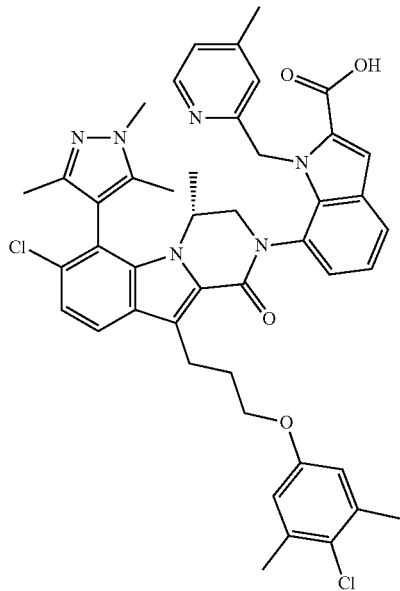 [SMILES: Cc1ccnc(Cn2c(C(=O)O)cc3cccc(N4C[C@@H](C)n5c(c(CCCOc6cc(C)c(Cl)c(C)c6)c6ccc(Cl)c(-c7c(C)nn(C)c7C)c65)C4=O)c32)c1]
I-371
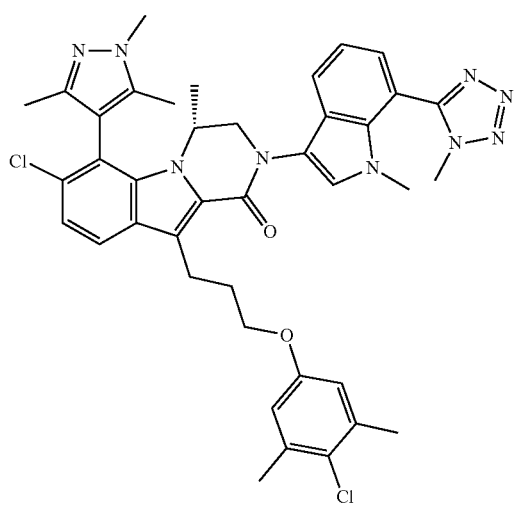 [SMILES: Cc1cc(OCCCc2c3n(c4c(-c5c(C)nn(C)c5C)c(Cl)ccc24)[C@H](C)CN(c2cn(C)c4c(-c5nnnn5C)cccc24)C3=O)cc(C)c1Cl]
I-372

TABLE 1-continued
Exemplary compounds.
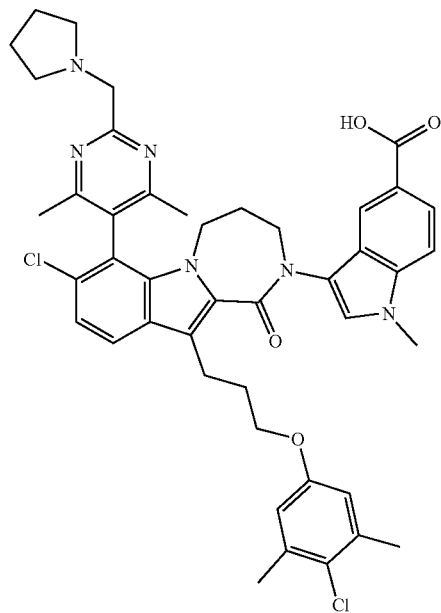 [SMILES: Cc1cc(OCCCc2c3n(c4c(-c5c(C)nc(CN6CCCC6)nc5C)c(Cl)ccc24)CCCN(c2cn(C)c4ccc(C(=O)O)cc24)C3=O)cc(C)c1Cl]
I-373
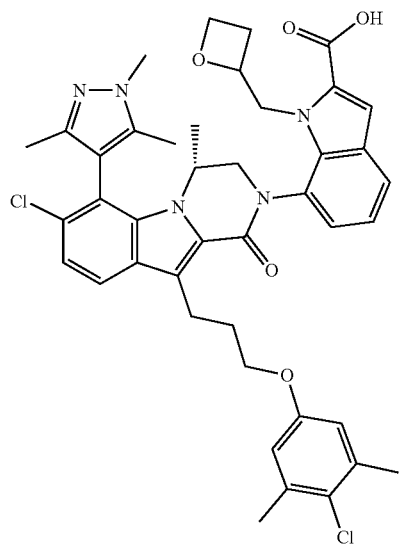 [SMILES: Cc1cc(OCCCc2c3n(c4c(-c5c(C)nn(C)c5C)c(Cl)ccc24)[C@H](C)CN(c2cccc4cc(C(=O)O)n(CC5CCO5)c24)C3=O)cc(C)c1Cl]
I-374

TABLE 1-continued
Exemplary compounds.
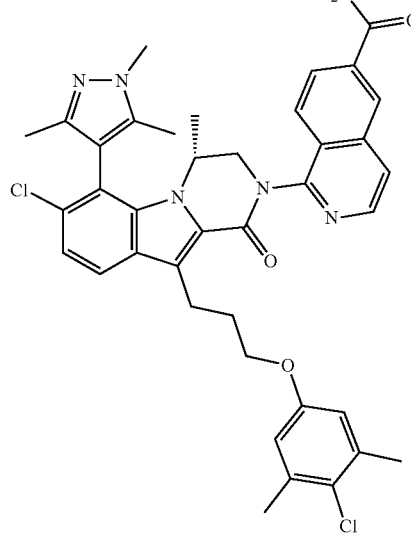
I-375
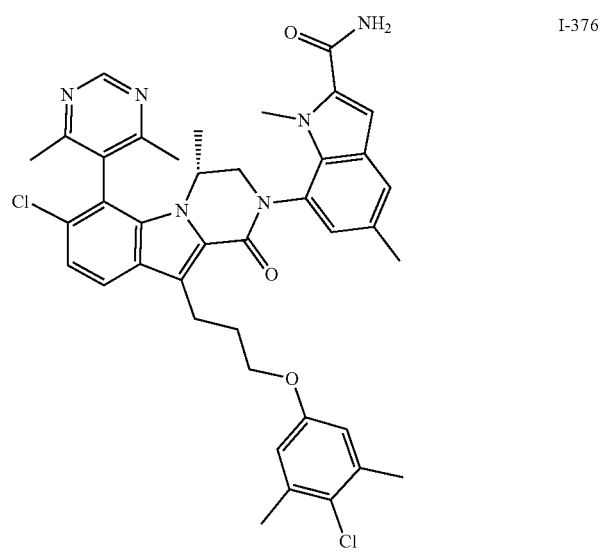
I-376

TABLE 1-continued
Exemplary compounds.
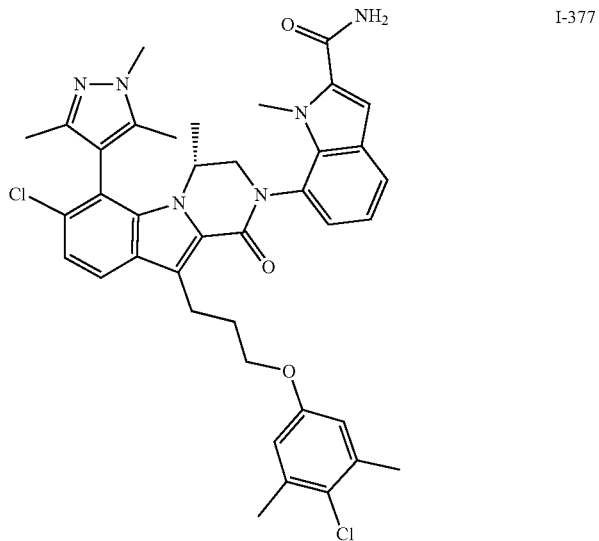
I-377
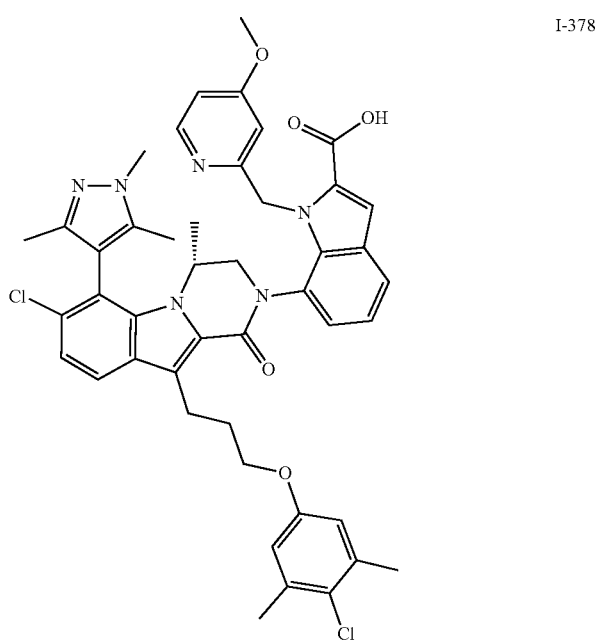
I-378

TABLE 1-continued
Exemplary compounds.
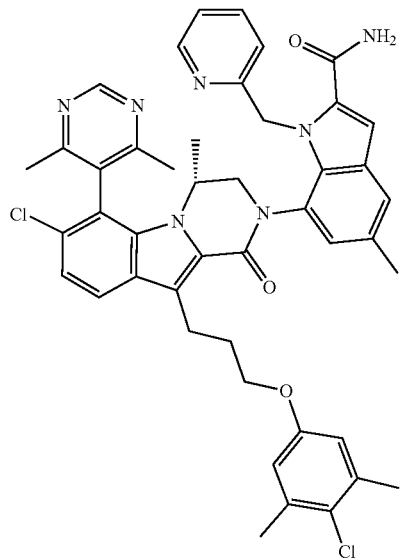 [SMILES: Cc1cc(N2C[C@@H](C)n3c(c(CCCOc4cc(C)c(Cl)c(C)c4)c4ccc(Cl)c(-c5c(C)ncnc5C)c43)C2=O)c2c(c1)cc(C(N)=O)n2Cc1ccccn1]
I-379
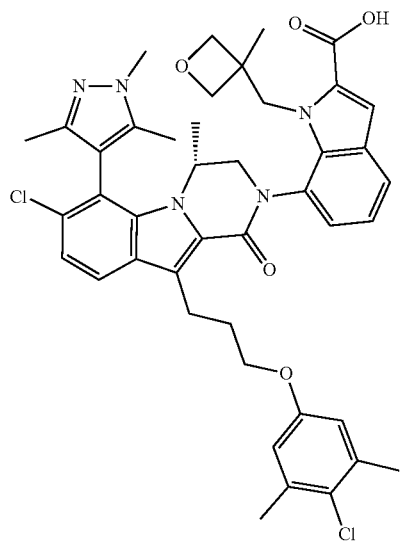 [SMILES: Cc1cc(OCCCc2c3n(c4c(-c5c(C)nn(C)c5C)c(Cl)ccc24)[C@H](C)CN(c2cccc4cc(C(=O)O)n(CC5(C)COC5)c24)C3=O)cc(C)c1Cl]
I-380

TABLE 1-continued
Exemplary compounds.
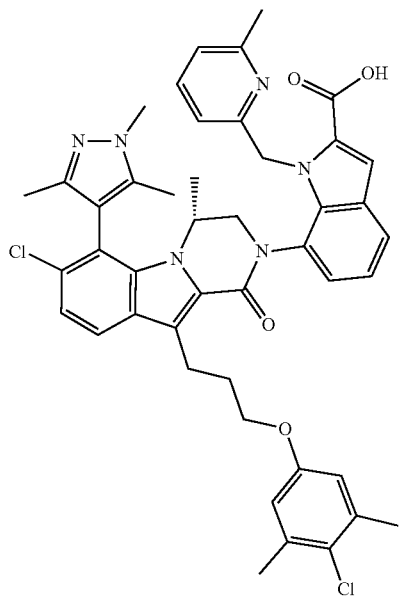 [SMILES: Cc1cccc(Cn2c(C(=O)O)cc3cccc(N4C[C@@H](C)n5c(c(CCCOc6cc(C)c(Cl)c(C)c6)c6ccc(Cl)c(-c7c(C)nn(C)c7C)c65)C4=O)c32)n1]
I-381
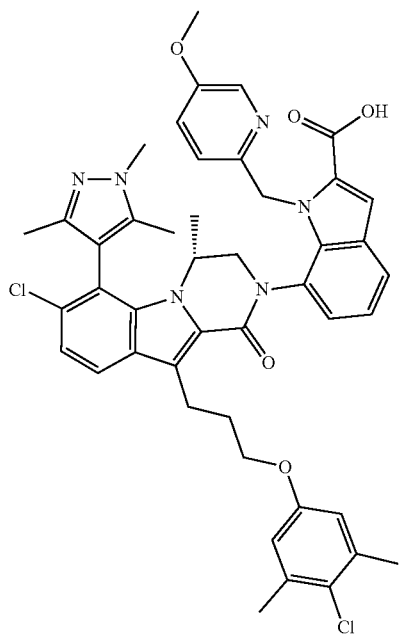 [SMILES: COc1ccc(Cn2c(C(=O)O)cc3cccc(N4C[C@@H](C)n5c(c(CCCOc6cc(C)c(Cl)c(C)c6)c6ccc(Cl)c(-c7c(C)nn(C)c7C)c65)C4=O)c32)nc1]
I-382

TABLE 1-continued
Exemplary compounds.
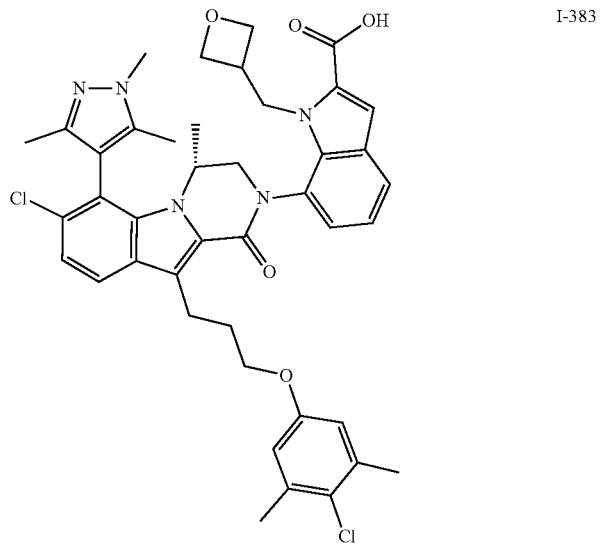
I-383
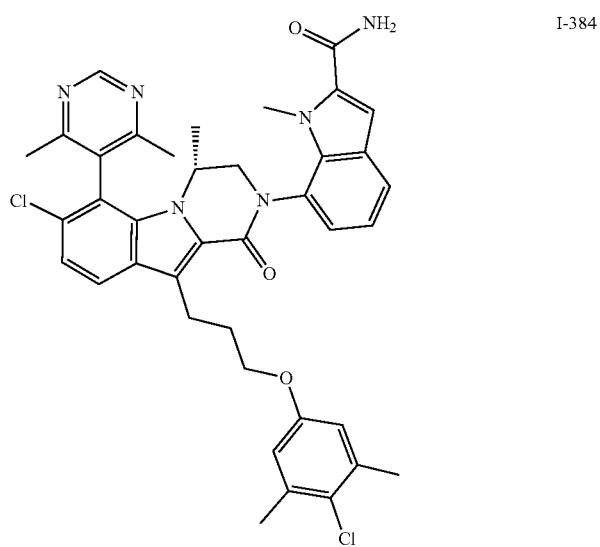
I-384

331
TABLE 1-continued
Exemplary compounds.
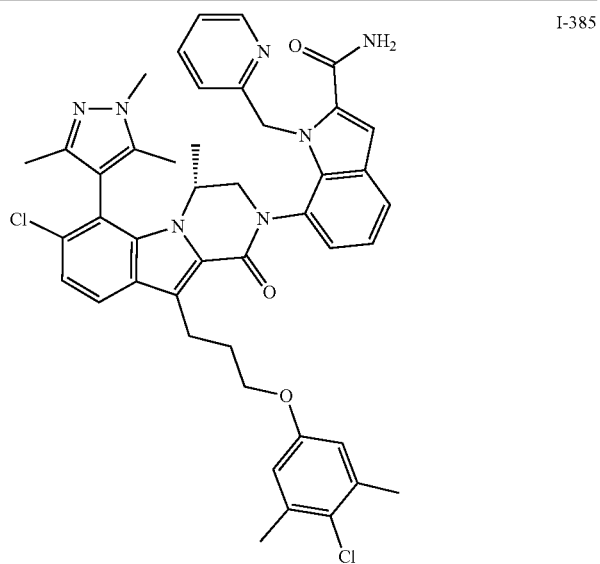
I-385
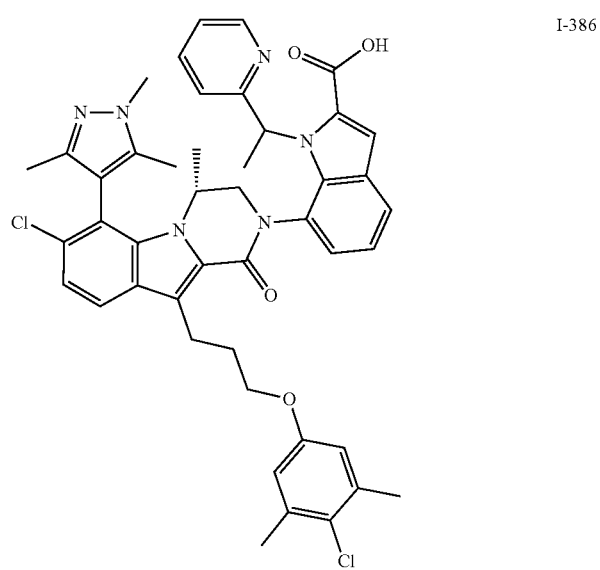
I-386

TABLE 1-continued
Exemplary compounds.
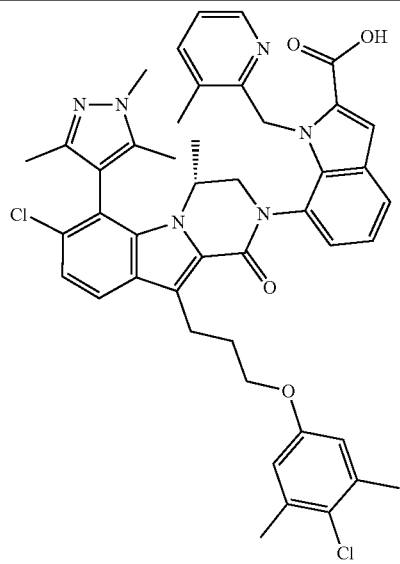
I-387
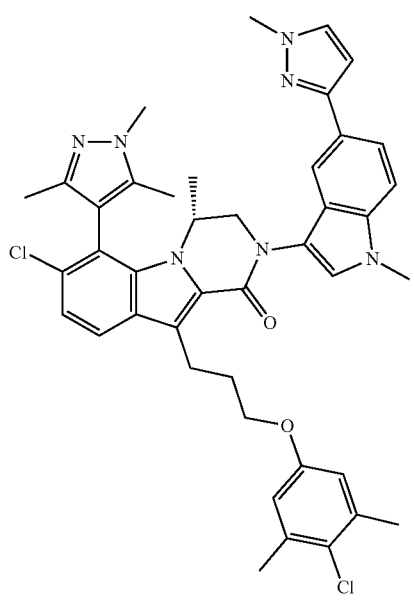 [SMILES: Cc1cc(OCCCc2c3n(c4c(-c5c(C)nn(C)c5C)c(Cl)ccc24)[C@H](C)CN(c2cn(C)c4ccc(-c5ccn(C)n5)cc24)C3=O)cc(C)c1Cl]
I-388

TABLE 1-continued
Exemplary compounds.
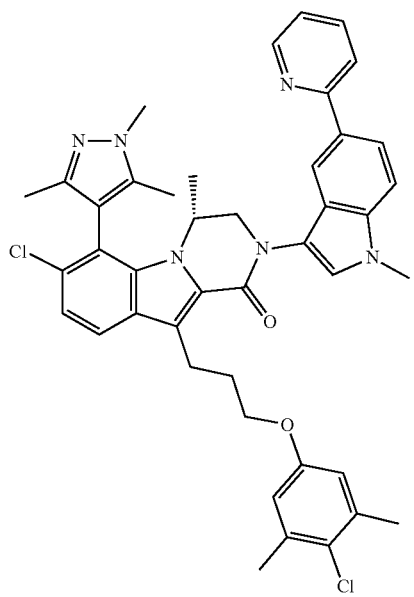 [SMILES: Cc1cc(OCCCc2c3n(c4c(-c5c(C)nn(C)c5C)c(Cl)ccc24)[C@H](C)CN(c2cn(C)c4ccc(-c5ccccn5)cc24)C3=O)cc(C)c1Cl]
I-389
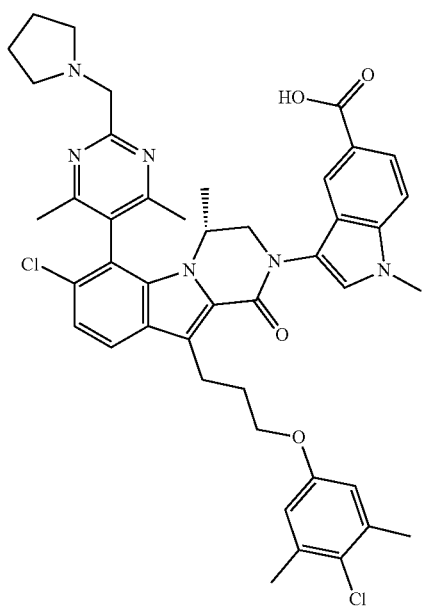 [SMILES: Cc1cc(OCCCc2c3n(c4c(-c5c(C)nc(CN6CCCC6)nc5C)c(Cl)ccc24)[C@H](C)CN(c2cn(C)c4ccc(C(=O)O)cc24)C3=O)cc(C)c1Cl]
I-390

TABLE 1-continued
Exemplary compounds.
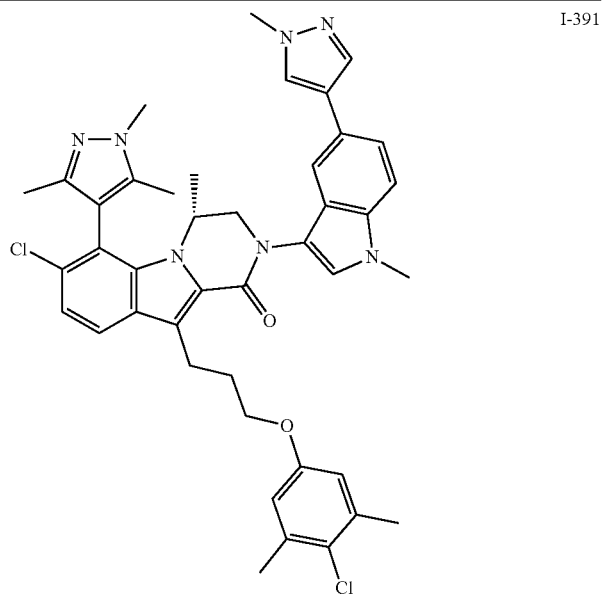
I-391
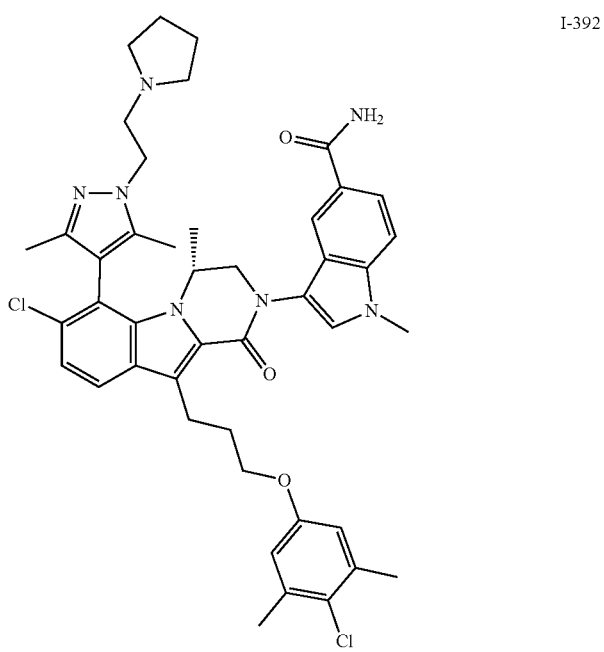
I-392

TABLE 1-continued
Exemplary compounds.
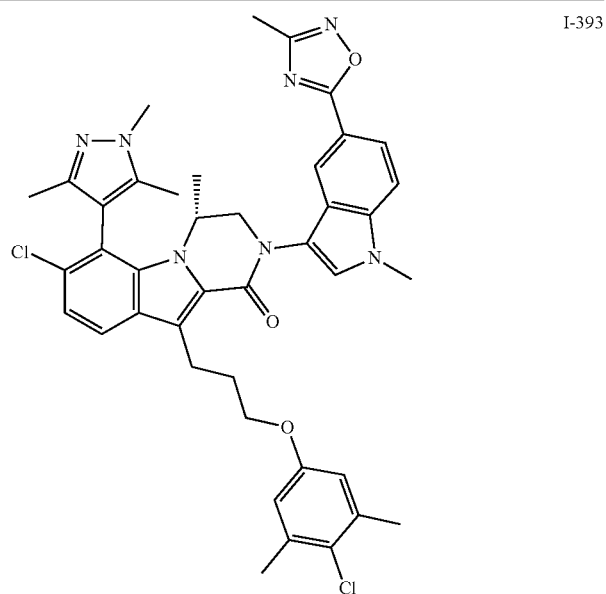
I-393
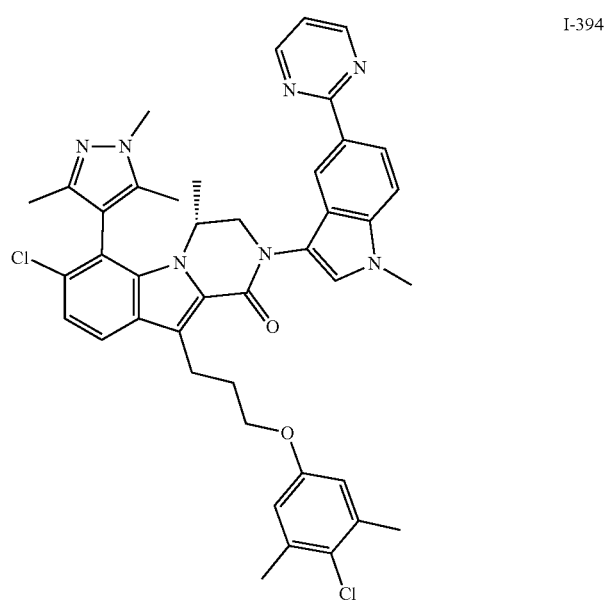
I-394

341
342
TABLE 1-continued
Exemplary compounds.
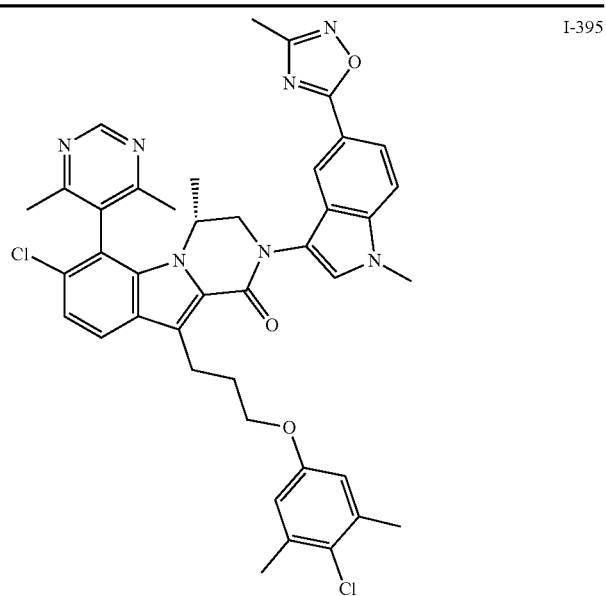
I-395
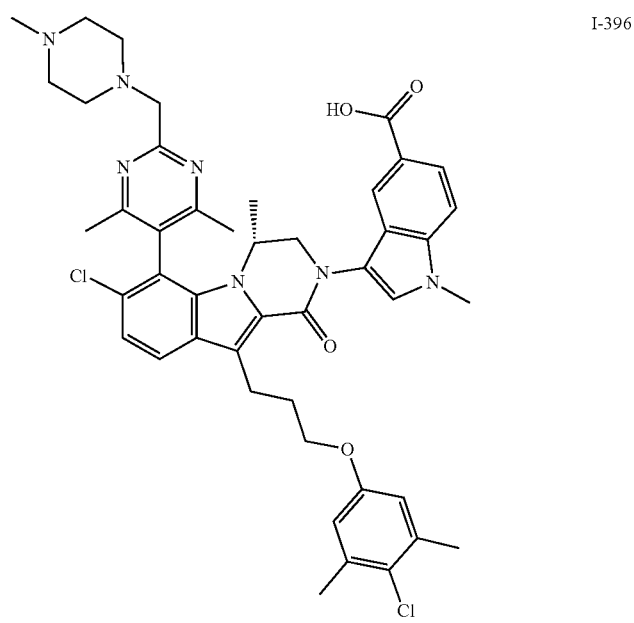
I-396

TABLE 1-continued
Exemplary compounds.
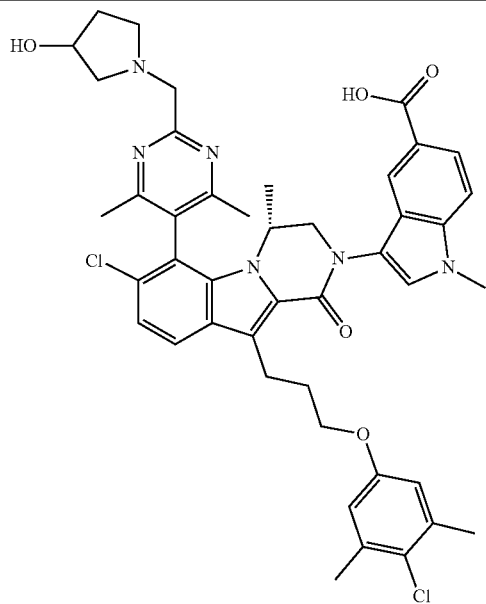
I-397
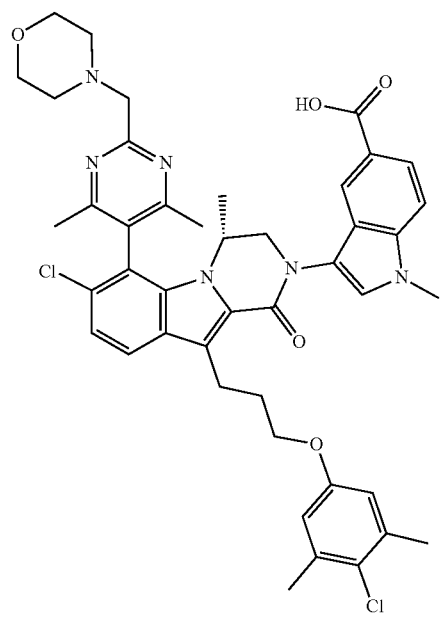 [SMILES: Cc1cc(OCCCc2c3n(c4c(-c5c(C)nc(CN6CCOCC6)nc5C)c(Cl)ccc24)[C@H](C)CN(c2cn(C)c4ccc(C(=O)O)cc24)C3=O)cc(C)c1Cl]
I-398

TABLE 1-continued
Exemplary compounds.
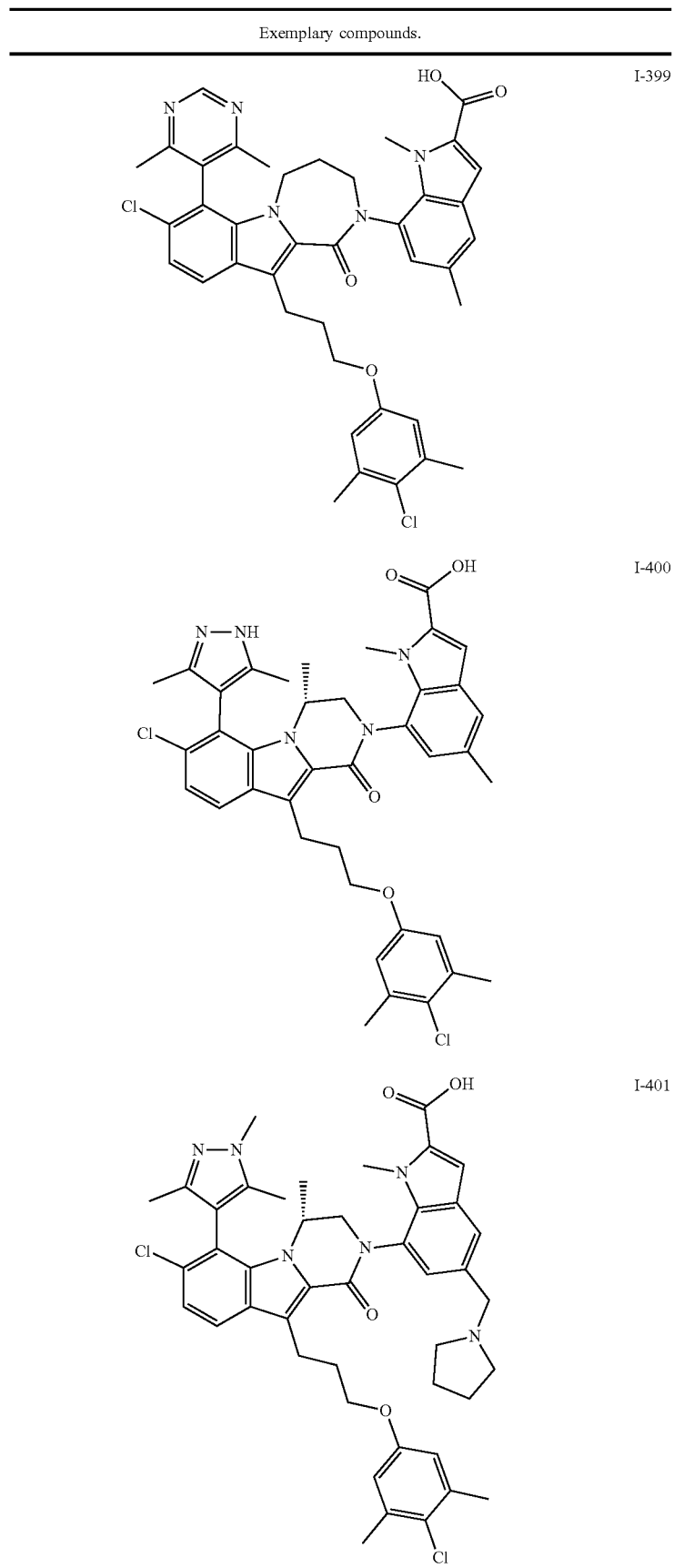
I-399
I-400
I-401

TABLE 1-continued
Exemplary compounds.
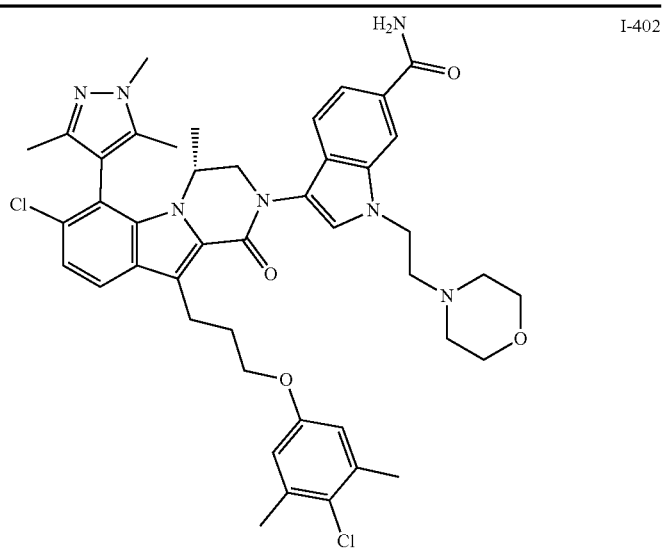
I-402
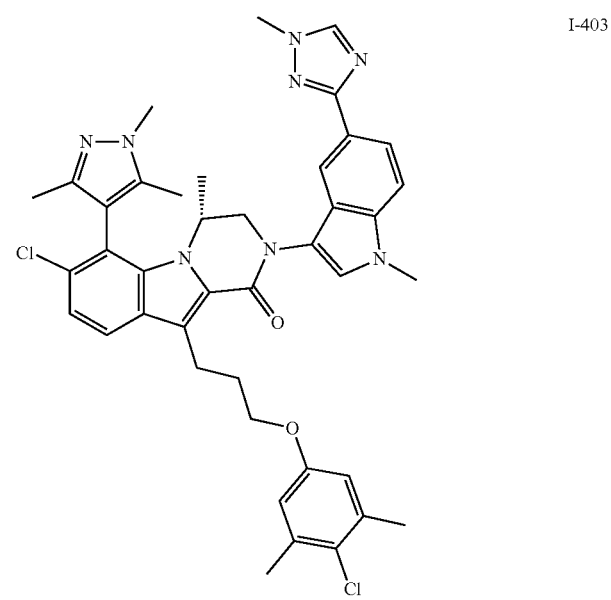
I-403
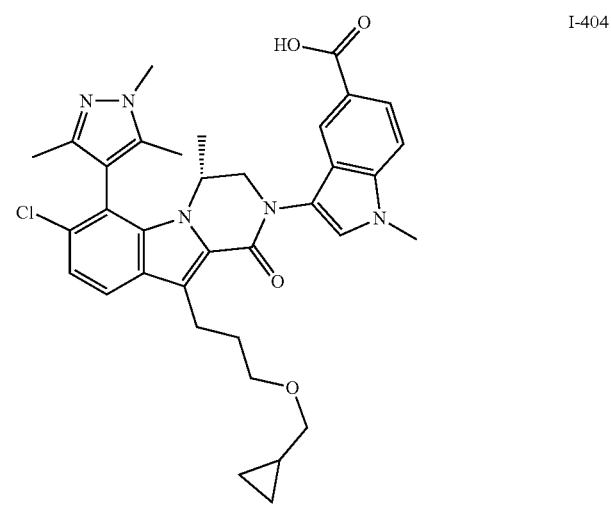
I-404

TABLE 1-continued
Exemplary compounds.
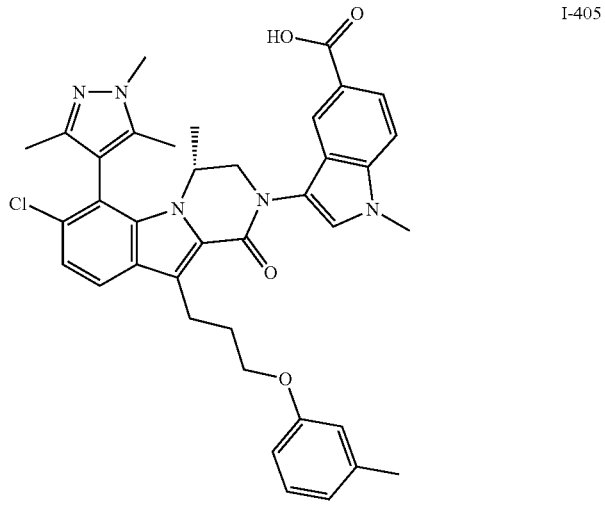
I-405
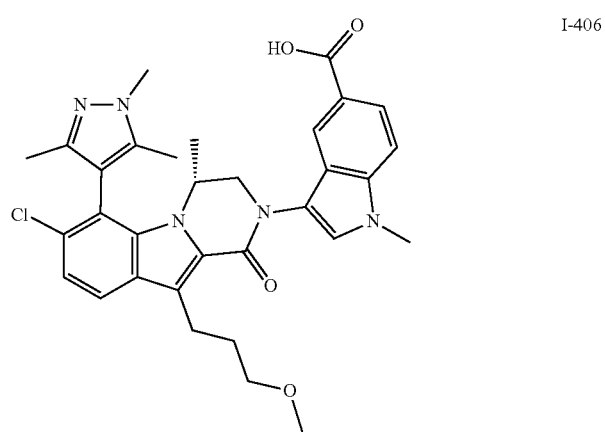
I-406
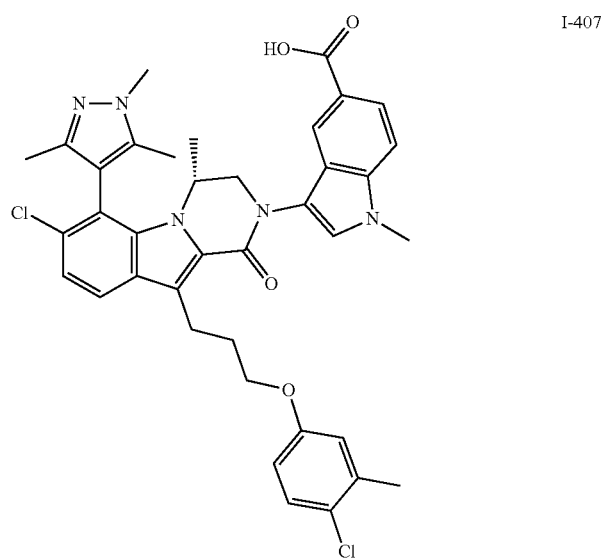
I-407

TABLE 1-continued
Exemplary compounds.
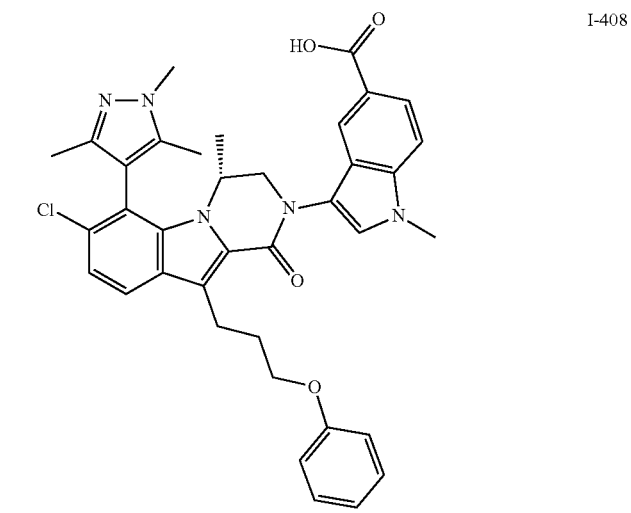
I-408
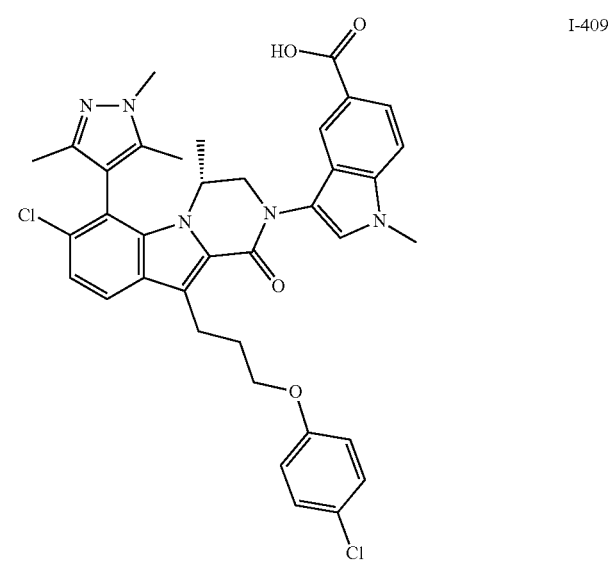
I-409
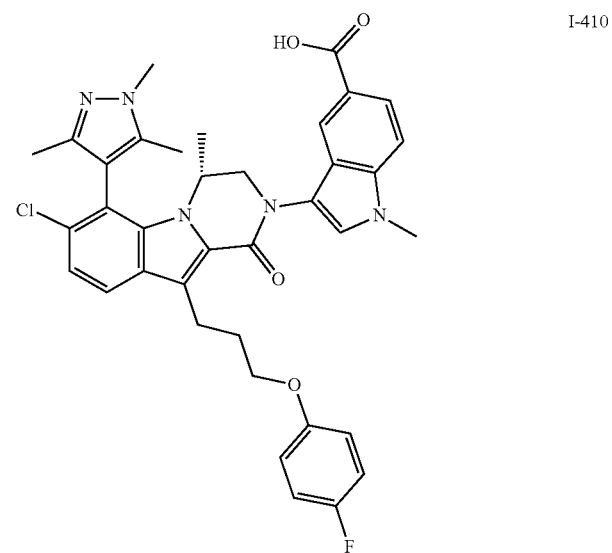
I-410

TABLE 1-continued
Exemplary compounds.
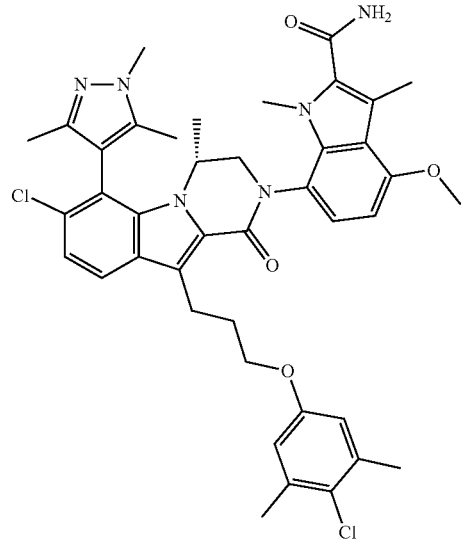 [SMILES: COc1ccc(N2C[C@@H](C)n3c(c(CCCOc4cc(C)c(Cl)c(C)c4)c4ccc(Cl)c(-c5c(C)nn(C)c5C)c43)C2=O)c2c1c(C)c(C(N)=O)n2C]
I-411
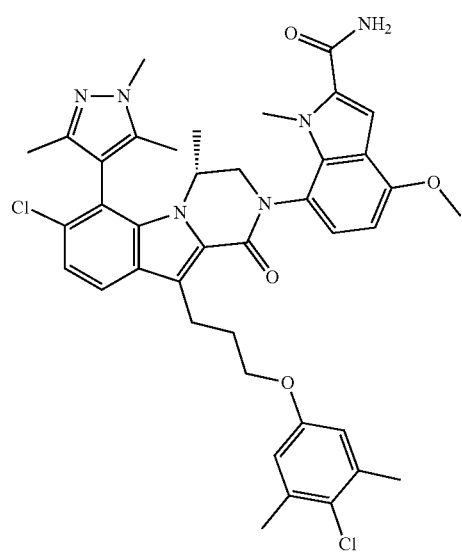 [SMILES: COc1ccc(N2C[C@@H](C)n3c(c(CCCOc4cc(C)c(Cl)c(C)c4)c4ccc(Cl)c(-c5c(C)nn(C)c5C)c43)C2=O)c2c1cc(C(N)=O)n2C]
I-412

TABLE 1-continued
Exemplary compounds.
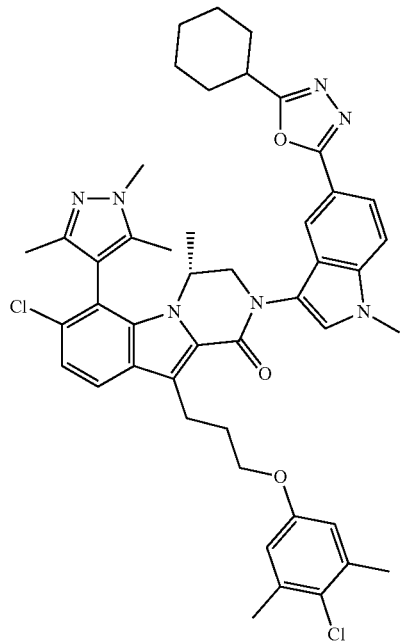 [SMILES: Cc1cc(OCCCc2c3n(c4c(-c5c(C)nn(C)c5C)c(Cl)ccc24)[C@H](C)CN(c2cn(C)c4ccc(-c5nnc(C6CCCCC6)o5)cc24)C3=O)cc(C)c1Cl]
I-413
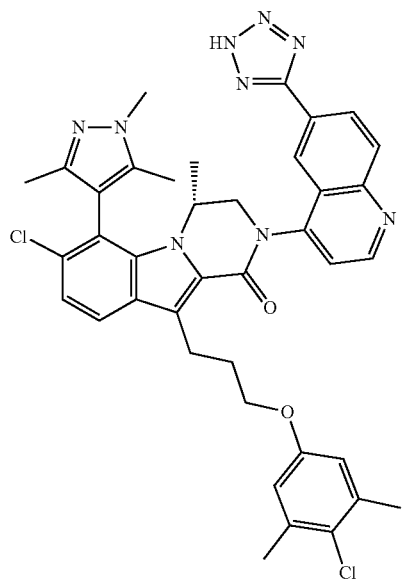 [SMILES: Cc1cc(OCCCc2c3n(c4c(-c5c(C)nn(C)c5C)c(Cl)ccc24)[C@H](C)CN(c2ccnc4ccc(-c5nn[nH]n5)cc24)C3=O)cc(C)c1Cl]
I-414

TABLE 1-continued
Exemplary compounds.
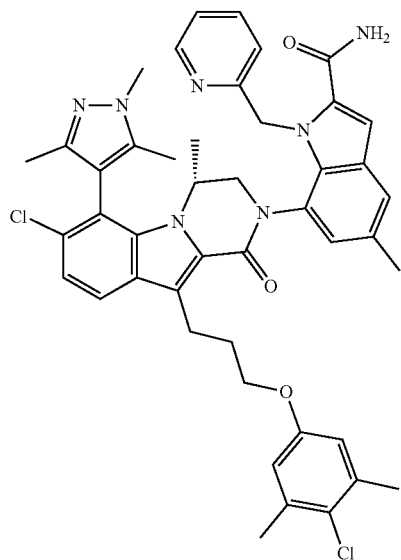 [SMILES: Cc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(N)=O)n2Cc1ccccn1]
I-415
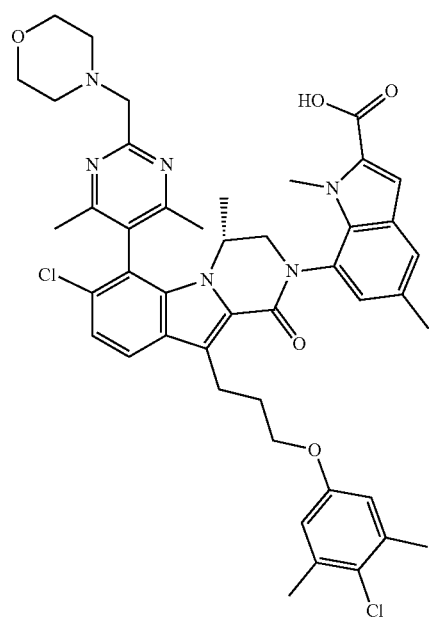 [SMILES: Cc1cc(N2C[C@@H](C)n3c(c(CCCOc4cc(C)c(Cl)c(C)c4)c4ccc(Cl)c(-c5c(C)nc(CN6CCOCC6)nc5C)c43)C2=O)c2c(c1)cc(C(=O)O)n2C]
I-416

TABLE 1-continued
Exemplary compounds.
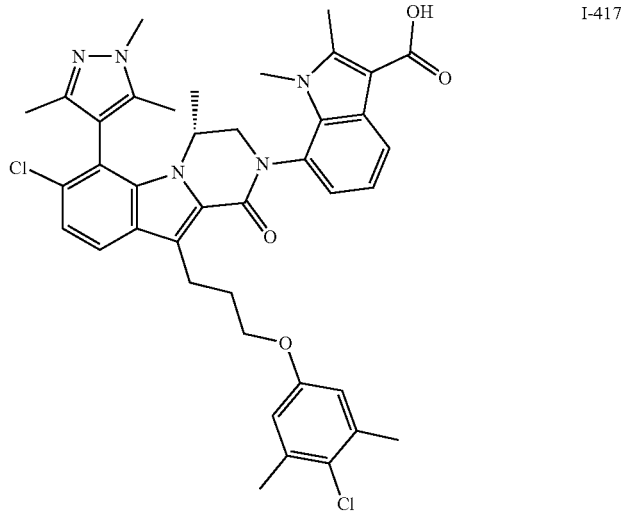
I-417
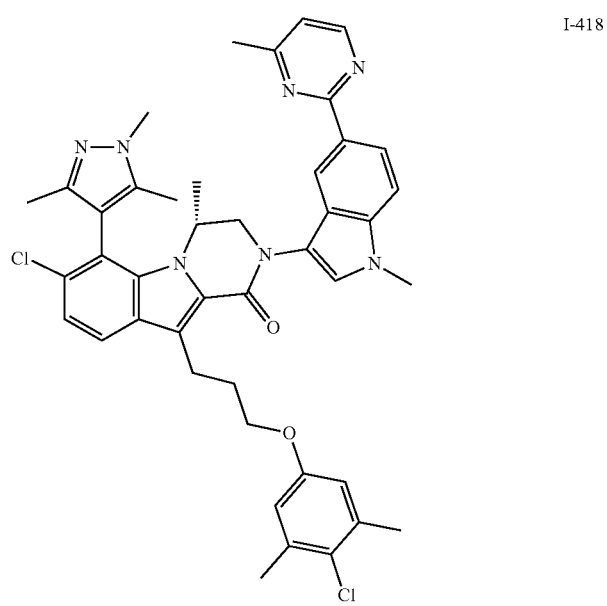
I-418

TABLE 1-continued
Exemplary compounds.
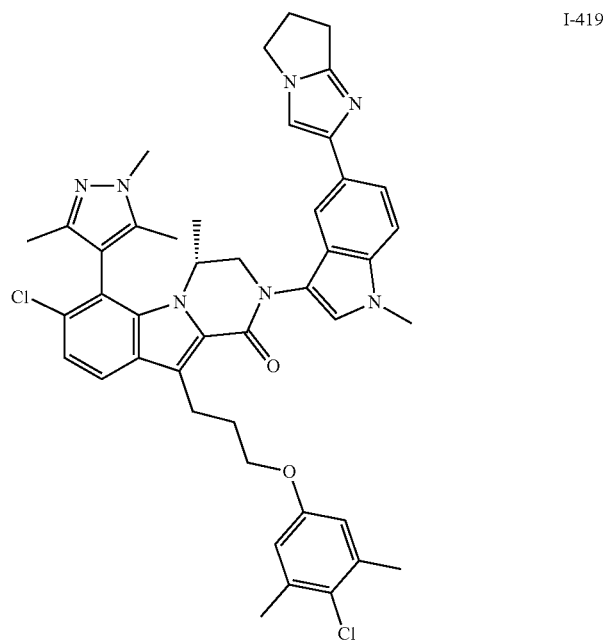
I-419
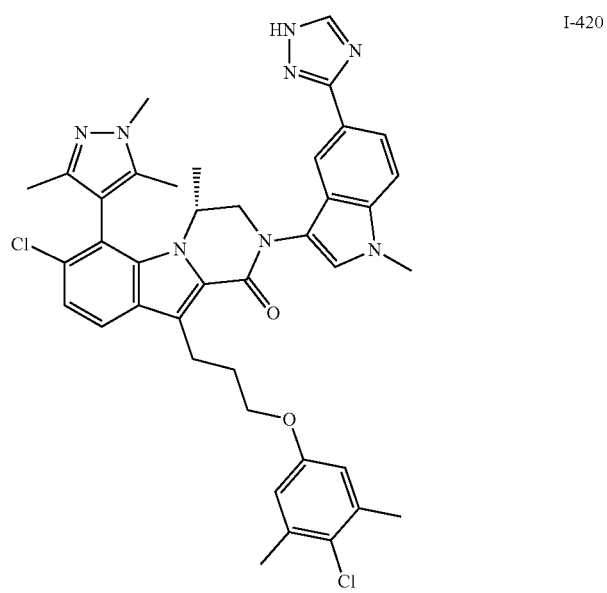
I-420

TABLE 1-continued
Exemplary compounds.
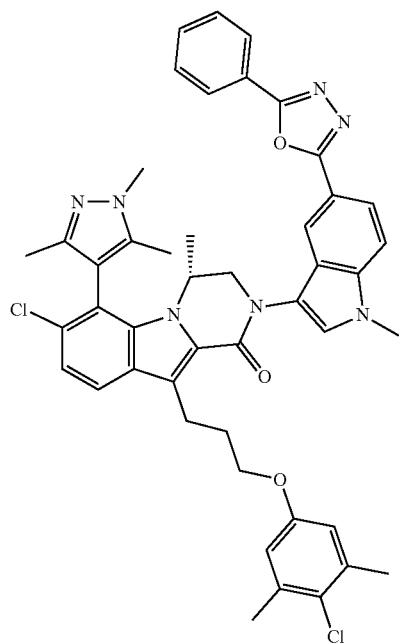 [SMILES: Cc1cc(OCCCc2c3n(c4c(-c5c(C)nn(C)c5C)c(Cl)ccc24)[C@H](C)CN(c2cn(C)c4ccc(-c5nnc(-c6ccccc6)o5)cc24)C3=O)cc(C)c1Cl]
I-421
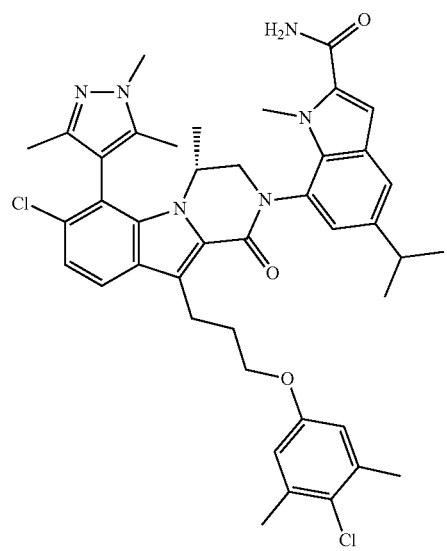 [SMILES: Cc1cc(OCCCc2c3n(c4c(-c5c(C)nn(C)c5C)c(Cl)ccc24)[C@H](C)CN(c2cc(C(C)C)cc4cc(C(N)=O)n(C)c24)C3=O)cc(C)c1Cl]
I-422

TABLE 1-continued
Exemplary compounds.
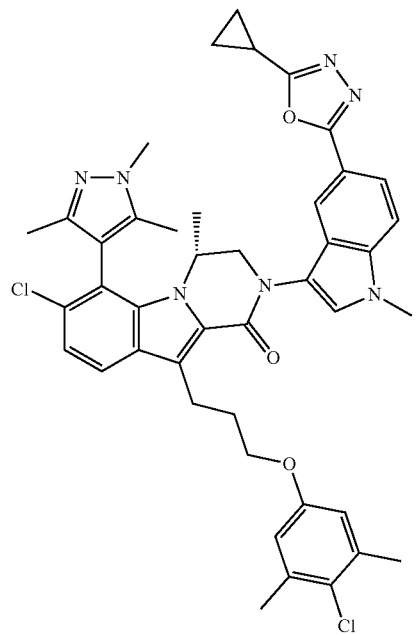 [SMILES: Cc1cc(OCCCc2c3n(c4c(-c5c(C)nn(C)c5C)c(Cl)ccc24)[C@H](C)CN(c2cn(C)c4ccc(-c5nnc(C6CC6)o5)cc24)C3=O)cc(C)c1Cl]
I-423
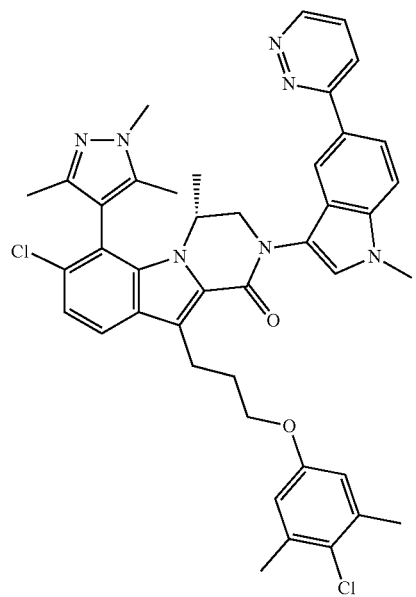 [SMILES: Cc1cc(OCCCc2c3n(c4c(-c5c(C)nn(C)c5C)c(Cl)ccc24)[C@H](C)CN(c2cn(C)c4ccc(-c5cccnn5)cc24)C3=O)cc(C)c1Cl]
I-424

TABLE 1-continued
Exemplary compounds.
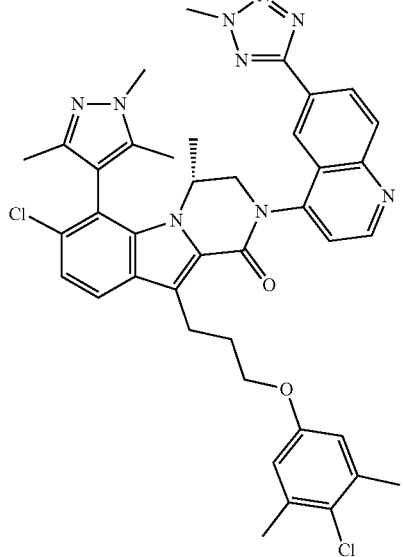
I-425
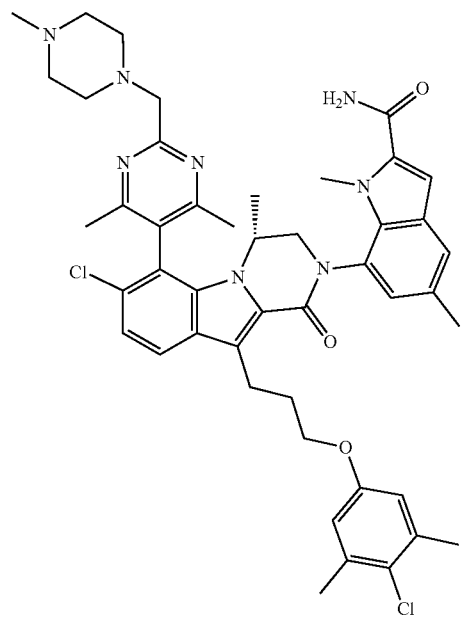
I-426

TABLE 1-continued
Exemplary compounds.
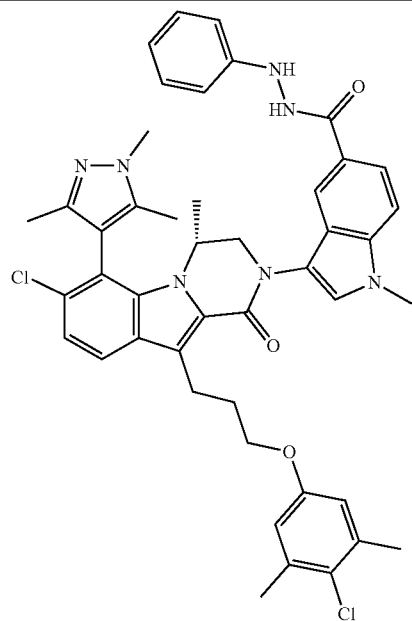
I-427
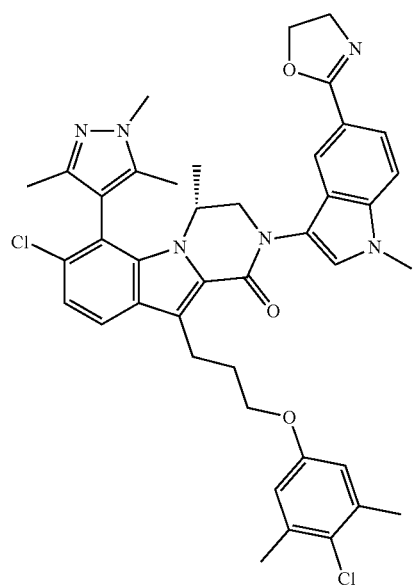 [SMILES: Cc1cc(OCCCc2c3n(c4c(-c5c(C)nn(C)c5C)c(Cl)ccc24)[C@H](C)CN(c2cn(C)c4ccc(C5=NCCO5)cc24)C3=O)cc(C)c1Cl]
I-428

TABLE 1-continued
Exemplary compounds.
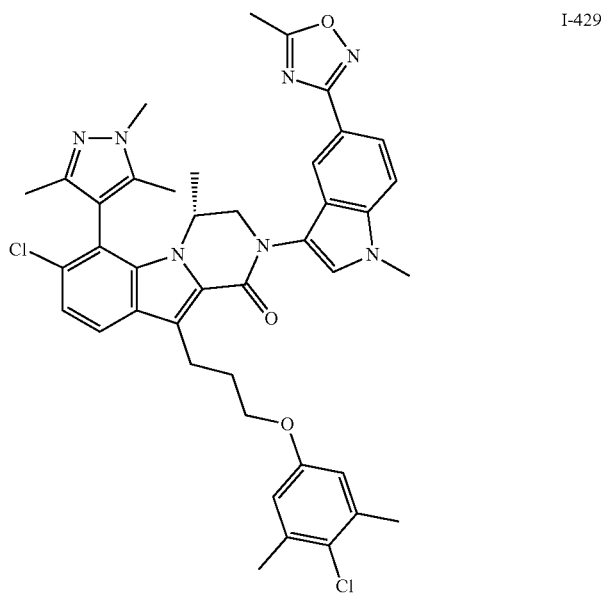
I-429
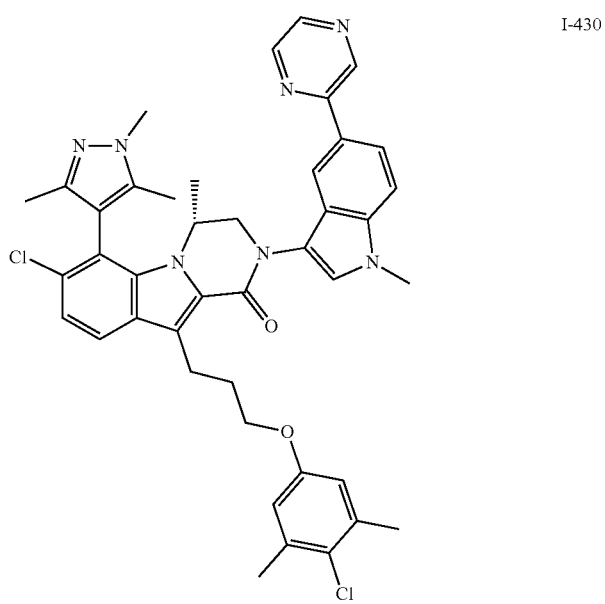
I-430

TABLE 1-continued
Exemplary compounds.
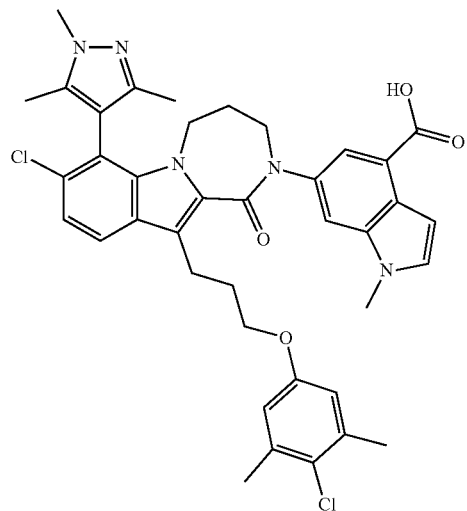 [SMILES: Cc1cc(OCCCc2c3n(c4c(-c5c(C)nn(C)c5C)c(Cl)ccc24)CCCN(c2cc(C(=O)O)c4ccn(C)c4c2)C3=O)cc(C)c1Cl]
I-431
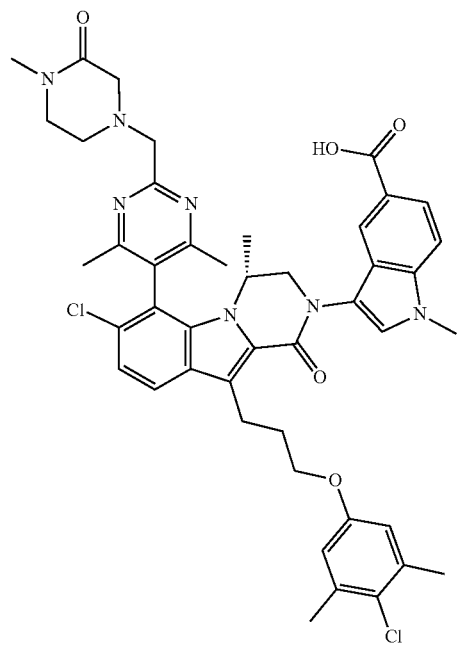
I-432

TABLE 1-continued
Exemplary compounds.
I-433
I-434

TABLE 1-continued
Exemplary compounds.
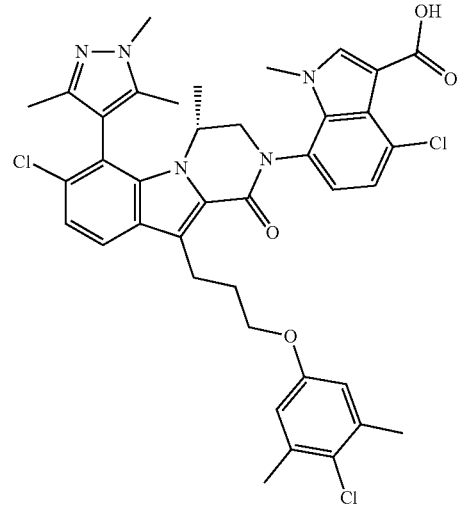
I-435
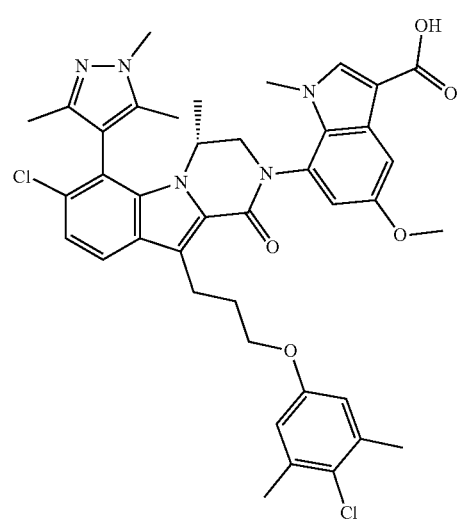 [SMILES: COc1cc(N2C[C@@H](C)n3c(c(CCCOc4cc(C)c(Cl)c(C)c4)c4ccc(Cl)c(-c5c(C)nn(C)c5C)c43)C2=O)c2c(c1)c(C(=O)O)cn2C]
I-436

TABLE 1-continued
Exemplary compounds.
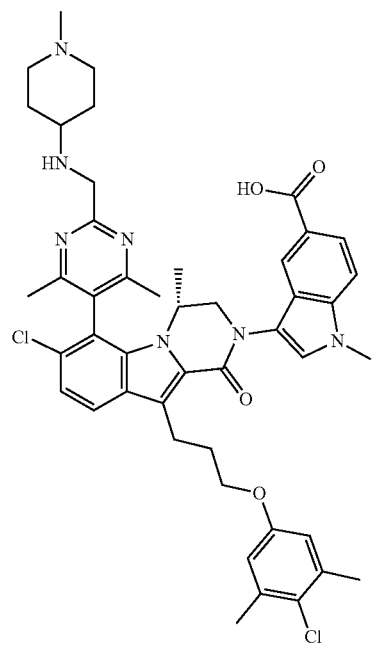 [SMILES: Cc1cc(OCCCc2c3n(c4c(-c5c(C)nc(CNC6CCN(C)CC6)nc5C)c(Cl)ccc24)[C@H](C)CN(c2cn(C)c4ccc(C(=O)O)cc24)C3=O)cc(C)c1Cl]
I-437
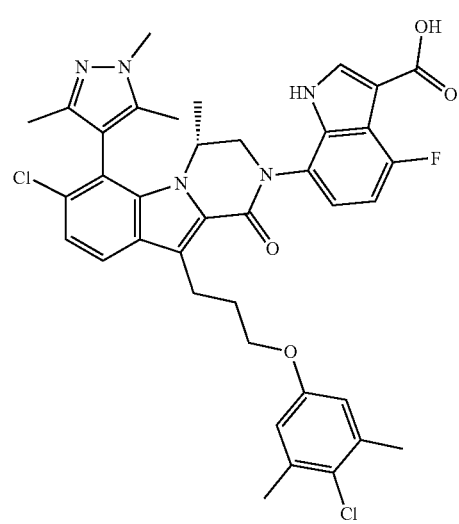 [SMILES: Cc1cc(OCCCc2c3n(c4c(-c5c(C)nn(C)c5C)c(Cl)ccc24)[C@H](C)CN(c2ccc(F)c4c(C(=O)O)c[nH]c24)C3=O)cc(C)c1Cl]
I-438

TABLE 1-continued
Exemplary compounds.
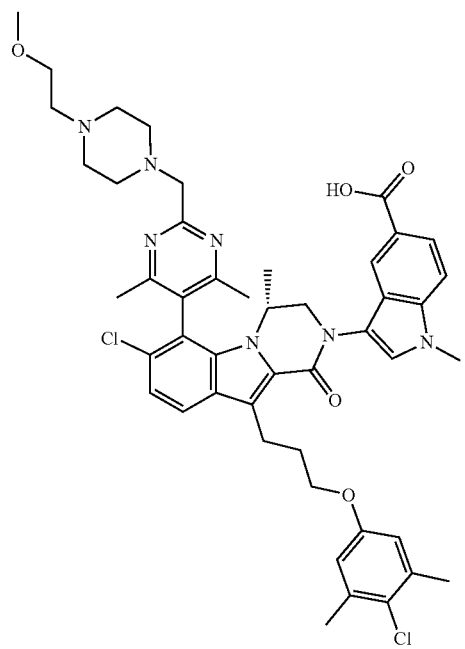 [SMILES: COCCN1CCN(Cc2nc(C)c(-c3c(Cl)ccc4c(CCCOc5cc(C)c(Cl)c(C)c5)c5n(c34)[C@H](C)CN(c3cn(C)c4ccc(C(=O)O)cc34)C5=O)c(C)n2)CC1]
I-439
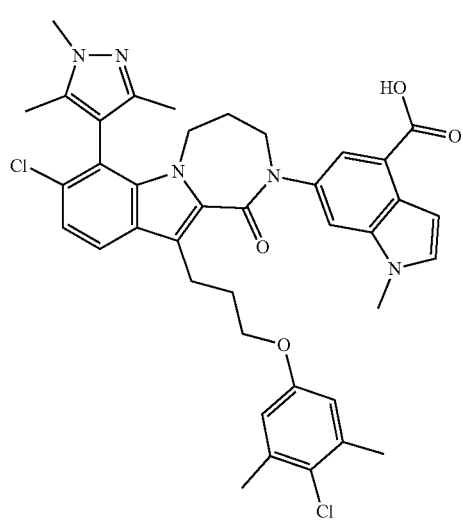 [SMILES: Cc1cc(OCCCc2c3n(c4c(-c5c(C)nn(C)c5C)c(Cl)ccc24)CCCN(c2cc(C(=O)O)c4ccn(C)c4c2)C3=O)cc(C)c1Cl]
I-440

TABLE 1-continued
Exemplary compounds.
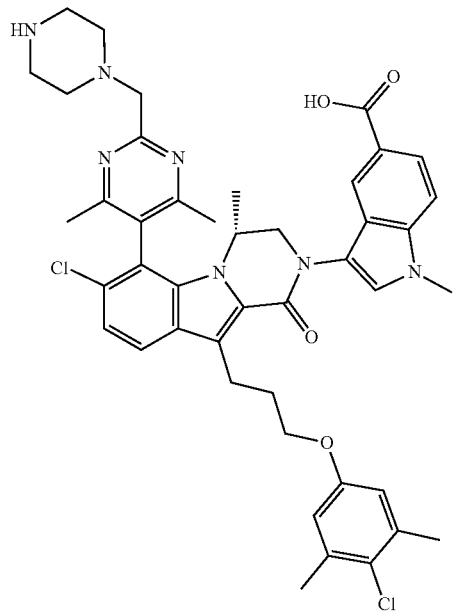 [SMILES: Cc1cc(OCCCc2c3n(c4c(-c5c(C)nc(CN6CCNCC6)nc5C)c(Cl)ccc24)[C@H](C)CN(c2cn(C)c4ccc(C(=O)O)cc24)C3=O)cc(C)c1Cl]
I-441
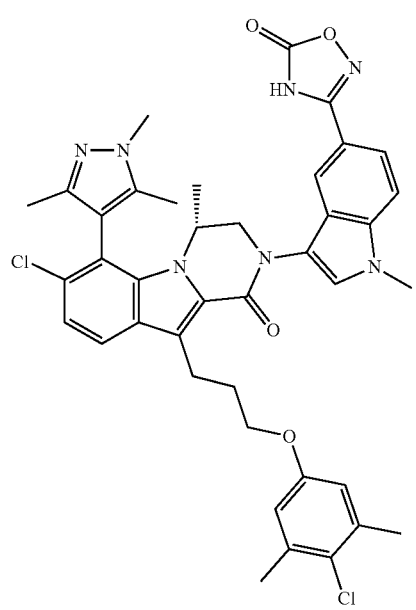 [SMILES: Cc1cc(OCCCc2c3n(c4c(-c5c(C)nn(C)c5C)c(Cl)ccc24)[C@H](C)CN(c2cn(C)c4ccc(-c5noc(=O)[nH]5)cc24)C3=O)cc(C)c1Cl]
I-442

TABLE 1-continued
Exemplary compounds.
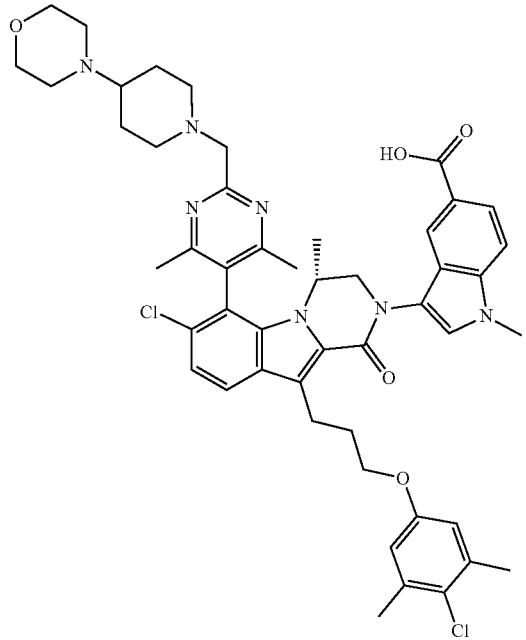 [SMILES: Cc1cc(OCCCc2c3n(c4c(-c5c(C)nc(CN6CCC(N7CCOCC7)CC6)nc5C)c(Cl)ccc24)[C@H](C)CN(c2cn(C)c4ccc(C(=O)O)cc24)C3=O)cc(C)c1Cl]
I-443
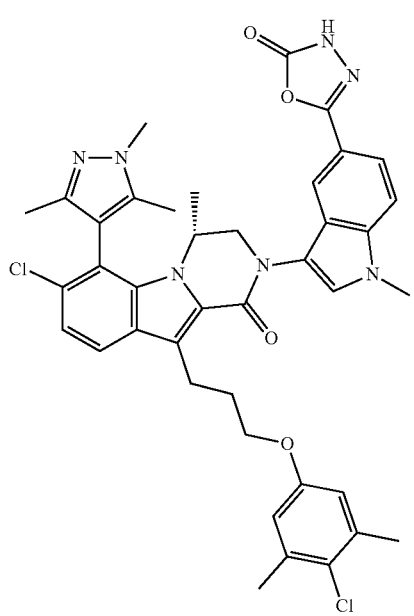 [SMILES: Cc1cc(OCCCc2c3n(c4c(-c5c(C)nn(C)c5C)c(Cl)ccc24)[C@H](C)CN(c2cn(C)c4ccc(-c5n[nH]c(=O)o5)cc24)C3=O)cc(C)c1Cl]
I-444

TABLE 1-continued
Exemplary compounds.
I-445
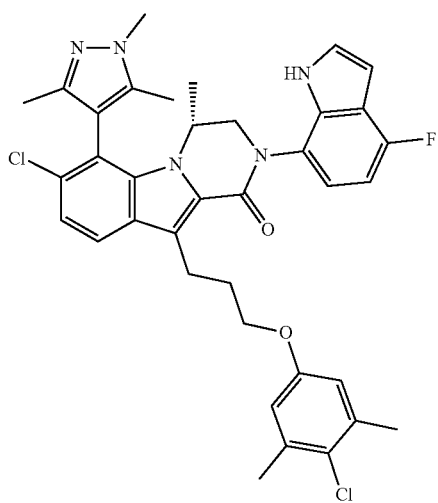 [SMILES: Cc1cc(OCCCc2c3n(c4c(-c5c(C)nn(C)c5C)c(Cl)ccc24)[C@H](C)CN(c2ccc(F)c4cc[nH]c24)C3=O)cc(C)c1Cl]
I-446
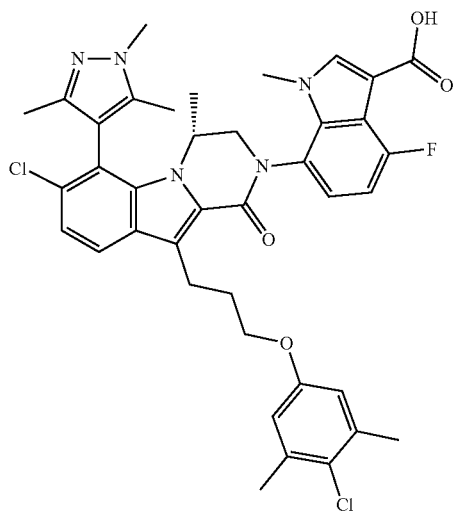 [SMILES: Cc1cc(OCCCc2c3n(c4c(-c5c(C)nn(C)c5C)c(Cl)ccc24)[C@H](C)CN(c2ccc(F)c4c(C(=O)O)cn(C)c24)C3=O)cc(C)c1Cl]
I-447

TABLE 1-continued
Exemplary compounds.
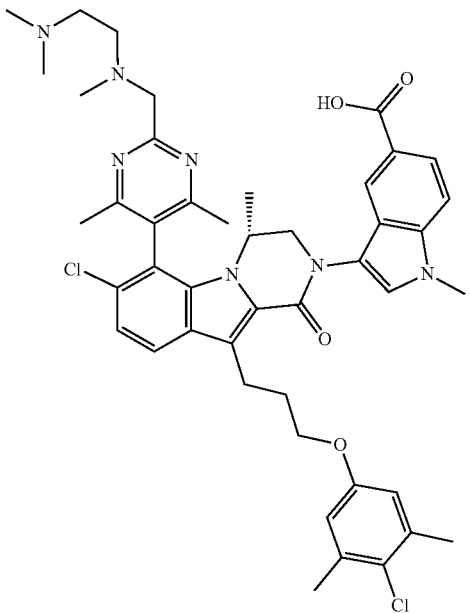
I-448
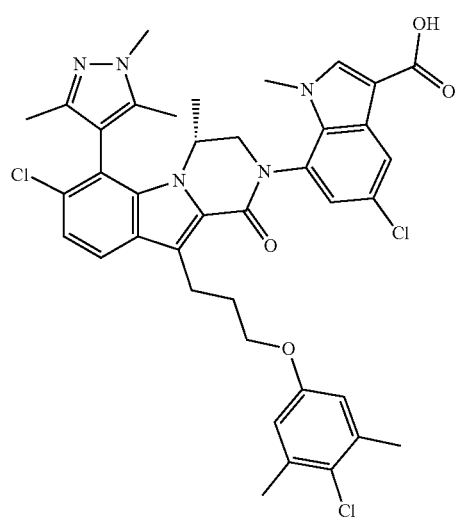 [SMILES: Cc1cc(OCCCc2c3n(c4c(-c5c(C)nn(C)c5C)c(Cl)ccc24)[C@H](C)CN(c2cc(Cl)cc4c(C(=O)O)cn(C)c24)C3=O)cc(C)c1Cl]
I-449

TABLE 1-continued
Exemplary compounds.
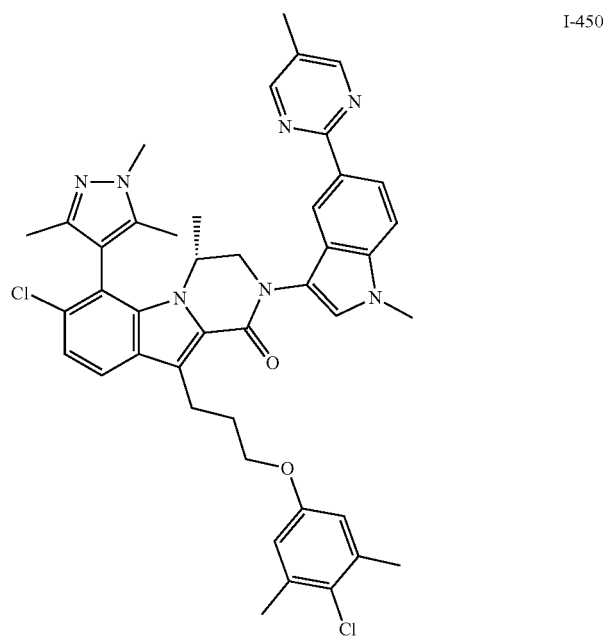 I-450
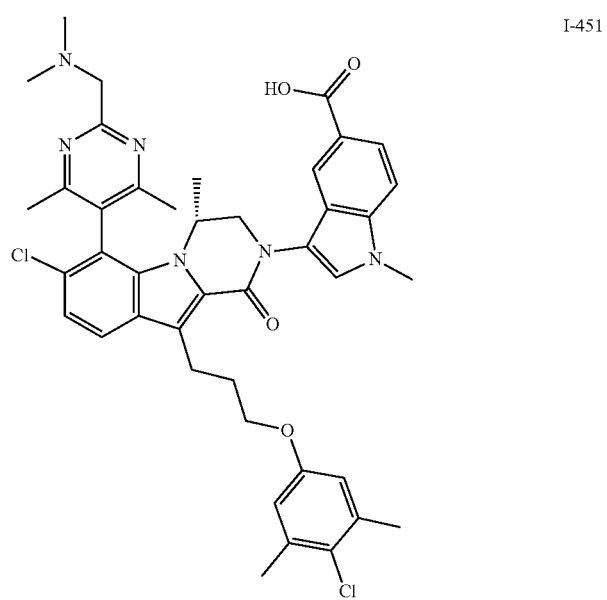 I-451

TABLE 1-continued
Exemplary compounds.
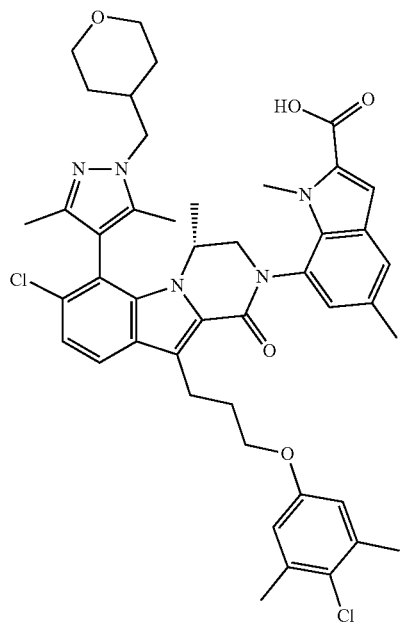 [SMILES: Cc1cc(N2C[C@@H](C)n3c(c(CCCOc4cc(C)c(Cl)c(C)c4)c4ccc(Cl)c(-c5c(C)nn(CC6CCOCC6)c5C)c43)C2=O)c2c(c1)cc(C(=O)O)n2C]
I-452
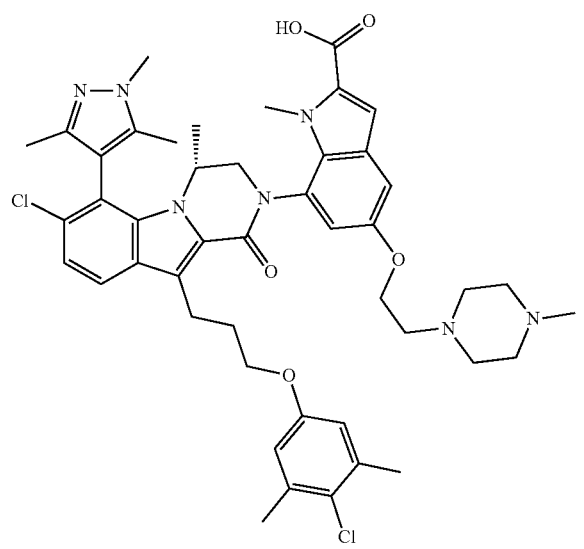 [SMILES: Cc1cc(OCCCc2c3n(c4c(-c5c(C)nn(C)c5C)c(Cl)ccc24)[C@H](C)CN(c2cc(OCCN4CCN(C)CC4)cc4cc(C(=O)O)n(C)c24)C3=O)cc(C)c1Cl]
I-453

TABLE 1-continued
Exemplary compounds.
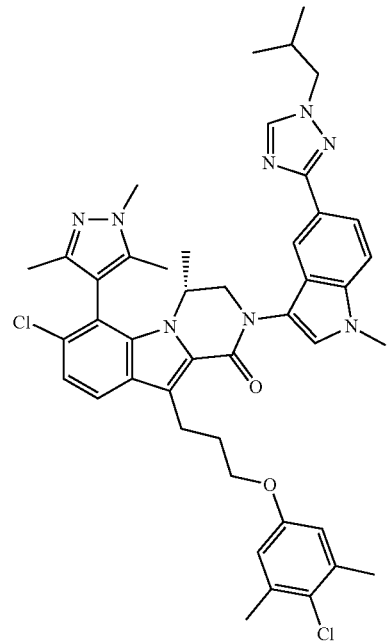 [SMILES: Cc1cc(OCCCc2c3n(c4c(-c5c(C)nn(C)c5C)c(Cl)ccc24)[C@H](C)CN(c2cn(C)c4ccc(-c5ncn(CC(C)C)n5)cc24)C3=O)cc(C)c1Cl]
I-454
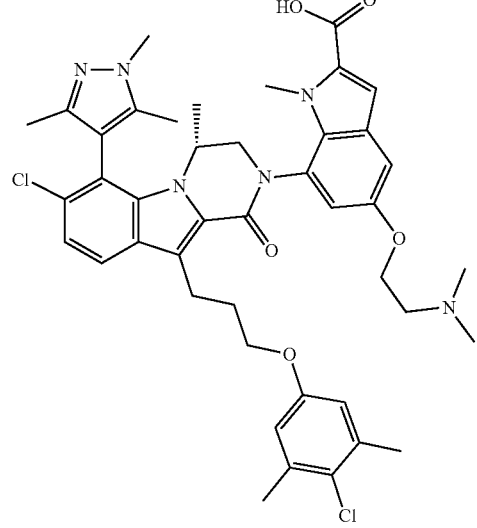
I-455

TABLE 1-continued
Exemplary compounds.
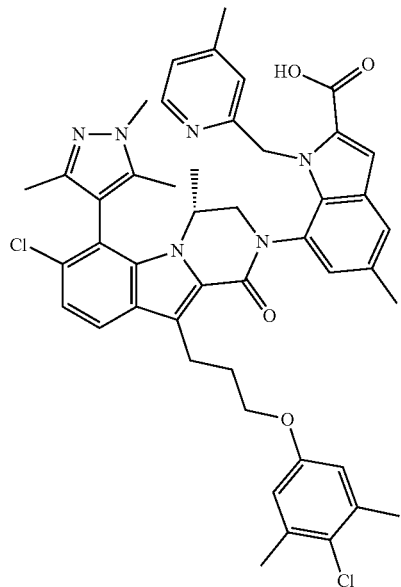 [SMILES: Cc1ccnc(Cn2c(C(=O)O)cc3cc(C)cc(N4C[C@@H](C)n5c(c(CCCOc6cc(C)c(Cl)c(C)c6)c6ccc(Cl)c(-c7c(C)nn(C)c7C)c65)C4=O)c32)c1]
I-456
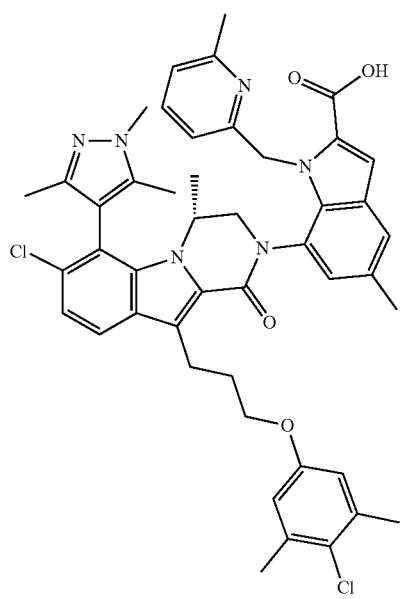 [SMILES: Cc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(=O)O)n2Cc1cccc(C)n1]
I-457

TABLE 1-continued
Exemplary compounds.
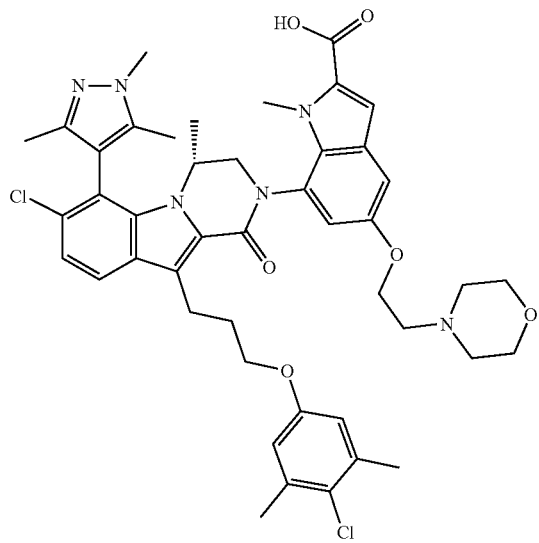 [SMILES: Cc1cc(OCCCc2c3n(c4c(-c5c(C)nn(C)c5C)c(Cl)ccc24)[C@H](C)CN(c2cc(OCCN4CCOCC4)cc4cc(C(=O)O)n(C)c24)C3=O)cc(C)c1Cl]
I-458
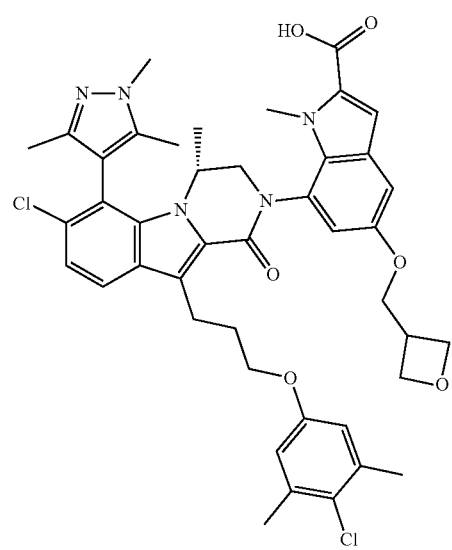 [SMILES: Cc1cc(OCCCc2c3n(c4c(-c5c(C)nn(C)c5C)c(Cl)ccc24)[C@H](C)CN(c2cc(OCC4COC4)cc4cc(C(=O)O)n(C)c24)C3=O)cc(C)c1Cl]
I-459
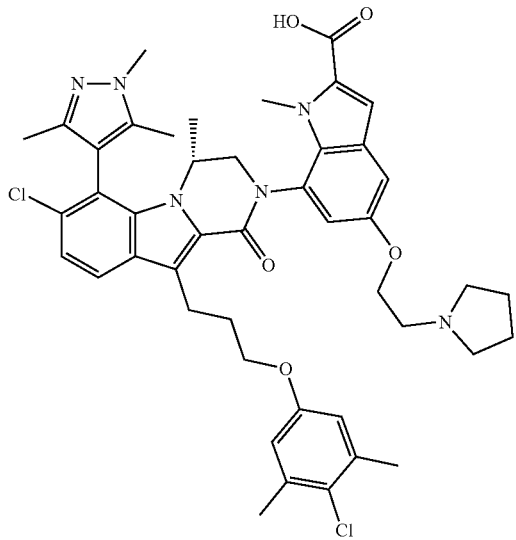 [SMILES: Cc1cc(OCCCc2c3n(c4c(-c5c(C)nn(C)c5C)c(Cl)ccc24)[C@H](C)CN(c2cc(OCCN4CCCC4)cc4cc(C(=O)O)n(C)c24)C3=O)cc(C)c1Cl]
I-460

TABLE 1-continued
Exemplary compounds.
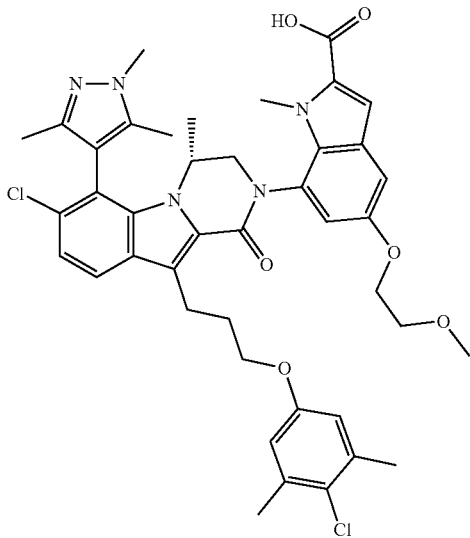 [SMILES: COCCOc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(=O)O)n2C]
I-461
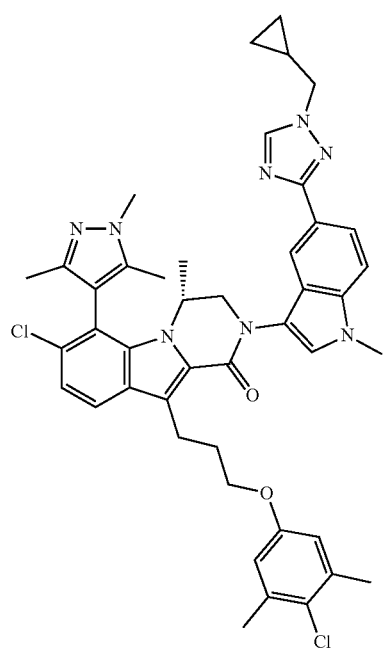 [SMILES: Cc1cc(OCCCc2c3n(c4c(-c5c(C)nn(C)c5C)c(Cl)ccc24)[C@H](C)CN(c2cn(C)c4ccc(-c5ncn(CC6CC6)n5)cc24)C3=O)cc(C)c1Cl]
I-462

TABLE 1-continued
Exemplary compounds.
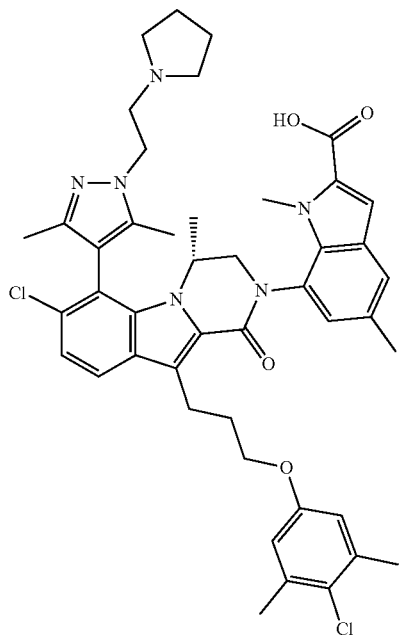 [SMILES: Cc1cc(N2C[C@@H](C)n3c(c(CCCOc4cc(C)c(Cl)c(C)c4)c4ccc(Cl)c(-c5c(C)nn(CCN6CCCC6)c5C)c43)C2=O)c2c(c1)cc(C(=O)O)n2C]
I-463
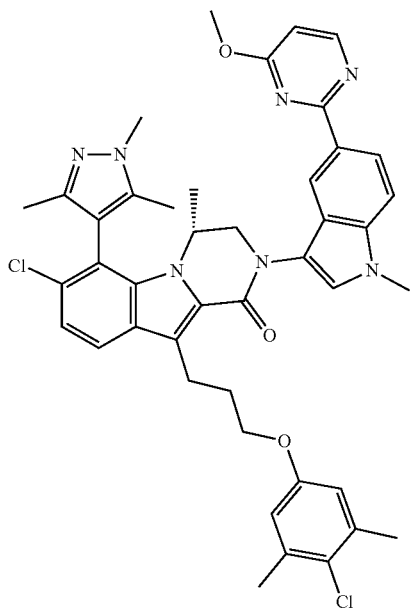 [SMILES: COc1ccnc(-c2ccc3c(c2)c(N2C[C@@H](C)n4c(c(CCCOc5cc(C)c(Cl)c(C)c5)c5ccc(Cl)c(-c6c(C)nn(C)c6C)c54)C2=O)cn3C)n1]
I-464

TABLE 1-continued
Exemplary compounds.
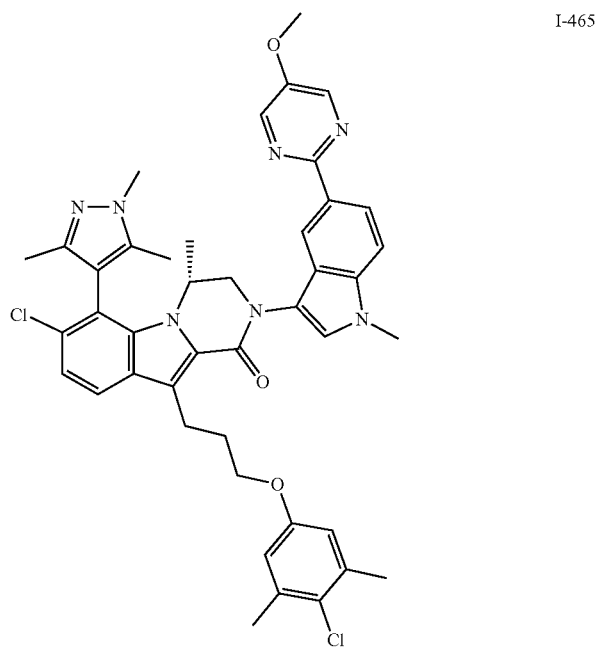
I-465
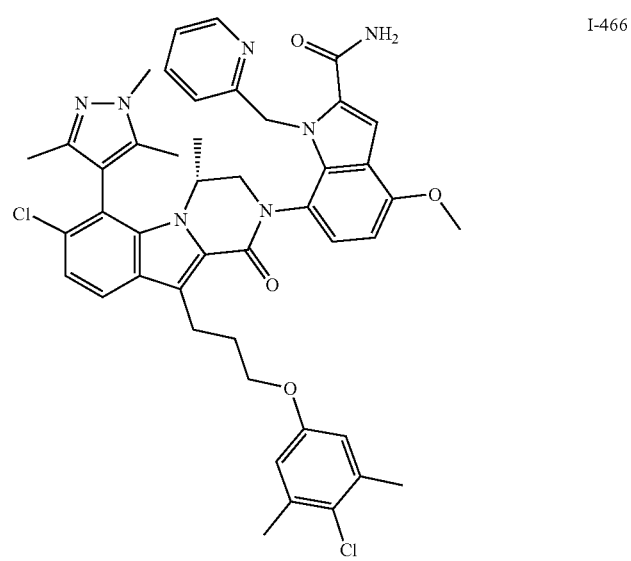
I-466

407                                                                                                          408
TABLE 1-continued
Exemplary compounds.
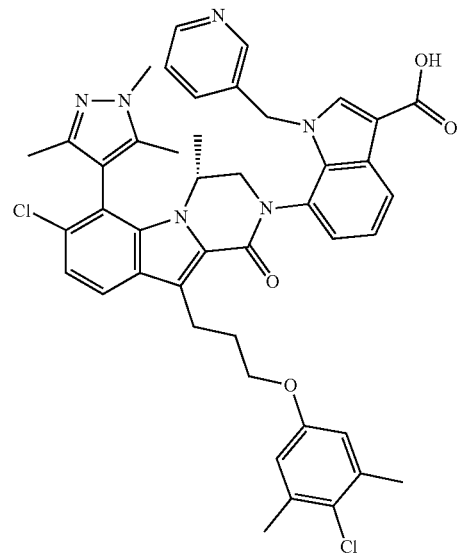 [SMILES: Cc1cc(OCCCc2c3n(c4c(-c5c(C)nn(C)c5C)c(Cl)ccc24)[C@H](C)CN(c2cccc4c(C(=O)O)cn(Cc5cccnc5)c24)C3=O)cc(C)c1Cl]
I-467
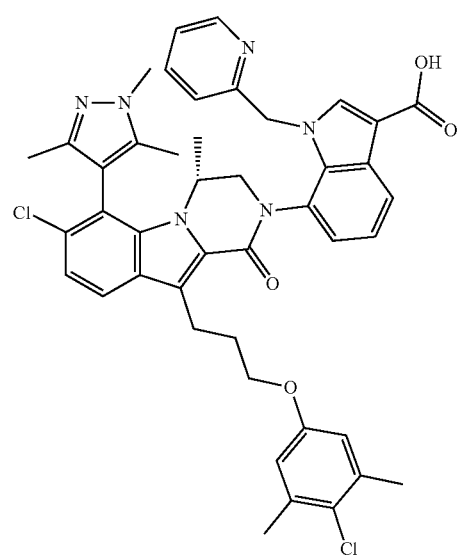 [SMILES: Cc1cc(OCCCc2c3n(c4c(-c5c(C)nn(C)c5C)c(Cl)ccc24)[C@H](C)CN(c2cccc4c(C(=O)O)cn(Cc5ccccn5)c24)C3=O)cc(C)c1Cl]
I-468

409
410
TABLE 1-continued
Exemplary compounds.
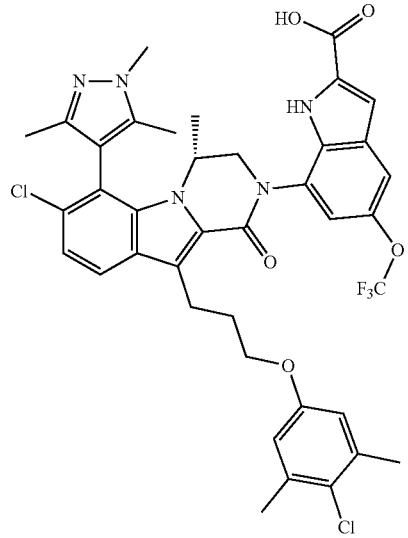 [SMILES: Cc1cc(OCCCc2c3n(c4c(-c5c(C)nn(C)c5C)c(Cl)ccc24)[C@H](C)CN(c2cc(OC(F)(F)F)cc4cc(C(=O)O)[nH]c24)C3=O)cc(C)c1Cl]
I-469
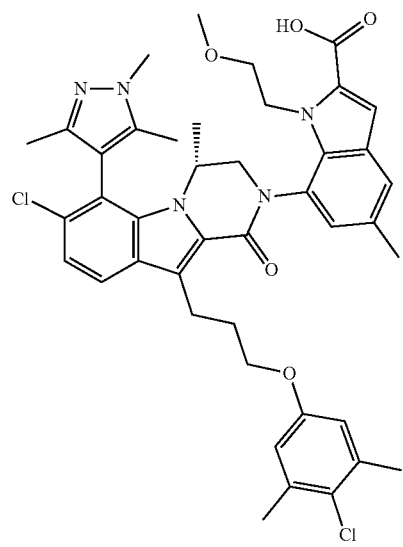 [SMILES: COCCn1c(C(=O)O)cc2cc(C)cc(N3C[C@@H](C)n4c(c(CCCOc5cc(C)c(Cl)c(C)c5)c5ccc(Cl)c(-c6c(C)nn(C)c6C)c54)C3=O)c21]
I-470

TABLE 1-continued
Exemplary compounds.
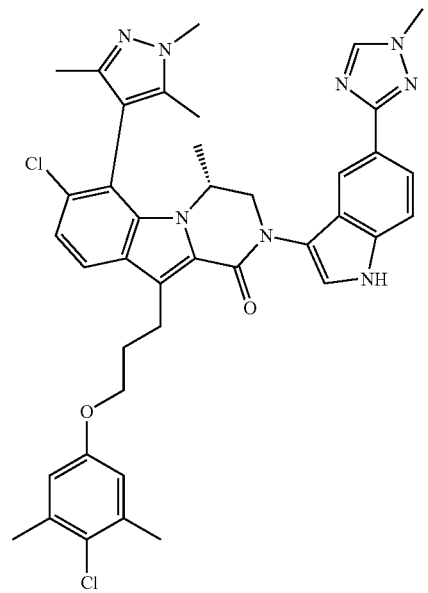
I-471
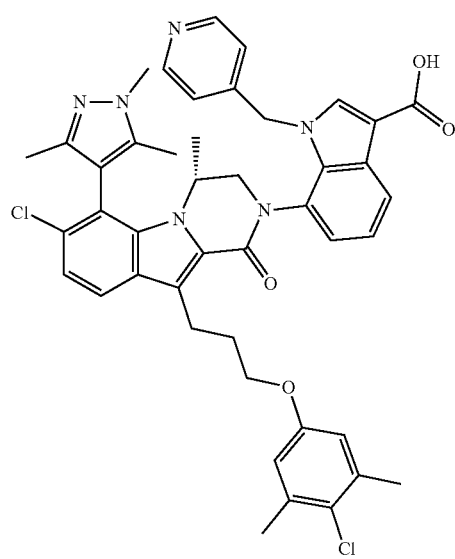 [SMILES: Cc1cc(OCCCc2c3n(c4c(-c5c(C)nn(C)c5C)c(Cl)ccc24)[C@H](C)CN(c2cccc4c(C(=O)O)cn(Cc5ccncc5)c24)C3=O)cc(C)c1Cl]
I-472

TABLE 1-continued
Exemplary compounds.
I-473
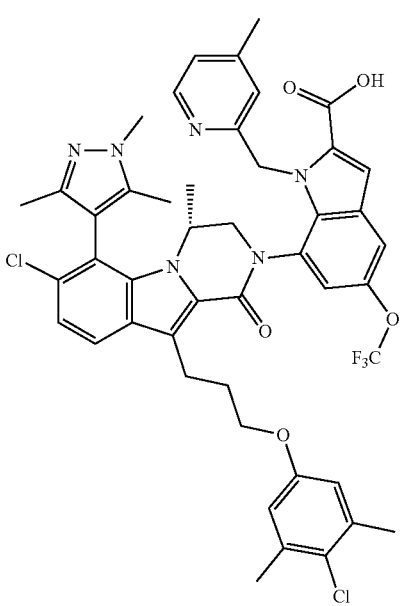 [SMILES: Cc1ccnc(Cn2c(C(=O)O)cc3cc(OC(F)(F)F)cc(N4C[C@@H](C)n5c(c(CCCOc6cc(C)c(Cl)c(C)c6)c6ccc(Cl)c(-c7c(C)nn(C)c7C)c65)C4=O)c32)c1]
I-474

415
416
TABLE 1-continued
Exemplary compounds.
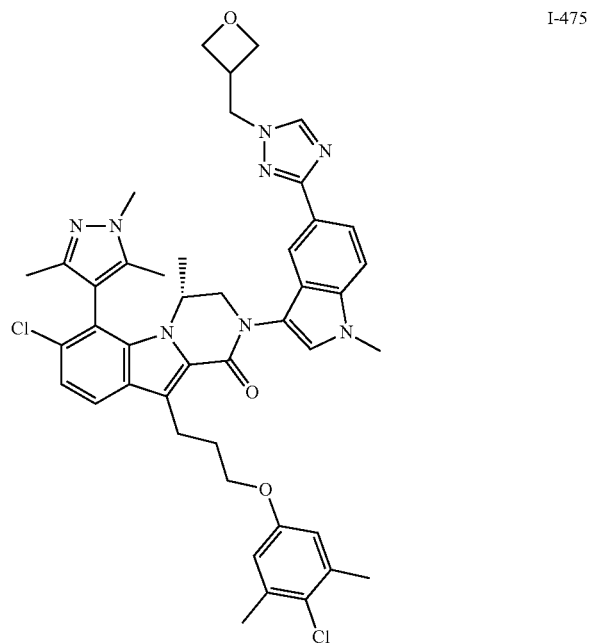
I-475
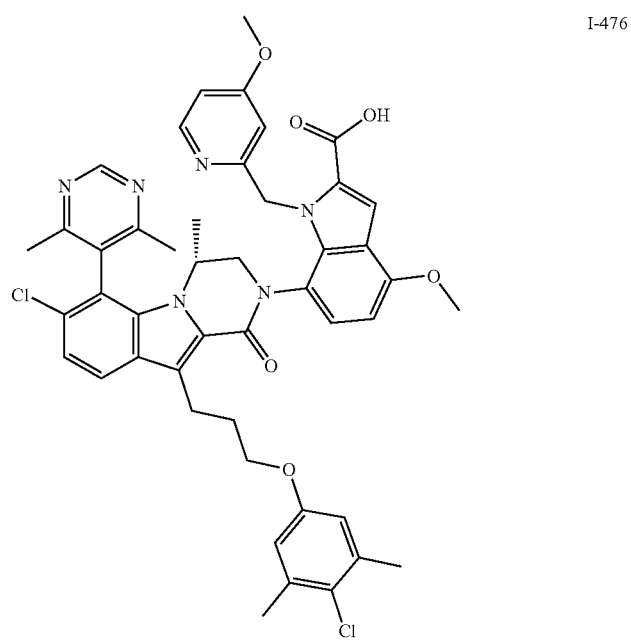
I-476

TABLE 1-continued
Exemplary compounds.
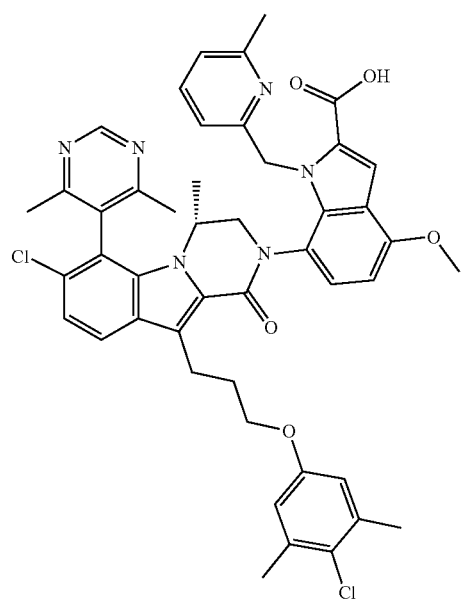 [SMILES: COc1ccc(N2C[C@@H](C)n3c(c(CCCOc4cc(C)c(Cl)c(C)c4)c4ccc(Cl)c(-c5c(C)ncnc5C)c43)C2=O)c2c1cc(C(=O)O)n2Cc1cccc(C)n1]
I-477
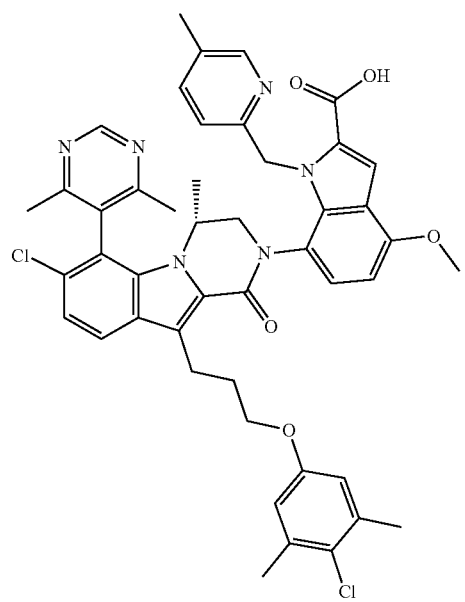 [SMILES: COc1ccc(N2C[C@@H](C)n3c(c(CCCOc4cc(C)c(Cl)c(C)c4)c4ccc(Cl)c(-c5c(C)ncnc5C)c43)C2=O)c2c1cc(C(=O)O)n2Cc1ccc(C)cn1]
I-478

TABLE 1-continued
Exemplary compounds.
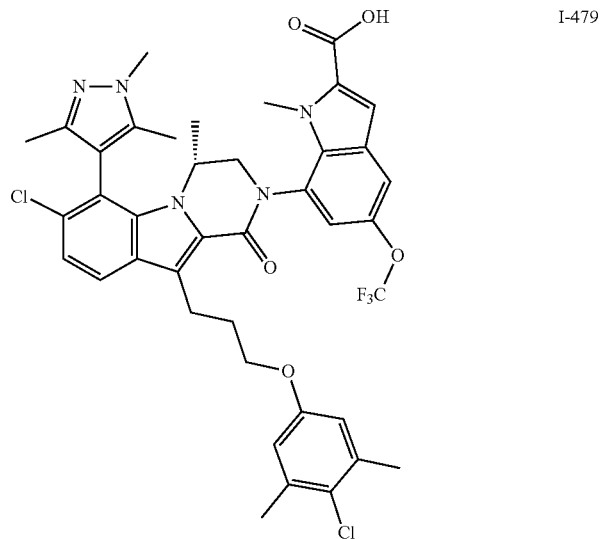
I-479
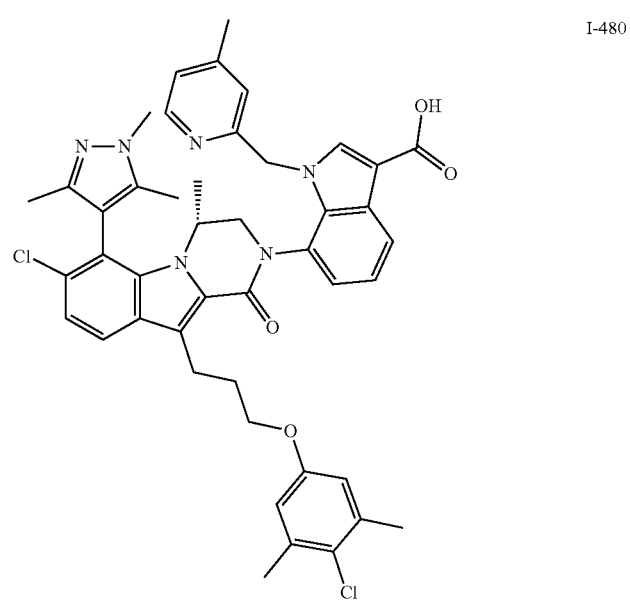
I-480

TABLE 1-continued
Exemplary compounds.
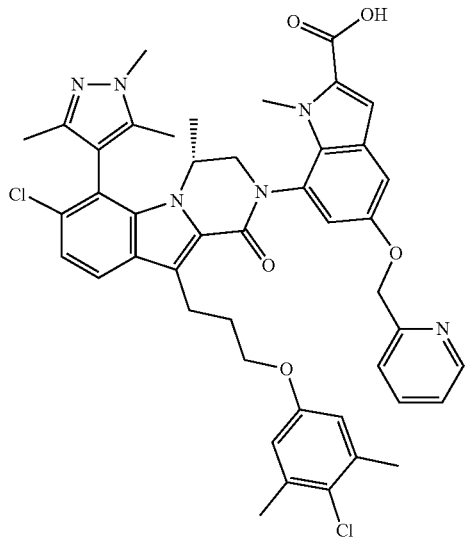 [SMILES: Cc1cc(OCCCc2c3n(c4c(-c5c(C)nn(C)c5C)c(Cl)ccc24)[C@H](C)CN(c2cc(OCc4ccccn4)cc4cc(C(=O)O)n(C)c24)C3=O)cc(C)c1Cl]
I-481
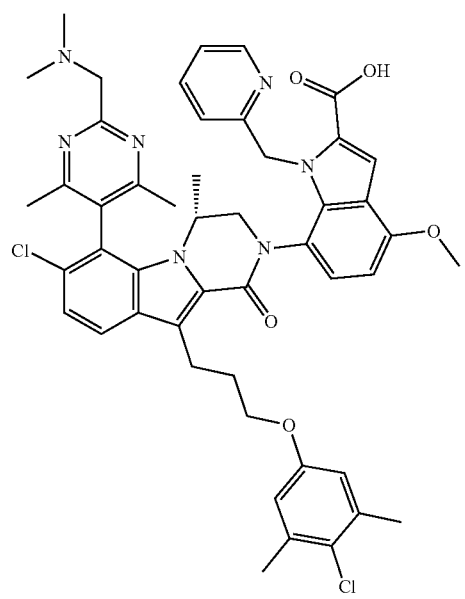 [SMILES: COc1ccc(N2C[C@@H](C)n3c(c(CCCOc4cc(C)c(Cl)c(C)c4)c4ccc(Cl)c(-c5c(C)nc(CN(C)C)nc5C)c43)C2=O)c2c1cc(C(=O)O)n2Cc1ccccn1]
I-482

423
424
TABLE 1-continued
Exemplary compounds.
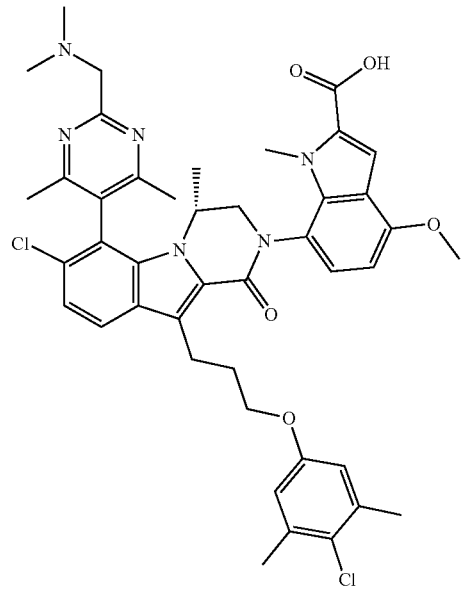 [SMILES: COc1ccc(N2C[C@@H](C)n3c(c(CCCOc4cc(C)c(Cl)c(C)c4)c4ccc(Cl)c(-c5c(C)nc(CN(C)C)nc5C)c43)C2=O)c2c1cc(C(=O)O)n2C]
I-483
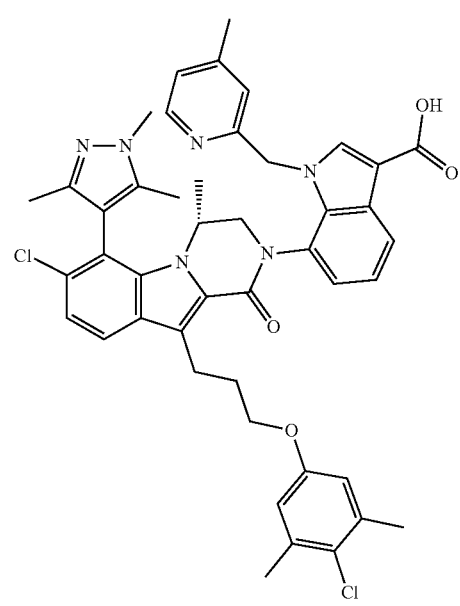 [SMILES: Cc1ccnc(Cn2cc(C(=O)O)c3cccc(N4C[C@@H](C)n5c(c(CCCOc6cc(C)c(Cl)c(C)c6)c6ccc(Cl)c(-c7c(C)nn(C)c7C)c65)C4=O)c32)c1]
I-484

TABLE 1-continued
Exemplary compounds.
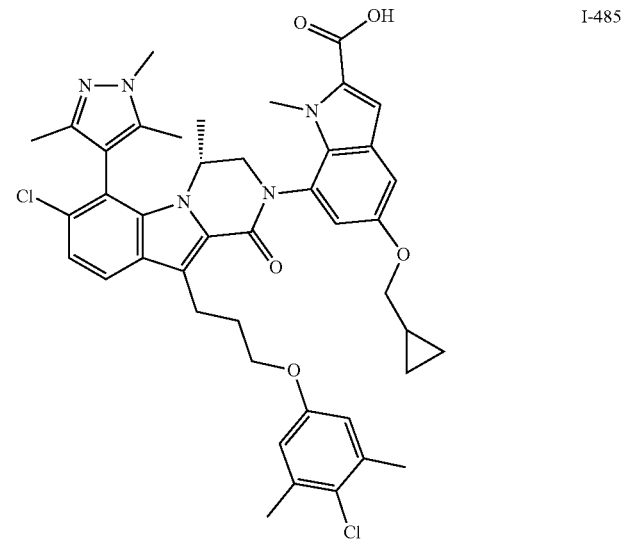
I-485
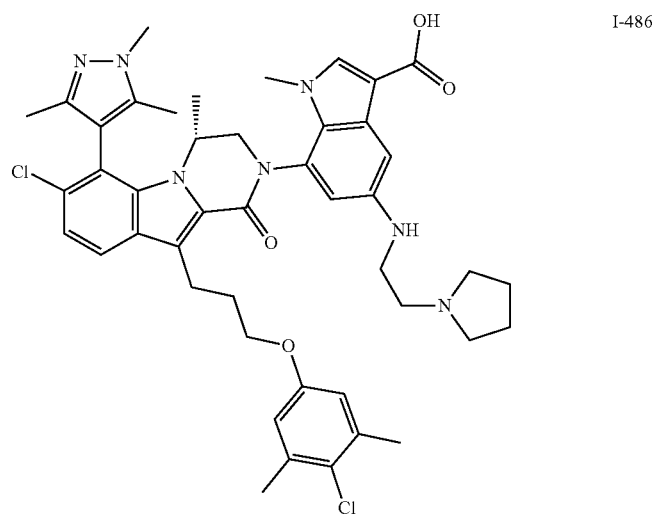
I-486
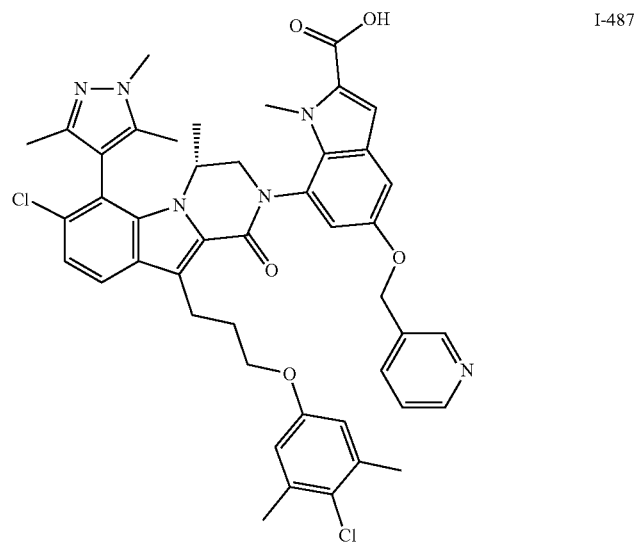
I-487

427
428
TABLE 1-continued
Exemplary compounds.
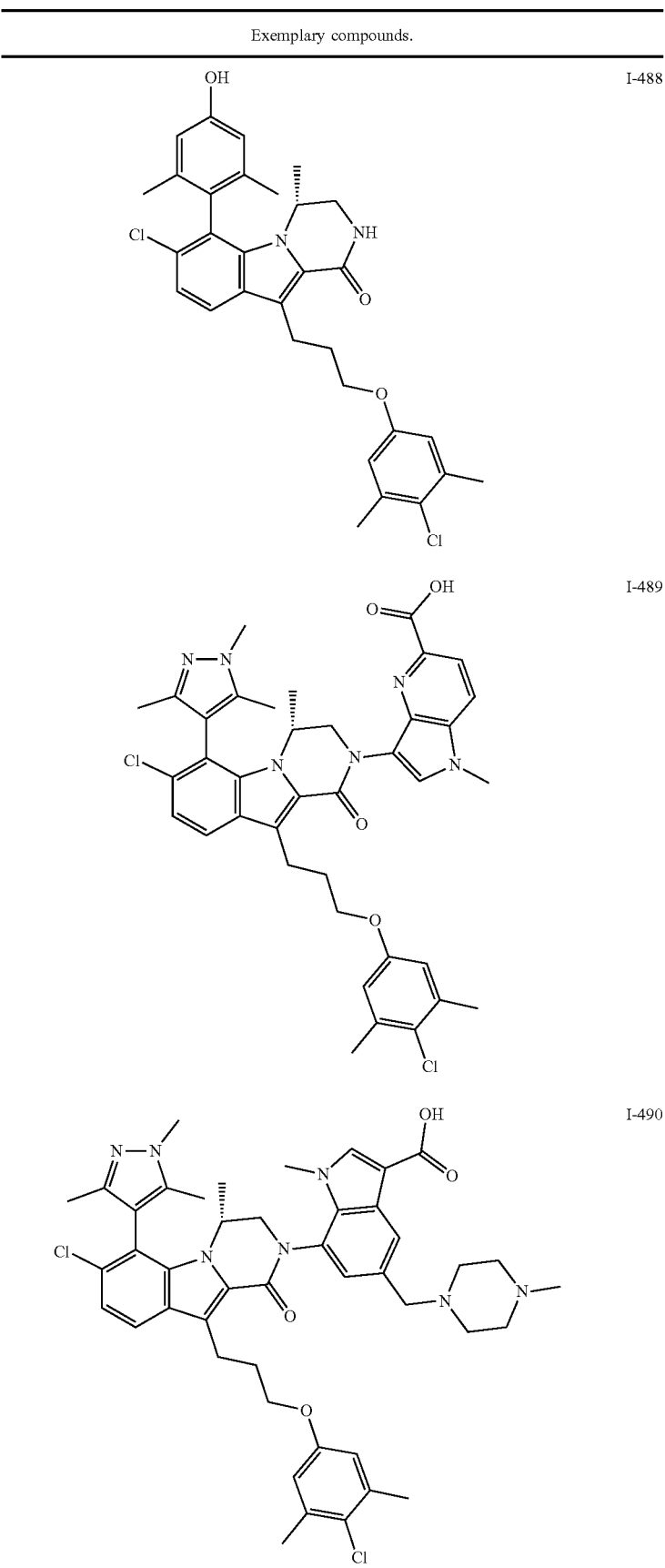
I-488
I-489
I-490

429
430
TABLE 1-continued
Exemplary compounds.
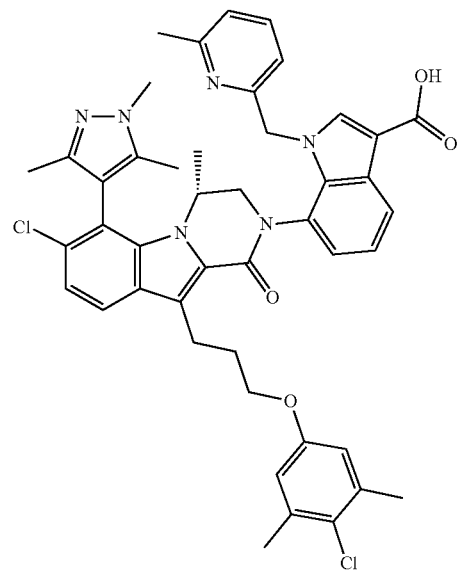 [SMILES: Cc1cccc(Cn2cc(C(=O)O)c3cccc(N4C[C@@H](C)n5c(c(CCCOc6cc(C)c(Cl)c(C)c6)c6ccc(Cl)c(-c7c(C)nn(C)c7C)c65)C4=O)c32)n1]
I-491
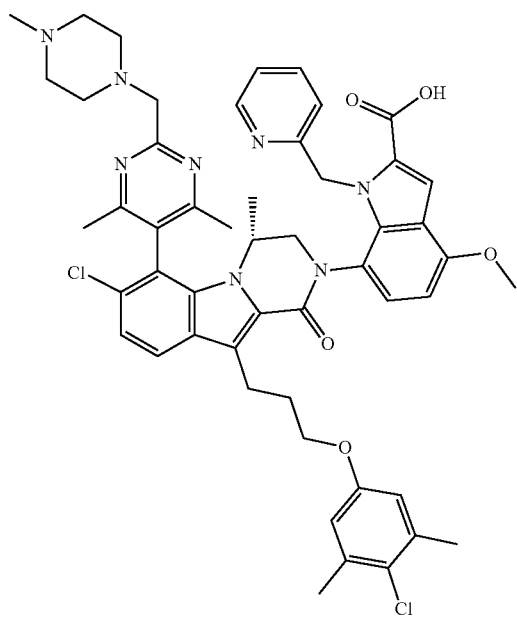
I-492

TABLE 1-continued
Exemplary compounds.
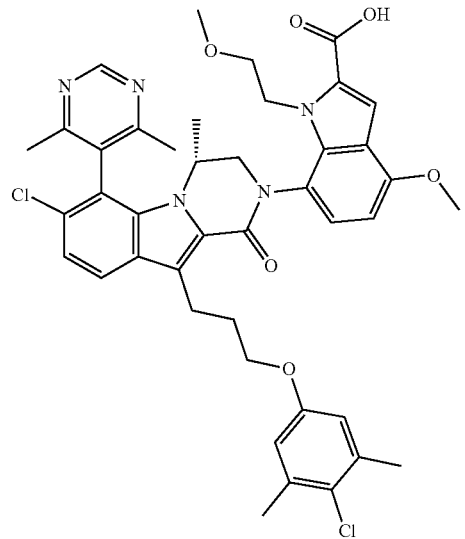 [SMILES: COCCn1c(C(=O)O)cc2c(OC)ccc(N3C[C@@H](C)n4c(c(CCCOc5cc(C)c(Cl)c(C)c5)c5ccc(Cl)c(-c6c(C)ncnc6C)c54)C3=O)c21]
I-493
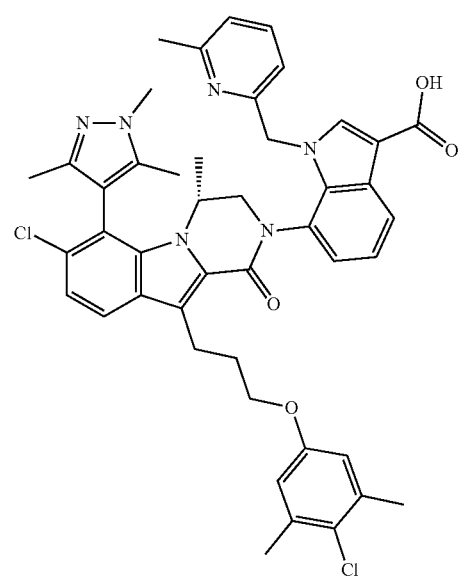 [SMILES: Cc1cccc(Cn2cc(C(=O)O)c3cccc(N4C[C@@H](C)n5c(c(CCCOc6cc(C)c(Cl)c(C)c6)c6ccc(Cl)c(-c7c(C)nn(C)c7C)c65)C4=O)c32)n1]
I-494

TABLE 1-continued
Exemplary compounds.
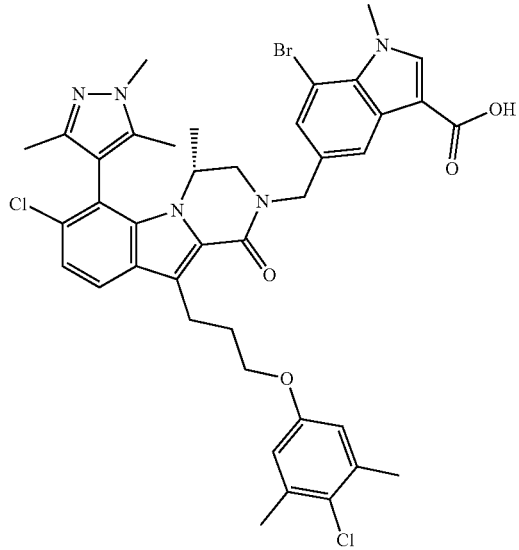 [SMILES: Cc1cc(OCCCc2c3n(c4c(-c5c(C)nn(C)c5C)c(Cl)ccc24)[C@H](C)CN(Cc2cc(Br)c4c(c2)c(C(=O)O)cn4C)C3=O)cc(C)c1Cl]
I-495
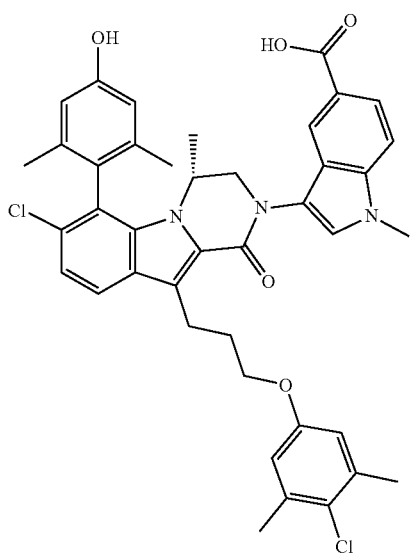 [SMILES: Cc1cc(OCCCc2c3n(c4c(-c5c(C)cc(O)cc5C)c(Cl)ccc24)[C@H](C)CN(c2cn(C)c4ccc(C(=O)O)cc24)C3=O)cc(C)c1Cl]
I-496

TABLE 1-continued
Exemplary compounds.
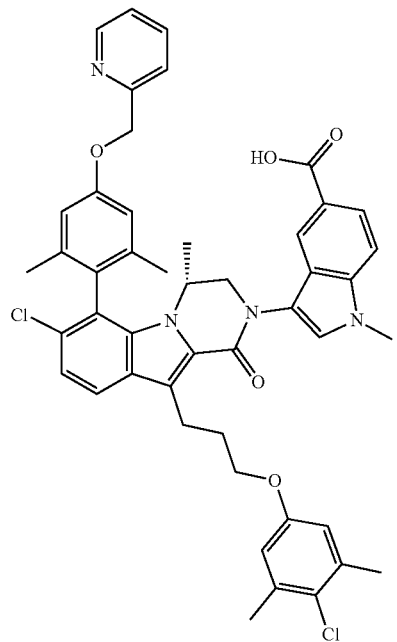 [SMILES: Cc1cc(OCCCc2c3n(c4c(-c5c(C)cc(OCc6ccccn6)cc5C)c(Cl)ccc24)[C@H](C)CN(c2cn(C)c4ccc(C(=O)O)cc24)C3=O)cc(C)c1Cl]
I-497
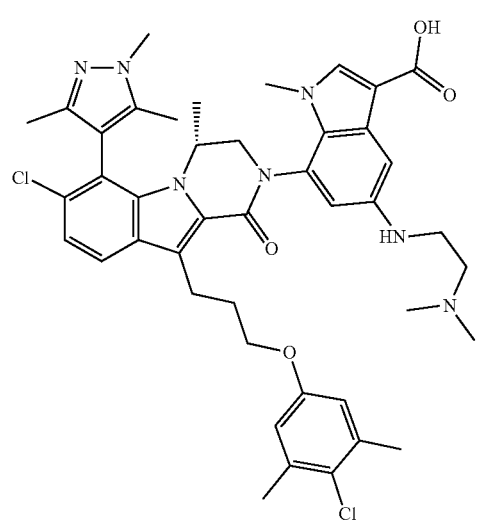 [SMILES: Cc1cc(OCCCc2c3n(c4c(-c5c(C)nn(C)c5C)c(Cl)ccc24)[C@H](C)CN(c2cc(NCCN(C)C)cc4c(C(=O)O)cn(C)c24)C3=O)cc(C)c1Cl]
I-498

TABLE 1-continued
Exemplary compounds.
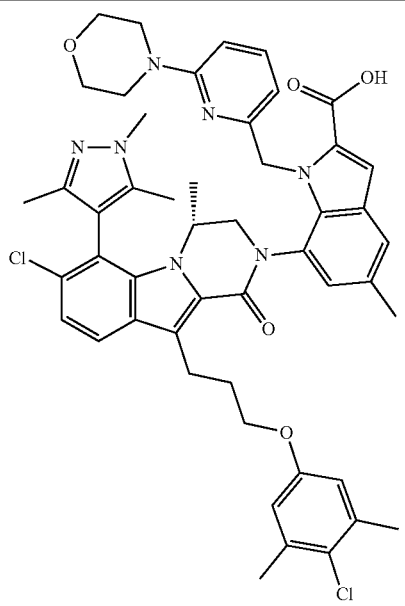
I-499
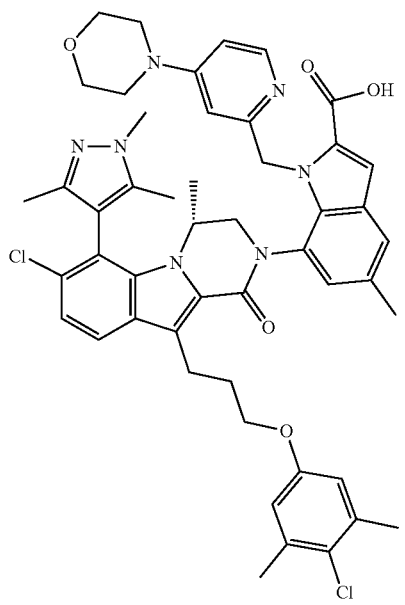 [SMILES: Cc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(=O)O)n2Cc1cc(N2CCOCC2)ccn1]
I-500

TABLE 1-continued
Exemplary compounds.
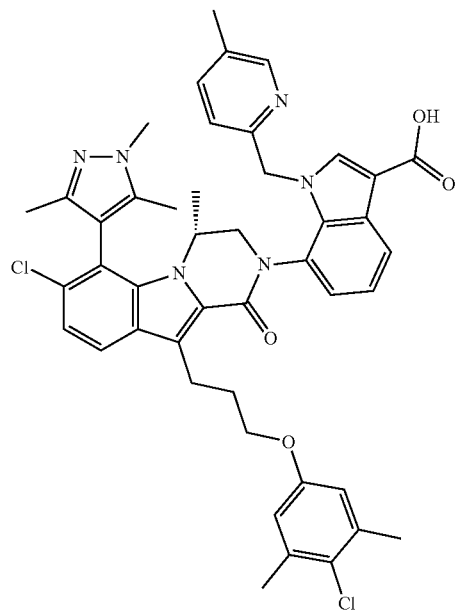 [SMILES: Cc1ccc(Cn2cc(C(=O)O)c3cccc(N4C[C@@H](C)n5c(c(CCCOc6cc(C)c(Cl)c(C)c6)c6ccc(Cl)c(-c7c(C)nn(C)c7C)c65)C4=O)c32)nc1]
I-501
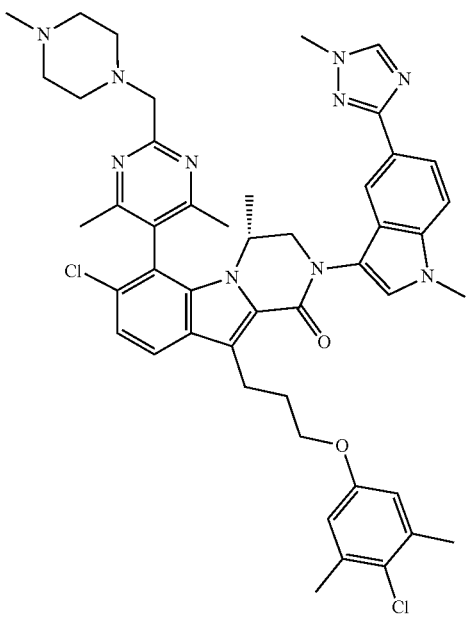
I-502

TABLE 1-continued
Exemplary compounds.
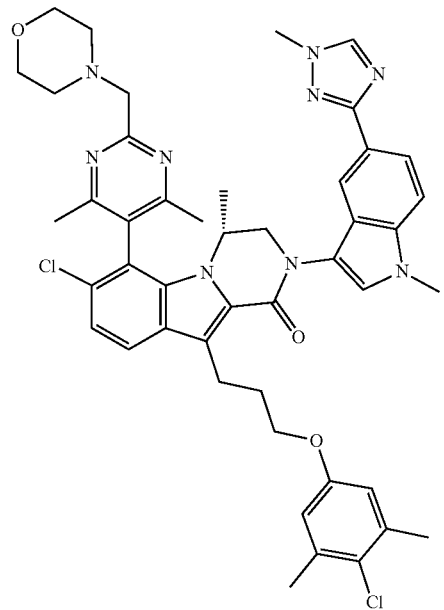 [SMILES: Cc1cc(OCCCc2c3n(c4c(-c5c(C)nc(CN6CCOCC6)nc5C)c(Cl)ccc24)[C@H](C)CN(c2cn(C)c4ccc(-c5ncn(C)n5)cc24)C3=O)cc(C)c1Cl]
I-503
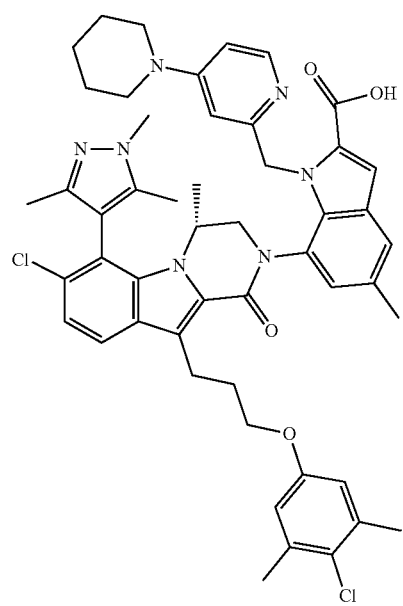
I-504

TABLE 1-continued
Exemplary compounds.
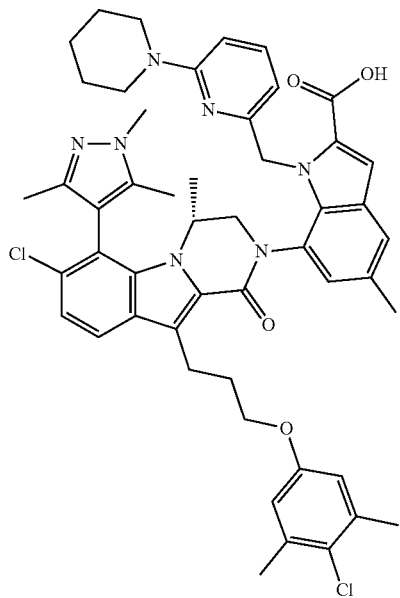 [SMILES: Cc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(=O)O)n2Cc1cccc(N2CCCCC2)n1]
I-505
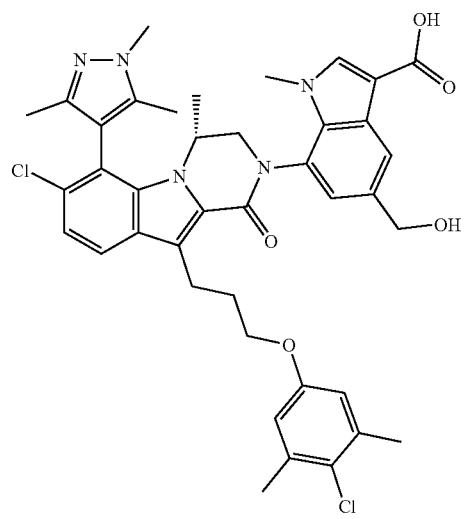 [SMILES: Cc1cc(OCCCc2c3n(c4c(-c5c(C)nn(C)c5C)c(Cl)ccc24)[C@H](C)CN(c2cc(CO)cc4c(C(=O)O)cn(C)c24)C3=O)cc(C)c1Cl]
I-506

TABLE 1-continued
Exemplary compounds.
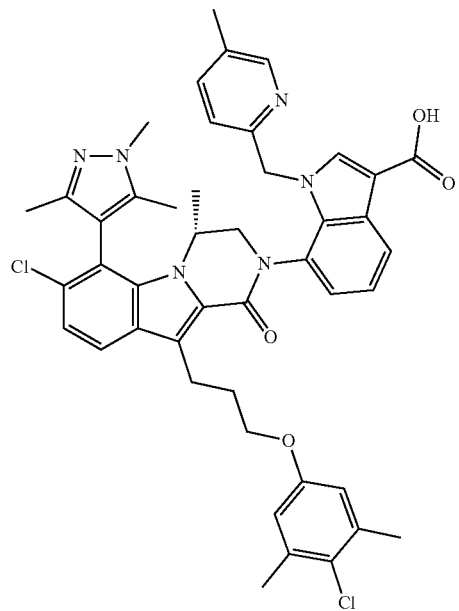 [SMILES: Cc1ccc(Cn2cc(C(=O)O)c3cccc(N4C[C@@H](C)n5c(c(CCCOc6cc(C)c(Cl)c(C)c6)c6ccc(Cl)c(-c7c(C)nn(C)c7C)c65)C4=O)c32)nc1]
I-507
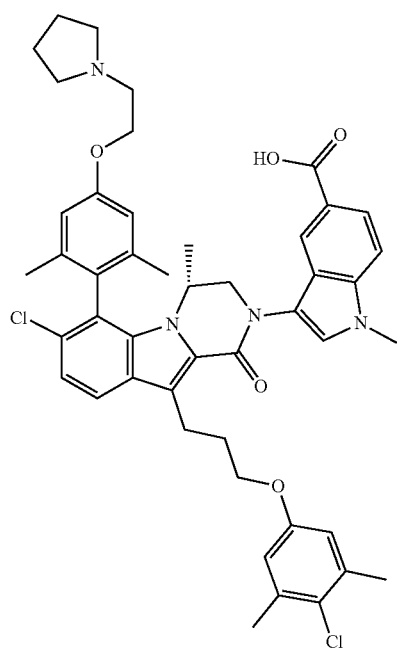 [SMILES: Cc1cc(OCCCc2c3n(c4c(-c5c(C)cc(OCCN6CCCC6)cc5C)c(Cl)ccc24)[C@H](C)CN(c2cn(C)c4ccc(C(=O)O)cc24)C3=O)cc(C)c1Cl]
I-508

TABLE 1-continued
Exemplary compounds.
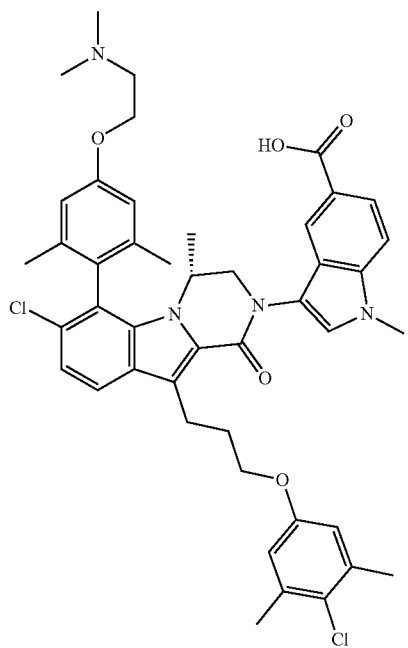 [SMILES: Cc1cc(OCCCc2c3n(c4c(-c5c(C)cc(OCCN(C)C)cc5C)c(Cl)ccc24)[C@H](C)CN(c2cn(C)c4ccc(C(=O)O)cc24)C3=O)cc(C)c1Cl]
I-509
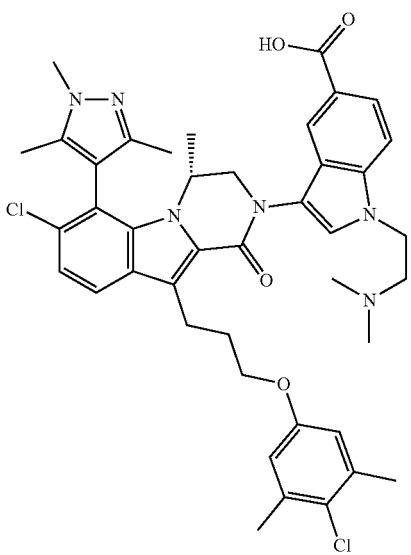 [SMILES: Cc1cc(OCCCc2c3n(c4c(-c5c(C)nn(C)c5C)c(Cl)ccc24)[C@H](C)CN(c2cn(CCN(C)C)c4ccc(C(=O)O)cc24)C3=O)cc(C)c1Cl]
I-510

TABLE 1-continued
Exemplary compounds.
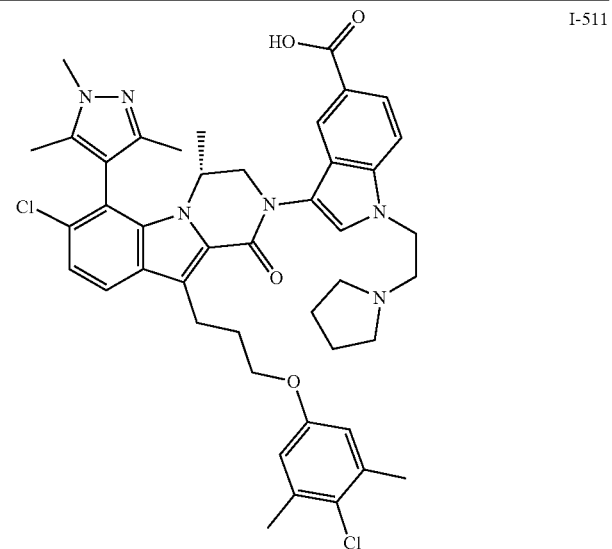
I-511
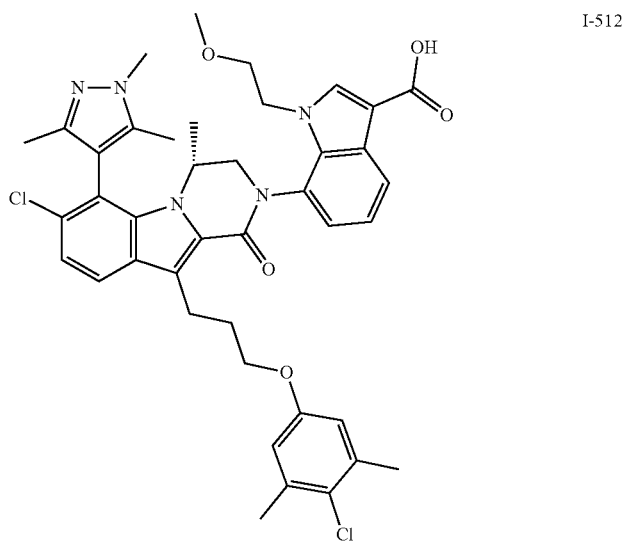
I-512
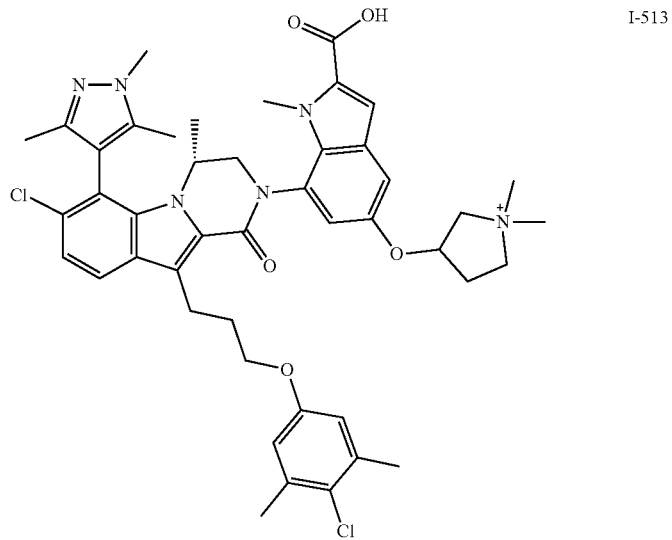
I-513

451
TABLE 1-continued
Exemplary compounds.
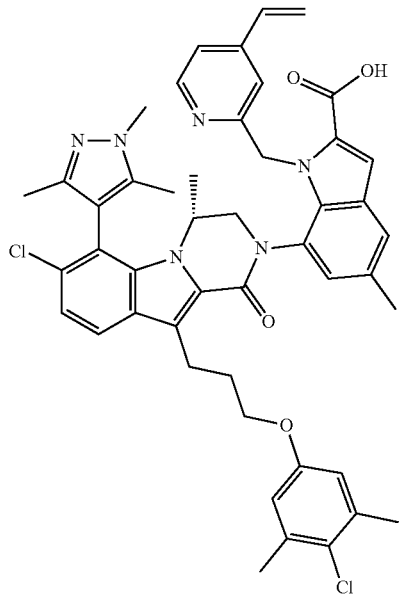 [SMILES: C=Cc1ccnc(Cn2c(C(=O)O)cc3cc(C)cc(N4C[C@@H](C)n5c(c(CCCOc6cc(C)c(Cl)c(C)c6)c6ccc(Cl)c(-c7c(C)nn(C)c7C)c65)C4=O)c32)c1]
I-514
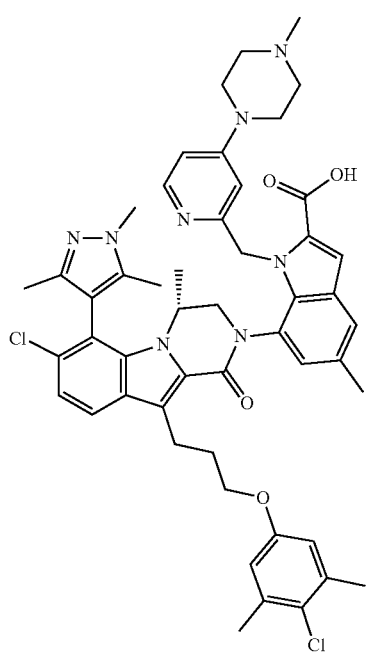 [SMILES: Cc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(=O)O)n2Cc1cc(N2CCN(C)CC2)ccn1]
I-515

TABLE 1-continued
Exemplary compounds.
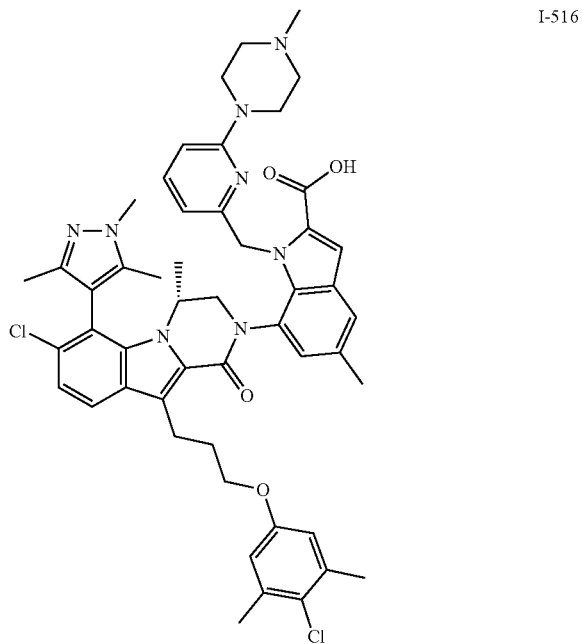
I-516
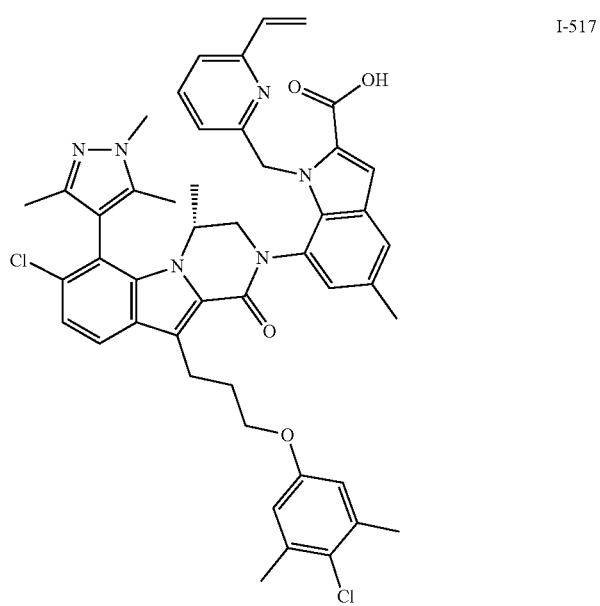
I-517

TABLE 1-continued
Exemplary compounds.
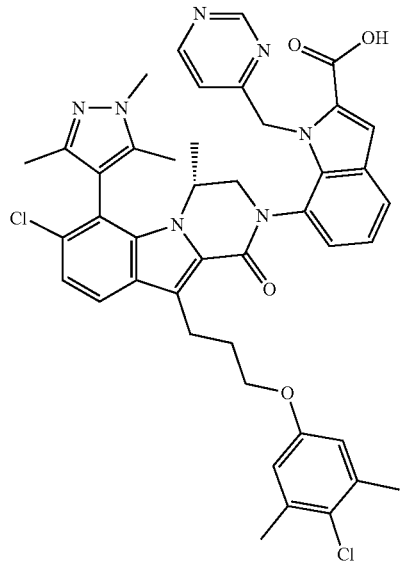 [SMILES: Cc1cc(OCCCc2c3n(c4c(-c5c(C)nn(C)c5C)c(Cl)ccc24)[C@H](C)CN(c2cccc4cc(C(=O)O)n(Cc5ccncn5)c24)C3=O)cc(C)c1Cl]
I-518
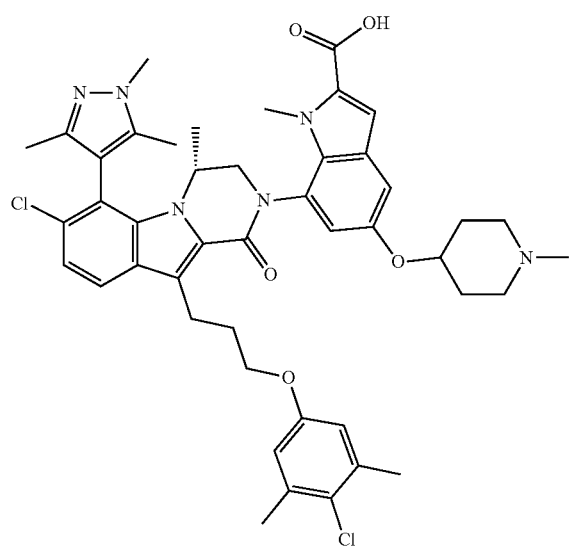 [SMILES: Cc1cc(OCCCc2c3n(c4c(-c5c(C)nn(C)c5C)c(Cl)ccc24)[C@H](C)CN(c2cc(OC4CCN(C)CC4)cc4cc(C(=O)O)n(C)c24)C3=O)cc(C)c1Cl]
I-519

TABLE 1-continued
Exemplary compounds.
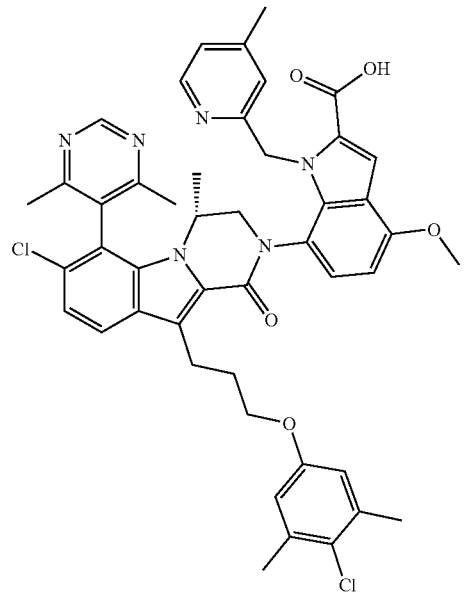 [SMILES: COc1ccc(N2C[C@@H](C)n3c(c(CCCOc4cc(C)c(Cl)c(C)c4)c4ccc(Cl)c(-c5c(C)ncnc5C)c43)C2=O)c2c1cc(C(=O)O)n2Cc1cc(C)ccn1]
I-520
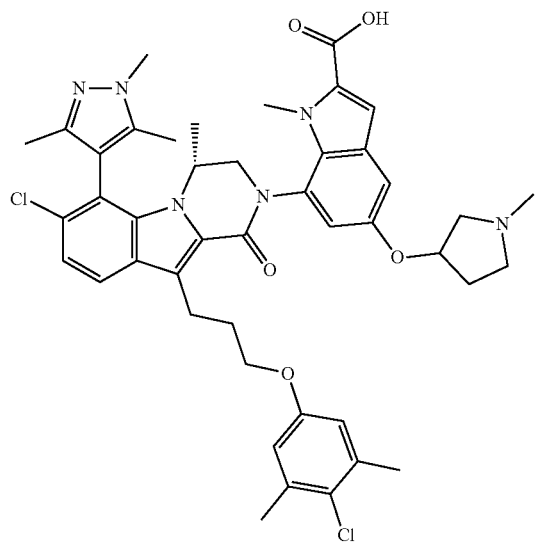 [SMILES: Cc1cc(OCCCc2c3n(c4c(-c5c(C)nn(C)c5C)c(Cl)ccc24)[C@H](C)CN(c2cc(OC4CCN(C)C4)cc4cc(C(=O)O)n(C)c24)C3=O)cc(C)c1Cl]
I-521

TABLE 1-continued
Exemplary compounds.
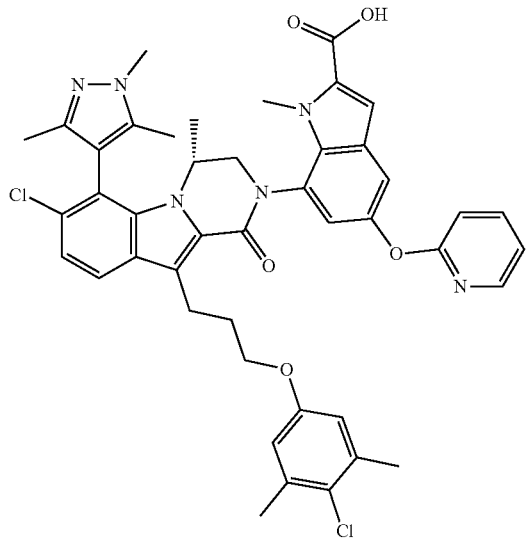 [SMILES: Cc1cc(OCCCc2c3n(c4c(-c5c(C)nn(C)c5C)c(Cl)ccc24)[C@H](C)CN(c2cc(Oc4ccccn4)cc4cc(C(=O)O)n(C)c24)C3=O)cc(C)c1Cl]
I-522
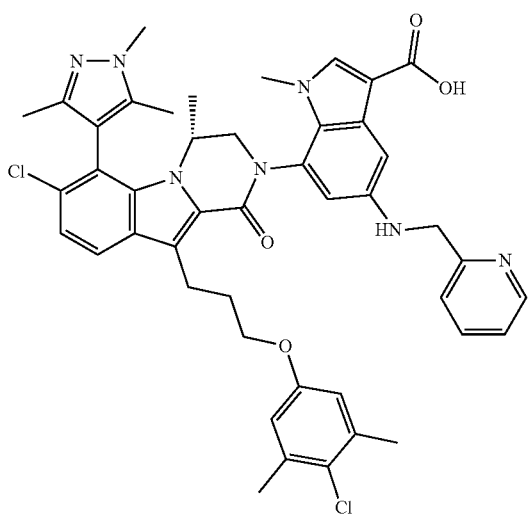 [SMILES: Cc1cc(OCCCc2c3n(c4c(-c5c(C)nn(C)c5C)c(Cl)ccc24)[C@H](C)CN(c2cc(NCc4ccccn4)cc4c(C(=O)O)cn(C)c24)C3=O)cc(C)c1Cl]
I-523

TABLE 1-continued
Exemplary compounds.
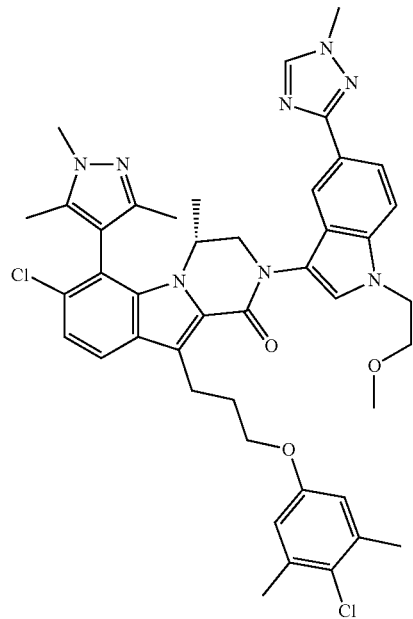 [SMILES: COCCn1cc(N2C[C@@H](C)n3c(c(CCCOc4cc(C)c(Cl)c(C)c4)c4ccc(Cl)c(-c5c(C)nn(C)c5C)c43)C2=O)c2cc(-c3ncn(C)n3)ccc21]
I-524
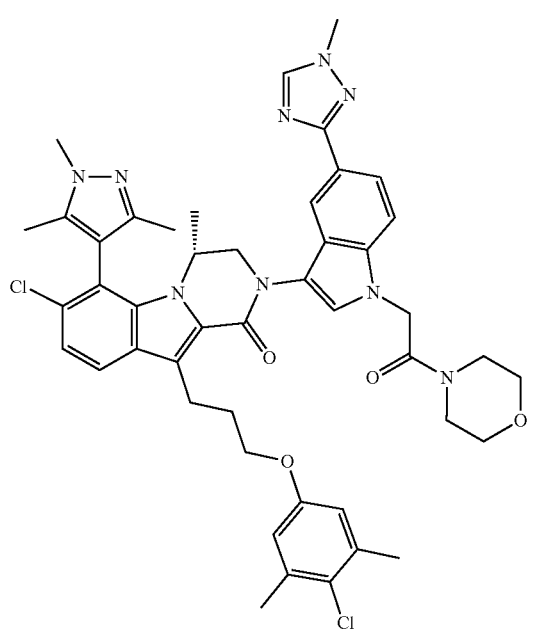 [SMILES: Cc1cc(OCCCc2c3n(c4c(-c5c(C)nn(C)c5C)c(Cl)ccc24)[C@H](C)CN(c2cn(CC(=O)N4CCOCC4)c4ccc(-c5ncn(C)n5)cc24)C3=O)cc(C)c1Cl]
I-525

TABLE 1-continued
Exemplary compounds.
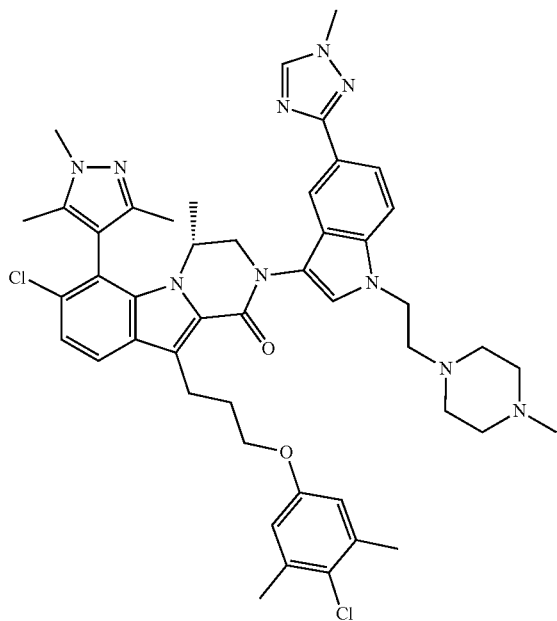
I-526
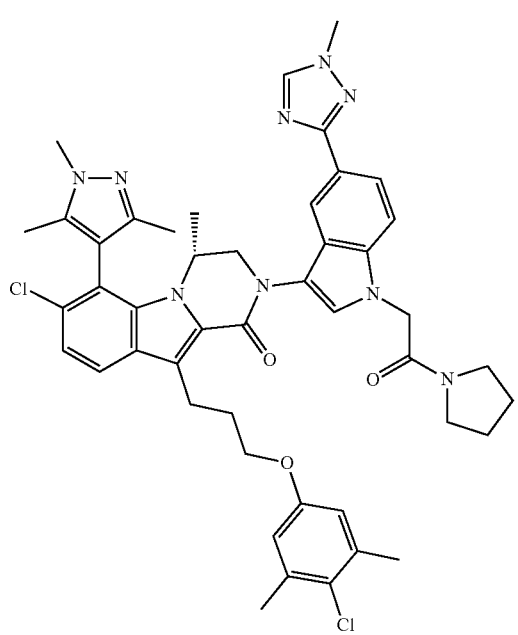 [SMILES: Cc1cc(OCCCc2c3n(c4c(-c5c(C)nn(C)c5C)c(Cl)ccc24)[C@H](C)CN(c2cn(CC(=O)N4CCCC4)c4ccc(-c5ncn(C)n5)cc24)C3=O)cc(C)c1Cl]
I-527

TABLE 1-continued
Exemplary compounds.
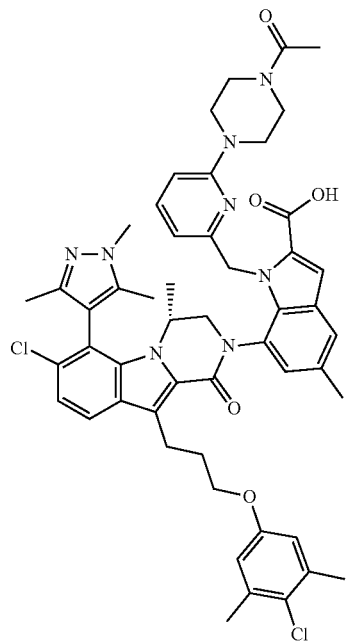 [SMILES: CC(=O)N1CCN(c2cccc(Cn3c(C(=O)O)cc4cc(C)cc(N5C[C@@H](C)n6c(c(CCCOc7cc(C)c(Cl)c(C)c7)c7ccc(Cl)c(-c8c(C)nn(C)c8C)c76)C5=O)c43)n2)CC1]
I-528
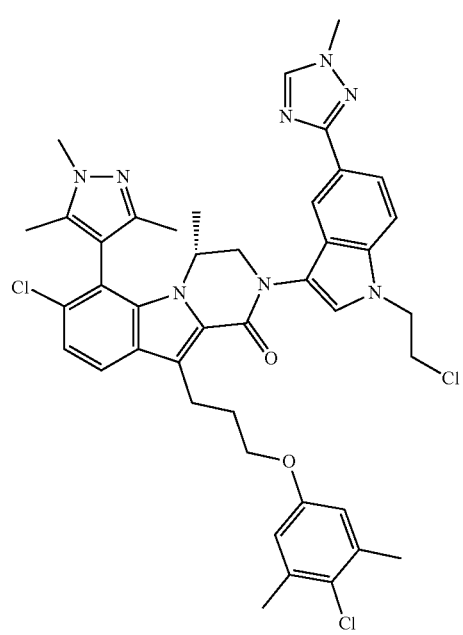 [SMILES: Cc1cc(OCCCc2c3n(c4c(-c5c(C)nn(C)c5C)c(Cl)ccc24)[C@H](C)CN(c2cn(CCCl)c4ccc(-c5ncn(C)n5)cc24)C3=O)cc(C)c1Cl]
I-529

TABLE 1-continued
Exemplary compounds.
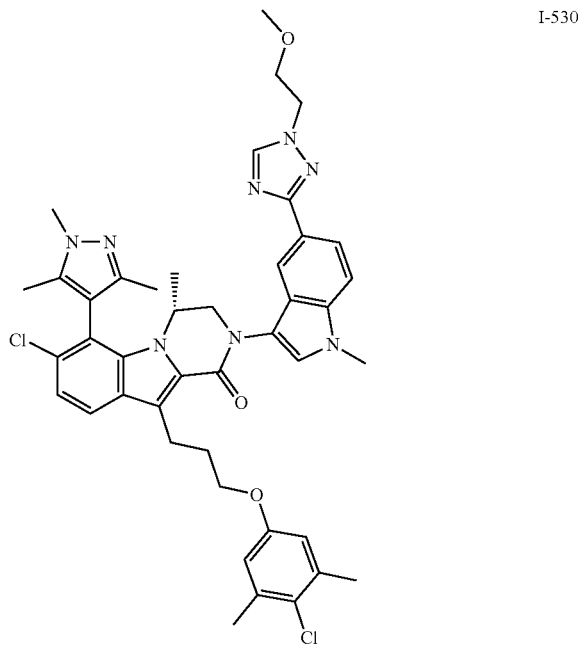
I-530
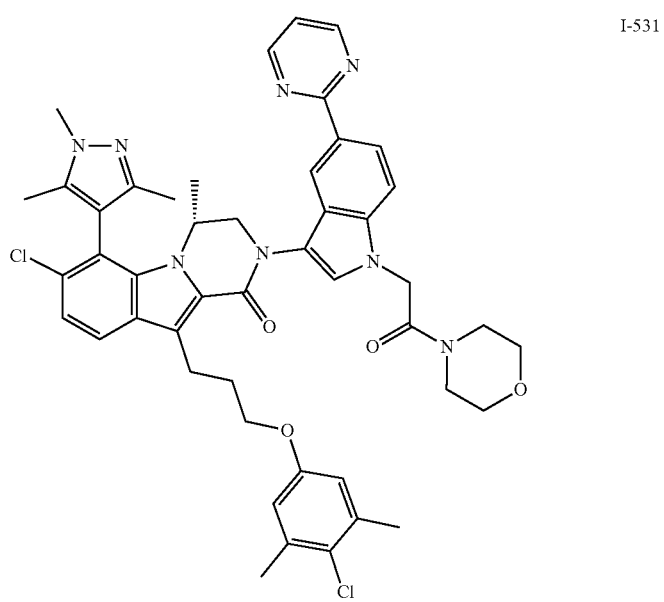
I-531

TABLE 1-continued
Exemplary compounds.
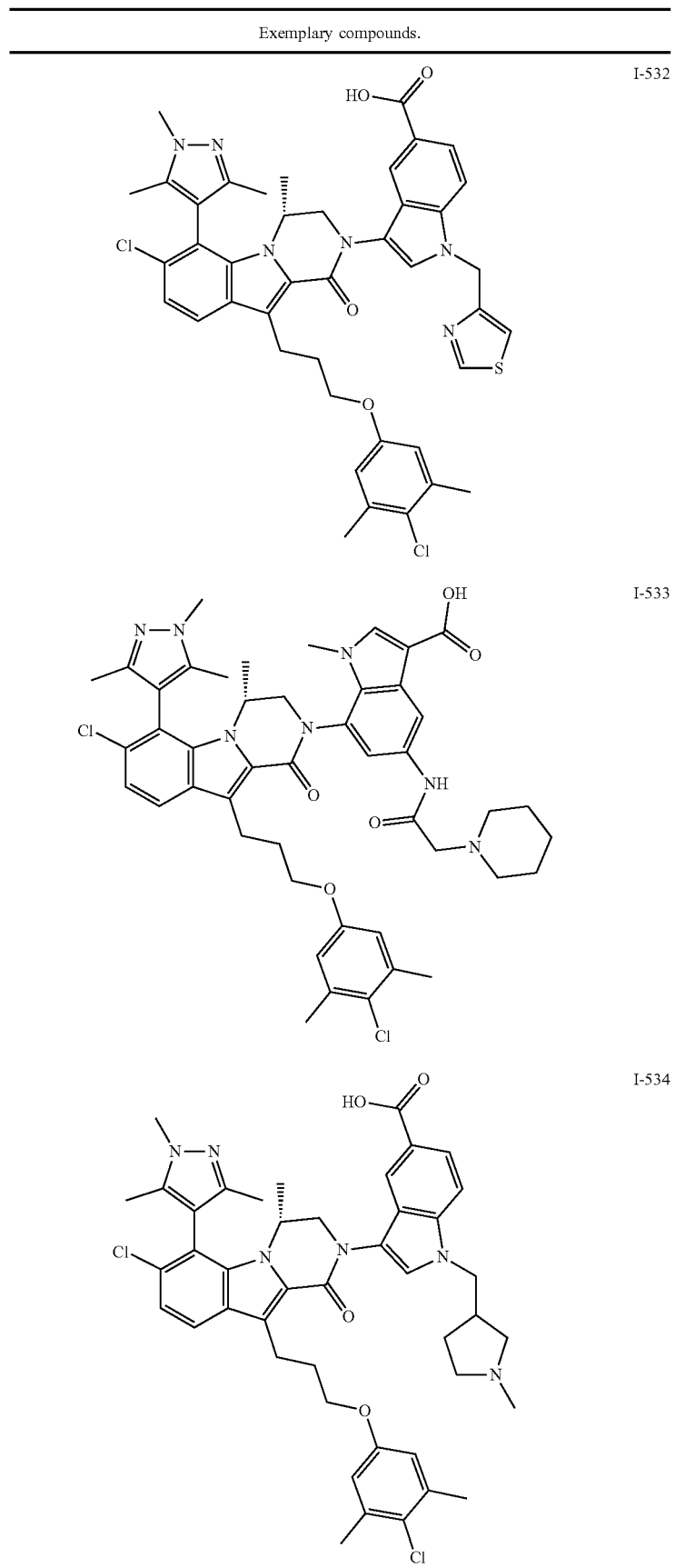
I-532
I-533
I-534

471
472
TABLE 1-continued
Exemplary compounds.
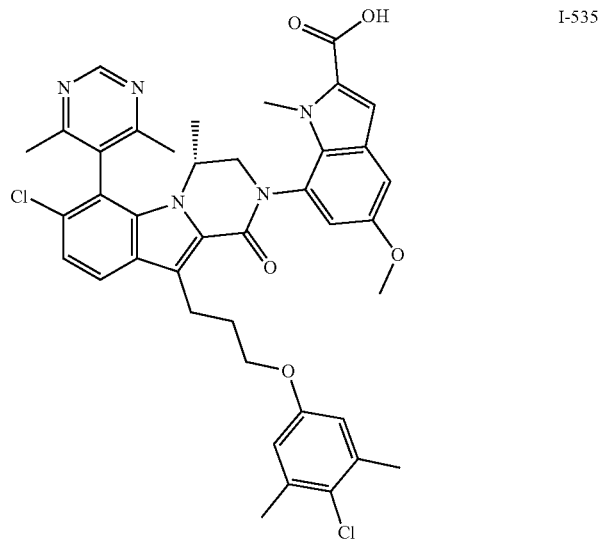
I-535
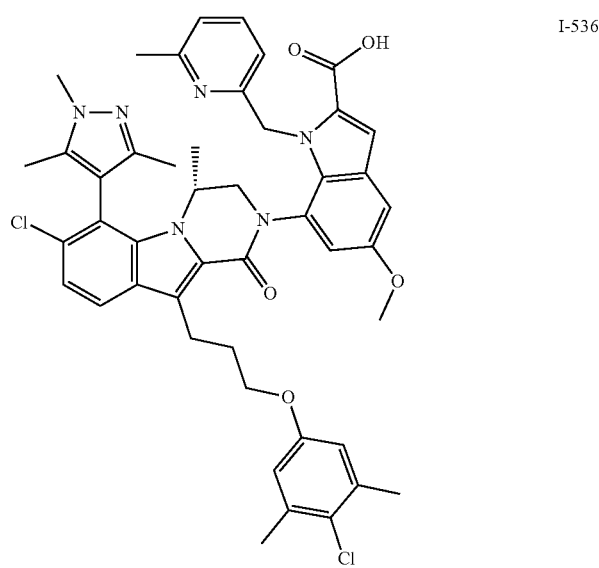
I-536

TABLE 1-continued
Exemplary compounds.
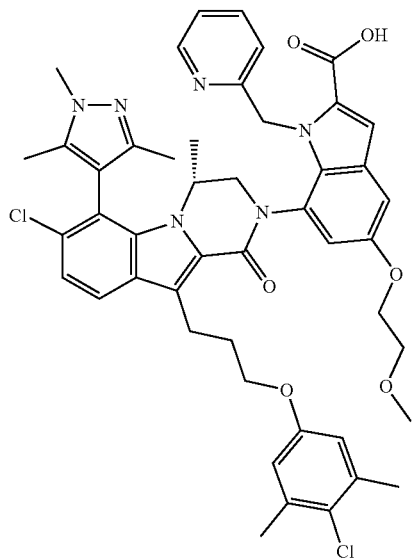
I-537
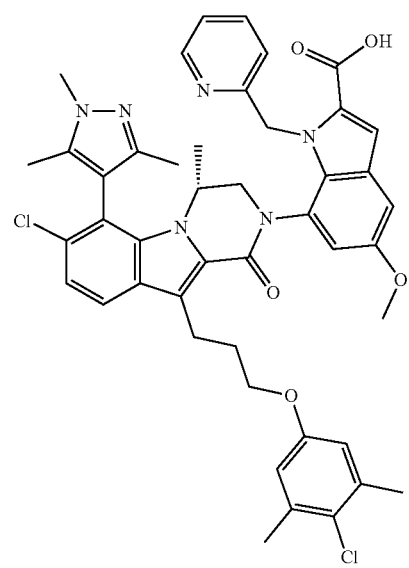
I-538

475
TABLE 1-continued
Exemplary compounds.
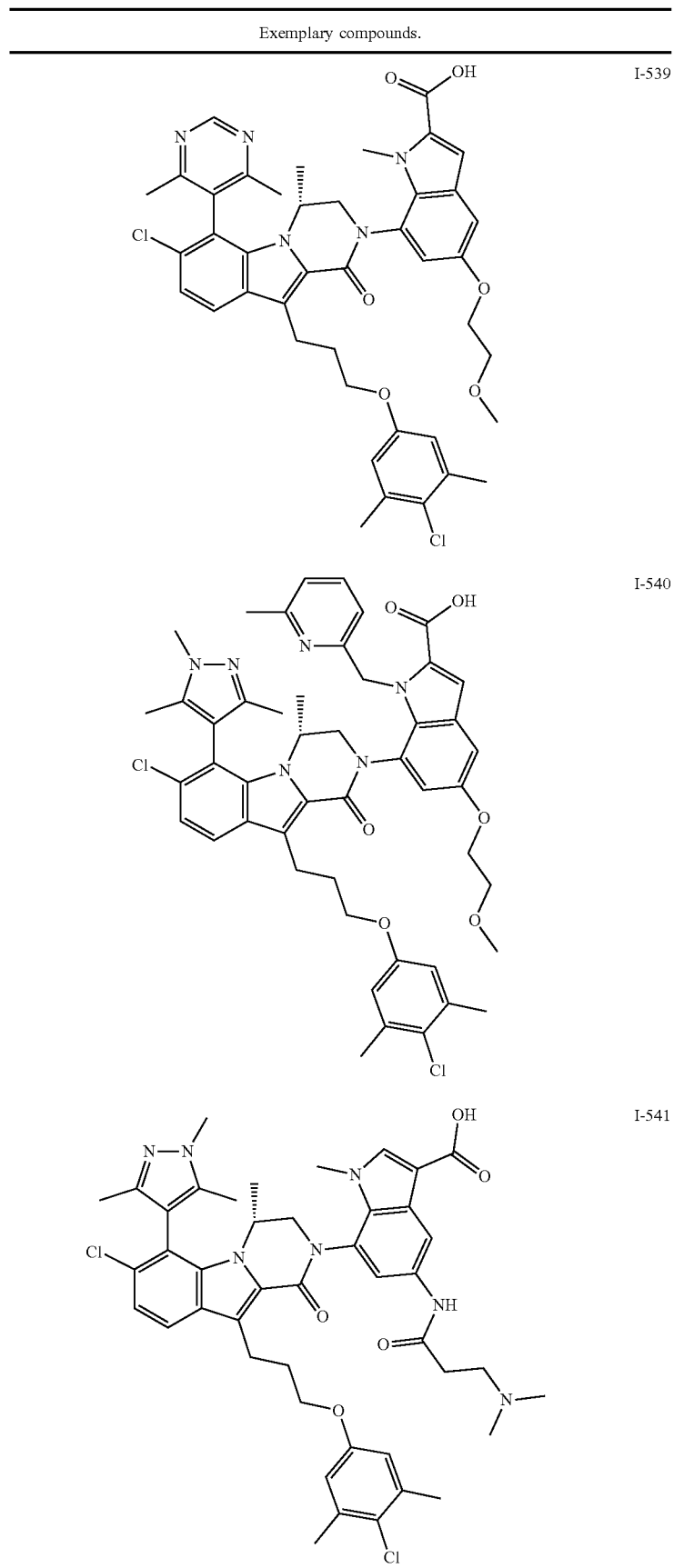
I-539
I-540
I-541
476

TABLE 1-continued
Exemplary compounds.
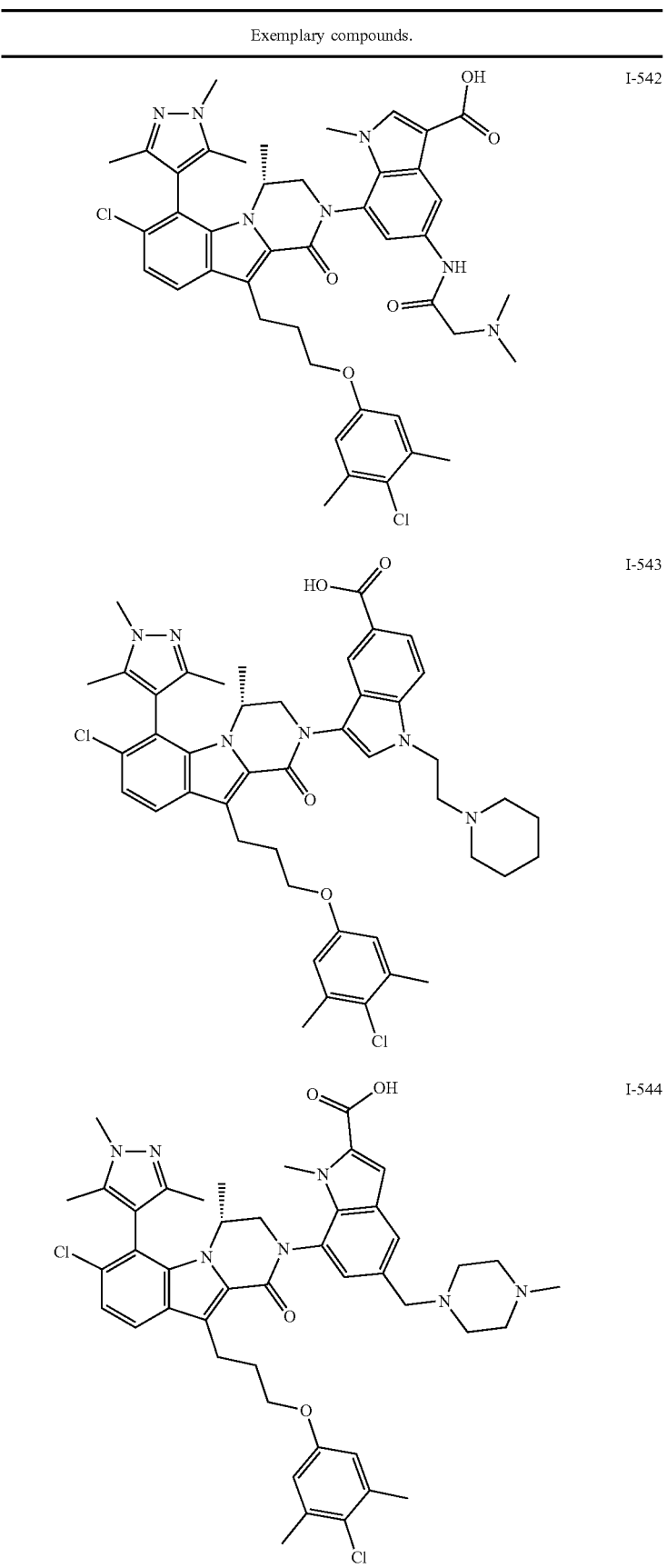

TABLE 1-continued
Exemplary compounds.
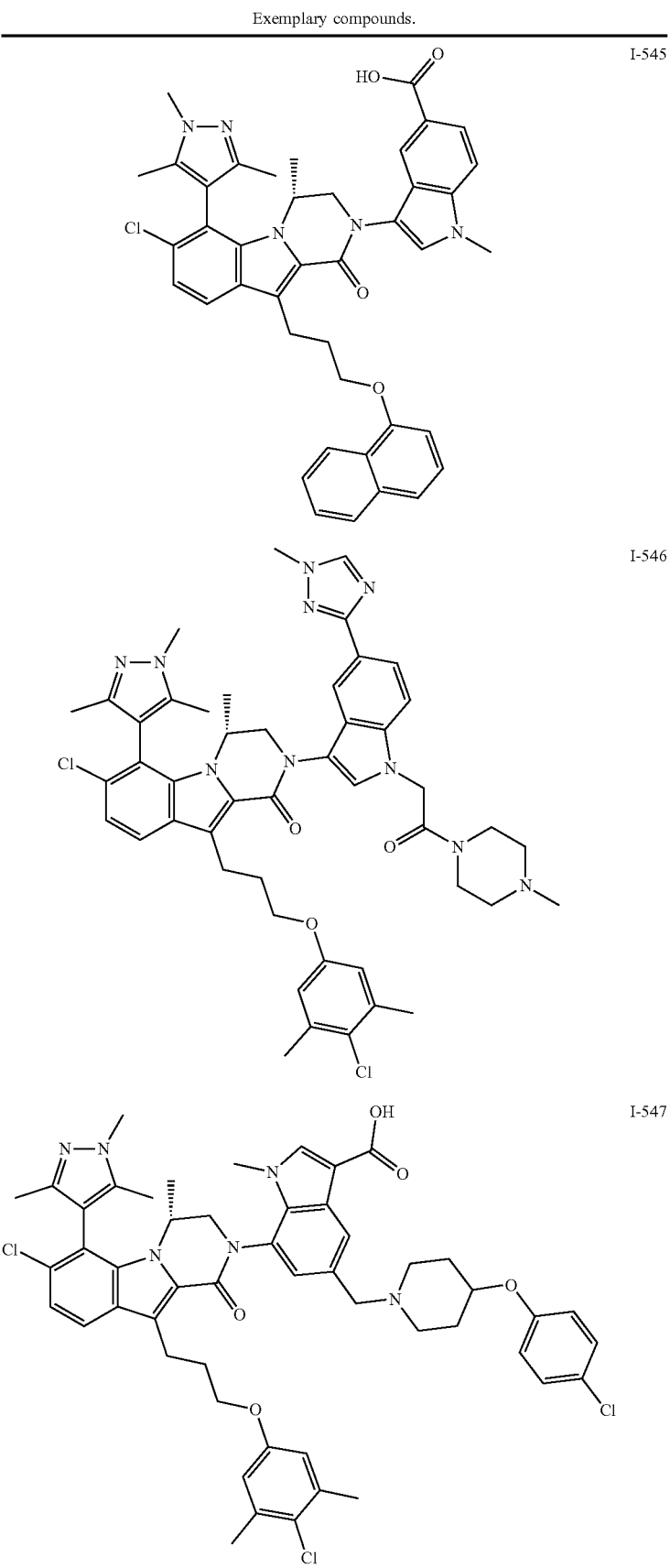
I-545
I-546
I-547

TABLE 1-continued
Exemplary compounds.
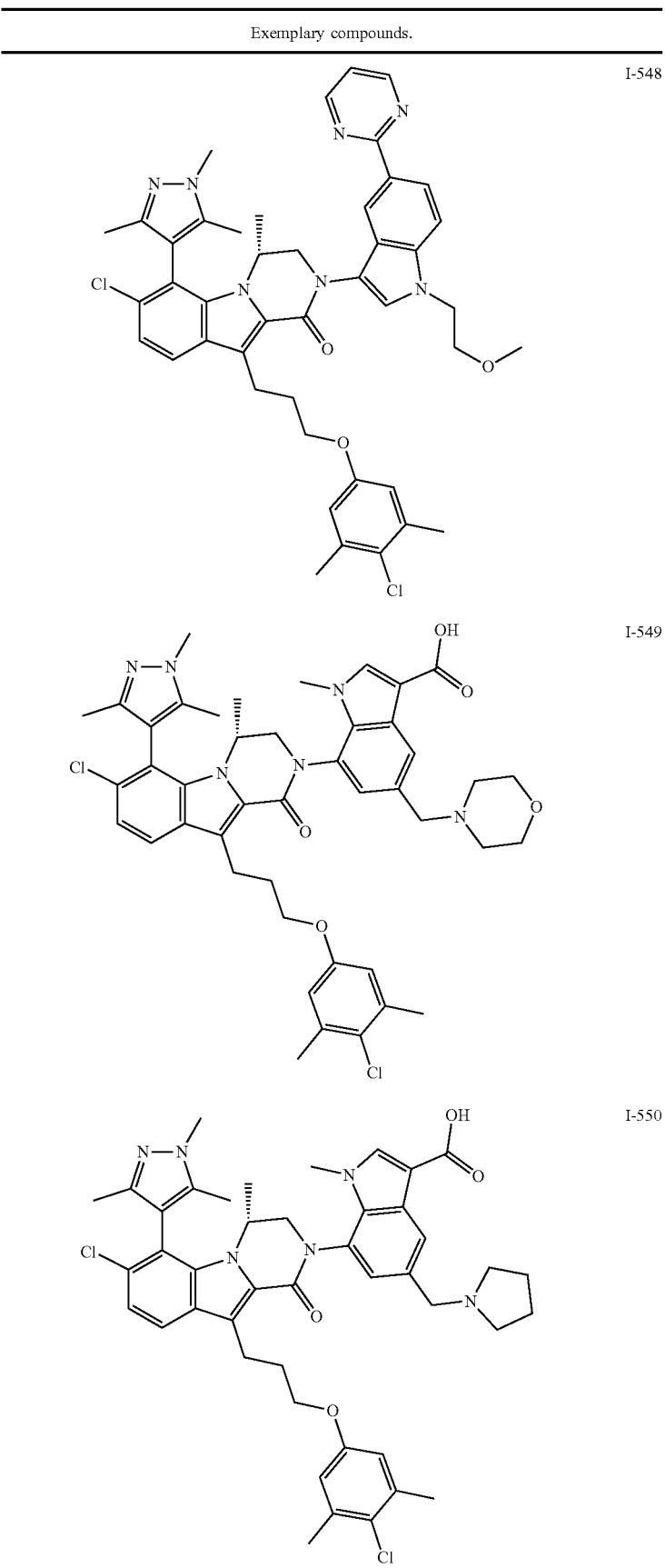
I-548
I-549
I-550

TABLE 1-continued
Exemplary compounds.
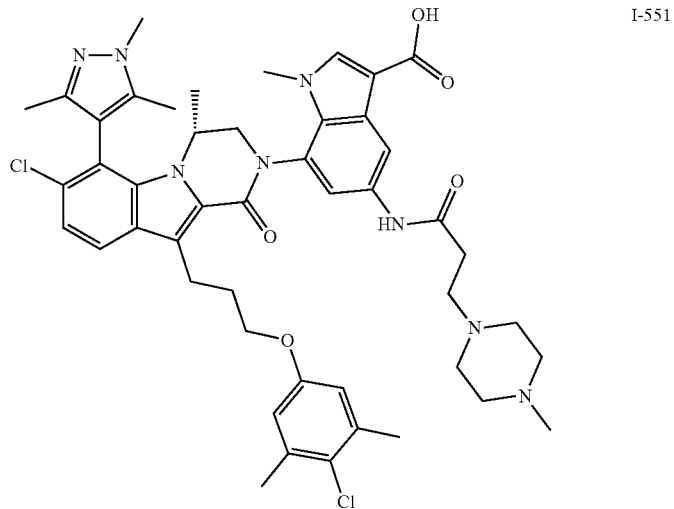
I-551
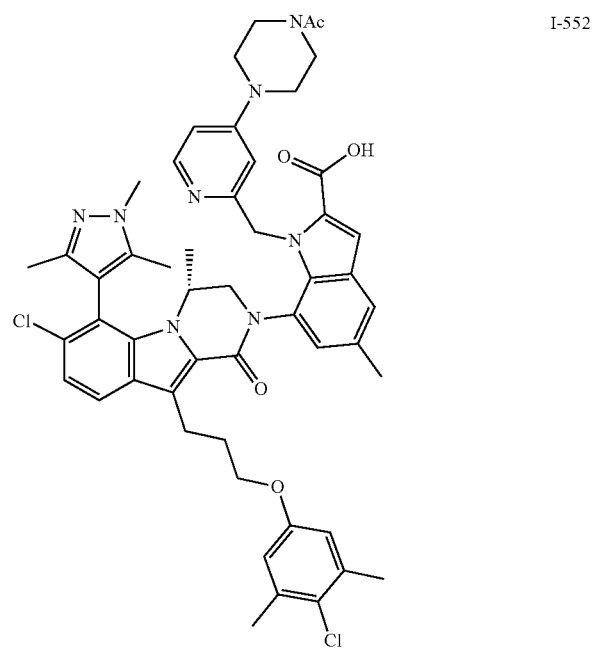
I-552

TABLE 1-continued
Exemplary compounds.
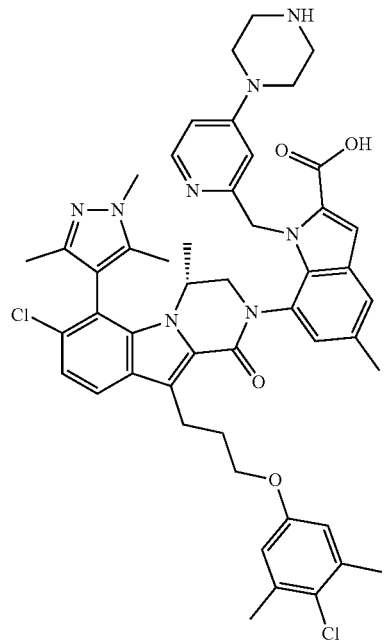
I-553
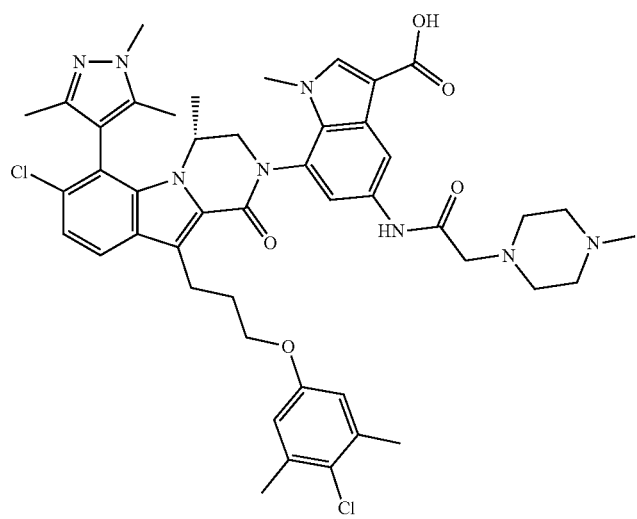
I-554

TABLE 1-continued
Exemplary compounds.
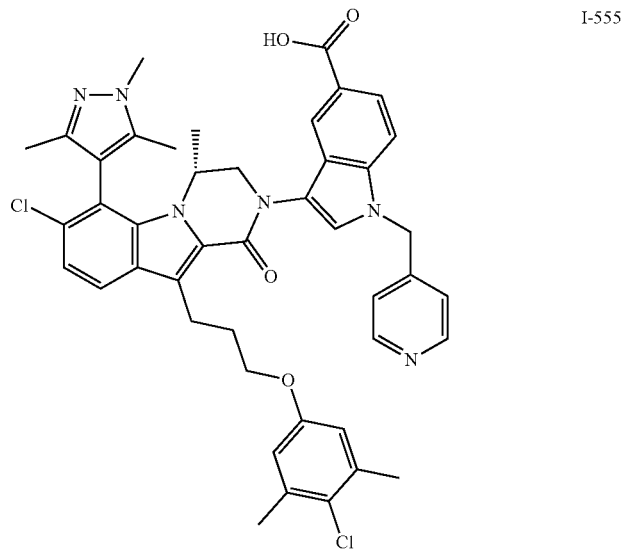
I-555
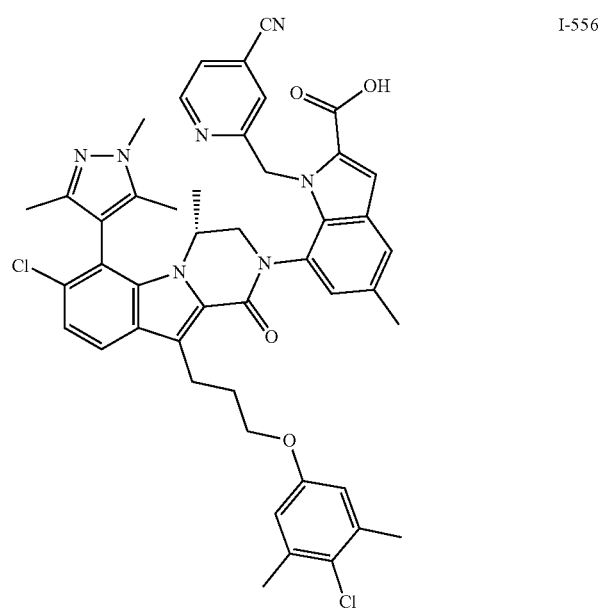
I-556

489
490
TABLE 1-continued
Exemplary compounds.
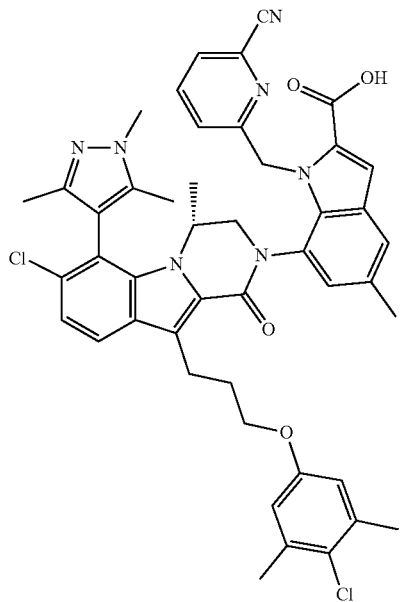
I-557
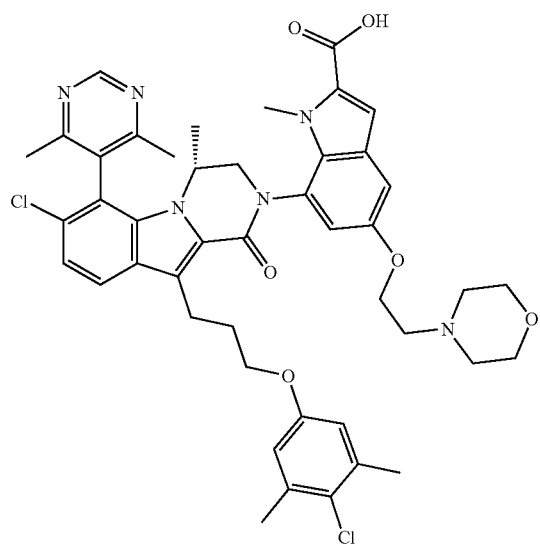 [SMILES: Cc1cc(OCCCc2c3n(c4c(-c5c(C)ncnc5C)c(Cl)ccc24)[C@H](C)CN(c2cc(OCCN4CCOCC4)cc4cc(C(=O)O)n(C)c24)C3=O)cc(C)c1Cl]
I-558

TABLE 1-continued
Exemplary compounds.
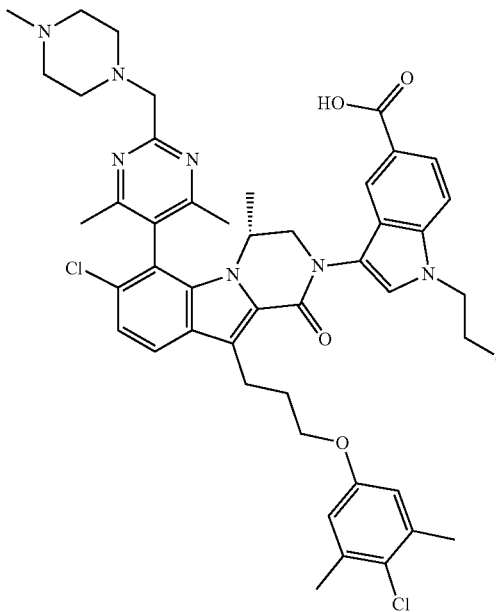
I-559
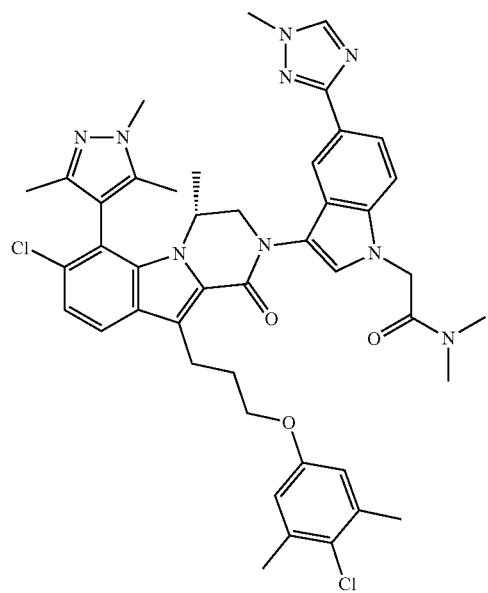
I-560

TABLE 1-continued
Exemplary compounds.
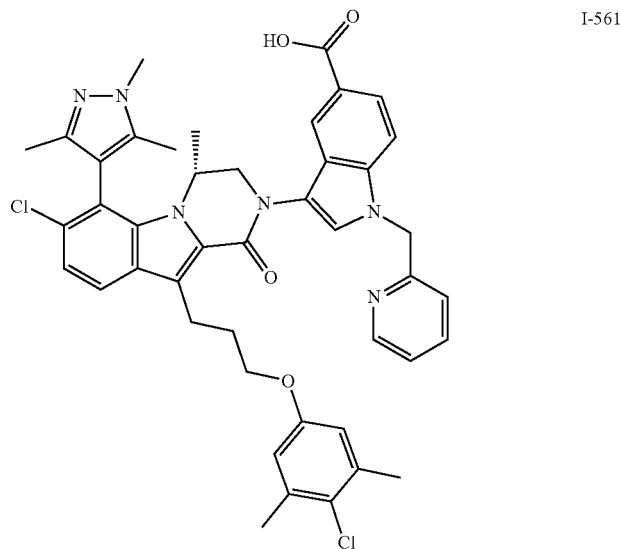
I-561
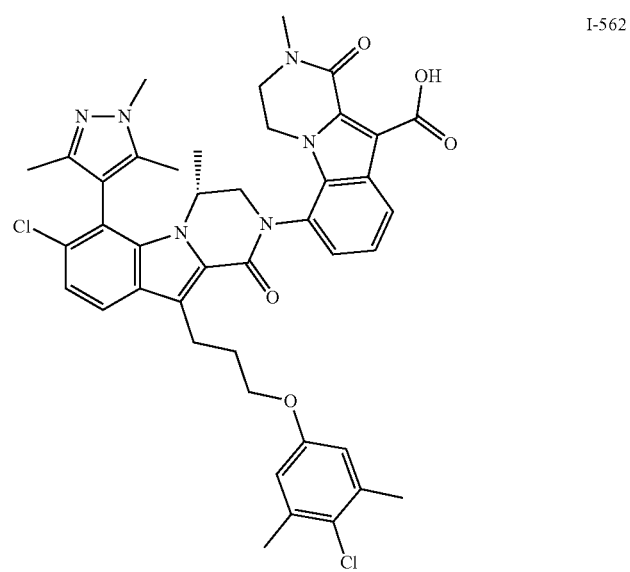
I-562

TABLE 1-continued
Exemplary compounds.
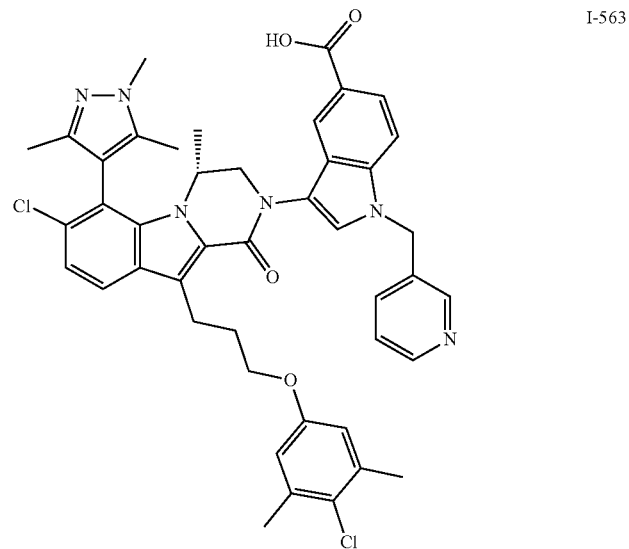
I-563
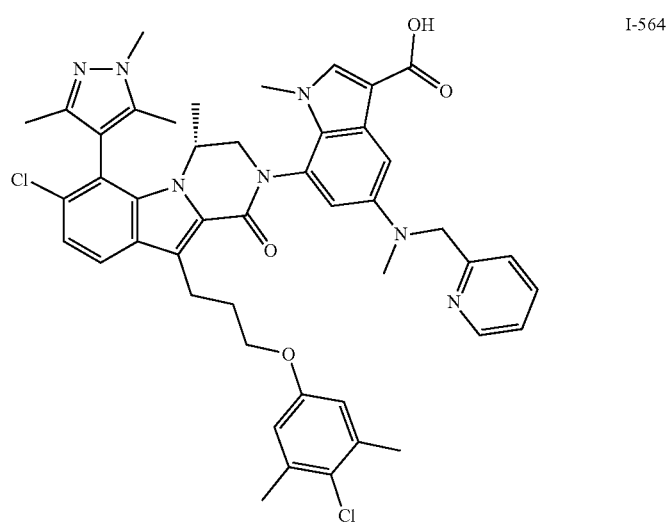
I-564

TABLE 1-continued
Exemplary compounds.
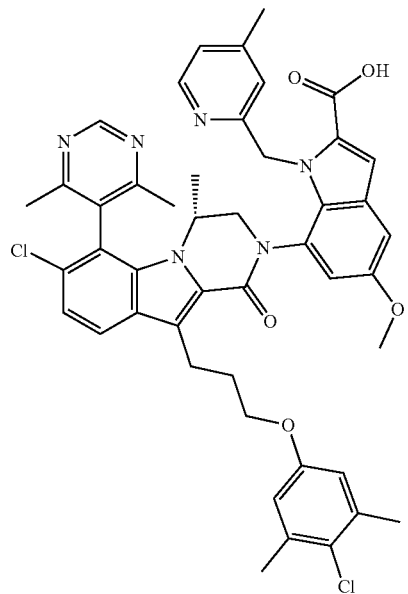 [SMILES: COc1cc(N2C[C@@H](C)n3c(c(CCCOc4cc(C)c(Cl)c(C)c4)c4ccc(Cl)c(-c5c(C)ncnc5C)c43)C2=O)c2c(c1)cc(C(=O)O)n2Cc1cc(C)ccn1]
I-565
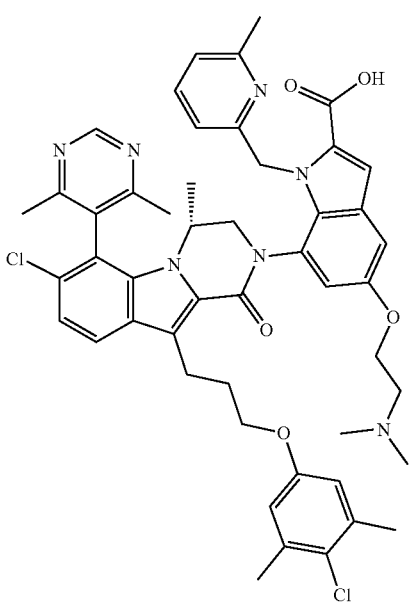 [SMILES: Cc1cccc(Cn2c(C(=O)O)cc3cc(OCCN(C)C)cc(N4C[C@@H](C)n5c(c(CCCOc6cc(C)c(Cl)c(C)c6)c6ccc(Cl)c(-c7c(C)ncnc7C)c65)C4=O)c32)n1]
I-566

TABLE 1-continued
Exemplary compounds.
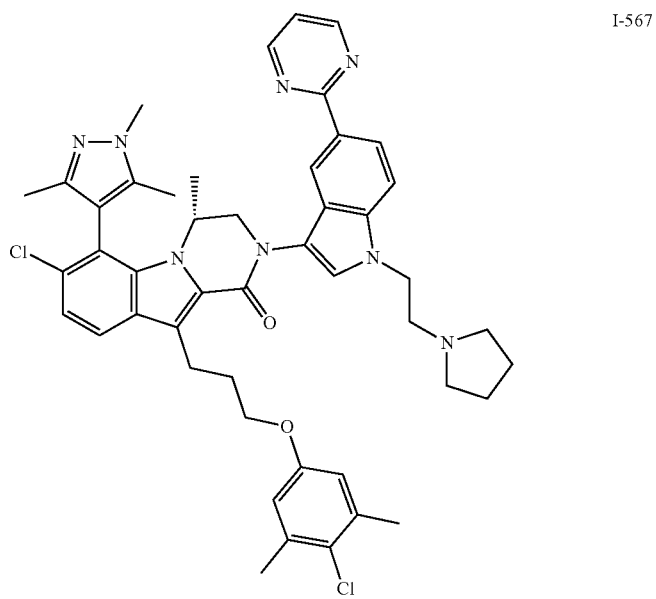
I-567
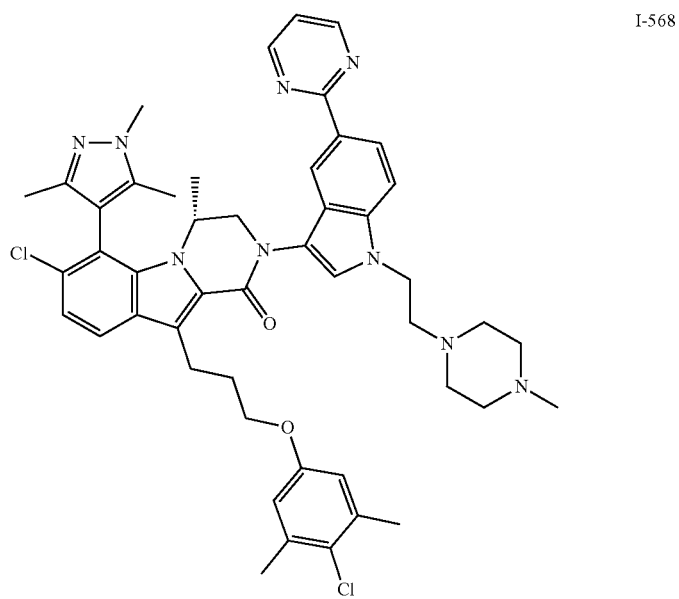
I-568

TABLE 1-continued
Exemplary compounds.
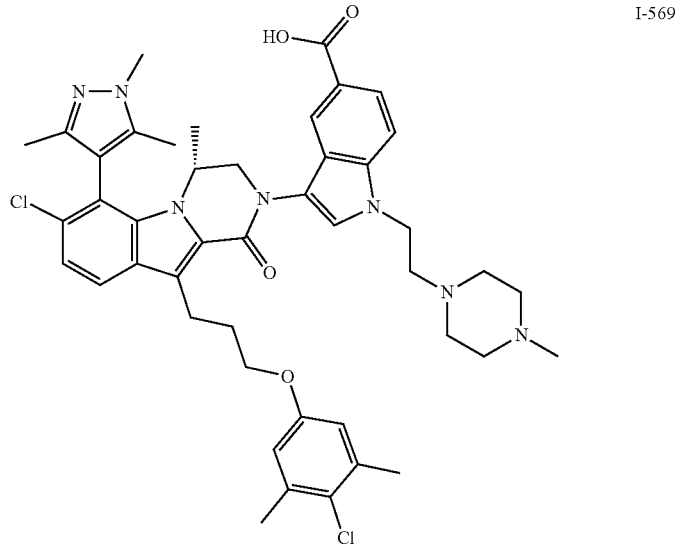
I-569
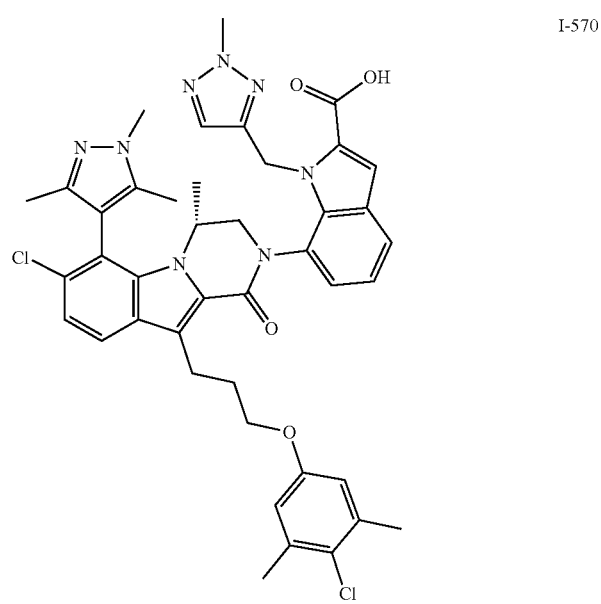
I-570

TABLE 1-continued
Exemplary compounds.
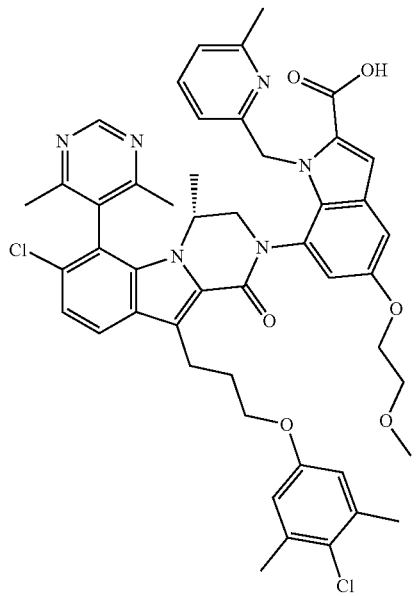 [SMILES: COCCOc1cc(N2C[C@@H](C)n3c(c(CCCOc4cc(C)c(Cl)c(C)c4)c4ccc(Cl)c(-c5c(C)ncnc5C)c43)C2=O)c2c(c1)cc(C(=O)O)n2Cc1cccc(C)n1]
I-571
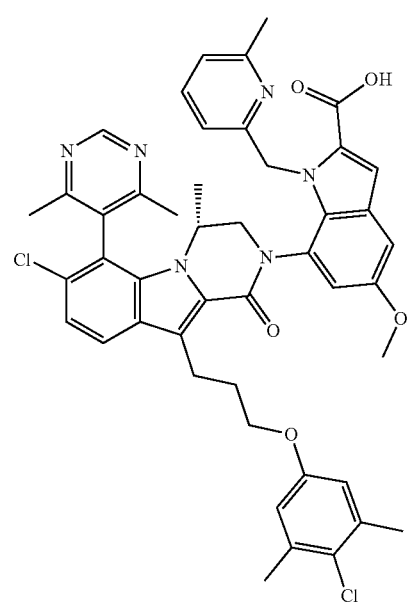 [SMILES: COc1cc(N2C[C@@H](C)n3c(c(CCCOc4cc(C)c(Cl)c(C)c4)c4ccc(Cl)c(-c5c(C)ncnc5C)c43)C2=O)c2c(c1)cc(C(=O)O)n2Cc1cccc(C)n1]
I-572

TABLE 1-continued
Exemplary compounds.
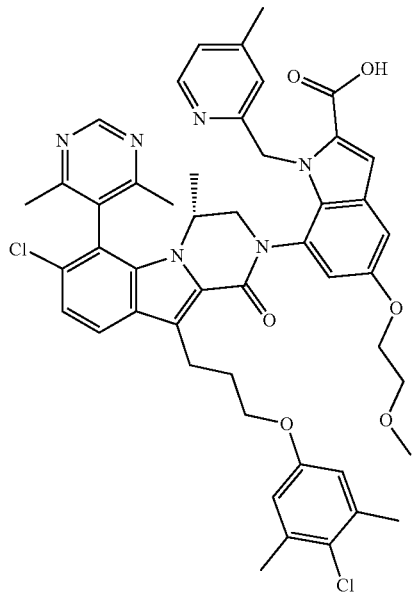 [SMILES: COCCOc1cc(N2C[C@@H](C)n3c(c(CCCOc4cc(C)c(Cl)c(C)c4)c4ccc(Cl)c(-c5c(C)ncnc5C)c43)C2=O)c2c(c1)cc(C(=O)O)n2Cc1cc(C)ccn1]
I-573
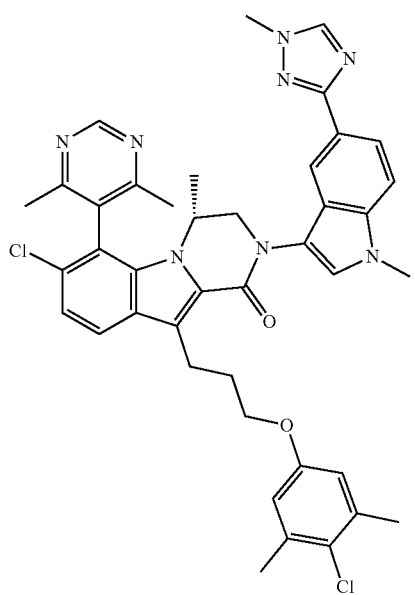 [SMILES: Cc1cc(OCCCc2c3n(c4c(-c5c(C)ncnc5C)c(Cl)ccc24)[C@H](C)CN(c2cn(C)c4ccc(-c5ncn(C)n5)cc24)C3=O)cc(C)c1Cl]
I-574

TABLE 1-continued
Exemplary compounds.
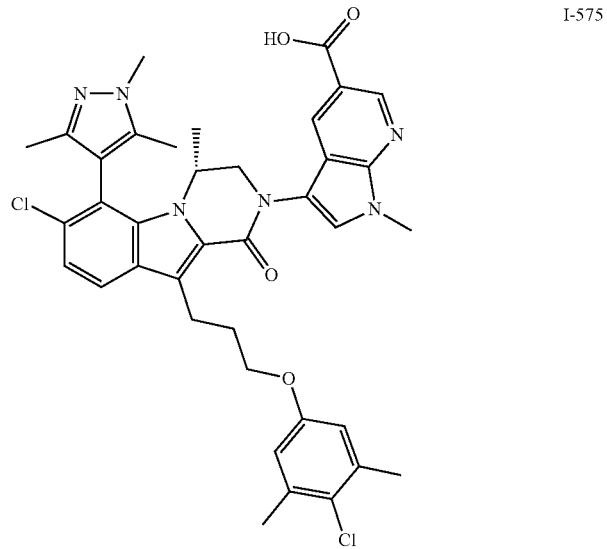
I-575
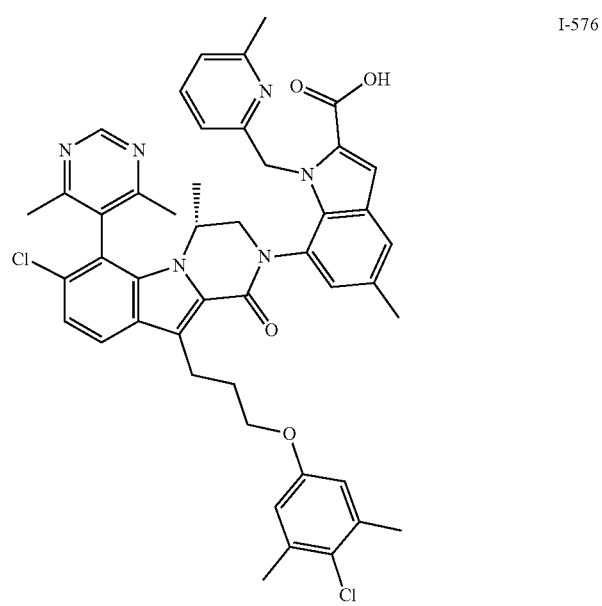
I-576

TABLE 1-continued
Exemplary compounds.
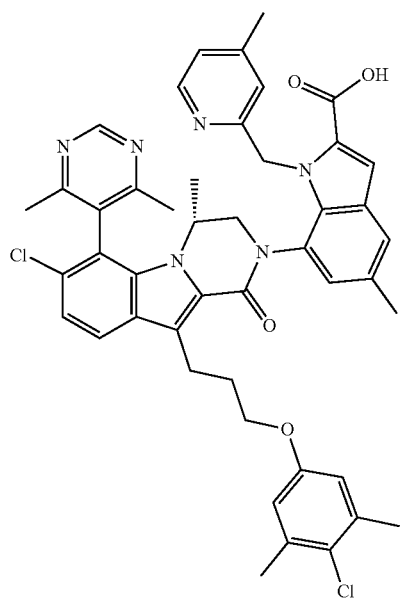 [SMILES: Cc1ccnc(Cn2c(C(=O)O)cc3cc(C)cc(N4C[C@@H](C)n5c(c(CCCOc6cc(C)c(Cl)c(C)c6)c6ccc(Cl)c(-c7c(C)ncnc7C)c65)C4=O)c32)c1]
I-577
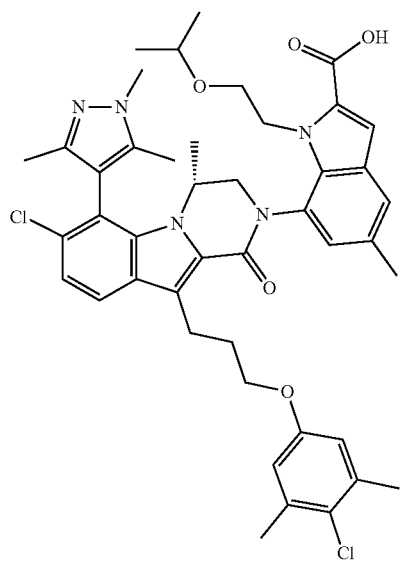
I-578

TABLE 1-continued
Exemplary compounds.
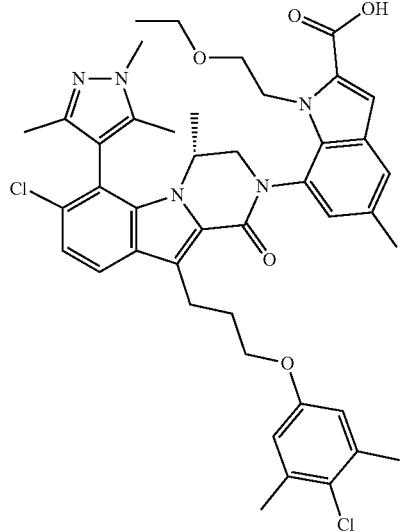
I-579
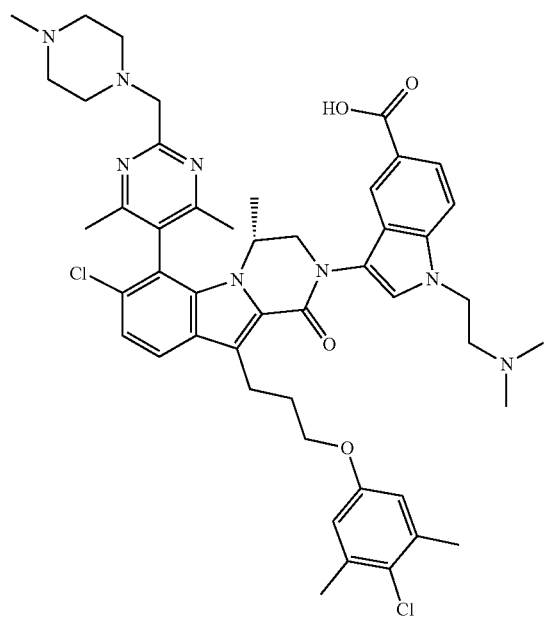
I-580

TABLE 1-continued
Exemplary compounds.
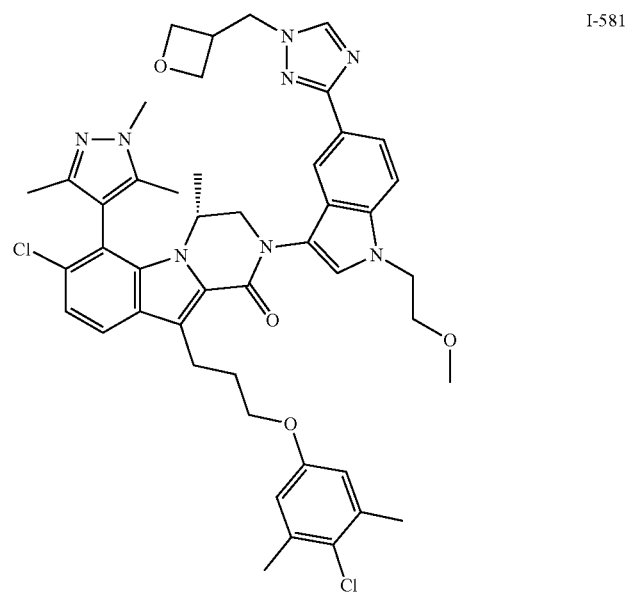
I-581
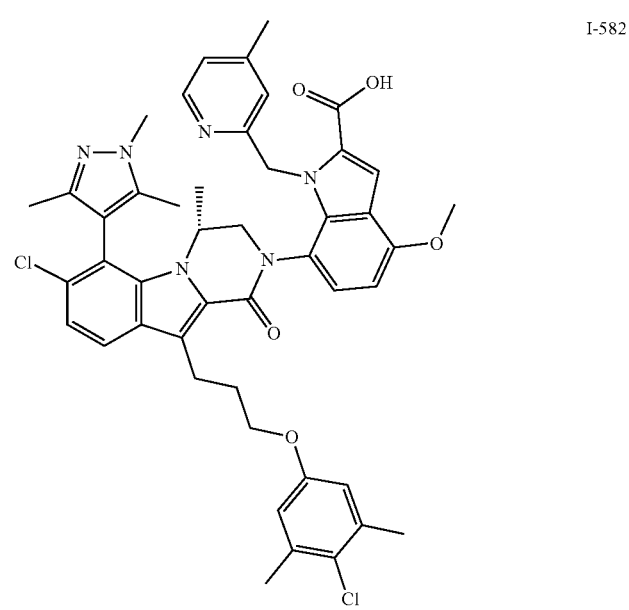
I-582

TABLE 1-continued
Exemplary compounds.
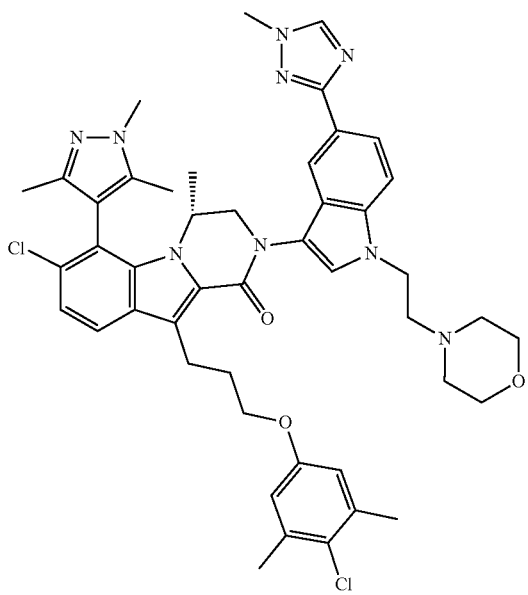 [SMILES: Cc1cc(OCCCc2c3n(c4c(-c5c(C)nn(C)c5C)c(Cl)ccc24)[C@H](C)CN(c2cn(CCN4CCOCC4)c4ccc(-c5ncn(C)n5)cc24)C3=O)cc(C)c1Cl]
I-583
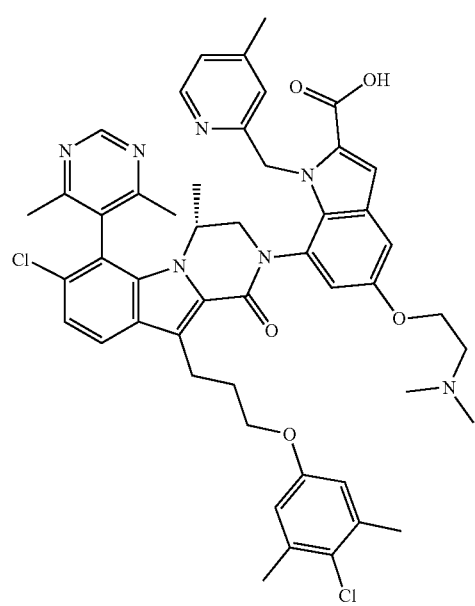 [SMILES: Cc1ccnc(Cn2c(C(=O)O)cc3cc(OCCN(C)C)cc(N4C[C@@H](C)n5c(c(CCCOc6cc(C)c(Cl)c(C)c6)c6ccc(Cl)c(-c7c(C)ncnc7C)c65)C4=O)c32)c1]
I-584

TABLE 1-continued
Exemplary compounds.
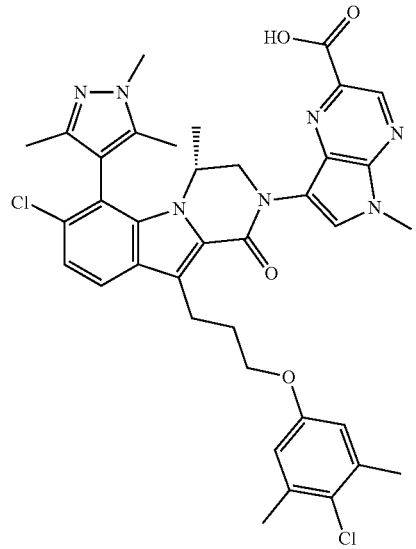
I-585
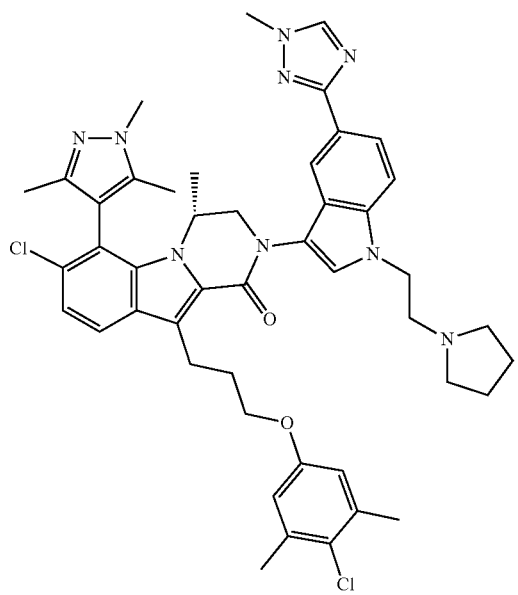 [SMILES: Cc1cc(OCCCc2c3n(c4c(-c5c(C)nn(C)c5C)c(Cl)ccc24)[C@H](C)CN(c2cn(CCN4CCCC4)c4ccc(-c5ncn(C)n5)cc24)C3=O)cc(C)c1Cl]
I-586

TABLE 1-continued
Exemplary compounds.
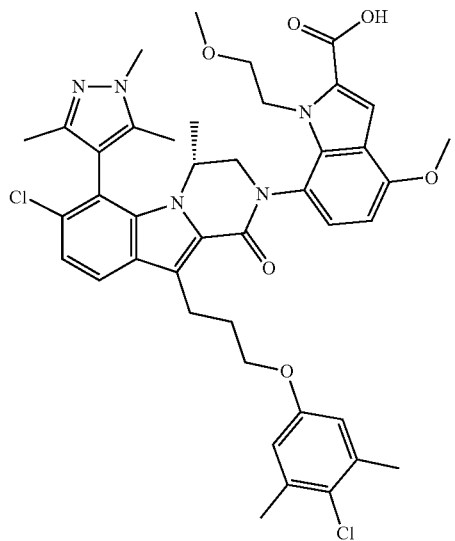
I-587
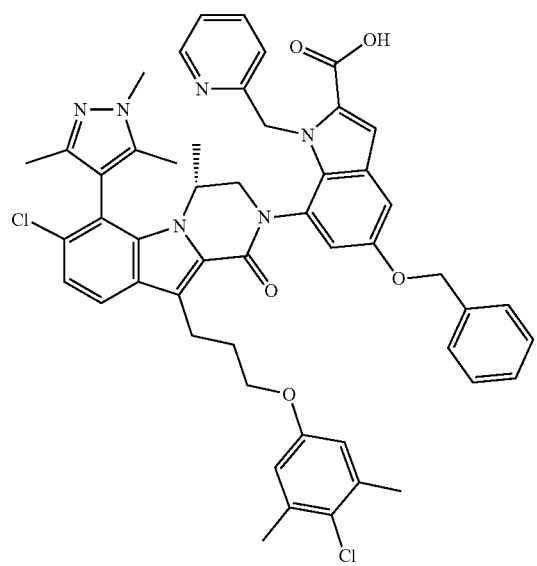 [SMILES: Cc1cc(OCCCc2c3n(c4c(-c5c(C)nn(C)c5C)c(Cl)ccc24)[C@H](C)CN(c2cc(OCc4ccccc4)cc4cc(C(=O)O)n(Cc5ccccn5)c24)C3=O)cc(C)c1Cl]
I-588

TABLE 1-continued
Exemplary compounds.
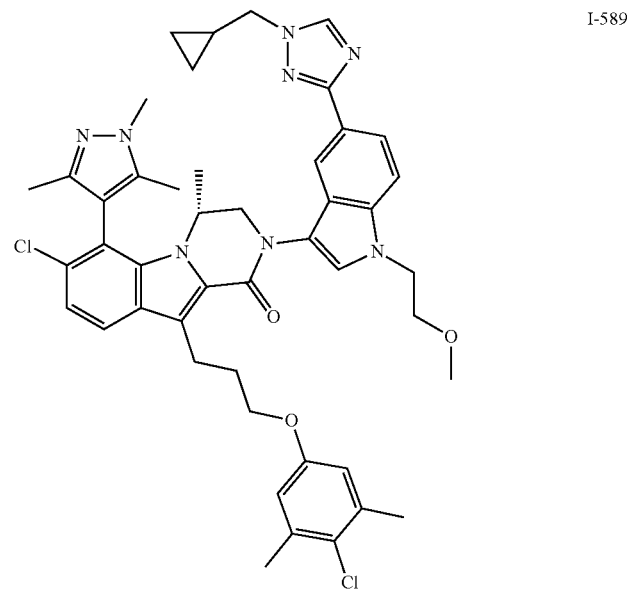
I-589
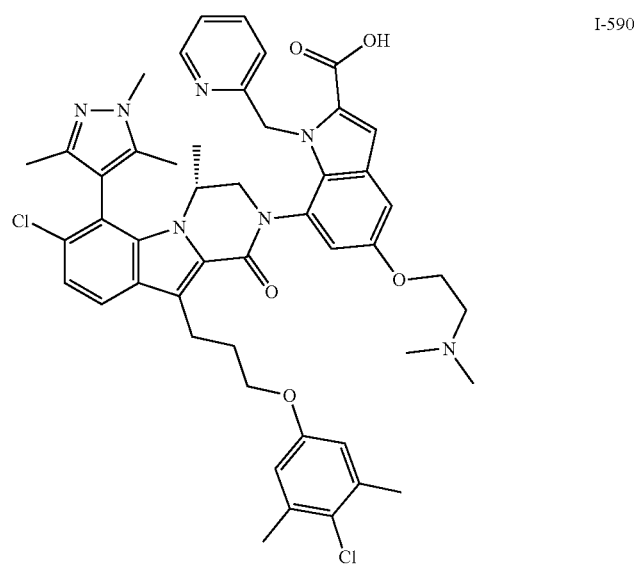
I-590

TABLE 1-continued
Exemplary compounds.
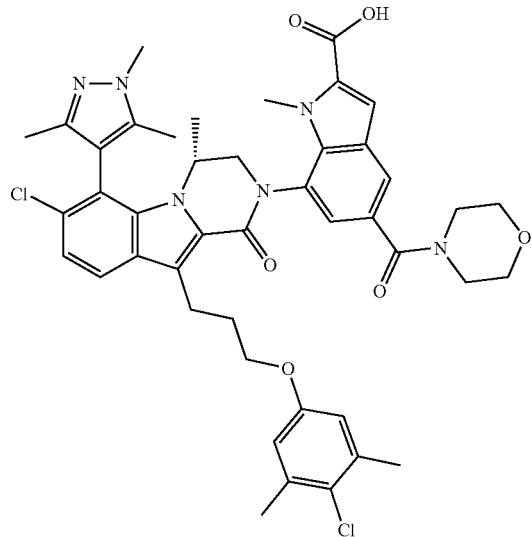 [SMILES: Cc1cc(OCCCc2c3n(c4c(-c5c(C)nn(C)c5C)c(Cl)ccc24)[C@H](C)CN(c2cc(C(=O)N4CCOCC4)cc4cc(C(=O)O)n(C)c24)C3=O)cc(C)c1Cl]
I-591
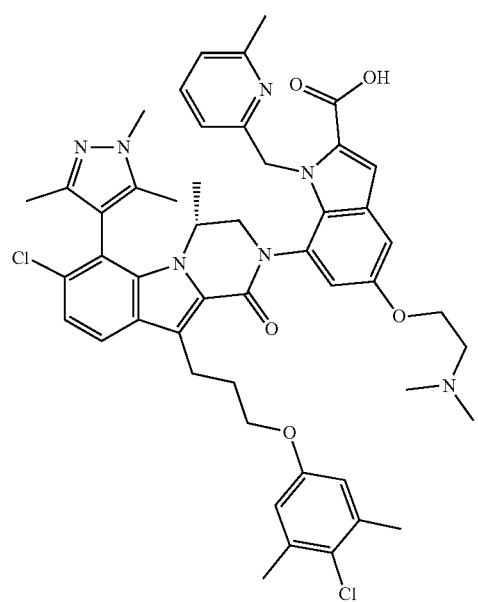
I-592

TABLE 1-continued
Exemplary compounds.
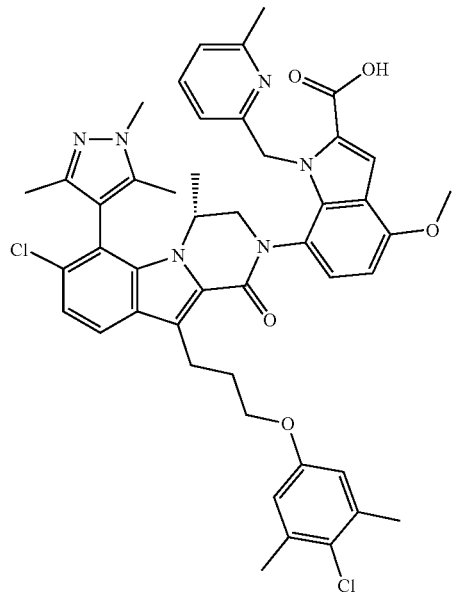
I-593
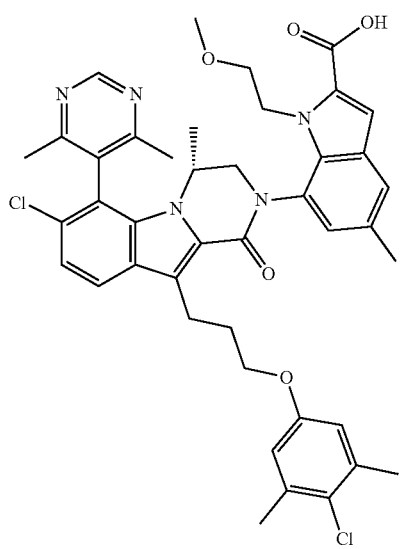 [SMILES: COCCn1c(C(=O)O)cc2cc(C)cc(N3C[C@@H](C)n4c(c(CCCOc5cc(C)c(Cl)c(C)c5)c5ccc(Cl)c(-c6c(C)ncnc6C)c54)C3=O)c21]
I-594

527
528
TABLE 1-continued
Exemplary compounds.
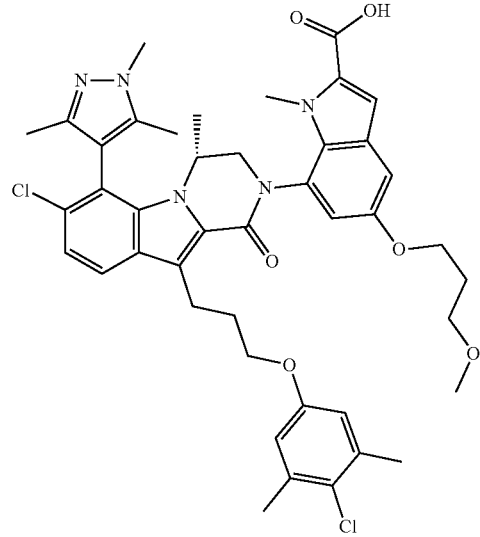 [SMILES: COCCCOc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(=O)O)n2C]
I-595
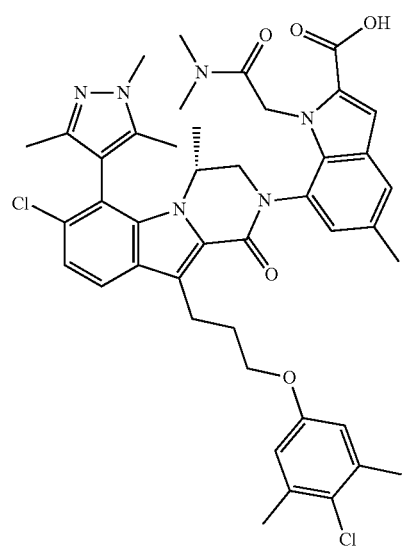
I-596

TABLE 1-continued
Exemplary compounds.
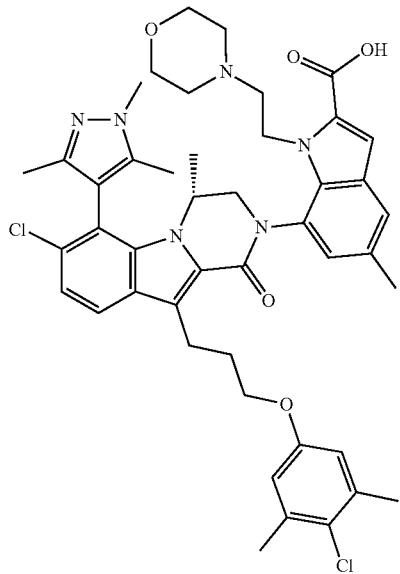
I-597
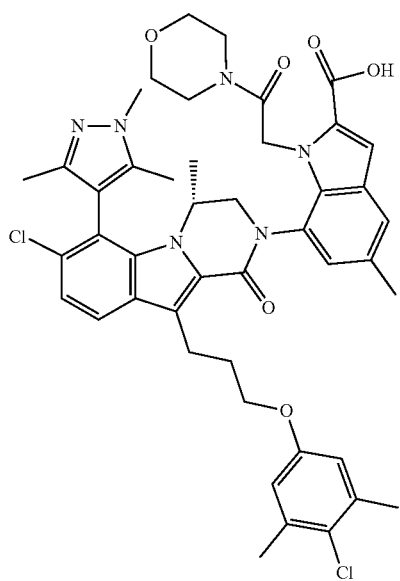
I-598

TABLE 1-continued
Exemplary compounds.
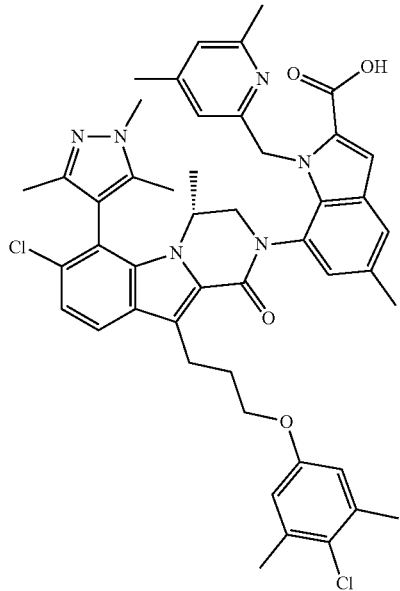
I-599
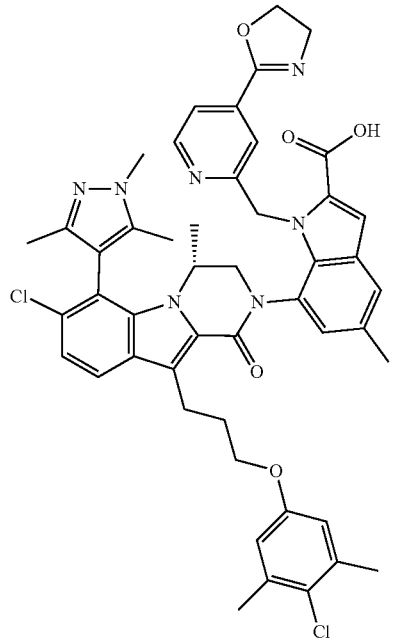 [SMILES: Cc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(=O)O)n2Cc1cc(C2=NCCO2)ccn1]
I-600

TABLE 1-continued
Exemplary compounds.
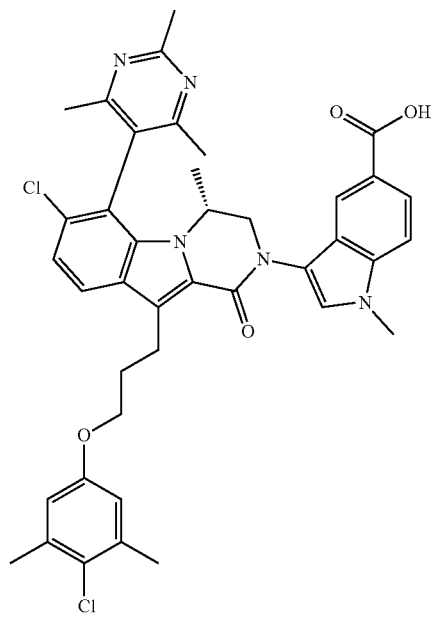 [SMILES: Cc1nc(C)c(-c2c(Cl)ccc3c(CCCOc4cc(C)c(Cl)c(C)c4)c4n(c23)[C@H](C)CN(c2cn(C)c3ccc(C(=O)O)cc23)C4=O)c(C)n1]
I-601
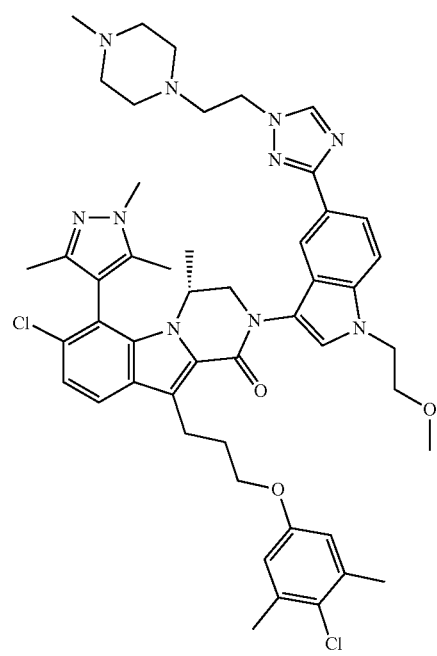
I-602

TABLE 1-continued
Exemplary compounds.
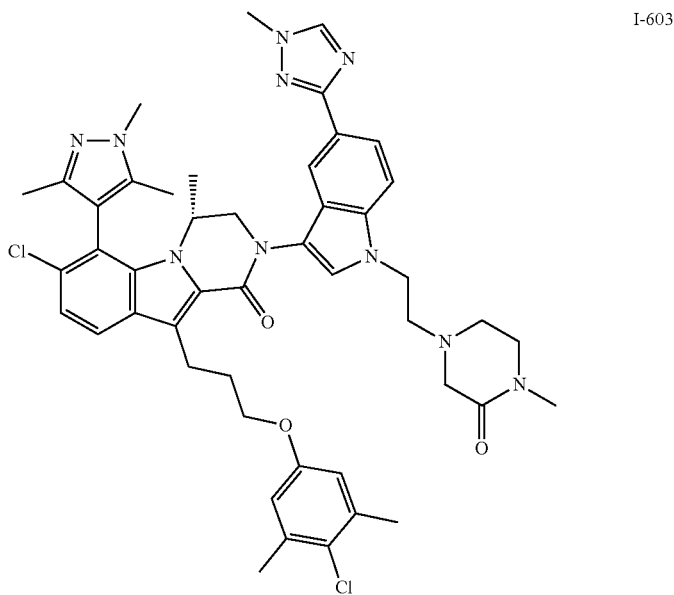
I-603
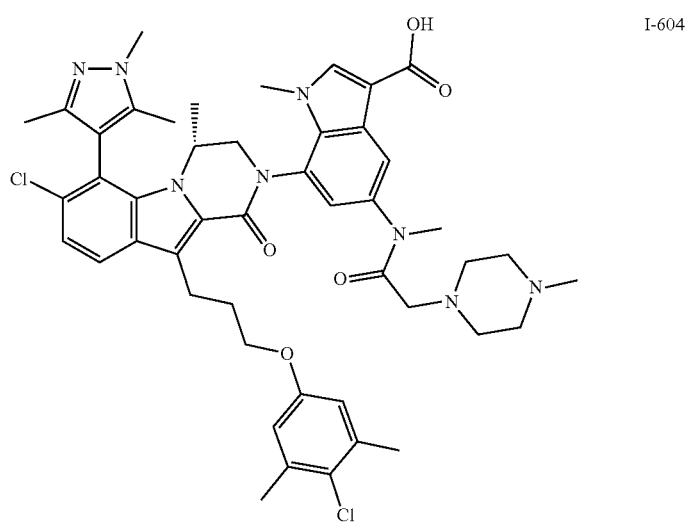
I-604

TABLE 1-continued
Exemplary compounds.
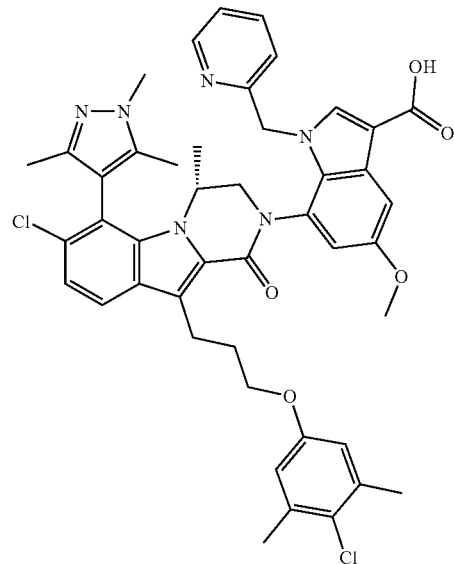 [SMILES: COc1cc(N2C[C@@H](C)n3c(c(CCCOc4cc(C)c(Cl)c(C)c4)c4ccc(Cl)c(-c5c(C)nn(C)c5C)c43)C2=O)c2c(c1)c(C(=O)O)cn2Cc1ccccn1]
I-605
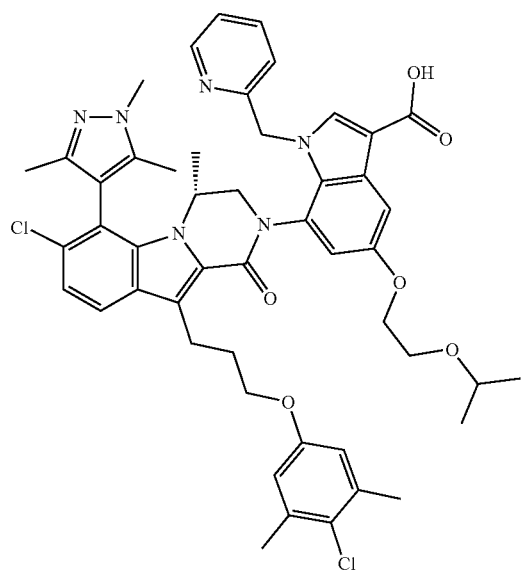 [SMILES: Cc1cc(OCCCc2c3n(c4c(-c5c(C)nn(C)c5C)c(Cl)ccc24)[C@H](C)CN(c2cc(OCCOC(C)C)cc4c(C(=O)O)cn(Cc5ccccn5)c24)C3=O)cc(C)c1Cl]
I-606

TABLE 1-continued
Exemplary compounds.
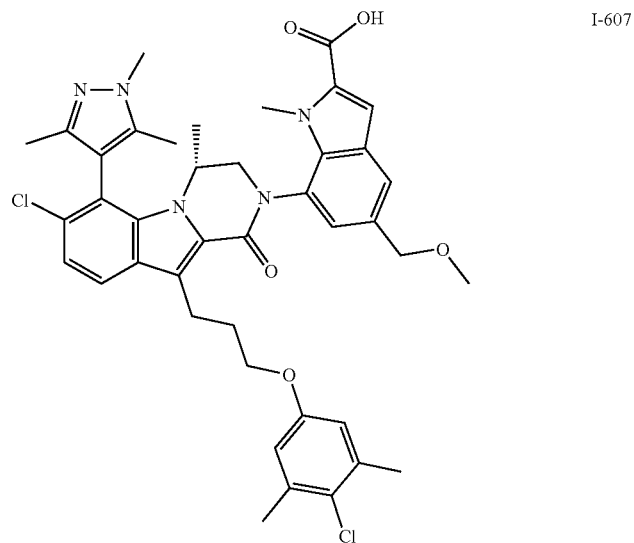
I-607
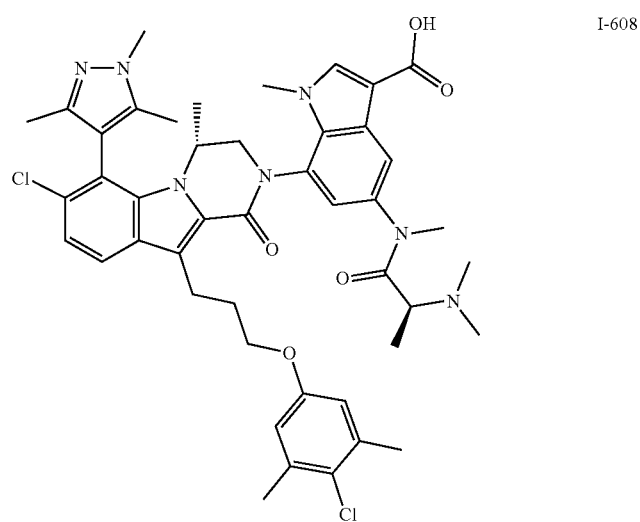
I-608
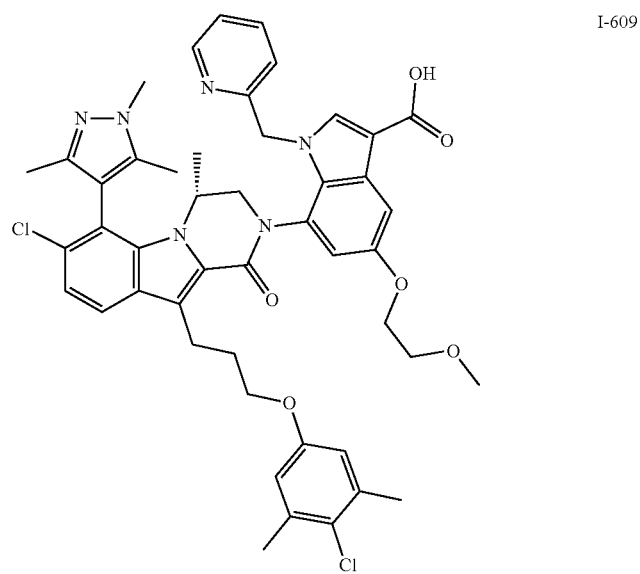
I-609

TABLE 1-continued
Exemplary compounds.
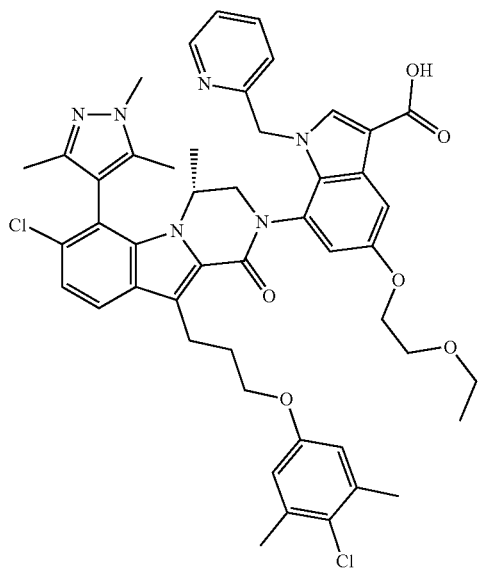 [SMILES: CCOCCOc1cc(N2C[C@@H](C)n3c(c(CCCOc4cc(C)c(Cl)c(C)c4)c4ccc(Cl)c(-c5c(C)nn(C)c5C)c43)C2=O)c2c(c1)c(C(=O)O)cn2Cc1ccccn1]
I-610
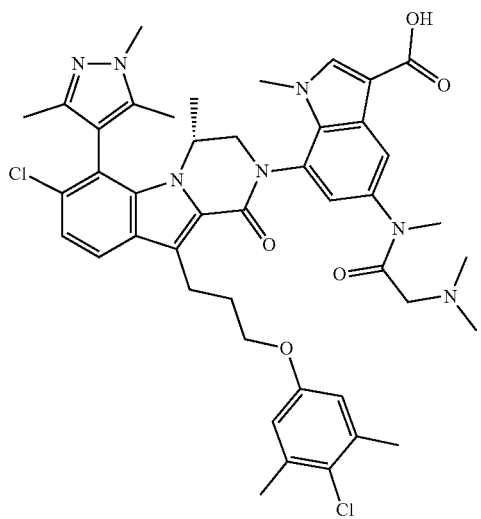
I-611
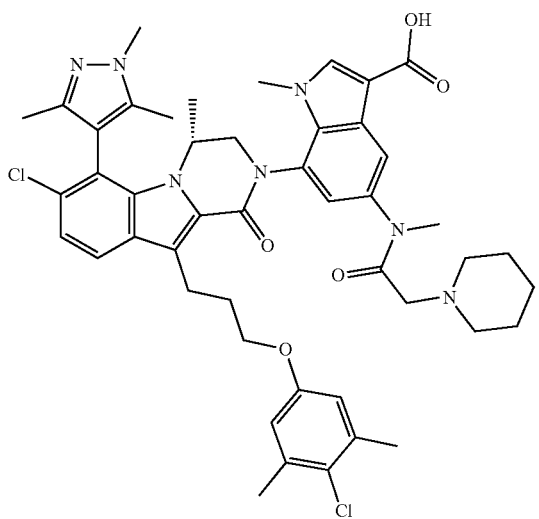 [SMILES: Cc1cc(OCCCc2c3n(c4c(-c5c(C)nn(C)c5C)c(Cl)ccc24)[C@H](C)CN(c2cc(N(C)C(=O)CN4CCCCC4)cc4c(C(=O)O)cn(C)c24)C3=O)cc(C)c1Cl]
I-612

TABLE 1-continued
Exemplary compounds.
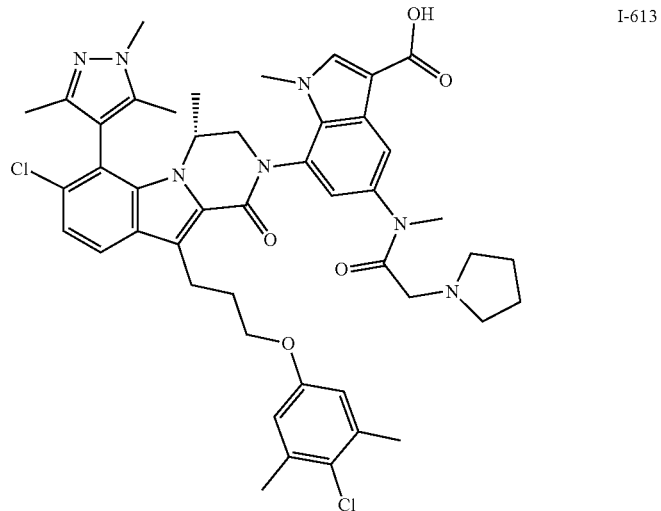
I-613
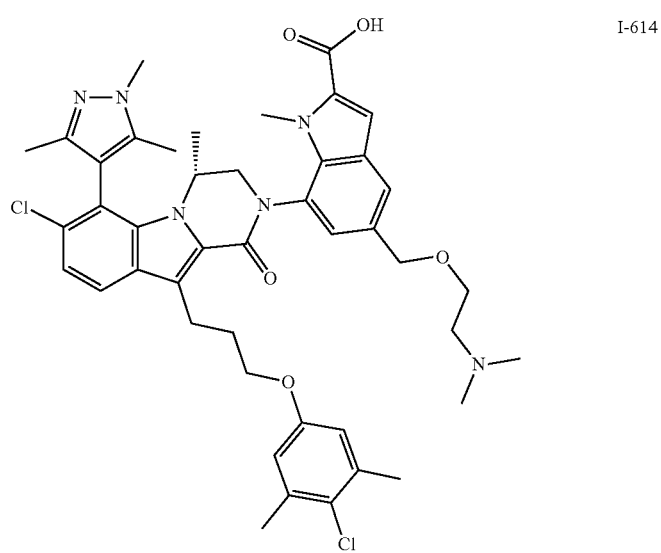
I-614

TABLE 1-continued
Exemplary compounds.
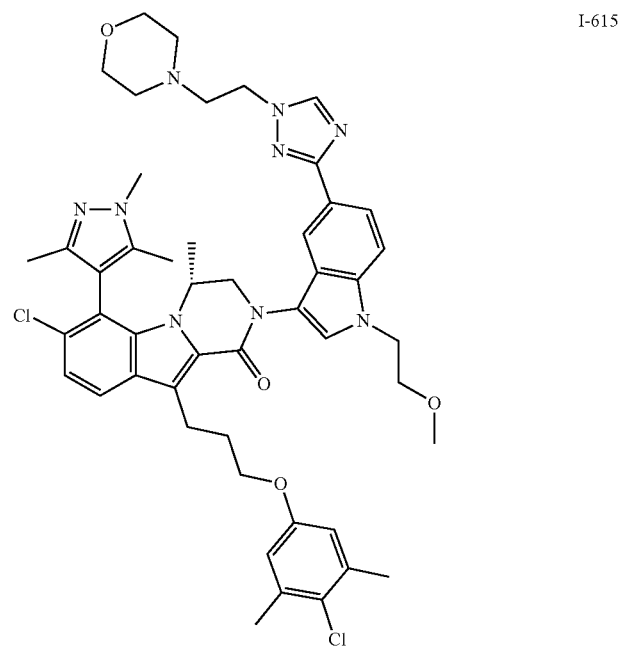
I-615
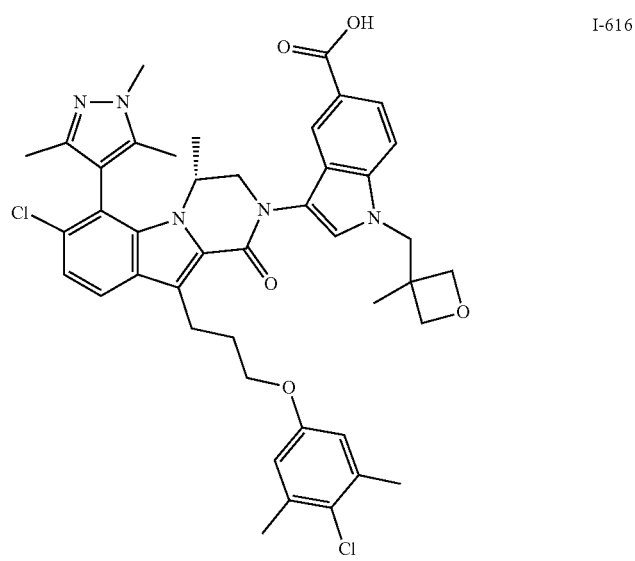
I-616

TABLE 1-continued
Exemplary compounds.
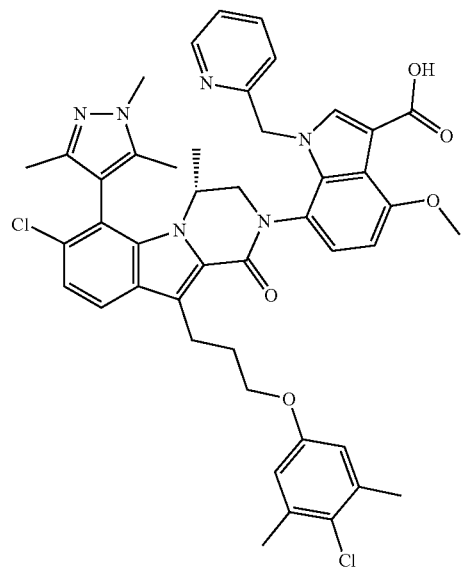
I-617
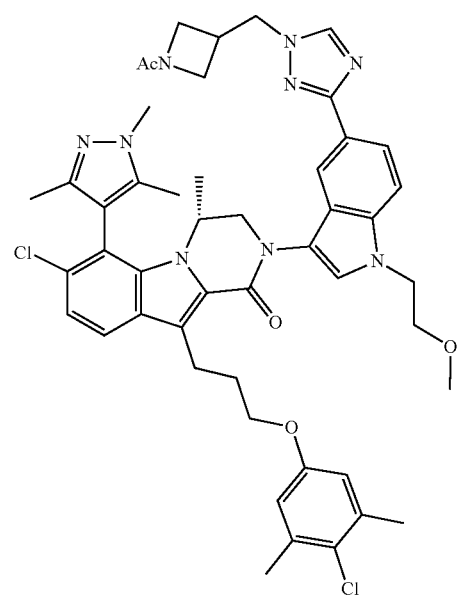
I-618

TABLE 1-continued
Exemplary compounds.
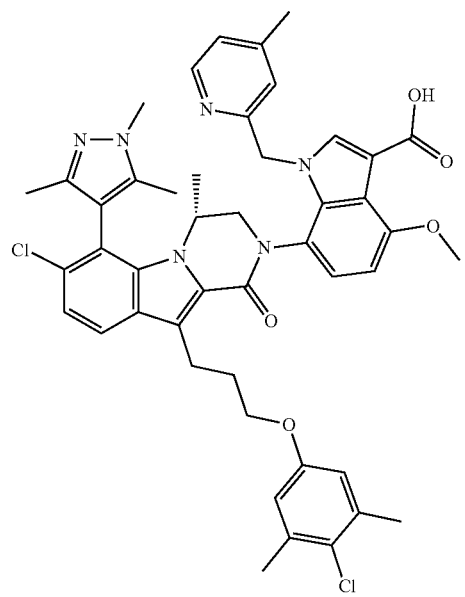
I-619
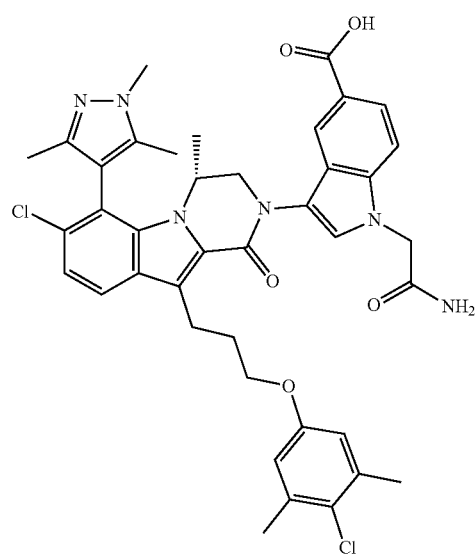 [SMILES: Cc1cc(OCCCc2c3n(c4c(-c5c(C)nn(C)c5C)c(Cl)ccc24)[C@H](C)CN(c2cn(CC(N)=O)c4ccc(C(=O)O)cc24)C3=O)cc(C)c1Cl]
I-620

TABLE 1-continued
Exemplary compounds.
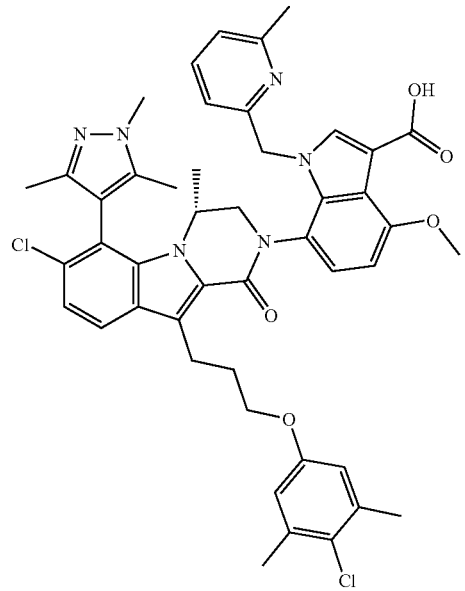
I-621
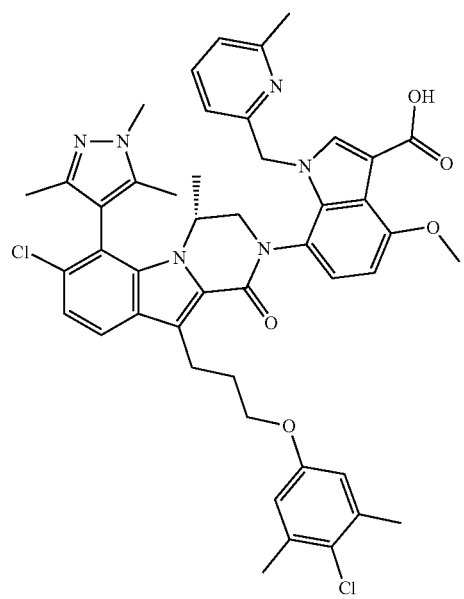
I-622

TABLE 1-continued
Exemplary compounds.
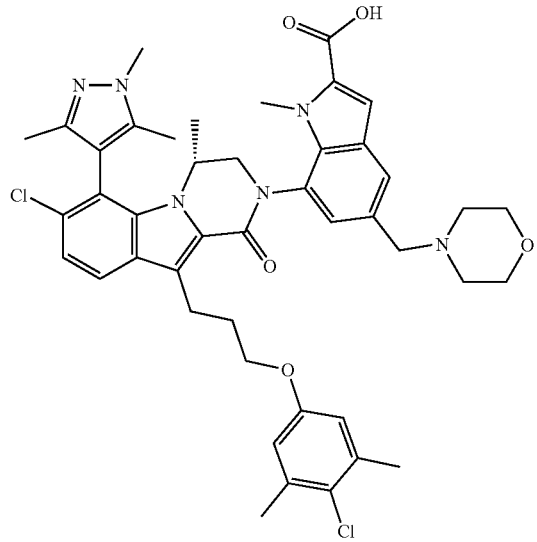 [SMILES: Cc1cc(OCCCc2c3n(c4c(-c5c(C)nn(C)c5C)c(Cl)ccc24)[C@H](C)CN(c2cc(CN4CCOCC4)cc4cc(C(=O)O)n(C)c24)C3=O)cc(C)c1Cl]
I-623
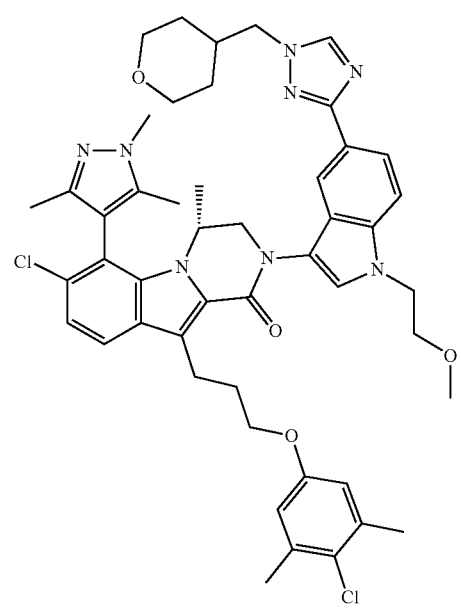 [SMILES: COCCn1cc(N2C[C@@H](C)n3c(c(CCCOc4cc(C)c(Cl)c(C)c4)c4ccc(Cl)c(-c5c(C)nn(C)c5C)c43)C2=O)c2cc(-c3ncn(CC4CCOCC4)n3)ccc21]
I-624

TABLE 1-continued
Exemplary compounds.
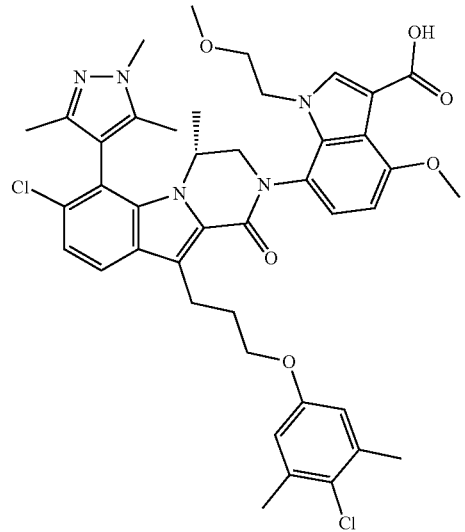
I-625
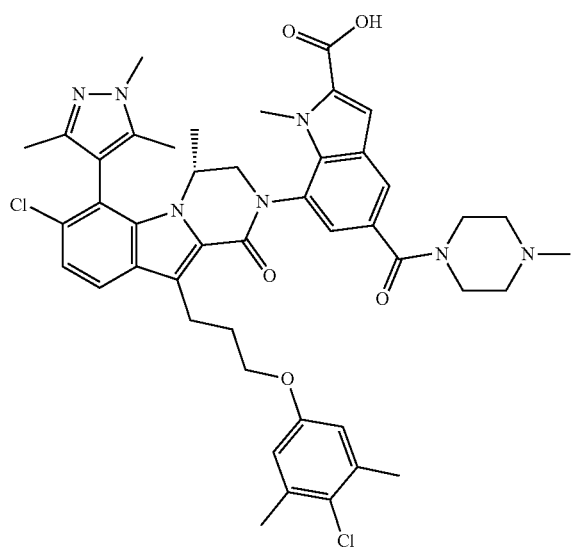
I-626

TABLE 1-continued
Exemplary compounds.
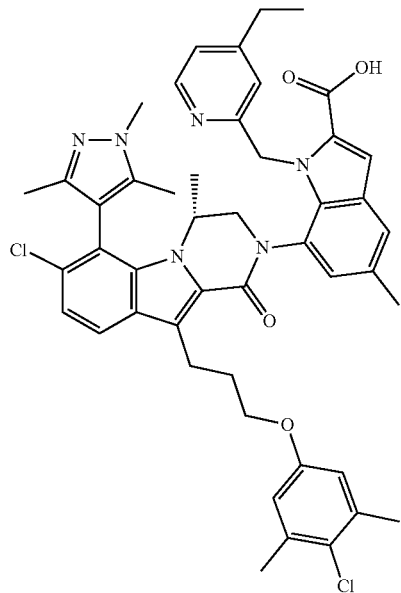
I-627
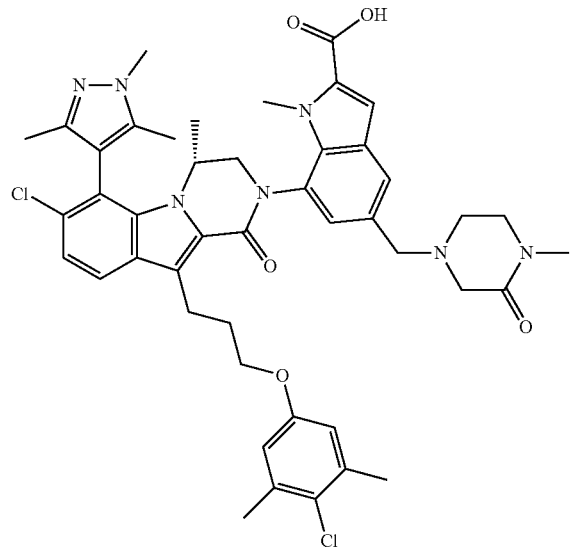
I-628

TABLE 1-continued
Exemplary compounds.
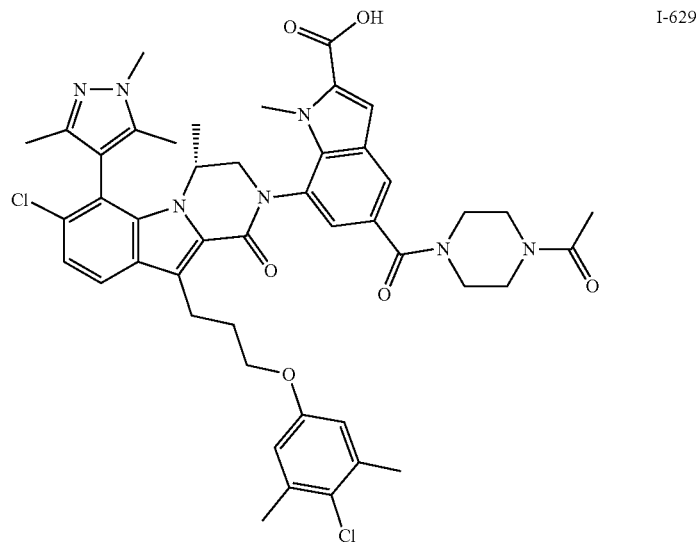
I-629
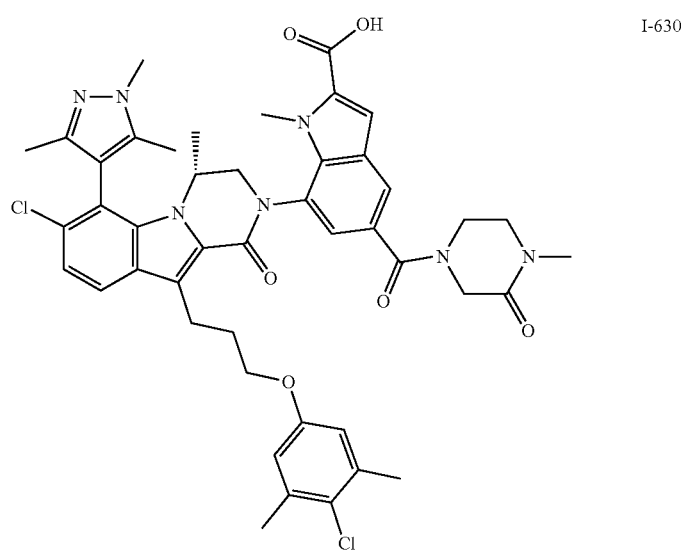
I-630
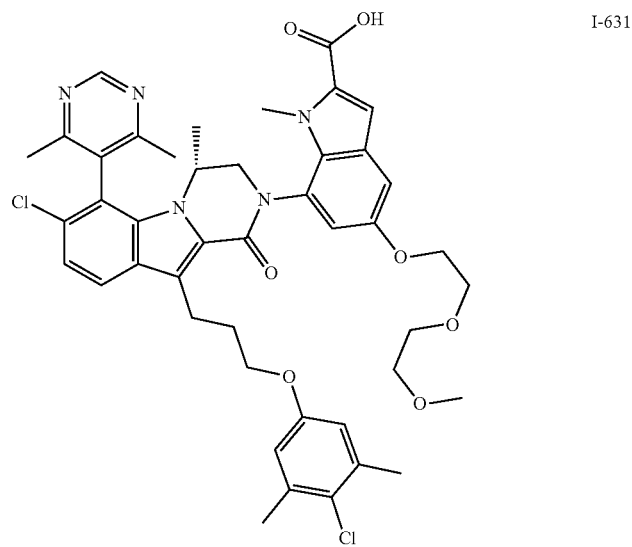
I-631

TABLE 1-continued
Exemplary compounds.
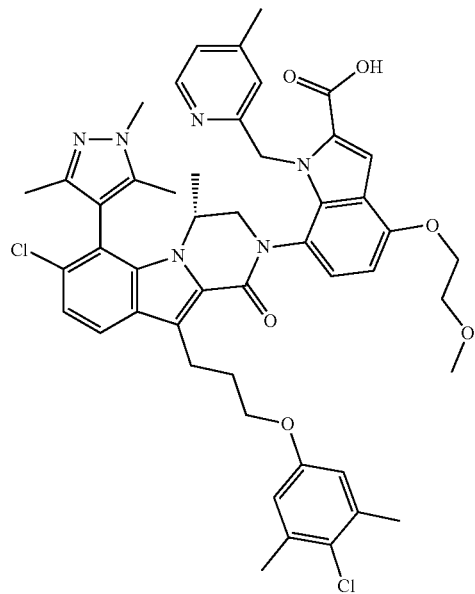 [SMILES: COCCOc1ccc(N2C[C@@H](C)n3c(c(CCCOc4cc(C)c(Cl)c(C)c4)c4ccc(Cl)c(-c5c(C)nn(C)c5C)c43)C2=O)c2c1cc(C(=O)O)n2Cc1cc(C)ccn1]
I-632
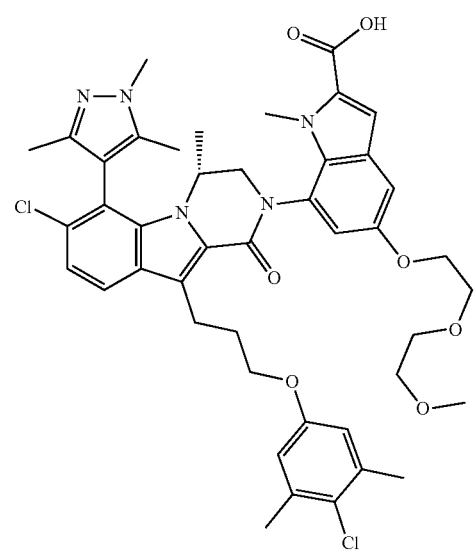 [SMILES: COCCOCCOc1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(=O)O)n2C]
I-633

TABLE 1-continued
Exemplary compounds.
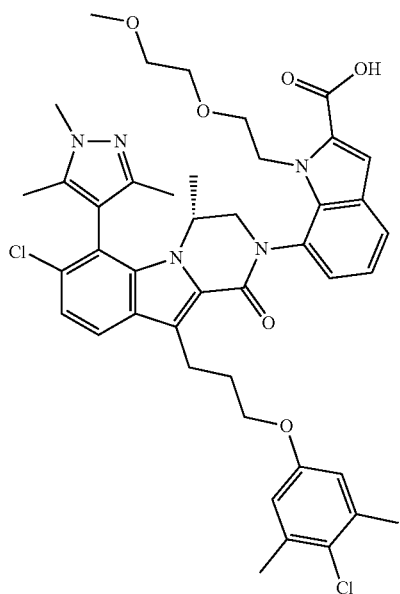
I-634
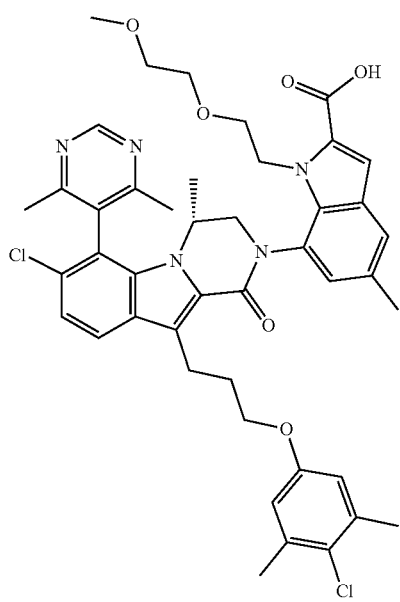 [SMILES: COCCOCCn1c(C(=O)O)cc2cc(C)cc(N3C[C@@H](C)n4c(c(CCCOc5cc(C)c(Cl)c(C)c5)c5ccc(Cl)c(-c6c(C)ncnc6C)c54)C3=O)c21]
I-635

TABLE 1-continued
Exemplary compounds.
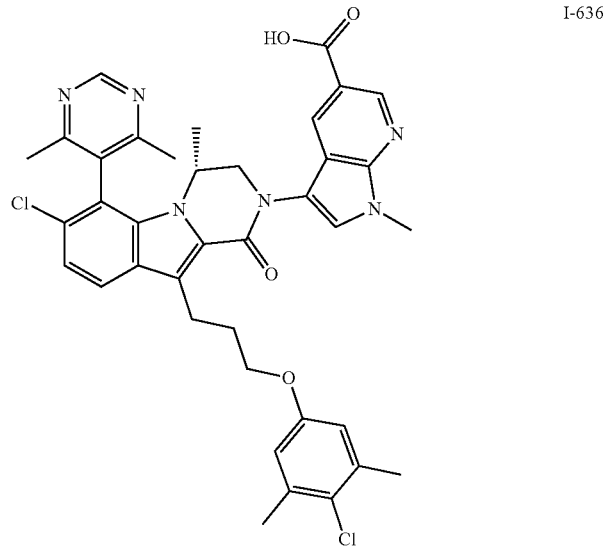
I-636
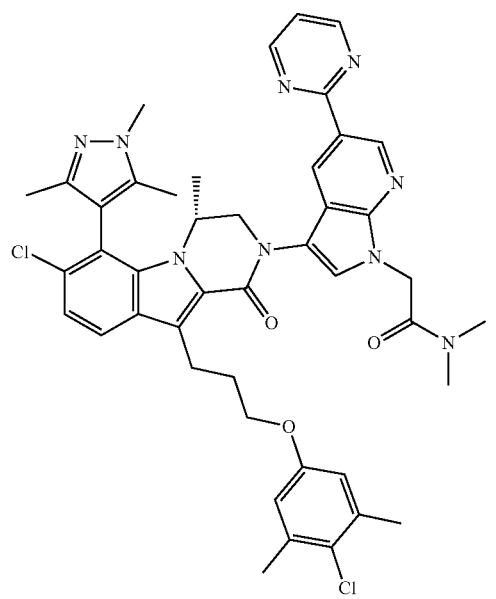
I-637

TABLE 1-continued
Exemplary compounds.
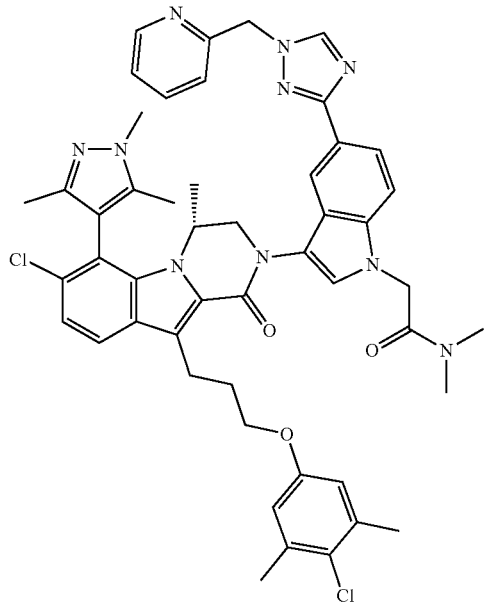
I-638
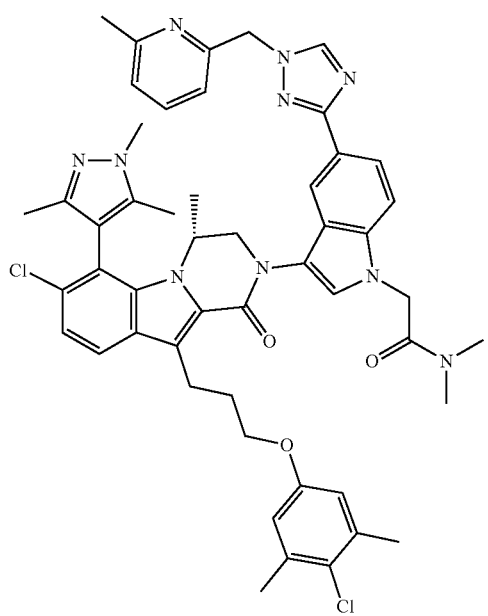
I-639

TABLE 1-continued
Exemplary compounds.
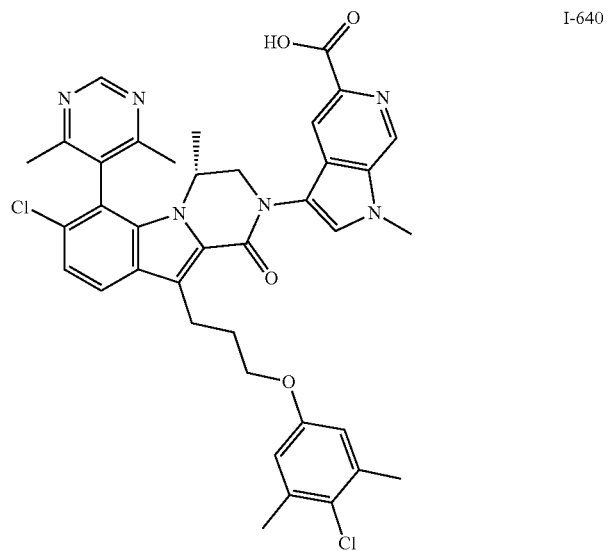
I-640
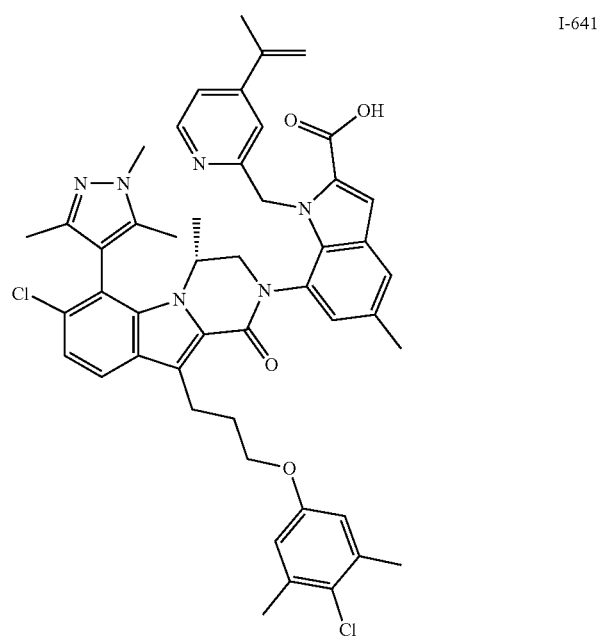
I-641

571
TABLE 1-continued
Exemplary compounds.
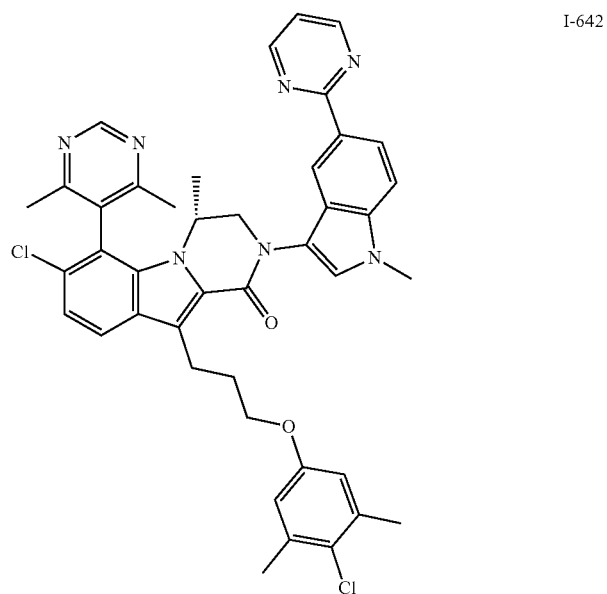
I-642
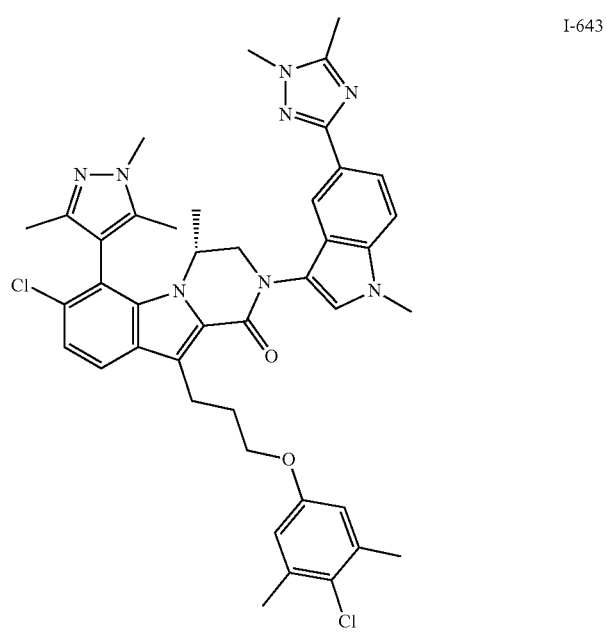
I-643

TABLE 1-continued
Exemplary compounds.
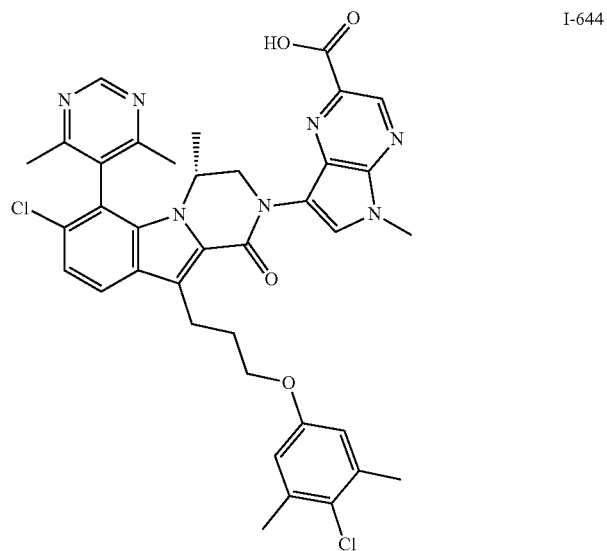
I-644
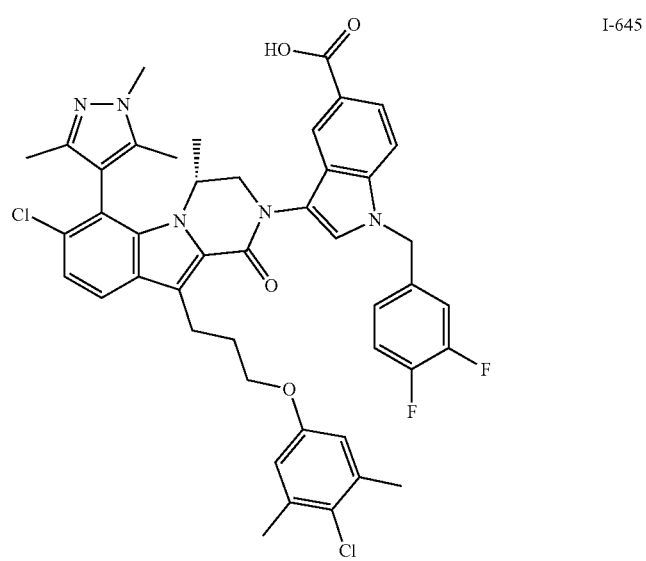
I-645

575
576
TABLE 1-continued
Exemplary compounds.
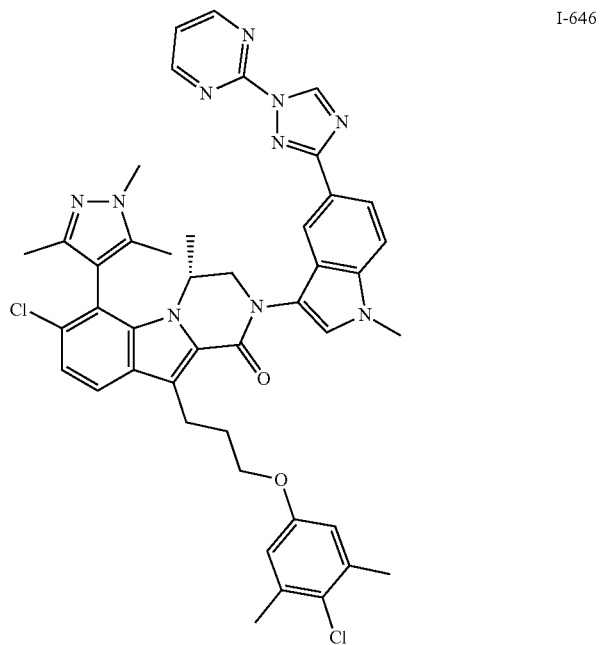 I-646
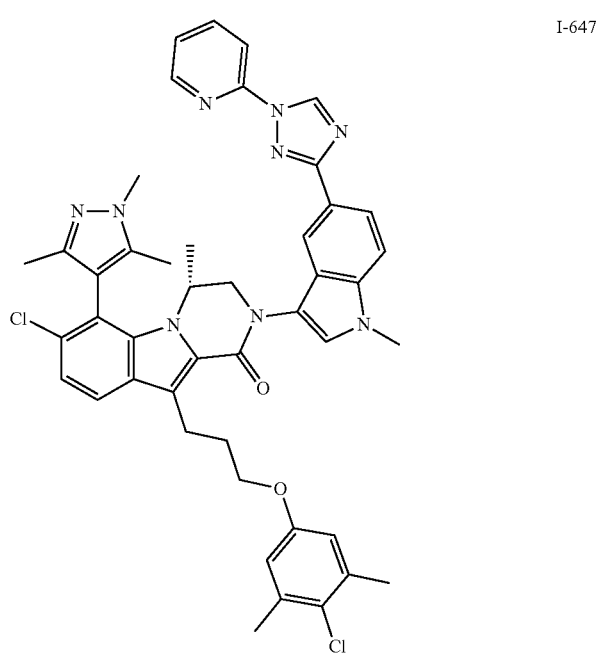 I-647

TABLE 1-continued
Exemplary compounds.
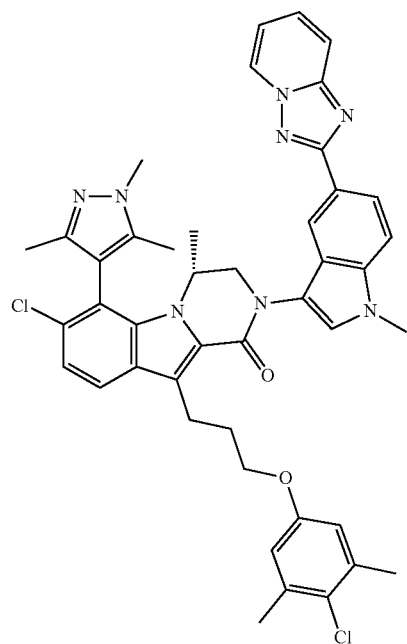
I-648
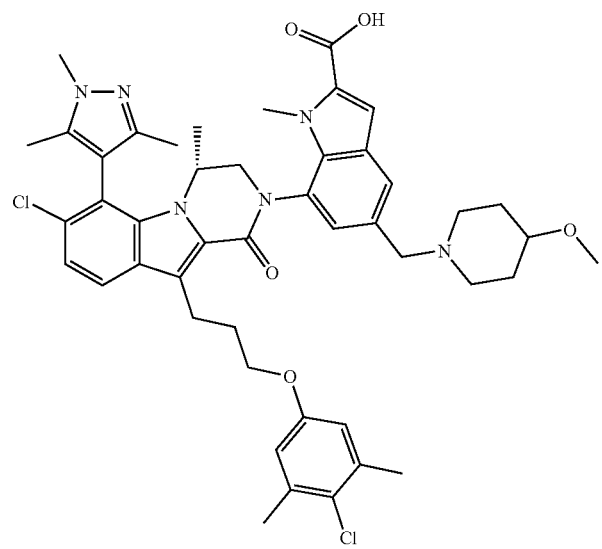
I-649

TABLE 1-continued
Exemplary compounds.
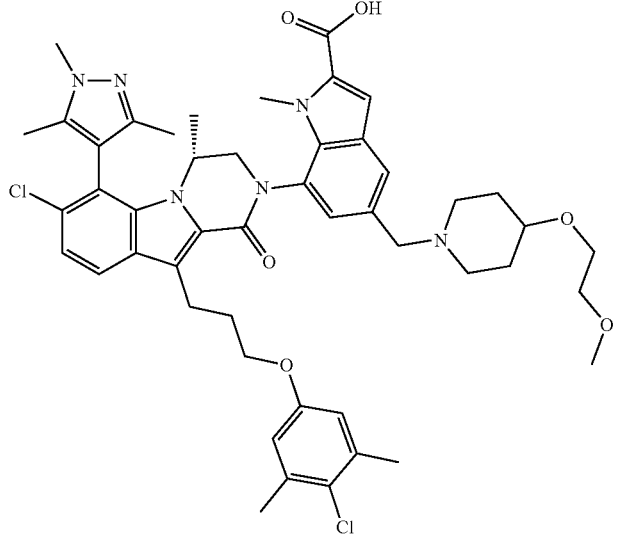 [SMILES: COCCOC1CCN(Cc2cc(N3C[C@@H](C)n4c(c(CCCOc5cc(C)c(Cl)c(C)c5)c5ccc(Cl)c(-c6c(C)nn(C)c6C)c54)C3=O)c3c(c2)cc(C(=O)O)n3C)CC1]
I-650
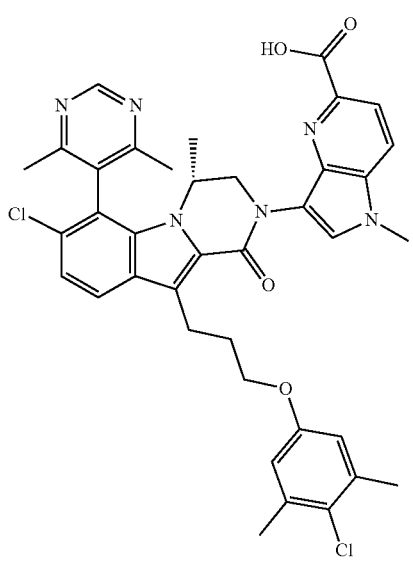 [SMILES: Cc1cc(OCCCc2c3n(c4c(-c5c(C)ncnc5C)c(Cl)ccc24)[C@H](C)CN(c2cn(C)c4ccc(C(=O)O)nc24)C3=O)cc(C)c1Cl]
I-651

TABLE 1-continued
Exemplary compounds.
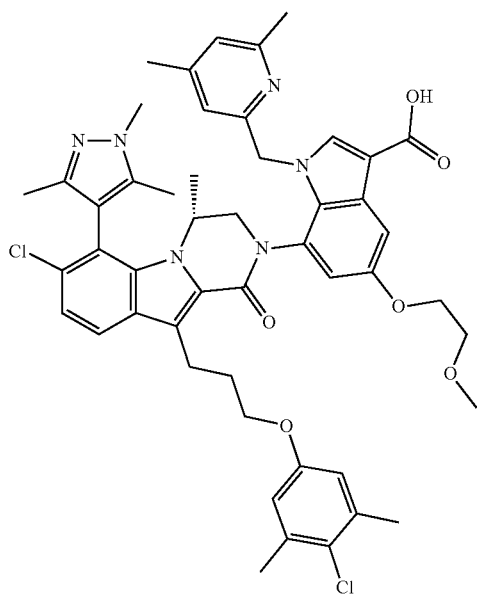
I-652
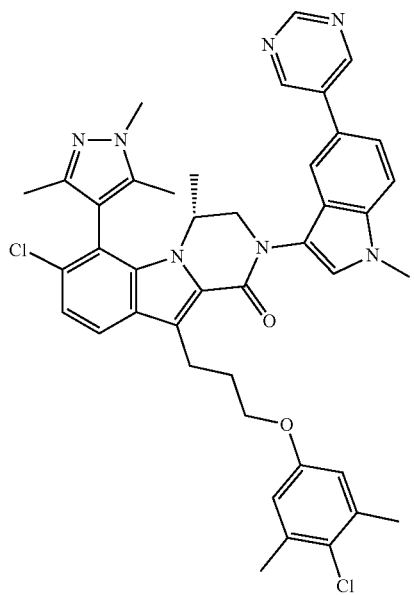
I-653

TABLE 1-continued
Exemplary compounds.
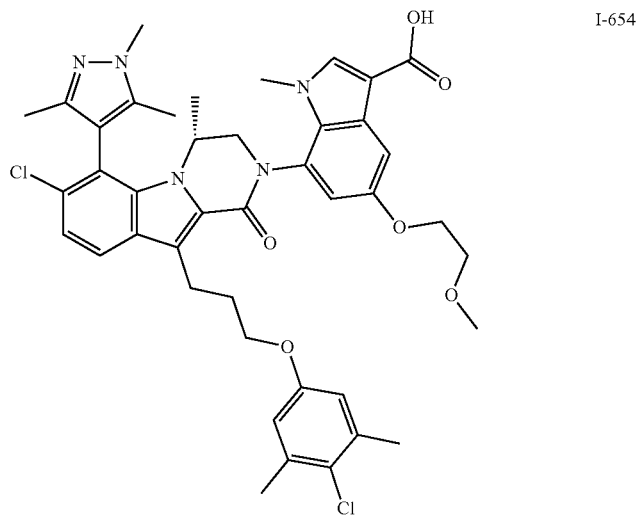
I-654
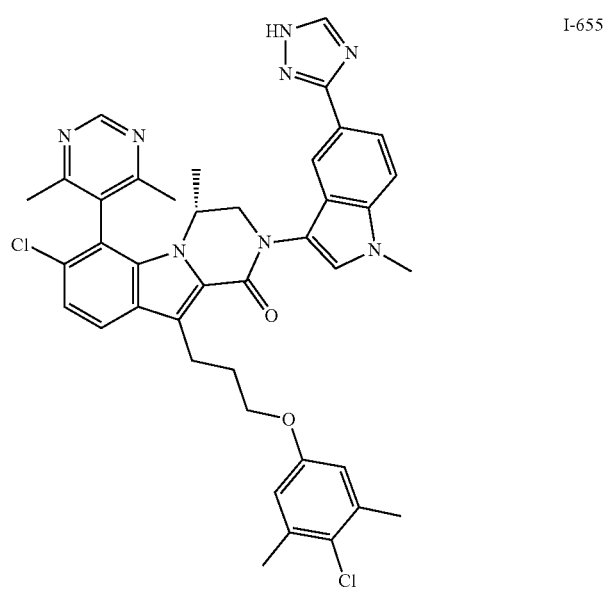
I-655

TABLE 1-continued
Exemplary compounds.
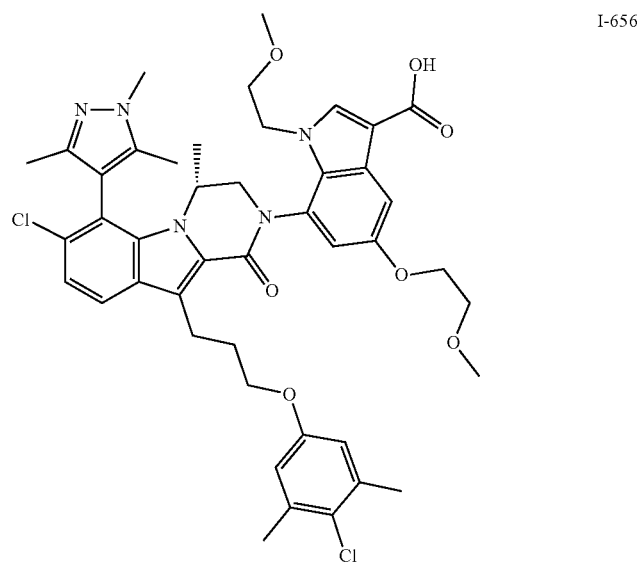
I-656
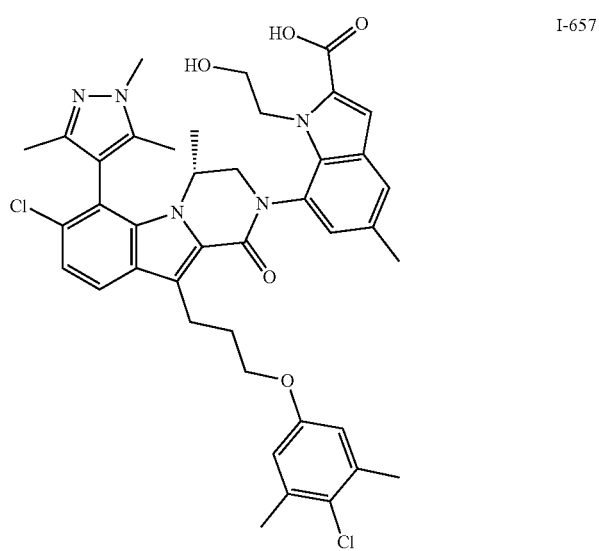
I-657

TABLE 1-continued
Exemplary compounds.
I-658
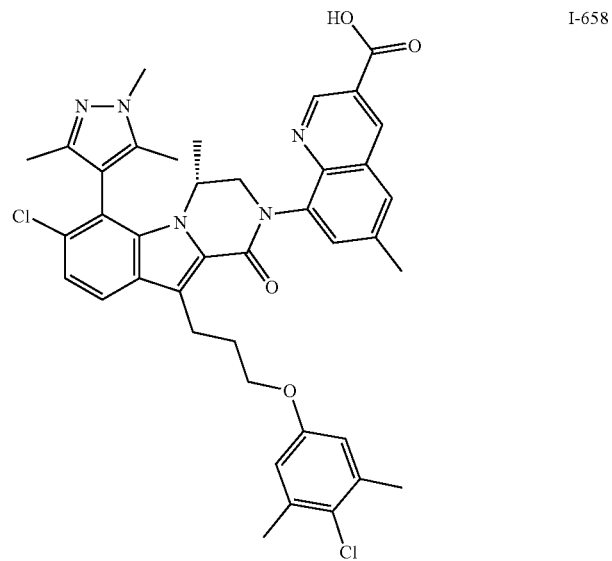
I-659
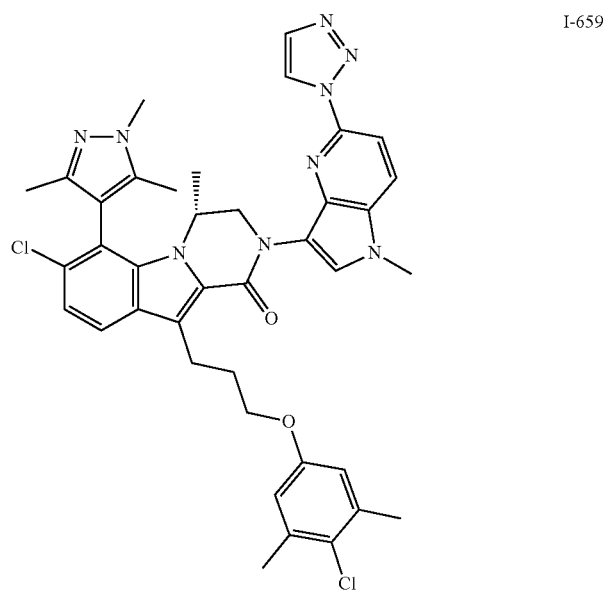

TABLE 1-continued
Exemplary compounds.
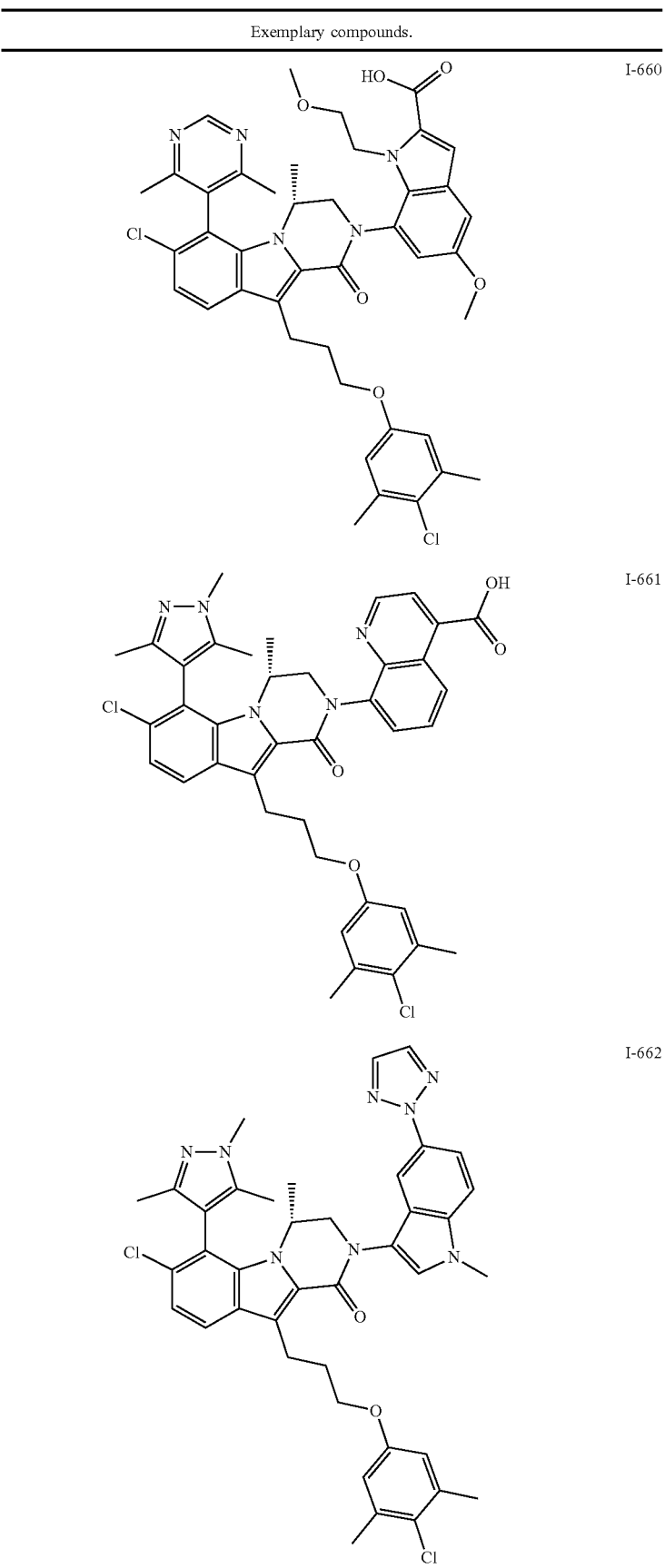
I-660
I-661
I-662

TABLE 1-continued
Exemplary compounds.
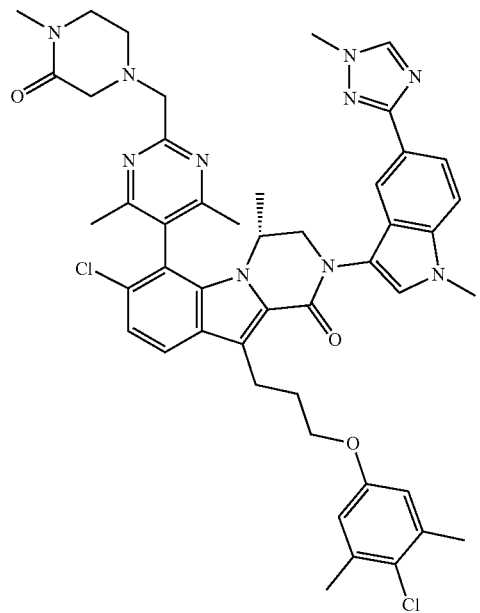
I-663
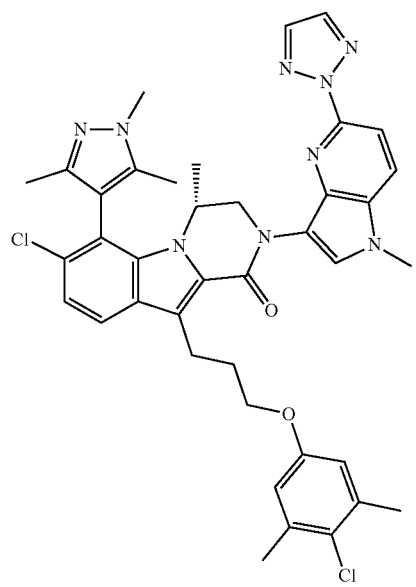
I-664

TABLE 1-continued
Exemplary compounds.
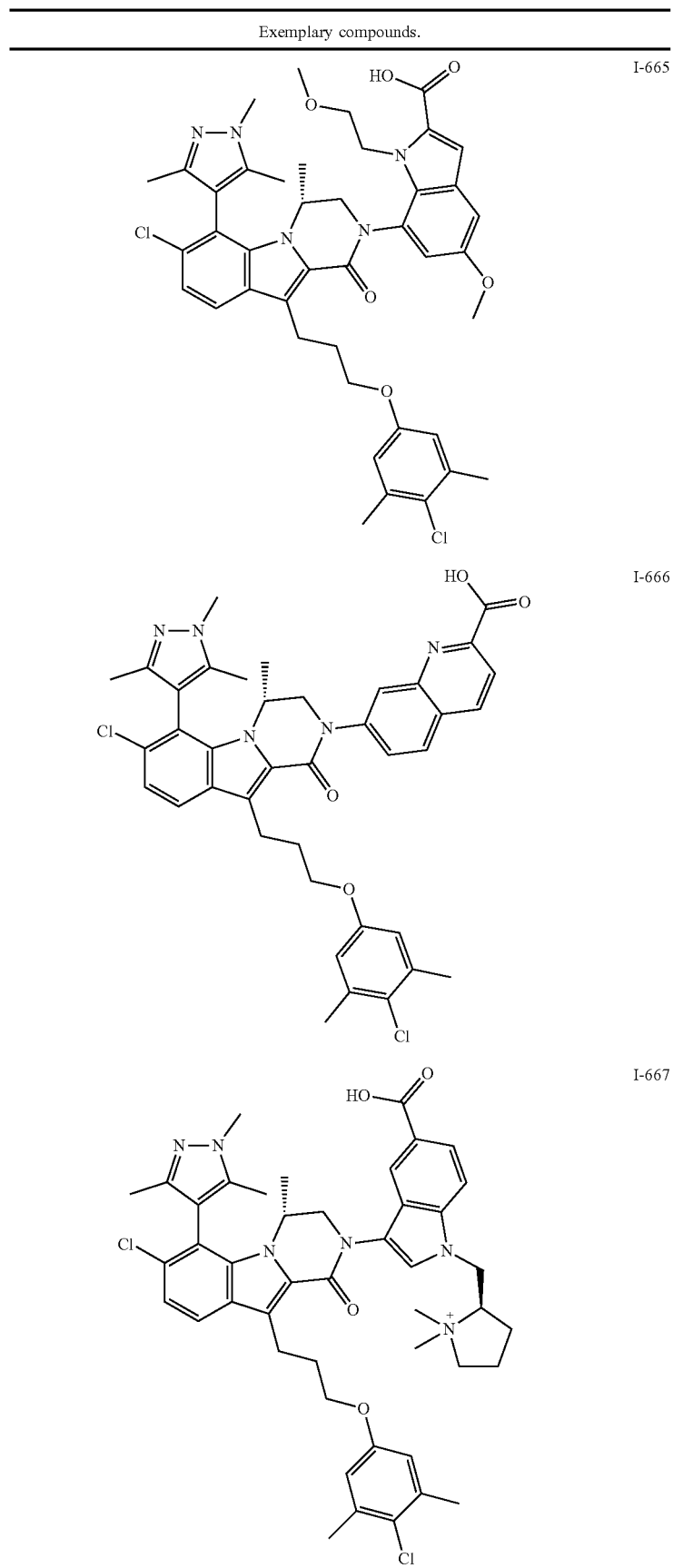

TABLE 1-continued
Exemplary compounds.
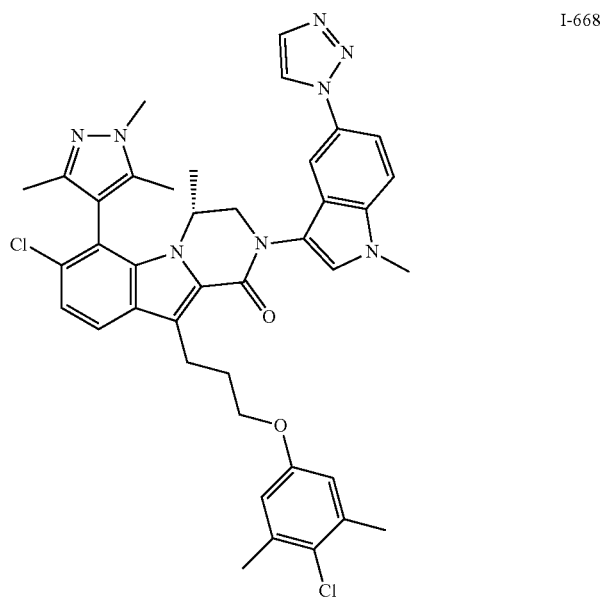
I-668
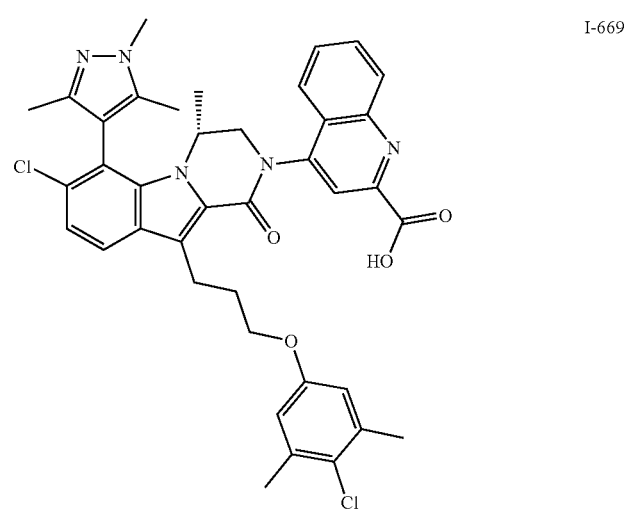
I-669

TABLE 1-continued
Exemplary compounds.
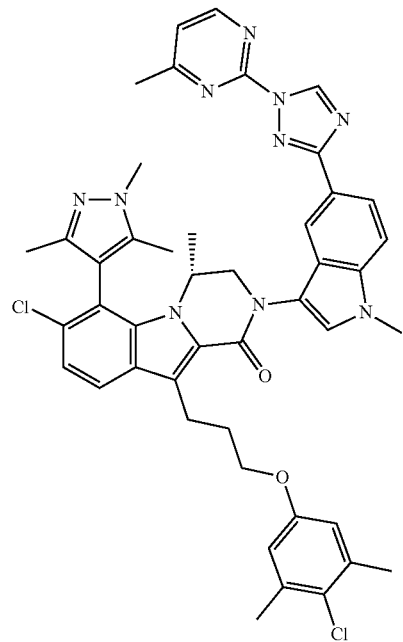
I-670
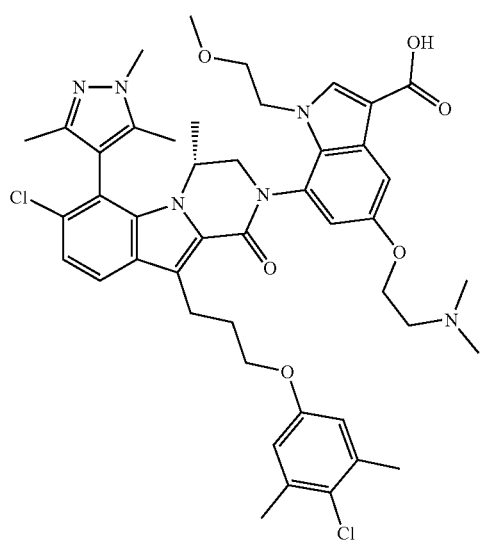
I-671

TABLE 1-continued
Exemplary compounds.
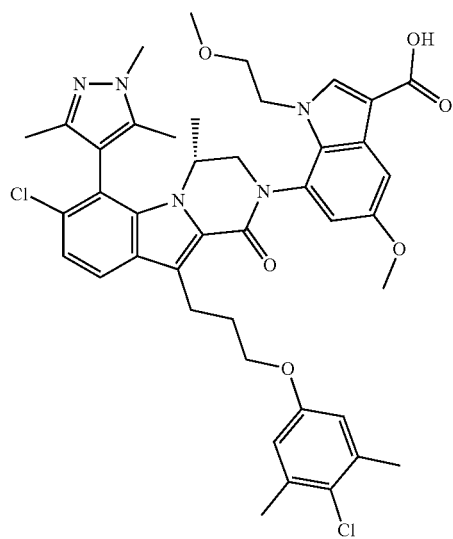 [SMILES: COCCn1cc(C(=O)O)c2cc(OC)cc(N3C[C@@H](C)n4c(c(CCCOc5cc(C)c(Cl)c(C)c5)c5ccc(Cl)c(-c6c(C)nn(C)c6C)c54)C3=O)c21]
I-672
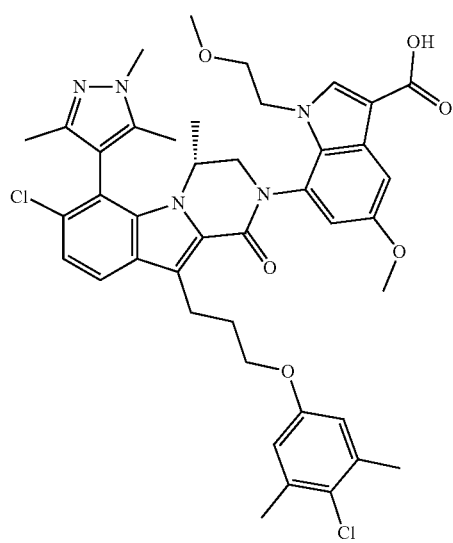 [SMILES: COCCn1cc(C(=O)O)c2cc(OC)cc(N3C[C@@H](C)n4c(c(CCCOc5cc(C)c(Cl)c(C)c5)c5ccc(Cl)c(-c6c(C)nn(C)c6C)c54)C3=O)c21]
I-673

TABLE 1-continued
Exemplary compounds.
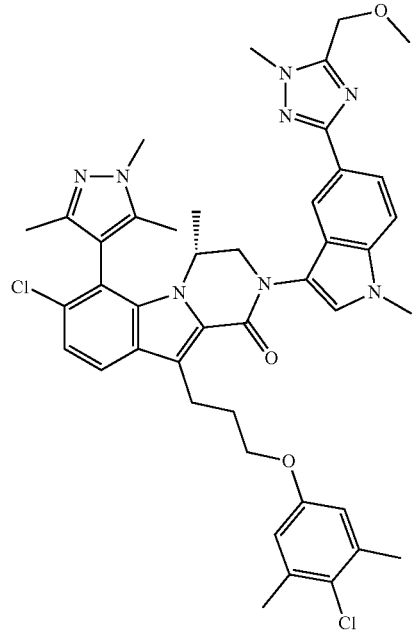
I-674
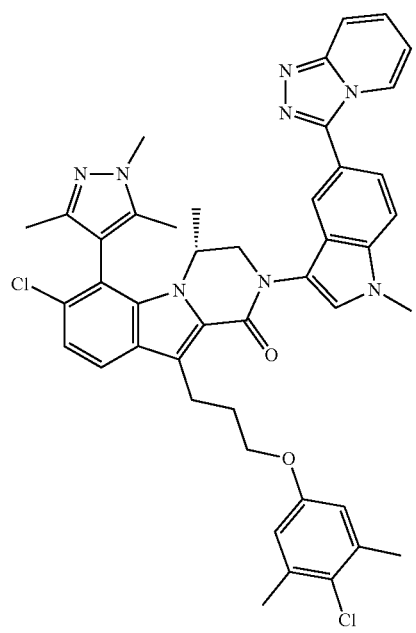
I-675

TABLE 1-continued
Exemplary compounds.
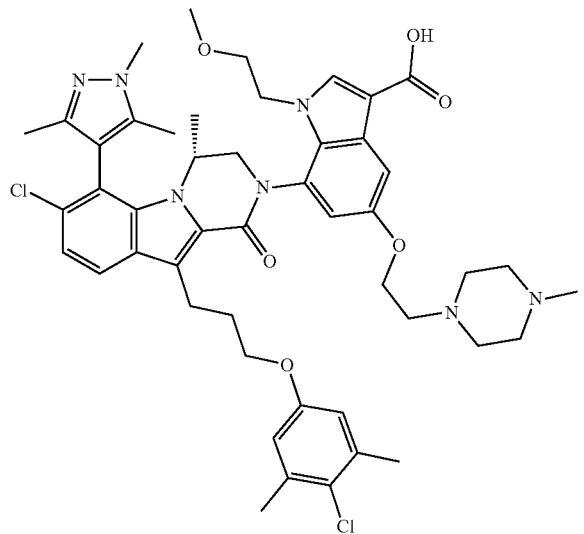
I-676
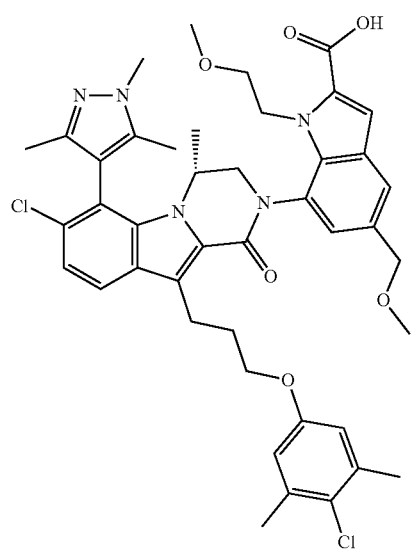
I-677

TABLE 1-continued
Exemplary compounds.
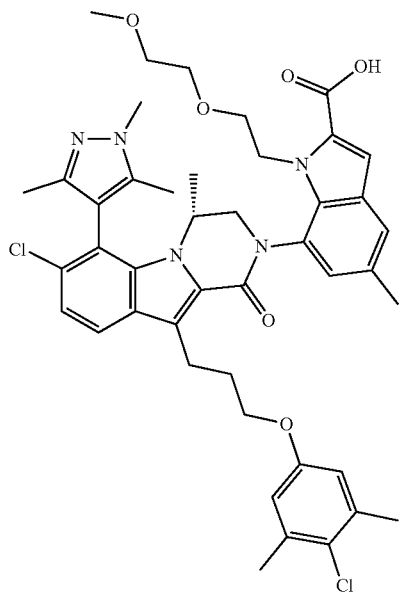
I-678
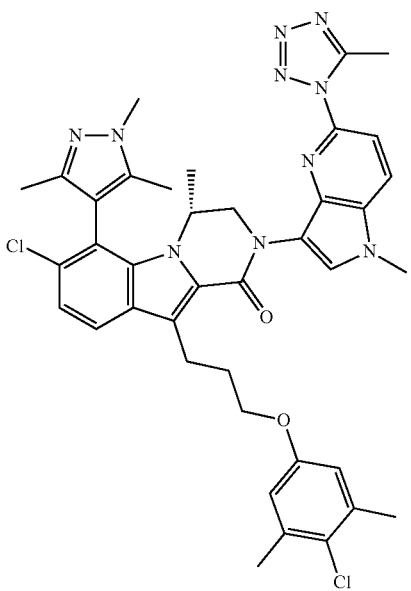
I-679

TABLE 1-continued
Exemplary compounds.
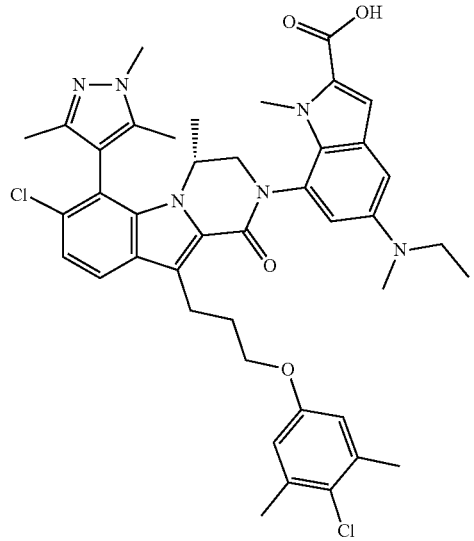 [SMILES: CCN(C)c1cc(N2C[C@@H](C)n3c(c(CCCOc4cc(C)c(Cl)c(C)c4)c4ccc(Cl)c(-c5c(C)nn(C)c5C)c43)C2=O)c2c(c1)cc(C(=O)O)n2C]
I-680
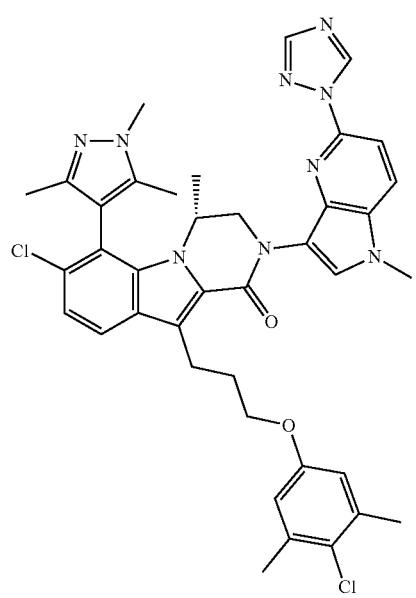
I-681

TABLE 1-continued
Exemplary compounds.
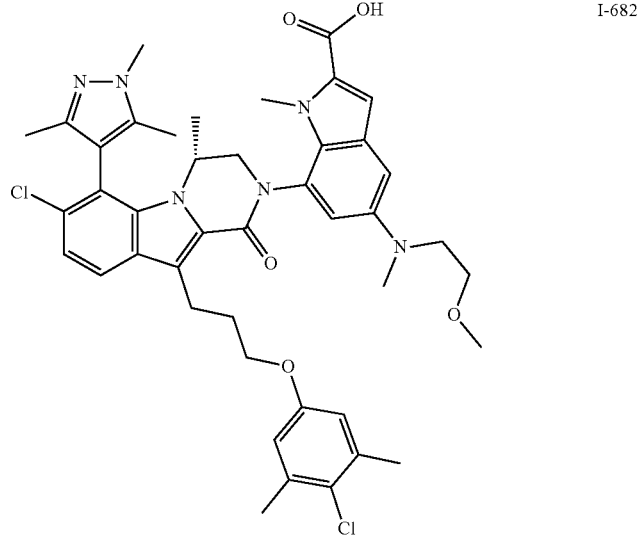
I-682
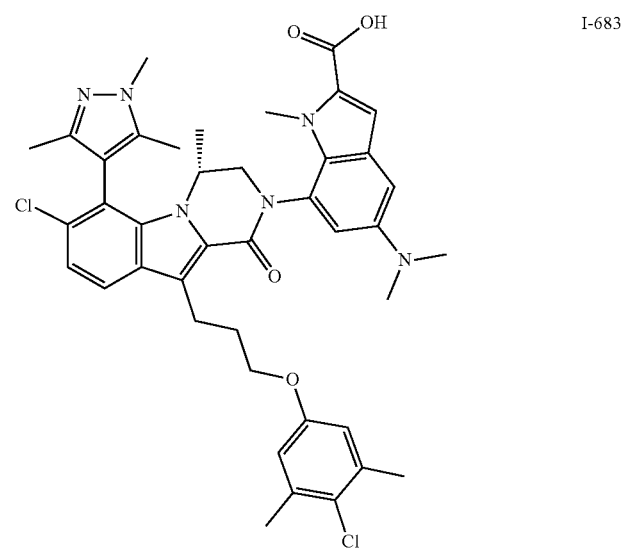
I-683

TABLE 1-continued
Exemplary compounds.
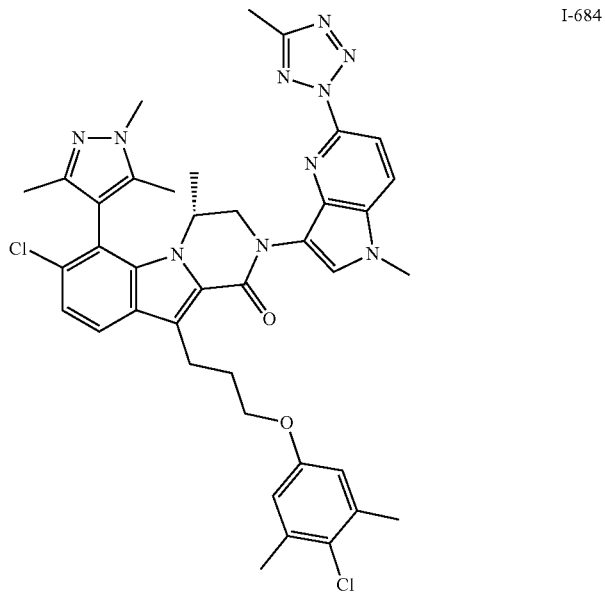
I-684
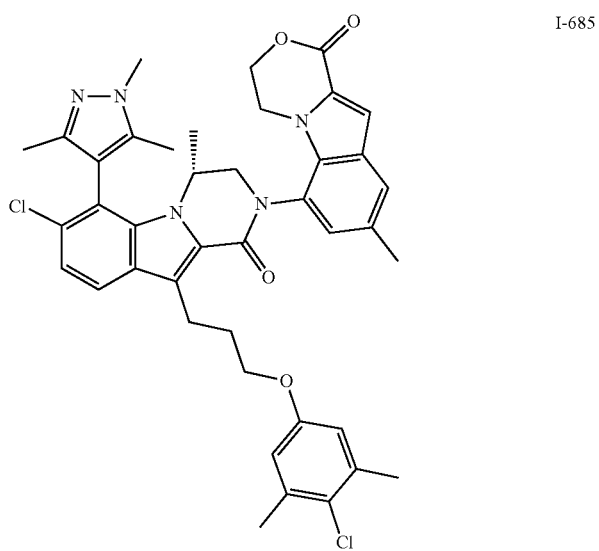
I-685

TABLE 1-continued
Exemplary compounds.
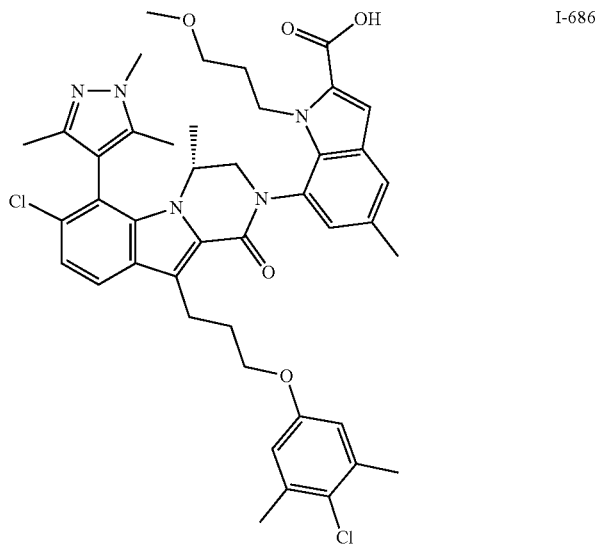
I-686
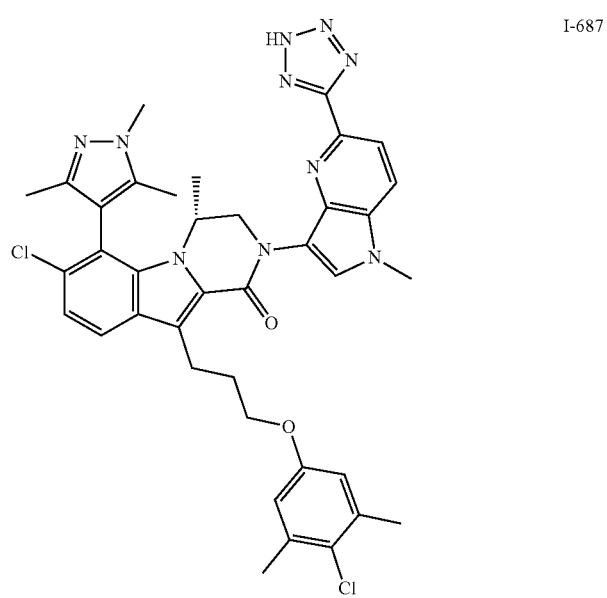
I-687

TABLE 1-continued
Exemplary compounds.
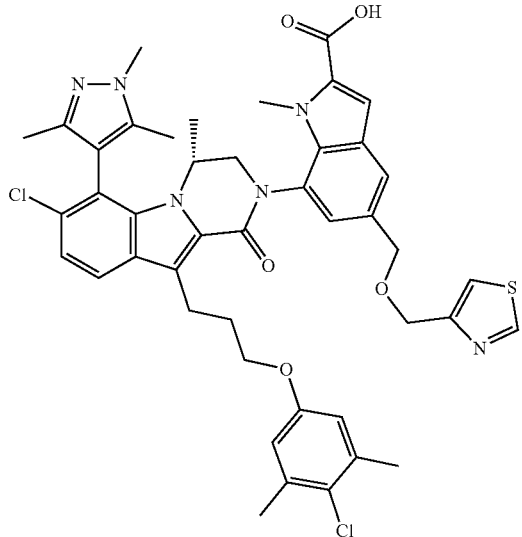 [SMILES: Cc1cc(OCCCc2c3n(c4c(-c5c(C)nn(C)c5C)c(Cl)ccc24)[C@H](C)CN(c2cc(COCc4cscn4)cc4cc(C(=O)O)n(C)c24)C3=O)cc(C)c1Cl]
I-688
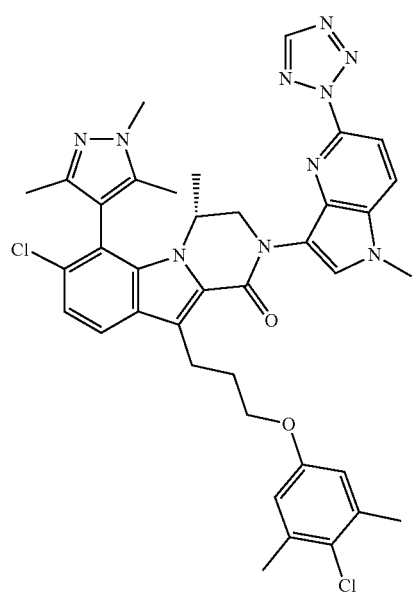
I-689

TABLE 1-continued
Exemplary compounds.
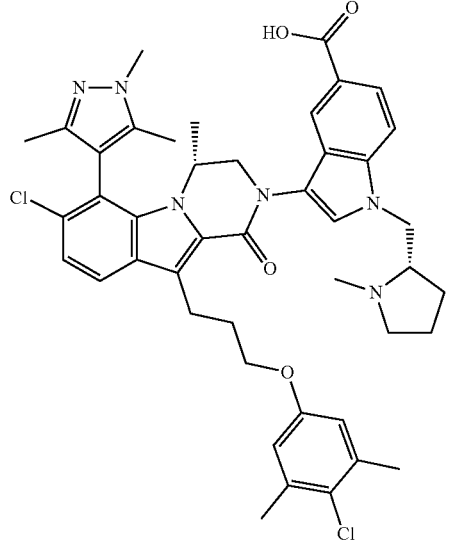 [SMILES: Cc1cc(OCCCc2c3n(c4c(-c5c(C)nn(C)c5C)c(Cl)ccc24)[C@H](C)CN(c2cn(C[C@@H]4CCCN4C)c4ccc(C(=O)O)cc24)C3=O)cc(C)c1Cl]
I-690
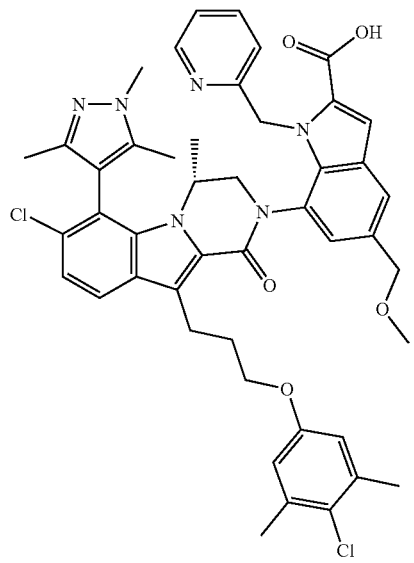
I-691

TABLE 1-continued
Exemplary compounds.
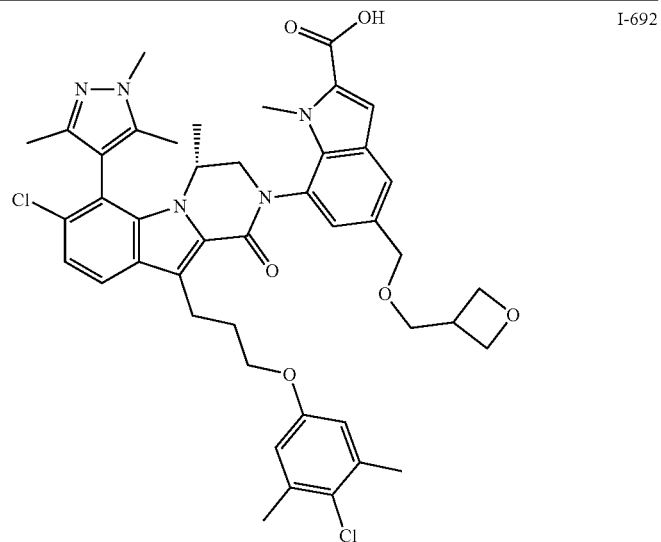
I-692
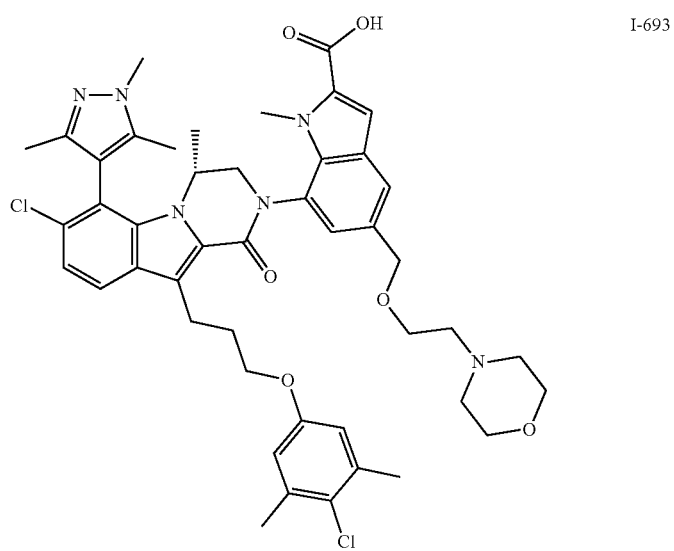
I-693
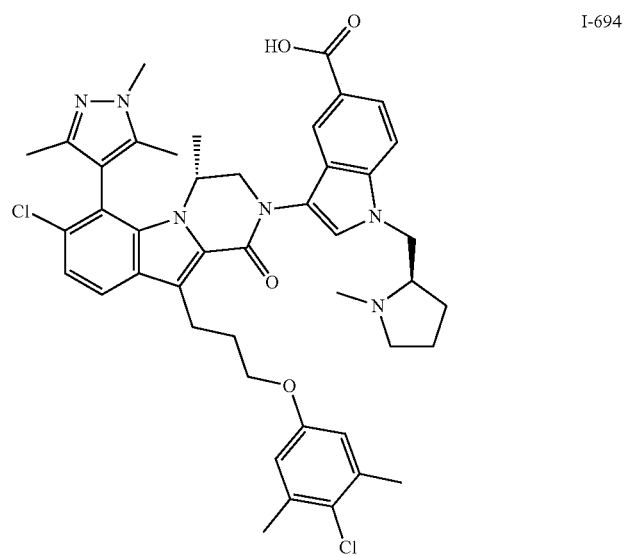
I-694

621
TABLE 1-continued
Exemplary compounds.
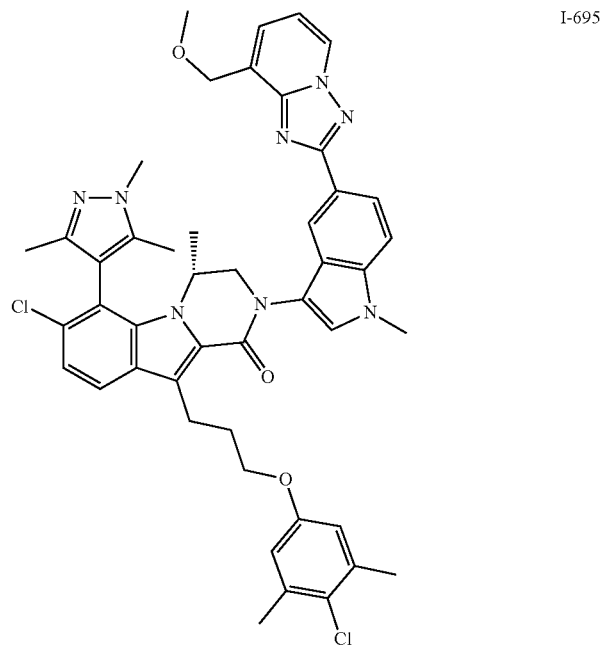
I-695
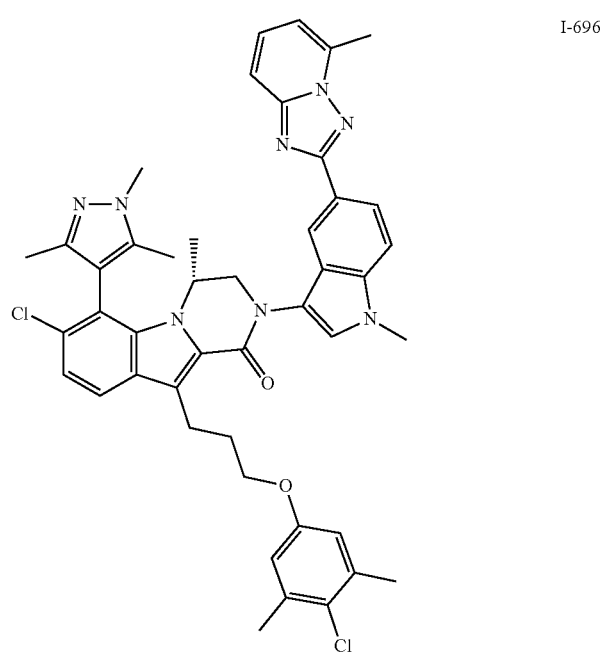
I-696

TABLE 1-continued
Exemplary compounds.
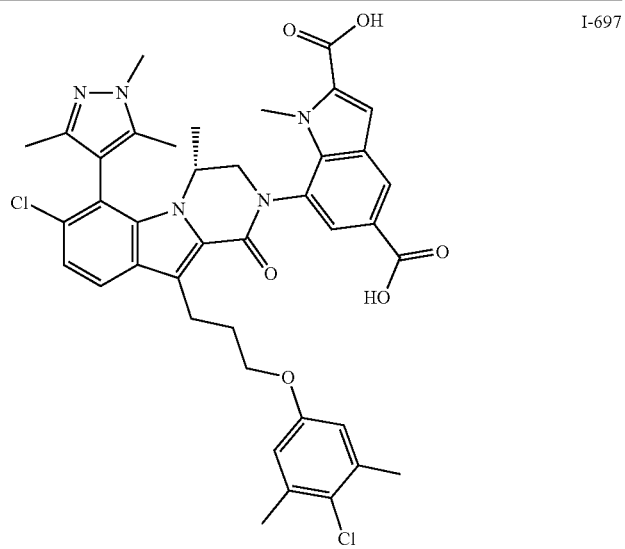
I-697
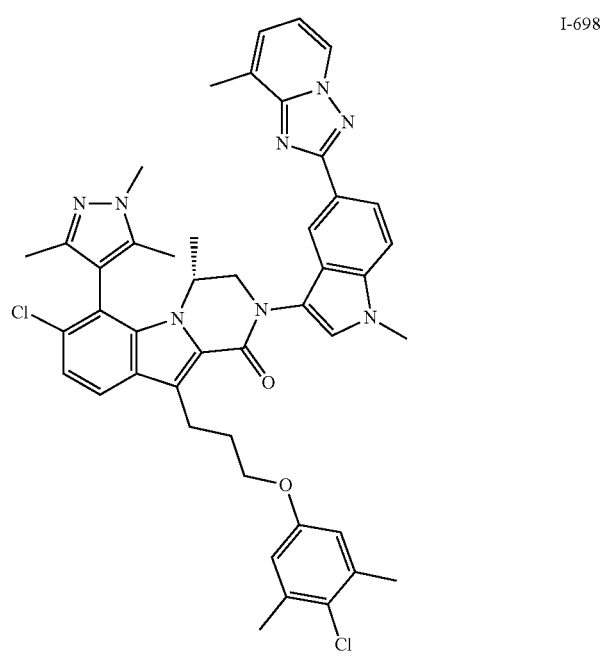
I-698

TABLE 1-continued
Exemplary compounds.
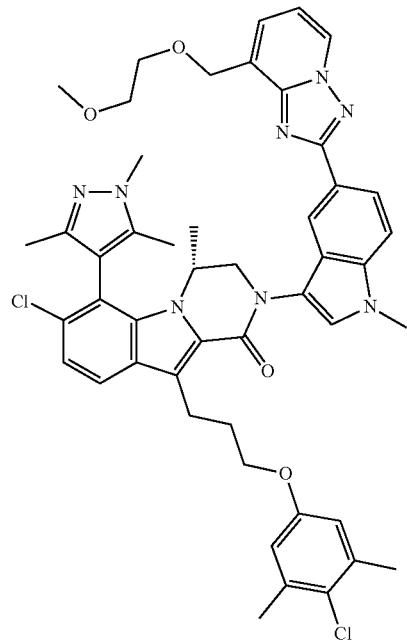
I-699
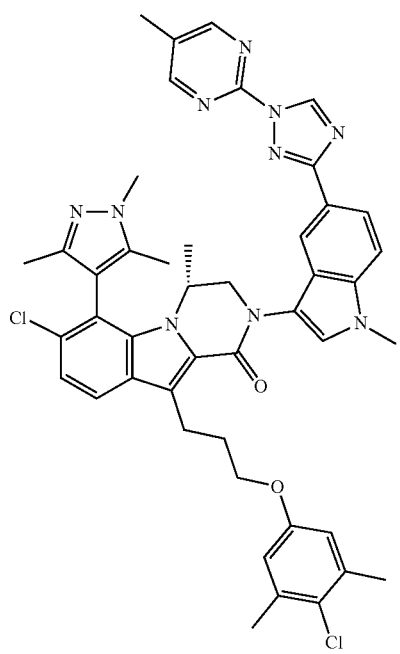
I-700

TABLE 1-continued
Exemplary compounds.
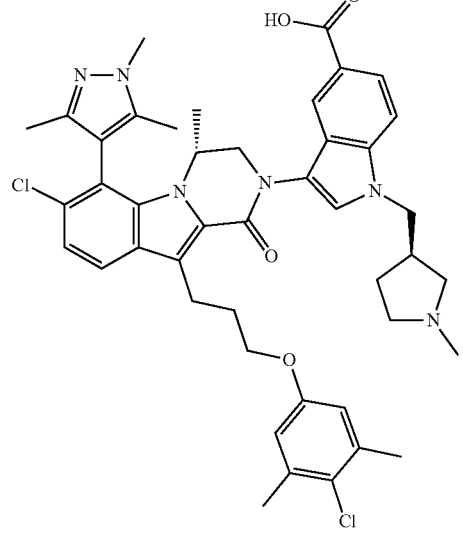
I-701
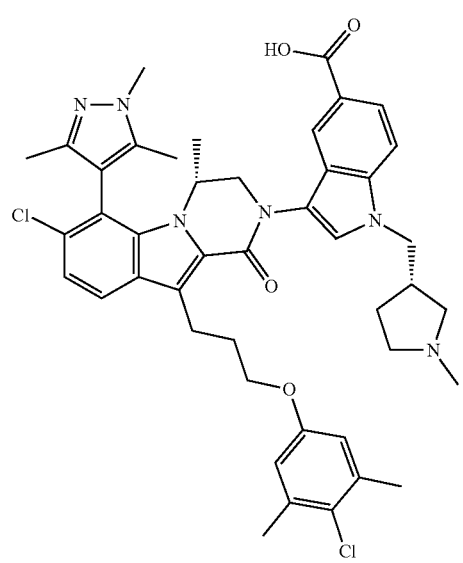
I-702

TABLE 1-continued
Exemplary compounds.
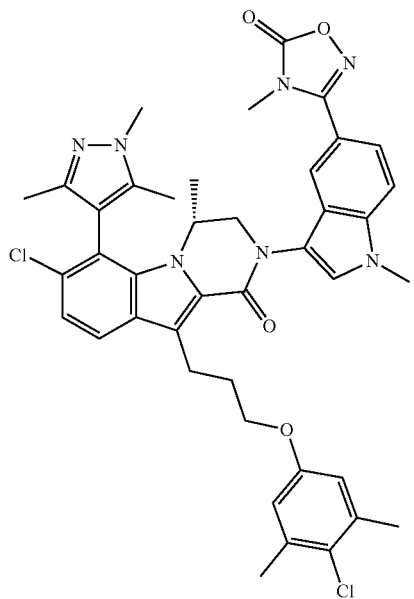
I-703
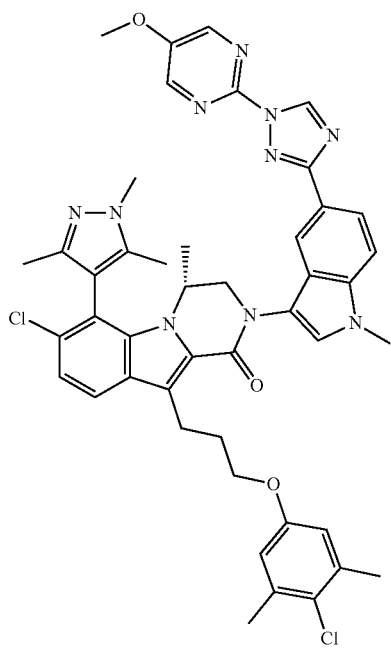
I-704

TABLE 1-continued
Exemplary compounds.
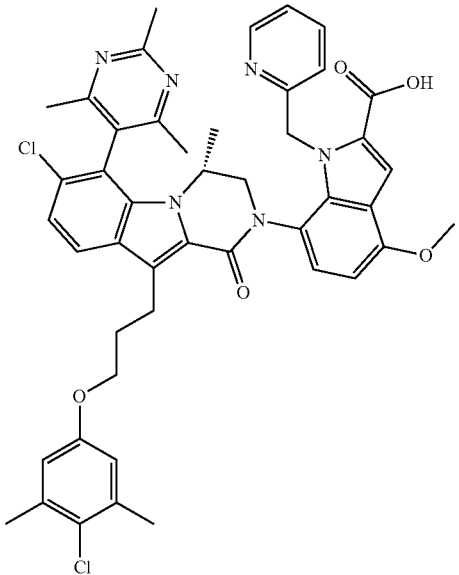
I-705
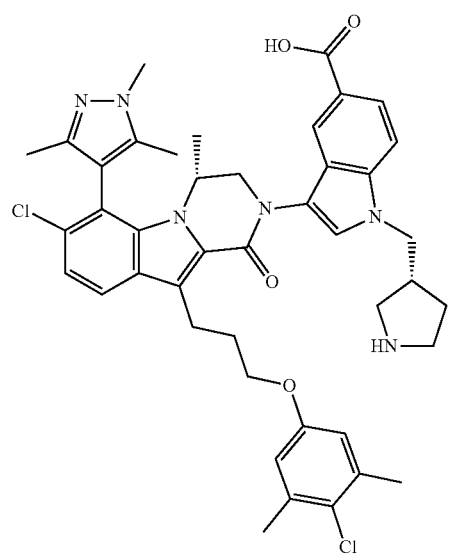 [SMILES: Cc1cc(OCCCc2c3n(c4c(-c5c(C)nn(C)c5C)c(Cl)ccc24)[C@H](C)CN(c2cn(C[C@@H]4CCNC4)c4ccc(C(=O)O)cc24)C3=O)cc(C)c1Cl]
I-706

TABLE 1-continued
Exemplary compounds.
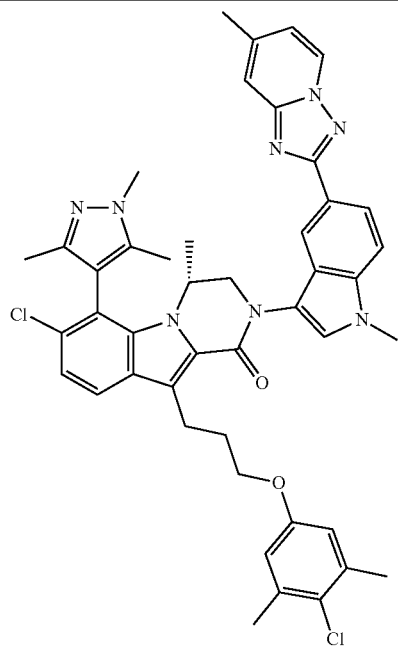
I-707
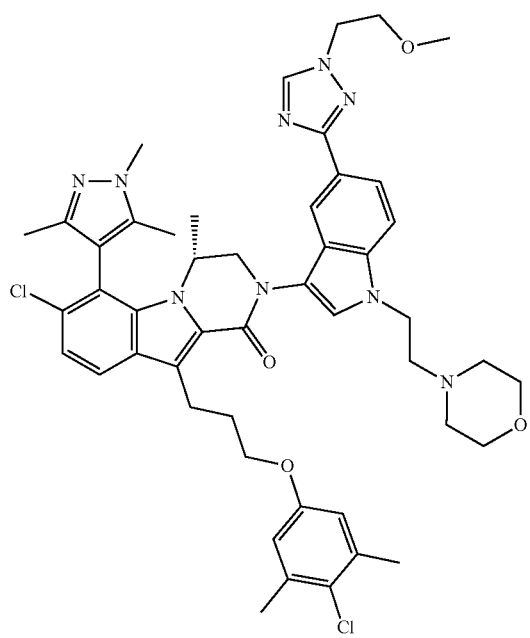 [SMILES: COCCn1cnc(-c2ccc3c(c2)c(N2C[C@@H](C)n4c(c(CCCOc5cc(C)c(Cl)c(C)c5)c5ccc(Cl)c(-c6c(C)nn(C)c6C)c54)C2=O)cn3CCN2CCOCC2)n1]
I-708

TABLE 1-continued
Exemplary compounds.
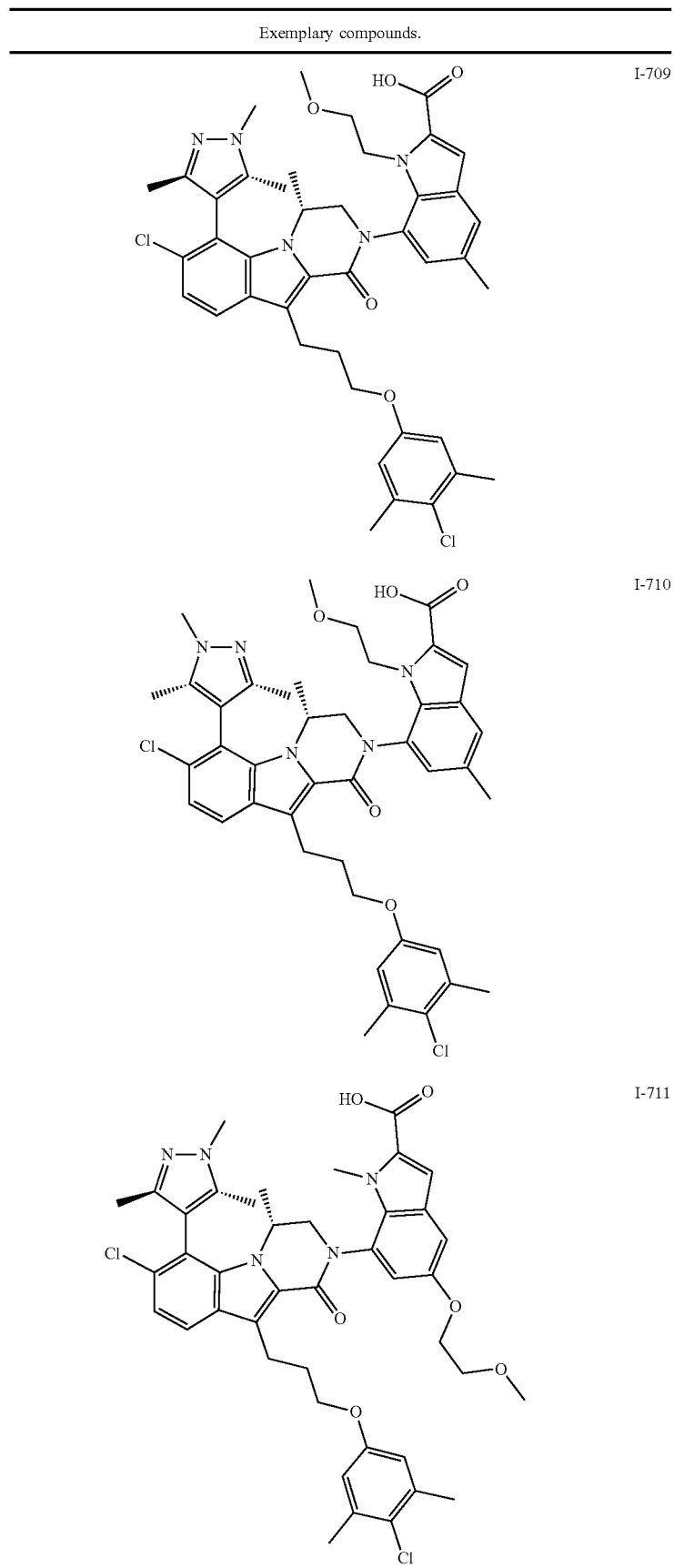
I-709
I-710
I-711

TABLE 1-continued
Exemplary compounds.
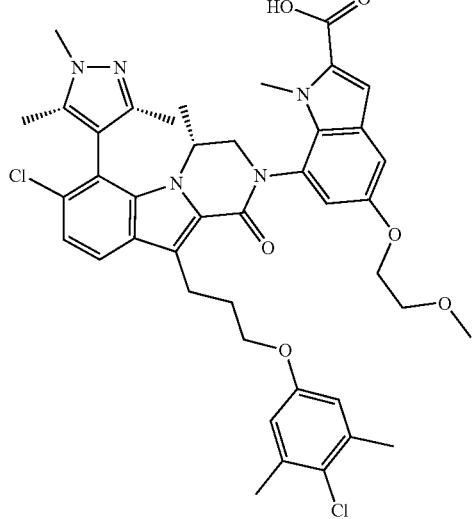
I-712
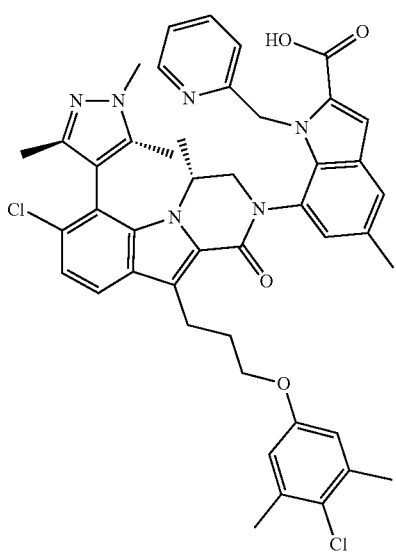
I-713
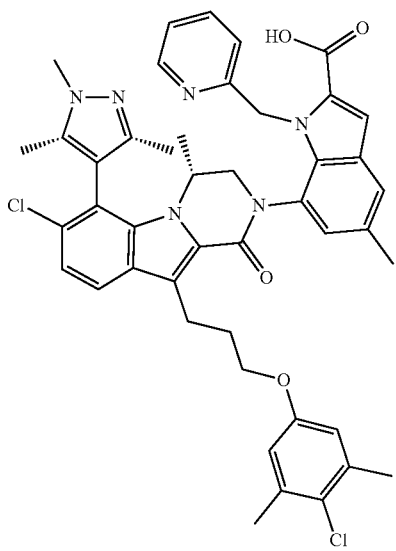
I-714

TABLE 1-continued
Exemplary compounds.
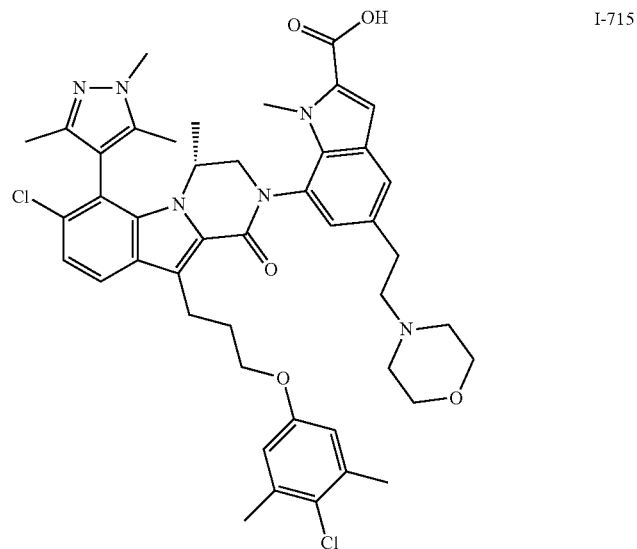
I-715
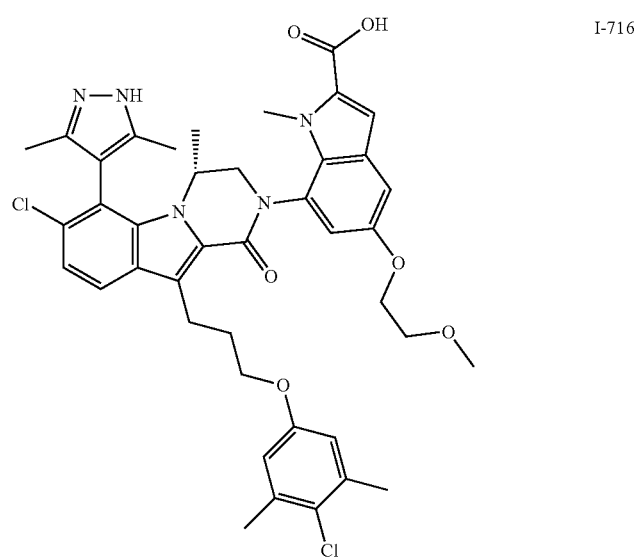
I-716

TABLE 1-continued
Exemplary compounds.
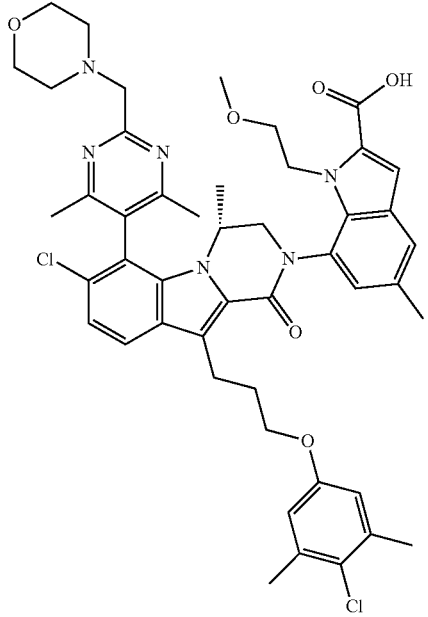 [SMILES: COCCn1c(C(=O)O)cc2cc(C)cc(N3C[C@@H](C)n4c(c(CCCOc5cc(C)c(Cl)c(C)c5)c5ccc(Cl)c(-c6c(C)nc(CN7CCOCC7)nc6C)c54)C3=O)c21]
I-717
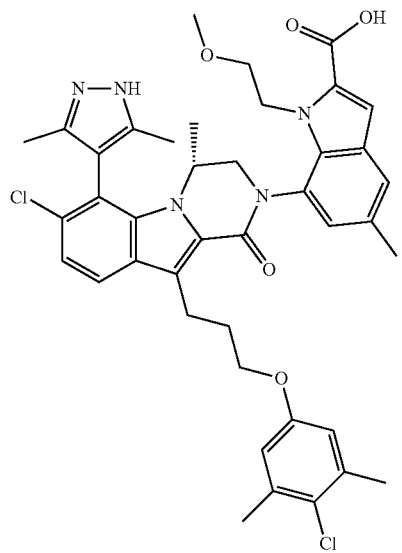
I-718

TABLE 1-continued
Exemplary compounds.
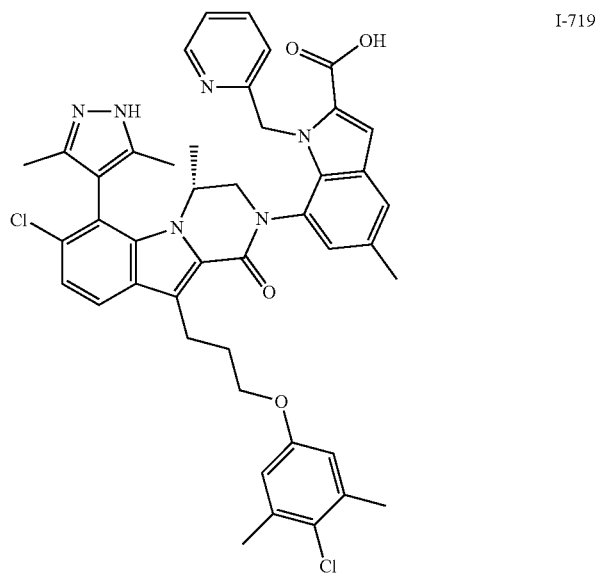
I-719
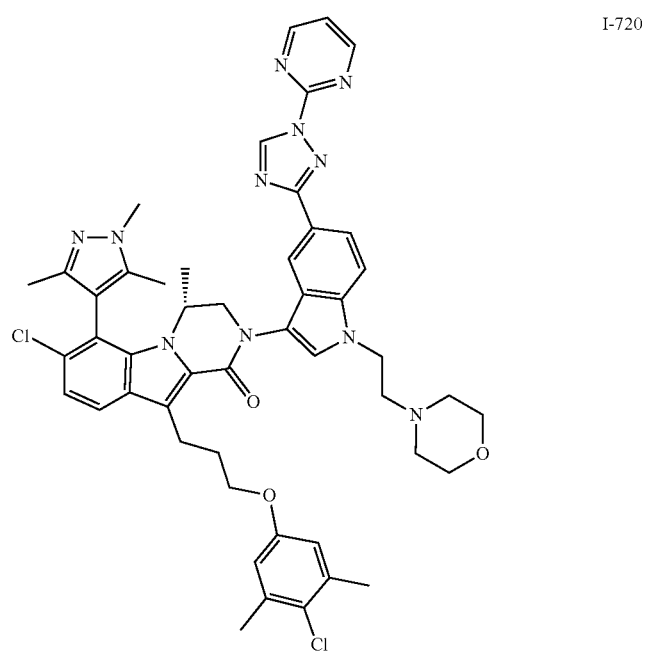
I-720

TABLE 1-continued
Exemplary compounds.
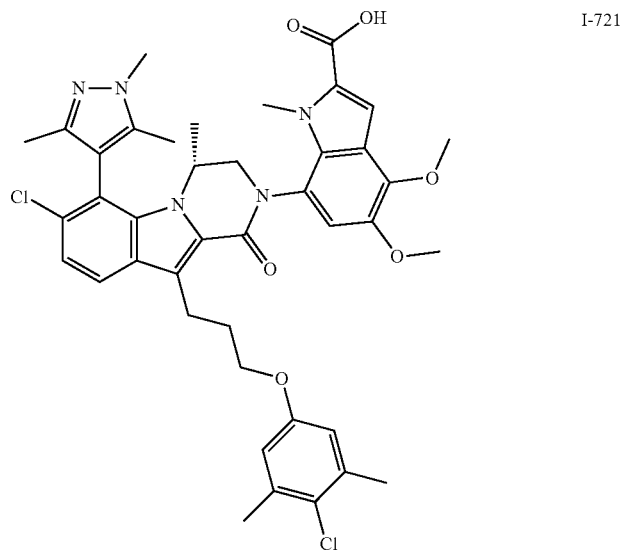
I-721
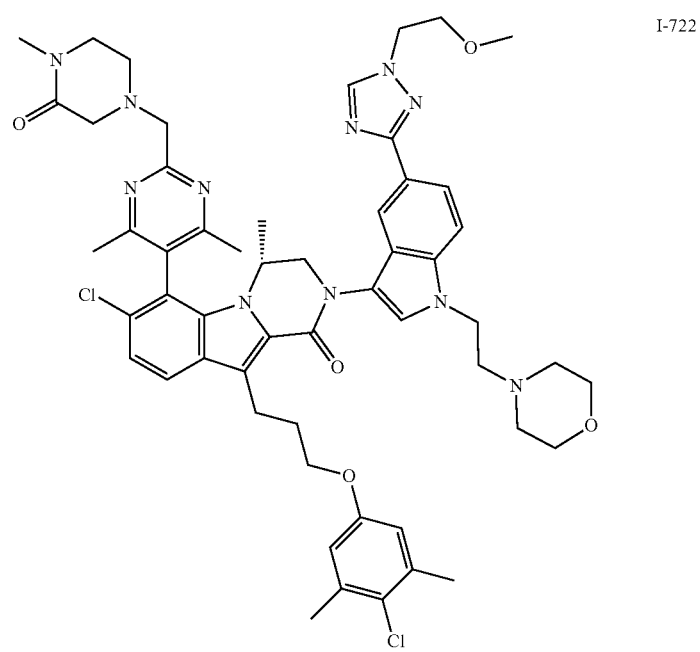
I-722

TABLE 1-continued
Exemplary compounds.
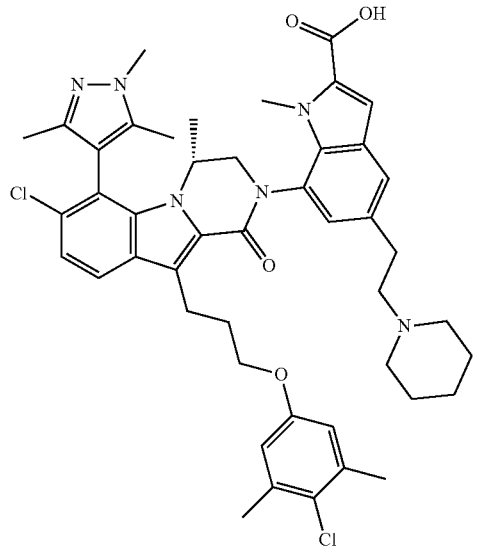
I-723
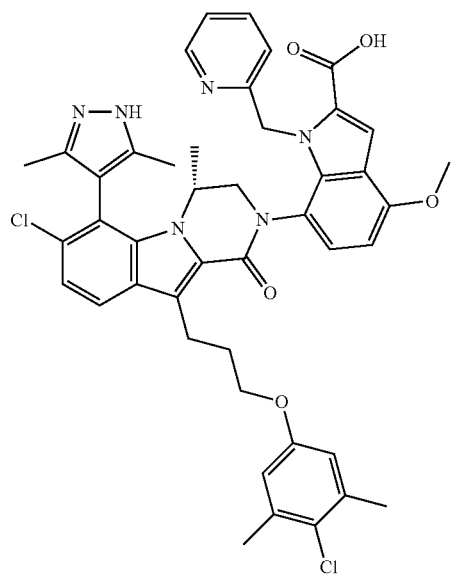
I-724

TABLE 1-continued
Exemplary compounds.
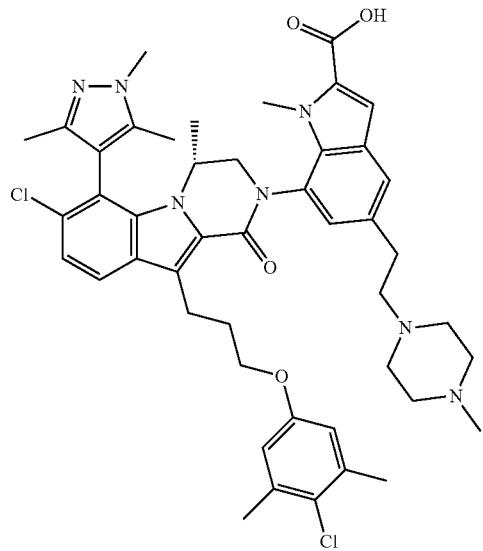
I-725
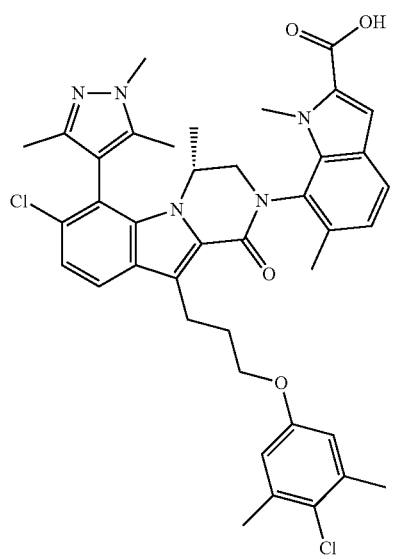 [SMILES: Cc1cc(OCCCc2c3n(c4c(-c5c(C)nn(C)c5C)c(Cl)ccc24)[C@H](C)CN(c2c(C)ccc4cc(C(=O)O)n(C)c24)C3=O)cc(C)c1Cl]
I-726

TABLE 1-continued
Exemplary compounds.
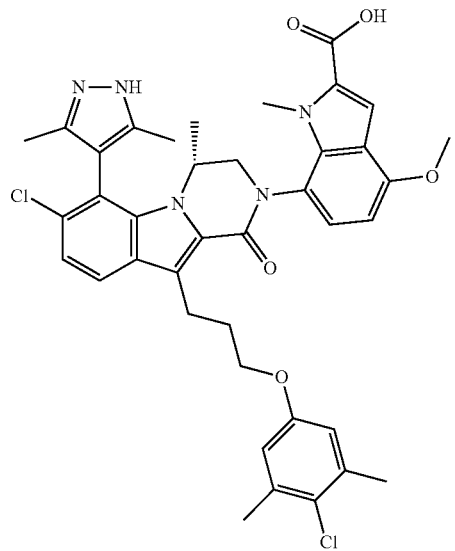
I-727
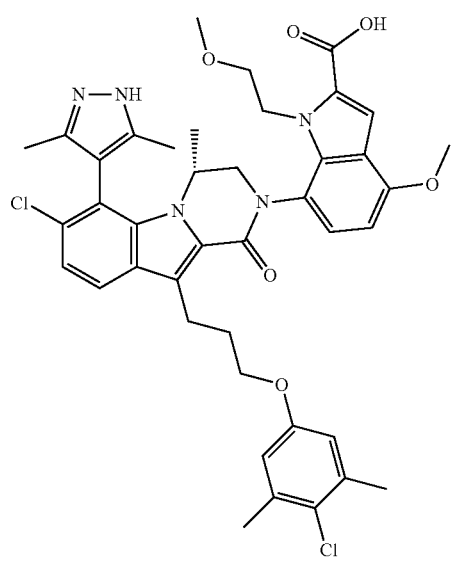
I-728

TABLE 1-continued
Exemplary compounds.
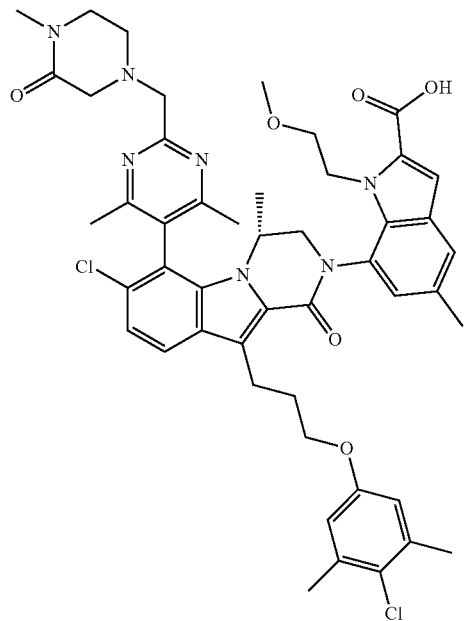
I-729
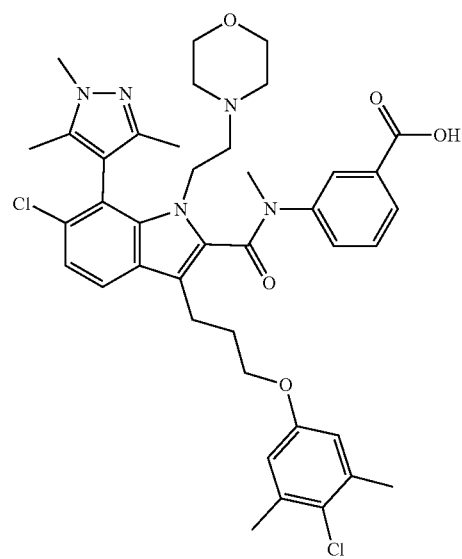 [SMILES: Cc1cc(OCCCc2c(C(=O)N(C)c3cccc(C(=O)O)c3)n(CCN3CCOCC3)c3c(-c4c(C)nn(C)c4C)c(Cl)ccc23)cc(C)c1Cl]
I-730

TABLE 1-continued
Exemplary compounds.
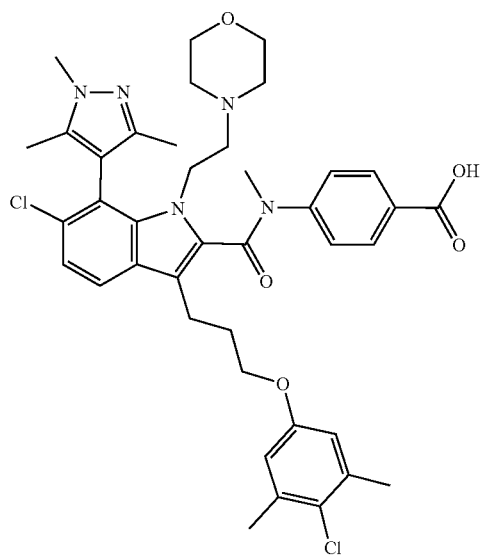 [SMILES: Cc1cc(OCCCc2c(C(=O)N(C)c3ccc(C(=O)O)cc3)n(CCN3CCOCC3)c3c(-c4c(C)nn(C)c4C)c(Cl)ccc23)cc(C)c1Cl]
I-731
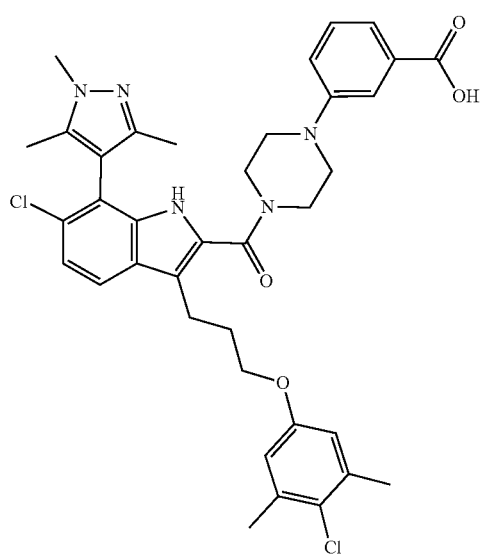 [SMILES: Cc1cc(OCCCc2c(C(=O)N3CCN(c4cccc(C(=O)O)c4)CC3)[nH]c3c(-c4c(C)nn(C)c4C)c(Cl)ccc23)cc(C)c1Cl]
I-732

TABLE 1-continued
Exemplary compounds.
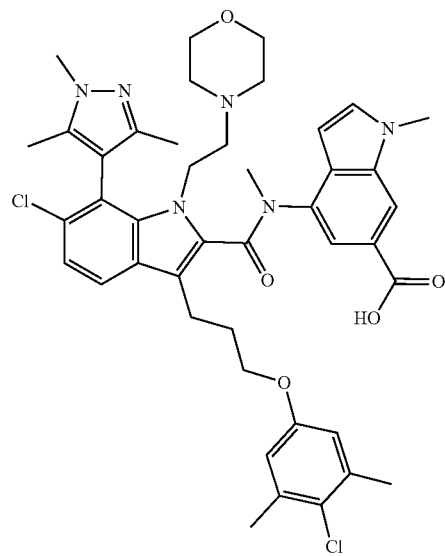 [SMILES: Cc1cc(OCCCc2c(C(=O)N(C)c3cc(C(=O)O)cc4c3ccn4C)n(CCN3CCOCC3)c3c(-c4c(C)nn(C)c4C)c(Cl)ccc23)cc(C)c1Cl]
I-733
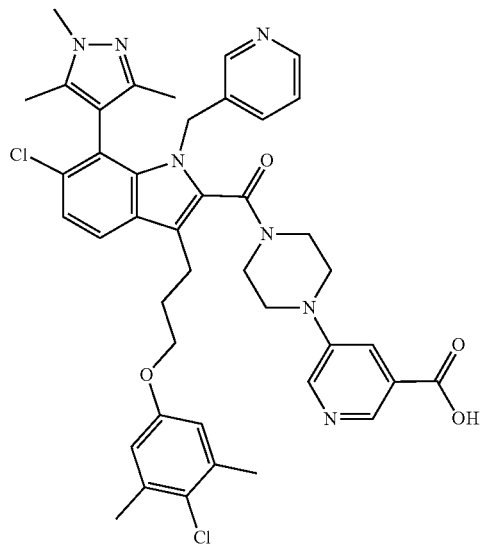 [SMILES: Cc1cc(OCCCc2c(C(=O)N3CCN(c4cncc(C(=O)O)c4)CC3)n(Cc3cccnc3)c3c(-c4c(C)nn(C)c4C)c(Cl)ccc23)cc(C)c1Cl]
I-734

TABLE 1-continued
Exemplary compounds.
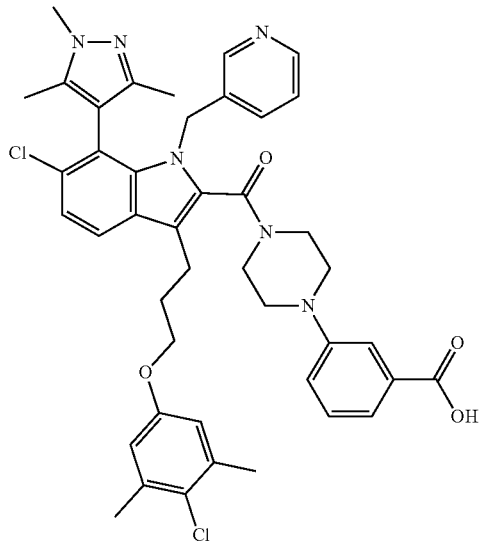 [SMILES: Cc1cc(OCCCc2c(C(=O)N3CCN(c4cccc(C(=O)O)c4)CC3)n(Cc3cccnc3)c3c(-c4c(C)nn(C)c4C)c(Cl)ccc23)cc(C)c1Cl]
I-735
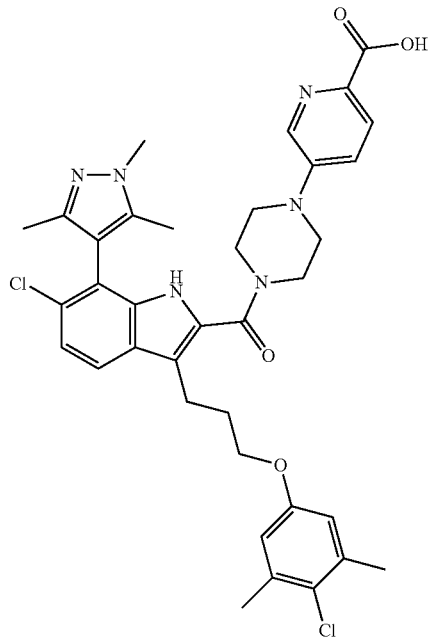 [SMILES: Cc1cc(OCCCc2c(C(=O)N3CCN(c4ccc(C(=O)O)nc4)CC3)[nH]c3c(-c4c(C)nn(C)c4C)c(Cl)ccc23)cc(C)c1Cl]
I-736

TABLE 1-continued
Exemplary compounds.
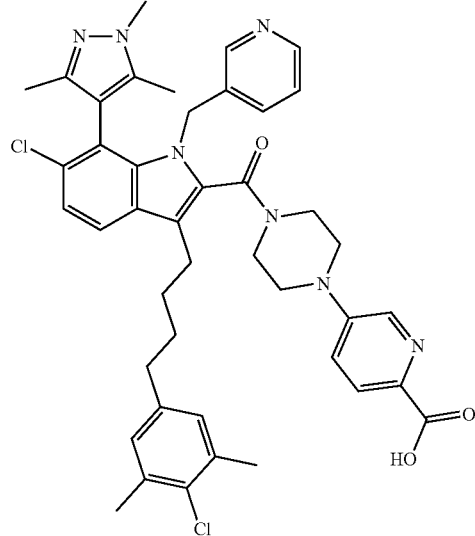 [SMILES: Cc1cc(CCCCc2c(C(=O)N3CCN(c4ccc(C(=O)O)nc4)CC3)n(Cc3cccnc3)c3c(-c4c(C)nn(C)c4C)c(Cl)ccc23)cc(C)c1Cl]
I-737
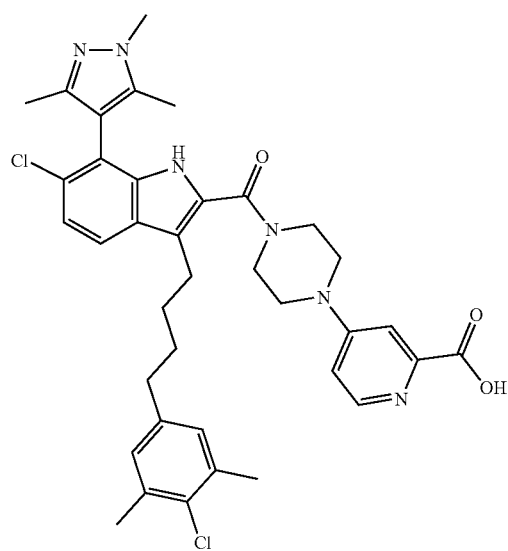 [SMILES: Cc1cc(CCCCc2c(C(=O)N3CCN(c4ccnc(C(=O)O)c4)CC3)[nH]c3c(-c4c(C)nn(C)c4C)c(Cl)ccc23)cc(C)c1Cl]
I-738

TABLE 1-continued
Exemplary compounds.
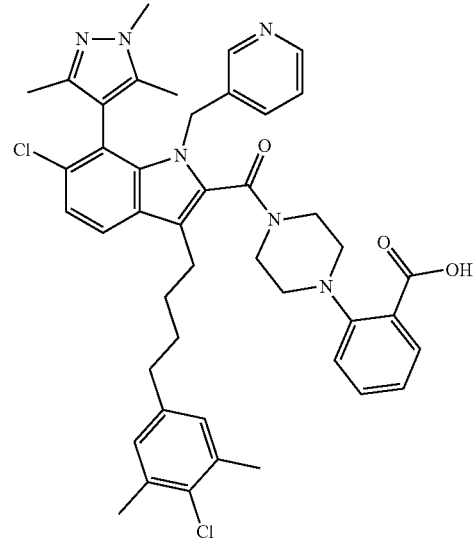 [SMILES: Cc1cc(CCCCc2c(C(=O)N3CCN(c4ccccc4C(=O)O)CC3)n(Cc3cccnc3)c3c(-c4c(C)nn(C)c4C)c(Cl)ccc23)cc(C)c1Cl]
I-739
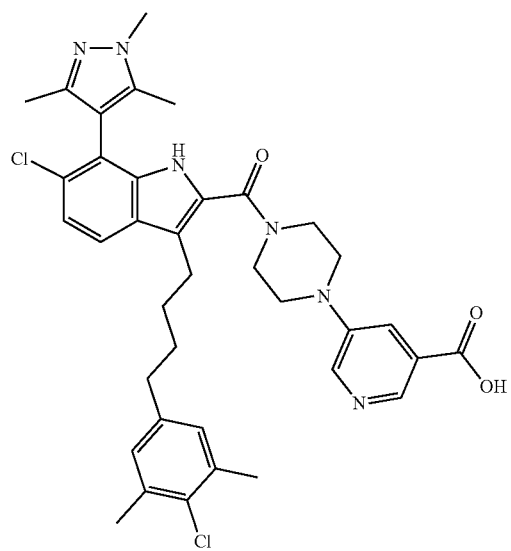
I-740

TABLE 1-continued
Exemplary compounds.
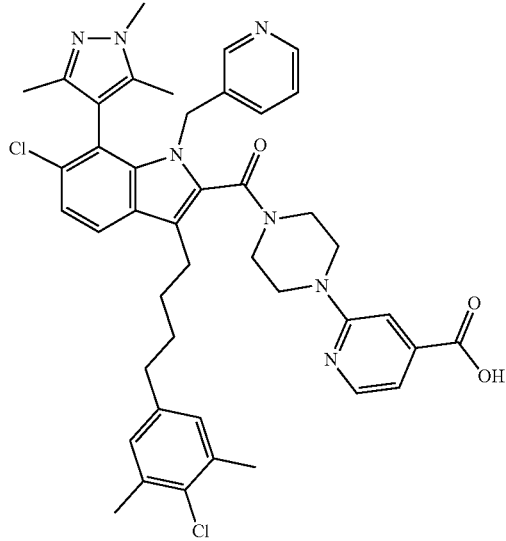 [SMILES: Cc1cc(CCCCc2c(C(=O)N3CCN(c4cc(C(=O)O)ccn4)CC3)n(Cc3cccnc3)c3c(-c4c(C)nn(C)c4C)c(Cl)ccc23)cc(C)c1Cl]
I-741
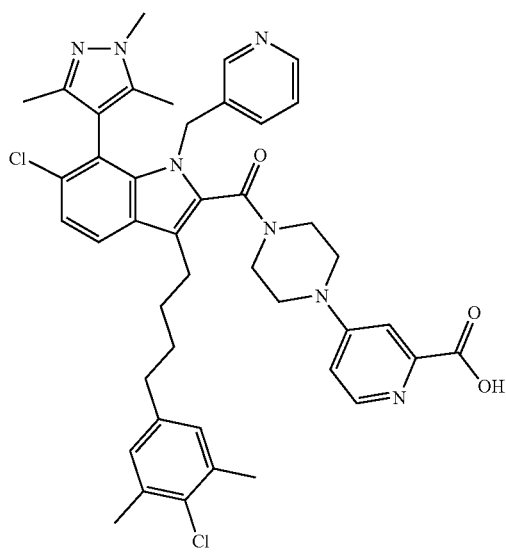 [SMILES: Cc1cc(CCCCc2c(C(=O)N3CCN(c4ccnc(C(=O)O)c4)CC3)n(Cc3cccnc3)c3c(-c4c(C)nn(C)c4C)c(Cl)ccc23)cc(C)c1Cl]
I-742

TABLE 1-continued
Exemplary compounds.
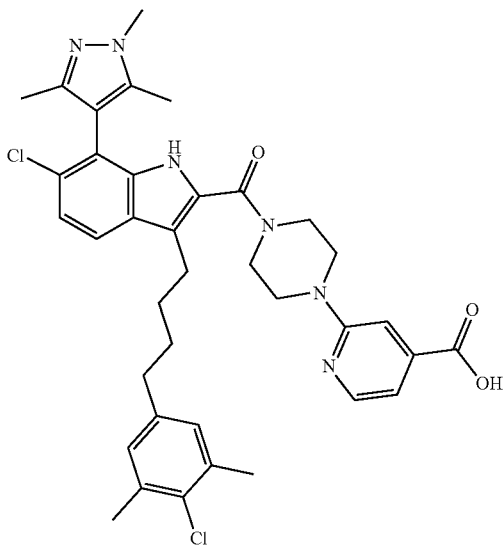 [SMILES: Cc1cc(CCCCc2c(C(=O)N3CCN(c4cc(C(=O)O)ccn4)CC3)[nH]c3c(-c4c(C)nn(C)c4C)c(Cl)ccc23)cc(C)c1Cl]
I-743
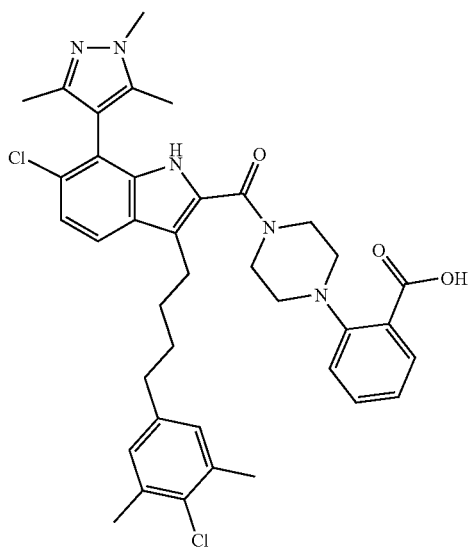 [SMILES: Cc1cc(CCCCc2c(C(=O)N3CCN(c4ccccc4C(=O)O)CC3)[nH]c3c(-c4c(C)nn(C)c4C)c(Cl)ccc23)cc(C)c1Cl]
I-744
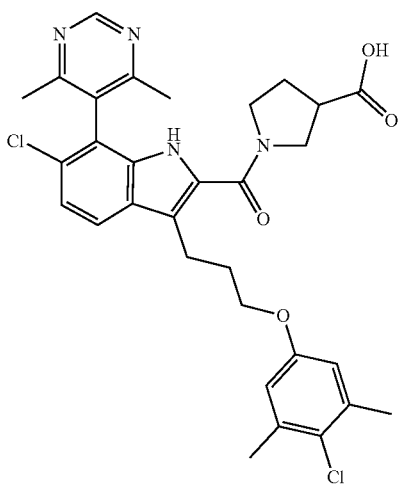 [SMILES: Cc1cc(OCCCc2c(C(=O)N3CCC(C(=O)O)C3)[nH]c3c(-c4c(C)ncnc4C)c(Cl)ccc23)cc(C)c1Cl]
I-745

TABLE 1-continued
Exemplary compounds.
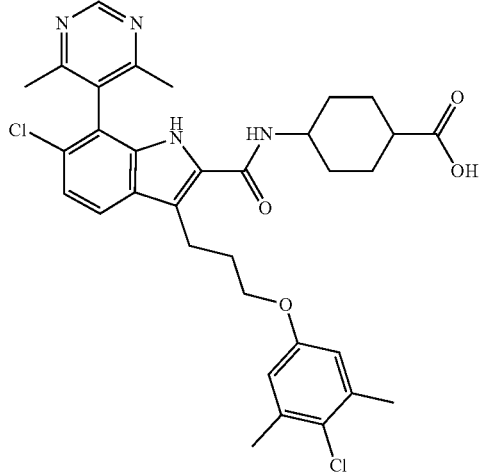 [SMILES: Cc1cc(OCCCc2c(C(=O)NC3CCC(C(=O)O)CC3)[nH]c3c(-c4c(C)ncnc4C)c(Cl)ccc23)cc(C)c1Cl]
I-746
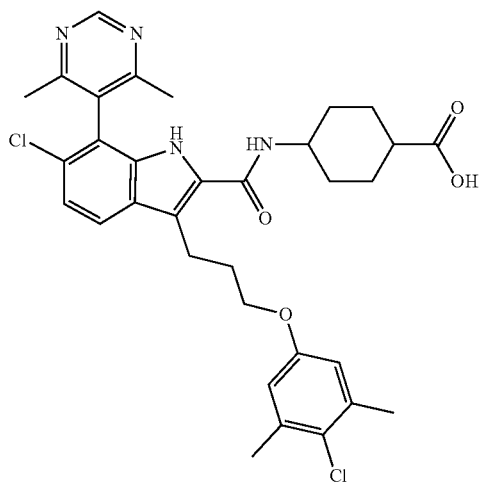 [SMILES: Cc1cc(OCCCc2c(C(=O)NC3CCC(C(=O)O)CC3)[nH]c3c(-c4c(C)ncnc4C)c(Cl)ccc23)cc(C)c1Cl]
I-747
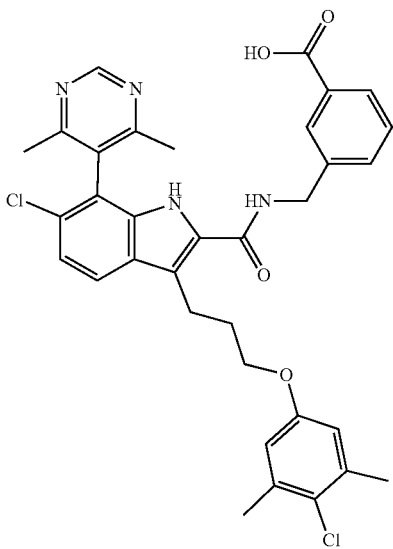 [SMILES: Cc1cc(OCCCc2c(C(=O)NCc3cccc(C(=O)O)c3)[nH]c3c(-c4c(C)ncnc4C)c(Cl)ccc23)cc(C)c1Cl]
I-748

SYNTHESIS

The compounds of the present disclosure can be prepared in a number of ways well known to one skilled in the art of organic synthesis. The compounds of the present disclosure can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference as to the subject matter referenced herein.

The compounds of the disclosure may be prepared using the exemplary reactions and techniques described in this section. The reactions are performed in solvents appropriate to the reagents and materials employed and are suitable for the transformations being effective. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One having ordinary skill in the art may adjust one or more of the conditions described herein. One skilled in the art of organic synthesis understands that the functionality present on various portions of the edict molecule must be compatible with the reagents and reactions proposed. Not all compounds of the disclosure falling into a given class may be compatible with some of the reaction conditions required in some of the methods described. Such restrictions to the substituents, which are compatible with the reaction conditions, will be readily apparent to one skilled in the art and alternate methods can be used.

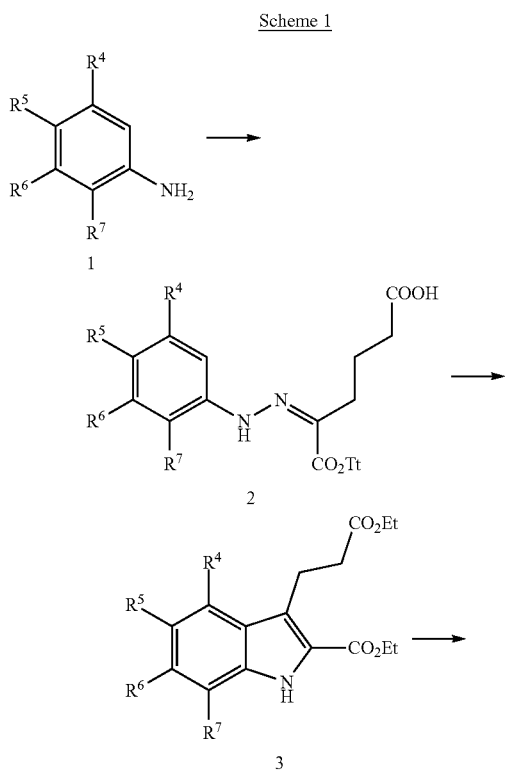

Scheme 1

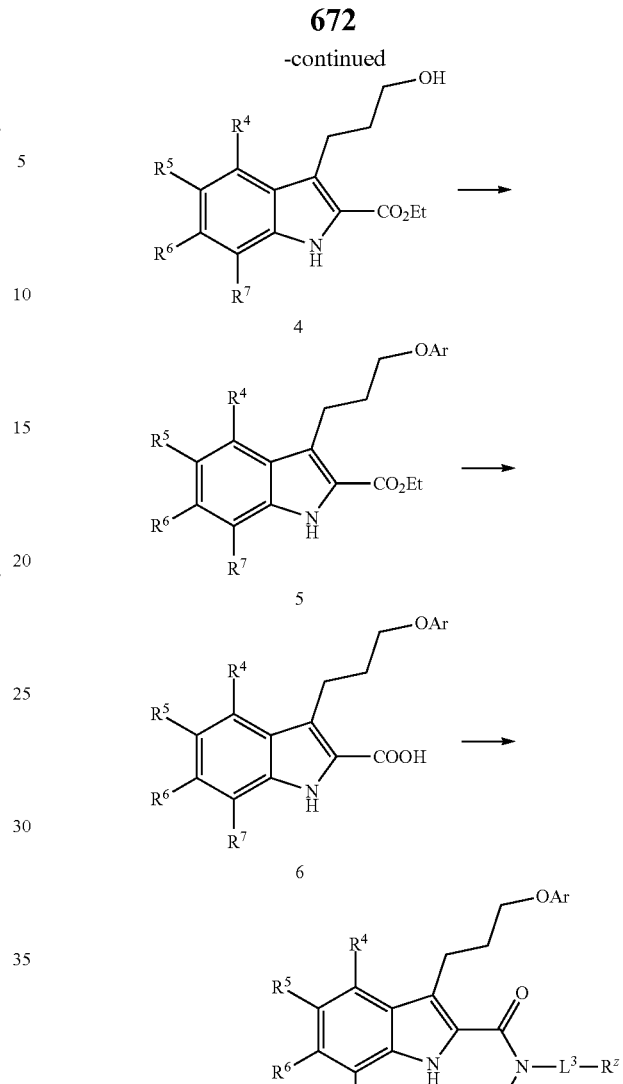

In some embodiments, provided compounds of this invention may be prepared as shown in Scheme 1. Indole 3 can be assembled by using Japp-Klingemann reaction described by, but not limited to, F. G. Salituro, et al. *J. Med. Chem.* (1990) 33, 2944-2946 as follows. Aniline 1 is converted to the corresponding benzenediazonium intermediate followed by condensation with ethyl 2-oxocyclopentanecarboxylate to give hydrazone 2. Intramolecular Fisher indole cyclization of the intermediate 2 is followed to give indole 3. The ethyl ester functional group at the flexible linker of indole 3 can be selectively reduced with excess $BH_3$, and the resulting alcohol 4 can be condensed with phenols or hydroxyheterocycles via Mitsunobu reaction to give the ether 5 using, but not limited to, DEAD or Dt-BuAD. Indole acid 6 can be generated by saponification of compounds 5 with appropriate bases, such as $Cs_2CO_3$, $K_2CO_3$, LiOH or NaOH, at a number of conditions that are routine for those skilled in the art of organic synthesis. Indole amides 7 can be produced by coupling of compounds 6 with suitable amines using coupling reagents, but not limited to, PyBOP, DCC, EDC, HBTU, or TBTU at a number of conditions that are routine for those skilled in the art of organic synthesis.

Scheme 2

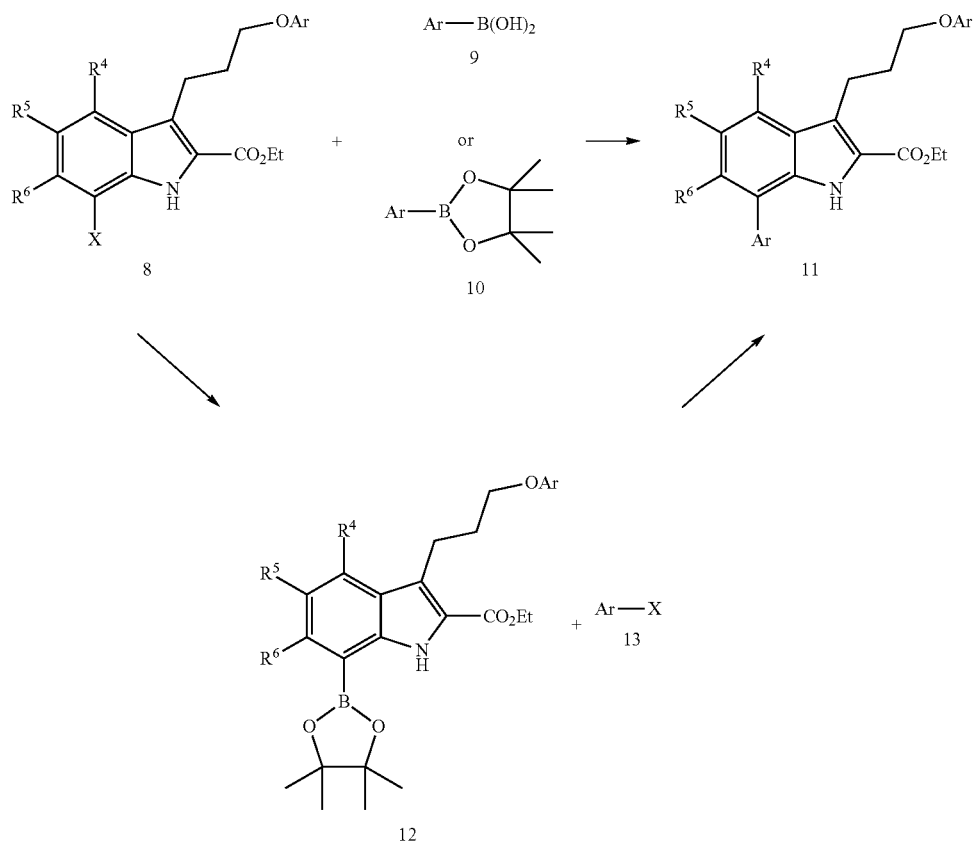

In some embodiments, compounds of Formula 11 containing Ar or heteroaryl substituents as $R^7$ group may be synthesized by procedures illustrated in Scheme 2. Compounds of Formula 8, wherein X=Cl, Br, I, triflates or diazoderivatives, can be prepared as previously described in Scheme 1. A variety of boronic acids 9 or borates 10, which are commercially available or can be prepared, can be coupled with intermediates 8 via e.g., Suzuki coupling protocol to afford biaryl adducts 11 (Miyaura, N., Suzuki, A., Chem. Rev. (1995), 2457). In some embodiments, one exemplary such procedure entails treatment of the aryl bromide or iodide 8 with an aryl boronic acid in the presence of a catalytic Pd species, such as $Pd(PPh_3)_4$, $Pd(PPh_3)_2Cl_2$, $Pd(OAc)_2$, $Pd_2(dba)_3$ and a suitable ligand such as $PPh_3$, $AsPh_3$, etc., or other such Pd catalyst, and a base such as $Na_2CO_3$, $Cs_2CO_3$, $K_2CO_3$, $Ba(OH)_2$ or $Et_3N$. Alternatively, biaryl adducts 11 can be prepared from Pinacolborates 12 which can be prepared from compounds 8 via Pd, such as $Pd(PPh_3)_4$, $Pd(PPh_3)_2Cl_2$, $Pd(OAc)_2$, $Pd_2(dba)_3$, catalyzed coupling of bis(pinacolato)diboron. Intermediates 12 can be coupled with a variety of aryl-halides or heteroaryl-halides 13 using Suzuki coupling protocol described above to give compounds 11. In some embodiments, a provided approach allows for great diversity in the subsequent coupling of indole boronic acids or borates with commercially available haloaromatic derivatives.

Scheme 3

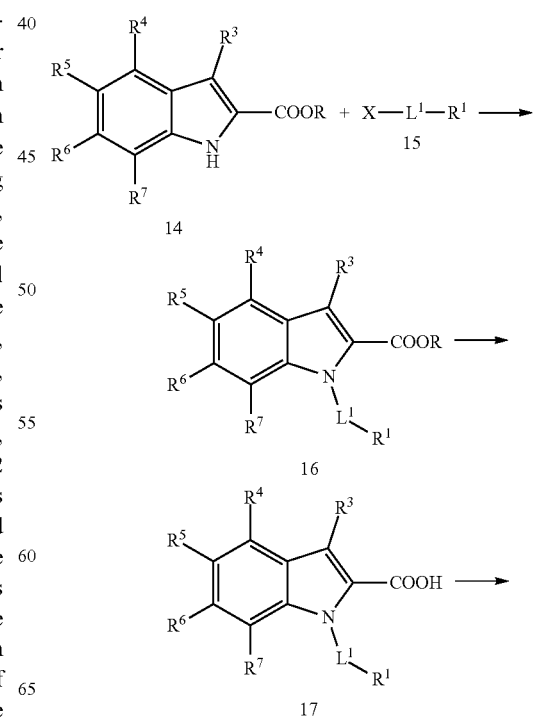

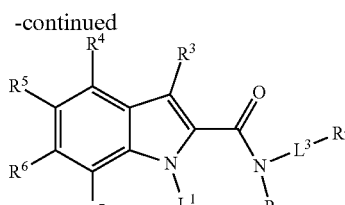

18

In some embodiments, provided compounds of Formula 18 may be prepared by procedures outlined in Scheme 3. Compounds of Formula 14 can be reacted with compounds of Formula 15, wherein X is Cl, Br, I, OMs, or OTs with a base such as NaH, $K_2CO_3$, $Cs_2CO_3$, $Et_3N$, or DIPEA in a suitable solvent such as DMF, THF, ether, DME, or the like, to give compounds of Formula 16. Applying the same reaction sequence as described in Scheme 1, compounds of Formula 16 can undergo saponification followed by coupling reaction to give compounds of Formula 18.

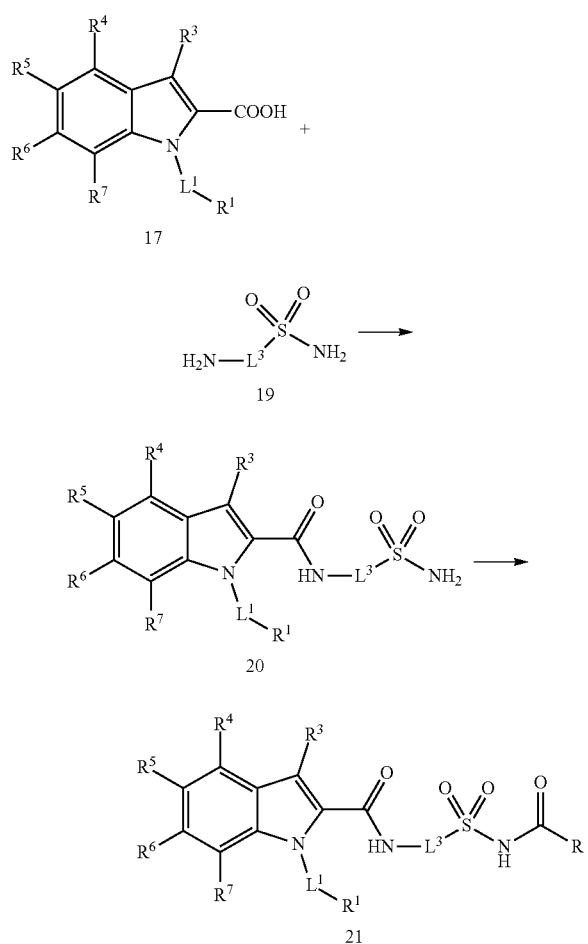

In some embodiments, compounds of Formula 21 can be synthesized by procedures depicted in Scheme 4 via selective sequential coupling reactions in one-pot. An amino group of compounds 19 can be coupled with compounds of Formula 17 as illustrated in Scheme 1 to afford intermediates 20. In the same pot, suitable carboxylic acids can be coupled to the sulfonamide group of compounds of Formula 20 using coupling reagents, but not limited to, PyBOP, DCC, EDC, HBTU, or TBTU at a number of conditions that are routine for those skilled in the art of organic synthesis, to yield acylsulfonamides of Formula 21.

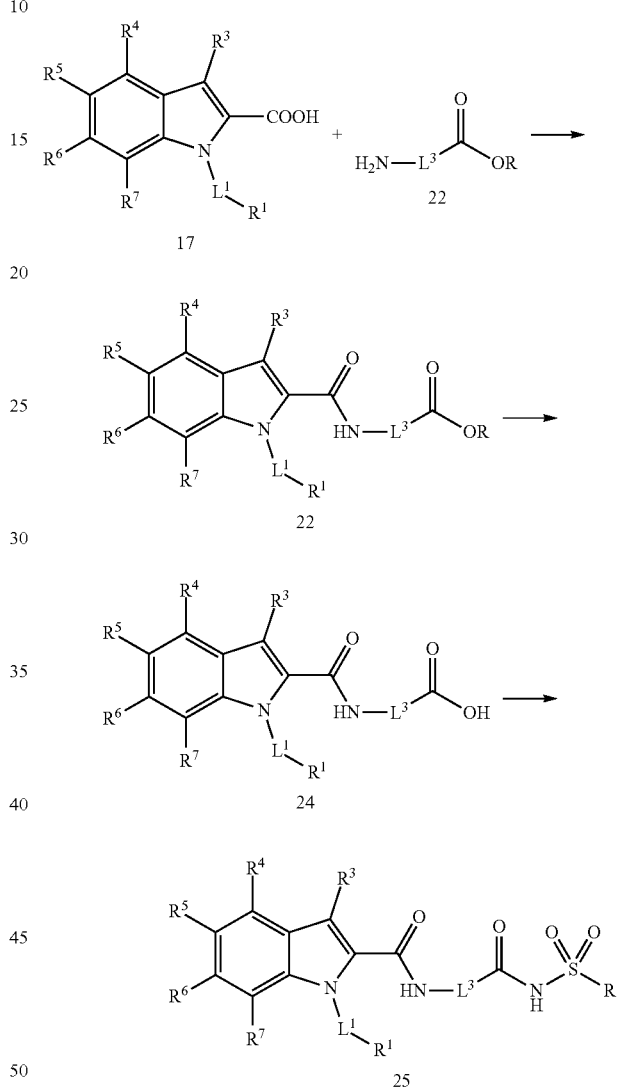

Alternatively, compounds of Formula 25 can be prepared by procedures illustrated in Scheme 5 by similar sequential coupling reactions. Compounds of Formula 17 can undergo coupling reactions with an amine functional group of compounds 22 as shown Scheme 1 to give intermediates 23. An ester group of Formula 23 can be saponificated using aqueous based, such as $Cs_2CO_3$, $K_2CO_3$, LiOH or NaOH, at a number of conditions that are routine for those skilled in the art of organic synthesis to generated compounds of Formula 24. Subsequent coupling reactions of acids 24 with suitable sulfonamides using coupling reagents at a number of conditions that are routine for those skilled in the art of organic synthesis to afford reverse acylsulfonamides of Formula 25.

Scheme 6

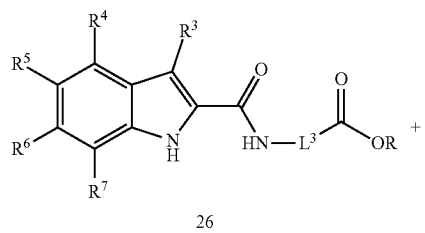

26

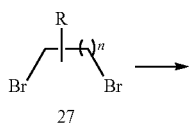

27

-continued

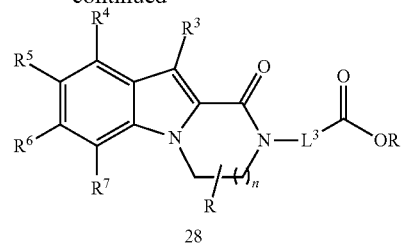

28

Exemplary method for preparing compounds of Formula 28, wherein the N1 position of indole and the amide NH is tethered to form rings, is described in Scheme 6 and proceeds from compounds of Formula 26. Optionally substituted di-bromo alkanes 27 can be used to react with indole amides 26. The cyclization may be accomplished with a variety of bases, but not limited to, DBU, $Et_3N$, DIPEA, $Cs_2CO_3$, $K_2CO_3$, NaH, or t-BuONa in a suitable solvent such as DMF, toluene, THF, DME, $CH_3CN$, 1,4-dioxane or the like, to afford compounds of Formula 28 at a number of conditions that are routine for those skilled in the art of organic synthesis. Compounds of Formula 28 can be employed to subsequent reactions as depicted in above Schemes.

Scheme 7

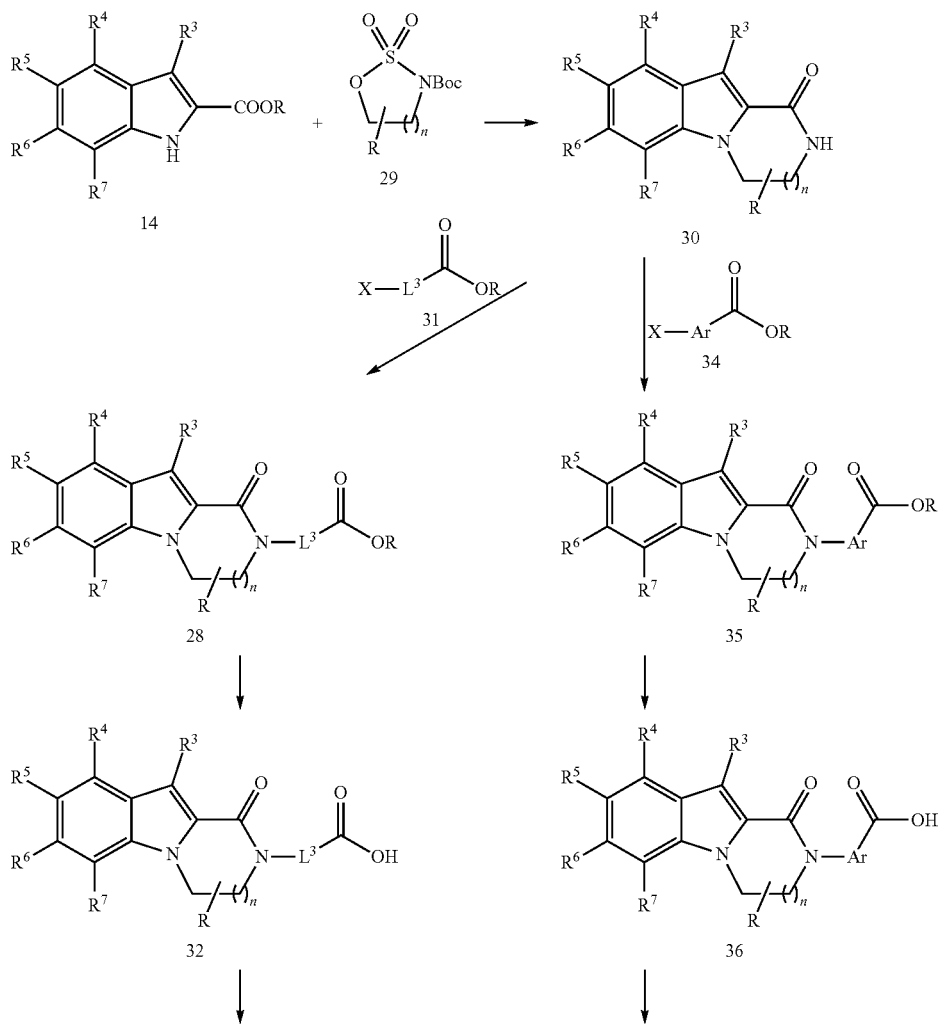

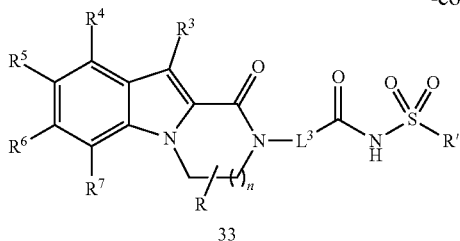

33

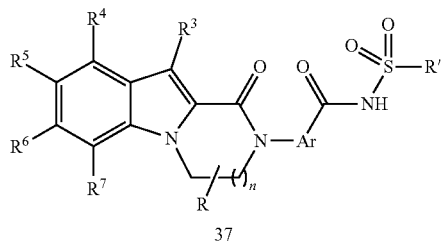

37

An alternate route to substituted tricyclic indole amides is shown in Scheme 7 and described here. The tricyclic amide intermediates of Formula 30 can be prepared by alkylation of the indole NH of ester 14 with optionally substituted cyclic sulfamidates 29 followed by cyclization upon removal of the Boc-protecting group (see, for example, Richter H. G. F. Bioorg. Med. Chem. Lett. 2010, 5713). The size and stereochemistry of the newly formed cyclic amide can be controlled by size and preset stereo-configuration of the reagent 29. The NH group of Formula 30 can undergo alkylation reactions with compounds of Formula 31, wherein X is Cl, Br, I, OMs, or OTs with a base such as NaH, $K_2CO_3$, $Cs_2CO_3$, $Et_3N$, or DIPEA in a suitable solvent such as DMF, THF, ether, DME, or the like, to give compounds of Formula 28. Corresponding compounds of Formulae 32 and 33 can be prepared from the ester 28 by saponification and coupling of sulfonamides to the carboxylic acid functional group of compounds 32 as described in Scheme 5. Alternatively, a variety of aryl or heteroaryl halides of Formula 34, wherein X is Br, I, or OTf can be coupled to the NH group of Formula 30 in the presence of a catalytic Pd species, such as $Pd(OAc)_2$, $Pd_2(dba)_3$ and a suitable ligand such as Xantphos and a base such as $Na_2CO_3$, $Cs_2CO_3$, or $K_2CO_3$ to generate compounds of Formula 35. Same saponification and coupling of sulfonamide coupling protocols described above can also be applied to prepare corresponding compounds of Formulae 36 and 37.

Scheme 8

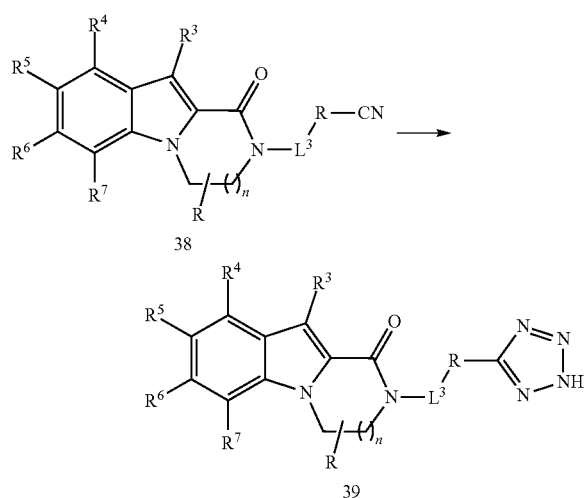

In some embodiments, compounds of Formula 39 containing tetrazole moiety can be generated by the procedure depicted in Scheme 8. A nitrile group of compounds 38 can undergo cyclization reaction with $NaN_3$ in the presence salt such as $NH_3Cl$, $Et_3N.HCl$ or catalytic amount of $I_2$, $AlCl_3$ or TMSCl in a suitable solvent such as DMF, $PhNO_2$ or NMP at a number of conditions that are routine for those skilled in the art of organic synthesis to give tetrazoles of Formula 39.

Scheme 9

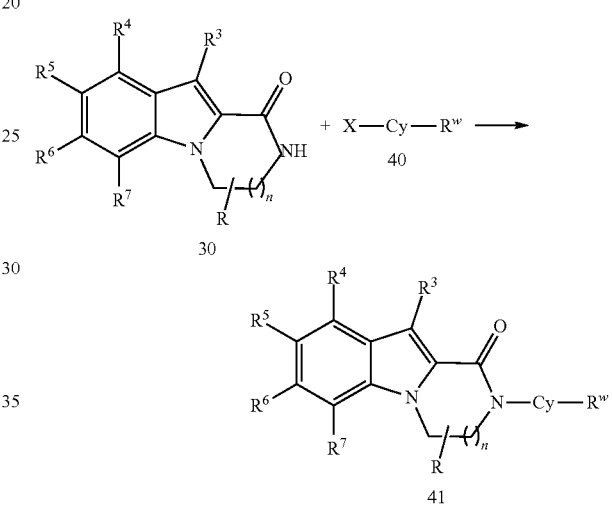

The NH group of Formula 30 can undergo cross-coupling reactions with a variety of aryl or heteroaryl halides of Formula 40, wherein X is Br, I, or OTf in the presence of a catalytic Pd species, such as $Pd(OAc)_2$, $Pd_2(dba)_3$ and a suitable ligand such as Xantphos and a base such as $Na_2CO_3$, $Cs_2CO_3$, or $K_2CO_3$ to generate compounds of Formula 22. Alternatively, compounds of Formula 30 can be produced using the Ullman coupling conditions in the presence of CuI and a suitable ligand such as (trans)-1,2-N,N'-dimethylaminocyclohexane or L-Proline and a base such as $Cs_2CO_3$, $K_2CO_3$ or $K_3PO_4$ in a suitable solvent such as toluene or DMF. The $R^7$ and $R^w$ of Formula 21 and 22 can be further elaborated such as saponification, substitution, alkylation of NH or OH, halogenation, amidation and construction of heterocycles under a number of functional group modification conditions that are routine for those skilled in the art of organic synthesis.

ABBREVIATIONS

The following abbreviations are employed in the Examples and elsewhere herein:
Dt-BuAD=di-tert-butyl azodicarboxylate
DCM=dichloromethane
EDC=1-Ethyl-3-(3-dimethylaminopropyl)carbodiimide
TEA=triethylamine
DMAP=dimethylamino pyridine
HOBT=hydroxybenzotriazole DBU=1,8-Diazabicycloundec-7-ene
DMF=dimethylformamide
DMSO=dimethylsulfoxide
THF=tetrahydrofuran
$K_2CO_3$=potassium carbonate
$Cs_2CO_3$=cesium carbonate
DME=1,2-dimethoxyethane
t-BuONa=sodium tert-butoxide
LDA=lithium di-isopropylamide
NaHMDS=sodium hexamethyldisilazide
LiHMDS=lithium hexamethyldisilazide
n-BuLi=n-butyl lithium
ether=diethyl ether
NaOH=sodium hydroxide
KOH=potassium hydroxide
EtOAc=ethyl acetate
$Na_2CO_3$=sodium carbonate
$Na_2SO_4$=sodium sulfate
$MgSO_4$=magnesium sulfate
$SiO_2$=silicon dioxide
$CH_2Cl_2$=methylene chloride
MeOH=methanol
EtOH=ethanol
Hex=hexanes
HCl=hydrochloric acid
Pd(dppf)$Cl_2$=[1,1'-bis(diphenylphosphino)ferrocene]dichloropalladium (II)
$Pd_2(dba)_3$=tris(dibenzylideneacetone)dipalladium (0)
Pd($PPh_3)_4$=tetrakis(triphenylphosphine)palladium(0)
TFA=trifluoroacetic acid
$Et_3N$=triethylamine
DIPEA=N,N-diisopropylethylamine
$SnCl_2$=tin(II) chloride
DEAD=diethyl azodicarboxylate
TBAD=dit-butyl azodicarboxylate
NaH=sodium hydride
$NaNO_2$=sodium nitrite
$CH_3COONa$=sodium acetate
$NaN_3$=sodium azid
MsCl=methanesulfonyl chloride
TBAI=tetrabutylammonium iodide
EtI=ethyl iodide
EtBr=ethyl bromide
TBAF=tetrabutyl ammonium fluoride
NMM=1H-N-Methylmorpholine
NMO=N-Methylmorpholine N-oxide
DBU=1,8-Diazabicyclo(5.4.0)undec-7-ene
PCC=Pyridinium chlorochromate
BOP=(Benzotriazol-1-yloxy)tris(dimethylamino)phosphonium hexafluorophosphate
MsCl=mesyl chloride
PPA=polyphosphoric acid
min=minute(s)
h or hr=hour(s)
mL or ml=milliliter
g=gram(s)
mg=milligram(s)
mmol=millimole(s)
RT or rt=room temperature
LRMS=low resolution mass spectrometry
NMR=nuclear magnetic resonance

EXAMPLES

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

General Coupling Procedure A:

A mixture of lactam (1.0 eq), bromide (2.0 eq), $Pd_2(dba)_3$ (0.1 eq), Xantphos (0.2 eq), and $Cs_2CO_3$ (2.5 eq) 1,4-Dioxane (1 mL) was sparged with Ar gas for 5 minutes. The reaction mixture was sealed and heated to 110° C. for 18 h. The reaction mixture was cooled to ambient temperature, poured to DCM/water (10 mL, 1:1). The organic layer was separated and the aqueous layer was extracted with DCM (2×5 mL). The combined organic solution was dried over $MgSO_4$, filtered and concentrated in vacuo. The crude residue was purified by reverse phase HPLC or flash chromatography.

General Coupling Procedure B:

A mixture of lactam (1.0 eq), bromide (2.0 eq), CuI (0.5 eq), (trans)-1,2-N,N'-dimethylaminocyclohexane (1.0 eq), and $K_2CO_3$ (2.5 eq) in toluene (1 mL) was sparged with Ar gas for 5 min. The reaction mixture was sealed and heated to 110° C. for 18 h. Same work up and purification protocols described in general coupling procedure A were followed to obtain a desire product.

General Coupling Procedure C:

A mixture of lactam (1.0 eq), bromide (2.0 eq), CuI (0.5 eq), (trans)-1,2-N,N'-dimethylaminocyclohexane (1.0 eq), and $K_3PO_4$ (2.5 eq) in DMF (1 mL) was sparged with Ar gas 5 minutes. The reaction mixture was sealed and heated to 120° C. for 18 h. Same work up and purification protocols described in general coupling procedure A were followed to obtaine a desire product.

General Saponification Procedure D:

To a solution of ester in a mixture of THF, MeOH, and $H_2O$ (3 mL, 0.5 mL, 0.5 mL), was added LiOH (5 mg). The reaction was heated to 50° C. for 3 h then cooled to ambient temperature. The crude reaction mixture was concentrated in vacuo, and the residue was purified by reverse phase HPLC.

General Peptide Coupling Procedure E:

To a solution of (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol) and HATU (8 mg, 0.021 mmol) in DMF (1 mL) was added diisopropylethylamine (5 mg, 0.039 mmol), and the reaction was stirred at room temperature for 15 min. The appropriate amine was added, and the reaction was stirred at room temperature until complete by LCMS. Same work up and purification protocols described in general coupling procedure A were followed to obtain a desire product.

General Procedure F: Headpiece Bromination & Alkylation

To a solution of indole or indazole (0.28 mmol) in DMF (2 mL) was added NBS (51 mg, 0.28 mmol) at 0° C., and the reaction was stirred 1 h. The reaction as diluted into DCM/$H_2O$ (20 mL, 1:1), the layers separated, and the aqueous layer was extracted with DCM (2×10 mL). The combined organic layers were washed with 10% aqueous $Na_2S_2O_3$ (10 mL), dried over $MgSO_4$, filtered, and concentrated in vacuo. The crude residue was dissolved in DMF (2 mL), sodium hydride was added (14 mg, 0.34 mmol), and the reaction was allowed to stir 5 min at room temperature. Alkyl iodide (0.34 mmol) was added and the reaction was allowed to stir for 1 h. The reaction was diluted with DCM (10 mL), quenched with $H_2O$ (10 mL), the layers separated and the aqueous layer was extracted with DCM (2×10 mL). The combined organic extracts were concentrated in vacuo. The crude residue was purified by flash chromatography.

General Procedure G: Headpiece Alkylation

To asolution of substituted indole/indazole or naphthoic acid/quinolone carboxylic acid (0.20 mmol) in DMF (2 mL) was added NaH (10 mg, 0.24 mmol) at room temperature and stirred for 5 min at room temperature. Alkyl iodide (0.24 mmol) was added, and the reaction was stirred for 1 h. The work up described in general coupling procedure A was followed. The crude residue was purified by flash chromatography.

General Procedure H: Alkylation of Indole Hydroxy Group

A mixture of hydroxyl-indole (1.0 eq), $Cs_2CO_3$ (3.0 eq) and the appropriate electrophile in DMF (0.05 M) was heated to 60 to 90° C. until complete by LCMS. The work up described in general coupling procedure A was followed. The crude residue was purified by flash chromatography.

General Procedure I: Alkylation of Indole Nitrogen after Coupling to Tricyclic Core A mixture of NH-indole (1.0 eq), $Cs_2CO_3$ (3.0 eq) and the appropriate electrophile in DMF (0.05 M) was heated to 60 to 90° C. until complete by LCMS. The work up described in general coupling procedure A was followed. The crude residue was purified by flash chromatography.

General Procedure J: Mesylation and SN2 Displacement of 2-Hydroxymethyl Pyrimidine To a solution of hydroxymethyl-pyrimidine (1.0 eq) in DCM (0.03 M) was added DIPEA (5.0 eq) followed by mesyl chloride (3.0 eq). The reaction mixture was stirred at RT for 2 h then concentrated in vacuo. The residue was dissolved in DMF (0.05 M), and DIPEA (5.0 eq) and the appropriate amine (5-10 eq) were added in sequence. The reaction mixture was stirred from 25 to 50° C. until complete by LCMS. The work up described in general coupling procedure A was followed. The crude reaction mixture was used for subsequent saponification without further purification.

Example 1

Ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate Step A. Preparation of 5-(2-(2-bromo-3-chlorophenyl)hydrazono)-6-ethoxy-6-oxohexanoic acid To a stirring mixture of 2-bromo-3-chloroaniline (20 mmol) in 1M HCl (25 mL) and water (5 mL) at 0° C. was added $NaNO_2$ (1.38 g, 20 mmol) in water (20 mL), $CH_3COONa$ (9.23 g, 112 mmol) in water (25 mL) and ethyl 2-oxocyclopentane carboxylate (3.0 mL, 20 mmol) in sequence. The reaction mixture was stirred for 15 min at 0° C. then warmed to 20° C. over 2 h and extracted with $CH_2Cl_2$, dried over $MgSO_4$, filtered and concentrated in vacuo to give the title compound as a red oil in 7.1 g (90% crude).

Step B. Preparation of ethyl 7-bromo-6-chlor-3-(3-ethoxy-3-oxopropyl)-1H-indole-2-carboxylate To a solution of 5-(2-(2-bromo-3-chlorophenyl)hydrazono)-6-ethoxy-6-oxohexanoic acid (7.1 g, 18 mmol) in EtOH (30 mL) was added conc. $H_2SO_4$ (7.5 mL), slowly. The reaction mixture was refluxed for 1.5 h. The reaction was quenched by pouring into ice then extracted with $CH_2Cl_2$. The combined organic layer was washed with sat. $NaHCO_3$, water, brine, dried over $MgSO_4$, filtered and concentrated in vacuo. The residue was purified by flash chromatography (Combi-flash Rf Hex/EtOAc 25% gradient) to give the title compound as an off-white solid in 4.4 g (11 mmol). MS (ES) 402.0 (M+H).

Step C. Preparation of ethyl 7-bromo-6-chloro-3-(3-hydroxypropyl)-1H-indole-2-carboxylate To a solution of ethyl 7-bromo-6-chloro-3-(3-ethoxy-3-oxopropyl)-1H-indole-2-carboxylate (1.9 g, 4.8 mmol) in THF (20 mmol) was added $BH_3$ in THF (20 mL, 20 mmol) at 20° C. The reaction mixture was stirred for 15 h at 20° C. and quenched by addition of MeOH then concentrated in vacuo. The residue was purified by flash chromatography (Combi-flash Rf Hexane/EtOAc gradient 0-50%) to give the title compound as a white solid (1.4 g, 3.9 mmol). MS (ES) 360.1 (M+H).

Step D. Preparation of ethyl 7-bromo-6-chloro-3-(3-(4-chloro-3,5-dimethylphenoxy)propyl)-1H-indole-2-carboxylate To a solution of ethyl 7-bromo-6-chloro-3-(3-hydroxypropyl)-1H-indole-2-carboxylate (101 mg, 0.28 mmol), $PPh_3$ (110 mg, 0.51 mmol) and 3,5-diMe-4-Cl-phenol (81 mg, 0.52 mmol) in THF (3.5 mL) was added Dt-BuAD (99 mg, 0.51 mmol) at 20° C. The reaction mixture was stirred for 15 h at 20° C. then concentrated in vacuo. The residue was purified by flash chromatography (Combi-flash Rf Hexane/EtOAc gradient 0-10%) to give the title compound (105 mg, 0.21 mmol) as a colorless oil. MS (ES) 498.0 (M+H).

Step E. Preparation of ethyl 6-chloro-3-(3-(4-chloro-3,5-dimethylphenoxy)propyl)-7-(1,3,5-trimethyl-1H-pyrazol-4-yl)-1H-indole-2-carboxylate To a solution of ethyl 7-bromo-6-chloro-3-(3-(4-chloro-3,5-dimethylphenoxy)propyl)-1H-indole-2-carboxylate (319 mg, 0.64 mmol) in dioxane (3.0 ml) and water (2.0 ml) at 20 was added 1,3,5-trimethyl-4-(4,4,5,5-tetramethyl-1,3,2-dioxaborolan-2-yl)-1H-pyrazole (168 mg, 0.71 mmol), $Pd(PPh_3)_4$ (37 mg, 0.032 mmol) and $K_2CO_3$ (267 mg, 1.94 mmol). The mixture was degased then heated to 125° C. in Biotage Initiator for 40 min. The reaction was quenched by addition of water, extracted with EtOAc, dried over $MgSO_4$, filtered and concentrated in vacuo. The residue was purified by flash chromatography (Combi-flash Rf Hexane/EtOAc gradient 0-15%) to give the title compound (238 mg, 0.45 mmol) as a white solid. MS (ES) 528.2 (M+H).

Step F. Preparation of ethyl (R)-1-(1-((tert-butoxycarbonyl)amino)propan-2-yl)-6-chloro-3-(3-(4-chloro-3,5-dimethylphenoxy)propyl)-7-(1,3,5-trimethyl-1H-pyrazol-4-yl)-1H-indole-2-carboxylate To a solution of ethyl 6-chloro-3-(3-(4-chloro-3,5-dimethylphenoxy)propyl)-7-(1,3,5-trimethyl-1H-pyrazol-4-yl)-1H-indole-2-carboxylate (360 mg, 0.68 mmol) in anhydrous DMF (2 mL) was added NaH (60%) (25 mg, 0.70 mmol) at 0° C. and stirred for 3 min. tert-Butyl (S)-5-methyl-1,2,3-oxathiazolidine-3-carboxylate 2,2-dioxide (0.70 mmol) was added. The reaction mixture was stirred in the ice bath for 20 min and then at RT for overnight. The reaction mixture was diluted with ethyl acetate (50 mL) and washed with brine (2×30 mL), dried with anhydrous MgSO$_4$, filtered and concentrated in vacuo. The residue was purified by flash chromatography (Combi-flash Rf, Hex/acetone=80:20) to give the title compound (305 mg, 65%). MS (ES) 686.3 (M+H), Rf=1.29.

Step G. Preparation of (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one To a solution of ethyl (R)-1-(1-((tert-butoxycarbonyl)amino)propan-2-yl)-6-chloro-3-(3-(4-chloro-3,5-dimethylphenoxy)propyl)-7-(1,3,5-trimethyl-1H-pyrazol-4-yl)-1H-indole-2-carboxylate (218 mg, 0.32 mol) in anhydrous DCM (5.0 mL) at 0° C. was added TFA (1.5 mL) dropwise. The reaction mixture was warmed to RT and stirred for 2 h then concentrated in vacuo. The residue was dissolved in anhydrous ethanol (10 mL) then anhydrous K$_2$CO$_3$ (829 mg, 1.92 mmols) was added. The reaction mixture was stirred at RT for overnight then diluted with ethyl acetate (60 mL) and washed with brine (2×30 mL). The organic layers were dried over anhydrous MgSO$_4$, filtered and concentrated. The residue was purified by flash chromatography (Combi-flash Rf, DCM/methanol=0-10% gradient) to give the title compound (150 mg, 87%). MS (ES) 539.5 (M+H), Rf=0.95.

Step H. Example 1

The title compound (210 mg, 52%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (300 mg, 0.55 mmol), ethyl 7-bromo-1H-indole-2-carboxylate (300 mg, 1.10 mmol), copper iodide (50 mg, 0.26 mmol), (trans)-N$^1$,N$^2$-dimethylcyclohexane-1,2-diamine (80 mg, 0.56 mmol), and K$_2$CO$_3$ (250 mg, 1.81 mmol). MS (ES) 726.3 (M+H).

Example 2

3-Bromo-6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-4-carboxylic acid Step A. Preparation of ethyl 1-(3-((tert-butoxycarbonyl)amino)propyl)-6-chloro-3-(3-(4-chloro-3,5-dimethylphenoxy)propyl)-7-(1,3,5-trimethyl-1H-pyrazol-4-yl)-1H-indole-2-carboxylate To a solution of ethyl 6-chloro-3-(3-(4-chloro-3,5-dimethylphenoxy)propyl)-7-(1,3,5-trimethyl-1H-pyrazol-4-yl)-1H-indole-2-carboxylate (360 mg, 0.683 mol) in anhydrous DMF (2 mL) was added NaH (60%) (25 mg, 0.62 mol) at 0° C. and stirred for 3 min. tert-Butyl 2-oxo-1,3-oxazinane-3-carboxylate was added. The reaction mixture was stirred in the ice bath for 20 min then at RT overnight. The reaction mixture was diluted with ethyl acetate (50 mL) and washed with brine (2×30 mL), dried over anhydrous MgSO$_4$, filtered and concentrated in vacuo. The residue was purified by flash chromatography (Combi-flash Rf, eluent 20% ethyl acetate in hexanes) to give the title compound (305 mg, 65%). $^1$H NMR; δ 7.58 (d, J=10.7 Hz, 1H), 7.23 (d, J=10.7 Hz, 1H), 6.64 (s, 2H), 4.42-4.35 (m, 3H), 4.32-4.24 (m, 1H), 4.18-4.08 (m, 1H), 3.98 (t, J=7.5 Hz, 2H), 3.88 (s, 3H), 3.24 (t, J=9.0 Hz, 2H), 2.76 (q, J=7.0 Hz, 2H), 2.34 (s, 6H), 2.13 (t, J=7.0 Hz, 2H), 2.09 (s, 3H), 2.03 (s, 3H), 1.48 (t, J=7.0 Hz, 2H), 1.43 (t, J=9.0 Hz, 3H), 1.42 (s, 9H): $^{13}$C NMR: (125 MHz in CDCl$_3$) δ 162.3, 156.7, 155.6, 146.4, 138.0, 137.2, 136.9, 134.2, 126.8, 126.1, 126.0, 125.0, 121.7, 120.9, 116.4, 114.4, 113.5, 78.9, 67.4, 60.7, 42.8, 37.9, 36.2, 31.2, 30.5, 28.3, 21.8, 20.9, 14.3, 12.3, 10.3; LCMS: R$_T$=2.320 min; >98% purity at 215 nm and 254 nm; MS (ES) 685.0 (M+H).

Step B. Preparation of 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one To a solution of ethyl 1-(3-((tert-butoxycarbonyl)amino)propyl)-6-chloro-3-(3-(4-chloro-3,5-dimethylphenoxy)propyl)-7-(1,3,5-trimethyl-1H-pyrazol-4-yl)-1H-indole-2-carboxylate (218 mg, 0.32 mol) in anhydrous CH$_2$Cl$_2$ at 0° C. was added TFA (1.5 mL) dropwise. The reaction mixture was warmed to RT, stirred for 2 h then concentrated in vacuo. The residue was dissolved in anhydrous ethanol (10 mL) then anhydrous K$_2$CO$_3$ (829 mg, 1.92 mmols) was added. The reaction mixture was stirred at RT for overnight. The reaction mixture was diluted with ethyl acetate (60 mL) and washed with brine (2×30 mL). The organic layers were dried with anhydrous MgSO$_4$, filtered and concentrated in vacuo. The residue was purified by flash chromatography (Combi-flash Rf, CH$_2$Cl$_2$/methanol=0-10% gradient) to give the title compound (150 mg, 87%). $^1$H NMR: (500 MHz in CDC$_3$) δ 7.62 (d, J=10.7 Hz, 2H), 7.25 (d, J=10.7 Hz, 2H), 6.65 (s, 2H), 6.23 (t, J=7.5 Hz, 1H), 4.06-3.93 (m, 4H), 3.90 (s, 3H), 3.22-3.15 (m, 4H), 2.35 (s, 6H), 2.20 (quint., J=8.7 Hz, 2H), 2.06 (s, 3H), 2.04 (s, 3H), 1.82-1.66 (m, 2H); $^{13}$C NMR: (125 MHz in CDCl$_3$) δ 166.4, 156.8, 145.8, 138.1, 136.9, 135.8, 132.9, 131.6, 126.7, 125.9, 121.7, 121.2, 120.8, 115.1, 114.5, 113.5, 67.4, 41.0, 38.5 36.1, 30.2, 30.1, 20.9, 20.4, 12.1, 10.0; LCMS: R$_T$=1.896 min., >98% purity at 215 nm and 254 nm; MS (ES) 539.0 (M+H).

Step C. Preparation of Methyl 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoate The title compound (66 mg, 76%) was prepared following General coupling procedure B using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (70 mg, 0.13 mmol, 1.0 eq), methyl 3-bromobenzoate (55 mg, 0.26 mmol, 2.0 eq), CuI (10 mg, 0.052 mmol, 0.40 eq), rac-N,N'-dimethylcyclohexane-1,2-diamine (15 mg, 0.105 mmol, 0.81 eq), and K$_2$CO$_3$ (55 mg, 0.40 mmol, 3.0 eq). $^1$H NMR: (500 MHz in CDCl$_3$) δ 7.98-7.94 (m, H), 7.61 (d, J=8.5 Hz, 1H), 7.51-7.46 (m, 2H), 7.24 (d, J=8.5 Hz, 1H), 6.61 (s, 2H), 4.16-4.06 (m, 2H), 3.96 (t, J=6.0, 2H), 3.91 (s, 3H), 3.85 (s, 3H), 3.76-3.67 (m, 2H), 3.16 (oct, J=7.5 Hz, 2H), 2.29 (s, 6H), 2.23-2.16 (m, 2H), 2.06 (s, 3H), 2.05 (s, 3H), 1.92-1.80 (m, 2H); $^{13}$C NMR: (125 MHz in CDCl$_3$) δ 166.2, 164.0, 156.8, 146.0, 142.3, 137.7, 136.9, 135.2, 133.0, 132.0, 131.4, 130.7, 129.3, 127.8, 126.7, 126.6, 125.9, 121.5, 121.2, 120.7, 115.5, 114.5, 113.2, 67.3, 52.2, 48.2, 40.7, 36.2, 30.2, 29.5, 20.8, 20.6, 12.3, 10.0; LCMS: R$_T$=2.092 mm, >98% purity at 215 nm and 254 nm; MS (ES) 673.0 (M+H).

Step D. Example 2

To a solution of methyl 6-(8-chloro-11-(3-(4-chloro-3,5-dimethylphenoxy)propyl)-1-oxo-7-(1,3,5-trimethyl-1H- pyrazol-4-yl)-4,5-dihydro-1H-[1,4]diazepino[1,2-a]indol-2(3H)-yl)-1-methyl-1H-indole-4-carboxylate (40 mg, 0.055 mmol) in THF (0.5 mL) was added NBS (10 mg, 0.058 mmol) then stirred for 15 h at RT. LiOH (0.14 ml, 0.28 mmol, 2N) was added, and the mixture was heated to 70° C. for additional 6 h. The reaction was concentrated in vacuo, and the crude residue was dissolved in DMSO (1 mL) and filtered. The DMSO solution was purified by reverse phase HPLC (Phenomenex Gemini C18, $H_2O/CH_3CN$ gradient from 30-90% $CH_3CN$, 0.1% TFA) to yield the title compound (28 mg, 65%) as an off-white solid. MS (ES) 790.2 (M+H).

Example 3

3-Chloro-6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-4-carboxylic acid The title compound was prepared (22 mg, 0.029 mmol) as a white solid according to procedures described in Example 2 Step D substituting NBS with NCS (7.4 mg, 0.055 mmol). MS (ES) 746.2 (M+H).

Example 4

6-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-1-methyl-benzotriazole-4-carboxylic acid The title compound (6.2 mg, 16%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 6-bromo-1-methyl-1H-benzo[d][1,2,3]triazole-4-carboxylate (19 mg, 0.070 mmol), $Pd_2(dba)_3$ (8 mg, 0.0087 mmol), Xantphos (12 mg, 0.021 mmol), and $Cs_2CO_3$ (60 mg, 0.19 mmol) followed by saponification using General Procedure D. LCMS: $R_T$=1.288 min, MS (ES) 714.1 (M+H).

Example 5

6-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-3-methyl-benzotriazole-4-carboxylic acid The title compound (3.7 mg, 9.3%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 5-bromo-1-methyl-1H-benzo[d][1,2,3]triazole-7-carboxylate (25 mg, 0.092 mmol), $Pd_2(dba)_3$ (8 mg, 0.0087 mmol), Xantphos (12 mg, 0.021 mmol), and $Cs_2CO_3$ (60 mg, 0.19 mmol) followed by saponification using General Procedure D. LCMS: $R_T$=1.360 min, MS (ES) 714.1 (M+H).

Example 6

7-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-1-methyl-indole-3-carbonitrile The title compound (13 mg, 34%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), 7-bromo-1-methyl-1H-indole-3-carbonitrile (30 mg, 0.14 mmol), $Pd_2(dba)_3$ (8 mg, 0.0087 mmol), Xantphos (12 mg, 0.021 mmol), and $Cs_2CO_3$ (60 mg, 0.19 mmol). LCMS: $R_T$=1.555 min, MS (ES) 693.1 (M+H).

Example 7

6-[8-chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-1-methyl-benzimidazole-4-carboxylic acid

Step A. Preparation of methyl 6-bromo-1-methyl-1H-benzo[d]imidazole-4-carboxylate To a solution of 6-bromo-1H-benzo[d]imidazole-4-carboxylic acid (200 mg, 0.84 mmol) in THF (5 mL) and MeOH (1 mL) at 0° C. was added trimethylsilyldiazomethane in $Et_2O$ (2.0 M, 0.63 mL, 1.3 mmol). The reaction was stirred for 1 h at 0° C. then warmed to RT. The reaction was quenched by addition of AcOH dropwise and concentrated in vacuo. The crude residue was diluted with DCM (20 mL) and washed with brine (10 mL). The organic layer was dried over $MgSO_4$, filtered, and concentrated in vacuo. To a solution of the crude residue in DMF (2 mL) was added NaH (30 mg, 1.25 mmol) at RT and stirred for 30 min. Methyl iodide (120 mg, 0.84 mmol) was added, and the reaction was stirred for 4 h at RT. The reaction mixture was cooled to −78° C. and quenched with MeOH. The mixture was diluted into $DCM/H_2O$ (20 mL, 1:1), the organic layer separated and the aqueous layer was extracted with DCM (2×5 mL). The combined organic extracts were dried over $MgSO_4$, filtered, and concentrated in vacuo. The crude residue was purified by reverse phase preparative HPLC (Phenomenex Gemini C18, $H_2O/CH_3CN$ gradient to 20-80% MeCN 0.1% TFA) to afford the title compound (83 mg, 37%).

Step B. Example 7

The title compound (3 mg, 8%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 6-bromo-1-methyl-1H-benzo[d]imidazole-4-carboxylate (35 mg, 0.13 mmol), $Pd_2(dba)_3$ (8 mg, 0.0087 mmol), Xantphos (12 mg, 0.021 mmol), and $Cs_2CO_3$ (60 mg, 0.19 mmol) followed by saponification using General Procedure D. LCMS: $R_T$=1.048 min, MS (ES) 713.0 (M+H).

Example 8

2-(4-(Tert-butoxycarbonyl)piperazin-1-yl)-6-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)isonicotinic acid The title compound (67 mg, 76%) was prepared following General coupling procedure A using methyl 2-chloro-6-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)isonicotinate (72 mg, 0.1 mmol), tert-butyl piperazine-1-carboxylate (22 mg, 0.12 mmol), Pd$_2$(dba)$_3$ (2 mg, 0.002 mmol), Xantphos (3.5 mg, 0.006 mmol), and Cs$_2$CO$_3$ (49 mg, 0.15 mmol) followed by saponification using General Procedure D. LCMS: R$_T$=2.025 min, MS (ES) 858.3 (M+H).

Example 9

2-((8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(4-(furan-2-carbonyl)piperazin-1-yl)isonicotinic acid Step A. Preparation of methyl 2-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(piperazin-1-yl)isonicotinate To a solution of tert-butyl 4-(6-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-4-(methoxycarbonyl)pyridin-2-yl)piperazine-1-carboxylate in CH$_2$Cl$_2$ (1 mL) was added TFA (0.5 mL) and the mixture was stirred at room temperature for 12 h. The reaction mixture was extracted in CH$_2$Cl$_2$ (3×15 mL), dried (anhyd. Na$_2$SO$_4$) and concentrated in vacuo to give the crude title compound. MS (ES) 772.2 (M+H).

Step B. Example 9

To a solution of methyl 2-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(piperazin-1-yl)isonicotinate (15 mg, 0.02 mmol), in CH$_2$Cl$_2$ (1 mL) at room temperature was added triethylamine (6 µL, 0.04 mmol) followed by furan-2-carbonyl chloride (4 µL, 0.04 mmol) and the mixture was stirred at room temperature for 1 h. The mixture was diluted with water (2 mL) and extracted in CH$_2$Cl$_2$ (3×5 mL), dried and concentrated in vacuo. The residue was dissolved in THF, MeOH, and H$_2$O (3 mL, 0.5 mL, 0.5 mL), and LiOH (5 mg) was added and the reaction was heated to 50° C. for 3 h. The crude was purified by reverse phase HPLC (Phenomenex Gemini C18, H$_2$O/CH$_3$CN gradient to 35-95% MeCN 0.1% TFA) to afford the title compound (16 mg, 94%). LCMS: R$_T$=1.785 min, MS (ES) 852.4 (M+H).

Example 10

2-((8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(piperazin-1-yl)isonicotinic acid Title compound (54 mg, 63%) was prepared according to General saponification procedure D using methyl 2-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(piperazin-1-yl)isonicotinate (87 mg, 0.11 mmol). LCMS: R$_T$=1.605 min, MS (ES) 758.3 (M+H).

Example 11

4-(8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-(2-(dimethylamino)ethyl)-1H-indole-6-carboxylic acid Step A. Preparation of methyl 4-amino-1-(2-(dimethylamino)ethyl)-1H-indole-6-carboxylate To a solution of methyl 4-amino-1H-indole-6-carboxylate (100 mg, 0.526 mmol) in DMF (3 mL) was added NaH (63 mg, 1.6 mmol) and stirred at RT for 15 min. 2-Bromo-N,N-dimethylethan-1-amine (96 mg, 0.631 mmol) was added, and the resulting mixture was stirred for 30 min then quenched by TFA (0.081 mL, 1.0 mmol). The reaction mixture was concentrated, and the residue was purified by reverse phase HPLC (Phenomenex Gemini C18, H$_2$O/CH$_3$CN gradient to 0-50% MeCN 0.1% TFA) to give the title compound (50 mg, 36%) product. MS (ES) 262.3 (M+H).

Step B. Preparation of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-1-(2-(dimethylamino)ethyl)-1H-indole-6-carboxylate To a solution of 6-chloro-3-(3-(4-chloro-3,5-dimethylphenoxy)propyl)-7-(1,3,5-trimethyl-1H-pyrazol-4-yl)-1H-indole-2-carboxylic acid (70 mg, 0.14 mmol), methyl 4-amino-1-(2-(dimethylamino)ethyl)-1H-indole-6-carboxylate (40 mg, 0.15 mmol) and DMAP (34 mg, 0.28 mmol) in DCM (2 mL) was added EDC (54 mg, 0.28 mmol) and stirred at RT for 16 h. The reaction mixture was concentrated, and the residue was purified by reverse phase HPLC (Phenomenex Gemini C18, H$_2$O/CH$_3$CN gradient to 0-50% MeCN 0.1% TFA) to give the title compound (24 mg, 23%). LCMS: R$_T$=1.695 min, MS (ES) 742.8 (M+H).

Step C. Example 11

To a solution of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-1-(2-(dimethylamino)ethyl)-1H-indole-6-carboxylate (24 mg, 0.032 mmol) and 1,3-dibromopropane (9.8 µl, 0.097 mmol) in DMF (0.5 mL) was added Cs$_2$CO$_3$ (53 mg, 0.16 mmol) then stirred at rt for 20 h. The reaction mixture was filtered, and the filterate was concentrated. The residue was dissolved in THF (1 mL) and LiOH (0.2 mL, 2N) and stirred at 60° C. overnight. The reaction mixture was concentrated, and the residue was purified by reverse phase HPLC (Phenomenex Gemini C18, H$_2$O/CH$_3$CN gradient to 30-80% MeCN 0.1% TFA) to give the title compound (9 mg, 36%). LCMS: R$_T$=1.671 min, MS (ES) 768.7 (M+H).

Example 12

6-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-2-(2-morpholinoethyl)indazole-4-carboxylic acid Step A. Preparation of methyl 6-bromo-2-(2-morpholinoethyl)-2H-indazole-4-carboxylate To a solution of methyl 6-bromo-1H-indazole-4-carboxylate (100 mg, 0.392 mmol) in DMF (5 mL) was added NaH (30 mg, 1.25 mmol) at RT. The reaction mixture was stirred for 30 min, followed by addition of 4-(2-bromoethyl)morpholine (120 mg, 0.619 mmol). After 4 h, the reaction was quenched with water then concentrated in vacuo. The residue was purified by reverse phase preparative HPLC (Phenomenex Gemini C18. $H_2O/CH_3CN$ gradient to 20-75% MeCN 0.1% TFA) to separate the regioisomeric indazole intermediates. The desire region-isomer was dissolved in THF (5 mL) and MeOH (1 mL) and trimethylsilyldiazomethane (2.0 M in $Et_2O$, 0.25 mL, 0.50 mmol) was added. The reaction was stirred for 30 min at RT then quenched by addition of AcOH dropwise and concentrated in vacuo to afford the title compound (21 mg, 15%).

Step B. Example 12

The title compound (4.6 mg, 10%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 6-bromo-2-(2-morpholinoethyl)-2H-indazole-4-carboxylate (20 mg, 0.054 mmol), $Pd_2(dba)_3$ (8 mg, 0.0087 mmol), Xantphos (12 mg, 0.021 mmol), and $Cs_2CO_3$ (60 mg, 0.19 mmol) followed by, saponification using General Procedure D. LCMS: $R_T$=1.048 min, MS (ES) 812.1 (M+H).

Example 13

7-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-1-methyl-indazole-3-carboxylic acid The title compound (2.7 mg, 7%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 7-bromo-1-methyl-1H-indazole-3-carboxylate (12 mg, 0.045 mmol), $Pd_2(dba)_3$ (8 mg, 0.0087 mmol), Xantphos (12 mg, 0.021 mmol), and $Cs_2CO_3$ (60 mg, 0.19 mmol) followed by saponification using General Procedure D. LCMS: $R_T$=1.843 min, MS (ES) 712.7 (M+H).

Example 14

6-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-1-(2-morpholinoethyl)indazole-4-carboxylic acid Step A. Preparation of methyl 6-bromo-1-(2-morpholinoethyl)-1H-indazole-4-carboxylate The title compound (34 mg, 24%) was prepared following the same procedure as Example 12, Step A.

Step B. Example 14

The title compound (7.4 mg, 17%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 6-bromo-1-(2-morpholinoethyl)-1H-indazole-4-carboxylate (34 mg, 0.092 mmol), $Pd_2(dba)_3$ (8 mg, 0.0087 mmol), Xantphos (12 mg, 0.021 mmol), and $Cs_2CO_3$ (60 mg, 0.19 mmol) followed by saponification using General Procedure D. LCMS: $R_T$=1.661 min, MS (ES) 811.8 (M+H).

Example 15

8-Chloro-11-[3-(4-chloro-3,5-dimethyl-phenoxy)propyl]-2-[1-methyl-3-(2H-tetrazol-5-yl)indol-7-yl]-7-(1,3,5-trimethylpyrazol-4-yl)-4,5-dihydro-3H-[1,4]diazepino[1,2-a]indol-1-one To a solution of 7-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-3-carbonitrile (10 mg, 0.014 mmol) in DMF (1 mL) was added $NaN_3$ (10 mg, 0.15 mmol) and ammonium chloride (10 mg, 0.19 mmol). The reaction was capped and heated to 130° C. for 72 h then cooled to RT. The work up described in general coupling procedure A was followed then purified by reverse phase HPLC (Phenomenex Gemini C18, $H_2O/CH_3CN$ gradient 35-95% MeCN 0.1% TFA) to afford the title compound (2 mg, 19%). LCMS: $R_T$=1.980 min, MS (ES) 735.9 (M+H).

Example 16

7-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-2-methyl-indazole-3-carboxylic acid The title compound (6.1 mg, 16%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 7-bromo-2-methyl-2H-indazole-3-carboxylate (12 mg, 0.045 mmol), $Pd_2(dba)_3$ (8 mg, 0.0087 mmol), Xantphos (29 mg, 0.11 mmol), and $Cs_2CO_3$ (60 mg, 0.19 mmol) followed by saponification using General Procedure D. LCMS: $R_T$=1.463 min, MS (ES) 713.0 (M+H).

Example 17

2-(4-acetylpiperazin-1-yl)-6-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)isonicotinic acid To a solution of methyl 2-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(piperazin-1-yl)isonicotinate (15 mg, 0.02 mmol), in $CH_2Cl_2$ (1 mL) at RT was added triethylamine (6 μL, 0.04 mmol) followed by acetyl chloride (3 μL, 0.04 mmol) and the mixture was stirred at room temperature for 1 h. The mixture was diluted with water (2 mL) and extracted in $CH_2Cl_2$ (3×5 mL), dried and evaporated. The crude material was subjected to saponification conditions following General Procedure D followed by purification by reverse phase HPLC (Phenomenex Gemini C18, $H_2O/CH_3CN$ gradient to 35-95% MeCN 0.1% TFA) to afford the title compound (14 mg, 88%). LCMS: $R_T$=1.721 min, MS (ES) 800.4 (M+H).

Example 18

5-[8-chloro-11-[3-(4-chloro-3,5-dimethyl-phenoxy) propyl]-1-oxo-7-(1,3,5-trimethylpyrazol-4-yl)-4,5-dihydro-3H-[1,4]diazepino[1,2-a]indol-2-yl]-2,3-dihydrobenzofuran-7-carboxylic acid The title compound (2 mg, 5%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 5-bromo-2,3-dihydrobenzofuran-7-carboxylate (30 mg, 0.12 mmol), $Pd_2(dba)_3$ (8 mg, 0.0087 mmol), Xantphos (29 mg, 0.11 mmol), and $Cs_2CO_3$ (60 mg, 0.19 mmol) followed by saponification using General Procedure D. LCMS: $R_T$=1.825 min, MS (ES) 700.8 (M+H).

Example 19

(R)-5-(7-chloro-10-(3-(4-chloro-3,5-dimethylphenoxy)propyl)-3-ethyl-1-oxo-6-(1,3,5-trimethyl-1H-pyrazol-4-yl)-3,4-dihydropyrazino[1,2-a]indol-2(1H)-yl)quinoline-8-carboxylic acid The title compound (53% yield) was prepared following General coupling procedure A using (R)-7-chloro-10-(3-(4-chloro-3,5-dimethylphenoxy)propyl)-3-ethyl-6-(1,3,5-trimethyl-1H-pyrazol-4-yl)-3,4-dihydropyrazino[1,2-a]indol-(2H)-one and methyl 5-bromoquinoline-8-carboxylate followed by saponification using General Procedure D. MS (ES) 724.3 (M+H).

Example 20

(R)-6-((7-chloro-10-(3-(4-chloro-3,5-dimethylphenoxy)propyl)-3-ethyl-1-oxo-6-(1,3,5-trimethyl-1H-pyrazol-4-yl)-3,4-dihydropyrazino[1,2-a]indol-2(1H)-yl)methyl)nicotinic acid To a solution of (R)-7-chloro-10-(3-(4-chloro-3,5-dimethylphenoxy)propyl)-3-ethyl-6-(1,3,5-trimethyl-1H-pyrazol-4-yl)-3,4-dihydropyrazino[1,2-a]indol-1(2H)-one (25 mg, 46 mmol) in anhydrous DMF (2 mL) was added NaH (60%) (3 mg, 78 mmol) at 0° C. under $N_2$ atmosphere and stirred for 10 min. Methyl 6-(bromomethyl)nicotinate (1.7 eq.) was added to the reaction mixture and stirred for 10 min at 0° C. and 1 h at RT. The reaction mixture was diluted with ethyl acetate (20 mL), washed with brine (2×10 mL), dried over anhydrous $MgSO_4$ and concentrated in vacuo. The crude material was subjected to saponification conditions following General Procedure D followed by purification by reverse phase HPLC (Phenomenex Gemini C18, $H_2O/CH_3CN$ gradient to 50-95% MeCN 0.1% TFA) to give the title compound (68% yield). MS (ES) 688.3 (M+H) Rf=0.79.

Example 21

(R)-3-(7-chloro-10-(3-(4-chloro-3,5-dimethylphenoxy)propyl)-3-ethyl-t-oxo-6-(1,3,5-trimethyl-1H-pyrazol-4-yl)-3,4-dihydropyrazino[1,2-a]indol-2(1H)-yl)benzoic acid The title compound (52% yield) was prepared following General coupling procedure A using (R)-7-chloro-10-(3-(4-chloro-3,5-dimethylphenoxy)propyl)-3-ethyl-6-(1,3,5-trimethyl-1H-pyrazol-4-yl)-3,4-dihydropyrazino[1,2-a]indol-1(2H)-one and methyl 3-bromobenzoate followed by saponification using General Procedure D. MS (ES) 673.2 (M+H).

Example 22

2-(5-(8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indol-3-yl)acetic acid The title compound (56 mg, 77%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (54 mg, 0.1 mmol), methyl 2-(5-bromo-1-methyl-1H-indol-3-yl)acetate (34 mg, 0.12 mmol), $Pd_2(dba)_3$ (2 mg, 0.002 mmol), Xantphos (3.5 mg, 0.006 mmol), and $Cs_2CO_3$ (49 mg, 0.15 mmol) followed by saponification using General Procedure D. LCMS: $R_T$=1.756 min, MS (ES) 726.3 (M+H).

Example 23

(R)-4-(7-chloro-10-(3-(4-chloro-3,5-dimethylphenoxy)propyl)-3-ethyl-1-oxo-6-(1,3,5-trimethyl-1H-pyrazol-4-yl)-3,4-dihydropyrazino[1,2-a]indol-2(1H)-yl)benzoic acid The title compound (85% yield) was prepared following General coupling procedure A using (R)-7-chloro-1043-(4-chloro-3,5-dimethylphenoxy)propyl)-3-ethyl-6-(1,3,5-trimethyl-1H-pyrazol-4-yl)-3,4-dihydropyrazino[1,2-a]indol-1(2H)-one and methyl 4-bromobenzoate followed by saponification using General Procedure D. MS (ES) 673.2 (M+H); $^1$H-NMR (CDCl$_3$) δ 8.14 (d, 2H, J=8 Hz), 8.10 (m, 1H), 7.47 (d, 1H, J=8 Hz) 7.75 (m, 1H), 7.32-7.28 (m, 1H), 6.65 (s, 2H), 4.11 (tr, 2H, J=8 Hz), 3.97 (multiple s, m, 5H), 3.52-3.34 (m, 2H), 2.33 (s, 6H), 2.30-2.09 (overlapped multiple s, tr, 10H), 1.64 (m, 2H), 0.57 (tr, 3H, J=8 Hz).

Example 24

(R)-7-chloro-10-(3-(4-chloro-3,5-dimethylphenoxy) propyl)-3-ethyl-6-(1,3,5-trimethyl-1H-pyrazol-4-yl)-3,4-dihydropyrazino[1,2-a]indol-1(2H)-one To a solution of ethyl 6-chloro-3-(3-(4-chloro-3,5-dimethylphenoxy)propyl)-7-(4,6-dimethylpyrimidin-5-yl)-1H-indole-2-carboxylate (1.25 g, 2.37 mmol) in anhydrous acetonitrile (20 mL) was added cesium carbonate (1.5 g, 4.74 mmol) follow by tert-butyl (R)-4-ethyl-1,2,3-oxathiazolidine-3-carboxylate 2,2-dioxide (3.8 mmols). The reaction mixture was stirred at 80° C. for overnight. Additional cesium carbonate (0.5 eq) and tert-butyl (R)-4-ethyl-1,2,3-oxathiazolidine-3-carboxylate 2,2-dioxide (0.5 eq) were added to the mixture and the reaction was heated for additional 6 h at 80° C. The reaction mixture was cooled to abient temperature, diluted with ethyl acetate (100 mL). The solution was washed with brine (3×50 mL), dried with anhydrous $MgSO_4$, filtered and concentrated in vacuo. The residue was dissolved in anhydrous DCM (30 mL) and cooled to 0° C. then TFA (10 eq) was added dropwise. The reaction mixture was stirred at room temperature for 4 h. The reaction mixture was concentrated to driness then re-dissolved in anhydrous EtOH (20 mL). Anhydrous $K_2CO_3$ (15 eq.) was added and the reaction mixture was stirred at RT for 2 h then concentrated to ⅓ of original volume and diluted with ethyl acetate (100 mL). The solution was washed with brine (3×50 mL), dried over anhydrous $MgSO_4$, filtered and concentrated in vacuo. The residue was purified by flash chromatography (Combi-flash Rf, DCM/methanol=0-5% gradient) to give the title compound (80% for 3 steps). MS (ES) 553.2 (M+H), Rf=0.84; $^1$H-NMR ($CDCl_3$) δ 7.66 (d, 1H, J=8 Hz), 7.24 (d, 1H, J=8 Hz), 6.65 (s, 2H), 5.77 (m, 1H), 4.03 (tr, 2H, J=8 Hz), 3.99 (s, 3H), 3.52-3.50 (m, 1H), 3.49-3.38 (m, 1H), 3.38-3.34 (m, 2H), 2.35 (s, 6H), 2.19 (tr, 2H, J=8 Hz), 2.09 (2s, 6H), 1.59 (m, 2H), 1.26 (tr, 3H, J=8 Hz).

Example 25

7-(8-Chloro-11-(3-(4-chloro-3,5-dimethylphenoxy) propyl)-1-oxo-7-(1,3,5-trimethyl-1H-pyrazol-4-yl)-4,5-dihydro-1H-[1,4]diazepino[1,2-a]indol-2(3H)-yl)-2,3-dihydrobenzo[b][1,4]dioxine-5-carboxylic acid The title compound was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one and methyl 7-bromo-2,3-dihydrobenzo[b][1,4]dioxine-5-carboxylate followed by saponification using General Procedure D. MS (ES) 717.2 (M+H).

Example 26

(R)-8-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-2,3-dihydrobenzo[b][1,4]dioxine-6-carboxylic acid The title compound (45% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 8-bromo-2,3-dihydrobenzo[b][1,4]dioxine-6-carboxylate followed by saponification using General Procedure D. MS (ES) 717.2 (M+H).

Example 27

2-((8-chloro-11-(3-(4-chloro-3,5-dimethylphenoxy) propyl)-1-oxo-7-(1,3,5-trimethyl-1H-pyrazol-4-yl)-4,5-dihydro-1H-[1,4]diazepino[1,2-a]indol-2(3H)-yl) methyl)-6-(4-((5-methylfuran-2-yl)sulfonyl) piperazin-1-yl)isonicotinic acid To a solution of methyl 2-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2 (3H)-yl)methyl)-6-(piperazin-1-yl)isonicotinate (15 mg, 0.02 mmol), in $CH_2Cl_2$ (1 mL) at RT was added $Et_3N$ (6 μL, 0.04 mmol) followed by 5-methylfuran-2-sulfonyl chloride (6 μL, 0.04 mmol) and the mixture was stirred at room temperature for 1 h. The mixture was diluted with water (2 mL) and extracted in $CH_2Cl_2$ (3×5 mL), dried and concentrated. The crude material was subjected to saponification conditions following General Procedure D and purified by reverse phase HPLC (Phenomenex Gemini C18, $H_2O$/$CH_3CN$ gradient to 35-95% MeCN 0.1% TFA) to afford the title compound (13 mg, 69%). LCMS: $R_T$=2.019 min, MS (ES) 902.3 (M+H).

Example 28

4-[8-chloro-11-[3-(4-chloro-3,5-dimethyl-phenoxy) propyl]-1-oxo-7-(1,3,5-trimethylpyrazol-4-yl)-4,5-dihydro-3H-[1,4]diazepino[1,2-a]indol-2-yl]-2-[2-(dimethylamino)ethyl]indazole-6-carboxylic acid Step A. Preparation of methyl 4-bromo-2-(2-(dimethylamino)ethyl)-2H-indazole-6-carboxylate The title compound (28 mg, 22%) was prepared following General Procedure G using methyl 4-bromo-1H-indazole-6-carboxylate (100 mg, 0.393 mmol), NaH (15 mg, 0.625 mmol), and 2-bromo-N,N-dimethylethan-1-amine (120 mg, 0.515 mmol).

Step B. Example 28

The title compound (22 mg, 51%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 4-bromo-2-(2-(dimethylamino)ethyl)-2H-indazole-6-carboxylate (20 mg, 0.061 mmol), $Pd_2(dba)_3$ (5 mg, 0.0054 mmol), Xantphos (8 mg, 0.013 mmol), and $Cs_2CO_3$ (60 mg, 0.19 mmol) followed by saponification using General Procedure D using LiOH (5 mg, 0.21 mmol). LCMS: $R_T$=1.631 min, MS (ES) 770.2 (M+H); $^1$H NMR (400 MHz, DMSO-$d_6$) δ 8.71 (s, 1H), 8.24 (d, J=1.2 Hz, 1H), 7.73 (d, J=8.6 Hz, 1H), 7.48 (d, J=1.1 Hz, 1H), 7.27 (d, J=8.6 Hz, 1H), 6.73 (s, 2H), 4.98 (t, J=6.7 Hz, 2H), 4.13 (t, J=6.8 Hz, 2H), 3.98 (t, J=6.4 Hz, 2H), 3.78 (s, 3H), 3.76-3.74 (m, 4H), 3.09-3.00 (m, 2H), 2.77 (s, 3H), 2.76 (s, 3H), 2.24 (s, 6H), 2.13-1.99 (m, 5H), 1.93 (s, 3H), 1.75 (quint, J=8.0 Hz, 2H).

Example 29

(R)-6-(7-chloro-10-(3-(4-chloro-3,5-dimethylphenoxy)propyl)-3-ethyl-1-oxo-6-(1,3,5-trimethyl-1H-pyrazol-4-yl)-3,4-dihydropyrazino[1,2-a]indol-2 (1H)-yl)-1-methyl-1H-indole-4-carboxylic acid The title compound (45% yield) was prepared following General coupling procedure A using (R)-7-chloro-10-(3-(4-chloro-3,5-dimethylphenoxy)propyl)-3-ethyl-6-(1,3,5-trimethyl-1H-pyrazol-4-yl)-3,4-dihydropyrazino[1,2-a]indol-1 (2H)-one and methyl 6-bromo-1-methyl-1H-indole-4-carboxylate followed by saponification using General Procedure D. MS (ES) 727.2 (M+H).

Example 30

6-[8-Chloro-11-[3-(4-chloro-3,5-dimethyl-phenoxy) propyl]-1-oxo-7-(1,3,5-trimethylpyrazol-4-yl)-4,5-dihydro-3H-[1,4]diazepino[1,2-a]indol-2-yl]-1-[2-(dimethylamino)ethyl]indazole-4-carboxylic acid Step A. Preparation of methyl 6-bromo-1-(2-(dimethylamino)ethyl)-1H-indazole-4-carboxylate The title compound (39 mg, 30%) was prepared following the procedure described Example 12, Step A using methyl 6-bromo-1H-indazole-4-carboxylate (100 mg, 0.392 mmol), NaH (30 mg, 1.25 mmol), 2-bromo-N,N-dimethylethan-1-amine HBr salt (130 mg, 0.56 mmol), and trimethylsilyldiazomethane (2.0 M in Et$_2$O, 0.1 mL, 0.2 mmol).

Step B. Example 30

The title compound (17 mg, 40%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 6-bromo-1-(2-(dimethylamino)ethyl)-1H-indazole-4-carboxylate (20 mg, 0.061 mmol), Pd$_2$(dba)$_3$ (5 mg, 0.0054 mmol), Xantphos (8 mg, 0.013 mmol), and Cs$_2$CO$_3$ (60 mg, 0.19 mmol) followed by saponification using General Procedure D using LiOH (5 mg, 0.21 mmol). LCMS: R$_T$=1.656 min, MS (ES) 770.3 (M+H); $^1$H NMR (400 MHz, DMSO-d$_6$) δ 8.44 (d, J=0.8 Hz, 1H), 8.25 (t, J=1.3 Hz, 1H), 7.90 (d, J=1.7 Hz, 1H), 7.73 (d, J=8.6 Hz, 1H), 7.27 (d, J=8.5 Hz, 1H), 6.74 (s, 2H), 4.97 (t, J=6.7 Hz, 2H), 4.08 (t, J=8.0 Hz, 2H), 3.98 (t, J=6.3 Hz, 2H), 3.83-3.70 (m, 5H), 3.62-3.59 (m, 2H), 3.06 (t, J=8.0 Hz, 2H), 2.78 (s, 3H), 2.77 (s, 3H), 2.22 (s, 6H), 2.15-2.00 (m, 5H), 1.96-1.83 (m, 5H).

Example 31

6-(8-chloro-11-(3-(4-chloro-3,5-dimethylphenoxy) propyl)-1-oxo-7-(1,3,5-trimethyl-1H-pyrazol-4-yl)-4,5-dihydro-1H-[1,4]diazepino[1,2-a]indol-2(3H)-yl)-1-(2-morpholinoethyl)-1H-indole-4-carboxylic acid Step A. Preparation of methyl 6-bromo-1-((2-(trimethylsilyl)ethoxy)methyl)-1H-indole-4-carboxylate To a solution of methyl 6-bromo-1H-indole-4-carboxylate (200 mg, 0.79 mmol) in DMF (5 mL) was added NaH (38 mg, 0.95 mmol) and stirred at rt for 15 min. (2-(Chloromethoxy)ethyl)trimethylsilane (197 mg, 1.2 mmol) was added, and the resulting mixture was stirred for additional 30 min. The reaction was quenched by addition of MeOH (1 mL) then concentrated in vacuo. The residue was purified by flash chromatography (Combi-flash Rf, Hex/EtOAc=0-25% gradient) to give the title compound (270 mg, 89%) as a colorless oil. LCMS: R$_T$=1.939 min, MS (ES) 384.1 (M+H)

Step B. Preparation of methyl 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4] diazepino[1,2-a]indol-2(3H)-yl)-1-((2-(trimethylsilyl)ethoxy)methyl)-1H-indole-4-carboxylate The title compound (187 mg, 80%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (150 mg, 0.278 mmol), methyl 6-bromo-1-((2-(trimethylsilyl)ethoxy)methyl)-1H-indole-4-carboxylate (128 mg, 0.334 mmol), Pd$_2$(dba)$_3$ (5 mg, 0.0054 mmol), Xantphos (8 mg, 0.013 mmol), and Cs$_2$CO$_3$ (181 mg, 0.556 mmol). LCMS: R$_T$=2.461 min, MS (ES) 842.3 (M+H).

Step C. Preparation of methyl 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4] diazepino[1,2-a]indol-2(3H)-yl)-1H-indole-4-carboxylate A mixture of methyl 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2 (3H)-yl)-1-((2-(trimethylsilyl)ethoxy)methyl)-1H-indole-4-carboxylate (170 mg, 0.202 mmol), TBAF (2.0 ml, 2.0 mmol) was heated to 100° C. under microwave irradiation in Biotage Initiator for 20 min. The reaction was quenched by addition of H$_2$O (5 mL) then extracted with DCM (10 mL×2). The combined organic solution was concentrated and purified by reverse phase HPLC (Phenomenex Gemini C18, H$_2$O/CH$_3$CN gradient to 35-95% MeCN 0.1% TFA) to give the title compound (80 mg, 56%). LCMS: R$_T$=2.065 min, MS (ES) 712.3 (M+H).

Step D. Example 31

To a solution of methyl 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2 (3H)-yl)-1H-indole-4-carboxylate (20 mg, 0.028 mmol) in DMF (0.5 mL) was added NaH (4.5 mg, 0.11 mmol) then stirred for 20 min. 4-(2-Bromoethyl)morpholine (16 mg, 0.084 mmol) was added, and the resulting mixture was stirred at rt for 20 h. The reaction was quenched by MeOH (0.5 mL), acidified with TFA and purified by reverse phase HPLC (Phenomenex Gemini C18, H$_2$O/CH$_3$CN gradient to 30-80% MeCN 0.1% TFA) to give the title compound (9.8 mg, 43%). LCMS: R$_T$=1.670 min, MS (ES) 811.3 (M+H).

Example 32

4-(8-Chloro-11-(3-(4-chloro-3,5-dimethylphenoxy) propyl)-1-oxo-7-(1,3,5-trimethyl-1H-pyrazol-4-yl)-4,5-dihydro-1H-[1,4]diazepino[1,2-a]indol-2(3H)-yl)-1-(methylsulfonyl)-1H-indole-6-carboxylic acid Step A. Preparation of methyl 4-bromo-1-((2-(trimethylsilyl)ethoxy)methyl)-1H-indole-6-carboxylate e The title compounds were prepared according to procedures described in Example 31 Step A using methyl 4-bromo-1H-indole-6-carboxylate. MS (ES) 384.1 (M+H).

Step B. Preparation of methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4] diazepino[1,2-a]indol-2(3H)-yl)-1-((2-(trimethylsilyl)ethoxy)methyl)-1H-indole-6-carboxylate The title compound was prepared according to the procedure in Example 31 Step B substituting methyl 6-bromo-1-((2-(trimethylsilyl)ethoxy)methyl)-1H-indole-4-carboxylate with methyl 4-bromo-1-((2-(trimethylsilyl)ethoxy) methyl)-1H-indole-6-carboxylate. MS (ES) 842.3 (M+H).

Step C. Preparation of methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1H-indole-6-carboxylate The title compound (50 mg, 59%) was prepared according to the procedure in Example 31 Step C using methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-((2-(trimethylsilyl)ethoxy)methyl)-1H-indole-6-carboxylate (100 mg, 0.12 mmol) and TBAF (0.593 mL, 0.593 mmol). LCMS: $R_T$=2.056 min, MS (ES) 712.2 (M+H).

Step D. Example 32

To a solution of methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1H-indole-6-carboxylate (25 mg, 0.035 mmol) in DMF (1 mL) was added NaH (4.21 mg, 0.105 mmol) and stirred for 15 min. MsCl (8.20 µl, 0.11 mmol) was added and the resulting mixture was stirred overnight. The reaction mixture was concentrated and the residue was dissolved into THF (0.3 mL) and LIOH (0.2 mL, 2 N) then stirred at 60° C. for 4 h. The reaction mixture was concentrated, and the residue was purified by reverse phase HPLC (Phenomenex Gemini C18, $H_2O$/$CH_3CN$ gradient to 40-90% MeCN 0.1% TFA) to give the title compound (4 mg, 15%) as an off-white solid. LCMS: $R_T$=1.979 min, MS (ES) 775.9 (M+H).

Example 33

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)benzo[d][1,3]dioxole-5-carboxylic acid The title compound (42% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-bromobenzo[d][1,3]dioxole-5-carboxylate followed by saponification using General Procedure D. MS (ES) 703.2 (M+H).

Example 34

2-((8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(4-(dimethylcarbamoyl)piperazin-1-yl)isonicotinic acid To a solution of methyl 2-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(piperazin-1-yl)isonicotinate (15 mg, 0.02 mmol), in $CH_2Cl_2$ (1 mL) at room temperature was added triethylamine (6 µL, 0.04 mmol) followed by dimethylcarbamic chloride (4 µL, 0.04 mmol) then the mixture was stirred at RT for 1 h. The mixture was diluted with water (2 mL) and extracted with $CH_2Cl_2$ (3×5 mL), dried and concentrated. The crude material was subjected to saponification conditions following General Procedure D and purified by reverse phase HPLC (Phenomenex Gemini C18, $H_2O$/$CH_3CN$ gradient to 35-95% MeCN 0.1% TFA) to afford the title compound (11 mg, 66%). LCMS: $R_T$=1.761 min, MS (ES) 829.3 (M+H).

Example 35

(R)-2-chloro-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)benzoic acid The title compound (88% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 4-bromo-2-chlorobenzoate followed by saponification using General Procedure D. MS (ES) 693.2 (M+H).

Example 36

4-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-2-methyl-indazole-6-carboxylic acid The title compound (26 mg, 65%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 4-bromo-2-methyl-2H-indazole-6-carboxylate (20 mg, 0.074 mmol), $Pd_2(dba)_3$ (5 mg, 0.0054 mmol), Xantphos (8 mg, 0.013 mmol), and $Cs_2CO_3$ (60 mg, 0.19 mmol) followed by saponification using General Procedure D using LiOH (5 mg, 0.21 mmol). LCMS: $R_T$=1.873 min, MS (ES) 713.1 (M+H).

Example 37

5-(8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1H-1,2,4-triazole-3-carboxylic acid To a solution of 6-chloro-3-(3-(4-chloro-3,5-dimethylphenoxy)propyl)-7-(1,3,5-trimethyl-1H-pyrazol-4-yl)-1H-indole-2-carboxylic acid (50 mg, 0.1 mmol) in DMF (2 mL) were added methyl 5-amino-1H-1,2,4-triazole-3-carboxylate (15 mg, 0.1 mmol), HBTU (76 mg, 0.2 mmol), triethylamine (42 µL, 0.3 mmol), and the mixture was stirred at RT for 10 h. Water (5 mL) was added to the mixture and extracted with $CH_2Cl_2$ (3×5 mL). The organic layer was dried (anhyd. $Na_2SO_4$) and concentrated. To the solution crude in DMF (3 mL) were added 1,3-dibromopropane (42 µL, 0.4 mmol) and $Cs_2CO_3$ (130 mg, 0.4 mmol). The mixture was stirred at 40° C. for 6 h, filtered, diluted with water (5 mL) and extracted with $CH_2Cl_2$ (3×5 mL). The organic layer was dried (anhyd. $Na_2SO_4$) and concentrated in vacuo. The crude material was subjected to saponification conditions following General Procedure D and purified by reverse phase HPLC (Phenomenex Gemini C18, $H_2O$/$CH_3CN$ gradient to 35-95% MeCN 0.1% TFA) to afford the title compound (34 mg, 52%). LCMS: $R_T$=2.088 min, MS (ES) 650.2 (M+H).

Example 38

2-((8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(4-(phenethylsulfonyl)piperazin-1-yl)isonicotinic acid To a solution of methyl 2-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(piperazin-1-yl)isonicotinate (15 mg, 0.02 mmol), in $CH_2Cl_2$ (1 mL) at room temperature was added triethylamine (6 µL, 0.04 mmol) followed by 2-phenylethane-1-sulfonyl chloride (8 mg, 0.04 mmol) and the mixture was stirred at RT for 1 h. The mixture was diluted with water (2 mL) and extracted with $CH_2Cl_2$ (3×5 mL), dried and concentrated. The crude material was subjected to saponification conditions following General Procedure D and purified by reverse phase HPLC (Phenomenex Gemini C18, $H_2O/CH_3CN$ gradient to 35-95% MeCN 0.1% TFA) to afford the title compound (17 mg, 92%). LCMS: $R_T$=1.959 min, MS (ES) 926.3 (M+H).

Example 39

6-[8-chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-1-ethyl-indazole-4-carboxylic acid

Step A. Preparation of methyl 6-bromo-1-ethyl-1H-indazole-4-carboxylate

The title compound (44 mg, 39%) was prepared following the procedure described Example 12, Step A using methyl 6-bromo-1H-indazole-4-carboxylate (100 mg, 0.392 mmol) and ethyl bromide (85 mg, 0.78 mmoL).

Step B. Example 39

The title compound (6 mg, 18%) was prepared following General Procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol), methyl 6-bromo-1-ethyl-1H-indazole-4-carboxylate (20 mg, 0.071 mmol), $Pd_2(dba)_3$ (4 mg, 0.0044 mmol), Xantphos (6 mg, 0.010 mmol), and $Cs_2CO_3$ (60 mg, 0.19 mmol) followed by saponification using General Procedure D. LCMS: $R_T$=1.977 min, MS (ES) 727.2 (M+H).

Example 40

4-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-1-[2-(dimethylamino)ethyl]indazole-6-carboxylic acid

Step A. Preparation of methyl 4-bromo-1-(2-(dimethylamino)ethyl)-1H-indazole-6-carboxylate The title compound (70 mg, 55%) was prepared following the procedure described Example 12, Step A using methyl 4-bromo-1H-indazole-6-carboxylate (100 mg, 0.393 mmol) and 2-bromo-N,N-dimethylethan-1-amine (120 mg, 0.515 mmol).

Step B. Example 40

The title compound (26 mg, 60%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 4-bromo-1-(2-(dimethylamino)ethyl)-1H-indazole-6-carboxylate (20 mg, 0.061 mmol), $Pd_2(dba)_3$ (5 mg, 0.0054 mmol), Xantphos (8 mg, 0.013 mmol), and $Cs_2CO_3$ (60 mg, 0.19 mmol) followed by saponification using General Procedure D. LCMS: $R_T$=1.666 min, MS (ES) 770.3 (M+H).

Example 41

(R)-5-(7-chloro-10-(3-(4-chloro-3,5-dimethylphenoxy)propyl)-3-ethyl-1-oxo-6-(1,3,5-trimethyl-1H-pyrazol-4-yl)-3,4-dihydropyrazino[1,2-a]indol-2(1H)-yl)-1-methyl-1H-indole-7-carboxylic acid The title compound (48% yield) was prepared following General coupling procedure A using (R)-7-chloro-10-(3-(4-chloro-3,5-dimethylphenoxy)propyl)-3-ethyl-6-(1,3,5-trimethyl-1H-pyrazol-4-yl)-3,4-dihydropyrazino[1,2-a]indol-1(2H)-one and methyl 5-bromo-1-methyl-1H-indole-7-carboxylate followed by saponification using General Procedure D. MS (ES) 726.2 (M+H).

Example 42

6-[8-chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-2-[2-(dimethylamino)ethyl]indazole-4-carboxylic acid

Step A. Preparation of methyl 6-bromo-2-(2-(dimethylamino)ethyl)-2H-indazole-4-carboxylate The title compound (13 mg, 10%) was prepared following the procedure described Example 12, Step A using methyl 6-bromo-1H-indazole-4-carboxylate (100 mg, 0.392 mmol), sodium hydride (30 mg, 1.25 mmol), 2-bromo-N,N-dimethylethan-1-amine HBr salt (130 mg, 0.56 mmol).

Step B. Example 42

The title compound (12 mg, 28%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 6-bromo-2-(2-(dimethylamino)ethyl)-2H-indazole-4-carboxylate (13 mg, 0.039 mmol), $Pd_2(dba)_3$ (5 mg, 0.0054 mmol), Xantphos (8 mg, 0.013 mmol), and $Cs_2CO_3$ (60 mg, 0.19 mmol) followed by saponification using General Procedure D. LCMS: $R_T$=1.662 mm. MS (ES) 770.2 (M+H); $^1$H NMR (400 MHz, DMSO-$d_6$) δ 8.81 (s, 1H), 7.90-7.83 (m, 1H), 7.80 (d, J=1.7 Hz, 1H), 7.72 (d, J=8.6 Hz, 1H), 7.26 (d, J=8.5 Hz, 1H), 6.73 (s, 2H), 5.03 (t, J=6.6 Hz, 2H), 4.04 (t, J=7.1 Hz, 2H), 3.96 (t, J=6.3 Hz, 2H), 3.78 (s, 3H), 3.69 (dt, J=25.3, 6.3 Hz, 4H), 3.06 (t, J=7.4 Hz, 2H), 2.78 (s, 3H), 2.77 (s, 3H), 2.22 (s, 6H), 2.08 (q, J=6.8 Hz, 2H), 2.02 (s, 3H), 1.91 (s, 3H), 1.79 (q, J=7.9, 7.3 Hz, 2H).

Example 43

2-((8-Chloro-11-(3-(4-chloro-3,5-dimethylphenoxy) propyl)-1-oxo-7-(1,3,5-trimethyl-1H-pyrazol-4-yl)-4,5-dihydro-1H-[1,4]diazepino[1,2-a]indol-2(3H)-yl) methyl)isonicotinic acid To a solution of 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (54 mg, 0.1 mmol) in DMF (2 mL) was added NaH (5 mg, 0.12 mmol) and the mixture was stirred at RT for 10 min. Methyl 2-(bromomethyl)isonicotinate (28 mg, 0.12 mmol, 1.2 eqv.) was added to the mixture followed by TBAI (37 mg, 0.1 mmol) and stirred for additional 2 h. The mixture was diluted with water (5 mL) and extracted with $CH_2Cl_2$ (3×5 mL). The organic layer was dried over $Na_2SO_4$ and concentrated in vacuo. The crude material was subjected to saponification conditions following General Procedure D using 2M LiOH (1 mL) and purified by reverse phase HPLC (Phenomenex Gemini C18, $H_2O/CH_3CN$ gradient to 35-95% MeCN 0.1% TFA) to afford the title compound (59 mg, 88%). LCMS: $R_T$=1.849 min, MS (ES) 674.2 (M+H).

Example 44

6-[8-chloro-11-[3-(4-chloro-3,5-dimethyl-phenoxy) propyl]-1-oxo-7-(1,3,5-trimethylpyrazol-4-yl)-4,5-dihydro-3H-[1,4]diazepino[1,2-a]indol-2-yl]-1H-indazole-4-carboxylic acid

Step A. Preparation of methyl 6-bromo-1-((2-(trimethylsilyl)ethoxy)methyl)-1H-indazole-4-carboxylate The title compound (154 mg, 93%) was prepared using the procedure described in Example 39 Step A using methyl 6-bromo-1H-indazole-4-carboxylate (110 mg, 0.43 mmol), (2-(chloromethoxy)ethyl)trimethylsilane (110 mg, 0.65 mmol), and sodium hydride (10 mg, 0.43 mmol) and purified by flash chromatography (Combi-flash Rf, Hex/EtOAc=0-100% gradient).

Step B. Preparation of methyl 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-((2-(trimethylsilyl)ethoxy)methyl)-1H-indazole-4-carboxylate The title compound was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 6-bromo-1-((2-(trimethylsilyl)ethoxy)methyl)-1H-indazole-4-carboxylate (32 mg, 0.083 mmol), $Pd_2(dba)_3$ (8 mg, 0.0087 mmol), Xantphos (12 mg, 0.021 mmol), and $Cs_2CO_3$ (50 mg, 0.15 mmol).

Step C. Example 44

Methyl 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-((2-(trimethylsilyl)ethoxy)methyl)-1H-indazole-4-carboxylate was dissolved in TBAF (1.0 M in THF, 3 mL). The reaction was irradiated in the microwave at 100° C. for 1 h. Water (0.5 mL) and LiOH (5 mg, 0.21 mmol) were added, and the reaction was heated to 50° C. for additional 1 h. The work up described in general coupling procedure A was followed then purified by reverse phase HPLC (Phenomenex Gemini C18, $H_2O/CH_3CN$ gradient 35-95% MeCN 0.1% TFA) to afford the title compound (8 mg, 20% two Steps). LCMS: $R_T$=1.837 min, MS (ES) 699.3 (M+H).

Example 45

4-[8-chloro-11-[3-(4-chloro-3,5-dimethyl-phenoxy) propyl]-1-oxo-7-(1,3,5-trimethylpyrazol-4-yl)-4,5-dihydro-3H-[1,4]diazepino[1,2-a]indol-2-yl]-1-methyl-indazole-6-carboxylic acid The title compound (21 mg, 52%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 4-bromo-1-methyl-1H-indazole-6-carboxylate (20 mg, 0.074 mmol), $Pd_2(dba)_3$ (5 mg, 0.0054 mmol), Xantphos (8 mg, 0.013 mmol), and $Cs_2CO_3$ (60 mg, 0.19 mmol) followed by saponification using General Procedure D. LCMS: $R_T$=1.849 min, MS (ES) 713.2 (M+H), $^1$H NMR (400 MHz, DMSO-$d_6$) δ 8.25 (s, 1H), 8.06 (d, J=1.0 Hz, 1H), 7.73 (d, J=8.6 Hz, 1H), 7.58 (d, J=1.1 Hz, 1H), 7.27 (d, J=8.6 Hz, 1H), 6.72 (s, 2H), 4.15 (s, 3H), 4.12 (t, J=6.0 Hz, 2H) 3.97 (t, J=6.3 Hz, 2H), 3.78 (s, 3H), 3.76 (t, J=3.8 Hz, 2H), 3.04 (d, J=8.0 Hz, 2H), 2.23 (s, 6H), 2.13-2.00 (m, 5H), 1.93 (s, 3H), 1.75 (m, 2H).

Example 46

2-(6-(8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2 (3H)-yl)-3,4-dihydroquinolin-1(2H)-yl)acetic acid To a solution of 6-chloro-3-(3-(4-chloro-3,5-dimethylphenoxy)propyl)-7-(1,3,5-trimethyl-1H-pyrazol-4-yl)-1H-indole-2-carboxylic acid (50 mg, 0.1 mmol) in DMF (2 mL) were added tert-butyl 6-amino-3,4-dihydroquinoline-1 (2H)-carboxylate (25 mg, 0.1 mmol), HBTU (76 mg, 0.2 mmol), triethylamine (42 µL, 0.3 mmol), and the mixture was stirred at RT for 10 h. Water (5 mL) was added to the mixture and it was extracted in $CH_2Cl_2$ (3×5 mL). The organic layer was dried over $Na_2SO_4$ and concentrated. To the solution of crude in DMF (3 mL) were added 1,3-dibromopropane (42 µL, 0.4 mmol), $Cs_2CO_3$ (130 mg, 0.4 mmol), and the mixture was stirred at 40° C. for 6 h. The mixture was filtered, diluted with water (5 mL) and extracted with $CH_2Cl_2$ (3×5 mL). The organic layer was dried over $Na_2SO_4$ and concentrated. The crude residue was dissolved in $CH_2Cl_2$ (2 mL) and TFA (2 mL) was added. The mixture was stirred at room temperature for 6 h. Saturated aqueous $NaHCO_3$ (8 ML) was added to the mixture and extracted with DCM (3×5 mL). The organic layer was dried over $Na_2SO_4$, and concentrated. To a solution of crude in DMF (1 mL) was added NaH (5 mg, 0.12 mmol) and the mixture was stirred at room temperature for 10 min. Ethyl bromoacetate (14 µL, 0.12 mmol) was added to the mixture and stirred at RT for 2 h. The reaction mixture was quenched with water (5 mL) and extracted with $CH_2Cl_2$ (3×5 mL). The organic layer was dried over $Na_2SO_4$ and concentrated in vacuo. The crude material was subjected to saponification conditions following General Procedure D and purified by reverse phase HPLC (Phenomenex Gemini C18, $H_2O/CH_3CN$ gradient to 35-95% MeCN 0.1% TFA) to afford the title compound (15 mg, 21%). LCMS: $R_T$=2.023 min, MS (ES) 728.2 (M+H).

Example 47

2-((8-Chloro-11-(3-(4-chloro-3,5-dimethylphenoxy) propyl)-1-oxo-7-(1,3,5-trimethyl-1H-pyrazol-4-yl)-4,5-dihydro-1H-[1,4]diazepino[1,2-a]indol-2(3H)-yl) methyl)-6-(4-(cyclopropylsulfonyl)piperazin-1-yl) isonicotinic acid The title compound (10 mg, 58%) was prepared following the procedure described Example 38 using methyl 2-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(piperazin-1-yl)isonicotinate (15 mg, 0.02 mmol) and cyclopropanesulfonyl chloride (6 μL, 0.04 mmol) followed by saponification conditions following General Procedure D. LCMS: $R_T$=1.931 min, MS (ES) 862.3 (M+H).

Example 48

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-methyl-1H-indazole-6-carboxylic acid The title compound (40% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 3-bromo-1-methyl-1H-indazole-6-carboxylate followed by saponification using General Procedure D. MS (ES) 713.2 (M+H).

Example 49

3-(8-chloro-11-(3-(4-chloro-3,5-dimethylphenoxy) propyl)-1-oxo-7-(1,3,5-trimethyl-1H-pyrazol-4-yl)-4,5-dihydro-1H-[1,4]diazepino[1,2-a]indol-2(3H)-yl)-1-(2-morpholinoethyl)-1H-indazole-6-carboxylic acid Step A. Preparation of methyl 3-bromo-1-(2-morpholinoethyl)-1H-indazole-6-carboxylate To a solution of methyl 3-bromo-1H-indazole-6-carboxylate (0.27 mmol) in DMF (3 mL) was added sodium hydride (10 mg, 0.69 mmol), and the reaction was stirred 5 min at RT. 4-(2-Chloroethyl)morpholine (1.1 mmol) was added, and the reaction was stirred for additional 1 h. The reaction was diluted with EtOAc (10 mL), washed with $H_2O$ (3×10 mL), dried over $MgSO_4$ and concentrated in vacuo. The residue was purified by flash chromatography (Combi-flash Rf, Hex/EtOAc=0-40% gradient) to afford the title compound (76 mg, 75%).

Step B. Example 49

A flame dried flask was charged with $Pd_2(dba)_3$ (1 mg, 0.5 mol %), Xantphos (2 mg, 1 mol %), cesium carbonate (27 mg, 0.084 mmol), 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 3-bromo-1-(2-morpholinoethyl)-1H-indazole-6-carboxylate (24 mg, 0.067 mmol), and 1,4-dioxane (1 mL). The reaction mixture was degassed for 10 min under argon and stirred for 16 h at 110° C. then concentrated in vacuo. The residue was filtered through silica pad with DCM/MeOH (3/1) then concentrated in vacuo. To a solution of crude methyl 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-(2-morpholinoethyl)-1H-indazole-6-carboxylate (0.056 mmol) in mixture of methanol and dioxane (1 mL/2 mL) was added sodium hydroxide (0.2 mL, 2M solution). The reaction mixture was stirred for 3 h at room temperature and then concentrated in vacuo. The residue was purified by reverse phase preparatory HPLC (Phenomenex Gemini C18, $H_2O$/$CH_3CN$ gradient to 5-95% $CH_3CN$ 0.1% TFA) to afford the title compound (17 mg, 36%). LCMS: $R_T$=0.669 min (non polar method, >99%, ELSD); MS (ES) 812.2 [M+H]; $^1$H NMR (DMSO, 400 MHz) δ (ppm) 8.41 (s, 1H), 7.79 (d, J=8.4 Hz, 1H), 7.74 (d, J=8.4 Hz, 1H), 7.69 (dd, J=8.4, 1.2 Hz, 1H), 7.28 (d, J=8.8 Hz, 1H), 6.71 (s, 2H), 4.92-4.79 (m, 2H), 4.05 (t, J=6.0 Hz, 2H), 3.99-3.95 (m, 4H), 3.85 (t, J=6.0 Hz, 2H), 3.76 (s, 3H), 3.71-3.55 (m, 6H), 3.26-3.10 (m, 2H), 3.07 (t, J=6.8 Hz, 2H), 2.21 (s, 6H), 2.12-2.01 (m, 2H), 2.02 (s, 3H), 1.92 (s, 3H), 1.85-1.62 (m, 2H).

Example 50

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-(2-morpholinoethyl)-1H-indazole-6-carboxylic acid The title compound (40 mg, 87%) was prepared according to procedures described in Example 49 Step B by substituting 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one with (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a] indol-1(2H)-one (30 mg, 0.056 mmol). LCMS: $R_T$=0.697 min (non polar method, >99%, ELSD); MS (ES) 812.3 [M+H]; $^1$H NMR (DMSO, 400 MHz) δ (ppm) 8.41 (s, 1H), 7.78 (d, J=8.4 Hz, 1H), 7.75 (d, J=8.4 Hz, 1H), 7.72 (dd, J=8.4, 1.2 Hz, 1H), 7.31 (d, J=8.4 Hz, 1H), 6.71 (s, 2H), 4.91-4.85 (m, 2H), 4.48-4.43 (m, 2H), 4.25-4.18 (m, 2H), 4.02-3.99 (m, 4H), 3.96-3.92 (m, 1H), 3.77 (s, 3H), 3.75-3.51 (m, 4H), 3.39-3.16 (m, 4H), 3.23 (s, 6H), 2.10 (s, 1.5H), 2.10 (s, 1.5H), 2.10-1.97 (m, 2H), 1.89 (s, 1.5H), 1.02 (d, J=6.0 Hz, 3H).

Example 51

(R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-methyl-1H-indole-7-carboxylic acid The title compound (84% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one and methyl 4-bromo-1-methyl-1H-indole-7-carboxylate followed by saponification using General Procedure D. MS (ES) 712.3 (M+H); $^1$H-NMR (CDCl$_3$) δ 7.89 (d, 1H, J=8 Hz), 7.79 (d, 1H, J=8 Hz), 7.34 (d, 1H, J=8 Hz) 7.11 (m, 1H), 7.02 (m, 1H), 6.62 (s, 2H), 6.40 (m, 1H), 4.5 (m, 1H), 4.18 (tr, 2H, J=8 Hz), 4.02 (s, 3H), 3.97 (s, 3H), 3.90-3.88 (m, 2H), 3.52-3.36 (m, 2H), 2.33 (s, 6H), 2.30-2.09 (overlapped multiples, tr, 8H), 1.28 (two d, 3H, J=8 Hz).

Example 52

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-4-carboxylic acid The title compound (84% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-bromo-1-methyl-1H-indole-4-carboxylate followed by saponification using General Procedure D. MS (ES) 712.3 (M+H); $^1$H-NMR (CDCl$_3$) δ 7.95 (d, 1H, J=8 Hz), 7.75 (d, 1H, J=8 Hz), 7.35 (d, 1H, J=8 Hz) 7.13 (m, 1H), 7.02 (m, 1H), 6.99 (m, 1H), 6.62 (s, 2H), 4.02 (s, 3H), 4.00 (tr, 2H, J=8 Hz), 3.78 (s, 3H), 3.90-3.88 (m, 1H), 3.52-3.35 (m, 2H), 2.33 (s, 6H), 2.30-2.18 (overlapped multiples, tr, m, 10H), 1.28 (two d, 3H, J=8 Hz).

Example 53

(R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indazole-4-carboxylic acid The title compound (6.0 mg, 18%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 6-bromo-1-methyl-1H-indazole-4-carboxylate (20 mg, 0.074 mmol), Pd$_2$(dba)$_3$ (4 mg, 0.0044 mmol), Xantphos (6 mg, 0.010 mmol), and Cs$_2$CO$_3$ (60 mg, 0.19 mmol) followed by saponification using General Procedure D. LCMS: R$_T$=2.014 min, MS (ES) 713.2 (M+H).

Example 54

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-2-methyl-2H-indazole-3-carboxylic acid The title compound (7.3 mg, 22%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 7-bromo-2-methyl-2H-indazole-3-carboxylate (20 mg, 0.074 mmol), Pd$_2$(dba)$_3$ (4 mg, 0.0044 mmol), Xantphos (6 mg, 0.010 mmol), and Cs$_2$CO$_3$ (60 mg, 0.19 mmol) followed by saponification using General Procedure D. LCMS: R$_T$=2.066 min, MS (ES) 713.2 (M+H).

Example 55

7-(8-Chloro-11-(3-(4-chloro-3,5-dimethylphenoxy)propyl)-1-oxo-7-(1,3,5-tri methyl-1H-pyrazol-4-yl)-4,5-dihydro-1H-[1,4]diazepino[1,2-a]indol-2(3H)-yl)-1-methyl-1H-indole-4-carboxylic acid The title compound (25 mg, 62%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one and methyl 7-bromo-1-methyl-1H-indole-4-carboxylate followed by saponification using General Procedure D. MS (ES) 712.3 (M+H); $^1$H NMR (DMSO, 400 MHz) δ (ppm) 7.73 (s, 1H), 7.70 (s, 1H), 7.44 (d, J=2.8 Hz, 1H), 7.26 (d, J=8.4 Hz, 1H), 7.10 (dd, J=12.0, 8.0 Hz, 1H), 7.02 (d, J=3.2 Hz, 1H), 6.73 (s, 2H), 4.20-4.08 (m, 2H), 4.00 (t, J=6.0 Hz, 2H), 3.79 (s, 3H), 3.77 (s, 3H), 3.75-3.68 (m, 1H), 3.53-3.45 (m, 1H), 3.16-3.08 (m, 1H), 2.99-2.91 (m, 1H), 2.25 (s, 6H), 2.15-2.03 (m, 2H), 2.05 (s, 1.5H), 2.00 (s, 1.5H), 1.94 (s, 1.5H), 1.89 (s, 1.5H), 1.8-1.6 (m, 2H).

Example 56

(R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-morpholinoethyl)-1H-indazole-4-carboxylic acid Step A. Preparation of methyl 6-bromo-1-(2-morpholinoethyl)-1H-indazole-4-carboxylate The title compound (74 mg, 26%) was prepared following General Procedure G using methyl 6-bromo-1H-indazole-4-carboxylate (200 mg, 0.784 mmol), NaH (36 mg, 1.5 mmol), and 4-(2-bromoethyl)morpholine (225 mg, 1.16 mmol).

Step B. Example 56

The title compound (7.1 mg, 19%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 6-bromo-1-(2-morpholinoethyl)-1H-indazole-4-carboxylate (30 mg, 0.081 mmol), Pd$_2$(dba)$_3$ (4 mg, 0.0044 mmol), Xantphos (6 mg, 0.010 mmol), and Cs$_2$CO$_3$ (60 mg, 0.19 mmol) followed by saponification using General Procedure D. LCMS: R$_T$=1.783 min, MS (ES) 811.9 (M+H).

Example 57

(R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-2-(2-morpholinoethyl)-2H-indazole-4-carboxylic acid Step A. Preparation of methyl 6-bromo-2-(2-morpholinoethyl)-2H-indazole-4-carboxylate The title compound (42 mg, 15%) was prepared following General Procedure G using methyl 6-bromo-1H-indazole-4-carboxylate (200 mg, 0.784 mmol), NaH (36 mg, 1.5 mmol), and 4-(2-bromoethyl)morpholine (225 mg, 1.16 mmol).

Step B. Example 57

The title compound (5.4 mg, 14%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 6-bromo-2-

(2-morpholinoethyl)-2H-indazole-4-carboxylate (30 mg, 0.081 mmol), Pd$_2$(dba)$_3$ (4 mg, 0.0044 mmol), Xantphos (6 mg, 0.010 mmol), and Cs$_2$CO$_3$ (60 mg, 0.19 mmol) followed by saponification using General Procedure D. LCMS: R$_T$=1.726 min, MS (ES) 812.3 (M+H).

Example 58

6-(8-Chloro-11-(3-(4-chloro-3,5-dimethylphenoxy) propyl)-7-(3,5-dimethyl-1H-pyrazol-4-yl)-1-oxo-4,5-dihydro-1H-[1,4]diazepino[1,2-a]indol-2(3H)-yl)-1-methyl-1H-indole-4-carboxylic acid Step A. Preparation of 3,5-dimethyl-4-(4,4,5,5-tetramethyl-1,3,2-dioxaborolan-2-yl)-1-((2-(trimethylsilyl)ethoxy)methyl)-1H-pyrazole To a solution of 3,5-dimethyl-4-(4,4,5,5-tetramethyl-1,3,2-dioxaborolan-2-yl)-1H-pyrazole (6.456 g, 28.67 mmol) in DMF (57 ml) was added NaH (1.72 g, 43.0 mmol) and stirred for 15 min. (2-(Chloromethoxy)ethyl)trimethylsilane (6.59 ml, 37.28 mmol) was added to the reaction mixture and stirred at RT for additional 2 h. The reaction was diluted with DCM (50 mL) then quenched by H$_2$O (50 mL). The layers were separated and aqueous phase was extracted with DCM (2×50 mL). The combined organic layer was dried over MgSO$_4$ and concentrated in vacuo. The residue was purified by flash chromatography (Combi-flash Rf, DCM/MeOH=0-10% gradient) to afford the title product (5.23 g, 52%). LCMS: R$_T$=1.318 min, MS (ES) 353.2 (M+H).

Step B. Preparation of ethyl 6-chloro-3-(3-(4-chloro-3,5-dimethylphenoxy)propyl)-7-(3,5-dimethyl-1-((2-(trimethylsilyl)ethoxy)methyl)-1H-pyrazol-4-yl)-1H-indole-2-carboxylate A solution of ethyl 7-bromo-6-chloro-3-(3-(4-chloro-3,5-dimethylphenoxy)propyl)-1H-indole-2-carboxylate (1.76 g, 3.55 mmol), 3,5-dimethyl-4-(4,4,5,5-tetramethyl-1,3,2-dioxaborolan-2-yl)-1-((2-(trimethylsilyl)ethoxy)methyl)-1H-pyrazole (1.50 g, 4.26 mmol), Pd(PPh$_3$)$_4$ (0.250 g, 0.178 mmol) and K$_2$CO$_3$ (1.47 g, 10.65 mmol) in 1,4-dioxane (12 mL) and water (4 mL) was irradiated at 140° C. for 45 min under microwave. The reaction mixture was concentrated in vacuo and purified by flash chromatography (Combi-flash Rf, Hex/EtOAc=0-70% gradient) to afford the title as a white solid (1.60 g, 70%). LCMS: R$_T$=1.30 min, MS (ES) 644.2 (M+H).

Step C. Preparation of ethyl 1-(3-((tert-butoxycarbonyl)amino)propyl)-6-chloro-3-(3-(4-chloro-3,5-dimethylphenoxy)propyl)-7-(3,5-dimethyl-1-((2-(trimethylsilyl)ethoxy)methyl)-1H-pyrazol-4-yl)-1H-indole-2-carboxylate To a solution of ethyl 6-chloro-3-(3-(4-chloro-3,5-dimethylphenoxy)propyl)-7-(3,5-dimethyl-1-((2-(trimethylsilyl)ethoxy)methyl)-1H-pyrazol-4-yl)-1H-indole-2-carboxylate (150 mg, 0.233 mmol) and tert-butyl 1,2,3-oxathiazinane-3-carboxylate 2,2-dioxide (66.2 mg, 0.279 mmol) in DMF (2 ml) was added NaH (12 mg, 0.30 mmol), and the resulting mixture was stirred at rt for 2 h. Satureated aq. NH$_4$Cl (20 mL) was added to quench the reaction. The mixture was extracted with DCM (20 mL×3). The combined organics were concentrated, and the residue was purified by flash chromatography (Combi-flash Rf, Hex/EtOAc=0-30% gradient) to give the title product. LCMS: R$_T$=2.232 min, MS (ES) 801.4 (M+H).

Step D. Preparation of ethyl 1-(3-aminopropyl)-6-chloro-3-(3-(4-chloro-3,5-dimethylphenoxy)propyl)-7-(3,5-dimethyl-1-((2-(trimethylsilyl)ethoxy) methyl)-1H-pyrazol-4-yl)-1H-indole-2-carboxylate To a stirred solution of ethyl 1-(3-((tert-butoxycarbonyl) amino)propyl)-6-chloro-3-(3-(4-chloro-3,5-dimethylphenoxy)propyl)-7-(3,5-dimethyl-1-((2-(trimethylsilyl)ethoxy) methyl)-1H-pyrazol-4-yl)-1H-indole-2-carboxylate (115 mg, 0.143 mmol) in DCM (3 mL) was added TFA (0.055 mL, 0.717 mmol), and the resulting solution was stirred at 40° C. overnight. The reaction was quenched with saturated aq. NaHCO$_3$ (5 mL), the mixture was extracted with DCM (10 mL×3). The combined organic solution was dried and concentrated to give the crude title compound, which was used for the next step without further purification. LCMS: R$_T$=1.288 min, MS (ES) 701.4 (M+H).

Step E. Preparation of 8-chloro-11-(3-(4-chloro-3,5-dimethylphenoxy)propyl)-7-(3,5-dimethyl-1-((2-(trimethylsilyl)ethoxy)methyl)-1H-pyrazol-4-yl)-2,3,4,5-tetrahydro-1H-[1,4]diazepino[1,2-a]indol-1-one To a solution of ethyl 1-(3-aminopropyl)-6-chloro-3-(3-(4-chloro-3,5-dimethylphenoxy)propyl)-7-(3,5-dimethyl-1-((2-(trimethylsilyl)ethoxy)methyl)-1H-pyrazol-4-yl)-1H-indole-2-carboxylate (100 mg, 0.142 mmol) in MeOH (2 mL) was added K$_2$CO$_3$ (98 mg, 0.712 mmol), and the mixture was stirred for 2 h at 50° C. then filtered. The filtrate was concentrated and purified by flash chromatography (Combi-flash Rf, MeOH/DCM=0-10% gradient) to give the title compound (74 mg, 79% two steps). LCMS: R$_T$=1.617 min, MS (ES) 655.3 (M+H).

Step F. Preparation of methyl 6-(8-chloro-11-(3-(4-chloro-3,5-dimethylphenoxy)propyl)-7-(3,5-dimethyl-1-((2-(trimethylsilyl)ethoxy)methyl)-1H-pyrazol-4-yl)-1-oxo-4,5-dihydro-1H-[1,4]diazepino[1,2-a]indol-2(3H)-yl)-1-methyl-1H-indole-4-carboxylate The title compound (38 mg, 34%) was prepared following General coupling procedure A using 8-chloro-11-(3-(4-chloro-3,5-dimethylphenoxy)propyl)-7-(3,5-dimethyl-1-((2-(trimethylsilyl)ethoxy)methyl)-1H-pyrazol-4-yl)-2,3,4,5-tetrahydro-1H-[1,4]diazepino[1,2-a]indol-1-one (74 mg, 0.113 mmol), methyl 6-bromo-1-methyl-1H-indole-4-carboxylate (36.3 mg, 0.135 mmol), Pd$_2$(dba)$_3$ (2 mg, 0.0023 mmol), Xantphos (3.9 mg, 0.0068 mmol), and Cs$_2$CO$_3$ (74 mg, 0.23 mmol). LCMS: R$_T$=1.807 min, MS (ES) 842.4 (M+H).

Step G. Example 58

A mixture of methyl 6-(8-chloro-11-(3-(4-chloro-3,5-dimethylphenoxy)propyl)-7-(3,5-dimethyl-1-((2-(trimethylsilyl)ethoxy)methyl)-1H-pyrazol-4-yl)-1-oxo-4,5-dihydro-1H-[1,4]diazepino[1,2-a]indol-2(3H)-yl)-1-methyl-1H-indole-4-carboxylate (32 mg, 0.038 mmol) and TBAF (380 μl, 0.380 mmol) was heated to 100° C. under microwave irradiation in Biotage Initiator for 30 min. The reaction mixture was concentrated, and the residue was purified by reverse phase HPLC (Phenomenex Gemini C18, H$_2$O/

CH₃CN gradient to 40-85% MeCN 0.1% TFA) to give the title compound (16 mg, 60%). LCMS: $R_T$=1.852 min, MS (ES) 698.2 (M+H).

Example 59

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indazole-3-carboxylic acid The title compound (6.2 mg, 18%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (25 mg, 0.046 mmol), methyl 7-bromo-1-methyl-1H-indazole-3-carboxylate (20 mg, 0.074 mmol), Pd₂(dba)₃ (4 mg, 0.0044 mmol), Xantphos (6 mg, 0.010 mmol), and Cs₂CO₃ (60 mg, 0.19 mmol) followed by saponification using General Procedure D. LCMS: $R_T$=1.984, 2.014 min, MS (ES) 713.2 (M+H); ¹H NMR (400 MHz, Chloroform-d) δ 8.22-8.11 (m, 1H), 7.67-7.59 (m, 1H), 7.34-7.23 (m, 2H), 7.19-7.07 (m, 1H), 6.53 (s, 1.3H), 6.50 (s, 0.7H), 4.50-4.32 (m, 1H), 4.28-4.17 (m, 1H), 4.14 (d, J=3.0 Hz, 1H), 4.06 (s, 1H), 4.01 (s, 1H), 3.96-3.82 (m, 5H), 3.58-3.20 (m, 3H), 2.24 (s, 6H), 2.19-2.15 (m, 3H), 2.14-2.07 (m, 2H), 2.03 (s, 0.7H), 2.02 (s, 0.3H), 1.98 (s, 2H), 1.25 (d, J=6.4 Hz, 0.6H), 1.19 (d, J=6.4 Hz, 1.4H), 1.14 (d, J=6.4 Hz, 0.3H), 1.08 (d, J=6.4 Hz 0.7H).

Example 60

Methyl 8-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-2,3-dihydrobenzo[b][1,4]dioxine-6-carboxylate The title compound was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one, methyl 8-bromo-2,3-dihydrobenzo[b][1,4]dioxine-6-carboxylate. MS (ES) 731.3 (M+H).

Example 61

5-[8-chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-4-methyl-2,3-dihydro-1,4-benzoxazine-7-carboxylic acid Step A. Preparation of methyl 5-bromo-3,4-dihydro-2H-benzo[b][1,4]oxazine-7-carboxylate To a solution of methyl 4-amino-3-bromo-5-hydroxybenzoate (250 mg, 1.02 mmol) in DMF (5 mL) was added dibromoethane (350 mg, 1.9 mmol) and K₂CO₃ (300 mg, 2.2 mmol). The reaction was heated to 80° C. for 20 h then cool to RT. The reaction was diluted with DCM/H₂O (40 mL, 1:1), the organic layer separated, and the aqueous layer extracted with DCM (2×20 mL). The combined organic layers were dried over MgSO₄, filtered, and concentrated in vacuo. The crude reaction mixture was purified by flash chromatography (Combi-flash Rf. Hex/EtOAc=0-100% gradient) to afford the title compound (90 mg, 32%).

Step B. Preparation of methyl 5-bromo-4-methyl-3,4-dihydro-2H-benzo[b][1,4]oxazine-7-carboxylate The title compound (35 mg, 74%) was prepared following General Procedure G using methyl 5-bromo-3,4-dihydro-2H-benzo[b][1,4]oxazine-7-carboxylate (45 mg, 0.17 mmol), sodium hydride (9 mg, 0.38 mmol), and methyl iodide (40 mg, 0.28 mmol).

Step C Example 69

The title compound (2.3 mg, 7%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol), methyl 5-bromo-4-methyl-3,4-dihydro-2H-benzo[b][1,4]oxazine-7-carboxylate (25 mg, 0.087 mmol), Pd₂(dba)₃ (4 mg, 0.0044 mmol), Xantphos (6 mg, 0.010 mmol), and Cs₂CO₃ (60 mg, 0.19 mmol) followed by saponification using General Procedure D. LCMS: $R_T$=1.953 min, MS (ES) 729.9 (M+H).

Example 62

3-[8-chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-4-(2-hydroxyethoxy)-5-methoxy-benzoic acid Step A. Preparation of methyl 3-bromo-4-(2-((tert-butyldimethylsilyl)oxy)ethoxy)-5-methoxybenzoate The title compound (43 mg, 27%) was prepared following the same procedure as described in Example 66 Step A using methyl 3-bromo-4-hydroxy-5-methoxybenzoate (100 mg, 0.381 mmol), Cs₂CO₃ (200 mg, 0.615 mmol) and (2-bromoethoxy)(tert-butyl)dimethylsilane (130 mg, 0.543 mmol).

Step B. Example 62

Crude Methyl 4-(2-((tert-butyldimethylsilyl)oxy)ethyl)-3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-methoxybenzoate was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (20 mg, 0.037 mmol), methyl 3-bromo-4-(2-((tert-butyldimethylsilyl)oxy)ethoxy)-5-methoxybenzoate (30 mg, 0.068 mmol), Pd₂(dba)₃ (4 mg, 0.0043 mmol), Xantphos (8 mg, 0.013 mmol), and Cs₂CO₃ (50 m, 0.153 mmol). To a solution of crude product in THF (3 mL) was added TBAF (1.0 M, 0.05 mL, 0.05 mmol). The reaction was stirred at 40° C. for 1 h then diluted into DCM/H₂O (10 mL, 1:1), extracted with DCM (2×5 mL) and concentrated in vacuo. The residue was then subjected to General Procedure D to afford the title compound (2 mg, 7%). LCMS: $R_T$=1.858 min, MS (ES) 749.2 (M+H).

Example 63

(R)-5-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-naphthoic acid The title compound (31 mg, 87%) was prepared following General coupling procedure A using (R)-7-chloro-10-(3-(4- chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 5-bromo-1-naphthoate (16 mg, 0.06 mmol). $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D. LCMS: $R_T$=2.083 min, MS (ES) 709.2 (M+H).

Example 64

2-(1,2-benzoxazol-6-yl)-8-chloro-11-[3-(4-chloro-3,5-dimethyl-phenoxy)propyl]-7-(1,3,5-trimethylpyrazol-4-yl)-4,5-dihydro-3H-[1,4]diazepino[1,2-a]indol-1-one The title compound (13 mg, 53%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (20 mg, 0.037 mmol), methyl 6-bromobenzo[d]isoxazole-3-carboxylate (20 mg, 0.078 mmol), $Pd_2(dba)_3$ (4 mg, 0.0043 mmol), Xantphos (8 mg, 0.013 mmol), and $Cs_2CO_3$ (50 m, 0.153 mmol). LCMS: $R_T$=1.995 min, MS (ES) 656.2 (M+H).

Example 65

3-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-4-[2-(2-fluorophenoxy)ethoxy]-5-methoxy-benzoic acid Step A. Preparation of methyl 3-bromo-4-(2-(2-fluorophenoxy)ethoxy)-5-methoxybenzoate The title compound (101 mg, 66%) was prepared following the procedure described in Example 66 step 1 using methyl 3-bromo-4-hydroxy-5-methoxybenzoate (100 mg, 0.381 mmol), 1-(2-bromoethoxy)-2-fluorobenzene (120 mg, 0.547 mmol), and $Cs_2CO_3$ (200 mg, 0.615 mmol).

Step B. Example 65

The title compound (4 mg, 13%) was obtained following the procedures described in General Procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (20 mg, 0.037 mmol), methyl 3-bromo-4-(2-(2-fluorophenoxy)ethoxy)-5-methoxybenzoate (30 mg, 0.074 mmol), $Pd_2(dba)_3$ (4 mg, 0.0043 mmol), Xantphos (8 mg, 0.013 mmol), and $Cs_2CO_3$ (50 m, 0.153 mmol) followed by General Procedure D. LCMS: $R_T$=2.051 min, MS (ES) 842.8 (M+H).

Example 66

3-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-5-methoxy-4-(2-phenylethoxy)benzoic acid Step A. Preparation of methyl 3-bromo-5-methoxy-4-phenethoxybenzoate To a solution of methyl 3-bromo-4-hydroxy-5-methoxybenzoate (100 mg, 0.381 mmol) in DMF (3 mL) was added $Cs_2CO_3$ (200 mg, 0.615 mmol) followed by (2-bromoethyl)benzene (100 mg, 0.541 mmol). The reaction was stirred at 50° C. until complete as determined by LCMS. The reaction was then cooled to RT, diluted into $DCM/H_2O$ (20 mL, 1:1). The layers were separated and the aqueous layer was extracted with DCM (2×10 mL) and the combined organic extracts were dried over $MgSO_4$, filtered, and concentrated in vacuo. The crude reaction mixture was purified by flash chromatography (Combi-flash Rf, Hex/EtOAc=0-100% gradient) to afford the title compound (80 mg, 57%).

Step B. Example 66

The title compound (8 mg, 27%) was obtained following the procedures described in General Procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (20 mg, 0.037 mmol), methyl 3-bromo-5-methoxy-4-phenethoxybenzoate (25 mg, 0.068 mmol), $Pd_2(dba)_3$ (4 mg, 0.0043 mmol), Xantphos (8 mg, 0.013 mmol), and $Cs_2CO_3$ (50 m, 0.153 mmol) followed by saponification using General Procedure D. LCMS: $R_T$=2.230 min, MS (ES) 809.2 (M+H).

Example 67

3-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-4-(3-hydroxypropoxy)-5-methoxy-benzoic acid Step A. Preparation of methyl 3-bromo-4-(3-((tert-butyldimethylsilyl)oxy)propoxy)-5-methoxybenzoate The title compound (107 mg, 64%) was prepared following the procedure described in Example 66 Step A substituting (2-bromoethyl)benzene with (3-bromopropoxy)(tert-butyl)dimethylsilane (130 mg, 0.514 mmol).

Step B. Example 67

The title compound (4 mg, 14%) was prepared following the same procedure as described in Example 62 Step B substituting methyl 3-bromo-4-(2-((tert-butyldimethylsilyl)oxy)ethoxy)-5-methoxybenzoate with methyl 3-bromo-4-(3-((tert-butyldimethylsilyl)oxy)propoxy)-5-methoxybenzoate (30 mg, 0.069 mmol). LCMS: $R_T$=1.847 min, MS (ES) 763.3 (M+H).

Example 68

3-(8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-6-carboxylic acid The title compound (32 mg, 90%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (27 mg, 0.05 mmol), methyl 3-bromo-1-methyl-1H-indole-6-carboxylate (16 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D. LCMS: $R_T$=1.992 min, MS (ES) 712.3 (M+H).

Example 69

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylic acid The title compound (22 mg, 31%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (54 mg, 0.1 mmol), methyl 7-bromo-1-methyl-1H-indole-3-carboxylate (32 mg, 0.12 mmol), Pd$_2$(dba)$_3$ (2 mg, 0.002 mmol), Xantphos (3.5 mg, 0.006 mmol), and Cs$_2$CO$_3$ (49 mg, 0.15 mmol) followed by saponification using General Procedure D. LCMS: R$_T$=2.043 min, MS (ES) 712.2 (M+H).

Example 70

(R)-6-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-4-carboxylic acid

Step A. Preparation of (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one The title compound was prepared following the procedure described Example 58 Step C to E using ethyl 6-chloro-3-(3-(4-chloro-3,5-dimethylphenoxy)propyl)-7-(3,5-dimethyl-1-((2-(trimethylsilyl)ethoxy)methyl)-1H-pyrazol-4-yl)-1H-indole-2-carboxylate, and tert-butyl (S)-5-methyl-1,2,3-oxathiazolidine-3-carboxylate 2,2-dioxide. MS (ES) 656.2 (M+H).

Step B. Preparation of methyl (R)-6-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1-methyl-1H-indole-4-carboxylate The title compound (30 mg, 47%) was prepared following General coupling procedure A using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one (50 mg, 0.076 mmol), methyl 6-bromo-1-methyl-1H-indole-4-carboxylate (25 mg, 0.092 mmol), Pd$_2$(dba)$_3$ (1.4 mg, 0.0015 mmol), Xantphos (2.7 mg, 0.0046 mmol), and Cs$_2$CO$_3$ (49 mg, 0.15 mmol). LCMS: R$_T$=2.011 min, MS (ES) 842.3 (M+H).

Step C. Example 70

The title compound (16 mg, 66%) was prepared following the procedure described Example 58 Step G using methyl (R)-6-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1-methyl-1H-indole-4-carboxylate (30 mg, 0.036 mmol) and TBAF (356 µl, 0.356 mmol). LCMS: R$_T$=1.893 min, MS (ES) 698.2 (M+H).

Example 71

(R)-4-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-6-carboxylic acid The title compound (29 mg, 59% two steps) was prepared according to procedures described in Example 70 B to C using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one (50 mg, 0.076 mmol) and methyl 4-bromo-1-methyl-1H-indole-6-carboxylate (25 mg, 0.092 mmol). LCMS: R$_T$=1.895 min, MS (ES) 698.2 (M+H).

Example 72

4-(8-chloro-11-(3-(4-chloro-3,5-dimethylphenoxy)propyl)-7-(3,5-dimethyl-1H-pyrazol-4-yl)-1-oxo-4,5-dihydro-1H-[1,4]diazepino[1,2-a]indol-2(3H)-yl)-1-methyl-1H-indole-6-carboxylic acid The title compound was prepared according to procedures described in Example 58 step F to G using 8-chloro-11-(3-(4-chloro-3,5-dimethylphenoxy)propyl)-7-(3,5-dimethyl-1-((2-(trimethylsilyl)ethoxy)methyl)-1H-pyrazol-4-yl)-2,3,4,5-tetrahydro-1H-[1,4]diazepino[1,2-a]indol-1-one and methyl 4-bromo-1-methyl-1H-indole-6-carboxylate. LCMS: R$_T$=1.843 min, MS (ES) 698.2 (M+H).

Example 73

5-(8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-3-hydroxy-1,4-dihydropyrazine-2-carboxylic acid The title compound (28 mg, 82%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (27 mg, 0.05 mmol), methyl 5-chloropyrazine-2-carboxylate (10 mg, 0.06 mmol). Pd$_2$(dba)$_3$ (1 mg, 0.001 mmol), Xantphos (2 mg, 0.003 mmol), and Cs$_2$CO$_3$ (25 mg, 0.075 mmol) followed by saponification using General Procedure D. LCMS: R$_T$=1.841 min, MS (ES) 679.2 (M+H).

Example 74

3-(8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-7-carboxylic acid

Step A. Preparation of methyl 3-bromo-1-methyl-1H-indole-7-carboxylate

The title compound (73 mg, 96%) was prepared following General Procedure F using methyl-indole-7-carboxylate (50 mg, 0.28 mmol), NBS (51 mg, 0.28 mmol), NaH (14 mg, 0.34 mmol) and MeI (21 µL, 0.34 mmol). LCMS: $R_T$=1.646 min, MS (ES) 268.1 (M+H).

Step B. Example 74

The title compound (23 mg, 65%) was prepared following General coupling procedure B using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (27 mg, 0.05 mmol), methyl 3-bromo-1-methyl-1H-indole-7-carboxylate (16 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol) followed by saponification using General Procedure D. LCMS: $R_T$=2.038 min, MS (ES) 712.2 (M+H).

Example 75

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-7-carboxylic acid The title compound (31 mg, 87%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-methyl-1H-indole-7-carboxylate (16 mg, 0.06 mmol). CuI (5 mg, 0.025 mmol), (trans)-1,2-N,N'-dimethylaminocyclohexane (8 µL, 0.05 mmol), and $K_2CO_3$ (25 mg, 0.075 mmol) followed by saponification using General Procedure D. LCMS: $R_T$=2.092 min, MS (ES) 712.2 (M+H); $^1$H NMR (400 MHz, DMSO-$d_6$) δ 7.76 (d, J=8.6 Hz, 1H), 7.62-7.53 (m, 2H), 7.49 (d, J=2.8 Hz, 1H), 7.30 (d, J=8.6 Hz, 1H), 7.09 (td, J=7.7, 2.2 Hz, 1H), 6.72 (s, 2H), 4.48 (dd, J=13.0, 3.8 Hz, 1H), 4.23-4.08 (m, 1H), 3.98 (dt, J=6.4, 3.4 Hz, 2H), 3.84 (s, 3H), 3.78 (s, 1.5H), 3.77 (s, 1.5H), 3.40-3.15 (m, 3H), 2.25 (s, 6H), 2.12 (s, 1.5H), 2.08 (d, J=12.0 Hz, 2H), 2.04 (s, 1.5H), 1.98 (s, 1.5H), 1.89 (s, 1.5H), 1.08 (d, J=6.4 Hz, 3H).

Example 76

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid The title compound (28 mg, 79%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-methyl-1H-indole-5-carboxylate (16 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol) followed by saponification using General Procedure D. LCMS: $R_T$=2.003 min, MS (ES) 712.3 (M+H); $^1$H NMR (400 MHz, DMSO-$d_6$) δ 8.11 (dd, J=3.5, 1.5 Hz, 1H), 7.87-7.71 (m, 2H), 7.57 (dd, J=9.4, 1.9 Hz, 2H), 7.30 (d, J=8.6 Hz, 1H), 6.73 (s, 2H), 4.48 (dd, J=13.0, 3.8 Hz, 1H) 4.24-4.09 (m, 1H) 3.99 (tt, J=6.4, 3.2 Hz, 2H), 3.85 (s, 3H), 3.79 (s, 1.5H), 3.77 (s, 1.5H), 3.72-3.59 (m, 1H), 3.23 (dt, J=13.4, 7.4 Hz, 2H), 2.24 (s, 6H), 2.12 (s, 1.5H), 2.07 (dd, J=12.7, 6.0 Hz, 2H), 2.03 (s, 1.5H), 1.98 (s, 1.5H), 1.89 (s, 1.5H), 1.19-0.93 (m, 3H).

Example 77

(P, R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (separated atropisomer A)

Example 91 was separated using reverse phase HPLC (Phenomenex Gemini C18. $H_2O/CH_3CN$ gradient to 35-95% MeCN 0.1% TFA, 10 mins gradient) to give the title compound as the first eluting atropisomer (13 mg, 37%). LCMS: $R_T$=1.970 min, MS (ES) 712.0 (M+H).

Example 78

(M, R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (separated atropisomer B)

Example 91 was separated using reverse phase HPLC (Phenomenex Gemini C18, $H_2O/CH_3CN$ gradient to 35-95% MeCN 0.1% TFA, 10 mins gradient) to give the title compound as a second eluting atropisomer (11 mg, 31%). LCMS: $R_T$=1.989 min, MS (ES) 712.0 (M+H).

Example 79

(R)-6-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylic acid The title compound (32 mg, 90%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 6-bromo-1-methyl-1H-indole-3-carboxylate (16 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D. LCMS: $R_T$=2.041 min, MS (ES) 712.3 (M+H); $^1$H NMR (400 MHz, DMSO-$d_6$) δ 8.08 (d, J=1.3 Hz, 1H), 8.00 (dd, J=8.5, 2.7 Hz, 1H), 7.75 (d, J=8.6 Hz, 1H), 7.56 (t, J=2.5 Hz, 1H), 7.30 (d, J=8.6 Hz, 1H), 7.21 (dt, J=8.5, 2.2 Hz, 1H), 6.74 (s, 2H), 4.49 (dd, J=13.0, 3.8 Hz, 1H), 4.21-4.09 (m, 1H), 3.99 (t, J=6.6 Hz, 2H), 3.84 (s, 3H), 3.79 (s, 1.5H), 3.78 (s, 1.5H), 3.40-3.13 (m, 3H), 2.26 (s, 6H), 2.12 (s, 1.5H), 2.07 (d, J=6.9 Hz, 2H), 2.03 (s, 1.5H), 1.98 (s, 1.5H), 1.89 (s, 1.5H), 1.05 (d, J=6.4 Hz, 3H).

Example 80

3-(8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-5-carboxylic acid The title compound (28 mg, 79%) was prepared following General coupling procedure B using 8-chloro-11-(3-(4- chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (27 mg, 0.05 mmol), methyl 3-bromo-1-methyl-1H-indole-5-carboxylate (16 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol) followed by saponification using General Procedure D. LCMS: $R_T$=1.942 min, MS (ES) 712.3 (M+H).

Example 81

6-(8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-3-carboxylic acid The title compound (20 mg, 70%) was prepared following General coupling procedure A using (8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (27 mg, 0.05 mmol), methyl 6-bromo-1-methyl-1H-indole-3-carboxylate (16 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D. LCMS: $R_T$=1.968 min, MS (ES) 712.3 (M+H).

Example 82

6-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-1-(2-methoxyethyl)indazole-4-carboxylic acid Step A. Preparation of methyl 6-bromo-1-(2-methoxyethyl)-1H-indazole-4-carboxylate To a solution of methyl 6-bromo-1H-indazole-4-carboxylate (200 mg, 0.79 mmol) in DMF (5 mL) was added NaH (40 mg, 1.63 mmol), and the reaction was stirred for 30 min at RT. 1-Bromo-2-methoxyethane (165 mg, 1.18 mmol) was added and the reaction was stirred overnight. The reaction was quenched with MeOH at −78° C., then diluted with $DCM/H_2O$ (60 mL, 1:1), the organic layer was separated, the aqueous layer was extracted with DCM (2×20 mL), the organic fractions combined, dried over $MgSO_4$, filtered, and concentrated in vacuo. The crude reaction mixture was purified by flash chromatography (Combi-flash Rf, Hex/EtOAc=0-100% gradient) to afford the title compound (39 mg, 16%).

Step B. Example 82

The title compound (4 mg, 11%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol), methyl 6-bromo-1-(2-methoxyethyl)-1H-indazole-4-carboxylate (20 mg, 0.064 mmol), $Pd_2(dba)_3$ (4 mg, 0.0043 mmol). Xantphos (6 mg, 0.010 mmol), and $Cs_2CO_3$ (50 mg, 0.153 mmol) followed by saponification using General Procedure D. LCMS: $R_T$=1.948 min, MS (ES) 757.3 (M+H).

Example 83

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-ethyl-1H-indole-7-carboxylic acid Step A. Preparation of methyl 3-bromo-1-ethyl-1H-indole-7-carboxylate The title compound (70 mg, 62%) was prepared following General Procedure F using methyl-indole-7-carboxylate (70 mg, 0.40 mmol), NBS (71 mg, 0.40 mmol), NaH (20 mg, 0.48 mmol) and ethyl iodide (38 µL, 0.48 mmol). LCMS: $R_T$=1.731 min, MS (ES) 282.1 (M+H).

Step B. Example 83

The title compound (34 mg, 96%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-ethyl-1H-indole-7-carboxylate (16 mg, 0.06 mmol). CuI (5 mg, 0.025 mmol). (trans)-1,2-N,N'-dimethylaminocyclohexane (8 µL, 0.05 mmol), and $K_2CO_3$ (25 mg, 0.075 mmol) followed by saponification using General Procedure D. LCMS: $R_T$=2.135 min, MS (ES) 726.3 (M+H); $^1$H NMR (400 MHz, DMSO-$d_6$) δ 7.76 (d, J=8.6 Hz, 1H), 7.65-7.44 (m, 3H), 7.30 (d, J=8.6 Hz, 1H), 7.15-7.03 (m, 1H), 6.72 (s, 2H), 4.48 (dd, J=13.0, 3.8 Hz, 1H), 4.43-4.26 (m, 2H), 4.24-4.09 (m, 2H), 3.99 (s, 3H), 3.78 (s, 1.5H), 3.77 (s, 1.5H), 3.68-3.57 (m, 2H), 3.41-3.14 (m, 2H), 2.25 (s, 6H), 2.12 (s, 1.5H), 2.11-2.04 (m, 2H), 2.04 (s, 1.5H), 1.98 (s, 1.5H), 1.89 (s, 1.5H), 1.26 (td, J=7.1, 1.4 Hz, 3H), 1.08 (d, J=6.4 Hz, 3H).

Example 84

(R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indazole-6-carboxylic acid The title compound (13 mg, 39%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 4-bromo-1-methyl-1H-indazole-6-carboxylate (20 mg, 0.074 mmol), $Pd_2(dba)_3$ (4 mg, 0.0043 mmol), Xantphos (8 mg, 0.014 mmol), and $Cs_2CO_3$ (50 mg, 0.153 mmol) followed by saponification using General Procedure D. LCMS: $R_T$=2.018 min, MS (ES) 713.2 (M+H).

Example 85

5-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-1-methyl-indazole-7-carboxylic acid The title compound (4 mg, 12%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol), methyl 5-bromo-1- methyl-1H-indazole-7-carboxylate (20 mg, 0.074 mmol), Pd$_2$(dba)$_3$ (4 mg, 0.0043 mmol), Xantphos (8 mg, 0.014 mmol), and Cs$_2$CO$_3$ (50 mg, 0.153 mmol) followed by saponification using General Procedure D. LCMS: R$_T$=1.934 min, MS (ES) 713.2 (M+H).

Example 86

8-Chloro-11-(3-(4-chloro-3,5-dimethylphenoxy) propyl)-7-(2,6-dimethylphenyl)-2,3,4,5-tetrahydro-1H-[1,4]diazepino[1,2-a]indol-1-one Step A. Preparation of ethyl 6-chloro-3-(3-(4-chloro-3,5-dimethylphenoxy)propyl)-7-(2,6-dimethylphenyl)-1H-indole-2-carboxylate A mixture of ethyl 7-bromo-6-chloro-3-(3-(4-chloro-3,5-dimethylphenoxy)propyl)-1H-indole-2-carboxylate (25 mg, 0.050 mmoL), (2,6-dimethylphenyl)boronic acid (10 mg, 0.068 mmol), Pd$_2$(dba)$_3$ (4 mg, 0.0043 mmol), dicyclohexyl (2-(phenanthren-9-yl)phenyl)phosphane (6 mg, 0.014 mmol), and potassium phosphate (30 mg, 0.142 mmol) was purged with Ar for 5 min then toluene (1 mL) was added. The reaction was heated to 110° C. for 16 h then cooled to RT. The reaction was diluted into DCM/H$_2$O (10 mL, 1:1), the layers were separated, and the aqueous layer was extracted with DCM (2×10 mL). The combined organic extracts were dried by passage through a phase separator, concentrated in vacuo, and purified by flash chromatography (Combi-flash Rf, Hex/EtOAc=0-100% gradient) to afford the title compound (22 mg, 88%).

Step B. Preparation of ethyl 1-(3-((tert-butoxycarbonyl)amino)propyl)-6-chloro-3-(3-(4-chloro-3,5-dimethylphenoxy)propyl)-7-(2,6-dimethylphenyl)-1H-indole-2-carboxylate To a solution of ethyl 6-chloro-3-(3-(4-chloro-3,5-dimethylphenoxy)propyl)-7-(2,6-dimethylphenyl)-1H-indole-2-carboxylate (96 mg, 0.18 mmol) and tert-butyl 1,2,3-oxathiazinane-3-carboxylate 2,2-dioxide (50 mg, 0.21 mmol) in DMF (4 mL) was added NaH (6 mg, 0.25 mmol), and the reaction was stirred for 16 h at RT. The work up described in general coupling procedure A was followed and purified by flash chromatography (Combi-flash Rf, Hex/EtOAc=0-100% gradient) to afford the title compound (72 mg, 57%).

Step C. Example 86

To a solution of ethyl 1-(3-((tert-butoxycarbonyl)amino)propyl)-6-chloro-3-(3-(4-chloro-3,5-dimethylphenoxy)propyl)-7-(2,6-dimethylphenyl)-1H-indole-2-carboxylate (72 mg, 0.11 mmol) in dioxane (3 mL) was added HCl (4.0 M in dioxanes, 0.5 mL, 2.0 mmol). The reaction was stirred for 16 h at RT then concentrated in vacuo. The residue was dissolved in MeOH (5 mL), and K$_2$CO$_3$ (50 mg, 0.30 mmol) was added. The reaction was allowed to stir 20 h at 50° C. The work up described in general coupling procedure A was followed and purified by flash chromatography (Combi-flash Rf, Hex/EtOAc=0-100% gradient) to afford the title compound (33 mg, 59%). LCMS: R$_T$=2.317 min, MS (ES) 535.2 (M+H).

Example 87

(R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-ethyl-1H-indazole-4-carboxylic acid The title compound (10 mg, 30%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 6-bromo-1-ethyl-1H-indazole-4-carboxylate (20 mg, 0.070 mmol), Pd$_2$(dba)$_3$ (4 mg, 0.0043 mmol), Xantphos (6 mg, 0.010 mmol), and cesium carbonate (50 mg, 0.153 mmol) followed by saponification using General Procedure D. LCMS: R$_T$=2.036 min, MS (ES) 727.2 (M+H).

Example 88

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-methyl-1H-indole-6-carboxylic acid The title compound (30 mg, 84%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-methyl-1H-indole-6-carboxylate (16 mg, 0.06 mmol), CuI (5 mg, 0.025 mmol), (trans)-1,2-N,N'-dimethylaminocyclohexane (8 μL, 0.05 mmol), and K$_2$CO$_3$ (25 mg, 0.075 mmol) followed by saponification using General Procedure D. LCMS: R$_T$=2.031 min, MS (ES) 712.3 (M+H); $^1$H NMR (400 MHz, DMSO-4) δ 8.12 (s, 1H), 7.76 (d, J=8.6 Hz, 1H), 7.70-7.60 (m, 2H), 7.48 (dd, J=8.4, 4.4 Hz, 1H), 7.30 (d, J=8.6 Hz, 1H), 6.72 (s, 2H), 4.48 (dd, J=12.9, 3.8 Hz, 1H), 4.25-4.07 (m, 1H), 3.99 (td, J=6.4, 2.0 Hz, 2H), 3.88 (s, 3H), 3.78 (s, 1.5H), 3.77 (s, 1.5H), 3.39-3.15 (m, 3H), 2.25 (s, 6H), 2.12 (s, 1.5H), 2.11-2.05 (m, 2H), 2.03 (s, 1.5H), 1.98 (s, 1.5H), 1.89 (s, 1.5H), 1.08 (d, J=6.4 Hz, 3H).

Example 89

3-(8-Chloro-11-(3-(4-chloro-3,5-dimethylphenoxy) propyl)-1-oxo-7-(1,3,5-trimethyl-1H-pyrazol-4-yl)-4,5-dihydro-1H-[1,4]diazepino[1,2-a]indol-2(3H)-yl)-1-(2-morpholinoethyl)-1H-indole-6-carboxylic acid Step A. Preparation of methyl 3-bromo-1-(2-morpholinoethyl)-1H-indole-6-carboxylate The title compound (36 mg, 49%) was prepared following General Procedure G using methyl 3-bromo-1H-indole-6-carboxylate (51 mg, 0.20 mmol), sodium hydride (10 mg, 0.24 mmol), 4-(2-chloroethyl)morpholine (36 mg, 0.24 mmol) and KI (40 mg, 0.24 mmol). LCMS: R$_T$=1.515 min, MS (ES) 367.1 (M+H).

Step B. Example 89

The title compound (8 mg, 20%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-(2-morpholinoethyl)-1H-indole-6-carboxylate (19 mg, 0.06 mmol), CuI (5 mg, 0.025 mmol), (trans)-1,2-N,N'-dimethylaminocyclohexane (8 μL, 0.05 mmol), and K$_2$CO$_3$ (25 mg, 0.075 mmol) followed by saponification using General Procedure D. LCMS: R$_T$=1.719 and 1.745 min, MS (ES) 810.9 (M+H).

Example 90

(R)-5-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-ethyl-3-oxo-3,4-dihydro-2H-benzo[b][1,4]oxazine-7-carboxylic acid

Step A. Preparation of methyl 5-bromo-4-ethyl-3-oxo-3,4-dihydro-2H-benzo[b][1,4]oxazine-7-carboxylate To a solution of methyl 4-amino-3-bromo-5-hydroxybenzoate (250 mg, 1.02 mmol) in THF (10 mL) was added $NaHCO_3$ (150 mg, 1.8 mmol) and chloroacetyl chloride (170 mg, 1.5 mmol) at 0° C. The reaction was stirred for 2 h and warm to RT. $K_2CO_3$ (150 mg, 1.1 mmol) was added, and the reaction was heated to 65° C. then cooled to RT. The mixture was diluted with $DCM/H_2O$ (40 mL, 1:1) and extracted with DCM (2×20 mL). The combined organic layers were dried over $MgSO_4$, filtered, and concentrated in vacuo. The crude reaction mixture was purified by flash chromatography (Combi-flash Rf, Hex/EtOAc=0-100% gradient) to afford methyl 5-bromo-3-oxo-3,4-dihydro-2H-benzo[b][1,4]oxazine-7-carboxylate (86 mg, 30%). The product (40 mg, 0.14 mmol) was dissolved in DMF (3 mL), NaH (7 mg, 0.30 mmol) was added. The reaction was stirred at RT for 30 min, and EtBr (30 mg, 0.28 mmol) was added. The reaction was stirred for 3 h at RT then diluted with $DCM/H_2O$ (20 mL, 1:1). The organic layer was separated, and the aqueous layer was extracted with DCM (2×10 mL). The combined organic extracts were dried by passage through a phase separator and concentrated in vacuo. The crude reaction mixture was purified by flash chromatography (Combi-flash Rf, Hex/EtOAc=0-100% gradient) to afford the title compound (28 mg, 65%).

Step B. Example 90

The title compound (1 mg, 4%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (20 mg, 0.037 mmol), methyl 5-bromo-4-ethyl-3-oxo-3,4-dihydro-2H-benzo[b][1,4]oxazine-7-carboxylate (20 mg, 0.063 mmol), $Pd_2(dba)_3$ (4 mg, 0.0043 mmol), Xantphos (6 mg, 0.010 mmol), and $Cs_2CO_3$ (35 mg, 0.107 mmol) followed by saponification using General Procedure D. LCMS: $R_T$=2.034 min, MS (ES) 757.8 (M+H).

Example 91

6-[8-Chloro-11-[3-(4-chloro-3,5-dimethyl-phenoxy)propyl]-7-(2,6-dimethylphenyl)-1-oxo-4,5-dihydro-3H-[1,4]diazepino[1,2-a]indol-2-yl]-1-methyl-indole-4-carboxylic acid The title compound (3 mg, 9%) was prepared following General coupling procedure A using 8-chloro-11-(3-(4-chloro-3,5-dimethylphenoxy)propyl)-7-(2,6-dimethylphenyl)-2,3,4,5-tetrahydro-1H-[1,4]diazepino[1,2-a]indol-1-one (25 mg, 0.037 mmol), methyl 6-bromo-1-methyl-1H-indole-4-carboxylate (20 mg, 0.063 mmol), $Pd_2(dba)_3$ (4 mg, 0.0043 mmol), Xantphos (6 mg, 0.010 mmol), and $Cs_2CO_3$ (35 mg, 0.107 mmol) followed by saponification using General Procedure D. LCMS: $R_T$=1.531 min, MS (ES) 708.3 (M+H).

Example 92

6-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-1-isopropyl-indazole-4-carboxylic acid

Step A. Preparation of methyl 6-bromo-1-isopropyl-1H-indazole-4-carboxylate

The title compound (43 mg, 18%) was prepared following the procedure described in Example 82 Step A substituting 1-bromo-2-methoxyethane with 2-bromopropane (190 mg, 1.54 mmol).

Step B. Example 92

The title compound (5 mg, 15%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol), methyl 6-bromo-1-isopropyl-1H-indazole-4-carboxylate (20 mg, 0.067 mmol). $Pd_2(dba)_3$ (4 mg, 0.0043 mmol), Xantphos (6 mg, 0.010 mmol), and $Cs_2CO_3$ (50 mg, 0.153 mmol) followed by saponification using General Procedure D. LCMS: $R_T$=2.048 min, MS (ES) 741.3 (M+H).

Example 93

(R)-6-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indazole-4-carboxylic acid The title compound (19 mg, 38% two steps) was prepared according to procedures described in Example 70 B to C using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one (50 mg, 0.076 mmol) and methyl 6-bromo-1-methyl-1H-indazole-4-carboxylate (23 mg, 0.084 mmol). LCMS: $R_T$=1.859 min, MS (ES) 699.2 (M+H).

Example 94

(R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-morpholinoethyl)-1H-indole-4-carboxylic acid

Step A. Preparation of methyl (R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-(trimethylsilyl)ethoxy)methyl)-1H-indole-4-carboxylate The title compound (138 mg, 88%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (100 mg, 0.184 mmol), methyl 6-bromo-1-((2-(trimethylsilyl)ethoxy)methyl)-1H-indole-4-carboxylate (78 mg, 0.20 mmol), $Pd_2(dba)_3$ (4 mg, 0.0043 mmol), Xantphos (6 mg, 0.010 mmol), and Cs$_2$CO$_3$ (121 mg, 0.37 mmol). MS (ES) 842.3 (M+H).

Step B. Preparation of methyl (R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-4-carboxylate A mixture of methyl (R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-(trimethylsilyl)ethoxy)methyl)-1H-indole-4-carboxylate (138 mg, 0.164 mmol). TBAF (0.819 mL, 0.819 mmol) in THF (1 mL) was heated at 100° C. under microwave irradiation in Biotage Initiator for 20 min. The reaction was quenched with H$_2$O (5 mL) then extracted with DCM (10 mL×2). The combined organic solution was concentrated and the residue was purified by flash chromatography (Combi-flash Rf, MeOH/DCM=0-5% gradient) to give the title compound (80 mg, 69%) as a white solid. LCMS: R$_T$=2.115 min, MS (ES) 712.2 (M+H).

Step C. Example 94

To a solution of methyl (R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-4-carboxylate (40 mg, 0.056 mmol) in DMF (0.5 mL) was added NaH (4.5 mg, 0.11 mmol) and stirred for 20 min. 4-(2-Bromoethyl)morpholine (22 mg, 0.11 mmol) was added, and the resulting mixture was heated to 50° C. for 2 days. The reaction was quenched by MeOH (0.5 mL) and acidified with TFA then concentrated in vacuo. The residue was purified by reverse phase HPLC (Phenomenex Gemini C18, H$_2$O/CH$_3$CN gradient to 30-85% MeCN 0.1% TFA) to give the title compound (14 mg, 30%). LCMS: R$_T$=1.714 min, MS (ES) 811.3 (M+H).

Example 95

6-(8-Chloro-1-(3-(4-chloro-3,5-dimethylphenoxy) propyl)-7-(3,5-dimethyl-1H-pyrazol-4-yl)-1-oxo-4,5-dihydro-1H-[1,4]diazepino[1,2-a]indol-2(3H)-yl)-1-methyl-1H-indazole-4-carboxylic acid The title compound (25 mg, 56% two steps) was prepared according to procedures described in Example 70 B to C using 8-chloro-11-(3-(4-chloro-3,5-dimethylphenoxy)propyl)-7-(3,5-dimethyl-1-((2-(trimethylsilyl)ethoxy)methyl)-1H-pyrazol-4-yl)-2,3,4,5-tetrahydro-1H-[1,4]diazepino[1,2-a]indol-1-one (50 mg, 0.076 mmol) and methyl 6-bromo-1-methyl-1H-indazole-4-carboxylate (23 mg, 0.084 mmol). LCMS: R$_T$=1.859 min, MS (ES) 699.2 (M+H).

Example 96

(R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-morpholinoethyl)-1H-indole-6-carboxylic acid The title compound (58% yield) was prepared according to procedures described in Example 94 Step A to C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one and methyl 4-bromo-1-((2-(trimethylsilyl)ethoxy)methyl)-1H-indole-6-carboxylate. LCMS: R$_T$=1.735 min, MS (ES) 811.3 (M+H).

Example 97

(R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-2-methyl-2H-indazole-1-carboxylic acid The title compound (6 mg, 18%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 4-bromo-2-methyl-2H-indazole-6-carboxylate (20 mg, 0.074 mmol), Pd$_2$(dba)$_3$ (4 mg, 0.0043 mmol), Xantphos (8 mg, 0.014 mmol), and Cs$_2$CO$_3$ (50 mg, 0.153 mmol) followed by saponification using General Procedure D. LCMS: R$_T$=1.949 min, MS (ES) 713.2 (M+H).

Example 98

(R)-5-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indazole-7-carboxylic acid The title compound (3 mg, 9%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 5-bromo-1-methyl-1H-indazole-7-carboxylate (20 mg, 0.074 mmol), Pd$_2$(dba)$_3$ (4 mg, 0.0043 mmol), Xantphos (8 mg, 0.014 mmol), and Cs$_2$CO$_3$ (50 mg, 0.153 mmol) followed by saponification using General Procedure D. LCMS: R$_T$=1.991 min, MS (ES) 713.2 (M+H).

Example 99

(R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-ethyl-1H-indole-4-carboxylic acid The title compound (12 mg, 38%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (40 mg, 0.074 mmol), methyl 6-bromo-1-ethyl-1H-indole-4-carboxylate (25 mg, 0.089 mmol), Pd$_2$(dba)$_3$ (1.4 mg, 0.0015 mmol), Xantphos (2.6 mg, 0.0045 mmol), and Cs$_2$CO$_3$ (48 mg, 0.15 mmol) followed by saponification using General Procedure D. LCMS: R$_T$=2.220 min, MS (ES) 740.3 (M+H).

Example 100

(R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-6-carboxylic acid The title compound was prepared along with Example 96 as a byproduct. MS (ES) 698.2 (M+H).

Example 101

(R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-4-carboxylic acid The title compound was prepared along with Example 94 as a byproduct. MS (ES) 698.2 (M+H).

Example 102

(R)-6-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-2-carboxylic acid The title compound (21 mg, 59%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (27 mg, 0.05 mmol), methyl 6-bromoquinoline-2-carboxylate (16 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D. LCMS: $R_T$=2.025 min, MS (ES) 710.2 (M+H); $^1$H NMR (400 MHz, DMSO-<6) δ 8.51 (dd, J=8.6, 1.7 Hz, 1H), 8.14 (t, J=8.6 Hz, 2H), 8.09-8.00 (m, 1H), 7.96 (ddd, J=9.0, 2.4, 1.0 Hz, 1H), 7.78 (d, J=8.6 Hz, 1H), 7.31 (d, J=8.6 Hz, 1H), 6.74 (s, 2H), 4.68-4.46 (m, 2H), 4.26-4.14 (m, 3H), 4.00 (s, 3H), 3.79 (s, 3H), 3.44-3.14 (m, 2H), 2.25 (s, 6H), 2.12 (s, 1.5H), 2.11-2.05 (m, 2H), 2.03 (s, 1.5H), 2.00 (s, 1.5H), 1.90 (s, 1.5H), 1.05 (d, J=6.4 Hz, 3H).

Example 103

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-ethyl-1H-indole-3-carboxylic acid

Step A. Preparation of ethyl 7-bromo-1-ethyl-1H-indole-3-carboxylate

The title compound (58 mg, 68%) was prepared following General Procedure G using 7-bromo-1H-indole-3-carboxylic acid (70 mg, 0.29 mmol), NaH (26 mg, 0.64 mmol) and EtI (51 μL, 0.64 mmol). LCMS: $R_T$=1.803 min, MS (ES) 296.1 (M+H).

Step B. Example 103

The title compound (8 mg, 22%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), ethyl 7-bromo-1-ethyl-1H-indole-3-carboxylate (14 mg, 0.06 mmol), CuI (5 mg, 0.025 mmol), (trans)-1,2-N,N'-dimethylaminocyclohexane (8 μL, 0.05 mmol), and $K_2CO_3$ (25 mg, 0.075 mmol) followed by saponification using General Procedure D. LCMS: $R_T$=2.042 min, MS (ES) 726.3 (M+H).

Example 104

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-ethyl-1H-indole-6-carboxylic acid

Step A. Preparation of methyl 3-bromo-1-ethyl-1H-indole-6-carboxylate

The title compound (76 mg, 95%) was prepared following General Procedure G using methyl 3-bromo-1H-indole-6-carboxylate (72 mg, 0.28 mmol), sodium hydride (14 mg, 0.34 mmol) and EtI (28 μL, 0.34 mmol). LCMS: $R_T$=1.682 min, MS (ES) 282.1 (M+H).

Step B. Example 104

The title compound (35 mg, 96%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-ethyl-1H-indole-6-carboxylate (14 mg, 0.06 mmol). CuI (5 mg, 0.025 mmol). (trans)-1,2-N,N'-dimethylaminocyclohexane (8 μL, 0.05 mmol), and $K_2CO_3$ (25 mg, 0.075 mmol) followed by saponification using General Procedure D. LCMS: $R_T$=2.064 min, MS (ES) 726.3 (M+H).

Example 105

(R)-8-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-3-carboxylic acid The title compound (34 mg, 96%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 8-bromoquinoline-3-carboxylate (16 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D. LCMS: $R_T$=2.010 min, MS (ES) 710.2 (M+H).

Example 106

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-4-carboxylic acid

Step A. Preparation of methyl 3-bromo-1-methyl-1H-indole-7-carboxylate

The title compound (39 mg, 51%) was prepared following General Procedure F using methyl 1H-indole-4-carboxylate (50 mg, 0.28 mmol), NBS (51 mg, 0.28 mmol), NaH (14 mg, 0.34 mmol), and MeI (21 μL, 0.34 mmol). LCMS: $R_T$=1.414 min, MS (ES) 268.1 (M+H).

Step B. Example 106

The title compound (16 mg, 45%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-methyl-1H-indole-4-carboxylate (14 mg, 0.06 mmol), CuI (5 mg, 0.025 mmol), (trans)-1,2-N,N'-dimethylaminocyclohexane (8 μL, 0.05 mmol), and $K_2CO_3$ (25 mg, 0.075 mmol) followed by saponification using General Procedure D. LCMS: $R_T$=1.936 and 1.963 min, MS (ES) 712.3 (M+H).

Example 107

6-[8-Chloro-11-[3-(4-chloro-3,5-dimethyl-phenoxy)propyl]-1-oxo-7-(1,3,5-trimethylpyrazol-4-yl)-4,5-dihydro-3H-[1,4]diazepino[1,2-a]indol-2-yl]-1-(2-hydroxyethyl)indazole-4-carboxylic acid

Step A. Preparation of methyl 6-bromo-1-(2-((tert-butyldimethylsilyl)oxy)ethyl)-1H-indazole-4-carboxylate The title compound (73 mg, 23%) was prepared following the procedure describe in Example 82 Step A substituting 1-bromo-2-methoxyethane with (2-bromoethoxy)(tert-butyl)dimethylsilane (375 mg, 1.57 mmol).

Step B. Example 107

The title compound (3 mg, 9%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol), methyl 6-bromo-1-(2-((tert-butyldimethylsilyl)oxy)ethyl)-1H-indazole-4-carboxylate (30 mg, 0.073 mmol), $Pd_2(dba)_3$ (4 mg, 0.0043 mmol), Xantphos (6 mg, 0.010 mmol), and $Cs_2CO_3$ (50 mg, 0.153 mmol). Following isolation of the coupling product, the crude residue was dissolved in THF (3 mL) and TBAF (1.0 M, 0.1 mL, 0.1 mmol) was added and the reaction was allowed to stir overnight at RT. The crude reaction mixture was concentrated and carried forward to saponification following General Procedure D. LCMS: $R_T$=1.786 min, MS (ES) 742.9 (M+H).

Example 108

(R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-3-carboxylic acid The title compound was prepared according to procedures described in Example 70 B to C using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one and methyl 7-bromo-1-methyl-1H-indole-3-carboxylate. MS (ES) 699.2 (M+H).

Example 109

(R)-3-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-6-carboxylic acid

Step A. Preparation of methyl (R)-3-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1-methyl-1H-indole-6-carboxylate The title compound (88 mg, 69%) was prepared following General Procedure B using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one (100 mg, 0.15 mmol), methyl 3-bromo-1-methyl-1H-indole-6-carboxylate (41 mg, 0.15 mmol), CuI (1.5 mg, 0.0078 mmol), (trans)-1,2-N,N'-dimethylaminocyclohexane (2.2 mg, 0.015 mmol), and $K_2CO_3$ (42 mg, 0.31 mmol). MS (ES) 842.3 (M+H).

Step B. Example 109

The title compound was prepared according to procedures described in Example 70 C using methyl (R)-3-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1-methyl-1H-indole-6-carboxylate. LCMS: $R_T$=1.900 min, MS (ES) 698.2 (M+H).

Example 110

(R)-6-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid The title compound (28 mg, 79%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 6-bromo-1-methyl-1H-indole-2-carboxylate (14 mg, 0.06 mmol), CuI (5 mg, 0.025 mmol), (trans)-1,2-N,N'-dimethylaminocyclohexane (8 μL, 0.05 mmol), and $K_2CO_3$ (25 mg, 0.075 mmol) followed by saponification using General Procedure D. LCMS: $R_T$=2.091 and 2.114 min, MS (ES) 712.3 (M+H).

Example 111

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)imidazo[1,5-a]pyridine-1-carboxylic acid The title compound (89% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 3-bromoimidazo[1,5-a]pyridine-1-carboxylate followed by saponification using General Procedure D. MS (ES) 701.3 (M+H); $^1$H NMR (DMSO, 400 MHz) δ (ppm) 8.08 (t, J=10.0 Hz, 2H), 7.79 (d, J=8.4 Hz, 1H), 7.31 (d, J=8.4 Hz, 1H), 7.29-7.26 (m, 1H), 6.93 (t, J=6.8 Hz, 1H), 6.71 (s, 2H), 4.55-4.50 (m, 1H), 4.30-4.25 (m, 2H), 3.97 (t, J=6.0 Hz, 2H), 3.77 (s, 3H), 3.33-3.15 (m, 2H), 2.23 (s, 6H), 2.11 (s, 1.5H), 2.09-2.01 (m, 2H), 2.02 (s, 1.5H), 1.97 (s, 1.5H), 1.88 (s, 1.5H), 1.09 (d, J=5.6 Hz, 3H).

Example 112

(R)-2-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)imidazo[1,2-a]pyridine-8-carboxylic acid The title compound (49% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 2-bromoimidazo[1,2-a]pyridine-8-carboxylate followed by saponification using General Procedure D. MS (ES) 701.4 (M+H).

Example 113

(R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid The title compound (26 mg, 73%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 4-bromo-1-methyl-1H-indole-2-carboxylate (14 mg, 0.06 mmol), CuI (5 mg, 0.025 mmol), (trans)-1,2-N,N'-dimethylaminocyclohexane (8 µL, 0.05 mmol), and K$_2$CO$_3$ (25 mg, 0.075 mmol) followed by saponification using General Procedure D. LCMS: R$_T$=2.076 min, MS (ES) 712.2 (M+H); $^1$H NMR (400 MHz, CDCl$_3$) δ 7.74 (d, J=3.1 Hz, 0.5H), 7.72 (d, J=3.1 Hz, 0.5H), 7.49-7.37 (m, 2H), 7.31 (dd, J=9.7, 5.1 Hz, 2H), 7.13-7.05 (m, 1H), 6.70-6.55 (m, 2H), 4.57-4.40 (m, H), 4.37-4.17 (m, 2H), 4.10 (s, 3H), 3.97 (s, 1.5H), 3.96 (s, 1.5H), 3.62 (dd, J=11.9, 4.2 Hz, 1H), 3.40 (ddt, J=42.4, 13.8, 7.3 Hz, 3H), 2.32 (s, 6H), 2.26 (s, 1.5H), 2.25 (s, 1.5H), 2.22 (d, J=7.0 Hz, 2H), 2.11 (s, 1.5H), 2.09 (s, 1.5H), 1.27 (d, J=6.4 Hz, 1.5H), 1.20 (d, J=6.5 Hz, 1.5H).

Example 114

(R)-5-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid The title compound (28 mg, 79%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 5-bromo-1-methyl-1H-indole-2-carboxylate (14 mg, 0.06 mmol), CuI (5 mg, 0.025 mmol), (trans)-1,2-N,N'-dimethylaminocyclohexane (8 µL, 0.05 mmol), and K$_2$CO$_3$ (25 mg, 0.075 mmol) followed by saponification using General Procedure D. LCMS: R$_T$=2.084 min, MS (ES) 712.3 (M+H); $^1$H NMR (400 MHz, DMSO-d$_6$) δ 7.75 (d, J=8.6 Hz, 1H), 7.66-7.54 (m, 2H), 7.36-7.26 (m, 2H), 7.23 (t, J=0.9 Hz, 1H), 6.73 (s, 2H), 4.44 (dd, 1=13.0, 3.8 Hz, 1H), 4.05 (s, 3H), 3.98 (tt, J=6.3, 2.9 Hz, 3H), 3.78 (s, 1.5H), 3.77 (s, 1.5H), 3.63 (t, J=13.5 Hz, 1H), 3.22 (dt, J=13.2, 7.2 Hz, 2H), 2.26 (s, 6H), 2.12 (s, 1.5H), 2.10-2.04 (m, 2H), 2.03 (s, 1.5H), 1.97 (s, 1.5H), 1.88 (s, 1.5H), 1.04 (d, J=6.4 Hz, 3H).

Example 115

(R)-2-(benzo[d]isoxazol-6-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one The title compound (41% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and 6-bromobenzo[d]isoxazole. MS (ES) 656.4 (M+H); $^1$H NMR (DMSO, 400 MHz) δ (ppm) 7.73 (d, J=8.8 Hz, 1H), 7.63 (dd, J=8.4, 2.8 Hz, 1H), 7.28 (d, J=8.4 Hz, 1H), 7.15 (s, 1H), 6.91 (d, J=8.8 Hz, 1H), 6.72 (s, 2H), 4.45-4.41 (m, 1H), 4.24-4.13 (m, 2H), 3.97 (t, J=6.0 Hz, 2H), 3.76 (s, 3H), 3.32-3.15 (m, 2H), 2.24 (s, 6H), 2.08 (s, 1.5H), 2.07-2.02 (m, 2H), 1.98 (s, 1.5H), 1.94 (s, 1.5H), 1.85 (s, 1.5H), 0.94 (d, J=6.4 Hz, 3H)

Example 116

(R)-5-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indazole-3-carboxylic acid The title compound (25 mg, 70%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 5-bromo-1-methyl-1H-indazole-3-carboxylate (14 mg, 0.06 mmol), CuI (5 mg, 0.025 mmol), (trans)-1,2-N,N'-dimethylaminocyclohexane (8 µL, 0.05 mmol), and K$_2$CO$_3$ (25 mg, 0.075 mmol) followed by saponification using General Procedure D. LCMS: R$_T$=1.998 min, MS (ES) 713.2 (M+H).

Example 117

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-2-ethyl-2H-indazole-3-carboxylic acid Step A. Preparation of methyl 7-bromo-2-ethyl-2H-indazole-3-carboxylate The title compound (54 mg, 48%) was prepared following the procedure described in Example 82 Step A using methyl 7-bromo-1H-indazole-3-carboxylate (100 mg, 0.392 mmol), sodium hydride (18 mg, 0.75 mmol), and EtBr (80 mg, 0.74 mmol).

Step B. Example 117

The title compound (9.5 mg, 29%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 7-bromo-2-ethyl-2H-indazole-3-carboxylate (20 mg, 0.071 mmol), Pd$_2$ (dba)₃ (4 mg, 0.0043 mmol), Xantphos (6 mg, 0.010 mmol), and Cs₂CO₃ (50 mg, 0.153 mmol) followed by saponification using General Procedure D. LCMS: $R_T$=2.138 min, MS (ES) 727.3 (M+H); ¹H NMR (400 MHz, Chloroform-d) δ 7.86 (ddd, J=8.4, 3.9, 0.9 Hz, 1H), 7.73 (dd, J=8.6, 2.9 Hz, 1H), 7.43-7.36 (m, 1H), 7.35-7.24 (m, 2H), 6.68-6.62 (m, 2H), 4.84 (q, J=7.2 Hz, 2H), 4.64-4.49 (m, 1H), 4.36-4.20 (m, 1H), 4.04 (t, J=6.4 Hz, 2H), 3.96 (d, J=2.7 Hz, 3H), 3.79 (t, J=13.5 Hz, 1H), 3.44 (ddt, J=17.8, 11.7, 6.3 Hz, 2H), 2.33 (s, 6H), 2.28-2.19 (m, 5H), 2.12 (s, 1.5H), 2.09 (s, 1.5H), 1.49 (td, J=7.2, 5.8 Hz, 3H), 1.34 (d, J=6.3 Hz, 1.5H), 1.26 (d, J=6.4 Hz, 1.5H).

Example 118

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-ethyl-1H-indazole-3-carboxylic acid Step A. Preparation of methyl 7-bromo-1-ethyl-1H-indazole-3-carboxylate The title compound (22 mg, 20%) was prepared in the same reaction as described in Example 117 Step A.

Step B. Example 118

The title compound (3 mg, 9%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 7-bromo-1-ethyl-1H-indazole-3-carboxylate (20 mg, 0.071 mmol), Pd₂(dba)₃ (4 mg, 0.0043 mmol), Xantphos (6 mg, 0.010 mmol), and Cs₂CO₃ (50 mg, 0.153 mmol) followed by saponification using General Procedure D. LCMS: $R_T$=2.058 min, MS (ES) 727.2 (M+H).

Example 119

7-[8-chloro-11-[3-(4-chloro-3,5-dimethyl-phenoxy)propyl]-7-(4,6-dimethylpyrimidin-5-yl)-1-oxo-4,5-dihydro-3H-[1,4]diazepino[1,2-a]indol-2-yl]-1-methyl-indole-3-carboxylic acid The title compound (1 mg, 3%) was prepared following General coupling procedure A using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (25 mg, 0.046 mmol), methyl 7-bromo-1-methyl-1H-indole-3-carboxylate (20 mg, 0.074 mmol), Pd₂(dba)₃ (4 mg, 0.0043 mmol). Xantphos (6 mg, 0.010 mmol), and Cs₂CO₃ (50 mg, 0.153 mmol) followed by saponification using General Procedure D. LCMS: $R_T$=2.032 min, MS (ES) 710.2 (M+H).

Example 120

8-Chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one Step A. Preparation of ethyl 6-chloro-3-(3-(4-chloro-3,5-dimethylphenoxy)propyl)-7-(4,6-dimethylpyrimidin-5-yl)-1H-indole-2-carboxylate Ethyl 7-bromo-6-chloro-3-(3-(4-chloro-3,5-dimethylphenoxy)propyl)-1H-indole-2-carboxylate (1.647 g, 3.30 mmol) was combined with (4,6-dimethylpyrimidin-5-yl)boronic acid (1.2 g, 7.90 mmol), Pd₂(dba)₃ (0.30 g, 0.33 mmol), and dicyclohexyl(2',6'-dimethoxy-[1,1'-biphenyl]-2-yl)phosphine (SPhos) (0.406 g, 0.990 mmol) in 30 mL 1:1 THF/Toluene in a pressure tube. The mixture was treated with K₃PO₄ (1.16 mL, 11.6 mmol) and was stirred 10 minutes at RT under Ar flush. The reaction was heated to 110° C. and stirred for 24 h. The mixture was cooled, poured in 150 mL EtOAc and stirred with 50 mL saturated ammonium chloride. The organic layer was dried over anhydrous MgSO₄ and was concentrated in vacuo. The crude material was purified by flash chromatography (EtOAc/DCM=0-50% gradient) to give the title compound (970 mg, 56%) as an amber foam. ¹H NMR (400 MHz, Chloroform-d) δ 9.09 (s, 1H), 8.93 (s, 1H), 7.68 (dd, J=8.6, 0.6 Hz, 1H), 7.25 (d, J=8.7 Hz, 1H), 6.62 (s, 2H), 4.33 (q, J=7.1 Hz, 2H), 3.97 (t, J=6.1 Hz, 2H), 3.28 (dd, J=8.1, 6.8 Hz, 2H), 2.32 (s, 6H), 2.20 (s, 6H), 2.21-2.10 (m, 2H), 1.36-1.20 (m, 3H); ¹³C NMR (101 MHz, cdcl₃) δ 165.98, 161.85, 157.76, 156.71, 137.03, 134.32, 130.42, 127.16, 127.11, 126.11, 124.93, 124.67, 121.97, 118.44, 114.45, 67.35, 61.10, 30.24, 22.26, 21.21, 20.96, 14.32.

Step B. Preparation of ethyl 1-(3-((tert-butoxycarbonyl)amino)propyl)-6-chloro-3-(3-(4-chloro-3,5-dimethylphenoxy)propyl)-7-(4,6-dimethylpyrimidin-5-yl)-1H-indole-2-carboxylate To a solution of ethyl 6-chloro-3-(3-(4-chloro-3,5-dimethylphenoxy)propyl)-7-(4,6-dimethylpyrimidin-5-yl)-1H-indole-2-carboxylate (500 mg, 0.952 mmol) and tert-butyl 1,2,3-oxathiazinane-3-carboxylate 2,2-dioxide (300 mg, 1.26 mmol) in DMF (20 mL) was added NaH (60 mg, 1.50 mmol), and the reaction was stirred at RT for 3 h. The reaction was diluted with DCM/H₂O (60 mL, 1:1), and the layers were separated. The aqueous layer was extracted with DCM (2×30 mL), and the combined organic extracts were dried over MgSO₄, filtered, and concentrated in vacuo. The crude reaction mixture was purified by flash chromatography (Combi-flash Rf, Hex/EtOAc=0-100% gradient) to afford the title compound (525 mg, 81%).

Step C. Example 120

To a solution of ethyl 1-(3-((tert-butoxycarbonyl)amino)propyl)-6-chloro-3-(3-(4-chloro-3,5-dimethylphenoxy)propyl)-7-(4,6-dimethylpyrimidin-5-yl)-1H-indole-2-carboxylate in dioxane (20 mL) was added HCl in dioxane (4.0 M, 3.0 mL, 12 mmol), and the reaction was stirred for 72 h at RT. The reaction was concentrated in vacuo, and the crude residue was taken up in MeOH (30 mL). K₂CO₃ (300 mg, 2.17 mmol) was added, and the reaction was stirred for 6 h at 50° C. The reaction was concentrated in vacuo, and the residue extracted with DCM (3×30 mL) and washed with H₂O (30 mL). The combined organic extracts were dried over MgSO₄, filtered, and concentrated in vacuo. The crude reaction mixture was then purified by flash chromatography (Combi-flash Rf, CH₂Cl₂/methanol=0-10% gradient) to afford the title compound (243 mg, 58%). LCMS: $R_T$=1.947 min, MS (ES) 537.3 (M+H).

Example 121

(R)-6-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indazole-3-carboxylic acid The title compound (19 mg, 53%) was prepared following General coupling procedure B using (R)-7-chloro-10-(3-(4- chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 6-bromo-1-methyl-1H-indazole-3-carboxylate (14 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol) followed by saponification using General Procedure D. LCMS: $R_T$=2.024 min, MS (ES) 713.2 (M+H); $^1$H NMR (400 MHz, DMSO-$d_6$) δ 8.57-7.98 (m, 1H), 7.82-7.69 (m, 1H), 7.63 (dd, J=12.1, 7.1 Hz, 1H), 7.29 (dd, J=8.6, 4.6 Hz, 2H), 6.74 (s, 2H), 4.74-4.45 (m, 1H), 4.45-4.32 (m, 1H), 4.25-4.08 (m, 2H), 4.01 (s, 3H), 4.00-3.95 (m, 1H), 3.79 (s, 1.5H), 3.78 (s, 1.5H), 3.74-3.60 (m, 1H), 2.77-2.62 (m, 1H), 2.26 (s, 6H), 2.12 (s, 1.5H), 2.06-2.00 (m, 2H), 1.98 (s, 1.5H), 1.89 (s, 1.5H), 1.76 (s, 1.5H), 1.05 (d, J=6.3 Hz, 3H).

Example 122

7-(8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-ethyl-1H-indazole-5-carboxylic acid Step A. Preparation of methyl 7-bromo-1-ethyl-1H-indazole-5-carboxylate The title compound (42 mg, 37%) was prepared following the procedure described in Example 82 Step A using methyl 7-bromo-1H-indazole-5-carboxylate (100 mg, 0.392 mmol), NaH (18 mg, 0.75 mmol), and EtBr (80 mg, 0.74 mmol).

Step B. Example 137

The title compound (3 mg, 9%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol), methyl 7-bromo-1-ethyl-1H-indazole-5-carboxylate (20 mg, 0.074 mmol), $Pd_2$(dba)$_3$ (4 mg, 0.0043 mmol), Xantphos (6 mg, 0.010 mmol), and $Cs_2CO_3$ (50 mg, 0.153 mmol) followed by saponification using General Procedure D. LCMS: $R_T$=2.033 min, MS (ES) 727.2 (M+H).

Example 123

7-(8-Chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indazole-5-carboxylic acid Step A. Preparation of methyl 7-bromo-1-methyl-1H-indazole-5-carboxylate The title compound (64 mg, 61%) was prepared following the procedure described in Example 82 Step A using methyl 7-bromo-1-methyl-1H-indazole-5-carboxylate (100 mg, 0.392 mmol), NaH (18 mg, 0.75 mmol), and MeI (75 mg, 0.52 mmol).

Step B. Example 123

The title compound (5 mg, 15%) was prepared following General coupling procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol), methyl 7-bromo-1-methyl-1H-indazole-5-carboxylate (20 mg, 0.074 mmol), $Pd_2$(dba)$_3$ (4 mg, 0.0043 mmol), Xantphos (6 mg, 0.010 mmol), and $Cs_2CO_3$ (50 mg, 0.153 mmol) followed by saponification using General Procedure D. LCMS: $R_T$=1.926 min, MS (ES) 712.9 (M+H).

Example 124

7-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-2-ethyl-2H-indazole-5-carboxylic acid Step A. Preparation of methyl 7-bromo-2-ethyl-2H-indazole-5-carboxylate The title compound (29 mg, 26%) was prepared in the same reaction as described in Example 122 Step A.

Step 2: Example 124

The title compound (3.9 mg, 12%) was prepared following General Procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol), methyl 7-bromo-2-ethyl-2H-indazole-5-carboxylate (20 mg, 0.074 mmol), $Pd_2$(dba)$_3$ (4 mg, 0.0043 mmol), Xantphos (6 mg, 0.010 mmol), and $Cs_2CO_3$ (50 mg, 0.153 mmol) followed by saponification using General Procedure D. LCMS: $R_T$=1.895 min, MS (ES) 726.9 (M+H).

Example 125

4-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indazole-3-carboxylic acid The title compound (4 mg, 11%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.050 mmol), methyl 4-bromo-1-methyl-1H-indazole-3-carboxylate (20 mg, 0.074 mmol), $Pd_2$(dba)$_3$ (5 mg, 0.0055 mmol), Xantphos (7 mg, 0.012 mmol), and $Cs_2CO_3$ (50 mg, 0.153 mmol) followed by saponification using General Procedure D. LCMS: $R_T$=1.944 min, MS (ES) 713.2 (M+H).

Example 126

4-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indazole-3-carboxylic acid (Separated Steroisomer A)

The title compound (8 mg, 20%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.052 mmol), methyl 4-bromo-1-methyl-1H-indazole-3-carboxylate (30 mg, 0.11 mmol), $Pd_2$(dba)$_3$ (5 mg, 0.0055 mmol), Xantphos (7 mg, 0.012 mmol), and $Cs_2CO_3$ (50 mg, 0.153 mmol) followed by saponification using General Procedure D. LCMS: $R_T$=1.944 min, MS (ES) 713.2 (M+H). The title compound was separated using reverse phase HPLC (Phenomenex Gemini C18, H$_2$O/CH$_3$CN gradient from 30-90% CH$_3$CN, 0.1% TFA) during the final purification step to give as a separated atropisomer (1$^{st}$ fraction, absolute stereochemistry underminded). MS (ES) 713.2 (M+H).

Example 127

4-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indazole-3-carboxylic acid (Separated Steroisomer B)

The title compound was separated along with Example 141 as a separated atropisomer (2$^{nd}$ fraction). MS (ES) 713.2 (M+H).

Example 128

(R)-7-(7-chloro-10-(3-(4-chloro-3,5-dimethylphenoxy)propyl)-6-(3,5-dimethyl-1-((tetrahydro-2H-pyran-4-yl)methyl)-1H-pyrazol-4-yl)-4-methyl-1-oxo-3,4-dihydropyrazino[1,2-a]indol-2(1H)-yl)-1-methyl-1H-indole-3-carboxylic acid Step A. Preparation of methyl (R)-7-(7-chloro-10-(3-(4-chloro-3,5-dimethylphenoxy)propyl)-6-(3,5-dimethyl-1-((tetrahydro-2H-pyran-4-yl)methyl)-1H-pyrazol-4-yl)-4-methyl-1-oxo-3,4-dihydropyrazino[1,2-a]indol-2(1H)-yl)-1-methyl-1H-indole-3-carboxylate To a solution of methyl (R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-3-carboxylate (20 mg, 0.028 mmol) in DMF (0.5 mL) was added NaH (1.4 mg, 0.034 mmol) and stirred for 15 min at RT. 4-(Bromomethyl)tetrahydro-2H-pyran (5.5 mg, 0.031 mmol) was added, and the resulting mixture was stirred overnight then concentrated in vacuo. The residue was purified by flash chromatography (Combi-flash Rf, Hex/EtOAc=0-70% gradient) to give the title compound (20 mg, 88%) as white foam. LCMS: R$_T$=2.107 min, MS (ES) 810.3 (M+H).

Step B. Example 128

The title compound (10 mg, 51%) was prepared following General Procedure D for saponification using methyl (R)-7-(7-chloro-10-(3-(4-chloro-3,5-dimethylphenoxy)propyl)-6-(3,5-dimethyl-1-((tetrahydro-2H-pyran-4-yl)methyl)-1H-pyrazol-4-yl)-4-methyl-1-oxo-3,4-dihydropyrazino[1,2-a]indol-2(1H)-yl)-1-methyl-1H-indole-3-carboxylate (20 mg, 0.025 mmol). LCMS: R$_T$=2.124 min, MS (ES) 796.3 (M+H).

Example 129

(R)-3-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-5-carboxylic acid The title compound was prepared following the procedure described in Example 109 Step A and B using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one and methyl 3-bromo-1-methyl-1H-indole-5-carboxylate. LCMS: R$_T$=1.872 min, MS (ES) 698.2 (M+H).

Example 130

6-[8-Chloro-11-[3-(4-chloro-3,5-dimethyl-phenoxy)propyl]-7-(4,6-dimethylpyrimidin-5-yl)-1-oxo-4,5-dihydro-3H-[1,4]diazepino[1,2-a]indol-2-yl]-1-methyl-indole-4-carboxylic acid The title compound (2 mg, 6%) was prepared following General coupling procedure A using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (25 mg, 0.046 mmol), methyl 6-bromo-1-methyl-1H-indole-4-carboxylate (20 mg, 0.067 mmol), Pd$_2$(dba)$_3$ (4 mg, 0.0043 mmol), Xantphos (6 mg, 0.010 mmol), and Cs$_2$CO$_3$ (50 mg, 0.153 mmol) followed by saponification using General Procedure D. LCMS: R$_T$=2.012 min, MS (ES) 710.2 (M+H).

Example 131

6-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-isopropyl-indazole-4-carboxylic acid The title compound (8 mg, 23%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 6-bromo-1-isopropyl-1H-indazole-4-carboxylate (20 mg, 0.067 mmol), Pd$_2$(dba)$_3$ (4 mg, 0.0043 mmol), Xantphos (6 mg, 0.010 mmol), and Cs$_2$CO$_3$ (50 mg, 0.153 mmol) followed by saponification using General Procedure D. LCMS: R$_T$=2.119 min, MS (ES) 741.3 (M+H).

Example 132

4-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-2-methyl-indazole-3-carboxylic acid The title compound (12 mg, 34%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.050 mmol), methyl 4-bromo-2-methyl-2H-indazole-3-carboxylate (25 mg, 0.074 mmol), Pd$_2$(dba)$_3$ (5 mg, 0.0055 mmol), Xantphos (7 mg, 0.012 mmol), and Cs$_2$CO$_3$ (50 mg, 0.153 mmol) followed by saponification using General Procedure D. LCMS: R$_T$=1.940, 1.971 min, MS (ES) 713.2 (M+H)

Example 133

4-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-2-methyl-indazole-3-carboxylic acid (Separated Steroisomer A)

The title compound was separated using reverse phase HPLC (Phenomenex Gemini C18, H$_2$O/CH$_3$CN gradient from 30-90% CH₃CN, 0.1% TFA) during the final purification step to give as a separated atropisomer (1ˢᵗ fraction, absolute stereochemistry undeterminded). LCMS: $R_T$=1972 min, MS (ES) 713.2 (M+H).

Example 134

(R)-2-(4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indol-1-yl)acetic acid Step A. Preparation of tert-butyl (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-1-carboxylate The title compound (35 mg, 93%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), tert-butyl 4-bromo-1H-indole-1-carboxylate (18 mg, 0.06 mmol), Pd₂(dba)₃ (1 mg, 0.001 mmol), Xantphos (2 mg, 0.003 mmol), and Cs₂CO₃ (25 mg, 0.075 mmol). LCMS: $R_T$=2.453 min, MS (ES) 754.30 (M+H).

Step B. Example 134

To a solution of tert-butyl (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-1-carboxylate (35 mg, 0.046 mmol) in DCM (2 mL) was added TFA (2 mL), and the mixture was stirred at room temperature for 6 h. Saturated aqueous NaHCO₃ (8 mL) was added to the mixture and extracted in DCM (3×5 mL). The organic layer was dried (anhyd. Na₂SO₄), evaporated. The residue was dissolved in DMF (1 mL), and NaH (5 mg, 0.12 mmol, 1.2 eqv.) was added then stirred at RT for 10 min. Ethyl bromoacetate (14 μL, 0.12 mmol, 1.2 eqv.) was added to the mixture and stirred at RT for 2 h. The reaction was quenched with water (5 mL) and extracted with DCM (3×5 mL). The organic layer was dried (anhyd. Na₂SO₄) and concentrated. The residue was subjected to saponification using General Procedure D and purified by reverse phase HPLC (Phenomenex Gemini C18, H₂O/CH₃CN gradient to 35-95% MeCN 0.1% TFA) to afford the title compound (16 mg, 45%). LCMS: $R_T$=1.748 min, MS (ES) 712.2 (M+H).

Example 135

(R)-2-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-[1,2,4]triazolo[1,5-a]pyridine-7-carboxylic acid The title compound (43% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 2-bromo-[1,2,4]triazolo[1,5-a]pyridine-7-carboxylate followed by saponification using General Procedure D. MS (ES) 700.4 (M+H); ¹H NMR (DMSO, 400 MHz) δ (ppm) 9.00 (dd, J=7.2, 3.6 Hz, 1H), 8.22 (d, J=8.0 Hz, 1H), 7.76 (d, J=8.8 Hz, 1H), 7.58 (dd, J=7.2, 1.2 Hz, 1H), 7.29 (d, J=8.8, 1.2 Hz, 1H), 6.73 (s, 2H), 4.37-4.19 (m, 3H), 4.13-3.95 (m, 2H), 3.76 (d, J=8.8 Hz, 3H), 3.36-3.15 (m, 2H), 2.24 (s, 6H), 2.09-2.05 (m, 2H), 2.08 (s, 1.5H), 1.99 (s, 1.5H), 1.97 (s, 1.5H), 1.87 (s, 1.5H), 0.95 (dd, J=9.2, 6.8 Hz, 3H).

Example 136

2-(4-(8-Chloro-11-(3-(4-chloro-3,5-dimethylphenoxy)propyl)-1-oxo-2-phenyl-2,3,4,5-tetrahydro-1H-[1,4]diazepino[1,2-a]indol-7-yl)-3,5-dimethyl-1H-pyrazol-1-yl)acetic acid Step A. Preparation of 8-chloro-11-(3-(4-chloro-3,5-dimethylphenoxy)propyl)-7-(3,5-dimethyl-1H-pyrazol-4-yl)-2-phenyl-2,3,4,5-tetrahydro-1H-[1,4]diazepino[1,2-a]indol-1-one The title compound was prepared according to procedures described in Example 58 step F to G using 8-chloro-11-(3-(4-chloro-3,5-dimethylphenoxy)propyl)-7-(3,5-dimethyl-1-((2-(trimethylsilyl)ethoxy)methyl)-1H-pyrazol-4-yl)-2,3,4,5-tetrahydro-1H-[1,4]diazepino[1,2-a]indol-1-one and aniline. MS (ES) 601.2 (M+H)

Step B. Example 136

To a solution of 8-chloro-11-(3-(4-chloro-3,5-dimethylphenoxy)propyl)-7-(3,5-dimethyl-1H-pyrazol-4-yl)-2-phenyl-2,3,4,5-tetrahydro-1H-[1,4]diazepino[1,2-a]indol-1-one (0.05 mmol) in DMF (1 mL) was added NaH (0.08 mmol) at RT, and the reaction was stirred for 30 min. Methyl 2-chloroacetate (0.1 mmol) was added, and the reaction was stirred for 5 h at RT then diluted with DCM/H₂O (20 mL, 1:1). The organic layer was separated and the aqueous layer was extracted with DCM (2×5 mL). The combined organic extracts were concentrated in vacuo. The crude reaction product was then saponified and purified following the procedure described in General Procedure D to afford the title compound (71% yield). MS (ES) 659.2 (M+H).

Example 137

(R)-7-(7-chloro-10-(3-(4-chloro-3,5-dimethylphenoxy)propyl)-6-(3,5-dimethyl-1-((1-methylpiperidin-4-yl)methyl)-1H-pyrazol-4-yl)-4-methyl-1-oxo-3,4-dihydropyrazino[1,2-a]indol-2(1H)-yl)-1-methyl-1H-indole-3-carboxylic acid Step A. Preparation of methyl (R)-7-(7-chloro-10-(3-(4-chloro-3,5-dimethylphenoxy)propyl)-6-(3,5-dimethyl-1-((1-methylpiperidin-4-yl)methyl)-1H-pyrazol-4-yl)-4-methyl-1-oxo-3,4-dihydropyrazino[1,2-a]indol-2(1H)-yl)-1-methyl-1H-indole-3-carboxylate To a solution of methyl (R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-3-carboxylate (20 mg, 0.028 mmol) and (1-methylpiperidin-4-yl)methanol (7.25 mg, 0.056 mmol) in Toluene (932 μl) was added 2-(tributyl-15-phosphanylidene)acetonitrile (140 μl, 0.056 mmol) and stirred at 50° C. for 20 h. The reaction mixture was concentrated, and the residue was purified by flash chromatography (Combi-flash Rf, DCM/MeOH=0-10% gradient) to give the title compound (15 mg, 65%). LCMS: $R_T$=1.901 min, MS (ES) 823.3 (M+H).

Step B. Example 137

The title compound (5 mg, 34%) was prepared according to General Procedure G using methyl (R)-7-(7-chloro-10-(3-(4-chloro-3,5-dimethylphenoxy)propyl)-6-(3,5-dimethyl-1-((1-methylpiperidin-4-yl)methyl)-1H-pyrazol-4-yl)-4-methyl-1-oxo-3,4-dihydropyrazino[1,2-a]indol-2(1H)-yl)-1-methyl-1H-indole-3-carboxylate (15 mg, 0.018) and methyl 6-(bromomethyl)nicotinate. LCMS: $R_T$=1.740 min, MS (ES) 809.4 (M+H).

Example 138

(R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)quinoline-8-carboxylic acid The title compound (66% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 6-bromoquinoline-8-carboxylate followed by saponification using General Procedure D. MS (ES) 710.2 (M+H); $^1$H-NMR (MeOH-d$_3$) δ 9.12 (dd, 1H, J1=2 Hz, J1=5 Hz), 9.90 (dd, 1H, J1=2 Hz, J1=5 Hz), 8.81 (m, 1H), 8.33 (m, 1H) 7.93 (m, 1H), 7.78 (d, 1H, J=8 Hz), 7.32 (d, 1H, J=8 Hz), 6.63 (s, 2H), 4.46 (m, 2H), 4.35 (m, 1H), 4.01-3.96 (m, 2H), 3.87 (multiple s, 3H), 3.77-3.74 (m, 1H), 3.49-3.38 (m, 2H), 3.11-3.08 (m, 1H), 2.27 (s, 6H), 2.23-2.02 (multiple s and in, 8H), 1.18 and 1.16 (two d, 3H J=8 Hz).

Example 139

(R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)imidazo[1,2-a]pyridine-2-carboxylic acid The title compound (78% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 6-bromoimidazo[1,2-a]pyridine-2-carboxylate followed by saponification using General Procedure D. MS (ES) 699.2 (M+H).

Example 140

(3R,4R)-7-chloro-10-(3-(4-chloro-3,5-dimethylphenoxy)propyl)-3,4-dimethyl-6-(1,3,5-trimethyl-1H-pyrazol-4-yl)-3,4-dihydropyrazino[1,2-a]indol-1 (2H)-one The title compound (74% yield) was prepared following same procedures described in Example 24 substituting tert-butyl (R)-4-ethyl-1,2,3-oxathiazolidine-3-carboxylate 2,2-dioxide with tert-butyl (4R,5S)-4,5-dimethyl-1,2,3-oxathiazolidine-3-carboxylate 2,2-dioxide. MS (ES) 553.4 (M+H); $^1$H-NMR (CDCl$_3$) δ 7.70 (d, 1H, J=8 Hz), 7.29 (d, 1H, J=8 Hz), 6.64 (s, 2H), 5.82 (m, 1H), 4.05-3.90 (m, 6H), 3.52-3.50 (m, 1H), 3.47-3.31 (m, 3H), 2.35 (s, 6H), 2.17 (over-lapped tr and multiple s, 8H), 1.21 (d, 0.75H, J=8 Hz), 1.19 (d, 0.75H, J=8 Hz), 1.05 (d, 1.5H, J=8 Hz), 1.03 (d, 1.5H, J=8 Hz), 0.88 (d, 0.75H, J=8 Hz), 0.82 (d, 0.75H, J=8 Hz)

Example 141

3-((3R,4R)-7-chloro-10-(3-(4-chloro-3,5-dimethylphenoxy)propyl)-3,4-dimethyl-1-oxo-6-(1,3,5-trimethyl-1H-pyrazol-4-yl)-3,4-dihydropyrazino[1,2-a]indol-2(1H)-yl)benzoic acid The title compound (62% yield) was prepared following General coupling procedure A using (3R,4R)-7-chloro-10-(3-(4-chloro-3,5-dimethylphenoxy)propyl)-3,4-dimethyl-6-(1,3,5-trimethyl-1H-pyrazol-4-yl)-3,4-dihydropyrazino[1,2-a]indol-1(2H)-one and methyl 3-bromobenzoate followed by saponification using General Procedure D. MS (ES) 673.2 (M+H).

Example 142

4-((3R,4R)-7-chloro-10-(3-(4-chloro-3,5-dimethylphenoxy)propyl)-3,4-dimethyl-1-oxo-6-(1,3,5-trimethyl-1H-pyrazol-4-yl)-3,4-dihydropyrazino[1,2-a]indol-2(1H)-yl)benzoic acid The title compound (73% yield) was prepared following General coupling procedure A using (3R,4R)-7-chloro-10-(3-(4-chloro-3,5-dimethylphenoxy)propyl)-3,4-dimethyl-6-(1,3,5-trimethyl-1H-pyrazol-4-yl)-3,4-dihydropyrazino[1,2-a]indol-1(2H)-one and methyl 4-bromobenzoate followed by saponification using General Procedure D. MS (ES) 673.3 (M+H).

Example 143

6-((3R,4R)-7-chloro-10-(3-(4-chloro-3,5-dimethylphenoxy)propyl)-3,4-dimethyl-1-oxo-6-(1,3,5-trimethyl-1H-pyrazol-4-yl)-3,4-dihydropyrazino[1,2-a]indol-2(1H)-yl)-1-methyl-1H-indole-4-carboxylic acid The title compound (8% yield) was prepared following General coupling procedure A using (3R,4R)-7-chloro-10-(3-(4-chloro-3,5-dimethylphenoxy)propyl)-3,4-dimethyl-6-(1,3,5-trimethyl-1H-pyrazol-4-yl)-3,4-dihydropyrazino[1,2-a]indol-1(2H)-one and methyl 6-bromo-1-methyl-1H-indole-4-carboxylate followed by saponification using General Procedure D. MS (ES) 726.3 (M+H).

Example 144

2-(4-(8-Chloro-11-(3-(4-chloro-3,5-dimethylphenoxy)propyl)-1-oxo-2-(quinolin-8-yl)-2,3,4,5-tetrahydro-1H-[1,4]diazepino[1,2-a]indol-7-yl)-3,5-dimethyl-1H-pyrazol-1-yl)acetic acid The title compound (55% yield) was prepared according to procedures described in Example 136 step A and B by substituting aniline with 8-bromoquinoline. MS (ES) 710.2 (M+H)

Example 145

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,7-dimethyl-1H-indole-5-carboxylic acid

Step A. Preparation of ethyl 1,7-dimethyl-1H-indole-5-carboxylate

A mixture of ethyl 7-bromo-1-methyl-1H-indole-5-carboxylate (200 mg, 0.71 mmol), methylboronic acid (57.9 mg, 0.97 mmol), dicyclohexyl(2',6'-dimethoxy-[1,1'-biphenyl]-2-yl)phosphane (79 mg, 0.193 mmol), $K_3PO_4$ (253 mg, 1.29 mmol) and $PdOAc_2$ (22 mg, 0.097 mmol) was degased for 10 min under Ar. Toluene (1.5 ml) was added and the resulting mixture was heated at 100° C. for 3 h. The reaction mixture was concentrated, and the residue was purified by flash chromatography (Combi-flash Rf. Hex/EtOAc=0-20% gradient) to give the title compound (140 mg, 99%). LCMS: $R_T$=1.558 min, MS (ES) 218.2 (M+H).

Step B. Preparation of ethyl 3-bromo-1,7-dimethyl-1H-indole-5-carboxylate

To a stirred solution of ethyl 1,7-dimethyl-1H-indole-5-carboxylate (140 mg, 0.64 mmol) in DMF (2 mL) was added NBS (115 mg, 0.64 mmol) at 0° C. After 1 h, the reaction was quenched by addition of $H_2O$ (10 mL). The mixture was extracted with DCM (10 mL×2). The combined organic solution was washed with $H_2O$ (20 mL), dried and concentrated. The residue was purified by flash chromatography (Combi-flash Rf, Hex/EtOAc=0-10% gradient) to give the title compound (176 mg, 92%) as a yellow solid.

Step C. Example 145

The title compound (33 mg, 50%) was prepared following General coupling procedure B using R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (50 mg, 0.093 mmol), ethyl 3-bromo-1,7-dimethyl-1H-indole-5-carboxylate (33 mg, 0.11 mmol), CuI (0.9 mg, 0.005 mmol), (trans)-1,2-N,N'-dimethylaminocyclohexane (1.3 mg, 0.0093 mmol), and $K_2CO_3$ (26 mg, 0.19 mmol) followed by saponification using General Procedure D. LCMS: $R_T$=2.018 min, MS (ES) 726.3 (M+H).

Example 146

(R)-3-(7-chloro-10-(3-(4-chloro-3,5-dimethylphenoxy)propyl)-6-(3,5-dimethyl-1-((1-methylpiperidin-4-yl)methyl)-1H-pyrazol-4-yl)-4-methyl-1-oxo-3,4-dihydropyrazino[1,2-a]indol-2(1H)-yl)-1-methyl-1H-indole-5-carboxylic acid The title compound (14 mg, 60%) was prepared according to procedures described in Example 137 Step A and B using methyl (R)-3-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-5-carboxylate (20 mg, 0.028 mmol) and (1-methylpiperidin-4-yl)methanol (18 mg, 0.14 mmol). MS (ES) 698.2 (M+H).

Example 147

5-[8-Chloro-11-[3-(4-chloro-3,5-dimethyl-phenoxy)propyl]-7-(4,6-dimethylpyrimidin-5-yl)-1-oxo-4,5-dihydro-3H-[1,4]diazepino[1,2-a]indol-2-yl]quinoline-8-carboxylic acid The title compound (12.7 mg, 38%) was prepared following General coupling procedure A using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (25 mg, 0.046 mmol), methyl 5-bromoquinoline-8-carboxylate (20 mg, 0.075 mmol), $Pd_2(dba)_3$ (4 mg, 0.0043 mmol), Xantphos (6 mg, 0.010 mmol), and $Cs_2CO_3$ (50 mg, 0.153 mmol) followed by saponification using General Procedure D. LCMS: $R_T$=2.008 min, MS (ES) 708.3 (M+H); $^1$H NMR (600 MHz, Chloroform-d) δ 9.20 (s, 1H), 9.00 (dd, J=4.4, 1.6 Hz, 1H), 8.87 (d, J=7.8 Hz, 1H), 8.32 (dd, J=8.6, 1.6 Hz, 1H), 7.81 (d, J=8.6 Hz, 1H), 7.64 (dd, J=8.6, 4.3 Hz, 1H), 7.56 (d, J=7.8 Hz, 1H), 7.39 (d, J=8.6 Hz, 1H), 6.61 (s, 2H), 3.99 (h, J=6.4 Hz, 5H), 3.77 (dt, J=14.2, 5.7 Hz, 1H), 3.20 (dt, J=12.5, 7.4 Hz, 2H), 2.42 (s, 3H), 2.39 (s, 3H), 2.33 (s, 6H), 2.21 (quint. J=6.0 Hz, 2H), 1.95-1.92 (m, 1H), 1.83-1.78 (m, 1H).

Example 148

5-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]naphthalene-1-carboxylic acid The title compound (8.3 mg, 25%) was prepared following General coupling procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (25 mg, 0.046 mmol), methyl 5-bromo-1-naphthoate (20 mg, 0.075 mmol), CuI (5 mg, 0.026 mmol), (trans)-1,2-N,N'-dimethylaminocyclohexane (8 mg, 0.056 mmol), and $K_2CO_3$ (20 mg, 0.14 mmol) followed by saponification using General Procedure D. LCMS: $R_T$=2.107 min, MS (ES) 707.2 (M+H); $^1$H NMR (500 MHz, Chloroform-d) δ 9.14 (s, 1H), 9.05 (t, J=9.7 Hz, 1H), 8.33 (dd, J=7.3, 4.3 Hz, 1H), 8.17 (d, J=10.0 Hz, 0.5H), 7.91 (d, J=10.0 Hz, 0.5H), 7.81 (dd, J=8.7, 1.7 Hz, 1H), 7.63 (dt, J=15.9, 8.0 Hz, 1H), 7.52 (q, J=8.5 Hz, 1H), 7.44 (d, J=10.0 Hz, 0.5H), 7.36 (dd, J=11.5, 8.0 Hz, 1.5H), 6.60 (d, J=9.0 Hz, 2H), 4.42 (dd, J=12.9, 3.8 Hz, 1H), 4.01 (q, J=6.0 Hz, 2H), 3.83-3.75 (m, 1H), 3.49-3.33 (m, 3H), 2.48 (s, 1.5H), 2.46 (s, 1.5H), 2.31 (s, 9H), 2.22 (h, J=7.5 Hz, 2H), 1.31 (d, J=3.9 Hz, 1.5H), 1.29 (d, J=3.9 Hz, 1.5H).

Example 150

8-Chloro-11-(3-(4-chloro-3,5-dimethylphenoxy)propyl)-7-(3,5-dimethyl-1H-pyrazol-4-yl)-2-(quinolin-8-yl)-2,3,4,5-tetrahydro-1H-[1,4]diazepino[1,2-a]indol-1-one The title compound was prepared following the procedure described in Example 109 Step A and B using 8-chloro-11-(3-(4-chloro-3,5-dimethylphenoxy)propyl)-7-(3,5-dimethyl-1-((2-(trimethylsilyl)ethoxy)methyl)-1H-pyrazol-4-yl)-2,3,4,5-tetrahydro-1H-[1,4]diazepino[1,2-a]indol-1-one and 8-bromoquinoline. MS (ES) 698.2 (M+H).

Example 151

5-[8-Chloro-11-[3-(4-chloro-3,5-dimethyl-phenoxy)propyl]-7-(4,6-dimethylpyrimidin-5-yl)-1-oxo-4,5-dihydro-3H-[1,4]diazepino[1,2-a]indol-2-yl]naphthalene-1-carboxylic acid The title compound (6.3 mg, 19%) was prepared following General coupling procedure A using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (25 mg, 0.046 mmol), methyl 5-bromo-1-naphthoate (20 mg, 0.074 mmol), $Pd_2(dba)_3$ (4 mg, 0.0043 mmol), Xantphos (6 mg, 0.010 mmol), and $Cs_2CO_3$ (50 mg, 0.153 mmol) followed by saponification using General Procedure D. LCMS: $R_T$=2.079 min, MS (ES) 707.2 (M+H).

Example 152

6-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-1-methyl-indole-4-carboxylic acid The title compound (8.1 mg, 25%) was prepared following General coupling procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (25 mg, 0.046 mmol), methyl 6-bromo-1-methyl-1H-indole-4-carboxylate (20 mg, 0.075 mmol), CuI (5 mg, 0.026 mmol), (trans)-1,2-N,N'-dimethylaminocyclohexane (8 mg, 0.056 mmol), and $K_2CO_3$ (20 mg, 0.14 mmol) followed by saponification using General Procedure D. LCMS: $R_T$=2.075 min, MS (ES) 710.2 (M+H); $^1H$ NMR (500 MHz, Chloroform-d) δ 9.15 (s, 1H), 7.82-7.72 (m, 2H), 7.64 (s, 1H), 7.33 (d, J=8.6 Hz, 1H), 7.24 (d, J=3.1 Hz, 1H), 7.14 (d, J=3.2 Hz, 1H), 6.62 (s, 2H), 4.41 (dd, J=13.0, 3.6 Hz, 1H), 4.00 (t, J=6.2 Hz, 2H), 3.83 (s, 3H), 3.73 (d, J=6.0 Hz, 1H), 3.60 (d, J=12.7 Hz, 1H), 3.47-3.32 (m, 2H), 2.46 (s, 3H), 2.31 (s, 6H), 2.28 (s, 3H), 2.22 (q, J=6.9 Hz, 2H), 1.20 (d, J=6.4 Hz, 3H).

Example 153

3-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-1-methyl-indole-6-carboxylic acid The title compound (16.3 mg, 49%) was prepared following General coupling procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (25 mg, 0.046 mmol), methyl 3-bromo-1-methyl-1H-indole-6-carboxylate (20 mg, 0.075 mmol), CuI (5 mg, 0.026 mmol), (trans)-1,2-N,N'-dimethylaminocyclohexane (8 mg, 0.056 mmol), and $K_2CO_3$ (20 mg, 0.14 mmol) followed by saponification using General Procedure D. LCMS: $R_T$=2.061 min, MS (ES) 710.2 (M+H); $^1H$ NMR (600 MHz, Chloroform-d) δ 9.25 (s, 1H), 7.79 (d, J=8.6 Hz, 1H), 7.63 (d, J=1.9 Hz, 1H), 7.58-7.51 (m, 1H), 7.34 (d, J=8.6 Hz, 1H), 6.65 (s, 2H), 4.35-4.30 (m, 4H), 4.01 (t, J=6.2 Hz, 2H), 3.88 (s, 2H), 3.66 (s, 2H), 3.18 (t, J=7.5 Hz, 2H), 2.45 (s, 6H), 2.34 (s, 6H), 2.23 (dd, J=10.0, 4.5 Hz, 2H), 1.73 (s, 2H).

Example 154

5-[8-Chloro-11-[3-(4-chloro-3,5-dimethyl-phenoxy)propyl]-7-(4,6-dimethylpyrimidin-5-yl)-1-oxo-4,5-dihydro-3H-[1,4]diazepino[1,2-a]indol-2-yl]-2,3-dihydro-1,4-benzodioxine-7-carboxylic acid The title compound (5.7 mg, 17%) was prepared following General coupling procedure A using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (25 mg, 0.046 mmol), methyl 8-bromo-2,3-dihydrobenzo[b][1,4]dioxine-6-carboxylate (20 mg, 0.074 mmol), $Pd_2(dba)_3$ (4 mg, 0.0043 mmol), Xantphos (6 mg, 0.010 mmol), and $Cs_2CO_3$ (50 mg, 0.153 mmol) followed by saponification using General Procedure D. LCMS: $R_T$=1.975 min, MS (ES) 715.2 (M+H); $^1H$ NMR (600 MHz, Chloroform-d) δ 9.25 (s, 1H), 7.79 (d, J=8.6 Hz, 1H), 7.63 (d, J=1.9 Hz, 1H), 7.58-7.51 (m, 1H), 7.34 (d, J=8.6 Hz, 1H), 6.65 (s, 2H), 4.35-4.30 (m, 4H), 4.01 (t, J=6.2 Hz, 2H), 3.88 (s, 2H), 3.66 (s, 2H), 3.18 (t, J=7.5 Hz, 2H), 2.45 (s, 6H), 2.34 (s, 6H), 2.23 (dd, J=10.0, 4.5 Hz, 2H), 1.73 (s, 2H).

Example 155

6-[8-Chloro-11-[3-(4-chloro-3,5-dimethyl-phenoxy)propyl]-7-(4,6-dimethylpyrimidin-5-yl)-1-oxo-4,5-dihydro-3H-[1,4]diazepino[1,2-a]indol-2-yl]-1-methyl-indazole-4-carboxylic acid The title compound (9 mg, 27%) was prepared following General coupling procedure A using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (25 mg, 0.046 mmol), methyl 6-bromo-1-methyl-1H-indazole-4-carboxylate (20 mg, 0.074 mmol), $Pd_2(dba)_3$ (4 mg, 0.0043 mmol), Xantphos (6 mg, 0.010 mmol), and $Cs_2CO_3$ (50 mg, 0.153 mmol) followed by saponification using General Procedure D. LCMS: $R_T$=1.960 min, MS (ES) 711.3 (M+H); $^1H$ NMR (600 MHz, Chloroform-d) δ 9.22 (s, 1H), 8.51 (d, J=0.9 Hz, 1H), 7.83-7.76 (m, 2H), 7.74-7.70 (m, 1H), 7.36 (d, J=8.6 Hz, 1H), 6.65 (s, 2H), 4.11 (s, 3H), 4.02 (t, J=6.1 Hz, 2H), 3.89 (t, J=6.4 Hz, 2H), 3.83 (t, J=6.0 Hz, 2H), 3.22 (dd, J=8.3, 6.5 Hz, 2H), 2.40 (s, 6H), 2.32 (s, 6H), 2.20 (s, 2H), 1.90-1.85 (m, 2H).

Example 156

3-[8-Chloro-11-[3-(4-chloro-3,5-dimethyl-phenoxy)propyl]-7-(4,6-dimethylpyrimidin-5-yl)-1-oxo-4,5-dihydro-3H-[1,4]diazepino[1,2-a]indol-2-yl]-1-methyl-indole-5-carboxylic acid The title compound (7.5 mg, 23%) was prepared following General coupling procedure A using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (25 mg, 0.046 mmol), methyl 3-bromo-1-methyl-1H-indole-5-carboxylate (20 mg, 0.074 mmol), $Pd_2(dba)_3$ (4 mg, 0.0043 mmol), Xantphos (6 mg, 0.010 mmol), and $Cs_2CO_3$ (50 mg, 0.153 mmol) followed by saponification using General Procedure D. LCMS: $R_T$=1.964 min, MS (ES) 710.2 (M+H); $^1H$ NMR (600 MHz, Chloroform-d) δ 9.21 (s, 1H), 8.25 (s, 1H), 8.02 (ddd, J=8.8, 4.1, 1.5 Hz, 1H), 7.79 (dd, J=8.6, 6.2 Hz, 1H), 7.37 (dd, J=24.7, 8.6 Hz, 2H), 7.16 (s, 1H), 6.65 (d, J=4.6 Hz, 2H), 4.01 (t, J=6.1 Hz, 2H), 3.90 (s, 2H), 3.84 (s, 3H), 3.79 (t, J=6.0 Hz, 2H), 3.21 (t, J=9.0 Hz, 2H), 2.40 (s, 6H), 2.32 (s, 6H), 2.25 (quint. J=6.0 Hz, 2H), 1.84-1.80 (m, 2H).

Example 157

(R)-2-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-5-carboxylic acid The title compound (22 mg, 62%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 2-chloroquinoline-5-carboxylate (16 mg, 0.06 mmol), Pd$_2$(dba)$_3$ (1 mg, 0.001 mmol), Xantphos (2 mg, 0.003 mmol), and Cs$_2$CO$_3$ (25 mg, 0.075 mmol) followed by saponification using General Procedure D. LCMS: R$_T$=1.323 min, MS (ES) 710.2 (M+H).

Example 158

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-propyl-1H-indole-5-carboxylic acid Step A. Preparation of propyl 3-bromo-1-propyl-1H-indole-5-carboxylate The title compound (56 mg, 61%) was prepared following General Procedure F using 1H-indole-5-carboxylic acid (46 mg, 0.28 mmol), NBS (51 mg, 0.28 mmol), NaH (25 mg, 0.62 mmol) and 1-iodopropane (61 μL, 0.48 mmol). LCMS: R$_T$=1.761 min, MS (ES) 324.2 (M+H).

Step B. Example 158

The title compound (29 mg, 78%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), propyl 3-bromo-1-propyl-1H-indole-5-carboxylate (15 mg, 0.06 mmol), CuI (5 mg, 0.025 mmol), (trans)-1,2-N,N'-dimethylaminocyclohexane (8 μL, 0.05 mmol), and K$_2$CO$_3$ (25 mg, 0.075 mmol) followed by saponification using General Procedure D. LCMS: R$_T$=2.104 min, MS (ES) 740.2 (M+H); $^1$H NMR (400 MHz, DMSO-d$_6$) δ 8.11 (d, J=1.6 Hz, 1H), 7.84-7.69 (m, 2H), 7.62 (dd, J=8.2, 1.7 Hz, 2H), 7.29 (d, J=8.6 Hz, 1H), 6.73 (s, 2H), 4.48 (dt, J=12.7, 3.2 Hz, 1H), 4.28-4.10 (m, 4H), 3.98 (s, 3H), 3.78 (s, 1.5H), 3.77 (s, 1.5H), 3.71-3.56 (m, 2H), 3.44-3.10 (m, 2H), 2.24 (s, 6H), 2.12 (s, 1.5H), 2.11-2.04 (m, 2H), 2.03 (s, 1.5H), 1.98 (s, 1.5H), 1.89 (s, 1.5H), 1.80 (h, J=7.4 Hz, 2H), 1.09 (d, J=6.4 Hz, 3H), 0.88 (td, J=7.4, 2.7 Hz, 3H).

Example 159

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,5-dimethyl-1H-indole-3-carboxylic acid (Separated Stereoisomer A)

Step A. Preparation of 7-bromo-5-methyl-1H-indole-3-carboxylic acid

To a stirred solution of 7-bromo-5-methyl-1H-indole (300 mg, 1.43 mmol) in DMF (1 mL) was added TFAA (0.24 mL, 1.71 mmol) dropwise at at 0° C. The reaction solution was warmed up to rt and stirred overnight. The reaction was quenched with H$_2$O (10 mL) then extracted with DCM (10 mL×2). The combined organic solution was dried and concentrated in vacuo. The residue was dissolved in H$_2$O (1 mL) and NaOH (200 mg, 5.00 mmol) was added. The reaction mixture was refluxing for 3 h then neutralized with HCl (6 N). The resulting mixture was extracted with EtOAc (20 mL×2). The combined organic solution was dried, concentrated and purified by reverse phase HPLC (Phenomenex Gemini C18, H$_2$O/CH$_3$CN gradient to 20-80% MeCN 0.1% TFA) to give the title compound (100 mg, 30%). LCMS: R$_T$=1.252 min, MS (ES) 254.1 (M+H).

Step B. Preparation of methyl 7-bromo-1,5-dimethyl-1H-indole-3-carboxylate

To a stirred solution of 7-bromo-5-methyl-1H-indole-3-carboxylic acid (100 mg, 0.394 mmol) in DMF (1 mL) was added NaH (38 mg, 1.57 mmol) at 0° C. After 15 min, MeI (0.098 mL, 1.574 mmol) was added, and the resulting mixture was stirred for 1 h. The reaction was quenched with H$_2$O (3 mL) then extracted with DCM (10 mL×2). The combined organic solution was dried, concentrated to give the title compound. It was used for next step without further purification. MS (ES) 282.1 (M+H)

Step C. Example 159

The title compound (70 mg, 60%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (200 mg, 0.37 mmol), methyl 7-bromo-1,5-dimethyl-1H-indole-3-carboxylate (115 mg, 0.41 mmol), Pd$_2$(dba)$_3$ (20 mg, 0.022 mmol), Xantphos (43 mg, 0.074 mmol), and Cs$_2$CO$_3$ (242 mg, 0.74 mmol) followed by saponification using General Procedure D. During the final purification step, the title compound was isolated as a separated atropisomer (1$^{st}$ fraction, absolute stereochemistry undetermined). LCMS: R$_T$=2.044 min, MS (ES) 726.3 (M+H).

Example 160

(R)-3-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1,7-dimethyl-1H-indole-5-carboxylic acid The title compound was prepared following the procedure described in Example 109 Step A and B using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one and ethyl 3-bromo-1,7-dimethyl-1H-indole-5-carboxylate. MS (ES) 712.2 (M+H).

Example 161

(R)-3-(7-chloro-10-(3-(4-chloro-3,5-dimethylphenoxy)propyl)-6-(3,5-dimethyl-1-((1-methylpiperidin-4-yl)methyl)-1H-pyrazol-4-yl)-4-methyl-1-oxo-3,4-dihydropyrazino[1,2-a]indol-2(1H)-yl)-1,7-dimethyl-1H-indole-5-carboxylic acid The title compound (25 mg, 74%) was prepared according to procedures described in Example 137 Step A and B using ethyl (R)-3-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1,7-dimethyl-1H-indole-5-carboxylate (34 mg, 0.046 mmol) and (1-methylpiperidin-4-yl)methanol (30 mg, 0.23 mmol). LCMS: $R_T$=1.767 min, MS (ES) 823.3 (M+H).

Example 162

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,5-dimethyl-1H-indole-3-carboxylic acid (Separated Stereoisomer B)

The title compound was isolated along with Example 159 as a separated atropisomer ($2^{nd}$ fraction, absolute stereochemistry underminded). LCMS: $R_T$=2.074 min, MS (ES) 726.3 (M+H).

Example 163

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indazole-5-carboxylic acid The title compound (20 mg, 56%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-methyl-1H-indazole-5-carboxylate (17 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D. LCMS: $R_T$=1.994 min, MS (ES) 713.2 (M+H).

Example 164

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-ethyl-1H-indole-5-carboxylic acid Step A. Preparation of ethyl 3-bromo-1-ethyl-1H-indole-5-carboxylate The title compound (51 mg, 61%) was prepared following General Procedure F using 1H-indole-5-carboxylic acid (46 mg, 0.28 mmol), NBS (51 mg, 0.28 mmol), NaH (25 mg, 0.62 mmol) and EtI (53 μL, 0.62 mmol). LCMS: $R_T$=1.756 min, MS (ES) 296.1 (M+H).

Step B. Example 164

The title compound (34 mg, 94%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), ethyl 3-bromo-1-ethyl-1H-indole-5-carboxylate (15 mg, 0.06 mmol), CuI (5 mg, 0.025 mmol), (trans)-1,2-N,N'-dimethylaminocyclohexane (8 μL, 0.05 mmol), and $K_2CO_3$ (25 mg, 0.075 mmol) followed by saponification using General Procedure D. LCMS: $R_T$=1.155 min, MS (ES) 726.3 (M+H).

Example 165

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indazole-7-carboxylic acid The title compound (27 mg, 76%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-methyl-1H-indazole-7-carboxylate (15 mg, 0.06 mmol), CuI (5 mg, 0.025 mmol), (trans)-1,2-N,N'-dimethylaminocyclohexane (8 μL, 0.05 mmol), and $K_2CO_3$ (25 mg, 0.075 mmol) followed by saponification using General Procedure D. LCMS: $R_T$=2.058 min, MS (ES) 713.2 (M+H).

Example 166

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-isopropyl-1H-indole-5-carboxylic acid Step A. Preparation of isopropyl 3-bromo-1-isopropyl-1H-indole-5-carboxylate The title compound (28 mg, 30%) was prepared following General Procedure F using 1H-indole-5-carboxylic acid (46 mg, 0.28 mmol), NBS (51 mg, 0.28 mmol), NaH (25 mg, 0.62 mmol) and 2-iodopropane (61 μL, 0.62 mmol). LCMS: $R_T$=1.765 min, MS (ES) 324.2 (M+H).

Step B. Example 166

The title compound (13 mg, 37%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), isopropyl 3-bromo-1-isopropyl-1H-indole-5-carboxylate (15 mg, 0.06 mmol), CuI (5 mg, 0.025 mmol), (trans)-1,2-N,N'-dimethylaminocyclohexane (8 μL, 0.05 mmol), and $K_2CO_3$ (25 mg, 0.075 mmol) followed by saponification using General Procedure D. LCMS: $R_T$=2.087 min, MS (ES) 740.2 (M+H).

Example 167

(R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-pyrrolo[2,3-b]pyridine-6-carboxylic acid The title compound (87% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 4-bromo-1-methyl-1H-pyrrolo[2,3-b]pyridine-6-carboxylate followed by saponification using General Procedure D. MS (ES) 713.3 (M+H); $^1$H NMR (DMSO, 400 MHz) δ (ppm) 7.83 (d, J=4.8 Hz, 1H), 7.78 (d, J=8.8 Hz, 1H), 7.75 (d, J=3.2 Hz, 1H), 7.29 (d, J=8.8 Hz, 1H), 6.70 (s, 2H), 6.44 (dd, J=8.4, 3.2 Hz, 1H), 4.71-4.64 (m, 1H), 4.20-4.10 (m, 2H), 3.99-3.95 (m, 2H), 3.89 (s, 3H), 3.73 (s, 3H), 3.33-3.20 (m, 2H), 2.23 (s, 6H), 2.09 (s, 1.5H), 2.09-2.03 (m, 2H), 2.00 (s, 1.5H), 1.98 (s, 1.5H), 1.89 (s, 1.5H), 1.00 (dd, J=6.4, 3.6 Hz, 3H).

Example 168

7-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-1-methyl-indole-3-carboxylic acid The title compound (3.8 mg, 12%) was prepared following General coupling procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (25 mg, 0.046 mmol), methyl 7-bromo-1-methyl-1H-indole-3-carboxylate (20 mg, 0.075 mmol), CuI (5 mg, 0.026 mmol), (trans)-1,2-N,N'-dimethylaminocyclohexane (8 mg, 0.056 mmol), and $K_2CO_3$ (20 mg, 0.14 mmol) followed by saponification using General Procedure D. LCMS: $R_T$=2.056 min, MS (ES) 710.1 (M+H); $^1$H NMR (500 MHz, Chloroform-d) δ 9.12 (s, 1H), 8.25 (d, J=7.9 Hz, 0.7H), 8.21 (d, J=7.9 Hz, 0.3H), 7.79 (s, 0.7H), 7.77 (s, 1.3H), 7.36 (d, J=8.9 Hz, 1.3H), 7.32 (d, J=7.8 Hz, 0.7H), 7.05 (d, J=7.6 Hz, 1.3H), 7.00 (d, J=7.6 Hz, 0.7H), 6.62 (s, 1.3H), 6.57 (s, 0.7H), 4.16 (dd, J=13.5, 3.5 Hz, 1H), 4.08-3.96 (m, 2H), 3.93 (s, 1H), 3.84-3.71 (m, 3H) 3.54 (dd, J=23.0, 13.2 Hz, 1H), 3.37 (dq, J=14.4, 7.2 Hz, 2H), 2.44 (s, 3H), 2.34-2.28 (m, 6H), 2.26 (s, 3H), 2.23-2.16 (m, 2H), 1.30 (d, J=6.5 Hz, 2H), 1.19 (d, J=6.5 Hz, 1H).

Example 169

(R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-pyrrolo[2,3-b]pyridine-2-carboxylic acid The title compound (90% yield) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 4-bromo-1-methyl-1H-pyrrolo[2,3-b]pyridine-2-carboxylate followed by saponification using General Procedure D. MS (ES) 713.3 (M+H); $^1$H NMR (DMSO, 400 MHz) δ (ppm) 8.47 (d, J=4.8 Hz, 1H), 7.76 (d, J=8.8 Hz, 1H), 7.29 (d, J=8.4 Hz, 1H), 7.15 (d, J=5.2 Hz, 1H), 7.08 (s, 1H), 6.70 (s, 2H), 4.68-4.63 (m, 1H), 4.18-4.09 (m, 2H), 4.06 (s, 3H), 4.02-3.95 (m, 2H), 3.76 (s, 3H), 3.37-3.16 (m, 2H), 2.25 (s, 3H), 2.22 (s, 6H), 2.06 (s, 1.5H), 2.03-1.99 (m, 2H), 1.98 (s, 1.5H), 1.89 (s, 1.5H), 0.99 (d, J=6.4 Hz, 3H).

Example 170

2-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-4-carboxylic acid Step A. Preparation of methyl 2-bromo-1H-indole-4-carboxylate To a solution of methyl 2-oxoindoline-4-carboxylate (100 mg, 0.523 mmol) in DCE (5 mL) were added $POBr_3$ (880 mg, 3.05 mmol) and imidazole (140 mg, 2.06 mmol). The reaction was heated to 80° C. and stirred for 16 h. The reaction was cooled to RT, quenched with $H_2O$ (20 mL) and extracted with DCM (3×20 mL). The combined organic extracts were dried over $MgSO_4$, filtered, and concentrated in vacuo. The crude reaction mixture was purified by flash chromatography (Combi-flash Rf, Hex/EtOAc=0-100% gradient) to afford the title compound (27 mg, 20%).

Step B. Preparation of methyl 2-bromo-1-methyl-1H-indole-4-carboxylate

The title compound (21 mg, 75%) was prepared following General Procedure F using methyl 2-bromo-1H-indole-4-carboxylate, NaH (6 mg, 0.25 mmol) and MeI (30 mg, 0.211 mmol).

Step C. Example 170

The title compound (9.7 mg, 29%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (25 mg, 0.046 mmol), methyl 2-bromo-1-methyl-1H-indole-4-carboxylate (20 mg, 0.075 mmol), CuI (5 mg, 0.026 mmol), (trans)-1,2-N,N'-dimethylaminocyclohexane (8 mg, 0.056 mmol), and $K_2CO_3$ (20 mg, 0.14 mmol) followed by saponification using General Procedure D. LCMS: $R_T$=2.116 min, MS (ES) 712.1 (M+H); $^1$H NMR (600 MHz, Chloroform-d) δ 7.84 (dt, J=7.7, 1.4 Hz, 1H), 7.56 (dd, J=8.6, 5.8 Hz, 1H), 7.41 (t, J=7.4 Hz, 1H), 7.22-7.14 (m, 2H), 6.88 (s, 1H), 6.46 (d, J=1.5 Hz, 2H), 4.29-4.09 (m, 2H), 3.87-3.83 (m, 2H), 3.79 (s, 3H), 3.52 (s, 1.5H), 3.51 (s, 1.5H), 3.47-3.37 (m, 1H), 3.27 (dtd, J=12.5, 7.3, 5.0 Hz, 1H), 3.19 (dt, J=13.6, 7.4 Hz, 1H), 2.17 (s, 6H), 2.10 (s, 1.5H), 2.09 (s, 1.5H), 2.05-2.02 (m, 2H), 1.93 (s, 1.5H), 1.91 (s, 15H), 1.07 (br. s, 1.5H), 1.03 (br. S, 1.5H).

Example 171

(R)-5-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylic acid The title compound (30 mg, 84%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 5-bromo-1-methyl-1H-indole-3-carboxylate (16 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D. LCMS: $R_T$=2.018 min, MS (ES) 712.2 (M+H); $^1$H NMR (400 MHz, DMSO-$d_6$) δ 8.10 (d, J=0.9 Hz, 1H), 7.94 (t, J=2.1 Hz, 1H), 7.74 (d, J=8.6 Hz, 1H), 7.56 (d, J=8.8 Hz, 1H), 7.29 (d, J=8.6 Hz, 1H), 7.23 (td, J=8.9, 2.1 Hz, 1H), 6.74 (s, 2H), 4.49 (dd, J=12.9, 3.8 Hz, 1H), 4.21-4.10 (m, 1H), 4.01-3.94 (m, 3H), 3.88 (s, 3H), 3.78 (s, 1.5H), 3.77 (s, 1.5H), 3.23 (h, J=6.9 Hz, 2H), 2.25 (s, 6H), 2.12 (s, 1.5H), 2.07 (q, J=7.1, 6.5 Hz, 2H), 2.03 (s, 1.5H), 1.98 (s, 1.5H), 1.88 (s, 1.5H), 1.05 (dd, J=6.5, 3.8 Hz, 3H).

Example 172

(R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-6-carboxylic acid The title compound (26 mg, 73%) was prepared following General coupling procedure A using (R)-7-chloro-10-(3-(4- chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 4-bromoquinoline-6-carboxylate (16 mg, 0.06 mmol). Pd$_2$(dba)$_3$ (1 mg, 0.001 mmol), Xantphos (2 mg, 0.003 mmol), and Cs$_2$CO$_3$ (25 mg, 0.075 mmol) followed by saponification using General Procedure D. LCMS: R$_T$=1.816 min, MS (ES) 710.2 (M+H).

Example 173

4-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-ethyl-indole-3-carboxylic acid Step A. Preparation of methyl 4-bromo-1-ethyl-1H-indole-3-carboxylate To a solution of 4-bromo-1H-indole-3-carboxylic acid (700 mg, 2.92 mmol) in THF (20 mL) and MeOH (0 mL) was added trimethylsilyldiazomethane (2.0 M solution in Et$_2$O, 1.6 mL, 3.2 mmol) was added at 0° C., and the reaction mixture was stirred for 2 h then warmed to RT. The reaction was quenched with AcOH, concentrated in vacuo, and the crude residue was purified by flash chromatography (Combi-flash Rf, Hex/EtOAc=0-100% gradient) to give methyl 4-bromo-1H-indole-3-carboxylic acid (513 mg, 69% yield). The title compound (52 mg, 93%) was prepared following General Procedure F using methyl 4-bromo-1H-indole-3-carboxylic acid (50 mg, 0.20 mmol), NaH (9 mg, 0.375 mmol) and EtBr (40 mg, 0.367 mmol).

Step B. Example 173

The title compound (11.6 mg, 35%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 4-bromo-1-ethyl-1H-indole-3-carboxylate (20 mg, 0.071 mmol), CuI (5 mg, 0.026 mmol), (trans)-1,2-N,N'-dimethylaminocyclohexane (8 mg, 0.056 mmol), and K$_2$CO$_3$ (20 mg, 0.14 mmol) followed by saponification using General Procedure D. LCMS: R$_T$=1.996, 2.029 min, MS (ES) 726.1 (M+H).

Example 174

2-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-5-carboxylic acid Step A. Preparation of methyl 2-bromo-1-methyl-1H-indole-5-carboxylate The title compound (33 mg, 23%) was prepared following the procedures described in Example 170 Step A using methyl 2-oxoindoline-5-carboxylate (100 mg, 0.52 mmol), POBr$_3$ (400 mg, 1.4 mmol), imidazole (100 mg, 1.47 mmol), and Step B using NaH (6 mg, 0.25 mmol) and MeI (30 mg, 0.21 mmol).

Step B. Example 174

The title compound (8.9 mg, 27%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 2-bromo-1-methyl-1H-indole-5-carboxylate (20 mg, 0.074 mmol), CuI (5 mg, 0.026 mmol), (trans)-1,2-N,N'-dimethylaminocyclohexane (8 mg, 0.056 mmol), and K$_2$CO$_3$ (20 mg, 0.14 mmol) followed by saponification using General Procedure D. LCMS: R$_T$=2.097 min, MS (ES) 712.2 (M+H); $^1$H NMR (600 MHz, Chloroform-d) δ 8.38 (s, 1H), 8.00 (ddd, J=8.6, 3.0, 1.6 Hz, 1H), 7.72 (dd, J=8.6, 4.6 Hz, 1H), 7.39-7.30 (m, 2H), 6.62 (s, 2H), 6.41 (d, J=2.4 Hz, 1H), 4.44-4.24 (m, 2H), 4.03-4.00 (m, 2H), 3.96 (s, 3H), 3.69 (s, 1.5H), 3.68 (s 1.5H), 3.62-3.53 (m, 1H), 3.44 (dt, J=14.1, 7.3 Hz, 1H), 3.35 (dt, J=13.1, 7.5 Hz, 1H), 2.33 (d, J=1.3 Hz, 6H), 2.26 (s, 1.5H), 2.24 (s, 1.5H), 2.23-2.18 (m, 2H), 2.09 (s, 1.5H), 2.08 (s, 1.5H), 1.23 (d, J=6.2 Hz, 1.5H), 1.22 (d, J=6.2 Hz, 1.5H).

Example 175

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indazole-4-carboxylic acid The title compound (9 mg, 25%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-methyl-1H-indazole-4-carboxylate (17 mg, 0.06 mmol), Pd$_2$(dba)$_3$ (1 mg, 0.001 mmol), Xantphos (2 mg, 0.003 mmol), and Cs$_2$CO$_3$ (25 mg, 0.075 mmol) followed by saponification using General Procedure D. LCMS: R$_T$=1.948 min, MS (ES) 713.2 (M+H).

Example 176

3-[8-Chloro-11-[3-(4-chloro-3,5-dimethyl-phenoxy)propyl]-7-(4,6-dimethylpyrimidin-5-yl)-1-oxo-4,5-dihydro-3H-[1,4]diazepino[1,2-a]indol-2-yl]-1-methyl-indole-6-carboxylic acid The title compound (5.4 mg, 20%) was prepared following General coupling procedure B using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (20 mg, 0.037 mmol), methyl 3-bromo-1-methyl-1H-indole-6-carboxylate (20 mg, 0.074 mmol), CuI (5 mg, 0.026 mmol), (trans)-1,2-N,N'-dimethylaminocyclohexane (8 mg, 0.056 mmol), and K$_2$CO$_3$ (40 mg, 0.29 mmol) followed by saponification using General Procedure D. LCMS: R$_T$=2.020 min, MS (ES) 710.2 (M+H).

Example 177

3-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-1-methyl-indole-5-carboxylic acid The title compound (11.2 mg, 43%) was prepared following General coupling procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-(2H)-one (20 mg, 0.037 mmol), methyl 3-bromo-1-methyl-1H-indole-5-carboxylate (20 mg, 0.074 mmol), CuI (5 mg, 0.026 mmol), (trans)-1,2-N,N'-dimethylaminocyclohexane (8 mg, 0.056 mmol), and K₂CO₃ (40 mg, 0.29 mmol) followed by saponification using General Procedure D. LCMS: $R_T$=2.018 min, MS (ES) 710.2 (M+H); ¹H NMR (500 MHz, Chloroform-d) δ 9.16 (s, 1H), 8.30 (s, 1H), 8.00 (d, J=10.0 Hz, 1H), 7.77 (d, J=8.5 Hz, 1H), 7.36 (d, J=5.0 Hz, 1H), 7.35 (d, J=10.0 Hz, 1H), 6.62 (s, 2H), 4.38 (dd, J=13.1, 3.7 Hz, 1H), 4.00 (s, 2H), 3.83 (s, 3H), 3.74 (s, 1H), 3.62 (d, J=12.7 Hz, 1H), 3.39 (m, 2H), 2.44 (s, 3H), 2.31 (s, 6H), 2.29 (s, 3H), 2.25-2.18 (m, 3H), 1.24 (d, J=6.5 Hz, 3H).

Example 178

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid Step A. Preparation of ethyl 7-bromo-1-methyl-1H-indole-2-carboxylate The title compound (45 mg, 80%) was prepared following General Procedure G using ethyl 7-bromo-1H-indole-2-carboxylate (54 mg, 0.20 mmol), NaH (10 mg, 0.24 mmol) and MeI (15 µL, 0.24 mmol). LCMS: $R_T$=1.882 min, MS (ES) 282.1 (M+H).

Step B. Example 178

The title compound (16 mg, 45%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), ethyl 7-bromo-1-methyl-1H-indole-2-carboxylate (14 mg, 0.06 mmol), CuI (5 mg, 0.025 mmol), (trans)-1,2-N,N'-dimethylaminocyclohexane (8 µL, 0.05 mmol), and K₂CO₃ (25 mg, 0.075 mmol) followed by saponification using General Procedure D. LCMS: $R_T$=2.059 min, MS (ES) 712.2 (M+H).

Example 179

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indazole-4-carboxylic acid (Separated Stereoisomer, 2ⁿᵈ Eluting Atropisomer)

The title compound (absoluted configuration unknown, 6 mg, 17%) was isolated from Example 175 using reverse phase HPLC (Phenomenex Gemini C18, H₂O/CH₃CN gradient to 35-95% MeCN 0.1% TFA, 10 mins gradient) as the second eluting stereoisomer. LCMS: $R_T$=1.961 min, MS (ES) 713.2 (M+H).

Example 180

2-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-6-carboxylic acid Step A. Preparation of methyl 2-bromo-1-methyl-1H-indole-6-carboxylate The title compound (74 mg, 53%) was prepared following the procedures described in Example 170 Step A using methyl 2-oxoindoline-6-carboxylate (100 mg, 0.52 mmol). POBr₃ (400 mg, 1.39 mmol), and imidazole (100 mg, 1.47 mmol) and Step B using NaH (15 mg, 0.63 mmol) and MeI (60 mg, 0.42 mmol).

Step B. Example 180

The title compound (11.9 mg, 36%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 2-bromo-1-methyl-1H-indole-6-carboxylate (20 mg, 0.074 mmol), CuI (5 mg, 0.026 mmol), (trans)-1,2-N,N'-dimethylaminocyclohexane (8 mg, 0.056 mmol), and K₂CO₃ (20 mg, 0.14 mmol) followed by saponification using General Procedure D. LCMS: $R_T$=2.096 min, MS (ES) 712.2 (M+H); ¹H NMR (600 MHz, Chloroform-d) δ 7.96 (d, J=3.0 Hz, 1H), 7.66 (dt, J=8.3, 1.8 Hz, 1H), 7.52 (dd, J=8.6, 4.6 Hz, 1H), 7.41 (dd, J=8.3, 1.5 Hz, 1H), 7.13 (dd, J=8.6, 6.0 Hz, 1H), 6.42 (d, =2.2 Hz, 2H), 6.16 (s, 1H), 4.28-4.02 (m, 2H), 3.90-3.78 (m, 2H), 3.74 (s, 3H), 3.51 (s, 1.5H), 3.50 (s, 1.5H), 3.41-3.31 (m, 1H), 3.29-3.22 (m, 1H), 3.14 (m, 1H), 2.13 (s, 6H), 2.05 (s, 1.5H), 2.03 (s, 1.5H), 2.02-1.97 (m, 2H), 1.88 (d, J=6.2 Hz, 3H), 1.03 (d, J=3.9 Hz, 1.5H), 0.97 (d, J=5.6 Hz, 1.5H).

Example 181

4-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-(2-methoxyethyl)indole-3-carboxylic acid Step A. Preparation of methyl 4-bromo-1-(2-methoxyethyl)-1H-indole-3-carboxylate The title compound (58 mg, 94%) was prepared following the procedure described in Example 173 Step A using methyl 4-bromo-1H-indole-3-carboxylate (50 mg, 0.20 mmol), NaH (9 mg, 0.38 mmol), and 1-bromo-2-methoxyethane (50 mg, 0.36 mmol).

Step B. Example 181

The title compound (13.7 mg, 39%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(21H)-one (25 mg, 0.046 mmol), methyl 4-bromo-1-(2-methoxyethyl)-1H-indole-3-carboxylate (25 mg, 0.080 mmol), CuI (5 mg, 0.026 mmol), (trans)-1,2-N,N'-dimethylaminocyclohexane (8 mg, 0.056 mmol), and K₂CO₃ (20 mg, 0.14 mmol) followed by saponification using General Procedure D. LCMS: $R_T$=1.956, 1.908 min, MS (ES) 756.1 (M+H).

Example 182

4-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-3-carboxylic acid Step A. Preparation of methyl 4-bromo-1-methyl-1H-indole-3-carboxylate The title compound (51 mg, 97% yield) was prepared following the procedure described in Example 173 Step A using methyl 4-bromo-1H-indole-3-carboxylate (50 mg, 0.20 mmol), NaH (9 mg, 0.38 mmol), and MeI (50 mg, 0.35 mmol).

Step B. Example 182

The title compound (11 mg, 34%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 4-bromo-1-methyl-1H-indole-3-carboxylate (20 mg, 0.074 mmol), CuI (5 mg, 0.026 mmol), (trans)-1,2-N,N'-dimethylaminocyclohexane (8 mg, 0.056 mmol), and $K_2CO_3$ (20 mg, 0.14 mmol) followed by saponification using General Procedure D. LCMS: $R_T$=1.952, 1.988 min, MS (ES) 712.00 (M+H).

Example 183

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,5-dimethyl-1H-indole-3-carboxylic acid The title compound was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-bromo-1,5-dimethyl-1H-indole-3-carboxylate followed by saponification using General Procedure D. MS (ES) 726.3 (M+H).

Example 184

(R)-5-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-2-carboxylic acid The title compound was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 5-bromoquinoline-2-carboxylate followed by saponification using General Procedure D. MS (ES) 710.2 (M+H); $^1$H NMR (MeOD, 400 MHz) δ (ppm) 8.56 (d, J=8.4 Hz, 1H), 8.22 (d, J=8.8 Hz, 1H), 8.08 (dd, J=7.6, 1.2 Hz, 1H), 7.83 (s, 1H), 7.79 (d, J=7.6 Hz, 1H), 7.76 (d, J=8.4 Hz, 1H), 7.29 (d, J=7.6 Hz, 1H), 6.70 (s, 2H), 4.33-4.29 (m, 1H), 3.97 (t, J=6.0 Hz, 2H), 3.85 (s, 3H), 3.72-3.62 (m, 2H), 3.51-3.31 (m, 2H), 2.28 (s, 6H), 2.24 (s, 1.5H), 2.22-2.15 (m, 2H), 2.17 (s, 1.5H), 2.09 (s, 1.5H), 2.09 (s, 1.5H), 2.02 (s, 1.5H), 1.31 (s, 3H).

Example 185

(R)-6-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-2-naphthoic acid The title compound (28 mg, 79%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (27 mg, 0.05 mmol), methyl 6-bromo-2-naphthoate (16 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D. LCMS: $R_T$=2.120 min, MS (ES) 709.0 (M+H).

Example 186

(R)-5-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-2-naphthoic acid (Separated Stereoisomer, 1$^{st}$ Eluting Atropisomer)

The title compound was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 5-bromo-2-naphthoate (16 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D and purified by reverse phase HPLC (Phenomenex Gemini C18, $H_2O/CH_3CN$ gradient to 35-95% MeCN 0.1% TFA) to afford the title compound as the first eluting stereoisomer (absoluted configuration unknown). LCMS: $R_T$=2.047 min, MS (ES) 709.0 (M+H); $^1$H NMR (400 MHz, $CDCl_3$) δ 8.84-8.65 (m, 1H), 8.16-7.94 (m, 2H), 7.86-7.67 (m, 2H), 7.68-7.56 (m, 1H), 7.49 (td, J=21.2, 7.8 Hz, 1H), 7.37-7.31 (m, 1H), 6.71-6.49 (m, 2H), 4.50 (qd, J=12.8, 4.0 Hz, 1H), 4.42-4.20 (m, 1H), 4.07-3.96 (m, 2H), 3.93 (s, 0.75H), 3.92 (s, 1.5H), 3.91 (s, 0.75H), 3.54-3.35 (m, 3H), 2.32 (s, 6H), 2.29-2.24 (m, 2H), 2.21 (s, 0.75H), 2.20 (s, 1.5H), 2.19 (s, 0.75H), 2.11 (s, 0.75H), 2.10 (s, 0.75H), 2.09 (s, 1.5H), 1.40-1.21 (m, 3H).

Example 187

(R)-5-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-2-naphthoic acid (Separated Stereoisomer, 2$^{nd}$ Eluting Atropisomer)

The title compound was isolated along with Example 186 as the second eluting stereoisomer (absoluted configuration unknown). MS (ES) 709.0 (M+H).

Example 188

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-naphthoic acid The title compound (29 mg, 82%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (27 mg, 0.05 mmol), methyl 3-bromo-1-naphthoate (16 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D. LCMS: $R_T$=2.123 and 2.140 min, MS (ES) 709.0 (M+H); $^1$H NMR (400 MHz, DMSO-$d_6$) δ 8.84 (dd, J=8.1, 1.8 Hz, 1H), 8.25 (t, J=1.9 Hz, 1H), 8.12 (s, 1H), 8.05-7.94 (m, 1H), 7.77 (d, J=8.6 Hz, 1H), 7.71-7.56 (m, 1H), 7.31 (d, J=8.5 Hz, 1H), 7.11 (s, 0.5H), 6.98 (s, 0.5H), 6.74 (s, 2H), 4.68-4.48 (m, 1H), 4.27-4.13 (m, 1H), 4.08-

3.92 (m, 2H), 3.79 (s, 3H), 3.29 (ddt, =41.8, 13.5, 6.4 Hz, 3H), 2.24 (s, 6H), 2.13 (s, 1.5H), 2.09 (s, 1.5H), 2.08-2.03 (m, 2H), 2.00 (s, 1.5H), 1.90 (s, 1.5H), 1.05 (dd, J=6.5, 1.6 Hz, 3H).

Example 189

(R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-naphthoic acid The title compound (21 mg, 59%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 4-bromo-1-naphthoate (16 mg, 0.06 mmol), Pd$_2$(dba)$_3$ (1 mg, 0.001 mmol), Xantphos (2 mg, 0.003 mmol), and Cs$_2$CO$_3$ (25 mg, 0.075 mmol) followed by saponification using General Procedure D. LCMS: R$_T$=2.091 min, MS (ES) 709.0 (M+H); $^1$H NMR (400 MHz, DMSO-d$_6$) δ 8.91 (dd, J=8.9, 3.3 Hz, 1H), 8.27-8.12 (m, 1H), 7.92 (t, J=9.3 Hz, 1H), 7.82-7.76 (m, 1H), 7.75-7.47 (m, 3H), 7.40-7.27 (m, 1H), 6.70 (d, J=4.6 Hz, 2H), 4.77-4.52 (m, 1H), 4.36-4.09 (m, 1H), 4.04-3.86 (m, 2H), 3.78 (s, 1.5H), 3.75 (s, 1.5H), 3.67-3.54 (m, 2H), 3.26-3.10 (m, 1H), 2.24 (s, 6H), 2.14 (s, 1.5H), 2.12-2.06 (m, 2H), 2.05 (s, 1.5H), 2.01 (s, 1.5H), 1.92 (s, 1.5H), 1.24-1.08 (m, 3H).

Example 190

(R)-1-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-2-naphthoic acid The title compound (18 mg, 51%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 1-bromo-2-naphthoate (16 mg, 0.06 mmol), Pd$_2$(dba)$_3$ (1 mg, 0.001 mmol). Xantphos (2 mg, 0.003 mmol), and Cs$_2$CO$_3$ (25 mg, 0.075 mmol) followed by saponification using General Procedure D. LCMS: R$_T$=2.065 and 2.092 min, MS (ES) 709.0 (M+H); $^1$H NMR (400 MHz, DMSO-d$_6$) δ 8.20-8.05 (m, 2.5H), 8.01 (dd, J=8.7, 2.1 Hz, 1H), 7.91-7.85 (m, 0.5), 7.78 (dd, J=8.6, 2.7 Hz, 1H), 7.74-7.60 (m, 1.5H), 7.58 (d, J=7.6 Hz, 0.5H), 7.33 (dd, J=8.6, 2.1 Hz, 1H), 6.70 (d, J=4.8 Hz, 2H), 4.40 (dq, J=10.5, 6.2, 5.2 Hz, 1H), 4.29-4.14 (m, 1H), 3.95 (t, J=6.5 Hz, 2H), 3.78 (s, 1.5H), 3.75 (s, 1.5H), 3.30-3.14 (m, 3H), 2.22 (s, 6H), 2.16 (s, 1H), 2.13 (s, 0.5H), 2.10 (s, 0.5H), 2.07 (s, 1H), 2.05 (s, 0.5H), 2.04-1.98 (m, 2H), 1.96 (s, 1H), 1.92 (s, 0.5H), 1.87 (s, 1H), 1.32-1.10 (m, 3H).

Example 191

(R)-8-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-naphthoic acid The title compound (7 mg, 20%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 8-bromo-1-naphthoate (16 mg, 0.06 mmol), Pd$_2$(dba)$_3$ (1 mg, 0.001 mmol), Xantphos (2 mg, 0.003 mmol), and Cs$_2$CO$_3$ (25 mg, 0.075 mmol) followed by saponification using General Procedure D. LCMS: R$_T$=2.012 min, MS (ES) 709.0 (M+H); $^1$H NMR (400 MHz, DMSO-d$_6$) δ 8.13 (dd, J=7.5, 2.1 Hz, 1H), 8.04 (dd, J=8.3, 1.2 Hz, 1H), 7.74 (d, J=8.6 Hz, 1H), 7.68 (t, J=7.8 Hz, 1H), 7.63-7.53 (m, 2H), 7.52-7.42 (m, 1H), 7.30 (d, J=8.6 Hz, 1H), 6.75 (s, 2H), 4.49 (dd, J=13.8, 3.9 Hz, 1H), 4.29-4.10 (m, 1H), 3.95 (q, J=6.4 Hz, 2H), 3.80 (s, 1.5H), 3.78 (s, 1.5H), 3.26-3.04 (m, 3H), 2.24 (s, 6H), 2.13 (s, 1.5H), 2.11-2.04 (m, 2H), 2.03 (s, 1.5H), 2.00 (s, 1.5H), 1.91 (s, 1.5H), 1.17 (d, J=6.5 Hz, 3H).

Example 192

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-methyl-1H-indole-2-carboxylic acid The title compound (11 mg, 30%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 7-bromo-4-methoxy-1-methyl-1H-indole-2-carboxylate (18 mg, 0.06 mmol), Pd$_2$(dba)$_3$ (1 mg, 0.001 mmol), Xantphos (2 mg, 0.003 mmol), and Cs$_2$CO$_3$ (25 mg, 0.075 mmol) followed by saponification using General Procedure D. LCMS: R$_T$=1.094 min, MS (ES) 742.0 (M+H).

Example 193

(4R)-7-chloro-10-[3-(4-chloro-3,5-dimethyl-phenoxy)propyl]-4-methyl-2-[1-methyl-5-(trifluoromethyl)indol-3-yl]-6-(1,3,5-trimethylpyrazol-4-yl)-3,4-dihydropyrazino[1,2-a]indol-1-one (Separated Stereoisomer, 2$^{nd}$ Eluting Atropisomer)

Step A. Preparation of 3-bromo-1-methyl-5-(trifluoromethyl)-1H-indole

The title compound (61 mg, 51%) was prepared following General procedure Fusing 5-(trifluoromethyl)-1H-indole (80 mg, 0.43 mmol), NBS (100 mg, 0.561 mmol), NaH (18 mg, 0.75 mmol), and MeI (90 mg, 0.63 mmol).

Step B. Example 193

The title compound (7.6 mg, 29%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (20 mg, 0.037 mmol), 3-bromo-1-methyl-5-(trifluoromethyl)-1H-indole (20 mg, 0.072 mmol), CuI (5 mg, 0.026 mmol), (trans)-1,2-N,N'-dimethylaminocyclohexane (8 mg, 0.056 mmol), and K$_2$CO$_3$ (20 mg, 0.14 mmol) followed by saponification using General Procedure D. The title compound was separated using reverse phase HPLC (Phenomenex Gemini C18, H$_2$O/CH$_3$CN gradient from 30-90% CH$_3$CN, 0.1% TFA) during the final purification step to give as a separated atropisomer (2$^{nd}$ fraction, absolute stereochemistry underminded). LCMS: R$_T$=2.293, min, MS (ES) 736.0 (M+H).

Example 194

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)benzofuran-2-carboxylic acid The title compound (19 mg, 54%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (27 mg, 0.05 mmol), methyl 7-bromobenzofuran-2-carboxylate (13 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol) followed by saponification using General Procedure D. LCMS: $R_T$=1.103 min, MS (ES) 699.0 (M+H).

Example 195

(R)-7-Chloro-10-(3-(4-chloro-3,5-dimethylphenoxy)propyl)-4-methyl-2-(3-oxo-2,3-dihydro-1H-inden-4-yl)-6-(1,3,5-trimethyl-1H-pyrazol-4-yl)-3,4-dihydropyrazino[1,2-a]indol-1(2H)-one The title compound (8 mg, 24%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), 7-bromo-2,3-dihydro-1H-inden-1-one (11 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol) followed by saponification using General Procedure D. LCMS: $R_T$=2.069 min, MS (ES) 669.1 (M+H).

Example 196

(R)-5-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)benzofuran-2-carboxylic acid The title compound (29 mg, 83%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 5-bromobenzofuran-2-carboxylate (14 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol) followed by saponification using General Procedure D. LCMS: $R_T$=1.130 min, MS (ES) 699.0 (M+H); $^1$H NMR (400 MHz, DMSO-$d_6$) δ 7.76 (d, J=2.2 Hz, 2H), 7.74 (d, J=2.5 Hz, 1H), 7.68 (d, J=1.0 Hz, 1H), 7.49 (ddd, J=8.9, 3.6, 2.2 Hz, 1H), 7.30 (d, J=8.6 Hz, 1H), 6.73 (s, 2H), 4.47 (d, J=11.4 Hz, 2H), 4.19-4.11 (m, 1H), 3.99 (s, 3H), 3.78 (s, 1.5H), 3.77 (s, 1.5H), 3.74-3.61 (m, 2H), 3.22 (dt, J=13.4, 7.4 Hz, 2H), 2.26 (s, 6H), 2.12 (s, 1.5H), 2.08 (d, J=13.1 Hz, 2H), 2.03 (s, 1.5H), 1.97 (s, 1.5H), 1.88 (s, 1.5H), 1.04 (d, J=6.4 Hz, 3H).

Example 197

(R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-isopropyl-1H-indole-2-carboxylic acid Step A. Preparation of methyl 4-bromo-1-isopropyl-1H-indole-2-carboxylate The title compound (35 mg, 59%) was prepared following General Procedure G using methyl 4-bromo-1H-indole-2-carboxylate (51 mg, 0.20 mmol), NaH (10 mg, 0.24 mmol) and 2-iodopropane (15 µL, 0.44 mmol). LCMS: $R_T$=1.901 min, MS (ES) 296.0 (M+H).

Step B. Example 197

The title compound (21 mg, 57%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 4-bromo-1-isopropyl-1H-indole-2-carboxylate (15 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D. LCMS: $R_T$=1.192 and 1.257 min, MS (ES) 740.1 (M+H).

Example 198

(R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((tetrahydro-2H-pyran-4-yl)methyl)-1H-indole-2-carboxylic acid Step A. Preparation of methyl 4-bromo-1-((tetrahydro-2H-pyran-4-yl)methyl)-1H-indole-2-carboxylate The title compound (53 mg, 75%) was prepared following General Procedure G using methyl 4-bromo-1H-indole-2-carboxylate (51 mg, 0.20 mmol), NaH (10 mg, 0.24 mmol) and 4-(bromomethyl)tetrahydro-2H-pyran (32 µL, 0.24 mmol). LCMS: $R_T$=1.776 min, MS (ES) 352.0 (M+H).

Step B. Example 198

The title compound (31 mg, 78%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 4-bromo-1-((tetrahydro-2H-pyran-4-yl)methyl)-1H-indole-2-carboxylate (21 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using Procedure D. LCMS: $R_T$=2.079 min, MS (ES) 796.0 (M+H).

Example 199

(4R)-7-chloro-10-[3-(4-chloro-3,5-dimethyl-phenoxy)propyl]-4-methyl-2-[1-methyl-6-(trifluoromethyl)indol-3-yl]-6-(1,3,5-trimethylpyrazol-4-yl)-3,4-dihydropyrazino[1,2-a]indol-1-one (Separated Stereoisomer, 2$^{nd}$ Eluting Atropisomer)

Step A. Preparation of 3-bromo-1-methyl-6-(trifluoromethyl)-1H-indole

The title compound (115 mg, 38%) was prepared following General procedure F using 6-(trifluoromethyl)-1H-indole (200 mg, 1.08 mmol), NBS (240 mg, 1.35 mmol), NaH (70 mg, 2.92 mmol), and MeI (220 mg, 1.55 mmol).

Step B. Example 199

The title compound (7.4 mg, 28%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (20 mg, 0.037 mmol), 3-bromo-1-methyl-6-(trifluoromethyl)-1H-indole (20 mg, 0.072 mmol), CuI (5 mg, 0.026 mmol), (trans)-1,2-N,N'-dimethylaminocyclohexane (8 mg, 0.056 mmol), and K$_2$CO$_3$ (20 mg, 0.14 mmol) followed by saponification using General Procedure D. The title compound was separated using reverse phase HPLC (Phenomenex Gemini C18, H$_2$O/CH$_3$CN gradient from 30-90% CH$_3$CN, 0.1% TFA) during the final purification step to give as a separated atropisomer (2$^{nd}$ fraction, absolute stereochemistry undetermined). LCMS: R$_T$=2.312 min, MS (ES) 736.0 (M+H); $^1$H NMR (400 MHz, Chloroform-d) δ 7.74 (dd, J=8.6, 3.5 Hz, 1H), 7.64 (d, J=8.8 Hz, 1H), 7.55 (d, J=8.4 Hz, 1H), 7.41-7.34 (m, 1H), 7.34-7.28 (m, 2H), 6.61 (s, 2H), 4.41 (d, J=11.9 Hz, 1H), 4.22 (s, 1H), 4.05 (s, 3H), 4.00 (tt, J=6.2, 3.1 Hz, 2H), 3.88 (s, 2H), 3.85 (s, 1H), 3.64 (d, J=12.6 Hz, 1H), 3.39 (m, 2H), 2.31 (d, J=2.0 Hz, 6H), 2.27 (s, 3H), 2.22 (m, 5H), 1.23 (d, J=5.5 Hz, 1H), 1.19 (d, =5.5 Hz, 2H).

Example 200

(4R)-7-chloro-10-[3-(4-chloro-3,5-dimethyl-phenoxy)propyl]-4-methyl-2-[1-methyl-5-(trifluoromethyl)indol-3-yl]-6-(1,3,5-trimethylpyrazol-4-yl)-3,4-dihydropyrazino[1,2-a]indol-1-one (Separated Stereoisomer, 1$^{st}$ Eluting Atropisomer)

The title compound (6.9 mg, 26%) was separated as the 1$^{st}$ eluting atropisomer with Example 193. LCMS: R$_T$=2.267 min, MS (ES) 736.0 (M+H).

Example 201

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,5-dimethyl-1H-indole-2-carboxylic acid

Step A. Preparation of methyl 7-bromo-1,5-dimethyl-1H-indole-2-carboxylate

The title compound (24 mg, 43%) was prepared following General Procedure G using 7-bromo-5-methyl-1H-indole-2-carboxylic acid (51 mg, 0.20 mmol), NaH (16 mg, 0.40 mmol) and MeI (26 µL, 0.40 mmol). LCMS: R$_T$=1.761 min, MS (ES) 282.1 (M+H).

Step B. Example 201

The title compound (22 mg, 61%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 7-bromo-1,5-dimethyl-1H-indole-2-carboxylate (17 mg, 0.06 mmol), Pd$_2$(dba)$_3$ (1 mg, 0.001 mmol), Xantphos (2 mg, 0.003 mmol), and Cs$_2$CO$_3$ (25 mg, 0.075 mmol) followed by saponification using General Procedure D. LCMS: R$_T$=1.163 mm, MS (ES) 726.1 (M+H).

Example 202

(4R)-7-chloro-10-[3-(4-chloro-3,5-dimethyl-phenoxy)propyl]-4-methyl-2-[1-methyl-6-(trifluoromethyl)indol-3-yl]-6-(1,3,5-trimethylpyrazol-4-yl)-3,4-dihydropyrazino[1,2-a]indol-1-one (Separated Stereoisomer, 1$^{st}$ Eluting Atropisomer)

The title compound (6.5 mg, 24%) was separated as the 1$^{st}$ eluting atropisomer with Example 199. LCMS: R$_T$=2.285 min, MS (ES) 736.0 (M+H); $^1$H NMR (400 MHz, Chloroform-d) δ 7.75 (d, J=8.6 Hz, 1H), 7.64 (d, J=9.1 Hz, 1H), 7.55 (d, J=8.4 Hz, 1H), 7.37 (d, J=8.3 Hz, 1H), 7.32 (dd, J=8.8, 3.8 Hz, 2H), 6.61 (s, 2H), 4.40 (s, 1H), 4.09 (s, 4H), 4.03-3.93 (m, 2H), 3.89 (s, 2H), 3.86 (s, 1H), 3.66 (s, 1H), 3.52-3.27 (m, 2H), 2.35 (s, 3H), 2.32 (s, 6H), 2.23-2.11 (m, 5H), 1.26 (s, 3H).

Example 203

(R)-7-Chloro-10-(3-(4-chloro-3,5-dimethylphenoxy)propyl)-4-methyl-2-(1-oxo-2,3-dihydro-1H-inden-4-yl)-6-(1,3,5-trimethyl-1H-pyrazol-4-yl)-3,4-dihydropyrazino[1,2-a]indol-1(2H)-one The title compound (24 mg, 72%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), 4-bromo-2,3-dihydro-1H-inden-1-one (11 mg, 0.06 mmol), CuI (5 mg, 0.025 mmol), (trans)-1,2-N,N'-dimethylaminocyclohexane (8 µL, 0.05 mmol), and K$_2$CO$_3$ (25 mg, 0.075 mmol) followed by saponification using General Procedure D. LCMS: R$_T$=2.104 min, MS (ES) 669.1 (M+H).

Example 204

Methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylate (Separated Stereoisomer, 1$^{st}$ Eluting Atropisomer)

The title compound (12 mg, 33%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-methyl-1H-indole-5-carboxylate (16 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol). The title compound was isolated as the first eluting stereoisomer from reverse phase HPLC (Phenomenex Gemini C18, $H_2O/CH_3CN$ gradient to 35-95% MeCN 0.1% TFA). LCMS: $R_T$=2.146 min, MS (ES) 726.1 (M+H), $^1H$ NMR (400 MHz, $CDCl_3$) δ 8.29 (dd, J=1.6, 0.6 Hz, 1H), 7.98 (dd, J=8.7, 1.6 Hz, 1H), 7.72 (d, J=8.6 Hz, 1H), 7.38 (dd, J=8.8, 0.7 Hz, 1H), 7.34-7.30 (m, 2H), 6.64 (s, 2H), 4.47 (dd, J=12.6, 3.8 Hz, 1H), 4.13 (s, 1H), 4.02 (t, J=6.3 Hz, 2H), 3.96 (s, 3H), 3.92 (s, 3H), 3.85 (s, 3H), 3.71 (dd, J=12.5, 1.7 Hz, 1H), 3.41 (ddt, J=37.4, 13.2, 7.4 Hz, 2H), 2.33 (s, 6H), 2.26 (s, 3H), 2.25-2.17 (m, 2H), 2.09 (s, 3H), 1.27 (d, J=6.5 Hz, 3H).

Example 205

Methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylate The title compound (26 mg, 36%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (54 mg, 0.1 mmol), methyl 7-bromo-1-methyl-1H-indole-3-carboxylate (32 mg, 0.12 mmol), $Pd_2(dba)_3$ (2 mg, 0.002 mmol), Xantphos (3.5 mg, 0.006 mmol), and $Cs_2CO_3$ (49 mg, 0.15 mmol). LCMS: $R_T$=2.162 and 2.193 min, MS (ES) 726.3 (M+H).

Example 206

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-6-carbonitrile The title compound (34 mg, 98%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), 3-bromo-1-methyl-1H-indole-6-carbonitrile (14 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol). LCMS: $R_T$=2.165 min, MS (ES) 693.1 (M+H).

Example 207

Methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylate (Separated Stereoisomer, $2^{nd}$ Eluting Atropisomer)

The title compound (10 mg, 27%) was isolated as the second eluting stereoisomer along with Example 204 from reverse phase HPLC (Phenomenex Gemini C18, $H_2O/CH_3CN$ gradient to 35-95% MeCN 0.1% TFA). LCMS: $R_T$=2.167 min, MS (ES) 726.1 (M+H); $^1H$ NMR (400 MHz, $CDCl_3$) δ 8.29 (d, J=1.5 Hz, 1H), 7.98 (dd, J=8.7, 1.6 Hz, 1H), 7.71 (d, J=8.6 Hz, 1H), 7.38 (d, J=8.7 Hz, 1H), 7.33-7.28 (m, 2H), 6.64 (s, 2H), 4.43 (dd, J=12.8, 3.8 Hz, 1H), 4.34-4.24 (m, 1H), 4.02 (tt, J=6.2, 3.3 Hz, 2H), 3.94 (s, 3H), 3.92 (s, 3H), 3.85 (s, 3H), 3.70 (dd, J=12.8, 1.6 Hz, 1H), 3.54-3.23 (m, 2H), 2.33 (s, 6H), 2.24 (s, 3H), 2.23-2.15 (m, 2H), 2.09 (s, 3H), 1.24 (d, J=6.5 Hz, 3H).

Example 208

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carbonitrile The title compound (33 mg, 95%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (27 mg, 0.05 mmol), 3-bromo-1-methyl-1H-indole-5-carbonitrile (14 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol). LCMS: $R_T$=1.214 min, MS (ES) 693.0 (M+H).

Example 209

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-7-carbonitrile The title compound (26 mg, 75%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (27 mg, 0.05 mmol), 3-bromo-1-methyl-1H-indole-7-carbonitrile (14 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol). MS (ES) 693.2 (M+H).

Example 210

4-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-1-methyl-indole-2-carboxylic acid The title compound (2 mg, 8%) was prepared following General coupling procedure B using ((R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (20 mg, 0.037 mmol), methyl 4-bromo-1-methyl-1H-indole-2-carboxylate (20 mg, 0.074 mmol), CuI (5 mg, 0.026 mmol), (trans)-1,2-N,N'-dimethylaminocyclohexane (8 mg, 0.056 mmol), and $K_2CO_3$ (20 mg, 0.14 mmol) followed by saponification using General Procedure D. LCMS: $R_T$=2.071 min, MS (ES) 710.1 (M+H).

Example 211

4-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-2-(trifluoromethyl)indole-6-carboxylic acid Step A. Preparation of methyl 4-bromo-1-methyl-2-(trifluoromethyl)-1H-indole-6-carboxylate A mixture of methyl 4-bromo-1H-indole-6-carboxylate (125 mg, 0.49 mmol), 1-(trifluoromethyl)-1$λ^3$-benzo[d][1, 2]iodaoxol-3(1H)-one (100 mg, 0.54 mmol), and copper (I) acetate (5 mg, 0.04 mmol) were dissolved in MeOH (5 mL). The reaction mixture was purged with Ar for 5 min, sealed, and stirred at RT for 4 h. The reaction was then heated to 40° C. for 36 h. The reaction was cooled to RT, diluted with DCM/H$_2$O (20 mL, 1:1), the layers separated, and the aqueous layer was extracted with DCM (2×10 mL). The combined organic extracts were dried over MgSO$_4$, filtered, and concentrated in vacuo. The crude reaction mixture was purified by flash chromatography (Combi-flash Rf, Hex/EtOAc=0-100% gradient) to afford methyl 4-bromo-2-(trifluoromethyl)-1H-indole-6-carboxylate (44 mg, 28% yield). The resultant product was methylated following General coupling procedure G using NaH (6 mg, 0.25 mmol) and MeI (40 mg, 0.28 mmol) to afford the title compound (28 mg, 61% two steps).

Step B. Example 211

The title compound (3 mg, 8%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 4-bromo-1-methyl-2-(trifluoromethyl)-1H-indole-6-carboxylate (28 mg, 0.083 mmol), CuI (5 mg, 0.026 mmol), (trans)-1,2-N,N'-dimethylaminocyclohexane (8 mg, 0.056 mmol), and K$_2$CO$_3$ (20 mg, 0.14 mmol) followed by saponification using General Procedure D. LCMS: R$_T$=2.187 min, MS (ES) 780.0 (M+H).

Example 212

(S)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid The title compound (8% yield) was prepared following General coupling procedure A using (S)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 3-bromo-1-methyl-1H-indole-5-carboxylate followed by saponification using General Procedure D. MS (ES) 712.2 (M+H).

Example 213

5-[8-Chloro-11-[3-(4-chloro-3,5-dimethyl-phenoxy)propyl]-7-(4,6-dimethylpyrimidin-5-yl)-1-oxo-4,5-dihydro-3H-[1,4]diazepino[1,2-a]indol-2-yl]naphthalene-2-carboxylic acid The title compound (4.8 mg, 18%) was prepared following General coupling procedure B using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (20 mg, 0.037 mmol), methyl 5-bromo-2-naphthoate (15 mg, 0.056 mmol), CuI (5 mg, 0.026 mmol), (trans)-1,2-N,N'-dimethylaminocyclohexane (8 mg, 0.056 mmol), and K$_2$CO$_3$ (20 mg, 0.14 mmol) followed by saponification using General Procedure D. LCMS: R$_T$=2.065 min, MS (ES) 707.0 (M+H).

Example 214

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylic acid (Separated Stereoisomer, 1$^{st}$ Eluting Atropisomer)

The title compound was isolated as a separated atropisomer (1$^{st}$ fraction, absolute stereochemistry undetermined) from mixture of atropisomers. MS (ES) 712.2 (M+H).

Example 215

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylic acid (Separated Stereoisomer, 2$^{nd}$ Eluting Atropisomer)

The title compound was isolated as a separated atropisomer (2$^{nd}$ fraction, absolute stereochemistry undetermined) from mixture of atropisomers. MS (ES) 712.2 (M+H).

Example 216

(P,R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one The title compound was separated from diasteromeric (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one using reverse phase HPLC. Absolute stereochemistry was determined by single crystal X-ray structure. $[\alpha]_d^{25}$=−138.7.

Example 217

(M,R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one The title compound was separated from diasteromeric (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one using reverse phase HPLC along with Example 216. Absolute stereochemistry was determined by single crystal X-ray structure. $[\alpha]_d^{25}$=−182.4.

Example 218

5-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]naphthalene-2-carboxylic acid The title compound (5.8 mg, 22%) was prepared following General coupling procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (20 mg, 0.037 mmol), methyl 5-bromo-2-naphthoate (15 mg, 0.057 mmol), CuI (5 mg, 0.026 mmol), (trans)-1,2-N,N'-dimethylaminocyclohexane (8 mg, 0.056 mmol), and K$_2$CO$_3$ (20 mg, 0.14 mmol) followed by saponification using General Procedure D. LCMS: R$_T$=2.037 min, MS (ES) 706.9 (M+H); ¹H NMR (400 MHz, Chloroform-d) δ 9.10 (s, 1H), 8.63 (d, J=1.6 Hz, 1H), 8.00 (dt, J=8.9, 1.1 Hz, 1H), 7.89 (dt, J=17.6, 8.8 Hz, 1.5H), 7.74 (dd, J=8.6, 2.1 Hz, 1H), 7.67 (d, J=8.8 Hz, 0.5H), 7.52 (ddd, J=13.5, 8.3, 7.3 Hz, 1H), 7.44 (dd, J=7.3, 1.2 Hz, 0.5H), 7.34 (dd, J=7.4, 1.1 Hz, 0.5H), 7.30 (s, 1H), 7.19 (s, 1H), 6.53 (s, 1H), 6.51 (s, 1H), 4.39 (dd, J=26.2, 11.3 Hz, 1H), 3.92 (q, J=5.9 Hz, 2H), 3.70 (s, 1H), 3.32 (dtt, J=27.9, 13.5, 7.1 Hz, 3H), 2.43 (s, 1.5H), 2.42 (s, 1.5H), 2.27 (s, 3H), 2.23 (s, 3H), 2.22 (s, 3H), 2.13 (q, J=6.9 Hz, 2H), 1.23 (d, J=6.8 Hz, 1.5H), 1.21 (d, J=6.8 Hz, 1.5H).

Example 219

7-[8-Chloro-11-[3-(4-chloro-3,5-dimethyl-phenoxy) propyl]-7-(4,6-dimethylpyrimidin-5-yl)-1-oxo-4,5-dihydro-3H-[1,4]diazepino[1,2-a]indol-2-yl]-1-methyl-indole-2-carboxylic acid The title compound (2.5 mg, 9%) was prepared following General coupling procedure B using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (20 mg, 0.037 mmol), ethyl 7-bromo-1-methyl-1H-indole-2-carboxylate (15 mg, 0.053 mmol), CuI (5 mg, 0.026 mmol), (trans)-1,2-N,N'-dimethylaminocyclohexane (8 mg, 0.056 mmol), and K₂CO₃ (20 mg, 0.14 mmol) followed by saponification using General Procedure D. LCMS: R$_T$=2.039 min, MS (ES) 710.1 (M+H).

Example 220

4-[8-Chloro-11-[3-(4-chloro-3,5-dimethyl-phenoxy) propyl]-7-(4,6-dimethylpyrimidin-5-yl)-1-oxo-4,5-dihydro-3H-[1,4]diazepino[1,2-a]indol-2-yl]quinoline-6-carboxylic acid The title compound (4.5 mg, 17%) was prepared following General coupling procedure B using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (20 mg, 0.037 mmol), methyl 4-bromoquinoline-6-carboxylate (10 mg, 0.037 mmol), CuI (5 mg, 0.026 mmol), (trans)-1,2-N,N'-dimethylaminocyclohexane (8 mg, 0.056 mmol), and K₂CO₃ (20 mg, 0.14 mmol) followed by saponification using General Procedure D. LCMS: R$_T$=1.786 min, MS (ES) 708.0 (M+H); ¹H NMR (400 MHz, Chloroform-d) δ 9.19 (s, 1H), 9.11 (s, 1H), 8.65 (s, 1H), 8.41 (q. J=8.8 Hz, 2H), 7.79 (d, J=8.6 Hz, 1H), 7.38 (d, J=8.6 Hz, 1H), 7.32 (d, J=4.5 Hz, 1H), 6.62 (s, 2H), 4.11-3.96 (m, 4H), 3.90 (s, 2H), 3.22 (t, J=7.4 Hz, 2H), 2.36 (s, 6H), 2.30 (s, 6H), 2.24 (quint, J=7.1, 6.6 Hz, 2H), 1.86 (br s, 2H).

Example 221

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-5-carboxamide The title compound (5.2 mg, 52%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (10 mg, 0.078 mmol), and 7M ammonia in MeOH (0.05 mL, 0.35 mmol). LCMS: R$_T$=1.924 min, MS (ES) 711.0 (M+H).

Example 222

(R)-7-chloro-10-(3-(4-chloro-3,5-dimethylphenoxy) propyl)-4-methyl-2-(1-methyl-6-(methylsulfonyl)-1H-indol-3-yl)-6-(1,3,5-trimethyl-1H-pyrazol-4-yl)-3,4-dihydropyrazino[1,2-a]indol-1(2H)-one Step A. Preparation of 3-bromo-1-methyl-6-(methylsulfonyl)-1H-indole To a solution of 6-(methylsulfonyl)-1H-indole (50 mg, 0.26 mmol) in DMF (3 mL) was added NaH (14 mg, 0.58 mmol) and stirred at RT for 30 min. MeI (70 mg, 0.49 mmol) was added and the reaction was stirred at RT for 3 h, diluted into DCM (10 mL), quenched with H₂O (10 mL). The layers were separated and the aqueous layer was extracted with DCM (2×10 mL). The combined organic extracts were dried and concentrated in vacuo. The residue was purified by flash chromatography (Combi-flash Rf, Hex/EtOAc=0-100% gradient) to give 1-methyl-6-(methylsulfonyl)-1H-indole. The product was dissolved in DMF (3 mL), cooled to 0° C., and NBS (60 mg, 0.34 mmol) was added. After 30 min, the reaction was diluted into DCM (20 mL), washed with 10% aqueous Na₂S₂O₃, dried over MgSO₄, filtered, and concentrated. The crude residue was purified by flash chromatography (Combi-flash Rf, Hex/EtOAc=0-100% gradient) to afford the title compound (52 mg, 70%).

Step B. Example 222

The title compound (18.3 mg, 65%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (20 mg, 0.037 mmol), 3-bromo-1-methyl-6-(methylsulfonyl)-1H-indole (20 mg, 0.069 mmol), CuI (5 mg, 0.026 mmol), (trans)-1,2-N,N'-dimethylaminocyclohexane (8 mg, 0.056 mmol), and K₂CO₃ (25 mg, 0.18 mmol). LCMS: R$_T$=2.015, 2.034 min, MS (ES) 745.9 (M+H); ¹H NMR (400 MHz, Chloroform-d) δ 8.04 (t, J=1.0 Hz, 1H), 7.75-7.60 (m, 3H), 7.39 (d, J=6.0 Hz, 1H), 7.31 (dd, J=8.0, 4.0 Hz, 1H), 6.62 (d, J=1.6 Hz, 2H), 4.42 (dt, J=12.2, 4.2 Hz, 1H), 4.35-4.18 (m, 1H), 4.01 (td. J=5.4, 4.5, 2.5 Hz, 2H), 3.94 (s, 3H), 3.92 (s, 3H), 3.66-3.56 (m, 1H), 3.51-3.29 (m, 2H), 3.10 (s, 3H), 2.33 (s, 6H), 2.28-2.14 (m, 5H), 2.09 (s, 1.5H), 2.07 (s, 1.5H), 1.26 (d, J=6.4 Hz, 1.5H), 1.19 (d, J=6.4 Hz, 1.5H).

Example 223

(4R)-7-chloro-10-[3-(4-chloro-3,5-dimethyl-phenoxy)propyl]-4-methyl-2-(1-methyl-5-nitro-indol-3-yl)-6-(1,3,5-trimethylpyrazol-4-yl)-3,4-dihydropyrazino[1,2-a]indol-1-one The title compound (17.4 mg, 67%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (20 mg, 0.037 mmol), 3-bromo-1-methyl-5-nitro-1H-indole (20 mg, 0.078 mmol), CuI (5 mg, 0.026 mmol), (trans)-1,2-N,N'-dimethylaminocyclohexane (8 mg, 0.056 mmol), and K₂CO₃ (25 mg, 0.18 mmol). LCMS: R$_T$=2.136, 2.159 min, MS (ES) 712.9 (M+H); ¹H NMR (400 MHz, Chloroform-d) δ 8.50 (dd, J=6.2, 2.2 Hz, 1H), 8.18 (dd, J=9.1, 2.2 Hz, 1H), 7.71 (dd, J=8.6, 2.2 Hz, 1H), 7.41 (d, J=9.2 Hz, 1H), 7.37 (s, 0.5H), 7.32-7.29 (m, 1.5H), 6.66-6.61 (m, 2H), 4.49-4.23 (m, 2H), 4.06-3.98 (m, 2H), 3.92 (s, 3H), 3.87 (s, 3H), 3.65 (dd, J=12.3, 7.2 Hz, 1H), 3.53-3.29 (m, 2H), 2.33 (s, 6H), 2.28-2.16 (m, 5H), 2.08 (d, J=1.4 Hz, 3H), 1.26 (d, J=6.4 Hz, 1.5H), 1.24 (d, J=6.4 Hz, 1.5H).

Example 224

8-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]quinoline-5-carboxylic acid The title compound (11.8 mg, 45%) was prepared following General coupling procedure B using (R)-7-chloro-10-(3 (4-chloro-3,5-dimethylphenoxy)propyl)-6-(4,6-dimethylpyrimidin-5-yl)-4-methyl-3,4-dihydropyrazino[1,2-a]indol-1 (2H)-one (20 mg, 0.037 mmol), methyl 8-bromoquinoline-5-carboxylate (20 mg, 0.075 mmol), CuI (5 mg, 0.026 mmol), (trans)-1,2-N,N'-dimethylaminocyclohexane (8 mg, 0.056 mmol), and K$_2$CO$_3$ (25 mg, 0.18 mmol) followed by saponification using General Procedure D. LCMS: R$_T$=1.990 min, MS (ES) 707.8 (M+H).

Example 225

8-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]quinoline-4-carboxylic acid The title compound (13.9 mg, 52%) was prepared following General coupling procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (20 mg, 0.037 mmol), methyl 8-bromoquinoline-4-carboxylate (20 mg, 0.075 mmol), CuI (5 mg, 0.026 mmol), (trans)-1,2-N,N'-dimethylaminocyclohexane (8 mg, 0.056 mmol), and K$_2$CO$_3$ (25 mg, 0.18 mmol) followed by saponification using General Procedure D. LCMS: R$_T$=2.012 min, MS (ES) 707.8 (M+H).

Example 226

(4R)-7-chloro-10-[3-(4-chloro-3,5-dimethyl-phenoxy)propyl]-4-methyl-2-(2-methyl-1-oxo-3,4-dihydropyrazino[1,2-a]indol-6-yl)-6-(1,3,5-trimethylpyrazol-4-yl)-3,4-dihydropyrazino[1,2-a]indol-1-one Step A. Preparation of 6-bromo-3,4-dihydropyrazino[1,2-a]indol-1(2H)-one The title compound (71 mg, 70%) was prepared following the procedure described in Example 86 Steps B and C using ethyl 7-bromo-1-methyl-1H-indole-2-carboxylate (100 mg, 0.56 mmol), tert-butyl 1,2,3-oxathiazolidine-3-carboxylate 2,2-dioxide (180 mg, 0.81 mmol), NaH (24 mg, 1.0 mmol), HCl (4.0 M in dioxanes, 2 mL, 8.0 mmol), and K$_2$CO$_3$ (150 mg, 1.09 mmol).

Step B. Preparation of 6-bromo-2-methyl-3,4-dihydropyrazino[1,2-a]indol-1(2H)-one The title compound (18 mg, 86%) was prepared following General Procedure G using 6-bromo-3,4-dihydropyrazino[1, 2-a]indol-1(2H)-one (20 mg, 0.075 mmol), NaH (3 mg, 0.13 mmol), and MeI (20 mg, 0.14 mmol).

Step C. Example 226

The title compound (6.1 mg, 18%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), 6-bromo-2-methyl-3,4-dihydropyrazino[1,2-a]indol-1(2H)-one (18 mg, 0.064 mmol), CuI (5 mg, 0.026 mmol), (trans)-1,2-N,N'-dimethylaminocyclohexane (8 mg, 0.056 mmol), and K$_2$CO$_3$ (20 mg, 0.15 mmol). MS (ES) 736.9 (M+H).

Example 227

8-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]quinoline-3-carboxylic acid The title compound (15.4 mg, 58%) was prepared following General coupling procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (20 mg, 0.037 mmol), methyl 8-bromoquinoline-3-carboxylate (20 mg, 0.075 mmol), CuI (5 mg, 0.026 mmol), (trans)-1,2-N,N'-dimethylaminocyclohexane (8 mg, 0.056 mmol), and K$_2$CO$_3$ (25 mg, 0.18 mmol) followed by saponification using General Procedure D. LCMS: R$_T$=2.002 min, MS (ES) 707.9 (M+H); $^1$H NMR (400 MHz, Chloroform-d) δ 9.39 (d, J=1.9 Hz, 1H), 9.22 (s, 1H), 8.88 (d, J=2.0 Hz, 1H), 7.96 (d, J=8.1 Hz, 1H), 7.88-7.77 (m, 2H), 7.72 (t, J=7.8 Hz, 1H), 7.36 (d, J=8.6 Hz, 1H), 6.62 (s, 2H), 4.71 (s, 1H), 4.00 (t, J=6.1 Hz, 2H), 3.75 (s, 1H), 3.52 (s, 1H), 3.39 (m, 2H), 2.53 (s, 3H), 2.36 (s, 3H), 2.31 (s, 6H), 2.23 (quint, J=7.0, 6.3 Hz, 2H), 1.33 (d, J=5.9 Hz, 3H).

Example 228

3-(8-Chloro-11-(3-(4-chloro-3,5-dimethylphenoxy)propyl)-7-(4,6-dimethyl-2-(4-methylpiperazin-1-yl)pyrimidin-5-yl)-1-oxo-4,5-dihydro-1H-[1,4]diazepino[1,2-a]indol-2(3H)-yl)-1-methyl-1H-indole-5-carboxylic acid Step A. Preparation of 4,6-dimethyl-2-(4-methylpiperazin-1-yl)pyrimidine A mixture of 2-chloro-4,6-dimethylpyrimidine (1.0 g, 7.0 mmol), 1-methylpiperazine (750 mg, 7.5 mmol), and K$_2$CO$_3$ (1.5 g, 10.9 mmol) in MeCN (10 mL) was heated to 50° C. for 72 h. Reaction was diluted with DCM/H$_2$O (60 mL, 1:1), the organic layer was separated, and the aqueous layer was extracted with DCM (2×30 mL). The combined organic layers were dried over MgSO$_4$, filtered, and concentrated in vacuo to afford the title compound (1.39 g, 96%).

Step B. Preparation of 5-bromo-4,6-dimethyl-2-(4-methylpiperazin-1-yl)pyrimidine To a solution of 4,6-dimethyl-2-(4-methylpiperazin-1-yl)pyrimidine (1.39 g, 6.75 mmol) in CHCl$_3$ (10 mL) and NBS (1.25 g, 7.02 mmol) was added. The reaction was heated to 65° C. for 10 min then cooled to RT. The reaction mixture was diluted with DCM/H$_2$O (60 mL, 1:1) and extracted with DCM (2×30 mL). The combined organic layers were dried over MgSO$_4$, filtered, and concentrated in vacuo. The residue was purified by flash chromatography (Combi-flash Rf, DCM/MeOH=0-10% gradient) to afford the title compound (1.66 g, 86%).

Step C. Preparation of (4,6-dimethyl-2-(4-methylpiperazin-1-yl)pyrimidin-5-yl)boronic acid To a solution of 5-bromo-4,6-dimethyl-2-(4-methylpiperazin-1-yl)pyrimidine (250 mg, 0.88 mmol) in toluene/THF (4 mL/1 mL) was added triisopropyl borate (250 mg, 1.33 mmol), and the reaction was cooled to −40° C. n-Butyllitium (2.5 M, 0.48 mL, 1.20 mmol) was added over 1 h and stirred for 30 min, then warmed to −20° C. over 1 h. The reaction was quenched with 1M HCl, the organic layer was removed, and the aqueous layer was adjusted to pH 7 with 1M NaOH. The aqueous layer was extracted with 10% iPrOH in CHCl$_3$ (3×30 mL), and the combined organic layers were dried over MgSO$_4$, filtered, and concentrated in vacuo to afford the title compound (140 mg, 56%).

Step D. Preparation of ethyl 6-chloro-3-(3-(4-chloro-3,5-dimethylphenoxy)propyl)-7-(4,6-dimethyl-2-(4-methylpiperazin-1-yl)pyrimidin-5-yl)-1H-indole-2-carboxylate A mixture of ethyl 7-bromo-6-chloro-3-(3-(4-chloro-3,5-dimethylphenoxy)propyl)-1H-indole-2-carboxylate (100 mg, 0.20 mmol), (4,6-dimethyl-2-(4-methylpiperazin-1-yl)pyrimidin-5-yl)boronic acid (75 mg, 0.32 mmol), Pd$_2$(dba)$_3$ (20 mg, 0.022 mmol), S-Phos (25 mg, 0.061 mmol), and potassium phosphate (130 mg, 0.61 mmol) in THF (3 mL) and toluene (3 mL) was sparged with Ar for 5 min. The reaction was heated to 110° C. for 24 h then cooled to RT and diluted with DCM/H$_2$O (20 mL, 1:1). The layers were separated, and the aqueous layer was extracted with DCM (2×10 mL). The combined organic layers were dried over MgSO$_4$, filtered, and concentrated in vacuo. The residue was purified by flash chromatography (Combi-flash Rf, Hex/EtOAc=0-100% gradient) to give the title compound (52 mg, 42%).

Step E. Preparation of 8-chloro-11-(3-(4-chloro-3,5-dimethylphenoxy)propyl)-7-(4,6-dimethyl-2-(4-methylpiperazin-1-yl)pyrimidin-5-yl)-2,3,4,5-tetrahydro-1H-[1,4]diazepino[1,2-a]indol-1-one The title compound (31 mg, 58%) was prepared following the procedures described in Example 120 Steps B and C using ethyl 6-chloro-3-(3-(4-chloro-3,5-dimethylphenoxy)propyl)-7-(4,6-dimethyl-2-(4-methylpiperazin-1-yl)pyrimidin-5-yl)-1H-indole-2-carboxylate (52 mg, 0.083 mmol), tert-butyl 1,2,3-oxathiazinane-3-carboxylate 2,2-dioxide (30 mg, 0.13 mmol), NaH (8 mg, 0.20 mmol), HCl in dioxanes (4.0 M, 0.5 mL, 2.0 mmol), and K$_2$CO$_3$ (30 mg, 0.22 mmol).

Step F. Example 228

The title compound (13 mg, 33%) was prepared following General coupling procedure B using 8-chloro-11-(3-(4-chloro-3,5-dimethylphenoxy)propyl)-7-(4,6-dimethyl-2-(4-methylpiperazin-1-yl)pyrimidin-5-yl)-2,3,4,5-tetrahydro-1H-[1,4]diazepino[1,2-a]indol-1-one (31 mg, 0.049 mmol), methyl 3-bromo-1-methyl-1H-indole-5-carboxylate (30 mg, 0.11 mmol), CuI (5 mg, 0.026 mmol), (trans)-1,2-N,N'-dimethylaminocyclohexane (8 mg, 0.056 mmol), and K$_2$CO$_3$ (25 mg, 0.18 mmol) followed by saponification using General Procedure D. LCMS: R$_T$=1.760 min, MS (ES) 808.0 (M+H); $^1$H NMR (400 MHz, Chloroform-d) δ 8.28 (s, 1H), 8.00 (d, J=8.8 Hz, 1H), 7.69 (d, J=8.8 Hz, 1H), 7.38 (d, J=8.8 Hz, 1H), 7.29 (d, J=8.6 Hz, 1H), 7.18 (s, 1H), 6.64 (s, 2H), 5.04 (d, J=11.2 Hz, 2H), 4.11 (t, J=6.4 Hz, 2H), 4.00 (t, J=6.1 Hz, 2H), 3.83 (s, 3H), 3.77 (t, J=6.2 Hz, 4H), 3.56 (s, 2H), 3.21 (t, J=7.4 Hz, 2H), 2.92 (s, 5H), 2.31 (s, 6H), 2.28-2.19 (m, 2H), 2.12 (s, 6H), 1.91 (d, J=6.0 Hz, 2H).

Example 229

(4R)-7-chloro-10-[3-(4-chloro-3,5-dimethyl-phenoxy)propyl]-2-(2-isopentyl-1-oxo-3,4-dihydropyrazino[1,2-a]indol-6-yl)-4-methyl-6-(1,3,5-trimethylpyrazol-4-yl)-3,4-dihydropyrazino[1,2-a]indol-1-one

Step A. Preparation of 6-bromo-2-isopentyl-3,4-dihydropyrazino[1,2-a]indol-1(2H)-one The title compound (15 mg, 59%) was prepared following General Procedure G using 6-bromo-3,4-dihydropyrazino[1,2-a]indol-1(2H)-one (20 mg, 0.075 mmol), NaH (3 mg, 0.13 mmol), and isovaleryl bromide (25 mg, 0.17 mmol).

Step B. Example 229

The title compound (4.7 mg, 13%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), 6-bromo-2-isopentyl-3,4-dihydropyrazino[1,2-a]indol-1(2H)-one (15 mg, 0.045 mmol), CuI (5 mg, 0.026 mmol), (trans)-1,2-N,N'-dimethylaminocyclohexane (8 mg, 0.056 mmol), and K$_2$CO$_3$ (25 mg, 0.18 mmol) followed by saponification using General Procedure D. LCMS: R$_T$=2.177 min, MS (ES) 793.0 (M+H).

Example 230

(R)-4-Chloro-8-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-2-carboxylic acid The title compound (11 mg, 30%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 8-bromo-4-chloroquinoline-2-carboxylate (19 mg, 0.06 mmol), Pd$_2$(dba)$_3$ (1 mg, 0.001 mmol), Xantphos (2 mg, 0.003 mmol), and Cs$_2$CO$_3$ (25 mg, 0.075 mmol) followed by saponification using General Procedure D. LCMS: R$_T$=2.089 min, MS (ES) 743.9 (M+H); $^1$H NMR (400 MHz, DMSO-d$_6$) δ 8.31 (dt, J=7.8, 1.5 Hz, 1H), 8.26 (d, J=1.8 Hz, 1H), 8.04-7.90 (m, 2H), 7.77 (d, =8.6 Hz, 1H), 7.31 (d, J=8.6 Hz, 1H), 6.72 (s, 2H), 4.77-4.55 (m, 1H), 4.27-4.12 (m, 1H), 3.96 (t, J=6.5 Hz, 2H), 3.78 (s, 1.5H), 3.76 (s, 1.5H), 3.35-3.12 (m, 3H), 2.23 (s, 6H), 2.13 (s, 1.5H), 2.11-2.04 (m, 2H), 2.02 (s, 1.5H), 1.98 (s, 1.5H), 1.89 (s, 1.5H), 1.37-1.16 (m, 3H).

Example 231

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-(trimethylsilyl)ethoxy)methyl)-1H-indole-5-carboxylic acid Step A. Preparation of methyl 3-bromo-1-((2-(trimethylsilyl)ethoxy)methyl)-1H-indole-5-carboxylate The title compound (96 mg, 88%) was prepared following General Procedure F using methyl 1H-indole-5-carboxylate (50 mg, 0.28 mmol), NBS (51 mg, 0.28 mmol), NaH (14 mg, 0.34 mmol) and (2-(chloromethoxy)ethyl)trimethylsilane (60 µL, 0.34 mmol). LCMS: $R_T$=1.979 min, MS (ES) 384.0 (M+H).

Step B. Example 231

The title compound (30 mg, 72%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-((2-(trimethylsilyl)ethoxy)methyl)-1H-indole-5-carboxylate (23 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol) followed by saponification using General Procedure D. LCMS: $R_T$=2.257 min, MS (ES) 828.0 (M+H).

Example 232

(R)-5Chloro-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)benzofuran-2-carboxylic acid (Separated Stereoisomer, 1st Eluting Atropisomer)

The title compound (11 mg, 30%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 7-bromo-5-chlorobenzofuran-2-carboxylate (19 mg, 0.06 mmol), $Pd_2(dba)_3$ (1 mg, 0.001 mmol), Xantphos (2 mg, 0.003 mmol), and $Cs_2CO_3$ (25 mg, 0.075 mmol) followed by saponification using General Procedure D The title compound was isolated as a separated atropisomer (1st fraction, absolute stereochemistry underminded) by reverse phase HPLC (Phenomenex Gemini C18, $H_2O/CH_3CN$ gradient to 35-95% MeCN 0.1% TFA). LCMS: $R_T$=2.138 min, MS (ES) 732.9 (M+H).

Example 233

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1H-indole-2-carboxylic acid (Separated Stereoisomer, 1st Eluting Atropisomer)

Step A. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate The title compound (210 mg, 52%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.55 mmol), ethyl 7-bromo-1H-indole-2-carboxylate (300 mg, 1.10 mmol), CuI (50 mg, 0.26 mmol), (trans)-$N^1,N^2$-dimethylcyclohexane-1,2-diamine (80 mg, 0.56 mmol), and $K_2CO_3$ (250 mg, 1.81 mmol).

Step B. Example 233

The title compound (6.8 mg, 35%) was obtained following General Procedure D using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (20 mg, 0.027 mmol) and isolated as a separated atropisomer (1st fraction, absolute stereochemistry underminded) by reverse phase HPLC (Phenomenex Gemini C18, $H_2O/CH_3CN$ gradient from 30-90% $CH_3CN$, 0.1% TFA). LCMS: $R_T$=1.954 min, MS (ES) 697.9 (M+H).

Example 234

(R)-7-Chloro-10-(3-(4-chloro-3,5-dimethylphenoxy)propyl)-4-methyl-2-(1-methyl-1H-indol-7-yl)-6-(1,3,5-trimethyl-1H-pyrazol-4-yl)-3,4-dihydropyrazino[1,2-a]indol-1(2H)-one Step A. Preparation of (R)-7-chloro-10-(3-(4-chloro-3,5-dimethylphenoxy)propyl)-2-(1H-indol-7-yl)-4-methyl-6-(1,3,5-trimethyl-1H-pyrazol-4-yl)-3,4-dihydropyrazino[1,2-a]indol-1(2H)-one The title compound was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), 7-bromo-1H-indole (12 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol).

Step B. Example 234

The title compound (17 mg, 51%) was prepared following General procedure G using (R)-7-chloro-10-(3-(4-chloro-3,5-dimethylphenoxy)propyl)-2-(1H-indol-7-yl)-4-methyl-6-(1,3,5-trimethyl-1H-pyrazol-4-yl)-3,4-dihydropyrazino[1,2-a]indol-1(2H)-one, NaH (5 mg, 0.12 mmol) and MeI (8 µL, 0.12 mmol). LCMS: $R_T$=2.169 and 2.194 min, MS (ES) 667.9 (M+H).

Example 235

(R)-7-Chloro-10-(3-(4-chloro-3,5-dimethylphenoxy)propyl)-4-methyl-2-(1-methyl-5-(1H-tetrazol-5-yl)-1H-indol-3-yl)-&(1,3,5-trimethyl-1H-pyrazol-4-yl)-3,4-dihydropyrazino[1,2-a]indol-1(2H)-one (Separated Stereoisomer, 2nd Eluting Atropisomer)

To a solution of (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carbonitrile (69 mg, 0.1 mmol) in DMF (2 mL) were added sodium azide (33 mg, 0.5 mmol), ammonium chloride (27 mg, 0.5 mmol) and the mixture was heated at 120° C. for 12 h then cooled to ambient temperature. The reaction mixture was quenched with H₂O (5 mL), extracted with CH₂Cl₂ (3×15 mL), dried (anhyd. Na₂SO₄), and concentrated. The residue was purified by reverse phase HPLC (Phenomenex Gemini C18, H₂O/CH₃CN gradient to 35-95% MeCN 0.1% TFA) to afford the title compound (25 mg, 34%) as the second eluting atropisomer (absolute configuration undetermined). LCMS: $R_T$=2.007 min, MS (ES) 736.0 (M+H).

Example 236

(R)-7-chloro-10-(3-(4-chloro-3,5-dimethylphenoxy) propyl)-4-methyl-2-(1-methyl-6-(2H-tetrazol-5-yl)-1H-indol-3-yl)-6-(1,3,5-trimethyl-1H-pyrazol-4-yl)-3,4-dihydropyrazino[1,2-a]indol-1(2H)-one The title compound (13 mg, 80%) was prepared according to the procedure for Example 235 using (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-6-carbonitrile (15 mg, 0.022 mmol). LCMS: $R_T$=2.045 min, MS (ES) 736.0 (M+H).

Example 237

(R)-2-(Benzofuran-3-yl)-7-chloro-10-(3-(4-chloro-3, 5-dimethylphenoxy)propyl)-4-methyl-6-(1,3,5-trimethyl-1H-pyrazol-4-yl)-3,4-dihydropyrazino[1,2-a] indol-1(2H)-one (Separated Stereoisomer, 1$^{st}$ Eluting Atropisomer)

The title compound (9 mg, 27%) was prepared following General coupling procedure B as the first eluting atropisomer (absolute configuration undetermined) using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), 3-bromobenzofuran (13 mg, 0.06 mmol), CuI (5 mg, 0.025 mmol), (trans)-1,2-N,N'-dimethylaminocyclohexane (8 µL, 0.05 mmol), and K₂CO₃ (25 mg, 0.075 mmol). LCMS: $R_T$=2.260 min, MS (ES) 655.0 (M+H).

Example 238

7-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-1-methyl-indole-2-carboxylic acid The title compound (23 mg, 58%) was prepared following General coupling procedure A using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1 (2H)-one (30 mg, 0.056 mmol), ethyl 7-bromo-1-methyl-1H-indole-2-carboxylate (30 mg, 0.11 mmol). Pd₂(dba)₃ (10 mg, 0.011 mmol), Xantphos (15 mg, 0.026 mmol), and Cs₂CO₃ (80 mg, 0.246 mmol) followed by saponification using General Procedure D. LCMS: $R_T$=1.957 min, MS (ES) 709.9 (M+H).

Example 239

(R)-8-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-4-methoxyquinoline-2-carboxylic acid The title compound (16 mg, 44%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 8-bromo-4-chloroquinoline-2-carboxylate (19 mg, 0.06 mmol), Pd₂(dba)₃ (1 mg, 0.001 mmol), Xantphos (2 mg, 0.003 mmol), and Cs₂CO₃ (25 mg, 0.075 mmol) followed by saponification using General Procedure D. LCMS: $R_T$=2.019 and 2.034 min, MS (ES) 739.9 (M+H); ¹H NMR (400 MHz, DMSO-d₆) δ 8.20 (dd, J=8.4, 1.3 Hz, 1H), 7.83 (ddd, J=7.4, 3.1, 1.5 Hz, 1H), 7.78-7.68 (m, 2H), 7.59 (d, J=1.6 Hz, 1H), 7.30 (d, J=8.6 Hz, 1H), 6.73 (s, 2H), 4.88-4.49 (m, 1H), 4.31-4.18 (m, 1H), 4.15 (s, 3H), 3.97 (t, J=6.4 Hz, 2H), 3.78 (s, 1.5H), 3.75 (s, 1.5H), 3.34-3.15 (m, 3H), 2.24 (s, 6H), 2.13 (s, 1.5H), 2.11-2.04 (m, 2H), 2.02 (s, 1.5H), 1.98 (s, 1.5H), 1.89 (s, 1.5H), 1.36-1.15 (m, 3H).

Example 240

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-(2-(tetrahydro-2H-pyran-4-yl)ethyl)-1H-indole-5-carboxylic acid To a solution of methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-(trimethylsilyl)ethoxy)methyl)-1H-indole-5-carboxylate (15 mg, 0.019 mmol) in DCM (1 mL) was added TFA (1 mL), and the mixture was stirred at RT for 6 h. Saturated aqueous NaHCO₃ (8 mL) was added to the mixture and extracted with DCM (3×5 mL). The organic layer was dried (anhyd. Na₂SO₄) and concentrated in vacuo. The crude product was alkylated following General procedure G using NaH (5 mg, 0.12 mmol) and 4-(2-bromoethyl) tetrahydro-2H-pyran (6 mg, 0.031 mmol) followed by saponification using General Procedure D to afford the title compound (8 mg, 52%). LCMS: $R_T$=2.168 min, MS (ES) 810.3 (M+H).

Example 241

1-Benzyl-7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a] indol-2-yl]indole-2-carboxylic acid To a solution of ethyl (R)-7-(7-chloro-10-(3-(4-chloro-3, 5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1H-indole-2-carboxylate (10 mg, 0.014 mmol) in DMF (1 mL) was added NaH (2 mg, 0.08 mmol), and the reaction was stirred at RT for 30 min. Benzyl bromide (5 mg, 0.029 mmol) was added, and the reaction was stirred for 16 h at RT then diluted with DCM/H₂O (20 mL, 1:1). The mixture was extracted with DCM (2×5 mL), dried by passing through a phase separator and concentrated in vacuo. The crude reaction product was then saponified and purified following General Procedure D to afford the title compound (6.9 mg, 64% yield). LCMS: $R_T$=2.084 min, MS (ES) 787.8 (M+H).

Example 242

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1H-indole-2-carboxylic acid (Separated Stereoisomer, $2^{nd}$ Eluting Atropisomer)

The title compound (8.1, 42% yield) was prepared in the same procedure as described in Example 233 as the $2^{nd}$ fraction. LCMS: $R_T$=1.953 min, MS (ES) 697.9 (M+H).

Example 243

Methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-(trimethylsilyl)ethoxy)methyl)-1H-indole-5-carboxylate The title compound (37 mg, 88%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1-((2-(trimethylsilyl)ethoxy)methyl)-1H-indole-5-carboxylate (23 mg, 0.06 mmol), CuI (5 mg, 0.025 mmol), (trans)-1,2-N,N'-dimethylaminocyclohexane (8 µL, 0.05 mmol), and K$_2$CO$_3$ (25 mg, 0.075 mmol). LCMS: $R_T$=2.451 min, MS (ES) 841.9 (M+H).

Example 244

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-7-cyano-1-methyl-1H-indole-5-carboxylic acid

Step A. Preparation of ethyl 3-bromo-7-cyano-1-methyl-1H-indole-5-carboxylate To a solution of ethyl 7-bromo-1H-indole-5-carboxylate (97 mg, 0.36 mmol) in DMF (2 mL) was added NaH (17 mg, 0.43 mmol) and the mixture was stirred at RT for 10 min. Methyl iodide (27 µL, 0.43 mmol) was added to the mixture and stirred at ambient temperature for 2 h. The mixture was diluted with water (5 mL) and was extracted in CH$_2$Cl$_2$ (3×5 mL). The organic layer was dried (anhyd. Na$_2$SO$_4$) and concentrated. The crude was subjected to General Procedure B using sodium cyanide (22 mg, 0.43 mmol), CuI (7 mg, 0.04 mmol), (trans)-1,2-N,N'-dimethylaminocyclohexane (57 µL, 0.36 mmol), and K$_2$CO$_3$ (120 mg, 0.72 mmol) and purified by flash chromatography (Combi-flash Rf, Hex/EtOAc=0-20% gradient). To a solution of resulted ethyl 7-cyano-1-methyl-1H-indole-5-carboxylate in DMF (2 mL) was added and NBS (51 mg, 0.28 mmol) at 0° C. and stirred for 1 h. Same work up and purification protocols described in general coupling procedure A were followed to afford the title compound (52 mg, 47%). LCMS: $R_T$=1.672 min, MS (ES) 307.0 (M+H).

Step B. Example 244

The title compound (25 mg, 68%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), ethyl 3-bromo-7-cyano-1-methyl-1H-indole-5-carboxylate (19 mg, 0.06 mmol), CuI (5 mg, 0.025 mmol), (trans)-1,2-N,N'-dimethylaminocyclohexane (8 µL, 0.05 mmol), and K$_2$CO$_3$ (25 mg, 0.075 mmol) followed by saponification using General Procedure D. LCMS: $R_T$=2.006 min, MS (ES) 736.9 (M+H).

Example 245

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-(3-pyridylmethyl)indole-2-carboxylic acid The title compound (7.3 mg, 84%) was prepared following the procedure described Example 241 using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (8 mg, 0.011 mmol), NaH (2 mg, 0.05 mmol) and 3-chloromethylpyridine HCl salt (5 mg, 0.031 mmol). LCMS: $R_T$=1.760, 1.786 min, MS (ES) 789.0 (M+H).

Example 246

(R)-2-(Benzofuran-3-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (Separated Stereoisomer, $2^{nd}$ Eluting Atropisomer)

The title compound (11 mg, 33%) was prepared following General coupling procedure B as the second eluting atropisomer (absolute configuration undetermined) along with Example 237. LCMS: $R_T$=2.238 min, MS (ES) 655.0 (M+H).

Example 247

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-(2-pyridylmethyl)indole-2-carboxylic acid The title compound (4 mg, 37%) was prepared following the procedure described Example 241 using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) NaH (2 mg, 0.05 mmol) and 2-bromomethylpyridine HBr salt (5 mg, 0.020 mmol). LCMS: $R_T$=1.839 min (major), 1.867 min (minor), MS (ES) 789.0 (M+H).

Example 248

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-(4-pyridylmethyl)indole-2-carboxylic acid The title compound (5.7 mg, 53%) was prepared following the same procedure as described for Example 247, substituting 3-bromomethylpryidine HBr with 4-bromom-

Example 249

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-(2-pyridylmethyl)indole-2-carboxylic acid (Separated Stereoisomer, 1$^{st}$ Eluting Atropisomer)

The title compound (2.1 mg, 19%) was separated from Example 247 by reverse phase HPLC (Phenomenex Gemini C18, H$_2$O/CH$_3$CN gradient 35-95% MeCN 0.1% TFA) as the 1$^{st}$ eluting atropisomer (absolute stereochemistry undetermined). LCMS: R$_T$=1.839 min, MS (ES) 789.0 (M+H).

Example 250

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,7-dimethyl-1H-indole-6-carboxylic acid

Step A. Preparation of methyl 3-bromo-1,7-dimethyl-1H-indole-6-carboxylate

The title compound (65 mg, 81%) was prepared following General Procedure F using methyl 7-methyl-1H-indole-6-carboxylate (50 mg, 0.28 mmol), NBS (51 mg, 0.28 mmol), NaH (14 mg, 0.34 mmol) and MeI (22 μL, 0.34 mmol). LCMS: R$_T$=1.602 min, MS (ES) 282.1 (M+H).

Step B. Example 250

The title compound (27 mg, 74%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 3-bromo-1,7-dimethyl-1H-indole-6-carboxylate (15 mg, 0.06 mmol), CuI (5 mg, 0.025 mmol), (trans)-1,2-N,N'-dimethylaminocyclohexane (8 μL, 0.05 mmol), and K$_2$CO$_3$ (25 mg, 0.075 mmol) followed by saponification using General Procedure D. LCMS: R$_T$=2.043 min, MS (ES) 726.0 (M+H); $^1$H NMR (400 MHz, DMSO-d$_6$) δ 7.75 (d, J=8.6 Hz, 1H), 7.49 (d, J=3.3 Hz, 1H), 7.39 (dd, J=8.4, 2.7 Hz, 1H), 7.29 (d, J=8.6 Hz, 1H), 7.21 (dd, J=8.4, 4.7 Hz, 1H), 6.72 (s, 2H), 4.44 (dd, J=13.0, 3.9 Hz, 2H), 4.11 (s, 3H), 3.98 (tt, J=6.4, 2.7 Hz, 2H), 3.78 (s, 1.5H), 3.77 (s, 1.5H), 3.58 (t, J=11.2 Hz, 1H), 3.39-3.16 (m, 2H), 2.95 (s, 3H), 2.25 (s, 6H), 2.12 (s, 1.5H), 2.11-2.04 (m, 2H), 2.04 (s, 1.5H), 1.97 (s, 1.5H), 1.88 (s, 1.5H), 1.07 (d, J=6.5 Hz, 3H).

Example 251

(R)-7-Chloro-10-(3-(4-chloro-3,5-dimethylphenoxy)propyl)-4-methyl-2-(1-methyl-5-(1H-tetrazol-5-yl)-1H-indol-3-yl)-6-(1,3,5-trimethyl-1H-pyrazol-4-yl)-3,4-dihydropyrazino[1,2-a]indol-1(2H)-one (Separated Stereoisomer, 1$^{st}$ Eluting Atropisomer)

The title compound (28 mg, 38%) was isolated along with Example 235 as the first eluting atropisomer (absolute configuration undetermined). LCMS: R$_T$=1.981 min, MS (ES) 736.0 (M+H).

ethylpyridine HBr salt (5 mg, 0.020 mmol). LCMS: R$_T$=1.817 min, MS (ES) 788.8 (M+H).

Example 252

4-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-1-methyl-indole-3-carboxylic acid The title compound (11.5 mg, 42%) was prepared following General coupling procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (20 mg, 0.037 mmol), methyl 4-bromo-1-methyl-1H-indole-3-carboxylate (20 mg, 0.075 mmol), CuI (5 mg, 0.026 mmol), (trans)-N$^1$,N$^2$-dimethylcyclohexane-1,2-diamine (8 mg, 0.056 mmol), and K$_2$CO$_3$ (25 mg, 0.18 mmol) followed by saponification using General Procedure D. LCMS: R$_T$=1.954 min, MS (ES) 709.9 (M+H); $^1$H NMR (400 MHz, Chloroform-d) δ 9.13 (s, 1H), 7.81 (d, J=8.6 Hz, 1H), 7.45-7.30 (m, 3H), 7.16 (dd, J=5.4, 3.0 Hz, 1H), 7.06 (d, J=4.4 Hz, 1H), 6.56 (s, 2H), 4.38 (dd, J=12.3, 4.0 Hz, 1H), 3.92 (qd, J=7.8, 6.3, 4.7 Hz, 2H), 3.80 (s, 3H), 3.71 (s, 1H), 3.49-3.17 (m, 3H), 2.52 (s, 3H), 2.33 (d, J=8.0 Hz, 1H), 2.29-2.19 (m, 8H), 2.17-2.04 (m, 2H), 1.28 (d, J=6.4 Hz, 3H).

Example 253

(R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-8-carboxylic acid The title compound (20 mg, 56%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), methyl 4-bromoquinoline-8-carboxylate (16 mg, 0.06 mmol), Pd$_2$(dba)$_3$ (1 mg, 0.001 mmol), Xantphos (2 mg, 0.003 mmol), and Cs$_2$CO$_3$ (25 mg, 0.075 mmol) followed by saponification using General Procedure D. LCMS: R$_T$=2.030 min, MS (ES) 709.9 (M+H); $^1$H NMR (400 MHz, DMSO-d$_6$) δ 9.21 (d, J=5.0 Hz, 1H), 8.70-8.48 (m, 1H), 8.19 (dt, J=8.5, 1.8 Hz, 1H), 7.83 (ddd, J=15.6, 8.6, 4.4 Hz, 3H), 7.34 (d, J=8.6 Hz, 1H), 6.70 (d, J=5.4 Hz, 2H), 4.92-4.62 (m, 1H), 4.40-4.12 (m, 2H), 3.97 (t, J=6.4 Hz, 2H), 3.79 (s, 3H), 3.39-3.13 (m, 2H), 2.23 (s, 6H), 2.14 (s, 1.5H), 2.04 (s, 3H), 2.02-1.97 (m, 2H), 1.92 (s, 1.5H), 1.15 (dd, J=6.5, 3.1 Hz, 3H).

Example 254

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-(cyclopropylmethyl)indole-2-carboxylic acid The title compound (7.6 mg, 92%) was prepared following the procedure described Example 241 using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (8 mg, 0.011 mmol), NaH (2 mg, 0.08 mmol) and bromomethylcyclopropane (5 mg, 0.075 mmol). LCMS: R$_T$=2.096 min, MS (ES) 751.9 (M+H).

Example 255

8-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl] naphthalene-1-carboxylic acid The title compound (1.3 mg, 5%) was prepared following General coupling procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (20 mg, 0.037 mmol), methyl 8-bromo-1-naphthoate (20 mg, 0.075 mmol), copper iodide (5 mg, 0.026 mmol), (trans)-$N^1,N^2$-dimethylcyclohexane-1,2-diamine (8 mg, 0.056 mmol), and $K_2CO_3$ (25 mg, 0.18 mmol) followed by saponification and purification following General Procedure D. LCMS: $R_T$=1.976 min, MS (ES) 706.9 (M+H).

Example 256

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-(2-methoxyethyl)indole-2-carboxylic acid The title compound (2.6 mg, 25% yield) was prepared following the same procedure as described in Example 245 substituting 3-chloromethylpyridine HCl with 1-bromo-2-methoxyethane (5 mg, 0.036 mmol). LCMS: $R_T$=2.016 min, MS (ES) 755.8 (M+H).

Example 257

N-[3-[(4R)-7-chloro-10-[3-(4-chloro-3,5-dimethylphenoxy)propyl]-4-methyl-1-oxo-6-(1,3,5-trimethylpyrazol-4-yl)-3,4-dihydropyrazino[1,2-a]indol-2-yl]-1-methyl-indol-5-yl]acetamide

Step A. Preparation of N-(3-bromo-1-methyl-1H-indol-5-yl)acetamide

To a solution of 1-methyl-1H-indol-5-amine (60 mg, 0.41 mmol) in DCM (3 mL) was added DIPEA (100 mg, 0.78 mmol) followed by acetyl chloride (40 mg, 0.513 mmol) at RT, and the reaction was stirred for 10 min. The reaction was quenched by the addition of MeOH, diluted into DCM/$H_2O$ (20 mL, 1:1), the layers were separated, and the aqueous layer was extracted with DCM (2×10 mL). The combined organic extracts were dried concentrated in vacuo. The crude residue was dissolved in DMF (3 mL), and NBS (75 mg, 0.42 mmol) was added. The reaction was stirred for 1 h at RT and determined to be complete by LCMS. The reaction was diluted into DCM (20 mL) and washed with 10% aqueous $Na_2S_2O_3$ solution. The organic layer was dried, concentrated, and purified by flash chromatography (Combi-flash Rf, Hex/EtOAc=0-100% gradient) to afford the title compound (40 mg, 36%).

Step B. Example 257

The title compound (15.2 mg, 75%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (15 mg, 0.028 mmol), N-(3-bromo-1-methyl-1H-indol-5-yl)acetamide (20 mg, 0.075 mmol), CuI (5 mg, 0.026 mmol), (trans)-1,2-N,N'-dimethylaminocyclohexane (8 mg, 0.056 mmol), and $K_2CO_3$ (30 mg, 0.22 mmol). MS (ES) 724.9 (M+H).

Example 258

(R)-7-Chloro-10-(3-(4-chloro-3,5-dimethylphenoxy)propyl)-4-methyl-2-(1-methyl-7-(1H-tetrazol-5-yl)-1H-indol-3-yl)-6-(1,3,5-trimethyl-1H-pyrazol-4-yl)-3,4-dihydropyrazino[1,2-a]indol-1(2H)-one The title compound (15 mg, 93%) was prepared according to the procedure for Example 235 using (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-7-carbonitrile (15 mg, 0.022 mmol) and sodium azide (7 mg, 0.11 mmol). LCMS: $R_T$=2.004 and 2.028 min, MS (ES) 736.0 (M+H).

Example 259

(R)-5-Chloro-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)benzofuran-2-carboxylic acid
(Separated Stereoisomer, $2^{nd}$ Eluting Atropisomer)

The title compound (12 mg, 33%) was isolated along with Example 232 as the $2^{nd}$ eluting atropisomer (absolute configuration undetermined). LCMS: $R_T$=2.245 min, MS (ES) 732.9 (M+H).

Example 260

(R)-2-(5-Acetyl-1-methyl-1H-indol-3-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one The title compound (21 mg, 59%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol), 1-(3-bromo-1-methyl-1H-indol-5-yl)ethan-1-one (13 mg, 0.06 mmol), CuI (5 mg, 0.025 mmol), (trans)-1,2-N,N'-dimethylaminocyclohexane (8 µL, 0.05 mmol), and $K_2CO_3$ (25 mg, 0.075 mmol). LCMS: $R_T$=2.078 and 2.099 min, MS (ES) 710.0 (M+H).

Example 261

3-((4R)-7-chloro-10-(3-(4-chloro-3,5-dimethylphenoxy)propyl)-6-(3,5-dimethyl-1-((1-methylpyrrolidin-3-yl)methyl)-1H-pyrazol-4-yl)-4-methyl-1-oxo-3,4-dihydro pyrazino[1,2-a]indol-2(1H)-yl)-1-methyl-1H-indole-5-carboxylic acid

Step A. Preparation of methyl (R)-3-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-5-carboxylate To solution of methyl (R)-3-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3, 4-dihydropyrazino[1,2-a]indol-2(1H)-yl)-1-methyl-1H-indole-5-carboxylate (100 mg, 0.12 mmol) in THF (2 mL) was added TBAF (0.59 mL, 0.59 mmol). The reaction mixture was heated to 100° C. for 20 min under microwave. The solvent was removed in vacuo and residue was purified by flash chromatography (Combi-flash Rf. DCM/MeOH=0-10% gradient) to afford the title compound as brown oil (75 mg, 88%). LCMS: $R_T$=0.984 min, MS (ES) 712.2 (M+H).

Step B. Example 261

To a solution of methyl (R)-3-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-5-carboxylate (41 mg, 0.057 mmol) in DMF (1.5 mL) was added NaH (5 mg, 0.11 mmol). After 15 min, 3-(bromomethyl)-1-methylpyrrolidine (20 mg, 0.11 mmol) was added to reaction mixture and stirred overnight. The solvent was concentrated in vacuo and residue was filtered through silica pad with DCM/MeOH (3/1) then solvent was removed in vacuo. The residue was redissolved in mixture of methanol and dioxane (1 mL/2 mL), and sodium hydroxide (0.2 mL, 2M solution) was added. The reaction mixture was stirred for 3 h at room temperature and then concentrated in vacuo. The residue was purified by reverse phase HPLC (Phenomenex Gemini C18, $H_2O$/$CH_3CN$ gradient to 35-95% MeCN 0.1,% TFA) to afford the title compound (18 mg, 49%). LCMS: $R_T$=non polar method: 0.712 min, MS (ES) 795.3 (M+H).

Example 262

(R)-3-(7-chloro-10-(3-(4-chloro-3,5-dimethylphenoxy)propyl)-6-(3,5-dimethyl-1-((tetrahydro-2H-pyran-4-yl)methyl)-1H-pyrazol-4-yl)-4-methyl-1-oxo-3,4-dihydro pyrazino[1,2-a]indol-2(1H)-yl)-1-methyl-1H-indole-5-carboxylic acid The title compound (15 mg, 41%) was prepared according to the procedure used in Example 261 Step B by substituting 3-(bromomethyl)-1-methylpyrrolidine for 4-(bromomethyl) tetrahydro-2H-pyran. LCMS: $R_T$=non polar method: 0.976 min, MS (ES) 796.3 (M+H).

Example 263

(R)-3-(7-chloro-10-(3-(4-chloro-3,5-dimethylphenoxy)propyl)-6-(3,5-dimethyl-1-(2-(pyrrolidin-1-yl)ethyl)-1H-pyrazol-4-yl)-4-methyl-1-oxo-3,4-dihydropyrazino[1,2-a]indol-2(1H)-yl)-1-methyl-1H-indole-5-carboxylic acid The title compound (13 mg, 40%) was prepared according to the procedure used in Example 261 Step B by substituting 3-(bromomethyl)-1-methylpyrrolidine for 1-(2-bromoethyl) pyrrolidine. LCMS: $R_T$=non polar method: 0.766 min, MS (ES) 795.3 (M+H); $^1$H NMR (MeOD, 400 MHz) δ (ppm) 8.27 (s, 1H), 7.95 (d, J=8.4 Hz, 1H), 7.78 (d, J=8.8 Hz, 1H), 7.53 (d, J=8.8 Hz, 1H), 7.39 (d, J=3.6 Hz, 1H), 7.30 (d, J=8.4 Hz, 1H), 6.64 (s, 2H), 4.62-4.47 (m, 3H), 4.32-4.30 (m, 1H), 4.02-3.95 (m, 2H), 3.89 (s, 2H), 3.78-3.68 (m, 4H), 3.52-3.30 (m, 2H), 3.20-3.13 (m, 2H), 2.68 (s, 2H), 2.29 (s, 6H), 2.25-2.03 (m, 4H), 2.20 (s, 3H), 2.04 (s, 3H), 1.25 (t, J=6.0 Hz, 3H).

Example 264

1-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]isoquinoline-6-carboxylic acid The title compound (14 mg, 53%) was prepared following General coupling procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (20 mg, 0.037 mmol), methyl 1-chloroisoquinoline-6-carboxylate (20 mg, 0.90 mmol), CuI (5 mg, 0.026 mmol), (trans)-$N^1$,$N^2$-dimethylcyclohexane-1,2-diamine (8 mg, 0.056 mmol), and $K_3PO_4$ (30 mg, 0.14 mmol) followed by saponification using General Procedure D. LCMS: $R_T$=2.299 min, MS (ES) 709.9 (M+H).

Example 265

(R)-7-chloro-10-(3-(4-chloro-3,5-dimethylphenoxy) propyl)-4-methyl-2-(1-methyl-5-(piperazin-1-ylsulfonyl)-1H-indol-3-yl)-6-(1,3,5-trimethyl-1H-pyrazol-4-yl)-3,4-dihydropyrazino[1,2-a]indol-1(2H)-one Step A. Preparation of tert-butyl 4-((3-bromo-1-methyl-1H-indol-5-yl)sulfonyl)piperazine-1-carboxylate To a solution of tert-butyl 4-((1-methyl-1H-indol-5-yl) sulfonyl)piperazine-1-carboxylate (65 mg, 0.17 mmol) in DMF (2 mL) was added NBS (35 mg, 0.20 mmol), and the reaction was stirred at RT until complete as determined by LCMS. The reaction was diluted into DCM (20 mL), washed with 10% aqueous $Na_2S_2O_3$ (10 mL), dried, and concentrated in vacuo to afford the title compound (66 mg, 85%).

Step B. Preparation of tert-butyl (R)-4-((3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indol-5-yl)sulfonyl)piperazine-1-carboxylate The title compound (25 mg, 49% crude) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (20 mg, 0.037 mmol), tert-butyl 4-((3-bromo-1-methyl-1H-indol-5-yl)sulfonyl)piperazine-1-carboxylate (30 mg, 0.066 mmol), CuI (5 mg, 0.026 mmol), (trans)-$N^1$,$N^2$-dimethylcyclohexane-1,2-diamine (8 mg, 0.056 mmol), and $K_2CO_3$.

Step C. Example 265

To a solution of the crude reaction product from Step B in dioxane (2 mL) was added HCl in dioxane (4.0 M, 0.5 mL, 2.0 mmol), and the reaction was stirred for 16 h at RT. The reaction mixture was concentrated in vacuo, and half of the material was purified by reverse phase HPLC (Phenomenex Gemini C18, $H_2O$/$CH_3CN$ gradient 35-95% MeCN 0.1% TFA) to afford the title compound (7.3 mg, 48% yield two steps). LCMS: $R_T$=1.848 min, MS (ES) 816.0 (M+H).

Example 266

4-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-2-carboxamide The title compound (4.8 mg, 48%) was prepared following General Procedure E employing (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid (10 mg, 0.014 mmol), HATU (10 mg, 0.026 mmol), DIPEA (10 mg, 0.078 mmol), and ammonia in MeOH (7.0 M, 0.05 mL, 0.35 mmol). LCMS: $R_T$=2.061 min, MS (ES) 711.0 (M+H).

Example 267

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-N,1-dimethyl-1H-indole-5-sulfonamide Step A. Preparation of 3-bromo-N,1-dimethyl-1H-indole-5-sulfonamide To a solution of I-methyl-1H-indole-5-sulfonyl chloride (40 mg, 0.17 mmol) in DCM (2 mL) was added DIPEA (40 mg, 0.31 mmol). Methylamine hydrochloride (30 mg, 0.45 mmol) was added, and the reaction was stirred at RT until complete by LCMS then concentrated in vacuo. The crude residue was then brominated following the procedure described in Example 265 Step A using NBS (35 mg, 0.20 mmol) to afford the title compound (37 mg, 71%).

Step B. Example 267

The title compound (9 mg, 32%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (20 mg, 0.037 mmol), 3-bromo-N,1-dimethyl-1H-indole-5-sulfonamide (25 mg, 0.083 mmol), CuI (5 mg, 0.026 mmol), (trans)-$N^1,N^2$-dimethylcyclohexane-1,2-diamine (8 mg, 0.056 mmol), and $K_2CO_3$ (25 mg, 0.18 mmol). LCMS: $R_T$=2.059 min, MS (ES) 760.9 (M+H); $^1$H NMR (400 MHz, Chloroform-d) δ 8.09 (d, J=11.2 Hz, 1H), 7.73 (ddd, J=9.3, 7.6, 1.8 Hz, 1H), 7.45 (d, J=8.7 Hz, 1H), 7.40-7.28 (m, 2H), 6.63 (s, 2H), 4.51 (dd, J=40.0, 11.5 Hz, 1H), 4.20 (d, J=21.5 Hz, 1H), 4.08 (s, 1.5H), 4.05 (s, 1.5H), 3.99 (t, J=6.2 Hz, 2H), 3.86 (s, 3H), 3.70 (t, J=12.6 Hz, 1H), 3.51-3.28 (m, 2H), 2.62 (s, 1.5H), 2.60 (s, 1.5H), 2.34 (s, 1.5H), 2.32 (s, 6H), 2.28 (s, 1.5H), 2.24-2.09 (m, 5H), 1.23 (d, J=5.9 Hz, 3H).

Example 268

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-methoxyethyl)-1H-indole-5-carboxylic acid Step A. Preparation of methyl 3-bromo-1-((2-(trimethylsilyl)ethoxy)methyl)-1H-indole-5-carboxylate The title compound (107 mg, 71%) was prepared following General Procedure G using methyl 3-bromo-1H-indole-5-carboxylate (100 mg, 0.39 mmol), NaH (24 mg, 0.59 mmol), and (2-(chloromethoxy)ethyl)trimethylsilane (0.11 mL, 98.5 mg, 0.59 mmol).

Step B. Preparation of methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-(trimethylsilyl)ethoxy)methyl)-1H-indole-5-carboxylate The title compound (93 mg, 82%) was prepared following General Procedure B using methyl 3-bromo-1-((2-(trimethylsilyl)ethoxy)methyl)-1H-indole-5-carboxylate (78 mg, 0.20 mmol), (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (61 mg, 0.11 mmol), (1R,2R)—$N^1,N^2$-dimethylcyclohexane-1,2-diamine (14 mg, 0.098 mmol), CuI (9.4 mg, 0.049 mmol) and $K_2CO_3$ (54.7 mg, 0.40 mmol). MS (ES) 842.3 (M+H).

Step C. Preparation of methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate To a solution of methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-(trimethylsilyl)ethoxy)methyl)-1H-indole-5-carboxylate (110 mg, 0.13 mmol) in THF (0.5 mL) was added TBAF (1.18 mL, 1.17 mmol, 1.0 M in THF), and the reaction mixture was stirred as 40° C. for 24 h. The reaction was cooled to RT, quenched with saturated $NH_4Cl$ aq. solution and extracted with EtOAc (3×5 mL). The combined organic layer was washed with brine, dried over $MgSO_4$, filtered, and concentrated in vacuo. The residue was purified by flash chromatography (Combi-flash Rf, Hex/EtOAc=0-100% gradient followed by DCM/MeOH=0-10% gradient) to afford the title compound (40 mg, 43%). MS (ES) 712.3 (M+H).

Step D. Example 268

The title compound (5.1 mg, 21%, 2 steps) was prepared following General Procedure G using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (23 mg, 0.032 mmol), NaH (1.9 mg, 0.048 mmol), 1-bromo-2-methoxyethane (30 mg, 0.275 mmol) followed by saponification and purification following General Procedure D. LCMS: $R_T$=1.947 min, MS (ES) 756.3 (M+H).

Example 269

3-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-1-methyl-indole-5-carboxamide The title compound (5.6 mg, 55%) was prepared following General Procedure E using ((R)-3-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]

indol-2(1H)-yl)-1-methyl-1H-indole-5-carboxylic acid (10 mg, 0.014 mmol), HATU (10 mg, 0.026 mmol), DIPEA (10 mg, 0.078 mmol), and ammonia in MeOH (7.0 M, 0.05 mL, 0.35 mmol). LCMS: $R_T$=2.015 min, MS (ES) 708.9 (M+H).

Example 270

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-2-carboxamide The title compound (6.8 mg, 68%) was prepared following General Procedure E using (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid (10 mg, 0.014 mmol), HATU (10 mg, 0.026 mmol), DIPEA (10 mg, 0.078 mmol), and ammonia in MeOH (7.0 M, 0.05 mL, 0.35 mmol). LCMS: $R_T$=2.001 min, MS (ES) 711.0 (M+H).

Example 271

(R)-7-(10-(3-(4-chloro-3,5-dimethylphenoxy)propyl)-6-(4,6-dimethylpyrimidin-5-yl)-4,7-dimethyl-1-oxo-3,4-dihydropyrazino[1,2-a]indol-2(1H)-yl)-1-(pyridin-2-ylmethyl)-1H-indole-2-carboxylic acid (partially separated the 1st Eluting Atropisomer)

Step A. Preparation of ethyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1H-indole-2-carboxylate The title compound (14 mg, 13%) was prepared following General Procedure B using ethyl 7-bromo-1H-indole-2-carboxylate (80 mg, 0.30 mmol), (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (80 mg, 0.15 mmol), (1R,2R)—$N^1,N^2$-dimethylcyclohexane-1,2-diamine (47 μL, 42.4 mg, 0.30 mmol), CuI (28.4 mg, 0.15 mmol) and $K_2CO_3$ (61.8 mg, 0.45 mmol). MS (ES) 704.3 (M+H).

Step B. Example 271

The title compound was prepared following General Procedure G using ethyl (R)-7-(10-(3-(4-chloro-3,5-dimethylphenoxy)propyl)-6-(4,6-dimethylpyrimidin-5-yl)-4,7-dimethyl-1-oxo-3,4-dihydropyrazino[1,2-a]indol-2(1H)-yl)-1H-indole-2-carboxylate (14 mg, 0.019 mmol), NaH (4.6 mg, 0.11 mmol), 2-(bromomethyl)pyridine hydrobromide (14.4 mg, 0.058 mmol) followed by saponification using General Procedure D. The title compound was isolated as a partially separated the first eluting isomer (2.2 mg, 15%, absolute configuration undetermined). LCMS: $R_T$=1.877 min, MS (ES) 767.3 (M+H).

Example 272

7-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-1,5-dimethyl-indole-2-carboxylic acid The title compound (14.9 mg, 37%) was prepared following General coupling procedure A using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (30 mg, 0.056 mmol), methyl 7-bromo-1,5-dimethyl-1H-indole-2-carboxylate (25 mg, 0.089 mmol), $Pd_2(dba)_3$ (6 mg, 0.0065 mmol), Xantphos (8 mg, 0.013 mmol), and $Cs_2CO_3$ (60 mg, 0.19 mmol) followed by saponification using General Procedure D. LCMS: $R_T$=2.092, 2.119 min, MS (ES) 723.9 (M+H); $^1$H NMR (400 MHz, Chloroform-d) δ 9.19 (s, 1H), 7.82 (dd, J=8.7, 1.1 Hz, 1H), 7.48 (s, 0.7H), 7.44 (s, 0.3H) 7.39-7.34 (m, 2H), 6.95 (d, J=1.5 Hz, 1H), 6.63 (s, 1.3H), 6.61 (s, 0.7H), 4.20 (d, J=21.5 Hz, 2H), 4.06-3.93 (m, 4H), 3.85-3.71 (m, 1H), 3.53 (dd, J=12.6, 5.4 Hz, 1H), 3.45-3.32 (m, 2H), 2.52 (s, 1H), 2.50 (s, 2H), 2.43 (s, 2H), 2.40 (s, 1H), 2.34 (s, 1H), 2.33 (s, 2H), 2.32 (s, 6H), 2.25-2.18 (m, 2H), 1.32 (d, J=6.4 Hz, 2H), 1.22 (d, J=6.5 Hz, 1H).

Example 273

3-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-1-methyl-indazole-4-carboxylic acid The title compound (13.2 mg, 39%) was prepared following General coupling procedure B using (R)-7-chloro-10-(3(4-chloro-3,5-dimethylphenoxy)propyl)-6-(4,6-dimethylpyrimidin-5-yl)-4-methyl-3,4-dihydropyrazino[1,2-a]indol-1(2H)-one (25 mg, 0.046 mmol), methyl 3-bromo-1-methyl-1H-indazole-4-carboxylate (20 mg, 0.075 mmol), CuI (5 mg, 0.026 mmol), (trans)-$N^1,N^2$-dimethylcyclohexane-1,2-diamine (8 mg, 0.056 mmol), and $K_2CO_3$ (30 mg, 0.22 mmol) followed by saponification using General Procedure D. LCMS: $R_T$=1.935 min, MS (ES) 711.0 (M+H); $^1$H NMR (400 MHz, Chloroform-d) δ 9.17 (s, 1H), 7.75 (d, J=8.7 Hz, 1H), 7.59 (d, J=7.7 Hz, 1H), 7.34 (dd, J=7.8, 5.4 Hz, 3H), 6.51 (s, 2H), 4.36 (s, 1H), 4.07 (s, 3H), 3.92 (s, 2H), 3.74 (s, 2H), 3.36 (s, 1H), 3.21 (dt, J=13.7, 7.4 Hz, 1H), 2.49 (s, 3H), 2.26 (s, 6H), 2.24-2.10 (m, 5H), 1.27 (d, J=5.7 Hz, 3H).

Example 274

(R)-7-chloro-10-(3-(4-chloro-3,5-dimethylphenoxy)propyl)-4-methyl-2-(1-methyl-5-((4-methylpiperazin-1-yl)sulfonyl)-1H-indol-3-yl)-6-(1,3,5-trimethyl-1H-pyrazol-4-yl)-3,4-dihydropyrazino[1,2-a]indol-1(2H)-one Step A. Preparation of 3-bromo-1-methyl-5-((4-methylpiperazin-1-yl)sulfonyl)-1H-indole The title compound (49 mg, 75%) was prepared following the procedure described in Example 265 Step A using 1-methyl-5-((4-methylpiperazin-1-yl)sulfonyl)-1H-indole (80 mg, 0.17 mmol) and NBS (35 mg, 0.20 mmol).

Step B. Example 274

The title compound (22.6 mg, 73%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (20 mg, 0.037 mmol), 3-bromo-1-methyl-5-((4-methylpiperazin-1-yl)sulfonyl)-1H-indole (30 mg, 0.081 mmol), CuI (5 mg, 0.026 mmol), (trans)-$N^1,N^2$-dimethylcyclohexane-1,2-diamine (8 mg, 0.056 mmol), and K$_2$CO$_3$ (25 mg, 0.18 mmol) followed by saponification using General Procedure D. LCMS: R$_T$=1.868 min, MS (ES) 829.9 (M+H); $^1$H NMR (400 MHz, Chloroform-d) δ 7.97 (d, J=1.6 Hz, 0.5H), 7.90 (d, J=2.0 Hz, 0.5H) 7.75 (dd, J=8.6, 5.5 Hz, 1H), 7.63 (ddd, J=13.7, 8.7, 1.7 Hz, 1H), 7.51 (s, 0.5H), 7.49 (s, 0.5H), 7.37 (s, 1H), 7.32 (dd, J=8.6, 1.9 Hz, 1H), 6.65 (s, 1H), 6.64 (s, 1H), 4.50 (dd, J=12.8, 4.01 Hz, 0.5H), 4.28 (d, J=12.4 Hz, 1.5H), 4.11-3.96 (m, 5H), 3.94-3.70 (m, 7H), 3.64-3.27 (m, 3H), 3.15-2.87 (m, 4H), 2.82 (s, 15H), 2.79 (s, 1.5H), 2.34 (s, 3H), 2.33 (s, 3H), 2.32 (s, 1.5H), 2.28 (s, 1.5H), 2.25-2.19 (m, 2H), 2.14 (d, J=2.6 Hz, 3H), 1.32 (d, J=6.1 Hz, 1.5H), 1.18 (d, J=6.3 Hz, 1.5H).

Example 275

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1,2-dimethyl-indole-5-carboxylic acid Step A. Preparation of methyl 3-bromo-1,2-dimethyl-1H-indole-5-carboxylate The title compound (98 mg, 81%) was prepared following General Procedure F using 2-methyl-1H-indole-5-carboxylic acid (75 mg, 0.43 mmol), NBS (90 mg, 0.51 mmol). NaH (42 mg, 1.75 mmol), and MeI (200 mg, 1.41 mmol).

Step B. Example 275

The title compound (12.5 mg, 35%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), methyl 3-bromo-1,2-dimethyl-1H-indole-5-carboxylate (30 mg, 0.11 mmol), CuI (5 mg, 0.026 mmol), (trans)-N$^1$,N$^2$-dimethylcyclohexane-1,2-diamine (8 mg, 0.056 mmol), and K$_2$CO$_3$ (30 mg, 0.22 mmol) followed by saponification using General Procedure D. LCMS: R$_T$=2.109 min, MS (ES) 726.0 (M+H).

Example 276

(R)-7-(10-(3-(4-chloro-3,5-dimethylphenoxy)propyl)-6-(4,6-dimethylpyrimidin-5-yl)-4,7-dimethyl-1-oxo-3,4-dihydropyrazino[1,2-a]indol-2(1H)-yl)-1-(pyridin-2-ylmethyl)-1H-indole-2-carboxylic acid (partially separated the 2$^{nd}$ Eluting Atropisomer)

The title compound was isolated by reverse phase HPLC (Phenomenex Gemini C18, H$_2$O/CH$_3$CN gradient to 35-95% MeCN 0.1% TFA, 10 mins gradient) as a partially separated the 2$^{nd}$ eluting isomer (absolute configuration undetermined). LCMS: R$_T$=1.897 min, MS (ES) 767.3 (M+H).

Example 277

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-6-carboxamide The title compound (3.2 mg, 32%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-6-carboxylic acid (10 mg, 0.014 mmol), HATU (10 mg, 0.026 mmol), DIPEA (10 mg, 0.078 mmol), and ammonia in MeOH (7.0 M, 0.05 mL, 0.35 mmol). LCMS: R$_T$=2.011 min, MS (ES) 711.0 (M+H).

Example 278

(R)-2-(5-((4-acetylpiperazin-1-yl)sulfonyl)-1-methyl-1H-indol-3-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one To a solution of (R)-7-chloro-10-(3-(4-chloro-3,5-dimethylphenoxy)propyl)-4-methyl-2-(1-methyl-5-(piperazin-1-ylsulfonyl)-1H-indol-3-yl)-6-(1,3,5-trimethyl-1H-pyrazol-4-yl)-3,4-dihydropyrazino[1,2-a]indol-1(2H)-one (15 mg, 0.018 mmol) in DCM (3 mL) was added DIPEA (10 mg, 0.078 mmol) followed by acetyl chloride (5 mg, 0.037 mmol). The reaction was stirred at RT for 10 min. The reaction was quenched with MeOH, diluted with DCM/H$_2$O (10 mL, 1:1) and extracted with DCM (2×5 mL). The combined organic extracts were dried, concentrated in vacuo, and purified by reverse phase HPLC (Phenomenex Gemini C18, H$_2$O/CH$_3$CN gradient 35-95% MeCN 0.1% TFA) to afford the title compound (12.1 mg, 77%). LCMS: R$_T$=2.245, 2.262 min, MS (ES) 858.0 (M+H).

Example 279

7-(8-Chloro-11-(3-(4-chloro-3,5-dimethylphenoxy)propyl)-7-(4,6-dimethylpyrimidin-5-yl)-1-oxo-4,5-dihydro-1H-[1,4]diazepino[1,2-a]indol-2(3H)-yl)-1-(pyridin-2-ylmethyl)-1H-indole-2-carboxylic acid Step A. Preparation of ethyl 7-(8-chloro-11-(3-(4-chloro-3,5-dimethylphenoxy)propyl)-7-(4,6-dimethylpyrimidin-5-yl)-1-oxo-4,5-dihydro-1H-[1,4]diazepino[1,2-a]indol-2(3H)-yl)-1H-indole-2-carboxylate The title compound (21 mg, 20% yield) was prepared following General Procedure B using ethyl 7-bromo-1H-indole-2-carboxylate (79.8 mg, 0.30 mmol), 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one (80 mg, 0.15 mmol), (1R,2R)—N$^1$,N$^2$-dimethylcyclohexane-1,2-diamine (47 μL, 42.4 mg, 0.30 mmol), CuI (28.4 mg, 0.15 mmol) and K$_2$CO$_3$ (61.8 mg, 0.45 mmol). MS (ES) 724.3 (M+H).

Step B. Example 279

The title compound (5.7 mg, 32%, 2 steps) was prepared following General Procedure G using ethyl 7-(8-chloro-11-(3-(4-chloro-3,5-dimethylphenoxy)propyl)-7-(4,6-dimethylpyrimidin-5-yl)-1-oxo-4,5-dihydro-1H-[1,4]diazepino[1,2-a]indol-2(3H)-yl)-1H-indole-2-carboxylate (17 mg, 0.023 mmol), NaH (2.8 mg, 0.069 mmol), 2-(bromomethyl)pyridine hydrobromide (8.9 mg, 0.035 mmol) followed by saponification using General Procedure D. LCMS: R$_T$=1.845 min, MS (ES) 787.1 (M+H). $^1$H NMR (400 MHz, CDCl$_3$) δ 9.18 (s, 1H), 8.59 (s, 1H), 8.01-7.97 (m, 1H), 7.78 (d, J=8.0 Hz, 1H), 7.65 (d, J=8.6 Hz, 1H), 7.59 (s, 1H), 7.39-7.34 (m, 1H), 7.30-7.23 (m, 2H), 7.06 (d, J=7.3 Hz, 1H), 6.84 (d, J=8.0 Hz, 1H), 6.59 (s, 2H), 6.41 (d, J=17.8 Hz, 1H), 6.12 (d, J=17.0 Hz, 1H), 4.09-3.97 (m, 2H), 3.84-3.79 (m, 1H), 3.70-3.59 (m, 2H), 3.38-3.36 (m, 1H), 2.89-2.84 (m, 1H), 2.42 (s, 3H), 2.32 (s, 6H), 2.28 (s, 3H), 2.16-2.12 (m, 1H), 2.05-1.94 (m, 2H), 1.88-1.83 (m, 1H), 1.64-1.57 (m, 1H).

Example 280

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-N-(2-pyridyl)indole-5-carboxamide The title compound (3.5 mg, 31%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (20 mg, 0.155 mmol), and 2-aminopyridine (5 mg, 0.053 mmol). The reaction was stirred for 16 h at room temperature followed by 8 h at 50° C. LCMS: $R_T$=1.994 min, MS (ES) 787.9 (M+H).

Example 281

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-N-(2-pyridylmethyl)indole-5-carboxamide The title compound (6.6 mg, 58%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (20 mg, 0.155 mmol), and pyridin-2-ylmethanamine (5 mg, 0.046 mmol). After 16 hr the reaction was complete. LCMS: $R_T$=1.861 min, MS (ES) 802.0 (M+H).

Example 282

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-N,1-dimethyl-N-(3-pyridylmethyl)indole-5-carboxamide The title compound (8.5 mg, 75%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (20 mg, 0.155 mmol), and N-methyl-1-(pyridin-3-yl)methanamine (5 mg, 0.041 mmol). After 16 h the reaction was complete. LCMS: $R_T$=1.860 min, MS (ES) 816.0 (M+H).

Example 283

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-N-(4-pyridyl)indole-5-carboxamide The title compound (6.6 mg, 58%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (20 mg, 0.155 mmol), and 4-aminopyridine (5 mg, 0.053 mmol). The reaction was stirred for 16 h at room temperature followed by 8 h at 50° C. LCMS: $R_T$=1.875 min, MS (ES) 787.9 (M+H).

Example 284

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-N-(4-pyridylmethyl)indole-5-carboxamide The title compound (8.3 mg, 73%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (20 mg, 0.155 mmol), and pyridin-4-ylmethanamine (5 mg, 0.046 mmol). After 16 h the reaction was be complete. LCMS: $R_T$=1.825 min, MS (ES) 802.0 (M+H).

Example 285

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-N-phenyl-indole-5-carboxamide The title compound (6.3 mg, 57%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (20 mg, 0.155 mmol), and aniline (5 mg, 0.053 mmol). The reaction was stirred for 16 h at room temperature followed by 8 h at 50° C. LCMS: $R_T$=2.234 min, MS (ES) 787.0 (M+H).

Example 286

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-N,1-dimethyl-1H-indole-5-carboxamide The title compound (6.8 mg, 67%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (20 mg, 0.155 mmol), and methylamine hydrochloride (5 mg, 0.074 mmol). After 16 h the reaction was complete. LCMS: $R_T$=2.029 min, MS (ES) 725.0 (M+H).

Example 287

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-N-(3-pyridylmethyl)indole-5-carboxamide The title compound (8.8 mg, 78%) was prepared following General Procedure E employing (R)-3-(7-chloro-10-(3-

(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (20 mg, 0.155 mmol), and pyridin-3-ylmethanamine (5 mg, 0.046 mmol). After 16 h the reaction was complete. LCMS: $R_T$=1.841 min, MS (ES) 802.0 (M+H).

Example 288

(R)-7-chloro-10-(3-(4-chloro-3,5-dimethylphenoxy)propyl)-4-methyl-2-(1-methyl-1H-indol-3-yl)-6-(1,3,5-trimethyl-1H-pyrazol-4-yl)-3,4-dihydropyrazino[1,2-a]indol-1(2H)-one The title compound (14.6 mg, 78%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (15 mg, 0.028 mmol), 3-bromo-1-methyl-1H-indole (11.7 mg, 0.056 mmol), (1R,2R)—$N^1,N^2$-dimethylcyclohexane-1,2-diamine (8.9 μL, 8.0 mg, 0.056 mmol), CuI (5.3 mg, 0.028 mmol) and $K_2CO_3$ (11.6 mg, 0.084 mmol). LCMS: $R_T$=2.151 min, MS (ES) 667.9 (M+H); $^1$H NMR (400 MHz, CDCl$_3$) δ 7.59 (dd, J=8.6, 2.3 Hz, 1H), 7.40 (dd, J=7.9, 3.8 Hz, 1H), 7.28-7.26 (m, 1H), 7.22-7.21 (m, 1H), 7.18-7.16 (m, 1H), 7.10 (d, J=5.3 Hz, 1H), 7.05 (t, J=7.5 Hz, 1H), 6.54 (s, 2H), 4.31-4.26 (m, 1H), 4.24-4.10 (m, 1H), 3.95-3.90 (m, 2H), 3.80 (d, J=3.2 Hz, 3H), 3.73 (s, 3H), 3.56 (ddd, J=12.5, 7.9, 1.5 Hz, 1H), 3.40-3.33 (m, 1H), 3.31-3.24 (m 1H), 2.24 (s, 6H), 2.12 (s, 3H), 1.95 (d, J=2.9 Hz, 3H), 1.19-1.15 (m, 2H), 1.10 (d, J=6.4 Hz, 3H).

Example 289

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-N,N,1-trimethyl-indole-5-carboxamide The title compound (8.0 mg, 76%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (20 mg, 0.155 mmol), and dimethylamine hydrochloride (5 mg, 0.061 mmol). After 16 h the reaction was complete. LCMS: $R_T$=2.085 min, MS (ES) 739.0 (M+H).

Example 290

(4R)-7-chloro-10-[3-(4-chloro-3,5-dimethyl-phenoxy)propyl]-4-methyl-2-[1-methyl-5-(pyrrolidine-1-carbonyl)indol-3-yl]-6-(1,3,5-trimethylpyrazol-4-yl)-3,4-dihydropyrazino[1,2-a]indol-1-one The title compound (7.8, 72%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (20 mg, 0.155 mmol), and pyrrolidine (5 mg, 0.070 mmol). After 16 hr the reaction was complete. LCMS: $R_T$=2.193 min, MS (ES) 765.0 (M+H); $^1$H NMR (400 MHz, Chloroform-d) δ 7.85-7.69 (m, 2H), 7.48-7.28 (m, 4H), 6.62 (d, J=1.8 Hz, 2H), 4.53-4.36 (m, 1H), 4.15-4.09 (m, 4H), 3.99 (t, J=6.1 Hz, 2H), 3.88-3.79 (m, 3H), 3.74-3.49 (s, 4H), 3.37 (ddt, J=34.7, 13.6, 7.1 Hz, 2H), 2.34 (s, 1.5H), 2.32 (s, 3H), 2.31 (s, 3H), 2.28 (s, 1.5H), 2.22-2.13 (m, 6H), 2.05-1.81 (br. s, 4H), 1.24 (m, 3H).

Example 291

3-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-N-(3-pyridyl)indole-5-carboxamide The title compound (6.7 mg, 60%) was prepared following General Procedure E employing (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol), HATU (10 mg, 0.026 mmol), DIPEA (20 mg, 0.155 mmol), and 3-aminopyridine (5 mg, 0.053 mmol). The reaction was stirred for 16 h at room temperature followed by 8 h at 50° C. LCMS: $R_T$=1.882 min, MS (ES) 787.9 (M+H).

Example 292

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-morpholinoethyl)-1H-indole-6-carboxylic acid (separated the $2^{nd}$ Eluting Atropisomer)

Step A. Preparation of methyl 3-bromo-1-(2-morpholinoethyl)-1H-indole-6-carboxylate The title compound (27 mg, 19%) was prepared following General Procedure G using methyl 3-bromo-1H-indole-6-carboxylate (100 mg, 0.39 mmol), NaH (94.6 mg, 2.36 mmol) and 4-(2-chloroethyl)morpholine hydrochloride (220 mg, 1.2 mmol). MS (ES) 367.0 (M+H).

Step B. Example 292

The title compound (2.5 mg, 6%, 2 steps) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.056 mmol), methyl 3-bromo-1-(2-morpholinoethyl)-1H-indole-6-carboxylate (27 mg, 0.074 mmol), (1R,2R)—$N^1,N^2$-dimethylcyclohexane-1,2-diamine (7.0 μL, 6.4 mg, 0.044 mmol), CuI (4.3 mg, 0.022 mmol) and $K_2CO_3$ (27.0 mg, 0.21 mmol) followed by saponification using General Procedure D. The title compound was isolated as the $2^{nd}$ eluting isomer from the final purification by reverse phase HPLC (absolute configuration undetermined). LCMS: $R_T$=1.837 min, MS (ES) 811.3 (M+H).

Example 293

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-morpholinoethyl)-1H-indole-6-carboxylic acid (separated the 1$^{st}$ Eluting Atropisomer)

The title compound (11.5 mg, 25%, 2 steps) was isolated as the 1$^{st}$ eluting isomer from the final reverse phase HPLC along with Example 292. LCMS: $R_T$=1.815 min, MS (ES) 811.3 (M+H).

Example 294

3-[7-[2-(benzyloxymethyl)-4,6-dimethyl-pyrimidin-5-yl]-8-chloro-11-[3-(4-chloro-3,5-dimethyl-phenoxy)propyl]-1-oxo-4,5-dihydro-3H-[1,4]diazepino[1,2-a]indol-2-yl]-1-methyl-indole-5-carboxylic acid

Step A. Preparation of ethyl 7-(2-((benzyloxy)methyl)-4,6-dimethylpyrimidin-5-yl)-1-(3-((tert-butoxycarbonyl)amino)propyl)-6-chloro-3-(3-(4-chloro-3,5-dimethylphenoxy)propyl)-1H-indole-2-carboxylate A mixture of ethyl 7-(2-((benzyloxy)methyl)-4,6-dimethylpyrimidin-5-yl)-6-chloro-3-(3-(4-chloro-3,5-dimethylphenoxy)propyl)-1H-indole-2-carboxylate (180 mg, 0.278 mmol), tert-butyl 1,2,3-oxathiazinane-3-carboxylate 2,2-dioxide (100 mg, 0.42 mmol), and Cs$_2$CO$_3$ (200 mg, 0.61 mmol) in MeCN (10 mL) was heated to 80° C. for 16 h. After which time, an additional portion of tert-butyl 1,2,3-oxathiazinane-3-carboxylate 2,2-dioxide (30 mg, 0.013 mmol) was added. The reaction was heated an additional 6 h, cooled to RT then diluted with EtOAc/H$_2$O (40 mL, 1:1). The organic layer was separated, and the aqueous layer was extracted with EtOAc (2×20 mL). The combined organic layers were dried over MgSO$_4$, filtered, and concentrated in vacuo. The crude reaction mixture was purified by flash chromatography (Combi-flash Rf, Hex/EtOAc=0-100% gradient) to afford the title compound (194 mg, 87%).

Step B. Preparation of 7-(2-((benzyloxy)methyl)-4,6-dimethylpyrimidin-5-yl)-8-chloro-11-(3-(4-chloro-3,5-dimethylphenoxy)propyl)-2,3,4,5-tetrahydro-1H-[1,4]diazepino[1,2-a]indol-1-one To a solution of ethyl 7-(2-((benzyloxy)methyl)-4,6-dimethylpyrimidin-5-yl)-1-(3-((tert-butoxycarbonyl)amino)propyl)-6-chloro-3-(3-(4-chloro-3,5-dimethylphenoxy)propyl)-1H-indole-2-carboxylate (194 mg, 0.24 mmol) in 1,4-dioxane (20 mL) was added a solution of 4M HCl in dioxanes (1 mL, 4 mmol). The reaction was stirred overnight then concentrated in vacuo. The crude residue taken up in MeOH (10 mL) then K$_2$CO$_3$ (300 mg, 2.17 mmol) was added. The reaction was heated to 50° C. for 5 h, concentrated then dissolved in DCM/H$_2$O (60 mL, 1:1). The organic layer was separated, and the aqueous layer was extracted with DCM (2×20 mL). The combined organic layers were dried over MgSO$_4$, filtered, and concentrated in vacuo. The crude reaction mixture was purified by flash chromatography (Combi-flash Rf, Hex/EtOAc=0-100% gradient) to afford the title compound (117 mg, 74% 2 steps).

Step C. Preparation of methyl 3-(7-(2-((benzyloxy)methyl)-4,6-dimethylpyrimidin-5-yl)-8-chloro-11-(3-(4-chloro-3,5-dimethylphenoxy)propyl)-1-oxo-4,5-dihydro-1H-[1,4]diazepino[1,2-a]indol-2(3H)-yl)-1-methyl-1H-indole-5-carboxylate The title compound (78 mg, 53%) was prepared following General coupling procedure B using 7-(2-((benzyloxy)methyl)-4,6-dimethylpyrimidin-5-yl)-8-chloro-11-(3-(4-chloro-3,5-dimethylphenoxy)propyl)-2,3,4,5-tetrahydro-1H-[1,4]diazepino[1,2-a]indol-1-one (115 mg, 0.17 mmol), methyl 3-bromo-1-methyl-1H-indole-5-carboxylate (100 mg, 0.37 mmol), CuI (10 mg, 0.052 mmol), (trans)-1,2-N,N'-dimethylaminocyclohexane (15 mg, 0.10 mmol), and K$_2$CO$_3$ (75 mg, 0.54 mmol).

Step D. Example 294

The title compound (4 mg, 80%) was prepared following General Procedure D using methyl 3-(7-(2-((benzyloxy)methyl)-4,6-dimethylpyrimidin-5-yl)-8-chloro-11-(3-(4-chloro-3,5-dimethylphenoxy)propyl)-1-oxo-4,5-dihydro-1H-[1,4]diazepino[1,2-a]indol-2(3H)-yl)-1-methyl-1H-indole-5-carboxylate (5 mg, 0.0059 mmol) and LiOH (2 mg, 0.083 mmol). LCMS: $R_T$=2.155 min, MS (ES) 829.9 (M+H).

Example 295

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-5-methyl-1-(2-pyridylmethyl)indole-2-carboxylic acid

Step A. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate The title compound was prepared following General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.055 mmol), methyl 7-bromo-5-methyl-1H-indole-2-carboxylate (30 mg, 0.112 mmol), CuI (5 mg, 0.026 mmol), (trans)-1,2-N,N'-dimethylaminocyclohexane (8 mg, 0.056 mmol). K$_3$PO$_4$ (40 mg, 0.19 mmol).

Step B. Example 295

The title compound (9.3 mg, 21%, 2 steps) was prepared following the same procedure as described for Example 247 using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate NaH (6 mg, 0.25 mmol) and 2-(Bromomethyl)pyridine HBr salt (30 mg, 0.119 mmol) followed by saponification using General Procedure D. LCMS: $R_T$=2.096, 2.121 min, MS (ES) 802.9 (M+H).

Example 296

7-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-5-methyl-1-(2-pyridylmethyl)indole-2-carboxylic acid Step A. Preparation of methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methyl-1H-indole-2-carboxylate The title compound was prepared following General Procedure C using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (30 mg, 0.056 mmol), methyl 7-bromo-5-methyl-1H-indole-2-carboxylate (30 mg, 0.112 mmol), CuI (5 mg, 0.026 mmol), (trans)-1,2-N,N'-dimethylaminocyclohexane (8 mg, 0.056 mmol), $K_3PO_4$ (40 mg, 0.19 mmol).

Step B. Example 296

The title compound (5.7 mg, 13%, 2 steps) was prepared following the same procedure as described for Example 247 using methyl methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methyl-1H-indole-2-carboxylate, NaH (6 mg, 0.25 mmol) and 2-(Bromomethyl)pyridine HBr salt (30 mg, 0.119 mmol) followed by saponification using General Procedure D. LCMS: $R_T$=1.956 min, MS (ES) 801.0 (M+H).

Example 297

(P, R)-6-(benzyloxy)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid The title compound was prepared following General coupling procedure B using (P,R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one, methyl 6-(benzyloxy)-4-bromo-1-methyl-1H-indole-2-carboxylate, CuI, (trans)-1,2-N,N'-dimethylaminocyclohexane, and $K_2CO_3$ followed by saponification and purification following General Procedure D. LCMS: $R_T$=2.337 min, MS (ES) 818.2 (M+H).

Example 298

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-(thiazol-2-ylmethyl)indole-2-carboxylic acid To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (20 mg, 0.028 mmol) in DMF (2 mL) was added $Cs_2CO_3$ (40 mg, 0.123 mmol), KI (20 mg, 0.12 mmol), and 2-(chloromethyl)thiazole (25 mg, 0.19 mmol), and the reaction was heated to 90° C. for 4 h. The reaction was then cooled to RT and diluted with $DCM/H_2O$ (20 mL, 1:1). The organic layer was separated, and the aqueous layer was extracted with DCM (2×5 mL). The combined organic extracts were dried and concentrated in vacuo. The crude product was saponified and purified following the procedure described in General Procedure D to afford the title compound (2.2 mg, 10%, 2 steps). LCMS: $R_T$=2.067 min, MS (ES) 795.0 (M+H).

Example 299

(P, R)-7-(benzyloxy)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid The title compound was prepared following General coupling procedure B using (P,R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one, methyl 7-(benzyloxy)-4-bromo-1-methyl-1H-indole-2-carboxylate, CuI, (trans)-1,2-N,N'-dimethylaminocyclohexane, and $K_2CO_3$ followed by saponification and purification following General Procedure D. LCMS: $R_T$=2.329 min, MS (ES) 817.9 (M+H).

Example 300

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-2-carbonitrile The title compound (11.7 mg, 32%) was prepared following General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol), 7-bromo-1-methyl-1H-indole-2-carbonitrile (17 mg, 0.068 mmol), CUI (5 mg, 0.026 mmol), (trans)-1,2-N,N'-dimethylaminocyclohexane (8 mg, 0.056 mmol), $K_3PO_4$ (30 mg, 0.14 mmol). LCMS: $R_T$=2.221 min, MS (ES) 693.0 (M+H).

Example 301

4-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-2-carbonitrile Step A. Preparation of 4-bromo-1-methyl-1H-indole-2-carboxamide The title compound (47 mg, 47%) was prepared following General Procedure E using 4-bromo-1-methyl-1H-indole-2-carboxylic acid (100 mg, 0.39 mmol), HATU (200 mg, 0.526 mmol), DIPEA (200 mg, 1.55 mmol), and ammonia in methanol (7.0 M, 0.25 mL, 1.75 mmol).

Step B. Preparation of 4-bromo-1-methyl-1H-indole-2-carbonitrile

A solution of 4-bromo-1-methyl-1H-indole-2-carboxamide (47 mg, 0.17 mmol) in $POCl_3$ (2 mL) was heated to 100° C. for 2 h. The reaction was cooled to RT and poured into ice/aqueous $NaHCO_3$. The aqueous layer was extracted with DCM (3×10 mL), the combined organic reactions were dried over MgSO$_4$, filtered, and concentrated in vacuo. The crude reaction mixture was purified by flash chromatography (Combi-flash Rf, Hex/EtOAc=0-100%) to afford the title compound (32 mg, 73% yield).

Step C. Example 301

The title compound (25 mg, 65%) was prepared following General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.056 mmol), 4-bromo-1-methyl-1H-indole-2-carbonitrile (26 mg, 0.11 mmol), CuI (5 mg, 0.026 mmol), (trans)-1,2-N,N'-dimethylaminocyclohexane (8 mg, 0.056 mmol), K$_3$PO$_4$ (50 mg, 0.24 mmol). LCMS: R$_T$=2.276 min, MS (ES) 693.0 (M+H); $^1$H NMR (400 MHz, Chloroform-d) δ 7.74 (dd, J=8.6, 1.7 Hz, 1H), 7.53-7.43 (m, 1H), 7.40-7.27 (m, 2H), 7.13-7.02 (m, 2H), 6.65-6.60 (m, 2H), 4.48 (d, J=11.6 Hz, 1H), 4.32-4.14 (m, 2H), 4.05-4.00 (m, 4H), 3.95 (s, 3H), 3.59 (d, J=12.4 Hz, 1H), 3.46 (dt, J=14.2, 7.5 Hz, 1H), 3.33 (dt, J=14.0, 7.5 Hz, 1H), 2.33 (s, 5H), 2.29 (s, 1.5H), 2.26 (1.5H), 2.22-2.17 (m, 3H), 2.15 (s, 1.5H), 2.10 (s, 1.5H), 1.24 (d, J=4.8 Hz, 1.5H), 1.18 (d, J=6.4 Hz, 1.5H).

Example 302

7-[(4R)-7-chloro-10-[3-(4-chloro-3,5-dimethyl-phenoxy)propyl]-6-(4,6-dimethylpyrimidin-5-yl)-4-methyl-1-oxo-3,4-dihydropyrazino[1,2-a]indol-2-yl]-4-methoxy-1-(2-pyridylmethyl)indole-2-carboxylic acid Step A. Preparation of methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-JH-indole-2-carboxylate The title compound (15 mg, 36%) was prepared following General Procedure C using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (30 mg, 0.056 mmol), methyl 7-bromo-4-methoxy-1H-indole-2-carboxylate (30 mg, 0.11 mmol), CuI (5 mg, 0.026 mmol), (trans)-1,2-N,N'-dimethylaminocyclohexane (8 mg, 0.056 mmol), K$_3$PO$_4$ (40 mg, 0.19 mmol).

Step B. Example 302

The title compound (7.2 mg, 43%) was prepared following the procedure described Example 247 using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-1H-indole-2-carboxylate, NaH (6 mg, 0.25 mmol) and 2-(bromomethyl)pyridine HBr salt (30 mg, 0.12 mmol). LCMS: R$_T$=2.061 min, MS (ES) 816.9 (M+H).

Example 303

(P, R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-6-hydroxy-1-methyl-1H-indole-2-carboxylic acid To a solution of (P, R)-6-(benzyloxy)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid (6 mg, 0.0072 mmol) in MeOH (3 mL) was added Pd/C (10% wt, 2 mg, 0.0018 mmol). The reaction was flushed with hydrogen then stirred under H$_2$ for 6 h at RT. The reaction was filtered, concentrated in vacuo, and purified by reverse phase HPLC (Phenomenex Gemini C18, H$_2$O/CH$_3$CN gradient 35-95% MeCN 0.1% TFA) to afford the title compound (4 mg, 72% yield). LCMS: R$_T$=2.007 min, MS (ES) 727.9 (M+H).

Example 304

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-(thiazol-4-ylmethyl)indole-2-carboxylic acid The title compound (6.3 mg, 58%) was prepared following the procedure described Example 247 using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol), NaH (5 mg, 0.12 mmol) and 4-(chloromethyl)thiazole (10 mg, 0.075 mmol) followed by saponification using General Procedure D. LCMS: R$_T$=2.099, 2.129 min, MS (ES) 794.9 (M+H).

Example 305

(M, R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-6-hydroxy-1-methyl-1H-indole-2-carboxylic acid (Singlr Atropisomer)

The title compound (3.3 mg, 59%) was prepared following the same procedure as Example 303 using (M R)-6-(benzyloxy)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid (6 mg, 0.0072 mmol) and Pd/C (10% wt, 2 mg, 0.0019 mmol). LCMS: R$_T$=2.020 min, MS (ES) 727.9 (M+H).

Example 306

(R)-3-(7-chloro-10-(3-(4-chloro-3,5-dimethylphenoxy)propyl)-6-(3,5-dimethyl-1-(2-(pyrrolidin-1-yl)ethyl)-1H-pyrazol-4-yl)-4-methyl-1-oxo-3,4-dihydropyrazino[1,2-a]indol-2(1H)-yl)-1-methyl-1H-indole-6-carboxylic acid The title compound was prepared according to the procedure used in Example 261 Step B by substituting 3-(bromomethyl)-1-methylpyrrolidine with 1-(2-bromoethyl)pyrrolidine. LCMS: R$_T$=non polar method: 0.976 min, MS (ES) 795.3 (M+H).

Example 307

(4R)-7-chloro-10-[3-(4-chloro-3,5-dimethyl-phenoxy)propyl]-4-methyl-2-[1-methyl-2-(2H-tetrazol-5-yl)indol-4-yl]-6-(1,3,5-trimethylpyrazol-4-yl)-3,4-dihydropyrazino[1,2-a]indol-1-one The title compound (4 mg, 21%) was prepared according to the procedure for Example 235 using (R)-4-(7-chloro-10-

(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carbonitrile (18 mg, 0.026 mmol) and sodium azide (10 mg, 0.15 mmol). LCMS: $R_T$=2.145, 2.172 min, MS (ES) 736.0 (M+H).

Example 308

(R)-3-(7-chloro-10-(3-(4-chloro-3,5-dimethylphenoxy)propyl)-6-(3,5-dimethyl-1-((tetrahydro-2H-pyran-4-yl)methyl)-1H-pyrazol-4-yl)-4-methyl-1-oxo-3,4-dihydropyrazino[1,2-a]indol-2(1H)-yl)-1-methyl-1H-indole-6-carboxylic acid The title compound was prepared according to the procedure used in Example 261 Step B by substituting 3-(bromomethyl)-1-methylpyrrolidine with 4-(bromomethyl)tetrahydro-2H-pyran. MS (ES) 796.3 (M+H), $^1$H-NMR (MeOH-$d_3$) δ 8.19 (d, 1H, J=8 Hz), 7.79-7.75 (m, 2H), 7.48-7.47 (m, 2H) 7.31 (d, 1H, J=8 Hz), 6.62 (s, 2H), 4.50-4.47 (m, 1H), 4.30-4.28 (m, 1H) 4.06 (tr, 2H, J=8 Hz), 3.99 (s, 3H), 3.92 (s, 3H), 3.36-3.60 (m, 2H), 3.50-3.40 (m, 4H), 2.33 (s, 6H), 2.29-2.16 (multiples s (3H), tr (2H), total 5H), 2.08 (s, 1.5H), 2.01 (s, 1.5H), 1.54-1.46 (m, 2H), 1.45-1.40 (m, 2H), 1.31 (m, 1H), 1.23-1.19 (multiple d, 3H).

Example 309

(R)-3-(7-chloro-10-(3-(4-chloro-3,5-dimethylphenoxy)propyl)-6-(1-(2-(dimethylamino)ethyl)-3,5-dimethyl-1H-pyrazol-4-yl)-4-methyl-1-oxo-3,4-dihydropyrazino[1,2-a]indol-2(1H)-yl)-1-methyl-1H-indole-6-carboxylic acid The title compound was prepared according to the procedure used in Example 261 Step B by substituting 3-(bromomethyl)-1-methylpyrrolidine with 2-bromo-N,N-dimethylethan-1-amine. MS (ES) 769.3 (M+H)

Example 310

(M, R)-6-(benzyloxy)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid The title compound (5.5 mg, 92%) was prepared following General Procedure D using methyl (M, R)-6-benzyloxy-4-[7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-2-carboxylate (6 mg, 0.0072 mmol). LCMS: $R_T$=2.349 min, MS (ES) 817.9 (M+H).

Example 311

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-(pyrimidin-5-ylmethyl)indole-2-carboxylic acid The title compound (2 mg, 31%) was prepared according to the procedure used in Example 298 using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (6 mg, 0.0083 mmol), $Cs_2CO_3$ cesium carbonate (20 mg, 0.061 mmol), KI (10 mg, 0.0.060 mmol), and 5-(chloromethyl)pyrimidine (20 mg, 0.15 mmol) followed by saponification using General Procedure D. LCMS: $R_T$=2.006 min, MS (ES) 790.0 (M+H).

Example 312

(M, R)-7-(benzyloxy)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid The title compound (4 mg, 81%) was prepared following General Procedure D using methyl (M, R)-7-benzyloxy-4-[7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-methyl-indole-2-carboxylate (5 mg, 0.0060 mmol). LCMS: $R_T$=2.192 min, MS (ES) 817.9 (M+H).

Example 313

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-4-methoxy-1-(2-pyridylmethyl)indole-2-carboxylic acid Step A. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H-indole-2-carboxylate The title compound was prepared following General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.056 mmol), methyl 7-bromo-4-methoxy-1H-indole-2-carboxylate (30 mg, 0.11 mmol), CuI (5 mg, 0.026 mmol), (trans)-1,2-N,N'-dimethylaminocyclohexane (8 mg, 0.056 mmol), $K_3PO_4$ (40 mg, 0.19 mmol).

Step B. Example 313

The title compound (12.8 mg, 28% 3 steps) was prepared following the procedure described Example 241 using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H-indole-2-carboxylate (from Step A), NaH (6 mg, 0.25 mmol) and 2-(bromomethyl)pyridine HBr salt (30 mg, 0.12 mmol) followed by saponification using General Procedure D. LCMS: $R_T$=1.941, 1.965 min, MS (ES) 819.0 (M+H).

Example 314

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-[(5-methyl-1,2,4-oxadiazol-3-yl)methyl]indole-2-carboxylic acid The title compound (4.2 mg, 19%) was prepared following the procedure described Example 298 using ethyl (R)-

7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (20 mg, 0.028 mmol), Cs$_2$CO$_3$ (40 mg, 0.123 mmol), KI (20 mg, 0.12 mmol), and 3-(chloromethyl)-5-methyl-1,2,4-oxadiazole (25 mg, 0.186 mmol) followed by saponification using General Procedure D to afford the title compound. LCMS: R$_T$=2.063 min, MS (ES) 793.9 (M+H).

Example 315

7-[(4R)-7-chloro-10-[3-(4-chloro-3,5-dimethyl-phenoxy)propyl]-4-methyl-1-oxo-6-(1,3,5-trimethylpyrazol-4-yl)-3,4-dihydropyrazino[1,2-a]indol-2-yl]-1-[(5-methyl-1,3,4-oxadiazol-2-yl)methyl]indole-2-carboxylic acid The title compound (4.9 mg, 45%) was prepared following the procedure described Example 241 using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol), NaH (3 mg, 0.12 mmol), and 2-(chloromethyl)-5-methyl-1,3,4-oxadiazole (10 mg, 0.076 mmol) followed by saponification using General Procedure D. LCMS: R$_T$=2.072 min, MS (ES) 793.9 (M+H).

Example 316

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,3-dimethyl-1H-indole-2-carboxylic acid Step A. Preparation of methyl 7-bromo-3-methyl-1H-indole-2-carboxylate To a solution of (2-bromophenyl)hydrazine hydrochloride (223 mg, 1.0 mmol) in MeOH (5 mL) was added ethyl pyruvate (0.1 mL, 116 mg 1.0 mmol) followed by conc. HCl (5 mL). The reaction mixture was stirred at 70° C. for 4 h then cooled to RT, quenched with sat. NaHCO$_3$ aq. solution and extracted with DCM (3×5 mL). The combined organic layer was washed with brine, dried over MgSO$_4$, filtered, and concentrated in vacuo. The residue was purified by flash chromatography (Combi-flash Rf, Hex/EtOAc=0-100% gradient) to afford the title compound (227 mg, 85% yield). LCMS: R$_T$=1.618 min, MS (ES) 268.0 (M+H).

Step B. Preparation of methyl 7-bromo-1,3-dimethyl-1H-indole-2-carboxylate

The title compound (38 mg, 37% yield) was prepared following General Procedure G using methyl 7-bromo-3-methyl-1H-indole-2-carboxylate (100 mg, 0.37 mmol). LCMS: R$_T$=1.828 min, MS (ES) 282.0 (M+H); $^1$H NMR (400 MHz, CDCl$_3$) δ 7.50 (d, J=7.9 Hz, 1H), 7.42 (d, J=7.5 Hz, 1H), 6.87 (t, J=7.8 Hz, 1H), 4.25 (s, 3H), 3.87 (s, 3H), 2.44 (s, 3H).

Step C. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,3-dimethyl-1H-indole-2-carboxylate The title compound (20 mg, 33%) was prepared following General Procedure B, using methyl 7-bromo-1,3-dimethyl-1H-indole-2-carboxylate (35 mg, 0.124 mmol) and (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (44.6 mg, 0.083 mmol). LCMS: R$_T$=2.244, 2.267 min, MS (ES) 739.9 (M+H).

Step D. Example 316

The title compound (3.1 mg, 15%) was prepared following General procedure D using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,3-dimethyl-1H-indole-2-carboxylate (20 mg, 0.027 mmol). LCMS: R$_T$=2.096 min, MS (ES) 726.0 (M+H); $^1$H NMR (400 MHz, CDCl$_3$) δ 7.78 (d, J=8.0 Hz, 1H), 7.74-7.68 (m, 1H), 7.36-7.33 (m, 1H), 7.23-7.10 (m, 2H), 6.64-6.59 (m, 2H), 4.52-4.46 (m, 1H), 4.30-4.25 (m, 2H), 4.13-4.11 (m, 4H), 4.01-3.97 (m, 4H), 3.42-3.36 (m, 2H), 2.63-2.61 (m, 3H), 2.39-2.32 (m, 9H), 2.24-2.15 (m, 5H), 1.31-1.28 (m, 3H).

Example 317

(R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,6-dimethyl-1H-indole-2-carboxylic acid The title compound was prepared according to General Procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one and methyl 4-bromo-1,6-dimethyl-1H-indole-2-carboxylate followed by saponification using General Procedure D. LCMS: R$_T$=2.71 min, MS (ES) 726.2 (M+H) (LC method III). $^1$H NMR (400 MHz, Chloroform-d) δ 7.68 (d, J=8.8 Hz, 1H), 7.28 (d, J=8.8 Hz, 1H), 7.26 (s, 1H), 7.22 (s, 1H), 6.92 (s, 1H), 6.60 (s, 2H), 4.40 (dd, J=12.4, 3.6 Hz, 1H), 4.19 (d, J=4.8 Hz, 1H), 4.03-3.96 (m, 5H), 3.90 (s, 3H), 3.58 (d, J=12.4 Hz, 1H), 3.49-3.31 (m, 2H), 2.51 (s, 3H), 2.30 (s, 6H), 2.21-2.17 (m, 5H), 2.04 (s, 3H), 1.24 (d, J=6.4 Hz, 3H).

Example 318

(R)-4-(7-Chloro-10-(3-(4-chloro-3,5-dimethylphenoxy)propyl)-6-(3,5-dimethyl-1-(2-(pyrrolidin-1-yl)ethyl)-1H-pyrazol-4-yl)-4-methyl-1-oxo-3,4-dihydropyrazino[1,2-a]indol-2(1H)-yl)-1-methyl-1H-indole-2-carboxylic acid Step A. Preparation of methyl (R)-4-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1-methyl-1H-indole-2-carboxylate The title compound was prepared following General coupling procedure B using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one and methyl 4-bromo-1-methyl-1H-indole-2-carboxylate. MS (ES) 842.3 (M+H).

Step B. Preparation of methyl (R)-4-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-2-carboxylate The title compound (77 mg, 90%) was prepared following the procedure described Example 261 Step A using methyl (R)-4-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1-methyl-1H-indole-2-carboxylate (100 mg, 0.12 mmol) and TBAF (0.59 mL, 0.59 mmol). MS (ES) 712.2 (M+H).

Step C. Example 318

The title compound (17 mg, 38% 2 steps) was prepared following the procedure described Example 261 Step B using methyl (R)-4-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-methyl-1H-indole-2-carboxylate (41 mg, 0.057 mmol), NaH (5 mg, 0.113 mmol) and 1-(2-bromoethyl)pyrrolidine (20 mg, 0.113 mmol) followed by saponification using General Procedure D. LCMS: $R_T$=0.863 min (LC method IV), MS (ES) 795.8 (M+H); $^1$H NMR (DMSO, 400 MHz) δ (ppm) 7.79 (d, J=8.4 Hz, 1H), 7.55 (d, J=8.4 Hz, 1H), 7.38 (t, J=8.4 Hz, 1H), 7.30 (d, J=8.4 Hz, 1H), 7.06 (s, 2H), 6.70 (s, 2H), 4.59-4.40 (m, 2H), 4.20-4.11 (m, 1H), 4.04 (s, 3H), 3.97-3.93 (m, 2H), 3.65-3.60 (m, 2H), 3.55-3.50 (m, 2H), 3.12-2.90 (m, 2H), 2.53 (s, 3H), 2.22 (s, 6H), 2.18 (s, 2H), 2.05 (d, J=4.0 Hz, 3H), 2.03-1.90 (m, 2H), 2.05 (s, 3H), 1.85-1.82 (m, 2H), 1.08-1.05 (m, 4H).

Example 319

4-((M, R)-7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-7-((1-methylpyrrolidin-3-yl)methoxy)-1H-indole-2-carboxylic acid Step A. Preparation of methyl (M, R)-7-(benzyloxy)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylate The title compound was prepared according to General Procedure B using (M, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-(benzyloxy)-4-bromo-1-methyl-1H-indole-2-carboxylate. LCMS: $R_T$=1.772 min, MS (ES) 831.8 (M+H) (LC method II).

Step B. Preparation of methyl (M, R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-7-hydroxy-1-methyl-1H-indole-2-carboxylate To a solution of methyl (R)-7-(benzyloxy)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylate (25 mg, 0.030 mmol) in MeOH (5 mL) was added Pd/C (10 wt. %, 5 mg, 0.0046 mmol), and the reaction was stirred for 18 h under $H_2$ atmosphere at RT. The reaction mixture was filtered through celite and concentrated to afford the title compound (21 mg, 94%). LCMS: $R_T$=2.090 min, MS (ES) 742.0 (M+H).

Step C. Example 319

The title compound (4.0 mg, 36%) was prepared according to General Procedure H using methyl (M, R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-7-hydroxy-1-methyl-1H-indole-2-carboxylate (10 mg, 0.014 mmol) and 3-(bromomethyl)-1-methylpyrrolidine (10 mg, 0.056 mmol) followed by saponification using General Procedure D. LCMS: $R_T$=1.825 min, MS (ES) 825.0 (M+H).

Example 320

7-((R)-7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((1-methylpyrrolidin-3-yl)methyl)-1H-indole-2-carboxylic acid The title compound (3.0 mg, 27%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 3-(bromomethyl)-1-methylpyrrolidine (10 mg, 0.056 mmol) followed by saponification using General Procedure K. LCMS: $R_T$=1.876 min, MS (ES) 795.0 (M+H).

Example 321

(M, R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-hydroxy-1-methyl-1H-indole-2-carboxylic acid Step A. Preparation of methyl (M, R)-4-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylate The title compound was prepared according to General Procedure B using (M, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 4-(benzyloxy)-7-bromo-1-methyl-1H-indole-2-carboxylate. MS (ES) 832.2 (M+H).

Step B. Preparation of methyl (M, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-hydroxy-1-methyl-1H-indole-2-carboxylate The title compound (17 mg, 45%) was prepared following the procedure described Example 319 Step B using methyl (M, R)-4-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylate (42 mg, 0.051 mmol) and Pd/C (10 wt %, 20 mg, 0.019 mmol). LCMS: $R_T$=1.944 min, MS (ES) 727.9 (M+H).

Step C. Example 321

The title compound (4.4 mg, 64%) was prepared according to General Procedure D using methyl (M, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-hydroxy-1-methyl-1H-indole-2-carboxylate (7 mg, 0.0094 mmol). LCMS: $R_T$=1.946 min, MS (ES) 727.9 (M+H).

Example 322

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-(dimethylamino)ethyl)-1H-indole-2-carboxylic acid The title compound (2.9 mg, 27%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-bromo-N,N-dimethylethan-1-amine (10 mg, 0.066 mmol) followed by saponification using General Procedure D. LCMS: $R_T$=1.861, 1.882 min, MS (ES) 769.0 (M+H).

Example 323

(M, R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-7-(2-methoxyethoxy)-1-methyl-1H-indole-2-carboxylic acid The title compound (4.3 mg, 41%) was prepared according to General Procedure H using methyl (M, R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-7-hydroxy-1-methyl-1H-indole-2-carboxylate (10 mg, 0.014 mmol) and 1-bromo-2-methoxyethane (10 mg, 0.072 mmol) followed by saponification using General Procedure D. LCMS: $R_T$=2.044 min, MS (ES) 786.0 (M+H).

Example 324

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((tetrahydro-2H-pyran-4-yl)methyl)-1H-indole-2-carboxylic acid Step A. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate The title compound (44 mg, 61%) was prepared according to General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (54 mg, 0.1 mmol) and methyl 7-bromo-5-methyl-1H-indole-2-carboxylate (80 mg, 0.3 mmol). LCMS: $R_T$=2.221 min, MS (ES) 726.0 (M+H).

Step B. Example 324

The title compound (6 mg, 53%) was prepared according to General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (10 mg, 0.014 mmol) and 4-(bromomethyl)tetrahydro-2H-pyran (5 mg, 0.028 mmol) followed by saponification using General Procedure D. LCMS: $R_T$=2.217 MS (ES) 809.8 (M+H); $^1$H NMR (500 MHz, DMSO-$d_6$) δ 7.76 (d, J=8.6 Hz, 1H), 7.48 (s, 0.75H), 7.44 (s, 0.25H), 7.34-7.28 (m, 1H), 7.26-7.23 (m, 1H), 6.98 (d, J=8.7 Hz, 1H), 6.69 (s, 1.5H), 6.68 (s, 0.5H), 4.33-4.26 (m, 2H), 4.25-4.18 (m, 2H), 3.78 (s, 1.5H), 3.76 (s, 0.5H), 3.75 (s, 1H), 3.63-3.60 (m, 1H), 3.33-3.13 (m, 3H), 3.06-2.91 (m, 3H), 2.37 (s, 2H), 2.35 (s, 1H), 2.23 (s, 6H), 2.14 (s, 0.5H), 2.13 (s, 1H), 2.08 (s, 1.5H), 2.06-1.96 (m, 4H), 1.93 (s, 1H), 1.90 (s, 0.5H), 1.83 (s, 1.5H), 1.17-1.08 (m, 3H), 1.05-0.96 (m, 2H), 0.93-0.75 (m, 3H).

Example 325

(M, R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-(2-methoxyethoxy)-1-methyl-1H-indole-2-carboxylic acid The title compound (3.6 mg, 33%) was prepared according to General Procedure H using methyl (M, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-hydroxy-1-methyl-1H-indole-2-carboxylate (10 mg, 0.013 mmol) and 1-bromo-2-methoxyethane (10 mg, 0.072 mmol) followed by saponification using General Procedure D. LCMS: $R_T$=2.047 min, MS (ES) 786.0 (M+H).

Example 326

7-((R)-7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((tetrahydrofuran-2-yl)methyl)-1H-indole-2-carboxylic acid The title compound (2.7 mg, 25%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-(bromomethyl)tetrahydrofuran (10 mg, 0.061 mmol) followed by saponification using General Procedure D. LCMS: $R_T$=2.105 min, MS (ES) 781.9 (M+H).

Example 327

(P, R)-7-(Benzyloxy)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid The title compound was prepared according to General Procedure B using (P, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-(benzyloxy)-4-bromo-1-methyl-1H-indole-2-carboxylate followed by saponification using General Procedure D. LCMS: $R_T$=2.99 min, MS (ES) 818.0 (M+H) (LC method III). $^1$H NMR (400 MHz, Chloroform-d) δ 7.66 (d, J=8.8 Hz, 1H), 7.47-7.22 (m, 7H), 6.93 (d, J=8.4 Hz, 1H), 6.78 (d, J=8.4 Hz, 1H), 6.60 (s, 2H), 5.20 (s, 2H), 4.48-4.26 (m, 5H), 3.97-3.94 (m, 5H), 3.78-3.27 (m, 3H), 2.29 (s, 6H), 2.20-2.16 (m, 5H), 2.03 (s, 3H), 1.13 (d, J=6.4 Hz, 3H).

Example 328

(M, R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-6-(2-methoxyethoxy)-1-methyl-1H-indole-2-carboxylic acid Step A. Preparation of methyl (M, R)-6-(benzyloxy)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylate The title compound was prepared according to General Procedure B using (M, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 6-(benzyloxy)-4-bromo-1-methyl-1H-indole-2-carboxylate followed by saponification using General Procedure K. LCMS: $R_T$=1.823 min, MS (ES) 831.8 (M+H) (LC method II).

Step B. Preparation of methyl (M, R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-6-hydroxy-1-methyl-1H-indole-2-carboxylate The title compound (34 mg, 77%) was prepared following the procedure described Example 319 Step B using methyl (M, R)-6-(benzyloxy)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylate (50 mg, 0.06 mmol) and Pd/C (10 wt. %, 7 mg, 0.0065 mmol). LCMS: $R_T$=2.067 min, MS (ES) 742.0 (M+H).

Step C. Example 328

The title compound (5.1 mg, 60%) was prepared according to General Procedure H using methyl (M, R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-6-hydroxy-1-methyl-1H-indole-2-carboxylate (8 mg, 0.011 mmol) and 1-bromo-2-methoxyethane (10 mg, 0.072 mmol) followed by saponification using General Procedure K. LCMS: $R_T$=2.029 min, MS (ES) 786.0 (M+H).

Example 329

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyrimidin-2-ylmethyl)-1H-indole-2-carboxylic acid The title compound (3.6 mg, 17%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-(chloromethyl)pyrimidine (20 mg, 0.16 mmol), followed by saponification using General Procedure D. LCMS: $R_T$=2.026 min, MS (ES) 790.0 (M+H).

Example 330

7-((R)-7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((1-methylpyrrolidin-3-yl)methyl)-1H-indole-2-carboxylic acid The title compound (7 mg, 62%) was prepared according to General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (10 mg, 0.014 mmol) and 3-(bromomethyl)-1-methylpyrrolidine hydrobromide (7 mg, 0.028 mmol) followed by saponification using General Procedure D. LCMS: $R_T$=1.962 MS (ES) 808.9 (M+H); $^1$H NMR (500 MHz, DMSO-$d_6$) δ 9.69 (bs, 1H), 7.90-7.73 (m, 1H), 7.60-7.47 (m, 1H), 7.41-7.29 (m, 2H), 7.28-7.16 (m, 0.5H), 7.09-6.98 (m, 0.5H), 6.71 (s, 2H), 4.58-4.49 (m, 3H), 4.42-4.09 (m, 3H), 4.08-4.01 (m, 1H), 3.99 (s, 3H), 3.77 (s, 1.5H), 3.75 (s, 1.5H), 3.30-3.13 (m, 3H), 2.75-2.62 (m, 3H), 2.37 (s, 1.5H), 2.35 (s, 1.5H), 2.24 (s, 6H), 2.12 (s, 1.5H), 2.07 (s, 1.5H), 2.06-2.04 (m, 2H), 2.04-2.03 (m, 1H), 2.03-2.01 (m, 2H), 1.99 (s, 1.5H), 1.91 (s, 1.5H), 1.17-1.05 (m, 3H).

Example 331

4-((M, R)-7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-6-((1-methylpyrrolidin-3-yl)methoxy)-1H-indole-2-carboxylic acid The title compound (4.1 mg, 46%) was prepared according to General Procedure H using methyl (M, R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-6-hydroxy-1-methyl-1H-indole-2-carboxylate (8 mg, 0.011 mmol) and 3-(bromomethyl)-1-methylpyrrolidine (10 mg, 0.056 mmol) followed by saponification using General Procedure D. LCMS: $R_T$=1.795 min, MS (ES) 825.0 (M+H).

Example 332

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,5-dimethyl-1H-indole-2-carboxamide The title compound (7 mg, 70%) was prepared according to General Procedure E using (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,5-dimethyl-1H-indole-2-carboxylic acid (10 mg, 0.014 mmol) and ammonia in MeOH (7.0 M, 0.25 mL). LCMS: $R_T$=2.017, 2.043 min, MS (ES) 724.9 (M+H).

Example 333

(M, R)-5-(Benzyloxy)-7-(7-chlor-10-(3-(4-chloro-3,
5-dimethylphenoxy)propyl)-4 methyl-1-oxo-6-(1,3,
5-trimethyl-1H-pyrazol-4-yl)-3,4-dihydropyrazino[1,
2-a]indol-2(1H)-yl)-1-methyl-1H-indole-2-
carboxylic acid The title compound was prepared according to General Procedure B using (M, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 5-(benzyloxy)-7-bromo-1-methyl-1H-indole-2-carboxylate followed by saponification using General Procedure D. LCMS: $R_T$=2.430, 2.457 min, MS (ES) 817.8 (M+H). $^1$H NMR (400 MHz, Chloroform-d) δ 7.68 (d, J=8.8 Hz, 1H), 7.32-7.30 (m, 7H), 7.14 (s, 1H), 6.93 (d, J=8.8 Hz, 1H), 6.61 (s, 1.5H) 6.59 (s, 0.5H), 5.07 (s, 2H), 4.24-4.17 (m, 3H), 4.03-3.88 (m, 7H), 3.41-3.29 (m, 3H), 2.29 (s, 6H), 2.22-2.18 (m, 5H), 2.03 (s, 3H), 1.25 (d, J=6.0 Hz, 2H), 1.18 (d, J=6.0 Hz, 1H).

Example 334

(M, R)-4-(7-Chloro-10-(3-(4-chloro-3,5-dimeth-
ylphenoxy)propyl)-4-methyl-1-oxo-6-(1,3,5-trim-
ethyl-1H-pyrazol-4-yl)-3,4-dihydropyrazino[1,2-a]
indol-2(1H)-yl)-6-methoxy-1-methyl-1H-indole-2-
carboxylic acid The title compound (4.8 mg, 48%) was prepared according to General Procedure H using methyl (M, R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-6-hydroxy-1-methyl-1H-indole-2-carboxylate (10 mg, 0.0138 mmol) and MeI (5 mg, 0.035 mmol) followed by saponification using General Procedure D. LCMS: $R_T$=2.034 min, MS (ES) 742.0 (M+H). $^1$H NMR (400 MHz, Chloroform-d) δ 7.72 (d, J=8.6 Hz, 1H), 7.31 (d, J=8.6 Hz, 1H), 7.23 (s, 1H), 6.80-6.72 (m, 2H), 6.63 (s, 2H), 4.46-4.36 (m, 1H), 4.18 (s, 1H), 4.05 (s, 3H), 4.02-3.94 (m, 5H), 3.93 (s, 3H), 3.59 (d, J=12.4 Hz, 1H), 3.48-3.30 (m, 2H), 2.32 (s, 6H), 2.27-2.17 (m, 5H), 2.08 (s, 3H), 1.25 (d, J=6.2 Hz, 3H).

Example 335

(R)-3-(7-Chloro-10-(3-(4-chloro-3,5-dimethylphe-
noxy)propyl)-4-methyl-1-oxo-6-(1,3,5-trimethyl-1H-
pyrazol-4-yl)-3,4-dihydropyrazino[1,2-a]indol-2
(1H)-yl)-N-hydroxy-1-methyl-1H-indole-6-
carboximidamide To a solution of (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-6-carbonitrile (15 mg, 0.02 mmol) in EtOH (1 mL) at RT was added $NH_2OH \cdot HCl$ (6 mg, 0.088 mmol) followed by $K_2CO_3$ (9 mg, 0.066 mmol). The mixture was heated at 80° C. for 8 h then concentrated in vacuo. The crude material was purified by reverse phase HPLC (Phenomenex Gemini C18, $H_2O/CH_3CN$ gradient to 35-95% MeCN 0.1% TFA) to afford the title compound (12 mg, 75%). LCMS: $R_T$=1.791 min, MS (ES) 726.0 (M+H).

Example 336

(R)-7-(7-Chloro-10-(3-(4-chloro-3,5-dimethylphe-
noxy)propyl)-4-methyl-1-oxo-6-(1,3,5-trimethyl-1H-
pyrazol-4-yl)-3,4-dihydropyrazino[1,2-a]indol-2
(1H)-yl)-1,3,5-trimethyl-1H-indole-2-carboxylic
acid

Step A. Preparation of methyl 7-bromo-1,3,5-trimethyl-1H-indole-2-carboxylate The title compound (52 mg, 88%) was prepared following General Procedure G using 7-bromo-5-methyl-1H-indole-2-carboxylic acid (51 mg, 0.20 mmol) and MeI (39 μL, 0.80 mmol). LCMS: $R_T$=1.783 min, MS (ES) 296.2 (M+H).

Step B. Example 336

The title compound (11 mg, 30%) was prepared according to General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and methyl 7-bromo-1,3,5-trimethyl-1H-indole-2-carboxylate (18 mg, 0.06 mmol) followed by saponification using General Procedure D. LCMS: $R_T$=2.137 MS (ES) 739.9 (M+H); $^1$H NMR (500 MHz, DMSO-$d_6$) δ 7.83-7.68 (m, 1H), 7.48 (s, 0.5H), 7.43 (s, 0.5H), 7.33-7.24 (m, 1H), 7.16 (s, 0.5H), 6.94 (s, 0.25H), 6.93 (s, 0.25H), 6.69 (s, 1H), 6.68 (s, 1H), 4.36-4.27 (m, 1H), 4.26-4.09 (m, 1H), 4.02-3.93 (m, 2H), 3.91 (s, 1.5H), 3.92 (s, 1.5H), 3.80 (s, 0.75H), 3.77 (s, 0.75H), 3.76 (0.75H), 3.75 (s, 0.75H), 3.71-3.61 (m, 2H), 3.21-3.11 (m, 1H), 2.39 (s, 1.5H), 2.36 (s, 1.5H), 2.22 (s, 6H), 2.10 (s, 1.5H), 2.08 (s, 1.5H), 2.06-2.03 (m, 2H), 1.96 (s, 1.5H), 1.94 (s, 1.5H), 1.91 (s, 3H), 1.87 (s, 1.5H), 1.15 (d, J=6.2 Hz, 1.5H), 1.04 (d, J=6.2 Hz, 1.5H).

Example 337

(R)-7-Chloro-10-(3-(4-chloro-3,5-dimethylphenoxy)
propyl)-4-methyl-2-(1-methyl-5-(5-methyl-1,3,4-
oxadiazol-2-yl)-1H-indol-3-yl)-6-(1,3,5-trimethyl-
1H-pyrazol-4-yl)-3,4-dihydropyrazino[1,2-a]indol-1
(2H)-one

Step A. Preparation of (R)—N'-acetyl-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carbohydrazide The title compound (32 mg, 74%) was prepared according to General Procedure E using (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (40 mg, 0.056 mmol) and acetohydrazide (15 mg, 0.20 mmol). LCMS: $R_T$=2.098 min, MS (ES) 768.0 (M+H).

Step B. Example 337

(R)—N'-acetyl-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carbohydrazide (10 mg, 0.013 mmol) was dissolved in $POCl_3$ (1 mL) and heated to 95° C. for 1 h. The reaction mixture was cooled to RT, poured into ice/aqueous NaHCO$_3$ (50 mL), and the mixture was then stirred for 15 min. The aqueous layer was extracted with DCM (3×15 mL). The combined organic extracts were dried over MgSO$_4$, filtered, and concentrated. The crude reaction mixture was purified by reverse phase HPLC (Phenomenex Gemini C18, H$_2$O/CH$_3$CN gradient 35-95% MeCN 0.1% TFA) to afford the title compound (5.3 mg, 54%). LCMS: R$_T$=2.051 min, MS (ES) 750.0 (M+H).

Example 338

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-2-ylmethyl)-1H-indole-6-carboxylic acid Step A. Preparation of methyl 3-bromo-1-((2-(trimethylsilyl)ethoxy)methyl)-1H-indole-5-carboxylate The title compound (107 mg, 71%) was prepared following General Procedure G using methyl 3-bromo-1H-indole-5-carboxylate (100 mg, 0.39 mmol) and (2-(chloromethoxy)ethyl)trimethylsilane (0.11 mL, 98.5 mg, 0.59 mmol). LCMS: R$_T$=1.977 min, MS (ES) 384.0 (M+H).

Step B. Preparation of methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-(trimethylsilyl)ethoxy)methyl)-1H-indole-5-carboxylate The title compound (93 mg, 82%) was prepared following General Procedure B using methyl 3-bromo-1-((2-(trimethylsilyl)ethoxy)methyl)-1H-indole-5-carboxylate (78 mg, 0.20 mmol) and (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (60.8 mg, 0.11 mmol). LCMS: R$_T$=2.393 min, MS (ES) 842.0 (M+H).

Step C. Preparation of methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate To a solution of methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-(trimethylsilyl)ethoxy)methyl)-1H-indole-5-carboxylate (110 mg, 0.13 mmol) in THF (0.5 mL) was added TBAF (1.18 mL, 1.17 mmol, 1.0 M in THF), and the reaction mixture was stirred at 40° C. for 24 h. The reaction was quenched with sat. NH$_4$Cl aq. solution and extracted with EtOAc (3×5 mL). The combined organic layer was washed with brine, dried over MgSO$_4$, filtered, and concentrated in vacuo. The residue was purified by flash chromatography (Combi-flash Rf, DCM/MeOH=0-10% gradient) to afford the title compound (40 mg, 43%). LCMS: R$_T$=2.077 min, MS (ES) 711.9 (M+H).

Step D. Example 338

The title compound (7 mg, 81%, 2 steps) was prepared following General Procedure G, using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (8 mg, 0.011 mmol) and 2-(bromomethyl)pyridine hydrobromide (4.2 mg, 0.017 mmol) followed by General Procedure D. LCMS: R$_T$=1.887 min, MS (ES) 789.0 (M+H). $^1$H NMR (500 MHz, DMSO-d$_6$) δ 8.52 (s, 2H), 8.11 (s, 2H), 7.85 (s, 2H), 7.82 (t, J=7.3 Hz, 2H), 7.74 (d, J=8.7 Hz, 2H), 7.62 (d, J=8.1 Hz, 2H), 7.47 (d, J=8.4 Hz, 2H), 7.37-7.34 (m, 2H), 7.28 (d, J=8.6 Hz, 2H), 7.16 (t, J=7.1 Hz, 2H), 6.71 (s, 4H), 5.63 (s, 4H), 4.50-4.47 (m, 2H), 4.16-4.13 (m, 2H), 3.97 (m, 4H), 3.77-3.76 (m, 6H), 3.70 (d, J=13.0 Hz, 1H), 3.66 (d, J=13.1 Hz, 1H), 3.32-3.29 (m, 2H), 3.25-3.20 (m, 2H), 2.23 (s, 12H), 2.11 (s, 3H), 2.07-2.04 (m, 4H), 2.02 (s, 3H), 1.96 (s, 3H), 1.87 (s, 3H), 1.07 (d, J=6.2 Hz, 6H).

Example 339

(R)-7-(7-Chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1,3,5-trimethyl-1H-indole-2-carboxylic acid The title compound (13 mg, 35%) was prepared according to General Procedure C using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (27 mg, 0.05 mmol) and methyl 7-bromo-1,3,5-trimethyl-1H-indole-2-carboxylate (18 mg, 0.06 mmol) followed by saponification using General Procedure D. LCMS: R$_T$=2.191 MS (ES) 738.0 (M+H).

Example 340

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-(dimethylamino)ethyl)-1H-indole-6-carboxylic acid The title compound (4.3 mg, 37%) was prepared following General Procedure G using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate and 2-bromo-N,N-dimethylethan-1-amine hydrobromide (5.4 mg, 0.023 mmol) followed by saponification using General Procedure D. LCMS: R$_T$=1.824 min, MS (ES) 769.0 (M+H).

Example 341

(R)-7-Chloro-10-(3-(4-chloro-3,5-dimethylphenoxy)propyl)-4-methyl-2-(1-methyl-2-(1,3,4-oxadiazol-2-yl)-1H-indol-7-yl)-6-(1,3,5-trimethyl-1H-pyrazol-4-yl)-3,4-dihydropyrazino[1,2-a]indol-1(2H)-one A solution of (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid (10 mg, 0.014 mmol) and N-isocyano-1,1,1-triphenyl-$\lambda^5$-phosphanimine (20 mg, 0.066 mmol) in DCM (2 mL) was stirred at 40° C. for 7 days. The reaction mixture was then diluted with DCM (10 mL), washed with H$_2$O (5 mL), dried by passage through a phase separator, and concentrated. The crude reaction mixture was purified by reverse phase HPLC (Phenomenex Gemini C18, H$_2$O/CH$_3$CN gradient 35-95% MeCN 0.1% TFA) to afford the title compound (4.4 mg, 43%). LCMS: R$_T$=2.083 min, MS (ES) 736.0 (M+H).

Example 342

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methoxy-1-methyl-1H-indole-2-carboxylic acid Step A. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate The title compound (252 mg, 94%) was prepared following the procedure described Example 319 Step B using ethyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylate (300 mg, 0.35 mmol) and Pd/C (10 wt. %, 40 mg, 0.037 mmol). LCMS: R$_T$=2.093 min, MS (ES) 755.8 (M+H).

Step B. Example 342

The title compound (13.6 mg, 69%) was prepared according to General Procedure H using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (20 mg, 0.026 mmol) and MeI (10 mg, 0.070 mmol) followed by saponification using General Procedure D. LCMS: R$_T$=2.028 min, MS (ES) 742.0 (M+H). $^1$H NMR (400 MHz, Chloroform-d) δ 7.73 (d, J=8.6 Hz, 1H), 7.40-7.29 (m, 2H), 7.10 (d, J=2.3 Hz, 0.66H), 7.06 (d, J=2.3 Hz, 0.34H), 6.88-6.83 (m, 1H), 6.63 (s, 1.3H), 6.61 (s, 0.7H), 4.47-4.18 (m, 2H), 4.06-3.95 (m, 7H), 3.91 (s, 0.7H), 3.90 (s, 0.3H), 3.87 (s, 2H), 3.86 (s, 1H), 3.58 (d, J=12.2 Hz, 0.3H),3.53 (d, J=12.2 Hz, 0.7H), 3.45-3.30 (m, 2H), 2.32 (s, 6H), 2.28 (s, 3H), 2.22-2.15 (m, 2H), 2.10 (s, 1H), 2.08 (s, 2H), 1.30 (d, J=6.5 Hz, 2H), 1.22 (d, J=6.6 Hz, 1H).

Example 343

(R)-7-Chloro-10-(3-(4-chloro-3,5-dimethylphenoxy)propyl)-4-methyl-2-(1-methyl-6-(1,3,4-oxadiazol-2-yl)-1H-indol-3-yl)-6-(1,3,5-trimethyl-1H-pyrazol-4-yl)-3,4-dihydropyrazino[1,2-a]indol-1(2H)-one The title compound (2.8 mg, 26%) was prepared following the procedure described Example 341 using (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-6-carboxylic acid (10 mg, 0.014 mmol) and N-isocyano-1,1,1-triphenyl-λ$^5$-phosphanimine (20 mg, 0.066 mmol). LCMS: R$_T$=2.115 min, MS (ES) 736.0 (M+H).

Example 344

(M, R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-7-methoxy-1-methyl-1H-indole-2-carboxylic acid The title compound (7.1 mg, 71%) was prepared according to General Procedure H using methyl (M, R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-7-hydroxy-1-methyl-1H-indole-2-carboxylate (10 mg, 0.014 mmol) and MeI (5 mg, 0.035 mmol) followed by saponification using General Procedure D. LCMS: R$_T$=2.044 min, MS (ES) 742.0 (M+H). $^1$H NMR (400 MHz, Chloroform-d) δ 7.71 (d, J=8.6 Hz, 1H), 7.31 (d, J=8.6 Hz, 1H), 7.21 (s, 1H), 6.95 (d, J=8.1 Hz, 1H), 6.73 (d, J=8.2 Hz, 1H), 6.62 (s, 2H), 4.37 (s, 4H), 4.17 (s, 1H), 4.04-3.94 (m, 8H), 3.54 (d, J=12.5 Hz, 1H), 3.46-3.27 (m, 2H), 2.32 (s, 6H), 2.26 (s, 3H), 2.24-2.14 (m, 2H), 2.08 (s, 3H), 1.27 (d, J=6.4 Hz, 3H).

Example 345

(P, R)-5-(Benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid The title compound was prepared according to General Procedure B using (P, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 5-(benzyloxy)-7-bromo-1-methyl-1H-indole-2-carboxylate followed by saponification using General Procedure D. LCMS: R$_T$=2.430, 2.457 min, MS (ES) 817.8 (M+H).

Example 346

(R)-7-Chloro-10-(3-(4-chloro-3,5-dimethylphenoxy)propyl)-4-methyl-2-(1-methyl-5-(1,3,4-oxadiazol-2-yl)-1H-indol-3-yl)-6-(1,3,5-trimethyl-1H-pyrazol-4-yl)-3,4-dihydropyrazino[1,2-a]indol-1(2H)-one The title compound (2.2 mg, 21%) was prepared following the procedure described Example 341 using (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.014 mmol) and N-isocyano-1,1,1-triphenyl-λ$^5$-phosphanimine (20 mg, 0.066 mmol). LCMS: R$_T$=2.043 min, MS (ES) 736.0 (M+H).

Example 347

(R)-7-Chloro-10-(3-(4-chloro-3,5-dimethylphenoxy)propyl)-4-methyl-2-(1-methyl-2-(1,3,4-oxadiazol-2-yl)-1H-indol-4-yl)-6-(1,3,5-trimethyl-1H-pyrazol-4-yl)-3,4-dihydropyrazino[1,2-a]indol-1(2H)-one The title compound (1.8 mg, 17%) was prepared following the procedure described Example 341 using (R)-4-(7-chloro-10-(3-(4-chloro-3,5-dimethylphenoxy)propyl)-4- methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid (10 mg, 0.014 mmol) and N-isocyano-1,1,1-triphenyl-$\lambda^5$-phosphanimine (20 mg, 0.066 mmol). LCMS: $R_T$=2.089 min, MS (ES) 735.9 (M+H).

Example 348

(P, R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-6-fluoro-1-methyl-1H-indole-5-carboxylic acid The title compound was prepared according to General Procedure B using (P, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 3-bromo-6-fluoro-1-methyl-1H-indole-5-carboxylate followed by saponification using General Procedure D. LCMS: $R_T$=2.176 min, MS (ES) 729.9 (M+H).

Example 349

(M, R)-8-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-2-naphthoic acid The title compound was prepared according to General Procedure B using (M, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 8-bromo-2-naphthoate followed by saponification using General Procedure D. LCMS: $R_T$=2.233 min, MS (ES) 708.9 (M+H).

Example 350

(R)-7-Chloro-10-(3-(4-chloro-3,5-dimethylphenoxy)propyl)-4-methyl-2-(1-methyl-5-(2-methyl-2H-tetrazol-5-yl)-1H-indol-3-yl)-6-(1,3,5-trimethyl-1H-pyrazol-4-yl)-3,4-dihydropyrazino[1,2-a]indol-1(2H)-one The title compound (12 mg, 60%) was prepared following General Procedure G using (R)-7-chloro-10-(3-(4-chloro-3,5-dimethylphenoxy)propyl)-4-methyl-2-(1-methyl-5-(1H-tetrazol-5-yl)-1H-indol-3-yl)-6-(1,3,5-trimethyl-1H-pyrazol-4-yl)-3,4-dihydropyrazino[1,2-a]indol-1(2H)-one (20 mg, 0.03 mmol) and MeI (4 µL, 0.05 mmol) and isolated as the first eluting isomer by reverse phase HPLC (Phenomenex Gemini C18, H$_2$O/CH$_3$CN gradient to 40-90% MeCN 0.1% TFA). LCMS: $R_T$=2.033 min, MS (ES) 750.0 (M+H).

Example 351

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1,3-dimethyl-1H-indole-2-carboxylic acid Step A. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-JH-indole-2-carboxylate The title compound (35 mg, 94%) was prepared according to General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and methyl 7-bromo-4-methoxy-1H-indole-2-carboxylate (43 mg, 0.15 mmol). LCMS: $R_T$=2.116 min, MS (ES) 742.0 (M+H) 51.

The title compound (6 mg, 53% yield) was prepared according to General Procedure G using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H-indole-2-carboxylate (15 mg, 0.02 mmol) and MeI (5 µL, 0.08 mmol) followed by saponification using General Procedure D. LCMS: $R_T$=1.766 MS (ES) 756.0 (M+H).

Example 352

(R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-2-ylmethyl)-1H-indole-2-carboxylic acid Step A. Preparation of methyl 4-bromo-1-((2-(trimethylsilyl)ethoxy)methyl)-1H-indole-2-carboxylate The title compound (115 mg, 76%) was prepared following General Procedure G using methyl 4-bromo-1H-indole-2-carboxylate (100 mg, 0.39 mmol) and (2-(chloromethoxy)ethyl)trimethylsilane (0.11 mL, 98.5 mg, 0.59 mmol).

Step B. Preparation of methyl (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-(trimethylsilyl)ethoxy)methyl)-1H-indole-2-carboxylate The title compound (125 mg, 99%) was prepared following General Procedure B using methyl 4-bromo-1-((2-(trimethylsilyl)ethoxy)methyl)-1H-indole-2-carboxylate (96 mg, 0.25 mmol) and (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one (85 mg, 0.139 mmol). LCMS: $R_T$=2.466 min, MS (ES) 842.0 (M+H).

Step C. Preparation of methyl (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate To a solution of methyl (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-(trimethylsilyl)ethoxy)methyl)-1H-indole-2-carboxylate (125 mg, 0.148 mmol) in THF (0.5 mL) was added TBAF (3.7 mL, 3.7 mmol, 1.0 M in THF), and the reaction mixture was irradiated under microwave for 10 h at 120° C. The reaction was cooled to RT, quenched with sat. NH$_4$Cl aq. solution and extracted with EtOAc (3×5 mL). The combined organic layer was washed with brine, dried over MgSO$_4$, filtered and concentrated. The residue was redissolved in THF (6 mL) and MeOH (0.6 mL) then trimethylsilyl diazomethane (0.114 mL, 0.228 mmol, 2.0 M in Et$_2$O) was added. After 1 h of stirring at RT, the reaction was quenched with glacial acetic acid then concentrated.

The residue was purified by flash chromatography (Combi-flash Rf, DCM/MeOH=0-10% gradient) (57 mg, 54% yield, 2 steps). LCMS: $R_T$=2.090 min, MS (ES) 712.0 (M+H).

Step D. Example 352

The title compound (8 mg, 53%, 2 steps) was prepared following General Procedure G using methyl (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-di-hydropyrazino[1,2-a]indol-2(1H)-yl)-1H-indole-2-carboxylate (13 mg, 0.019 mmol) and 2-(bromomethyl)pyridine hydrobromide (6.2 mg, 0.025 mmol) followed by saponification using General Procedure D. LCMS: $R_T$=1.869 min, MS (ES) 788.9 (M+H).

Example 353

(R)-4-(7-Chloro-10-(3-(4-chloro-3,5-dimethylphe-noxy)propyl)-4-methyl-1-oxo-6-(1,3,5-trimethyl-1H-pyrazol-4-yl)-3,4-dihydropyrazino[1,2-a]indol-2(1H)-yl)-1-(2-methoxyethyl)-1H-indole-2-carboxylic acid The title compound (11 mg, 75%, 2 steps) was prepared following General Procedure G using methyl (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-di-hydropyrazino[1,2-a]indol-2(1H)-yl)-1H-indole-2-carboxylate (13 mg, 0.019 mmol) and 1-bromo-2-methoxyethane (3 µL, 4.4 mg, 0.032 mmol) followed by saponification using General Procedure D. LCMS: $R_T$=2.040 min, MS (ES) 756.0 (M+H).

Example 354

(R)-7-(7-Chloro-10-(3-(4-chloro-3,5-dimethylphe-noxy)propyl)-4-methyl-1-oxo-6-(1,3,5-trimethyl-1H-pyrazol-4-yl)-3,4-dihydropyrazino[1,2-a]indol-2(1H)-yl)-1-(2-methoxyethyl)-1H-indole-2-carboxamide The title compound (4.5 mg, 45%) was prepared according to General Procedure E using (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-methoxyethyl)-1H-indole-2-carboxylic acid (10 mg, 0.013 mmol) and ammonia in MeOH (7.0 M, 0.25 mL). LCMS: $R_T$=2.012 min, MS (ES) 754.9 (M+H).

Example 355

(M, R)-3-(7-Chloro-10-(3-(4-chloro-3,5-dimeth-ylphenoxy)propyl)-4-methyl-1-oxo-6-(1,3,5-trim-ethyl-1H-pyrazol-4-yl)-3,4-dihydropyrazino[1,2-a]indol-2(1H)-yl)-6-fluoro-1-methyl-1H-indole-5-carboxylic acid The title compound was prepared according to General Procedure B using (M, R)-7-chloro-10-(3-(4-chloro-3,5-di-methylphenoxy)propyl)-4-methyl-6-(1,3,5-trimethyl-1H-pyrazol-4-yl)-3,4-dihydropyrazino[1,2-a]indol-1(2H)-one and methyl 3-bromo-6-fluoro-1-methyl-1H-indole-5-car-boxylate followed by saponification using General Proce-dure D. LCMS: $R_T$=2.74 min, MS (ES) 730.0 (M+H) (LC method III).

Example 356

(R)-7-(7-Chloro-10-(3-(4-chloro-3,5-dimethylphe-noxy)propyl)-4-methyl-1-oxo-6-(1,3,5-trimethyl-1H-pyrazol-4-yl)-3,4-dihydropyrazino[1,2-a]indol-2(1H)-yl)-5-isopropyl-1-methyl-1H-indole-2-carboxylic acid Step A. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-isopropyl-1H-indole-2-carboxylate The title compound (22 mg, 58%) was prepared according to General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and methyl 7-bromo-5-isopropyl-1H-indole-2-carboxylate (45 mg, 0.15 mmol). LCMS: $R_T$=2.295 min, MS (ES) 754.0 (M+H).

Step B. Example 356

The title compound (12 mg, 80%) was prepared according to General Procedure G using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropy-razino[1,2-a]indol-2(1H)-yl)-5-isopropyl-1H-indole-2-carboxylate (15 mg, 0.02 mmol) and MeI (5 µL, 0.08 mmol) followed by saponification using General Procedure D. LCMS: $R_T$=2.186 MS (ES) 754.0 (M+H).

Example 357

(R)-7-(7-Chloro-10-(3-(4-chloro-3,5-dimethylphe-noxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxamide To a solution of (R)-7-(7-chloro-10-(3-(4-chloro-3,5-di-methylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylic acid (20 mg, 0.028 mmol) in DCM (1 mL) was added DMF (1 µL) and oxalyl chloride (3.8 µL), sequentially. The reaction mixture was stirred for 30 min at RT then concentrated. The residue was dissolved in dry DCM (1 mL) and ammonia (10 µL, 0.5M in 1,4-dioxane) was added. The reaction mixture was stirred at RT for 15 min then concentrated. The residue was purified by HPLC (Phenomenex Gemini C18. $H_2O/CH_3CN$ gradient from 50% to 100% $CH_3CN$ for 5 min, 0.1% TFA) to give the title compound (16 mg, 80%). MS (ES) 712.1 (M+H), Rf=0.88

Example 358

(R)-7-Chloro-10-(3-(4-chloro-3,5-dimethylphenoxy)propyl)-4-methyl-2-(1-methyl-5-(1-methyl-1H-tetra-zol-5-yl)-1H-indol-3-yl)-6-(1,3,5-trimethyl-1H-pyra-zol-4-yl)-3,4-dihydropyrazino[1,2-a]indol-1(2H)-one The title compound (4 mg, 20%) was isolated as the second eluting isomer along with Example 350. LCMS: $R_T$=2.110 min, MS (ES) 749.9 (M+H).

Example 359

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-isopropyl-1-(pyridin-2-ylmethyl)-1H-indole-2-carboxylic acid The title compound (16 mg, 96%) was prepared according to General Procedure G using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-isopropyl-1H-indole-2-carboxylate (15 mg, 0.02 mmol) and 2-(bromomethyl)pyridine hydrobromide (7.6 mg, 0.03 mmol) followed by saponification using General Procedure D. LCMS: $R_T$=1.971 MS (ES) 831.0 (M+H).

Example 360

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((6-methoxypyridin-2-yl)methyl)-1H-indole-2-carboxylic acid The title compound (7.2 mg, 64% yield) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-(chloromethyl)-6-methoxypyridine (10 mg, 0.064 mmol) followed by saponification using General Procedure D. LCMS: $R_T$=2.105 min, MS (ES) 819.0 (M+H).

Example 361

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-N-hydroxy-1-methyl-1H-indole-5-carboxamide To a solution of (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (115 mg, 0.16 mmol) in DCM (3 mL) was added NMM (18 mg, 0.18 mmol), hydroxylamine hydrochloride (13 mg, 0.18 mmol) and DMAP (2 mg, 0.02 mmol). The reaction mixture was stirred at RT for 12 h then quenched with water (5 mL). The mixture was extracted with DCM (3×5 mL). The organic layer was dried and concentrated. The residue was purified by reverse phase HPLC (Phenomenex Gemini C18, H₂O/CH₃CN gradient to 35-95% MeCN 0.1% TFA) to afford the title compound (49 mg, 42%). LCMS: $R_T$=1.897 min, MS (ES) 726.9 (M+H).

Example 362

(R)-7-Chloro-10-(3-(4-chloro-3,5-dimethylphenoxy)propyl)-4-methyl-2-(1-methyl-7-(2-methyl-2H-tetrazol-5-yl)-1H-indol-3-yl)-6-(1,3,5-trimethyl-1H-pyrazol-4-yl)-3,4-dihydropyrazino[1,2-a]indol-1(2H)-one The title compound (11 mg, 54%) was prepared following General Procedure G using (R)-7-chloro-10-(3-(4-chloro-3,5-dimethylphenoxy)propyl)-4-methyl-2-(1-methyl-7-(1H-tetrazol-5-yl)-1H-indol-3-yl)-6-(1,3,5-trimethyl-1H-pyrazol-4-yl)-3,4-dihydropyrazino[1,2-a]indol-1(2H)-one (20 mg, 0.03 mmol) and methyl iodide (4 μL, 0.05 mmol) and isolated as the first eluting isomer. LCMS: $R_T$=2.074 min, MS (ES) 750.0 (M+H).

Example 363

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((5-methylpyridin-2-yl)methyl)-1H-indole-2-carboxylic acid The title compound (8.9 mg, 80%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-(chloromethyl)-5-methylpyridine (10 mg, 0.070 mmol) followed by saponification using General Procedure D. LCMS: $R_T$=1.885 min, MS (ES) 802.9 (M+H).

Example 364

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-isopropyl-1-(2-methoxyethyl)-1H-indole-2-carboxylic acid The title compound (12 mg, 75%) was prepared according to General Procedure G using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-isopropyl-1H-indole-2-carboxylate (15 mg, 0.02 mmol) and 1-bromo-2-methoxyethane (4.2 mg, 0.03 mmol) followed by saponification using General Procedure D. LCMS: $R_T$=2.208 MS (ES) 798.0 (M+H).

Example 365

(R)-6-Chloro-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid The title compound was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 3-bromo-6-chloro-1-methyl-1H-indole-5-carboxylate followed by saponification using General Procedure D. LCMS: $R_T$=2.81 min, MS (ES) 745.9 (M+H). (LC method III).

Example 366

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carbohydrazide To a solution of methyl (R)-3-(7-chloro-10-(3-(4-chloro-3,5-dimethylphenoxy)propyl)-4-methyl-1-oxo-6-(1,3,5- trimethyl-1H-pyrazol-4-yl)-3,4-dihydropyrazino[1,2-a]indol-2(1H)-yl)-1-methyl-1H-indole-5-carboxylate (15 mg, 0.02 mmol) in DMF (1 mL) was added hydrazine hydrate (0.5 mL, 2.4 mmol, 50% solution), and the mixture was heated at 60° C. for 6 h. The reaction was quenched with water (5 mL) and extracted with $CH_2Cl_2$ (3×5 mL). The organic layer was dried (anhyd. $Na_2SO_4$) and concentrated. The residue was purified by reverse phase HPLC (Phenomenex Gemini C18, $H_2O/CH_3CN$ gradient to 35-95% MeCN 0.1% TFA) to afford the title compound (13 mg, 89%). LCMS: $R_T$=1.768 min, MS (ES) 726.0 (M+H).

Example 367

(R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-morpholinoethyl)-1H-indole-2-carboxylic acid The title compound (2.5 mg, 16%, 2 steps) was prepared following General Procedure G using methyl (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (13 mg, 0.019 mmol) and 4-(2-chloroethyl)morpholine hydrochloride (5.1 mg, 0.027 mmol) followed by saponification using General Procedure D. LCMS: $R_T$=1.843 min, MS (ES) 811.0 (M+H).

Example 368

(P, R)-8-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-2-naphthoic acid The title compound was prepared according to General Procedure I using (P, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 8-bromo-2-naphthoate followed by saponification using General Procedure D. LCMS: $R_T$=2.237 min, MS (ES) 708.9 (M+H).

Example 369

(R)-4-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-(pyrrolidin-1-yl)ethyl)-1H-indole-2-carboxylic acid The title compound (3 mg, 20%, 2 steps) was prepared following General Procedure G using methyl (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (13 mg, 0.019 mmol) and 1-(2-bromoethyl)pyrrolidine hydrobromide (10.2 mg, 0.039 mmol) followed by saponification using General Procedure D. LCMS: $R_T$=1.855 min, MS (ES) 795.0 (M+H).

Example 370

(R)-7-Chloro-10-(3-(4-chloro-3,5-dimethylphenoxy)propyl)-4-methyl-2-(1-methyl-6-(2-methyl-2H-tetrazol-5-yl)-1H-indol-3-yl)-6-(1,3,5-trimethyl-1H-pyrazol-4-yl)-3,4-dihydropyrazino[1,2-a]indol-1(2H)-one The title compound (14 mg, 69%) was prepared following General Procedure G using (R)-7-chloro-10-(3-(4-chloro-3,5-dimethylphenoxy)propyl)-4-methyl-6-(1H-tetrazol-5-yl)-1H-indol-3-yl)-6-(1,3,5-trimethyl-1H-pyrazol-4-yl)-3,4-dihydropyrazino[1,2-a]indol-1(2H)-one (20 mg, 0.03 mmol) and MeI (4 μL, 0.05 mmol). LCMS: $R_T$=2.125 min, MS (ES) 750.0 (M+H).

Example 371

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4-methylpyridin-2-yl)methyl)-1H-indole-2-carboxylic acid The title compound (6.6 mg, 60% yield) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-(chloromethyl)-4-methylpyridine (10 mg, 0.070 mmol) followed by saponification using General Procedure D. LCMS: $R_T$=1.842, 1.862 min, MS (ES) 802.9 (M+H).

Example 372

(R)-7-Chloro-10-(3-(4-chloro-3,5-dimethylphenoxy)propyl)-4-methyl-2-(1-methyl-7-(1-methyl-1H-tetrazol-5-yl)-1H-indol-3-yl)-6-(1,3,5-trimethyl-1H-pyrazol-4-yl)-3,4-dihydropyrazino[1,2-a]indol-1(2H)-one The title compound (6 mg, 30%) was isolated as the second eluting isomer along with Example 362. LCMS: $R_T$=2.119 min, MS (ES) 749.9 (M+H).

Example 373

3-(8-Chloro-11-(3-(4-chloro-3,5-dimethylphenoxy)propyl)-7-(4,6-dimethyl-2-(pyrrolidin-1-ylmethyl)pyrimidin-5-yl)-1-oxo-4,5-dihydro-1H-[1,4]diazepino[1,2-a]indol-2(3H)-yl-1-methyl-1H-indole-5-carboxylic acid Step A. Preparation of 2-((benzyloxy)methyl)-4,6-dimethyl-5-(4,4,5,5-tetramethyl-1,3,2-dioxaborolan-2-yl)pyrimidine A mixture of 2-((benzyloxy)methyl)-5-bromo-4,6-dimethylpyrimidine (800 mg, 2.26 mmol), 4,4,4',4',5,5,5',5'-octamethyl-2,2'-bi(1,3,2-dioxaborolane) (864 mg, 3.4 mmol), Pd(dppf)Cl₂ (165 mg, 0.23 mmol) and KOAc (353 mg, 4.5 mmol) in 1,4-dioxane (20 mL) was sparged for 1 min with $N_2$ gas. The reaction mixture was stirred at 100° C. for 15 h. The reaction mixture was cooled to RT, quenched with $H_2O$ and extracted with EtOAc. The combined organic solution was dried over MgSO$_4$, filtered and concentrated in vacuo. The crude residue was purified by flash chromatography (Combi-flash Rf, Hex/EtOAc=0-25% gradient) to afford the title compound (560 mg, 70%).

Step B. Preparation of 2-((benzyloxy)methyl)-4,6-dimethyl-5-(trifluoro-14-boranyl)pyrimidine potassium salt To a solution of 2-((benzyloxy)methyl)-4,6-dimethyl-5-(4,4,5,5-tetramethyl-1,3,2-dioxaborolan-2-yl)pyrimidine (2.2 g, 6.2 mmol) in MeOH (30 mL) was added aqueous KH$_2$F (4.5 M, 15 mL). The mixture was stirred at RT for 15 min then concentrated in vacuo. The residue was dissolved in hot acetone then filtered. The filtrate was concentrated in vacuo, and the residue was recrystallized in hot acetone and Et$_2$O to afford the title compound as a white solid (1.6 g, 77%).

Step C. Preparation of (2-((benzyloxy)methyl)-4,6-dimethylpyrimidin-5-yl)boronic acid To a solution of 2-((benzyloxy)methyl)-4,6-dimethyl-5-(trifluoro-14-boranyl)pyrimidine potassium salt (1.4 g, 4.2 mmol) in MeCN (20 mL) was added H$_2$O (13 μM, 12.6 mmol) and TMSCl (1.35 g, 12.6 mmol). The reaction mixture was stirred at room temperature for 1 h then concentrated in vacuo. The residue was purified by flash chromatography (Combi-flash Rf, DCM/MeOH=0-10% gradient) to afford the title compound (790 mg, 69%).

Step D. Preparation of ethyl 7-(2-((benzyloxy)methyl)-4,6-dimethylpyrimidin-5-yl)-6-chloro-3-(3-(4-chloro-3,5-dimethylphenoxy)propyl)-1H-indole-2-carboxylate A mixture of ethyl 7-bromo-6-chloro-3-(3-(4-chloro-3,5-dimethylphenoxy)propyl)-1H-indole-2-carboxylate (260 mg, 0.52 mmol), (2-((benzyloxy)methyl)-4,6-dimethylpyrimidin-5-yl)boronic acid (214 mg, 0.78 mmol), dicyclohexyl(2-(phenanthren-9-yl)phenyl)phosphane (25 mg, 0.055 mmol), Pd$_2$(dba)$_3$ (19 mg, 0.018 mmol), and K$_2$CO$_3$ (136 mg, 1.0 mmol) in PhMe (2.0 mL)/THF (2.0 mL)/H$_2$O (0.2 mL) was degassed and heated at 110° C. for 24 h. The reaction mixture was quenched with H$_2$O and extracted with EtOAc. The combined organic layer was dried, filtered and concentrated. The residue was purified by flash chromatography (Combi-flash Rf, Hex/EtOAc=0-100% gradient) to afford the title compound (210 mg, 62%). MS (ES) 646.2 (M+H)

Step E. Preparation of ethyl 7-(2-((benzyloxy)methyl)-4,6-dimethylpyrimidin-5-yl)-1-(3-((tert-butoxycarbonyl)amino)propyl)-6-chloro-3-(3-(4-chloro-3,5-dimethylphenoxy)propyl)-1H-indole-2-carboxylate To a solution of ethyl 7-(2-((benzyloxy)methyl)-4,6-dimethylpyrimidin-5-yl)-6-chloro-3-(3-(4-chloro-3,5-dimethylphenoxy)propyl)-1H-indole-2-carboxylate (180 mg, 0.28 mmol) and tert-butyl 1,2,3-oxathiazinane-3-carboxylate 2,2-dioxide (150 mg, 0.63 mmol) in MeCN (10 mL) was added Cs$_2$CO$_3$ (200 mg, 0.62 mmol). The reaction was heated at 80° C. for 24 h, then cooled to RT. The reaction mixture was diluted with DCM/H$_2$O (50 mL, 1:1) then layers were separated. The aqueous layer was extracted with DCM (2×20 mL). The combined organic extracts were dried over MgSO$_4$, filtered, and concentrated. The residue was purified by flash chromatography (Combi-flash Rf, Hex/EtOAc=0-100% gradient) to afford the title compound (194 mg, 87%). LCMS: R$_T$=1.724 min, MS (ES) 803.0 (M+H) (LC method II).

Step F. Preparation of 7-(2-((benzyloxy)methyl)-4,6-dimethylpyrimidin-5-yl)-8-chloro-11-(3-(4-chloro-3,5-dimethylphenoxy)propyl)-2,3,4,5-tetrahydro-1H-[1,4]diazepino[1,2-a]indol-1-one To a solution of ethyl 7-(2-((benzyloxy)methyl)-4,6-dimethylpyrimidin-5-yl)-1-(3-((tert-butoxycarbonyl)amino)propyl)-6-chloro-3-(3-(4-chloro-3,5-dimethylphenoxy)propyl)-1H-indole-2-carboxylate (194 mg, 0.24 mmol) 1,4-dioxane (10 mL) was added HCl in dioxanes (4.0 M, 1.0 mL, 4.0 mmol), and the reaction mixture was stirred at RT overnight. The reaction was concentrated, and the residue was dissolved in MeOH (20 mL). K$_2$CO$_3$ (300 mg, 2.2 mmol) was added, and the reaction mixture was stirred at 50° C. for 5 h. The reaction mixture was concentrated, and the residue was dissolved in DCM/H$_2$O (40 mL, 1:1). The layers were separated, and the aqueous layer was extracted with DCM (2×20 mL). The combined organic layers were dried over MgSO$_4$, filtered, and concentrated. The residue was purified by flash chromatography (Combi-flash Rf, Hex/EtOAc=0-100% gradient) to afford the title compound (117 mg, 74%). LCMS: R$_T$=2.219 min, MS (ES) 657.0 (M+H).

Step G. preparation of methyl 3-(7-(2-((benzyloxy)methyl)-4,6-dimethylpyrimidin-5-yl)-8-chloro-11-(3-(4-chloro-3,5-dimethylphenoxy)propyl)-1-oxo-4,5-dihydro-1H-[1,4]diazepino[1,2-a]indol-2(3H)-yl)-1-methyl-1H-indole-5-carboxylate The title compound (78 mg, 53%) was prepared according to General Procedure B using 7-(2-((benzyloxy)methyl)-4,6-dimethylpyrimidin-5-yl)-8-chloro-11-(3-(4-chloro-3,5 dimethylphenoxy)propyl)-2,3,4,5-tetrahydro-1H-[1,4]diazepino[1,2-a]indol-1-one (115 mg, 0.17 mmol) and methyl 3-bromo-1-methyl-1H-indole-5-carboxylate (100 mg, 0.37 mmol). LCMS: R$_T$=2.439 min, MS (ES) 843.9 (M+H).

Step H. Preparation of methyl 3-(8-chloro-11-(3-(4-chloro-3,5-dimethylphenoxy)propyl)-7-(2-(hydroxymethyl)-4,6-dimethylpyrimidin-5-yl)-1-oxo-4,5-dihydro-1H-[1,4]diazepino[1,2-a]indol-2(3H)-yl)-1-methyl-1H-indole-5-carboxylate To a solution of methyl 3-(7-(2-((benzyloxy)methyl)-4,6-dimethylpyrimidin-5-yl)-8-chloro-11-(3-(4-chloro-3,5-dimethylphenoxy)propyl)-1-oxo-4,5-dihydro-1H-[1,4]diazepino[1,2-a]indol-2(3H)-yl)-1-methyl-1H-indole-5-carboxylate (78 mg, 0.092 mmol) in a mixture of EtOH/MeOH/EtOAc (2 mL/1 mL/1 mL) was added HCl in dioxanes (4.0 M, 0.25 mL, 1.0 mmol) followed by Pd/C (10 wt. %, 20 mg, 0.018 mmol). The reaction mixture was stirred under H$_2$ atmosphere at RT for 96 h. The reaction mixture was filtered through celite, rinsed with DCM and concentrated. The residue was purified by flash chromatography (Combi-flash Rf, Hex/EtOAc=0-100% gradient) to afford the title compound (34 mg, 49%). LCMS: R$_T$=2.023 min, MS (ES) 753.9.0 (M+H).

Step I. Example 373

The title compound (5.2 mg, 15%) was prepared according to General Procedure J using methyl 3-(8-chloro-11-(3-

(4-chloro-3,5-dimethylphenoxy)propyl)-7-(2-(hydroxymethyl)-4,6-dimethylpyrimidin-5-yl)-1-oxo-4,5-dihydro-1H-[1,4]diazepino[1,2-a]indol-2(3H)-yl)-1-methyl-1H-indole-5-carboxylate (34 mg, 0.045 mmol) and pyrrolidine (15 mg, 0.21 mmol) followed by saponification using General Procedure D. LCMS: $R_T$=1.778 min, MS (ES) 793.0 (M+H).

Example 374

7-((R)-7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-(oxetan-2-ylmethyl)-1H-indole-2-carboxylic acid The title compound (2 mg, 18%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-(bromomethyl)oxetane (10 mg, 0.066 mmol) followed by saponification using General Procedure D. LCMS: $R_T$=2.034 min, MS (ES) 767.9 (M+H).

Example 375

(R)-1-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)isoquinoline-6-carboxamide The title compound (4.3 mg, 72% yield) was prepared according to General Procedure L using (R)-1-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)isoquinoline-6-carboxylic acid (6 mg, 0.0085 mmol) and ammonia in MeOH (7.0 M, 0.25 mL). LCMS: $R_T$=1.940 min, MS (ES) 708.9 (M+H).

Example 376

(R)-7-(7-Chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2 (1H)-yl)-1,5-dimethyl-1H-indole-2-carboxamide The title compound (2.4 mg, 48%) was prepared according to General Procedure E using (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1,5-dimethyl-1H-indole-2-carboxylic acid (5 mg, 0.0069 mmol) and ammonia in MeOH (7.0 M, 0.25 mL). LCMS: $R_T$=2.064 min, MS (ES) 723.0 (M+H). $^1$H NMR (400 MHz, Chloroform-d) δ 9.19 (s, 1H), 7.82 (dd, J=8.6, 2.3 Hz, 1H), 7.52-7.34 (m, 3H), 7.02-6.90 (m, 1H), 6.64 (s, 1.5H), 6.61 (s, 0.5H), 4.30-4.10 (m, 2H), 4.07-03.93 (m, 4H), 3.85-3.70 (m, 1H), 3.58-3.48 (m, 1H), 3.42-3.33 (m, 2H), 2.54 (s, 0.75H), 2.52 (s, 2.25H), 2.47 (s, 0.75H), 2.44 (s, 2.25H), 2.40-2.35 (m, 2H), 2.34 (s, 6H), 2.24-2.17 (m, 3H), 1.36-1.20 (m, 3H).

Example 377

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-methyl-1H-indole-2-carboxamide The title compound was prepared according to General Procedure E using (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid and ammonia in MeOH. LCMS: $R_T$=2.004 min, MS (ES) 711.2 (M+H).

Example 378

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-((4-methoxypyridin-2-yl)methyl)-1H-indole-2-carboxylic acid The title compound (7.8 mg, 69%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-(chloromethyl)-4-methoxypyridine hydrochloride salt (5 mg, 0.026 mmol) followed by saponification using General Procedure D. LCMS: $R_T$=1.835, 1.858 min, MS (ES) 819.0 (M+H).

Example 379

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2 (1H)-yl)-5-methyl-1-(pyridin-2-ylmethyl)-1H-indole-2-carboxamide To a solution of methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methyl-1-(pyridin-2-ylmethyl)-1H-indole-2-carboxylate (10 mg, 0.012 mmol) in DMF (0.5 mL) was added NH$_4$OH (1 mL). The reaction mixture was stirred at 90° C. for 72 h. The crude reaction mixture was purified by reverse phase HPLC (Phenomenex Gemini C18, H$_2$O/CH$_3$CN gradient 35-95% MeCN 0.1% TFA) to afford the title compound (2.0 mg, 20%). LCMS: $R_T$=1.869 min, MS (ES) 799.9 (M+H).

Example 380

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-((3-methyloxetan-3-yl)methyl)-1H-indole-2-carboxylic acid The title compound (7.4 mg, 69%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 3-(bromomethyl)-3-methyloxetane (10 mg, 0.061 mmol) followed by saponification using General Procedure D. LCMS: $R_T$=2.035 min, MS (ES) 781.9 (M+H).

Example 381

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-((6-methylpyridin-2-yl)methyl)-1H-indole-2-carboxylic acid The title compound (7.9 mg, 72%) was prepared according to General Procedure I using ethyl (R)-7-(7-chloro-10-

(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-(chloromethyl)-6-methylpyridine (5 mg, 0.035 mmol) followed by saponification using General Procedure D. LCMS: $R_T$=1.850 min, MS (ES) 802.9 (M+H).

Example 382

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((5-methoxypyridin-2-yl)methyl)-1H-indole-2-carboxylic acid The title compound (10.2 mg, 90%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-(chloromethyl)-5-methoxypyridine hydrochloride salt (10 mg, 0.053 mmol) followed by saponification using General Procedure D. LCMS: $R_T$=1.911 min, MS (ES) 819.0 (M+H).

Example 383

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(oxetan-3-ylmethyl)-1H-indole-2-carboxylic acid The title compound (3.3 mg, 91%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 3-(bromomethyl)oxetane (10 mg, 0.066 mmol) followed by saponification using General Procedure D. LCMS: $R_T$=2.009 min, MS (ES) 768.0 (M+H).

Example 384

(R)-7-(7-Chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-methyl-1H-indole-2-carboxamide The title compound (7.2 mg, 72%) was prepared according to General Procedure E using (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-methyl-1H-indole-2-carboxylic acid (10 mg, 0.0069 mmol) and ammonia in MeOH (7.0 M, 0.25 mL). LCMS: $R_T$=2.018 min, MS (ES) 708.9 (M+H).

Example 385

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-2-ylmethyl)-1H-indole-2-carboxamide The title compound (2.5 mg, 17%) was prepared following the procedure described Example 379 using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-2-ylmethyl)-1H-indole-2-carboxylate (15 mg, 0.019 mmol) and NH₄OH (1 mL). LCMS: $R_T$=1.809, 1.831 min, MS (ES) 787.9 (M+H). ¹H NMR (400 MHz, Chloroform-d) δ 9.18 (s, 1H), 7.82 (dd, J=8.6, 2.6 Hz, 1H), 7.67 (d, J=7.9 Hz, 0.75H), 7.62 (d, J=7.9 Hz, 0.25H), 7.38 (d, J=8.6 Hz, 0.25H), 7.37 (d, J=8.6 Hz, 0.75H), 7.25-6.95 (m, 3H), 6.64 (s, 1.5H), 6.60 (s, 0.5H), 4.46-4.13 (m, 2H), 4.05-3.97 (m, 4H), 3.85-3.71 (m, 1H), 3.55-3.32 (m, 3H), 2.51 (s, 0.75H), 2.49 (s, 2.25H), 2.33 (s, 9H), 2.25-2.17 (m, 2H), 1.31 (d, J=6.5 Hz, 2.25H), 1.22 (d, J=6.5 Hz, 0.75H).

Example 386

7-((R)-7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(1-(pyridin-2-yl)ethyl)-1H-indole-2-carboxylic acid The title compound (3.7 mg, 33%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-(1-chloroethyl)pyridine hydrochloride (10 mg, 0.056 mmol) followed by saponification using General Procedure D. LCMS: $R_T$=1.862 min, MS (ES) 802.9 (M+H).

Example 387

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((3-methylpyridin-2-yl)methyl)-1H-indole-2-carboxylic acid The title compound (2.3 mg, 21%) was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (10 mg, 0.014 mmol) and 2-(chloromethyl)-3-methylpyridine hydrochloride (10 mg, 0.056 mmol) followed by saponification using General Procedure D. LCMS: $R_T$=1.850 min, MS (ES) 802.9 (M+H).

Example 388

(R)-7-Chloro-10-(3-(4-chloro-3,5-dimethylphenoxy)propyl)-4-methyl-2-(1-methyl-5-(1-methyl-1H-pyrazol-3-yl)-1H-indol-3-yl)-6-(1,3,5-trimethyl-1H-pyrazol-4-yl)-3,4-dihydropyrazino[1,2-a]indol-1(2H)-one Step A. Preparation of 1-methyl-5-(1-methyl-1H-pyrazol-3-yl)-1H-indole 3-Bromo-1-methyl-1H-pyrazole (100 mg, 0.62 mmol), PdCl₂(dppf).DCM (25 mg, 0.03 mmol), K₂CO₃ (745 μL, 1.86 mmol, 2.5 M aq. solution) were added to a solution of 1-methyl-5-(4,4,5,5-tetramethyl-1,3,2-dioxaborolan-2-yl)-1H-indole (196 mg, 0.76 mmol) in MeCN (2.5 mL). The reaction mixture was degassed using Ar then stirred at 95° C. for 13 hr. The reaction mixture was cooled to RT, filtered through Celite pad and extracted with DCM (3×5 mL). The combined organic layers were dried and concentrated. The residue was purified by flash chromatography (Combi-flash Rf, Hex/EtOAc=0-25% gradient) to provide the title compound (120 mg, 91%). LCMS: $R_T$=1.237 min, MS (ES) 212.2 (M+H).

Step B. Preparation of 3-iodo-1-methyl-5-(1-methyl-1H-pyrazol-3-yl)-1H-indole

NIS (134 mg, 0.60 mmol) was added to a solution of 1-methyl-5-(1-methyl-1H-pyrazol-3-yl)-1H-indole (120 mg, 0.57 mmol) in DMF (5.7 mL) at 0° C. The reaction was warmed to RT and stirred for 2 h. The reaction was quenched with water and extracted with EtOAc (3×10 mL). The combined organic layer was washed with water, dried and concentrated. The residue was purified by flash chromatography (Combi-flash Rf, Hex/EtOAc=0-50% gradient) to afford the title compound (95 mg, 50%). LCMS: $R_T$=1.491 min, MS (ES) 337.9 (M+H).

Step B. Example 388

The title compound (23 mg, 66%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol) and 3-iodo-1-methyl-5-(1-methyl-1H-pyrazol-3-yl)-1H-indole (30 mg, 0.089 mmol). LCMS: $R_T$=2.057 min, MS (ES) 748.9 (M+H).

Example 389

(R)-7-Chloro-10-(3-(4-chloro-3,5-dimethylphenoxy)propyl)-4-methyl-2-(1-methyl-5-(pyridin-2-yl)-1H-indol-3-yl)-6-(1,3,5-trimethyl-1H-pyrazol-4-yl)-3,4-dihydropyrazino[1,2-a]indol-1(2H)-one Step A. Preparation of 1-methyl-5-(pyridin-2-yl)-1H-indole The title compound (110 mg, 83%) was prepared following the procedure described Example 388, Step A using 2-bromopyridine (60 μL, 0.63 mmol) and 1-methyl-5-(4,4,5,5-tetramethyl-1,3,2-dioxaborolan-2-yl)-1H-indole (200 mg, 0.78 mmol). LCMS: $R_T$=0.973 min, MS (ES) 209.1 (M+H).

Step B. Preparation of 3-iodo-1-methyl-5-(pyridin-2-yl)-1H-indole

The title compound (160 mg, 91%) was prepared following the procedure described Example 388, Step B using 1-methyl-5-(pyridin-2-yl)-1H-indole (110 mg, 0.53 mmol). LCMS: $R_T$=1.146 min, MS (ES) 334.9 (M+H).

Step B. Example 389

The title compound (37 mg, 88%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.056 mmol) and 3-iodo-1-methyl-5-(pyridin-2-yl)-1H-indole (36 mg, 0.11 mmol). LCMS: $R_T$=1.895 min, MS (ES) 745.0 (M+H).

Example 390

(R)-3-(7-Chloro-10-(3-(4-chloro-3,5-dimethylphenoxy)propyl)-6-(4,6-dimethyl-2-(pyrrolidin-1-ylmethyl)pyrimidin-5-yl)-4-methyl-1-oxo-3,4-dihydropyrazino[1,2-a]indol-2(1H)-yl)-1-methyl-1H-indole-5-carboxylic acid Step A. Preparation of ethyl (R)-7-(2-((benzyloxy)methyl)-4,6-dimethylpyrimidin-5-yl)-1-(1-((tert-butoxycarbonyl)amino)propan-2-yl)-6-chloro-3-(3-(4-chloro-3,5-dimethylphenoxy)propyl)-1H-indole-2-carboxylate The title compound (259 mg, 84%) was prepared following the procedure described Example 373, Step E using of ethyl 7-(2-((benzyloxy)methyl)-4,6-dimethylpyrimidin-5-yl)-6-chloro-3-(3-(4-chloro-3,5-dimethylphenoxy)propyl)-1H-indole-2-carboxylate (250 mg, 0.39 mmol), tert-butyl (S)-5-methyl-1,2,3-oxathiazolidine-3-carboxylate 2,2-dioxide (150 mg, 0.63 mmol) and Cs$_2$CO$_3$ (250 mg, 0.77 mmol). LCMS: $R_T$=1.737 min, MS (ES) 803.0 (M+H).

Step B. Preparation of (R)-6-(2-((benzyloxy)methyl)-4,6-dimethylpyrimidin-5-yl)-7-chloro-10-(3-(4-chloro-3,5-dimethylphenoxy)propyl)-4-methyl-3,4-dihydropyrazino[1,2-a]indol-1(2H)-one The title compound (143 mg, 68%) was prepared following the procedure described Example 373, Step F using ethyl (R)-7-(2-((benzyloxy)methyl)-4,6-dimethylpyrimidin-5-yl)-1-(1-((tert-butoxycarbonyl)amino)propan-2-yl)-6-chloro-3-(3-(4-chloro-3,5-dimethylphenoxy) propyl)-1H-indole-2-carboxylate (259 mg, 0.32 mmol), HCl in dioxanes (4.0 M, 1.0 mL, 4.0 mmol) and K$_2$CO$_3$ (250 mg, 1.8 mmol). LCMS: $R_T$=1.270 min, MS (ES) 657.0 (M+H).

Step C. Preparation of methyl (R)-3-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-1-methyl-1H-indole-5-carboxylate The title compound (123 mg, 67%) was prepared according to General Procedure B using (R)-6-(2-((benzyloxy)methyl)-4,6-dimethylpyrimidin-5-yl)-7-chloro-10-(3-(4-chloro-3,5-dimethylphenoxy)propyl)-4-methyl-3,4-dihydropyrazino[1,2-a]indol-1(2H)-one (143 mg, 0.22 mmol) and methyl 3-bromo-1-methyl-1H-indole-5-carboxylate (120 mg, 0.45 mmol). LCMS: $R_T$=2.336 min, MS (ES) 843.9 (M+H).

Step D. Preparation of methyl (R)-3-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1-methyl-1H-indole-5-carboxylate To a solution of methyl (R)-3-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-1-methyl-1H-indole-5-carboxylate (123 mg, 0.15 mmol) in MeOH (5 mL) and EtOAc (1 mL) was added HCl in dioxane (4.0 M, 0.25 mL, 1.0 mmol) followed by Pd/C (10 wt. %, 10 mg, 0.0093 mmol). The reaction mixture was stirred under H$_2$ atmosphere at 35° C. for 24 h. The reaction was filtered through celite, rinsed with DCM, and concentrated to afford the title compound (92 mg, 84%). LCMS: $R_T$=2.066 min, MS (ES) 754.0 (M+H).

Step E. Example 390

The title compound (8.2 mg, 60%) was prepared according to General Procedure J using methyl (R)-3-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1-methyl-1H-indole-5-carboxylate (13 mg, 0.017 mmol) and pyrrolidine (50 mg, 0.70 mmol) followed by saponification using General Procedure D. LCMS: $R_T$=1.841 min, MS (ES) 793.0 (M+H). $^1$H NMR (400 MHz, Chloroform-d) δ 8.27 (s, 1H), 7.95 (dd, J=8.8, 1.5 Hz, 1H), 7.78 (d, J=8.6 Hz, 1H), 7.32 (dd, J=8.7, 4.7 Hz, 2H), 6.64 (s, 2H), 4.61 (s, 2H), 4.43-4.11 (m, 3H), 4.01 (t, J=6.2 Hz, 2H), 3.82 (s, 3H), 3.81-3.78 (m, 1H), 3.67 (d, J=13.0 Hz, 1H), 3.50-3.26 (m, 2H), 3.23-3.08 (m, 2H), 2.41 (s, 3H), 2.33 (s, 6H), 2.28-2.14 (m, 9H), 1.23 (d, J=6.3 Hz, 3H).

Example 391

(R)-7-Chloro-10-(3-(4-chloro-3,5-dimethylphenoxy)propyl)-4-methyl-2-(1-methyl-5-(1-methyl-1H-pyrazol-4-yl)-1H-indol-3-yl)-6-(1,3,5-trimethyl-1H-pyrazol-4-yl)-3,4-dihydropyrazino[1,2-a]indol-1(2H)-one Step A. Preparation of (R)-2-(5-bromo-1-methyl-1H-indol-3-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one The title compound (50 mg, 72%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (50 mg, 0.090 mmol) and 5-bromo-3-iodo-1-methyl-1H-indole (60 mg, 0.18 mmol). LCMS: $R_T$=2.277 min, MS (ES) 746.8 (M+H).

Step B. Example 391

1-Methylpyrazole-4-boronic acid pinacol ester (20 mg, 0.094 mmol), PdCl$_2$(dppf).DCM (2 mg, 0.002 mmol), K$_2$CO$_3$ (56 µL, 0.14 mmol, 2.5 M aq. solution) were added to a solution of (R)-2-(5-bromo-1-methyl-1H-indol-3-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (35 mg, 0.047 mmol) in MeCN (1 mL). The reaction mixture was degassed using Ar and stirred at 95° C. for 1 h. The cooled reaction mixture was filtered through Celite followed by silica gel and the filtrate was concentrated. The residue was purified by reverse phase HPLC (Phenomenex Gemini C18, H$_2$O/MeCN gradient to 30-95% MeCN 0.1% TFA) to afford the title compound (25 mg, 71%). LCMS: $R_T$=2.071 min, MS (ES) 748.0 (M+H).

Example 392

(R)-3-(7-chloro-10-(3-(4-chloro-3,5-dimethylphenoxy)propyl)-6-(3,5-dimethyl-1-(2-(pyrrolidin-1-yl)ethyl)-1H-pyrazol-4-yl)-4-methyl-1-oxo-3,4-dihydropyrazino[1,2-a]indol-2(1H)-yl)-1-methyl-1H-indole-5-carboxamide To a solution of (R)-3-(7-chloro-10-(3-(4-chloro-3,5-dimethylphenoxy)propyl)-6-(3,5-dimethyl-1-(2-(pyrrolidin-1-yl)ethyl)-1H-pyrazol-4-yl)-4-methyl-1-oxo-3,4-dihydropyrazino[1,2-a]indol-2(1H)-yl)-1-methyl-1H-indole-5-carboxylic acid (9 mg, 0.0113 mmol) in DCM (1 mL) was added oxalyl chloride (2.2 µL, 0.026 mmol), followed by catalytic amount of DMF. The reaction mixture was stirred for 1 h at RT then concentrated in vacuo. The residue was re-dissolved in dry DCM (1 mL), and ammonia (10 uL, 0.5M in 1-4-dioxane) was added. The reaction mixture was stirred at RT for 15 min and concentrated. The residue was purified by reverse phase HPLC (Phenomenex Gemini C18, H$_2$O/CH$_3$CN gradient to 25-95% MeCN 0.1% TFA) to give the title compound (3.2 mg, 36%). LCMS: $R_T$=0.783 min (LC method IV), MS (ES) 794.1 (M+H).

Example 393

(R)-7-Chloro-10-(3-(4-chloro-3,5-dimethylphenoxy)propyl)-4-methyl-2-(1-methyl-5-(3-methyl-1,2,4-oxadiazol-5-yl)-1H-indol-3-yl)-6-(1,3,5-trimethyl-1H-pyrazol-4-yl)-3,4-dihydropyrazino[1,2-a]indol-1(2H)-one Step A. Preparation of (R)—N-((3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carbonyl)oxy)acetimidamide The title compound was prepared according to General Procedure E using (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (25 mg, 0.035 mmol) and N-hydroxyacetimidamide (10 mg, 0.135 mmol). The crude product was carried forward to Step B without further purification. LCMS: $R_T$=1.916 min, MS (ES) 768.0 (M+H).

Step B. Example 393

To a solution of (R)—N-((3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carbonyl)oxy)acetimidamide from Step A in EtOH/H$_2$O (3:1, 4 mL) was added sodium acetate (10 mg, 0.121 mmol), and the mixture was stirred at 70° C. for 16 h. The reaction was cooled to RT and diluted into DCM/H$_2$O (10 mL, 1:1). The layers were separated, and the aqueous layer was extracted with DCM (2×5 mL). The combined organic layer was dried and concentrated. The residue was purified by reverse phase HPLC (Phenomenex Gemini C18, H$_2$O/CH$_3$CN gradient 35-95% MeCN 0.1% TFA) to afford the title compound (8.1 mg, 31%). LCMS: $R_T$=2.138 min, MS (ES) 749.8 (M+H). $^1$H NMR (400 MHz, Chloroform-d) δ 8.30 (d, J=2.0 Hz, 1H), 8.04 (d, J=8.7 Hz, 1H), 7.78 (dd, J=8.6, 2.1 Hz, 1H), 7.50 (dd, J=8.6, 1.8 Hz, 1H), 7.38-7.24 (m, 2H), 6.63 (s, 2H), 4.56-4.36 (m, 1H), 4.27-4.13 (m, 1H), 4.08-3.96 (m, 5H), 3.86 (s, 3H), 3.70 (d, J=12.3 Hz, 1H), 3.50-3.30 (m, 2H), 2.49 (s, 1.5H), 2.47 (s, 1.5H), 2.34 (s, 1.5H), 2.32 (s, 6H), 2.31 (s, 1.5H), 2.24-2.18 (m, 5H), 1.30-1.23 (m, 3H).

Example 394

(R)-7-Chloro-10-(3-(4-chloro-3,5-dimethylphenoxy)propyl)-4-methyl-2-(1-methyl-5-(pyrimidin-2-yl)-1H-indol-3-yl)-6-(1,3,5-trimethyl-1H-pyrazol-4-yl)-3,4-dihydropyrazino[1,2-a]indol-1(2H)-one

Step A. Preparation of 1-methyl-5-(pyrimidin-2-yl)-1H-indole

The title compound (61 mg, 58%) was prepared following the procedure described Example 388, Step A using 2-bromopyrimidine (80 mg, 0.50 mmol) and 1-methyl-5-(4,4,5,5-tetramethyl-1,3,2-dioxaborolan-2-yl)-1H-indole (159 mg, 0.62 mmol). LCMS: $R_T$=1.103 min, MS (ES) 210.1 (M+H).

Step B. Preparation of 3-iodo-1-methyl-5-(pyrimidin-2-yl)-1H-indole

The title compound (82 mg, 84%) was prepared following the procedure described Example 388, Step B using 1-methyl-5-(pyrimidin-2-yl)-1H-indole (61 mg, 0.29 mmol). LCMS: $R_T$=1.456 min, MS (ES) 335.9 (M+H).

Step C. Example 394

The title compound (15 mg, 43%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol) and 3-iodo-1-methyl-5-(pyrimidin-2-yl)-1H-indole (30 mg, 0.089 mmol). LCMS: $R_T$=2.086 min, MS (ES) 746.9 (M+H). ¹H NMR (400 MHz, Chloroform-d) δ 8.77 (d, J=4.8 Hz, 1H), 8.76 (d, J=4.9 Hz, 1H), 8.63 (dd, J=5.1, 1.5 Hz, 1H), 8.38 (dt, J=9.0, 1.5 Hz, 1H), 7.68 (dd, J=8.5, 2.6 Hz, 1H), 7.44 (dd, J=9.0, 2.9 Hz, 1H), 7.30-7.25 (m, 2H), 7.12 (dt, J=8.5, 4.8 Hz, 1H), 6.61 (s, 2H), 4.53-4.46 (m, 1H), 4.35-4.20 (m, 1H), 4.02-3.97 (m, 1H), 3.89 (s, 3H), 3.84 (s, 3H), 3.75 (ddd, J=16.3, 12.7, 1.5 Hz, 1H), 3.47-3.31 (m, 2H), 2.29 (s, 6H), 2.24-2.19 (m, 5H), 2.06 (d, J=2.1 Hz, 3H), 1.29 (d, J=6.8 Hz, 1.4H), 1.22 (d, J=6.4 Hz, 1.5H).

Example 395

(R)-7-Chloro-10-(3-(4-chloro-3,5-dimethylphenoxy)propyl)-6-(4,6-dimethylpyrimidin-5-yl)-4-methyl-2-(1-methyl-5-(3-methyl-1,2,4-oxadiazol-5-yl)-1H-indol-3-yl)-3,4-dihydropyrazino[1,2-a]indol-1(2H)-one

Step A. Preparation of (R)—N-((3-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-methyl-1H-indole-5-carbonyl)oxy)acetimidamide The title compound was prepared according to General Procedure E using (R)-3-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-methyl-1H-indole-5-carboxylic acid (20 mg, 0.028 mmol) and N-hydroxyacetimidamide (10 mg, 0.135 mmol). The crude product was carried forward to Step 2 without purification. LCMS: $R_T$=1.930 min, MS (ES) 766.0 (M+H).

Step B. Example 395

The title compound (8.1 mg, 31%) was prepared following the procedure described Example 393 Step B using (R)—N-((3-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-methyl-1H-indole-5-carbonyl)oxy)acetimidamide and sodium acetate (10 mg, 0.121 mmol). LCMS: $R_T$=2.187 min, MS (ES) 747.8 (M+H). ¹H NMR (400 MHz, Chloroform-d) δ 9.23 (s, 1H), 8.31-8.18 (m, 1H), 8.03 (dd, J=8.7, 1.6 Hz, 1H), 7.88-7.80 (m, 1H), 7.49 (d, J=8.7 Hz, 1H), 7.38 (m, 1H), 7.25 (s, 1H), 6.64 (s, 2H), 4.42 (dd, J=24.4, 9.9 Hz, 1H), 4.02 (t, J=6.1 Hz, 2H), 3.87 (s, 2H), 3.85 (d, J=2.5 Hz, 1H), 3.72-3.69 (m, 1H), 3.61 (d, J=12.6 Hz, 1H), 3.52-3.30 (m, 2H), 2.54 (s, 3H), 2.47 (s, 3H), 2.38 (s, 3H), 2.32 (s, 6H), 2.23 (t, J=6.9 Hz, 2H), 1.27 (d, J=6.5 Hz, 3H).

Example 396

(R)-3-(7-Chloro-10-(3-(4-chloro-3,5-dimethylphenoxy)propyl)-6-(4,6-dimethyl-2-((4-methylpiperazin-1-yl)methyl)pyrimidin-5-yl)-4-methyl-1-oxo-3,4-dihydropyrazino[1,2-a]indol-2(1H)-yl)-1-methyl-1H-indole-5-carboxylic acid The title compound (9.5 mg, 48%) was prepared according to General Procedure J using methyl (R)-3-(7-chloro-10-(3-(4-chloro-3,5-dimethylphenoxy)propyl)-6-(2-(hydroxylmethyl)-4,6-dimethylpyrimidin-5-yl)-4-methyl-1-oxo-3,4-dihydropyrazino[1,2-a]indol-2(1H)-yl)-1-methyl-1H-indole-5-carboxylate (18 mg, 0.024 mmol) and N-methyl piperazine (100 mg, 1.0 mmol) followed by saponification using General Procedure D. LCMS: $R_T$=1.799 min, MS (ES) 821.8 (M+H). ¹H NMR (400 MHz, Chloroform-d) δ 8.25 (s, 1H), 7.92 (dd, J=8.7, 1.5 Hz, 1H), 7.80 (d, J=8.6 Hz, 1H), 7.36-7.26 (m, 3H), 6.64 (s, 2H), 4.57 (s, 2H), 4.33 (dd, J=13.3, 3.2 Hz, 1H), 4.06-3.87 (m, 6H), 3.81 (s, 3H), 3.81-3.68 (m, 6H), 3.51-3.30 (m, 2H), 2.95 (s, 3H), 2.40 (s, 3H), 2.33 (s, 6H), 2.25-2.17 (m, 5H), 1.24 (d, J=6.4 Hz, 3H).

Example 397

3-((4R)-7-Chloro-10-(3-(4-chloro-3,5-dimethylphenoxy)propyl)-6-(2-((3-hydroxypyrrolidin-1-yl)methyl)-4,6-dimethylpyrimidin-5-yl)-4-methyl-1-oxo-3,4-dihydropyrazino[1,2-a]indol-2(1H)-yl)-1-methyl-1H-indole-5-carboxylic acid The title compound (5.5 mg, 29%) was prepared according to General Procedure J using methyl (R)-3-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1-methyl-1H-indole-5-carboxylate (18 mg, 0.024 mmol) and 3-hydroxypyrrolidine (100 mg, 1.4 mmol) followed by saponification using General Procedure D. LCMS: $R_T$=1.787 min, MS (ES) 808.9 (M+H). ¹H NMR (400 MHz, Chloroform-d) δ 8.26 (s, 1H), 7.92 (d, J=8.7 Hz, 1H), 7.79 (d, J=8.6 Hz, 1H), 7.34-7.26 (m, 3H), 6.64 (s, 2H), 4.70 (s, 2H), 4.38-3.89 (m, 6H), 3.82 (s, 3H), 3.81-3.59 (m, 4H), 3.50-3.30 (m, 2H), 2.41 (s, 3H), 2.33 (s, 6H), 2.26-2.17 (m, 7H), 1.24 (d, J=4.4 Hz, 3H).

Example 398

(R)-3-(7-Chloro-10-(3-(4-chloro-3,5-dimethylphenoxy)propyl)-6-(4,6-dimethyl-2-(morpholinomethyl)pyrimidin-5-yl)-4-methyl-1-oxo-3,4-dihydropyrazino[1,2-a]indol-2(1H)-yl)-1-methyl-1H-indole-5-carboxylic acid The title compound (9 mg, 46%) was prepared according to General Procedure J using methyl (R)-3-(7-chloro-10-(3-

(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1-methyl-1H-indole-5-carboxylate (18 mg, 0.024 mmol) and morpholine (100 mg, 1.4 mmol) followed by saponification using General Procedure D. LCMS: $R_T$=1.809, min, MS (ES) 808.9 (M+H).

Example 399

7-(8-Chloro-11-(3-(4-chloro-3,5-dimethylphenoxy) propyl)-7-(4,6-dimethylpyrimidin-5-yl)-1-oxo-4,5-dihydro-1H-[1,4]diazepino[1,2-a]indol-2(3H)-yl)-1, 5-dimethyl-1H-indole-2-carboxylic acid The title compound was prepared following General Procedure B using 8-chloro-11-(3-(4-chloro-3,5-dimethylphenoxy)propyl)-7-(4,6-dimethylpyrimidin-5-yl)-2,3,4,5-tetrahydro-1H-[1,4]diazepino[1,2-a]indol-1-one and methyl 7-bromo-1,5-dimethyl-1H-indole-2-carboxylate followed by saponification using General Procedure D. MS (ES) 724.2 (M+H).

Example 400

(R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2 (1H)-yl)-1,5-dimethyl-1H-indole-2-carboxylic acid Step A. Preparation of methyl (R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1,5-dimethyl-1H-indole-2-carboxylate The title compound was prepared according to procedures described in Example 318 step A and B using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one and methyl 7-bromo-1,5-dimethyl-1H-indole-2-carboxylate. MS (ES) 726.2 (M+H).

Step B. Example 400

The title compound was prepared following General Procedure D using methyl (R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1,5-dimethyl-1H-indole-2-carboxylate. LCMS: $R_T$=0.873 min (LC method IV), MS (ES) 712.6 (M+H); $^1$H NMR (DMSO, 400 MHz) δ (ppm) 7.72 (d, J=8.8 Hz, 1H), 7.47 (s, 1H), 7.29 (dd, J=8.8, 2.8 Hz, 1H), 7.25 (s, 1H), 6.98 (s, 1H), 6.92 (s, 2H), 4.37-4.16 (m, 1H), 4.03 (s, 3H), 3.98 (t, J=6.0 Hz, 2H), 3.68-3.62 (m, 1H), 3.46-3.40 (m, 1H), 2.43 (s, 3H), 2.28 (s, 6H), 2.22 (s, 3H), 2.17 (t, J=6.4 Hz, 2H), 2.08-2.03 (m, 2H), 2.04 (s, 3H), 1.29 (d, J=6.0 Hz, 3H).

Example 401

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-methyl-5-(pyrrolidin-1-ylmethyl)-1H-indole-2-carboxylic acid Step A. Preparation of 1-(tert-butyl) 2-methyl 7-bromo-5-methyl-1H-indole-1,2-dicarboxylate To a solution of 7-bromo-5-methyl-1H-indole-2-carboxylic acid (1.5 g, 5.9 mmol) in THF (50 mL) and MeOH (6 mL) was added trimethylsilyl diazomethane (4.4 mL, 8.9 mmol, 2.0 M in Et$_2$O), and the reaction mixture was stirred at RT for 1 h. The reaction was quenched with glacial acetic acid then concentrated. The residue was dissolved in DCM (30 mL), and Et$_3$N (2.94 mL, 2.15 g, 21.1 mmol), DMAP (0.144 g, 1.18 mmol) and di-tert-butyl dicarbonate (1.76 mL, 1.67 g, 7.67 mmol) were added. The reaction mixture was stirred at RT for 3 h then quenched with sat. NH$_4$Cl aq. solution and extracted with DCM (3×25 mL). The combined organic layer was washed with brine, dried over MgSO$_4$, filtered, and concentrated. The residue was purified by flash chromatography (Combi-flash Rf, Hex/EtOAc=0-100% gradient) to afford the title compound (1.7 g, 78%, 2 steps). LCMS: $R_T$=1.900 min, MS (ES) 390.0 (M+Na); $^1$H NMR (400 MHz, CDCl$_3$) δ 7.45 (d, J=3.2 Hz, 2H), 7.21 (s, 1H), 3.92 (s, 3H), 2.41 (s, 3H), 1.69 (s, 9H).

Step B. Preparation of 1-(tert-butyl) 2-methyl 7-bromo-5-formyl-1H-indole-1,2-dicarboxylate To a solution of 1-(tert-butyl) 2-methyl 7-bromo-5-methyl-1H-indole-1,2-dicarboxylate (1.7 g, 4.6 mmol) in CCl$_4$ (46 mL) was added AIBN (189 mg, 1.15 mmol) and NBS (822 mg, 4.6 mmol). The reaction mixture was reflux for 3 h then concentrated. The residue was purified by flash chromatography (Combi-flash Rf, Hex/EtOAc=0-100% gradient). The crude mixture of products obtained was dissolved in MeCN (25 mL) then NMO (1.77 g, 15.2 mmol) and molecular sieves (4 Å, 6 g) were added. The reaction mixture was stirred at RT for 4 h then quenched with sat. NH$_4$Cl aq. solution and extracted with EtOAc (3×20 mL). The combined organic layer was washed with brine, dried over MgSO$_4$, filtered, and concentrated. The residue was purified by flash chromatography (Combi-flash Rf, Hex/EtOAc=0-100% gradient) to afford the title compound (500 mg, 29%, 2 steps). LCMS: $R_T$=1.699 min, MS (ES) 403.8 (M+Na); $^1$H NMR (400 MHz, CDCl$_3$) δ 9.88 (s, 1H), 8.04 (d, J=1.2 Hz, 1H), 7.99 (d, J=1.2 Hz, 1H), 7.28 (s, 1H), 3.85 (s, 3H), 1.63 (s, 9H).

Step C. Preparation of methyl 7-bromo-1-methyl-5-(pyrrolidin-1-ylmethyl)-1H-indole-2-carboxylate To a solution of 1-(tert-butyl) 2-methyl 7-bromo-5-formyl-1H-indole-1,2-dicarboxylate (220 mg, 0.58 mmol) in DCM (3.5 mL) was added TFA (0.6 mL, 0.894 g, 7.8 mmol) and stirred at RT for 16 h. The reaction mixture was quenched with sat. NH$_4$Cl aq. solution and extracted with DCM (3×10 mL). The combined organic layer was dried over MgSO$_4$, filtered and concentrated. The residue was re-dissolved in DMF (5.5 mL) then K$_2$CO$_3$ (0.56 g, 4.1 mmol) and MeI (72 μL, 163 mg, 1.15 mmol) were added and stirred for 4 h at 60° C. The reaction was quenched with sat. NH$_4$Cl aq. solution and extracted with DCM (3×10 mL). The combined organic layer was dried over MgSO$_4$, filtered and concentrated. The residue was re-dissolved in DCM (5.6 mL) and Et$_3$N (1 mL). Pyrrolidine (52 μL, 44 mg, 0.624 mmol) and Na(OAc)$_3$BH (220 mg, 1.04 mmol) were added and stirred at RT for 4 h. The reaction mixture was quenched with aqueous saturated NaHCO$_3$ solution and extracted with DCM (3×10 mL). The combined organic layer was dried over MgSO$_4$, filtered and concentrated. The residue was purified by flash chromatography (Combi-flash Rf, Hex/EtOAc=0-100% gradient) to afford the title compound (118 mg, 58%, 3 steps). LCMS: $R_T$=1.246 min, MS (ES) 351.0 (M+H). $^1$H NMR (400 MHz, CDCl$_3$) δ 7.46 (s, 1H), 7.44 (s, 1H), 7.13 (s, 1H), 4.37 (s, 3H), 3.83 (s, 3H), 3.57 (s, 2H), 2.47-2.43 (m, 4H), 1.73-1.70 (m, 4H).

Step D. Example 401

The title compound (1.1 mg, 3%, 2 steps) was prepared following General Procedure B using methyl 7-bromo-1-methyl-5-(pyrrolidin-1-ylmethyl)-1H-indole-2-carboxylate (20 mg, 0.057 mmol) and (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.057 mmol) followed by saponification using General Procedure D. LCMS: $R_T$=1.851 min, MS (ES) 794.8 (M+H).

Example 402

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-morpholinoethyl)-1H-indole-6-carboxamide The title compound (1.5 mg, 74%) was prepared following General Procedure E using (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-morpholinoethyl)-1H-indole-6-carboxylic acid (2.0 mg, 2.5 µmol). LCMS: $R_T$=1.782 min, MS (ES) 810.0 (M+H).

Example 403

(R)-7-Chloro-10-(3-(4-chloro-3,5-dimethylphenoxy)propyl)-4-methyl-2-(1-methyl-5-(1-methyl-1H-1,2,4-triazol-3-yl)-1H-indol-3-yl)-6-(1,3,5-trimethyl-1H-pyrazol-4-yl)-3,4-dihydropyrazino[1,2-a]indol-1(2H)-one

Step A. Preparation of 1-methyl-5-(1-methyl-1H-1,2,4-triazol-3-yl)-1H-indole The title compound (48 mg, 43%) was prepared following the procedure described Example 388, Step A using 2-bromo-1-methyl-1H-1,2,4-triazole (85 mg, 0.525 mmol) and 1-methyl-5-(4,4,5,5-tetramethyl-1,3,2-dioxaborolan-2-yl)-1H-indole (165 mg, 0.65 mmol) LCMS: $R_T$=1.077 min, MS (ES) 213.1 (M+H).

Step B. Preparation of 3-iodo-1-methyl-5-(1-methyl-1H-1,2,4-triazol-3-yl)-1H-indole The title compound (46 mg, 61%) was prepared following the procedure described Example 388, Step B using 1-methyl-5-(1-methyl-1H-1,2,4-triazol-3-yl)-1H-indole (48 mg, 0.23 mmol). LCMS: $R_T$=1.306 min, MS (ES) 338.7 (M+H).

Step C. Example 403

The title compound (15 mg, 43%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol) and 3-iodo-1-methyl-5-(1-methyl-1H-1,2,4-triazol-3-yl)-1H-indole (30 mg, 0.089 mmol). LCMS: $R_T$=1.953 min, MS (ES) 749.9 (M+H). $^1$H NMR (400 MHz, Chloroform-d) δ 8.23 (s, 1H), 8.86 (d, J=1.8 Hz, 1H), 8.01 (d, J=8.3 Hz, 1H), 7.67 (dd, J=8.6, 2.5 Hz, 1H), 7.40 (d, J=8.6 Hz, 1H), 7.29-7.22 (m, 2H), 6.61 (s, 2H), 4.47 (dt, J=12.6, 3.0 Hz, 1H), 4.34-4.19 (m, 1H), 4.01-3.97 (m, 2H), 3.95 (d, J=3.2 Hz, 3H), 3.87 (s, 3H), 3.82 (s, 3H), 3.72-3.65 (m, 1H), 3.45-3.30 (m, 2H), 2.29 (s, 6H), 2.23-2.16 (m, 5H), 2.04 (s, 3H), 1.25 (d, J=6.7 Hz, 1.5H), 1.20 (d, J=6.5 Hz, 1.5H).

Example 404

(R)-3-(7-chloro-10-(3-(cyclopropylmethoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid

Step A. Preparation of (R)-3-(10-(3-bromopropyl)-7-chloro-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid To a solution of methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylate (225 mg, 0.31 mmol) in DCM (20 mL) at 0° C. was added BBr$_3$ (1.0 M, 1.0 mL, 1.0 mmol), and the mixture was stirred for 1 h. The reaction was diluted with DCM (20 mL) and quenched with H$_2$O (10 mL). The layers were separated, and the aqueous layer was extracted with DCM (2×10 mL). The combined organic layer was washed with sat. aq. NaHCO$_3$ (20 mL), dried over MgSO$_4$, filtered, and concentrated to afford the crude title compound (122 mg, 62% yield), which was used in subsequent reactions without further purification. LCMS: $R_T$=1.687 min, MS (ES) 637.9 (M+H).

Step B. Example 404

To a solution of cyclopropyl methanol (50 mg, 0.69 mmol) in DMF (2 mL) was added NaH (60 wt. %, 25 mg, 0.625 mmol) at RT, and the mixture was stirred for 30 min. (R)-3-(10-(3-Bromopropyl)-7-chloro-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (15 mg, 0.024 mmol) was added to the mixture, and the reaction was stirred at 50° C. for 15 h. The reaction was diluted DCM/H$_2$O (10 mL, 1:1). The organic layer was separated and the aqueous layer was extracted with DCM (2×5 mL). The combined organic layers were dried and concentrated. The crude reaction mixture was purified by reverse phase HPLC (Phenomenex Gemini C18, H$_2$O/CH$_3$CN gradient 35-95% MeCN 0.1% TFA) to afford the title compound (7.8 mg, 53%). LCMS: $R_T$=1.666 min, MS (ES) 628.0 (M+H). $^1$H NMR (400 MHz, Chloroform-d) δ 8.30 (s, 1H), 7.97 (dd, J=8.7, 1.5 Hz, 1H), 7.76 (dd, J=8.6, 2.8 Hz, 1H), 7.38-7.27 (m, 3H), 4.41 (d, J=11.5 Hz, 1H), 4.28-4.10 (m, 1H), 3.97 (s, 3H), 3.83 (s, 3H), 3.68 (d, J=12.0 Hz, 1H), 3.50 (t, J=6.5 Hz, 2H), 3.37-3.20 (m, 4H), 2.25 (d, J=10.1 Hz, 3H), 2.13-1.97 (m, 5H), 1.28-1.18 (m, 3H), 1.11-1.01 (m, 1H), 0.56-0.46 (m, 2H), 0.22-0.16 (m, 2H).

Example 405

(R)-3-(7-Chloro-4-methyl-1-oxo-10-(3-(m-tolyloxy)propyl)-6-(1,3,5-trimethyl-1H-pyrazol-4-yl)-3,4-dihydropyrazino[1,2-a]indol-2(1H)-yl)-1-methyl-1H-indole-5-carboxylic acid To a solution of (R)-3-(10-(3-bromopropyl)-7-chloro-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (15 mg, 0.024 mmol) in DMF (2 mL) was added 3-hydroxytoluene (20 mg, 0.19 mmol) and Cs$_2$CO$_3$ (30 mg, 0.092 mmol). The reaction was stirred at 50° C. for 15 h then diluted with DCM/120 (10 mL, 1:1). The organic layer was separated, and the aqueous layer was extracted with DCM (2×5 mL). The combined organic layer was dried and concentrated. The residue was purified by reverse phase HPLC (Phenomenex Gemini C18, H$_2$O/CH$_3$CN gradient 35-95% MeCN 0.1% TFA) to afford the title compound (5.8 mg, 37%). LCMS: R$_T$=1.822 min, MS (ES) 664.0 (M+H). $^1$H NMR (400 MHz, Chloroform-d) δ 8.30 (s, 1H), 7.98 (d, J=8.8, 1.6 Hz, 1H), 7.73 (dd, J=8.6, 2.4 Hz, 1H), 7.36 (d, J=8.7 Hz, 1H), 7.32-7.27 (m, 2H), 7.12 (t, J=7.8 Hz, 1H), 6.76-6.66 (m, 3H), 4.45-4.37 (m, 1H), 4.26-4.13 (m, 1H), 4.07-3.93 (m, 5H), 3.84 (s, 3H), 3.68 (d, J=12.8 Hz, 1H), 3.49-3.31 (m, 2H), 2.31-2.18 (m, 8H), 2.12 (s, 1.5H), 2.08 (s, 1.5H), 1.28-1.20 (m, 3H).

Example 406

(R)-3-(7-Chloro-10-(3-methoxypropyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid The title compound (5.0 mg, 36%) was prepared following the procedure described Example 404 Step B using methanol (50 mg, 1.56 mmol), NaH (60 wt. %, 25 mg, 0.625 mmol) and (R)-3-(10-(3-Bromopropyl)-7-chloro-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (15 mg, 0.024 mmol). LCMS: R$_T$=1.525 min, MS (ES) 588.0 (M+H).

Example 407

(R)-3-(7-Chloro-10-(3-(4-chloro-3-methylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid The title compound (4.5 mg, 27%) was prepared following the procedure described Example 405 using (R)-3-(10-(3-bromopropyl)-7-chloro-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (15 mg, 0.024 mmol) and 4-chloro-3-methylphenol (20 mg, 0.14 mmol). LCMS: R$_T$=1.909 min, MS (ES) 697.9 (M+H). $^1$H NMR (400 MHz, Chloroform-d) δ 8.30 (s, 1H), 7.98 (d, J=8.6 Hz, 1H), 7.71 (dd, J=8.6, 2.6 Hz, 1H), 7.37 (d, J=8.8 Hz, 1H), 7.29-7.25 (m, 2H), 7.17 (d, J=8.7 Hz, 1H), 6.75 (s, 1H), 6.64 (dd, J=8.8, 3.0 Hz, 1H), 4.41 (d, J=12.6 Hz, 1H), 4.22-4.12 (m, 1H), 4.05-3.95 (m, 5H), 3.83 (s, 3H), 3.68 (d, J=13.9 Hz, 1H), 3.45-3.29 (m, 2H), 2.29 (s, 4.5H), 2.25 (s, 1.5H), 2.20 (t, J=6.5 Hz, 2H), 2.13 (s, 1.5H), 1.98 (s, 1.5H), 1.18-1.07 (m, 3H).

Example 408

(R)-3-(7-Chloro-4-methyl-1-oxo-10-(3-phenoxypropyl)-6-(1,3,5-trimethyl-1H-pyrazol-4-yl)-3,4-dihydropyrazino[1,2-a]indol-2(1H)-yl)-1-methyl-1H-indole-5-carboxylic acid The title compound (4.3 mg, 28%) was prepared following the procedure described Example 405 using (R)-3-(10-(3-bromopropyl)-7-chloro-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (15 mg, 0.024 mmol) and phenol (20 mg, 0.21 mmol). LCMS: R$_T$=1.765 min, MS (ES) 649.9 (M+H). $^1$H NMR (400 MHz, Chloroform-d) δ 8.33 (s, 1H), 8.00 (dd, J=8.7, 1.6 Hz, 1H), 7.75 (dd, J=8.6, 2.4 Hz, 1H), 7.39 (d, J=8.7 Hz, 1H), 7.35-7.24 (m, 4H), 6.96-6.85 (m, 3H), 4.46-4.18 (m, 2H), 4.09-3.99 (m, 5H), 3.86 (s, 3H), 3.70 (d, J=12.7 Hz, 1H), 3.56-3.31 (m, 2H), 2.31 (s, 1H), 2.26 (s, 2H), 2.25-2.22 (m, 2H), 2.14 (s, 2H), 2.11 (s, 1H), 1.27 (d, J=5.8 Hz, 1H), 1.24 (d, =5.1 Hz, 2H).

Example 409

(R)-3-(7-Chloro-10-(3-(4-chlorophenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid The title compound (4.7 mg, 29%) was prepared following the procedure described Example 405 using (R)-3-(10-(3-bromopropyl)-7-chloro-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (15 mg, 0.024 mmol) and 4-chlorophenol (20 mg, 0.16 mmol). LCMS: R$_T$=1.845 min, MS (ES) 684.0 (M+H). $^1$H NMR (400 MHz, Chloroform-d) δ 8.30 (s, 1H), 7.98 (d. J=8.8 Hz, 1H), 7.71 (dd, J=8.6, 2.6 Hz, 1H), 7.37 (d, J=8.7 Hz, 1H), 7.32-7.28 (m, 2H), 7.21-7.15 (m, 2H), 6.84-6.75 (m, 2H), 4.41 (d, J=12.6 Hz, 1H), 4.26-4.11 (m, 1H), 4.04-3.94 (m, 5H), 3.84 (s, 3H), 3.68 (d, J=10.4 Hz, 1H), 3.50-3.31 (m, 2H), 2.31-2.16 (m, 5H), 2.11 (s, 1.5H), 2.09 (s, 1.5H), 1.25 (d, J=5.2 Hz, 1.5H), 1.22 (d, J=5.2 Hz, 1.5H).

Example 410

(R)-3-(7-Chloro-10-(3-(4-fluorophenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid The title compound (4.8 mg, 31%) was prepared following the procedure described Example 405 using (R)-3-(10-(3-bromopropyl)-7-chloro-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (15 mg, 0.024 mmol) and 4-fluorophenol (20 mg, 0.18 mmol). LCMS: R$_T$=1.776 min, MS (ES) 667.9 (M+H). $^1$H NMR (400 MHz, Chloroform-d) δ 8.32 (s, 1H), 8.00 (dd, J=8.7, 1.6 Hz, 1H), 7.73 (dd, J=8.5, 2.6 Hz, 1H), 7.39 (d, J=8.7 Hz, 1H), 7.36-7.28 (m, 2H), 7.00-6.90 (m, 2H), 6.88-6.75 (m, 2H), 4.44-4.19 (m, 2H), 4.05-3.96 (m, 5H), 3.86 (s, 3H), 3.70 (d, J=12.6 Hz, 1H), 3.50-3.30 (m, 2H), 2.30 (s, 1.5H), 2.27 (s, 1.5H), 2.22 (p, J=6.8 Hz, 2H), 2.13 (s, 1.5H), 2.11 (s, 1.5H), 1.27 (d, J=5.1 Hz, 1.5H), 1.24 (d, J=5.1 Hz, 1.5H).

Example 411

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1,3-dimethyl-1H-indole-2-carboxamide The title compound (8 mg, 80%) was prepared following General Procedure E using (R)-7-(7-chloro-10-(3-(4-chloro- 3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1,3-dimethyl-1H-indole-2-carboxylic acid (10 mg, 0.013 mmol). LCMS: $R_T$=1.752 min, MS (ES) 754.9 (M+H).

Example 412

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-methyl-1H-indole-2-carboxamide The title compound (6.3 mg, 62%) was prepared following General Procedure E using (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-methyl-1H-indole-2-carboxylic acid (10 mg, 0.013 mmol). LCMS: $R_T$=2.002 min, MS (ES) 741.0 (M+H).

Example 413

(R)-7-Chloro-10-(3-(4-chloro-3,5-dimethylphenoxy)propyl)-2-(5-(5-cyclohexyl-1,3,4-oxadiazol-2-yl)-1-methyl-1H-indol-3-yl)-4-methyl-6-(1,3,5-trimethyl-1H-pyrazol-4-yl)-3,4-dihydropyrazino[1,2-a]indol-1(2H)-one Example A. Preparation of 3-bromo-N'-(cyclohexanecarbonyl)-1-methyl-1H-indole-5-carbohydrazide To a solution of 3-bromo-1-methyl-1H-indole-5-carboxylic acid (75 mg, 0.30 mmol) and DIPEA (100 mg, 0.78 mmol) in DMF (2 mL) was added HATU (120 mg, 0.32 mmol). The reaction mixture was stirred at RT for 10 min then cyclohexanecarbohydrazide (50 mg, 0.35 mmol) was added. The reaction was allowed to stir for 2 h at RT. The reaction was diluted into DCM/H$_2$O (20 mL, 1:1), and the layers were separated. The aqueous layer was extracted with DCM (2×10 mL), and the combined organic layer was dried and concentrated. The crude reaction mixture was purified by flash chromatography (Combi-flash Rf, Hex/EtOAc=0-100% gradient) to afford the title compound (66 mg, 59%). LCMS: $R_T$=1.361 min, MS (ES) 379.9 (M+H).

Example B. Preparation of 2-(3-bromo-1-methyl-1H-indol-5-yl)-5-cyclohexyl-1,3,4-oxadiazole A solution of 3-bromo-N'-(cyclohexanecarbonyl)-1-methyl-1H-indole-5-carbohydrazide (66 mg, 0.17 mmol) in POCl$_3$ (2 mL) was heated to 95° C. for 1 h. The cooled reaction mixture was quenched by pouring into ice/sat. aq. NaHCO$_3$ (50 mL), and the resulting mixture was stirred for 15 min then extracted with DCM (3×15 mL). The combined organic layer was dried over MgSO$_4$, filtered, and concentrated. The residue was purified by flash chromatography (Combi-flash Rf, Hex/EtOAc=0-100% gradient) to afford the title compound (32 mg, 51%). LCMS: $R_T$=1.814 min, MS (ES) 360.0 (M+H).

Step C. Example 413

The title compound (12.4 mg, 41%) was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (20 mg, 0.038 mmol) and 2-(3-bromo-1-methyl-1H-indol-5-yl)-5-cyclohexyl-1,3,4-oxadiazole (21 mg, 0.61 mmol) followed by saponification using General Procedure D. LCMS: $R_T$=1.674, 1.706 min, MS (ES) 817.9 (M+H) (Ultra aqueous method).

Example 414

(R)-2-(6-(2H-Tetrazol-5-yl)quinolin-4-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one Step A. Preparation of (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-6-carbonitrile The title compound (31 mg, 90%) was prepared according to General Procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and 4-bromo quinoline-6-carbonitrile (16 mg, 0.06 mmol). LCMS: $R_T$=2.039 min, MS (ES) 691.0 (M+H).

Step B. Example 414

The title compound (26 mg, 80%) was prepared according to the procedure for Example 235 using (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-6-carbonitrile (30 mg, 0.04 mmol), sodium azide (14 mg, 0.22 mmol) and ammonium chloride (12 mg, 0.22 mmol). LCMS: $R_T$=1.844 min, MS (ES) 733.9 (M+H).

Example 415

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-(pyridin-2-ylmethyl)-1H-indole-2-carboxamide The title compound (2.9 mg, 29%) was prepared following the procedure described Example 379 using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-(pyridin-2-ylmethyl)-1H-indole-2-carboxylate (10 mg, 0.012 mmol) and NH$_4$OH (1 mL). LCMS: $R_T$=1.900, 1.934 min, MS (ES) 801.9 (M+H).

Example 416

(R)-7-(7-Chloro-10-(3-(4-chloro-3,5-dimethylphenoxy)propyl)-6-(4,6-dimethyl-2-(morpholinomethyl)pyrimidin-5-yl)-4-methyl-1-oxo-3,4-dihydropyrazino[1,2-a]indol-2(1H)-yl)-1,5-dimethyl-1H-indole-2-carboxylic acid Step A. Preparation of methyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-5-methyl-1H-indole-2-carboxylate The title compound (279 mg, 72%) was prepared according to General Procedure B using (R)-6-(2-((benzyloxy)methyl)-4,6-dimethylpyrimidin-5-yl)-7-chloro-10-(3-(4-chloro-3,5-dimethylphenoxy)propyl)-4-methyl-3,4-dihydropyrazino[1,2-a]indol-1(2H)-one (300 mg, 0.46 mmol) and methyl 7-iodo-5-methyl-1H-indole-2-carboxylate (300 mg, 0.952 mmol). LCMS: $R_T$=2.387 min, MS (ES) 843.9 (M+H).

Step B. Preparation of methyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-1,5-dimethyl-1H-indole-2-carboxylate The title compound was prepared according to General Procedure I using methyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-5-methyl-1H-indole-2-carboxylate (48 mg, 0.057 mmol) and MeI (14 mg, 0.10 mmol). LCMS: $R_T$=2.464 min, MS (ES) 857.9 (M+H).

Step C. Preparation of methyl (R)-7-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1,5-dimethyl-1H-indole-2-carboxylate The title compound (33 mg, 73%. Steps B and C) was prepared following the procedure described Example 390 step D using methyl (R)-7-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1,5-dimethyl-1H-indole-2-carboxylate (0.057 mmol). LCMS: $R_T$=2.175, 2.208 min, MS (ES) 767.9 (M+H).

Step D. Example 416

The title compound (7.6 mg, 44%) was prepared according to General Procedure J using methyl (R)-7-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1,5-dimethyl-1H-indole-2-carboxylate (16 mg, 0.021 mmol) and morpholine (50 mg, 0.57 mmol) followed by saponification using General Procedure D. LCMS: $R_T$=1.959, 2.022 min, MS (ES) 822.9 (M+H). $^1$H NMR (400 MHz, Chloroform-d) δ 7.79 (d, J=8.6 Hz, 0.25H), 7.78 (d, J=8.6 Hz, 0.75H), 7.38-7.25 (m, 3H), 6.95-6.83 (s, 1H), 6.63 (s, 1.5H), 6.61 (s, 0.5H), 4.64 (d, J=14.7 Hz, 1H), 4.52-4.40 (m, 2H), 4.25-4.03 (m, 4H), 4.02-3.96 (m, 2H), 3.93 (s, 3H), 3.88-3.78 (s, 2H), 3.45-3.31 (m, 3H), 2.48 (s, 3H), 2.41 (s, 2.25H), 2.40 (s, 0.75H), 2.33 (s, 6H), 2.26-2.17 (m, 5H), 1.31-1.14 (m, 3H).

Example 417

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,2-dimethyl-1H-indole-3-carboxylic acid The title compound was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-bromo-1,2-dimethyl-1H-indole-3-carboxylate followed by saponification using General Procedure D. LCMS: $R_T$=2.87 min, MS (ES) 726.2 (M+H) (LC method III). $^1$H NMR (400 MHz, Chloroform-d) δ 8.27 (d, J=8.0 Hz, 1H), 7.67 (d, J=8.0 Hz, 1H), 7.31-7.26 (m, 2H), 6.98 (d, J=8.0 Hz, 1H), 6.61 (s, 1.5H), 6.58 (s, 0.5H), 4.51-4.20 (m, 2H), 3.99-3.81 (m, 6H), 3.71-3.32 (m, 5H), 2.77 (s, 2H), 2.76 (s, 1H), 2.31 (s, 6H), 2.21-2.17 (m, 5H), 2.07-2.03 (m, 3H), 1.25 (d, J=6.0 Hz, 2H), 1.13 (d, J=6.0 Hz, 1H).

Example 418

(R)-7-Chloro-10-(3-(4-chloro-3,5-dimethylphenoxy)propyl)-4-methyl-2-(1-methyl-5-(4-methylpyrimidin-2-yl)-1H-indol-3-yl)-6-(1,3,5-trimethyl-1H-pyrazol-4-yl)-3,4-dihydropyrazino[1,2-a]indol-1(2H)-one Step A. Preparation of 1-methyl-5-(4-methylpyrimidin-2-yl)-1H-indole The title compound (110 mg, 95%) was prepared following the procedure described Example 388 Step A using 2-bromo-4-methylpyrimidine (90 mg, 0.52 mmol). LCMS: $R_T$=0.901 min, MS (ES) 224.1 (M+H).

Step B. Preparation of 3-iodo-1-methyl-5-(4-methylpyrimidin-2-yl)-1H-indole

The title compound (110 mg, 64%) was prepared following the procedure described Example 388 Step B using 1-methyl-5-(4-methylpyrimidin-2-yl)-1H-indole (110 mg, 0.49 mmol). LCMS: $R_T$=1.489 min, MS (ES) 349.9 (M+H).

Step C. Example 418

The title compound (22 mg, 62%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol) and 3-iodo-1-methyl-5-(4-methylpyrimidin-2-yl)-1H-indole (31 mg, 0.089 mmol). LCMS: $R_T$=2.060 min, MS (ES) 760.9 (M+H).

Example 418

(R)-7-Chloro-10-(3-(4-chloro-3,5-dimethylphenoxy)propyl)-2-(5-(6,7-dihydro-5H-pyrrolo[1,2-a]imidazol-2-yl)-1-methyl-1H-indol-3-yl)-4-methyl-6-(1,3,5-trimethyl-1H-pyrazol-4-yl)-3,4-dihydropyrazino[1,2-a]indol-1(2H)-one Step A. Preparation of 5-(6,7-dihydro-5H-pyrrolo[1,2-a]imidazol-2-yl)-1-methyl-1H-indole The title compound (60 mg, 39%) was prepared following the procedure described Example 388 Step A using 2-bromo-6,7-dihydro-5H-pyrrolo[1,2-a]imidazole (120 mg, 0.64 mmol) and 1-methyl-5-(4,4,5,5-tetramethyl-1,3,2-dioxaborolan-2-yl)-1H-indole (203 mg, 0.79 mmol). LCMS: $R_T$=0.925 min, MS (ES) 238.2 (M+H).

Step B. Preparation of 5-(6,7-dihydro-5H-pyrrolo[1,2-a]imidazol-2-yl)-3-iodo-1-methyl-1H-indole The title compound (75 mg, 82%) was prepared following the procedure described Example 388 Step B using 5-(6,7-dihydro-5H-pyrrolo[1,2-a]imidazol-2-yl)-1-methyl-1H-indole (60 mg, 0.25 mmol). LCMS: $R_T$=1.240 min, MS (ES) 363.9 (M+H).

Step C. Example 419

The title compound (20 mg, 56%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol) and 5-(6,7-dihydro-5H-pyrrolo[1,2-a]imidazol-2-yl)-3-iodo-1-methyl-1H-indole (32 mg, 0.089 mmol). LCMS: $R_T$=1.932 min, MS (ES) 774.9 (M+H).

Example 420

(R)-7-Chloro-10-(3-(4-chloro-3,5-dimethylphenoxy)propyl)-4-methyl-2-(1-methyl-5-(1H-1,2,4-triazol-3-yl)-1H-indol-3-yl)-6-(1,3,5-trimethyl-1H-pyrazol-4-yl)-3,4-dihydropyrazino[1,2-a]indol-1(2H)-one Step A. Preparation of 1-methyl-5-(1-(tetrahydro-2H-pyran-2-yl)-1H-1,2,4-triazol-3-yl)-1H-indole The title compound (80 mg, 39%) was prepared following the procedure described Example 388 Step A using 3-bromo-1-(tetrahydro-2H-pyran-2-yl)-1H-1,2,4-triazol (170 mg, 0.73 mmol) and 1-methyl-5-(4,4,5,5-tetramethyl-1,3,2-dioxaborolan-2-yl)-1H-indole (245 mg, 0.95 mmol). LCMS: $R_T$=1.339 min, MS (ES) 283.0 (M+H).

Step B. Preparation of 3-iodo-1-methyl-5-(1-(tetrahydro-2H-pyran-2-yl)-1H-1,2,4-triazol-3-yl)-1H-indole The title compound (100 mg, 72%) was prepared following the procedure described Example 388 Step B using 1-methyl-5-(1-(tetrahydro-2H-pyran-2-yl)-1H-1,2,4-triazol-3-yl)-1H-indole (80 mg, 0.28 mmol). LCMS: $R_T$=1.561 min, MS (ES) 408.9 (M+H).

Step C. Preparation of (4R)-7-chloro-10-(3-(4-chloro-3,5-dimethylphenoxy)propyl)-4-methyl-2-(1-methyl-5-(1-(tetrahydro-2H-pyran-2-yl)-1H-1,2,4-triazol-3-yl)-1H-indol-3-yl)-6-(1,3,5-trimethyl-1H-pyrazol-4-yl)-3,4-dihydropyrazino[1,2-a]indol-1(2H)-one The title compound (20 mg, 38%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (35 mg, 0.065 mmol) and 3-iodo-1-methyl-5-(1-(tetrahydro-2H-pyran-2-yl)-1H-1,2,4-triazol-3-yl)-1H-indole (51 mg, 0.13 mmol). LCMS: $R_T$=2.104 min, MS (ES) 818.9 (M+H).

Step C. Example 420

TFA (1 mL) was added to a solution of (4R)-7-chloro-10-(3-(4-chloro-3,5-dimethylphenoxy)propyl)-4-methyl-2-(1-methyl-5-(1-(tetrahydro-2H-pyran-2-yl)-1H-1,2,4-triazol-3-yl)-1H-indol-3-yl)-6-(1,3,5-trimethyl-1H-pyrazol-4-yl)-3,4-dihydropyrazino[1,2-a]indol-1(2H)-one (20 mg, 0.020 mmol) in DCM (2 mL) at 0° C. The reaction mixture was stirred at RT for 18 h. The reaction mixture was diluted DCM and washed with water. Sat. aq. NaHCO₃ was added at 0° C. and extracted with DCM (3×5 mL). The combined organic layer was dried and concentrated. The residue was purified by flash chromatography (Combi-flash Rf, DCM/MeOH=0-2% gradient) to afford the title compound (17 mg, 95%). LCMS: $R_T$=1.906 min, MS (ES) 735.9 (M+H).

Example 421

(R)-7-chloro-10-(3-(4-chloro-3,5-dimethylphenoxy)propyl)-4-methyl-2-(1-methyl-5-(5-phenyl-1,3,4-oxadiazol-2-yl)-1H-indol-3-yl)-6-(1,3,5-trimethyl-1H-pyrazol-4-yl)-3,4-dihydropyrazino[1,2-a]indol-1(2H)-one Example A. Preparation of N'-benzoyl-3-bromo-1-methyl-1H-indole-5-carbohydrazide The title compound (49 mg, 45%) was prepared following General coupling procedure E using 3-bromo-1-methyl-1H-indole-5-carboxylic acid (75 mg, 0.30 mmol), DIPEA (100 mg, 0.78 mmol), HATU (120 mg, 0.32 mmol) and benzohydrazide (50 mg, 0.37 mmol). LCMS: $R_T$=1.278 min, MS (ES) 373.9 (M+H).

Example B. Preparation of 2-(3-bromo-1-methyl-1H-indol-5-yl)-5-phenyl-1,3,4-oxadiazole The title compound (22 mg, 47%) was prepared following the procedure described Example 413 Step B using N'-benzoyl-3-bromo-1-methyl-1H-indole-5-carbohydrazide (49 mg, 0.13 mmol). LCMS: $R_T$=1.742 min, MS (ES) 353.9 (M+H).

Step C. Example 421

The title compound (17.8 mg, 59% yield) was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (20 mg, 0.038 mmol) and 2-(3-bromo-1-methyl-1H-indol-5-yl)-5-phenyl-1,3,4-oxadiazole (22 mg, 0.062 mmol) followed by saponification using General Procedure D. LCMS: $R_T$=2.470, 2.503 min, MS (ES) 811.9 (M+H). ¹H NMR (400 MHz, Chloroform-d) δ 8.40-8.32 (m, 1H), 8.18-8.10 (m, 2H), 8.03 (ddd, J=8.7, 4.9, 1.5 Hz, 2H), 7.78 (dd, J=8.6, 2.1 Hz, 1H), 7.62-7.49 (m, 3H), 7.39-7.27 (m, 2H), 6.63 (s, 2H), 4.61-4.45 (m, 1H), 4.28-4.15 (m, 1H), 4.07-3.95 (m, 5H), 3.90 (s, 3H), 3.73 (d, J=12.5 Hz, 1H), 3.52-3.31 (m, 2H), 2.38-2.29 (m, 9H), 2.29-2.13 (m, 5H), 1.29 (d, J=6.5 Hz, 3H).

Example 422

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-isopropyl-1-methyl-1H-indole-2-carboxamide The title compound (5.2 mg, 52%) was prepared following General Procedure E using (R)-7-(7-chloro-10-(3-(4- chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-isopropyl-1-methyl-1H-indole-2-carboxylic acid (10 mg, 0.013 mmol). LCMS: $R_T$=2.111 min, MS (ES) 753.0 (M+H).

Example 423

(R)-7-Chloro-10-(3-(4-chloro-3,5-dimethylphenoxy)propyl)-2-(5-(5-cyclopropyl-1,3,4-oxadiazol-2-yl)-1-methyl-1H-indol-3-yl)-4-methyl-6-(1,3,5-trimethyl-1H-pyrazol-4-yl)-3,4-dihydropyrazino[1,2-a]indol-1(2H)-one Step A. Preparation of N'-(cyclopropanecarbonyl)-1-methyl-1H-indole-5-carbohydrazide The title compound (41 mg, 43%) was prepared following the procedure described Example 413 Step A using 1-methyl-1H-indole-5-carbohydrazide (70 mg, 0.37 mmol) and cyclopropanecarbonyl chloride (110 mg, 1.06 mmol). LCMS: $R_T$=0.907 min, MS (ES) 258.1 (M+H).

Step B. Preparation of 2-cyclopropyl-5-(1-methyl-1H-indol-5-yl)-1,3,4-oxadiazole The title compound (I1 mg, 28% yield) was prepared following the procedure described Example 413 Step B using N'-(cyclopropanecarbonyl)-1-methyl-1H-indole-5-carbohydrazide (41 mg, 0.16 mmol). LCMS: $R_T$=1.341 min, MS (ES) 240.1 (M+H).

Step C. Preparation of 2-(3-bromo-1-methyl-1H-indol-5-yl)-5-cyclopropyl-1,3,4-oxadiazole The title compound (12 mg, 82% yield) was prepared according to General Procedure F using 2-cyclopropyl-5-(1-methyl-1H-indol-5-yl)-1,3,4-oxadiazole (11 mg, 0.046 mmol). LCMS: $R_T$=1.538 min, MS (ES) 318.0 (M+H).

Step D. Example 423

The title compound (11.2 mg, 39%) was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (20 mg, 0.037 mmol) and 2-(3-bromo-1-methyl-1H-indol-5-yl)-5-cyclopropyl-1,3,4-oxadiazole (12 mg, 0.038 mmol) followed by saponification using General Procedure B. LCMS: $R_T$=2.314, 2.342 min, MS (ES) 775.9 (M+H). $^1$H NMR (400 MHz, Chloroform-d) δ 8.26-8.16 (m, 1H), 7.89 (t, J=7.5 Hz, 1H), 7.77 (dd, J=8.6, 2.0 Hz, 1H), 7.47 (dd, J=8.7, 1.0 Hz, 1H), 7.34 (d, J=2.6 Hz, 1H), 7.35-7.28 (m, 1H), 6.63 (s, 2H), 4.55-4.45 (m, 1H), 4.27-4.13 (m, 1H), 4.08-3.96 (m, 5H), 3.87 (s, 3H), 3.70 (d, J=12.5 Hz, 1H), 3.50-3.29 (m, 2H), 2.38-2.27 (m, 9H), 2.27-2.12 (m, 5H), 1.25 (m, 8H).

Example 424

(R)-7-Chloro-10-(3-(4-chloro-3,5-dimethylphenoxy)propyl)-4-methyl-2-(1-methyl-5-(pyridazin-3-yl)-1H-indol-3-yl)-6-(1,3,5-trimethyl-1H-pyrazol-4-yl)-3,4-dihydropyrazino[1,2-a]indol-1(2H)-one Step A. Preparation of 1-methyl-5-(pyridazin-3-yl)-1H-indole The title compound (143 mg, 91%) was prepared following the procedure described Example 388 Step A using 3-bromopyridazine (120 mg, 0.76 mmol) and 1-methyl-5-(4,4,5,5-tetramethyl-1,3,2-dioxaborolan-2-yl)-1H-indole (239 mg, 0.93 mmol). LCMS: $R_T$=1.005 min, MS (ES) 210.1 (M+H).

Step B. Preparation of 3-iodo-1-methyl-5-(pyridazin-3-yl)-1H-indole

The title compound (160 mg, 80%) was prepared following the procedure described Example 388 Step B using 1-methyl-5-(pyridazin-3-yl)-1H-indole (143 mg, 0.60 mmol). LCMS: $R_T$=1.251 min, MS (ES) 335.8 (M+H).

Step C. Example 424

The title compound (20 mg, 59%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol) and 3-iodo-1-methyl-5-(pyridazin-3-yl)-1H-indole (30 mg, 0.089 mmol). LCMS: $R_T$=1.938 min, MS (ES) 746.8 (M+H).

Example 425

(R)-7-Chloro-10-(3-(4-chloro-3,5-dimethylphenoxy)propyl)-4-methyl-2-(6-(2-methyl-2H-tetrazol-5-yl)quinolin-4-yl)-6-(1,3,5-trimethyl-1H-pyrazol-4-yl)-3,4-dihydropyrazino[1,2-a]indol-1(2H)-one The title compound (14 mg, 69%) was prepared following General Procedure N General Procedure G using (R)-2-(6-(2H-tetrazol-5-yl)quinolin-4-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (20 mg, 0.03 mmol) and methyl iodide (4 μL, 0.05 mmol). LCMS: $R_T$=1.909 min, MS (ES) 747.9 (M+H).

Example 426

(R)-7-(7-Chloro-10-(3-(4-chloro-3,5-dimethylphenoxy)propyl)-6-(4,6-dimethyl-2-((4-methylpiperazin-1-yl)methyl)pyrimidin-5-yl)-4-methyl-1-oxo-3,4-dihydropyrazino[1,2-a]indol-2(1H)-yl)-1,5-dimethyl-1H-indole-2-carboxylic acid The title compound (12.7 mg, 73%) was prepared according to General Procedure J using methyl (R)-7-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1,5-dimethyl-1H-indole-2-carboxylate (16 mg, 0.021 mmol) and N-methyl piperazine (50 mg, 0.20 mmol) followed by saponification using General Procedure D. LCMS: $R_T$=1.841, 1.871 min, MS (ES) 835.9 (M+H). $^1$H NMR (400 MHz, Chloroform-d) 7.78 (dd, J=8.7, 2.5 Hz, 1H), 7.37-7.20 (m, 3H), 6.92-6.76 (m, 1H), 6.62 (s, 1.5H), 6.60 (s, 0.5H), 4.62 (d, J=15.5 Hz, 1H), 4.47-4.38 (m, 2H), 4.09 (s, 1H), 4.03-3.61 (m, 13H), 3.34 (t, J=7.5 Hz, 2H), 3.16-3.06 (m, 1H), 2.92 (s, 2.25H), 2.89 (s, 0.75H), 2.44 (s, 2.25H), 2.42

(s, 0.75H), 2.41 (s, 2.25H), 2.39 (s, 0.75H), 2.28-2.16 (m, 5H), 1.23 (d, J=6.4 Hz, 2.25H), 1.13 (d, J=6.4 Hz, 0.75H).

Example 427

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-N'-phenyl-1H-indole-5-carbohydrazide The title compound (7.6 mg, 73%) was prepared following General Procedure E using (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (10 mg, 0.013 mmol) and phenylhydrazine hydrochloride (4 mg, 0.026 mmol). LCMS: $R_T$=2.079 min, MS (ES) 802.0 (M+H).

Example 428

(R)-7-Chloro-10-(3-(4-chloro-3,5-dimethylphenoxy)propyl)-2-(5-(4,5-dihydrooxazol-2-yl)-1-methyl-1H-indol-3-yl)-4-methyl-6-(1,3,5-trimethyl-1H-pyrazol-4-yl)-3,4-dihydropyrazino[1,2-a]indol-1(2H)-one Step A. Preparation of 2-(1-methyl-1H-indol-5-yl)-4,5-dihydrooxazole Aminoethanol (193 μL, 3.20 mmol) and $ZnCl_2$ (6 μL, 0.13 mmol) were added to a solution of 1-methyl-1H-indole-5-carbonitrile (100 mg, 0.64 mmol) in toluene (3 mL). The reaction mixture was stirred at 135° C. for 4 days. The reaction solution was cooled and concentrated. The residue was diluted with water and extracted with DCM (3×10 mL). The combined organic layer was dried, filtered and concentrated. The residue was purified by flash chromatography (Combi-flash Rf, DCM/MeOH=0-5% gradient) to afford the title compound (30 mg, 23%). LCMS: $R_T$=0.775 min, MS (ES) 201.1 (M+H).

Step B. Preparation of 2-(3-iodo-1-methyl-1H-indol-5-yl)-4,5-dihydrooxazole

The title compound was prepared following the procedure described Example 388, Step B using 2-(1-methyl-1H-indol-5-yl)-4,5-dihydrooxazole (15 mg, 0.070 mmol). The crude compound (25 mg) was used for the next step without further purification. LCMS: $R_T$=1.142 min, MS (ES) 326.9 (M+H).

Step C. Example 428

The title compound (25 mg, 73%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol) and 2-(3-iodo-1-methyl-1H-indol-5-yl)-4,5-dihydrooxazole (24 mg, 0.074 mmol). LCMS: $R_T$=1.883 min, MS (ES) 737.8 (M+H).

Example 429

(R)-7-Chloro-10-(3-(4-chloro-3,5-dimethylphenoxy)propyl)-4-methyl-2-(1-methyl-5-(5-methyl-1,2,4-oxadiazol-3-yl)-1H-indol-3-yl)-6-(1,3,5-trimethyl-1H-pyrazol-4-yl)-3,4-dihydropyrazino[1,2-a]indol-1(2H)-one Step A. Preparation of 5-methyl-3-(1-methyl-1H-indol-5-yl)-1,2,4-oxadiazole Hydroxylamine hydrochloride (116 mg, 1.66 mmol) and $K_3PO_4$ (408 mg, 1.92 mmol) were added to a solution of 1-methyl-1H-indole-5-carbonitrile (200 mg, 1.28 mmol) in DMF (4 mL). The reaction mixture was stirred at 95° C. for 16 h then acetyl chloride (137 μL, 1.92 mmol) was added at RT. The solution was stirred at 105° C. for additional 36 h. The reaction mixture was diluted EtOAc and washed with water, dried and concentrated. The residue was purified by flash chromatography (Combi-flash Rf, DCM/MeOH=0-3% gradient) to afford the title compound (21 mg, 64%). LCMS: $R_T$=1.304 min, MS (ES) 214.1 (M+H).

Step B. Preparation of 3-(3-iodo-1-methyl-1H-indol-5-yl)-5-methyl-1,2,4-oxadiazole The title compound was prepared following the procedure described Example 388, Step B using 5-methyl-3-(1-methyl-1H-indol-5-yl)-1,2,4-oxadiazole (21 mg, 0.10 mmol). The crude compound (55 mg) was used for the next step without further purification. LCMS: $R_T$=1.594 min, MS (ES) 339.9 (M+H).

Step C. Example 429

The title compound (22 mg, 63%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol) and 3-(3-iodo-1-methyl-1H-indol-5-yl)-5-methyl-1,2,4-oxadiazole (25 mg, 0.074 mmol). LCMS: $R_T$=2.121 min, MS (ES) 750.8 (M+H).

Example 430

(R)-7-Chloro-10-(3-(4-chloro-3,5-dimethylphenoxy)propyl)-4-methyl-2-(1-methyl-5-(pyrazin-2-yl)-1H-indol-3-yl)-6-(1,3,5-trimethyl-1H-pyrazol-4-yl)-3,4-dihydropyrazino[1,2-a]indol-1(2H)-one Step A. Preparation of 1-methyl-5-(pyrazin-2-yl)-1H-indole The title compound (90 mg, 98%) was prepared following the procedure described Example 388 Step A using 2-bromopyrazine (70 mg, 0.44 mmol) and 1-methyl-5-(4,4,5,5-tetramethyl-1,3,2-dioxaborolan-2-yl)-1H-indole (170 mg, 0.66 mmol). LCMS: $R_T$=1.296 min, MS (ES) 210.1 (M+H).

Step B. Preparation of 3-iodo-1-methyl-5-(pyrazin-2-yl)-1H-indole

The title compound was prepared following the procedure described Example 388 Step B using 1-methyl-5-(pyrazin-2-yl)-1H-indole (90 mg, 0.43 mmol). The crude compound (120 mg) was used for the next step without further purification. LCMS: $R_T$=1.530 min, MS (ES) 335.8 (M+H).

Step C. Example 430

The title compound (28 mg, 67%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.056 mmol) and 3-iodo-1-methyl-5-(pyrazin-2-yl)-1H-indole (30 mg, 0.089 mmol). LCMS: $R_T$=2.096 min, MS (ES) 746.9 (M+H).

Example 431

6-(8-Chloro-11-(3-(4-chloro-3,5-dimethylphenoxy) propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-4-carboxylic acid
(Separated atropisomer 1, absolute stereochemistry unknown)

Step A. Separation of 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one Racemic mixture of atropisomeric 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one was separated by preparative normal phase HPLC using chiral AD column. Optically pure atropisomers were isolated and absolute configurations were undetermined. $1^{st}$ eluted isomer $[\alpha]_D^{25}$=+9.9°, $2^{nd}$ eluted isomer $[\alpha]_D^{25}$=+6.1°

Step B. Example 431

The title compound was prepared according to General Procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one ($1^{st}$ eluted isomer) and 6-bromo-1-methyl-1H-indole-4-carboxylic acid followed by saponification using General Procedure D. LCMS: $R_T$=2.163 min, MS (ES) 711.9 (M+H).

Example 432

(R)-3-(7-Chloro-10-(3-(4-chloro-3,5-dimethylphenoxy)propyl)-6-(4,6-dimethyl-2-((4-methyl-3-oxopiperazin-1-yl)methyl)pyrimidin-5-yl)-4-methyl-1-oxo-3,4-dihydropyrazino[1,2-a]indol-2(1H)-yl)-1-methyl-1H-indole-5-carboxylic acid The title compound (4.2 mg, 38%) was prepared according to General Procedure J using methyl (R)-3-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1-methyl-1H-indole-5-carboxylate (10 mg, 0.013 mmol) and 1-methylpiperazin-2-one (10 mg, 0.088 mmol) followed by saponification using General Procedure D. LCMS: $R_T$=1.782 min, MS (ES) 835.9 (M+H).

Example 433

(R)-3-(6-(2-((4-Acetylpiperazin-1-yl)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-1-methyl-1H-indole-5-carboxylic acid To a solution of methyl (R)-3-(7-chloro-10-(3-(4-chloro-3,5-dimethylphenoxy)propyl)-6-(4,6-dimethyl-2-(piperazin-1-ylmethyl)pyrimidin-5-yl)-4-methyl-1-oxo-3,4-dihydropyrazino[1,2-a]indol-2(1H)-yl)-1-methyl-1H-indole-5-carboxylate (8 mg, 0.0098 mmol) in DCM (1 mL) was added DIPEA (5 mg, 0.038 mmol) followed by acetyl chloride (3 mg, 0.038 mmol) in DCM (0.5 mL) at 0° C. The reaction mixture was stirred for 15 min at 0° C. then quenched with MeOH. The quenched mixture was diluted with DCM (5 mL) and washed with $H_2O$ (5 mL). The organic layer was dried and concentrated. The residue was purified by reverse phase HPLC (Phenomenex Gemini C18, $H_2O/CH_3CN$ gradient 35-95% MeCN 0.1% TFA) to afford the title compound (2.1 mg, 25%). LCMS: $R_T$=1.789 min, MS (ES) 849.9 (M+H).

Example 434

(R)-7-Chloro-10-(3-(4-chloro-3,5-dimethylphenoxy)propyl)-4-methyl-6-(1,3,5-trimethyl-1H-pyrazol-4-yl)-3,3',4,4'-tetrahydro-1H-[2,6'-bipyrazino[1,2-a]indole]-1,1'(2'H)-dione Step A. Preparation of ethyl (R)-1-(2-((tert-butoxycarbonyl)amino)ethyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (15 mg, 0.021 mmol) and tert-butyl 1,2,3-oxathiazolidine-3-carboxylate 2,2-dioxide (10 mg, 0.045 mmol) in MeCN (1 mL) was added $Cs_2CO_3$ (15 mg, 0.0416 mmol), and the reaction mixture was stirred at 80° C. for 18 h. The reaction was cooled to RT and diluted into $DCM/H_2O$ (10 mL, 1:1). The layers were separated and extracted with DCM (2×5 mL). The combined organic layer was dried and concentrated to give the crude title compound which was used without further purification. LCMS: $R_T$=2.289 min, MS (ES) 890.9 (M+Na).

Step B. Example 434

To a solution of crude ethyl (R)-1-(2-((tert-butoxycarbonyl)amino)ethyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate in DCM (3 mL) was added TFA (0.5 mL), and the reaction mixture was stirred for 6 h at RT then concentrated. The residue was dissolved in MeOH (3 mL), and $K_2CO_3$ (10 mg, 0.072 mmol) was added. The reaction mixture was stirred at 50° C. for 4 h then concentrated. The residue was dissolved in $DCM/H_2O$ (10 mL, 1:1). The layers were separated and extracted with DCM (2×5 mL). The combined organic layer was dried and concentrated. The residue was purified by reverse phase HPLC (Phenomenex Gemini C18, $H_2O/CH_3CN$ gradient 35-95% MeCN 0.1% TFA) to afford the title compound (5.3 mg, 35%). LCMS: R$_T$=2.116, 2.153 min, MS (ES) 723.0 (M+H).

Example 435

(R)-4-Chloro-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylic acid The title compound was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-bromo-4-chloro-1-methyl-1H-indole-3-carboxylate followed by saponification using General Procedure D. LCMS: R$_T$=2.212, 2.254 min, MS (ES) 745.8 (M+H).

Example 436

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methoxy-1-methyl-1H-indole-3-carboxylic acid The title compound was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-bromo-5-methoxy-1-methyl-1H-indole-3-carboxylate followed by saponification using General Procedure D. LCMS: R$_T$=2.182, 2.217 min, MS (ES) 741.9 (M+H).

Example 437

(R)-3-(7-Chloro-10-(3-(4-chloro-3,5-dimethylphenoxy)propyl)-6-(4,6-dimethyl-2-(((1-methylpiperidin-4-yl)amino)methyl)pyrimidin-5-yl)-4-methyl-1-oxo-3,4-dihydropyrazino[1,2-a]indol-2(1H)-yl)-1-methyl-1H-indole-5-carboxylic acid The title compound (6.9 mg, 62%) was prepared according to General Procedure J using methyl (R)-3-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1-methyl-1H-indole-5-carboxylate (10 mg, 0.013 mmol) and 1-methylpiperidin-4-amine (20 mg, 0.18 mmol) followed by saponification using General Procedure D. LCMS: R$_T$=1.762 min, MS (ES) 835.9 (M+H).

Example 438

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-fluoro-1H-indole-3-carboxylic acid The title compound was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-bromo-4-fluoro-1H-indole-3-carboxylate followed by saponification using General Procedure D. LCMS: R$_T$=2.70, 2.73 min, MS (ES) 716.2 (M+H) (LC method III).

Example 439

(R)-3-(7-Chloro-10-(3-(4-chloro-3,5-dimethylphenoxy)propyl)-6-(2-((4-(2-methoxyethyl)piperazin-1-yl)methyl)-4,6-dimethylpyrimidin-5-yl)-4-methyl-1-oxo-34-dihydropyrazino[1,2-a]indol-2(1H)-yl)-1-methyl-1H-indole-5-carboxylic acid The title compound (8.9 mg, 77%) was prepared according to General Procedure J using methyl (R)-3-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1-methyl-1H-indole-5-carboxylate (10 mg, 0.013 mmol) and 1-(2-methoxyethyl)piperazine (40 mg, 0.28 mmol) followed by saponification using General Procedure D. LCMS: R$_T$=1.850 min, MS (ES) 865.9 (M+H). $^1$H NMR (400 MHz, Chloroform-d) δ 8.26 (s, 1H), 7.92 (dd, J=8.8, 1.4 Hz, 1H), 7.78 (d, J=8.6 Hz, 1H), 7.35-7.28 (m, 3H), 6.64 (s, 2H), 4.51-4.38 (m, 2H), 4.30 (dd, J=13.5, 3.8 Hz, 1H), 4.01 (dt, J=6.2, 3.0 Hz, 2H), 3.91-3.71 (m, 14H), 3.44-3.29 (m, 8H), 2.39 (s, 3H), 2.33 (s, 6H), 2.29-2.19 (m, 5H), 1.25 (d, J=6.4 Hz, 3H).

Example 440

6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-4-carboxylic acid (Separated Atropisomer 2, Absolute Stereochemistry Unknown)

The title compound was prepared according to General Procedure A using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one ($2^{nd}$ eluted isomer) and 6-bromo-1-methyl-1H-indole-4-carboxylic acid followed by saponification using General Procedure D. LCMS: R$_T$=2.163 min, MS (ES) 711.9 (M+H).

Example 441

(R)-3-(7-Chloro-10-(3-(4-chloro-3,5-dimethylphenoxy)propyl)-6-(4,6-dimethyl-2-(piperazin-1-ylmethyl)pyrimidin-5-yl)-4-methyl-1-oxo-3,4-dihydropyrazino[1,2-a]indol-2(1H)-yl)-1-methyl-1H-indole-5-carboxylic acid The title compound (17 mg, 79%) was prepared according to General Procedure J using methyl (R)-3-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1-methyl-1H-indole-5-carboxylate (20 mg, 0.039 mmol) and piperazine (50 mg, 0.58 mmol) followed by saponification using General Procedure D. LCMS: R$_T$=1.727 min, MS (ES) 807.9 (M+H).

Example 442

(R)-3-(3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indol-5-yl)-1,2,4-oxadiazol-5(4H)-one To a solution of methyl (R)-3-(7-chloro-10-(3-(4-chloro-3,5-dimethylphenoxy)propyl)-4-methyl-1-oxo-6-(1,3,5- trimethyl-1H-pyrazol-4-yl)-3,4-dihydropyrazino[1,2-a]indol-2(1H)-yl)-1-methyl-1H-indole-5-carboxylate (30 mg, 0.04 mmol) in DMF (1 mL) was added sodium acetate (14 mg, 0.16 mmol) and hydroxylamine hydrochloride (11 mg, 0.16 mmol), and the mixture was stirred at RT for 15 h. The reaction was quenched with water (10 mL) then extracted with DCM (3×5 mL). The organic layer was dried and concentrated. The residue was dissolved in THF (1 mL) and 1,1'-carbonyldiimidazole (17 mg, 0.08 mmol) and DBU (18 µL, 12 mmol) were added. The mixture was irradiated in a Biotage microwave at 120° C. for 20 min then concentrated. The residue was purified by reverse phase HPLC (Phenomenex Gemini C18, H$_2$O/CH$_3$CN gradient to 35-95% MeCN 0.1% TFA) to afford the title compound (7.8 mg, 26%). LCMS: R$_T$=2.033 min, MS (ES) 751.8 (M+H).

Example 443

(R)-3-(7-Chloro-10-(3-(4-chloro-3,5-dimethylphenoxy)propyl)-6-(4,6-dimethyl-2-((4-(tetrahydro-2H-pyran-4-yl)piperazin-1-yl)methyl)pyrimidin-5-yl)-4-methyl-1-oxo-3,4-dihydropyrazino[1,2-a]indol-2(1H)-yl)-1-methyl-1H-indole-5-carboxylic acid The title compound (10.6 mg, 89%) was prepared according to General Procedure J using methyl (R)-3-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1-methyl-1H-indole-5-carboxylate (10 mg, 0.013 mmol) and 4-(piperidin-4-yl)morpholine (50 mg, 0.29 mmol) followed by saponification using General Procedure D. LCMS: R$_T$=1.848 min, MS (ES) 891.9 (M+H).

Example 444

(R)-5-(3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indol-5-yl)-1,3,4-oxadiazol-2(3H)-one To a solution of (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carbohydrazide (15 mg, 0.02 mmol) in DMF (1 mL) was added 1,1'-carbonyldiimidazole (7 mg, 0.04 mmol) followed by Et$_3$N (6 µL, 0.04 mmol), and the mixture was stirred at RT for 6 h then concentrated. The residue was purified by reverse phase HPLC (Phenomenex Gemini C18, H$_2$O/CH$_3$CN gradient to 35-95% MeCN 0.1% TFA) to afford the title compound (6.1 mg, 40%). LCMS: R$_T$=1.982 min, MS (ES) 751.8 (M+H).

Example 445

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-methyl-1H-indole-3-carboxylic acid The title compound was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and 7-bromo-4-methoxy-1-methyl-1H-indole-3-carboxylic acid followed by saponification using General Procedure D. LCMS: R$_T$=2.76, 2.81 min, MS (ES) 742.2 (M+H) (LC method III). $^1$H NMR (400 MHz, Chloroform-d) δ 7.88 (d, J=8.0 Hz, 1H), 7.68 (d, J=8.0 Hz, 1H), 7.32-7.26 (m, 1H), 7.02-7.00 (m, 1H), 6.80-6.77 (m, 1H), 6.60 (s, 2H), 4.23-4.18 (m, 2H), 4.13 (s, 3H), 3.98-3.87 (m, 5H), 3.71-3.32 (m, 5H), 3.77 (s, 3H), 3.56-3.52 (m, 1H), 3.35-3.31 (m, 2H), 2.31 (s, 6H), 2.21-2.15 (m, 5H), 2.03 (s, 3H), 1.23-1.17 (m, 3H).

Example 446

(R)-7-Chloro-10-(3-(4-chloro-3,5-dimethylphenoxy)propyl)-2-(4-fluoro-1H-indol-7-yl)-4-methyl-6-(1,3,5-trimethyl-1H-pyrazol-4-yl)-3,4-dihydropyrazino[1,2-a]indol-1(2H)-one The title compound was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and 7-bromo-4-fluoro-1H-indole followed by saponification using General Procedure D. LCMS: R$_T$=3.04 min, MS (ES) 672.0 (M+H) (LC method III).

Example 447

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-fluoro-1-methyl-1H-indole-3-carboxylic acid The title compound was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and 7-bromo-4-fluoro-1-methyl-1H-indole-3-carboxylic acid followed by saponification using General Procedure D. LCMS: R$_T$=2.77 min, MS (ES) 730.1 (M+H) (LC method III).

Example 448

(R)-3-(7-Chloro-10-(3-(4-chloro-3,5-dimethylphenoxy)propyl)-6-(2-(((2-(dimethylamino)ethyl)(methyl)amino)methyl)-4,6-dimethylpyrimidin-5-yl)-4-methyl-1-oxo-3,4-dihydropyrazino[1,2-a]indol-2(1H)-yl)-1-methyl-1H-indole-5-carboxylic acid The title compound (5.3 mg, 48%) was prepared according to General Procedure J using methyl (R)-3-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1-methyl-1H-indole-5-carboxylate (10 mg, 0.013 mmol) and N$^1$,N$^1$,N$^2$-trimethylethane-1,2-diamine (30 mg, 0.29 mmol) followed by saponification using General Procedure D. LCMS: R$_T$=1.788 min, MS (ES) 823.9 (M+H).

Example 449

(R)-5Chloro-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylic acid The title compound was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-bromo-5-chloro-1-methyl-1H-indole-3-carboxylate followed by saponification using General Procedure D. LCMS: $R_T$=2.284 min, MS (ES) 745.8 (M+H).

Example 450

(R)-7-Chloro-10-(3-(4-chloro-3,5-dimethylphenoxy) propyl)-4-methyl-2-(1-methyl-5-(5-methylpyrimidin-2-yl)-1H-indol-3-yl)-6-(1,3,5-trimethyl-1H-pyrazol-4-yl)-3,4-dihydropyrazino[1,2-a]indol-1(2H)-one Step A. Preparation of 1-methyl-5-(5-methylpyrimidin-2-yl)-1H-indole The title compound (70 mg, 78%) was prepared following the procedure described Example 388 Step A using 2-bromo-5-methylpyrimidine (70 mg, 0.44 mmol) and 1-methyl-5-(4,4,5,5-tetramethyl-1,3,2-dioxaborolan-2-yl)-1H-indole (156 mg, 0.61 mmol). LCMS: $R_T$=1.156 min, MS (ES) 224.1 (M+H).

Step B. Preparation of 3-iodo-1-methyl-5-(5-methylpyrimidin-2-yl)-1H-indole

The title compound was prepared following the procedure described Example 388 Step B using 1-methyl-5-(5-methylpyrimidin-2-yl)-1H-indole (70 mg, 0.31 mmol). The crude compound (100 mg) was used for the next step without further purification. LCMS: $R_T$=1.507 min, MS (ES) 350.8 (M+H).

Step C. Example 450

The title compound (29 mg, 69%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.056 mmol) and 3-iodo-1-methyl-5-(5-methylpyrimidin-2-yl)-1H-indole (31 mg, 0.089 mmol). LCMS: $R_T$=2.132 min, MS (ES) 760.9 (M+H).

Example 451

(R)-3-(7-Chloro-10-(3-(4-chloro-3,5-dimethylphenoxy)propyl)-6-(2-((dimethylamino)methyl)-4,6-dimethylpyrimidin-5-yl)-4-methyl-1-oxo-3,4-dihydropyrazino[1,2-a]indol-2(1H)-yl)-1-methyl-1H-indole-5-carboxylic acid The title compound (5.9 mg, 58%) was prepared according to General Procedure J using methyl (R)-3-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-1-methyl-1H-indole-5-carboxylate (10 mg, 0.013 mmol) and dimethylamine hydrochloride salt (20 mg, 0.25 mmol) followed by saponification using General Procedure D. LCMS: $R_T$=1.811 min, MS (ES) 766.9 (M+H).

Example 452

(R)-7-(7-Chloro-10-(3-(4-chloro-3,5-dimethylphenoxy)propyl)-6-(3,5-dimethyl-1-((tetrahydro-2H-pyran-4-yl)methyl)-1H-pyrazol-4-yl) 4-methyl-1-oxo-3,4-dihydropyrazino[1,2-a]indol-2(1H)-yl)-1,5-dimethyl-1H-indole-2-carboxylic acid The title compound was prepared following the procedure described Example 318 Step C using methyl (R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1,5-dimethyl-1H-indole-2-carboxylate and 4-(bromomethyl)tetrahydro-2H-pyran. LCMS: $R_T$=1.63 min, MS (ES) 810.7 (M+H); $^1$H NMR (DMSO, 400 MHz) δ (ppm) 7.76 (dd, J=8.8.1.6 Hz, 1H), 7.48 (s, 1H), 7.29 (dd, J=8.8, 1.6 Hz, 1H), 7.21 (d, J=1.6 Hz, 1H), 6.95 (s, 1H), 6.70 (s, 2H), 4.39-4.31 (m, 1H), 4.20-4.16 (m, 2H), 3.97-3.94 (m, 2H), 3.91 (s, 3H), 3.86-3.80 (m, 2H), 2.67-2.63 (m, 2H), 2.53 (s, 3H), 2.37 (s, 3H), 2.35-2.31 (m, 2H), 2.22 (s, 6H), 2.12 (s, 3H), 2.01 (s, 3H), 1.95-1.95 (m, 2H), 1.89-1.87 (m, 2H), 1.43-1.29 (m, 1H), 1.17-1.03 (m, 4H).

Example 453

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-methyl-5-(2-(4-methylpiperazin-1-yl) ethoxy)-1H-indole-2-carboxylic acid To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (10 mg, 0.013 mmol), PPh$_3$ (10 mg, 0.038 mmol) and 2-(4-methylpiperazin-1-yl)ethan-1-ol (8 mg, 0.055 mmol) in THF (1 mL) was added di-tert-butyl (E)-diazene-1,2-dicarboxylate (10 mg, 0.044 mmol) at RT. The reaction mixture was stirred for 18 h at RT, then heated to 60° C. for additional 5 h. The reaction was cooled to RT and diluted with DCM/H$_2$O (10 mL, 1:1). The aqueous layer was extracted with DCM (2×5 mL). The combined organic layer was dried and concentrated. The crude product was saponified following General Procedure D. The crude reaction mixture was purified by reverse phase HPLC (Phenomenex Gemini C18, H$_2$O/CH$_3$CN gradient 35-95% MeCN 0.1% TFA) to afford the title compound (2.2 mg, 19%). LCMS: $R_T$=1.779 min, MS (ES) 853.9 (M+H).

Example 454

(R)-7-Chloro-10-(3-(4-chloro-3,5-dimethylphenoxy) propyl)-2-(5-(1-isobutyl-1H-1,2,4-triazol-3-yl)-1-methyl-1H-indol-3-yl)-4-methyl-6-(1,3,5-trimethyl-1H-pyrazol-4-yl)-3,4-dihydropyrazino[1,2-a]indol-1 (2H)-one Step A. Preparation of 3-iodo-1-methyl-5-(1H-1,2,4-triazol-3-yl)-1H-indole 2N HCl (2 mL) was added to a solution of 3-iodo-1-methyl-5-(1-(tetrahydro-2H-pyran-2-yl)-1H-1,2,4-triazol-3-yl)-1H-indole (150 mg, 0.37 mmol) in MeOH (1 mL) at 0° C. The reaction was warmed to RT and stirred for 4 h. The reaction mixture was diluted with EtOAc, quenched with Sat. aq. NaHCO$_3$ at 0° C. and extracted with EtOAc (3×5 mL). The combined organic layer was dried and concentrated to give the title compound (80 mg), which was used for the next step without further purification. LCMS: $R_T$=0.211 min, MS (ES) 324.9 (M+H).

Step B. Preparation of 3-iodo-5-(1-isobutyl-1H-1,2,4-triazol-3-yl)-1-methyl-1H-indole NaH (4 mg, 0.15 mmol) was added to a solution of 3-iodo-1-methyl-5-(1H-1,2,4-triazol-3-yl)-1H-indole (40 mg, 0.12 mmol) in DMF (1 mL) at 0° C. After 10 min, 1-bromo-2-methylpropane (16.1 µL 0.15 mmol) was added slowly. The reaction was warmed to RT and stirred for 15 h. The reaction was quenched with water and extracted with EtOAc (3×10 mL). The combined organic layer was washed with water, dried and concentrated. The residue was purified by flash chromatography (Combi-flash Rf, Hex/EtOAc=0-20% gradient) to provide the title compound (35 mg, 74%). LCMS: $R_T$=1.564 min, MS (ES) 380.8 (M+H).

Step C. Example 454

The title compound (40 mg, 91%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.056 mmol) and 3-iodo-5-(1-isobutyl-1H-1,2,4-triazol-3-yl)-1-methyl-1H-indole (34 mg, 0.089 mmol). LCMS: $R_T$=2.132 min, MS (ES) 791.9 (M+H). $^1$H NMR (400 MHz, Chloroform-d) δ 8.31 (d, J=24.5 Hz, 1H), 8.20 (d, J=11.2 Hz, 1H), 7.98 (dd, J=9.0, 1.7 Hz, 1H), 7.68 (dd, J=8.8, 3.0 Hz, 1H), 7.41 (d, J=8.8 Hz, 1H), 7.29-7.23 (m, 2H), 6.61 (s, 2H), 4.50-4.41 (m, 1H), 4.31-4.20 (m, 1H), 4.00-3.95 (m, 4H), 3.90 (s, 3H), 3.83 (s, 3H), 3.74-3.67 (m, 1H), 3.46-3.30 (m, 2H), 2.34-2.27 (m, 7H), 2.22-2.18 (m, 5H), 2.06 (s, 3H), 1.26 (d, J=6.4 Hz, 1.5H), 1.23 (d, J=6.9 Hz, 1.5H), 0.97 (d, J=6.9 Hz, 6H).

Example 455

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-(dimethylamino)ethoxy)-1-methyl-1H-indole-2-carboxylic acid The title compound (2.6 mg, 24%) was prepared following the procedure described Example 453 using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (10 mg, 0.013 mmol) and 2-(dimethylamino)ethan-1-ol (5 mg, 0.056 mmol). LCMS: $R_T$=1.810 min, MS (ES) 798.9 (M+H).

Example 456

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((4-methylpyridin-2-yl)methyl)-1H-indole-2-carboxylic acid Step A. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-3-carboxylate The title compound (30 mg, 45%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (50 mg, 0.09 mmol) and methyl 7-bromo-5-methyl-1H-indole-2-carboxylate (58 mg, 0.19 mmol). LCMS: $R_T$=2.16 min, MS (ES) 726 (M+H).

Step B. Example 456

The title compound (25 mg, 34%) was prepared following General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-3-carboxylate (60 mg, 0.08 mmol) and 2-(chloromethyl)-4-methylpyridine HCl (29 mg, 0.17 mmol) followed by saponification using General Procedure D. LCMS: $R_T$=1.38 min, MS (ES) 817 (M+H).

Example 457

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((6-methylpyridin-2-yl)methyl)-1H-indole-2-carboxylic acid Step A. Preparation of pentyl 7-iodo-5-methyl-1H-indole-2-carboxylate To a mixture of methyl 7-bromo-5-methyl-1H-indole-2-carboxylate (200 mg, 0.75 mmol) followed by CuI (7 mg, 0.04 mmol) and NaI (224 mg, 1.5 mmol) was added a solution of (trans)-1,2-N,N'-dimethylaminocyclohexane (11 mg, 0.07 mmol) in 1-pentanol (1 mL). The reaction mixture was sealed and stirred at 120° C. for 24 h. The reaction was cooled to RT and diluted with 30% NH$_4$OH (5 mL) in water (20 mL) and extracted with DCM. The combined organics were dried and concentrated. The residue was purified by flash chromatography (Combi-flash Rf, Hex/EtOAc=0-5% gradient) to give the title compound (205 mg, 74%). LCMS: $R_T$=2.04 min, MS (ES) 372 (M+H).

Step B. Preparation of pentyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate The title compound (80 mg, 73%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (75 mg, 0.14 mmol) and pentyl 7-iodo-5-methyl-1H-indole-2-carboxylate (103 mg, 0.28 mmol). LCMS: $R_T$=2.42 min, MS (ES) 782 (M+H).

Step C. Example 457

The title compound (45 mg, 68%) was prepared following General Procedure I using pentyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (80 mg, 0.10 mmol) and 2-(chloromethyl)-6-methylpyridine (36 mg, 0.26 mmol) followed by saponification using General Procedure D as TFA salt. LCMS: $R_T$=1.40 min, MS (ES) 817 (M+H); $^1$H NMR (400 MHz, DMSO-d$_6$) δ 7.75 (d, J=8.6 Hz, 1H), 7.56 (s, 1H), 7.40 (s, 1H), 7.27 (d, J=8.6 Hz, 1H), 7.01 (m, 1H), 6.87 (s, 0.5H), 6.86 (s, 0.5H), 6.74 (s, 1H), 6.70 (s, 1H), 6.11-6.24 (m, 2H), 5.74 (s, 2H), 4.01 (m, 2H), 3.88 (m, 1H), 3.73 (s, 1.5H), 3.70 (s, 1.5H), 3.24-3.28 (m, 1H), 3.08 (m, 1H), 2.32-2.38 (m, 5H), 2.23 (s, 3H), 2.21 (s, 3H), 2.08 (s, 15H), 2.06 (s, 1.5H), 1.95-1.99 (m, 2H), 1.91 (s, 1.5H), 1.89 (s, 1.5H), 1.85 (s, 15H), 1.75 (s, 1.5H), 1.03 (t, J=6.8 Hz, 3H).

Example 458

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-methyl-5-(2-morpholinoethoxy)-1H-indole-2-carboxylic acid The title compound (4.7 mg, 42%) was prepared following the procedure described Example 453 using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (10 mg, 0.013 mmol) and 2-morpholinoethan-1-ol (8 mg, 0.061 mmol). LCMS: $R_T$=1.794 min, MS (ES) 840.9 (M+H).

Example 459

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-methyl-5-(oxetan-3-ylmethoxy)-1H-indole-2-carboxylic acid The title compound (3.7 mg, 35%) was prepared according to General Procedure H using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (10 mg, 0.013 mmol) and 3-(bromomethyl)oxetane (5 mg, 0.033 mmol) followed by saponification using General Procedure D. LCMS: $R_T$=1.990 min, MS (ES) 797.8 (M+H).

Example 460

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-methyl-5-(2-(pyrrolidin-1-yl)ethoxy)-1H-indole-2-carboxylic acid The title compound (2.1 mg, 19%) was prepared following the procedure described Example 453 using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (10 mg, 0.013 mmol) and 2-(pyrrolidin-1-yl)ethan-1-ol (8 mg, 0.069 mmol). LCMS: $R_T$=1.799 min, MS (ES) 824.9 (M+H).

Example 461

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-5-(2-methoxyethoxy)-1-methyl-1H-indole-2-carboxylic acid The title compound (5.2 mg, 50%) was prepared according to General Procedure H using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (10 mg, 0.013 mmol) and 1-bromo-2-methoxyethane (5 mg, 0.036 mmol) followed by saponification using General Procedure D. LCMS: $R_T$=2.009 min, MS (ES) 785.8 (M+H).

Example 462

(R)-7-Chloro-10-(3-(4-chloro-3,5-dimethylphenoxy) propyl)-2-(5-(1-(cyclopropylmethyl)-1H-1,2,4-triazol-3-yl)-1-methyl-1H-indol-3-yl)-4-methyl-6-(1,3,5-trimethyl-1H-pyrazol-4-yl)-3,4-dihydropyrazino[1,2-a]indol-1(2H)-one Step A. Preparation of 5-(1-(cyclopropylmethyl)-1H-1,2,4-triazol-3-yl)-3-iodo-1-methyl-1H-indole The title compound (35 mg, 75%) was prepared following the procedure described Example 454 Step B using 3-iodo-1-methyl-5-(1H-1,2,4-triazol-3-yl)-1H-indole (40 mg, 0.12 mmol) and (bromomethyl)cyclopropane (14.4 µL, 0.15 mmol). LCMS: $R_T$=1.498 min, MS (ES) 378.9 (M+H).

Step B. Example 462

The title compound (38 mg, 87%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.056 mmol) and 5-(1-(cyclopropylmethyl)-1H-1,2,4-triazol-3-yl)-3-iodo-1-methyl-1H-indole (34 mg, 0.089 mmol). LCMS: $R_T$=2.034 min, MS (ES) 789.0 (M+H).

Example 463

(R)-7-(7-Chloro-10-(3-(4-chloro-3,5-dimethylphenoxy)propyl)-6-(3,5-dimethyl-1-(2-(pyrrolidin-1-yl) ethyl)-1H-pyrazol-4-yl)-4-methyl-1-oxo-3,4-dihydropyrazino[1,2-a]indol-2(1H)-yl)-1,5-dimethyl-1H-indole-2-carboxylic acid The title compound was prepared following the procedure described Example 318 Step C using methyl (R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1,5-dimethyl-1H-indole-2-carboxylate and 1-(2-bromoethyl)pyrrolidine. LCMS: $R_T$=1.37 min, MS (ES) 809.7 (M+H); $^1$H NMR (DMSO, 400 MHz) δ (ppm) 7.90 (d, J=8.8 Hz, 1H), 7.49 (s, 1H), 7.31 (dd, J=8.8, 2.0 Hz, 1H), 7.22 (d, J=2.0 Hz, 1H), 6.96 (d, J=10.0 Hz, 1H), 6.69 (s, 2H), 4.46-4.36 (m, 2H), 4.17-4.11 (m, 1H), 3.98-3.91 (m, 2H), 3.92 (s, 3H), 3.65-3.60 (m, 2H), 3.09-3.01 (m, 2H), 2.64-2.61 (m, 2H), 2.53 (s, 3H), 2.38 (s, 3H), 2.32-2.31 (m, 2H), 2.22 (s, 6H), 2.05 (d, J=4.0 Hz, 3H), 2.06-1.95 (m, 2H), 1.93 (s, 3H), 1.90-1.84 (m, 2H), 1.22-1.05 (m, 4H).

Example 464

(R)-7-Chloro-10-(3-(4-chloro-3,5-dimethylphenoxy) propyl)-2-(5-(4-methoxypyrimidin-2-yl)-1-methyl-1H-indol-3-yl)-4-methyl-6-(1,3,5-trimethyl-1H-pyrazol-4-yl)-3,4-dihydropyrazino[1,2-a]indol-1(2H)-one Step A. Preparation of 5-(4-methoxypyrimidin-2-yl)-1-methyl-1H-indole 2-Chloro-4-methoxypyrimidine (80 mg, 0.55 mmol), Pd[P(t-Bu)$_3$]$_2$ (28 mg, 0.060 mmol). Cs$_2$CO$_3$ (270 mg, 0.83 mmol) were added to a solution of 1-methyl-5-(4,4,5,5-tetramethyl-1,3,2-dioxaborolan-2-yl)-1H-indole (185 mg, 0.72 mmol) in dioxane (2.2 mL). The reaction mixture was degassed using Ar. The reaction was stirred at 90° C. for 5 h, quenched with water and extracted with DCM (3×5 mL). The combined organic layer was dried and concentrated. The residue was purified by flash chromatography (Combiflash Rf, Hex/EtOAc=0-20% gradient) to provide the title compound (19 mg, 14%). LCMS: $R_T$=0.163 min, MS (ES) 240.1 (M+H).

Step B. Preparation of 3-iodo-5-(4-methoxypyrimidin-2-yl)-1-methyl-1H-indole

The title compound was prepared following the procedure described Example 388 Step B using 5-(4-methoxypyrimidin-2-yl)-1-methyl-1H-indole (19 mg, 0.080 mmol). The crude compound (30 mg) was used for the next step without further purification. LCMS: $R_T$=1.248 min, MS (ES) 365.8 (M+H).

Step C. Example 464

The title compound (35 mg, 80%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.056 mmol) and 3-iodo-5-(4-methoxypyrimidin-2-yl)-1-methyl-1H-indole (30 mg, 0.089 mmol). LCMS: $R_T$=2.106 min, MS (ES) 776.8 (M+H).

Example 465

(R)-7-Chloro-10-(3-(4-chloro-3,5-dimethylphenoxy) propyl)-2-(5-(5-methoxypyrimidin-2-yl)-1-methyl-1H-indol-3-yl)-4-methyl-6-(1,3,5-trimethyl-1H-pyrazol-4-yl)-3,4-dihydropyrazino[1,2-a]indol-1(2H)-one Step A. Preparation of 5-(5-methoxypyrimidin-2-yl)-1-methyl-1H-indole The title compound (63 mg, 48%) was prepared following the procedure described Example 464 Step A using 2-chloro-5-methoxypyrimidine (80 mg, 0.55 mmol) and 1-methyl-5-(4,4,5,5-tetramethyl-1,3,2-dioxaborolan-2-yl)-1H-indole (185 mg, 0.72 mmol). LCMS: $R_T$=1.086 min, MS (ES) 240.1 (M+H).

Step B. Preparation of 3-iodo-5-(5-methoxypyrimidin-2-yl)-1-methyl-1H-indole

The title compound was prepared following the procedure described Example 388 Step B using 5-(5-methoxypyrimidin-2-yl)-1-methyl-1H-indole (63 mg, 0.26 mmol). The crude compound (85 mg) was used for the next step without further purification. LCMS: $R_T$=1.601 min, MS (ES) 365.8 (M+H).

Step C. Example 465

The title compound (35 mg, 80%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.056 mmol) and 3-iodo-5-(5-methoxypyrimidin-2-yl)-1-methyl-1H-indole (32 mg, 0.089 mmol). LCMS: $R_T$=2.106 min, MS (ES) 776.8 (M+H). $^1$H NMR (400 MHz, Chloroform-d) δ 8.51 (d, J=8.1 Hz, 2H), 8.47 (dd, J=6.6, 1.4 Hz, 1H), 8.26 (ddd, J=8.7, 3.6, 1.7 Hz, 1H), 7.70 (dd, J=8.6, 2.7 Hz, 1H), 7.43 (dd, J=8.7, 2.8 Hz, 1H), 7.30-7.24 (m, 2H), 6.60 (s, 2H), 7.48 (td, J=13.4, 3.7 Hz, 1H), 4.30-4.19 (m, 1H), 4.02-3.98 (m, 2H), 3.95-3.93 (m, 6H), 3.83-3.73 (m, 4H), 3.47-3.30 (m, 2H), 2.28 (s, 6H), 2.25-2.18 (m, 5H), 2.09 (d, J=5.3 Hz, 3H), 1.30 (d, J=6.5 Hz, 1.5H), 1.22 (d, J=6.6 Hz, 1.5H).

Example 466

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-(pyridin-2-ylmethyl)-1H-indole-2-carboxamide The title compound (6 mg, 37%) was prepared according to General Procedure G using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H-indole-2-carboxylate (15 mg, 0.02 mmol) and 2-(bromomethyl)pyridine hydrobromide (7.6 mg, 0.03 mmol) followed by primary carboxamide formation using General Procedure E. LCMS: $R_T$=1.859 MS (ES) 817.9 (M+H).

Example 467

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-3-ylmethyl)-1H-indole-3-carboxylic acid Step A. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate The title compound (32 mg, 90%) was prepared according to General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and methyl 7-bromo-1H-indole-3-carboxylate (39 mg, 0.15 mmol). LCMS: $R_T$=2.070 min, MS (ES) 711.9 (M+H).

Step B. Example 467

The title compound (10.1 mg, 63%) was prepared according to General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate (15 mg, 0.02 mmol) and 3-(chloromethyl)pyridine hydrochloride (7 mg, 0.04 mmol) followed by saponification using General Procedure D. LCMS: $R_T$=1.806 MS (ES) 788.8 (M+H); $^1$H NMR (500 MHz, DMSO-$d_6$) δ 8.47-8.39 (m, 1H), 8.20-8.14 (m, 2H), 8.00-7.91 (m, 1H), 7.76 (d, J=8.8 Hz, 1H), 7.33-7.28 (m, 2H), 7.20-7.11 (m, 1H), 7.04-6.94 (m, 1H), 6.72 (s, 2H), 5.65-5.58 (m, 1H), 4.02-3.97 (m, 2H), 3.93-3.88 (m, 2H), 3.74 (s, 1.5H), 3.72 (s, 1.5H), 3.42-3.34 (m, 1H), 3.16-3.11 (m, 2H), 2.96-2.87 (m, 2H), 2.23 (s, 6H), 2.07 (s, 1.5H), 2.06-2.02 (m, 2H), 1.98 (s, 1.5H), 1.90 (s, 1.5H), 1.80 (s, 1.5H), 1.06-1.00 (m, 3H).

Example 468

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-2-ylmethyl)-1H-indole-3-carboxylic acid The title compound (8.7 mg, 55%) was prepared according to General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate (15 mg, 0.02 mmol) and 2-(bromomethyl)pyridine hydrobromide (10 mg, 0.04 mmol) followed by saponification using General Procedure D. LCMS: $R_T$=1.923 MS (ES) 788.8 (M+H); $^1$H NMR (500 MHz, DMSO-$d_6$) δ 8.23 (s, 1H), 8.14 (d, J=8.4 Hz, 1H), 7.77 (d, J=8.4 Hz, 1H), 7.58 (t, J=7.8 Hz, 1H), 7.38-7.24 (m, 2H), 7.23-7.16 (m, 1H), 6.97-6.89 (m, 1H), 6.72 (s, 2H), 6.50-6.42 (m, 1H), 5.71-5.58 (m, 1H), 4.04-3.99 (m, 3H), 3.83-3.78 (m, 2H), 3.73 (s, 1.5H), 3.70 (s, 1.5H), 3.42-3.31 (m, 1H), 3.31-3.23 (m, 1H), 3.22-3.12 (m, 1H), 2.68-2.56 (m, 1H), 2.15-2.09 (m, 2H), 2.22 (s, 6H), 2.08 (s, 1.5H), 1.98 (s, 1.5H), 1.84 (s, 1.5H), 1.74 (s, 1.5H), 1.06-0.94 (m, 3H).

Example 469

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(trifluoromethoxy)-1H-indole-2-carboxylic acid The title compound (20 mg, 57%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (75 mg, 0.14 mmol) and ethyl 7-bromo-5-(trifluoromethoxy)-1H-indole-2-carboxylate (98 mg, 0.28 mmol) followed by saponification following General Procedure D. LCMS: $R_T$=2.07 min, MS (ES) 782 (M+H); $^1$H NMR (400 MHz, DMSO-$d_6$) δ 7.74 (d, J=8.6 Hz, 1H), 7.68 (bs, 1H), 7.28 (d, J=8.6 Hz, 1H), 7.23 (d, J=2.0 Hz, 1H), 7.16 (bs, 1H), 6.72 (s, 2H), 4.66-4.69 (m, 1H), 4.11-4.18 (m, 1H), 3.98 (m, 2H), 3.77 (s, 1.5H), 3.76 (s, 1.5H), 3.45-3.53 (m, 1H), 3.18-3.36 (m, 2H), 2.22 (s, 6H), 2.03-2.12 (m, 5H), 1.98 (s, 1.5H), 1.89 (s, 1.5H), 1.11 (d, J=6.4 Hz, 3H).

Example 470

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-methoxyethyl)-5-methyl-1H-indole-2-carboxylic acid The title compound (35 mg, 61%) was prepared following General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (70 mg, 0.10 mmol) and 2-bromoethyl methyl ether (20 mg, 0.14 mmol) followed by saponification using General Procedure D. LCMS: $R_T$=2.06 min, MS (ES) 770 (M+H); $^1$H NMR (400 MHz, DMSO-$d_6$) δ 7.76 (d, J=8.4 Hz, 1H), 7.50 (s, 0.5H), 7.45 (s, 0.5H), 7.33 (m, 1H), 7.27 (m, 1H), 6.96 (s, 0.5H), 6.94 (s, 0.5H), 6.71 (s, 1H), 6.70 (s, 1H), 4.94 (m, 1H), 4.68 (m, 2H), 4.43 (m, 2H), 4.18 (m, 1H), 3.99 (t, J=5.5 Hz, 2H), 3.79 (s, 1.5H), 3.77 (s, 1.5H), 3.71 (m, 1H), 3.35 (m, 2H), 3.22 (m, 2H), 3.0 (s, 1.5H), 2.95 (s, 1.5H), 2.39 (s, 1.5H), 2.36 (s, 1.5H), 2.24 (s, 6H), 2.14 (m, 1H), 1.88-2.07 (m, 5H), 1.17 (d, J=6.4 Hz, 1.5H), 1.06 (d, J=6.4 Hz, 1.5H).

Example 471

(R)-7-chloro-10-(3-(4-chloro-3,5-dimethylphenoxy)propyl)-4-methyl-2-(5-(1-methyl-1H-1,2,4-triazol-3-yl)-1H-indol-3-yl)-6-(1,3,5-trimethyl-1H-pyrazol-4-yl)-3,4-dihydropyrazino[1,2-a]indol-1(2H)-one Step A. Preparation of 5-(1-methyl-1H-1,24-triazol-3-yl)-1-((2-(trimethylsilyl)ethoxy) methyl)-1H-indole The title compound (310 mg, 77%) was prepared following the procedure described Example 388 Step A using 3-bromo-1-methyl-1H-1,2,4-triazole (200 mg, 1.23 mmol) and 5-(4,4,5,5-tetramethyl-1,3,2-dioxaborolan-2-yl)-1-((2-(trimethylsilyl)ethoxy)methyl)-1H-indole (567 mg, 1.52 mmol). LCMS: $R_T$=1.488 min, MS (ES) 329.1 (M+H).

Step B. Preparation of 3-iodo-5-(1-methyl-1H-1,2,4-triazol-3-yl)-1-((2-(trimethylsilyl) ethoxy)methyl)-1H-indole The title compound (380 mg, 89%) was prepared following the procedure described Example 388 Step B using 5-(1-methyl-1H-1,2,4-triazol-3-yl)-1-((2-(trimethylsilyl)ethoxy) methyl)-1H-indole (310 mg, 0.94 mmol). LCMS: $R_T$=1.740 min, MS (ES) 454.9 (M+H).

Step C. Preparation of (R)-7-chloro-10-(3-(4-chloro-3,5-dimethylphenoxy)propyl)-4-methyl-2-(5-(1-methyl-1H-1,2,4-triazol-3-yl)-1-((2-(trimethylsilyl)ethoxy)methyl)-1H-indol-3-yl)-6-(1,3,5-trimethyl-1H-pyrazol-4-yl)-3,4-dihydropyrazino[1,2-a]indol-1(2H)-one The title compound (150 mg, 63%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (150 mg, 0.28 mmol) and 3-iodo-5-(1-methyl-1H-1,2,4-triazol-3-yl)-1-((2-(trimethylsilyl)ethoxy)methyl)-1H-indole (202 mg, 0.45 mmol). LCMS: $R_T$=2.209 min, MS (ES) 865.9 (M+H).

Step D. Example 471

TBAF (2 mL, 1 M solution in THF) was added to a solution of (R)-7-chloro-10-(3-(4-chloro-3,5-dimethylphenoxy)propyl)-4-methyl-2-(5-(1-methyl-1H-1,2,4-triazol-3-yl)-1-((2-(trimethylsilyl)ethoxy)methyl)-1H-indol-3-yl)-6-(1,3,5-trimethyl-1H-pyrazol-4-yl)-3,4-dihydropyrazino[1,2-a]indol-1(2H)-one (150 mg, 0.17 mmol) in THF (1.7 mL). The reaction was irradiated under microwave at 70° C. for 30 mm (3 times). Additional TBAF (1 mL) was added to the reaction then irradiated under microwave at 75° C. for 1 h (3 times). The reaction was quenched with water and extracted with DCM (3×10 mL). The combined organic layer was dried and concentrated. The residue was purified by flash chromatography (Combi-flash Rf, DCM/MeOH=0-3% gradient) to provide the title compound (95 mg, 75%). LCMS: $R_T$=1.864 min, MS (ES) 735.9 (M+H).

Example 472

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-4-ylmethyl)-1H-indole-3-carboxylic acid The title compound (12.6 mg, 80%) was prepared according to General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate (15 mg, 0.02 mmol) and 4-(bromomethyl)pyridine hydrobromide (10 mg, 0.04 mmol) followed by saponification using General Procedure D. LCMS: $R_T$=1.751 MS (ES) 788.8 (M+H); $^1$H NMR (500 MHz, DMSO-$d_6$) δ 8.55-8.47 (m, 1H), 8.40-8.32 (m, 1H), 8.28-8.21 (m, 1H), 8.17 (d, J=8.0 Hz, 1H), 7.80-7.68 (m, 1H), 7.37-7.23 (m, 2H), 7.09-7.00 (m, 1H), 6.96 (t, J=8.1 Hz, 1H), 6.72 (s, 1H), 6.68 (s, 1H), 5.75-5.61 (m, 1H), 4.06-3.95 (m, 3H), 3.89-3.85 (m, 2H), 3.73 (s, 1.5H), 3.70 (s, 15H), 3.39-3.27 (m, 2H), 3.18-3.06 (m, 1H), 2.74-2.65 (m, 1H), 2.23 (s, 6H), 2.08 (s, 1.5H), 2.06-2.02 (m, 2H), 1.98 (s, 1.5H), 1.87 (s, 1.5H), 1.75 (s, 1.5H), 1.05-0.96 (m, 3H).

Example 473

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)imidazo[1,2-a]pyridine-6-carboxylic acid The title compound (30 mg, 43%) was prepared following General coupling procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (60 mg, 0.111 mmol) and methyl 3-bromoimidazo[1,2-a]pyridine-6-carboxylate (40 mg, 0.156 mmol) followed by saponification using General Procedure D. LCMS: $R_T$=0.858 min (LC method IV), MS (ES) 699.5 (M+H), $^1$H NMR (DMSO, 400 MHz) δ (ppm) 8.81 (s, 1H), 7.92 (d, J=10.0 Hz, 2H), 7.82 (d, J=10.0 Hz, 1H), 7.78 (d, J=8.8 Hz, 1H), 7.31 (d, J=8.8 Hz, 1H), 6.70 (s, 2H), 4.67-4.63 (m, 1H), 4.20-4.18 (m, 2H), 3.97-3.95 (m, 2H), 3.78 (s, 3H), 2.49 (s, 6H), 2.22-2.15 (m, 2H), 2.06 (s, 3H), 2.00-1.95 (m, 2H), 1.87 (s, 3H), 1.10 (d, J=6.8 Hz, 3H).

Example 474

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4-methylpyridin-2-yl)methyl)-5-(trifluoromethoxy)-1H-indole-2-carboxylic acid To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(trifluoromethoxy)-1H-indole-2-carboxylate (34 mg, 0.04 mmol) and 2-(chloromethyl)-4-methylpyridine HCl (22 mg, 0.13 mmol) in DMF (0.7 mL) was added $Cs_2CO_3$ (68 mg, 0.21 mmol). The mixture was stirred under Ar at 80° C. overnight then an additional 2-(chloromethyl)-4-methylpyridine HCl (22 mg, 0.13 mmol) and $Cs_2CO_3$ (100 mg) were added. The reaction was stirred under Ar at 100° C. for 24 h. The title compound (21 mg, 50%) was isolated according to work up and purification protocols described in general coupling procedure A followed by saponification using General Procedure D as TFA salt. LCMS: $R_T$=2.00 min, MS (ES) 887 (M+H).

Example 475

(R)-7-Chloro-10-(3-(4-chloro-3,5-dimethylphenoxy)propyl)-4-methyl-2-(1-methyl-5-(1-(oxetan-3-ylmethyl)-1H-1,2,4-triazol-3-yl)-1H-indol-3-yl)-6-(1,3,5-trimethyl-1H-pyrazol-4-yl)-3,4-dihydropyrazino[1,2-a]indol-1(2H)-one Step A. Preparation of 3-iodo-1-methyl-5-(1-(oxetan-3-ylmethyl)-1H-1,2,4-triazol-3-yl)-1H-indole The title compound (39 mg, 32%) was prepared following the procedure described Example 454 Step B using 3-iodo-1-methyl-5-(1H-1,2,4-triazol-3-yl)-1H-indole (100 mg, 0.31 mmol) and 3-(chloromethyl)oxetane (30 µL, 0.090 mmol). LCMS: $R_T$=1.339 min, MS (ES) 395.8 (M+H). LCMS: $R_T$=1.498 min, MS (ES) 378.9 (M+H).

Step B. Example 475

The title compound (22 mg, 59%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.046 mmol) and 3-iodo-1-methyl-5-(1-(oxetan-3-ylmethyl)-1H-1,2,4-triazol-3-yl)-1H-indole (37 mg, 0.093 mmol). LCMS: $R_T$=1.963 min, MS (ES) 805.9 (M+H).

Example 476

(R)-7-(7-Chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-1-((4-methoxypyridin-2-yl)methyl)-1H-indole-2-carboxylic acid The title compound (6.6 mg, 38%) was prepared according to General Procedure I using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-1H-indole-2-carboxylate (15 mg, 0.020 mmol) and 2-(chloromethyl)-4-methoxypyridine HCl salt (10 mg, 0.052 mmol) followed by saponification using General Procedure D. LCMS: $R_T$=1.883 min, MS (ES) 846.8 (M+H).

Example 477

(R)-7-(7-Chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-1-((6-methylpyridin-2-yl)methyl)-1H-indole-2-carboxylic acid The title compound (7.5 mg, 45%) was prepared according to General Procedure I using methyl (R)-7-(7-chloro- 10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-1H-indole-2-carboxylate (15 mg, 0.020 mmol) and 2-(chloromethyl)-6-methylpyridine (10 mg, 0.071 mmol) followed by saponification using General Procedure D. LCMS: $R_T$=1.895 min, MS (ES) 830.8 (M+H).

Example 478

(R)-7-(7-Chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-1-((5-methylpyridin-2-yl)methyl)-1H-indole-2-carboxylic acid The title compound (5.2 mg, 31%) was prepared according to General Procedure I using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-1H-indole-2-carboxylate (15 mg, 0.020 mmol) and 2-(chloromethyl)-5-methylpyridine HCl salt (10 mg, 0.056 mmol) followed by saponification using General Procedure D. LCMS: $R_T$=1.909 min, MS (ES) 830.8 (M+H).

Example 479

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(trifluoromethoxy)-1H-indole-2-carboxylic acid The title compound was prepared according to General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(trifluoromethoxy)-1H-indole-2-carboxylate (45 mg, 0.06 mmol) and MeI (16 mg, 0.11 mmol) followed by saponification using General Procedure D. LCMS: $R_T$=2.12 min, MS (ES) 796 (M+H).

Example 480

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4-methylpyridin-2-yl)methyl)-1H-indole-3-carboxylic acid ($2^{nd}$ Eluted Atropisomer, Absolute Configuration Underminded)

The title compound (7.2 mg, 45%) was prepared according to General Procedure G using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-J H-indole-3-carboxylate (15 mg, 0.02 mmol) and 2-(chloromethyl)-4-methylpyridine HCl (7 mg, 0.04 mmol) followed by saponification using General Procedure D. The title compound was isolate as the $2^{nd}$ eluting stereoisomer by reverse phase HPLC (Phenomenex Gemini C18, $H_2O/CH_3CN$ gradient to 40-900% MeCN 0.1% TFA). LCMS: $R_T$=1.888 min, MS (ES) 802.9 (M+H); $^1$H NMR (400 MHz, CDCl$_3$) δ 8.42 (d, J=5.6 Hz, 0.5H), 8.38 (d, J=5.6 Hz, 0.5H), 8.28 (t, J=8.0 Hz, 1H), 7.90 (s, 0.5H), 7.84 (s, 0.5H), 7.68-7.61 (m, 1H), 7.40-7.29 (m, 2H), 7.10-7.02 (m, 2H), 6.61 (s, 1H), 6.60 (s, 1H), 5.80-5.75 (m, 1H), 4.51-4.34 (m, 1H), 4.23-4.07 (m, 1H), 3.98 (s, 1.5H), 3.97 (s, 1.5H), 3.94-3.75 (m, 3H), 3.58-3.49 (m, 0.5H), 3.47-3.39 (m, 0.5H), 3.20-2.86 (m, 2H), 2.80-2.60 (m, 1H), 2.44 (s, 3H), 2.34 (s, 3H), 2.33 (s, 3H), 2.28 (s, 1.5H), 2.24 (s, 1.5H), 2.10 (s, 1.5H), 2.07 (s, 1.5H), 2.04-1.96 (m, 1H), 1.94-1.86 (m, 1H), 1.26 (d, J=6.8 Hz, 1.5H), 1.19 (d, J=6.8 Hz, 1.5H).

Example 481

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(pyridin-2-ylmethoxy)-1H-indole-2-carboxylic acid The title compound (3.6 mg, 33%) was prepared according to General Procedure H using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (10 mg, 0.013 mmol) and 2-(bromomethyl)pyridine HBr salt (10 mg, 0.040 mmol) followed by saponification using General Procedure D. LCMS: $R_T$=1.859 min, MS (ES) 818.8 (M+H).

Example 482

(R)-7-(7-Chloro-10-(3-(4-chloro-3,5-dimethylphenoxy)propyl)-6-(2-((dimethylamino)methyl)-4,6-dimethylpyrimidin-5-yl)-4-methyl-1-oxo-3,4-dihydropyrazino[1,2-a]indol-2(1H)-yl)-4-methoxy-1-(pyridin-2-ylmethyl)-1H-indole-2-carboxylic acid Step A. Preparation of methyl 7-iodo-4-methoxy-1H-indole-2-carboxylate A solution of methyl 4-(benzyloxy)-7-bromo-1H-indole-2-carboxylate (200 mg, 0.71 mmol), CuI (10 mg, 0.052 mmol), (trans)-N$^1$,N$^2$-dimethylcyclohexane-1,2-diamine (15 mg, 0.11 mmol), and NaI (250 mg, 1.67 mmol) in 1,4-dioxane (2 mL) was sparged with Ar for 5 min, then sealed and heated to 110° C. for 48 h. The reaction was cooled to RT and diluted with DCM (20 mL). The organic solution was washed with 10% aq. NH$_4$OH (20 mL), and the aqueous layer was extracted with DCM. The combined organic layer was dried and concentrated. The residue was purified by flash chromatography (Combi-flash Rf, Hex/EtOAc=0-100% gradient) to afford the title compound (196 mg, 84%). LCMS: $R_T$=1.433 min, MS (ES) 331.8 (M+H).

Step B. Preparation of methyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-4-methoxy-1H-indole-2-carboxylate The title compound (156 mg, 61%) was prepared according to General Procedure B using (R)-6-(2-((benzyloxy)methyl)-4,6-dimethylpyrimidin-5-yl)-7-chloro-10-(3-(4-chloro-3,5-dimethylphenoxy)propyl)-4-methyl-3,4-dihydropyrazino[1,2-a]indol-1(2H)-one (200 mg, 0.30 mmol) and methyl 7-iodo-4-methoxy-1H-indole-2-carboxylate (196 mg, 0.59 mmol). LCMS: $R_T$=2.293 min, MS (ES) 859.8 (M+H).

Step C. Preparation of methyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-4-methoxy-1-(pyridin-2-ylmethyl)-1H-indole-2-carboxylate The title compound (26 mg, 47%) was prepared according to General Procedure I using methyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-4-methoxy-1-(pyridin-2-ylmethyl)-1H-indole-2-carboxylate (50 mg, 0.058 mmol) and 2-(bromomethyl)pyridine HBr salt (40 mg, 0.16 mmol). LCMS: $R_T$=2.175 min, MS (ES) 950.8 (M+H).

Step D. Preparation of methyl (R)-7-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-4-methoxy-1-(pyridin-2-ylmethyl)-1H-indole-2-carboxylate The title compound was prepared following the procedure described Example 390 Step D using methyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-4-methoxy-1-(pyridin-2-ylmethyl)-1H-indole-2-carboxylate (26 mg, 0.027 mmol) and carried forward without further purification. LCMS: $R_T$=0.864 min, MS (ES) 860.8 (M+H) (LC method II).

Step E. Example 482

The title compound (4.0 mg, 33% 2 steps) was prepared according to General Procedure J using methyl (R)-7-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-4-methoxy-1-(pyridin-2-ylmethyl)-1H-indole-2-carboxylate (12 mg, 0.014 mmol) and dimethylamine HCl salt (25 mg, 0.31 mmol) followed by saponification using General Procedure D. LCMS: $R_T$=1.754 min, MS (ES) 873.9 (M+H).

Example 483

(R)-7-(7-Chloro-10-(3-(4-chloro-3,5-dimethylphenoxy)propyl)-6-(2-((dimethylamino)methyl)-4,6-dimethylpyrimidin-5-yl)-4-methyl-1-oxo-3,4-dihydropyrazino[1,2-a]indol-2(1H)-yl)-4-methoxy-1-methyl-1H-indole-2-carboxylic acid Step A. Preparation of methyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-4-methoxy-1-methyl-1H-indole-2-carboxylate The title compound (11 mg, 19%) was prepared according to General Procedure I using methyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-4-methoxy-1H-indole-2-carboxylate (50 mg, 0.058 mmol) and MeI (25 mg, 0.18 mmol). LCMS: $R_T$=2.386 min, MS (ES) 873.9 (M+H).

Step B. Preparation of methyl (R)-7-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-4-methoxy-1-methyl-5-(pyridin-2-yl)-1H-indole-2-carboxylate The crude title compound was prepared following the procedure described Example 390 Step D using methyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-4-methoxy-1-methyl-1H-indole-2-carboxylate (11 mg, 0.013 mmol). LCMS: $R_T$=2.101 min, MS (ES) 783.9 (M+H).

Step C. Example 483

The title compound (3.0 mg, 29% 2 steps) was prepared according to General Procedure J using methyl (R)-7-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-4-methoxy-1-(pyridin-2-ylmethyl)-1H-indole-2-carboxylate (10 mg, 0.013 mmol) and dimethylamine HCl salt (25 mg, 0.31 mmol) followed by saponification using General Procedure D. LCMS: $R_T$=1.860 min, MS (ES) 796.9 (M+H).

Example 484

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4-methylpyridin-2-yl)methyl)-1H-indole-3-carboxylic acid (1$^{st}$ Eluted Atropisomer, Absolute Configuration Undetermined)

The title compound (5.6 mg, 35%) was isolated as the 1$^{st}$ eluting stereoisomer along with Example 480. LCMS: $R_T$=1.870 min, MS (ES) 802.9 (M+H); $^1$H NMR (400 MHz, CDCl$_3$) δ 8.56-8.42 (m, 0.75H), 8.40-8.35 (m, 0.25H), 8.33-8.21 (m, 1H), 7.90 (s, 0.25H), 7.84 (s, 0.75H), 7.72-7.57 (m, 1H), 7.43-7.29 (m, 2H), 7.16-7.06 (m, 2H), 6.61 (s, 1H), 6.58 (s, 1H), 5.84-5.66 (m, 1H), 4.24-4.13 (m, 2H), 396 (s, 2H), 3.94 (s, 1H), 3.92-3.86 (m, 1H), 3.83-3.70 (m, 2H), 3.63-3.51 (m, 1H), 3.48-3.34 (m, 1H), 3.25-2.87 (m, 2H), 2.43 (s, 2H), 2.41 (s, 1H), 2.34 (s, 6H), 2.31 (s, 1H), 2.26 (s, 2H), 2.23 (s, 2H), 2.12-2.06 (m, 2H), 2.05 (s, 1H), 1.28-1.16 (m, 1H), 1.23-1.04 (m, 2H).

Example 485

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(cyclopropylmethoxy)-1-methyl-1H-indole-2-carboxylic acid The title compound (7.3 mg, 71%) was prepared according to General Procedure H using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (10 mg, 0.013 mmol) and (bromomethyl)cyclopropane (8 mg, 0.059 mmol) followed by saponification using General Procedure D. LCMS: $R_T$=2.337, 2.378 min, MS (ES) 781.9 (M+H).

Example 486

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-((2-(pyrrolidin-1-yl)ethyl)amino)-1H-indole-3-carboxylic acid Step A. Preparation of 1-(7-bromo-5-nitro-1H-indol-3-yl)-2,2,2-trifluoroethan-1-one To a solution of 7-bromo-5-nitro-1H-indole (1 g, 4.1 mmol) in DMF (12 mL) was added trifluoroacetic anhydride (3.3 mL, 16.4 mmol) at 0° C. The reaction mixture was warmed to RT and stirred for overnight then poured into brine and extracted with ethyl acetate. The organic layer was dried and concentrated. The residue was purified by flash chromatography (Combi-flash Rf, hex/EtOAc=0-100% gradient) to give the title compound. (1.30 g, 94%) $^1$H-NMR (DMSO-d$^6$) δ 8.98 (d, 1H, J=4 Hz), 8.7 (s, 1H), 8.43 (d, 1H, J=4 Hz), $^{19}$F NMR −75.2 (s)

Step B. Preparation of 7-bromo-5-nitro-1H-indole-3-carboxylic acid 1-(7-Bromo-5-nitro-1H-indol-3-yl)-2,2,2-trifluoroethan-1-one (1.30 g, 3.9 mmol) was refluxed in NaOH aq. solution (30 mL, 20%) for 2 h. The reaction mixture was cooled to RT and neutralized with conc. HCl. The mixture was extracted with EtOAc, and the organic layer was dried and concentrated to yield the title compound (0.9 g, 98%). $^1$H NMR (DMSO-d$^6$) δ 8.90 (d, 1H, J=4 Hz), 8.30 (s, 1H), 8.27 (d, 1H, J=4 Hz).

Step C. Preparation of methyl 7-bromo-5-nitro-1H-indole-3-carboxylate

To a suspension of 7-bromo-5-nitro-1H-indole-3-carboxylic acid (0.9 g, 3.8 mmol) in MeOH (30 mL) was added $H_2SO_4$ (0.3 mL). The reaction mixture was refluxed for overnight then concentrated. The residue was dissolved in EtOAc, washed with sat. NaHCO$_3$ aq. Solution, dried and concentrated to yield the title compound. (0.8 g, 84%). $^1$H NMR (DMSO-d$^6$) δ 8.82 (d, 1H, J=4 Hz), 8.31 (s, 1H), 8.20 (d, 1H, J=4 Hz), 3.85 (s, 3H).

Step D. Preparation of methyl 7-bromo-1-methyl-5-nitro-1H-indole-3-carboxylate

The title compound (0.75 g, 89%) was prepared following General Procedure G using methyl 7-bromo-5-nitro-1H-indole-3-carboxylate (0.8 g, 2.7 mol) in DMF (10 mL) and MeI (340 μL, 5.4 mmol). $^1$H NMR (DMSO-d$^6$) δ 8.87 (d, 1H, J=4 Hz), 8.48 (s, 1H), 8.27 (d, 1H, J=4 Hz), 4.24 (s, 3H), 3.88 (s, 3H).

Step E. Preparation of methyl 5-amino-7-bromo-1-methyl-1H-indole-3-carboxylate

To a solution of methyl 7-bromo-1-methyl-5-nitro-1H-indole-3-carboxylate (0.75 g, 2.4 mmol) in 1,4-dioxane (60 mL) was added HCl aq. solution (30 mL, 1.2 N) followed by Tin chloride (2.7 g, 1.2 mmol). The reaction mixture was refluxed for 3 h, cooled to RT, neutralized with NaOH and extracted with EtOAc. The organic layer was dried, concentrated and the residue was purified by flash chromatography (Combi-flash Rf, DCM/MeOH=0-15% gradient) to give the title compound (0.55 g, 82%). $^1$H NMR (DMSO-d$^6$) δ 7.96 (d, 1H, J=4 Hz), 7.22 (s, 1H), 6.81 (d, 1H, J=4 Hz), 5.0 (broad s, 2H), 4.00 (s, 3H), 3.76 (s, 3H).

Step F. Preparation of methyl 7-bromo-5-((tert-butoxycarbonyl)amino)-1-methyl-1H-indole-3-carboxylate To a solution of methyl 5-amino-7-bromo-1-methyl-1H-indole-3-carboxylate (0.55 g, 2.0 mmol) in THF (5 mL) was added 1.2 N aq. NaOH aq. solution (5 mL, 6.0 mM) and (Boc)$_{2O}$ (920 mg, 4.0 mmol). The reaction mixture was stirred overnight at RT then quenched with MeOH and water (50 mL). The mixture was extracted with EtOAc and the combined organic layer was dried, concentrated and the residue was purified by flash chromatography (Combi-flash Rf, hex/EtO=0-100% gradient) to give the title compound (0.60 g, 81%). $^1$H NMR (DMSO-d$^6$) δ 9.42 (broad s, 1H), 8.23 (d, 1H, J=4 Hz), 8.12 (s, 1H), 7.60 (d, 1H, J=4 Hz), 4.11 (s, 3H), 3.79 (s, 3H), 1.49 (s, 9H).

Step G. Preparation of methyl (R)-5-((tert-butoxycarbonyl)amino)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylate The title compound (400 mg, 78%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (330 mg, 0.6 mmol) and methyl 7-bromo-5-((tert-butoxycarbonyl)amino)-1-methyl-1H-indole-3-carboxylate (350 mg, 0.9 mmol). MS (ES) 841.2 (M+H).

Step H. Example 486

To a solution of methyl (R)-5-((tert-butoxycarbonyl)amino)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylate (40 mg, 0.047 mol) in DMF (2 mL) was added NaH (60%, 3.8 mg, 0.094 mol) under $N_2$ at 0° C. and stirred for 10 min. 1-(2-Bromoethyl)pyrrolidine (14.5 mg, 0.080 mmol) was added and the mixture was stirred for 10 min at 0° C. then at RT for 1 h. The reaction mixture was diluted with EtOAc (20 mL), washed with brine (2×10 mL), dried, filtered and concentrated. The residue was purified by flash chromatography (Combi-flash Rf, DCM/MeOH=0-10% gradient). The purified intermediate was dissolved in 4N HCl in 1,4-dioxane and the reaction mixture was heated at 60° C. for 5 h then concentrated. The residue was dissolved in a mixture of 1,4-dioxane and MeOH (4 mL, 1:1) and aq. NaOH solution (2M, 1 mL) was added. The reaction was stirred for 3 h at RT then neutralized with aq. HCl (1.2M). The mixture was concentrated and purified by HPLC (Phenomenex Gemini C18, $H_2O$/CH$_3$CN gradient from 50% to 95% CH$_3$CN for 4 min, 0.1% TFA) to give the title compound. MS (ES) 824.2 (M+H)

Example 487

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(pyridin-3-ylmethoxy)-1H-indole-2-carboxylic acid The title compound (7.1 mg, 66%) was prepared according to General Procedure H using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (10 mg, 0.013 mmol) and 3-(chlorrmethyl)pyridine HCl salt (8 mg, 0.049 mmol) followed by saponification using General Procedure D. LCMS: $R_T$=1.913, 1.944 min, MS (ES) 818.8 (M+H).

Example 488

(R)-7-chloro-10-(3-(4-chloro-3,5-dimethylphenoxy)propyl)-6-(4-hydroxy-2,6-dimethylphenyl)-4-methyl-3,4-dihydropyrazino[1,2-a]indol-1(2H)-one

Step A. Preparation of ethyl-6-chloro-3-(3-(4-chloro-3,5-dimethylphenoxy)propyl)-7-(4-(methoxymethoxy)-2,6-dimethylphenyl)-1H-indole-2-carboxylate Ethyl-7-bromo-6-chloro-3-(3-((4-chloro-3,5-dimethylhexa-2,4-dien-1-yl)oxy)propyl)-1H-indole-2-carboxylate (1.6 g, 3.0 mmol), $Pd_2(dba)_3$ (550 g, 0.6 mmol), Sphos (0.62 g, 1.5 mmol), $K_2CO_3$ (1.24 g, 9 mmol) and (4-(methoxymethoxy)-2,6-dimethylphenyl)boronic acid (1.26 g, 6.0 mmol) were dissolved in 1,4-dioxane (10 mL) and water (2 mL). The mixture was sparged with Ar for 5 min then irradiated under microwave for 1 h at 110° C. in Biotage Initiator. The reaction mixture was cooled to RT, diluted with EtOAc/water (80 mL, 1:1). The aqueous layer was extracted with EtOAc, and the combined organic layer was dried over $MgSO_4$ and concentrated in vacuo. The residue was purified by flash chromatography (Combi-flash Rf, Hex/EtOAc=0-60% gradient) to give the title compound. (1.5 g, 85%). $^1$H-NMR (CDCl$_3$) δ 8.24 (s, 1H), 7.62 (d, 1H, J=8 Hz), 7.24 (d, 1H, J=8 Hz), 6.91 (s, 2H), 6.64 (s, 1H), 6.55 (s, 1H), 5.27 (s, 2H) 5.27 (q, 2H, J$_1$=12 Hz, J$_2$=8 Hz), 4.01 (tr, 1H, J=8 Hz), 3.58 (s, 3H), 3.29 (tr, 2H, J=4 Hz), 2.36 (s, 3H), 2.30 (s, 3H), 2.19 (tr, 2H, J=4 Hz), 1.98 (s, 6H), 1.41 (tr, 3H, J=8 Hz).

Step B. Preparation of ethyl (R)-1-(1-((tert-butoxycarbonyl)amino)propan-2-yl)-6-chloro-3-(3-(4-chloro-3,5-dimethylphenoxy)propyl)-7-(4-(methoxymethoxy)-2,6-dimethylphenyl)-1H-indole-2-carboxylate To a solution of ethyl-6-chloro-3-(3-(4-chloro-3,5-dimethylphenoxy)propyl)-7-(4-(methoxymethoxy)-2,6-dimethylphenyl)-1H-indole-2-carboxylate (1.45 g, 0.0025 mol) in MeCN (30 mL) was added $Cs_2CO_3$ (1.2 g, 0.0037 mol) and tert-butyl (S)-5-methyl-1,2,3-oxathiazolidine-3-carboxylate 2,2-dioxide (0.88 gr, 0.0037 mol), and the mixture was stirred at 80° C. for overnight. Additional $Cs_2CO_3$ (0.5 eq) and tert-butyl (S)-5-methyl-1,2,3-oxathiazolidine-3-carboxylate 2,2-dioxide (0.5 eq) were added to the reaction and stirred for additional 6 h at 80° C. The reaction mixture was concentrated to half of its original volume then diluted with EtOAc (150 mL). The solution was washed with brine, dried and concentrated to give the crude title compound. It was used for the next step without purification. $^1$H-NMR (CDCl$_3$) δ 7.59 (d, 1H, J=8 Hz), 7.24 (d, 1H, J=8 Hz), 6.92 (s, 2H), 6.53 (s, 2H), 5.27 (s, 2H) 4.41 (q, 2H, J$_1$=12 Hz, J$_2$=8 Hz), 4.12-4.10 (m, 1H), 4.01 (tr, 1H, J=8 Hz), 3.83-3.81 (m, 1H), 3.73-3.71 (m, 1H), 3.54 (s, 3H), 3.17 (m, 1H), 2.34 (s, 6H), 2.16 (tr, 2H, J=4 Hz), 2.06 (s, 3H), 2.00 (s, 3H), 2.19 (tr, 2H, J=4 Hz), 1.46 (tr, 3H, J=8 Hz), 1.38 (s, 9H), 1.20 (d, 3H, J=8 Hz).

Step C. Preparation of (R)-7-Chloro-10-(3-(4-chloro-3,5-dimethylphenoxy)propyl)-6-(4-(methoxymethoxy)-2,6-dimethylphenyl)-4-methyl-3,4-dihydropyrazino[1,2-a]indol-1(2H)-one Ethyl (R)-1-(1-((tert-butoxycarbonyl)amino)propan-2-yl)-6-chloro-3-(3-(4-chloro-3,5-dimethylphenoxy)propyl)-7-(4-(methoxymethoxy)-2,6-dimethylphenyl)-1H-indole-2-carboxylate was dissolved in 1,4-dioxane (10 mL) and TFA (1.9 mL, 0.025 mol) and the reaction mixture was heated at 70° C. for overnight, then concentrated. The residue was purified by flash chromatography (Combi-flash Rf, Hex/EtOAc=0-50% gradient) to give the title compound (1.1 gr, 74% for 2 steps). $^1$H-NMR (CDCl$_3$) δ 7.66 (d, 1H, J=8 Hz), 7.24 (d, 1H, J=8 Hz), 6.90 (d, 1H, J=4 Hz), 6.86 (d, 1H, J=4 Hz), 6.65 (s, 2H), 5.84 (broad s, 1H) 5.25 (s, 2H), 3.79 (tr, 2H, J=4 Hz), 4.01-3.78 (m, 1H), 3.68 (dd, 1H, J$_1$=2 Hz, J$_2$=12 Hz), 3.56 (s, 3H), 3.42-3.38 (m, 2H), 3.34-3.11 (m, 1H), 2.35 (s, 6H), 2.23 (tr, 2H, J=4 Hz), 2.11 (s, 3H), 2.06 (s, 3H), 1.02 (d, 3H, J=8 Hz).

Step D. Example 488

(R)-7-Chloro-10-(3-(4-chloro-3,5-dimethylphenoxy)propyl)-6-(4-(methoxymethoxy)-2,6-dimethylphenyl)-4-methyl-3,4-dihydropyrazino[1,2-a]indol-1(2H)-one was dissolved in 1,4-dioxane (2 mL) and 4N HCl in 1,4-dioxane (20 μL) and stirred at 50° C. for overnight. The reaction mixture was concentrated and the residue was purified by HPLC (Phenomenex Gemini C18, $H_2O/CH_3CN$ gradient from 50% to 95% $CH_3CN$ for 4 min, 0.1% TFA) to give the title compound. $^1$H-NMR (CDCl$_3$) δ 7.65 (d, 1H, J=8 Hz), 7.24 (d, 1H, J=8 Hz), 6.73 (d, 1H, J=4 Hz), 6.69 (d, 1H, J=4 Hz), 6.68 (d, 1H, J=4 Hz) 6.65 (s, 2H), 5.79 (broad s, 1H), 4.04 (tr, 2H, J=4 Hz), 4.01-3.78 (m, 1H), 3.68 (dd, 1H, 31=2 Hz, J=12 Hz), 3.45-3.35 (m, 2H), 3.13-3.10 (m, 1H), 3.09 (s, 6H), 2.23 (tr, 2H, J=4 Hz), 2.23 (s, 3H), 1.87 (s, 3H), 1.02 (d, 3H, J=8 Hz); MS (ES) 551.3 (M+H).

Example 489

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-pyrrolo[3,2-b]pyridine-5-carboxylic acid

Step A. Preparation of methyl 3-bromo-1-methyl-1H-pyrrolo[3,2-b]pyridine-5-carboxylate The title compound (72 mg, 95%) was prepared following General Procedure F using 1H-pyrrolo[3,2-b]pyridine-6-carboxylic acid (46 mg, 0.28 mmol) and MeI (53 μL, 0.85 mmol). LCMS: $R_T$=1.704 min, MS (ES) 268.3 (M+H).

Step B. Example 489

The title compound (18 mg, 50%) was prepared according to General Procedure I using (R)-7-chloro-10-(3-(4-chloro- 3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and methyl 3-bromo-1-methyl-1H-pyrrolo[3,2-b]pyridine-5-carboxylate (16.1 mg, 0.06 mmol) followed by saponification using General Procedure D. LCMS: $R_T$=1.894 MS (ES) 712.9 (M+H); $^1$H NMR (500 MHz, DMSO-d$_6$) δ 8.14 (d, J=8.1 Hz, 1H), 8.08 (d, J=8.1 Hz, 1H), 7.93 (d, J=8.7 Hz, 1H), 7.74 (d, J=8.7 Hz, 1H), 7.27 (d, J=8.0 Hz, 1H), 6.73 (s, 2H), 4.51 (d, J=13.1 Hz, 1H), 4.47 (d, J=13.1 Hz, 1H), 4.39-4.28 (m, 1H), 4.00-3.92 (m, 2H), 3.88 (s, 3H), 3.78 (s, 1.5H), 3.77 (s, 1.5H), 3.40-3.30 (m, 1H), 3.28-3.18 (m, 1H), 2.24 (s, 6H), 2.11 (s, 1.5H), 2.09-2.04 (m, 2H), 2.02 (s, 1.5H), 1.96 (s, 1.5H), 1.87 (s, 1.5H), 1.15 (d, J=6.3 Hz, 1.5H), 1.12 (d, J=6.3 Hz, 1.5H).

Example 490

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-((4-methylpiperazin-1-yl)methyl)-1H-indole-3-carboxylic acid Step A. Preparation of ethyl 7-bromo-1,5-dimethyl-1H-indole-3-carboxylate To a solution of 7-bromo-5-methyl-1H-indole (100 mg, 0.45 mmol) in DMF (3 mL) was added K$_2$CO$_3$ (435 mg, 3.15 mmol) and MeI (60 μL, 135 mg, 0.90 mmol). The reaction mixture was stirred at 60° C. for 4 h then quenched with sat. NH$_4$Cl aq. solution and extracted with DCM. The combined organic layer was dried over MgSO$_4$, filtered and concentrated. The residue was dissolved in toluene (0.4 mL), and ethylchloroformate (46 μL, 52.3 mg, 0.48 mmol) and Me$_2$AlCl (0.4 mL, 0.4 mmol, 1.0 M solution in hexanes) were added. The reaction mixture was stirred at RT for 15 min then quenched with sat. NH$_4$Cl aq. solution and extracted with EtOAc. The combined organic layer was dried over MgSO$_4$, filtered, and concentrated. The residue was purified by flash chromatography (Combi-flash Rf, Hex/EtOAc=0-1100% gradient) to afford the title compound (110 mg, 93% 2 steps). LCMS: $R_T$=1.770 min, MS (ES) 295.9 (M+H).

Step B. Preparation of ethyl 7-bromo-5-(bromomethyl)-1-methyl-1H-indole-3-carboxylate To a solution of ethyl 7-bromo-1,5-dimethyl-1H-indole-3-carboxylate (110 mg, 0.37 mmol) in CCl$_4$ (4 mL) was added AIBN (15.2 mg, 0.093 mmol) and NBS (66 mg, 0.37 mmol) at 60° C. The reaction mixture was refluxed for 3 h then concentrated. The residue was purified by flash chromatography (Combi-flash Rf, Hex/EtOAc=0-100% gradient) to afford the title compound (120 mg, 90%). LCMS: $R_T$=1.772 min, MS (ES) 375.9 (M+H).

Step C. Preparation of ethyl 5-(acetoxymethyl)-7-bromo-1-methyl-1H-indole-3-carboxylate To a solution of ethyl 7-bromo-5-(bromomethyl)-1-methyl-1H-indole-3-carboxylate (31 mg, 0.083 mmol) in DMF (0.8 mL) was added NaOAc (13.6 mg, 0.166 mmol), and the reaction mixture was stirred at RT for 24 h. The reaction was quenched with sat. NH$_4$Cl aq. solution and extracted with DCM. The combined organic layer was dried and concentrated. The residue was purified by flash chromatography (Combi-flash Rf. Hex/EtOAc=0-100% gradient) to afford the title compound (25 mg, 85%). LCMS: $R_T$=1.620 min, MS (ES) 375.9 (M+Na); $^1$H NMR (400 MHz, CDCl$_3$) δ 8.08 (d, J=1.2 Hz, 1H), 7.64 (s, 1H), 7.35 (d, J=1.3 Hz, 1H), 5.09 (s, 2H), 4.30 (q, J=7.1 Hz, 2H), 4.10 (s, 3H), 2.04 (s, 3H), 1.34 (t, J=7.1 Hz, 3H).

Step D. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-3-carboxylate The title compound (8 mg, 32% yield) was prepared following General Procedure A using ethyl 5-(acetoxymethyl)-7-bromo-1-methyl-1H-indole-3-carboxylate (12 mg, 0.033 mmol) and (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (18.3 mg, 0.033 mmol). LCMS: $R_T$=2.031, 2.055 min, MS (ES) 769.9 (M+H).

Step E. Example 490

To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-3-carboxylate (20 mg, 0.026 mmol) in DCM (0.2 mL) was added 4 Å molecular sieves (50 mg) and PCC (12 mg, 0.052 mmol), and the reaction mixture was stirred at rt for 30 min then quenched with sat. NH$_4$Cl aq. solution and extracted with DCM. The combined organic layer was dried and concentrated. The residue was re-dissolved in DCM (0.2 mL) and Et$_3$N (0.03 mL) then N-methyl piperazine (2 μL, 1.7 mg, 0.017 mmol) and Na(OAc)$_3$BH (5.9 mg, 0.028 mmol) were added. The reaction mixture was stirred at rt for 4 h then quenched with sat. NaHCO$_3$ aq. solution and extracted with DCM. The combined organic layer was dried and concentrated. Subsequent saponification was carried out following General Procedure D. The crude was purified by reverse phase HPLC (Phenomenex Gemini C18, H$_2$O/CH$_3$CN gradient 35-95% MeCN, 0.1% TFA) to afford the title compound (2.1 mg, 10%, 3 steps). LCMS: $R_T$=1.809 min, MS (ES) 823.9 (M+H).

Example 491

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((6-methylpyridin-2-yl)methyl)-1H-indole-3-carboxylic acid (2$^{nd}$ Eluted Atropisomer, Absolute Configuration Underminded)

The title compound (6.8 mg, 42%) was prepared according to General Procedure G using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate (15 mg, 0.02 mmol) and 2-(chloromethyl)-6-methylpyridine (6 mg, 0.04 mmol) followed by saponification using General Procedure D. The title compound was isolate as the 2$^{nd}$ eluting stereoisomer by reverse phase HPLC (Phenomenex Gemini C18, H$_2$O/CH$_3$CN gradient to 40-90% MeCN 0.1% TFA). LCMS: $R_T$=1.917 min, MS (ES) 802.9 (M+H).

Example 492

(R)-7-(7-Chloro-10-(3-(4-chloro-3,5-dimethylphenoxy)propyl)-6-(4,6-dimethyl-2-((4-methylpiperazin-1-yl)methyl)pyrimidin-5-yl)-4-methyl-1-oxo-3,4-dihydropyrazino[1,2-a]indol-2(1H)-yl)-4-methoxy-1-(pyridin-2-ylmethyl)-1H-indole-2-carboxylic acid The title compound (4.7 mg, 34% 2 steps) was prepared according to General Procedure J using methyl (R)-7-(7-chloro-10-(3-(4-chloro-3,5-dimethylphenoxy)propyl)-6-(2-(hydroxymethyl)-4,6-dimethylpyrimidin-5-yl)-4-methyl-1-oxo-3,4-dihydropyrazino[1,2-a]indol-2(1H)-yl)-4-methoxy-1-(pyridin-2-ylmethyl)-1H-indole-2-carboxylate (13 mg, 0.015 mmol) and N-methylpiperazine (30 mg, 0.30 mmol) followed by saponification using General Procedure D. LCMS: $R_T$=1.771 min, MS (ES) 928.8 (M+H).

Example 493

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-1-(2-methoxyethyl)-1H-indole-2-carboxylic acid The title compound (8.3 mg, 52%) was prepared according to General Procedure I using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-1H-indole-2-carboxylate (15 mg, 0.020 mmol) and 1-bromo-2-methoxyethane (5 mg, 0.036 mmol) followed by saponification using General Procedure D. LCMS: $R_T$=2.048 min, MS (ES) 783.8 (M+H).

Example 494

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((6-methylpyridin-2-yl)methyl)-1H-indole-3-carboxylic acid (1$^{st}$ Eluted Atropisomer, Absolute Configuration Undeterminded)

The title compound (4.2 mg, 26%) was isolated along with Example 491 as a separated atropisomer (1$^{st}$ fraction, absolute stereochemistry undeterminded). LCMS: $R_T$=1.888 min, MS (ES) 802.9 (M+H).

Example 495

(R)-7-Bromo-5-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)-1-methyl-1H-indole-3-carboxylic acid The title compound (4.6 mg, 10%, 2 steps) was isolated along with ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-3-carboxylate from Example Step D as a byproduct followed by saponification following General Procedure D. LCMS: $R_T$=2.173, 2.227 min, MS (ES) 805.7 (M+H).

Example 496

(R)-3-(7-chloro-10-(3-(4-chloro-3,5-dimethylphenoxy)propyl)-6-(4-hydroxy-2,6-dimethylphenyl)-4-methyl-1-oxo-3,4-dihydropyrazino[1,2-a]indol-2(1H)-yl)-1-methyl-1H-indole-5-carboxylic acid Step A. Preparation of methyl-(R)-3-(7-chloro-10-(3-(4-chloro-3,5-dimethylphenoxy) propyl)-6-(4-(methoxymethoxy)-2,6-dimethylphenyl)-4-methyl-1-oxo-3,4-dihydropyrazino[1,2-a]indol-2(1H)-yl)-1-methyl-1H-indole-5-carboxylate The title compound (160 mg, 86%) was prepared following General Procedure B using (R)-7-chloro-10-(3-(4-chloro-3,5-dimethylphenoxy)propyl)-6-(4-(methoxymethoxy)-2,6-dimethylphenyl)-4-methyl-3,4-dihydropyrazino[1,2-a]indol-1(2H)-one (120 mg, 2.0 mmol) and methyl 3-bromo-1-methyl-1H-indole-5-carboxylate (110 mg, 4.0 mol). MS (ES) 782.4 (M+H).

Step B. Example 496

The title compound (16 mg, 86%) was prepared following the procedure described Example 488 Step D using methyl-(R)-3-(7-chloro-10-(3-(4-chloro-3,5-dimethylphenoxy) propyl)-6-(4-(methoxymethoxy)-2,6-dimethylphenyl)-4-methyl-1-oxo-3,4-dihydropyrazino[1,2-a]indol-2(1H)-yl)-1-methyl-1H-indole-5-carboxylate (20 mg, 0.026 mmol) followed by saponification following General Procedure D. $^1$H-NMR (DMSO-d$^6$) δ 9.45 (broad s, 1H), 8.09 (s, 1H), 7.95 (s, 1H), 7.80 (d, 1H, J=8 Hz), 7.75 (d, 1H, J=8 Hz), 7.55 (d, 1H, J=8 Hz), 7.50 (s, 1H), 7.30 (d, 1H, J=8 Hz), 6.72 (s, 2H), 6.65 (d, 1H, J=8 Hz), 4.38 (dd, 1H, $J_1$=2 Hz, $J_2$=12 Hz), 3.97 (tr, 2H, J=4 Hz), 3.82 (s, 3H), 3.62 (m, 1H), 3.68 (dd, 1H, $J_1$=2 Hz, $J_2$=12 Hz), 3.45-3.35 (m, 1H), 2.27 (s, 6H), 2.06 (tr, 2H, J=4 Hz), 1.96 (s, 3H), 1.82 (s, 3H), 1.01 (d, 3H, J=8 Hz); MS (ES) 724.2 (M+H).

Example 497

(R)-3-(7-chloro-10-(3-(4-chloro-3,5-dimethylphenoxy)propyl)-6-(2,6-dimethyl-4-(pyridin-2-ylmethoxy)phenyl)-4-methyl-1-oxo-3,4-dihydropyrazino[1,2-a]indol-2(1H)-yl)-1-methyl-1H-indole-5-carboxylic acid Step A. Preparation of methyl 3-((R)-7-chloro-10-(3-(4-chloro-3,5-dimethylphenoxy)propyl)-6-(4-hydroxy-2,6-dimethylphenyl)-4-methyl-1-oxo-3,4-dihydropyrazino[1,2-a]indol-2(1H)-yl)-1-methyl-3a,7a-dihydro-1H-indole-5-carboxylate The title compound (140 mg, 93%) was prepared following the procedure described Example 488 Step D using methyl 3-((R)-7-chloro-10-(3-(4-chloro-3,5-dimethylphenoxy) propyl)-6-(4-(methoxymethoxy)-2,6-dimethylphenyl)-4-methyl-1-oxo-3,4-dihydropyrazino[1,2-a]indol-2(1H)-yl)-1-methyl-3a,7a-dihydro-1H-indole-5-carboxylate (160 mg, 0.2 mmol). $^1$H-NMR (CDCl$_3$) δ 8.27 (s, 1H), 7.95 (d, 1H, J=8 Hz), 7.67 (d, 1H, J=8 Hz), 7.37 (d, 1H, J=8 Hz), 6.73 (d, 1H, J=4 Hz), 6.69 (d, 1H, J=4 Hz) 6.63 (s, 2H), 4.34 (dd, 1H, $J_1$=2 Hz, $J_2$=12 Hz), 4.00 (tr, 2H, J=4 Hz), 3.79 (s, 3H), 3.80 (m, 2H), 3.62 (dd, 1H, $J_1$=2 Hz, $J_2$=12 Hz), 3.45-3.35 (m, 1H), 2.35 (s, 6H), 2.23 (tr, 2H, J=4 Hz), 2.09 (s, 3H), 1.95 (s, 3H), 1.22 (d, 3H, J=8 Hz).

Step B. Example 497

To a solution of methyl 3-((R)-7-chloro-10-(3-(4-chloro-3,5-dimethylphenoxy)propyl)-6-(4-hydroxy-2,6-dimethylphenyl)-4-methyl-1-oxo-3,4-dihydropyrazino[1,2-a]indol-2(1H)-yl)-1-methyl-3a,7a-dihydro-1H-indole-5-carboxylate (20 mg, 0.027 mol) in anhydrous DMF (2 mL) was added NaH (60%, 3.8 mg, 0.094 mol) at 0° C. under $N_2$ atmosphere. The reaction mixture was stirred for 10 min then 2-(bromomethyl)pyridine (7.9 mg, 0.046 mmol) was added. The reaction mixture was stirred at 0° C. for 10 min then warmed to RT and stirred for additional 1 h. The reaction mixture was diluted with ethyl acetate (20 mL), washed with brine, dried and concentrated. The residue was dissolved in a mixture of 1,4-dioxane and MeOH (4 mL, 1:1) and aq. NaOH (2M, 1 mL) solution was added. The reaction was stirred for 5 h at RT then neutralized with aq. HCl (1.2M). The mixture was concentrated and purified by reverse phase HPLC (Phenomenex Gemini C18, $H_2O$/$CH_3CN$ gradient to 45-95% MeCN 0.1% TFA) to give the title compound. $^1$H-NMR (DMSO-$d_6$) δ 8.61 (s, 1H), 8.10 (d, 1H, J=2 Hz), 7.93-7.91 (m, 1H), 7.80-7.78 (m, 1H), 7.77 (d, 1H, J=8 Hz), 7.63 (m, 1H), 7.56 (d, 1H, J=8 Hz), 7.51 (s, 1H), 7.39 (m, 1H), 7.32 (d, 1H, J=8 Hz), 7.29 (s, 1H), 6.97 (s, 1H), 6.72 (s, 2H), 5.52 (s, 2H), 4.39 (dd, 1H, $J_1$=2 Hz, $J_2$=12 Hz), 4.03 (tr, 2H, J=4 Hz), 3.82 (s, 3H), 3.75 (m, 2H), 3.48 (dd, 1H, $J_1$=2 Hz, $J_2$=12 Hz), 3.45-3.35 (m, 1H), 2.24 (s, 6H), 2.07 (tr, 2H, J=4 Hz), 1.89 (s, 3H), 1.82 (s, 3H), 1.08 (d, 3H, J=8 Hz); MS (ES) 815.3 (M+H).

Example 498

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((2-(dimethylamino)ethyl)amino)-1-methyl-1H-indole-3-carboxylic acid The title compound was prepared following the procedure described Example 486 Step H using methyl (R)-5-((tert-butoxycarbonyl)amino)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylate (40 mg, 0.047 mol) and 2-bromo-N,N-dimethylethan-1-amine (12.3 mg, 0.080 mmol). MS (ES) 798.2 (M+H).

Example 499

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((6-morpholinopyridin-2-yl)methyl)-1H-indole-2-carboxylic acid Step A. Preparation of ethyl (R)-1-((6-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate The title compound (167 mg, 91%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (150 mg, 0.20 mmol) and 2-bromo-6-(bromomethyl)pyridine (102 mg, 0.41 mmol). LCMS: $R_T$=2.37 min, MS (ES) 909 (M+H).

Step B. Example 499

A solution of ethyl (R)-1-((6-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (25 mg, 0.03 mmol) in morpholine (0.5 mL) was stirred at 110° C. for overnight. The reaction mixture was diluted with water and EtOAc. The aqueous layer was extracted with EtOAc. The combined organic layer was dried and concentrated. The residue was saponified following General Procedure D to give the title compound (15 mg, 56%) as TFA salt. LCMS: $R_T$=2.05 min, MS (ES) 888 (M+H); $^1$H NMR (400 MHz, DMSO-$d_6$) δ 7.74 (d, J=8.6 Hz, 1H), 7.54 (s, 1H), 7.37 (s, 1H), 7.29-7.34 (m, 2H), 6.83 (m, 1H), 6.77 (s, 2H), 6.50 (m, 1H), 6.22 (m, 1H), 5.58 (m, 1H), 5.25 (m, 1H), 4.59 (m, 1H), 4.05 (m, 2H), 3.8 (m, 1H), 3.72 (s, 1.5H), 3.69 (s, 1.5H), 3.37-3.40 (m, 1H), 3.13-3.26 (m, 4H), 2.98-3.08 (m, 2H), 2.90-2.96 (m, 2H), 2.65-2.72 (m, 2H), 2.36 (s, 3H), 2.22 (s, 6H), 2.04 (s, 3H), 1.77-1.94 (m, 5H), 1.02 (m, 3H).

Example 500

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((4-morpholinopyridin-2-yl)methyl)-1H-indole-2-carboxylic acid Step A. Preparation of ethyl (R)-1-((4-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate The title compound (104 mg, 85%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (150 mg, 0.20 mmol) and 4-bromo-2-(chloromethyl)pyridine. LCMS: $R_T$=2.33 min, MS (ES) 909 (M+H).

Step B. Example 500

The title compound (18 mg, 66%) was prepared following the procedure described in Example 499 Step B using ethyl (R)-1-((4-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (25 mg, 0.03 mmol). LCMS: $R_T$=1.96 min, MS (ES) 888 (M+H).

Example 501

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((5-methylpyridin-2-yl)methyl)-1H-indole-3-carboxylic acid (1$^{st}$ Eluted Atropisomer, Absolute Configuration Undetermined)

The title compound (5.9 mg, 37%) was prepared according to General Procedure I using methyl (R)-7-(7-chloro- 10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate (15 mg, 0.02 mmol) and 2-(chloromethyl)-5-methylpyridine hydrochloride (3.5 mg, 0.04 mmol) followed by saponification using General Procedure D. The title compound was isolate as the 1$^{st}$ eluting stereoisomer by reverse phase HPLC (Phenomenex Gemini C18, H$_2$O/CH$_3$CN gradient to 40-90% MeCN 0.1% TFA). LCMS: R$_T$=2.047 min, MS (ES) 802.9 (M+H).

Example 502

(R)-7-chloro-10-(3-(4-chloro-3,5-dimethylphenoxy)propyl)-6-(4,6-dimethyl-2-((4-methylpiperazin-1-yl)methyl)pyrimidin-5-yl)-4-methyl-2-(1-methyl-5-(1-methyl-1H-1,2,4-triazol-3-yl)-1H-indol-3-yl)-3,4-dihydropyrazino[1,2-a]indol-1(2H)-one Step A. Preparation of (R)-6-(2-((benzyloxy)methyl)-4,6-dimethylpyrimidin-5-yl)-7-chloro-10-(3-(4-chloro-3,5-dimethylphenoxy)propyl)-4-methyl-2-(1-methyl-5-(1-methyl-1H-1,2,4-triazol-3-yl)-1H-indol-3-yl)-3,4-dihydropyrazino[1,2-a]indol-1(2H)-one The title compound (60 mg, 76%) was prepared following General Procedure B using (R)-6-(2-((benzyloxy)methyl)-4,6-dimethylpyrimidin-5-yl)-7-chloro-10-(3-(4-chloro-3,5-dimethylphenoxy)propyl)-4-methyl-3,4-dihydropyrazino[1,2-a]indol-1(2H)-one (60 mg, 0.090 mmol) and 3-iodo-1-methyl-5-(1-methyl-1H-1,2,4-triazol-3-yl)-1H-indole (62 mg, 0, 18 mmol). LCMS: R$_T$=2.166 min, MS (ES) 867.9 (M+H).

Step B. Preparation of (R)-7-chloro-10-(3-(4-chloro-3,5-dimethylphenoxy)propyl)-6-(2-(hydroxymethyl)-4,6-dimethylpyrimidin-5-yl)-4-methyl-2-(1-methyl-5-(1-methyl-1H-1,2,4-triazol-3-yl)-1H-indol-3-yl)-3,4-dihydropyrazino[1,2-a]indol-1(2H)-one To a solution of (R)-6-(2-((benzyloxy)methyl)-4,6-dimethylpyrimidin-5-yl)-7-chloro-10-(3-(4-chloro-3,5-dimethylphenoxy)propyl)-4-methyl-2-(1-methyl-5-(1-methyl-1H-1,2,4-triazol-3-yl)-1H-indol-3-yl)-3,4-dihydropyrazino[1,2-a]indol-1(2H)-one (600 mg, 0.070 mmol) in MeOH (4.6 mL) was added HCl solution (1 mL) followed by Pd/C (50 mg). The reaction mixture was stirred at RT for 20 h under Hz atmosphere. The reaction mixture was filtered, and the filtrate was concentrated. The crude title compound (45 mg) was used for the next step without further purification. LCMS: R$_T$=1.961 min, MS (ES) 777.9 (M+H).

Step C. Preparation of (R)-(5-(7-chloro-10-(3-(4-chloro-3,5-dimethylphenoxy)propyl)-4-methyl-2-(1-methyl-5-(1-methyl-1H-1,2,4-triazol-3-yl)-1H-indol-3-yl)-1-oxo-1,2,3,4-tetrahydropyrazino[1,2-a]indol-6-yl)-4,6-dimethylpyrimidin-2-yl)methyl methanesulfonate DIPEA (13.1 µL, 0.080 mmol) and MsCl (5.4 µL, 0.070 mmol) were added to a solution of (R)-7-chloro-10-(3-(4-chloro-3,5-dimethylphenoxy)propyl)-6-(2-(hydroxymethyl)-4,6-dimethylpyrimidin-5-yl)-4-methyl-2-(1-methyl-5-(1-methyl-1H-1,2,4-triazol-3-yl)-1H-indol-3-yl)-3,4-dihydropyrazino[1,2-a]indol-1(2H)-one (45 mg, 0.060 mmol) in DCM (0.5 mL) at 0° C. The reaction was warm to RT and stirred for 1 h then concentrated. The crude compound (40 mg) was used for the next step without further purification. LCMS: R$_T$=2.079 min, MS (ES) 855.8 (M+H).

Step D. Example 502

1-Methylpiperazine (15.6 µL 0.14 mmol) was added to a solution of (R)-(5-(7-chloro-10-(3-(4-chloro-3,5-dimethylphenoxy)propyl)-4-methyl-2-(1-methyl-5-(1-methyl-1H-1,2,4-triazol-3-yl)-1H-indol-3-yl)-1-oxo-1,2,3,4-tetrahydropyrazino[1,2-a]indol-6-yl)-4,6-dimethylpyrimidin-2-yl)methyl methanesulfonate (20 mg, 0.020 mmol) in DMF (1 mL). The reaction was stirred at 60° C. for 1 h, quenched with water then extracted with DCM. The combined organic layer was dried and concentrated. The residue was purified by reverse phase HPLC (Phenomenex Gemini C18, H$_2$O/MeCN gradient to 42-95% MeCN 0.1% TFA). The isolated TFA salt was neutralized using sat. aq. NaHCO$_3$ to afford the title compound (7 mg, 35% yield). LCMS: R$_T$=1.814 min, MS (ES) 859.9 (M+H). $^1$H NMR (400 MHz, Chloroform-d) δ 8.19 (d, J=1.0 Hz, 1H), 8.05 (s, 1H), 8.01 (dd, J=8.5, 1.2 Hz, 1H), 7.75 (d, J=8.7 Hz, 1H), 7.38 (d, J=8.7 Hz, 1H), 7.30 (d, J=8.6 Hz, 1H), 7.25 (d, J=8.6 Hz, 1H), 6.61 (s, 2H), 4.40 (dd, J=12.5, 3.3 Hz, 1H), 4.00-3.97 (m, 4H), 3.94 (s, 3H), 3.81 (s, 3H), 3.79-3.66 (m, 3H), 3.51-3.30 (m, 6H), 3.12-2.97 (m, 3H), 2.76 (s, 3H), 2.39 (s, 3H), 2.29 (s, 6H), 2.26 (s, 3H), 2.24-2.19 (m, 2H), 1.23 (d, J=6.5 Hz, 3H).

Example 503

(R)-7-chloro-10-(3-(4-chloro-3,5-dimethylphenoxy)propyl)-6-(4,6-dimethyl-2-(morpholinomethyl)pyrimidin-5-yl)-4-methyl-2-(1-methyl-5-(1-methyl-1H-1,2,4-triazol-3-yl)-1H-indol-3-yl)-3,4-dihydropyrazino[1,2-a]indol-1(2H)-one The title compound (12 mg, 61%) was prepared following the procedure described Example 502 Step D using morpholine (12.1 µL, 0.14 mmol) and (R)-(5-(7-chloro-10-(3-(4-chloro-3,5-dimethylphenoxy)propyl)-4-methyl-2-(1-methyl-5-(1-methyl-1H-1,2,4-triazol-3-yl)-1H-indol-3-yl)-1-oxo-1,2,3,4-tetrahydropyrazino[1,2-a]indol-6-yl)-4,6-dimethylpyrimidin-2-yl)methyl methanesulfonate (20 mg, 0.020 mmol). LCMS: R$_T$=1.878 min, MS (ES) 846.8 (M+H).

Example 504

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((4-(piperidin-1-yl)pyridin-2-yl)methyl)-1H-indole-2-carboxylic acid The title compound (15 mg, 55%) was prepared following the procedure described in Example 499 Step B using ethyl (R)-1-((4-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (25 mg, 0.03 mmol) and piperidine (0.5 mL). LCMS: R$_T$=2.08 min, MS (ES) 886 (M+H).

Example 505

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((6-(piperidin-1-yl)pyridin-2-yl)methyl)-1H-indole-2-carboxylic acid The title compound (21 mg, 78%) was prepared following the procedure described in Example 517 Step B using ethyl (R)-1-((6-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (25 mg, 0.03 mmol) and piperidine (0.5 mL). LCMS: $R_T$=2.09 min, MS (ES) 886 (M+H); $^1$H NMR (400 MHz, DMSO-$d_6$) δ 7.73 (d, J=8.4 Hz, 1H), 7.54 (s, 1H), 7.37 (s, 1H), 7.22-7.29 (m, 2H), 6.84 (s, 1H), 6.76 (s, 2H), 6.50 (bs, 1H), 6.19-6.22 (bs, 1H), 5.30-5.48 (m, 2H), 4.57 (m, 1H), 4.04 (bs, 2H), 3.83 (m, 1H), 3.73 (s, 1.5H), 3.69 (s, 1.5H), 3.39 (m, 1H), 3.14-3.26 (m, 3H), 2.97 (m, 2H), 2.76 (m, 2H), 2.36 (s, 3H), 2.22 (s, 6H), 2.04 (s, 3H), 1.94 (s, 1H), 1.85 (s, 1H), 1.75 (bs, 2H), 1.16-1.25 (m, 6H), 1.03 (m, 3H).

Example 506

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-3-carboxylic acid The title compound (1.5 mg, 25%) was prepared following General Procedure D using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-3-carboxylate (6.2 mg, 0.008 mmol). LCMS: $R_T$=2.041, 2.066 min, MS (ES) 741.9 (M+H).

Example 507

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((5-methylpyridin-2-yl)methyl)-1H-indole-3-carboxylic acid (2$^{nd}$ Eluted Atropisomer, Absolute Configuration Undeterminded)

The title compound (6.3 mg, 39% yield) was isolated along with Example 501 as a separated atropisomer (2$^{nd}$ fraction, absolute stereochemistry undetermined). LCMS: $R_T$=2.155 min, MS (ES) 802.9 (M+H).

Example 508

(R)-3-(7-chloro-10-(3-(4-chloro-3,5-dimethylphenoxy)propyl)-6-(2,6-dimethyl-4-(2-(pyrrolidin-1-yl)ethoxy)phenyl)-4-methyl-1-oxo-3,4-dihydropyrazino[1,2-a]indol-2(1H)-yl)-1-methyl-1H-indole-5-carboxylic acid The title compound was prepared following the procedure described Example 497 Step B using methyl 3-((R)-7-chloro-10-(3-(4-chloro-3,5-dimethylphenoxy)propyl)-6-(4-hydroxy-2,6-dimethylphenyl)-4-methyl-1-oxo-3,4-dihydropyrazino[1,2-a]indol-2(1H)-yl)-1-methyl-3a,7a-dihydro-1H-indole-5-carboxylate (20 mg, 0.027 mol) and 1-(2-bromoethyl)pyrrolidine (8.5 mg, 0.046 mmol). $^1$H-NMR (MeOH-$d^4$) δ 8.23 (d, 1H, J=1 Hz), 7.94 (dd, 1H, J=1.5 Hz, J=10 Hz), 7.75 (d, 1H, J=8 Hz), 7.50 (d, 1H, J=8 Hz), 7.34 (s, 1H), 7.30 (d, 1H, J=8 Hz), 6.96 (s, 1H), 6.91 (s, 1H), 6.64 (s, 2H), 4.41 (tr, 2H, J=4 Hz), 4.39 (dd, 1H, $J_1$=2 Hz, $J_2$=12 Hz), 3.99-3.67 (m, 2H), 3.87 (s, 3H), 3.75 (m, 2H), 3.69 (tr, 2H, J=4 Hz), 3.58 (dd, 1H, $J_1$=2 Hz, $J_2$=12 Hz), 3.49-3.45 (m, 1H), 2.31 (s, 6H), 2.21 (tr, 2H, J=4 Hz), 2.20-2.18 (m, 4H), 2.12 (s, 3H), 2.09-2.06 (m, 4H), 1.98 (s, 3H), 1.23 (d, 3H, J=8 Hz); MS (ES) 821.3 (M+H),

Example 509

(R)-3-(7-chloro-10-(3-(4-chloro-3,5-dimethylphenoxy)propyl)-6-(4-(2-(dimethylamino)ethoxy)-2,6-dimethylphenyl)-4-methyl-1-oxo-3,4-dihydropyrazino[1,2-a]indol-2(1H)-yl)-1-methyl-1H-indole-5-carboxylic acid The title compound was prepared following the procedure described Example 497, Step B using methyl 3-((R)-7-chloro-10-(3-(4-chloro-3,5-dimethylphenoxy)propyl)-6-(4-hydroxy-2,6-dimethylphenyl)-4-methyl-1-oxo-3,4-dihydropyrazino[1,2-a]indol-2(1H)-yl)-1-methyl-3a,7a-dihydro-1H-indole-5-carboxylate (20 mg, 0.027 mol) and 2-bromo-N,N-dimethylethan-1-amine (7.0 mg, 0.046 mmol). MS (ES) 795.5 (M+H),

Example 510

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-(dimethylamino)ethyl)-1H-indole-5-carboxylic acid The title compound (3.6 mg, 33%) was prepared according to General Procedure G using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (10 mg, 0.01 mmol) and 2-bromo-N,N-dimethylethan-1-amine hydrobromide (7 mg, 0.03 mmol) followed by saponification using General Procedure D. LCMS: $R_T$=1.844 min, MS (ES) 768.9 (M+H).

Example 511

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-(pyrrolidin-1-yl)ethyl)-1H-indole-5-carboxylic acid The title compound (7.2 mg, 65%) was prepared according to General Procedure G using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (10 mg, 0.01 mmol) and 1-(2-bromoethyl)pyrrolidine hydrobromide (7 mg, 0.03 mmol) followed by saponification using General Procedure D. LCMS: $R_T$=1.899 min, MS (ES) 794.9 (M+H).

Example 512

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-methoxyethyl)-1H-indole-3-carboxylic acid The title compound (11.9 mg, 79%) was prepared according to General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate (15 mg, 0.02 mmol) and 1-bromo-2-methoxyethane (3 mg, 0.04 mmol) followed by saponification using General Procedure D. LCMS: $R_T$=2.234 min, MS (ES) 755.8 (M+H).

Example 513

3-((2-Carboxy-7-((R)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indol-5-yl)oxy)-1,1-dimethylpyrrolidin-1-ium 2,2,2-trifluoroacetate To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (20 mg, 0.026 mmol) in DMF (1 mL) was added $Cs_2CO_3$ (25 mg, 0.77 mmol) and tert-butyl 3-bromopyrrolidine-1-carboxylate (15 mg, 0.060 mmol). The reaction was heated to 80° C. for 16 h, then diluted with $DCM/H_2O$ (10 mL, 1:1). The layers were separated, and the aqueous layer was extracted with DCM (2×5 mL). The combined organic extracts were dried by passage through a phase separator and concentrated. LCMS: $R_T$=2.373 min, MS (ES) 946.8 (M+Na). The crude reaction product was dissolved in DCM (3 mL) and TFA (0.5 mL) was added. The reaction was stirred for 4 h at RT then concentrated. LCMS: $R_T$=2.017, 2.088 min, MS (ES) 824.8 (M+H). The residue was dissolved in MeCN (2 mL) and $K_2CO_3$ (20 mg, 0.14 mmol) and MeI (8 mg, 0.057 mmol) were added in sequence. The reaction was stirred for 1 h at RT then diluted with $DCM/H_2O$ (10 mL, 1:1). The layers were separated, and the aqueous layer was extracted with DCM. The combined organic extracts were dried and concentrated. LCMS: $R_T$=2.062, 2.116 min, MS (ES) 952.9 (M). The residue was saponified according to General Procedure D to afford the title compound (3 mg, 14% yield). LCMS: $R_T$=1.868 min, MS (ES) 824.8 (M).

Example 514

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((4-vinylpyridin-2-yl)methyl)-1H-indole-2-carboxylic acid A solution of ethyl (R)-1-((4-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (50 mg, 0.06 mmol), $Pd(OAc)_2$ (1 mg, 0.005 mmol), tricyclohexylphosphine tetrafluoroborate (4 mg, 0.011 mmol). $K_3PO_4$ (23 mg, 0.11 mmol), Vinylboronic acid pinacol ester (0.011 mL, 0.07 mmol) in 5:1 DME/water (1 mL) was purged with Ar and stirred at 80° C. overnight. The solution was cooled to RT, diluted with EtOAc, filtered through Celite, washing with EtOAc and concentrated. The residue was purified by flash chromatography (Combi-flash Rf, Hex/EtOAc=0-100% gradient) followed by saponification following General Procedure D to give the title compound (28 mg, 78%) as TFA salt. LCMS: $R_T$=2.09 min, MS (ES) 829 (M+H); $^1$H NMR (400 MHz, DMSO-$d_6$) δ 8.20 (m, 1H), 7.73 (d, J=8.6 Hz, 1H), 7.57 (s, 1H), 7.40 (s, 1H), 7.26-7.32 (m, 2H), 6.86 (m, 1H), 6.71 (s, 2H), 6.57 (bs, 1H), 6.40-6.50 (m, 1H), 6.08-6.27 (m, 1H), 5.73-5.81 (m, 1H), 5.45-5.60 (m, 1H), 5.31-5.35 (m, 1H), 3.96 (m, 2H), 3.84 (m, 1H), 3.73 (s, 3H), 3.26-3.34 (m, 1H), 3.06 (m, 1H), 2.53 (m, 2H), 2.37 (s, 3H), 2.21 (s, 6H), 2.07 (s, 3H), 1.70-1.97 (m, 5H), 1.02 (m, 3H).

Example 515

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((4-(4-methylpiperazin-1-yl)pyridin-2-yl)methyl)-1H-indole-2-carboxylic acid The title compound (15 mg, 54% TFA salt) was prepared following the procedure described in Example 499 Step B using ethyl (R)-1-((4-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (32 mg, 0.04 mmol) and 1-methylpiperazine (0.5 mL, 4.6 mmol). LCMS: $R_T$=1.75 min. MS (ES) 901 (M+H).

Example 516

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((6-(4-methylpiperazin-1-yl)pyridin-2-yl)methyl)-1H-indole-2-carboxylic acid The title compound (18 mg, 55% TFA salt) was prepared following the procedure described in Example 499 Step B using ethyl (R)-1-((6-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (30 mg, 0.03 mmol) and 1-methylpiperazine (0.5 mL, 4.6 mmol). LCMS: $R_T$=2.02 min, MS (ES) 901 (M+H).

Example 517

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((6-vinylpyridin-2-yl)methyl)-1H-indole-2-carboxylic acid The title compound (21 mg, 49%) was prepared following the procedure described in Example 514 using ethyl (R)-1-((6-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]

indol-2(1H)-yl)-5-methyl-1H-indole-2-carboxylate (50 mg, 0.06 mmol). LCMS: $R_T$=2.24 min, MS (ES) 829 (M+H).

Example 518

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyrimidin-4-ylmethyl)-1H-indole-2-carboxylic acid The title compound (5.8 mg, 29%) was prepared according to General Procedure G using (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyrimidin-4-ylmethyl)-1H-indole-2-carboxylic acid (18 mg, 0.025 mmol) and pyrimidin-4-ylmethyl methanesulfonate (15 mg, 0.080 mmol) followed by saponification using General Procedure D. LCMS: $R_T$=2.021 min, MS (ES) 789.8 (M+H).

Example 519

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-((1-methylpiperidin-4-yl)oxy)-1H-indole-2-carboxylic acid To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (10 mg, 0.013 mmol), triphenylphosphine (10 mg, 0.038 mmol) and 1-methylpiperidin-4-ol (20 mg, 0.17 mmol) in THF (1 mL) was added di-tert-butyl (E)-diazene-1,2-dicarboxylate (10 mg, 0.044 mmol) at RT. The reaction was stirred for 18 h at RT, then heated to 60° C. for 16 h. The reaction was cooled to RT, diluted with DCM/H₂O (10 mL, 1:1) and extracted with DCM. The combined organic extracts were dried and concentrated. The crude product was saponified following General Procedure D and purified by reverse phase HPLC (Phenomenex Gemini C18, H₂O/CH₃CN gradient 35-95% MeCN 0.1% TFA) to afford the title compound (4.5 mg, 42%). LCMS: $R_T$=1.839 min, MS (ES) 824.8 (M+H).

Example 520

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-1-((4-methylpyridin-2-yl)methyl)-1H-indole-2-carboxylic acid The title compound (14 mg, 83%) was prepared according to General Procedure I using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-4-methoxy-1H-indole-2-carboxylate (15 mg, 0.020 mmol) and 2-(chloromethyl)-4-methylpyridine HCl salt (10 mg, 0.056 mmol) followed by saponification using General Procedure D. LCMS: $R_T$=2.022 min, MS (ES) 830.8 (M+H).

Example 521

7-((R)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-((1-methylpyrrolidin-3-yl)oxy)-1H-indole-2-carboxylic acid The title compound (8.6 mg, 41%) was isolated along with Example 513 following the procedure described in Example 513. LCMS: $R_T$=1.897, 1.929 min, MS (ES) 810.9 (M+H).

Example 522

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(pyridin-2-yloxy)-1H-indole-2-carboxylic acid The title compound (1.5 mg, 14%) was prepared according to General Procedure H using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (10 mg, 0.013 mmol) and 2-fluoropyridine (8 mg, 0.082 mmol) followed by saponification using General Procedure D. LCMS: $R_T$=2.207, 2.246 min. MS (ES) 804.9 (M+H).

Example 523

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-((pyridin-2-ylmethyl)amino)-1H-indole-3-carboxylic acid The title compound was prepared following the procedure described Example 486 Step H using methyl (R)-5-((tert-butoxycarbonyl)amino)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylate (40 mg, 0.047 mol) and 2-(bromomethyl)pyridine (13.8 mg, 0.080 mmol). MS (ES) 818.2 (M+H), Example 524

(R)-7-Chloro-10-(3-(4-chloro-3,5-dimethylphenoxy)propyl)-2-(1-(2-methoxyethyl)-5-(1-methyl-1H-1,2,4-triazol-3-yl)-1H-indol-3-yl)-4-methyl-6-(1,3,5-trimethyl-1H-pyrazol-4-yl)-3,4-dihydropyrazino[1,2-a]indol-1(2H)-one Step A. Preparation of 1-(2-methoxyethyl)-5-(1-methyl-1H-1,2,4-triazol-3-yl)-1H-indole NaH (8.5 mg, 0.35 mmol) was added to a solution of 5-(1-methyl-1H-1,2,4-triazol-3-yl)-1H-indole (35 mg, 0.18 mmol) in DMF (2 mL) at 0° C. After 30 min, 2-bromoethyl methyl ether (22 μL, 0.23 mmol) was added slowly. The reaction was warmed to RT and stirred for 1 h. The reaction was quenched with water and extracted with EtOAc (3×10 mL). The combined organic layer was washed with water, dried and concentrated to give the crude title compound (34 mg), which was used for the next step without further purification. LCMS: $R_T$=1.172 min, MS (ES) 257.1 (M+H).

Step B. Preparation of 3-iodo-1-(2-methoxyethyl)-5-(1-methyl-1H-1,2,4-triazol-3-yl)-1H-indole NIS (30 mg, 0.13 mmol) was added to a solution of 1-(2-methoxyethyl)-5-(1-methyl-1H-1,2,4-triazol-3-yl)-1H-indole (34 mg, 0.13 mmol) in DMF (1.3 mL) at 0° C., and the reaction mixture was stirred at 0° C. for 1 h. The reaction was quenched with water and extracted with EtOAc. The combined organic layer was washed with water, dried and concentrated to give the crude title compound (50 mg), which was used for the next step without further purification. LCMS: $R_T$=1.241 min, MS (ES) 383.8 (M+H).

Step C. Example 524

The title compound (30 mg, 68%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.060 mmol) and 3-iodo-1-(2-methoxyethyl)-5-(1-methyl-1H-1,2,4-triazol-3-yl)-1H-indole (50 mg, 0.11 mmol). LCMS: $R_T$=2.167 mm, MS (ES) 793.9 (M+H); $^1$H NMR (400 MHz, DMSO-$d_6$) δ 8.44 (s, 1H), 8.05 (s, 1H), 7.84 (d, J=8.8 Hz, 1H), 7.75 (d, J=8.6 Hz, 1H), 7.60 (d, J=8.8 Hz, 1H), 7.50 (s, 1H), 7.29 (d, J=8.6 Hz, 1H), 6.72 (s, 2H), 4.50-4.44 (m, 1H), 4.36 (t, J=4.5 Hz, 2H), 4.19-4.16 (m, 2H), 3.98 (t, J=7.0 Hz, 2H), 3.87 (s, 3H), 3.77 (d, J=4.8 Hz, 3H), 3.70 (d, J=5.2 Hz, 2H), 3.66-3.63 (m, 1H), 3.39-3.31 (m, 1H), 3.25-3.19 (m, 4H), 2.22 (s, 5H), 2.12-2.03 (m, 5H), 1.97-1.88 (m, 3H), 1.10 (d, J=6.2 Hz, 3H).

Example 525

(R)-7-Chloro-10-(3-(4-chloro-3,5-dimethylphenoxy)propyl)-4-methyl-2-(5-(1-methyl-1H-1,2,4-triazol-3-yl)-1-(2-morpholino-2-oxoethyl)-1H-indol-3-yl)-6-(1,3,5-trimethyl-1H-pyrazol-4-yl)-3,4-dihydropyrazino[1,2-a]indol-1(2H)-one Step A. Preparation of 1-morpholino-2-(5-(4,4,5,5-tetramethyl-1,3,2-dioxaborolan-2-yl)-1H-indol-1-yl)ethan-1-one Bis(pinacolato)diboron (434 mg, 1.71 mmol), KOAc (419 mg, 4.27 mmol) and PdCl$_2$(dppf).DCM (58 mg, 0.07 mmol) were added to a solution of 2-(5-bromo-1H-indol-1-yl)-1-morpholinoethan-1-one (460 mg, 1.42 mmol) in toluene (2.9 mL) under Ar atmosphere. The reaction was stirred at 90° C. for 18 h then filtered through Celite and concentrated. The residue was purified by flash chromatography (Combi-flash Rf, DCM/MeOH=0-1% gradient) to provide the title compound (520 mg, quant.). LCMS: $R_T$=1.527 min, MS (ES) 371.1 (M+H).

Step B. Preparation of 2-(5-(1-methyl-1H-1,2,4-triazol-3-yl)-1H-indol-1-yl)-1-morpholinoethan-1-one 3-Bromo-1-methyl-1H-1,2,4-triazole (50 mg, 0.31 mmol), PdCl$_2$(dppf).DCM (13 mg, 0.020 mmol), K$_2$CO$_3$ (370 μL, 0.93 mmol, 2.5 M aq. solution) were added to a solution of 1-morpholino-2-(5-(4,4,5,5-tetramethyl-1,3,2-dioxaborolan-2-yl)-1H-indol-1-yl)ethan-1-one (149 mg, 0.40 mmol) in MeCN (1.5 mL). The reaction mixture was degassed using Ar and stirred at 85° C. for 16 h. The reaction mixture was filtered through Celite, and the filtrate concentrated. The residue was purified by flash chromatography (Combi-flash Rf, DCM/MeOH=0-3% gradient) to provide the title compound (100 mg, quant.). LCMS: $R_T$=1.155 min, MS (ES) 323.1 (M+H).

Step C. Preparation of 2-(3-iodo-5-(1-methyl-1H-1,2,4-triazol-3-yl)-1H-indol-1-yl)-1-morpholinoethan-1-one The crude title compound (65 mg) was prepared following the procedure described Example 524 Step B using 2-(5-(1-methyl-1H-1,2,4-triazol-3-yl)-1H-indol-1-yl)-1-morpholinoethan-1-one (55 mg, 0.17 mmol). LCMS: $R_T$=1.245 min, MS (ES) 451.8 (M+H).

Step D. Example 543

The title compound (15 mg, 31%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.060 mmol) and 2-(3-iodo-5-(1-methyl-1H-1,2,4-triazol-3-yl)-1H-indol-1-yl)-1-morpholinoethan-1-one (50 mg, 0.11 mmol). LCMS: $R_T$=2.008 min, MS (ES) 862.9 (M+H).

Example 526

(R)-7-Chloro-10-(3-(4-chloro-3,5-dimethylphenoxy)propyl)-4-methyl-2-(5-(1-methyl-1H-1,2,4-triazol-3-yl)-1-(2-(4-methylpiperazin-1-yl)ethyl)-1H-indol-3-yl)-6-(1,3,5-trimethyl-1H-pyrazol-4-yl)-3,4-dihydropyrazino[1,2-a]indol-1(2H)-one Step A. Preparation of 1-(2-((tert-butyldimethylsilyl)oxy)ethyl)-5-(1-methyl-1H-1,2,4-triazol-3-yl)-1H-indole The title compound (270 mg, 82%) was prepared following the procedure described Example 525 Step B using 3-Bromo-1-methyl-1H-1,2,4-triazole (150 mg, 0.93 mmol) and 1-(2-((tert-butyldimethylsilyl)oxy)ethyl)-5-(4,4,5,5-tetramethyl-1,3,2-dioxaborolan-2-yl)-1H-indole (483 mg, 1.20 mmol). LCMS: $R_T$=1.858 min, MS (ES) 357.1 (M+H).

Step B. Preparation of 1-(2-((tert-butyldimethylsilyl)oxy)ethyl)-3-iodo-5-(1-methyl-1H-1,2,4-triazol-3-yl)-1H-indole The title compound (100 mg, 27%) was prepared following the procedure described Example 524 Step B using 1-(2-((tert-butyldimethylsilyl)oxy)ethyl)-5-(1-methyl-1H-1,2,4-triazol-3-yl)-1H-indole (270 mg, 0.76 mmol). LCMS: $R_T$=2.077 min, MS (ES) 483.0 (M+H).

Step C. Preparation (R)-2-(1-(2-((tert-butyldimethylsilyl)oxy)ethyl)-5-(1-methyl-1H-1,2,4-triazol-3-yl)-1H-indol-3-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one The title compound (67 mg, 67%) was prepared following General Procedure B using (R)-7-chloro-10-(3-(4-chloro-3,5-dimethylphenoxy)propyl)-4-methyl-6-(1,3,5-trimethyl- 1H-pyrazol-4-yl)-3,4-dihydropyrazino[1,2-a]indol-1(2H)-one (60 mg, 0.11 mmol) and 1-(2-((tert-butyldimethylsilyl)oxy)ethyl)-3-iodo-5-(1-methyl-1H-1,2,4-triazol-3-yl)-1H-indole (99 mg, 0.21 mmol). LCMS: $R_T$=1.683 min, MS (ES) 893.0 (M+H).

Step D. Preparation of (R)-7-chloro-10-(3-(4-chloro-3,5-dimethylphenoxy)propyl)-2-(1-(2-hydroxyethyl)-5-(1-methyl-1H-1,2,4-triazol-3-yl)-1H-indol-3-yl)-4-methyl-6-(1,3,5-trimethyl-1H-pyrazol-4-yl)-3,4-dihydropyrazino[1,2-a]indol-1(2H)-one TBAF (75 µL, 0.070 mmol) was added to a solution of (R)-2-(1-(2-((tert-butyldimethylsilyl)oxy)ethyl)-5-(1-methyl-1H-1,2,4-triazol-3-yl)-1H-indol-3-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (67 mg, 0.070 mmol) in THF (1 mL) at 0° C. The reaction was stirred at 0° C. for 30 min then concentrated. The residue was purified by flash chromatography (Combi-flash Rf, DCM/MeOH=0-2% gradient) to afford the title compound (34 mg, 59%). LCMS: $R_T$=2.005 min, MS (ES) 779.9 (M+H).

Step E. Preparation of (R)-2-(3-(7-chloro-10-(3-(4-chloro-3,5-dimethylphenoxy)propyl)-4-methyl-t-oxo-6-(1,3,5-trimethyl-1H-pyrazol-4-yl)-3,4-dihydropyrazino[1,2-a]indol-2(1H)-yl)-5-(1-methyl-1H-1,2,4-triazol-3-yl)-1H-indol-1-yl)ethyl methanesulfonate The crude title compound (37 mg) was prepared following the procedure described Example 502 Step C using (R)-7-chloro-10-(3-(4-chloro-3,5-dimethylphenoxy)propyl)-2-(1-(2-hydroxyethyl)-5-(1-methyl-1H-1,2,4-triazol-3-yl)-1H-indol-3-yl)-4-methyl-6-(1,3,5-trimethyl-1H-pyrazol-4-yl)-3,4-dihydropyrazino[1,2-a]indol-1(2H)-one (34 mg, 0.060 mmol). DIPEA (9.9 µL, 0.060 mmol) and MsCl (4.1 µL, 0.050 mmol). LCMS: $R_T$=2.056 min, MS (ES) 857.9 (M+H).

Step F. Example 526

1-Methylpiperazine (29 µL 0.26 mmol) was added to a solution of (R)-2-(3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(1-methyl-1H-1,2,4-triazol-3-yl)-1H-indol-1-yl)ethyl methanesulfonate (37 mg, 0.040 mmol) in DMF (1 mL). The reaction was stirred at 90° C. for 5 days. The reaction mixture was quenched with water and extracted with DCM. The combined organic layer was dried and concentrated. The residue was purified by reverse phase HPLC (Phenomenex Gemini C18, H₂O/MeCN gradient to 45-95% MeCN 0.1% TFA) followed by neutralization using sat. aq. NaHCO₃ to provide the title compound (9 mg, 24%) LCMS: $R_T$=1.827 min, MS (ES) 861.9 (M+H).

Example 527

(R)-7-Chloro-10-(3-(4-chloro-3,5-dimethylphenoxy)propyl)-4-methyl-2-(5-(1-methyl-1H-1,2,4-triazol-3-yl)-1-(2-oxo-2-(pyrrolidin-1-yl)ethyl)-1H-indol-3-yl)-6-(1,3,5-trimethyl-1H-pyrazol-4-yl)-3,4-dihydropyrazino[1,2-a]indol-1(2H)-one Step A. Preparation of 2-(5-(4,4,5,5-tetramethyl-1,3,2-dioxaborolan-2-yl)-1H-indol-1-yl)acetic acid LiOH (2.22 mL, 4.44 mmol, 2M Solution) was added to a solution of methyl 2-(5-(4,4,5,5-tetramethyl-1,3,2-dioxaborolan-2-yl)-1H-indol-1-yl)acetate (700 mg, 2.22 mmol) in THF/MeOH/H₂O (8.9 mL, 4:1:1) at 0° C. The reaction was stirred at 0° C. for 1 h then concentrated. The residue was diluted with water and acidified with 2 N HCl. The mixture was extracted with EtOAc. The combined organic layer was dried and concentrated to give the crude title compound (630 mg), which was used for the next step without further purification. LCMS: $R_T$=1.473 min, MS (ES) 302.1 (M+H).

Step B. Preparation of 1-(pyrrolidin-1-yl)-2-(5-(4,4,5,5-tetramethyl-1,3,2-dioxaborolan-2-yl)-1H-indol-1-yl)ethan-1-one BOP (441 mg, 1.00 mmol), pyrrolidine (273 µL, 3.32 mmol) and N-methylmorpholine (456 µL, 4.15 mmol) were added to a solution of 2-(5-(4,4,5,5-tetramethyl-1,3,2-dioxaborolan-2-yl)-1H-indol-1-yl)acetic acid (250 mg, 0.83 mmol) in DMF (5.5 mL). The reaction mixture was stirred at RT for 1 h. The reaction mixture was quenched with water and extracted with EtOAc. The combined organic layer was washed with water, dried and concentrated. The residue was purified by flash chromatography (Combi-flash Rf, DCM/MeOH=0-2% gradient) to afford the title compound (150 mg, 51%). LCMS: $R_T$=1.606 min, MS (ES) 355.0 (M+H).

Step C. Preparation of 2-(5-(1-methyl-1H-1,2,4-triazol-3-yl)-1H-indol-1-yl)-1-(pyrrolidin-1-yl)ethan-1-one The title compound (38 mg, 44% yield) was prepared following the procedure described Example 525 Step B using 3-Bromo-1-methyl-1H-1,2,4-triazole (45 mg, 0.28 mmol) and 1-(pyrrolidin-1-yl)-2-(5-(4,4,5,5-tetramethyl-1,3,2-dioxaborolan-2-yl)-1H-indol-1-yl)ethan-1-one (157 mg, 0.44 mmol). LCMS: $R_T$=1.087 min, MS (ES) 310.0 (M+H).

Step D. Preparation of 2-(3-iodo-5-(1-methyl-1H-1,2,4-triazol-3-yl)-1H-indol-1-yl)-1-(pyrrolidin-1-yl)ethan-1-one The crude title compound (45 mg) was prepared following the procedure described Example 524 Step B using 2-(5-(1-methyl-1H-1,2,4-triazol-3-yl)-1H-indol-1-yl)-1-(pyrrolidin-1-yl)ethan-1-one (38 mg, 0.12 mmol). LCMS: $R_T$=0.177 min, MS (ES) 435.9 (M+H).

Step E. Example 527

The title compound (15 mg, 32% yield) was prepared following General Procedure I using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.060 mmol) and 2-(3-iodo-5-(1-methyl-1H-1,2,4-triazol-3-yl)-1H-indol-1-yl)-1-(pyrrolidin-1-yl)ethan-1-one (48 mg, 0.11 mmol). LCMS: $R_T$=2.081 min, MS (ES) 846.9 (M+H).

Example 528

(R)-1-((6-(4-acetylpiperazin-1-yl)pyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylic acid Step A. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((6-(piperazin-1-yl)pyridin-2-yl)methyl)-1H-indole-2-carboxylate A solution of ethyl (R)-1-((6-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (50 mg, 0.05 mmol) and piperazine (24 mg, 0.27 mmol) in dioxane (0.5 mL) was stirred in a sealed vial at 110° C. overnight. The solution was diluted with EtOAc and water. The aqueous layer was extracted with EtOAc. The combined organic solution were washed with brine, dried and concentrated. The residue was purified by flash chromatography (Combi-flash Rf, DCM/MeOH=0-8% gradient, with 1% conc. NH$_4$OH) to give the title compound (30 mg, 60%). LCMS: R$_T$=2.20 min, MS (ES) 915 (M+H).

Step B. Example 528

To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((6-(piperazin-1-yl)pyridin-2-yl)methyl)-1H-indole-2-carboxylate (30 mg, 0.03 mmol) and Et$_3$N (0.01 mL, 0.08 mmol) in DCM (0.50 mL) at 0° C. under Ar was added dropwise a solution of acetyl chloride (5 mg, 0.07 mmol) in DCM (0.2 mL). After 15 minutes, the ice-bath was removed and the solution was stirred at RT for 2 h. The reaction mixture was diluted with DCM and methanol, and concentrated. The residue was saponified following General Procedure D to give the title compound (15 mg, 44%) as TFA salt. LCMS: R$_T$=2.11 min, MS (ES) 929 (M+H); $^1$H NMR (400 MHz, DMSO-d$_6$) δ 7.77 (d, J=8.6 Hz, 1H), 7.54 (s, 1H), 7.38 (s, 1H), 7.25-7.34 (m, 2H), 6.86 (m, 1H), 6.78 (s, 2H), 6.51 (d, J=8.5 Hz, 1H), 6.23 (m, 1H), 5.57 (m, 1H), 5.29 (m, 1H), 4.12-4.45 (bm, 4H), 4.07 (m, 2H), 3.80 (m, 1H), 3.72 (s, 3H), 3.43 (m, 1H), 2.95-3.35 (m, 5H), 2.89 (m, 3H), 2.72 (m, 1H), 2.36 (s, 3H), 2.22 (s, 6H), 2.04-2.19 (m, 3H), 1.72-1.94 (m, 6H), 1.04 (m, 3H).

Example 529

(R)-7-Chloro-10-(3-(4-chloro-3,5-dimethylphenoxy)propyl)-2-(1-(2-chloroethyl)-5-(1-methyl-1H-1,2,4-triazol-3-yl)-1H-indol-3-yl)-4-methyl-6-(1,3,5-trimethyl-1H-pyrazol-4-yl)-3,4-dihydropyrazino[1,2-a]indol-1(2H)-one The title compound (5 mg, 15% yield) was isolated as a byproduct from the reaction of Example 526 Step E. LCMS: R$_T$=2.209 min, MS (ES) 797.8 (M+H).

Example 530

(R)-7-Chloro-10-(3-(4-chloro-3,5-dimethylphenoxy)propyl)-2-(S-(1-(2-methoxyethyl)-1H-1,2,4-triazol-3-yl)-1-methyl-1H-indol-3-yl)-4-methyl-6-(1,3,5-trimethyl-1H-pyrazol-4-yl)-3,4-dihydropyrazino[1,2-a]indol-1(2H)-one Step A. Preparation of 3-iodo-5-(1-(2-methoxyethyl)-1H-1,2,4-triazol-3-yl)-1-methyl-1H-indole The title compound (75 mg, 53%) was prepared following the procedure described Example 524 Step A using 3-iodo-1-methyl-5-(1H-1,2,4-triazol-3-yl)-1H-indole (120 mg, 0.37 mmol), NaH (18 mg, 0.74 mmol) and 2-bromoethyl methyl ether (45 μL, 0.48 mmol). LCMS: R$_T$=1.527 min, MS (ES) 382.9 (M+H).

Step B. Example 530

The title compound (20 mg, 45%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.060 mmol) and 3-iodo-5-(1-(2-methoxyethyl)-1H-1,2,4-triazol-3-yl)-1-methyl-1H-indole (43 mg, 0.11 mmol). LCMS: R$_T$=2.211 min, MS (ES) 793.9 (M+H).

Example 531

(R)-7-Chloro-10-(3-(4-chloro-3,5-dimethylphenoxy)propyl)-4-methyl-2-(1-(2-morpholino-2-oxoethyl)-5-(pyrimidin-2-yl)-1H-indol-3-yl)-6-(1,3,5-trimethyl-1H-pyrazol-4-yl)-3,4-dihydropyrazino[1,2-a]indol-1(2H)-one Step A. Preparation of 1-morpholino-2-(5-(pyrimidin-2-yl)-1H-indol-1-yl)ethan-1-one The title compound (100 mg, quant.) was prepared following the procedure described Example 525 Step B using 2-bromopyrimidine (50 mg, 0.31 mmol) and 1-morpholino-2-(5-(4,4,5,5-tetramethyl-1,3,2-dioxaborolan-2-yl)-1H-indol-1-yl)ethan-1-one (151 mg, 0.41 mmol). LCMS: R$_T$=1.155 min, MS (ES) 323.1 (M+H).

Step B. Preparation of 2-(3-iodo-5-(pyrimidin-2-yl)-1H-indol-1-yl)-1-morpholinoethan-1-one The crude title compound (100 mg) was prepared following the procedure described Example 524 Step B using 1-morpholino-2-(5-(pyrimidin-2-yl)-1H-indol-1-yl)ethan-1-one (100 mg, 0.31 mmol). LCMS: R$_T$=1.439 min, MS (ES) 448.8 (M+H).

Step B. Example 531

The title compound (10 mg, 22%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.060 mmol) and 2-(3-iodo-5-(pyrimidin-2-yl)-1H-indol-1-yl)-1-morpholinoethan-1-one (50 mg, 0.11 mmol). LCMS: R$_T$=2.184 min, MS (ES) 860.8 (M+H).

Example 532

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(thiazol-4-ylmethyl)-1H-indole-5-carboxylic acid The title compound (5.2 mg, 47%) was prepared according to General Procedure G using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (10 mg, 0.01 mmol) and 4-(chloromethyl)thiazole HCl (5 mg, 0.03 mmol) followed by saponification using General Procedure D. LCMS: $R_T$=2.085 min, MS (ES) 794.8 (M+H).

Example 533

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(2-(piperidin-1-yl)acetamido)-1H-indole-3-carboxylic acid To a solution of 2-(piperidin-1-yl)acetic acid (8.6 mg, 0.06 mmol) in DMF (0.5 mL) were added HATU (23 mg, 0.06 mmol) and DIPEA (11 µL, 0.06 mmol) at 0° C. The reaction mixture was stirred for 30 min at 0° C. then methyl (R)-5-amino-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylate (30 mg, 0.04 mmol) was added at 0° C. The reaction mixture was warmed to RT and stirred for 10 h. The reaction mixture was diluted with ethyl acetate (10 mL), washed with brine, dried and concentrated. The residue was saponified in a mixture of 1,4-dioxane and MeOH (4 mL, 1:1) using NaOH (2M, 1 mL). The crude was purified by reverse phase HPLC (Phenomenex Gemini C18, H₂O/CH₃CN gradient from 45% to 95% CH₃CN, 0.1% TFA) to give the title compound, 1H-NMR (MeOH-d₄) δ 8.35 and 8.29 (two d, total 1H, J=8 Hz), 7.91 (s, 1H), 7.79 (d, 1H, J=8 Hz), 7.63 and 7.61 (two d, total 1H, J=8 Hz), 7.73 (d, 1H, J=8 Hz), 6.64 and 6.62 (two s, total 2H), 4.70-7.60 (m, 1H), 4.50-4.34 (m, 2H), 4.14 (s, 2H), 3.98-3.72 (multiples s, total 6H), 3.80-3.78 (m, 2H), 3.66-3.63 (m, 2H), 3.15-3.10 (m, 4H), 2.28 (s, 6H), 2.16-1.96 (multiples and tr, total 8H), 1.90-1.87 (multiple m, total 4H), 1.60 (m, 2H), 1.30 and 1.19 (multiple d, total 3H); MS (ES) 852.2 (M+H).

Example 534

3-((R)-7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((1-methylpyrrolidin-3-yl)methyl)-1H-indole-5-carboxylic acid The title compound (4.8 mg, 43%) was prepared according to General Procedure G using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (10 mg, 0.01 mmol) and 3-(bromomethyl)-1-methylpyrrolidine hydrobromide (7 mg, 0.03 mmol) followed by saponification using General Procedure D. LCMS: $R_T$=1.817 min, MS (ES) 794.9 (M+H).

Example 535

(R)-7-(7-Chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methoxy-1-methyl-1H-indole-2-carboxylic acid Step A. Preparation of methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1H-indole-2-carboxylate The title compound (391 mg, 53%) was prepared according to General Procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (500 mg, 0.93 mmol) and methyl 5-(benzyloxy)-7-iodo-1H-indole-2-carboxylate (600 mg, 1.43 mmol). LCMS: $R_T$=1.764 min, MS (ES) 815.8 (M+H).

Step B. Preparation of methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-methyl-1H-indole-2-carboxylate The title compound (164 mg, 90%) was prepared according to General Procedure I using methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1H-indole-2-carboxylate (180 mg, 0.22 mmol) and methyl iodide (75 mg, 0.53 mmol). LCMS: $R_T$=1.959 min (LC method II), MS (ES) 829.8 (M+H) (Ultra Aqueous method).

Step C. Preparation of methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-methyl-1H-indole-2-carboxylate To a solution of methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-methyl-1H-indole-2-carboxylate (164 mg, 0.20 mmol) in MeOH (10 mL) was added HCl in dioxane (4.0 M, 0.5 mL) followed by Pd/C (10 wt. %, 20 mg, 0.019 mmol). The reaction mixture was stirred for 24 h under H₂ atmosphere, filtered through celite, rinsed with DCM, and concentrated. The residue was purified by flash chromatography (Combi-flash Rf, Hex/EtOAc=0-100% gradient) to afford the title compound (141 mg, 96%). LCMS: $R_T$=1.335 min (LC method II), MS (ES) 739.9 (M+H).

Step D. Example 535

The title compound (6.1 mg, 31%) was prepared according to General Procedure H using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-methyl-1H-indole-2-carboxylate (20 mg, 0.027 mmol) and MeI (10 mg, 0.070 mmol) followed by saponification using General Procedure D. LCMS: $R_T$=2.212 min, MS (ES) 739.9 (M+H).

Example 536

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methoxy-1-((6-methylpyridin-2-yl)methyl)-1H-indole-2-carboxylic acid Step A. Preparation of methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate The title compound (320 mg, 53%) was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (400 mg, 0.74 mmol) and methyl 5-(benzyloxy)-7-iodo-1H-indole-2-carboxylate (400 mg, 0.98 mmol). LCMS: $R_T$=1.722 min, MS (ES) 817.9 (M+H).

Step B. Preparation of methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((6-methylpyridin-2-yl)methyl)-1H-indole-2-carboxylate The title compound (72 mg, 65%) was prepared according to General Procedure I using methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (100 mg, 0.12 mmol) and 2-(chloromethyl)-6-methylpyridine hydrochloride salt (75 mg, 0.53 mmol). LCMS: $R_T$=1.375 min (LC method II), MS (ES) 922.9 (M+H).

Step C. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-((6-methylpyridin-2-yl)methyl)-1H-indole-2-carboxylate The title compound (59 mg, 91%) was prepared following the procedure described Example 535, Step C using methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((6-methylpyridin-2-yl)methyl)-1H-indole-2-carboxylate (72 mg, 0.078 mmol). LCMS: $R_T$=0.930 min (LC method II), MS (ES) 832.8 (M+H).

Step D. Example 536

The title compound (6.4 mg, 43%) was prepared according to General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-((6-methylpyridin-2-yl)methyl)-1H-indole-2-carboxylate (15 mg, 0.018 mmol) and MeI (5 mg, 0.035 mmol) followed by saponification using General Procedure D. LCMS: $R_T$=1.959, 1.990 min, MS (ES) 832.8 (M+H).

Example 537

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-methoxyethoxy)-1-(pyridin-2-ylmethyl)-1H-indole-2-carboxylic acid Step A. Preparation of methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-2-ylmethyl)-1H-indole-2-carboxylate The title compound (88 mg, 41%) was prepared according to General Procedure I using methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (200 mg, 0.24 mmol) and 2-(bromomethyl)pyridine hydrobromide salt (200 mg, 0.80 mmol). LCMS: $R_T$=1.384 mm (LC method II), MS (ES) 908.8 (M+H).

Step B. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(pyridin-2-ylmethyl)-1H-indole-2-carboxylate The title compound (74 mg, 94%) was prepared following the procedure described Example 535 Step C using methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-2-ylmethyl)-1H-indole-2-carboxylate (88 mg, 0.090 mmol). LCMS: $R_T$=0.926 min (LC method II), MS (ES) 818.8 (M+H).

Step C. Example 537

The title compound (7.5 mg, 48%) was prepared according to General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(pyridin-2-ylmethyl)-1H-indole-2-carboxylate (15 mg, 0.018 mmol) and 1-bromo-2-methoxyethane (5 mg, 0.036 mmol) followed by saponification using General Procedure D. LCMS: $R_T$=1.953 min, MS (ES) 862.9 (M+H).

Example 538

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methoxy-1-(pyridin-2-ylmethyl)-1H-indole-2-carboxylic acid The title compound (6.6 mg, 44%) was prepared according to General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(pyridin-2-ylmethyl)-1H-indole-2-carboxylate (15 mg, 0.018 mmol) and MeI (5 mg, 0.035 mmol) followed by saponification using General Procedure D. LCMS: $R_T$=1.972 min, MS (ES) 818.8 (M+H).

Example 539

(R)-7-(7-Chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-(2-methoxyethoxy)-1-methyl-1H-indole-2-carboxylic acid The title compound (6.1 mg, 29%) was prepared according to General Procedure H using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-methyl-1H-indole-2-carboxylate (20 mg, 0.027 mmol) and 1-bromo-2-methoxyethane (10 mg, 0.072 mmol) followed by saponification using General Procedure D. LCMS: $R_T$=2.181 min, MS (ES) 783.9 (M+H). $^1$H NMR (400 MHz, DMSO-d$^6$) δ 9.08 (s, 1H), 7.92-7.87 (m, 1H), 7.42-7.38 (m, 1H), 7.18 (d, J=2.2 Hz, 0.7H), 7.13-7.08 (m, 1H), 6.98 (d, J=2.2 Hz, 0.3H), 6.71 (s, 1.5H), 6.67 (s, 1.5H), 4.69-4.63 (m, 0.5H), 4.36-4.30 (m, 0.5H), 4.08 (quart, J=5.6 Hz, 2H), 4.01 (s, 1H), 4.00-3.94 (m, 2H), 3.90 (s, 2H), 3.72-3.59 (m, 4H), 3.29 (s, 3H), 3.27-3.16 (m, 2H), 2.30 (s, 1H), 2.25 (s, 2H), 2.23 (s, 4H), 2.22 (s, 2H), 2.18 (s, 2H), 2.16 (s, 1H), 2.07-2.03 (m, 2H), 1.17 (d, J=6.5 Hz, 2H), 1.08 (d, J=6.5 Hz, 1H)

Example 540

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-methoxyethoxy)-1-((6-methylpyridin-2-yl)methyl)-1H-indole-2-carboxylic acid The title compound (4.4 mg, 28%) was prepared according to General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-((6-methylpyridin-2-yl)methyl)-1H-indole-2-carboxylate (15 mg, 0.018 mmol) and 1-bromo-2-methoxyethane (5 mg, 0.036 mmol) followed by saponification using General Procedure D. LCMS: $R_T$=1.944 min, MS (ES) 876.9 (M+H).

Example 541

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(3-(dimethylamino)propanamido)-1-methyl-1H-indole-3-carboxylic acid The title compound was prepared following the procedure described Example 533 using methyl (R)-5-amino-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylate (30 mg, 0.04 mmol) and 3-(dimethylamino)propanoic acid (7.0 mg, 0.06 mmol). MS (ES) 826.2 (M+H).

Example 542

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-(dimethylamino)acetamido)-1-methyl-1H-indole-3-carboxylic acid The title compound was prepared following the procedure described Example 533 using methyl (R)-5-amino-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylate (30 mg, 0.04 mmol) and dimethylglycine (6.2 mg, 0.06 mmol). MS (ES) 812.2 (M+H).

Example 543

(R)-3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-(piperidin-1-yl)ethyl)-1H-indole-5-carboxylic acid The title compound (3.6 mg, 32%) was prepared according to General Procedure G using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (10 mg, 0.01 mmol) and 1-(2-bromoethyl)piperidine hydrobromide (8 mg, 0.03 mmol) followed by saponification using General Procedure D. LCMS: $R_T$=1.909 min, MS (ES) 808.9 (M+H).

Example 544

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-((4-methylpiperazin-1-yl)methyl)-1H-indole-2-carboxylic acid Step A. Preparation of methyl 7-bromo-5-((methoxymethoxy)methyl)-1H-indole-2-carboxylate To a solution of 1-tert-butyl) 2-methyl 7-bromo-5-formyl-1H-indole-1,2-dicarboxylate (295 mg, 0.77 mmol) in DCM (7.3 mL) was added TFA (0.71 mL, 1.06 g, 9.3 mmol), and the reaction mixture was stirred at RT for 16 h. The reaction was quenched with sat. NH$_4$Cl aq. solution and extracted with DCM. The combined organic layer was dried, filtered and concentrated. The residue was re-dissolved in MeOH (6 mL)/THF (0.9 mL) and NaBH$_4$ (42 mg, 1.2 mmol) were added at RT. The reaction mixture was stirred for 30 min then quenched with sat. NH$_4$Cl aq. solution and extracted with DCM. The combined organic layer was dried, filtered and concentrated. The crude product was re-dissolved in DCM (4 mL), and MOMCl (92 μL, 98 mg, 1.22 mmol) and $^i$Pr$_2$EtN (0.56 mL, 414 mg, 3.2 mmol) were added in sequence. The reaction mixture was stirred at RT for 24 h then quenched with sat. NH$_4$Cl aq. solution and extracted with DCM. The combined organic layer was dried, filtered and concentrated. The residue was purified by flash chromatography (Combi-flash Rf, Hex/EtOAc=0-100% gradient) to afford the title compound (80 mg, 32% 3 steps). LCMS: $R_T$=1.512 min, MS (ES) 327.8 (M+H). $^1$H NMR (400 MHz, CDCl$_3$) δ 9.00 (br s, 1H), 7.63 (s, 1H), 7.54 (d, J=1.2 Hz, 1H), 7.28 (d, J=2.2 Hz, 1H), 4.74 (s, 2H), 4.67 (s, 2H), 3.98 (s, 3H), 3.45 (s, 3H).

Step B. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((methoxymethoxy)methyl)-1H-indole-2-carboxylate The title compound was prepared according to General Procedure A using methyl 7-bromo-5-((methoxymethoxy)methyl)-1H-indole-2-carboxylate. (20 mg, 0.061 mmol) and (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (32 mg, 0.061 mmol). MS (ES) 786.2 (M+H).

Step C. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((methoxymethoxy)methyl)-1-methyl-1H-indole-2-carboxylate The title compound was prepared according to General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((methoxymethoxy)methyl)-1H-indole-2-carboxylate. MS (ES) 800.2 (M+H).

Step D. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate To a solution of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((methoxymethoxy)methyl)-1-methyl-1H-indole-2-carboxylate in THF (1 mL) and MeOH (0.5 mL) was added conc. HCl (0.3 mL) at RT. The reaction mixture was stirred for 16 h at RT. The reaction was quenched with sat. NaHCO$_3$ aq. solution and extracted with DCM (3×10 mL). The combined organic layer was dried, filtered and concentrated to give the crude title compound, which was used to the next step directly.

Step E. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-formyl-1-methyl-1H-indole-2-carboxylate The crude methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate was dissolved in DCM (0.15 mL), and Dess-Martin periodinane (5 mg, 0.011 mmol) was added. The reaction mixture was stirred at RT for 1 h. The reaction was quenched with sat. sodium thiosulfate aq. solution and extracted with DCM. The combined organic layer was dried over MgSO$_4$, filtered and concentrated. The crude reaction mixture was purified by flash chromatography (Combi-flash Rf, Hex/EtOAc=0-100% gradient) to afford the title compound (9 mg, 20% 4 steps). LCMS: R$_T$=2.445 min, MS (ES) 753.9 (M+H).

Step F. Example 544

To a solution of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-formyl-1-methyl-1H-indole-2-carboxylate (9 mg, 0.012 mmol) in DCM (0.15 mL) and Et$_3$N (0.03 mL) were added N-methyl piperazine (2 µL, 1.7 mg, 0.017 mmol) and Na(OAc)$_3$BH (5.9 mg, 0.028 mmol) at RT. The reaction mixture was stirred at RT for 4 h. The reaction was quenched with sat. NaHCO$_3$ aq. solution and extracted with DCM. The combined organic layer was dried over MgSO$_4$, filtered and concentrated. Subsequent saponification was carried out following General Procedure D then purified by reverse phase HPLC (Phenomenex Gemini C18, H$_2$O/CH$_3$CN gradient 35-95% MeCN, 0.1% TFA) to afford the title compound (2.3 mg, 21%, 2 steps). LCMS: R$_T$=1.762 min, MS (ES) 823.9 (M+H).

Example 545

(R)-3-(7-Chloro-4-methyl-10-(3-(naphthalen-1-yloxy)propyl)-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid To a solution of (R)-3-(10-(3-bromopropyl)-7-chloro-4-methyl-1-oxo-6-(1,3,5-trimethyl-1H-pyrazol-4-yl)-3,4-dihydropyrazino[1,2-a]indol-2(1H)-yl)-1-methyl-1H-indole-5-carboxylic acid (15 mg, 0.024 mmol) in DMF (2 mL) were added 1-naphthol (20 mg, 0.14 mmol) and Cs$_2$CO$_3$ (30 mg, 0.092 mmol). The reaction was heated to 50° C. until complete by LCMS. The reaction was diluted with DCM/H$_2$O (10 mL, 1:1). The organic layer was separated and the aqueous layer was extracted with DCM. The combined organic layer was dried and concentrated. The residue was purified by reverse phase HPLC (Phenomenex Gemini C18, H$_2$O/CH$_3$CN gradient 35-95% MeCN 0.1% TFA) to afford the title compound (11.6 mg, 69%). LCMS: R$_T$=2.066 min, MS (ES) 699.9 (M+H). $^1$H NMR (400 MHz, Chloroform-d$^6$) δ 8.31 (s, 1H), 8.29-8.25 (m, 1H), 7.98 (dt, J=8.7, 1.5 Hz, 1H), 7.79-7.72 (m, 2H), 7.49-7.29 (m, 6H), 7.26-7.24 (m, 1H), 6.76 (d, J=7.5 Hz, 1H), 4.43-4.33 (m, 1H), 4.24-4.10 (m, 3H), 4.03-3.94 (m, 3H), 3.83 (s, 3H), 3.71-3.44 (m, 3H), 2.40 (quint, J=6.6 Hz, 2H), 2.27 (s, 1.5H), 2.20 (s, 1.5H), 2.11 (s, 1.5H), 2.05 (s, 1.5H), 1.20 (d, J=5.0 Hz, 1.5H), 1.16 (d, J=5.0 Hz, 1.5H).

Example 546

(R)-7-Chloro-10-(3-(4-chloro-3,5-dimethylphenoxy)propyl)-4-methyl-2-(5-(1-methyl-1H-1,2,4-triazol-3-yl)-1-(2-(4-methylpiperazin-1-yl)-2-oxoethyl)-1H-indol-3-yl)-6-(1,3,5-trimethyl-1H-pyrazol-4-yl)-3,4-dihydropyrazino[1,2-a]indol-1(2H)-one Step A. Preparation of 1-(4-methylpiperazin-1-yl)-2-(5-(4,4,5,5-tetramethyl-1,3,2-dioxaborolan-2-yl)-1H-indol-1-yl)ethan-1-one BOP reagent (529 mg, 1.20 mmol), 1-methylpiperazine (442 µL, 3.98 mmol) and N-methylmorpholine (548 µL, 4.98 mmol) were added to a solution of 2-(5-(4,4,5,5- tetramethyl-1,3,2-dioxaborolan-2-yl)-1H-indol-1-yl)acetic acid (300 mg, 1.00 mmol) in DMF (6.6 mL). The reaction mixture was stirred at RT for 1 h. The reaction mixture was quenched with water and extracted with EtOAc. The combined organic layers were washed with water, dried and concentrated. The residue was purified by flash chromatography (Combi-flash Rf, DCM/MeOH=0-2% gradient) to afford the title compound (240 mg, 63%). LCMS: $R_T$=1.128 min, MS (ES) 384.1 (M+H).

Step B. Preparation of 2-(5-(1-methyl-1H-1,2,4-triazol-3-yl)-1H-indol-1-yl)-1-(4-methylpiperazin-1-yl)ethan-1-one The title compound (68 mg, 65%) was prepared following the procedure described Example 388 Step A using 1-(4-methylpiperazin-1-yl)-2-(5-(4,4,5,5-tetramethyl-1,3,2-dioxaborolan-2-yl)-1H-indol-1-yl)ethan-1-one (154 mg, 0.40 mmol) and 3-bromo-1-methyl-1H-1,2,4-triazole (50 mg, 0.31 mmol). LCMS: $R_T$=0.885 min, MS (ES) 339.1 (M+H).

Step C. Preparation of 2-(3-iodo-5-(1-methyl-1H-1,2,4-triazol-3-yl)-1H-indol-1-yl)-1-(4-methylpiperazin-1-yl)ethan-1-one The title crude compound (44 mg) was prepared following the procedure described Example 388 Step B using 2-(5-(1-methyl-1H-1,2,4-triazol-3-yl)-1H-indol-1-yl)-1-(4-methylpiperazin-1-yl)ethan-1-one (68 mg, 0.20 mmol). LCMS: $R_T$=0.224 min, MS (ES) 464.8 (M+H).

Step D. Example 546

The title compound (5 mg, 10%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 2-(3-iodo-5-(1-methyl-1H-1,2,4-triazol-3-yl)-1H-indol-1-yl)-1-(4-methylpiperazin-1-yl)ethan-1-one (44 mg, 0.10 mmol). LCMS: $R_T$=1.794 min, MS (ES) 874.9 (M+H).

Example 547

(R)-7-(7-chloro-10-(3-(4-chloro-3,5-dimethylphenoxy)propyl)-4-methyl-t-oxo-6-(1,3,5-trimethyl-1H-pyrazol-4-yl)-3,4-dihydropyrazino[1,2-a]indol-2(1H)-yl)-5-((4-(4-chlorophenoxy)piperidin-1-yl)methyl)-1-methyl-1H-indole-3-carboxylic acid Step A. Preparation of ethyl 7-bromo-5-((methoxymethoxy)methyl)-1-methyl-1H-indole-3-carboxylate To a solution of ethyl 7-bromo-5-(bromomethyl)-1-methyl-1H-indole-3-carboxylate (292 mg, 0.78 mmol) in MeCN (14 mL) were added NMO (44 mg, 0.38 mmol) and 4 Å molecular sieves (250 mg) and stirred at RT for 4 h. The reaction was quenched with aq. sat. NH$_4$Cl solution and extracted with EtOAc. The combined organic layer was washed with brine solution, dried over MgSO$_4$, filtered, and concentrated. The residue was purified by flash chromatography (Combi-flash Rf, Hex/EtOAc=0-60% gradient) to afford ethyl 7-bromo-5-formyl-1-methyl-1H-indole-3-carboxylate. The title compound (120 mg, 43% 3 steps) was prepared following the procedure described Example 544 Step A using ethyl 7-bromo-5-formyl-1-methyl-1H-indole-3-carboxylate. LCMS: $R_T$=1.850 min, MS (ES) 377.9 (M+Na). $^1$H NMR (400 MHz, CDCl$_3$) δ 8.15 (s, 1H), 7.70 (s, 1H), 7.46 (s, 1H), 4.74 (s, 2H), 4.67 (s, 2H), 4.38 (q, J=7.1 Hz, 2H), 4.17 (s, 3H), 3.45 (s, 3H), 1.42 (t, J=7.1 Hz, 3H).

Step B. Preparation of ethyl (R)-7-(7-chloro-10-(3-(4-chloro-3,5-dimethylphenoxy)propyl)-4-methyl-t-oxo-6-(1,3,5-trimethyl-1H-pyrazol-4-yl)-3,4-dihydropyrazino[1,2-a]indol-2(1H)-yl)-5-((methoxymethoxy)methyl)-1-methyl-1H-indole-3-carboxylate The title compound was prepared following General coupling procedure A using ethyl 7-bromo-5-((methoxymethoxy)methyl)-1-methyl-1H-indole-3-carboxylate (57 mg, 0.161 mmol) and (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (86 mg, 0.161 mmol).

Step C. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-formyl-1-methyl-1H-indole-3-carboxylate To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((methoxymethoxy)methyl)-1-methyl-1H-indole-3-carboxylate (from Step B) in THF (3 mL) and MeOH (1.5 mL) was added Conc. HCl (0.9 mL) and stirred for 16 h ar RT. The reaction mixture was quenched with aq. sat. NaHCO$_3$ solution and extracted with DCM. The combined organic layer was dried over MgSO$_4$, filtered and concentrated. The crude product obtained was re-dissolved in DCM (1.6 mL). Dess-Martin periodinane (68 mg, 0.16 mmol) was added and stirred at RT for 1 h. Then, the reaction mixture was quenched with aq. sat. Na$_2$S$_2$O$_3$ solution and extracted with DCM. The combined organic layer was dried over MgSO$_4$, filtered and concentrated. The residue was purified by flash chromatography (Combi-flash Rf, DCM/MeOH=0-10% gradient) to afford the title compound (57 mg, 47%, 3 steps). LCMS: $R_T$=2.386, 2.406, 2.449 min, MS (ES) 767.8 (M+H).

Step D. Example 547

To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-formyl-1-methyl-1H-indole-3-carboxylate (19 mg, 0.025 mmol) in DCM (0.25 mL) and Et$_3$N (0.05 mL) was added 4-(4-chlorophenoxy)piperidine (2.6 mg, 0.030 mmol) followed by Na(OAc)$_3$BH (10.6 mg, 0.050 mmol). After stirring at RT for 4 h, the reaction mixture was quenched with aq. sat. NH$_4$Cl solution (2 mL) and extracted with DCM (3×5 mL). The combined organic layer was dried over MgSO$_4$, filtered and concentrated. Subsequent saponification was carried out following general procedure D using 2M NaOH. The crude was purified by reverse phase HPLC (Phenomenex Gemini C18, H$_2$O/CH$_3$CN gradient 35-95% MeCN, 0.1% TFA) and concentrated to afford the title compound (4.3 mg, 21%, 2 steps). LCMS: $R_T$=2.078, 2.104 min, MS (ES) 934.8 (M+H). $^1$H NMR (600 MHz, DMSO-d$_6$) δ 8.02-7.95 (m, 2H), 7.76 (d, J=8.6 Hz, 1H), 7.32-7.29 (m, 1H), 7.28 (d, J=8.9 Hz, 2H), 7.18 (d, J=9.6 Hz, 0.5H), 6.98-6.95 (m, 2.5H), 6.70 (d, J=14.5 Hz, 2H), 4.24-4.13 (m, 1H), 4.00-3.93 (m, 2H), 3.82 (s, 1H), 3.79-3.77 (m, 2.2H), 3.75-3.73 (m, 2.6H), 3.68 (d, J=13.0 Hz, 0.6H), 3.64 (d, J=13.0 Hz, 0.4H), 3.62-3.56 (m, 1.7H), 3.54-3.48 (m, 0.4H), 3.30-3.27 (m, 0.7H), 3.27-3.15 (m, 1.4H), 2.69 (br s, 2H), 2.29-2.22 (m, 7.6H), 2.12-2.11 (m, 2H), 2.06-1.99 (m, 4H), 1.96 (s, 1H), 1.94-1.89 (m, 2.5H), 1.88 (s, 1.5H), 1.62-1.54 (m, 2H), 1.19-1.15 (m, 2H), 1.06 (dd, J=6.6, 2.2 Hz, 1H).

Example 548

(R)-7-Chloro-10-(3-(4-chloro-3,5-dimethylphenoxy)propyl)-2-(1-(2-methoxyethyl)-5-(pyrimidin-2-yl)-1H-indol-3-yl)-4-methyl-6-(1,3,5-trimethyl-1H-pyrazol-4-yl)-3,4-dihydropyrazino[1,2-a]indol-1(2H)-one Step A. Preparation of 1-(2-methoxyethyl)-5-(pyrimidin-2-yl)-1H-indole The title compound (100 mg, 90%) was prepared following the procedure described Example 388 Step A using 1-(2-methoxyethyl)-5-(4,4,5,5-tetramethyl-1,3,2-dioxaborolan-2-yl)-1H-indole (172 mg, 0.57 mmol) and 2-bromopyrimidine (70 mg, 0.44 mmol). LCMS: $R_T$=1.329 min, MS (ES) 254.1 (M+H).

Step B. Preparation of 3-iodo-1-(2-methoxyethyl)-5-(pyrimidin-2-yl)-1H-indole

The title compound (133 mg, 89%) was prepared following the procedure described Example 388 Step B using 1-(2-methoxyethyl)-5-(pyrimidin-2-yl)-1H-indole (100 mg, 0.39 mmol). LCMS: $R_T$=1.658 min, MS (ES) 379.9 (M+H).

Step C. Example 548

The title compound (40 mg, 82%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-(2-methoxyethyl)-5-(pyrimidin-2-yl)-1H-indole (42 mg, 0.10 mmol). LCMS: $R_T$=2.243 min, MS (ES) 790.9 (M+H).

Example 549

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(morpholinomethyl)-1H-indole-3-carboxylic acid The title compound was prepared (4.3 mg, 21%, 2 steps) following the procedure described in Example 547 step D using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-formyl-1-methyl-1H-indole-3-carboxylate (19 mg, 0.025 mmol) and morpholine (2.6 mg, 2.6 µL, 0.030 mmol). LCMS: $R_T$=1.886, 1.922 min. MS (ES) 810.9 (M+H).

Example 550

(R)-7-(7-chloro-10-(3-(4-chloro-3,5-dimethylphenoxy)propyl)-4-methyl-t-oxo-6-(1,3,5-trimethyl-1H-pyrazol-4-yl)-3,4-dihydropyrazino[1,2-a]indol-2(1H)-yl)-1-methyl-5-(pyrrolidin-1-ylmethyl)-1H-indole-3-carboxylic acid The title compound was prepared (4.0 mg, 20%, 2 steps) following the procedure described in Example 547 step D using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-formyl-1-methyl-1H-indole-3-carboxylate (19 mg, 0.025 mmol) and pyrrolidine (2.1 mg, 0.030 mmol). LCMS: $R_T$=1.907, 1.943 min, MS (ES) 794.8 (M+H).

Example 551

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5(3-(4-methylpiperazin-1-yl)propanamido)-1H-indole-3-carboxylic acid The title compound (60%) was prepared following the procedure described Example 533 using methyl (R)-5-amino-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylate and 3-(4-methylpiperazin-1-yl)propanoic acid. MS (ES) 881.2 (M+H).

Example 552

(R)-1-((4-(4-acetylpiperazin-1-yl)pyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylic acid Step A. Preparation of ethyl (R)-1-((4-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate The title compound (222 mg, 72%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (250 mg, 0.34 mmol) and 4-bromo-2-(chloromethyl)-pyridine (174 mg, 0.84 mmol). LCMS: $R_T$=2.43 min., MS (ES) 909 (M+H).

Step B. Preparation of pentyl (R)-7-(7-chloro-10-(3-(4-chloro-3,5-dimethylphenoxy)-propyl)-4-methyl-1-oxo-6-(1,3,5-trimethyl-1H-pyrazol-4-yl)-3,4-dihydropyrazino[1,2-a]indol-2(1H)-yl)-5-methyl-1-((4-(piperazin-1-yl)pyridin-2-yl)methyl)-1H-indole-2-carboxylate To a solution of ethyl (R)-1-((4-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (85 mg, 0.09 mol) in pentanol (0.5 mL) was added piperazine (40 mg, 0.47 mmol). The reaction was sealed and stirred at 125° C. overnight. The reaction mixture was cooled to RT and diluted with EtOAc and water. The aqueous layer was separated and extracted with EtOAc. The combined organic layer was washed with brine, dried over MgSO$_4$, filtered and concentrated in vacuo. The residue was purified by flash chromatography (Combi-flash Rf, DCM/methanol=0-6% gradient) to give the title compound (66 mg, 74%). LCMS: $R_T$=1.92 min., MS (ES) 957 (M+H).

Step C. Preparation of pentyl (R)-1-((4-(4-acetylpiperazin-1-yl)pyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate To a solution of pentyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((4-(piperazin-1-yl)pyridin-2-yl)methyl)-1H-indole-2-carboxylate (66 mg, 0.07 mol) in DCM (1.0 mL) at 0° C. under Ar was added Et$_3$N (17 mg, 0.17 mmol) followed by acetyl chloride (11 mg, 0.14 mmol) then diluted with DCM (0.4 mL). The reaction was warmed to RT and stirred 3 h. The reaction was diluted with DCM and water. The aqueous layer was separated and extracted with DCM. The combined organic layers were washed with brine, dried over MgSO$_4$, filtered and concentrated in vacuo to give the crude title compound (69 mg, 100%). LCMS: $R_T$=2.06 min., MS (ES) 999 (M+H).

Step D. Example 552

The title compound (40 mg, 62%, 2 steps) was prepared following General Procedure D using pentyl (R)-1-((4-(4-acetylpiperazin-1-yl)pyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (69 mg, 0.07 mmol). LCMS: $R_T$=1.87 min., MS (ES) 929 (M+H).

Example 553

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((4-(piperazin-1-yl)pyridin-2-yl)methyl)-1H-indole-2-carboxylic acid The title compound was obtained as a byproduct of Example 552 step D. LCMS: $R_T$=1.71 min., MS (ES) 887 (M+H).

Example 554

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(2-(4-methylpiperazin-1-yl)acetamido)-1H-indole-3-carboxylic acid The title compound (62%) was prepared following the procedure described Example 533 using methyl (R)-5-amino-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylate and 2-(4-methylpiperazin-1-yl) acetic acid. MS (ES) 867.2 (M+H).

Example 555

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-4-ylmethyl)-1H-indole-5-carboxylic acid The title compound (9.6 mg, 61%) was prepared according to General Procedure I using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (15 mg, 0.02 mmol) and 4-(bromomethyl)pyridine HBr (10 mg, 0.04 mmol) followed by saponification using General Procedure D. LCMS: $R_T$=1.811 min, MS (ES) 788.80 (M+H). $^1$H NMR (400 MHz, DMSO-d$_6$) δ 8.74 (d, J=5.7 Hz, 2H), 8.16 (s, 1H), 7.82-7.74 (m, 3H), 7.56 (d, J=8.7 Hz, 1H), 7.50 (t, J=6.7 Hz, 2H), 7.30 (d, J=8.7 Hz, 1H), 6.73 (s, 2H), 5.76 (s, 2H), 4.53 (t, J=3.4 Hz, 0.5H), 4.50 (t, J=3.6 Hz, 0.5H), 4.28-4.11 (m, 1H), 3.99 (dt, J=6.2 & 2.2 Hz, 2H), 3.78 (s, 1.5H), 3.77 (s, 1.5H), 3.75-3.69 (m, 1H), 3.41-3.29 (m, 1H), 3.28-3.18 (m, 1H), 2.24 (s, 6H), 2.13 (s, 1.5H), 2.10-2.04 (m, 2H), 2.03 (s, 1.5H), 1.98 (s, 1.5H), 1.89 (s, 1.5H), 1.10 (d, J=6.4 Hz, 3H).

Example 556

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4-cyanopyridin-2-yl)methyl)-5-methyl-1H-indole-2-carboxylic acid Step A. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4-cyanopyridin-2-yl)methyl)-5-methyl-1H-indole-2-carboxylate To a solution of ethyl (R)-1-((4-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (102 mg, 0.11 mol) in DMF (1.0 mL) was added Zn(CN)$_2$ (18 mg, 0.16 mmol) and Pd(PPh$_3$)$_4$ (13 mg, 0.01 mmol). The reaction mixture was degassed, sealed and stirred at 110° C. for 3 h. The reaction mixture was cooled to RT and diluted with EtOAc and water. The aqueous layer was separated and extracted with EtOAc. The combined organic layer was washed with brine, dried over Na$_2$SO$_4$, filtered and concentrated in vacuo. The residue was purified by flash chromatography (Combi-flash Rf, DCM/methanol=0-2.5% gradient) to give the title compound (74 mg, 77%). LCMS: $R_T$=1.65 min., MS (ES) 856 (M+H).

Step B. Example 556

The title compound (40 mg, 62%) was prepared following General Procedure D using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4-cyanopyridin-2-yl)methyl)-5-methyl-1H-indole-2-carboxylate (74 mg, 0.09 mmol). LCMS: $R_T$=2.25 min., MS (ES) 828 (M+H). $^1$H NMR (400 MHz, DMSO-d$_6$) δ 8.51 (d, J=5.0 Hz, 0.5H), 8.42 (d, J=5.0 Hz, 0.5H), 7.68 (m, 1H), 7.54 (m, 2H), 7.38 (m, 1H), 7.25 (m, 1H), 6.81 (m, 2H), 6.71 (s, 2H), 6.02 (m, 1H), 5.62-5.88 (bm, 1H), 4.54 (m, 1H), 3.87-3.95 (bm, 3H) 3.74 (s, 1.5H), 3.72 (s, 1.5H), 3.39 (m, 1H), 3.03-3.21 (bm, 3H), 2.38 (s, 3H), 2.24 (s, 3H), 2.22 (s, 3H), 1.99-2.08 (bm, 4H), 1.86 (s, 1.5H), 1.74 (s, 1.5H) 1.01 (m, 3H).

Example 557

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((6-cyanopyridin-2-yl)methyl)-5-methyl-1H-indole-2-carboxylic acid Step A. Preparation of ethyl (R)-1-((6-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate The title compound (293 mg, 95%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (250 mg, 0.34 mmol, 1.0 eq) and 2-bromo-6-(bromomethyl)-pyridine (119 mg, 0.47 mmol). LCMS: $R_T$=2.44 min., MS (ES) 909 (M+H).

Step B. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((6-cyanopyridin-2-yl)methyl)-5-methyl-1H-indole-2-carboxylate The title compound (53 mg, 84%) was prepared following the procedure described Example 556, Step A using ethyl (R)-1-((6-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (67 mg, 0.07 mol). LCMS: $R_T$=1.62 min., MS (ES) 856 (M+H).

Step C. Example 557

The title compound (17 mg, 29%) was prepared following General Procedure D using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((6-cyanopyridin-2-yl)methyl)-5-methyl-1H-indole-2-carboxylate (53 mg, 0.06 mmol). LCMS: $R_T$=2.23 min., MS (ES) 828 (M+H).

Example 558

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-methyl-5-(2-morpholinoethoxy)-1H-indole-2-carboxylic acid The title compound (6.1 mg, 27%) was prepared following General Procedure H using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-methyl-1H-indole-2-carboxylate (20 mg, 0.027 mmol) and 4-(2-chloroethyl)morpholine HCl (10 mg, 0.054 mmol) followed by saponification using General Procedure D. LCMS: $R_T$=1.853 min, MS (ES) 838.9 (M+H).

Example 559

(R)-3-(7-chloro-10-(3-(4-chloro-3,5-dimethylphenoxy)propyl)-6-(4,6-dimethyl-2-((4-methylpiperazin-1-yl)methyl)pyrimidin-5-yl)-4-methyl-1-oxo-3,4-dihydropyrazino[1,2-a]indol-2(1H)-yl)-1-(2-methoxyethyl)-1H-indole-5-carboxylic acid Step A. (R)-7-chloro-10-(3-(4-chloro-3,5-dimethylphenoxy)propyl)-6-(2-(hydroxymethyl)-4,6-dimethylpyrimidin-5-yl)-4-methyl-3,4-dihydropyrazino[1,2-a]indol-1(2H)-one The title compound (94 mg, 95%) was prepared following the procedure described Example 390 Step D using (R)-6-(2-((benzyloxy)methyl)-4,6-dimethylpyrimidin-5-yl)-7-chloro-10-(3-(4-chloro-3,5-dimethylphenoxy)propyl)-4-methyl-3,4-dihydropyrazino[1,2-a]indol-1(2H)-one (115 mg, 0.175 mmol) and Pd/C (10 wt %, 20 mg, 0.019 mmol) by hydrogenating in MeOH (5 mL) with HCl (4.0 M in dioxanes, 0.5 mL) for 6 h at 40°C. LCMS: $R_T$=0.946 min (Method B), MS (ES) 566.9 (M+H).

Step B. (R)-7-chloro-10-(3-(4-chloro-3,5-dimethylphenoxy)propyl)-6-(4,6-dimethyl-2-((4-methylpiperazin-1-yl)methyl)pyrimidin-5-yl)-4-methyl-3,4-dihydropyrazino[1,2-a]indol-1(2H)-one The title compound (55 mg, 96%) was prepared following General Procedure J using (R)-7-chloro-10-(3-(4-chloro-3,5-dimethylphenoxy)propyl)-6-(2-(hydroxymethyl)-4,6-dimethylpyrimidin-5-yl)-4-methyl-3,4-dihydropyrazino[1,2-a]indol-1(2H)-one (50 mg, 0.088 mmol). MsCl (30 mg, 0.26 mmol), and N-methyl piperazine (50 mg, 0.50 mmol). The crude reaction product was carried forward without further purification. LCMS: $R_T$=1.658 min, MS (ES) 648.9 (M+H).

Step C. Example 559

The title compound was prepared (2.4 mg, 9%) following General Procedure B using: (R)-7-chloro-10-(3-(4-chloro-3,5-dimethylphenoxy)propyl)-6-(4,6-dimethyl-2-((4-methylpiperazin-1-yl)methyl)pyrimidin-5-yl)-4-methyl-3,4-dihydropyrazino[1,2-a]indol-1(2H)-one (20 mg, 0.031 mmol) and methyl 3-bromo-1-(2-methoxyethyl)-1H-indole-5-carboxylate (25 mg, 0.081 mmol) followed by saponification using General Procedure D. LCMS: $R_T$=1.769 min, MS (ES) 865.9 (M+H).

Example 560

(R)-2-(3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(1-methyl-1H-1,2,4-triazol-3-yl)-1H-indol-1-yl)-N,N-dimethylacetamide Step A. Preparation of N,N-dimethyl-2-(5-(1-methyl-1H-1,2,4-triazol-3-yl)-1H-indol-1-yl)acetamide The title crude compound (120 mg) was prepared following the procedure described Example 388 Step A using N,N-dimethyl-2-(5-(4,4,5,5-tetramethyl-1,3,2-dioxaborolan-2-yl)-1H-indol-1-yl)acetamide (152 mg, 0.46 mmol) and 3-bromo-1-methyl-1H-1,2,4-triazole (50 mg, 0.31 mmol). LCMS: $R_T$=0.169 min, MS (ES) 284.1 (M+H).

Step B. Preparation of 2-(3-iodo-5-(1-methyl-1H-1,2,4-triazol-3-yl)-1H-indol-1-yl)-N,N-dimethylacetamide The title compound (70 mg, 40%) was prepared following the procedure described Example 388 Step B using N,N-dimethyl-2-(5-(1-methyl-1H-1,2,4-triazol-3-yl)-1H-indol-1-yl)acetamide (120 mg, 0.42 mmol). LCMS: $R_T$=1.118 min, MS (ES) 409.9 (M+H)

Step C. Example 560

The title compound (9.5 mg, 21%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 2-(3-iodo-5-(1-methyl-1H-1,2,4-triazol-3-yl)-1H-indol-1-yl)-N,N-dimethylacetamide (46 mg, 0.11 mmol). LCMS: $R_T$=1.971 min, MS (ES) 819.9 (M+H).

Example 561

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-2-ylmethyl)-1H-indole-5-carboxylic acid The title compound (16 mg, 99%) was prepared according to General Procedure I using methyl (R)-3-(7-chloro-10-(3-(4-chloro-3,5-dimethylphenoxy)propyl)-4-methyl-1-oxo-6-(1,3,5- trimethyl-1H-pyrazol-4-yl)-3,4-dihydropyrazino[1,2-a]indol-2(1H)-yl)-1H-indole-5-carboxylate (15 mg, 0.02 mmol) and 2-(bromomethyl)pyridine HBr (10 mg, 0.04 mmol) followed by saponification using General Procedure D. LCMS: $R_T$=1.913 min (Method B), MS (ES) 788.80 (M+H). $^1$H NMR (400 MHz, DMSO-d$_6$) δ 8.57 (d, J=4.8 Hz, 1H), 8.12 (s, 1H), 7.84-7.76 (m, 2H), 7.75-7.71 (m, 2H), 7.59 (d, J=8.6 Hz, 1H), 7.34 (t, J=5.7 Hz, 1H), 7.29 (d, J=8.6 Hz, 1H), 7.20-7.14 (m, 1H), 6.73 (s, 2H), 5.57 (s, 2H), 4.59-4.43 (m, 1H), 4.23-4.08 (m, 1H), 3.98 (dt, J=6.0 & 2.7 Hz, 2H), 3.78 (s, 1.5H), 3.77 (s, 1.5H), 3.74-3.64 (m, 1H), 3.40-3.28 (m, 1H), 3.28-3.17 (m, 1H), 2.23 (s, 6H), 2.12 (s, 1.5H), 2.10-2.04 (m, 2H), 2.03 (s, 1.5H), 1.97 (s, 1.5H), 1.88 (s, 1.5H), 1.09 (d, J=6.4 Hz, 3H).

Example 562

(R)-7-chloro-10-(3-(4-chloro-3,5-dimethylphenoxy)propyl)-2',4-dimethyl-1,1'-dioxo-6-(1,3,5-trimethyl-1H-pyrazol-4-yl)-1',2',3,3',4,4'-hexahydro-1H-[2,6'-bipyrazino[1,2-a]indole]-10'-carboxylic acid Step A. Preparation of 1,2-bis(2-bromophenyl)hydrazine To a solution of 1-bromo-2-nitrobenzene (0.97 g, 4.8 mmol) in 50% aq. NaOH (0.3 mL) was added Zn dust (0.9 g, 13.9 mmol) in small portions while maintaining the reaction temperature below 80° C. The mixture was diluted with water (6 mL) and 20% aq. NaOH (12 mL) then zinc dust (1.2 g, 18.7 mmol) was added in one portion. The resulting mixture was heated at 80° C. for 1 h, cooled to RT and poured slowly to 10% sulfuric acid (20 mL) at 0° C. The mixture was stirred for 30 min then extracted with diethyl ether. The combined organic layer was dried over MgSO$_4$, filtered and concentrated. The residue was purified by flash chromatography (Combi-flash Rf, Hex/EtOAc=0-80% gradient) to afford the title compound (165 mg, 20%). LCMS: $R_T$=1.818 min, MS (ES) 340.8 (M+H).

Step B. Preparation of dimethyl 7-bromo-1H-indole-2,3-dicarboxylate

To a solution of 1,2-bis(2-bromophenyl)hydrazine (165 mg, 0.5 mmol) in MeOH (5 mL), dimethyl but-2-ynedioate (41 µL, 92 mg, 0.65 mmol) was added and refluxed for 16 h. The reaction was quenched with aq. sat. NH$_4$Cl solution and extracted with DCM. The combined organic layer was dried over MgSO$_4$, filtered and concentrated. The residue was purified by flash chromatography (Combi-flash Rf, Hex/EtOAc=0-80% gradient) to afford the title compound (30 mg, 19%). $^1$H NMR (400 MHz, CDCl$_3$) δ 9.34 (br s, 1H), 8.02 (d, J=8.2 Hz, 1H), 7.54 (dd, J=7.6, 0.8 Hz, 1H), 7.17 (t, J=8.1 Hz, 1H), 4.03 (s, 3H), 4.00 (s, 3H).

Step C. Preparation of methyl 6-bromo-2-methyl-1-oxo-1,2,3,4-tetrahydropyrazino[1,2-a]indole-10-carboxylate To a solution of dimethyl 7-bromo-1H-indole-2,3-dicarboxylate (30 mg, 0.10 mmol) in MeCN (1 mL) was added Cs$_2$CO$_3$ (78.2 mg, 0.24 mmol) followed by tert-butyl 1,2,3-oxathiazolidine-3-carboxylate 2,2-dioxide (26.8 mg, 0.12 mmol). The reaction was heated at 75° C. for 16 h then quenched with aq. sat. NH$_4$Cl solution and extracted with EtOAc. The combined organic layer was washed with brine, dried over MgSO$_4$, filtered, and concentrated. The crude product was re-dissolved in DCM (0.6 mL), TFA (138 mg, 1.2 mmol) was added and stirred at RT for 16 h. The reaction was quenched with aq. sat. NaHCO$_3$ and extracted with DCM. The combined organic layer was dried over MgSO$_4$, filtered and concentrated. The crude product was redissolved in CH$_3$CN (1.6 mL). Cs$_2$CO$_3$ (78 mg, 0.24 mmol) was added and heated at 70° C. for 12 h. Then, the reaction mixture was quenched with aq. sat. NH$_4$Cl solution and extracted with DCM. The combined organic layer was dried over MgSO$_4$, filtered and concentrated. The crude product was re-dissolved in DMF (1 mL). NaH (12 mg, 0.3 mmol) followed by MeI (63 µL, 142 mg, 1.0 mmol) were added and stirred at RT for 1 h. Then, the reaction mixture was quenched with aq. sat. NH$_4$Cl solution and extracted with DCM. The residue was purified by flash chromatography (Combi-flash Rf, Hex/EtOAc=0-100% gradient) to afford the title compound (7 mg, 20% yield, 4 steps). LCMS: $R_T$=1.337 min, MS (ES) 337.0 (M+H).

Step D. Example 562

The title compound (1.5 mg, 10%, 2 steps) was prepared following General coupling procedure A using methyl 6-bromo-2-methyl-1-oxo-1,2,3,4-tetrahydropyrazino[1,2-a]indole-10-carboxylate (7 mg, 0.02 mmol) and (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (11 mg, 0.02 mmol) followed by saponification using General Procedure D. LCMS: $R_T$=2.154, 2.186 min, MS (ES) 780.9 (M+H).

Example 563

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-3-ylmethyl)-1H-indole-5-carboxylic acid The title compound (12 mg, 76%) was prepared according to General Procedure I using methyl (R)-3-(7-chloro-10-(3-(4-chloro-3,5-dimethylphenoxy)propyl)-4-methyl-1-oxo-6-(1,3,5- trimethyl-1H-pyrazol-4-yl)-3,4-dihydropyrazino[1,2-a]indol-2(1H)-yl)-1H-indole-5-carboxylate (15 mg, 0.02 mmol) and 3-(bromomethyl)pyridine HBr (10 mg, 0.04 mmol) followed by saponification using General Procedure D. LCMS: $R_T$=1.804 min (Method B). MS (ES) 788.80 (M+H). $^1$H NMR (400 MHz, DMSO-d$_6$) δ 8.72-8.65 (m, 1H), 8.64-8.57 (m, 1H), 8.12 (s, 1H), 7.86 (t, J=7.6 Hz, 1H), 7.83-7.80 (m, 1H), 7.79 (d, J=8.5 Hz, 1H), 7.75 (d, J=8.6 Hz, 1H), 7.69 (d, J=8.6 Hz, 1H), 7.59-7.52 (m, 1H), 7.29 (d, J=8.5 Hz, 1H), 6.73 (s, 2H), 5.59 (s, 2H), 4.50 (t, J=3.5 Hz, 0.5H), 4.47 (t, J=3.6 Hz, 0.5H), 4.25-4.09 (m, 1H), 3.98 (dt, J=6.3 & 2.2 Hz, 2H), 3.78 (s, 1.5H), 3.77 (s, 1.5H), 3.75-3.65 (m, 1H), 3.39-3.28 (m, 1H), 3.27-3.17 (m, 1H), 2.23 (s, 6H), 2.12 (s, 1.5H), 2.10-2.04 (m, 2H), 2.03 (s, 1.5H), 1.97 (s, 1.5H), 1.88 (s, 1.5H), 1.09 (d, J=6.5 Hz, 3H).

Example 564

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(methyl(pyridin-2-ylmethyl)amino)-1H-indole-3-carboxylic acid Step A. Preparation of methyl 7-bromo-5-((tert-butoxycarbonyl)(methyl)amino)-1-methyl-1H-indole-3-carboxylate To a solution of methyl 7-bromo-5-((tert-butoxycarbonyl)amino)-1-methyl-1H-indole-3-carboxylate (450 mg, 1.17 mmol) in DMF (5 mL) was added NaH (95 mg, 2.4 mmol) at 0° C. under N$_2$ stirred for 10 min. MeI (2.0 mmol) was added to the reaction mixture and stirred at 0° C. for 10 min then at RT for 1 h. The reaction mixture was diluted with EtOAc, washed with brine, dried and concentrated. The residue was purified by flash chromatography (Combi-flash Rf, DCM/MeOH=0-10% gradient) to afford the title compound (440 mg, 94%). $^1$H-NMR (DMSO-d$_6$) δ 8.0 (s, 1H), 7.73 (s, 1H), 7.34 (s, 1H), 4.20 (s, 3H), 3.91 (s, 3H), 3.31 (s, 1H), 1.49 (s, 9H).

Step B. Preparation of methyl (R)-5-((tert-butoxycarbonyl)(methyl)amino)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-3-carboxylate The title compound (78%) was prepared following General coupling procedure A using methyl 7-bromo-5-((tert-butoxycarbonyl)(methyl)amino)-1-methyl-1H-indole-3-carboxylate and (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one. MS (ES) 855.3 (M+H)

Step C. Preparation of methyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-1-methyl-5-(methylamino)-1H-indole-3-carboxylate (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(methylamino)-1H-indole-3-carboxylate was dissolved in DCM/TFA (5/1) and stirred for 2 h at RT. The reaction mixture was concentrated in vacuo to afford the title compound (95%) which was carried to the next step without further purification.

Step D. Example 564

The title compound (65%) was prepared following General procedure G using methyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-1-methyl-5-(methylamino)-1H-indole-3-carboxylate and 2-(bromomethyl)pyridine followed by saponification using General Procedure D. MS (ES) 832.1 (M+H)

Example 565

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methoxy-1-((4-methylpyridin-2-yl)methyl)-1H-indole-2-carboxylic acid Step A. Preparation of methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-((4-methylpyridin-2-yl)methyl)-1H-indole-2-carboxylate The title compound (84 mg, 93%) was prepared following General Procedure I using methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1H-indole-2-carboxylate (80 mg, 0.098 mmol) and 2-(chloromethyl)-4-methylpyridine HCl (30 mg, 0.17 mmol). LCMS: $R_T$=1.299 min (Method B), MS (ES) 920.8 (M+H).

Step B. Preparation of methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1)-yl)-5-hydroxy-1-((4-methylpyridin-2-yl)methyl)-1H-indole-2-carboxylate The title compound (73 mg, 96%) was prepared following the procedure described Example 390 Step D using methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-((4-methylpyridin-2-yl)methyl)-1H-indole-2-carboxylate (84 mg, 0.092 mmol) and Pd/C (10 wt. %, 10 mg, 0.0092 mmol) by hydrogenating in MeOH (5 mL) with HCl for 5 h at RT. LCMS: $R_T$=0.839, 0.864 min (Method B), MS (ES) 830.8 (M+H).

Step C. Example 565

The title compound (5.9 mg, 39%) was prepared following General Procedure H using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-((4-methylpyridin-2-yl)methyl)-1H-indole-2-carboxylate (15 mg, 0.018 mmol) and MeI (10 mg, 0.070 mmol) followed by saponification using General Procedure D. LCMS: $R_T$=1.979 min, MS (ES) 830.8 (M+H).

Example 566

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-(2-(dimethylamino)ethoxy)-1-((6-methylpyridin-2-yl)methyl)-1H-indole-2-carboxylic acid Step A. Preparation of methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-((6-methylpyridin-2-yl)methyl)-1H-indole-2-carboxylate The title compound (86 mg, 96%) was prepared following General Procedure I using methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1H-indole-2-carboxylate (80 mg, 0.098 mmol) and 2-(chloromethyl)-6-methylpyridine (30 mg, 0.21 mmol). LCMS: $R_T$=1.319, 1.354 min (Method B), MS (ES) 920.8 (M+H).

Step 2: Preparation of methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-((6-methylpyridin-2-yl)methyl)-1H-indole-2-carboxylate The title compound (51 mg, 66%) was prepared following the procedure described Example 390 Step D using methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-((6-methylpyridin-2-yl)methyl)-1H-indole-2-carboxylate (86 mg, 0.093 mmol) and Pd/C (10 wt. %, 10 mg, 0.0092 mmol) by hydrogenating in MeOH (5 mL) with HCl for 5 h at RT. LCMS: $R_T$=0.888 min (Method B), MS (ES) 830.8 (M+H).

Step 3: Example 566

The title compound (7.1 mg, 39%) was prepared following General Procedure H using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-((6-methylpyridin-2-yl)methyl)-1H-indole-2-carboxylate (17 mg, 0.020 mmol) and 2-bromo-N,N-dimethylethan-1-amine (10 mg, 0.043 mmol) followed by saponification using General Procedure D. LCMS: $R_T$=0.476 min (Method B), MS (ES) 887.8 (M+H). $^1$H NMR (CDCl$_3$, 400 MHz) δ (ppm) 9.18 (s, 0.34H), 9.14 (s, 0.66H), 7.85-7.81 (m, 1H), 7.66-7.63 (m, 1H), 7.31 (dd, J=8.6, 2.3 Hz, 1H), 7.16 (t, J=7.8 Hz, 1H), 7.00-6.92 (m, 1H), 6.87-6.65 (m, 3H), 6.58 (s, 1.34H), 6.54 (s, 0.66H), 6.24-6.11 (m, 1.34H), 5.88-5.65 (m, 0.66H), 4.59-4.55 (m, 1H), 4.43 (dd, J=13.0, 4.0 Hz, 0.66H), 4.28-4.22 (m, 1.34H), 3.92-3.56 (m, 4H), 3.41-3.30 (m, 2H), 3.01 (s, 1H), 2.98 (s, 2H), 2.92 (s, 3H), 2.89-2.81 (m, 1H), 2.66 (s, 1H), 2.64 (s, 1H), 2.50 (s, 2H), 2.47 (s, 1H), 2.40 (s, 2H), 2.35 (s, 2H), 2.33 (s, 6H), 2.25 (s, 1H), 1.86-1.72 (m, 2H), 1.45 (d, J=5.8 Hz, 1H), 1.21 (d, J=6.8 Hz, 2H).

Example 567

(R)-7-Chloro-10-(3-(4-chloro-3,5-dimethylphenoxy)propyl)-4-methyl-2-(5-(pyrimidin-2-yl)-1-(2-(pyrrolidin-1-yl)ethyl)-1H-indol-3-yl)-6-(1,3,5-trimethyl-1H-pyrazol-4-yl)-3,4-dihydropyrazino[1,2-a]indol-1(2H)-one Step A. Preparation of 1-(2-((tert-butyldimethylsilyl)oxy)ethyl)-5-(pyrimidin-2-yl)-1H-indole The title compound (220 mg, 66%) was prepared following the procedure described Example 388 Step A using 1-(2-((tert-butyldimethylsilyl)oxy)ethyl)-5-(4,4,5,5-tetramethyl-1,3,2-dioxaborolan-2-yl)-1H-indole (492 mg, 1.23 mmol) and 2-bromopyrimidine (150 mg, 0.94 mmol). LCMS: $R_T$=2.077 min, MS (ES) 354.1 (M+H).

Step B. Preparation of 2-(5-(pyrimidin-2-yl)-1H-indol-1-yl)ethan-1-ol

The title compound (140 mg, 94%) was prepared following the procedure described Example 420 Step C using 1-(2-((tert-butyldimethylsilyl)oxy)ethyl)-5-(pyrimidin-2-yl)-1H-indole (220 mg, 0.62 mmol). LCMS: $R_T$=1.122 min, MS (ES) 240.1 (M+H).

Step C. Preparation of 5-(pyrimidin-2-yl)-1-(2-(pyrrolidin-1-yl)ethyl)-1H-indole The title compound (78 mg, 85%) was prepared following General Procedure J using 2-(5-(pyrimidin-2-yl)-1H-indol-1-yl)ethan-1-ol (140 mg, 0.59 mmol) and pyrrolidine (233 μL, 2.84 mmol). LCMS: $R_T$=0.167 min, MS (ES) 293.1 (M+H).

Step D. Preparation of 3-iodo-5-(pyrimidin-2-yl)-1-(2-(pyrrolidin-1-yl)ethyl)-1H-indole The title compound (37 mg, 33%) was prepared following the procedure described Example 388 Step B using 5-(pyrimidin-2-yl)-1-(2-(pyrrolidin-1-yl)ethyl)-1H-indole (78 mg, 0.27 mmol). LCMS: $R_T$=1.282 min, MS (ES) 418.9 (M+H).

Step E. Example 567

The title compound (16.5 mg, 31%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (35 mg, 0.06 mmol) and 3-iodo-5-

(pyrimidin-2-yl)-1-(2-(pyrrolidin-1-yl)ethyl)-1H-indole (37 mg, 0.09 mmol). LCMS: $R_T$=1.959 min, MS (ES) 828.9 (M+H).

Example 568

(R)-7-Chloro-10-(3-(4-chloro-3,5-dimethylphenoxy)propyl)-4-methyl-2-(1-(2-(4-methylpiperazin-1-yl)ethyl)-5-(pyrimidin-2-yl)-1H-indol-3-yl)-6-(1,3,5-trimethyl-1H-pyrazol-4-yl)-3,4-dihydropyrazino[1,2-a]indol-1(2H)-one The title compound (13 mg, 23%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (35 mg, 0.06 mmol) and 3-iodo-1-(2-(4-methylpiperazin-1-yl)ethyl)-5-(pyrimidin-2-yl)-1H-indole (44 mg, 0.10 mmol). LCMS: $R_T$=1.870 min, MS (ES) 858.0 (M+H).

Example 569

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-(4-methylpiperazin-1-yl)ethyl)-1H-indole-5-carboxylic acid The title compound (10.4 mg, 63%) was prepared according to General Procedure I using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (15 mg, 0.02 mmol) and 1-(2-Bromoethyl)-4-methylpiperazine dihydrobromide (15 mg, 0.04 mmol) followed by saponification using General Procedure D. LCMS: $R_T$=1.745 min, MS (ES) 823.90 (M+H).

Example 570

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((2-methyl-2H-1,2,3-triazol-4-yl)methyl)-1H-indole-2-carboxylic acid The title compound (7.2 mg, 43%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (15 mg, 0.021 mmol) and 4-(bromomethyl)-2-methyl-2H-1,2,3-triazole (10 mg, 0.039 mmol) followed by saponification using General Procedure D. LCMS: $R_T$=2.165, 2.138 min, MS (ES) 792.8 (M+H). $^1$H NMR (CDCl$_3$, 400 MHz) δ (ppm) 7.72-7.66 (m, 2H), 7.50 (s, 0.34H), 7.49 (s, 0.66H), 7.30 (d, J=8.6 Hz, 0.34), 7.29 (d, J=8.6 Hz, 0.66H), 7.23-7.02 (m, 3H), 6.61 (s, 1.34H), 6.58 (s, 0.66H), 6.21 (d, J=16.6 Hz, 1H), 6.17 (d, J=16.6 Hz, 1H), 5.85-5.55 (m, 1H), 4.48-4.19 (m, 2H), 4.15-3.93 (m, 4H), 3.89 (s, 4H), 3.88-3.83 (m, 1.5H), 3.72-3.64 (m, 0.5H), 3.46-3.24 (m, 3H), 2.30 (s, 2H), 2.29 (s, 4H), 2.23-2.10 (m, 5H), 2.07-2.00 (m, 3H), 1.25 (d, J=6.5 Hz, 1H), 1.19 (d, J=6.5 Hz, 2H).

Example 571

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-(2-methoxyethoxy)-1-((6-methylpyridin-2-yl)methyl)-1H-indole-2-carboxylic acid The title compound (9.8 mg, 55%) was prepared following General Procedure H using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-((6-methylpyridin-2-yl)methyl)-1H-indole-2-carboxylate (17 mg, 0.020 mmol) and 1-bromo-2-methoxyethane (10 mg, 0.072 mmol) followed by saponification using General Procedure D. LCMS: $R_T$=1.959 min, MS (ES) 874.8 (M+H). $^1$H NMR (CDCl$_3$, 400 MHz) δ (ppm) 9.11 (s, 0.66H), 9.10 (s, 0.34H), 7.81 (t, J=7.6 Hz, 1H), 7.69-7.65 (m, 1H), 7.41 (s, 0.34H), 7.36 (s, 0.66H), 7.33-7.28 (m, 1H), 7.21-7.08 (m, 2H), 6.91 (d, J=2.2 Hz, 0.34H), 6.86 (d, J=2.2 Hz, 0.66H), 6.78-6.69 (m, 0.66H), 6.65-6.60 (m, 0.33H), 6.57 (s, 1.3H), 6.56 (s, 0.66H), 6.26-5.82 (m, 2H), 4.39-4.08 (m, 3H), 3.83-3.64 (m, 5H), 3.45 (s, 3H), 3.37-3.21 (m, 1H), 3.12-2.94 (m, 1H), 2.60 (s, 1H), 2.48 (s, 2H), 2.43 (s, 1H), 2.38 (s, 2H), 2.35-2.28 (m, 9H), 2.22 (s, 1H), 1.90-1.67 (m, 2H), 1.21 (d, J=6.4 Hz, 2H), 1.09-0.98 (m, 1H).

Example 572

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methoxy-1-((6-methylpyridin-2-yl)methyl)-1H-indole-2-carboxylic acid The title compound (8.3 mg, 49%) was prepared following General Procedure H using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-((6-methylpyridin-2-yl)methyl)-1H-indole-2-carboxylate (17 mg, 0.020 mmol) and MeI (10 mg, 0.070 mmol) followed by saponification using General Procedure D. LCMS: $R_T$=1.984 min, MS (ES) 830.8 (M+H). $^1$H NMR (CDCl$_3$, 400 MHz) δ (ppm) 9.14 (s, 0.66H), 9.13 (s, 0.34H), 7.90-7.84 (m, 1H), 7.71-7.66 (m, 1H), 7.44-7.39 (m, 1H), 7.31 (t, J=8.5 Hz, 1H), 7.23 (d, J=7.8 Hz, 0.34H), 7.17 (d, J=7.8 Hz, 0.66H), 7.10 (d, J=2.3 Hz, 1H), 6.83 (d, J=2.4 Hz, 0.34H), 6.80 (d, J=2.4 Hz, 0.66H), 6.78-6.64 (m, 1H), 6.57 (s, 1.34H), 6.55 (s, 0.66H), 6.26-6.21 (m, 1.34H), 5.93 (d, J=17.8 Hz, 0.66H), 4.49 (d, J=12.4 Hz, 0.66H), 4.34 (dd, J=13.0, 3.9 Hz, 0.34H), 3.86 (s, 3H), 3.82-3.68 (m, 3H), 3.41 (d, J=13.3 Hz, 1H), 3.12-2.96 (m, 1H), 2.62 (s, 1H), 2.58-2.54 (m, 3H), 2.45 (s, 1H), 2.41 (s, 2H), 2.35 (s, 2H), 2.33 (s, 6H), 2.25 (s, 1H), 1.8-1.72 (m, 2H), 1.22 (d, J=6.5 Hz, 2H), 1.18-1.11 (m, 1H).

Example 573

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-(2-methoxyethoxy)-1-((4-methylpyridin-2-yl)methyl)-1H-indole-2-carboxylic acid The title compound (6.7 mg, 42%) was prepared following General Procedure H using methyl (R)-7-(7-chloro-10-

(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-((4-methylpyridin-2-yl)methyl)-1H-indole-2-carboxylate (15 mg, 0.018 mmol) and 1-bromo-2-methoxyethane (10 mg, 0.072 mmol) followed by saponification using General Procedure D. LCMS: $R_T$=1.954 min, MS (ES) 874.9 (M+H). $^1$H NMR (CDCl$_3$, 400 MHz) δ (ppm) 9.11 (s, 1H), 8.39 (d, J=5.8 Hz, 0.34H), 8.31 (d, J=5.8 Hz, 0.66H), 7.68-7.64 (m, 1H), 7.45 (s, 1H), 7.30 (d, J=8.6 Hz, 0.34H), 7.29 (d, J=8.6 Hz, 0.66H), 7.28-7.20 (m, 1H), 7.15 (d, J=2.2 Hz, 0.66H), 7.13 (d, J=2.2 Hz, 0.34H), 6.91 (d, J=2.2 Hz, 0.34H), 6.88 (d, J=2.2 Hz, 0.66H), 6.87-6.76 (m, 1H), 6.57 (s, 2H), 6.23-6.13 (m, 1H), 5.84 (d, J=16.9 Hz, 1H), 4.32-4.10 (m, 3H), 3.86-3.66 (m, 5H), 3.45 (s, 3H), 3.40-3.33 (m, 1H), 3.02-2.97 (m, 1H), 2.73-2.62 (m, 1H), 2.41 (s, 1H), 2.38 (s, 2H), 2.36 (s, 1H), 2.35-2.31 (m, 8H), 2.29 (s, 2H), 2.21 (s, 1H), 1.89-1.77 (m, 2H), 1.20 (d, J=6.5 Hz, 2H), 1.09-1.04 (m, 1H).

Example 574

(R)-7-Chloro-10-(3-(4-chloro-3,5-dimethylphenoxy)propyl)-6-(4,6-dimethylpyrimidin-5-yl)-4-methyl-2-(1-methyl-5-(1-methyl-1H-1,2,4-triazol-3-yl)-1H-indol-3-yl)-3,4-dihydropyrazino[1,2-a]indol-1(2H)-one The title compound (32 mg, 77%) was prepared following General Procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (30 mg, 0.06 mmol) and 3-iodo-1-methyl-5-(1-methyl-1H-1,2,4-triazol-3-yl)-1H-indole (38 mg, 0.11 mmol). LCMS: $R_T$=2.098 min, MS (ES) 746.8 (M+H).

Example 575

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-pyrrolo[2,3-b]pyridine-5-carboxylic acid Step A. Preparation of methyl 3-bromo-1-methyl-1H-pyrrolo[2,3-b]pyridine-6-carboxylate The title compound (88.6 mg, 88%) was prepared following General Procedure F using 1H-pyrrolo[2,3-b]pyridine-6-carboxylic acid (46 mg, 0.28 mmol), NBS (51 mg, 0.28 mmol), and MeI (53 µL, 0.85 mmol). LCMS: $R_T$=1.712 min, MS (ES) 269.0 (M+H).

Step B. Example 575

The title compound (22 mg, 62%) was prepared according to General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and 3-bromo-1-methyl-1H-pyrrolo[2,3-b]pyridine-6-carboxylate (22 mg, 0.06 mmol) followed by saponification using General Procedure D. LCMS $R_T$=2.063 min (Method B), MS (ES) 712.8 (M+H). $^1$H NMR (400 MHz, DMSO-d$_6$) δ 8.87 (t, J=1.6 Hz, 1H), 8.44 (t, J=1.6 Hz, 1H), 7.80-7.73 (m, 2H), 7.30 (d, J=8.6 Hz, 1H), 6.72 (s, 2H), 4.56-4.49 (m, 2H), 4.25-4.10 (m, 1H), 4.04-3.93 (m, 2H), 3.88 (s, 3H), 3.78 (s, 1.5H), 3.77 (s, 1.5H), 3.43-3.29 (m, 1H), 3.28-3.17 (m, 1H), 2.23 (s, 6H), 2.12 (s, 1.5H), 2.09 (s, 1.5H), 2.07-2.02 (m, 2H), 1.98 (s, 1.5H), 1.89 (s, 1.5H), 1.06 (d, J=6.5 Hz, 3H).

Example 576

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methyl-1-((6-methylpyridin-2-yl)methyl)-1H-indole-2-carboxylic acid Step A, methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methyl-1H-indole-2-carboxylate The title compound (145 mg, 54%) was prepared following General Procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (200 mg, 0.37 mmol) and methyl 7-bromo-5-methyl-1H-indole-2-carboxylate (200 mg, 0.746 mmol). LCMS: $R_T$=1.581 min, MS (ES) 723.9 (M+H).

Step B. Example 576

The title compound (13.3 mg, 48%) was prepared following General Procedure I using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methyl-1H-indole-2-carboxylate (25 mg, 0.034 mmol) and 2-(chloromethyl)-6-methylpyridine (10 mg, 0.071 mmol) followed by saponification using General Procedure D. LCMS: $R_T$=2.023 min, MS (ES) 814.8 (M+H).

Example 577

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methyl-1-((4-methylpyridin-2-yl)methyl)-1H-indole-2-carboxylic acid The title compound (13.2 mg, 47%) was prepared following General Procedure I using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methyl-1H-indole-2-carboxylate (25 mg, 0.034 mmol) and 2-(chloromethyl)-4-methylpyridine HCl (10 mg, 0.056 mmol) followed by saponification using General Procedure D. LCMS: $R_T$=2.012 min, MS (ES) 814.8 (M+H).

Example 578

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-isopropoxyethyl)-5-methyl-1H-indole-2-carboxylic acid The title compound (37 mg, 74%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (50 mg, 0.07 mmol) and 2-(2-bromoethoxy)propane (28 mg, 0.17 mmol) followed by saponification using General Procedure D. LCMS: $R_T$=2.32 min, MS (ES) 798 (M+H).

Example 579

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-ethoxyethyl)-5-methyl-1H-indole-2-carboxylic acid The title compound (40 mg, 75%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (50 mg, 0.07 mmol) and 2-bromoethyl ethyl ether (18 mg, 0.12 mmol) followed by saponification using General Procedure D. LCMS: $R_T$=2.28 min, MS (ES) 784 (M+H). $^1$H NMR (400 MHz, DMSO-d$_4$) δ 7.77 (s, 0.5H), 7.75 (s, 0.5H), 7.48 (s, 0.5H), 7.43 (s, 0.5H), 7.29 (m, 1H), 7.20 (m, 1H), 6.93 (m, 1H), 6.70 (s, 1H), 6.67 (s, 1H), 4.94 (m, 1H), 4.88 (m, 1H), 4.63 (m, 1H), 4.41 (m 2H), 4.15 (m, 1H), 3.94 (t, J=6.2 Hz, 2H), 3.77 (s, 1.5H), 3.75 (s, 1.5H), 3.71 (m, 1H), 3.45 (m, 1H), 3.36 (m, 1H), 3.07-3.26 (bm, 4H), 2.37 (s, 1.5H), 2.35 (s, 1.5H), 2.22 (s, 3H), 2.21 (s, 3H), 2.11 (m, 2H), 2.00 (m, 3H), 1.91-1.95 (m, 1H), 1.86 (s, 1H), 1.15 (d, J=6.5 Hz, 1.5H), 1.04 (d, J=6.5 Hz, 1.5H), 0.74 (m, 3H).

Example 580

(R)-3-(7-chloro-10-(3-(4-chloro-3,5-dimethylphenoxy)propyl)-6-(4,6-dimethyl-2-((4-methylpiperazin-1-yl)methyl)pyrimidin-5-yl)-4-methyl-1-oxo-3,4-dihydropyrazino[1,2-a]indol-2(1H)-yl)-1-(2-(dimethylamino)ethyl)-1H-indole-5-carboxylic acid Step A, methyl 3-bromo-1-(2-(dimethylamino)ethyl)-1H-indole-5-carboxylate The title compound (74 mg, 58%) was prepared following General Procedure G using methyl 3-bromo-1H-indole-5-carboxylate (100 mg, 0.39 mmol) and 2-bromo-N,N-dimethylethan-1-amine HBr (180 mg, 0.77 mmol). LCMS: $R_T$=1.154 min, MS (ES) 324.9 (M+H).

Step B. Example 580

The title compound (6.3 mg, 23% yield) was prepared following General Procedure B using (R)-7-chloro-10-(3-(4-chloro-3,5-dimethylphenoxy)propyl)-6-(4,6-dimethyl-2-((4-methylpiperazin-1-yl)methyl)pyrimidin-5-yl)-4-methyl-3,4-dihydropyrazino[1,2-a]indol-1(2H)-one (20 mg, 0.031 mmol) and methyl 3-bromo-1-(2-(dimethylamino)ethyl)-1H-indole-5-carboxylate (20 mg, 0.062 mmol) followed by saponification using General Procedure D. LCMS: $R_T$=0.476 min, MS (ES) 887.8 (M+H).

Example 581

(R)-7-Chloro-10-(3-(4-chloro-3,5-dimethylphenoxy)propyl)-2-(1-(2-methoxyethyl)-5-(1-(oxetan-3-ylmethyl)-1H-1,2,4-triazol-3-yl)-1H-indol-3-yl)-4-methyl-6-(1,3,5-trimethyl-1H-pyrazol-4-yl)-3,4-dihydropyrazino[1,2-a]indol-1(2H)-one Step A. Preparation of 1-(2-methoxyethyl)-5-(1-(tetrahydro-2H-pyran-2-yl)-1H-1,2,4-triazol-3-yl)-1H-indole The title compound (480 mg, 57%) was prepared following the procedure described Example 388 Step A using 1-(2-methoxyethyl)-5-(4,4,5,5-tetramethyl-1,3,2-dioxaborolan-2-yl)-1H-indole (934 mg, 3.10 mmol) and 3-bromo-1-(tetrahydro-2H-pyran-2-yl)-1H-1,2,4-triazole (600 mg, 2.59 mmol). LCMS: $R_T$=1.408 min, MS (ES) 327.1 (M+H).

Step B. Preparation of 3-iodo-1-(2-methoxyethyl)-5-(1-(tetrahydro-2H-pyran-2-yl)-1H-1,2,4-triazol-3-yl)-1H-indole The title compound (650 mg, 98%) was prepared following the procedure described Example 388 Step B using 1-(2-methoxyethyl)-5-(1-(tetrahydro-2H-pyran-2-yl)-1H-1,2,4-triazol-3-yl)-1H-indole (480 mg, 1.47 mmol). LCMS: $R_T$=1.674 min, MS (ES) 452.8 (M+H).

Step C. Preparation of 3-iodo-1-(2-methoxyethyl)-5-(1H-1,2,4-triazol-3-yl)-1H-indole 2N HCl (3 mL) was added to a solution of 3-iodo-1-(2-methoxyethyl)-5-(1-(tetrahydro-2H-pyran-2-yl)-1H-1,2,4-triazol-3-yl)-1H-indole (650 mg, 1.44 mmol) in DMF (15 mL) at 0° C. After 5 h, the reaction mixture was diluted with EtOAc, iPrOH and Sat. aq. NaHCO$_3$ at 0° C. The solution was extracted with EtOAc. The combined organic layers were dried and concentrated to afford the crude title compound (500 mg), which was used for the next step without further purification. LCMS: $R_T$=0.188 min, MS (ES) 368.8 (M+H).

Step D. Preparation of iodo-1-(2-methoxyethyl)-5-(1-(oxetan-3-ylmethyl)-1H-1,2,4-triazol-3-yl)-1H-indole The title crude compound (73 mg) was prepared following General Procedure G using 3-iodo-1-(2-methoxyethyl)-5-(1H-1,2,4-triazol-3-yl)-1H-indole (60 mg, 0.160 mmol) and 3-(chloromethyl)oxetane (17.4 μL, 0.18 mmol). LCMS: $R_T$=1.336 min, MS (ES) 438.9 (M+H).

Step E. Example 581

The title compound (29 mg, 61%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and iodo-1-(2-methoxyethyl)-5-(1-(oxetan-3-ylmethyl)-1H-1,2,4-triazol-3-yl)-1H-indole (49 mg, 0.11 mmol). LCMS: $R_T$=2.077 min, MS (ES) 848.8 (M+H).

Example 582

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-((4-methylpyridin-2-yl)methyl)-1H-indole-2-carboxylic acid Step A, methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H-indole-2-carboxylate The title compound (69 mg, 28%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (180 mg, 0.33 mmol) and methyl 7-iodo-4-methoxy-1H-indole-2-carboxylate (200 mg, 0.60 mmol). LCMS: $R_T$=1.386, 1.422 min, (Method B) MS (ES) 741.9 (M+H).

Step B. Example 582

The title compound (12.5 mg, 44%) was prepared following General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H-indole-2-carboxylate (23 mg, 0.031 mmol) and 2-(chloromethyl)-4-methylpyridine hydrochloride (10 mg, 0.056 mmol) followed by saponification using General Procedure D. LCMS: $R_T$=1.952, 1.982 min, MS (ES) 832.8 (M+H).

Example 583

(R)-7-Chloro-10-(3-(4-chloro-3,5-dimethylphenoxy)propyl)-4-methyl-2-(5-(1-methyl-1H-1,2,4-triazol-3-yl)-1-(2-morpholinoethyl)-1H-indol-3-yl)-4-(1,3,5-trimethyl-1H-pyrazol-4-yl)-3,4-dihydropyrazino[1,2-a]indol-1(2H)-one Step A. Preparation of 4-(2-(5-(1-methyl-1H-1,2,4-triazol-3-yl)-1H-indol-1-yl)ethyl) morpholine The title compound (42 mg, 41%) was prepared following General Procedure J using 2-(5-(1-methyl-1H-1,2,4-triazol-3-yl)-1H-indol-1-yl)ethan-1-ol (105 mg, 0.33 mmol) and morpholine (283 µL, 3.28 mmol). LCMS: $R_T$=0.163 min, MS (ES) 312.1 (M+H).

Step B. Preparation of 4-(2-(3-iodo-5-(1-methyl-1H-1,2,4-triazol-3-yl)-1H-indol-1-yl)ethyl) morpholine The title compound (55 mg, 93%) was prepared following the procedure described Example 388 Step B using 4-(2-(5-(1-methyl-1H-1,2,4-triazol-3-yl)-1H-indol-1-yl)ethyl)morpholine (42 mg, 0.13 mmol). LCMS: $R_T$=0.168 min, MS (ES) 437.8 (M+H).

Step C. Example 583

The title compound (30 mg, 64%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 4-(2-(3-iodo-5-(1-methyl-1H-1,2,4-triazol-3-yl)-1H-indol-1-yl)ethyl)morpholine (49 mg, 0.11 mmol). LCMS: $R_T$=1.825 min, MS (ES) 847.9 (M+H). $^1$H NMR (400 MHz, DMSO-$d_6$) δ 8.45 (s, 1H), 8.11 (s, 1H), 7.92 (d, J=8.6 Hz, 1H), 7.76 (d, J=8.6 Hz, 1H), 7.69 (d, J=8.9 Hz, 1H), 7.62 (s, 1H), 7.30 (d, J=8.6 Hz, 1H), 6.72 (s, 2H), 4.62 (t, J=7.2 Hz, 2H), 4.51-4.46 (m, 1H), 4.20-4.18 (m, 1H), 4.00-3.95 (m, 3H), 3.88 (s, 3H), 3.77 (d, J=4.8 Hz, 3H), 3.70 (dd, J=11.6, 7.4 Hz, 3H), 3.62-3.57 (m, 2H), 3.36-3.19 (m, 4H), 2.54 (s, 3H), 2.22 (s, 6H), 2.12-2.04 (m, 5H), 1.98-1.89 (m, 3H), 1.12-1.10 (m, 3H).

Example 584

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-(2-(dimethylamino)ethoxy)-1-((4-methylpyridin-2-yl)methyl)-1H-indole-2-carboxylic acid The title compound (6.1 mg, 38%) was prepared following General Procedure H using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-((4-methylpyridin-2-yl)methyl)-1H-indole-2-carboxylate (15 mg, 0.018 mmol) and 2-bromo-N,N-dimethylethan-1-amine hydrobromide (10 mg, 0.043 mmol) followed by saponification using General Procedure D. LCMS: $R_T$=1.660 min, MS (ES) 887.8 (M+H).

Example 585

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-5H-pyrrolo[2,3-b]pyrazine-2-carboxylic acid Step A. Preparation of methyl 7-bromo-5-methyl-5H-pyrrolo[2,3-b]pyrazine-2-carboxylate The title compound (65.1 mg, 85%) was prepared following General Procedure F using methyl 5H-pyrrolo[2,3-b]pyrazine-2-carboxylate (49 mg, 0.28 mmol), NBS (51 mg, 0.28 mmol), and MeI (53 µL, 0.85 mmol). LCMS: $R_T$=1.165 min, MS (ES) 269.9 (M+H).

Step B. Example 585

The title compound (19.5 mg, 55%) was prepared according to General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and methyl 7-bromo-5-methyl-5H-pyrrolo[2,3-b]pyrazine-2-carboxylate (22 mg, 0.06 mmol) followed by saponification using General Procedure D. LCMS: $R_T$=2.154 min (Method B), MS (ES) 713.8 (M+H). $^1$H NMR (400 MHz, DMSO-$d_6$) δ 8.99 (s, 1H), 8.48 (s, 0.5H), 8.45 (s, 0.5H), 7.76 (d, J=8.6 Hz, 1H), 7.30 (d, J=8.6 Hz, 1H), 6.74 (s, 2H), 4.61-4.52 (m, 0.5H), 4.50-4.44 (m, 0.5H), 4.41-4.30 (m, 1H), 4.27-4.15 (m, 1H), 3.99 (d, J=5.8 Hz, 2H), 3.92 (s, 3H), 3.80 (s, 1.5H), 3.78 (s, 1.5H), 3.30-3.20 (m, 2H), 2.24 (s, 6H), 2.12 (s, 1.5H), 2.08

(t, J=6.9 Hz, 1H), 2.03 (s, 1.5H), 1.98 (s, 1.5H), 1.89 (s, 1.5H), 1.12 (d, J=6.6 Hz, 3H).

Example 586

(R)-7-Chloro-10-(3-(4-chloro-3,5-dimethylphenoxy) propyl)-4-methyl-2-(5-(1-methyl-1H-1,2,4-triazol-3-yl)-1-(2-(pyrrolidin-1-yl)ethyl)-1H-indol-3-yl)-6-(1,3,5-trimethyl-1H-pyrazol-4-yl)-3,4-dihydropyrazino[1,2-a]indol-1(2H)-one Step A. Preparation of 5-(1-methyl-1H-1,2,4-triazol-3-yl)-1-(2-(pyrrolidin-1-yl)ethyl)-1H-indole The title compound (54 mg, 56%) was prepared following General Procedure J using 2-(5-(1-methyl-1H-1,2,4-triazol-3-yl)-1H-indol-1-yl)ethan-1-ol (105 mg, 0.33 mmol) and pyrrolidine (161 µL, 1.97 mmol). LCMS: $R_T$=0.158 min, MS (ES) 296.1 (M+H).

Step B. Preparation of 3-iodo-5-(1-methyl-1H-1,2,4-triazol-3-yl)-1-(2-(pyrrolidin-1-yl)ethyl)-1H-indole The title compound (40 mg, 52%) was prepared following the procedure described Example 388 Step B using 5-(1-methyl-1H-1,2,4-triazol-3-yl)-1-(2-(pyrrolidin-1-yl)ethyl)-1H-indole (54 mg, 0.18 mmol). LCMS: $R_T$=1.122 min, MS (ES) 421.9 (M+H).

Step C. Example 586

The title compound (40 mg, 87%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-5-(1-methyl-1H-1,2,4-triazol-3-yl)-1-(2-(pyrrolidin-1-yl)ethyl)-1H-indole (40 mg, 0.10 mmol). LCMS: $R_T$=1.855 min, MS (ES) 831.9 (M+H).

Example 587

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-(2-methoxyethyl)-1H-indole-2-carboxylic acid The title compound (13.8 mg, 57%) was prepared following General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H-indole-2-carboxylate (23 mg, 0.031 mmol) and 1-bromo-2-methoxyethane (10 mg, 0.072 mmol) followed by saponification using General Procedure D. LCMS: $R_T$=2.165, 2.196 min, MS (ES) 785.8 (M+H).

Example 588

(R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-2-ylmethyl)-1H-indole-2-carboxylic acid Step A. Preparation of ethyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate The title compound (39 mg, 94%) was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and ethyl 5-(benzyloxy)-7-bromo-1H-indole-3-carboxylate (22 mg, 0.06 mmol). LCMS: $R_T$=1.619 min, MS (ES) 831.9 (M+H).

Step B. Example 588

The title compound (33 mg, 79%) was prepared according to General Procedure I using methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate (39 mg, 0.02 mmol) and 2-(bromomethyl)pyridine HBr (19 mg, 0.074 mmol) followed by saponification using General Procedure D. LCMS: $R_T$=1.502 min, MS (ES) 895.9 (M+H).

Example 589

(R)-7-Chloro-10-(3-(4-chloro-3,5-dimethylphenoxy)propyl)-2-(5-(1-(cyclopropylmethyl)-1H-1,2,4-triazol-3-yl)-1-(2-methoxyethyl)-1H-indol-3-yl)-4-methyl-6-(1,3,5-trimethyl-1H-pyrazol-4-yl)-3,4-dihydropyrazino[1,2-a]indol-1(2H)-one Step A. Preparation of 5-(1-(cyclopropylmethyl)-1H-1,2,4-triazol-3-yl)-3-iodo-1-(2-methoxyethyl)-1H-indole The crude title compound (65 mg) was prepared following General Procedure G using 3-iodo-1-(2-methoxyethyl)-5-(1H-1,2,4-triazol-3-yl)-1H-indole (60 mg, 0.16 mmol) and (bromomethyl)cyclopropane (19 µL, 0.20 mmol). LCMS: $R_T$=1.605 min, MS (ES) 422.9 (M+H).

Step B. Example 589

The title compound (28 mg, 60%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 5-(1-(cyclopropylmethyl)-1H-1,2,4-triazol-3-yl)-3-iodo-1-(2-methoxyethyl)-1H-indole (47 mg, 0.11 mmol). LCMS: $R_T$=2.182 min, MS (ES) 832.9 (M+H).

Example 590

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-(dimethylamino)ethoxy)-1-(pyridin-2-ylmethyl)-1H-indole-2-carboxylic acid The title compound (2 mg, 12%) was prepared following General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(pyridin-2-ylmethyl)-1H-indole-2-carboxylate (15 mg, 0.019 mmol) and 2-bromo-N,N-dimethylethan-1-amine HBr (15 mg, 0.064 mmol)

followed by saponification using General Procedure D. LCMS: $R_T$=1.717 min, MS (ES) 875.8 (M+H).

Example 591

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-methyl-5-(morpholine-4-carbonyl)-1H-indole-2-carboxylic acid Step A. Preparation of ethyl 7-bromo-5-formyl-1-methyl-1H-indole-2-carboxylate To a solution of 1-(tert-butyl) 2-ethyl 7-bromo-5-formyl-1H-indole-1,2-dicarboxylate (585 mg, 1.47 mmol) in DCM (14 mL) was added TFA (1.13 mL, 14.7 mmol) and stirred at RT for 16 h. The reaction was quenched with aq. sat. NH$_4$Cl solution and extracted with DCM. The combined organic layer was washed with brine, dried over MgSO$_4$, filtered, and concentrated. The crude product was redissolved in DMF (8 mL). K$_2$CO$_3$ (1.22 g, 8.82 mmol) and MeI (275 μL, 626 mg, 4.41 mmol) were added and heated to 60° C. for 4 h. The reaction mixture was quenched with aq. sat. NH$_4$Cl solution and extracted with DCM. The combined organic layer was dried over MgSO$_4$, filtered and concentrated. The residue was purified by flash chromatography (Combi-flash Rf, Hex/EtOAc=0-60% gradient) to afford the title compound (360 mg, 79%, 2 steps). LCMS: $R_T$=1.886 min, MS (ES) 309.9 (M+H).

Step B. Preparation of ethyl 7-bromo-5-((methoxymethoxy)methyl)-1-methyl-1H-indole-2-carboxylate To a solution of the ethyl 7-bromo-5-formyl-1-methyl-1H-indole-2-carboxylate (356 mg, 1.15 mmol) in THF (1 mL) and MeOH (10 mL) was added NaBH$_4$ (65 mg, 1.72 mmol) and stirred at rt for 5 min. The reaction was quenched with aq. sat. NH$_4$Cl and extracted with DCM. The combined organic layer was dried over MgSO$_4$, filtered and concentrated. The crude product was redissolved in DCM. MOMCl (262 μL, 278 mg, 3.45 mmol) followed by $^i$Pr$_2$EtN (1 mL, 742 mg, 5.75 mmol) were added and stirred at RT for 16 h. The reaction was quenched with aq. sat. NH$_4$Cl and extracted with DCM. The combined organic layer was dried over MgSO$_4$, filtered and concentrated. The residue was purified by flash chromatography (Combi-flash Rf, Hex/EtOAc=0-50% gradient) to afford the title compound (336 mg, 82%, 2 steps). LCMS: $R_T$=1.971 min, MS (ES) 355.9 (M+H).

Step C. Ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate Coupling reaction was carried out following general procedure A using ethyl 7-bromo-5-((methoxymethoxy)methyl)-1-methyl-1H-indole-2-carboxylate (336 mg, 0.94 mmol) and (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (509 mg, 0.94 mmol). To a solution of the resulting ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((methoxymethoxy)methyl)-1-methyl-1H-indole-2-carboxylate in THF (10 mL) and MeOH (5 mL) was added Conc. HCl (2.4 mL), and the reaction mixture was stirred at RT for 16 h. The reaction was quenched with aq. sat. NaHCO$_3$ and extracted with DCM. The combined organic layer was dried over MgSO$_4$, filtered and concentrated. The residue was purified by flash chromatography (Combi-flash Rf, DCM/MeOH=0-10% gradient) to afford the title compound compound (289 mg, 40%, 2 steps). LCMS: $R_T$=2.274, 2.302, 2.324 min, MS (ES) 769.9 (M+H).

Step D. Example 591

To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (7.6 mg, 0.01 mmol) in acetone (0.12 mL) at 0° C. was added water (15 μL) and Conc. H$_2$SO$_4$ (5 μL). CrO$_3$ (3 mg, 0.03 mmol) was added to the reaction, slowly warmed to rt and stirred for 90 min. The reaction was quenched with $^i$PrOH (1 mL), filtered through Celite pad and washed with EtOAc. The filtrate was dried over MgSO$_4$, filtered and concentrated. The title compound (1.6 mg, 20%, 3 steps) was prepared following General Procedure E using crude (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-2-(ethoxycarbonyl)-1-methyl-1H-indole-5-carboxylic acid and morpholine (50 μL, 50 mg, 0.58 mmol) followed by saponification using General procedure D. LCMS: $R_T$=2.006, 2.035, 2.088 min, MS (ES) 824.8 (M+H).

Example 592

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-5-(2-(dimethylamino)ethoxy)-1-((6-methylpyridin-2-yl)methyl)-1H-indole-2-carboxylic acid The title compound (1.8 mg, 10%) was prepared following General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-((6-methylpyridin-2-yl)methyl)-1H-indole-2-carboxylate (15 mg, 0.019 mmol) and 2-bromo-N,N-dimethylethan-1-amine (15 mg, 0.064 mmol) followed by saponification using General Procedure D. LCMS: $R_T$=1.685 min, MS (ES) 889.8 (M+H).

Example 593

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-4-methoxy-1-((6-methylpyridin-2-yl) methyl)-1H-indole-2-carboxylic acid The title compound (13.3 mg, 51%) was prepared following General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H- indole-2-carboxylate (23 mg, 0.031 mmol) and 2-(chloromethyl)-6-methylpyridine (10 mg, 0.070 mmol) followed by saponification using General Procedure D. LCMS: $R_T$=1.985, 1.953 min, MS (ES) 832.8 (M+H).

Example 594

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-(2-methoxyethyl)-5-methyl-1H-indole-2-carboxylic acid The title compound (13.2 mg, 47%) was prepared following General Procedure I using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methyl-1H-indole-2-carboxylate (25 mg, 0.034 mmol) and 1-bromo-2-methoxyethane (10 mg, 0.072 mmol) followed by saponification using General Procedure D. LCMS: $R_T$=2.288, 2.302 min, MS (ES) 767.8 (M+H), $^1$H NMR (DMSO-$d_6$, 400 MHz) δ (ppm) 9.10 (s, 1H), 7.92 (d, J=8.6 Hz, 0.34H), 7.91 (d, J=8.6 Hz, 0.66H), 7.43 (d, J=8.6 Hz, 0.34H), 7.41 (d, J=8.6 Hz, 0.66H), 7.23-7.19 (m, 1H), 7.16-6.98 (m, 2H), 6.73 (s, 1.34H), 6.69 (s, 0.66H), 4.71-4.64 (m, 0.34H), 4.35 (dd, J=13.4, 3.4 Hz, 0.66H), 4.13-4.07 (m, 2H), 4.03 (s, 1H), 3.99 (t, J=6.0 Hz, 2H), 3.92 (s, 2H), 3.75-3.59 (m, 4H), 3.39-3.17 (m, 5H), 2.32 (s, 1H), 2.27 (s, 2H), 2.25 (s, 4H), 2.24 (s, 2H), 2.20 (s, 2H), 2.18 (s, 1H), 2.07 (quint, J=6.7 Hz, 2H), 1.19 (d, J=6.4 Hz, 2H), 1.10 (d, J=6.6 Hz, 1H).

Example 595

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((2-methoxyethoxy)methyl)-1-methyl-1H-indole-2-carboxylic acid To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (11 mg, 0.014 mmol) in DMF (0.1 mL) at 0° C. was added NaH (0.8 mg, 0.021 mmol) and stirring 10 min. 1-Bromo-2-methoxyethane (2 µL, 2.9 mg, 0.021 mmol) was added, warmed to rt and stirred for 4 h. The reaction was quenched with aq. sat. NH$_4$Cl and extracted with DCM. The combined organic layer was dried over MgSO$_4$, filtered and concentrated. Subsequent saponification was followed using General procedure D. The title compound (8.0 mg, 71%, 2 steps) was obtained by reverse phase HPLC (Phenomenex Gemini C18, H$_2$O/CH$_3$CN gradient to 35-95% MeCN 0.1% TFA). LCMS: $R_T$=2.147, 2.180, 2.234 min, MS (ES) 799.9 (M+H).

Example 596

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-(dimethylamino)-2-oxoethyl)-5-methyl-1H-indole-2-carboxylic acid The title compound (29 mg, 55%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (50 mg, 0.07 mmol), and 2-chloro-N,N-dimethylacetamide (10 mg, 0.08 mmol) followed by saponification using General Procedure D. LCMS: $R_T$=2.21 min, MS (ES) 797 (M+H). $^1$H NMR (400 MHz, DMSO-$d_6$) δ 7.75 (m, 1H), 7.50 (s, 0.5H), 7.45 (s, 0.5H), 7.32 (m, 0.5H), 7.30 (m, 10.5H), 7.26 (s, 0.5H), 7.23 (s, 0.5H), 6.86 (m, 1H), 6.70 (s, 1H), 6.69 (s, 1H), 5.84 (m, 1H), 4.92 (m, 1H), 4.55 (m, 1H), 4.10 (m, 1H), 3.97 (m, 2H), 3.75 (m, 3H), 3.58 (m, 1H), 3.22 (m, 2H), 2.60 (m, 3H), 3.51 (m, 3H), 2.37 (s, 1.5H), 2.35 (s, 1.5H), 2.22 (s, 6H), 2.11 (m, 2H), 1.97 (m, 3H), 1.89 (m, 1.5H), 1.84 (s, 1.5H), 1.11 (d, J=6.4 Hz, 3H).

Example 597

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-(2-morpholinoethyl)-1H-indole-2-carboxylic acid The title compound (40 mg, 70%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (50 mg, 0.07 mmol) and 4-(2-chloroethyl)-morpholine HCl (25 mg, 0.14 mmol) followed by saponification using General Procedure D. LCMS: $R_T$=2.03 min, MS (ES) 825 (M+H).

Example 598

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-(2-morpholino-2-oxoethyl)-1H-indole-2-carboxylic acid The title compound (20 mg, 36%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (50 mg, 0.07 mmol) and 4-(chloroacetyl)morpholine (13 mg, 0.08 mmol) followed by saponification using General Procedure D. LCMS: $R_T$=2.17 min, MS (ES) 839 (M+H).

Example 599

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4,6-dimethylpyridin-2-yl)methyl)-5-methyl-1H-indole-2-carboxylic acid The title compound (30 mg, 47%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (50 mg, 0.07 mmol) and 2-(chloromethyl)-4,6-dimethylpyridine (26 mg, 0.17 mmol) followed by saponification using General Procedure D. LCMS: $R_T$=2.05 min, MS (ES) 831 (M+H). $^1$H NMR (400 MHz, DMSO-$d_6$) δ 7.73 (m, 1H), 7.57 (bs, 1H), 7.41 (m, 1H), 7.27 (m, 2H), 6.96 (m, 1H), 6.87 (m, 1H), 6.69 (m, 2H), 6.09 (m, 2H), 4.61 (m, 1H), 3.96 (m, 2H) 3.87 (m, 1H), 3.72 (m, 3H), 3.50 (m, 1H), 3.24-3.33 (bm, 2H), 3.02-3.10 (bm, 2H), 2.39 (s, 1.5H), 2.37 (s, 1.5H), 2.23 (s, 3H), 2.21 (s, 3H), 2.04-2.10 (bm, 5H), 1.94-2.00 (bm, 3H), 1.87 (m, 1H), 1.78 (s, 2H), 1.03 (m, 3H).

Example 600

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4-(4,5-dihydrooxazol-2-yl)pyridin-2-yl)methyl)-5-methyl-1H-indole-2-carboxylic acid The title compound (25 mg, 42%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (40 mg, 0.05 mmol) and 2-(2-(chloromethyl)pyridin-4-yl)-4,5-dihydrooxazole (27 mg, 0.14 mmol) followed by saponification using General Procedure D. LCMS: $R_T$=2.14 min, MS (ES) 872 (M+H).

Example 601

(R)-3-(7-chloro-10-(3-(4-chloro-3,5-dimethylphenoxy)propyl)-4-methyl-1-oxo-6-(2,4,6-trimethylpyrimidin-5-yl)-3,4-dihydropyrazino[1,2-a]indol-2(1H)-yl)-1-methyl-1H-indole-5-carboxylic acid Step A. Preparation of (4,6-dimethylpyrimidin-2-yl)methanol To a solution of 4,6-Dimethylpyrimidine (7.17 g, 66.3 mmol) in MeOH (18 mL), $H_2O$ (66 mL) and $H_2SO_4$ (5.0 mL, conc.) was added ammonium persulfate (32.2 g, 141.2 mmol) at RT, and the reaction was heated to 60° C. and stirred overnight. The reaction mixture was concentrated to remove MeOH basified with aq. $K_2CO_3$, extracted with DCM followed by 10% i-PrOH in $CHCl_3$. Combined organic fractions were dried over $MgSO_4$, filtered, and concentrated. The crude title compound (8.69 g, 95%) was obtained as a yellow solid and carried forward without further purification. $^1H$ NMR: (400 MHz in $CDCl_3$) δ 6.96 (s, 1H), 4.77 (s, 2H), 2.51 (s, 6H); LCMS: RT=0.096 min, MS (ES) 139.17 (M+H).

Step B. Preparation of (4,6-dimethylpyrimidin-2-yl)methyl methanesulfonate

To a solution of (4,6-dimethyl pyrimidin-2-yl)methanol (3.0 g, 21.7 mmol) in DCM (72 mL) was added $Et_3N$ (6.06 mL, 43.4 mmol), followed by MsCl (2.86 mL, 36.9 mL) at 0° C. The reaction mixture was stirred for 3 h at RT, quenched with sat. $NH_4Cl$ (50 mL), and extracted with DCM. The combined organic layer was dried over $MgSO_4$, and concentrated in vacuo. The residue was purified by flash chromatography (Combi-flash Rf, Hex/EtOAc=0-90% gradient) to afford the title compound (4.32 g, 92%). $^{13}C$ NMR ($CDCl_3$, 100 MHz) δ 167.3, 162.4, 119.4, 71.2, 38.8, 23.8; LCMS: RT=0.344 min, MS (ES) 217.3 (M+H).

Step C. Preparation of 5-bromo-2-(bromomethyl)-4,6-dimethylpyrimidine

To a solution of (4,6-dimethylpyrimidin-2-yl)methyl methanesulfonate (4.68 g, 21.7 mmol) in EtOH (108 mL) was added bromine (3.34 mL, 65.13 mmol) at 0° C. The reaction was warmed to RT and stirred overnight. Solvent was removed in vacuo. The reaction mixture was diluted with DCM, washed with aqueous $Na_2S_2O_3$, and the combined organic layer was concentrated. The residue was purified by flash chromatography (Combi-flash Rf, Hex/EtOAc=0-50% gradient) to afford the title compound (4.5 g, 70%). $^1H$ NMR: (400 MHz in CDCl3) δ 4.47 (s, 2H), 2.63 (6H); LCMS: RT=0.754 min, MS (ES) 278.9 (M+H).

Step D. Preparation of 5-bromo-2, 4, 6-trimethylpyrimidine

To a solution of 5-bromo-2-(bromomethyl)-4,6-dimethyl pyrimidine (4.5 g, 16.4 mmol) in THF (160 mL) was added Raney-Nickel (30 g). The reaction mixture was vigorously stirred at RT overnight, diluted with DCM then filtered through Celite pad. The filtrate was dried over $MgSO_4$, filtered, concentrated to afford the crude title compound as a green solid obtained and carried forward without further purification. $^1H$ NMR: (400 MHz in MeOD) δ 2.55 (s, 6H), 2.51 (s, 3H); LCMS: RT=0.746 min, MS (ES) 201.07 (M+H).

Step E. Preparation of (2,4,6-trimethylpyrimidin-5-yl)boronic acid

A mixture of 5-bromo-2,4,6-trimethylpyrimidine (1.0 g, 4.97 mmol) and triisopropoxy borate (2.52 mL, 10.94 mmol) in THF (4.97 mL)/toluene (15.0 mL) was added n-BuLi (6.83 mL, 10.94 mmol) at −40° C. The reaction mixture was warmed to −20° C. quenched with HCl solution (1N, 10 mL), diluted with water and extracted with DCM. The combined organic layer was dried over $MgSO_4$ and concentrated to afford the crude title compound that was carried forward without further purification. $^1H$ NMR: (400 MHz in MeOD) δ 3.58 (s, OH), 2.46 (s, 6H), 2.42 (s, 3H); LCMS: RT=0.085 min, MS (ES) 166.09 (M+H).

Step F. Preparation of ethyl 6-chloro-3-(3-(4-chloro-3, 5-dimethylphenoxy)propyl)-7-(2,4,6-trimethylpyrimidin-5-yl)-1H-indole-2-carboxylate A solution of ethyl 3-(3-(11-oxidanyl)propyl)-7-bromo-6-chloro-1H-indole-2-carboxylate (124 mg, 0.25 mmol), (2,4,6-trimethylpyrimidin-5-yl)boronic acid (83 mg, 0.5 mmol), Sphos (51 mg, 0.125 mmol), $Pd_2(dba)_3$ (37 mg, 0.04 mmol) and $K_3PO_4$ (186 mg, 0.875 mmol) in THF (1.5 ml)/toluene (1.5 mL) was heated at 110° C. overnight. The Reaction mixture was concentrated in vacuo. The residue was purified by flash chromatography (Combi-flash Rf, Hex/EtOAc=0-80% gradient) to afford the title compound (40 mg, 30%). LCMS: RT=1.004 min, MS (ES) 540.21 (M+H).

Step G. Preparation of (R)-1-(1-((tert-butoxycarbonyl)amino)propan-2-yl)-6-chloro-3-(3-(4-chloro-3,5-dimethylphenoxy)propyl)-7-(2,4,6-trimethylpyrimidin-5-yl)-1H-indole-2-carboxylate A solution of ethyl 6-chloro-3-(3-(4-chloro-3, 5-dimethylphenoxy)propyl)-7-(2,4,6-trimethylpyrimidin-5-yl)-1H-indole-2-carboxylate (156 g, 0.29 mmol), tert-butyl (S)-5-methyl-1,2,3-oxathiazolidine-3-carboxylate 2,2-dioxide (9 mg, 0.41 mmol), and $Cs_2CO_3$ (151 mg, 0.46 mmol) in MeCN (3 ml) was stirred at 60° C. for 12 h. The reaction mixture was concentrated and the residue was diluted with EtOAc (10 mL)/water (10 mL), extracted with EtOAc, dried and concentrated. The residue was purified by flash chromatography (Combi-flash Rf, DCM/MeOH=0-30% gradient) to afford the title compound (192 mg, 95%). LCMS: RT=1.231 min, MS (ES) 697.31 (M+H).

Step H. Preparation of (R)-7-chloro-10-(3-(4-chloro-3,5-dimethylphenoxy)propyl)-4-methyl-6-(2,4,6-trimethyl pyrimidin-5-yl)-3,4-dihydropyrazino[1,2-a]indol-1(2H)-one The title compound (81 mg, 50%) was prepared following the procedure described Example 1 Step G using (R)-1-(1-((tert-butoxycarbonyl)amino)propan-2-yl)-6-chloro-3-(3-(4-chloro-3,5-dimethylphenoxy)propyl)-7-(2,4,6-trimethylpyrimidin-5-yl)-1H-indole-2-carboxylate (192 mg, 0.27 mmol), 1H NMR: (400 MHz in MeOD) δ 7.76 (d, J=8.4 Hz, 1H), 7.28 (d, J=8.4 Hz, 1H), 6.63 (s, 2H), 4.48-4.69 (m, 1H), 3.97 (dt, J=6.0, 1.6 Hz, 2H), 3.71-3.65 (m, 2H), 3.42-3.35 (m, 2H), 2.76 (s, 3H), 2.32 (s, 3H), 2.31 (s, 6H), 2.21-2.16 (m, 2H), 2.15 (s, 3H), 1.01 (d, J=6.0 Hz, 3H); LCMS: RT=0.857 min, >98% purity at 215 nm and 254 nm; MS (ES) 551.20 (M+H).

Step I. Example 601

The title compound was prepared following General Procedure C using (R)-7-chloro-10-(3-(4-chloro-3,5-dimethylphenoxy)propyl)-4-methyl-6-(2,4,6-trimethyl pyrimidin-5-yl)-3,4-dihydropyrazino[1,2-a]indol-1(2H)-one and methyl 3-bromo-1-methyl-1H-indole-5-carboxylate followed by saponification (29 mg, 0.07 mmol) using General Procedure D. $^1$H NMR: (400 MHz in MeOD) δ 8.25 (d, J=1.2 Hz, 1H), 7.94 (dd, J=8.8, 1.6 Hz, 1H), 7.88 (d, J=8.4 Hz, 1H), 7.51 (d, J=8.4 Hz, 1H), 7.38 (s, 1H), 7.37 (d, J=8.8 Hz, 1H), 6.65 (s, 2H), 4.43 (dd, J=12.8, 3.6 Hz, 1H), 3.99 (dt, J=6.0, 2.4 Hz, 2H), 3.88 (s, 3H), 3.90-3.75 (m, 1H), 3.67 (dd, J=12.8, 1.2 Hz, 1H), 3.55-3.46 (m, 1H), 3.41-3.34 (m, 1H), 2.77 (s, 3H), 2.39 (s, 3H), 2.29 (s, 6H), 2.24 (s, 3H), 2.28-2.15 (m, 2H), 1.26 (d, J=6.4 Hz, 3H); LCMS: $R_T$=0.766 min, >98% purity at 215 nm and 254 nm; MS (ES) 724.24 (M+H).

Example 602

(R)-7-Chloro-10-(3-(4-chloro-3,5-dimethylphenoxy)propyl)-2-(1-(2-methoxyethyl)-5-(1-(2-(4-methylpiperazin-1-yl)ethyl)-1H-1,2,4-triazol-3-yl)-1H-indol-3-yl)-4-methyl-6-(1,3,5-trimethyl-1H-pyrazol-4-yl)-3,4-dihydropyrazino[1,2-a]indol-1(2H)-one Step A. Preparation of 5-(1-(2-((tert-butyldimethylsilyl)oxy)ethyl)-1H-1,2,4-triazol-3-yl)-3-iodo-1-(2-methoxyethyl)-1H-indol The crude title compound (200 mg) was prepared following General Procedure G using 3-iodo-1-(2-methoxyethyl)-5-(1H-1,2,4-triazol-3-yl)-1H-indole (150 mg, 0.41 mmol) and (2-bromoethoxy)-tert-butyldimethylsilane (105 μL, 0.49 mmol). LCMS: $R_T$=0.196 min, MS (ES) 412.9 (M+H).

Step B. Preparation of 2-(3-(3-iodo-1-(2-methoxyethyl)-1H-indol-5-yl)-1H-1,2,4-triazol-1-yl)ethan-1-ol The title compound (110 mg, 70%) was prepared following the procedure described Example 420 Step C using 5-(I-(2-(((tert-butyldimethylsilyl)oxy)ethyl)-1H-1,2,4-triazol-3-yl)-3-iodo-1-(2-methoxyethyl)-1H-indol (200 mg, 0.38 mmol). LCMS: $R_T$=1.317 min, MS (ES) 412.9 (M+H).

Step C. Preparation of 3-iodo-1-(2-methoxyethyl)-5-(1-(2-(4-methylpiperazin-1-yl)ethyl)-1H-1,2,4-triazol-3-yl)-1H-indole The crude title compound (46 mg) was prepared following General Procedure J using 2-(3-(3-iodo-1-(2-methoxyethyl)-1H-indol-5-yl)-1H-1,2,4-triazol-1-yl)ethan-1-ol (110 mg, 0.27 mmol) and 1-methylpiperazine (82 μL, 0.73 mmol). LCMS: $R_T$=0.166 min, MS (ES) 494.8 (M+H).

Step D. Example 602

The title compound (27 mg, 54%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-(2-methoxyethyl)-5-(1-(2-(4-methylpiperazin-1-yl)ethyl)-1H-1,2,4-triazol-3-yl)-1H-indole (45 mg, 0.09 mmol). LCMS: $R_T$=1.879 min, MS (ES) 904.9 (M+H).

Example 603

(R)-7-Chloro-10-(3-(4-chloro-3,5-dimethylphenoxy)propyl)-4-methyl-2-(5-(1-methyl-1H-1,2,4-triazol-3-yl)-1-(2-(4-methyl-3-oxopiperazin-1-yl)ethyl)-1H-indol-3-yl)-6-(1,3,5-trimethyl-1H-pyrazol-4-yl)-3,4-dihydropyrazino[1,2-a]indol-1(2H)-one Step A. Preparation of 2-(3-iodo-5-(1-methyl-1H-1,2,4-triazol-3-yl)-1H-indol-1-yl)ethan-1-ol The crude title compound (210 mg) was prepared following the procedure described Example 388 Step B using 2-(5-(1-methyl-1H-1,2,4-triazol-3-yl)-1H-indol-1-yl)ethan-1-ol (160 mg, 0.66 mmol). LCMS: $R_T$=1.217 min, MS (ES) 368.8 (M+H).

Step B. Preparation of 4-(2-(3-iodo-5-(1-methyl-1H-1,2,4-triazol-3-yl)-1H-indol-1-yl)ethyl)piperazin-2-one The title compound (23 mg, 29%) was prepared following General Procedure J using 2-(3-iodo-5-(1-methyl-1H-1,2,4-triazol-3-yl)-1H-indol-1-yl)ethan-1-ol (210 mg, 0.57 mmol) and piperazin-2-one (54 mg, 0.54 mmol). LCMS: $R_T$=1.099 min, MS (ES) 450.9 (M+H).

Step C. Preparation of 4-(2-(3-iodo-5-(1-methyl-1H-1,2,4-triazol-3-yl)-1H-indol-1-yl)ethyl)-1-methylpiperazin-2-one The crude title compound (200 mg) was prepared following General Procedure G using 4-(2-(3-iodo-5-(1-methyl-1H-1,2,4-triazol-3-yl)-1H-indol-1-yl)ethyl)piperazin-2-one (23 mg, 0.05 mmol) and MeI (4 μL, 0.06 mmol). LCMS: $R_T$=1.123 min, MS (ES) 464.8 (M+H).

Step D. Example 603

The title compound (2.1 mg, 5%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)- one (25 mg, 0.05 mmol) and 4-(2-(3-iodo-5-(1-methyl-1H-1,2,4-triazol-3-yl)-1H-indol-1-yl)ethyl)-1-methylpiperazin-2-one (24 mg, 0.05 mmol). LCMS: $R_T$=1.855 min, MS (ES) 874.9 (M+H).

Example 604

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-t-methyl-5-(N-methyl-2-(4-methylpiperazin-1-yl)acetamido)-1H-indole-3-carboxylic acid The title compound (68%) was prepared following General procedure E using methyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-1-methyl-5-(methylamino)-1H-indole-3-carboxylate and 2-(4-methylpiperazin-1-yl)acetic acid followed by saponification using General Procedure D. $^1$H-NMR (MeOH-d$_4$), δ 8.16 and 8.12 (s, total 1H), 8.00 (s, 1H), 7.79 (d, 1H, J=12 Hz), 7.34 (d, 1H, J=12 Hz), 7.25 and 7.09 (two s, total 1H), 6.64 and 6.63 (two s, total 2H), 4.46-4.37 (m, 1H), 4.00-3.96 (m, 2H), 3.87-3.76 (multiples s, total 5H), 3.79-3.76 (m, 2H), 3.51-3.48 (m, 2H), 3.24-3.22 (m, 4H), 3.34 (s, 2H), 2.85 (s, 6H), 2.29 (s, 6H), 2.24-2.23 (multiple s, total 3H), 2.18 and 2.15 (multiple d, total 4H, J=4 Hz), 2.02 (m, 2H), 2.01 and 2.99 (multiple d, total 4H, J=4 Hz), 1.29-1.21 (multiple d, total 3H, J=8 Hz); MS (ES) 881.2 (M+H).

Example 605

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methoxy-1-(pyridin-2-ylmethyl)-1H-indole-3-carboxylic acid Step A. Preparation of ethyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-2-ylmethyl)-1H-indole-3-carboxylate The title compound (37 mg, 99%) was prepared according to General Procedure I using methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate (39 mg, 0.02 mmol) and 2-(bromomethyl)pyridine HBr (19 mg, 0.074 mmol). LCMS: $R_T$=2.443 MS (ES) 922.90 (M+H).

Step B. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(pyridin-2-ylmethyl)-1H-indole-3-carboxylate To a solution of ethyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(pyridin-2-ylmethyl)-1H-indole-3-carboxylate (37 mg, 0.04 mmol) in ethanol (2 mL) was added Pd/C (18.5 mg, 10%) and the mixture was stirred under H$_2$ for 10 h. The reaction mixture was filtered through a pad of silica gel and eluted with DCM. The filtrate was concentrated and purified by flash chromatography (Combiflash Rf, Hex/EtOAc=0-20% gradient) to afford the title compound (28 mg, 90%). LCMS $R_T$=1.988 min, MS (ES) 833.8 (M+H).

Step C. Example 605

The title compound (11 mg, 67%) was prepared according to General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(pyridin-2-ylmethyl)-1H-indole-3-carboxylate (17 mg, 0.02 mmol) and MeI (5 μL, 0.08 mmol) followed by saponification using General Procedure D. LCMS: $R_T$=2.122 min (Method B), MS (ES) 818.0 (M+H).

Example 606

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-isopropoxyethoxy)-1-(pyridin-2-ylmethyl)-1H-indole-3-carboxylic acid The title compound (13 mg, 73%) was prepared according to General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(pyridin-2-ylmethyl)-1H-indole-3-carboxylate (17 mg, 0.02 mmol) and 1-bromo-4-methylpentane (12 μL, 0.08 mmol) followed by saponification using General Procedure D. LCMS: $R_T$=2.153 min, MS (ES) 890.80 (M+H).

Example 607

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(methoxymethyl)-1-methyl-1H-indole-2-carboxylic acid The title compound was prepared (140 mg, 77%, 2 steps) following the procedure described Example 595 using ethyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (185 mg, 0.24 mmol) and MeI (22 μL, 51 mg, 0.36 mmol). LCMS: $R_T$=2.159, 2.193, 2.245 min, MS (ES) 755.8 (M+H). $^1$H NMR (400 MHz, DMSO-d$_6$) δ 7.77 (d, J=8.6 Hz, 1H), 7.66 (s, 0.6H), 7.61 (s, 0.3H), 7.35-7.27 (m, 2.4H), 7.08-7.05 (m, 0.6H), 6.74-6.67 (m, 2H), 4.73-4.65 (m, 0.4H), 4.49-4.44 (m, 2H), 4.37 (dd, J=13.2, 3.6 Hz, 0.6H), 4.29-4.14 (m, 1H), 4.06 (s, 1H), 4.02-3.92 (m, 4H), 3.82-3.75 (m, 3.2H), 3.74-3.63 (m, 1H), 3.29 (s, 3H), 3.27-3.14 (m, 1.4H), 2.23 (br s, 6H), 2.15-2.10 (m, 2H), 2.10-1.96 (m, 4.6H), 1.94-1.87 (m, 2H), 1.18 (d, J=6.4 Hz, 2H), 1.07 (d, J=6.1 Hz, 1.2H).

Example 608

7-((R)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((S)-2-(dimethylamino)-N-methylpropanamido)-1-methyl-1H-indole-3-carboxylic acid The title compound (70%) was prepared following General procedure E using methyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-1-methyl-5-(methylamino)-1H-indole-3-carboxylate and dimethyl-L-alanine followed by saponification using General Procedure D. MS (ES) 840.3 (M+H).

Example 609

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-methoxyethoxy)-1-(pyridin-2-ylmethyl)-1H-indole-3-carboxylic acid The title compound (16 mg, 93%) was prepared according to General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(pyridin-2-ylmethyl)-1H-indole-3-carboxylate (17 mg, 0.02 mmol) and 1-bromo-2-methoxyethane (8 µL, 0.08 mmol) followed by saponification using General Procedure D. LCMS: $R_T$=2.052 min, MS (ES) 862.8 (M+H).

Example 610

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-ethoxyethoxy)-1-(pyridin-2-ylmethyl)-1H-indole-3-carboxylic acid The title compound (11 mg, 63% yield) was prepared according to General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(pyridin-2-ylmethyl)-1H-indole-3-carboxylate (17 mg, 0.02 mmol) and 1-bromo-2-ethoxyethane (9 µL, 0.08 mmol) followed by saponification using General Procedure D. LCMS: $R_T$=2.126 min, MS (ES) 876.9 (M+H).

Example 611

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-(dimethylamino)-N-methylacetamido)-1-methyl-1H-indole-3-carboxylic acid The title compound (47%) was prepared following General procedure E using methyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-1-methyl-5-(methylamino)-1H-indole-3-carboxylate and dimethylglycine followed by saponification using General Procedure D. MS (ES) 826.2 (M+H).

Example 612

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(N-methyl-2-(piperidin-1-yl)acetamido)-1H-indole-3-carboxylic acid The title compound (75%) was prepared following General procedure E using methyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-1-methyl-5-(methylamino)-1H-indole-3-carboxylate and 2-(piperidin-1-yl)acetic acid followed by saponification using General Procedure D. $^1$H-NMR (MeOH-d$_4$), δ 8.18 and 8.13 (s, total 1H), 8.03 (s, 1H), 7.80 (d, 1H, J=12 Hz), 7.32 (d, 1H, J=12 Hz), 7.14 and 7.13 (two s, total 1H), 6.64 and 6.63 (two s, total 2H), 4.46-4.42 (m, 1H), 4.04-4.02 (m, 2H), 3.99-3.82 (multiples s, total 6H), 3.50-3.39 (m, 4H), 3.39 (multiples s, total 3H), 3.35-3.30 (m, 4H), 2.89-2.86 (m, 2H), 2.29 (s, 6H), 2.24-2.08 (multiple s, total 3H), 2.02 (m, 2H), 2.08 and 2.00 (two s, total 3H), 1.84-1.78 (m, 6H), 1.29-1.21 (multiple d, total 3H, J=8 Hz); MS (ES) 865.3 (M+H).

Example 613

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(N-methyl-2-(pyrrolidin-1-yl)acetamido)-1H-indole-3-carboxylic acid The title compound (82%) was prepared following General procedure E using methyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-1-methyl-5-(methylamino)-1H-indole-3-carboxylate and 2-(pyrrolidin-1-yl)acetic acid followed by saponification using General Procedure D. MS (ES) 852.3 (M+H).

Example 614

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((2-(dimethylamino)ethoxy)methyl)-1-methyl-1H-indole-2-carboxylic acid The title compound was prepared (1.2 mg, 11%, 2 steps) following the procedure described Example 595 using ethyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (11 mg, 0.014 mmol) and 2-bromo-N,N-dimethylethan-1-amine HCl (4.9 mg, 0.021 mmol). LCMS: $R_T$=1.900, 1.931 min, MS (ES) 812.8 (M+H).

Example 615

(R)-7-Chloro-10-(3-(4-chloro-3,5-dimethylphenoxy)propyl)-2-(1-(2-methoxyethyl)-5-(1-(2-morpholinoethyl)-1H-1,2,4-triazol-3-yl)-1H-indol-3-yl)-4-methyl-6-(1,3,5-trimethyl-1H-pyrazol-4-yl)-3,4-dihydropyrazino[1,2-a]indol-1(2H)-one Step A. Preparation of 4-(2-(3-(3-iodo-1-(2-methoxyethyl)-1H-indol-5-yl)-1H-1,2,4-triazol-1-yl)ethyl)morpholine The crude title compound (50 mg) was prepared following General Procedure J using 2-(3-(1-(2-methoxyethyl)-1H-indol-5-yl)-1H-1,2,4-triazol-1-yl)ethan-1-ol (110 mg, 0.27 mmol) and morpholine (35 µL, 0.41 mmol). LCMS: $R_T$=0.184 min, MS (ES) 481.9 (M+H).

Step B. Example 615

The title compound (11 mg, 22%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 4-(2-(3-(3-iodo-1-(2-methoxyethyl)-1H-indol-5-yl)-1H-1,2,4-triazol-1-yl)ethyl)morpholine (50 mg, 0.10 mmol). LCMS: $R_T$=1.920 min, MS (ES) 891.9 (M+H).

Example 616

((R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((3-methyloxetan-3-yl)methyl)-1H-indole-5-carboxylic acid The title compound (4.6 mg, 42%) was prepared according to General Procedure I using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (15 mg, 0.02 mmol) and 3-(bromomethyl)-3-methyloxetane (5 mg, 0.03 mmol) followed by saponification using General Procedure D. LCMS: $R_T$=2.111 min, MS (ES) 781.80 (M+H).

Example 617

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-(pyridin-2-ylmethyl)-1H-indole-3-carboxylic acid The title compound (15 mg, 91%) was prepared according to General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H-indole-3-carboxylate (15 mg, 0.02 mmol) and 2-(bromomethyl)pyridine HBr (10 mg, 0.04 mmol). LCMS: $R_T$=2.132 min, MS (ES) 818.8 (M+H).

Example 618

(R)-2-(5-(1-((1-Acetylazetidin-3-yl)methyl)-1H-1,2,4-triazol-3-yl)-1-(2-methoxyethyl)-1H-indol-3-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one Step A. Preparation of tert-butyl 3-((3-(3-iodo-1-(2-methoxyethyl)-1H-indol-5-yl)-1H-1,2,4-triazol-1-yl)methyl)azetidine-1-carboxylate The title compound (100 mg, 69%) was prepared following General Procedure G using 3-iodo-1-(2-methoxyethyl)-5-(1H-1,2,4-triazol-3-yl)-1H-indole (100 mg, 0.27 mmol) and 1-Boc-3-(bromomethyl)azetidine (136 mg, 0.54 mmol). LCMS: $R_T$=1.772 min, MS (ES) 481.8 (M+H).

Step B. Preparation of 5-(1-(azetidin-3-ylmethyl)-1H-1,2,4-triazol-3-yl)-3-iodo-1-(2-methoxyethyl)-1H-indole TFA (0.3 mL) was added to a solution of tert-butyl 3-((3-(3-iodo-1-(2-methoxyethyl)-1H-indol-5-yl)-1H-1,2,4-triazol-1-yl)methyl)azetidine-1-carboxylate (100 mg, 0.19 mmol) in DCM (0.5 mL) at 0° C. The reaction was stirred at RT for 1 h, concentrated and diluted with DCM. The solution was washed with sat. aq. NaHCO$_3$, dried and concentrated to afford the crude title compound (75 mg) that was used for the next step without further purification. LCMS: $R_T$=1.258 min, MS (ES) 437.8 (M+H).

Step C. Preparation of 1-(3-((3-(3-iodo-1-(2-methoxyethyl)-1H-indol-5-yl)-1H-1,2,4-triazol-1-yl)methyl)azetidin-1-yl)ethan-1-one Acetyl chloride (19 µL, 0.26 mmol) and DIPEA (48 µL, 0.27 mmol) was added to a solution of 5-(1-(azetidin-3-ylmethyl)-1H-1,2,4-triazol-3-yl)-3-iodo-1-(2-methoxyethyl)-1H-indole (75 mg, 0.17 mmol) in DCM (1 mL) at 0° C. The reaction was warm to RT and stirred for 3 h. The reaction mixture was diluted with water and extracted with DCM. The combined organic layers were dried and concentrated. The residue was purified by flash chromatography (Combi-flash Rf, DCM/MeOH=0-3% gradient) to afford the title compound (50 mg, 60%). LCMS: $R_T$=1.407 min, MS (ES) 479.8 (M+H).

Step D. Example 618

The title compound (22 mg, 44%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 1-(3-((3-(3-iodo-1-(2-methoxyethyl)-1H-indol-5-yl)-1H-1,2,4-triazol-1-yl)methyl)azetidin-1-yl)ethan-1-one (49 mg, 0.10 mmol). LCMS: $R_T$=2.033 min, MS (ES) 889.9 (M+H).

Example 619

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-((4-methylpyridin-2-yl)methyl)-1H-indole-3-carboxylic acid The title compound (8.8 mg, 53%) was prepared according to General Procedure I using methyl (R)-7-(7-chloro- 10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H-indole-3-carboxylate (15 mg, 0.02 mmol) and 2-(chloromethyl)-4-methylpyridine (10 mg, 0.04 mmol). LCMS: $R_T$=2.036 min, MS (ES) 832.8 (M+H).

Example 620

(R)-1-(2-amino-2-oxoethyl)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylic acid The title compound (8.2 mg, 54%) was prepared according to General Procedure I using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (15 mg, 0.02 mmol) and 2-bromoacetonitrile (5 mg, 0.04 mmol) followed by saponification using General Procedure D. LCMS: $R_T$=1.951 min, MS (ES) 755.80 (M+H).

Example 621

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-((6-methylpyridin-2-yl)methyl)-1H-indole-3-carboxylic add (2$^{nd}$ Eluted Atropisomer, Absolute Configuration Undeterminded)

The title compound (6.7 mg, 40%) was prepared according to General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H-indole-3-carboxylate (15 mg, 0.02 mmol) and 2-(chloromethyl)-6-methylpyridine (10 mg, 0.04 mmol) as the 2$^{nd}$ eluted isomer from reverse phase HPLC. LCMS: $R_T$=2.034 min, MS (ES) 832.8 (M+H).

Example 622

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-((6-methylpyridin-2-yl)methyl)-1H-indole-3-carboxylic acid (1$^{st}$ Eluted Atropisomer, Absolute Configuration Undeterminded)

The title compound (5.2 mg, 11%) was isolated along with Example 621 as the 1$^{st}$ eluted isomer from reverse phase HPLC. LCMS: $R_T$=1.998 min, MS (ES) 832.8 (M+H).

Example 623

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(morpholinomethyl)-1H-indole-2-carboxylic acid To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (135 mg, 0.175 mmol) in DCM (2 mL) was added $^i$Pr$_2$EtN (47 μL, 34 mg, 0.263 mmol) followed by MsCl (13.3 μL, 20 mg, 0.175 mmol). After stirring for 10 min, morpholine (46 μL, 46 mg, 0.53 mmol) was added and stirred for additional 30 min. The reaction was quenched with aq. sat. NH$_4$Cl and extracted with DCM. The combined organic layer was dried over MgSO$_4$, filtered and concentrated. Subsequent saponification following General procedure D to afford the title compound (100 mg, 70%, 2 steps). LCMS: $R_T$=1.913, 1.963 min, MS (ES) 810.9 (M+H). $^1$H NMR (400 MHz, DMSO-d$_6$) δ 7.79-7.73 (m, 1H), 7.51-7.46 (m, 0.9H), 7.34-7.28 (m, 1.1H), 7.16-7.12 (m, 0.3H), 7.02 (br s, 0.7H), 6.97-6.90 (m, 0.7H), 6.74-6.67 (m, 2H), 4.71-4.64 (m, 0.3H), 4.36-4.29 (m, 0.7H), 4.26-4.14 (m, 1.1H), 4.11 (s, 0.9H), 4.01 (s, 1.7H), 4.00-3.94 (m, 2.2H), 3.81-3.77 (m, 2.4H), 3.76 (br s, 0.9H), 3.73-3.60 (m, 1.2H), 3.59-3.54 (m, 4H), 3.53-3.45 (m, 2.2H), 3.39-3.26 (m, 2H), 3.25-3.15 (m, 1.2H), 2.27-2.19 (m, 6H), 2.15-2.10 (m, 2H), 2.08-2.02 (m, 2.8H), 2.01 (s, 0.8H), 1.97 (s, 0.8H), 1.92 (s, 0.7H), 1.89 (s, 1.3H), 1.75-1.66 (m, 0.3H), 1.63-1.44 (m, 0.7H), 1.20-1.15 (m, 2.1H), 1.09-1.03 (m, 1.3H).

Example 624

(R)-7-Chloro-10-(3-(4-chloro-3,5-dimethylphenoxy)propyl)-2-(1-(2-methoxyethyl)-5-(1-((tetrahydro-2H-pyran-4-yl)methyl)-1H-1,2,4-triazol-3-yl)-1H-indol-3-yl)-4-methyl-6-(1,3,5-trimethyl-1H-pyrazol-4-yl)-3,4-dihydropyrazino[1,2-a]indol-1(2H)-one Step A. Preparation of 3-iodo-1-(2-methoxyethyl)-5-(1-((tetrahydro-2H-pyran-4-yl)methyl)-1H-1,2,4-triazol-3-yl)-1H-indole The crude title compound (150 mg) was prepared following General Procedure G using 3-iodo-1-(2-methoxyethyl)-5-(1H-1,2,4-triazol-3-yl)-1H-indole (120 mg, 0.33 mmol) and 4-bromomethyltetrahydropyran (117 μL, 0.65 mmol). LCMS: $R_T$=1.517 min, MS (ES) 466.9 (M+H).

Step B. Example 624

The title compound (26 mg, 53%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-(2-methoxyethyl)-5-(1-((tetrahydro-2H-pyran-4-yl)methyl)-1H-1,2,4-triazol-3-yl)-1H-indole (52 mg, 0.11 mmol). LCMS: $R_T$=2.167 min, MS (ES) 876.9 (M+H).

Example 625

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1-(2-methoxyethyl)-1H-indole-3-carboxylic acid The title compound (14 mg, 89%) was prepared according to General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-methoxy-1H-indole-3-carboxylate (15

Example 626

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(4-methylpiperazine-1-carbonyl)-1H-indole-2-carboxylic acid The title compound has was (6.0 mg, 40%, 3 steps) following the procedure described Example 591 step D using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (13 mg, 0.018 mmol) and N-methyl piperazine (50 µL, 45 mg, 0.45 mmol). LCMS: $R_T$=1.852, 1.879 min, MS (ES) 837.9 (M+H).

Example 627

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4-ethylpyridin-2-yl)methyl)-5-methyl-1H-indole-2-carboxylic acid The title compound (39 mg, 61%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (50 mg, 0.07 mmol) and 2-(chloromethyl)-4-ethylpyridine (21 mg, 0.14 mmol) followed by saponification using General Procedure D. LCMS: $R_T$=2.07 min, MS (ES) 831 (M+H).

Example 628

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-((4-methyl-3-oxopiperazin-1-yl)methyl)-1H-indole-2-carboxylic acid To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (8 mg, 0.011 mmol) in DCM (0.1 mL) was added Dess-Martin periodinane reagent (5 mg, 0.011 mmol) and stirred at RT for 30 min. The reaction was quenched with aq. sat. $Na_2S_2O_3$ solution and extracted with DCM. The combined organic layer was washed with brine, dried over $MgSO_4$, filtered and concentrated. The resulting crude product was redissolved in DCM (0.2 mL) and $Et_3N$ (0.04 mL). 1-methylpiperazin-2-one (2.6 µL, 2.6 mg, 0.026 mmol) and $Na(OAc)_3BH$ (4.7 mg, 0.022 mmol) were added to the reaction mixture and stirred at RT for 4 h. The reaction was quenched with aq. sat. $NH_4Cl$ and extracted with DCM. The combined organic layer was washed with brine, dried over $MgSO_4$, filtered and concentrated. Subsequent saponification was followed using General procedure D to afford the title compound (1.5 mg, 17%, 3 steps). LCMS: $R_T$=1.856, 1.895 min, MS (ES) 837.9 (M+H).

Example 629

(R)-5-(4-acetylpiperazine-1-carbonyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylic acid The title compound was prepared (1.8 mg, 12%, 3 steps) following the procedures described Example 591 in step D using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (13 mg, 0.018 mmol) and 1-(piperazin-1-yl)ethan-1-one (50 µL, 0.39 mmol). LCMS: $R_T$=1.941, 1.966 min, MS (ES) 865.8 (M+H).

Example 630

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(4-methyl-3-oxopiperazine-1-carbonyl)-1H-indole-2-carboxylic acid The title compound was prepared (2.1 mg, 14%, 3 steps) following the procedures described in Example 591 step D using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (13 mg, 0.018 mmol) and 1-methylpiperazin-2-one (50 µL, 0.44 mmol). LCMS: $R_T$=1.966 min, MS (ES) 851.8 (M+H).

Example 631

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-(2-(2-methoxyethoxy)ethoxy)-1-methyl-1H-indole-2-carboxylic acid The title compound (2.2 mg, 13%) was prepared following General Procedure H using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-methyl-1H-indole-2-carboxylate (15 mg, 0.020 mmol) and 1-bromo-2-(2-methoxyethoxy)ethane (10 mg, 0.054 mmol) followed by saponification using General Procedure D. LCMS: $R_T$=2.181 min, MS (ES) 827.8 (M+H).

Example 632

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-(2-methoxyethoxy)-1-((4-methylpyridin-2-yl)methyl)-1H-indole-2-carboxylic acid Step A. Methyl (R)-4-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate The title compound (105 mg, 35%) was prepared following General Procedure B using (R)-7-chloro-10-(3-(4- chloro-3,5-dimethylphenoxy)propyl)-4-methyl-6-(1,3,5-trimethyl-1H-pyrazol-4-yl)-3,4-dihydropyrazino[1,2-a]indol-1(2H)-one (200 mg, 0.37 mmol) and methyl 4-(benzyloxy)-7-iodo-1H-indole-2-carboxylate (300 mg, 0.74 mmol). LCMS: $R_T$=1.596, 1.627 min, MS (ES) 817.8 (M+H).

Step B, methyl (R)-4-(benzyloxy)-7-(7-chloro-10-(3-(4-chloro-3,5-dimethylphenoxy)propyl)-4-methyl-t-oxo-6-(1,3,5-trimethyl-1H-pyrazol-4-yl)-3,4-dihydropyrazino[1,2-a]indol-2(1H)-yl)-1-((4-methylpyridin-2-yl)methyl)-1H-indole-2-carboxylate The title compound (31 mg, 78%) was prepared following General Procedure I using methyl (R)-4-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (35 mg, 0.043 mmol) and 2-(chloromethyl)-4-methylpyridine HBr (15 mg, 0.085 mmol). LCMS: $R_T$=1.314, 1.343, 1.403 min, MS (ES) 922.8 (M+H).

Step C. methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-hydroxy-1-((4-methylpyridin-2-yl)methyl)-1H-indole-2-carboxylate The title compound (16.2 mg, 58%) was prepared following the procedure described Example 390 Step D using methyl (R)-4-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4-methylpyridin-2-yl)methyl)-1H-indole-2-carboxylate (31 mg, 0.034 mmol) and Pd/C (10 wt. %, 10 mg, 0.0093 mmol) by hydrogenating in MeOH (5 mL) for 16 h at RT. LCMS: $R_T$=0.902, 0.860 min (Method B), MS (ES) 832.9 (M+H).

Step D. Example 632

The title compound (10.8 mg, 63%) was prepared following General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4-hydroxy-1-((4-methylpyridin-2-yl)methyl)-1H-indole-2-carboxylate (11 mg, 0.013 mmol) and 1-bromo-2-methoxyethane (5 mg, 0.036 mmol) followed by saponification using General Procedure D. LCMS: $R_T$=1.977, 2.005 min, MS (ES) 876.9 (M+H).

Example 633

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-(2-methoxyethoxy)ethoxy)-1-methyl-1H-indole-2-carboxylic acid The title compound (9.6 mg, 58%) was prepared following General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (15 mg, 0.020 mmol) and 1-bromo-2-(2-methoxyethoxy)ethane (10 mg, 0.054 mmol) followed by saponification using General Procedure D. LCMS: $R_T$=2.132, 2.161 min, MS (ES) 876.9 (M+H). $^1$H NMR (CDCl$_3$, 400 MHz) δ (ppm) (7.77 (d, J=8.6 Hz, 1H), 7.34-7.31 (m, 1H), 7.28-7.21 (m, 1H), 7.08-6.96 (m, 1H), 6.88-6.83 (m, 0.66H), 6.74-6.70 (m, 0.34H), 6.60 (s, 1.34H), 6.58 (s, 0.66H), 4.45-4.07 (m, 8H), 4.01-3.92 (m, 4H), 3.91-3.81 (m, 3H), 3.77-3.71 (m, 2H), 3.63-3.56 (m, 2H), 3.40 (s, 2H), 3.39 (s, 1H), 3.37-3.30 (m, 2H), 2.45 (s, 1H), 2.35-2.31 (m, 2H), 2.30 (s, 6H), 2.29-2.25 (m, 2H), 2.20-2.09 (m, 3H), 1.31-1.22 (m, 2H), 1.21-1.11 (m, 1H).

Example 634

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-(2-methoxyethoxy)ethyl)-1H-indole-2-carboxylic acid The title compound (10.2 mg, 46%) was prepared following General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (20 mg, 0.028 mmol) and 1-bromo-2-(2-methoxyethoxy)ethane (10 mg, 0.054 mmol) followed by saponification using General Procedure D. LCMS: $R_T$=2.182, 2.210 min, MS (ES) 799.9 (M+H).

Example 635

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-(2-(2-methoxyethoxy)ethyl)-5-methyl-1H-indole-2-carboxylic acid The title compound (6.4 mg, 38%) was prepared following General Procedure I using methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methyl-1H-indole-2-carboxylate (15 mg, 0.021 mmol) and 1-bromo-2-(2-methoxyethoxy)ethane (10 mg, 0.054 mmol) followed by saponification using General Procedure D. LCMS: $R_T$=2.292, 2.316 min, MS (ES) 811.8 (M+H).

Example 636

(R)-3-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-methyl-1H-pyrrolo[2,3-b]pyridine-5-carboxylic acid The title compound (6.4 mg, 18%) was prepared according to General Procedure C using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (27 mg, 0.05 mmol) and methyl 3-bromo-1-methyl-1H-pyrrolo[2,3-b]pyridine-5-carboxylate (16 mg, 0.06 mmol) followed by saponification using General Procedure D. LCMS: $R_T$=1.267 min, MS (ES) 710.8 (M+H).

Example 637

(R)-2-(3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(pyrimidin-2-yl)-1H-indol-1-yl)-N,N-dimethylacetamide Step A. Preparation of N,N-dimethyl-2-(5-(pyrimidin-2-yl)-1H-indol-1-yl)acetamide The title compound (135 mg, 96%) was prepared following the procedure described Example 388 Step A using N,N-dimethyl-2-(5-(4,4,5,5-tetramethyl-1,3,2-dioxaborolan-2-yl)-1H-indol-1-yl)acetamide (248 mg, 0.75 mmol) and 2-bromopyrimidine (80 mg, 0.50 mmol). LCMS: $R_T$=1.181 min, MS (ES) 281.1 (M+H).

Step B. Preparation of 2-(3-iodo-5-(pyrimidin-2-yl)-1H-indol-1-yl)-N,N-dimethylacetamide The crude title compound (150 mg) was prepared following the procedure described Example 388 Step B using N,N-dimethyl-2-(5-(pyrimidin-2-yl)-1H-indol-1-yl)acetamide (135 mg, 0.48 mmol). LCMS: $R_T$=1.384 min, MS (ES) 406.8 (M+H).

Step C. Example 637

The title compound (16 mg, 36%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 2-(3-iodo-5-(pyrimidin-2-yl)-1H-indol-1-yl)-N,N-dimethylacetamide (45 mg, 0.11 mmol). LCMS: $R_T$=2.123 min, MS (ES) 816.9 (M+H).

Example 638

(R)-2-(3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(1-(pyridin-2-ylmethyl)-1H-1,2,4-triazol-3-yl)-1H-indol-1-yl)-N,N-dimethylacetamide Step A. Preparation of N,N-dimethyl-2-(5-(1-(pyridin-2-ylmethyl)-1H-1,2,4-triazol-3-yl)-1H-indol-1-yl)acetamide The title compound (66) mg, 49%) was prepared following the procedure described Example 388 Step A using N,N-dimethyl-2-(5-(4,4,5,5-tetramethyl-1,3,2-dioxaborolan-2-yl)-1H-indol-1-yl)acetamide (185 mg, 0.56 mmol) and 2-((3-bromo-1H-1,2,4-triazol-1-yl)methyl)pyridine (90 mg, 0.38 mmol). LCMS: $R_T$=0.167 min, MS (ES) 361.0 (M+H).

Step B. Preparation of 2-(3-iodo-5-(1-(pyridin-2-ylmethyl)-1H-1,2,4-triazol-3-yl)-1H-indol-1-yl)-N,N-dimethylacetamide The crude title compound (100 mg) was prepared following the procedure described Example 388 Step B using N,N-dimethyl-2-(5-(1-(pyridin-2-ylmethyl)-1H-1,2,4-triazol-3-yl)-1H-indol-1-yl)acetamide (66 mg, 0.18 mmol). LCMS: $R_T$=0.199 min, MS (ES) 486.9 (M+H).

Step C. Example 638

The title compound (14 mg, 27%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 2-(3-iodo-5-(1-(pyridin-2-ylmethyl)-1H-1,2,4-triazol-3-yl)-1H-indol-1-yl)-N,N-dimethylacetamide (54 mg, 0.11 mmol). LCMS: $R_T$=1.943 min, MS (ES) 896.8 (M+H).

Example 639

(R)-2-(3-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(1-((6-methylpyridin-2-yl)methyl)-1H-1,2,4-triazol-3-yl)-1H-indol-1-yl)-N,N-dimethylacetamide Step A. Preparation of N,N-dimethyl-2-(5-(1-((6-methylpyridin-2-yl)methyl)-1H-1,2,4-triazol-3-yl)-1H-indol-1-yl)acetamide The title compound (130 mg, 98%) was prepared following the procedure described Example 388 Step A using N,N-dimethyl-2-(5-(4,4,5,5-tetramethyl-1,3,2-dioxaborolan-2-yl)-1H-indol-1-yl)acetamide (175 mg, 0.53 mmol) and 2-((3-bromo-1H-1,2,4-triazol-1-yl)methyl)-6-methylpyridine (90 mg, 0.36 mmol). LCMS: $R_T$=1.069 min, MS (ES) 375.0 (M+H).

Step B. Preparation of 2-(3-iodo-5-(1-((6-methylpyridin-2-yl)methyl)-1H-1,2,4-triazol-3-yl)-1H-indol-1-yl)-N,N-dimethylacetamide The title compound (100 mg, 58%) was prepared following the procedure described Example 388 Step B using N,N-dimethyl-2-(5-(1-((6-methylpyridin-2-yl)methyl)-1H-1,2,4-triazol-3-yl)-1H-indol-1-yl)acetamide (130 mg, 0.35 mmol). LCMS: $R_T$=1.231 min, MS (ES) 500.8 (M+H).

Step C. Example 639

The title compound (35 mg, 69%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 2-(3-iodo-5-(1-((6-methylpyridin-2-yl)methyl)-1H-1,2,4-triazol-3-yl)-1H-indol-1-yl)-N,N-dimethylacetamide (56 mg, 0.11 mmol). LCMS: $R_T$=1.895 min, MS (ES) 910.9 (M+H).

Example 640

(R)-3-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-methyl-1H-pyrrolo[2,3-c]pyridine-5-carboxylic acid Step A. Preparation of methyl 3-bromo-1-methyl-1H-pyrrolo[2,3-c]pyridine-5-carboxylate The title compound (26 mg, 34%) was prepared following General Procedure F using methyl 1H-pyrrolo[2,3-c]pyridine-5-carboxylate (49 mg, 0.28 mmol), NBS (51 mg, 0.28 mmol), and MeI (21 µL, 0.34 mmol). LCMS: $R_T$=1.083 min, MS (ES) 268.9 (M+H).

Step B. Example 640

The title compound (12 mg, 34%) was prepared according to General Procedure C using (R)-7-chloro-10-(3-(4-chloro- 3,5-dimethylphenoxy)propyl)-6-(4,6-dimethylpyrimidin-5-yl)-4-methyl-3,4-dihydropyrazino[1,2-a]indol-1(2H)-one (27 mg, 0.05 mmol) and methyl 3-bromo-1-methyl-1H-pyrrolo[2,3-c]pyridine-5-carboxylate (16 mg, 0.06 mmol) followed by saponification using General Procedure D. LCMS: $R_T$=2.131 MS (ES) 710.8 (M+H).

Example 641

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((4-(prop-1-en-2-yl)pyridin-2-yl)methyl)-1H-indole-2-carboxylic acid Step A. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((4-(prop-1-en-2-yl)pyridin-2-yl)methyl)-1H-indole-2-carboxylate To a solution of methyl (R)-1-((4-bromopyridin-2-yl)methyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (110 mg, 0.12 mol) in (4:1) dioxane/water (1.5 mL) was added 2-isopropenylboronic acid pinacol ester (41 mg, 0.25 mmol) and Pd(PPh$_3$)$_4$ (14 mg, 0.01 mmol) and K$_2$CO$_3$ (34 mg, 0.25 mmol). The reaction was stirred under Ar at 90° C. for 5 h then cooled to RT. The reaction mixture was diluted with EtOAc and water. The aqueous layer was separated and extracted with EtOAc. The combined organic layers were washed with brine, dried over Na$_2$SO$_4$, filtered and concentrated in vacuo. The residue was purified by flash chromatography (Combi-flash Rf, CH$_2$Cl$_2$/methanol=0-3% gradient) to give the title compound (75 mg, 71%). LCMS: $R_T$=1.41 min., MS (ES) 857 (M+H).

Step B. Example 641

The title compound (63 mg, 75%) was prepared following General Procedure D using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-((4-(prop-1-en-2-yl)pyridin-2-yl)methyl)-1H-indole-2-carboxylate (75 mg, 0.0) mmol). LCMS: $R_T$=2.11 min., MS (ES) 843 (M+H).

Example 642

(R)-7-Chloro-10-(3-(4-chloro-3,5-dimethylphenoxy)propyl)-6-(4,6-dimethylpyrimidin-5-yl)-4-methyl-2-(1-methyl-5-(pyrimidin-2-yl)-1H-indol-3-yl)-3,4-dihydropyrazino[1,2-a]indol-1(2H)-one The title compound (40 mg, 96%) was prepared following General Procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (30 mg, 0.06 mmol) and 3-iodo-1-methyl-5-(pyrimidin-2-yl)-1H-indole (37 mg, 0.11 mmol). LCMS: $R_T$=2.301 min, MS (ES) 743.8 (M+H).

Example 643

(R)-7-Chloro-10-(3-(4-chloro-3,5-dimethylphenoxy)propyl)-2-(5-(1,5-dimethyl-1H-1,2,4-triazol-3-yl)-1-methyl-1H-indol-3-yl)-4-methyl-6-(1,3,5-trimethyl-1H-pyrazol-4-yl)-3,4-dihydropyrazino[1,2-a]indol-1(2H)-one Step A. Preparation of 5-(1,5-dimethyl-1H-1,2,4-triazol-3-yl)-1-methyl-1H-indole The crude title compound (150 mg) was prepared following the procedure described Example 388 Step A using 1-methyl-5-(4,4,5,5-tetramethyl-1,3,2-dioxaborolan-2-yl)-1H-indole (176 mg, 0.68 mmol) and 3-bromo-1,5-dimethyl-1H-1,2,4-triazole (100 mg, 0.57 mmol). LCMS: $R_T$=1.153 min, MS (ES) 227.1 (M+H).

Step B. Preparation of 5-(1,5-dimethyl-1H-1,2,4-triazol-3-yl)-3-iodo-1-methyl-1H-indole The crude title compound (190 mg) was prepared following the procedure described Example 388 Step B using 5-(1,5-dimethyl-1H-1,2,4-triazol-3-yl)-1-methyl-1H-indole (150 mg, 0.66 mmol). LCMS: $R_T$=1.189 min, MS (ES) 352.9 (M+H).

Step C. Example 643

The title compound (28 mg, 66%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 5-(1,5-dimethyl-1H-1,2,4-triazol-3-yl)-3-iodo-1-methyl-1H-indole (39 mg, 0.11 mmol). LCMS: $R_T$=2.016 min, MS (ES) 762.9 (M+H).

Example 644

(R)-7-(7-chloro-10(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methyl-5H-pyrrolo[2,3-b]pyrazine-2-carboxylic acid The title compound (22 mg, 62%) was prepared according to General Procedure C using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (27 mg, 0.05 mmol) and methyl 7-bromo-5-methyl-5H-pyrrolo[2,3-b]pyrazine-2-carboxylate (16 mg, 0.06 mmol) followed by saponification using General Procedure D. LCMS: $R_T$=2.200 MS (ES) 711.9 (M+H).

Example 645

(R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(3,4-difluorobenzyl)-1H-indole-5-carboxylic acid The title compound (7 mg, 51%) was prepared according to General Procedure I using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (15 mg, 0.02 mmol) and 4-(bromomethyl)-1,2-difluorobenzene (5 mg, 0.03 mmol) followed by saponification using General Procedure D. LCMS: $R_T$=2.109 min (Method B), MS (ES) 823.8 (M+H).

Example 646

(R)-7-Chloro-10-(3-(4-chloro-3,5-dimethylphenoxy) propyl)-4-methyl-2-(1-methyl-5-(1-(pyrimidin-2-yl)-1H-1,2,4-triazol-3-yl)-1H-indol-3-yl)-6-(1,3,5-trimethyl-1H-pyrazol-4-yl)-3,4-dihydropyrazino[1,2-a]indol-1(2H)-one Step A. Preparation of 2-(3-bromo-1H-1,2,4-triazol-1-yl)pyrimidine $Cs_2CO_3$ (4.40 g, 13.5 mmol), CuI (257 mg, 1.35 mmol) and 2-bromopyrimidine (1.40 g, 8.79 mmol) were added to a solution of 5-bromo-1H-1,2,4-triazole (1.00 g, 6.76 mmol) in DMF (13.5 mL). The reaction mixture was stirred at 120° C. for 18 h under Ar. The reaction mixture was quenched with water and extracted with EtOAc. The combined organic layer was washed with water, dried and concentrated. The residue was purified by flash chromatography (Combi-flash Rf, Hex/EtOAc=0-70% gradient) to afford the title compound (340 mg, 22%). LCMS: $R_T$=0.194 min, MS (ES) 226.0 (M+H).

Step B. Preparation of 1-methyl-5-(1-(pyrimidin-2-yl)-1H-1,2,4-triazol-3-yl)-1H-indole The title compound (53 mg, 43%) was prepared following the procedure described Example 388 Step A using 1-methyl-5-(4,4,5,5-tetramethyl-1,3,2-dioxaborolan-2-yl)-1H-indole (137 mg, 0.53 mmol) and 2-(3-bromo-1H-1,2,4-triazol-1-yl)pyrimidine (100 mg, 0.44 mmol). LCMS: $R_T$=1.373 min, MS (ES) 227.0 (M+H).

Step C. Preparation of 3-iodo-1-methyl-5-(1-(pyrimidin-2-yl)-1H-1,2,4-triazol-3-yl)-1H-indole The crude title compound (35 mg) was prepared following the procedure described Example 388 Step B using 1-methyl-5-(1-(pyrimidin-2-yl)-1H-1,2,4-triazol-3-yl)-1H-indole (53 mg, 0.19 mmol). LCMS: $R_T$=1.614 min, MS (ES) 402.9 (M+H).

Step D. Example 646

The title compound (20 mg, 43%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-methyl-5-(1-(pyrimidin-2-yl)-1H-1,2,4-triazol-3-yl)-1H-indole (34 mg, 0.08 mmol). LCMS: $R_T$=2.205 min, MS (ES) 812.8 (M+H). $^1$H NMR (400 MHz, $CDCl_3$) δ 9.25 (d, J=5.0 Hz, 1H), 8.82 (dd, J=4.8, 2.5 Hz, 2H), 8.43 (s, 1H), 8.28-8.24 (m, 1H), 7.67 (dd, J=8.6, 2.7 Hz 1H), 7.43 (dd, J=8.7, 1.6 Hz, 1H), 7.33-7.28 (m, 2H), 7.27-7.22 (m, 1H), 6.61 (s, 2H), 4.47-4.51 (m, 1H), 4.35-4.23 (m, 1H), 3.99 (t, J=6.2 Hz, 1H), 3.86 (s, 3H), 3.84 (s, 3H), 3.66 (t, J=11.8 Hz, 1H), 3.47-3.30 (m, 2H), 2.29 (s, 6H), 2.24-2.17 (m, 5H), 2.0) (s, 3H), 1.26-1.20 (m, 3H).

Example 647

(R)-7-Chloro-10-(3-(4-chloro-3,5-dimethylphenoxy) propyl)-4-methyl-2-(1-methyl-5-(1-(pyridin-2-yl)-1H-1,2,4-triazol-3-yl)-1H-indol-3-yl)-6-(1,3,5-trimethyl-1H-pyrazol-4-yl)-3,4-dihydropyrazino[1,2-a]indol-1(2H)-one Step A. Preparation of 1-methyl-5-(1-(pyridin-2-yl)-1H-1,2,4-triazol-3-yl)-1H-indole The title compound (58 mg, 14%) was prepared following the procedure described Example 646 Step A using 1-methyl-5-(1H-1,2,4-triazol-3-yl)-1H-indole (300 mg, 1.51 mmol) and 2-bromopyridine (144 μL, 1.51 mmol). LCMS: $R_T$=2.205 min, MS (ES) 812.8 (M+H).

Step B. Preparation of 3-iodo-1-methyl-5-(1-(pyridin-2-yl)-1H-1,2,4-triazol-3-yl)-1H-indole The title compound (58 mg, 69%) was prepared following the procedure described Example 388 Step B using 1-methyl-5-(1-(pyridin-2-yl)-1H-1,2,4-triazol-3-yl)-1H-indole (58 mg, 0.21 mmol). LCMS: $R_T$=1.854 min, MS (ES) 401.8 (M+H).

Step C. Example 647

The title compound (30 mg, 67% yield) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-methyl-5-(1-(pyridin-2-yl)-1H-1,2,4-triazol-3-yl)-1H-indole (67 mg, 0.17 mmol). LCMS: $R_T$=2.357 min, MS (ES) 811.8 (M+H).

Example 648

(R)-2-(5-([1,2,4]Triazolo[1,5-a]pyridin-2-yl)-1-methyl-1H-indol-3-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one Step A. Preparation of 2-(1-methyl-1H-indol-5-yl)-[1,2,4]triazolo[1,5-a]pyridine The title compound (60 mg, 96%) was prepared following the procedure described Example 388 Step A using 1-methyl-5-(4,4,5,5-tetramethyl-1,3,2-dioxaborolan-2-yl)-1H-indole (78 mg, 0.30 mmol) and 2-Bromo-[1,2,4]triazolo[1,5-a]pyridine (50 mg, 0.25 mmol). LCMS: $R_T$=1.262 min, MS (ES) 249.1 (M+H).

Step B. Preparation of 2-(3-iodo-1-methyl-1H-indol-5-yl)-[1,2,4]triazolo[1,5-a]pyridine The crude title compound (56 mg) was prepared following the procedure described Example 388 Step B using 2-(1-methyl-1H-indol-5-yl)-[1,2,4]triazolo[1,5-a]pyridine (60 mg, 0.24 mmol). LCMS: $R_T$=1.605 min, MS (ES) 374.8 (M+H).

Step C. Example 648

The title compound (40 mg, 92%) was prepared following General Procedure B using (R)-7-chloro-10-(3-(4-chloro-3, 5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 2-(3-iodo-1-methyl-1H-indol-5-yl)-[1,2,4]triazolo[1,5-a]pyridine (52 mg, 0.14 mmol). LCMS: $R_T$=2.182 min, MS (ES) 784.9 (M+H). $^1$H NMR (400 MHz, DMSO-$d_6$) δ 8.89 (d, J=7.0 Hz, 1H), 8.30 (s, 1H), 8.08 (d, J=9.6 Hz, 1H), 7.78-7.75 (m, 2H), 7.64-7.60 (m, 2H), 7.51 (s, 1H), 7.31 (d, J=8.7 Hz, 1H), 7.14 (t, J=6.8 Hz, 1H), 6.70 (s, 2H), 4.53-4.48 (m, 1H), 4.21-4.18 (m, 1H), 4.05-3.98 (m, 2H), 3.85 (s, 3H), 3.77 (d, J=4.5 Hz, 3H), 3.72-3.67 (m, 1H), 3.83-3.22 (m, 2H), 2.19 (s, 6H), 2.13-2.04 (m, 5H), 1.99-1.90 (m, 3H), 1.13-1.11 (m, 3H).

Example 649

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((4-methoxypiperidin-1-yl)methyl)-1-methyl-1H-indole-2-carboxylic acid The title compound (5.1 mg, 46%, 3 steps) was prepared following the procedures described Example 628 using ethyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (10 mg, 0.013 mmol) and 4-methoxypiperidine (20 µL, 18.6 mg, 0.16 mmol). LCMS: $R_T$=1.961, 1.988 min MS (ES) 838.9 (M+H).

Example 650

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((4-(2-methoxyethoxy)piperidin-1-yl)methyl)-1-methyl-1H-indole-2-carboxylic acid The title compound (6.5 mg, 57%, 3 steps) was prepared following the procedures described Example 628 using ethyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (10 mg, 0.013 mmol) and 4-(2-methoxyethoxy)piperidine (20 µL, ~20 mg, 0.13). LCMS: $R_T$=1.953, 2.012 min, MS (ES) 882.9 (M+H).

Example 651

(R)-3-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-methyl-1H-pyrrolo[3,2-b]pyridine-5-carboxylic acid Step A. Preparation of methyl 3-bromo-1-methyl-1H-pyrrolo[3,2-b]pyridine-5-carboxylate The title compound (61 mg, 80%) was prepared following General Procedure F using methyl 1H-pyrrolo[3,2-b]pyridine-5-carboxylate (49 mg, 0.28 mmol), NBS (51 mg, 0.28 mmol), and MeI (53 µL, 0.85 mmol). LCMS: $R_T$=1.077 min, MS (ES) 268.9 (M+H).

Step B. Example 651

The title compound (17 mg, 48%) was prepared according to General Procedure C using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (27 mg, 0.05 mmol) and 3-bromo-1-methyl-1H-pyrrolo[3,2-b]pyridine-5-carboxylate (16 mg, 0.06 mmol) followed by saponification using General Procedure D. LCMS: $R_T$=2.051 MS (ES) 710.8 (M+H). $^1$H NMR (400 MHz, DMSO-$d_6$) δ 9.10 (s, 1H), 8.16 (s, 1H), 8.08 (d, J=8.7 Hz, 1H), 7.94 (d, J=8.6 Hz, 1H), 7.89 (d, J=8.6 Hz, 1H), 7.39 (d, J=8.7 Hz, 1H), 6.75 (s, 2H), 4.52-4.45 (m, 1H), 4.35-4.29 (m, 1H), 4.06-3.95 (m, 2H), 3.89 (s, 3H), 3.78-3.69 (m, 1H), 3.44-3.33 (m, 1H), 3.32-3.22 (m, 1H), 2.27 (s, 3H), 2.24 (s, 6H), 2.18 (s, 3H), 2.15-2.03 (m, 2H), 1.17 (d, J=6.4 Hz, 3H).

Example 652

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-((4,6-dimethylpyridin-2-yl)methyl)-5-(2-methoxyethoxy)-1H-indole-3-carboxylic acid The title compound (8.8 mg, 49%) was prepared following General Procedure I from ethyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate (17 mg, 0.02 mmol), 2-(chloromethyl)-4,6-dimethylpyridine hydrochloride (19 mg, 0.10 mmol) followed by hydrogenation procedure described in step B example 605. The crude material was subjected to General Procedure H using 1-bromo-2-methoxyethane (8 µL, 0.08 mmol) followed by saponification using General Procedure D. LCMS: $R_T$=1.965 min, MS (ES) 890.8 (M+H).

Example 653

(R)-7-Chloro-10-(3-(4-chloro-3,5-dimethylphenoxy)propyl)-4-methyl-2-(1-methyl-5-(pyrimidin-5-yl)-1H-indol-3-yl)-6-(1,3,5-trimethyl-1H-pyrazol-4-yl)-3,4-dihydropyrazino[1,2-a]indol-1(2H)-one Step A. Preparation of 1-methyl-5-(pyrimidin-5-yl)-1H-indole The title compound (100 mg, 95%) was prepared following the procedure described Example 388 Step A using 1-methyl-5-(4,4,5,5-tetramethyl-1,3,2-dioxaborolan-2-yl)-1H-indole (129 mg, 0.50 mmol) and 5-bromopyrimidine (80 mg, 0.50 mmol). LCMS: $R_T$=1.391 min, MS (ES) 210.1 (M+H).

Step B. Preparation of 3-iodo-1-methyl-5-(pyrimidin-5-yl)-1H-indole

The title compound (140 mg, 88%) was prepared following the procedure described Example 388 Step B using 1-methyl-5-(pyrimidin-5-yl)-1H-indole (100 mg, 0.48 mmol). LCMS: $R_T$=1.618 min, MS (ES) 335.8 (M+H).

Step C. Example 653

The title compound (30 mg, 72%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-methyl-5-(pyrimidin-5-yl)-1H-indole (22 mg, 0.07 mmol). LCMS: $R_T$=2.231 min, MS (ES) 745.9 (M+H). $^1$H NMR (400 MHz, DMSO-$d_6$) δ 9.13 (s, 2H), 9.11 (s, 1H), 7.88 (d, J=6.0 Hz, 1H), 7.75 (d, J=8.5 Hz, 1H), 7.65 (s, 2H), 7.53 (s, 1H), 7.29 (d, J=8.6 Hz, 1H), 6.71 (s, 2H), 4.57-4.52 (m, 1H), 4.21-4.12 (m, 1H), 4.00-3.96 (m, 2H), 3.85 (s, 3H), 3.77 (d, J=6.2 Hz, 4H), 3.37-3.18 (m, 2H), 2.21 (s, 6H), 2.11-2.03 (m, 5H), 1.98-1.89 (m, 3H), 1.12 (d, J=5.7 Hz, 3H).

Example 654

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-5-(2-methoxyethoxy)-1-methyl-1H-indole-3-carboxylic acid The title compound (6.3 mg, 40%) was prepared following General Procedure I from ethyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate (17 mg, 0.02 mmol), MeI (6 µL, 0.10 mmol) followed by hydrogenation procedure described in step B example 605. The crude material was subjected to General Procedure H using 1-bromo-2-methoxyethane (8 µL, 0.08 mmol) followed by saponification using General Procedure D. LCMS: $R_T$=2.172 min, MS (ES) 785.8 (M+H).

Example 655

(R)-7-Chloro-10-(3-(4-chloro-3,4-dimethylphenoxy) propyl)-6-(4,6-dimethylpyrimidin-5-yl)-4-methyl-2-(1-methyl-5-(1H-1,2,4-triazol-3-yl)-1H-indol-3-yl)-3,4-dihydropyrazino[1,2-a]indol-1(2H)-one Step A. Preparation of (4R)-7-chloro-10-(3-(4-chloro-3,5-dimethylphenoxy)propyl)-6-(4,6-dimethylpyrimidin-5-yl)-4-methyl-2-(1-methyl-5-(1-(tetrahydro-2H-pyran-2-yl)-1H-1,2,4-triazol-3-yl)-1H-indol-3-yl)-3,4-dihydropyrazino[1,2-a]indol-1(2H)-one The crude title compound (70 mg) was prepared following General Procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (30 mg, 0.06 mmol) and 3-iodo-1-methyl-5-(1-(tetrahydro-2H-pyran-2-yl)-1H-1,2,4-triazol-3-yl)-1H-indole (28 mg, 0.14 mmol). LCMS: $R_T$=2.320 min, MS (ES) 816.8 (M+H).

Step B. Example 655

The title compound (31 mg, 49%) was prepared following the procedure described Example 581 Step C using (4R)-7-chloro-10-(3-(4-chloro-3,5-dimethylphenoxy)propyl)-6-(4,6-dimethylpyrimidin-5-yl)-4-methyl-2-(1-methyl-5-(1-(tetrahydro-2H-pyran-2-yl)-1H-1,2,4-triazol-3-yl)-1H-indol-3-yl)-3,4-dihydropyrazino[1,2-a]indol-1(2H)-one (70 mg, 0.09 mmol). LCMS: $R_T$=2.046 min, MS (ES) 732.9 (M+H). $^1$H NMR (400 MHz, DMSO-$d_6$) δ 9.08 (s, 1H), 8.31 (br s, 1H), 7.88 (t, J=8.5 Hz, 1H), 7.60 (d, J=8.6 Hz, 1H), 7.49 (s, 1H), 7.40 (d, J=8.6 Hz, 1H), 6.73 (s, 2H), 4.46 (dd, J=13.1, 3.5 Hz, 1H), 3.99 (t, J=5.7 Hz, 5H), 3.83 (s, 6H), 3.71-3.60 (m, 2H), 3.39-3.22 (m, 2H), 2.28 (s, 3H), 2.23 (s, 6H), 2.18 (s, 3H), 2.12-2.05 (m, 2H), 1.13 (d, J=6.5 Hz, 3H).

Example 656

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-5-(2-methoxyethoxy)-1-(2-methoxyethyl)-1H-indole-3-carboxylic acid Step A. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(2-methoxyethyl)-1H-indole-3-carboxylate The title compound (15 mg, 94%) was prepared following General Procedure I from ethyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-3-carboxylate (17 mg, 0.02 mmol), 1-bromo-2-methoxyethane (8 µL, 0.08 mmol) followed by hydrogenation procedure described in step B example 605. LCMS: $R_T$=2.131 min, MS (ES) 799.7 (M+H).

Step B. Example 656

The title compound (12 mg, 72%) was prepared following General Procedure H from ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(2-methoxyethyl)-1H-indole-3-carboxylate (15 mg, 0.018 mmol), I-bromo-2-methoxyethane (8 µL, 0.08 mmol) followed by saponification using General Procedure D. LCMS: $R_T$=2.178 min, MS (ES) 829.8 (M+H).

Example 657

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-(2-hydroxyethyl)-5-methyl-1H-indole-2-carboxylic acid Step A. Methyl (R)-1-(2-((tert-butyldimethylsilyl) oxy)ethyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate The title compound (28 mg, 95%) was prepared following General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (24 mg, 0.033 mmol) and (2-bromoethoxy)(tert-butyl)dimethylsilane (20 mg, 0.084 mmol). LCMS: $R_T$=2.199, 2.232 min (Method B), MS (ES) 883.9 (M+H).

Step B. Example 657

To a solution of methyl (R)-1-(2-((tert-butyldimethylsilyl) oxy)ethyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (28 mg, 0.032 mmol) in THF (3 mL) was added TBAF (1.0 M, 200 uL, 0.20 mmol)

at RT, and the reaction mixture was stirred for 4 h. LiOH (10 mg, 0.42 mmol) was added to the reaction, followed by MeOH (1 mL) and $H_2O$ (1 mL). The reaction was heated to 35° C. and stirred for 18 h. The crude reaction was diluted with $DCM/H_2O$ (20 mL, 1:1). The layers were separated and extracted with DCM. The combined organic extract was dried and concentrated in vacuo. The crude reaction product was purified by reverse phase HPLC (Phenomenex Gemini C18, $H_2O/CH_3CN$ gradient from 30-95% $CH_3CN$, 0.1% TFA to yield the title compound (12.9 mg, 47%). LCMS: $R_T$=2.196, 2.228 min, MS (ES) 755.8 (M+H).

Example 658

(R)-8-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-6-methylquinoline-3-carboxylic acid The title compound (23 mg, 63%) was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and methyl 8-bromo-6-methylquinoline-3-carboxylate (16.8 mg, 0.06 mmol) followed by saponification using General Procedure D. LCMS: $R_T$=2.232 MS (ES) 723.9 (M+H). $^1$H NMR (400 MHz, DMSO-$d_6$) δ 9.19 (dd, J=4.6 & 1.9 Hz, 1H), 8.98 (t, J=1.6 Hz, 1H), 7.99 (s, 1H), 7.80-7.71 (m, 2H), 7.31 (d, J=8.5 Hz, 1H), 6.70 (s, 2H), 4.69-4.49 (m, 1H), 4.28-4.12 (m, 1H), 3.96 (t, J=6.3 Hz, 2H), 3.78 (s, 1.5H), 3.76 (s, 1.5H), 3.66-3.53 (m, 1H), 3.32-3.24 (m, 1H), 3.23-3.13 (m, 1H), 2.55 (s, 3H), 2.23 (s, 6H), 2.13 (s, 1.5H), 2.04 (s, 1.5H), 2.03-2.01 (m, 2H), 1.98 (s, 1.5H), 1.89 (s, 1.5H), 1.19 (d, J=5.9 Hz, 3H).

Example 659

(R)-7-Chloro-10-(3-(4-chloro-3,5-dimethylphenoxy)propyl)-4-methyl-2-(1-methyl-5-(1H-1,2,3-triazol-1-yl)-1H-pyrrolo[3,2-b]pyridin-3-yl)-6-(1,3,5-trimethyl-1H-pyrazol-4-yl)-3,4-dihydropyrazino[1,2-a]indol-1(2H)-one Step A. Preparation of 1-methyl-5-(1H-1,2,3-triazol-1-yl)-1H-pyrrolo[3,2-b]pyridine The title compound (100 mg, 53%) was prepared following the procedure described Example 646 Step A using 1H-1,2,3-triazole (71.4 μL 1.23 mmol) and 5-bromo-1-methyl-1H-pyrrolo[3,2-b]pyridine (200 mg, 0.95 mmol). LCMS: $R_T$=1.183 min, MS (ES) 200.1 (M+H).

Step B. Preparation of 3-iodo-1-methyl-5-(1H-1,2,3-triazol-1-yl)-1H-pyrrolo[3,2-b]pyridine The title compound (106 mg, 65%) was prepared following the procedure described Example 388 Step B using 1-methyl-5-(1H-1,2,3-triazol-1-yl)-1H-pyrrolo[3,2-b]pyridine (100 mg, 0.50 mmol). LCMS: $R_T$=1.512 min, MS (ES) 325.9 (M+H).

Step C. Example 659

The title compound (38 mg, 93%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-methyl-5-(1H-1,2,3-triazol-1-yl)-1H-pyrrolo[3,2-b]pyridine (27 mg, 0.08 mmol). LCMS: $R_T$=2.297 min, MS (ES) 735.9 (M+H). $^1$H NMR (400 MHz, DMSO-$d_6$) δ 8.74 (d, J=8.3 Hz, 1H), 8.27 (dd, J=8.9, 2.4 Hz, 1H), 8.07 (d, J=7.4 Hz, 1H), 7.96-7.94 (m, 2H), 7.75 (d, J=8.3 Hz, 1H), 7.29 (d, J=8.6 Hz, 1H), 6.73 (s, 2H), 4.42-4.34 (m, 1H), 4.27-4.22 (m, 2H), 4.03-3.97 (m, 2H), 3.93 (s, 3H), 3.78 (d, J=8.6 Hz, 3H), 3.37-3.21 (m, 2H), 2.23 (s, 6H), 2.12-2.03 (m, 5H), 1.97-1.88 (m, 3H), 1.16 (d, J=5.7 Hz, 3H).

Example 660

(R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-methoxy-1-(2-methoxyethyl)-1H-indole-2-carboxylic acid Step A, methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1H-indole-2-carboxylate The title compound (72 mg, 47%) was prepared following General Procedure B using (R)-7-chloro-10-(3-(4-chloro-3,5-dimethylphenoxy)propyl)-6-(4,6-dimethylpyrimidin-5-yl)-4-methyl-3,4-dihydropyrazino[1,2-a]indol-1(2H)-one (100 mg, 0.19 mmol) and methyl 5-(benzyloxy)-7-iodo-1H-indole-2-carboxylate (150 mg, 0.37 mmol). LCMS: $R_T$=1.834 min, MS (ES) 815.8 (M+H).

Step B, methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-(2-methoxyethyl)-1H-indole-2-carboxylate The title compound (70 mg, 88%) was prepared following General Procedure I using methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1H-indole-2-carboxylate (75 mg, 0.092 mmol) and 1-bromo-2-methoxyethane (30 mg, 0.22 mmol). LCMS: $R_T$=1.932, 1.959 min (Method B), MS (ES) 873.8 (M+H).

Step C. methyl (R)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-(2-methoxyethyl)-1H-indole-2-carboxylate The title compound (58 mg, 92%) was prepared following the procedure described Example 390 Step D using methyl (R)-5-(benzyloxy)-7-(7-chloro-10-(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-1-(2-methoxyethyl)-1H-indole-2-carboxylate (70 mg, 0.12 mmol) and Pd/C (10 wt. %, 20 mg, 0.019 mmol) by hydrogenating in MeOH (5 mL) for 16 h at RT. LCMS: $R_T$=1.515, 1.550 min, MS (ES) 783.9 (M+H).

Step D. Example 660

The title compound (9.4 mg, 47%) was prepared following General Procedure H using methyl (R)-7-(7-chloro-10-

(3-(4-chloro-3,5-dimethylphenoxy)propyl)-6-(4,6-dimethylpyrimidin-5-yl)-4-methyl-1-oxo-3,4-dihydropyrazino[1,2-a]indol-2(1H)-yl)-5-hydroxy-1-(2-methoxyethyl)-1H-indol-2-carboxylate (20 mg, 0.026 mmol) and MeI (10 mg, 0.070 mmol) followed by saponification using General Procedure D. LCMS: $R_T$=1.491 min, MS (ES) 783.9 (M+H).

Example 661

(R)-8-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-4-carboxylic acid The title compound (10 mg, 28%) was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and methyl 8-bromoquinoline-4-carboxylate (16 mg, 0.06 mmol) followed by saponification using General Procedure D. LCMS: $R_T$=2.184 MS (ES) 709.8 (M+H). $^1$H NMR (400 MHz, DMSO-$d_6$) δ 9.00 (t, J=4.8 Hz, 1H), 8.69 (d, J=8.2 Hz, 1H), 8.02-7.90 (m, 1H), 7.85-7.81 (m, 1H), 7.80 (d, J=8.2 Hz, 1H), 7.76 (d, J=8.5 Hz, 1H), 7.30 (d, J=8.5 Hz, 1H), 6.70 (s, 2H), 4.69-4.45 (m, 1H), 4.31-4.10 (m, 1H), 3.95 (t, J=6.6 Hz, 2H), 3.77 (s, 1.5H), 3.75 (s, 1.5H), 3.68-3.50 (m, 1H), 3.37-3.22 (m, 1H), 3.21-3.08 (m, 1H), 2.23 (s, 6H), 2.13 (s, 1.5H), 2.04 (s, 1.5H), 2.03-2.00 (m, 2H), 1.98 (s, 1.5H), 1.89 (s, 1.5H), 1.19 (d, J=5.7 Hz, 3H).

Example 662

(R)-7-Chloro-10-(3-(4-chloro-3,5-dimethylphenoxy)propyl)-4-methyl-2-(1-methyl-5-(2H-1,2,3-triazol-2-yl)-1H-indol-3-yl)-6-(1,3,5-trimethyl-1H-pyrazol-4-yl)-3,4-dihydropyrazino[1,2-a]indol-1(2H)-one Step A. Preparation of 1-methyl-5-(2H-1,2,3-triazol-2-yl)-1H-indole The title compound (50 mg, 18%) was prepared following the procedure described Example 646 Step A using 1H-1,2,3-triazole (108 μL, 1.86 mmol) and of 5-bromo-1-methyl-1H-indole (300 mg, 1.43 mmol). LCMS: $R_T$=1.516 min, MS (ES) 199.1 (M+H).

Step B. Preparation of 3-iodo-1-methyl-5-(2H-1,2,3-triazol-2-yl)-1H-indole

The title compound (80 mg, 98%) was prepared following the procedure described Example 388 Step B using 1-methyl-5-(2H-1,2,3-triazol-2-yl)-1H-indole (50 mg, 0.25 mmol). LCMS: $R_T$=1.830 min, MS (ES) 324.9 (M+H).

Step C. Example 662

The title compound (31 mg, 75%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-methyl-5-(2H-1,2,3-triazol-2-yl)-1H-indole (27 mg, 0.08 mmol). LCMS: $R_T$=2.345 min, MS (ES) 734.8 (M+H). $^1$H NMR (400 MHz, DMSO-$d_6$) δ 8.04-8.02 (m, 3H), 7.90 (d, J=8.6 Hz, 1H), 7.75 (d, J=8.6 Hz, 1H), 7.67 (d, J=8.8 Hz, 1H), 7.56 (d, J=3.1 Hz, 1H), 7.29 (d, J=8.4 Hz, 1H), 6.71 (s, 2H), 4.52-4.46 (m, 1H), 4.20-4.12 (m, 1H), 4.02-3.95 (m, 2H), 3.86 (s, 3H), 3.77 (d, J=5.2 Hz, 3H), 3.70-3.65 (m, 1H), 3.36-3.19 (m, 2H), 2.21 (s, 6H), 2.12-2.03 (m, 5H), 1.97-1.88 (m, 3H), 1.10 (d, J=6.4 Hz, 3H).

Example 663

(R)-7-chloro-10-(3-(4-chloro-3,5-dimethylphenoxy)propyl)-6-(4,6-dimethyl-2-((4-methyl-3-oxopiperazin-1-yl)methyl)pyrimidin-5-yl)-4-methyl-2-(1-methyl-5-(1-methyl-1H-1,2,4-triazol-3-yl)-1H-indol-3-yl)-3,4-dihydropyrazino[1,2-a]indol-1(2H)-one Step A. (R)-6-(2-((benzyloxy)methyl)-4,6-dimethylpyrimidin-5-yl)-7-chloro-10-(3-(4-chloro-3,5-dimethylphenoxy)propyl)-4-methyl-2-(1-methyl-5-(1-methyl-1H-1,2,4-triazol-3-yl)-1H-indol-3-yl)-3,4-dihydropyrazino[1,2-a]indol-1(2H)-one The title compound (96 mg, 74%) was prepared following General Procedure C using (R)-6-(2-((benzyloxy)methyl)-4,6-dimethylpyrimidin-5-yl)-7-chloro-10-(3-(4-chloro-3,5-dimethylphenoxy)propyl)-4-methyl-3,4-dihydropyrazino[1,2-a]indol-1(2H)-one (100 mg, 0.15 mmol) and 3-iodo-1-methyl-5-(1-methyl-1H-1,2,4-triazol-3-yl)-1H-indole (70 mg, 0.21 mmol). LCMS: $R_T$=1.616 min, MS (ES) 866.8 (M+H).

Step B. (R)-7-chloro-10-(3-(4-chloro-3,5-dimethylphenoxy)propyl)-6-(2-(hydroxymethyl)-4,6-dimethylpyrimidin-5-yl)-4-methyl-2-(1-methyl-5-(1-methyl-1H-1,2,4-triazol-3-yl)-1H-indol-3-yl)-3,4-dihydropyrazino[1,2-a]indol-1(2H)-one The title compound (80 mg, 93%) was prepared following the procedure described Example 390 Step D using (R)-6-(2-((benzyloxy)methyl)-4,6-dimethylpyrimidin-5-yl)-7-chloro-10-(3-(4-chloro-3,5-dimethylphenoxy)propyl)-4-methyl-2-(1-methyl-5-(1-methyl-1H-1,2,4-triazol-3-yl)-1H-indol-3-yl)-3,4-dihydropyrazino[1,2-a]indol-1(2H)-one (96 mg, 0.11 mmol) and Pd/C (10 wt. %, 15 mg, 0.014 mmol) by hydrogenating in MeOH (5 mL) with HCl (4.0 M in dioxanes, 0.5 mL) for 16 h at RT. LCMS: $R_T$=1.155 min, MS (ES) 776.8 (M+H).

Step C. Example 663

The title compound (8.4 mg, 37%) was prepared following General Procedure J using (R)-7-chloro-10-(3-(4-chloro-3,5-dimethylphenoxy)propyl)-6-(2-(hydroxymethyl)-4,6-dimethylpyrimidin-5-yl)-4-methyl-2-(1-methyl-1H-1,2,4-triazol-3-yl)-1H-indol-3-yl)-3,4-dihydropyrazino[1,2-a]indol-1(2H)-one (20 mg, 0.026 mmol) and 1-methylpiperazin-2-one (15 mg, 0.13 mmol). LCMS: $R_T$=0.962 min, MS (ES) 872.8 (M+H).

Example 664

(R)-7-Chloro-10-(3-(4-chloro-3,5-dimethylphenoxy)propyl)-4-methyl-2-(1-methyl-5-(2H-1,2,3-triazol-2-yl)-1H-pyrrolo[3,2-b]pyridin-3-yl)-6-(1,3,5-trimethyl-1H-pyrazol-4-yl)-3,4-dihydropyrazino[1,2-a]indol-1(2H)-one Step A. Preparation of 1-methyl-5-(2H-1,2,3-triazol-2-yl)-1f-pyrrolo[3,2-b]pyridine The title compound (100 mg) was isolated from Example 659 Step A. LCMS: $R_T$=0.195 min, MS (ES) 200.1 (M+H).

Step B. Preparation of 3-iodo-1-methyl-5-(2H-1,2, 3-triazol-2-yl)-1H-pyrrolo[3,2-b]pyridine The crude title compound (175 mg) was prepared following the procedure described Example 388 Step B using 1-methyl-5-(2H-1,2,3-triazol-2-yl)-1H-pyrrolo[3,2-b]pyridine (100 mg, 0.50 mmol). LCMS: $R_T$=1.272 min, MS (ES) 325.9 (M+H).

Step C. Example 664

The title compound (23 mg, 56%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-methyl-5-(2H-1,2,3-triazol-2-yl)-1H-pyrrolo[3,2-b]pyridine (27 mg, 0.08 mmol). LCMS: $R_T$=2.295 min, MS (ES) 735.9 (M+H).

Example 665

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-5-methoxy-1-(2-methoxyethyl)-1H-indole-2-carboxylic acid

Step A, methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3, 4-dihydropyrazino[1,2-a]indol-2(1H)-yl)-1-(2-methoxyethyl)-1H-indole-2-carboxylate The title compound (49 mg, 86%) was prepared following General Procedure I using methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (53 mg, 0.065 mmol) and 1-bromo-2-methoxyethane (25 mg, 0.18 mmol). LCMS: $R_T$=1.829, 1.858 min (Method B), MS (ES) 875.8 (M+H).

Step B, methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1H-indole-2-carboxylate The title compound (43 mg, 98%) was prepared following the procedure described Example 390 Step D using methyl (R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-methoxyethyl)-1H-indole-2-carboxylate (49 mg, 0.056 mmol) and Pd/C (10 wt. %, 10 mg, 0.0093 mmol) by hydrogenating in MeOH (5 mL) with HCl (4.0 M in dioxanes, 0.5 mL) for 16 h at RT. LCMS: $R_T$=1.461, 1.485 min, MS (ES) 785.8 (M+H).

Step C. Example 665

The title compound (7.8 mg, 39%) was prepared following General Procedure H using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1H-indole-2-carboxylate (20 mg, 0.025 mmol) and MeI (10 mg, 0.070 mmol) followed by saponification using General Procedure D. LCMS: $R_T$=2.262 min, MS (ES) 785.8 (M+H).

Example 666

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)quinoline-2-carboxylic acid The title compound (17 mg, 48%) was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and methyl 7-bromoquinoline-2-carboxylate (16 mg, 0.06 mmol) followed by saponification using General Procedure D. LCMS: $R_T$=2.223 MS (ES) 709.9 (M+H).

Example 667

(R)-2-((5-carboxy-3-((R)-7-chloro-10-(3-(4-chloro-3,5-dimethylphenoxy)propyl)-4-methyl-1-oxo-6-(1, 3,5-trimethyl-1H-pyrazol-4-yl)-3,4-dihydropyrazino [1,2-a]indol-2(1H)-yl)-1H-indol-1-yl)methyl)-1,1-dimethylpyrrolidin-1-ium The title compound (3.6 mg, 29%) was prepared according to General Procedure I using methyl 3-((R)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(((R)-pyrrolidin-2-yl)methyl)-1H-indole-5-carboxylate (10 mg, 0.013 mmol) and MeI (4 μL, 0.056 mmol) followed by saponification using General Procedure D. LCMS: $R_T$=1.913 min, MS (ES) 808.9 (M+H).

Example 668

(R)-7-Chloro-10-(3-(4-chloro-3,5-dimethylphenoxy) propyl)-4-methyl-2-(1-methyl-5-(1H-1,2,3-triazol-1-yl)-1H-indol-3-yl)-6-(1,3,5-trimethyl-1H-pyrazol-4-yl)-3,4-dihydropyrazino[1,2-a]indol-1(2H)-one

Step A. Preparation of 1-methyl-5-(1H-1,2,3-triazol-1-yl)-1H-indole

The title compound (75 mg, 27%) was isolated from Example 662 Step A. LCMS: $R_T$=1.335 min, MS (ES) 199.2 (M+H).

Step B. Preparation of 3-iodo-1-methyl-5-(1H-1,2, 3-triazol-1-yl)-1H-indole

The title compound (60 mg, 54%) was prepared following the procedure described Example 388 Step B using 1-methyl-5-(1H-1,2,3-triazol-1-yl)-1H-indole (75 mg, 0.38 mmol). LCMS: $R_T$=1.509 min, MS (ES) 324.9 (M+H).

Step C. Example 668

The title compound (35 mg, 86%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-methyl-5-(1H-1,2,3-triazol-1-yl)-1H-indole (27 mg, 0.08 mmol). LCMS:

R$_T$=2.212 min, MS (ES) 734.8 (M+H). $^1$H NMR (400 MHz, DMSO-d$_6$) δ 8.73 (s, 1H), 7.92-7.90 (m, 2H), 7.75 (d, J=8.8 Hz, 1H), 7.70 (s, 2H), 7.60 (s, 1H), 7.29 (d, J=8.5 Hz, 1H), 6.72 (s, 2H), 4.55-4.50 (m, 1H), 4.20-4.12 (m, 1H), 4.00-3.95 (m, 2H), 3.87 (s, 3H), 3.77 (d, J=5.3 Hz, 3H), 3.71-3.63 (m, 1H), 3.35-3.18 (m, 2H), 2.22 (s, 6H), 2.11-2.02 (m, 5H), 1.97-1.88 (m, 3H), 1.10 (d, J=6.5 Hz, 3H).

Example 669

(R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-2-carboxylic acid The title compound (28 mg, 79%) was prepared according to General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (27 mg, 0.05 mmol) and methyl 4-bromoquinoline-2-carboxylate (16 mg, 0.06 mmol) followed by saponification using General Procedure D. LCMS: R$_T$=1.489 min (Method B), MS (ES) 709.9 (M+H).

Example 670

(R)-7-Chloro-10-(3-(4-chloro-3,5-dimethylphenoxy)propyl)-4-methyl-2-(1-methyl-5-(1-(4-methylpyrimidin-2-yl)-1H-1,2,4-triazol-3-yl)-1H-indol-3-yl)-6-(1,3,5-trimethyl-1H-pyrazol-4-yl)-3,4-dihydropyrazino[1,2-a]indol-1(2H)-one Step A. Preparation of 2-(3-bromo-1H-1,2,4-triazol-1-yl)-4-methylpyrimidine The title compound (234 mg, 28%) was prepared following the procedure described Example 646 Step A using 2-bromomethylpyrimidine (775 mg, 4.48 mmol) and 5-bromo-1H-1,2,4-triazole (510 mg, 3.45 mmol). LCMS: R$_T$=1.125 min, MS (ES) 240.0 (M+H).

Step B. Preparation of 1-methyl-5-(1-(4-methylpyrimidin-2-yl)-1H-1,2,4-triazol-3-yl)-1H-indole The title compound (100 mg, 69%) was prepared following the procedure described Example 388 Step A using 1-methyl-5-(4,4,5,5-tetramethyl-1,3,2-dioxaborolan-2-yl)-1H-indole (192 mg, 0.75 mmol) and 2-(3-bromo-1H-1,2,4-triazol-1-yl)-4-methylpyrimidine (120 mg, 0.50 mmol). LCMS: R$_T$=1.409 min, MS (ES) 291.1 (M+H).

Step C. Preparation of 3-iodo-1-methyl-5-(1-(4-methylpyrimidin-2-yl)-1H-1,2,4-triazol-3-yl)-1H-indole The title compound (135 mg, 94%) was prepared following the procedure described Example 388 Step B using 1-methyl-5-(1-(4-methylpyrimidin-2-yl)-1H-1,2,4-triazol-3-yl)-1H-indole (100 mg, 0.34 mmol). LCMS: R$_T$=1.709 min, MS (ES) 416.8 (M+H).

Step D. Example 670

The title compound (36 mg, 78%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-methyl-5-(1-(4-methylpyrimidin-2-yl)-1H-1,2,4-triazol-3-yl)-1H-indole (35 mg, 0.08 mmol). LCMS: R$_T$=2.294 min, MS (ES) 826.8 (M+H). $^1$H NMR (400 MHz, DMSO-d$_6$) δ 9.39 (d, J=3.4 Hz, 1H), 8.76 (d, J=5.1 Hz, 1H), 8.23 (d, J=4.3 Hz, 1H), 8.02 (d, J=8.7 Hz, 1H), 7.76 (d, J=8.7 Hz, 1H), 7.63 (d, J=8.7 Hz, 1H), 7.51 (d, J=3.0 Hz, 1H), 7.45 (d, J=4.9 Hz, 1H), 7.30 (d, J=8.7 Hz, 1H), 6.70 (s, 2H), 4.53-4.47 (m, 1H), 4.21-4.15 (m, 1H), 4.00-3.97 (m, 2H), 3.85 (s, 3H), 3.77 (d, J=4.7 Hz, 3H), 3.73-3.67 (m, 1H), 3.39-3.20 (m, 2H), 2.58 (s, 3H), 2.12-2.04 (m, 5H), 1.98-1.89 (m, 3H), 1.13-1.11 (m, 3H).

Example 671

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-(dimethylamino)ethoxy)-1-(2-methoxyethyl)-1H-indole-3-carboxylic acid The title compound (3.7 mg, 22%) was prepared following General Procedure H using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(2-methoxyethyl)-1H-indole-3-carboxylate (17 mg, 0.02 mmol) and 2-bromo-N,N-dimethylethan-1-amine hydrobromide (9.3 mg, 0.04 mmol) followed by saponification using General Procedure D. LCMS: R$_T$=1.969 min, MS (ES) 842.9 (M+H).

Example 672

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methoxy-1-(2-methoxyethyl)-1H-indole-3-carboxylic acid The title compound (6 mg, 38%) was prepared following procedure described in Example 673 from ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(2-methoxyethyl)-1H-indole-3-carboxylate (17 mg, 0.02 mmol), MeI (6 μL, 0.08 mmol) followed by saponification using General Procedure D. The title compound was isolated as the second eluted isomer from the reverse phase HPLC purification. LCMS: R$_T$=2.239 min, MS (ES) 785.8 (M+H).

Example 673

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methoxy-1-(2-methoxyethyl)-1H-indole-3-carboxylic acid The title compound (5 mg, 32%) was prepared following General Procedure H from ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(2-methoxyethyl)-1H-indole-3-carboxylate (17 mg, 0.02 mmol), methyl iodide (6 μL, 0.08 mmol) followed by saponification using General Procedure D. The title compound was isolated as the first eluted

Example 674

(R)-7-Chloro-10-(3-(4-chloro-3,5-dimethylphenoxy) propyl)-2-(5-(5-(methoxymethyl)-1-methyl-1H-1,2, 4-triazol-3-yl)-1-methyl-1H-indol-3-yl)-4-methyl-6-(1,3,5-trimethyl-1H-pyrazol-4-yl)-3,4-dihydropyrazino[1,2-a]indol-1(2H)-one Step A. Preparation of 5-(5-(methoxymethyl)-1-methyl-1H-1,2,4-triazol-3-yl)-1-methyl-1H-indole The title compound (15 mg, 17%) was prepared following the procedure described Example 388 Step A using 1-methyl-5-(4,4,5,5-tetramethyl-1,3,2-dioxaborolan-2-yl)-1H-indole (105 mg, 0.41 mmol) and 3-bromo-5-(methoxymethyl)-1-methyl-1H-1,2,4-triazole (70 mg, 0.34 mmol). LCMS: $R_T$=1.363 min, MS (ES) 257.1 (M+H).

Step B. Preparation of 3-iodo-5-(5-(methoxymethyl)-1-methyl-1H-1,2,4-triazol-3-yl)-1-methyl-1H-indole The title compound (22 mg, quant.) was prepared following the procedure described Example 388 Step B using 5-(5-(methoxymethyl)-1-methyl-1H-1,2,4-triazol-3-yl)-1-methyl-1H-indole (15 mg, 0.06 mmol). LCMS: $R_T$=1.517 min, MS (ES) 382.9 (M+H).

Step C. Example 674

The title compound (27 mg, 61%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-5-(5-(methoxymethyl)-1-methyl-1H-1,2,4-triazol-3-yl)-1-methyl-1H-indole (22 mg, 0.06 mmol). LCMS: $R_T$=2.212 min, MS (ES) 792.9 (M+H).

Example 675

(R)-2-(5-([1,2,4]Triazolo[4,3-a]pyridin-3-yl)-1-methyl-1H-indol-3-yl)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one Step A. Preparation of 3-(1-methyl-1H-indol-5-yl)-[1,2,4]triazolo[4,3-a]pyridine The title compound (83 mg, 95%) was prepared following the procedure described Example 388 Step A using 1-methyl-5-(4,4,5,5-tetramethyl-1,3,2-dioxaborolan-2-yl)-1H-indole (109 mg, 0.42 mmol) and 3-bromo-[1,2,4]triazolo[4,3-a]pyridine (70 mg, 0.35 mmol). LCMS: $R_T$=0.210 min, MS (ES) 249.1 (M+H).

Step B. Preparation of 3-(3-iodo-1-methyl-1H-indol-5-yl)-[1,2,4]triazolo[4,3-a]pyridine The title compound (75 mg, 60%) was prepared following the procedure described Example 388 Step B using 3-(1-methyl-1H-indol-5-yl)-[1,2,4]triazolo[4,3-a]pyridine (83 mg, 0.33 mmol). LCMS: $R_T$=1.133 min, MS (ES) 374.8 (M+H).

Step C. Example 675

The title compound (50 mg, 86%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (40 mg, 0.07 mmol) and 3-(3-iodo-1-methyl-1H-indol-5-yl)-[1,2,4]triazolo[4,3-a]pyridine (36 mg, 0.10 mmol). LCMS: $R_T$=2.081 min, MS (ES) 784.9 (M+H). $^1$H NMR (400 MHz, DMSO-d$_6$) δ 8.62-8.57 (m, 1H), 7.96 (s, 1H), 7.92-7.87 (m, 1H), 7.75 (t, J=8.6 Hz, 2H), 7.68 (d, J=8.6 Hz, 1H), 7.61 (d, J=1.9 Hz, 1H), 7.57-7.51 (m, 1H), 7.28 (d, J=8.5 Hz, 1H), 7.11-7.06 (m, 1H), 6.69 (s, 2H), 4.53-4.49 (m, 1H), 4.19-4.10 (m, 1H), 4.00-3.95 (m, 2H), 3.90 (s, 3H), 3.77-3.70 (m, 4H), 3.33-3.20 (m, 2H), 2.20 (s, 6H), 2.10-2.01 (m, 5H), 1.96-1.87 (m, 3H), 1.08 (d, J=6.3 Hz, 3H).

Example 676

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-methoxyethyl)-5-(2-(4-methylpiperazin-1-yl)ethoxy)-1H-indole-3-carboxylic acid The title compound (11 mg, 61%) was prepared following General Procedure H using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-(2-methoxyethyl)-1H-indole-3-carboxylate (17 mg, 0.02 mmol) and 1-(2-bromoethyl)-4-methylpiperazine dihydrobromide (15 mg, 0.04 mmol) followed by saponification using General Procedure D. LCMS: $R_T$=1.887 min, MS (ES) 897.9 (M+H).

Example 677

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-methoxyethyl)-5-(methoxymethyl)-1H-indole-2-carboxylic acid Step A. Preparation of ethyl 7-bromo-5-formyl-1-(2-methoxyethyl)-1H-indole-2-carboxylate To a solution of 1-(tert-butyl) 2-ethyl 7-bromo-5-formyl-1H-indole-1,2-dicarboxylate (67 mg, 0.17 mmol) in DCM (1 mL) was added TFA (129 µL, 194 mg, 1.7 mmol) and stirred at RT for 16 h. The reaction was quenched with aq. sat. NH$_4$Cl and extracted with DCM. The combined organic layer was washed with brine, dried over MgSO$_4$, filtered, and concentrated. To a solution of the crude product in DMF (1 mL) was added Cs$_2$CO$_3$ (366 mg, 1.08 mmol) and 1-bromo-2-methoxyethane (78 µL, 114 mg, 0.82 mmol) and stirred at 40° C. for 16 h. The reaction was quenched with aq. sat. NH$_4$C and ßextracted with DCM. The combined organic layer was dried over MgSO$_4$, filtered and concentrated. The residue was purified by flash chromatography (Combi-flash Rf, Hex/EtOAc=0-60% gradient) to afford the title compound (29 mg, 49%, 2 steps). LCMS: $R_T$=1.893 min, MS (ES) 353.9 (M+H).

Step B. Preparation of ethyl 7-bromo-1-(2-methoxyethyl)-5-((methoxymethoxy)methyl)-1H-indole-2-carboxylate The title compound (30 mg, 68%, 2 steps) was prepared following the reduction by NaBH$_4$ and OH protection by MOMCl procedures described Example 544 Step A using ethyl 7-bromo-5-formyl-1-(2-methoxyethyl)-1H-indole-2-carboxylate (29 mg, 0.082 mmol). LCMS: R$_T$=2.010 min, MS (ES) 399.9 (M+H).

Step C. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-(2-methoxyethyl)-1H-indole-2-carboxylate The title compound (8 mg, 24%, 2 steps) was prepared following the procedure described Example 591 Step C using ethyl 7-bromo-1-(2-methoxyethyl)-5-((methoxymethoxy)methyl)-1H-indole-2-carboxylate (30 mg, 0.075 mmol) and (R)-7-chloro-10-(3-(4-chloro-3,5-dimethylphenoxy) propyl)-4-methyl-6-(1,3,5-trimethyl-1H-pyrazol-4-yl)-3,4-dihydropyrazino[1,2-a]indol-1(2H)-one (40 mg, 0.075 mmol). LCMS: R$_T$=1.574, 1.595, 1.643 min, (Method B) MS (ES) 813.9 (M+H).

Step D. Example 677

The title compound (2.2 mg, 27%, 2 steps) was prepared following the procedure described Example 595 using ethyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-(2-methoxyethyl)-1H-indole-2-carboxylate (8 mg, 0.01 mmol) and MeI (3.0 mg, 0.021 mmol). LCMS: R$_T$=2.245, 2.272, 2.318 min, MS (ES) 799.9 (M+H).

Example 678

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-(2-methoxyethoxy)ethyl)-5-methyl-1H-indole-2-carboxylic acid The title compound (8 mg, 29%) was prepared following General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (27 mg, 0.037 mmol) and 1-bromo-2-(2-methoxyethoxy)ethane (30 mg, 0.16 mmol) followed by saponification using General Procedure D. LCMS: R$_T$=1.517, 1.552 min, MS (ES) 813.9 (M+H).

Example 679

(R)-7-Chloro-10-(3-(4-chloro-3,5-dimethylphenoxy)propyl)-4-methyl-2-(1-methyl-5-(5-methyl-JH-tetrazol-1-yl)-1H-pyrrolo[3,2-b]pyridin-3-yl)-6-(1,3,5-trimethyl-1H-pyrazol-4-yl)-3,4-dihydropyrazino[1,2-a]indol-1(2H)-one Step A. Preparation of 1-methyl-5-(5-methyl-1H-tetrazol-1-yl)-1H-pyrrolo[3,2-b]pyridine 5-Methyl-1H-tetrazole (60 mg, 0.71 mmol), CuI (68 mg, 0.36 mmol), K$_2$CO$_3$ (308 mg, 2.23 mmol), trans-N,N'-dimethylcyclohexane-1,2-diamine (79 µL, 0.36 mmol) were added to a solution of 5-bromo-1-methyl-1H-pyrrolo[3,2-b]pyridine (196 mg, 0.93 mmol) in DMF (1.4 mL). The reaction mixture was stirred at 100° C. for 3 days under Ar. The reaction mixture was filtered through Celite pad. Water was added to the filtrate and extracted with EtOAc. The combined organic layers were washed with water, dried and concentrated. The residue was purified by flash chromatography (Combi-flash Rf, DCM/MeOH=0-2% gradient) to afford the title compound (90 mg, 59%). LCMS: R$_T$=0.205 min, MS (ES) 215.1 (M+H).

Step B. Preparation of 3-iodo-1-methyl-5-(5-methyl-1H-tetrazol-1-yl)-1H-pyrrolo[3,2-b]pyridine The crude title compound (90 mg) was prepared following the procedure described Example 388 Step B using 1-methyl-5-(5-methyl-2H-tetrazol-2-yl)-1H-pyrrolo[3,2-b]pyridine (90 mg, 0.42 mmol). LCMS: R$_T$=1.411 min, MS (ES) 340.9 (M+H).

Step C. Example 679

The title compound (38 mg, 64%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (40 mg, 0.07 mmol) and 3-iodo-1-methyl-5-(5-methyl-1H-tetrazol-1-yl)-1H-pyrrolo[3,2-b]pyridine (38 mg, 0.11 mmol). LCMS: R$_T$=2.315 min, MS (ES) 750.9 (M+H).

Example 680

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(ethyl(methyl)amino)-1-methyl-1H-indole-2-carboxylic acid Step A. Preparation of methyl (E)-2-(2-(2-bromo-4-(N-methylacetamido)phenyl)-2-methylhydrazono)propanoate To a solution of methyl (E)-2-(2-(4-acetamido-2-bromophenyl)hydrazono)propanoate (500 mg, 1.53 mmol) in dry DMF (2 mL) was added NaH (245 mg, 6.12 mmol) followed by MeI (285 µL, 4.6 mmol) at 0° C. The reaction mixture was warmed to RT and stirred for 5 h. The reaction was quenched by pouring into brine and extracted with EtOAc. The organic layer was dried and concentrated. The residue was purified by flash chromatography (Combi-flash Rf, DCM/MeOH=0-5% gradient) to afford the title compound (430 mg, 80%). $^1$H-NMR (CDCb$_3$) δ 7.50 (s, 1H), 7.22 (m, 1H), 7.14 (s, 1H), 3.87 (s, 2H), 3.39 (s, 3H), 3.26 (s, 1H), 1.92 (s, 3H), 1.70 (s, 1H).

Step B. Preparation of methyl 7-bromo-1-methyl-5-(N-methylacetamido)-1H-indole-2-carboxylate A solution of methyl (E)-2-(2-(2-bromo-4-(N-methylacetamido)phenyl)-2-methylhydrazono)propanoate (150 mg, 0.42 mmol) in glacial acetic acid (8 mL) and PPA (0.5 mL) was heated at 90° C. for 1 h. The reaction mixture was concentrated, and the residue was diluted with water. The mixture was extracted with EtOAc, and the organic layer was concentrated. The residue was purified by flash chromatography (Combi-flash Rf, Hex/EtOAc=0-30% gradient)

to afford the title compound (100 mg, 70%). ¹H-NMR (DMSO-d₆) δ 7.70 (s, 1H), 7.61 (s, 1H), 7.37 (s, 1H), 4.38 (s, 3H), 3.87 (s, 3H), 3.15 (s, 3H), 1.76 (s, 3H).

Step C. Preparation of methyl 7-bromo-1-methyl-5-(methylamino)-1H-indole-2-carboxylate To a solution of methyl 7-bromo-1-methyl-5-(N-methylacetamido)-1H-indole-2-carboxylate (100 mg, 0.30 mmol) in dioxane (2 mL) was added HCl (2 mL, 4M in dioxane). The reaction mixture was stirred at 55° C. for 3 h then concentrated to afford the title compound (83 mg, 95%), which was used in next step without further purification. MS (ES) 297/299 (M+H).

Step D. Preparation of methyl 7-bromo-5-(ethyl(methyl)amino)-1-methyl-1H-indole-2-carboxylate To a solution of methyl 7-bromo-1-methyl-5-(methylamino)-1H-indole-2-carboxylate (40 mg, 0.134 mmol) in DCE (2 mL) was added acetaldehyde (0.2 mmol) and stirred for 30 min at RT. NaBH(OAc)₃ (0.27 mmol) was added to the reaction mixture and stirred at RT for 3 h. The reaction mixture was removed concentrated and in vacuum and the residue was purified by flash chromatography (Combi-flash Rf, Hex/EtOAc=0-10% gradient) to afford the title compound. MS (ES) 325.3/327.3 (M+H).

Step E. Example 680

The title compound (28%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one and methyl 7-bromo-5-(ethyl(methyl)amino)-1-methyl-1H-indole-2-carboxylate followed by saponification using General Procedure D. MS (ES) 769.2 (M+H).

Example 681

(R)-7-Chloro-10-(3-(4-chloro-3,5-dimethylphenoxy)propyl)-4-methyl-2-(1-methyl-5-(1H-1,2,4-triazol-1-yl)-1H-indol-3-yl)-6-(1,3,5-trimethyl-1H-pyrazol-4-yl)-3,4-dihydropyrazino[1,2-a]indol-1(2H)-one Step A. Preparation of 3-iodo-1-methyl-5-(1H-1,2,4-triazol-1-yl)-1H-indole The crude title compound (43 mg) was prepared following the procedure described Example 388 Step B using 1-methyl-5-(1H-1,2,4-triazol-1-yl)-1H-indole (31 mg, 0.16 mmol). LCMS: $R_T$=1.469 min, MS (ES) 324.9 (M+H).

Step B. Example 681

The title compound (30 mg, 73%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-methyl-5-(1H-1,2,4-triazol-1-yl)-1H-indole (23 mg, 0.07 mmol). LCMS: $R_T$=2.263 min, MS (ES) 734.8 (M+H). ¹H NMR (400 MHz, DMSO-d₄) δ 9.18 (s, 1H), 8.16 (s, 1H), 7.86 (d, J=4.8 Hz, 1H), 7.75 (d, J=8.4 Hz, 1H), 7.67 (s, 2H), 7.57 (s, 1H), 7.29 (d, J=8.4 Hz, 1H), 6.71 (s, 2H), 4.54-4.48 (m, 1H), 4.21-4.12 (m, 1H), 4.00-3.95 (m, 2H), 3.86 (s, 3H), 3.77 (d, J=5.3 Hz, 3H), 3.70-3.63 (m, 1H), 3.36-3.18 (m, 2H), 2.22 (s, 6H), 2.12-2.03 (m, 5H), 1.97-1.88 (m, 3H), 1.10 (d, J=6.4 Hz, 3H).

Example 682

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((2-methoxyethyl)(methyl)amino)-1-methyl-1H-indole-2-carboxylic acid Step A. Preparation of methyl 7-bromo-5-((2-methoxyethyl)(methyl)amino)-1-methyl-1H-indole-2-carboxylate The title compound was prepared following the procedure described Example 680 Step D using methyl 7-bromo-1-methyl-5-(methylamino)-1H-indole-2-carboxylate and 2-methoxyacetaldehyde. MS (ES) 355.3/357.3 (M+H).

Step E. Example 682

The title compound (36%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-bromo-5-((2-methoxyethyl)(methyl)amino)-1-methyl-1H-indole-2-carboxylate followed by saponification using General Procedure D. ¹H-NMR (MeOH-d₄) δ 8.02 (s, 0.6H), 7.91 (s, 0.4H), 7.80 (d, 1H, J=12 Hz), 7.58 (s, 0.4), 749 (d, 1H. J=12 Hz), 7.35-7.32 (two s, 2H), 6.63 and 6.61 (two s, total 2H), 4.46-4.23 (m, 1H), 4.23 and 4.22 (two s, total 1H), 4.09 (two s, total 2H), 4.00 (m, 2H), 3.81 (s, 1H), 3.76-3.61 (m, 6H), 3.40 (two s, total 3H), 2.67 (two s, 6H), 2.25 (s, 6H), 2.18-2.15 (two s, total 3H), 2.02 (m, 2H), 2.00 (two s, total 3H), 1.31 (d, 2H, J=8 Hz), 1.19 (d, 1H, J=8 Hz); MS (ES) 799.2 (M+H)

Example 683

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(dimethylamino)-1-methyl-1H-indole-2-carboxylic acid Step A. Preparation of methyl 7-bromo-5-(dimethylamino)-1-methyl-1H-indole-2-carboxylate The title compound was prepared following the procedure described Example 680 Step D using methyl 7-bromo-1-methyl-5-(methylamino)-1H-indole-2-carboxylate and formaldehyde. MS (ES) 311.3/313.3 (M+H).

Step E. Example 683

The title compound (23%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 7-bromo-5-(dimethylamino)-1-methyl-1H-indole-2-carboxylate followed by saponification using General Procedure D. MS (ES) 755.3 (M+H).

Example 684

(R)-7-Chloro-10-(3-(4-chloro-3,5-dimethylphenoxy)propyl)-4-methyl-2-(1-methyl-5-(5-methyl-2H-tetrazol-2-yl)-1H-pyrrolo[3,2-b]pyridin-3-yl)-6-(1,3,5-trimethyl-1H-pyrazol-4-yl)-3,4-dihydropyrazino[1,2-a]indol-1(2H)-one The title compound (11 mg, 19% yield) was obtained along with Example 679 from Step C. LCMS: $R_T$=2.380 min, MS (ES) 772.8 (M+Na).

Example 685

(R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-8-methyl-3,4-dihydro-1H-[1,4]oxazino[4,3-a]indol-1-one The title compound (25 mg, 43%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (75 mg, 0.10 mmol) and 1-bromo-2-(trifluoromethoxy)ethane (49 mg, 0.25 mmol) followed by saponification using General Procedure D. LCMS: $R_T$=1.55 min, MS (ES) 738 (M+H).

Example 686

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(3-methoxypropyl)-5-methyl-1H-indole-2-carboxylic acid The title compound (25 mg, 43%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (75 mg, 0.10 mmol) and 1-bromo-3-methoxypropane (39 mg, 0.25 mmol) followed by saponification using General Procedure D. LCMS: $R_T$=1.55 min, MS (ES) 784 (M+H).

Example 687

(R)-7-chloro-10-(3-(4-chloro-3,5-dimethylphenoxy)propyl)-4-methyl-2-(1-methyl-5-(2H-tetrazol-5-yl)-1H-pyrrolo[3,2-b]pyridin-3-yl)-6-(1,3,5-trimethyl-1H-pyrazol-4-yl)-3,4-dihydropyrazino[1,2-a]indol-1(2H)-one Step A. Preparation of (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-pyrrolo[3,2-b]pyridine-5-carboxamide The title compound (13 mg, 93%) was prepared according to General Procedure E using (R)-3-(7-Chloro-10-(3-(4-chloro-3,5-dimethylphenoxy)propyl)-4-methyl-1-oxo-6-(1,3,5- trimethyl-1H-pyrazol-4-yl)-3,4-dihydropyrazino[1,2-a]indol-2(1H)-yl)-1-methyl-1H-pyrrolo[3,2-b]pyridine-5-carboxylic acid (14 mg, 0.02 mmol) and ammonia (100 μL, 2M in methanol). LCMS: $R_T$=1.873 min, MS (ES) 711.8 (M+H).

Step B. Preparation of (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-pyrrolo[3,2-b]pyridine-5-carbonitrile To a solution of (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-pyrrolo[3,2-b]pyridine-5-carboxamide (13 mg, 0.018 mmol) in DCM (1 mL) were added trifluoromethanesulfonic anhydride (7 μL, 0.04 mmol), triethylamine (6 μL, 0.04 mmol), and the mixture was stirred at room temperature for 2 h. Water (10 mL) was added to the mixture and extracted in DCM. The organic layers was dried and concentrated to afford the title compound (10 mg, 78%). LCMS: $R_T$=1.604 min (Method B), MS (ES) 693.90 (M+H).

Step C. Example 687

To a solution of (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-pyrrolo[3,2-b]pyridine-5-carbonitrile (10 mg, 0.014 mmol) in DMF (1 mL) were added sodium azide (6.5 mg, 0.11 mmol), ammonium chloride (5.5 mg, 0.11 mmol) and the mixture was heated at 120° C. for 6 h. The reaction mixture was extracted in DCM, dried and concentrated. The crude was purified by reverse phase HPLC (Phenomenex Gemini C18, $H_2O/CH_3CN$ gradient to 35-95% MeCN 0.1% TFA) to afford the title compound (7 mg, 68%). LCMS: $R_T$=1.342 min (Method B), MS (ES) 736.9 (M+H).

Example 688

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-((thiazol-4-ylmethoxy)methyl)-1H-indole-2-carboxylic acid The title compound was prepared (5.0 mg, 43%, 2 steps) following the procedures described Example 607 using ethyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (11 mg, 0.014 mmol) and 4-(chloromethyl)thiazole hydrochloride (5 mg, 0.021 mmol). LCMS: $R_T$=2.145, 2.172, 2.224 min, MS (ES) 838.8 (M+H).

Example 689

(R)-7-Chloro-10-(3-(4-chloro-3,5-dimethylphenoxy)propyl)-4-methyl-2-(1-methyl-5-(2H-tetrazol-2-yl)-1H-indol-3-yl)-6-(1,3,5-trimethyl-1H-pyrazol-4-yl)-3,4-dihydropyrazino[1,2-a]indol-1(2H)-one Step A. Preparation of 1-methyl-5-(2H-tetrazol-2-yl)-1H-indole 1-Methyl-1H-indole-5-diazonium tetrafluoroborate (200 mg, 0.82 mmol) and $AgNO_3$ (208 mg, 1.22 mmol) were suspended in THF (4 mL) under Ar and cooled at −78° C. Et$_3$N (171 μL, 1.22 mmol) was added dropwise and stirred for 10 min then TMSCHN$_2$ (408 μL, 0.98 mmol) was added slowly. The mixture was stirred 1 h at −78° C. and warmed to RT. A solution of CsF (124 mg, 0.82 mmol) in MeOH (0.5 mL) was added and the mixture was stirred 1.5 h at RT. EtOAc and brine were added and the organic phase was separated, dried and concentrated. The residue was purified by flash chromatography (Combi-flash Rf, Hex/EtOAc=0-30% gradient) to afford the title compound (50 mg, 30%). LCMS: R$_T$=1.493 min, MS (ES) 200.1 (M+H).

Step B. Preparation of 3-iodo-1-methyl-5-(2H-tetrazol-2-yl)-1H-indole

The crude title compound (45 mg) was prepared following the procedure described Example 388 Step B using 1-methyl-5-(2H-tetrazol-2-yl)-1H-indole (50 mg, 0.25 mmol). LCMS: R$_T$=1.752 min, MS (ES) 325.9 (M+H).

Step C. Example 689

The title compound (35 mg, 86%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-1-methyl-5-(2H-tetrazol-2-yl)-1H-indole (24 mg, 0.07 mmol). LCMS: R$_T$=2.279 min, MS (ES) 735.9 (M+H).

Example 690

3-((R)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(((S)-1-methylpyrrolidin-2-yl)methyl)-1H-indole-5-carboxylic acid Step A. Preparation of tert-butyl (S)-2-(((methylsulfonyl)oxy)methyl)pyrrolidine-1-carboxylate To a solution of tert-butyl (S)-2-(hydroxymethyl)pyrrolidine-1-carboxylate (201 mg, 1.0 mmol) in DCM (6 mL) was added Et$_3$N (279 μL, 2.0 mmol) followed by MsCl (117 μL, 1.5 mmol). The mixture was stirred at RT for 2 h. The reaction mixture was quenched with water and extracted with DCM. The organic layer was dried, concentrated and purified by flash chromatography (Combi-flash Rf. Hex 100%) to afford the title compound (166 mg, 59%). LCMS R$_T$=1.589 min, MS (ES) 224.1 (M+H−56).

Step B. Preparation of methyl 1-(((R)-1-(tert-butoxycarbonyl)pyrrolidin-2-yl)methyl)-3-((S)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate The title compound (12 mg, 96%) was prepared according to General Procedure I using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (15 mg, 0.02 mmol) and methyl tert-butyl (S)-2-(((methylsulfonyl)oxy)methyl)pyrrolidine-1-carboxylate (8 mg, 0.03 mmol). LCMS: R$_T$=1.864 min (Method B), MS (ES) 894.90 (M+H).

Step C. Preparation of methyl 3-((R)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(((S)-pyrrolidin-2-yl)methyl)-1H-indole-5-carboxylate To a solution of methyl 1-(((R)-1-(tert-butoxycarbonyl)pyrrolidin-2-yl)methyl)-3-((S)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (12 mg, 0.013 mmol) in DCM (1 mL) was added TFA (200 μL, 2.61 mmol), and the mixture was stirred at RT for 3 h. The reaction mixture was washed with sat. NaHCO$_3$ aq. solution (3 mL) and extracted with DCM. The organic layer was dried, concentrated and purified by flash chromatography (Combi-flash Rf, Hex/EtOAc=0-100% gradient) to afford the title compound (10 mg, 90%). LCMS R$_T$=1.892 min, MS (ES) 794.8 (M+H).

Step D. Example 690

To a solution of methyl 3-((R)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(((S)-pyrrolidin-2-yl)methyl)-1H-indole-5-carboxylate (10 mg, 0.012 mmol) in DCM (0.5 mL) were added Et$_3$N (4 μL, 0.028 mmol) and formaldehyde (1 mg, 0.028 mmol). The mixture was stirred at RT for 10 min then washed with water (3 mL) and extracted with DCM. The organic layer was dried, concentrated and saponified using General Procedure D to yield the title compound (7.7 mg, 69%). LCMS: R$_T$=1.918 MS (ES) 794.9 (M+H).

Example 691

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(methoxymethyl)-1-(pyridin-2-ylmethyl)-1H-indole-2-carboxylic acid Step A. Preparation of ethyl 7-bromo-5-((methoxymethoxy)methyl)-1H-indole-2-carboxylate The title compound (52 mg, 47%, 2 steps) was prepared following the procedure described Example 544 Step A using 1-(tert-butyl) 2-ethyl 7-bromo-5-formyl-1H-indole-1,2-dicarboxylate (127 mg, 0.32 mmol). LCMS: R$_T$=1.796 min, MS (ES) 341.9 (M+H).

Step B. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((methoxymethoxy)methyl)-1-(pyridin-2-ylmethyl)-1H-indole-2-carboxylate The title compound (10 mg, 13%, 2 steps) was prepared following General coupling procedure A using ethyl 7-bromo-5-((methoxymethoxy)methyl)-1H-indole-2-carboxylate (30 mg, 0.088 mmol) and (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (47 mg, 0.088 mmol) followed by NH alkylation using General procedure I with 2-(bromomethyl)

pyridine HBr (19 mg, 0.075 mmol) by substituting Cs$_2$CO$_3$ with K$_2$CO$_3$ (31 mg, 0.225 mmol). LCMS: R$_T$=2.277, 2.333 min, MS (ES) 890.9 (M+H).

Step C. Example 691

To a solution of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-((methoxymethoxy)methyl)-1-(pyridin-2-ylmethyl)-1H-indole-2-carboxylate (9 mg, 0.041 mmol) in THF (0.25 mL) and MeOH (0.15 mL) was added conc. HCl (0.02 mL). After stirring at RT for 16 h, the reaction was quenched with aq. sat. NaHCO$_3$ solution and extracted with DCM. The combined organic layer was dried over MgSO$_4$, filtered and concentrated. The residue was dissolved in DMF (0.5 mL), and NaH (3.0 mg, 0.061 mmol) was added at 0° C. After stirring at 0° C. for 5 min, MeI (3.8 µL, 8.7 mg, 0.061 mmol) was added then warmed to RT and stirred for 4 h. The reaction was quenched with aq. sat. NH$_4$Cl and extracted with DCM. The combined organic layer was dried over MgSO$_4$, filtered and concentrated. Subsequent saponification following general procedure D afforded the title compound (6.5 mg, 30%, 2 steps). LCMS: R$_T$=2.035, 2.057 min, MS (ES) 832.8 (M+H).

Example 692

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-((oxetan-3-ylmethoxy)methyl)-1H-indole-2-carboxylic acid The title compound was prepared (4.0 mg, 33%, 2 steps) following the procedures described Example 607 using ethyl (R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (11 mg, 0.014 mmol) and 3-(chloromethyl)oxetane (5 mg, 0.021 mmol). LCMS: R$_T$=2.129, 2.157, 2.207 min, MS (ES) 811.9 (M+H). $^1$H NMR (600 MHz, DMSO-d$_6$) δ 7.76-7.75 (m, 1H), 7.67-7.63 (m, 0.6H), 7.63-7.59 (m, 0.4H), 7.33-7.26 (m, 2.3H), 7.09-7.05 (m, 0.7H), 6.71 (s, 1.2H), 6.68 (s, 0.8H), 4.71-4.63 (m, 0.6H), 4.62-4.56 (m, 1.2H), 4.55-4.47 (m, 1.2H), 4.45-4.40 (m, 0.6H), 4.39-4.33 (m, 1H), 4.29 (dt, J=6.0, 3.0 Hz, 1.2H), 4.26-4.20 (m, 1H), 4.19-4.13 (m, 0.6H), 4.07-4.03 (m, 1H), 3.98-3.95 (m, 1.6H), 3.94 (s, 2H), 3.79-3.77 (m, 1.2H), 3.75 (s, 0.6H), 3.74-3.72 (m, 0.4H), 3.72-3.66 (m, 0.6H), 3.65-3.63 (m, 1H), 3.45-3.37 (m, 1.6H), 3.36-3.28 (m, 1H), 3.27-3.22 (m, 0.6H), 3.21-3.14 (m, 1H), 2.25-2.19 (m, 6.5H), 2.14-2.10 (m, 1.8H), 2.06-2.01 (m, 3.2H), 2.00-1.99 (m, 0.7H), 1.98-1.96 (m, 1H), 1.92-1.90 (m, 0.7H), 1.89 (s, 1.3H), 1.19-1.15 (m, 2.2H), 1.06 (d, J=6.6 Hz, 1.1H).

Example 693

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-((2-morpholinoethoxy)methyl)-1H-indole-2-carboxylic acid The title compound was prepared (4.0 mg, 35% B, 2 steps) following the procedures described in the synthesis of example 607 using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(hydroxymethyl)-1-methyl-1H-indole-2-carboxylate (11 mg, 0.014 mmol) and 4-(2-chloroethyl)morpholine HCl (3.8 mg, 0.021 mmol). LCMS: R$_T$=1.960, 1.989 min, MS (ES) 854.9 (M+H).

Example 694

3-((R)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(((R)-1-methylpyrrolidin-2-yl)methyl)-1H-indole-5-carboxylic acid Step A. Preparation of tert-butyl (R)-2-(((methylsulfonyl)oxy)methyl)pyrrolidine-1-carboxylate The title compound (174 mg, 62%) was prepared according to method described in Example 690 step A using tert-butyl (R)-2-(hydroxymethyl)pyrrolidine-1-carboxylate (201 mg, 1.0 mmol). LCMS R$_T$=1.522 min, MS (ES) 224.1 (M+H−56).

Step B. Example 694

The title compound (6 mg, 54%) was prepared according to steps B-D in Example 69 using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (10 mg, 0.014 mmol) and tert-butyl (R)-2-(((methylsulfonyl)oxy)methyl)pyrrolidine-1-carboxylate (8 mg, 0.028 mmol). LCMS: R$_T$=1.911 min, MS (ES) 794.9 (M+H).

Example 695

(R)-7-Chloro-10-(3-(4-chloro-3,5-dimethylphenoxy)propyl)-2-(5-(8-(methoxymethyl)-[1,2,4]triazolo[1,5-a]pyridin-2-yl)-1-methyl-1H-indol-3-yl)-4-methyl-6-(1,3,5-trimethyl-1H-pyrazol-4-yl)-3,4-dihydropyrazino[1,2-a]indol-1(2H)-one Step A. Preparation of 2-bromo-8-(bromomethyl)-[1,2,4]triazolo[1,5-a]pyridine AIBN (23 mg, 0.14 mmol) and NBS (92 mg, 0.52 mmol) were added to a solution of 2-bromo-8-methyl-[1,2,4]triazolo[1,5-a]pyridine (100 mg, 0.47 mmol) in CCl$_4$ (5 mL). The reaction mixture was stirred at 85° C. under Ar for 4 h then concentrated. The residue was purified by flash chromatography (Combi-flash Rf, DCM 100%) to afford the title compound (56 mg, 41%). LCMS: R$_T$=1.121 min, MS (ES) 289.7 (M+H).

Step B. Preparation of 2-bromo-8-(methoxymethyl)-[1,2,4]triazolo[1,5-a]pyridine

A mixture of MeOH (15.6 µL, 0.38 mmol) and NaH (9.3 mg, 0.38 mmol) in THF (2 mL) was added to a solution of 2-bromo-8-(bromomethyl)-[1,2,4]triazolo[1,5-a]pyridine (56 mg, 0.19 mmol) in THF (3 mL) at 0° C. The reaction mixture was stirred at RT for 30 min. The reaction was quenched with water and extracted with EtOAc. The combined organic layers were dried and concentrated. The crude compound (50 mg) was used for the next step without further purification. LCMS: $R_T$=0.205 min, MS (ES) 241.9 (M+H).

Step C. Preparation of 8-(methoxymethyl)-2-(1-methyl-1H-indol-5-yl)-[1,2,4]triazolo[1,5-a]pyridine The title compound (60 mg, quant.) was prepared following the procedure described Example 388 Step A using 1-methyl-5-(4,4,5,5-tetramethyl-1,3,2-dioxaborolan-2-yl)-1H-indole (64 mg, 0.25 mmol) and 2-bromo-8-(methoxymethyl)-[1,2,4]triazolo[1,5-a]pyridine (50 mg, 0.21 mmol). LCMS: $R_T$=1.531 min, MS (ES) 293.1 (M+H).

Step D. Preparation of 2-(3-iodo-1-methyl-1H-indol-5-yl)-8-(methoxymethyl)-[1,2,4]triazolo[1,5-a]pyridine The title compound (61 mg, 71%) was prepared following the procedure described Example 388 Step B using 8-(methoxymethyl)-2-(1-methyl-1H-indol-5-yl)-[1,2,4]triazolo[1,5-a]pyridine (60 mg, 0.21 mmol). LCMS: $R_T$=1.778 min, MS (ES) 418.9 (M+H).

Step E. Example 695

The title compound (40 mg, 86%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 2-(3-iodo-1-methyl-1H-indol-5-yl)-8-(methoxymethyl)-[1,2,4]triazolo[1,5-a]pyridine (28 mg, 0.07 mmol). LCMS: $R_T$=2.290 min, MS (ES) 828.9 (M+H).

Example 696

(R)-7-Chloro-10-(3-(4-chloro-3,5-dimethylphenoxy)propyl)-4-methyl-2-(1-methyl-5-(5-methyl-[1,2,4]triazolo[1,5-a]pyridin-2-yl)-1H-indol-3-yl)-6-(1,3,5-trimethyl-1H-pyrazol-4-yl)-3,4-dihydropyrazino[1,2-a]indol-1(2H)-one Step A. Preparation of 5-methyl-2-(1-methyl-1H-indol-5-yl)-[1,2,4]triazolo[1,5-a]pyridine The title compound (180 mg, 97%) was prepared following the procedure described Example 388 Step A using 1-methyl-5-(4,4,5,5-tetramethyl-1,3,2-dioxaborolan-2-yl)-1H-indole (218 mg, 0.85 mmol) and 2-bromo-5-methyl-[1,2,4]triazolo[1,5-a]pyridine (150 mg, 0.71 mmol). LCMS: $R_T$=1.654 min, MS (ES) 263.1 (M+H).

Step B. Preparation of 2-(3-iodo-1-methyl-1H-indol-5-yl)-5-methyl-[1,2,4]triazolo[1,5-a]pyridine The title compound (64 mg, 24%) was prepared following the procedure described Example 388 Step B using 5-methyl-2-(1-methyl-1H-indol-5-yl)-[1,2,4]triazolo[1,5-a]pyridine (180 mg, 0.69 mmol). LCMS: $R_T$=1.679 min, MS (ES) 388.9 (M+H).

Step C. Example 696

The title compound (40 mg, 90%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 2-(3-iodo-1-methyl-1H-indol-5-yl)-5-methyl-[1,2,4]triazolo[1,5-a]pyridine (26 mg, 0.07 mmol). LCMS: $R_T$=2.208 min, MS (ES) 798.9 (M+H).

Example 697

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2,5-dicarboxylic acid Step A. Preparation of 3-bromo-4-hydrazinylbenzoic acid To a solution of methyl 4-amino-3-bromo benzoate (1.41 g, 6.52 mmol) was added a solution of NaNO$_2$ (0.675 g, 9.78 mmol) in water (6.52 mL) at RT and stirred for 45 min. The reaction mixture was cooled to 0° C. then SnCl$_2$ (3.83 g, 20 mmol) in con. HCl (12.0 mL) was added. The reaction mixture was stirred for 3 h, diluted with water (30 mL). The precipitate was filtered and washed with ether to afford the title compound (0.994 g, 66%) as a white solid. $^1$H NMR: (400 MHz in MeOD) δ 8.23 (d, J=2.0 Hz, 1H), 8.05 (dd, J=8.4, 2.0 Hz, 1H), 7.02 (d, J=8.4 Hz, 1H); LCMS: $R_T$=0.135 min, MS (ES) 230.9 (M+H).

Step B. Preparation of (E)-3-bromo-4-(2-(1-methoxy-1-oxopropan-2-ylidene)hydrazinyl) benzoic acid To a solution of 3-bromo-4-hydrazinylbenzoic acid (1.14 g, 4.91 mmol) in EtOH (25 mL) was added methyl pyruvate (0.54 mL, 5.89 mmol) at 0° C. then stirred for 20 min. Precipitate was filtered and washed with ether to afford the title compound (1.05 g, 68%) as a yellow solid. $^1$H NMR: (400 MHz in MeOD) δ 8.15 (d, J=1.6 Hz, 1H), 7.95 (dd, J=8.4, 1.6 Hz, 1H), 7.85 (s, NH), 7.65 (d, J=8.4 Hz, 1H), 3.90 (s, 3H), 2.23 (s, 3H); LCMS: $R_T$=0.884 min, MS (ES) 314.9 (M+H).

Step C. Preparation of allyl (E)-3-bromo-4-(2-(1-methoxy-1-oxopropan-2-ylidene) hydrazinyl)benzoate To a solution of (E)-3-bromo-4-(2-(1-methoxy-1-oxopropan-2-ylidene)hydrazinyl) benzoic acid (0.4 g, 1.27 mmol) in DMF (6.4 mL) was added K$_2$CO$_3$ (0.70 g, 5.1 mmol), followed by allyl bromide (0.55 mL, 6.37 mmol). The reaction mixture was stirred for 3 h, diluted with EtOAc, and washed with water. The combined organic layer was dried and concentrated in vacuo. The residue was purified by flash chromatography (Combi-flash Rf, Hex/EtOAc=0-30% gradient) to afford the title compound (0.39 g, 87%). $^1$H NMR: (400 MHz in CDCl$_3$) δ 12.5 (s, NH), 8.19 (d, J=2.0 Hz, 1H), 7.96 (dd, J=8.8, 2.0 Hz, 1H), 7.63 (d, J=8.8 Hz, 1H), 6.09-5.97 (m, 1H), 5.43-5.37 (m, 1H), 5.31-5.27 (m, 1H), 4.80 (dt, J=5.6, 1.2 Hz, 2H), 3.88 (s, 3H), 2.22 (s, 3H); LCMS: $R_T$=1.215 min, MS (ES) 355.12 (M+H).

Step D. Preparation of allyl (E)-3-bromo-4-(2-(1-methoxy-1-oxopropan-2-ylidene)-1-methylhydrazinyl)benzoate To a solution of ally (E)-3-bromo-4-(2-(1-methoxy-1-oxopropan-2-ylidene)hydrazinyl) benzoate (132 mg, 0.372 mmol) in MeCN (3.0 mL)/DMF (1.0 mL) was added Cs$_2$CO$_3$ (182 mg, 0.56 mmol), followed by MeI (69 mg, 0.484 mmol). The reaction mixture was stirred for 3 h, diluted with EtOAc and washed with water. The combined organic layer was dried and concentrated. The residue was purified by flash chromatography (Combi-flash Rf, Hex/EtOAc=0-30% gradient) to afford the title compound (134 mg, 97%). LCMS: R$_T$=1.167 min, MS (ES) 369.04 (M+H).

Step E. Preparation of 5-allyl 2-methyl 7-bromo-1-methyl-1H-indole-2, 5-dicarboxylate A solution of allyl (E)-3-bromo-4-(2-(1-methoxy-1-oxopropan-2-ylidene)-1-methylhydrazinyl)benzoate (134 mg, 0.364 mmol) in AcOH (3 mL) was heated to 90° C. and PPA (0.3 mL) was added. The reaction mixture was stirred for 2 h at 90° C. then excess organic solvent was removed in vacuo. The residue was purified by flash chromatography (Combi-flash Rf, Hex/EtOAc=0-50% gradient) to afford the title compound (30 mg, 25%). $^1$H NMR: (400 MHz in CDCl$_3$) δ 8.33 (d, J=1.6 Hz, 1H), 8.18 (d, J=1.6 Hz, 1H), 7.33 (s, 1H), 6.10-6.01 (m, 1H), 5.42 (dd, J=17.2, 1.2 Hz, 1H), 5.31 (dd, J=10.4, 1.2 Hz, 1H), 4.83 (dt, J=5.6, 1.2 Hz, 2H), 4.48 (s, 3H), 3.92 (s, 3H): LCMS: R$_T$=1.311 min, MS (ES) 352.02 (M+H).

Step F. Example 697

The title compound was prepared following General Procedure C using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and 5-allyl 2-methyl 7-bromo-1-methyl-1H-indole-2, 5-dicarboxylate. $^1$H NMR: (400 MHz in MeOD) δ 8.44 (s, 1H), 7.81 (s, 1H), 7.72 (d, J=8.4 Hz, 1H), 7.47 (s, 1H), 7.29 (d, J=8.4 Hz, 1H), 6.61 (s, 2H), 4.39-4.35 (m, 1H), 4.10 (s, 3H), 3.98-3.92 (m, 2H), 3.87 (s, 3H), 3.86-3.84 (m, 2H), 3.46-3.38 (m, 2H), 2.28 (s, 6H), 2.23 (s, 3H), 2.21-2.16 (m, 2H), 2.01 (s, 3H), 1.31 (d, J=6.4 Hz, 3H): LCMS: R$_T$=0.856 mm. MS (ES) 756.23 (M+H).

Example 698

(R)-7-Chloro-10-(3-(4-chloro-3,5-dimethylphenoxy)propyl)-4-methyl-2-(1-methyl-5-(8-methyl-[1,2,4]triazolo[1,5-a]pyridin-2-yl)-1H-indol-3-yl)-6-(1,3,5-trimethyl-1H-pyrazol-4-yl)-3,4-dihydropyrazino[1,2-a]indol-1(2H)-one Step A. Preparation of 8-methyl-2-(1-methyl-1H-indol-5-yl)-[1,2,4]triazolo[1,5-a]pyridine The title compound (180 mg, 97%) was prepared following the procedure described Example 388 Step A using 1-methyl-5-(4,4,5,5-tetramethyl-1,3,2-dioxaborolan-2-yl)-1H-indole (218 mg, 0.85 mmol) and 2-bromo-8-methyl-[1,2,4]triazolo[1,5-a]pyridine (150 mg, 0.71 mmol). LCMS: R$_T$=1.404 min, MS (ES) 263.1 (M+H).

Step B. Preparation of 2-(3-iodo-1-methyl-1H-indol-5-yl)-8-methyl-[1,2,4]triazolo[1,5-a]pyridine The title compound (82 mg, 31%) was prepared following the procedure described Example 388 Step B using 8-methyl-2-(1-methyl-1H-indol-5-yl)-[1,2,4]triazolo[1,5-a]pyridine (180 mg, 0.69 mmol). LCMS: R$_T$=1.702 min, MS (ES) 388.9 (M+H).

Step C. Example 698

The title compound (34 mg, 76%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 2-(3-iodo-1-methyl-1H-indol-5-yl)-8-methyl-[1,2,4]triazolo[1,5-a]pyridine (26 mg, 0.07 mmol). LCMS: R$_T$=2.231 min, MS (ES) 798.9 (M+H). $^1$H NMR (400 MHz, DMSO-d$_6$) δ 8.71 (d, J=6.8 Hz, 1H), 8.30 (s, 1H), 7.10 (d, J=8.7 Hz, 1H), 7.77 (d, J=8.7 Hz, 1H), 7.62 (d, J=8.8 Hz, 1H), 7.51 (s, 1H), 7.42 (d, J=7.2 Hz, 1H), 7.31 (d, J=8.5 Hz, 1H), 7.04 (t, J=7.2 Hz, 1H), 6.69 (s, 2H), 4.54-4.48 (m, 1H), 4.22-4.15 (m, 1H), 3.99 (t, J=6.6 Hz, 2H), 3.85 (s, 3H), 3.78-3.67 (m, 4H), 3.41-3.21 (m, 2H), 2.55 (s, 3H), 2.18 (s, 6H), 2.12-2.04 (m, 5H), 1.99-1.90 (m, 3H), 1.12 (d, J=6.3 Hz, 3H).

Example 699

(R)-7-Chloro-10-(3-(4-chloro-3,5-dimethylphenoxy)propyl)-2-(5-(8-((2-methoxyethoxy)methyl)-[1,2,4]triazolo[1,5-a]pyridin-2-yl)-1-methyl-1H-indol-3-yl)-4-methyl-6-(1,3,5-trimethyl-1H-pyrazol-4-yl)-3,4-dihydropyrazino[1,2-a]indol-1(2H)-one Step A. Preparation of 2-bromo-[1,2,4]triazolo[1,5-a]pyridine-8-carbaldehyde 4-Methylmorpholine N-oxide (531 mg, 4.54 mmol) was added to a solution of 2-bromo-8-(bromomethyl)-[1,2,4]triazolo[1,5-a]pyridine (330 mg, 1.13 mmol) in THF (5 mL). The reaction was refluxed for 30 min. The reaction was quenched with water and extracted with EtOAc. The combined organic layer was washed with brine, dried and concentrated. The crude title compound (250 mg) was used for the next step without further purification. LCMS: R$_T$=0.977 min, MS (ES) 226.0 (M+H).

Step B. Preparation of (2-bromo-[1,2,4]triazolo[1,5-a]pyridin-8-yl)methanol

NaH (140.5 mg, 3.63 mmol) was added to a solution of 2-bromo-[1,2,4]triazolo[1,5-a]pyridine-8-carbaldehyde (410 mg, 1.81 mmol) in THF/MeOH (12 mL, 10:1) at 0° C. The reaction was stirred for 10 min and then refluxed for 30 min. The reaction mixture was quenched with water and extracted with EtOAc. The combined organic layer was washed with brine, dried and concentrated. The crude title compound (420 mg) was used for the next step without further purification. LCMS: R$_T$=0.974 min, MS (ES) 228.0 (M+H).

Step C. Preparation of 2-bromo-8-(((tert-butyldimethylsilyl)oxy)methyl)-[1,2,4]triazolo[1,5-a]pyridine tert-Butyldimethylsilyl chloride (833 mg, 5.53 mmol), 4-DMAP (22.5 mg, 0.180 mmol) and Et$_3$N (770 μL, 5.53 mmol) were added to a solution of (2-bromo-[1,2,4]triazolo[1,5-a]pyridin-8-yl)methanol (420 mg, 1.84 mmol) in DCM (8 mL) at 0° C. The reaction was stirred at RT for 20 h. The reaction was quenched with water and extracted with DCM. The combined organic layer was washed with brine, dried and concentrated. The residue was purified by flash chromatography (Combi-flash Rf. Hex/EtOAc=0-20% gradient)

to afford the title compound (270 mg, 43%). LCMS: $R_T$=2.099 min, MS (ES) 341.9 (M+H).

Step D. Preparation of 8-(((tert-butyldimethylsilyl) oxy)methyl)-2-(1-methyl-1H-indol-5-yl)-[1,2,4]triazolo[1,5-a]pyridine The title compound (45 mg, 15%) was prepared following the procedure described Example 388 Step A using 1-methyl-5-(4,4,5,5-tetramethyl-1,3,2-dioxaborolan-2-yl)-1H-indole (243 mg, 0.95 mmol) and 2-bromo-8-(((tert-butyldimethylsilyl)oxy)methyl)-[1,2,4]triazolo[1,5-a]pyridine (270 mg, 0.79 mmol). LCMS: $R_T$=2.176 min, MS (ES) 393.1 (M+H).

Step E. Preparation of 8-(((tert-butyldimethylsilyl) oxy)methyl)-2-(3-iodo-1-methyl-1H-indol-5-yl)-[1,2,4]triazolo[1,5-a]pyridine The title compound (58 mg, quant.) was prepared following the procedure described Example 388 Step B using 8-(((tert-butyldimethylsilyl)oxy)methyl)-2-(1-methyl-1H-indol-5-yl)-[1,2,4]triazolo[1,5-a]pyridine (45 mg, 0.11 mmol). LCMS: $R_T$=2.382 min, MS (ES) 518.8 (M+H).

Step F. Preparation of (2-(3-iodo-1-methyl-1H-indol-5-yl)-[1,2,4]triazolo[1,5-a]pyridin-8-yl)methanol The title compound (50 mg, quant.) was prepared following the procedure described Example 420 Step C using 8-(((tert-butyldimethylsilyl)oxy)methyl)-2-(3-iodo-1-methyl-1H-indol-5-yl)-[1,2,4]triazolo[1,5-a]pyridine (58 mg, 0.11 mmol). LCMS: $R_T$=1.558 min, MS (ES) 404.8 (M+H).

Step G. Preparation of 2-(3-iodo-1-methyl-1H-indol-5-yl)-8-((2-methoxyethoxy)methyl)-[1,2,4]triazolo[1,5-a]pyridine The title crude compound (31 mg) was prepared following General Procedure G using (2-(3-iodo-1-methyl-1H-indol-5-yl)-[1,2,4]triazolo[1,5-a]pyridin-8-yl)methanol (50 mg, 0.12 mmol) and 2-bromoethyl methyl ether (15.1 µL, 0.16 mmol). LCMS: $R_T$=1.763 min, MS (ES) 462.9 (M+H).

Step H. Example 699

The title compound (19 mg, 46%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (25 mg, 0.06 mmol) and 2-(3-iodo-1-methyl-1H-indol-5-yl)-8-((2-methoxyethoxy)methyl)-[1,2,4]triazolo[1,5-a]pyridine (26 mg, 0.06 mmol). LCMS: $R_T$=2.248 min, MS (ES) 872.8 (M+H).

Example 700

(R)-7-Chloro-10-(3-(4-chloro-3,5-dimethylphenoxy) propyl)-4-methyl-2-(1-methyl-5-(1-(5-methylpyrimidin-2-yl)-1H-1,2,4-triazol-3-yl)-1H-indol-3-yl)-6-(1,3,5-trimethyl-1H-pyrazol-4-yl)-3,4-dihydropyrazino[1,2-a]indol-1(2H)-one Step A. Preparation of 2-(3-bromo-1H-1,2,4-triazol-1-yl)-5-methylpyrimidine The title compound (220 mg, 45%) was prepared following the procedure described Example 646 Step A using 2-bromo-5-methylpyrimidine (421 mg, 2.43 mmol). LCMS: $R_T$=1.146 min, MS (ES) 240.0 (M+H).

Step B. Preparation of 1-methyl-5-(1-(5-methylpyrimidin-2-yl)-1H-1,2,4-triazol-3-yl)-1H-indole The title compound (250 mg, 94%) was prepared following the procedure described Example 388 Step A using 1-methyl-5-(4,4,5,5-tetramethyl-1,3,2-dioxaborolan-2-yl)-1H-indole (283 mg, 1.10 mmol) and 2-(3-bromo-1H-1,2,4-triazol-1-yl)-5-methylpyrimidine (220 mg, 0.92 mmol). LCMS: $R_T$=1.528 min, MS (ES) 291.1 (M+H).

Step C. Preparation of 3-iodo-1-methyl-5-(1-(5-methylpyrimidin-2-yl)-1H-1,2,4-triazol-3-yl)-1H-indole The title compound (45 mg, 13% yield) was prepared following the procedure described Example 388 Step B using 1-methyl-5-(1-(5-methylpyrimidin-2-yl)-1H-1,2,4-triazol-3-yl)-1H-indole (250 mg, 0.86 mmol). LCMS: $R_T$=1.748 min, MS (ES) 416.8 (M+H).

Step D. Example 700

The title compound (25 mg, 38%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (40 mg, 0.07 mmol) and 3-iodo-1-methyl-5-(1-(5-methylpyrimidin-2-yl)-1H-1,2,4-triazol-3-yl)-1H-indole (45 mg, 0.11 mmol). LCMS: $R_T$=2.269 min, MS (ES) 826.9 (M+H).

Example 701

3-((R)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-1-(((R)-1-methylpyrrolidin-3-yl)methyl)-1H-indole-5-carboxylic acid Step A. Preparation of tert-butyl (R)-3-(((methylsulfonyl)oxy)methyl)pyrrolidine-1-carboxylate The title compound (121 mg, 43%) was prepared according to method described in Example 690 step A using tert-butyl (R)-3-(hydroxymethyl)pyrrolidine-1-carboxylate (201 mg, 1.0 mmol). LCMS: $R_T$=1.441 min (Method B). MS (ES) 224.1 (M+H−56).

Step B. Example 701

The title compound (5.6 mg, 50%) was prepared according to steps B-D in Example 690 using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (10 mg, 0.014 mmol) and tert-butyl (R)-3-(((methylsulfonyl)oxy)methyl) pyrrolidine-1-carboxylate (8 mg, 0.028 mmol). LCMS: $R_T$=2.004 min, MS (ES) 794.9 (M+H).

Example 702

3-((R)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(((S)-1-methylpyrrolidin-3-yl)methyl)-1H-indole-5-carboxylic acid

Step A. Preparation of tert-butyl (S)-3-(((methylsulfonyl)oxy)methyl)pyrrolidine-1-carboxylate The title compound (178 mg, 64%) was prepared according to method described in Example 690 step A using tert-butyl (S)-3-(hydroxymethyl)pyrrolidine-1-carboxylate (201 mg, 1.0 mmol). LCMS: $R_T$=1.426 min, MS (ES) 224.1 (M+H−56).

Step B. Example 702

The title compound (10 mg, 90%) was prepared according to steps B-D in Example 690 using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (10 mg, 0.014 mmol) and tert-butyl (S)-3-(((methylsulfonyl)oxy)methyl) pyrrolidine-1-carboxylate (8 mg, 0.028 mmol). LCMS: $R_T$=1.849 min, MS (ES) 792.9 (M+H).

Example 703

(R)-3-(3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indol-5-yl)-4-methyl-1,2,4-oxadiazol-5(4H)-one The title compound (16.2 mg, 78%) was prepared according to General Procedure I using (R)-3-(3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indol-5-yl)-1,2,4-oxadiazol-5(4H)-one (20 mg, 0.027 mmol) and MeI (6 μL, 0.08 mmol). LCMS: $R_T$=2.249 min, MS (ES) 765.8 (M+H).

Example 704

(R)-7-Chloro-10-(3-(4-chloro-3,5-dimethylphenoxy)propyl)-2-(5-(1-(5-methoxypyrimidin-2-yl)-1H-1,2,4-triazol-3-yl)-1-methyl-1H-indol-3-yl)-4-methyl-6-(1,3,5-trimethyl-1H-pyrazol-4-yl)-3,4-dihydropyrazino[1,2-a]indol-1(2H)-one

Step A. Preparation of 2-(3-bromo-1H-1,2,4-triazol-1-yl)-5-methoxypyrimidine The title compound (310 mg, 83%) was prepared following the procedure described Example 646 Step A using 2-bromo-5-methoxypyrimidine (460 mg, 2.43 mmol). LCMS: $R_T$=0.222 min, MS (ES) 255.9 (M+H).

Step B. Preparation of 5-(1-(5-methoxypyrimidin-2-yl)-1H-1,2,4-triazol-3-yl)-1-methyl-1H-indole The title crude compound (400 mg) was prepared following the procedure described Example 388 Step A using 1-methyl-5-(4,4,5,5-tetramethyl-1,3,2-dioxaborolan-2-yl)-1H-indole (398 mg, 1.55 mmol) and 2-(3-bromo-1H-1,2,4-triazol-1-yl)-5-methoxypyrimidine (310 mg, 1.29 mmol). LCMS: $R_T$=1.529 min, MS (ES) 307.0 (M+H).

Step C. Preparation of 3-iodo-5-(1-(5-methoxypyrimidin-2-yl)-1H-1,2,4-triazol-3-yl)-1-methyl-1H-indole The title compound (260 mg, 46%) was prepared following the procedure described Example 388 Step B using 5-(1-(5-methoxypyrimidin-2-yl)-1H-1,2,4-triazol-3-yl)-1-methyl-1H-indole (400 mg, 1.31 mmol). LCMS: $R_T$=1.741 min, MS (ES) 432.9 (M+H).

Step D. Example 704

The title compound (29 mg, 62%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 3-iodo-5-(1-(5-methoxypyrimidin-2-yl)-1H-1,2,4-triazol-3-yl)-1-methyl-1H-indole (29 mg, 0.07 mmol). LCMS: $R_T$=2.176 min, MS (ES) 842.8 (M+H).

Example 705

(R)-7-(7-chloro-10-(3-(4-chloro-3,5-dimethylphenoxy)propyl)-4-methyl-1-oxo-6-(2,4,6-trimethylpyrimidin-5-yl)-3,4-dihydropyrazino[1,2-a]indol-2(1H)-yl)-4-methoxy-1-(pyridin-2-ylmethyl)-1H-indole-2-carboxylic acid The title compound was This compound was prepared following General Procedure C using (R)-7-chloro-10-(3-(4-chloro-3,5-dimethylphenoxy)propyl)-4-methyl-6-(2,4,6-trimethylpyrimidin-5-yl)-3,4-dihydropyrazino[1,2-a]indol-1(2H)-one and 7-iodo-4-methoxy-1H-indole-2-carboxylic acid followed by installation of the 2-methylpyridyl group using General Procedure G, and saponification using General Procedure D. $^1$H NMR: (400 MHz in MeOD) δ 8.47 (d, J=4.4 Hz, 1H), 8.06 (t, J=7.2 Hz, 1H), 7.83 (d, J=8.8 Hz, 1H), 7.64 (s, 1H), 7.56 (t, J=6.8 Hz, 1H), 7.36 (d, J=8.8 Hz, 1H), 7.14 (d, J=8.0 Hz, 1H), 7.04 (d, J=8.0 Hz, 1H), 6.76 (d, J=8.4 Hz, 1H), 6.65 (s, 2H), 6.10 (d, J=18.4 Hz, 1H), 5.95 (d, J=18.4 Hz, 1H), 4.03 (s, 3H), 3.89 (t, J=6.4 Hz, 2H), 3.86-3.69 (m, 2H), 3.48 (d, J=13.2 Hz, 1H), 3.15-3.06 (m, 1H), 2.89-2.79 (m, 1H), 2.75 (s, 3H), 2.35 (s, 3H), 2.31 (s, 6H), 2.18 (s, 3H), 2.01-1.94 (m, 2H), 1.21 (d, J=6.8 Hz, 3H); LCMS: $R_T$=0.850 min, MS (ES) 831.30 (M+H).ß

Example 706

3-((R)-7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(((R)-pyrrolidin-3-yl)methyl)-1H-indole-5-carboxylic acid The title compound (3.4 mg, 31%) was prepared according to steps B-C in Example 690 using methyl (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-5-carboxylate (10 mg, 0.014 mmol) and tert-butyl (R)-3-(((methylsulfonyl)oxy)methyl)pyrrolidine-1-carboxylate (8 mg, 0.028 mmol) followed by saponification using General Procedure D. LCMS: $R_T$=1.963 min, MS (ES) 780.8 (M+H).

Example 707

(R)-7-Chloro-10-(3-(4-chloro-3,5-dimethylphenoxy) propyl)-4-methyl-2-(1-methyl-5-(7-methyl-[1,2,4] triazolo[1,5-a]pyridin-2-yl)-1H-indol-3-yl)-6-(1,3,5-trimethyl-1H-pyrazol-4-yl)-3,4-dihydropyrazino[1,2-a]indol-1(2H)-one Step A. Preparation of 7-methyl-2-(1-methyl-1H-indol-5-yl)-[1,2,4]triazolo[1,5-a]pyridine The title compound (200 mg, 95%) was prepared following the procedure described Example 388 Step A using 1-methyl-5-(4,4,5,5-tetramethyl-1,3,2-dioxaborolan-2-yl)-1H-indole (247 mg, 0.96 mmol) and 2-bromo-7-methyl-[1,2,4]triazolo[1,5-a]pyridine (170 mg, 0.80 mmol). LCMS: $R_T$=1.309 min, MS (ES) 263.1 (M+H).

Step B. Preparation of 2-(3-iodo-1-methyl-1H-indol-5-yl)-7-methyl-[1,2,4]triazolo[1,5-a]pyridine The title compound (190 mg, 64%) was prepared following the procedure described Example 388 Step B using 7-methyl-2-(1-methyl-1H-indol-5-yl)-[1,2,4]triazolo[1,5-a]pyridine (200 mg, 0.76 mmol). LCMS: $R_T$=1.557 min, MS (ES) 388.9 (M+H).

Step C. Example 707

The title compound (7.5 mg, 17%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 2-(3-iodo-1-methyl-1H-indol-5-yl)-7-methyl-[1,2,4]triazolo[1,5-a]pyridine (28 mg, 0.07 mmol). LCMS: $R_T$=2.146 min, MS (ES) 798.9 (M+H).

Example 708

(R)-7-Chloro-10-(3-(4-chloro-3,5-dimethylphenoxy) propyl)-2-(5-(1-(2-methoxyethyl)-1H-1,2,4-triazol-3-yl)-1-(2-morpholinoethyl)-1H-indol-3-yl)-4-methyl-6-(1,3,5-trimethyl-1H-pyrazol-4-yl)-3,4-dihydropyrazino[1,2-a]indol-1(2H)-one Step A. Preparation of 4-(2-(3-iodo-5-(1-(tetrahydro-2H-pyran-2-yl)-1H-1,2,4-triazol-3-yl)-1H-indol-1-yl)ethyl)morpholine The crude title compound (250 mg) was prepared following General Procedure J using 2-(3-iodo-5-(1-(tetrahydro-2H-pyran-2-yl)-1H-1,2,4-triazol-3-yl)-1H-indol-1-yl)ethan-1-ol (210 mg, 0.48 mmol) and morpholine (376 µL, 4.36 mmol). LCMS: $R_T$=1.424 min, MS (ES) 407.9 (M+H).

Step B. Preparation of 4-(2-(3-iodo-5-(1H-1,2,4-triazol-3-yl)-1H-indol-1-yl)ethyl)morpholine The crude title compound (220 mg) was prepared following the procedure described Example 581 Step C using 4-(2-(3-iodo-5-(1-(tetrahydro-2H-pyran-2-yl)-1H-1,2,4-triazol-3-yl)-1H-indol-1-yl)ethyl)morpholine (250 mg, 0.49 mmol). LCMS: $R_T$=1.132 min, MS (ES) 423.9 (M+H).

Step C. Preparation of 4-(2-(3-iodo-5-(1-(2-methoxyethyl)-1H-1,2,4-triazol-3-yl)-1H-indol-1-yl) ethyl)morpholine The crude title compound (199 mg) was prepared following General Procedure G using 4-(2-(3-iodo-5-(1H-1,2,4-triazol-3-yl)-1H-indol-1-yl)ethyl)morpholine (220 mg, 0.52 mmol) and 2-bromoethyl methyl ether (63.5 µL, 0.68 mmol). LCMS: $R_T$=1.292 min, MS (ES) 481.9 (M+H).

Step D. Example 708

The title compound (25 mg, 49%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 4-(2-(3-iodo-5-(1-(2-methoxyethyl)-1H-1,2,4-triazol-3-yl)-1H-indol-1-yl)ethyl)morpholine (32 mg, 0.07 mmol). LCMS: $R_T$=1.982 min, MS (ES) 891.9 (M+H).

Example 709

(M, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-methoxyethyl)-5-methyl-1H-indole-2-carboxylic acid Step A. Separation of (M, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one Diastereomeric mixture of (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one was separated by HPLC (Chiralcel OZ-H column Hex/EtOAc 7/3).

Step B. Preparation of ethyl (M, R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate The title compound (206 mg, 75%) was prepared following General Procedure K using (M, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (200 mg, 0.37 mmol) and ethyl 7-iodo-5-methyl-1H-indole-2-carboxylate (200 mg, 0.61 mmol). LCMS: $R_T$=1.708 min, MS (ES) 739.9 (M+H).

Step C. Example 709

The title compound (138 mg, 64%) was prepared following General Procedure I using ethyl (M, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (206 mg, 0.28 mmol) and 1-bromo-2-methoxyethane (100 mg, 0.72 mmol) followed by saponification using General Procedure D. LCMS:

$R_T$=1.503 min, MS (ES) 769.9 (M+H). ¹H NMR (DMSO-d₆, 400 MHz) δ (ppm) 7.813 (d, J=8.7, Hz, 0.34H), 7.810 (d, J=8.7 Hz, 0.66H), 7.50-7.46 (m, 1H), 7.37 (d, J=8.7 Hz, 0.33H), 7.36 (d, J=8.4 Hz, 0.66H), 7.25-7.18 (m, 1.34H), 6.94 (s, 0.66H), 6.76 (s, 1.34H), 6.74 (s, 0.66H), 5.03-5.00 (m, 0.34H), 4.88-4.81 (m, 0.66H), 4.70 (dd, J=12.5, 4.4 Hz, 0.5H), 4.60-4.57 (m, 0.5H), 4.48-4.45 (m, 1H), 4.31-4.22 (m, 1H), 4.02 (t, J=6.2 Hz, 2H), 3.84 (s, 3H), 3.77 (d, J=13.1, 1H), 3.50-3.25 (m, 4H), 3.05 (s, 2H), 3.00 (s, 1H), 2.43 (s, 2H), 2.40 (s, 1H), 2.28 (s, 2.28, 4H), 2.27 (s, 2H), 2.19 (s, 1H), 2.18 (s, 2H), 2.14-2.04 (m, 2H), 1.97 (s, 1H), 1.92 (s, 2H), 1.21 (d, J=6.5 Hz, 2H), 1.10 (d, J=6.6 Hz, 1H).

Example 710

(P, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-(2-methoxyethyl)-5-methyl-1H-indole-2-carboxylic acid The title compound (131 mg, 46% yield) was prepared following the same procedure as Example 709 starting from (P, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (200 mg, 0.037 mmol). LCMS: $R_T$=1.466, 1.495 min (Method B), MS (ES) 769.9 (M+H). ¹H NMR (DMSO-d₆, 400 MHz) δ (ppm) 7.772 (d, J=8.6 Hz, 0.66H), 7.768 (d, J=8.6 Hz, 0.34H), 7.47-7.43 (m, 1H), 7.33 (d, J=8.7 Hz, 0.34H), 7.32 (d, J=08.7 Hz, 0.66H), 7.19 (s, 1.34H), 6.93 (s, 0.66H), 6.71 (s, 1.34H), 6.69 (s, 0.66H), 4.97-4.92 (m, 0.34H), 4.77-4.72 (m, 0.66H), 4.66 (dd, J=12.7, 4.4 Hz, 0.34H), 4.55-4.46 (m, 1H), 4.41 (dd, J=13.5, 3.7 Hz, 0.66H), 4.21-4.12 (m, 1H), 3.98 (t, J=6.3 Hz, 2H), 3.79 (s, 1H), 3.77 (s, 2H), 3.67 (d, J=12.8 Hz, 1H), 3.45-3.20 (m, 4H), 3.00 (s, 2H), 2.95 (s, 1H), 2.38 (s, 2H), 2.36 (s, 1H), 2.24 (s, 4H), 2.23 (s, 2H), 2.07-1.97 (m, 8H), 1.15 (d, J=6.5 Hz, 2H), 1.05 (d, J=6.6 Hz, 1H).

Example 711

(M, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-methoxyethoxy)-1-methyl-1H-indole-2-carboxylic acid Step A. Preparation of methyl (M, R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate The title compound (99 mg, 65%) was prepared following General Procedure K using (M, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (100 mg, 0.19 mmol) and methyl 5-(benzyloxy)-7-iodo-1H-indole-2-carboxylate (150 mg, 0.37 mmol). LCMS: $R_T$=1.756 min, MS (ES) 817.8 (M+H).

Step B. Preparation of methyl (M, R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylate The title compound (70 mg, 70%) was prepared following General Procedure I using methyl (M, R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1H-indole-2-carboxylate (99 mg, 0.12 mmol) and MeI (40 mg, 0.28 mmol). LCMS: $R_T$=1.847, 1.874 min, MS (ES) 831.9 (M+H).

Step C. Preparation of methyl (M, R)-7-(7-chloro-10-(3-(4-chloro-3,5-dimethylphenoxy) propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate The title compound (62 mg, 99%) was prepared following the procedure described Example 390 Step D using methyl (M, R)-5-(benzyloxy)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylate (70 mg, 0.084 mmol) and Pd/C (10 wt. %, 15 mg, 0.014 mmol) by hydrogenating in MeOH (5 mL) with HCl (4.0 M in dioxanes, 0.5 mL) for 16 h at RT. LCMS: $R_T$=1.462, 1.517 min, MS (ES) 741.9 (M+H).

Step D. Example 711

The title compound (36 mg, 53%) was prepared following General Procedure H using methyl (M, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-hydroxy-1-methyl-1H-indole-2-carboxylate (64 mg, 0.086 mmol) and 1-bromo-2-methoxyethane (35 mg, 0.25 mmol) followed by saponification using General Procedure D. LCMS: $R_T$=1.393 min, MS (ES) 785.8 (M+H).

Example 712

(P, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-methoxyethoxy)-1-methyl-1H-indole-2-carboxylic acid The title compound (23 mg, 15% overall yield) was prepared following the same procedure as Example 711 starting from (P, R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (100 mg, 0.19 mmol). LCMS: $R_T$=1.353, 1.388 min, MS (ES) 785.8 (M+H).

Example 713

(M, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1-(pyridin-2-ylmethyl)-1H-indole-2-carboxylic acid The title compound (30 mg, 29%) was prepared following General Procedure I using ethyl (M, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (94 mg, 0.13 mmol) and 2-(chloromethyl)pyridine hydrochlo-

Example 714

(P, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2 (1H)-yl)-5-methyl-1-(pyridin-2-ylmethyl)-1H-indole-2-carboxylic acid The title compound (72 mg, 31%) was prepared following General Procedure I using ethyl (P, R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-methyl-1H-indole-2-carboxylate (72 mg, 0.097 mmol) and 2-(chloromethyl)pyridine hydrochloride (40 mg, 0.24 mmol) followed by saponification using General Procedure D. LCMS: $R_T$=1.227 min, MS (ES) 802.8 (M+H).

Example 715

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(2-morpholinoethyl)-1H-indole-2-carboxylic acid

Step A. Preparation of 2-(4-amino-3-bromophenyl)ethan-1-ol

To a solution of 2-(4-Aminophenyl)ethan-1-ol (2.0 g, 145 mmol) in DMF (10 mL) was added NBS (2.5 g, 145 mmol) at 0° C. The reaction mixture was warmed to RT and stirred overnight then quenched with brine and extracted with EtOAc. The organic layers were dried and concentrated, and the residue was purified flash chromatography (Combi-flash Rf, hexane-ethyl acetate=0-50% gradient for 15 min) to give the title compound (2.5 g, 80%). $^1$H-NMR (DMSO-$d_6$) δ 7.18 (d, 1H, J=1.8 Hz), 6.91 (dd, 1H, $J_1$=1.8 Hz, $J_2$=12.0 Hz), 6.72 (d, 1H, J=12 Hz), 5.06 (s, 2H), 4.55 (s, 1H), 3.51 (m, 2H), 2.25 (tr, 2H, J=12 Hz).

Step B. Preparation of 2-(3-bromo-4-hydrazinylphenyl)ethan-1-ol

To a solution of 2-(4-Amino-3-bromophenyl)ethan-1-ol (2.5 g, 12 mmol) in conc. HCl (25 mL) at −5° C. was added a solution of sodium nitrate (0.2 g, 17 mmol) in water (3 mL) dropwise. The reaction mixture was stirred at −5° C. for 1 h then a solution of SnCl$_2$ (6.8 g, 36 mmol) conc. HCl (5 mL) was added slowly. The reaction mixture was warmed to RT and stirred for 5 h. The mixture was neutralized with NaOH and filtered. The filtrate was extracted with EtOAc and concentrated. The residue was purified by flash chromatography (Combi-flash Rf, Hex/EtOAc=0-40% gradient) to afford the title compound (1.9 g, 66%). $^1$H-NMR (DMSO-$d_6$) δ 7.21 (d, 1H, J=1.8 Hz), 7.10-7.06 (m, 2H), 6.05 (s, 1H), 4.56 (tr, 2H, J=6 Hz), 4.10 (s, 2H), 3.55 (m, 2H), 2.59 (tr, 2H, J=12 Hz).

Step C. Preparation of methyl (E)-2-(2-(2-bromo-4-(2-hydroxyethyl)phenyl)hydrazono) propanoate To a solution of 2-(3-bromo-4-hydrazinylphenyl)ethan-1-ol (1.9 g, 8 mmol) in THF (5 mL) was added methyl puravate (0.8 mL, 10 mmol). The reaction mixture was heated at 50° C. for 30 min then concentrated. The residue was purified by flash chromatography (Combi-flash Rf, DCM/MeOH=0-10% gradient) to afford the title compound (2.3 g, 90%). $^1$H-NMR (CDCl$_3$) δ 8.02 (d, 1H, J=1.8 Hz), 7.53 (dd, 1H, $J_1$=1.8 Hz, $J_2$=12.0 Hz), 7.32 (s, 1H), 7.15 (d, 1H, J=12 Hz), 3.78 (s, 3H), 2.84 (tr, 2H, J=12 Hz), 2.15 (s, 3H), 1.32 (tr, 2H, J=12 Hz).

Step D. Preparation of methyl (E)-2-(2-(2-bromo-4-(2-hydroxyethyl)phenyl)-2-methylhydrazono)propanoate To a solution of methyl (E)-2-(2-(2-bromo-4-(2-hydroxyethyl)phenyl)hydrazono) propanoate (2.3 g, 7 mmol) in MeCN (20 mL) was added Cs$_2$CO$_3$ (2.8 g, 84 mmol) followed by MeI (480 μL, 77 mmol) at RT. The reaction mixture was stirred at RT for 15 h. The reaction was quenched with brine, extracted with EtOAc and concentrated. The residue was purified by flash chromatography (Combi-flash Rf, DCM/MeOH=0-5% gradient) to afford the title compound (2.4 g, 94%).

Step E. Preparation of methyl 5-(2-acetoxyethyl)-7-bromo-1-methyl-1H-indole-2-carboxylate The title compound (650 mg, 30%) was prepared following the procedure described Example 680 Step B using methyl (E)-2-(2-(2-bromo-4-(2-hydroxyethyl)phenyl)-2-methylhydrazono)propanoate (2 g, 62 mmol) by heating at 90° C. for 6 h. $^1$H-NMR (CDCl$_3$) δ 7.44 (s, 1H), 7.41 (s, 1H), 7.18 (s, 1H), 4.47 (s, 3H), 4.31 (tr, 2H, J=12 Hz), 3.90 (s, 3H), 3.29 (tr, 2H, J=12 Hz), 2.06 (s, 3H).

Step F. Preparation of methyl (R)-5-(2-acetoxyethyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylate The title compound (98 mg, 80%) was prepared following General coupling procedure A using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-(2H)-one and methyl 5-(2-acetoxyethyl)-7-bromo-1-methyl-1H-indole-2-carboxylate. MS (ES) 812.3 (M+H)

Step G. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-hydroxyethyl)-1-methyl-1H-indole-2-carboxylate To a solution of methyl (R)-5-(2-acetoxyethyl)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-2-carboxylate (130 mg, 0.16 mmol) in MeOH/THF (3/1, 4 mL) was added solid NaOMe (10 mg, 0.176 mmol) at −40° C. The reaction mixture was wormed to RT over 1 h and few drops of water, methanol and silica gel were added then concentrated. The residue was purified by flash chromatography (Combi-flash Rf, DCM/MeOH=0-10% gradient) to afford the title compound (100 mg, 81%). MS (ES) 770.3 (M+H).

Step H. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(2-oxoethyl)-1H-indole-2-carboxylate To a solution of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-5-(2-hydroxyethyl)-1-methyl-1H-indole-2-carboxylate (110 mg, 0.143 mmol) in DCM was added Dess-Martin periodinane (91 mg, 0.22 mmol). The reaction mixture was stirred at RT for 1 h. The reaction mixture was diluted with DCM, washed with sat NaHCO$_3$, dried and concentrated to yield the title compound, which was used in next step without further purification. MS (ES) 768.3 (M+H).

Step I. Example 715

To a solution of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(2-oxoethyl)-1H-indole-2-carboxylate (30 mg, 0.039 mmol) in DCE (2 mL) was added morpholine (6 µL, 0.059 mmol) and stirred at R$_T$ for 30 min then NaBH(OAc)$_3$ was added. The reaction mixture was stirred at RT for 1 h then concentrated. The residue was subjected to saponification using General procedure D to give the title compound (20 mg. TFA salt, 54%). MS (ES) 825.3 (M+H).

Example 716

(R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-5-(2-methoxyethoxy)-1-methyl-1H-indole-2-carboxylic acid Step A. Preparation of methyl (R)-5-(benzyloxy)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1H-indole-2-carboxylate The title compound (206 mg, 36%) following General Procedure C using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one (400 mg, 0.61 mmol) and methyl 5-(benzyloxy)-7-iodo-1H-indole-2-carboxylate (420 mg, 1.03 mmol) in toluene instead of DMF. LCMS: R$_T$=2.153 min, MS (ES) 933.9 (M+H).

Step B. Preparation of methyl (R)-5-(benzyloxy)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1-methyl-1H-indole-2-carboxylate The title compound (33 mg, 64%) was prepared following General Procedure I using methyl (R)-5-(benzyloxy)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1H-indole-2-carboxylate (51 mg, 0.054 mmol) and MeI (20 mg, 0.14 mmol). LCMS: R$_T$=2.286 min (Method B), MS (ES) 947.8 (M+H).

Step C. Preparation of methyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-5-hydroxy-1-methyl-1H-indole-2-carboxylate The title compound (26 mg, 87%) was prepared following the procedure described Example 390 Step D using methyl (R)-5-(benzyloxy)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1-methyl-1H-indole-2-carboxylate (33 mg, 0.035 mmol) and Pd/C (10 wt. %, 10 mg, 0.0093 mmol) by hydrogenating in MeOH (5 mL) for 16 h at RT. LCMS: R$_T$=1.869, 1.928 min (Method B), MS (ES) 857.8 (M+H).

Step D. Preparation of methyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-5-(2-methoxyethoxy)-1-methyl-1H-indole-2-carboxylate The title compound was prepared following General Procedure H using methyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-5-hydroxy-1-methyl-1H-indole-2-carboxylate (26 mg, 0.030 mmol) and 1-bromo-2-methoxyethane (15 mg, 0.11 mmol). The crude reaction mixture was carried forward to the next step without further purification. LCMS: R$_T$=2.059, 2.139 min (Method B), MS (ES) 915.8 (M+H).

Step E. Example 716

In a microwave vial equipped with a stir bar, methyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-5-(2-methoxyethoxy)-1-methyl-1H-indole-2-carboxylate (from Step 4) was dissolved in THF (2 mL). Tetrabutylammonium fluoride (1.0 M, 0.75 mL, 0.75 mmol) was added and the reaction was capped and heated to 110° C. for 45 min. The reaction was diluted into DCM/H$_2$O (1:1, 10 mL) and the layers were separated. The aqueous layer was extracted with DCM (2×5 mL), and the combined organic layers were dried with a phase separator and concentrated in vacuo. The crude reaction product was purified by reverse phase HPLC (Phenomenex Gemini C18, H$_2$O/CH$_3$CN gradient from 30-95% CH$_3$CN, 0.1% TFA to yield the title compound (9 mg, 38% yield over Steps 4 and 5). LCMS: R$_T$=1.227 min (Method), MS (ES) 771.9 (M+H).

Example 717

(R)-7-(7-chloro-10-(3-(4-chloro-3,5-dimethylphenoxy)propyl)-6-(4,6-dimethyl-2-(morpholinomethyl)pyrimidin-5-yl)-4-methyl-1-oxo-3,4-dihydropyrazino[1,2-a]indol-2(1H)-yl)-1-(2-methoxyethyl)-5-methyl-1H-indole-2-carboxylic acid Step A. Preparation of ethyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-5-methyl-1H-indole-2-carboxylate The title compound (742 mg, 76%) was prepared following General Procedure C using (R)-6-(2-((benzyloxy)methyl)-4,6-dimethylpyrimidin-5-yl)-7-chloro-10-(3-(4-chloro-3,5-dimethylphenoxy)propyl)-4-methyl-3,4-dihydropyrazino[1,2-a]indol-1(2H)-one (750 mg, 1.14 mmol) and ethyl 7-iodo-5-methyl-1H-indole-2-carboxylate (600 mg, 1.82 mmol) in toluene instead of DMF. LCMS: $R_T$=1.944 min, MS (ES) 857.8 (M+H).

Step B. Preparation of ethyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-1-(2-methoxyethyl)-5-methyl-1H-indole-2-carboxylate The title compound (152 mg, 68%) was prepared following General Procedure I using ethyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-5-methyl-1H-indole-2-carboxylate (210 mg, 0.25 mmol) and 1-bromo-2-methoxyethane (80 mg, 0.58 mmol). LCMS: $R_T$=2.023, 2.050 min, MS (ES) 915.9 (M+H).

Step C. Example 717

The title compound (15.6 mg, 51%) was prepared following General Procedure J using ethyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-1-(2-methoxyethyl)-5-methyl-1H-indole-2-carboxylate (29 mg, 0.035 mmol) and morpholine (25 mg, 0.29 mmol) followed by saponification using General Procedure D. LCMS: $R_T$=2.021 min, MS (ES) 866.8 (M+H).

Example 718

(R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-1-(2-methoxyethyl)-5-methyl-1H-indole-2-carboxylic acid Step A. Preparation of ethyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-5-methyl-1H-indole-2-carboxylate The title compound (146 mg, 28%) was prepared following General Procedure C using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one (400 mg, 0.61 mmol) and ethyl 7-iodo-5-methyl-1H-indole-2-carboxylate (400 mg, 1.21 mmol) in toluene instead of DMF and stirred for 5 days. LCMS: $R_T$=2.092 min, MS (ES) 855.9 (M+H).

Step B. Preparation of ethyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1-(2-methoxyethyl)-5-methyl-1H-indole-2-carboxylate The title compound was prepared following General Procedure I using ethyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-5-methyl-1H-indole-2-carboxylate (55 mg, 0.064 mmol) and 1-bromo-2-methoxyethane (20 mg, 0.14 mmol). LCMS: $R_T$=2.217, 2.260 min (Method B), MS (ES) 913.9 (M+H).

Step C. Example 718

To a solution of ethyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-1-(2-methoxyethyl)-5-methyl-1H-indole-2-carboxylate in THF (2 mL) was added TBAF (1.0 M, 0.75 mL, 0.75 mmol), and the reaction was stirred at 110° C. for 45 min. The reaction was diluted into DCM/$H_2O$ (1:1, 10 mL) and the layers were separated. The aqueous layer was extracted with DCM, and the combined organic layer was dried and concentrated in vacuo. The crude reaction product was purified by reverse phase HPLC (Phenomenex Gemini C18, $H_2O$/$CH_3CN$ gradient from 40-95% $CH_3CN$, 0.1% TFA to yield the title compound (23.8 mg, 49% 2 steps). LCMS: $R_T$=2.129 min, MS (ES) 755.8 (M+H).

Example 719

(R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-5-methyl-1-(pyridin-2-ylmethyl)-1H-indole-2-carboxylic acid Step A. Preparation of ethyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-5-methyl-1-(pyridin-2-ylmethyl)-1H-indole-2-carboxylate The title compound (22 mg, 57%) was prepared following General Procedure I using ethyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-5-methyl-1H-indole-2-carboxylate (35 mg, 0.041 mmol) and 2-(chloromethyl)pyridine HCl (30 mg, 0.12 mmol). LCMS: $R_T$=1.838, 1.891 min, MS (ES) 946.9 (M+H).

Step B. Example 719

The title compound (9 mg, 49%) was prepared following the procedure described Example 718 Step C using ethyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-5-methyl-1-(pyridin-2-ylmethyl)-1H-indole-2-carboxylate (22 mg, 0.023 mmol). LCMS: $R_T$=1.998 min, MS (ES) 788.8 (M+H).

Example 720

(R)-7-Chloro-10-(3-(4-chloro-3,5-dimethylphenoxy) propyl)-4-methyl-2-(1-(2-morpholinoethyl)-5-(1-(pyrimidin-2-yl)-1H-1,2,4-triazol-3-yl)-1H-indol-3-yl)-6-(1,3,5-trimethyl-1H-pyrazol-4-yl)-3,4-dihydropyrazino[1,2-a]indol-1(2H)-one Step A. Preparation of 1-(2-((tert-butyldimethylsilyl)oxy)ethyl)-5-(1-(pyrimidin-2-yl)-1H-1,2,4-triazol-3-yl)-1H-indole The title compound (180 mg, 69%) was prepared following the procedure described Example 388 Step A using 1-(2-(tert-butyldimethylsilyl)oxy)ethyl)-5-(4,4,5,5-tetramethyl-1,3,2-dioxaborolan-2-yl)-1H-indole (273 mg, 0.68 mmol) and 2-(3-bromo-1H-1,2,4-triazol-1-yl)pyrimidine (140 mg, 0.62 mmol). LCMS: $R_T$=2.019 min, MS (ES) 421.0 (M+H).

Step B. Preparation of 1-(2-((tert-butyldimethylsilyl)oxy)ethyl)-3-iodo-5-(1-(pyrimidin-2-yl)-1H-1,2,4-triazol-3-yl)-1H-indole The crude title compound (170 mg) was prepared following the procedure described Example 388 Step B using 1-(2-((tert-butyldimethylsilyl)oxy)ethyl)-5-(1-(pyrimidin-2-yl)-1H-1,2,4-triazol-3-yl)-1H-indole (180 mg, 0.43 mmol). LCMS: $R_T$=2.183 min, MS (ES) 546.9 (M+H).

Step C. Preparation of 2-(3-iodo-5-(1-(pyrimidin-2-yl)-1H-1,2,4-triazol-3-yl)-1H-indol-1-yl)ethan-1-ol The crude title compound (170 mg) was prepared from the procedure described Example 420 Step C using 1-(2-((tert-butyldimethylsilyl)oxy)ethyl)-3-iodo-5-(1-(pyrimidin-2-yl)-1H-1,2,4-triazol-3-yl)-1H-indole (170 mg, 0.31 mmol). LCMS: $R_T$=1.275 min, MS (ES) 432.9 (M+H).

Step D. Preparation of 4-(2-(3-iodo-5-(1-(pyrimidin-2-yl)-1H-1,2,4-triazol-3-yl)-1H-indol-1-yl)ethyl) morpholine The crude title compound (250 mg) was prepared following General Procedure J using 2-(3-iodo-5-(1-(pyrimidin-2-yl)-1H-1,2,4-triazol-3-yl)-1H-indol-1-yl)ethan-1-ol (170 mg, 0.39 mmol) and morpholine (338 μL, 3.92 mmol). LCMS: $R_T$=1.317 min, MS (ES) 501.9 (M+H).

Step E. Example 720

The title compound (22 mg, 43%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (30 mg, 0.06 mmol) and 4-(2-(3-iodo-5-(1-(pyrimidin-2-yl)-1H-1,2,4-triazol-3-yl)-1H-indol-1-yl)ethyl)morpholine (36 mg, 0.07 mmol). LCMS: $R_T$=1.994 min, MS (ES) 911.8 (M+H).

Example 721

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4,5-dimethoxy-1-methyl-1H-indole-2-carboxylic acid Step A. Preparation of methyl (Z)-2-azido-3-(5-bromo-2,3-dimethoxyphenyl)acrylate A solution of 5-bromo-2,3-dimethoxybenzaldehyde (1.0 g, 4.1 mmol) was stirred at 0° C. under Ar in 1:1 MeOH/THF (4 mL). A solution of methyl azidoacetate (1.6 mL, 16.3 mmol) in MeOH (2 mL) was added. The reaction mixture was cooled to −20° C. and a mixture of NaOMe (881 mg, 16.3 mmol) in MeOH (12 mL) was added dropwise. After stirring 15 min, the reaction was placed in an ice-bath and stirred for about 6 h then was left to sit overnight in a freezer. The reaction was quenched with aq. Sat. NH$_4$Cl and diluted with water and EtOAc. The aqueous layer was separated and extracted with EtOAc. The combined organics was washed with brine, dried over MgSO$_4$ and concentrated. The residue was purified by flash chromatography (Combi-flash Rf, hex/EtOAc=0-12.5% gradient) to give the title compound (903 mg, 65%). LCMS: $R_T$=2.04 min; $^1$H NMR (400 MHz, DMSO-d$_6$) δ 7.87 (d, J=2.2 Hz, 1H), 7.27 (d, J=2.2 Hz, 1H), 7.04 (s, 1H), 3.86 (s, 3H), 3.83 (s, 3H), 3.72 (s, 3H).

Step B. Preparation of methyl 7-bromo-4,5-dimethoxy-1H-indole-2-carboxylate

A solution of methyl (Z)-2-azido-3-(5-bromo-2,3-dimethoxyphenyl)acrylate (523 mg, 1.53 mmol) in toluene (31 mL) was irradiated under microwave at 200° C. for 15 minutes. The reaction mixture was concentrated, and the residue was purified by flash chromatography (Combi-flash Rf, Hex/EtOAc=0-10% gradient) to give the title compound (282 mg, 59%). LCMS: $R_T$=1.71 min, MS (ES) 314 (M+H); $^1$H NMR (400 MHz, DMSO-d$_6$) δ 7.35 (s, 1H), 7.22 (s, 1H), 3.91 (s, 3H), 3.86 (s, 3H), 3.81 (s, 3H).

Step C. Preparation of methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4,5-dimethoxy-1H-indole-2-carboxylate The title compound (8 mg, 11%) was prepared following General Procedure B using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one (50 mg, 0.09 mmol), methyl 7-bromo-4,5-dimethoxy-1H-indole-2-carboxylate (58 mg, 0.19 mmol), CuI (9 mg, 0.05 mmol), (trans)-1,2-N,N'-dimethylaminocyclohexane (7 mg, 0.05 mmol), and K$_3$PO$_4$ (59 mg, 0.28 mmol). LCMS: $R_T$=1.52 min, MS (ES) 772 (M+H).

Step D. Example 721

The title compound (4 mg, 50%) was prepared following General Procedure I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-4,5-dimethoxy-1H-indole-2-carboxylate (8 mg, 0.01 mmol) and MeI (6 mg, 0.04 mmol) followed by saponification using General Procedure D. LCMS: $R_T$=2.18 min, MS (ES) 772 (M+H).

Example 722

(R)-7-Chloro-10-(3-(4-chloro-3,5-dimethylphenoxy) propyl)-6-(4,6-dimethyl-2-((4-methyl-3-oxopiperazin-1-yl)methyl)pyrimidin-5-yl)-2-(5-(1-(2-methoxyethyl)-1H-1,2,4-triazol-3-yl)-1-(2-morpholinoethyl)-1H-indol-3-yl)-4-methyl-3,4-dihydropyrazino[1,2-a]indol-1(2H)-one Step A. Preparation of (R)-6-(2-((benzyloxy) methyl)-4,6-dimethylpyrimidin-5-yl)-7-chloro-10-(3-(4-chloro-3,5-dimethylphenoxy)propyl)-2-(5-(1-(2-methoxyethyl)-1H-1,2,4-triazol-3-yl)-1-(2-morpholinoethyl)-1H-indol-3-yl)-4-methyl-3,4-dihydropyrazino[1,2-a]indol-1(2H)-one The title compound (66 mg, 72%) was prepared following General Procedure B using (R)-6-(2-((benzyloxy)methyl)-4,6-dimethylpyrimidin-5-yl)-7-chloro-10-(3-(4-chloro-3,5-dimethylphenoxy)propyl)-4-methyl-3,4-dihydropyrazino[1,2-a]indol-1(2H)-one (60 mg, 0.09 mmol) and 4-(2-(3-iodo-5-(1-(2-methoxyethyl)-1H-1,2,4-triazol-3-yl)-1H-indol-1-yl)ethyl) morpholine (57 mg, 0.12 mmol). LCMS: $R_T$=2.181 min, MS (ES) 1009.8 (M+H).

Step B. Preparation of (R)-7-chloro-10-(3-(4-chloro-3,5-dimethylphenoxy)propyl)-6-(2-(hydroxymethyl)-4,6-dimethylpyrimidin-5-yl)-2-(5-(1-(2-methoxyethyl)-1H-1,2,4-triazol-3-yl)-1-(2-morpholinoethyl)-1H-indol-3-yl)-4-methyl-3,4-dihydropyrazino[1,2-a]indol-1(2H)-one The title crude compound (19 mg, 33% yield) was prepared following the procedure described Example 390 Step D using (R)-6-(2-((benzyloxy)methyl)-4,6-dimethylpyrimidin-5-yl)-7-chloro-10-(3-(4-chloro-3,5-dimethylphenoxy) propyl)-2-(5-(1-(2-methoxyethyl)-1H-1,2,4-triazol-3-yl)-1-(2-morpholinoethyl)-1H-indol-3-yl)-4-methyl-3,4-dihydropyrazino[1,2-a]indol-1(2H)-one (66 mg, 0.07 mmol). LCMS: $R_T$=1.892 min, MS (ES) 919.9 (M+H).

Step C. Example 722

The title compound (6.5 mg, 32%) was prepared following General Procedure J using (R)-7-chloro-10-(3-(4-chloro-3,5-dimethylphenoxy)propyl)-6-(2-(hydroxymethyl)-4,6-dimethylpyrimidin-5-yl)-2-(5-(1-(2-methoxyethyl)-1H-1,2,4-triazol-3-yl)-1-(2-morpholinoethyl)-1H-indol-3-yl)-4-methyl-3,4-dihydropyrazino[1,2-a]indol-1(2H)-one (19 mg, 0.02 mmol). LCMS: $R_T$=2.080 min, MS (ES) 1015.9 (M+H).

Example 723

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(2-(piperidin-1-yl)ethyl)-1H-indole-2-carboxylic acid The title compound (30 mg, TFA salt, 81%) was prepared following the procedure described Example 715 Step I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(2-oxoethyl)-1H-indole-2-carboxylate (30 mg, 0.039 mmol) and piperidine (6 μL, 0.059 mmol). MS (ES) 823.3 (M+H).

Example 724

(R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-4-methoxy-1-(pyridin-2-ylmethyl)-1H-indole-2-carboxylic acid Step A. Preparation of methyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-4-methoxy-1H-indole-2-carboxylate The title compound (176 mg, 34%) was prepared following General Procedure C using (R)-7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-3,4-dihydropyrazino[1,2-a]indol-1(2H)-one (400 mg, 0.61 mmol) and methyl 7-iodo-4-methoxy-1H-indole-2-carboxylate (400 mg, 1.21 mmol) in toluene instead of DMF. LCMS: $R_T$=1.917 min, MS (ES) 857.8 (M+H).

Step B. Preparation of methyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-4-methoxy-1-(pyridin-2-ylmethyl)-1H-indole-2-carboxylate The title compound was prepared following General Procedure I using methyl (R)-7-(7-chloro-10-(3-(4-chloro-3,5-dimethylphenoxy)propyl)-6-(3,5-dimethyl-1-((2-(trimethylsilyl) ethoxy)methyl)-1H-pyrazol-4-yl)-4-methyl-1-oxo-3,4-dihydropyrazino[1,2-a]indol-2(1H)-yl)-4-methoxy-1H-indole-2-carboxylate (45 mg, 0.53 mmol) and 2-(chloromethyl)pyridine HCl (25 mg, 0.15 mmol). LCMS: $R_T$=1.811, 1.860 min (Method B), MS (ES) 948.9 (M+H).

Step C. Example 724

The title compound (6 mg, 14% 2 steps) was prepared following the procedure described Example 718 Step C using methyl (R)-7-(7-chloro-10-(3-(4-chloro-3,5-dimethylphenoxy)propyl)-6-(3,5-dimethyl-1-((2-(trimethylsilyl) ethoxy)methyl)-1H-pyrazol-4-yl)-4-methyl-1-oxo-3,4-dihydropyrazino[1,2-a]indol-2(1H)-yl)-4-methoxy-1-(pyridin-2-ylmethyl)-1H-indole-2-carboxylate. LCMS: $R_T$=1.066 min (Method B), MS (ES) 804.9 (M+H).

Example 725

(R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(2-(4-methylpiperazin-1-yl)ethyl)-1H-indole-2-carboxylic acid The title compound (30 mg, TFA salt, 71%) was prepared following the procedure described Example 715 Step I using methyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-5-(2-oxoethyl)-1H-indole-2-carboxylate (30 mg, 0.039 mmol) and 1-methylpiperazine (7 µL, 0.059 mmol). $^1$H-NMR (DMSO-d$_6$) δ 7.79 (d, 1H, J=6 Hz), 7.60 and 7.55 (s, total 1H), 7.34 (d, 1H, J=6 Hz), 7.31 and 7.30 (two s, total 1H), 7.02 and 7.00 (two s, total 1H), 6.71 and 6.69 (two s, total 2H), 4.62 (m, 1H), 4.39-4.36 (m, 2H), 4.05-3.98 (multiple s and m, total 7H), 3.76-3.66 (several s and m, total 8H), 3.37-3.24 (m, 6H), 3.14-2.98 (m, 2H), 2.85-2.82 (m, 2H), 2.26 (s, 6H), 2.14 and 2.13 (two s, total 2H), 2.06-2.04 (m, total 3H), 2.00 and 1.99 (two s, total 1H), 1.92 and 1.90 (two s, total 2H), 1.21 (d, 2H, J=8 Hz), 1.07 (d, 1H, J=8 Hz); MS (ES) 838.2 (M+H).

Example 726

(R)-7-(7-Chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,6-dimethyl-1H-indole-2-carboxylic acid Step A. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-6-methyl-1H-indole-2-carboxylate The title compound (25 mg, 10%) was prepared following General Procedure B using (R)-6-(2-((benzyloxy)methyl)-4,6-dimethylpyrimidin-5-yl)-7-chloro-10-(3-(4-chloro-3,5-dimethylphenoxy)propyl)-4-methyl-3,4-dihydropyrazino[1,2-a]indol-1(2H)-one (200 mg, 0.36 mmol) and ethyl 7-bromo-6-methyl-1H-indole-2-carboxylate (200 mg, 0.72 mmol). LCMS: $R_T$=2.206 min, MS (ES) 740.0 (M+H).

Step B. Preparation of ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,6-dimethyl-1H-indole-2-carboxylate The title compound (17 mg, 68%) was prepared following General Procedure I using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-6-methyl-1H-indole-2-carboxylate (25 mg, 0.03 mmol) and methyl iodide (2.3 µL, 0.04 mmol). LCMS: $R_T$=1.738 min, MS (ES) 753.9 (M+H).

Step C. Example 726

The title compound (6 mg, 37%) was prepared following General Procedure D using ethyl (R)-7-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1,6-dimethyl-1H-indole-2-carboxylate (17 mg, 0.02 mmol). LCMS: $R_T$=1.447 min, MS (ES) 725.8 (M+H).

Example 727

(R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-4-methoxy-1-methyl-1H-indole-2-carboxylic acid Step A. Preparation of methyl (R)-7-(7-chloro-10-(3-(4-chloro-3,5-dimethylphenoxy) propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-4-methoxy-1H-indole-2-carboxylate The title compound was prepared following General Procedure I using methyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-4-methoxy-1H-indole-2-carboxylate (48 mg, 0.056 mmol) and MeI (20 mg, 0.14 mmol). LCMS: $R_T$=2.040 min, MS (ES) 871.8 (M+H).

Step B. Example 727

The title compound (23.1 mg, 57% 2 steps) was prepared following the procedure described Example 718 Step C using methyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-4-methoxy-1H-indole-2-carboxylate. LCMS: $R_T$=2.071 min, MS (ES) 727.9 (M+H).

Example 728

(R)-7-(7-chloro-10-(3-(4-chloro-3,5-dimethylphenoxy)propyl)-6-(3,5-dimethyl-1H-pyrazol-4-yl)-4-methyl-1-oxo-3,4-dihydropyrazino[1,2-a]indol-2(1H)-yl)-4-methoxy-1-(2-methoxyethyl)-1H-indole-2-carboxylic acid Step A. Preparation of methyl (R)-7-(7-chloro-10-(3-(4-chloro-3,5-dimethylphenoxy) propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-4-methoxy-1-(2-methoxyethyl)-1H-indole-2-carboxylate The title compound was prepared following General Procedure I using methyl (R)-7-(7-chloro-10-(3-(4-chloro-3,5-dimethylphenoxy)propyl)-6-(3,5-dimethyl-1-((2-(trimethylsilyl) ethoxy)methyl)-1H-pyrazol-4-yl)-4-methyl-1-oxo-3,4-dihydropyrazino[1,2-a]indol-2(1H)-yl)-4-methoxy-1H-indole-2-carboxylate (48 mg, 0.056 mmol) and 1-bromo-2-methoxyethane (20 mg, 0.14 mmol). LCMS: $R_T$=2.086, 2.124 min (Method B), MS (ES) 915.8 (M+H).

Step B. Example 728

The title compound (12.1 mg, 28% 2 steps) was prepared following the procedure described Example 718 Step C using methyl (R)-7-(7-chloro-10-(3-(4-chloro-3,5-dimethylphenoxy)propyl)-6-(3,5-dimethyl-1-((2-(trimethylsilyl)ethoxy)methyl)-1H-pyrazol-4-yl)-4-methyl-1-oxo-3,4-dihydropyrazino[1,2-a]indol-2(1H)-yl)-4-methoxy-1-(2-methoxyethyl)-1H-indole-2-carboxylate. LCMS: $R_T$=2.081 min, MS (ES) 771.9 (M+H).

Example 729

(R)-7-(7-chloro-10-(3-(4-chloro-3,5-dimethylphenoxy)propyl)-6-(4,6-dimethyl-2-((4-methyl-3-oxopiperazin-1-yl)methyl)pyrimidin-5-yl)-4-methyl-1-oxo-3,4-dihydropyrazino[1,2-a]indol-2(1H)-yl)-1-(2-methoxyethyl)-5-methyl-1H-indole-2-carboxylic acid The title compound (10.2 mg, 34%) was prepared following General Procedure J using ethyl (R)-7-(6-(2-((benzyloxy)methyl)-4,6-dimethylpyrimidin-5-yl)-7-chloro-10-(3-(4-chloro-3,5-dimethylphenoxy)propyl)-4-methyl-1-oxo-3,4-dihydropyrazino[1,2-a]indol-2(1H)-yl)-1-(2-methoxyethyl)-5-methyl-1H-indole-2-carboxylate (29 mg, 0.035 mmol) and 1-methylpiperazin-2-one (20 mg, 0.18 mmol) followed by saponification using General Procedure D. LCMS: $R_T$=1.989, 2.021 min, MS (ES) 893.8 (M+H).

Example 730

3-[[6-chloro-3-[3-(4-chloro-3,5-dimethyl-phenoxy)propyl]-1-(2-morpholinoethyl)-7-(1,3,5-trimethylpyrazol-4-yl)indole-2-carbonyl]-methyl-amino] benzoic acid Step A. Preparation of 6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxylic acid To a solution of ethyl 6-chloro-3-(3-(4-chloro-3,5-dimethylphenoxy)propyl)-7-(1,3,5-trimethyl-1H-pyrazol-4-yl)-1H-indole-2-carboxylate (180 mg, 0.34 mmol) in DMF (10 mL) was added NaH (18 mg, 0.75 mmol) and stirred at RT for 30 min. 4-(2-Bromoethyl)morpholine (100 mg, 0.515 mmol) was added and the reaction mixture was stirred for 5 h at RT. The reaction was quenched with $H_2O$, diluted into DCM/brine (40 mL, 1:1), the organic layer was separated, and extracted with DCM. The combined organic extract was dried over $MgSO_4$, filtered, and concentrated in vacuo. The crude reaction mixture was purified by flash chromatography (Combi-flash Rf, DCM/MeOH=0-20% gradient) to afford the title compound (198 mg, 94% yield).

Step B. Example 730

To a solution of 6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxylic acid (20 mg, 0.033 mmol) in DCM (2 mL) and DMF (20 μL) was added oxalyl chloride (5 mg, 0.039 mmol) at RT and stirred for 30 min. $Et_3N$ (25 mg, 0.24 mmol) was added to the reaction mixture followed by methyl 3-(methylamino)benzoate (30 mg, 0.18 mmol), and the reaction was stirred at RT until complete by LCMS. The reaction was diluted into DCM/$H_2O$ (10 mL, 1:1) and extracted with DCM (2×5 mL). The combined organic extract was concentrated in vacuo and purified by reverse phase preparative HPLC (Phenomenex Gemini C18, $H_2O$/$CH_3CN$ gradient 35-95% MeCN 0.1% TFA). The resulting ester intermediate was saponified using General Procedure D to afford the title compound (4 mg, 16% yield). LCMS: $R_T$=1.661 min. MS (ES) 745.8 (M+H).

Example 731

4-[[6-Chloro-3-[3-(4-chloro-3,5-dimethyl-phenoxy)propyl]-1-(2-morpholinoethyl)-7-(1,3,5-trimethylpyrazol-4-yl)indole-2-carbonyl]-methyl-amino] benzoic acid The title compound (7 mg, 28% yield) was prepared following the same procedure as described in Example 730 employing 3-[[6-chloro-3-[3-(4-chloro-3,5-dimethyl-phenoxy)propyl]-1-(2-morpholinoethyl)-7-(1,3,5-trimethylpyrazol-4-yl)indole-2-carbonyl]-methyl-amino]benzoic acid (20 mg, 0.033 mmol) and 4-(methylamino)benzoate (30 mg, 0.18 mmol). LCMS: $R_T$=1.626 min, MS (ES) 745.8 (M+H).

Example 732

3-(4-(6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl)benzoic acid Step A. Preparation of methyl 3-(4-(6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl)benzoate The title compound was prepared following General procedure E using 6-chloro-3-(3-(4-chloro-3,5-dimethylphenoxy)propyl)-7-(1,3,5-trimethyl-1H-pyrazol-4-yl)-1H-indole-2-carboxylic acid (0.043 mmol) and methyl 3-(piperazin-1-yl)benzoate (0.086 mmol), HBTU (0.158 mmol). MS (ES) 702.3 (M+H).

Step B. Example 732

Methyl 3-(4-(6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl)benzoate was dissolved in THF and 2 N aq. LiOH solution (2:1), and the mixture was stirred for 24 h at ambient temperature. The reaction was acidified with 4M HCl to pH 7, extracted with EtOAc, dried over $Na_2SO_4$ and concentrated in vacuo. The residue was purified by the reverse phase HPLC (Phenomenex Gemini C18, $H_2O$/$CH_3CN$ gradient from 30-75% $CH_3CN$, 0.1% TFA) to give the title compound. MS (ES) 688.2 (M+H).

Example 733

4-[[6-chloro-3-[3-(4-chloro-3,5-dimethyl-phenoxy)propyl]-1-(2-morpholinoethyl)-7-(1,3,5-trimethylpyrazol-4-yl)indole-2-carbonyl]-methyl-amino]-1-methyl-indole-6-carboxylic acid Step A. preparation of 6-chloro-3-(3-(4-chloro-3,5-dimethylphenoxy)propyl)-N-methyl-1-(2-morpholinoethyl)-7-(1,3,5-trimethyl-1H-pyrazol-4-yl)-1H-indole-2-carboxamide The title compound was prepared following the same procedure described in Example 730 Step B using 6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxylic acid (20 mg, 0.033 mmol) and methylamine hydrochloride (25 mg, 0.38 mmol).

Step 2. Example 733

The title compound (1.4 mg, 5% yield) was prepared following General coupling procedure A using the product obtained in Step 1, methyl 4-bromo-1-methyl-1H-indole-6-carboxylate (15 mg, 0.056 mmol), Pd$_2$(dba)$_3$ (3 mg, 0.0032 mmol), Xantphos (6 mg, 0.010 mmol), and cesium carbonate (30 mg, 0.092 mmol), followed by subjection to General Procedure D using LiOH (5 mg, 0.21 mmol). LCMS: R$_T$=1.695 min, MS (ES) 798.7 (M+H).

Example 734

5-(4-(6-chloro-3-(3-(4-chloro-3,5-dimethylphenoxy) propyl)-1-(pyridin-3-ylmethyl)-7-(1,3,5-trimethyl-1H-pyrazol-4-yl)-1H-indole-2-carbonyl)piperazin-1-yl)nicotinic acid To a solution of 6-chloro-3-(3-(4-chloro-3,5-dimethylphenoxy)propyl)-7-(1,3,5-trimethyl-1H-pyrazol-4-yl)-1H-indole-2-carboxylic acid (25 mg, 0.05 mmol) in DMF (1 mL) were added methyl 5-(piperazin-1-yl)nicotinate (11 mg, 0.05 mmol), HBTU (70 mg, 0.185 mmol), triethylamine (56 μL, 0.4 mmol), and the mixture was stirred at RT for 10 h. The reaction was quenched with H$_2$O (5 mL) and extracted with DCM (3×5 mL). The combined organic layer was dried and concentrated in vacuo. The residue was dissolved in DMF (1 mL), and NaH (6 mg, 0.15 mmol) was added at RT. The reaction mixture was stirred for 30 min at RT then a solution of 3-(bromomethyl)pyridine hydrobromide (15 mg, 0.06 mmol) in DMF (1 mL) was added dropwise. The resulting reaction mixture was stirred for additional 2 h at RT. The reaction was quenched with water (4 mL) and extracted with DCM (3×5 mL). The organic layer was dried and concentrated. The residue was dissolved in THF (2 mL) and 2M aq. LiOH solution (1 mL) and the mixture was stirred at RT for 10 h. The reaction mixture was concentrated, acidified to pH 7 with 4M HCl, and extracted in EtOAc. The organic layer was dried, concentrated and purified by reverse phase HPLC (Phenomenex Gemini C18, H$_2$O/CH$_3$CN gradient from 30-70% CH$_3$CN, 0.1% TFA) to give the title compound (33 mg, 77%) as a white solid. MS (ES) 780.2 (M+H).

Example 735

3-(4-(6-chloro-3-(3-(4-chloro-3,5-dimethylphenoxy) propyl)-1-(pyridin-3-ylmethyl)-7-(1,3,5-trimethyl-1H-pyrazol-4-yl)-1H-indole-2-carbonyl)piperazin-1-yl)benzoic acid To a solution of methyl 3-(4-(6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl)benzoate (0.05 mmol) in DMF (1 mL) was added NaH (6 mg, 0.15 mmol) and stirred for 30 min at ambient temperature. A solution of 3-(bromomethyl)pyridine hydrobromide (15 mg, 0.06 mmol) in DMF (1 mL) was added dropwise to the reaction mixture at room temperature and stirred for additional 2 h. The title compound was obtained by following the saponification procedure described Example 734 (80% yield) as a white solid; MS (ES) 779.2 (M+H).

Example 736

5-(4-(6-Chloro-3-(3-(4-chloro-3,5-dimethylphenoxy) propyl)-7-(1,3,5-trimethyl-1H-pyrazol-4-yl)-1H-indole-2-carbonyl)piperazin-1-yl)picolinic acid The title compound was prepared following the procedure described Example 732 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid methyl 5-(piperazin-1-yl)picolinate. MS (ES) 689.1 (M+H).

Example 737

5-(4-(6-Chloro-3-(4-(4-chloro-3,5-dimethylphenyl) butyl)-1-(pyridin-3-ylmethyl)-7-(1,3,5-trimethyl-1H-pyrazol-4-yl)-1H-indole-2-carbonyl)piperazin-1-yl) picolinic acid The title compound was prepared following the procedure described Example 734 by substituting methyl 5-(piperazin-1-yl)nicotinate with methyl 5-(piperazin-1-yl)picolinate. MS (ES) 778.3 (M+H).

Example 738

4-(4-(6-Chloro-3-(4-(4-chloro-3,5-dimethylphenyl) butyl)-7-(1,3,5-trimethyl-1H-pyrazol-4-yl)-1H-indole-2-carbonyl)piperazin-1-yl)picolinic acid The title compound was prepared following the procedure described Example 732 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid and methyl 4-(piperazin-1-yl)nicotinate. MS (ES) 689.1 (M+H).

Example 739

2-(4-(6-Chloro-3-(4-(4-chloro-3,5-dimethylphenyl) butyl)-1-(pyridin-3-ylmethyl)-7-(1,3,5-trimethyl-1H-pyrazol-4-yl)-1H-indole-2-carbonyl)piperazin-1-yl) benzoic acid The title compound was prepared following the procedure described Example 734 by substituting methyl 5-(piperazin-1-yl)nicotinate with methyl 2-(piperazin-1-yl)benzoate. MS (ES) 777.3 (M+H).

Example 740

5-(4-(6-Chloro-3-(4-(4-chloro-3,5-dimethylphenyl) butyl)-7-(1,3,5-trimethyl-1H-pyrazol-4-yl)-1H-indole-2-carbonyl)piperazin-1-yl)nicotinic acid The title compound was prepared following the procedure described Example 732 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid and methyl 5-(piperazin-1-yl)nicotinate. MS (ES) 689.1 (M+H).

Example 741

2-(4-(6-Chloro-3-(4-(4-chloro-3,5-dimethylphenyl) butyl)-1-(pyridin-3-ylmethyl)-7-(1,3,5-trimethyl-1H-pyrazol-4-yl)-1H-indole-2-carbonyl)piperazin-1-yl) isonicotinic acid The title compound was prepared following the procedure described Example 734 by substituting methyl 5-(piperazin-1-yl)nicotinate with methyl 2-(piperazin-1-yl)isonicotinate. MS (ES) 778.3 (M+H).

Example 742

4-(4-(6-Chloro-3-(4-(4-chloro-3,5-dimethylphenyl) butyl)-1-(pyridin-3-ylmethyl)-7-(1,3,5-trimethyl-1H-pyrazol-4-yl)-1H-indole-2-carbonyl)piperazin-1-yl) picolinic acid The title compound was prepared following the procedure described Example 734 by substituting methyl 5-(piperazin-1-yl)nicotinate with methyl 4-(piperazin-1-yl)picolinate. MS (ES) 778.3 (M+H).

Example 743

2-(4-(6-Chloro-3-(4-(4-chloro-3,5-dimethylphenyl) butyl)-7-(1,3,5-trimethyl-1H-pyrazol-4-yl)-1H-indole-2-carbonyl)piperazin-1-yl)isonicotinic acid The title compound was prepared following the procedure described Example 732 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid and methyl 2-(piperazin-1-yl)isonicotinate. MS (ES) 689.1 (M+H).

Example 744

2-(4-(6-Chloro-3-(4-(4-chloro-3,5-dimethylphenyl) butyl)-7-(1,3,5-trimethyl-1H-pyrazol-4-yl)-1H-indole-2-carbonyl)piperazin-1-yl)benzoic acid The title compound was prepared following the procedure described Example 732 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid and methyl 2-(piperazin-1-yl)benzoate. MS (ES) 686.1 (M+H).

Example 745

1-[6-Chloro-3-[3-(4-chloro-3,5-dimethyl-phenoxy) propyl]-7-(4,6-dimethylpyrimidin-5-yl)-1H-indole-2-carbonyl]pyrrolidine-3-carboxylic acid To a solution of ethyl 6-chloro-3-(3-(4-chloro-3,5-dimethylphenoxy)propyl)-7-(4,6-dimethylpyrimidin-5-yl)-1H-indole-2-carboxylate (13 mg, 0.025 mmol in THF, MeOH, and H$_2$O (3 mL, 0.5 mL, 0.5 mL), and LiOH (5 mg, 0.21 mmol) was added. The reaction was heated to 50° C. for 3 h. The reaction was acidified with 2M HCl, diluted with brine (5 mL) and extracted with DCM (3×10 mL). The combined organic extracts were dried by passage through a phase separator and concentrated in vacuo. The crude residue was subjected to amide coupling following General Procedure E using methyl pyrrolidine-3-carboxylate (10 mg, 0.078 mmol), HATU (15 mg, 0.39 mmol), and DIPEA (20 mg, 0.15 mmol) followed by saponification using General Procedure D to afford the title compound (2 mg, 14% yield). LCMS: R$_T$=1.792 min, MS (ES) 595.2 (M+H).

Example 746

4-(6-Chloro-3-(3-(4-chloro-3,5-dimethylphenoxy) propyl)-7-(4,6-dimethylpyrimidin-5-yl)-1H-indole-2-carboxamido)cyclohexane-1-carboxylic acid (Separated Stereoisomer A)

The title compound (1.3 mg, 9% yield) was prepared following the reaction sequence and procedures described in Example 745 substituting methyl pyrrolidine-3-carboxylate with methyl 4-aminocyclohexane-1-carboxylate (10 mg, 0.070 mmol). LCMS: R$_T$=1.910 min, MS (ES) 623.2 (M+H). Described reaction sequence resulted in mixture of cis/trans isomers. They were separated but stereochemistry was not determined.

Example 747

4-(6-Chloro-3-(3-(4-chloro-3,5-dimethylphenoxy) propyl)-7-(4,6-dimethylpyrimidin-5-yl)-1H-indole-2-carboxamido)cyclohexane-1-carboxylic acid (Separated Stereoisomer B)

The title compound (1.2 mg, 8% yield) was obtained along with Example 746. LCMS: R$_T$=1.927 min, MS (ES) 623.2 (M+H). Stereochemistry was not determined.

Example 748

3-[[[6-Chloro-3-[3-(4-chloro-3,5-dimethyl-phenoxy) propyl]-7-(4,6-dimethylpyrimidin-5-yl)-1H-indole-2-carbonyl]amino]methyl]benzoic acid The title compound (2.8 mg, 18% yield) was prepared following the reaction sequence and procedures described in Example 745 substituting methyl pyrrolidine-3-carboxylate with methyl 3-(aminomethyl)benzoate (10 mg, 0.061 mmol). LCMS: R$_T$=1.925 min, MS (ES) 631.2 (M+H).

Example 749 Assays for Bcl-2 Family Proteins Activity

The in vitro modulation of Bcl-2 family proteins was determined as follows.

Bak Peptide Binding Assay
General

Provided compounds of the present invention can be demonstrated to compete for binding with fluorescently labeled peptides derived from relevant BH3 domains. In some embodiments, a provided compound exhibit selectivity for Mcl-1 over Bcl-xL and Bcl-2.

Fluorescence Polarization Anisotropy Competition Assay

Anisotropy measurements were carried out in 384-well, black, flat-bottom plates (Greiner Bio-one, Monroe, N.C., USA). The assay was run using either a fluorescein isothiocyanate-labeled BH3 peptide derived from Bak (FITC-AHx-GQVGRQLAIIGDDINR-NH$_2$) or a fluorescein isothiocyanate-labeled BH3 peptide derived from Bim (FITC-AHx-EARIAQELRRIGDEFNETYTR-NH$_2$) that were purchased from GenScript (Piscataway, N.J.) at >95% purity and used without further purification. 10 nM FITC-Bak peptide and 15 nM recombinant Mcl-1 (residues 172-327) were added to assay buffer (3 mM dithiothreitol, 50 mM NaCl, 20 mM Tris, pH 7.5). The Bim based assay was run with 1 nM FITC-Bim peptide and 1.5 nM recombinant Mcl-1 (residues 172-327) added to assay buffer (20 mM TRIS pH 7.5, 50 mM NaCl, 3 mM DTT, 0.01% CHAPS). For selectivity assays, 40 nM Bcl-2 (residues 1-207$^{A96T, G110R}$, Δ35-91, replaced with Bcl-xL$_{35-50}$) or 4 nM Bcl-xL (residues 1-209, loop 45-86 deleted) were incubated with 10 nM FITC-Bak in assay buffer.

Compounds are diluted in DMSO in a 10-point, 3-fold serial dilution scheme. For the FITC-BAK assay 2.5 uL compound is added to 47.5 μL of assay buffer containing FITC-Bak and protein, for a final DMSO concentration of 5% and a top concentration of 20 μM. A FITC-Bak peptide alone (100% inhibition) and peptide plus protein (0% inhibition) control is included on each assay plate. For the FITC-Bim assay, compound is added to 40 uL of assay buffer containing protein, 15 minutes prior to addition of 10 μL of the FITC-Bim peptide, for a final DMSO concentration of 0.165% and a top concentration of 200 nM. A FITC-Bim peptide alone (100% inhibition) and peptide plus protein (0% inhibition) control is included on each assay plate. The plate was mixed and incubated for 90 minutes at room temperature. Anisotropy is measured at excitation wavelength 480 nm and emission wavelength 535 nm using an EnVision Multi-label plate reader (PerkinElmer, Wellesley, Mass., USA) or a BioTek Cytation 3 (BioTek, Winooski, Vt., USA). Fluorescence anisotropy is plotted against compound concentration to generate an IC$_{50}$ (inhibitor concentration at which 50% of bound peptide is displaced) by fitting the data to a 4-parameter logistic model using XLFit software (Guildford, Surrey, UK). IC$_{50}$ is converted to a binding dissociation constant (K$_i$ value) according to the formula of Wang Z. FEBS Lett (1996) 3, 245.

$$K_i=[I]_{50}/([L]_{50}/K_d+[P]_0/K_d+1)$$

where [I]$_{50}$ is the concentration of the free inhibitor at 50% inhibition, [L]$_{50}$ is the concentration of the free labeled ligand at 50% inhibition, [P]$_0$ is the concentration of the free protein at 0% inhibition, K$_d$ represents the dissociation constant of the FITC peptide probe.

TR-FRET Binding Assay

Measurements were carried out in OptiPlate-384 White Opaque 384-well plates (Perkin Elmer. Shelton, Conn.). The assay was run using a fluorescein isothiocyanate-labeled BH3 peptide derived from Bak (FITC-AHx-GQVGRQLAIIGDDINR-NH$_2$) that was purchased from GenScript (Piscataway, N.J.) at >95% purity and used without further purification, 300 nM FITC-Bak peptide, 1 nM recombinant Maltose Binding Protein (MBP) tagged Mcl-1 (residues 172-327) and 1 nM terbium conjugated-MBP antibody were added to assay buffer (4.5 mM Monobasic potassium phosphate, 15.5 mM Dibasic potassium phosphate, 1 mM Sodium EDTA, 50 mM NaCl, 1 mM DTT, 0.05% Pluronic F-68, pH 7.5). Compounds are diluted in DMSO in a 16-point, semilog serial dilution scheme. For the BAK FITC TR-FRET assay 50 nL compound is added to 20 μL of assay buffer containing Bak-FITC. MBP tagged Mcl-1 protein and antibody, for a final DMSO concentration of 0.25% and a top concentration of 10 μM. A FITC-Bak peptide alone (100% inhibition) and peptide plus protein (0% inhibition) control is included on each assay plate. The plate was mixed and incubated for 3 hours at room temperature. TR-FRET signal (Delta F) is measured on a Biotek Cytation 3 multimode plate reader equipped with a filter cube containing an Ex 340/30 Em 620/10 nm filter and an Ex 340/30 Em 520 filter. TR-FRET signal is plotted and IC$_{50}$ and K$_i$ values are calculated in the same manner as the fluorescence polarization anisotropy based competition assays. The results for representative compounds are shown in Table 2 and 3.

TABLE 2

K$_i$ for Examplified Compounds for Inhibition of Mcl-1 by FPA assay

| Example | K$_i$ (nM) | Example | K$_i$ (nM) | Example | K$_i$ (nM) |
|---|---|---|---|---|---|
| 2 | <1 | 160 | 1.1 | 319 | 3.2 |
| 3 | 1.1 | 161 | 2.8 | 320 | 2.7 |
| 4 | 3.3 | 162 | <1 | 321 | <1 |
| 5 | 2.7 | 163 | <1 | 322 | 1.7 |
| 6 | 54 | 164 | 1.7 | 323 | <1 |
| 7 | 2.2 | 165 | 1 | 324 | <1 |
| 8 | 27 | 166 | <1 | 325 | <1 |
| 9 | 20 | 167 | <1 | 326 | <1 |
| 10 | 57 | 168 | 1.1 | 327 | 1.6 |
| 11 | 4 | 169 | <1 | 328 | <1 |
| 12 | 1.2 | 170 | 2.7 | 329 | <1 |
| 13 | <1 | 171 | <1 | 330 | 1.3 |
| 14 | <1 | 172 | <1 | 331 | 1.1 |
| 15 | 2.2 | 173 | 2.7 | 332 | 2.8 |
| 16 | <1 | 174 | 4.2 | 333 | 1.3 |
| 17 | 10 | 175 | <1 | 334 | <1 |
| 18 | 5.8 | 176 | <1 | 335 | 4.5 |
| 19 | 1.9 | 177 | <1 | 336 | <1 |
| 20 | 2.5 | 178 | <1 | 337 | 2.6 |
| 21 | 2.3 | 179 | <1 | 338 | <1 |
| 22 | 151 | 180 | 2.1 | 339 | <1 |
| 23 | <1 | 181 | 1.4 | 340 | 4.4 |
| 24 | 25 | 182 | <1 | 341 | 4.2 |
| 25 | 1.1 | 183 | <1 | 342 | <1 |
| 26 | 1.3 | 184 | <1 | 343 | 3.7 |
| 27 | 39 | 185 | 4.6 | 344 | <1 |
| 28 | 1.8 | 186 | <1 | 345 | 3.5 |
| 29 | 6.2 | 187 | <1 | 346 | 5.1 |
| 30 | 1.2 | 188 | 6.4 | 347 | 3.6 |
| 31 | <1 | 189 | 1.2 | 348 | 1.8 |
| 32 | <1 | 190 | <1 | 349 | 2.8 |
| 33 | <1 | 191 | <1 | 350 | <1 |
| 34 | 12.0 | 192 | <1 | 351 | <1 |
| 35 | 1.5 | 193 | 3.9 | 352 | 2.8 |
| 36 | <1 | 194 | <1 | 353 | 2.1 |
| 37 | 3 | 195 | 3.6 | 354 | 4.3 |
| 38 | 62 | 196 | <1 | 355 | 1.0 |
| 39 | 1.1 | 197 | <1 | 356 | 1.9 |
| 40 | 3.9 | 198 | <1 | 357 | 7.9 |
| 41 | 1.8 | 199 | 12 | 358 | 4.2 |
| 42 | 8 | 200 | 6.6 | 359 | 1.4 |
| 43 | 1.1 | 201 | <1 | 360 | 2.5 |
| 44 | <1 | 202 | 12 | 361 | 2.0 |
| 45 | 1.7 | 203 | 6 | 362 | 1.7 |
| 46 | 26 | 204 | 1.1 | 363 | 1.6 |
| 47 | 19 | 205 | 2.4 | 364 | 1.0 |
| 48 | <1 | 206 | <1 | 365 | 1.7 |
| 49 | <1 | 207 | <1 | 366 | 2.9 |
| 50 | <1 | 208 | <1 | 367 | 1.2 |
| 51 | <1 | 209 | 1.2 | 368 | 1.4 |
| 52 | <1 | 210 | 1.3 | 369 | 3.2 |
| 53 | <1 | 211 | 3.1 | 370 | 2.8 |
| 54 | <1 | 212 | 5.9 | 371 | <1 |
| 55 | 2.4 | 213 | <1 | 372 | 1.2 |
| 56 | <1 | 214 | <1 | 373 | 1.6 |
| 57 | <1 | 215 | <1 | 374 | 3.7 |
| 58 | <1 | 218 | <1 | 375 | 10 |
| 59 | <1 | 219 | 2.2 | 376 | 6.5 |
| 60 | <1 | 220 | <1 | 377 | 4.9 |
| 61 | 5.7 | 221 | 2.5 | 378 | 1.9 |
| 62 | <1 | 222 | 6.9 | 379 | 3.6 |
| 63 | <1 | 223 | 1.1 | 380 | 7.9 |
| 64 | 4.8 | 224 | <1 | 381 | 2.6 |
| 65 | 3.1 | 225 | <1 | 382 | 1.2 |
| 66 | 4.3 | 226 | 4.9 | 383 | 2.6 |
| 67 | <1 | 227 | <1 | 384 | 6.8 |
| 68 | <1 | 228 | 1.6 | 385 | 4.1 |
| 69 | <1 | 229 | 3.7 | 386 | 3.2 |
| 70 | <1 | 230 | <1 | 387 | 2.1 |
| 71 | <1 | 231 | 1.2 | 388 | 1.5 |

TABLE 2-continued

K$_i$ for Examplified Compounds for Inhibition of Mcl-1 by FPA assay

| Example | K$_i$ (nM) | Example | K$_i$ (nM) | Example | K$_i$ (nM) | Example | K$_i$ (nM) | Example | K$_i$ (nM) | Example | K$_i$ (nM) |
|---|---|---|---|---|---|---|---|---|---|---|---|
| 72 | <1 | 232 | <1 | 389 | <1 | 147 | 1.8 | 307 | 1.3 | 464 | 3.5 |
| 73 | <1 | 233 | <1 | 390 | 2.3 | 148 | <1 | 308 | <1 | 465 | 1.5 |
| 74 | <1 | 234 | <1 | 391 | 2.1 | 150 | 13 | 309 | <1 | 466 | 1.8 |
| 75 | <1 | 235 | <1 | 392 | 23 | 151 | <1 | 310 | 1.5 | 467 | 1.3 |
| 76 | <1 | 236 | <1 | 393 | 2.3 | 152 | <1 | 311 | <1 | 468 | <1 |
| 77 | <1 | 237 | 14 | 394 | 2.8 | 153 | <1 | 312 | 1.9 | 469 | 2.2 |
| 78 | <1 | 238 | <1 | 395 | 2.2 | 154 | <1 | 313 | <1 | 470 | <1 |
| 79 | <1 | 239 | <1 | 396 | 1.8 | 155 | <1 | 314 | <1 | 471 | 2.3 |
| 80 | <1 | 240 | <1 | 397 | 1.2 | 156 | <1 | 315 | <1 | 472 | 1.2 |
| 81 | 2.4 | 241 | <1 | 398 | <1 | 157 | 2.5 | 316 | <1 | 473 | 4.1 |
| 82 | <1 | 242 | <1 | 399 | 2.4 | 158 | <1 | 317 | <1 | 474 | 17 |
| 83 | <1 | 243 | 45 | 400 | 1.4 | 159 | <1 | 318 | 1.5 | 475 | 7.0 |
| 84 | <1 | 244 | <1 | 401 | <1 | 730 | 20 | 731 | >200 | 732 | 38.0 |
| 85 | 1.5 | 245 | <1 | 402 | 4.9 | 733 | 19 | 734 | >200 | 735 | 52.0 |
| 86 | 47 | 246 | 8.6 | 403 | 1.5 | 736 | 121 | 737 | 140 | 738 | 200 |
| 87 | <1 | 247 | <1 | 404 | 44 | 739 | 73 | 740 | 85 | 741 | >200 |
| 88 | <1 | 248 | <1 | 405 | <1 | 742 | >200 | 743 | 121 | 744 | 30.0 |
| 89 | <1 | 249 | <1 | 406 | >250 | 745 | 44 | 746 | 5.2 | 747 | 16 |
| 90 | 8.7 | 250 | <1 | 407 | 1.1 | 748 | 6.3 | | | | |
| 91 | 7.3 | 251 | <1 | 408 | 2.2 | | | | | | |
| 92 | <1 | 252 | 1.3 | 409 | 1.3 | | | | | | |
| 93 | <1 | 253 | 1.2 | 410 | 1.4 | | | | | | |
| 94 | <1 | 254 | <1 | 411 | 5.6 | | | | | | |
| 95 | <1 | 255 | 1.3 | 412 | 1.3 | | | | | | |
| 96 | 2.9 | 256 | <1 | 413 | 3.5 | | | | | | |
| 97 | <1 | 257 | 2.3 | 414 | <1 | | | | | | |
| 98 | <1 | 258 | <1 | 415 | 3.4 | | | | | | |
| 99 | <1 | 259 | <1 | 416 | <1 | | | | | | |
| 100 | <1 | 260 | <1 | 417 | 1.3 | | | | | | |
| 101 | <1 | 261 | <1 | 418 | 1.4 | | | | | | |
| 102 | 1.5 | 262 | <1 | 419 | 2.3 | | | | | | |
| 103 | <1 | 263 | 1.8 | 420 | 2 | | | | | | |
| 104 | <1 | 264 | <1 | 421 | 3.4 | | | | | | |
| 105 | <1 | 265 | 8.2 | 422 | <1 | | | | | | |
| 106 | <1 | 266 | 9.2 | 423 | 2.3 | | | | | | |
| 107 | <1 | 267 | 4.7 | 424 | 2.6 | | | | | | |
| 108 | <1 | 268 | <1 | 425 | 1.8 | | | | | | |
| 109 | <1 | 269 | 7.4 | 426 | <1 | | | | | | |
| 110 | <1 | 270 | 1.1 | 427 | 1.2 | | | | | | |
| 111 | <1 | 271 | <1 | 428 | 2 | | | | | | |
| 112 | 3.3 | 272 | <1 | 429 | 1.8 | | | | | | |
| 113 | <1 | 273 | <1 | 430 | 1.9 | | | | | | |
| 114 | <1 | 274 | 4.8 | 431 | 1.6 | | | | | | |
| 115 | 3.1 | 275 | <1 | 432 | <1 | | | | | | |
| 116 | <1 | 276 | <1 | 433 | 1.7 | | | | | | |
| 117 | <1 | 277 | 6.6 | 434 | 5.5 | | | | | | |
| 118 | <1 | 278 | 5.4 | 435 | <1 | | | | | | |
| 119 | <1 | 279 | 1 | 436 | 2.1 | | | | | | |
| 120 | 39 | 280 | 1.5 | 437 | 4.7 | | | | | | |
| 121 | 1.9 | 281 | 2.2 | 438 | 1.1 | | | | | | |
| 122 | 2.2 | 282 | 8.4 | 439 | 1.9 | | | | | | |
| 123 | <1 | 283 | 1.2 | 440 | 2.5 | | | | | | |
| 124 | <1 | 284 | 3.6 | 441 | 7 | | | | | | |
| 125 | <1 | 285 | <1 | 442 | 2.3 | | | | | | |
| 126 | <1 | 286 | 3.3 | 443 | 4.3 | | | | | | |
| 127 | <1 | 287 | 3 | 444 | 1.3 | | | | | | |
| 128 | <1 | 288 | 3 | 445 | 2.2 | | | | | | |
| 129 | <1 | 289 | 15 | 446 | 8.2 | | | | | | |
| 130 | <1 | 290 | 12 | 447 | <1 | | | | | | |
| 131 | <1 | 291 | 1.1 | 448 | 2.2 | | | | | | |
| 132 | <1 | 292 | <1 | 449 | 2.6 | | | | | | |
| 133 | <1 | 293 | <1 | 450 | 2.2 | | | | | | |
| 134 | <1 | 294 | <1 | 451 | <1 | | | | | | |
| 135 | <1 | 295 | <1 | 452 | 2.2 | | | | | | |
| 136 | <1 | 296 | <1 | 453 | 1.7 | | | | | | |
| 137 | 1.2 | 297 | 2.4 | 454 | 3.5 | | | | | | |
| 138 | 2.2 | 298 | <1 | 455 | <1 | | | | | | |
| 139 | 1.1 | 299 | 2 | 456 | <1 | | | | | | |
| 140 | 79 | 300 | 2 | 457 | <1 | | | | | | |
| 141 | 4.5 | 301 | 2.8 | 458 | 1.2 | | | | | | |
| 142 | 3.8 | 302 | <1 | 459 | 1.0 | | | | | | |
| 143 | 7.6 | 303 | <1 | 460 | 1.7 | | | | | | |
| 144 | <1 | 304 | <1 | 461 | <1 | | | | | | |
| 145 | <1 | 305 | <1 | 462 | 2.0 | | | | | | |
| 146 | 4 | 306 | 1.3 | 463 | 2.1 | | | | | | |

TABLE 3

K$_i$ for Examplified Compounds for Inhibition of Mcl-1 by TR-FRET assay

| Example | K$_i$ (nM) |
|---|---|
| 476 | <0.2 |
| 477 | <0.2 |
| 478 | 0.24 |
| 479 | 0.95 |
| 480 | <0.2 |
| 481 | <0.2 |
| 482 | <0.2 |
| 483 | <0.2 |
| 484 | <0.2 |
| 485 | 0.35 |
| 486 | 1.4 |
| 487 | 0.23 |
| 488 | 39 |
| 489 | <0.2 |
| 490 | 0.29 |
| 491 | <0.2 |
| 492 | <0.2 |
| 493 | <0.2 |
| 494 | 0.3 |
| 495 | 42 |
| 496 | 0.64 |
| 497 | 1.3 |
| 498 | 0.58 |
| 499 | 0.21 |
| 500 | <0.2 |
| 501 | 0.68 |
| 502 | 2.9 |
| 503 | 3.7 |
| 504 | 0.23 |
| 505 | 1.3 |
| 506 | <0.2 |
| 507 | 0.72 |
| 508 | 2.4 |
| 509 | 1.6 |
| 510 | <0.2 |
| 511 | <0.2 |
| 512 | <0.2 |
| 513 | <0.2 |
| 514 | <0.2 |
| 515 | <0.2 |
| 516 | <0.2 |
| 517 | 0.36 |
| 518 | <0.2 |
| 519 | 0.46 |
| 520 | <0.2 |

TABLE 3-continued

K$_i$ for Examplified Compounds for Inhibition of Mcl-1 by TR-FRET assay

| Example | K$_i$ (nM) |
|---|---|
| 521 | <0.2 |
| 522 | 0.32 |
| 523 | 0.50 |
| 524 | 0.28 |
| 525 | 0.41 |
| 526 | <0.2 |
| 527 | 0.36 |
| 528 | <0.2 |
| 529 | <0.2 |
| 530 | <0.2 |
| 531 | 0.48 |
| 532 | 0.20 |
| 533 | 0.69 |
| 534 | <0.2 |
| 535 | <0.2 |
| 536 | <0.2 |
| 537 | <0.2 |
| 538 | <0.2 |
| 539 | <0.2 |
| 540 | <0.2 |
| 541 | 0.53 |
| 542 | 0.48 |
| 543 | 2.9 |
| 544 | <0.2 |
| 545 | 0.39 |
| 546 | 0.38 |
| 547 | 10 |
| 548 | 0.94 |
| 549 | 0.34 |
| 550 | 0.52 |
| 551 | 0.3 |
| 552 | <0.2 |
| 553 | <0.2 |
| 554 | 0.26 |
| 555 | 0.26 |
| 556 | <0.2 |
| 557 | <0.2 |
| 558 | <0.2 |
| 559 | <0.2 |
| 560 | 0.53 |
| 561 | <0.2 |
| 562 | 0.97 |
| 563 | <0.2 |
| 564 | 0.46 |
| 565 | <0.2 |
| 566 | <0.2 |
| 567 | 9.6 |
| 568 | 1.8 |
| 569 | 0.49 |
| 570 | <0.2 |
| 571 | <0.2 |
| 572 | <0.2 |
| 573 | <0.2 |
| 574 | 2.4 |
| 575 | <0.2 |
| 576 | <0.2 |
| 577 | <0.2 |
| 578 | <0.2 |
| 579 | <0.2 |
| 580 | <0.2 |
| 581 | 3.7 |
| 582 | 0.28 |
| 583 | 0.73 |
| 584 | <0.2 |
| 585 | <0.2 |
| 586 | 2.6 |
| 587 | <0.2 |
| 588 | 1.4 |
| 589 | 1.7 |
| 590 | <0.2 |
| 591 | <0.2 |
| 592 | <0.2 |
| 593 | <0.2 |
| 594 | <0.2 |
| 595 | <0.2 |
| 596 | <0.2 |
| 598 | <0.2 |
| 599 | <0.2 |
| 600 | <0.2 |
| 602 | 5.9 |
| 603 | 0.89 |
| 604 | 0.73 |
| 605 | 0.45 |
| 606 | 0.47 |
| 607 | <0.2 |
| 608 | 0.91 |
| 609 | 0.26 |
| 610 | <0.2 |
| 611 | 1.1 |
| 612 | 1.2 |
| 613 | 1.9 |
| 614 | <0.2 |
| 615 | 9.6 |
| 616 | <0.2 |
| 617 | <0.2 |
| 618 | 3.8 |
| 619 | 0.26 |
| 620 | <0.2 |
| 621 | <0.2 |
| 622 | 0.76 |
| 623 | <0.2 |
| 624 | 9.6 |
| 625 | 0.22 |
| 626 | <0.2 |
| 627 | <0.2 |
| 628 | <0.2 |
| 629 | <0.2 |
| 630 | <0.2 |
| 631 | <0.2 |
| 632 | <0.2 |
| 633 | <0.2 |
| 634 | <0.2 |
| 635 | <0.2 |
| 636 | 0.5 |
| 637 | 1.3 |
| 638 | 1.7 |
| 639 | 4.2 |
| 640 | <0.2 |
| 641 | <0.2 |
| 642 | 3 |
| 643 | 1.3 |
| 644 | <0.2 |
| 645 | 3.3 |
| 646 | 0.3 |
| 647 | 0.32 |
| 648 | 0.23 |
| 649 | <0.2 |
| 650 | <0.2 |
| 651 | <0.2 |
| 652 | 0.28 |
| 653 | 15 |
| 654 | 0.34 |
| 655 | 1.6 |
| 656 | <0.2 |
| 657 | <0.2 |
| 658 | <0.2 |
| 659 | 0.96 |
| 660 | <0.2 |
| 661 | 0.23 |
| 662 | 0.93 |
| 663 | 0.52 |
| 664 | 0.64 |
| 665 | <0.2 |
| 666 | 7.2 |
| 667 | <0.2 |
| 668 | 7.6 |
| 669 | 1.0 |
| 670 | <0.2 |
| 671 | 0.32 |
| 672 | 0.43 |

TABLE 3-continued $K_i$ for Examplified Compounds for Inhibition of Mcl-1 by TR-FRET assay

| Example | $K_i$ (nM) |
|---|---|
| 673 | 0.31 |
| 674 | 2.1 |
| 675 | 28 |
| 676 | 0.56 |
| 677 | <0.2 |
| 678 | 0.22 |
| 679 | 3.1 |
| 680 | 0.33 |
| 681 | 5.5 |
| 682 | <0.2 |
| 683 | 0.21 |
| 684 | 0.6 |
| 685 | 3.2 |
| 686 | <0.2 |
| 687 | <0.2 |
| 688 | 0.22 |
| 689 | 2.1 |
| 690 | 0.26 |
| 691 | <0.2 |
| 692 | <0.2 |
| 693 | <0.2 |
| 694 | <0.2 |
| 695 | 0.57 |
| 696 | 1.1 |
| 697 | <0.2 |
| 698 | 1.8 |
| 699 | 1.2 |
| 700 | 0.73 |
| 709 | <0.2 |
| 710 | <0.2 |
| 711 | <0.2 |
| 712 | <0.2 |
| 713 | <0.2 |
| 714 | <0.2 |
| 715 | <0.2 |
| 716 | <0.2 |
| 717 | <0.2 |
| 718 | <0.2 |
| 719 | <0.2 |
| 720 | 0.51 |
| 721 | <0.2 |
| 722 | 3.1 |
| 723 | <0.2 |
| 724 | <0.2 |
| 725 | <0.2 |
| 726 | <0.2 |
| 727 | <0.2 |
| 728 | <0.2 |
| 729 | <0.2 |

Among other things, these data demonstrate the utility of representative compounds as selective inhibitors of the activity of Mcl-1 protein to bind peptides from relevant BH3 domains.

Cellular Viability of Human Tumor Cell Lines

Human cancer cell lines ALMC-1, ALMC-2, K562, H929, and OPM-2 were cultured in media supplemented with 10% fetal bovine serum (FBS). To evaluate compound effect on cellular proliferation, cells were plated at 1,000 cells/well in 96-well tissue culture plates in a total volume of 90 µL medium supplemented with 10% FBS (Sigma, Saint Louis, Mo.). 24 hours later, 10 µL of compound (in a 2-fold serial dilution) is added to the cells for a top concentration of 50 µM and a final DMSO concentration <1%. After 72 hours, 50 µL of Cell TiterGlo (Promega, Madison, Wis., USA) reagent is added to each well and plates are incubated at room temperature, in the dark, for 30 minutes. Luminescence is measured on a BioTek Cytation 3. Luminescence values are imported into a template in XLFit (Guildford, Surrey, UK) that uses a four-parameter fit to generate an $IC_{50}$ value for each compound dilution series on the plate.

TABLE 4

$GI_{50}$ (in µM) for representative compounds on cellular proliferation of H929 human cancer cell lines

| Example | $GI_{50}$ (µM) |
|---|---|
| 2 | 8.3 |
| 3 | 6.6 |
| 4 | 8.7 |
| 7 | 13 |
| 11 | 9.9 |
| 12 | 8.3 |
| 13 | 4.5 |
| 14 | 3.2 |
| 15 | 11 |
| 16 | 2.9 |
| 19 | 4.1 |
| 20 | 6.5 |
| 21 | 4.9 |
| 23 | 4.9 |
| 26 | 0.83 |
| 28 | 3.7 |
| 30 | 5.4 |
| 31 | 1.8 |
| 32 | 7.6 |
| 33 | 0.65 |
| 36 | 2.6 |
| 37 | 1.8 |
| 39 | 0.92 |
| 41 | 1.2 |
| 43 | 9.4 |
| 44 | 14 |
| 45 | 3.8 |
| 48 | 0.8 |
| 49 | 2.6 |
| 50 | 0.71 |
| 51 | 1.5 |
| 52 | 0.47 |
| 53 | 0.5 |
| 54 | 0.32 |
| 55 | 5.7 |
| 56 | 0.81 |
| 57 | 1.7 |
| 58 | 3 |
| 59 | 0.28 |
| 61 | 8.2 |
| 62 | 11 |
| 63 | 0.27 |
| 64 | 5.6 |
| 65 | 5.5 |
| 66 | 6.4 |
| 67 | 8.5 |
| 68 | 0.35 |
| 69 | <0.2 |
| 70 | 2.4 |
| 71 | 3.3 |
| 72 | 4.7 |
| 74 | 2.6 |
| 75 | 1.1 |
| 76 | <0.2 |
| 77 | <0.2 |
| 78 | <0.2 |
| 79 | 1.5 |
| 80 | 0.25 |
| 81 | 2.9 |
| 82 | 4.8 |
| 83 | 1.1 |
| 84 | 1.2 |
| 88 | 0.29 |
| 89 | 1.3 |
| 92 | 0.9 |
| 93 | 7.5 |
| 94 | 1.5 |
| 95 | 10 |
| 96 | 4.7 |
| 97 | 3.4 |

TABLE 4-continued

GI$_{50}$ (in µM) for representative compounds on cellular proliferation of H929 human cancer cell lines

| Example | GI$_{50}$ (µM) |
|---|---|
| 98 | 6.6 |
| 99 | 2.1 |
| 100 | 5.8 |
| 101 | 2.1 |
| 102 | 4.9 |
| 103 | 0.48 |
| 104 | 0.57 |
| 105 | 0.27 |
| 106 | 0.79 |
| 108 | 0.88 |
| 109 | 0.71 |
| 110 | 0.79 |
| 111 | 2.6 |
| 112 | 5.3 |
| 113 | 0.33 |
| 114 | 0.84 |
| 115 | 5.1 |
| 116 | 9.7 |
| 117 | 0.39 |
| 118 | 0.82 |
| 119 | 2.9 |
| 120 | 12 |
| 122 | 11 |
| 123 | 6.9 |
| 124 | 1.9 |
| 125 | 7.6 |
| 126 | 5.1 |
| 128 | 0.41 |
| 129 | 0.55 |
| 130 | 2.4 |
| 131 | 1.9 |
| 132 | 0.84 |
| 133 | 1.4 |
| 134 | 11 |
| 137 | 0.46 |
| 138 | 4.8 |
| 140 | 7.6 |
| 141 | 9.5 |
| 142 | 7.4 |
| 144 | 6.5 |
| 145 | 0.36 |
| 146 | 2.4 |
| 147 | 4.3 |
| 148 | 0.65 |
| 150 | 5.1 |
| 151 | 2.1 |
| 152 | 0.85 |
| 153 | 0.41 |
| 154 | 1.3 |
| 155 | 1.4 |
| 156 | 0.26 |
| 157 | 6.4 |
| 158 | 0.48 |
| 159 | 0.29 |
| 160 | 0.69 |
| 161 | 0.48 |
| 162 | 0.26 |
| 163 | 0.26 |
| 164 | 0.92 |
| 165 | 1.2 |
| 166 | 1.4 |
| 167 | 4.1 |
| 168 | 1 |
| 169 | 2.6 |
| 170 | 2.6 |
| 171 | 1.5 |
| 172 | 0.32 |
| 173 | 3.3 |
| 174 | 6.3 |
| 175 | 0.34 |
| 176 | 0.41 |
| 177 | 0.27 |
| 178 | <0.2 |
| 179 | 4.7 |
| 180 | 1.5 |
| 181 | 2 |
| 182 | 1.5 |
| 183 | 0.36 |
| 184 | 0.77 |
| 185 | 2.9 |
| 186 | <0.2 |
| 187 | <0.2 |
| 188 | 2.7 |
| 189 | 0.92 |
| 190 | 2.2 |
| 191 | 3.2 |
| 192 | <0.2 |
| 194 | 2.3 |
| 195 | 1.8 |
| 196 | 3.4 |
| 197 | 0.67 |
| 198 | 0.61 |
| 201 | <0.2 |
| 203 | 3.9 |
| 204 | 1 |
| 206 | 3.2 |
| 207 | 0.75 |
| 208 | 1.6 |
| 209 | 3.5 |
| 210 | 1.5 |
| 211 | 11 |
| 212 | 3.4 |
| 213 | <0.2 |
| 214 | 0.38 |
| 215 | 0.43 |
| 218 | <0.2 |
| 219 | 1.2 |
| 220 | 2 |
| 221 | 0.45 |
| 222 | 3 |
| 223 | 5 |
| 224 | 2.5 |
| 225 | 3.3 |
| 226 | 2.6 |
| 227 | 1.3 |
| 228 | 0.78 |
| 229 | 9.3 |
| 230 | 0.89 |
| 231 | 2.7 |
| 232 | 4 |
| 233 | 1.4 |
| 234 | 1.6 |
| 235 | 0.24 |
| 236 | 1.1 |
| 237 | 7.6 |
| 238 | 0.34 |
| 239 | 1.8 |
| 240 | 1.9 |
| 241 | 0.42 |
| 242 | 1.3 |
| 244 | 0.4 |
| 245 | 0.9 |
| 246 | 5.3 |
| 247 | <0.2 |
| 248 | 0.57 |
| 249 | 0.49 |
| 250 | 0.48 |
| 251 | 0.25 |
| 252 | 2 |
| 253 | 1.1 |
| 254 | 0.58 |
| 256 | 0.27 |
| 257 | 0.47 |
| 258 | 3.6 |
| 259 | 3.5 |
| 260 | 0.55 |
| 261 | 0.53 |
| 262 | 0.45 |
| 263 | 0.27 |
| 264 | 0.56 |

TABLE 4-continued

GI$_{50}$ (in μM) for representative compounds on cellular proliferation of H929 human cancer cell lines

| Example | GI$_{50}$ (μM) |
|---|---|
| 265 | 1.5 |
| 267 | 3.1 |
| 268 | 0.41 |
| 269 | 0.76 |
| 270 | 0.31 |
| 271 | 0.26 |
| 272 | 0.21 |
| 273 | 4.1 |
| 274 | 2.2 |
| 275 | 0.37 |
| 276 | 0.29 |
| 277 | 1.4 |
| 278 | 1.5 |
| 279 | 3.3 |
| 280 | 2.2 |
| 281 | 1.4 |
| 282 | 2.4 |
| 283 | 1.2 |
| 284 | 1.5 |
| 285 | 5.3 |
| 286 | 0.51 |
| 287 | 1.6 |
| 288 | 8.4 |
| 289 | 5.2 |
| 290 | 5.3 |
| 291 | 1 |
| 292 | 0.69 |
| 293 | 0.81 |
| 294 | 2 |
| 295 | <0.2 |
| 296 | 0.24 |
| 297 | 7.9 |
| 298 | 0.29 |
| 299 | 2.3 |
| 300 | 5.9 |
| 301 | 8.3 |
| 302 | <0.2 |
| 304 | 0.37 |
| 305 | 6.2 |
| 306 | 0.6 |
| 307 | 3.5 |
| 308 | 0.41 |
| 309 | 0.53 |
| 310 | 8.9 |
| 311 | 3.4 |
| 312 | 5.7 |
| 313 | <0.2 |
| 314 | 0.93 |
| 315 | 2.8 |
| 316 | 0.47 |
| 317 | 0.72 |
| 318 | 0.82 |
| 321 | 1.4 |
| 322 | 1.8 |
| 323 | 1.5 |
| 324 | 0.61 |
| 325 | 0.29 |
| 326 | 0.59 |
| 327 | 3.6 |
| 328 | 0.69 |
| 329 | 1.1 |
| 330 | 2.3 |
| 331 | 2.3 |
| 332 | 0.67 |
| 333 | 1.1 |
| 334 | 1.2 |
| 335 | 0.91 |
| 336 | 0.25 |
| 337 | 0.54 |
| 338 | 2 |
| 339 | 0.32 |
| 340 | 1.8 |
| 341 | 0.92 |
| 342 | 0.23 |
| 343 | 3.6 |
| 344 | 1.3 |
| 345 | 1.8 |
| 346 | 1.6 |
| 347 | 1.9 |
| 348 | 1.3 |
| 349 | 0.78 |
| 350 | 0.3 |
| 352 | 5.1 |
| 353 | 2.9 |
| 354 | 0.58 |
| 355 | 0.73 |
| 356 | 0.65 |
| 357 | 2 |
| 358 | 2.3 |
| 359 | 0.29 |
| 360 | 2.5 |
| 361 | 0.29 |
| 362 | 0.97 |
| 363 | 1.4 |
| 364 | 0.54 |
| 365 | 2.0 |
| 366 | 0.44 |
| 367 | 0.4 |
| 368 | 0.62 |
| 370 | 4.5 |
| 371 | 0.3 |
| 372 | 2.0 |
| 373 | 1.2 |
| 374 | 1.5 |
| 375 | 2.5 |
| 376 | 0.75 |
| 377 | 0.63 |
| 378 | 0.41 |
| 379 | 0.56 |
| 380 | 2.5 |
| 381 | 0.25 |
| 382 | 0.75 |
| 383 | 1.5 |
| 384 | 0.91 |
| 385 | 0.51 |
| 386 | 3.1 |
| 387 | 3.6 |
| 388 | 0.33 |
| 389 | 1.5 |
| 390 | 0.34 |
| 391 | 0.37 |
| 392 | 0.95 |
| 393 | 1.2 |
| 394 | 0.27 |
| 395 | 0.86 |
| 396 | <0.2 |
| 397 | 0.34 |
| 398 | 0.2 |
| 399 | 0.21 |
| 400 | 0.43 |
| 401 | 0.28 |
| 402 | 1.1 |
| 403 | <0.2 |
| 405 | 0.46 |
| 407 | 0.49 |
| 408 | 3.2 |
| 409 | 2.8 |
| 410 | 4 |
| 412 | 0.45 |
| 414 | 1.4 |
| 415 | 0.51 |
| 416 | <0.2 |
| 417 | 0.34 |
| 418 | 0.9 |
| 419 | 1.1 |
| 420 | 0.28 |
| 422 | 0.83 |
| 423 | 1.7 |
| 424 | 1.3 |
| 425 | 1.4 |

TABLE 4-continued

GI$_{50}$ (in μM) for representative compounds on cellular proliferation of H929 human cancer cell lines

| Example | GI$_{50}$ (μM) |
|---|---|
| 426 | 0.25 |
| 427 | 0.49 |
| 428 | 0.92 |
| 429 | 0.97 |
| 430 | 1.4 |
| 431 | 2.9 |
| 432 | 0.21 |
| 433 | 0.44 |
| 434 | 0.89 |
| 435 | 0.57 |
| 436 | 0.51 |
| 437 | 1.2 |
| 438 | 2.8 |
| 439 | <0.2 |
| 440 | 4.5 |
| 441 | 4.6 |
| 442 | 0.23 |
| 443 | 0.25 |
| 444 | 0.22 |
| 445 | 0.82 |
| 447 | 0.34 |
| 448 | 0.36 |
| 449 | 1.2 |
| 450 | 1.1 |
| 451 | <0.2 |
| 452 | 0.38 |
| 453 | 0.33 |
| 454 | 2.1 |
| 455 | 0.22 |
| 456 | <0.2 |
| 457 | <0.2 |
| 458 | 0.29 |
| 459 | 0.51 |
| 460 | 0.42 |
| 461 | <0.2 |
| 462 | 0.99 |
| 463 | 0.29 |
| 464 | 0.48 |
| 465 | 0.69 |
| 466 | 0.3 |
| 467 | 1.3 |
| 468 | 0.26 |
| 469 | 3.3 |
| 470 | <0.2 |
| 471 | 0.36 |
| 472 | 1.7 |
| 474 | 1.2 |
| 475 | 0.25 |
| 476 | <0.2 |
| 477 | <0.2 |
| 478 | 0.56 |
| 479 | 1.5 |
| 480 | 0.25 |
| 481 | 0.24 |
| 482 | 0.34 |
| 483 | 0.28 |
| 484 | 0.31 |
| 485 | 0.41 |
| 486 | 2.9 |
| 487 | 0.28 |
| 488 | 8.7 |
| 489 | <0.2 |
| 490 | 0.81 |
| 491 | 0.28 |
| 492 | 0.36 |
| 493 | <0.2 |
| 494 | 0.45 |
| 496 | 1.2 |
| 497 | 1.7 |
| 498 | 1.9 |
| 499 | 0.74 |
| 500 | 0.33 |
| 501 | 1.2 |
| 502 | <0.2 |
| 503 | <0.2 |
| 504 | 1.0 |
| 505 | 3.2 |
| 506 | 1.3 |
| 507 | 1.4 |
| 508 | 0.45 |
| 509 | 0.39 |
| 510 | 0.24 |
| 511 | 0.3 |
| 512 | 0.22 |
| 513 | 5.3 |
| 514 | <0.2 |
| 515 | 0.61 |
| 516 | 0.33 |
| 517 | 0.76 |
| 518 | 0.81 |
| 519 | 0.99 |
| 520 | <0.2 |
| 521 | 0.61 |
| 522 | 0.75 |
| 523 | 0.89 |
| 524 | 0.22 |
| 525 | 0.33 |
| 526 | <0.2 |
| 527 | 0.26 |
| 528 | 0.87 |
| 529 | 0.52 |
| 530 | 0.23 |
| 531 | 0.38 |
| 532 | 0.39 |
| 533 | 1.3 |
| 534 | 0.52 |
| 535 | 0.28 |
| 536 | <0.2 |
| 537 | <0.2 |
| 538 | <0.2 |
| 539 | <0.2 |
| 540 | <0.2 |
| 541 | 1.7 |
| 542 | 3.3 |
| 543 | 1.8 |
| 544 | 0.32 |
| 545 | 0.56 |
| 546 | 0.42 |
| 548 | 0.61 |
| 549 | 0.34 |
| 550 | 1.2 |
| 552 | 4.6 |
| 553 | 2.8 |
| 555 | 1.3 |
| 556 | 0.28 |
| 557 | 0.82 |
| 558 | 0.31 |
| 559 | 0.43 |
| 560 | 0.27 |
| 561 | 0.51 |
| 562 | 1.2 |
| 563 | 1.5 |
| 564 | 0.59 |
| 565 | <0.2 |
| 566 | 0.41 |
| 567 | 0.93 |
| 568 | 0.28 |
| 569 | 0.47 |
| 570 | 0.56 |
| 571 | <0.2 |
| 572 | 0.3 |
| 573 | <0.2 |
| 574 | 0.27 |
| 575 | 0.74 |
| 576 | 0.35 |
| 577 | 0.23 |
| 578 | 0.39 |
| 579 | 0.24 |
| 580 | 0.96 |
| 581 | 0.25 |

TABLE 4-continued

GI$_{50}$ (in μM) for representative compounds on cellular proliferation of H929 human cancer cell lines

| Example | GI$_{50}$ (μM) |
| --- | --- |
| 582 | 0.22 |
| 583 | <0.2 |
| 584 | 1 |
| 585 | 1.5 |
| 586 | 0.4 |
| 587 | <0.2 |
| 588 | 1.4 |
| 589 | 1.1 |
| 590 | 0.67 |
| 591 | 2.8 |
| 592 | 0.88 |
| 593 | <0.2 |
| 594 | 0.23 |
| 595 | <0.2 |
| 596 | 1.3 |
| 597 | 0.69 |
| 598 | 1.9 |
| 599 | <0.2 |
| 600 | 2.5 |
| 602 | 0.43 |
| 603 | <0.2 |
| 605 | 0.49 |
| 606 | 0.6 |
| 607 | <0.2 |
| 608 | 304 |
| 609 | 0.34 |
| 610 | 0.4 |
| 612 | 7.6 |
| 614 | 0.69 |
| 615 | 0.37 |
| 616 | 0.34 |
| 617 | 0.44 |
| 618 | 0.36 |
| 619 | 0.47 |
| 620 | 7.6 |
| 621 | 0.39 |
| 622 | 0.92 |
| 623 | <0.2 |
| 624 | 0.43 |
| 625 | 0.42 |
| 626 | 4.4 |
| 627 | <0.2 |
| 628 | 0.44 |
| 629 | 0.56 |
| 630 | 9 |
| 631 | 0.3 |
| 632 | 0.22 |
| 633 | <0.2 |
| 634 | 0.28 |
| 635 | <0.2 |
| 636 | 0.98 |
| 637 | 0.53 |
| 638 | 0.6 |
| 639 | 0.9 |
| 640 | 8.1 |
| 641 | 0.35 |
| 642 | 0.79 |
| 643 | 0.34 |
| 644 | 1.9 |
| 645 | 3.7 |
| 646 | 0.24 |
| 647 | 1.1 |
| 648 | 0.31 |
| 649 | <0.2 |
| 650 | 0.21 |
| 651 | 0.29 |
| 652 | 0.37 |
| 653 | 1.9 |
| 654 | 0.34 |
| 655 | 0.34 |
| 656 | 0.25 |
| 657 | 0.61 |
| 658 | 0.25 |
| 659 | 0.93 |
| 660 | 0.33 |
| 661 | 2.4 |
| 662 | 1.9 |
| 663 | <0.2 |
| 664 | 0.58 |
| 665 | 0.28 |
| 667 | 8.2 |
| 668 | 1.5 |
| 669 | 7.6 |
| 670 | <0.2 |
| 671 | 0.89 |
| 672 | 0.84 |
| 673 | 0.23 |
| 674 | 0.21 |
| 675 | 4.8 |
| 676 | 1.1 |
| 677 | <0.2 |
| 678 | <0.2 |
| 679 | 0.94 |
| 680 | 0.61 |
| 681 | 0.94 |
| 682 | 0.34 |
| 683 | 0.25 |
| 684 | 0.52 |
| 685 | 1.4 |
| 686 | 0.52 |
| 687 | 0.33 |
| 688 | 0.43 |
| 689 | 1.7 |
| 690 | 0.33 |
| 691 | <0.2 |
| 692 | 0.39 |
| 693 | 0.21 |
| 694 | 0.32 |
| 695 | 0.28 |
| 696 | 1.4 |
| 697 | 2 |
| 698 | 0.62 |
| 699 | 0.35 |
| 700 | 0.38 |
| 709 | <0.2 |
| 710 | <0.2 |
| 711 | <0.2 |
| 712 | <0.2 |
| 713 | <0.2 |
| 714 | <0.2 |
| 715 | <0.2 |
| 716 | 0.55 |
| 717 | <0.2 |
| 718 | 0.41 |
| 719 | 0.64 |
| 720 | 0.22 |
| 721 | <0.2 |
| 722 | <0.2 |
| 723 | <0.2 |
| 724 | 0.33 |
| 725 | <0.2 |
| 726 | 0.26 |
| 727 | 0.5 |
| 728 | 0.71 |
| 729 | 0.26 |

Apoptosis Assay Protocol (Caspase 3/7 Glo)

Induction of apoptosis was measured by quantifying caspase 3/7 activity using the commercially available Caspase-Glo reagent (Promega, Madison, Wis., USA). This assay relies on the cleavage of a proluminescent substrate by activated caspases, which is then detected on the BioTek Cytation 3, 5000 cells in 90 μL of media (+5% FBS) are plated in each well of a white 96-well plate and incubated overnight at 37° C. in a tissue culture incubator. The following day, compound is diluted in a 10-pt, 2-fold serial dilution scheme for a final top concentration of 50 μM. 10 μL of compound is added directly to the cell assay plate for a final volume of 100 μL Columns 11 and 12 are reserved for treatment with DMSO to serve as control wells. Plates are incubated for 3 hours. 100 μL of Caspase-Glo reagent is added to each well and plates are incubated at room temperature, in the dark, for 30 minutes. Luminescence is measured on the Cytation 3. Luminescence values are imported into a template in XLFit (Guildford. Surrey, UK) that uses a four-parameter fit to generate an $IC_{50}$ value for each compound dilution series on the plate.

Among other things, these data demonstrate the utility of representative compounds as inhibitors of cellular proliferation of human cancer cell lines and initiators of apoptosis via caspase 3 and 7 activation in a Mcl-1 sensitive human cancer cell line.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:
1. A compound having formula:

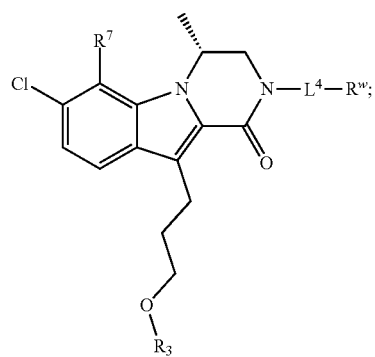
(I-a-1)

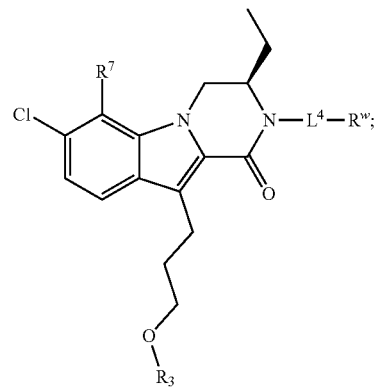
(I-a-2)

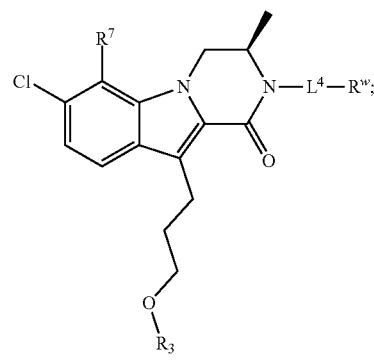
(I-a-3)

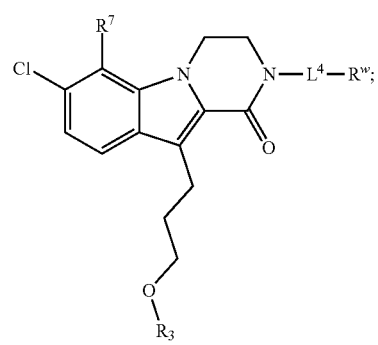
(I-a-4)

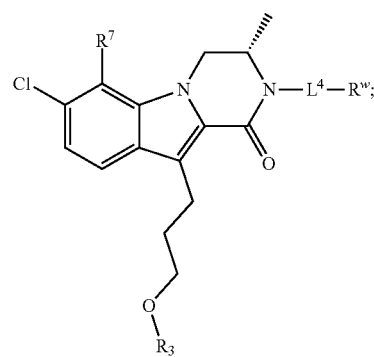
(I-a-5)

(I-a-6)
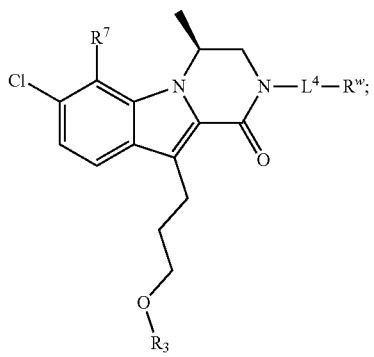

(I-b-1)
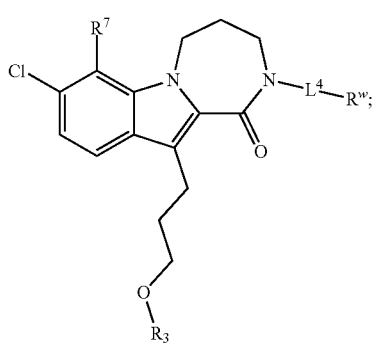

(I-b-2)
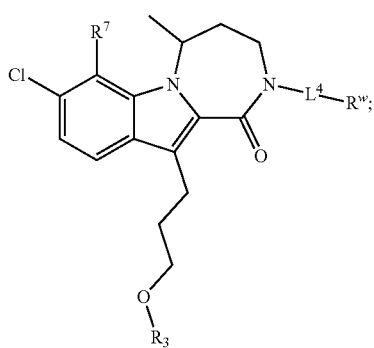

(I-b-3)
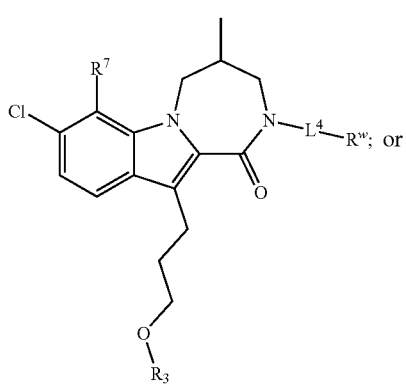

(I-b-4)
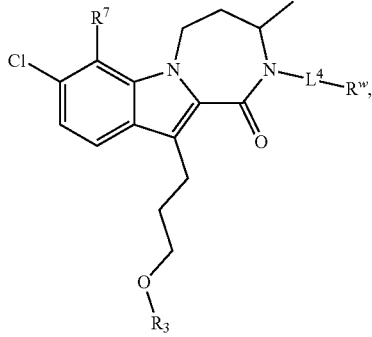

or a pharmaceutically acceptable salt thereof,
wherein:
$R^3$ is

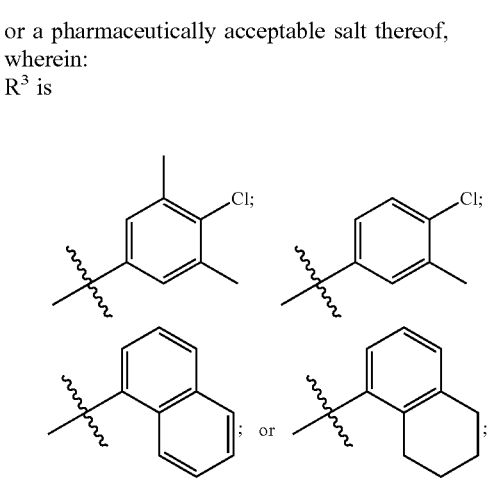

$R^7$ is

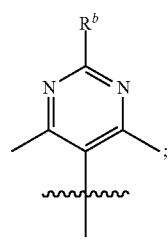

$R^b$ is hydrogen, hydroxy, alkyl, heteroalkyl, heterocyclyl, or heterocyclylalkyl, wherein said alkyl, heteroalkyl, heterocyclyl, and heterocyclylalkyl are independently substituted by 0, 1, 2, 3, 4, or 5 substituents independently selected from the group consisting of halogen, oxo (=O), =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocyclyl, cycloalkylalkyl, cycloalkenylalkyl, heteroarylalkyl, arylalkyl, heterocyclylalkyl, hydroxy, hydroxyalkyl, alkoxy, alkylthio, alkoxyalkyl, alkylene, aryloxy, arylthio, phenoxy, benzyloxy, amino, alkylamino, dialkylamino, acylamino, aminoalkyl, arylamino, diarylamino, sulfonylamino, sulfinylamino, sulfonyl, alkylsulfonyl, arylsulfonyl, aminosulfonyl, sulfinyl, —COOH, ketone, alkoxycarbonyl, aryloxycarbonyl, amide, carbamate, acyl, boronic acid, or boronic ester; and L⁴-Rʷ is an optionally substituted 8-10 membered bicyclic saturated, partially unsaturated or aryl ring, an optionally substituted 8-10 membered bicyclic saturated or partially unsaturated heterocyclic ring having 1-5 heteroatoms independently selected from nitrogen, oxygen, or sulfur, or an optionally substituted 8-10 membered bicyclic heteroaryl ring having 1-5 heteroatoms independently selected from nitrogen, oxygen, or sulfur.

2. The compound of claim 1, or a pharmaceutically acceptable salt thereof, wherein L⁴-Rʷ is an optionally substituted indolyl.

3. The compound of claim 1, or a pharmaceutically acceptable salt thereof, wherein
L⁴-Rʷ is

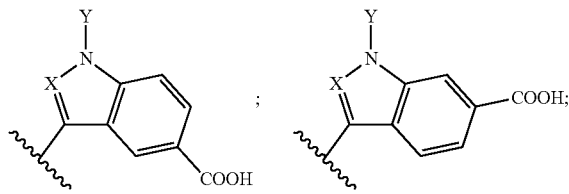

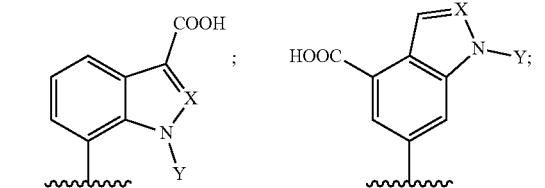

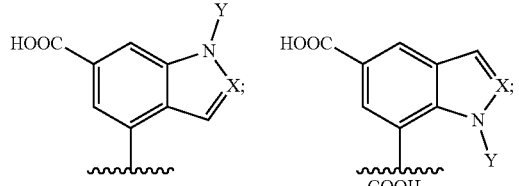

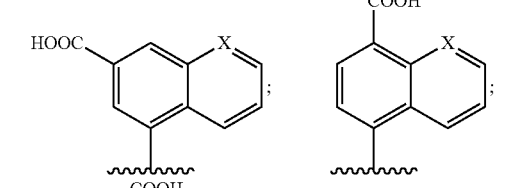

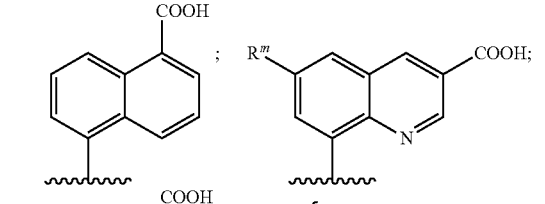

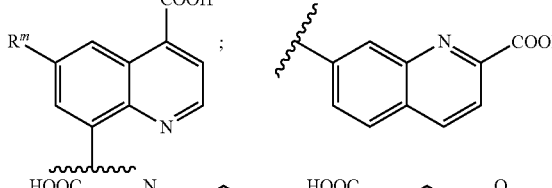

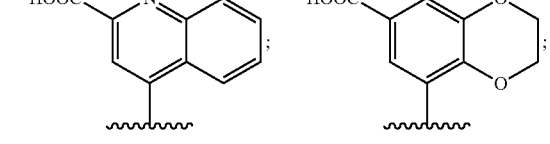

-continued

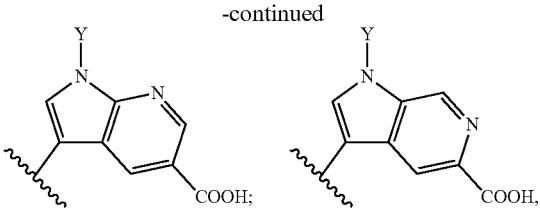

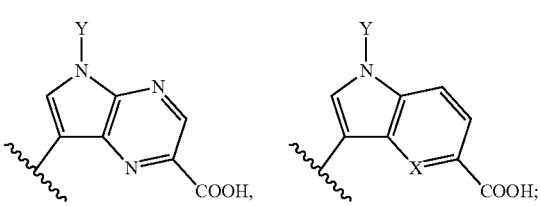

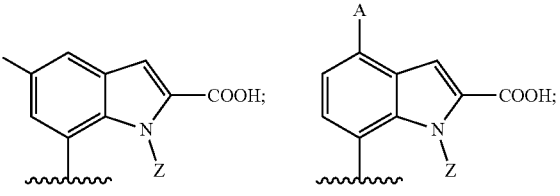

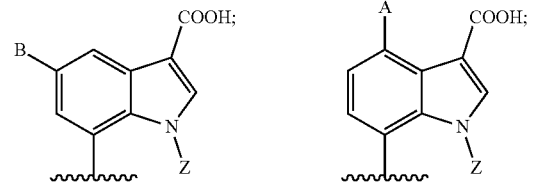

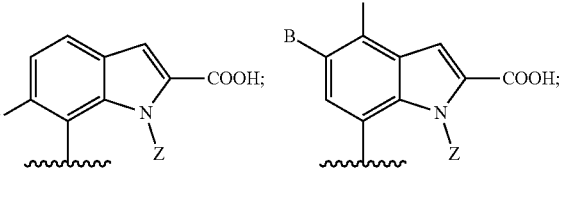

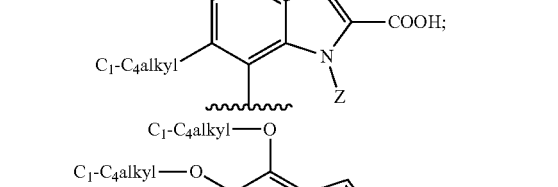

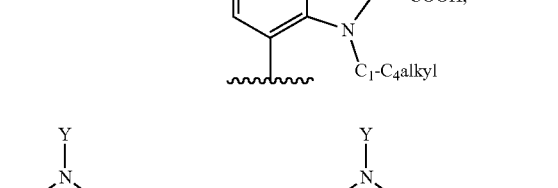

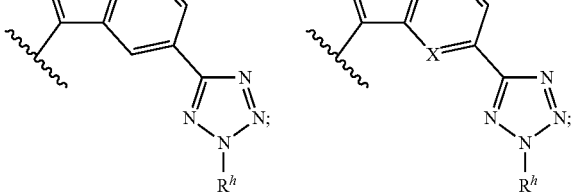

1035
-continued
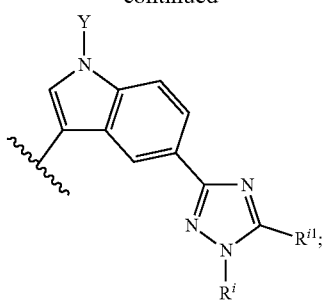
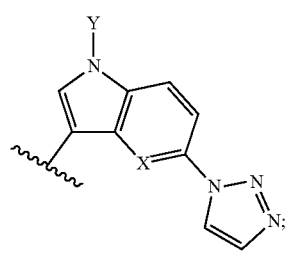
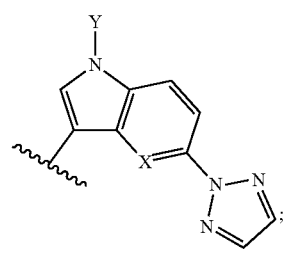
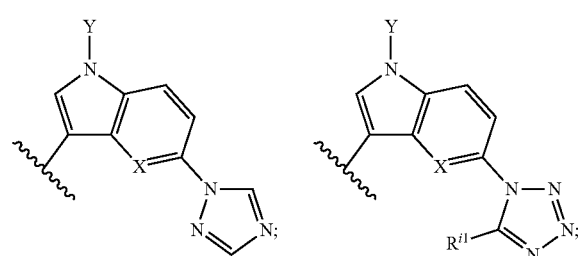
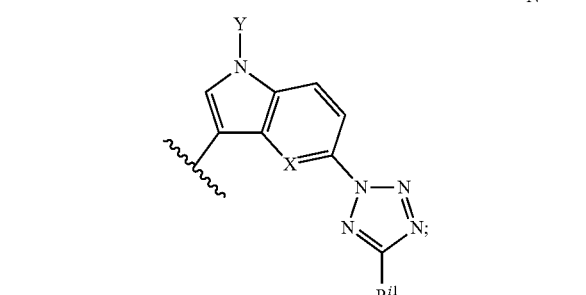
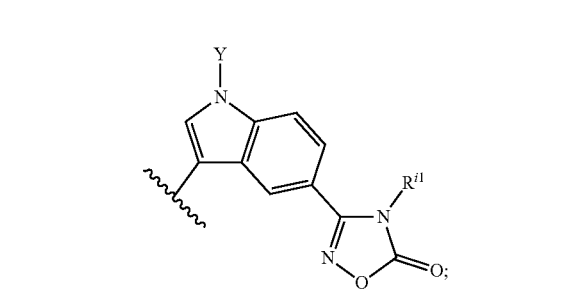
1036
-continued
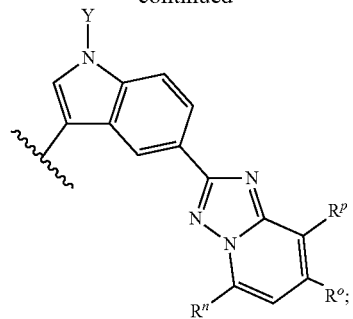
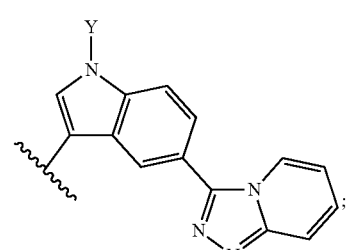
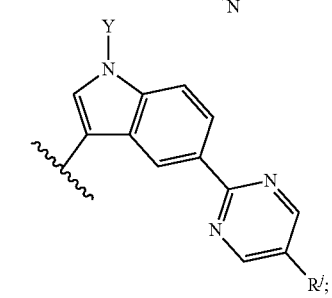
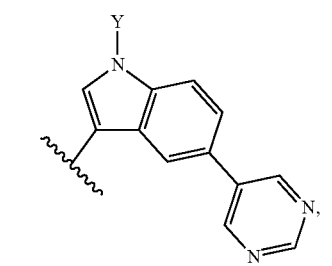
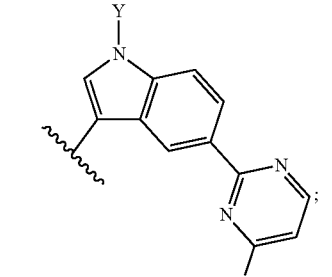
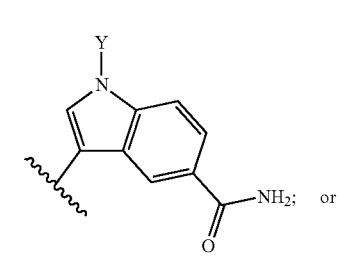 or

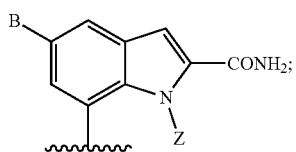

wherein

A and B are each independently hydrogen, halogen, C$_1$-C$_4$-alkyl, C$_1$-C$_4$-haloalkyl, C$_1$-C$_4$-alkoxy, C$_1$-C$_4$-haloalkoxy, halogen, —OR$^c$, —CH$_2$OR$^d$, CH$_2$CH$_2$OC$_1$-C$_4$alkyl, —NHC(O)R$^i$, —N(C$_1$-C$_4$alkyl)C(O)R$^i$, —NR$^c$R$^c$, CH$_2$N(R$^c$)$_2$, CH$_2$CH$_2$N(R$^c$)$_2$, COOH,

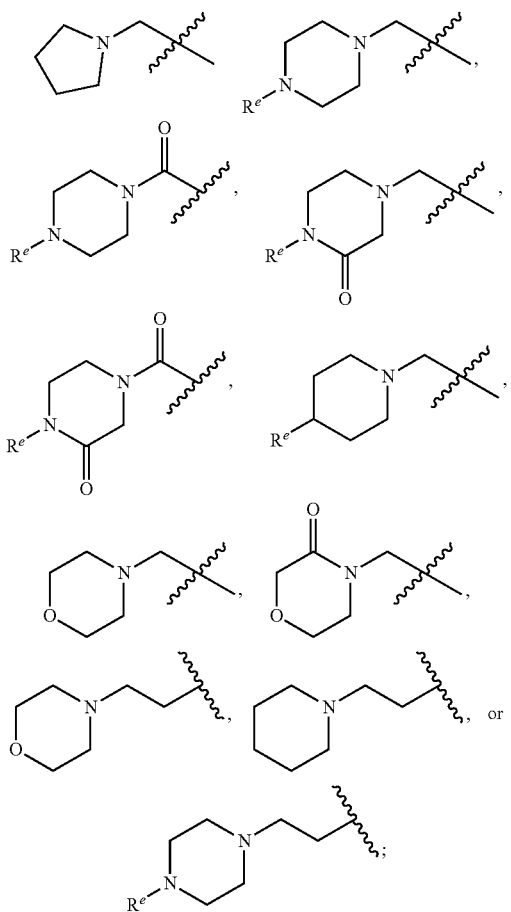

X is C(H), C(C$_1$-C$_4$-alkyl), C(C$_1$-C$_4$-haloalkyl) or N;
Y is hydrogen, C$_1$-C$_4$-alkyl,

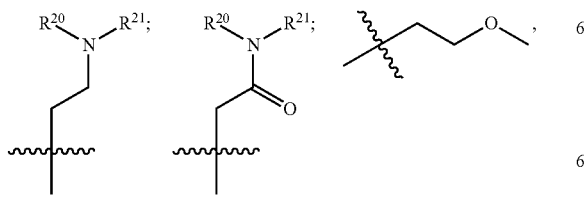

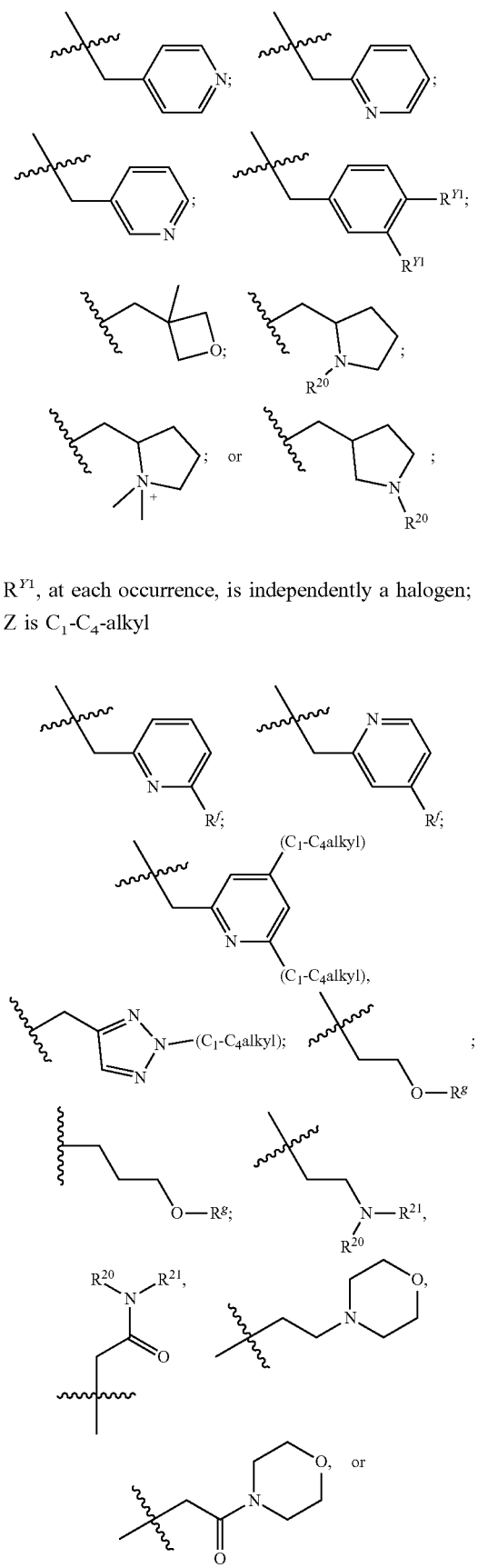

R$^{Y1}$, at each occurrence, is independently a halogen;
Z is C$_1$-C$_4$-alkyl -continued

[structure: CH2CH2-O-CH2CH2-O-C1-C4alkyl]

R²⁰ and R²¹ are each independently hydrogen or C₁-C₄-alkyl, or R²⁰ and R²¹ together with the nitrogen to which they are attached can form an optionally substituted 4-8 membered heterocyclic ring;

R^c, at each occurrence, is independently hydrogen, C₁-C₄-alkyl, C₂-C₄-alkenyl,

[structures: -CH2CH2-O-CH3, -CH2CH2-O-C1-C4alkyl,]

[structure: -CH2CH2-O-CH2CH2-O-C1-C4alkyl,]

[structures: -CH2CH2CH2-N(CH3)2, -CH2CH2CH2-morpholine,]

[structures: -CH2-phenyl, -CH2-pyridyl, or]

[structure: -CH2CH2CH2-N-methylpiperazine];

R^d is C₁-C₄-alkyl

[structures: -CH2CH2-O-CH3, -CH2CH2CH2-N(CH3)2,]

[structures: -CH2-thiazolyl, -CH2-oxetanyl,]

[structure: -CH2CH2CH2-morpholine];

R^e is C₁-C₄-alkyl, —OC₁-C₄-alkyl,

[structure: -O-CH2CH2-O-C1-C4alkyl,]

C(O)C₁-C₄-alkyl, or

[structure: -O-phenyl-R^e1], where R^e1 is halogen;

R^f is hydrogen, C₁-C₄-alkyl, C₂-C₄-alkenyl, cyano,

[structures: -N-piperazine-NH, -N-piperazine-C(O)CH3, or]

[structure: -oxazoline];

R^g is hydrogen or C₁-C₄-alkyl;
R^h is hydrogen or C₁-C₄-alkyl;
R^i is hydrogen, C₁-C₄-alkyl,

[structures: -CH2CH2-O-CH3, -CH2CH2-N(CH3)2,]

[structures: -CH2CH2-N(CH3)2, -CH(CH3)-N(CH3)2,]

[structures: -CH2CH2CH2-morpholine, -CH2-N-methylpiperazine,]

[structures: -CH2-piperidine, -CH2-pyrrolidine,]

[structures: -CH2-tetrahydropyran, -CH2-oxetane,]

[structures: -CH2-azetidine-C(O)CH3, -CH2-cyclopropyl,]

[structures: -CH2CH2-N-methylpiperazine, -CH2-pyridyl,]

[structures: -CH2-pyridyl-C1-C4alkyl, -pyrimidinyl,]

[structures: -pyrimidinyl-C1-C4alkyl, -pyrimidinyl-C1-C4alkyl,]

-continued

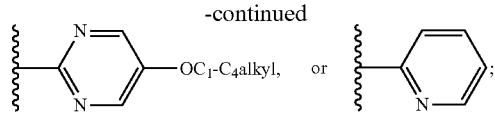

R$^{i1}$ is hydrogen, C$_1$-C$_4$-alkyl, CH$_2$—O—C$_1$-C$_4$alkyl;
R$^j$ is hydrogen, C$_1$-C$_4$-alkyl or C$_1$-C$_4$-alkoxy;
R$^k$ is C$_1$-C$_4$-alkyl;
R$^m$ is hydrogen or C$_1$-C$_4$alkyl;
R$^n$ is hydrogen or C$_1$-C$_4$alkyl;
R$^o$ is hydrogen or C$_1$-C$_4$alkyl; and
R$^p$ is hydrogen, C$_1$-C$_4$alkyl, CH$_2$OC$_1$-C$_4$alkyl, or

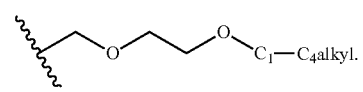

4. The compound of claim 1, or a pharmaceutically acceptable salt thereof, wherein L$^4$-R$^w$ is

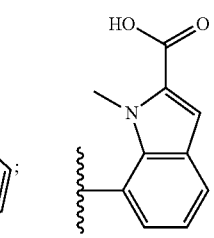

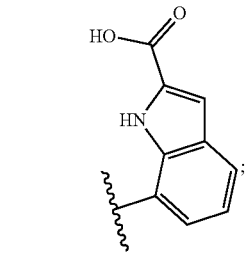

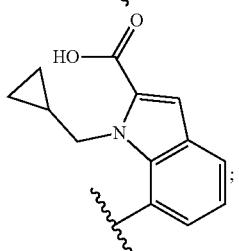

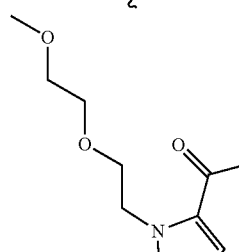

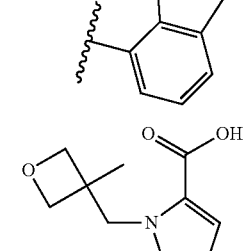

-continued

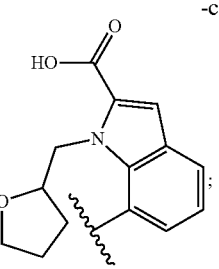

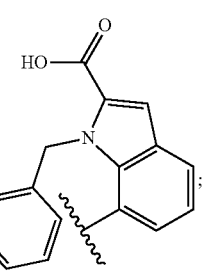 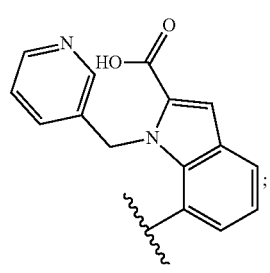

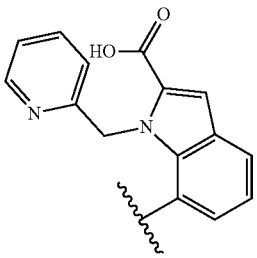 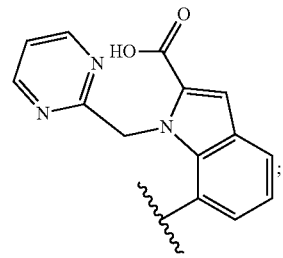

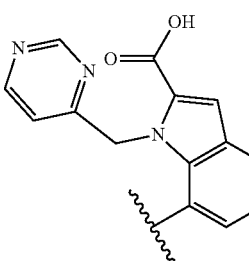 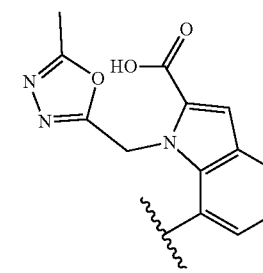

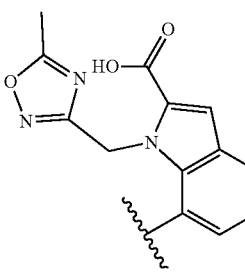 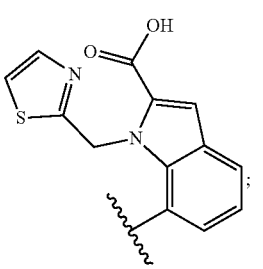

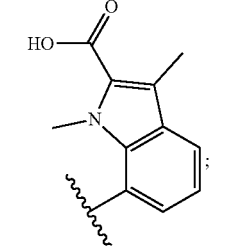

-continued
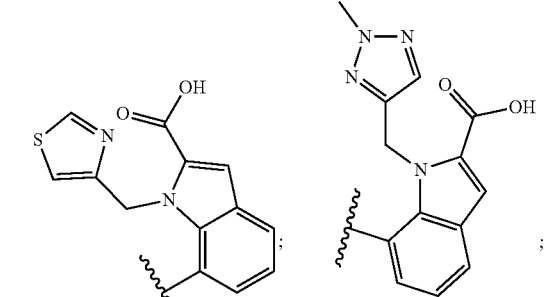
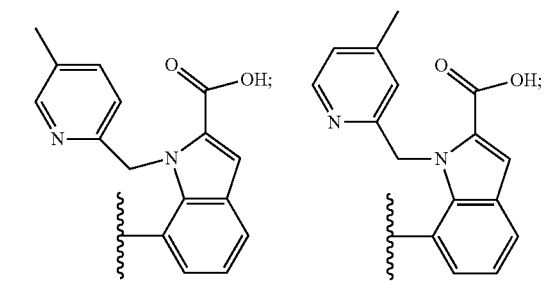
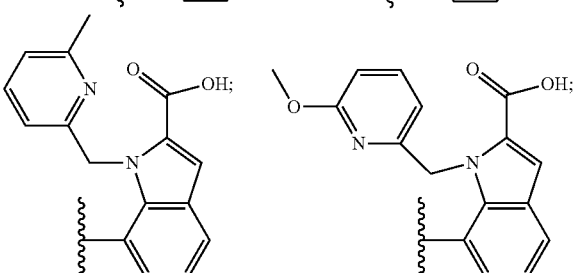
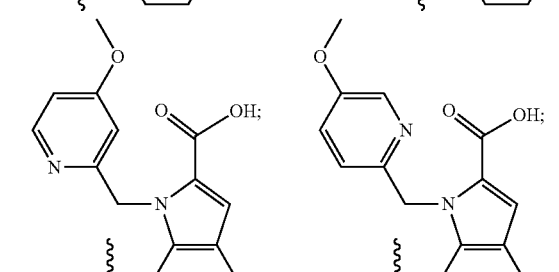
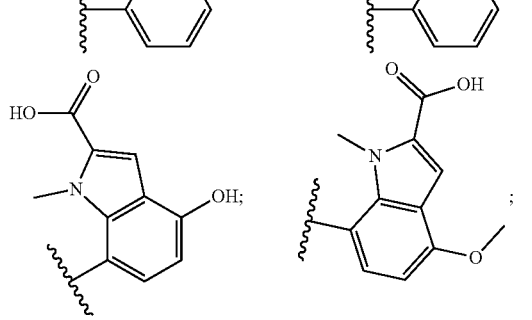
-continued
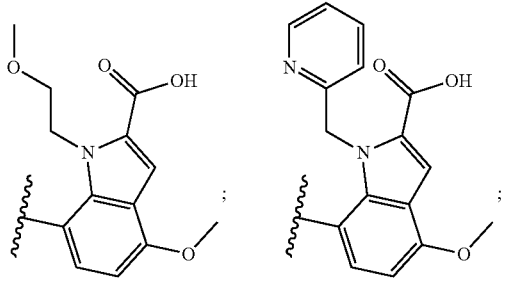
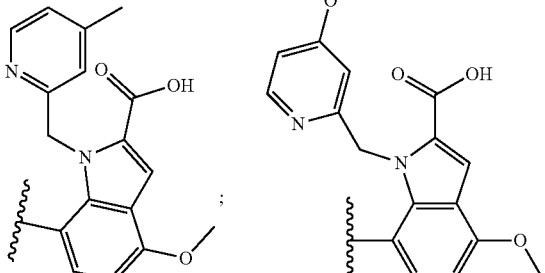
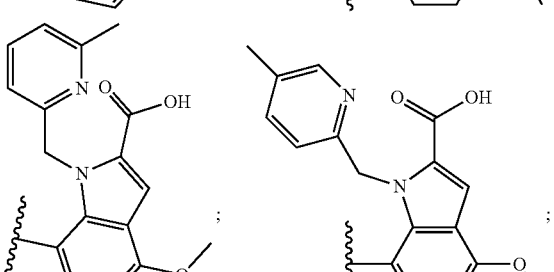
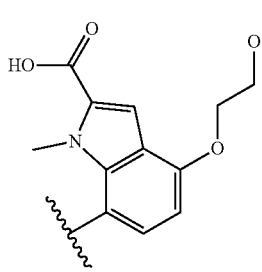
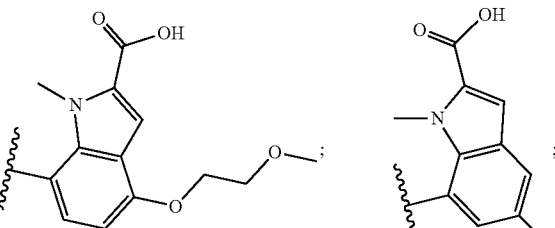
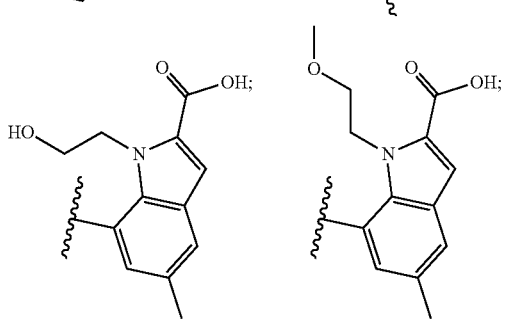

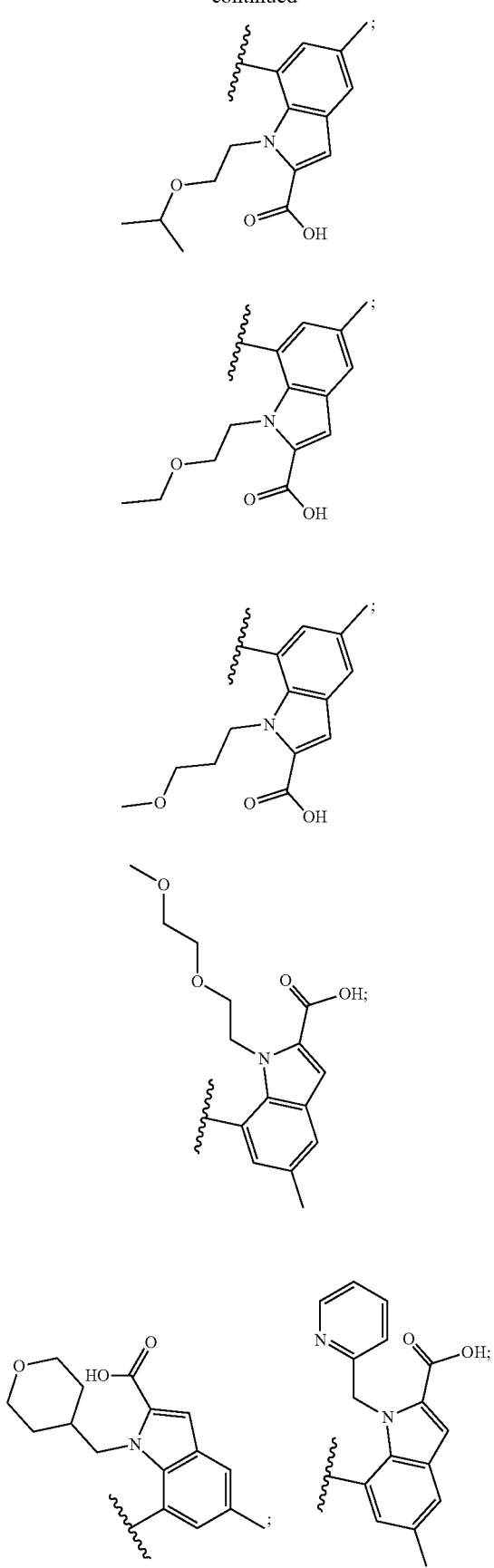

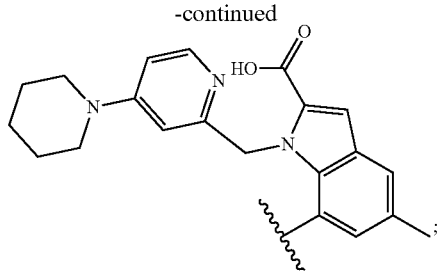
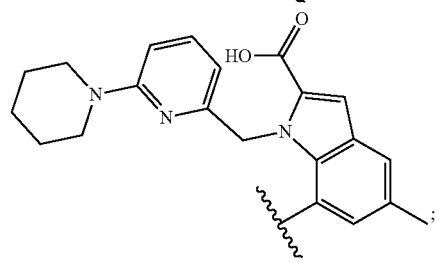
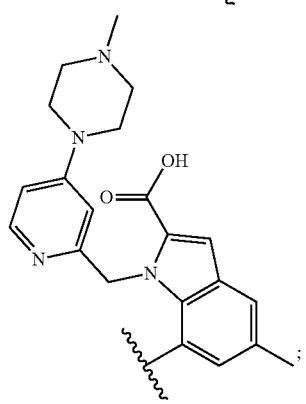
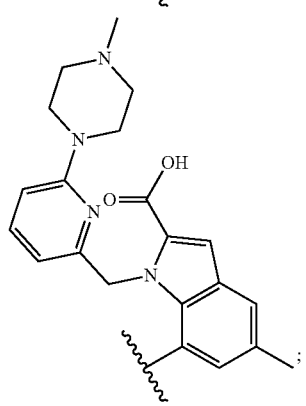
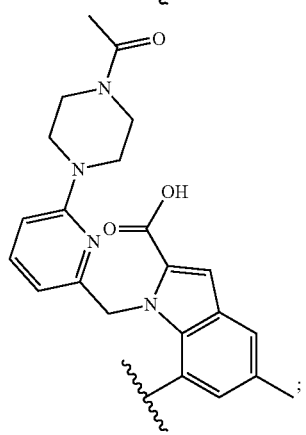
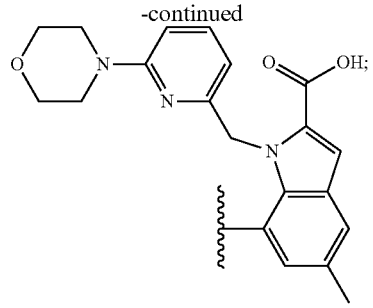
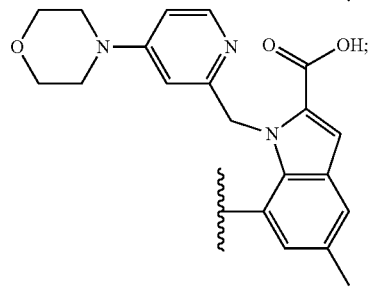
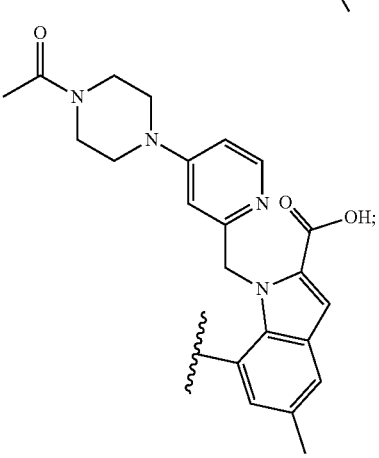
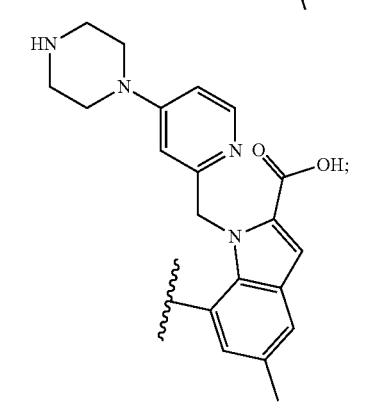
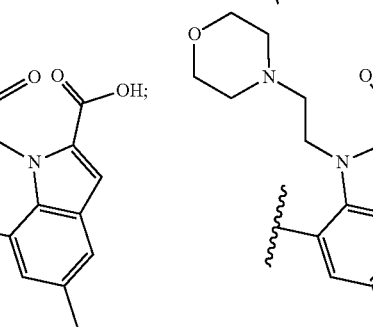

1049
-continued
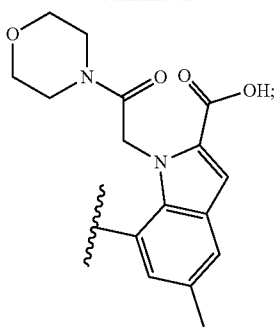
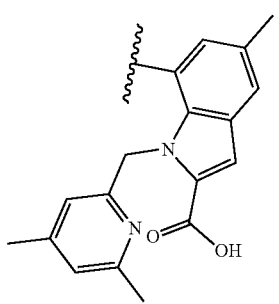
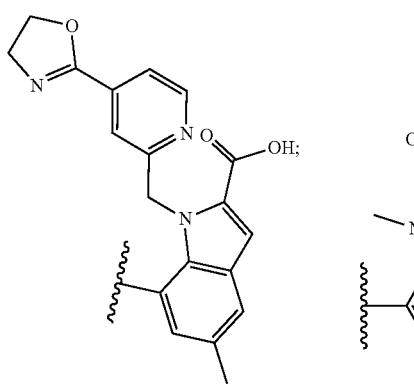
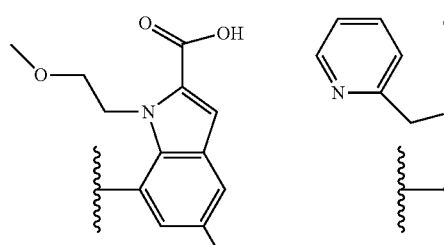
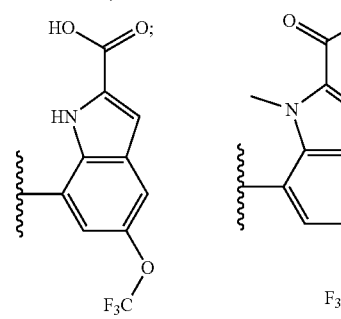
1050
-continued
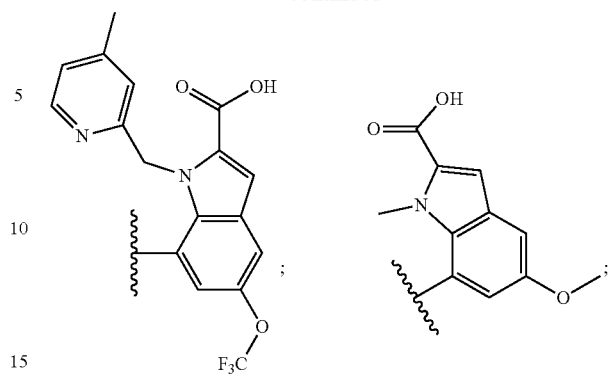
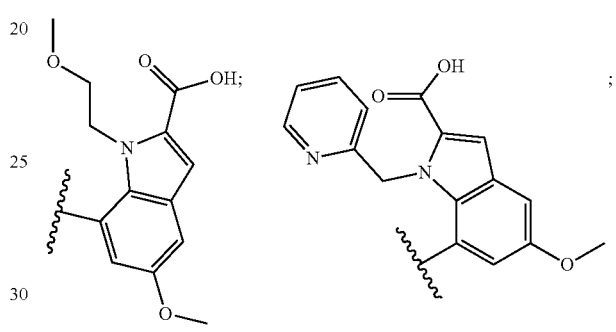
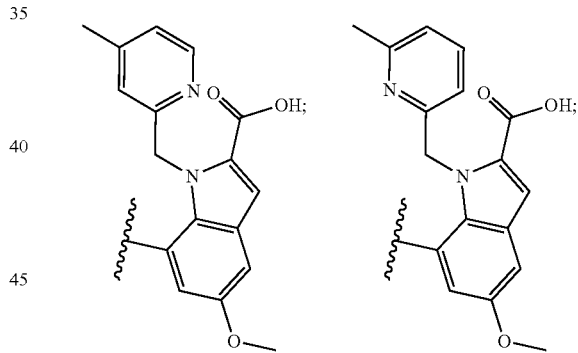
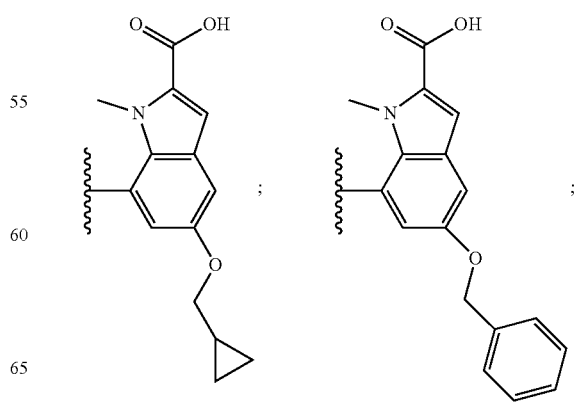

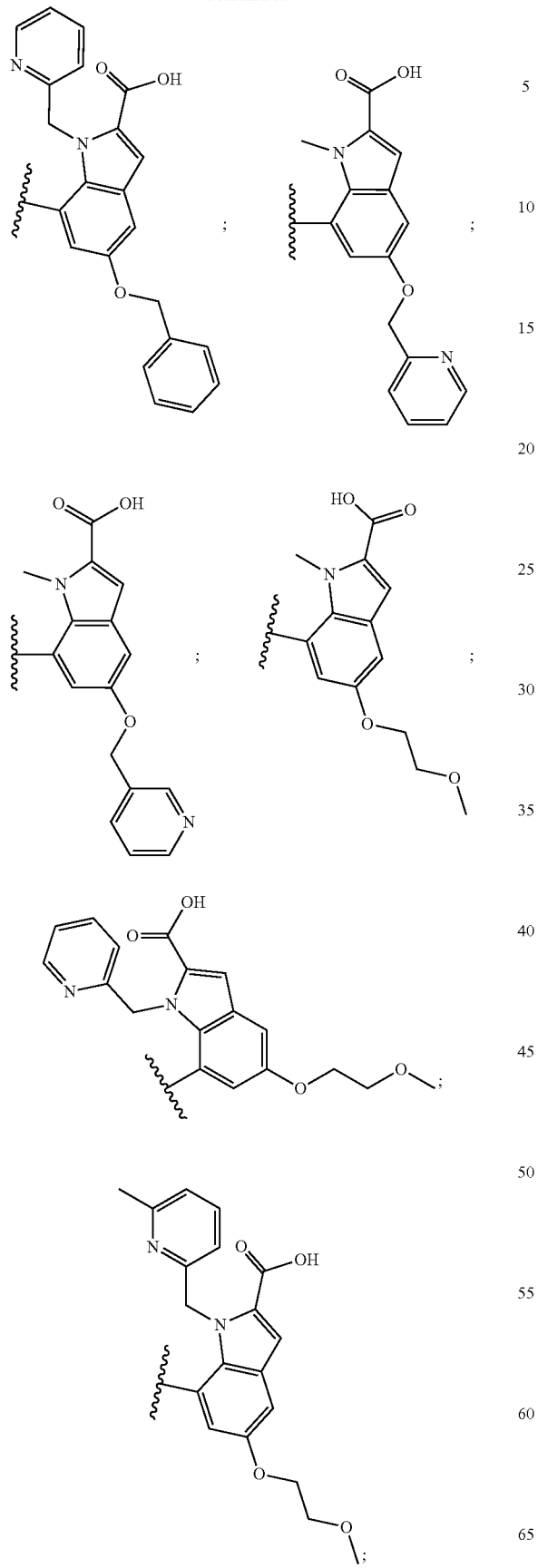
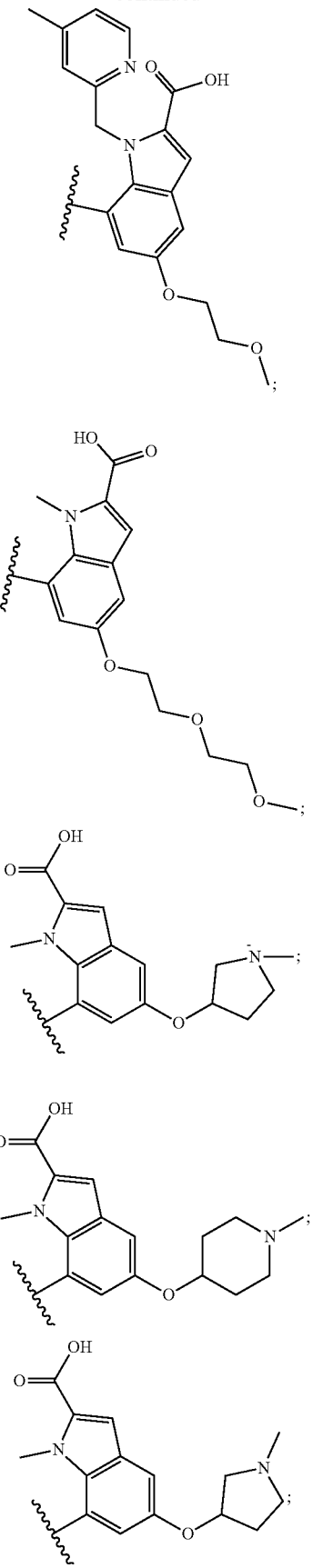

1053
-continued
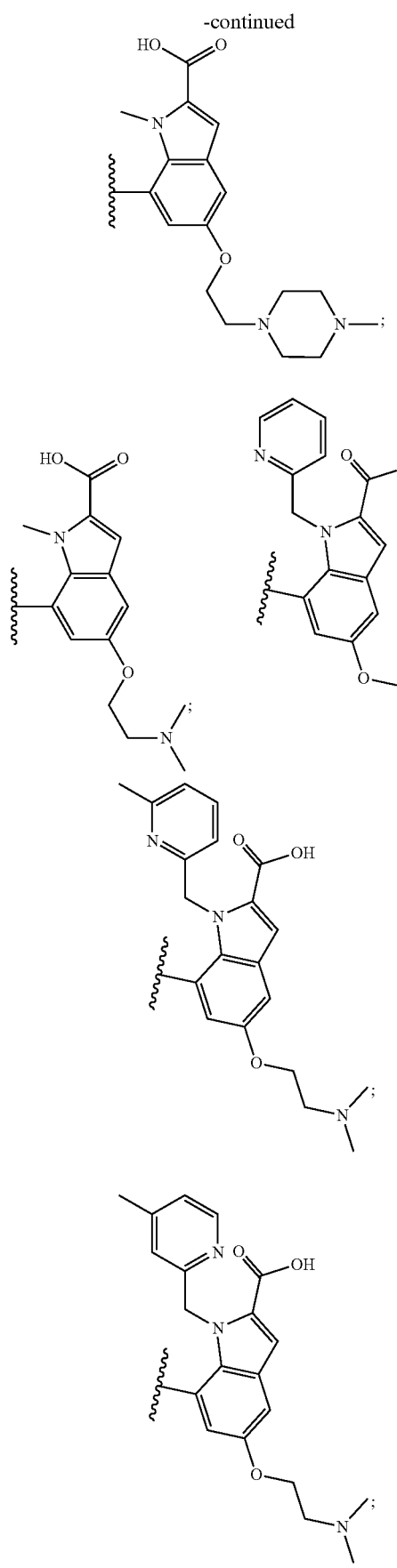
1054
-continued
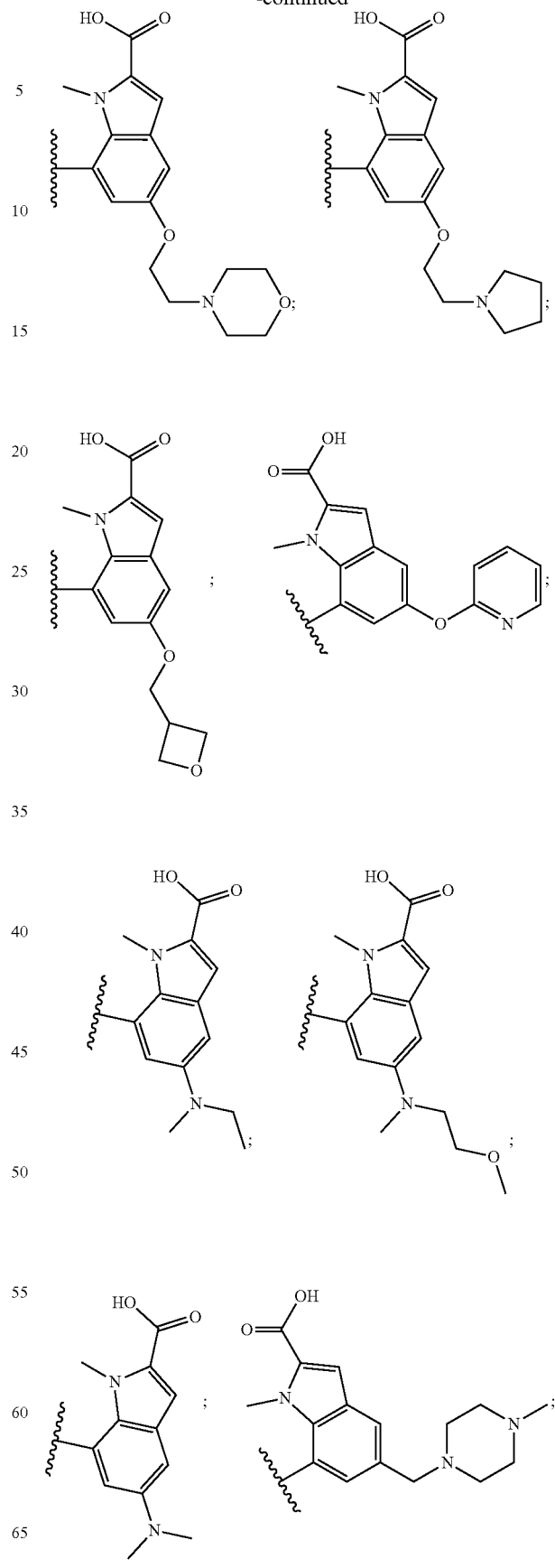

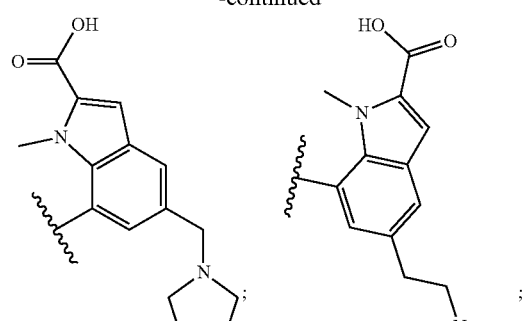
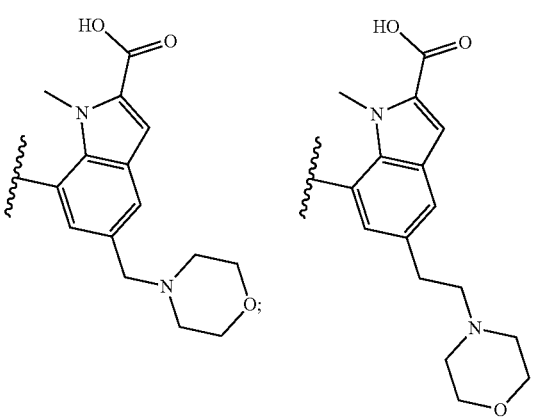
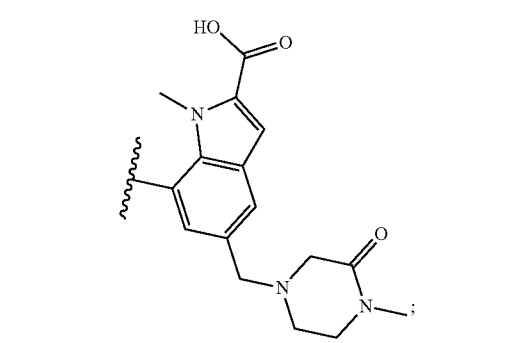
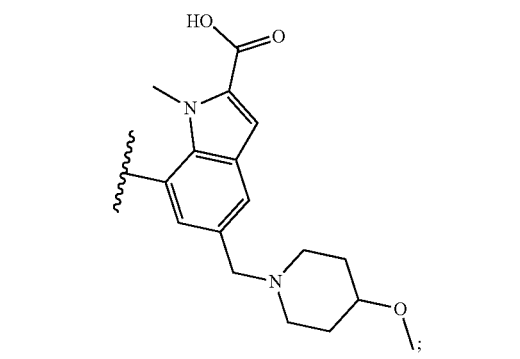
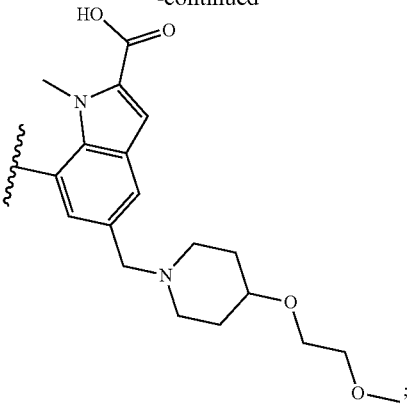
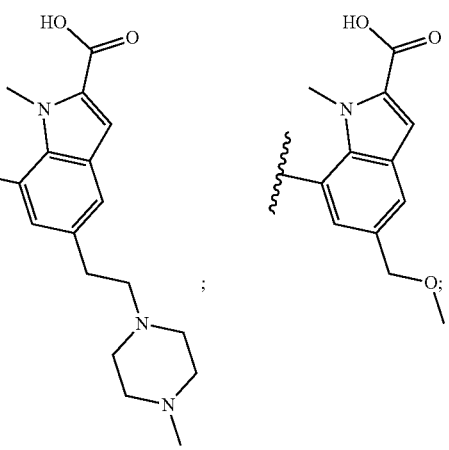
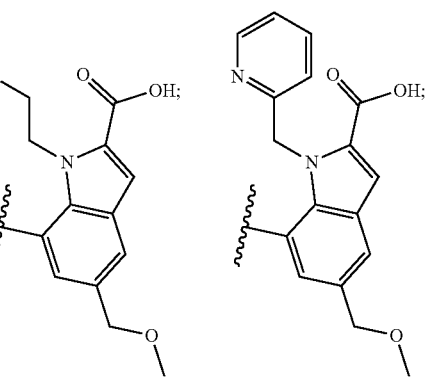
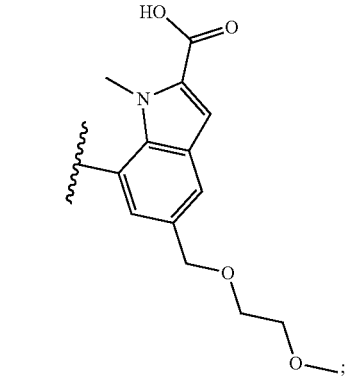

1057
-continued
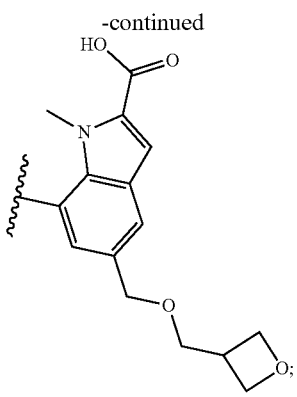
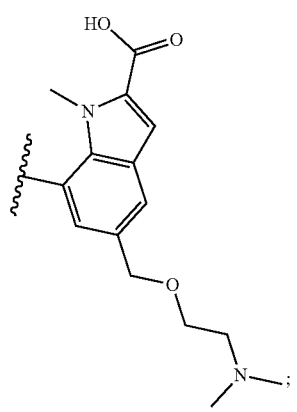
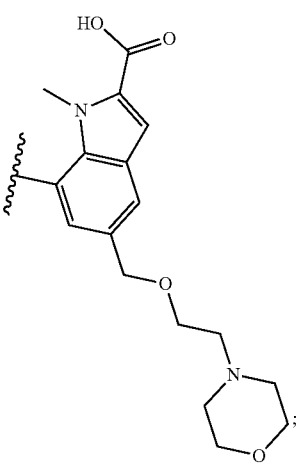
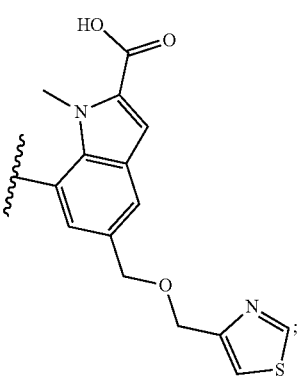
1058
-continued
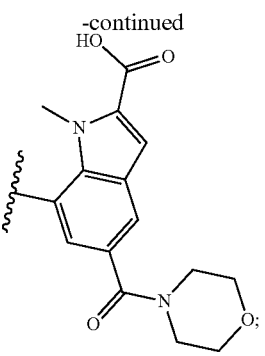
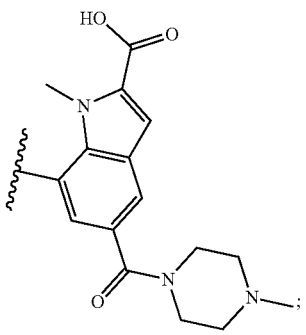
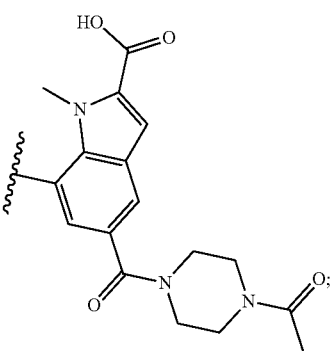
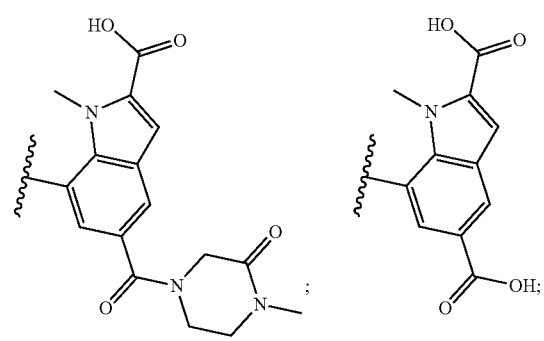
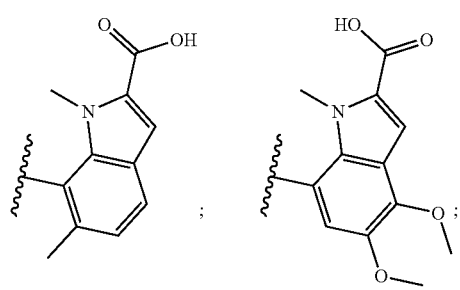

1059
-continued
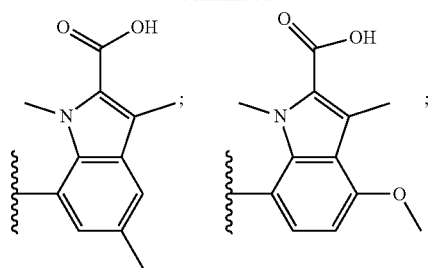
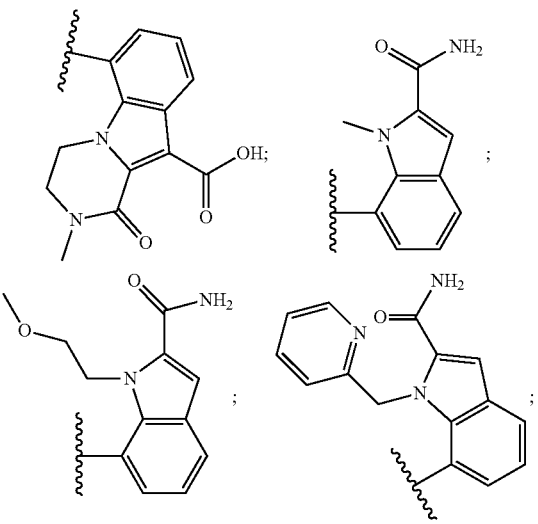
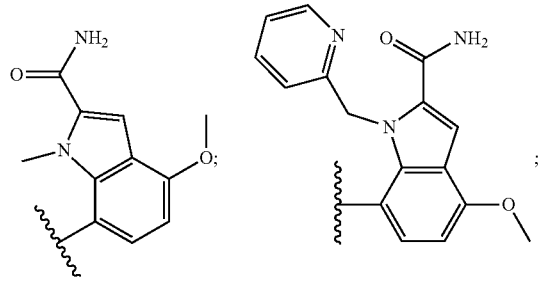
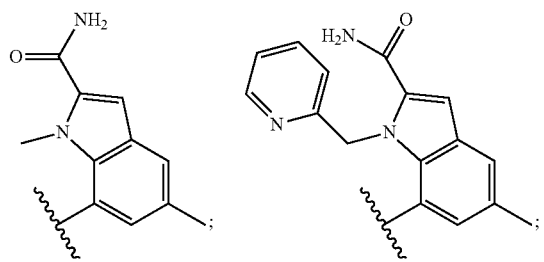
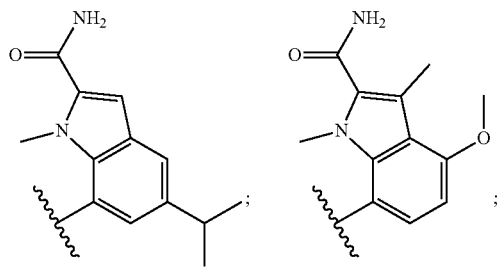
1060
-continued
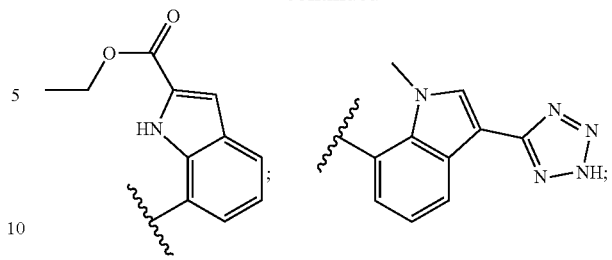
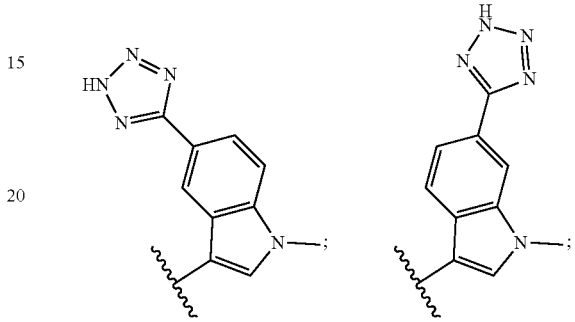
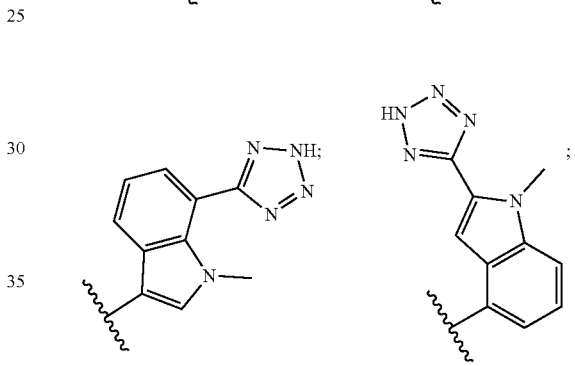
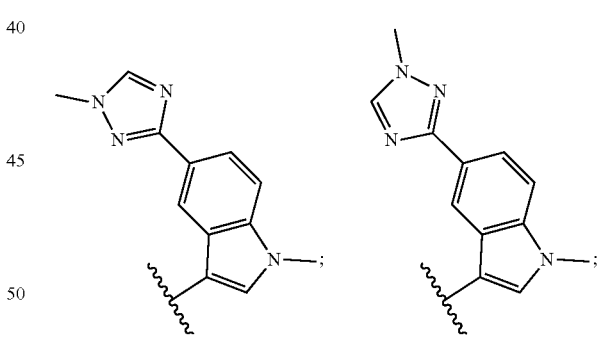
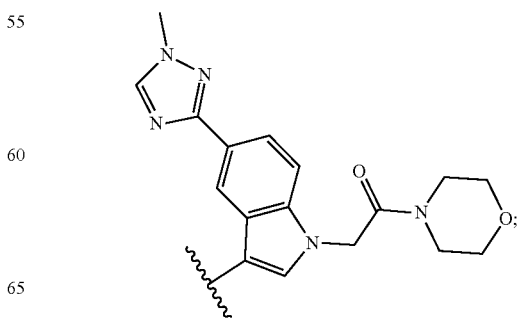

1061
-continued
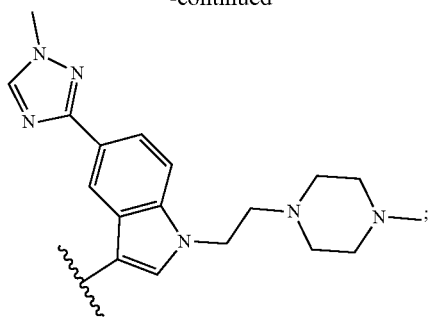
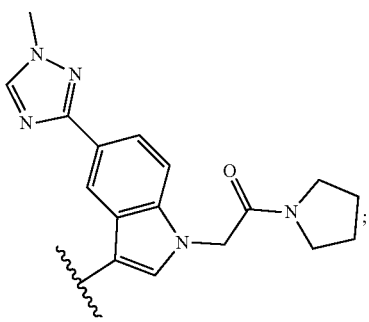
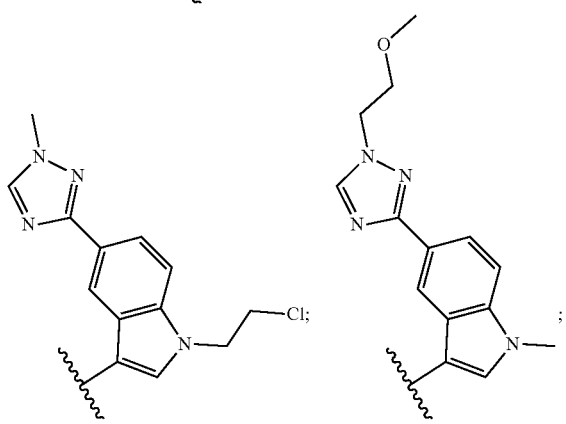
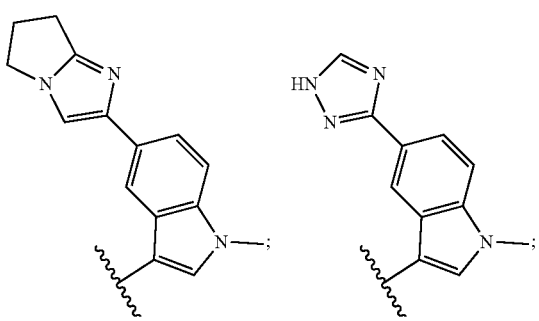
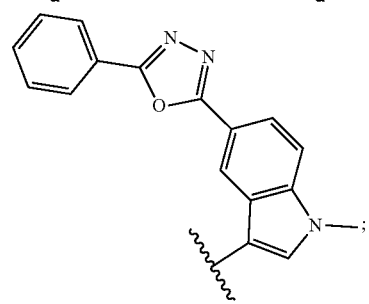
1062
-continued
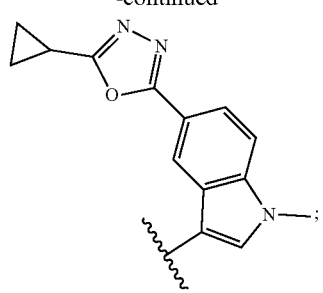
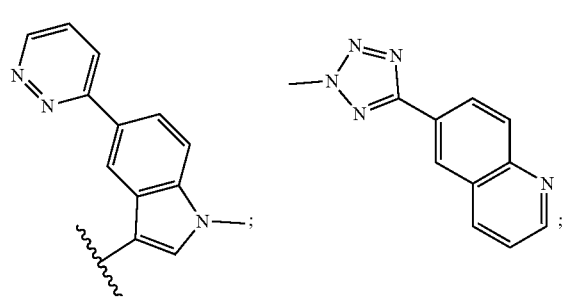
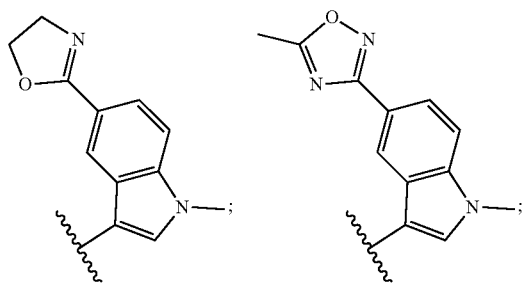
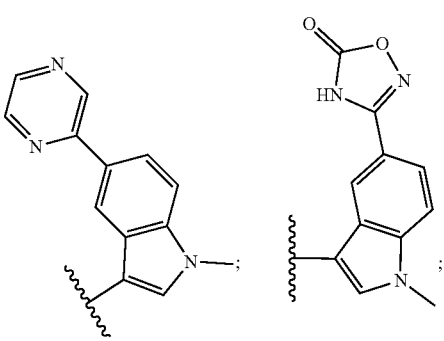
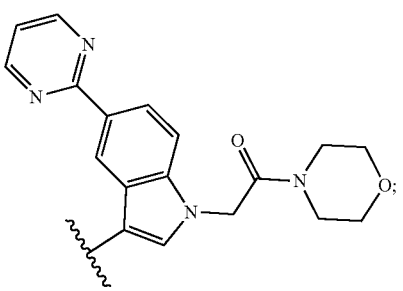

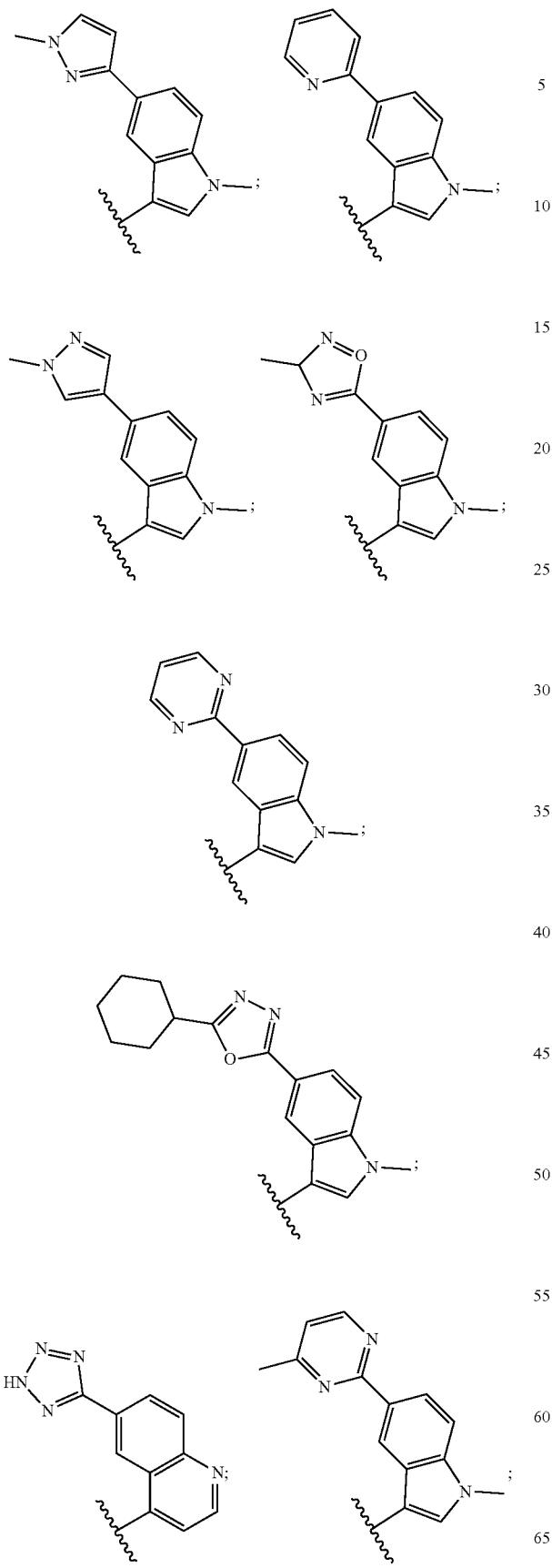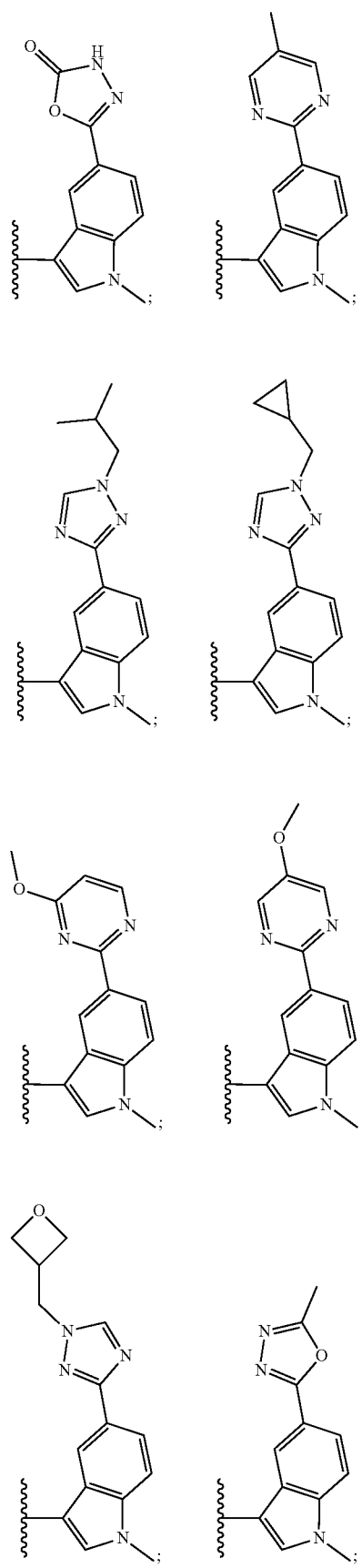

1065
-continued
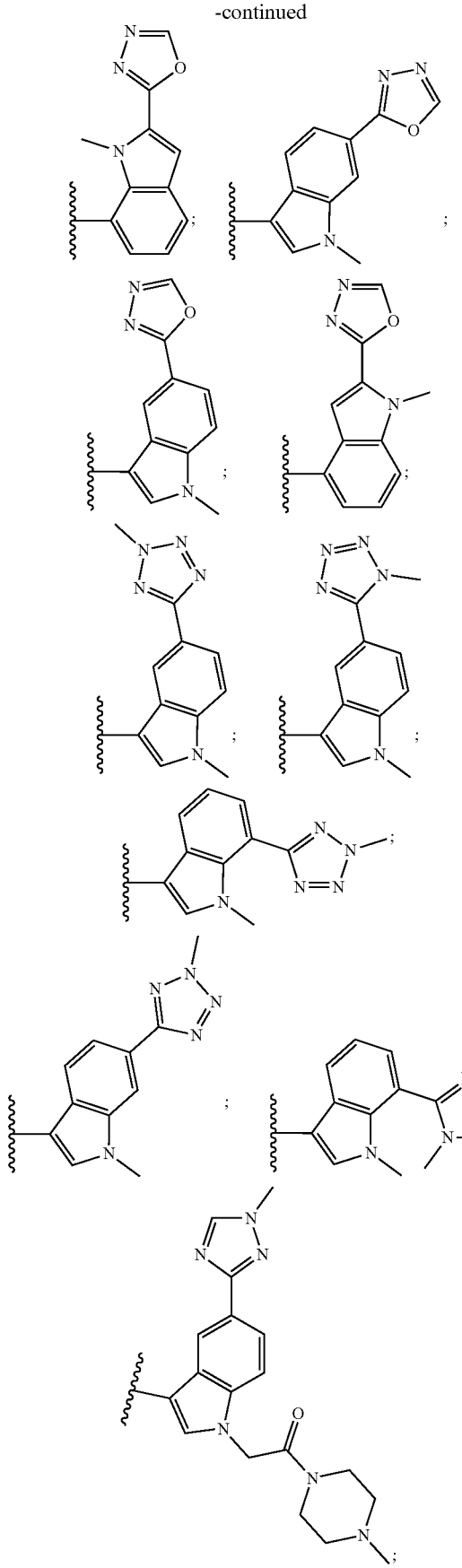
1066
-continued
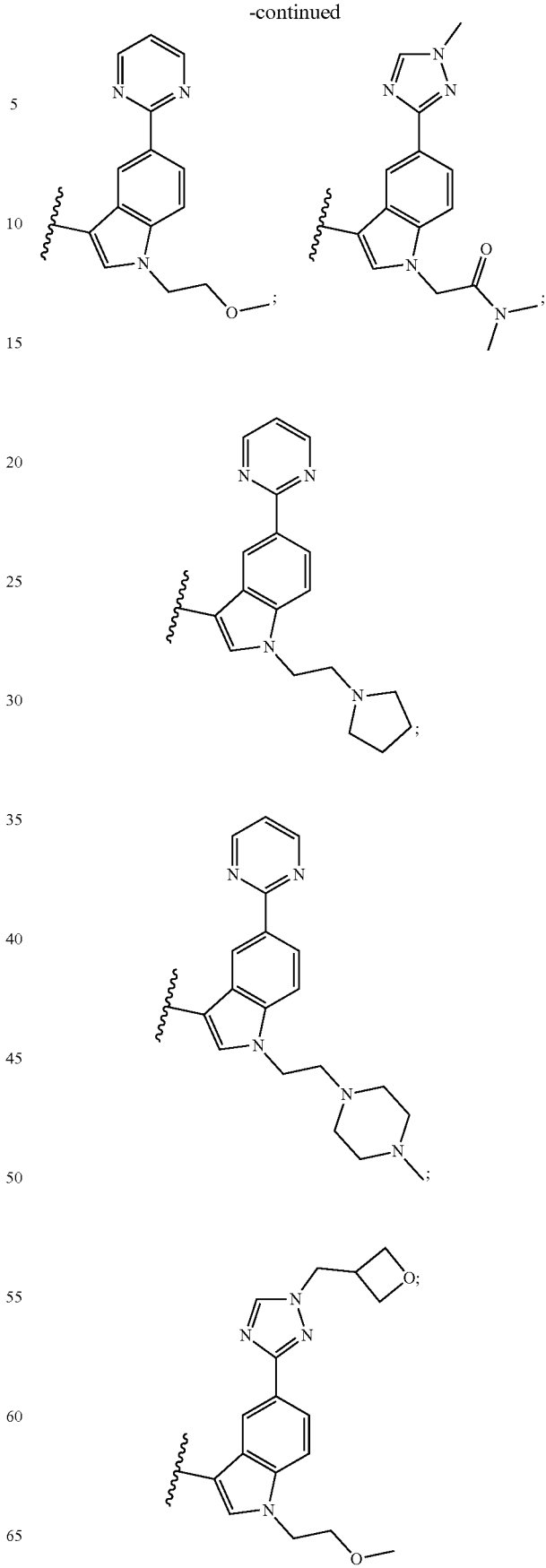

1067
-continued
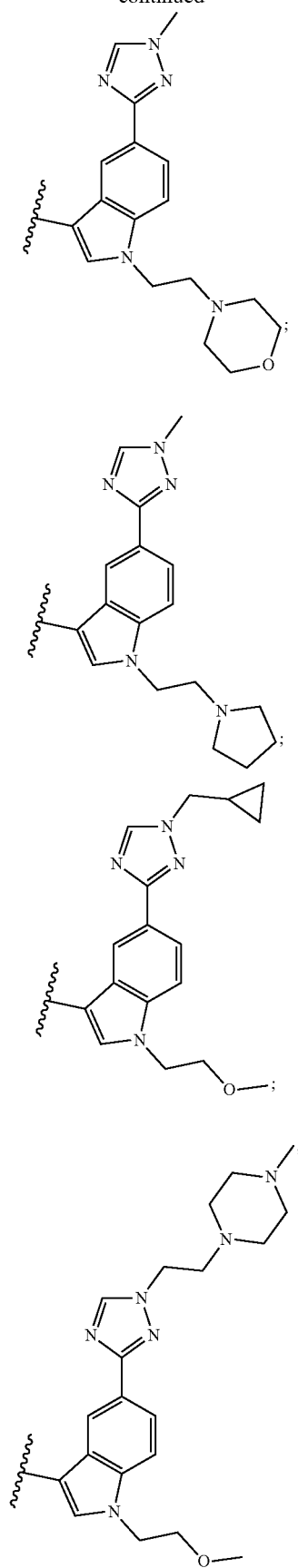
1068
-continued
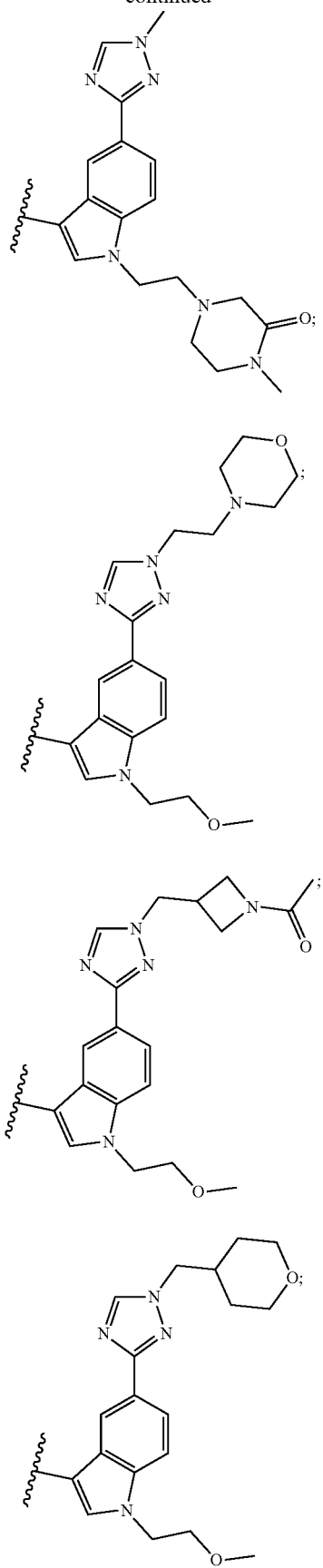

1069 -continued
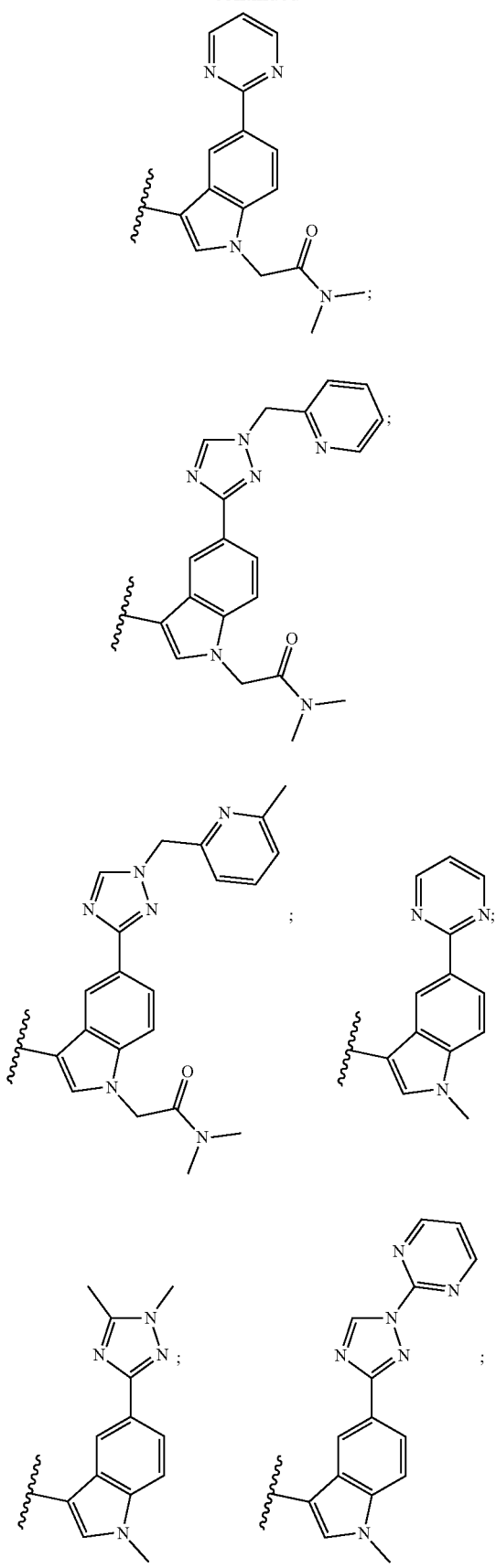
1070 -continued
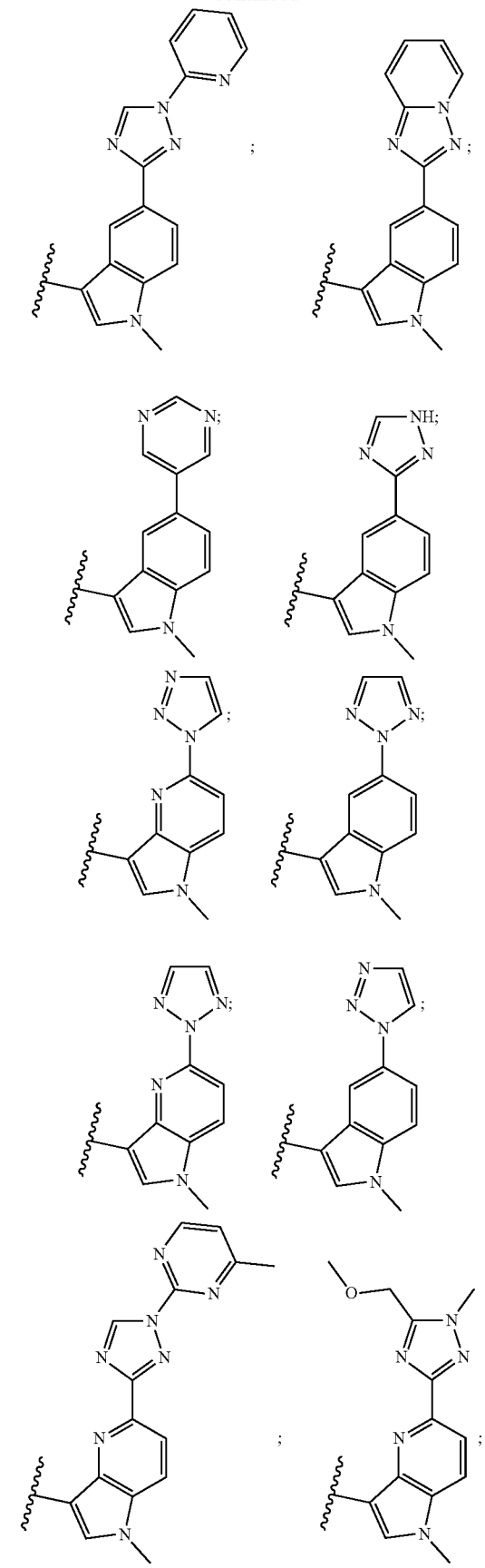

1071
-continued
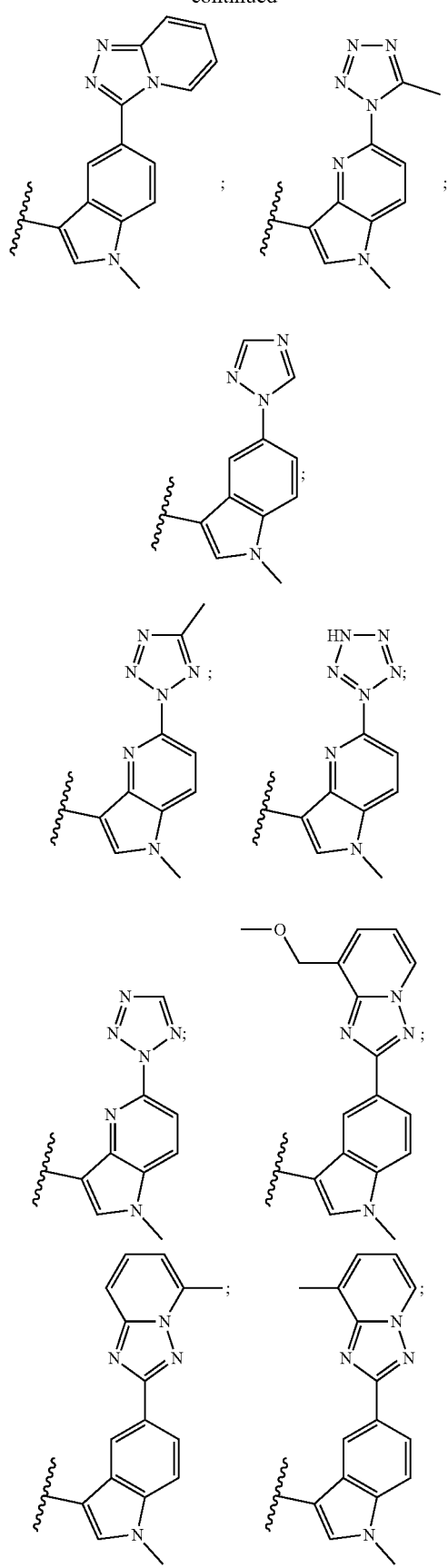
1072
-continued
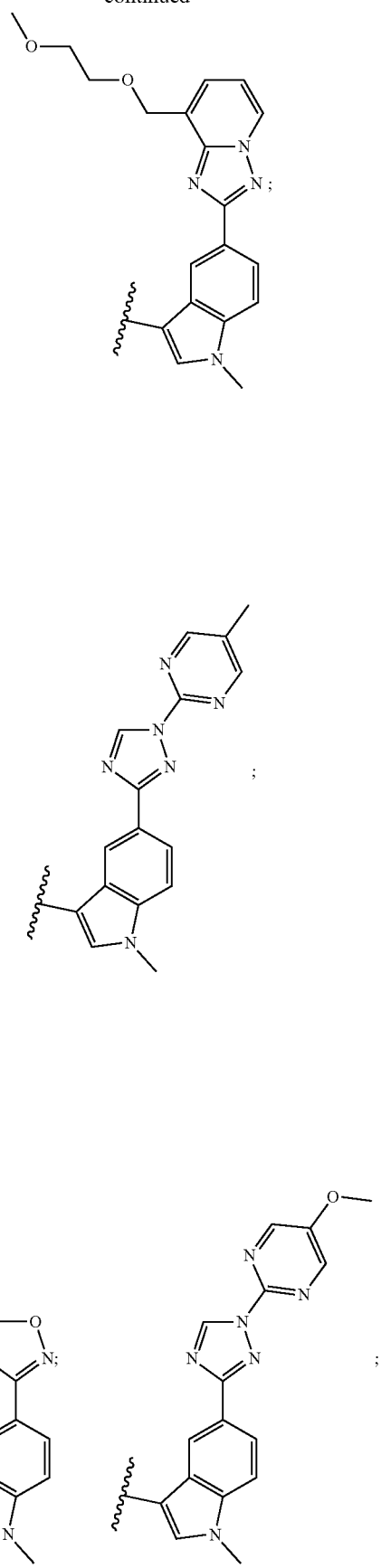

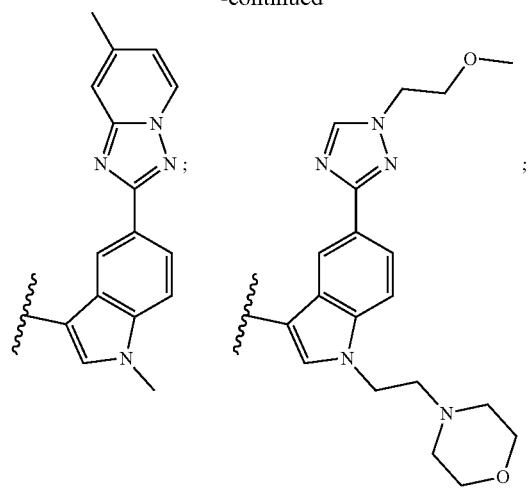
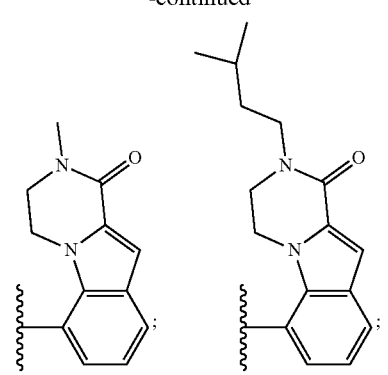
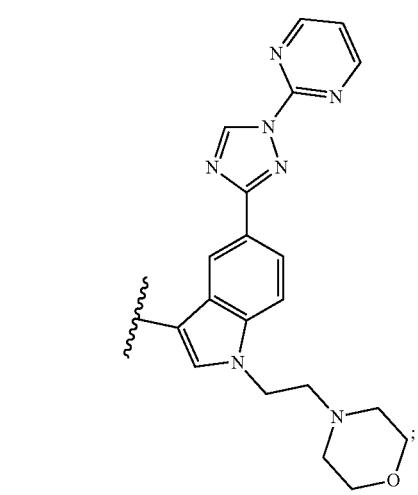
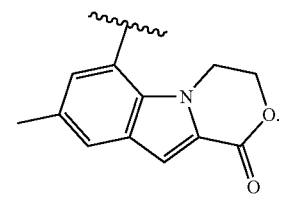
5. The compound of claim 4, or a pharmaceutically acceptable salt thereof, wherein $L^4$-$R^w$ is
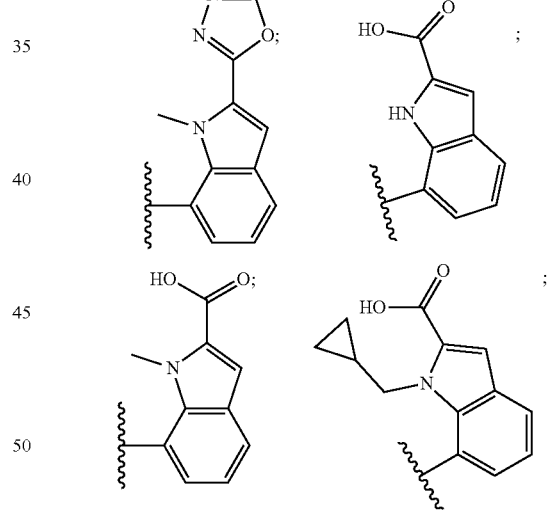
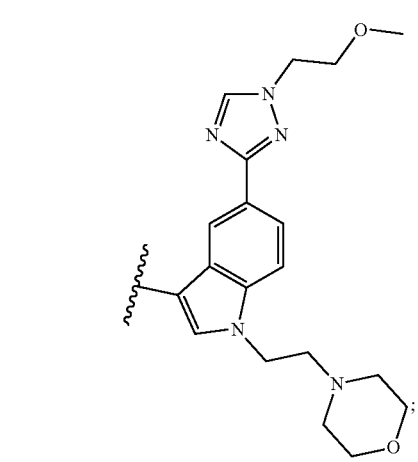
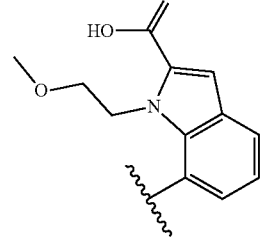
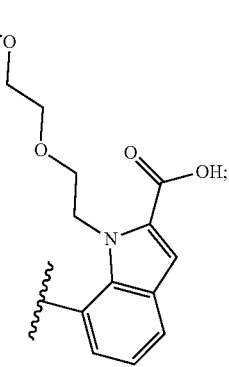

1075 -continued
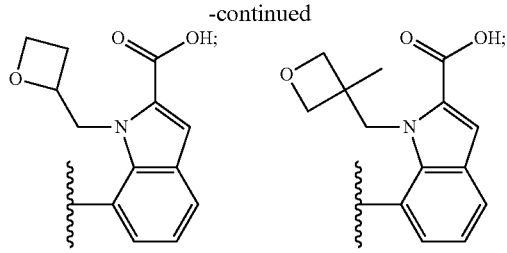
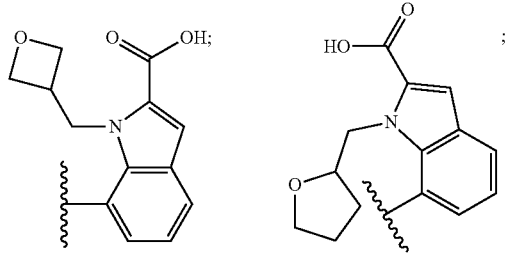
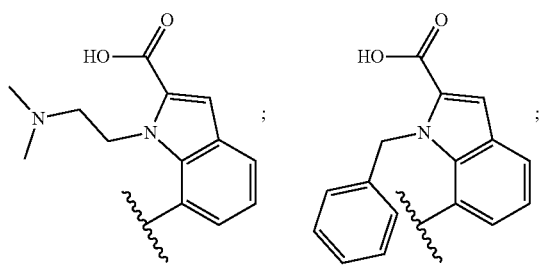
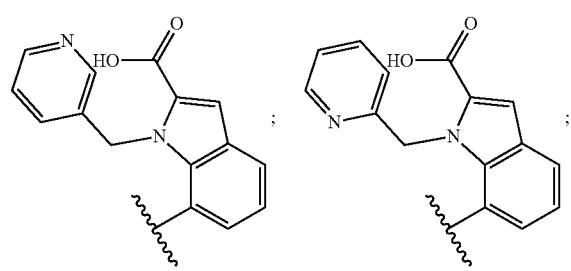
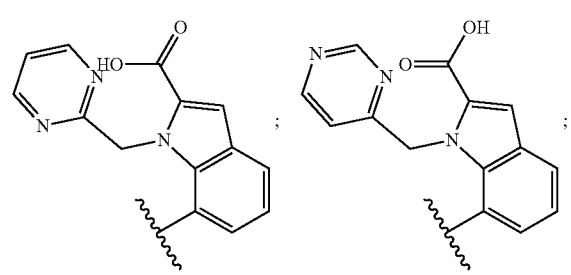
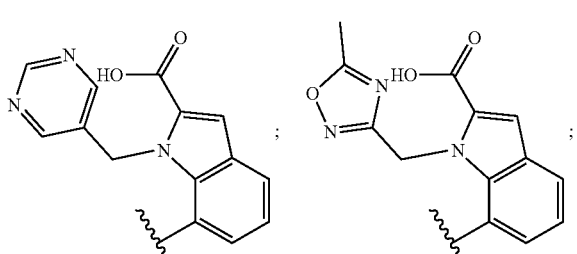
1076 -continued
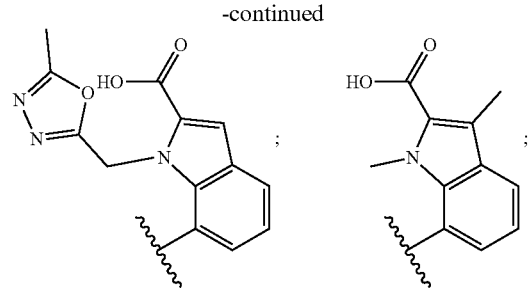
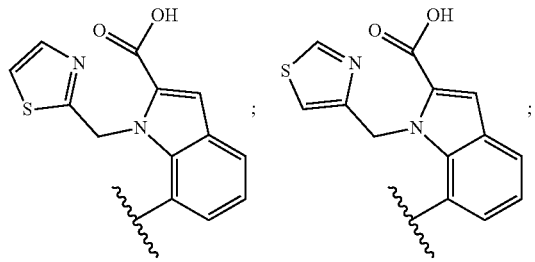
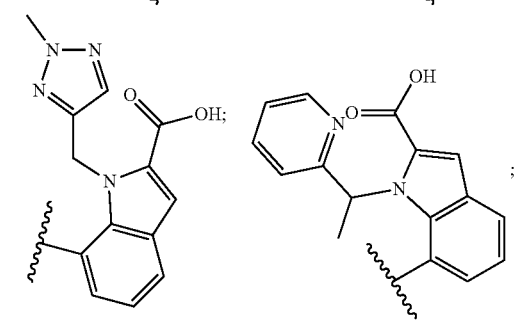
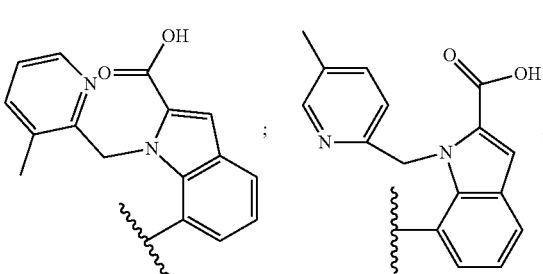
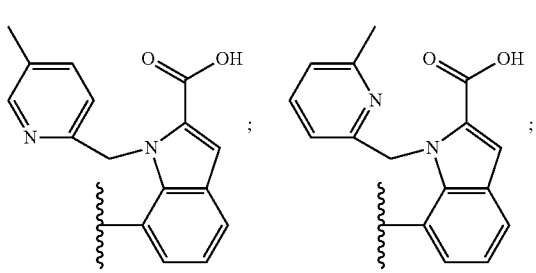
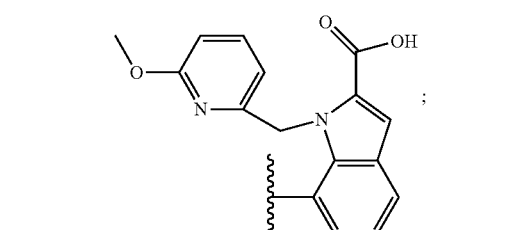

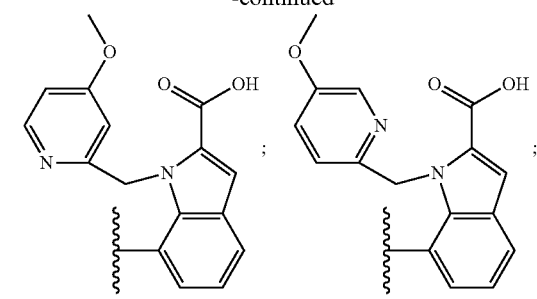
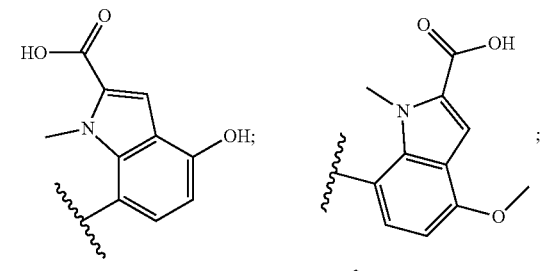
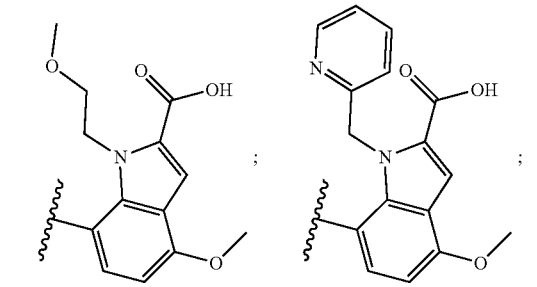
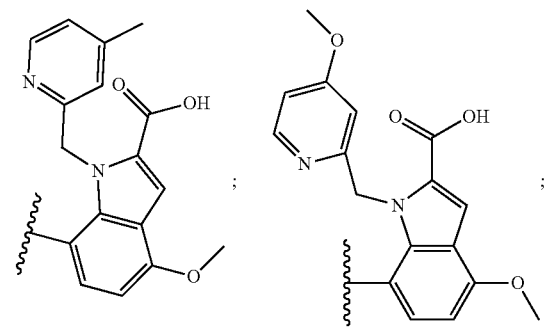
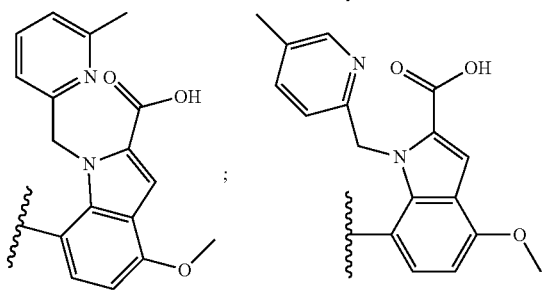
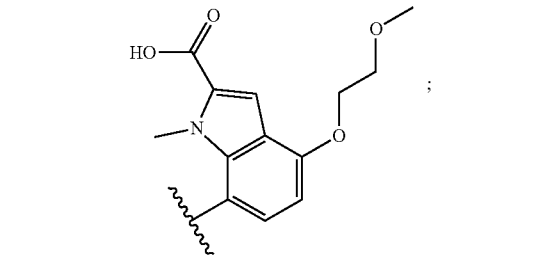
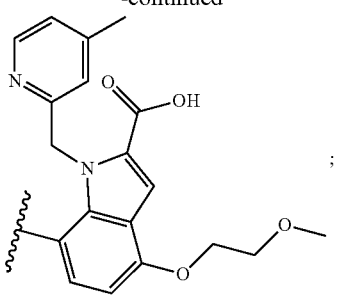
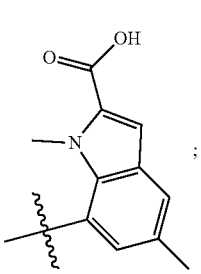
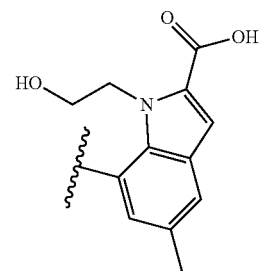
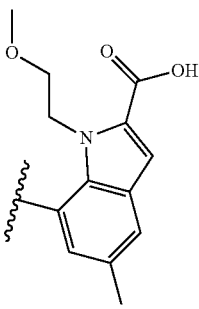
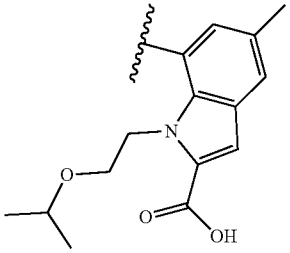
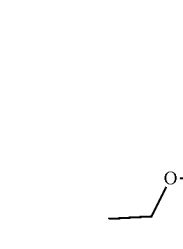
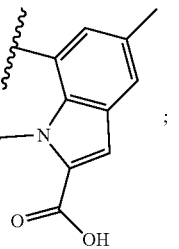
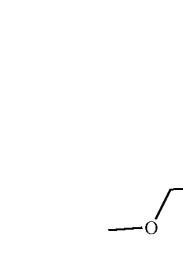
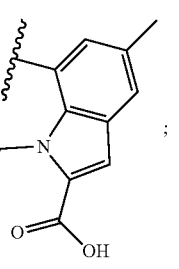

1079 -continued
1080 -continued
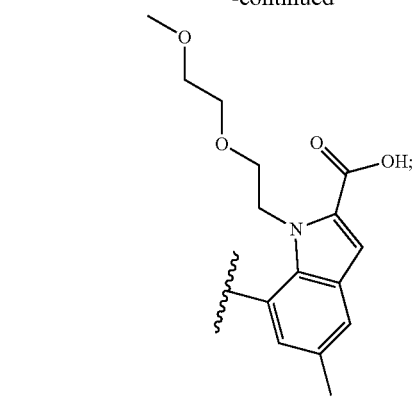
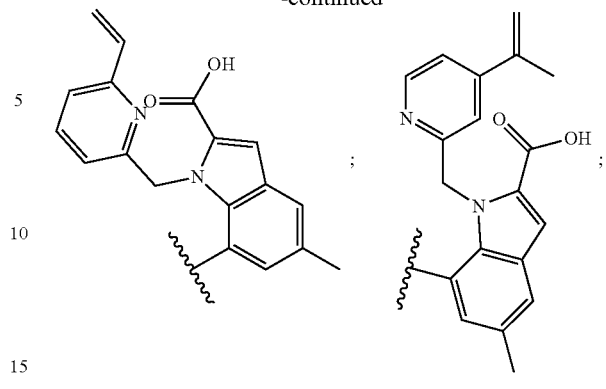
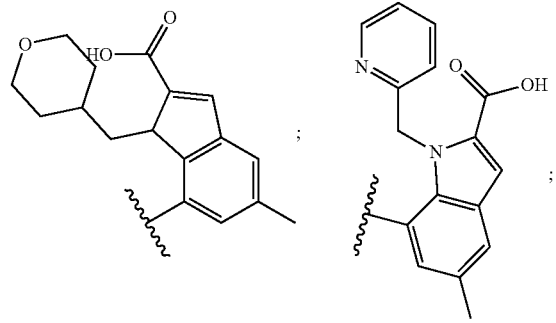
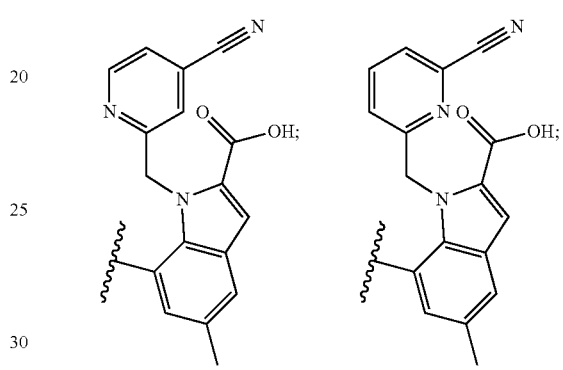
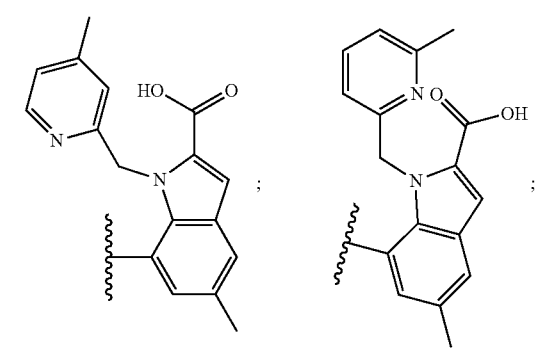
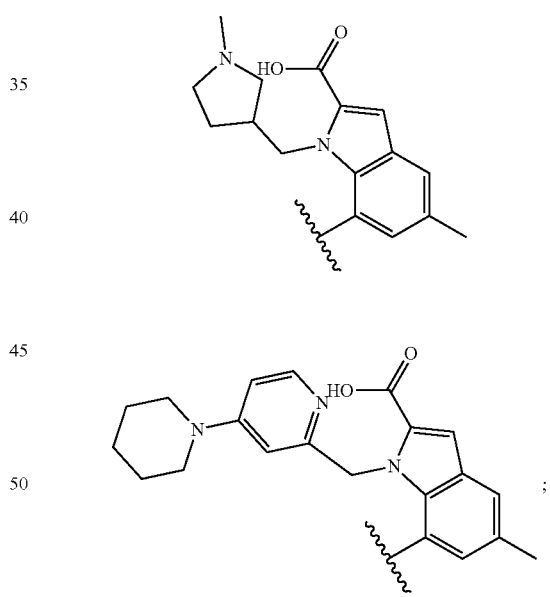
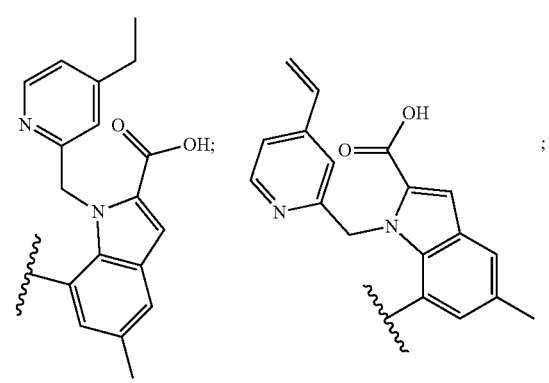
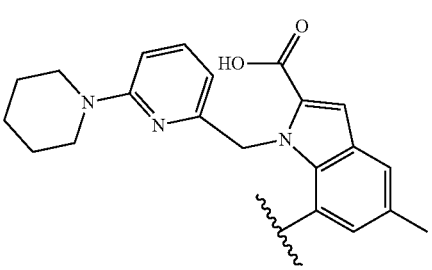

1081
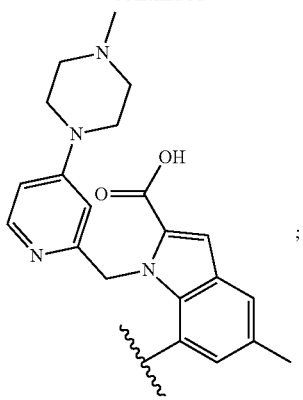
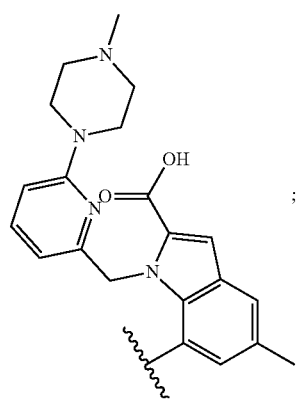
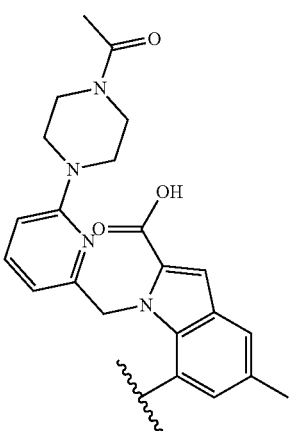
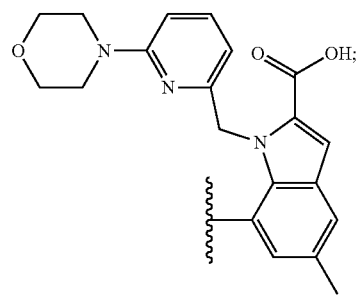
1082
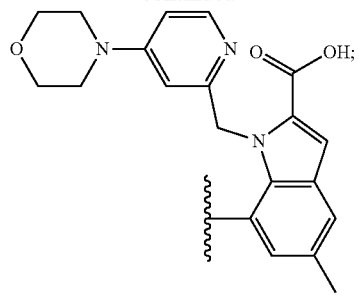
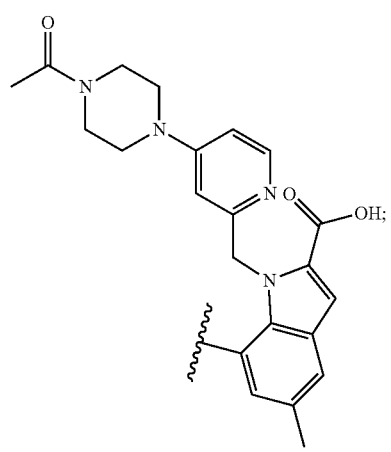
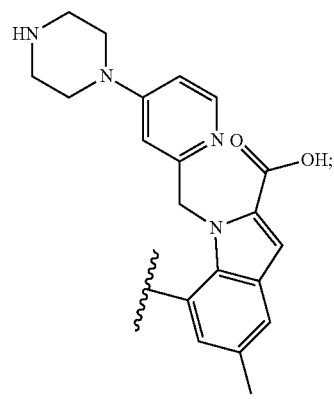
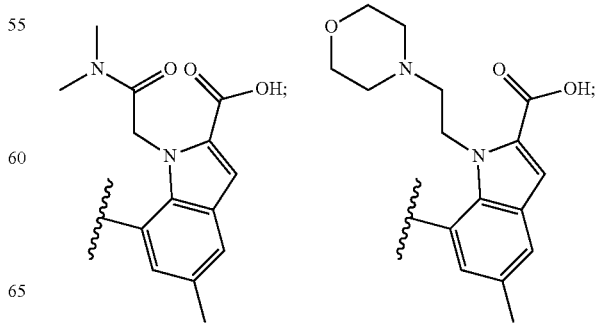

1083
-continued
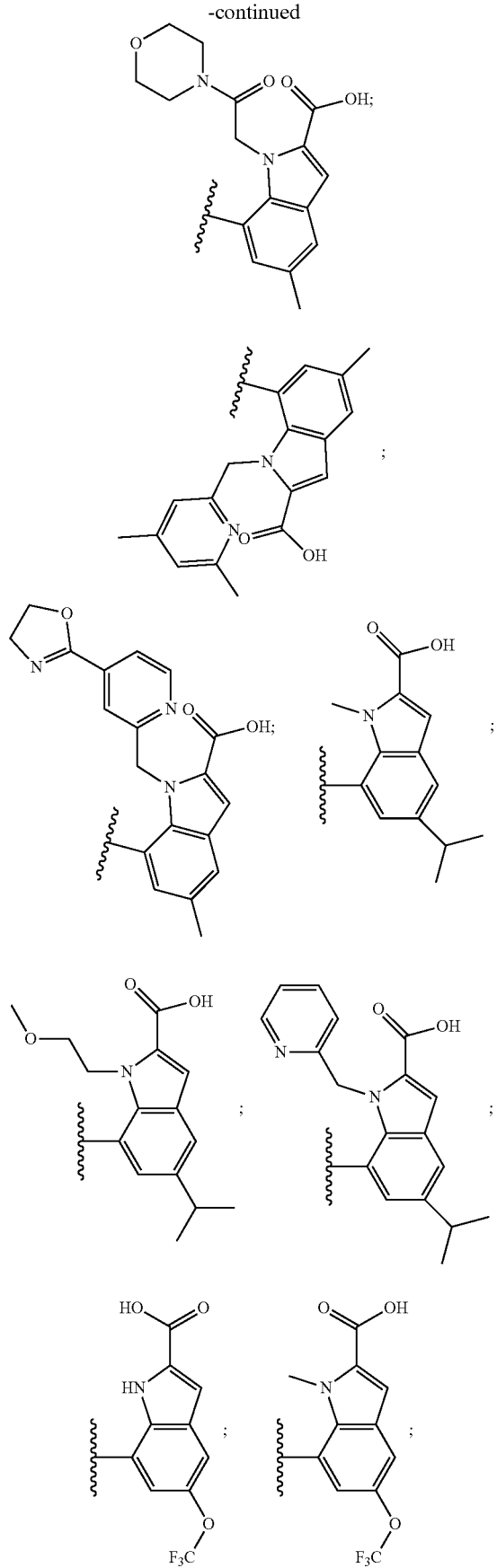
1084
-continued
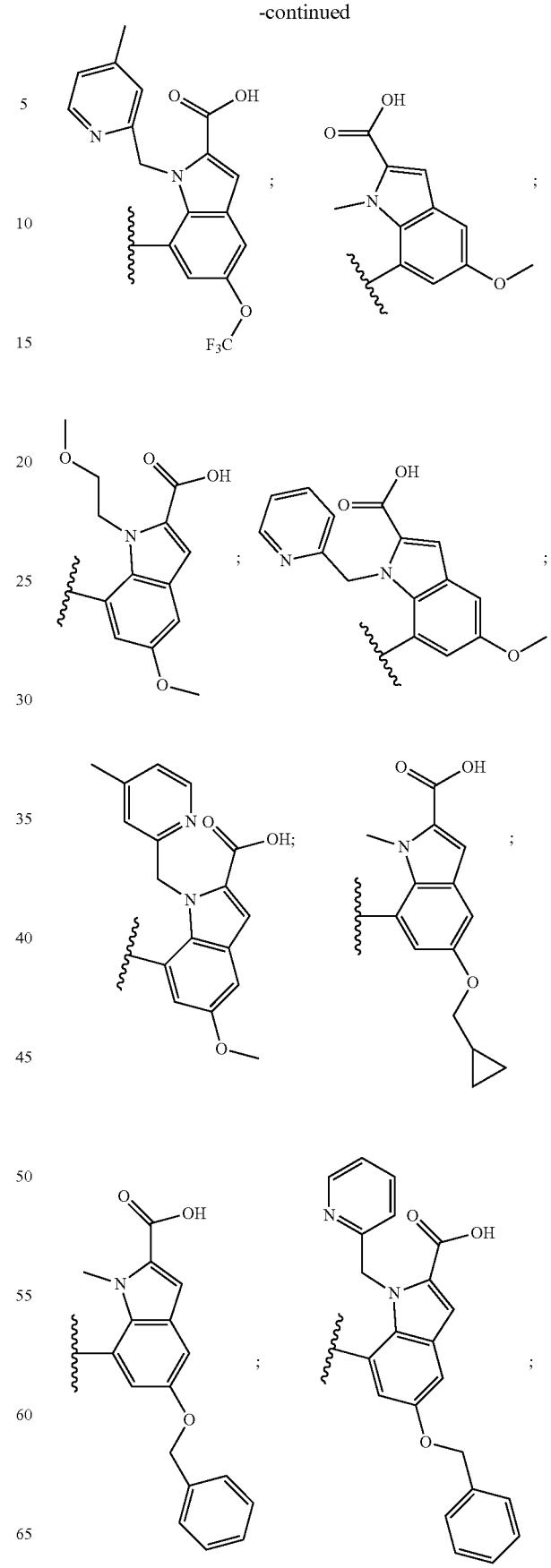

1085
-continued
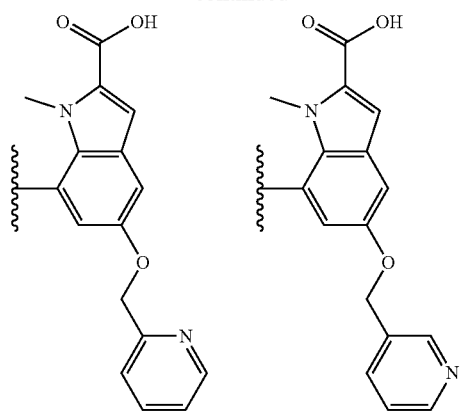
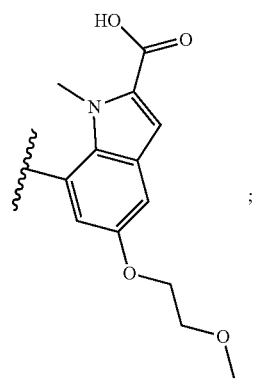
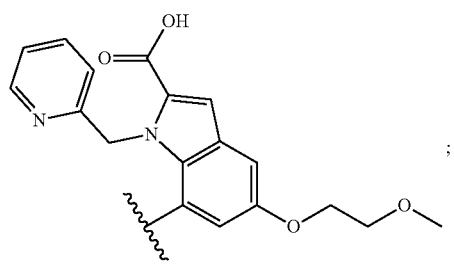
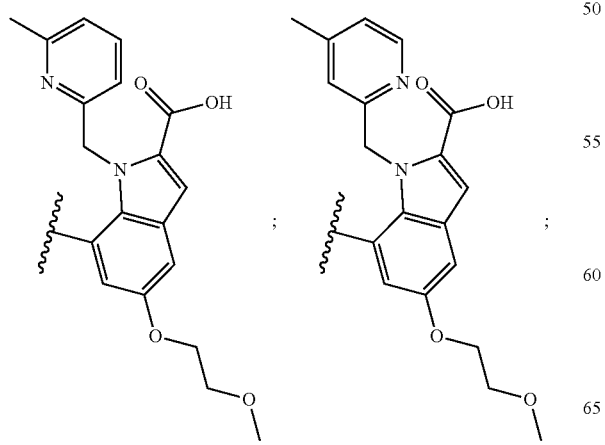
1086
-continued
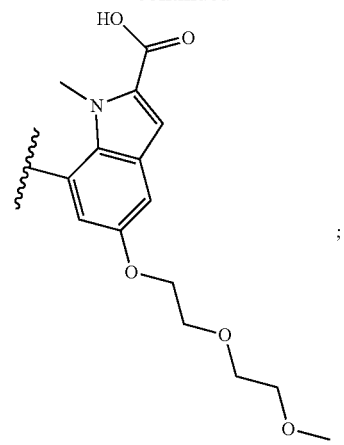
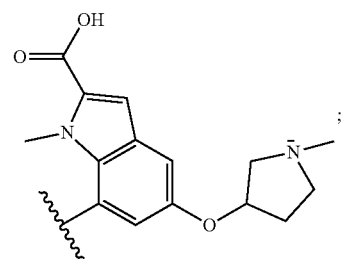
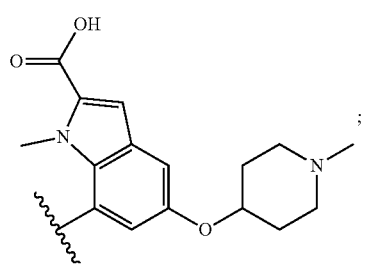
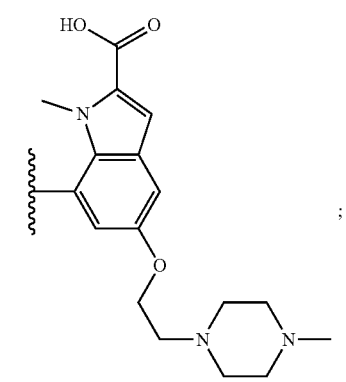

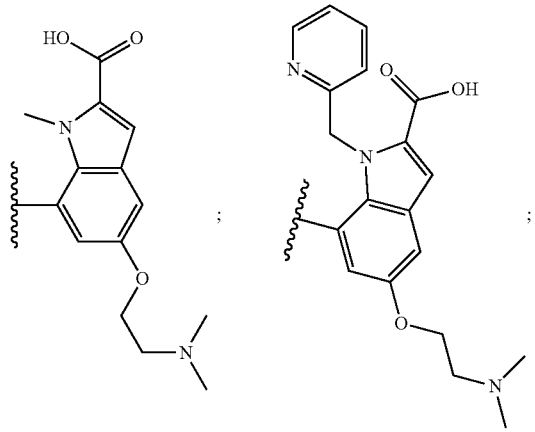
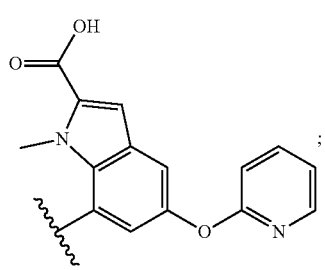
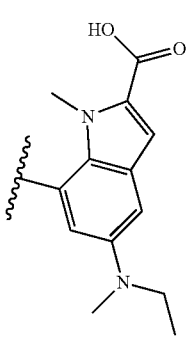
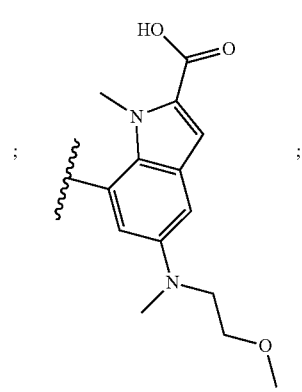
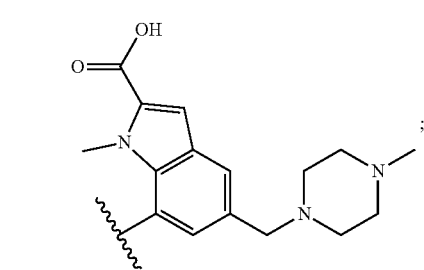
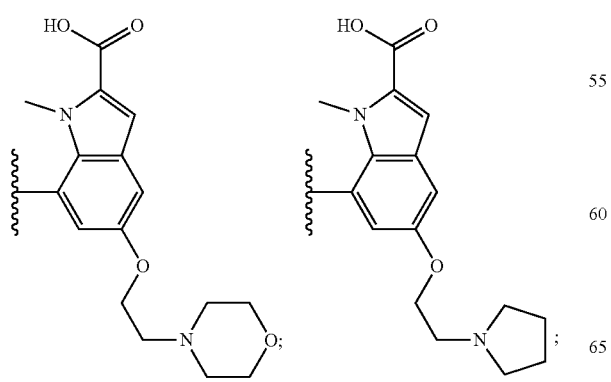

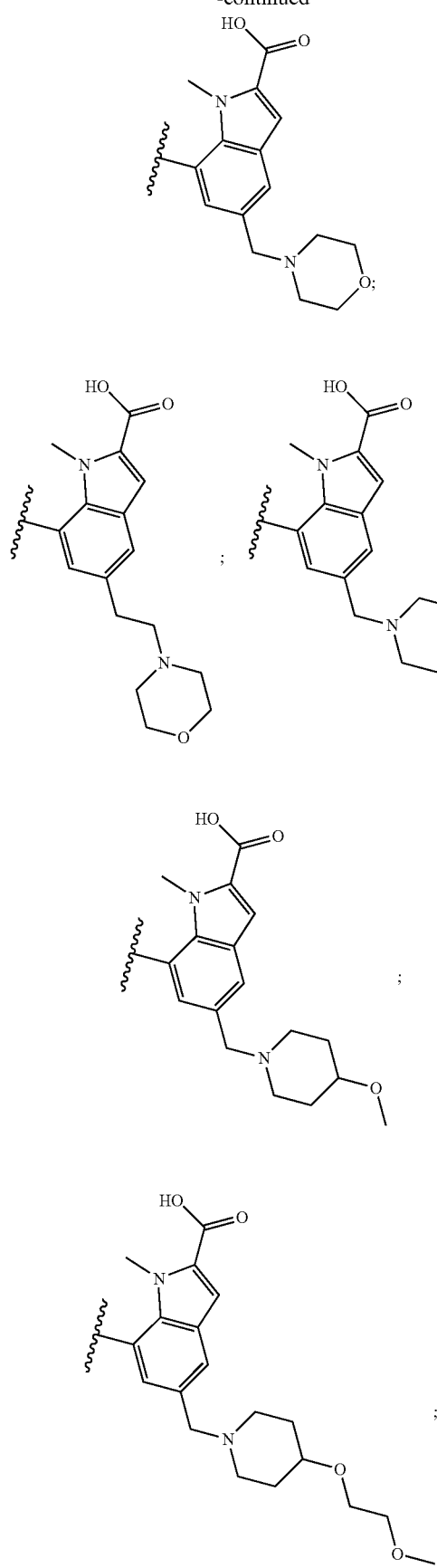
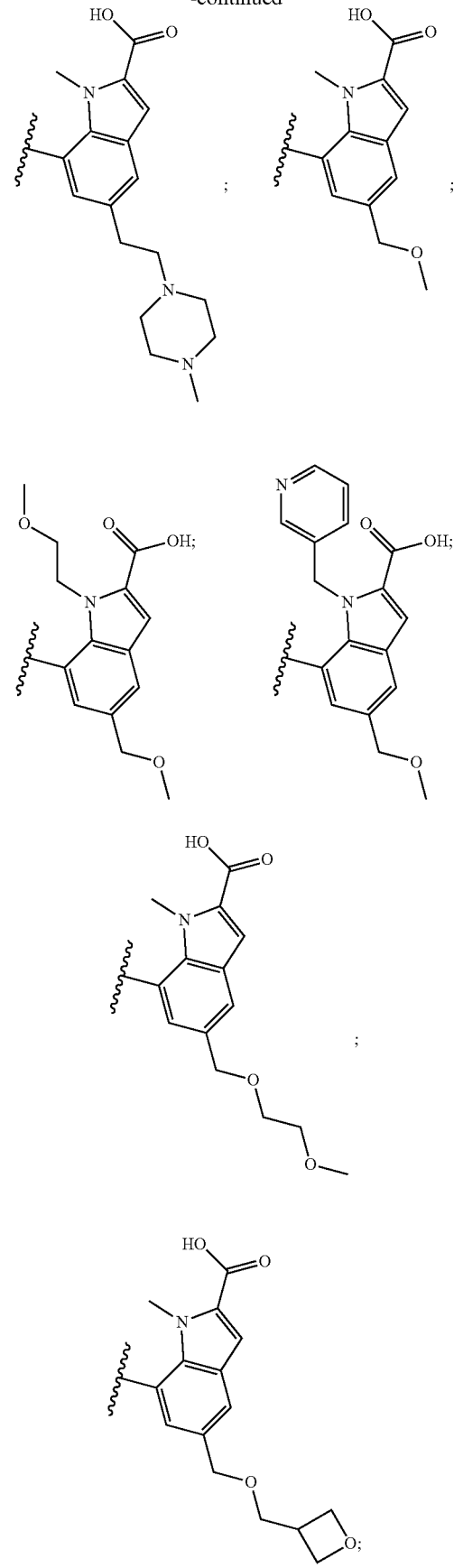

1091
-continued
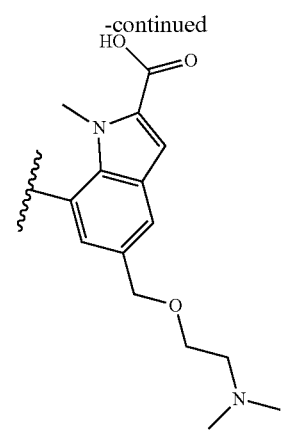
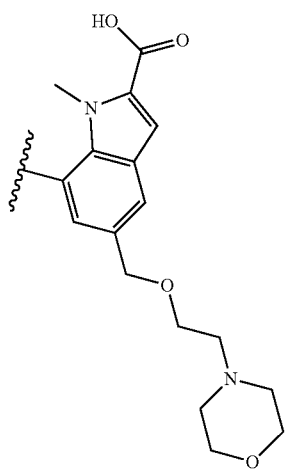
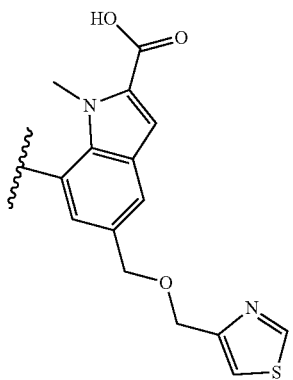
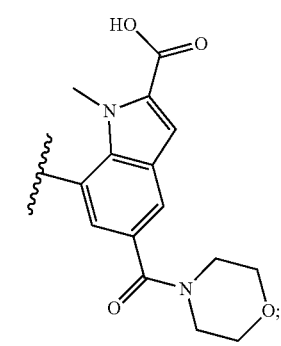
1092
-continued
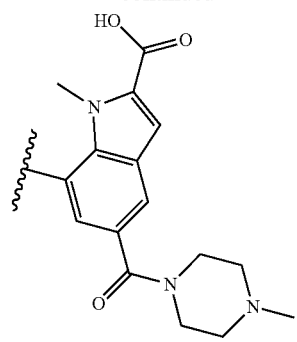
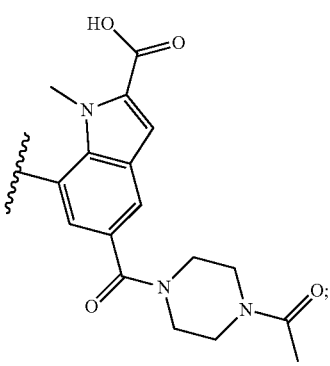
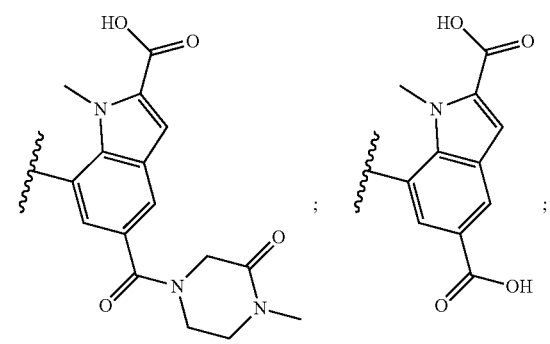
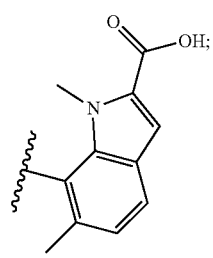 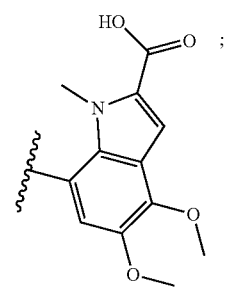
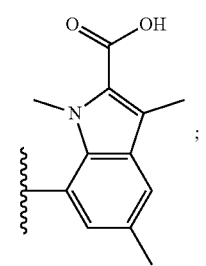 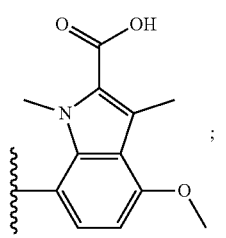

1093
-continued
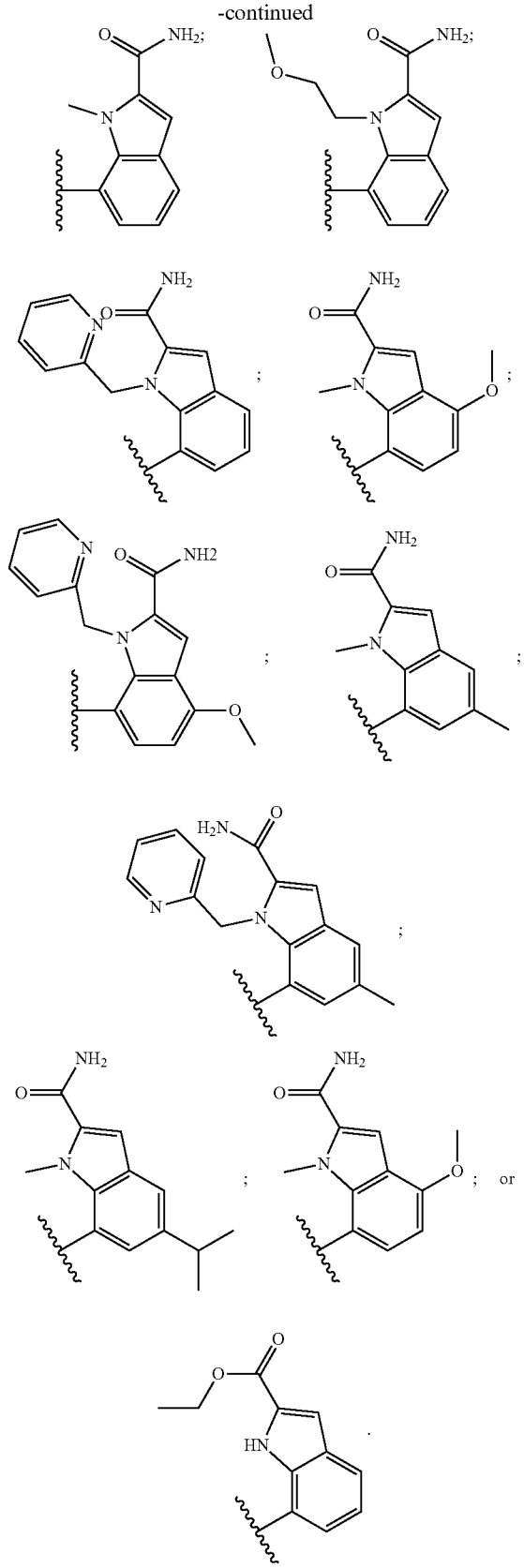
1094
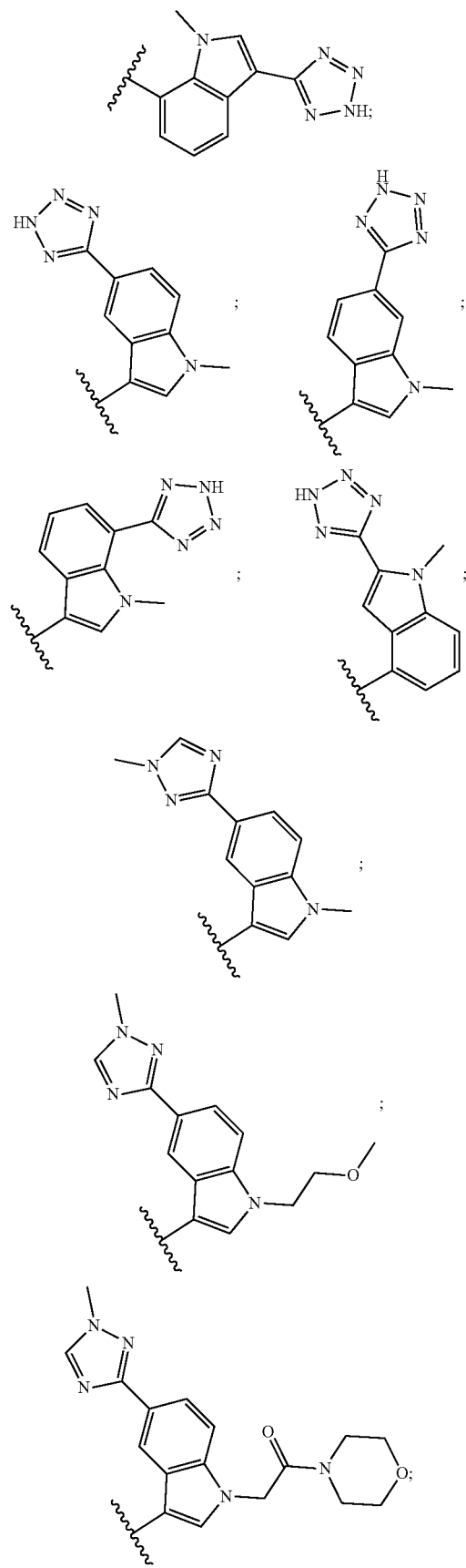
6. The compound of claim 4, or a pharmaceutically acceptable salt thereof, wherein $L^4$-$R^w$ is 1095
-continued
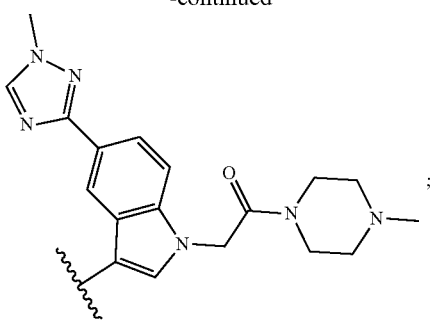
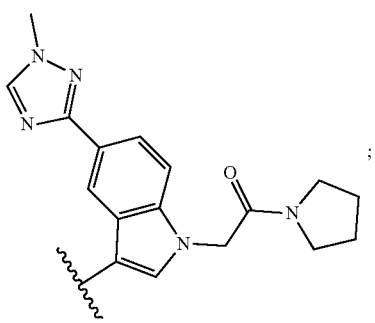
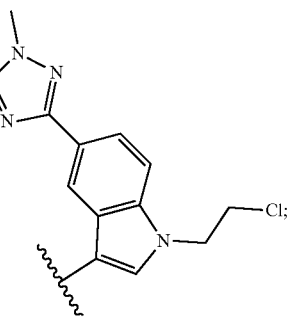
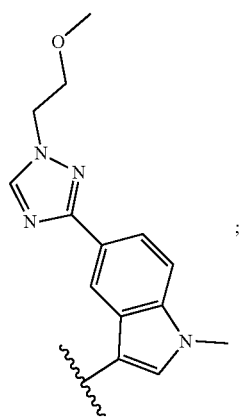
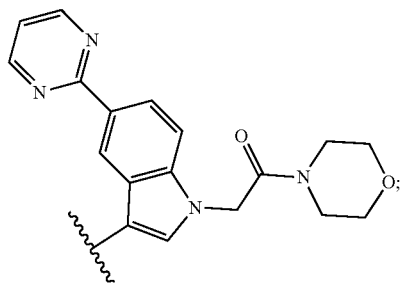
1096
-continued
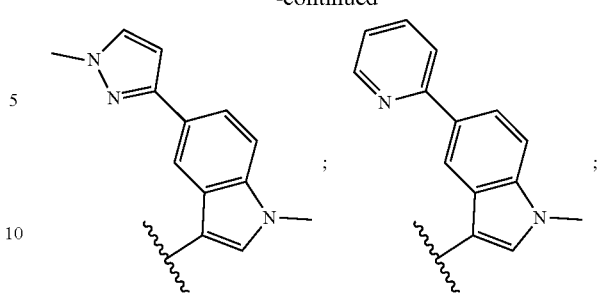
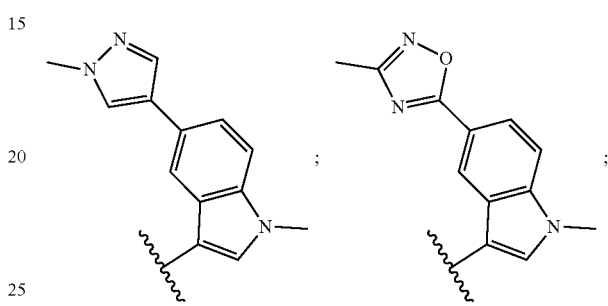
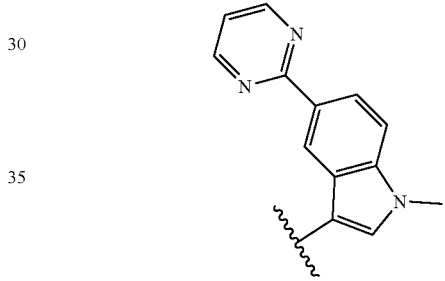
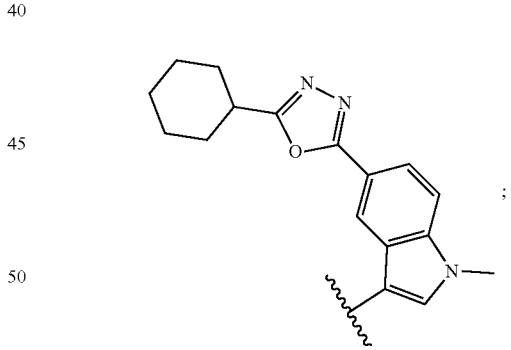
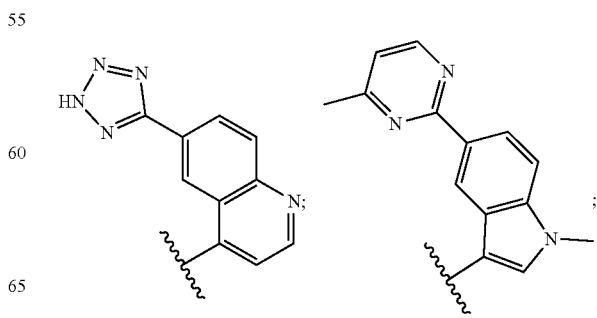

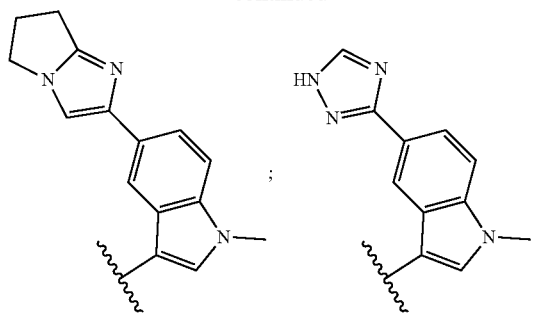
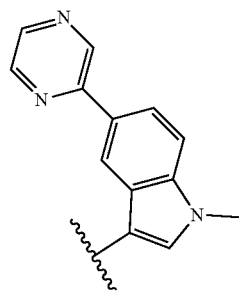
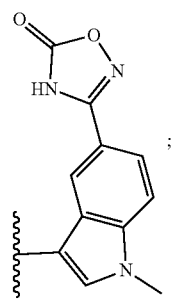
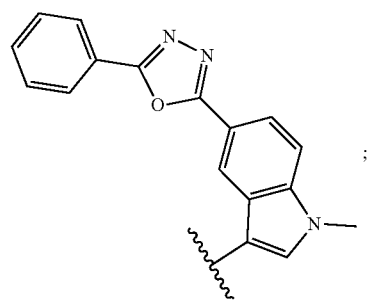
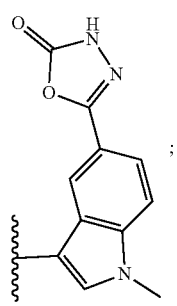
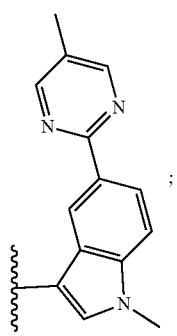
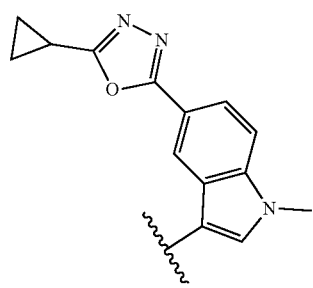
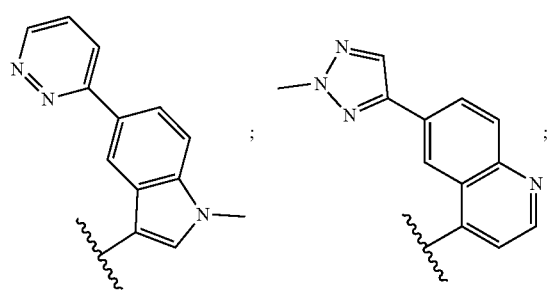
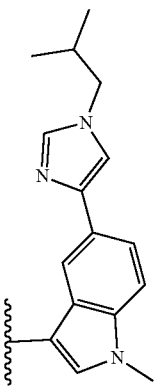
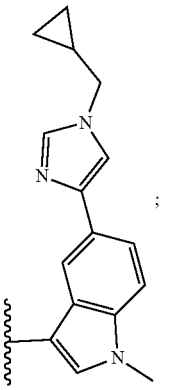
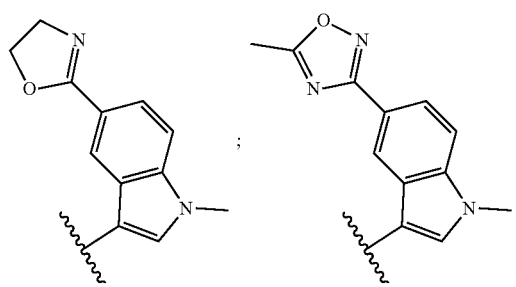
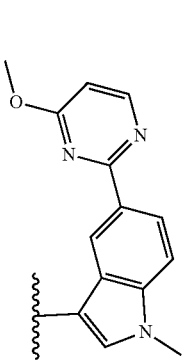
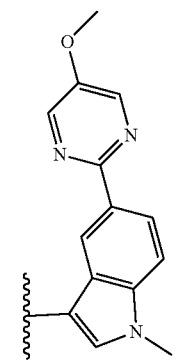

1099
-continued
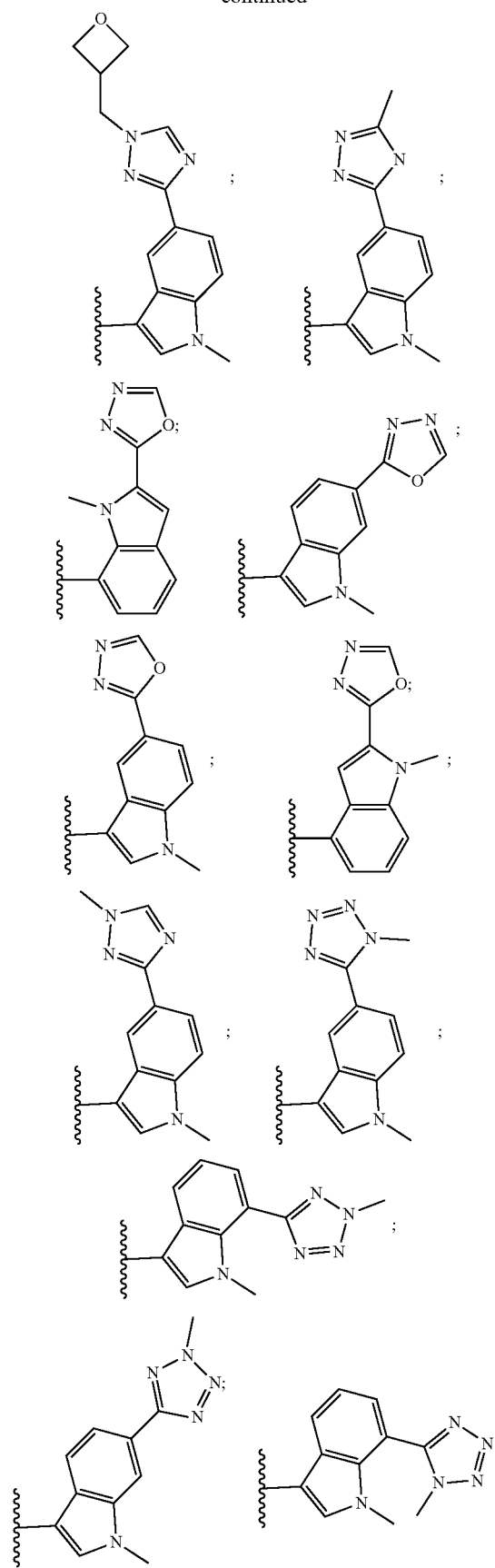
1100
-continued
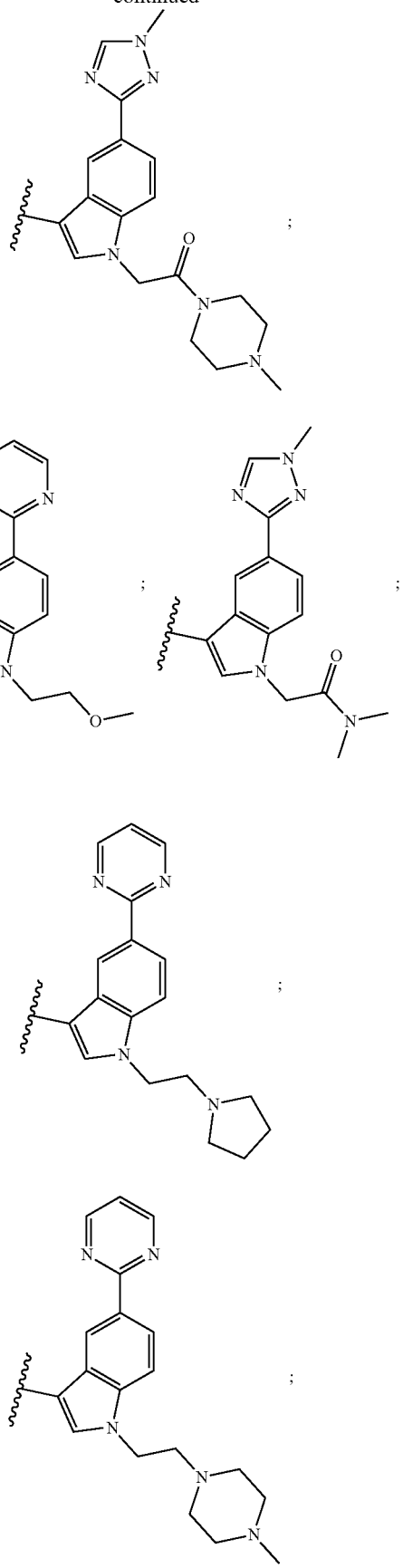

1101
-continued
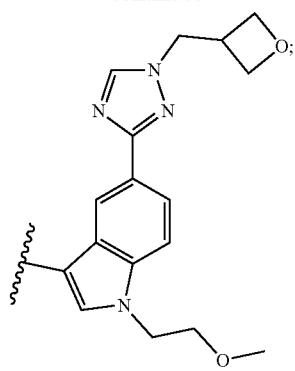
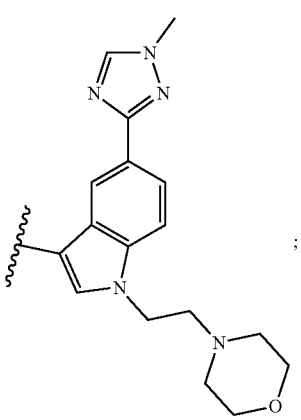
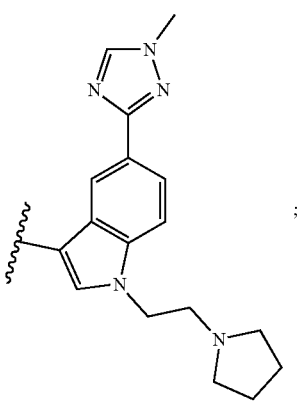
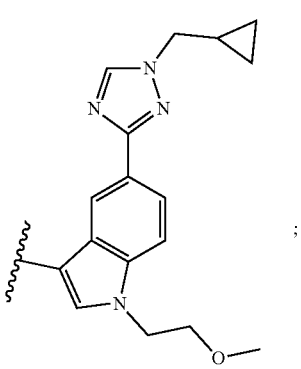
1102
-continued
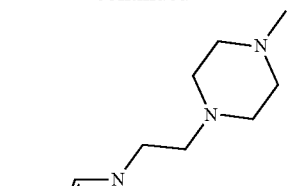
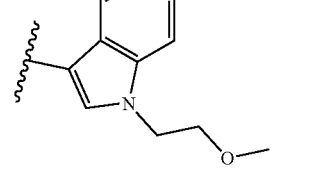
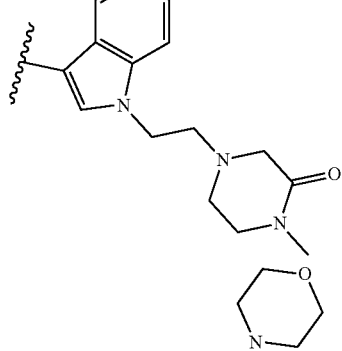
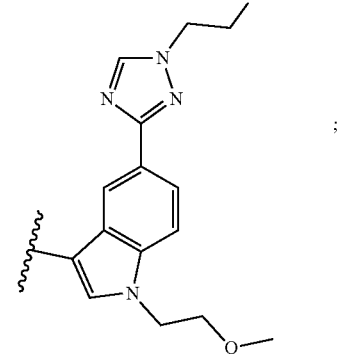
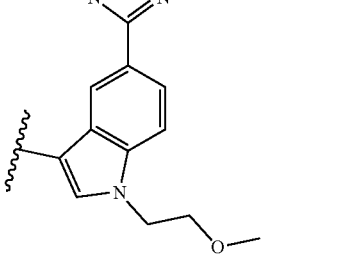

1103
-continued
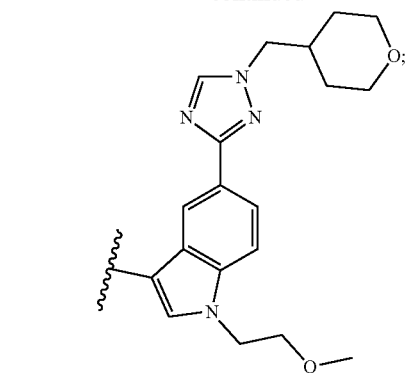
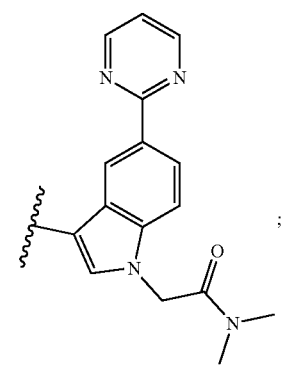
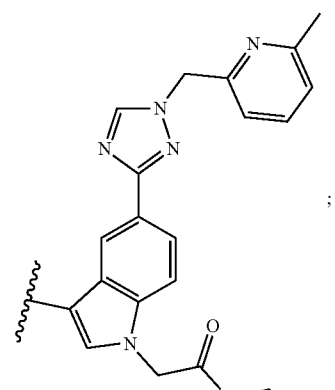
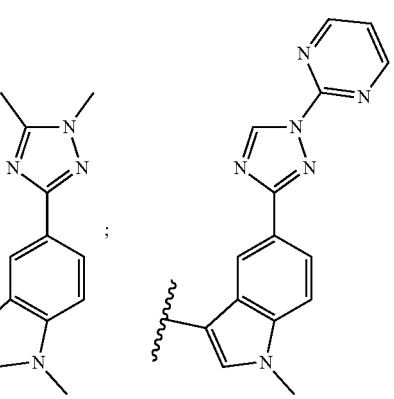
1104
-continued
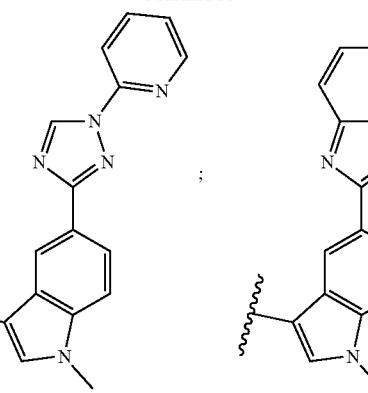
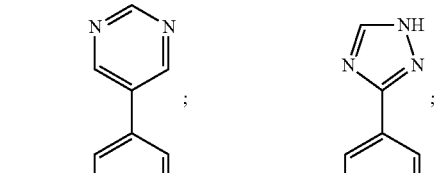
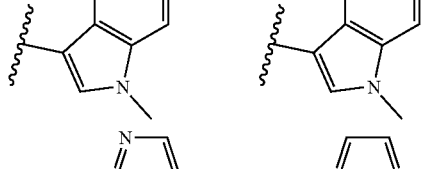
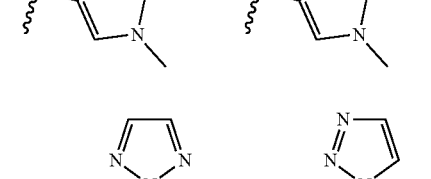
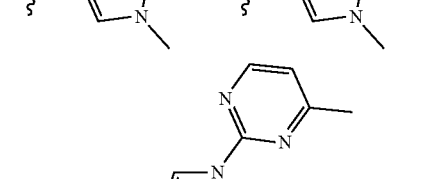

1105
-continued
1106
-continued
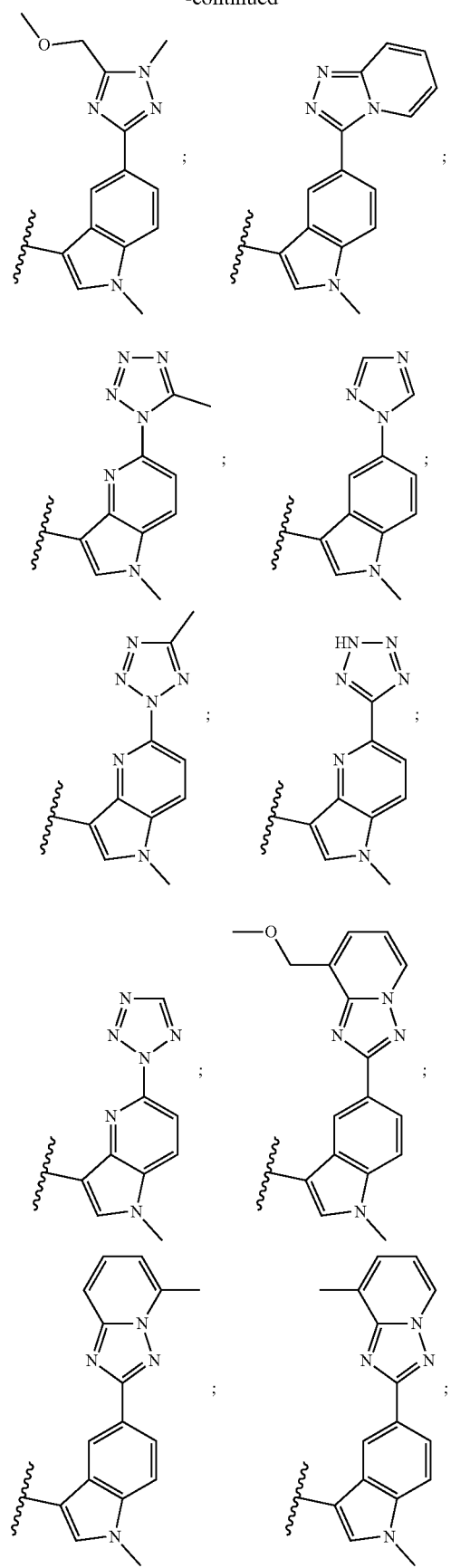
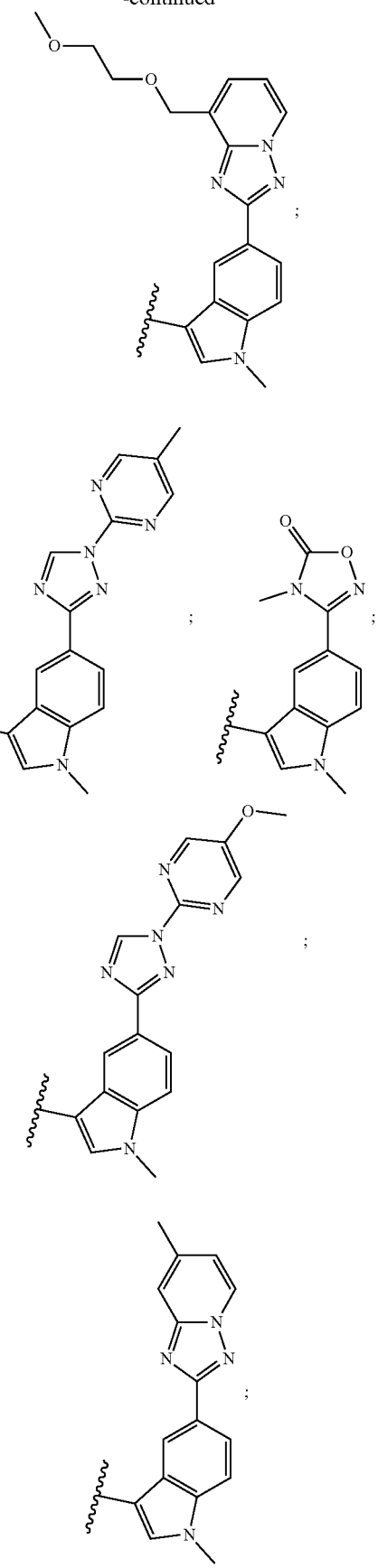

1107
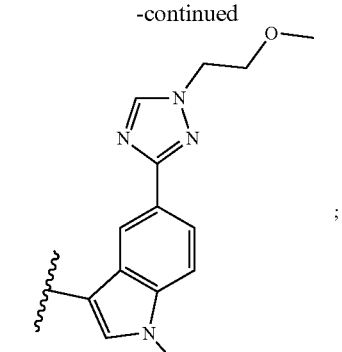
;
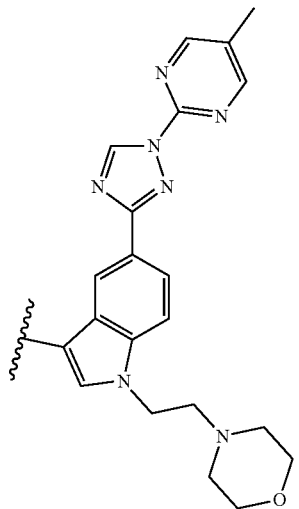
; or
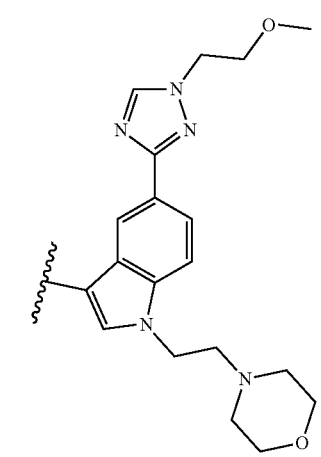
.
7. The compound of claim 4, or a pharmaceutically acceptable salt thereof, wherein $L^4$-$R^w$ is
1108
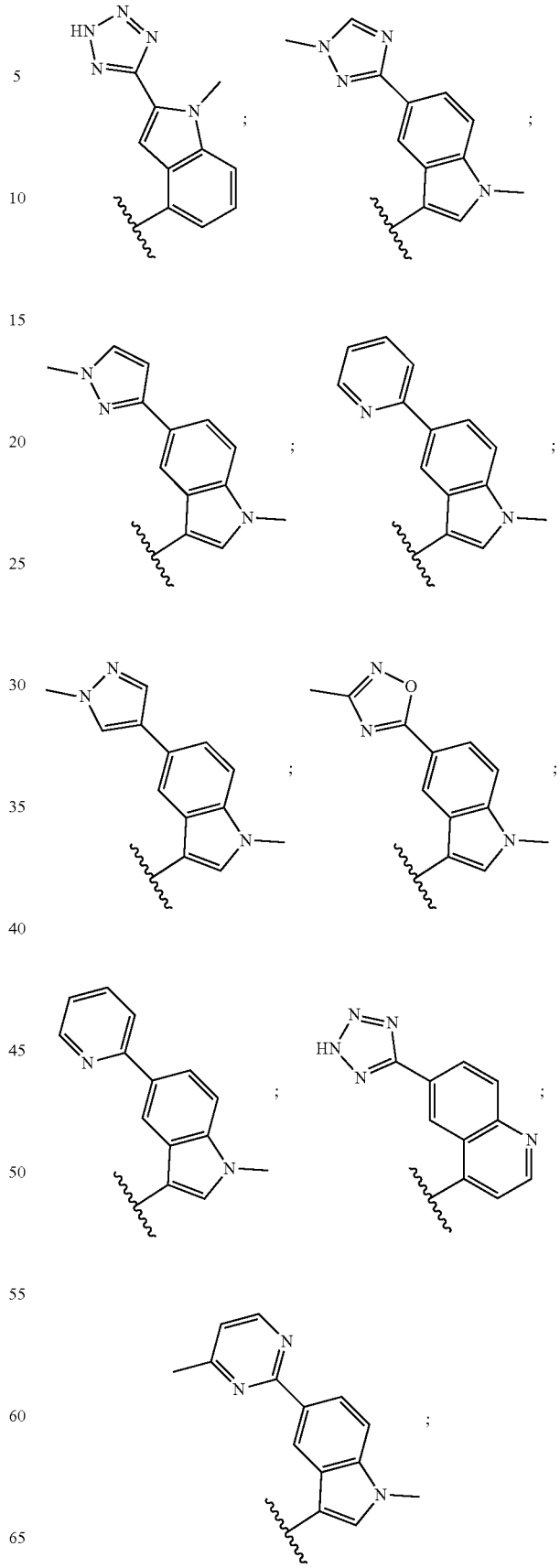

1109
-continued
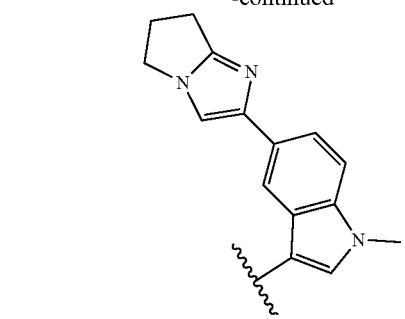
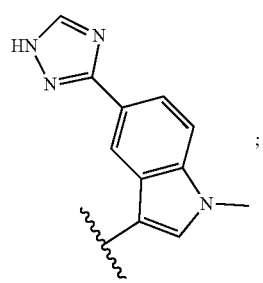 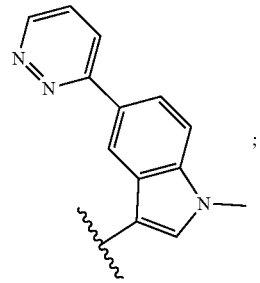
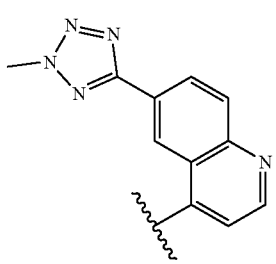 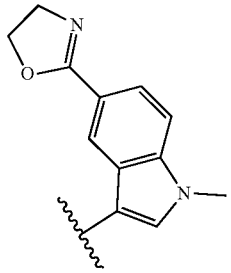
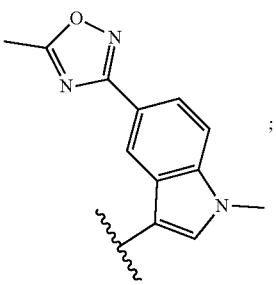 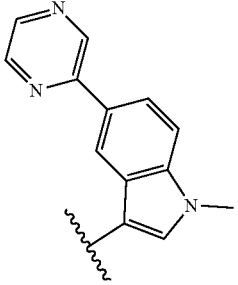
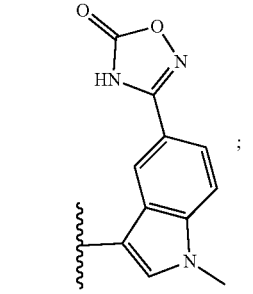 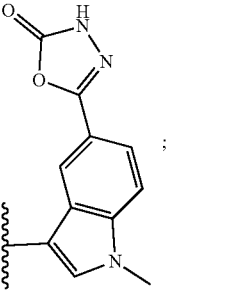
1110
-continued
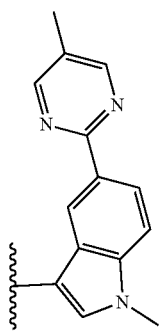 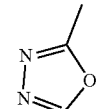
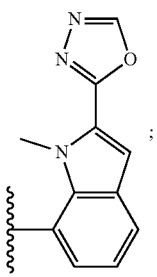
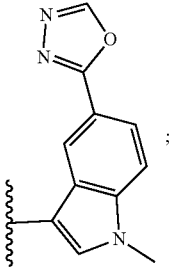 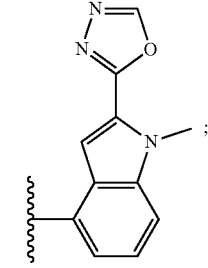
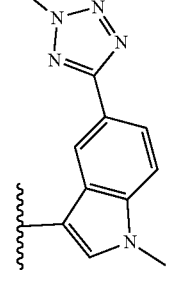 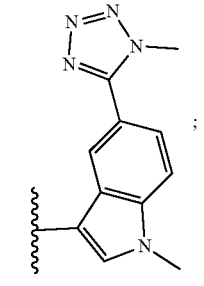
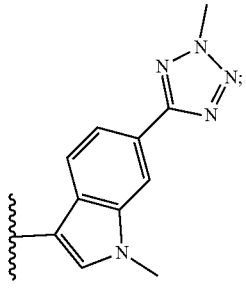 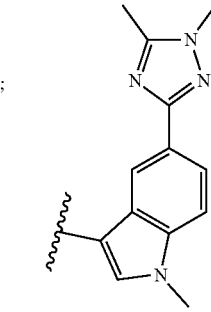

-continued
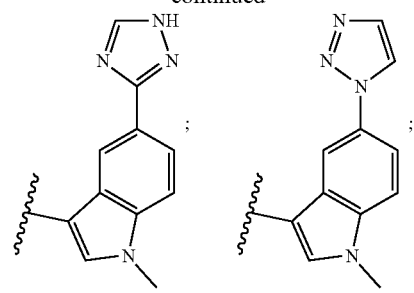
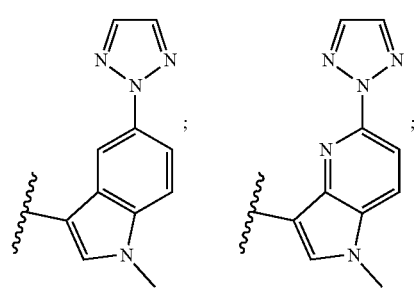
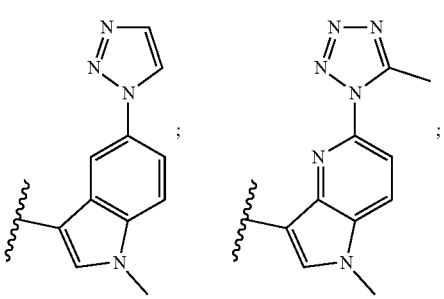
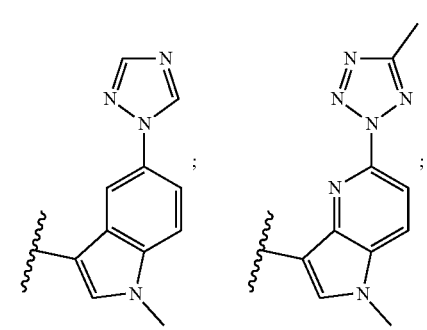
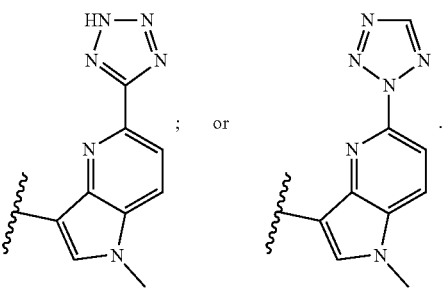
8. The compound of claim 1, or a pharmaceutically acceptable salt thereof, wherein $R^3$ is
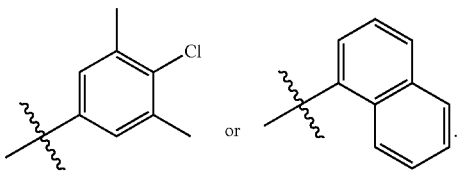
9. The compound of claim 1, or a pharmaceutically acceptable salt thereof, wherein $R^7$ is
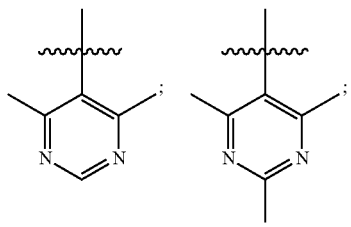
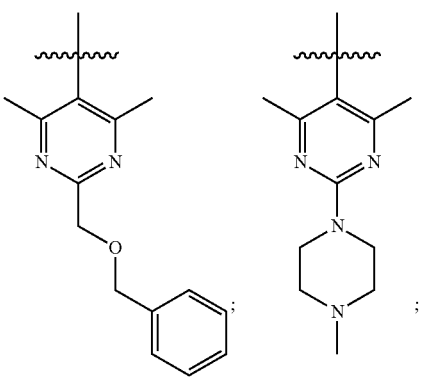
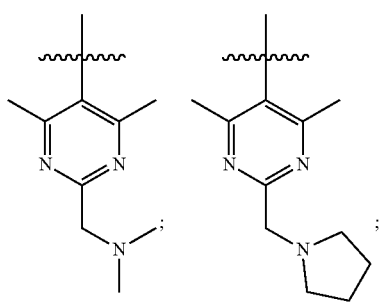
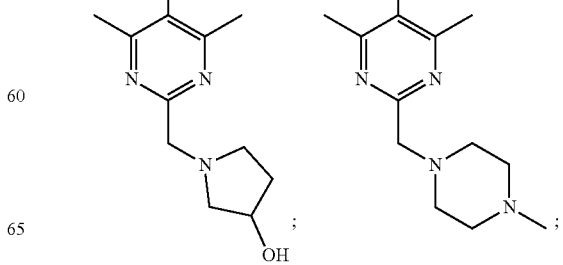

1113
-continued
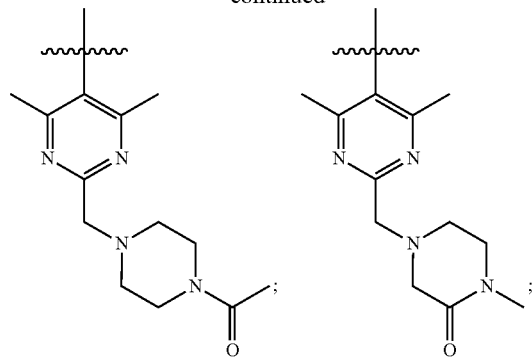
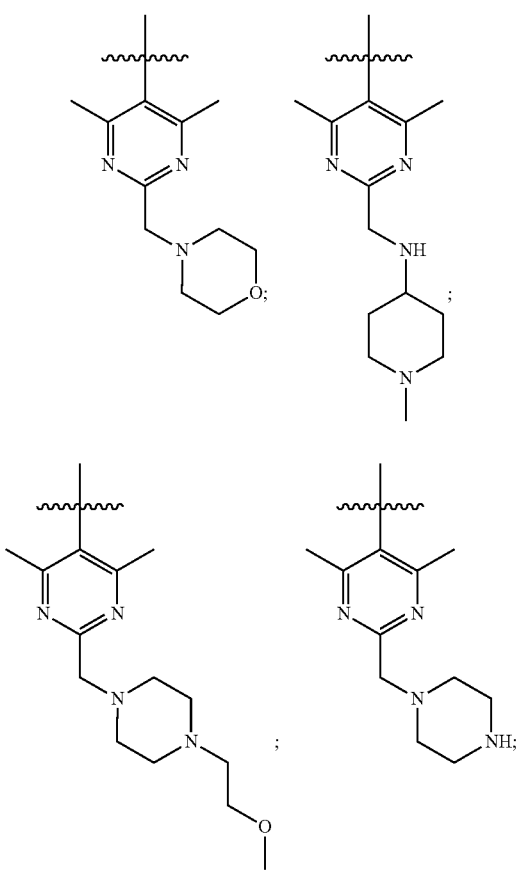
1114
-continued
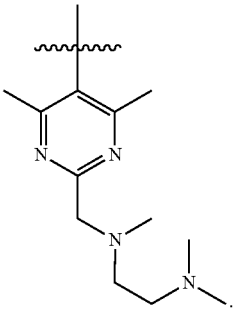
10. The compound of claim 1, or a pharmaceutically acceptable salt thereof, wherein $R^7$ is
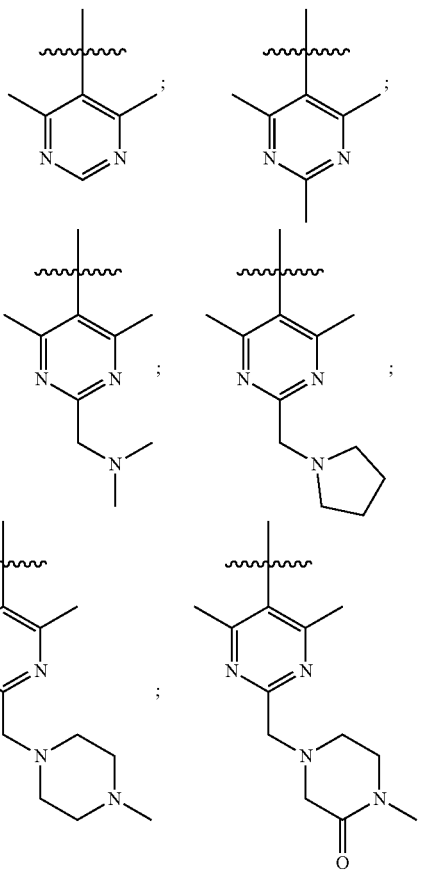
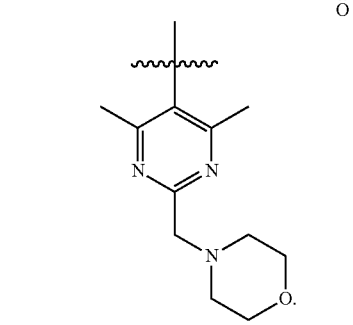
11. The compound of claim 1, or a pharmaceutically acceptable salt thereof, wherein $R^7$ is
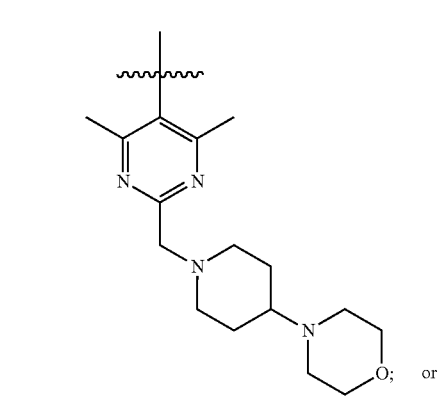

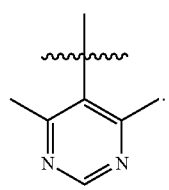
12. The compound of claim 1 selected from the group consisting of:
I-119
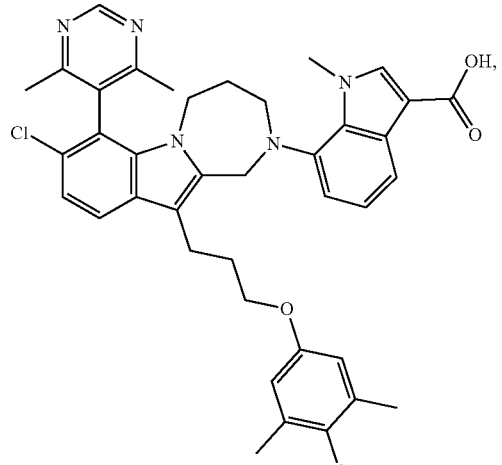
I-130
I-147
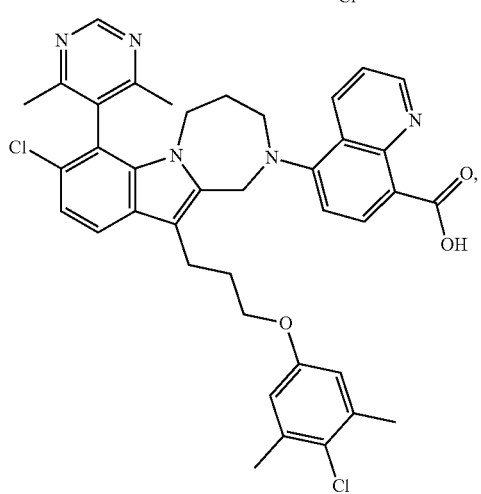
I-148
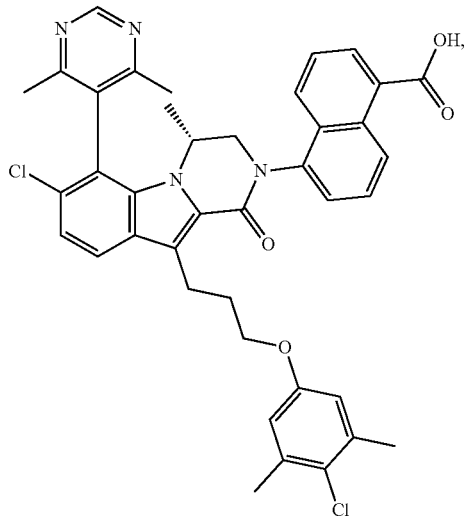
I-151
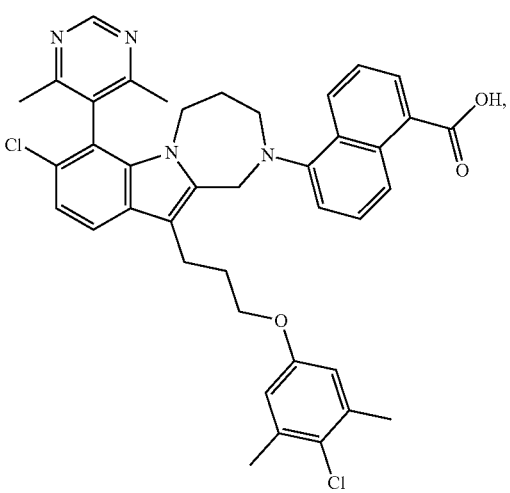
I-152
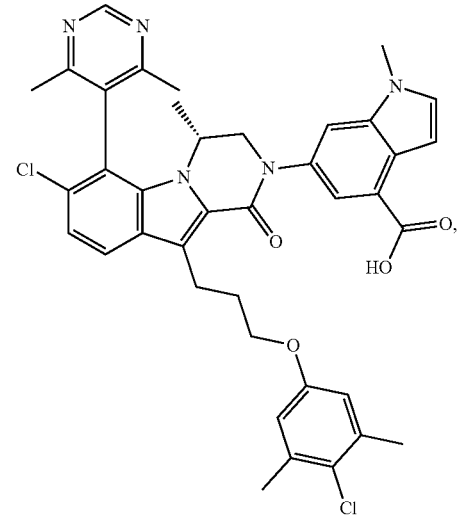

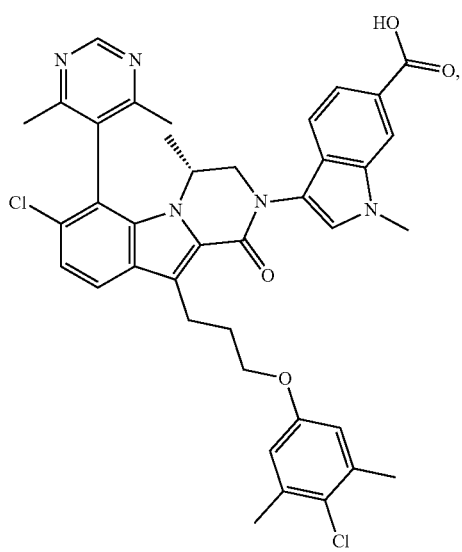
I-153
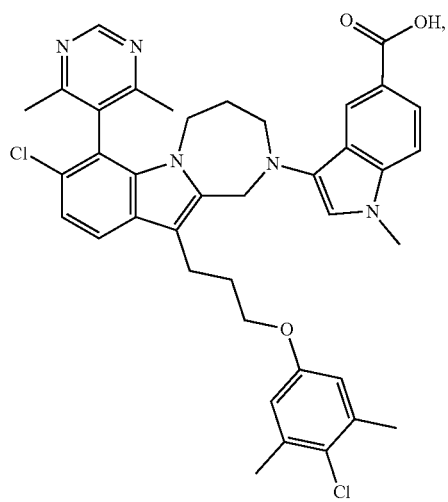
I-156
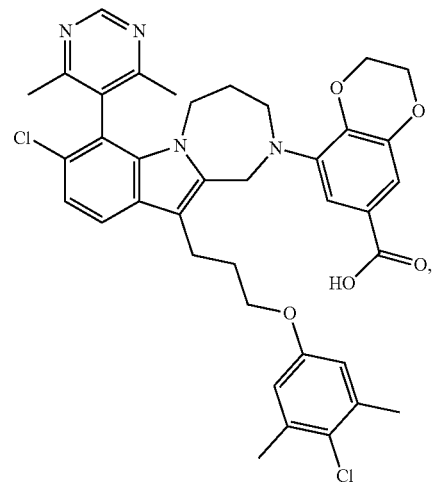
I-154
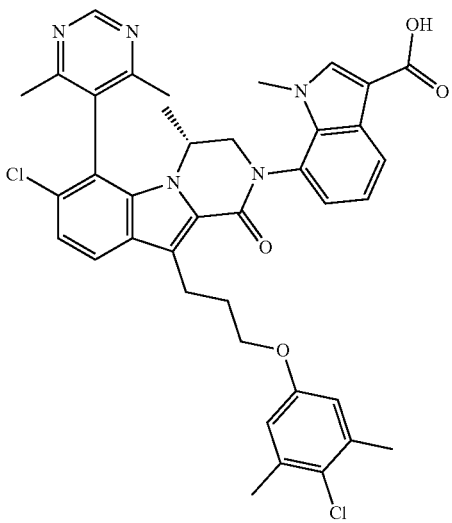
I-168
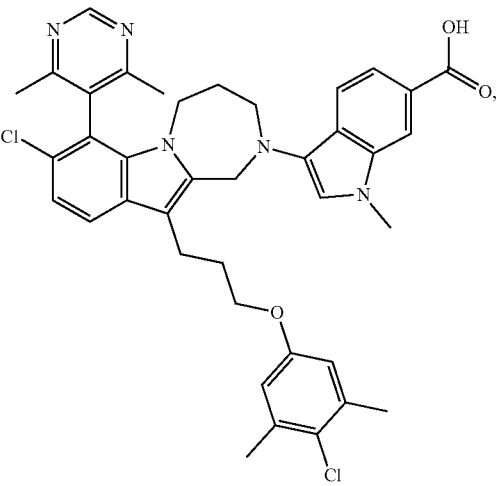
I-176
I-155

I-177
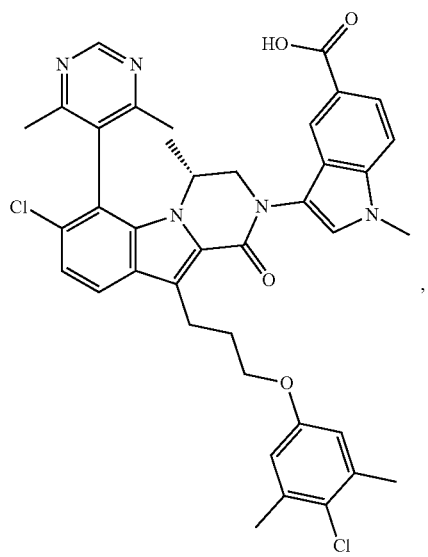
I-210
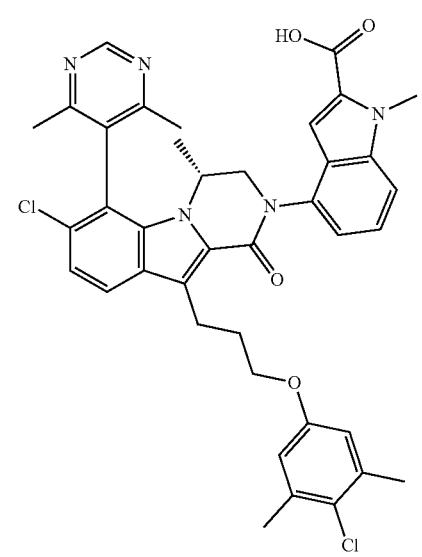
I-213
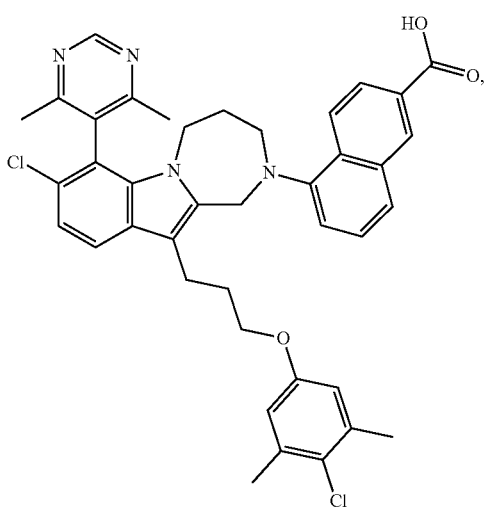
I-218
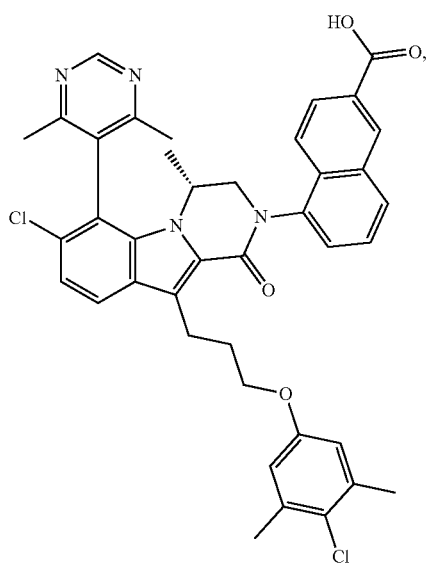
I-219
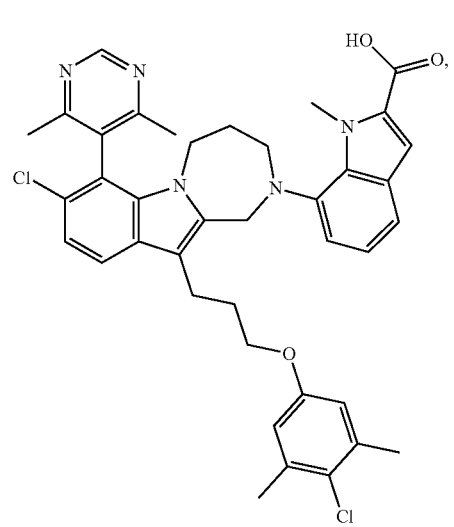
I-220
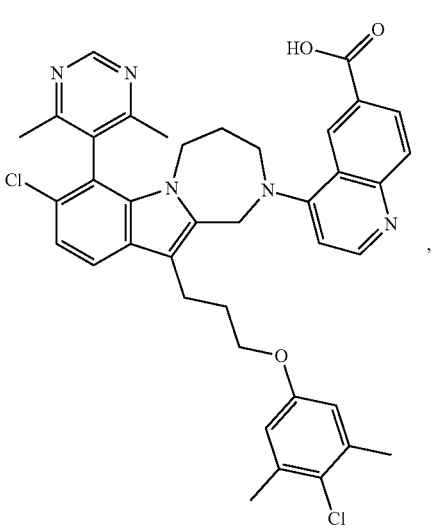

I-224
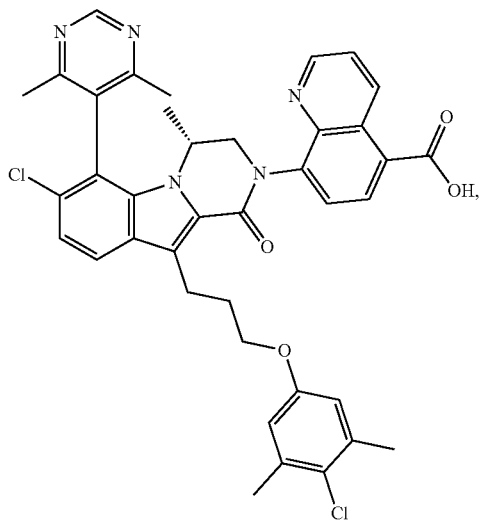
I-225
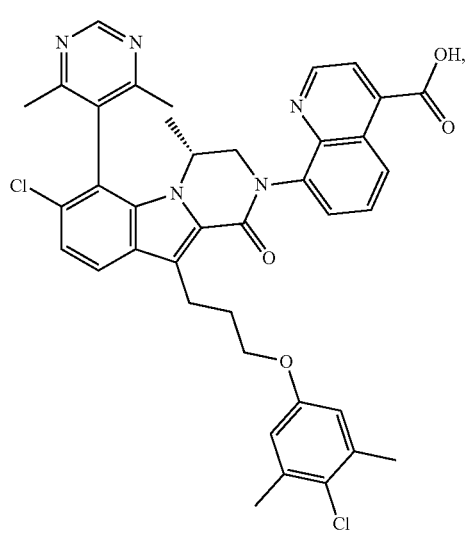
I-227
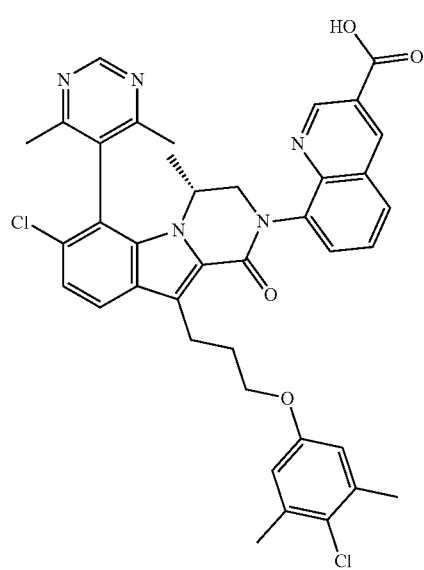
I-228
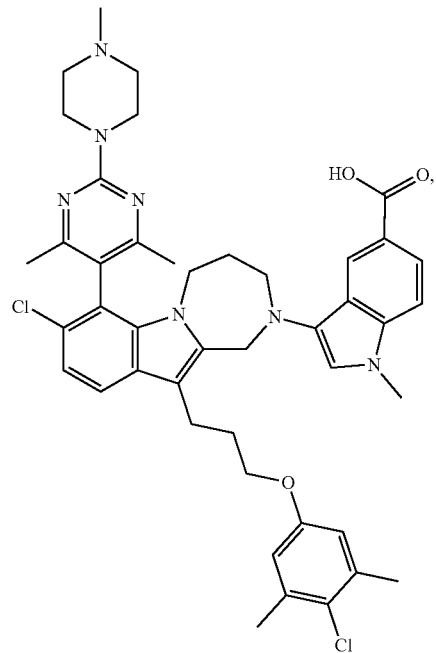
I-238
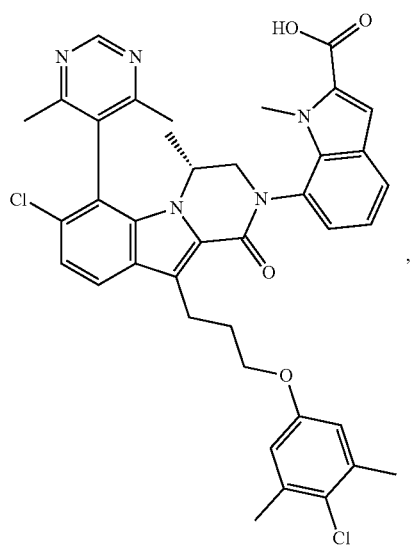

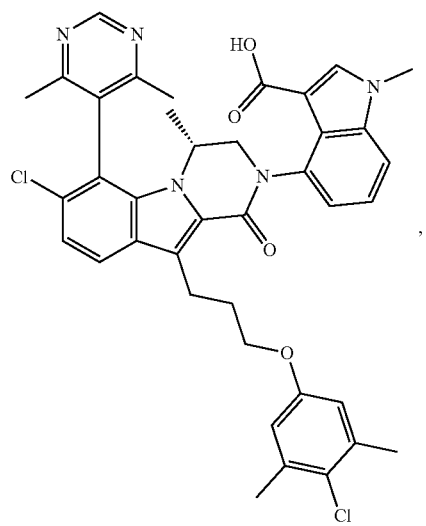
I-252
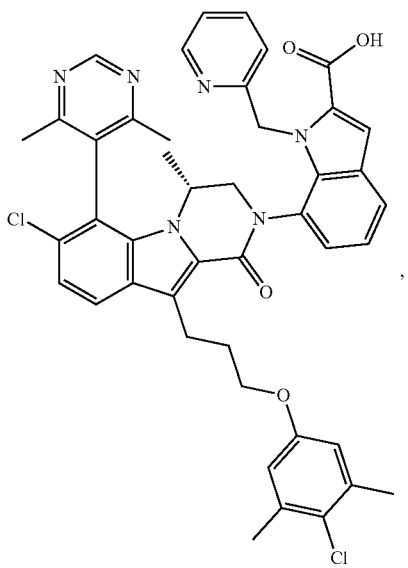
I-271
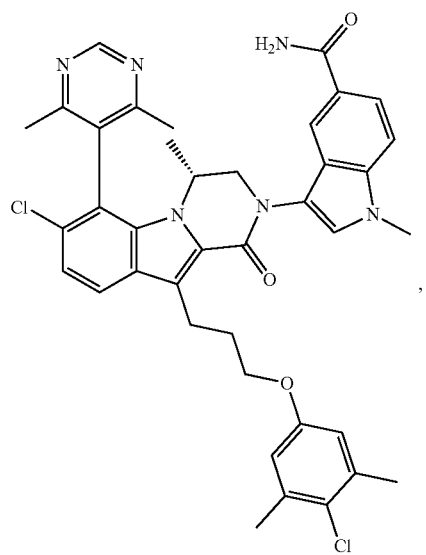
I-255
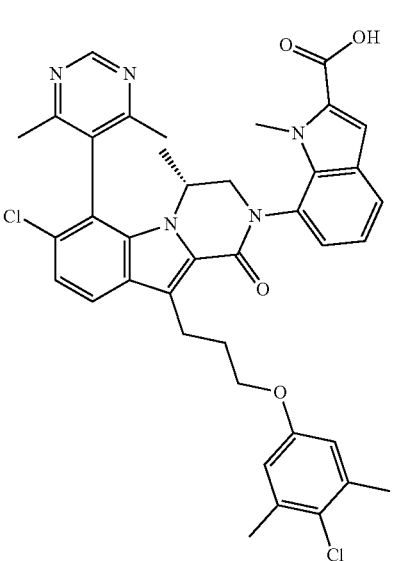
I-272
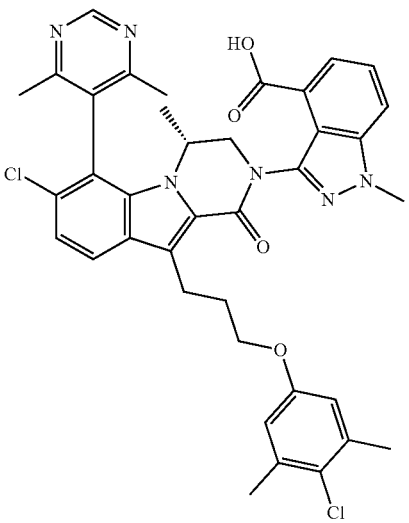
I-269
I-273

I-276
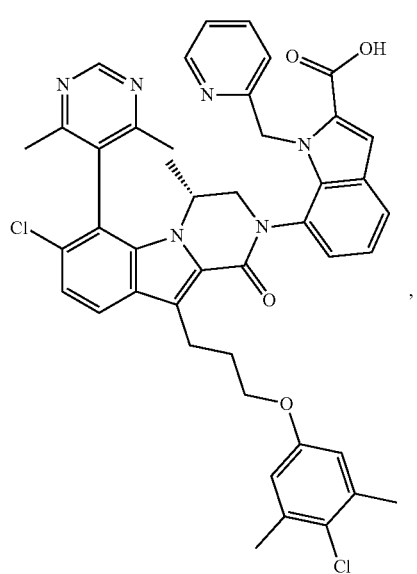
I-294
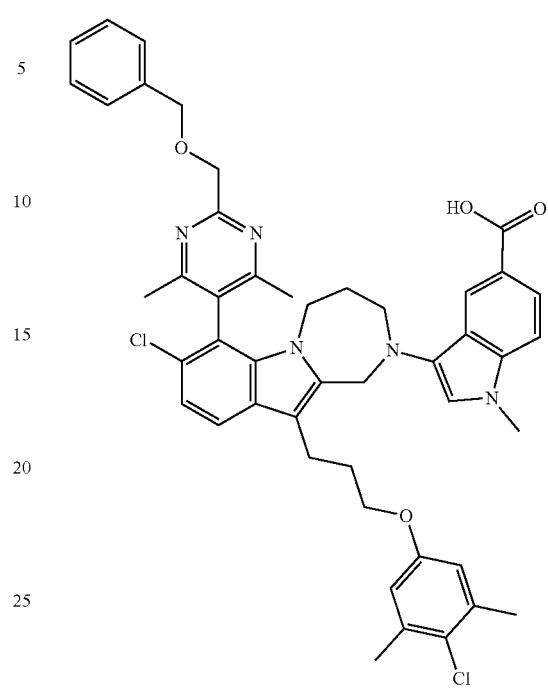
I-279
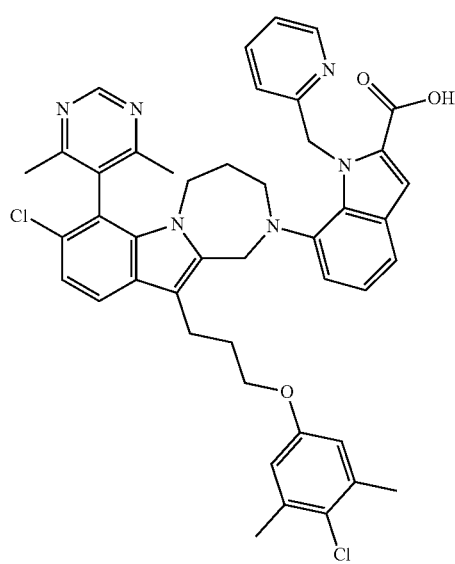
I-296
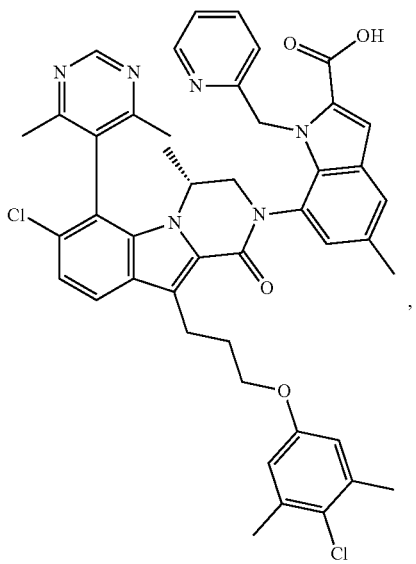

I-302

I-373

I-339

I-376

1129
-continued
I-379
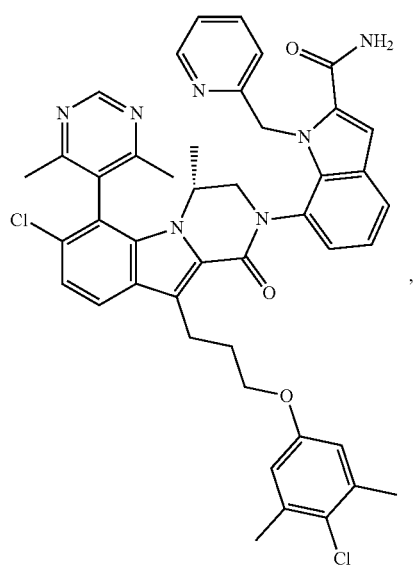
I-384
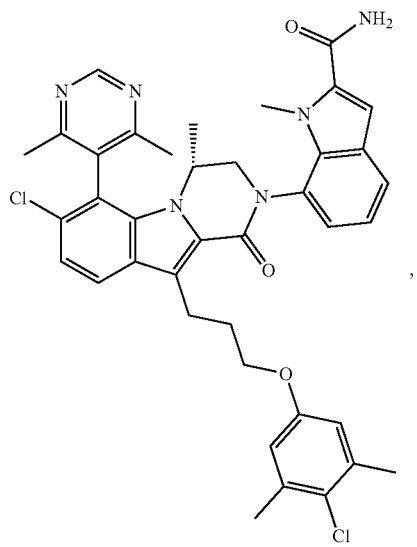
1130
-continued
I-390
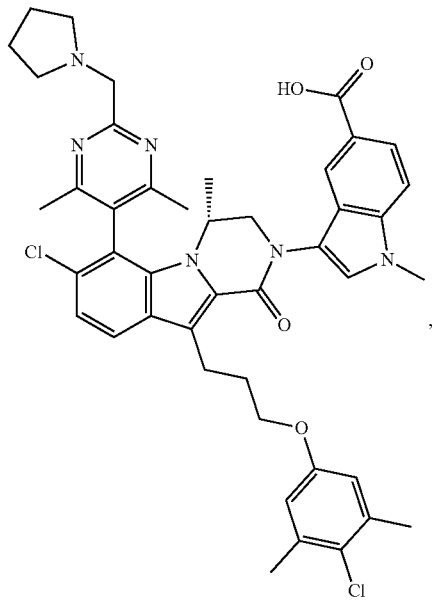
I-395
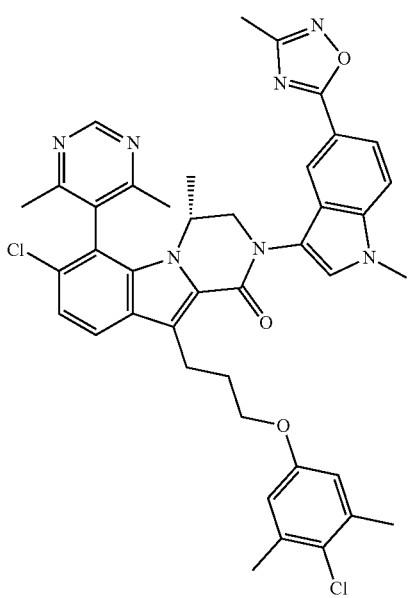

1131
-continued
I-396
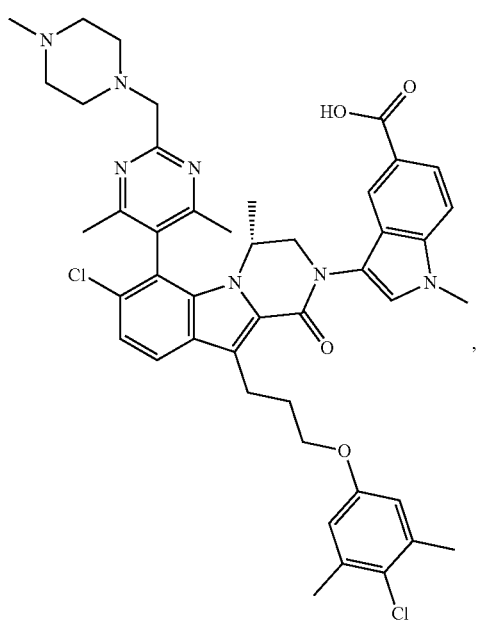
1132
-continued
I-398
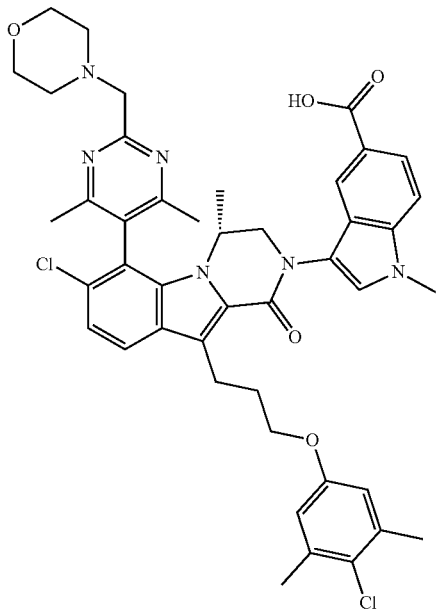
I-397
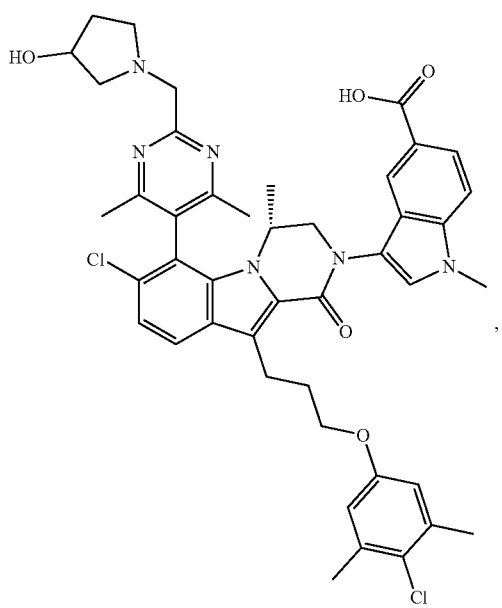
I-399
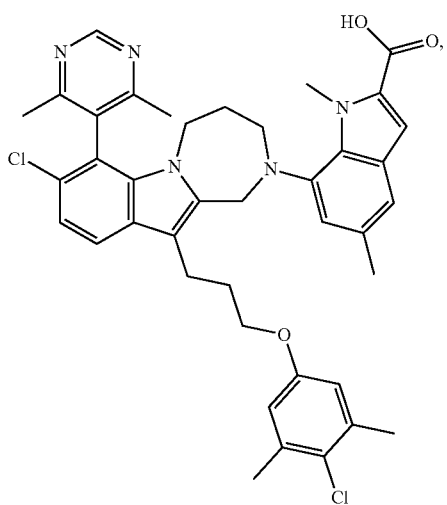

I-416
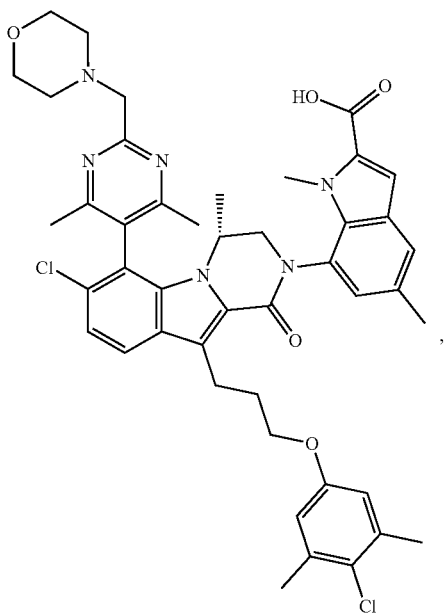
I-426
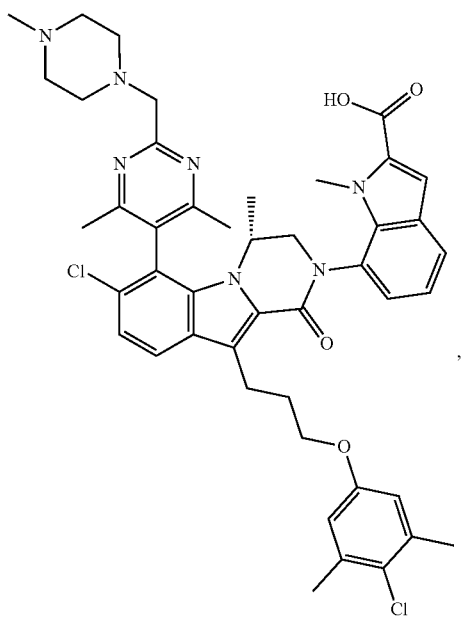
I-432
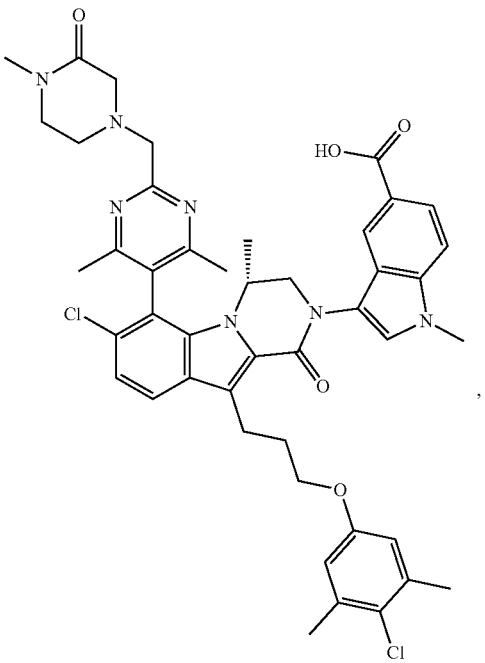
I-433
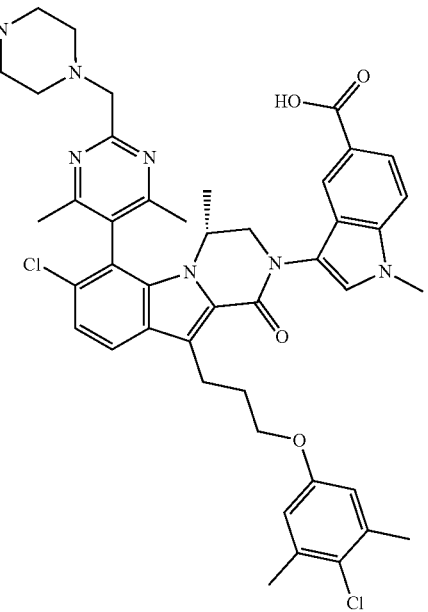

I-437
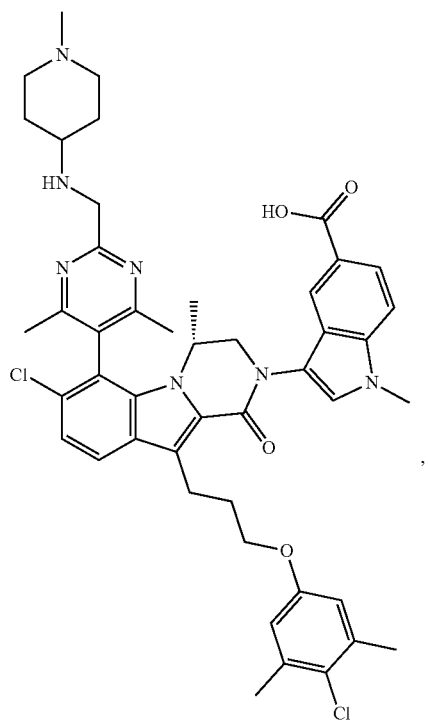
I-441
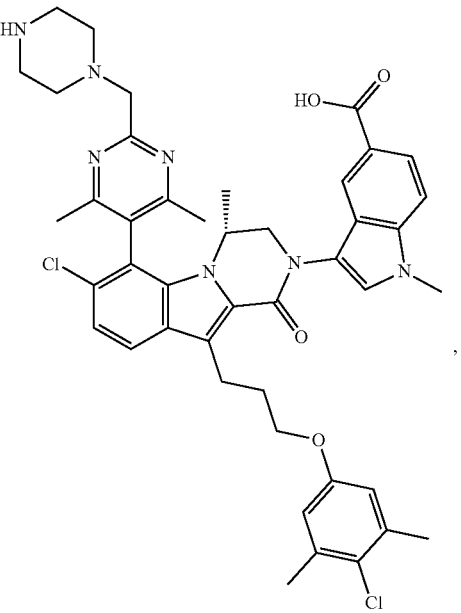
I-439
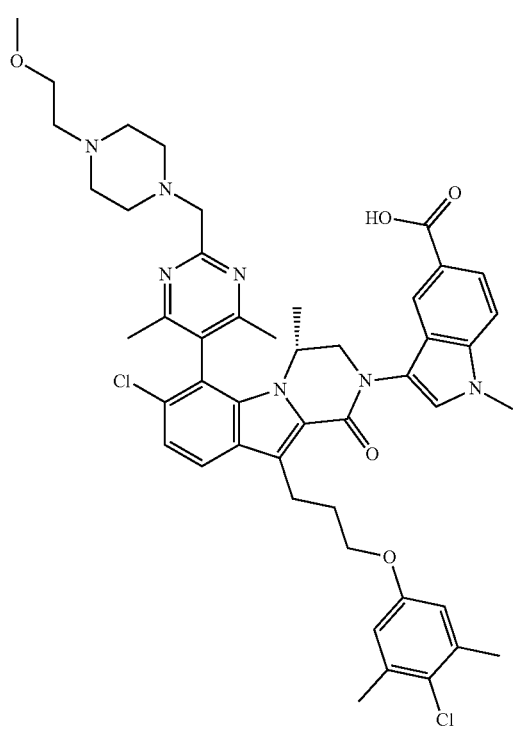
I-443
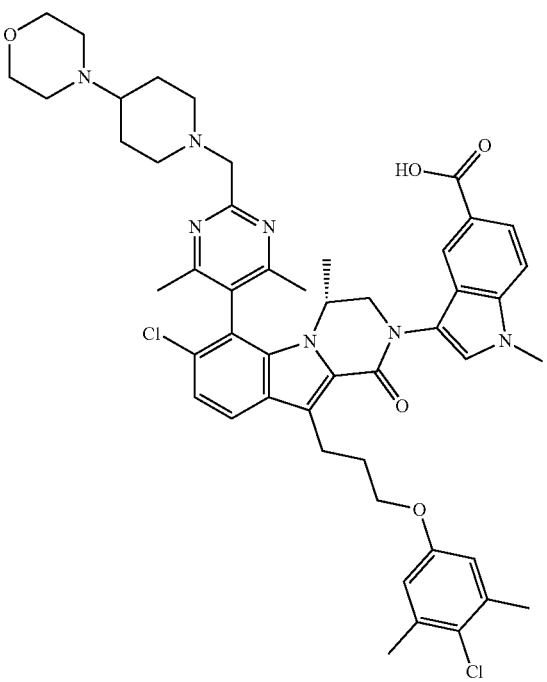

1137 1138
I-448
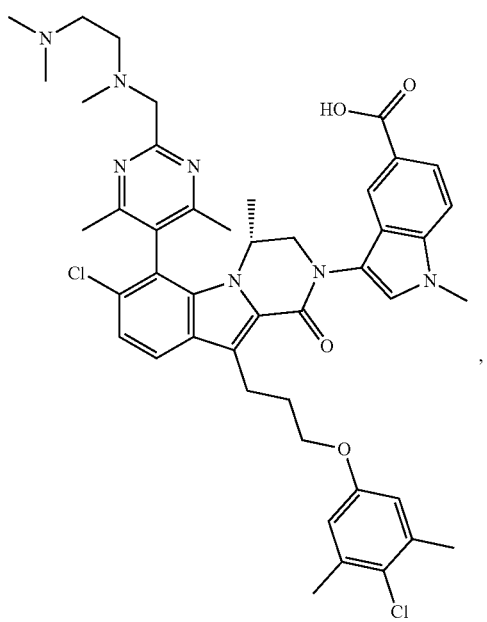
I-476
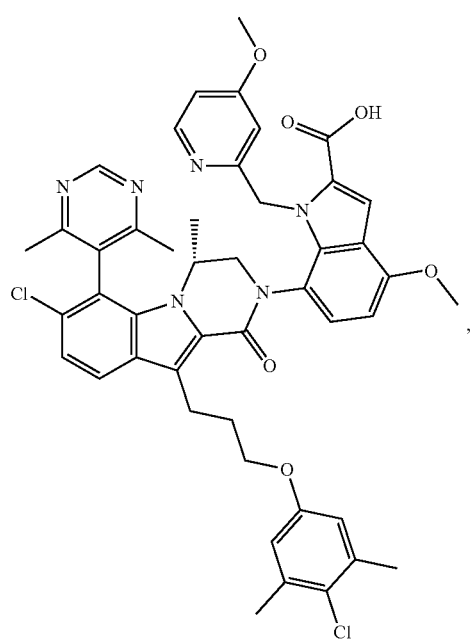
,
I-451
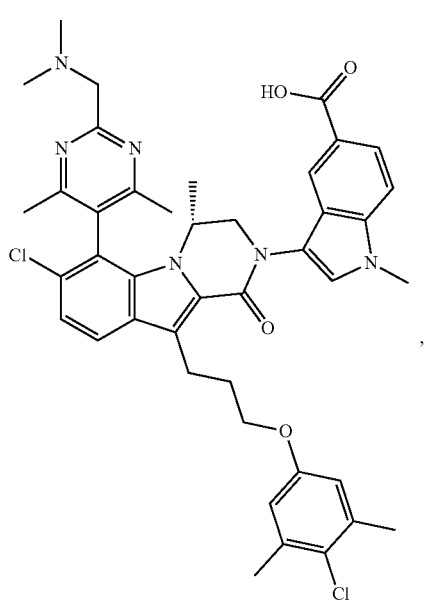
,
I-477
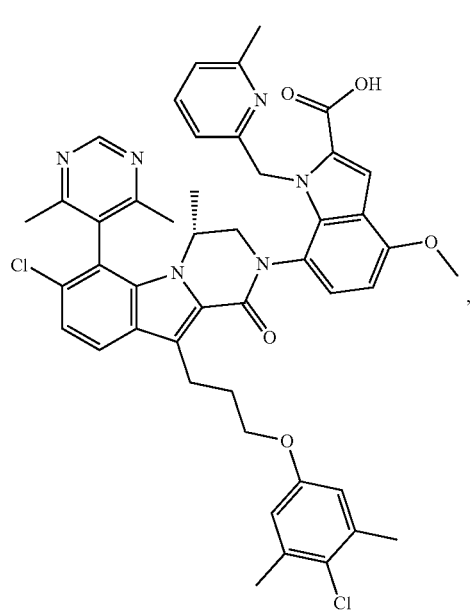
, I-478
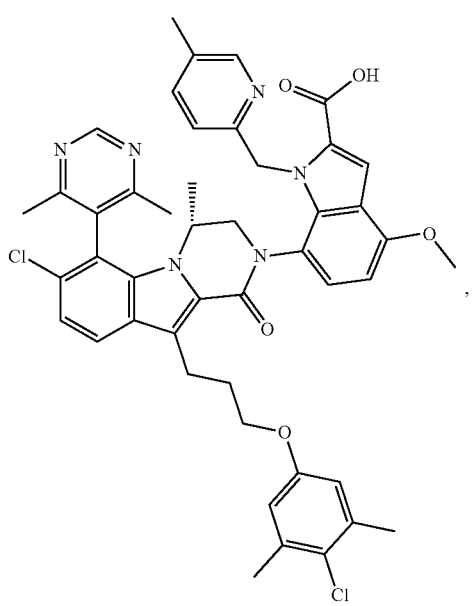
I-483
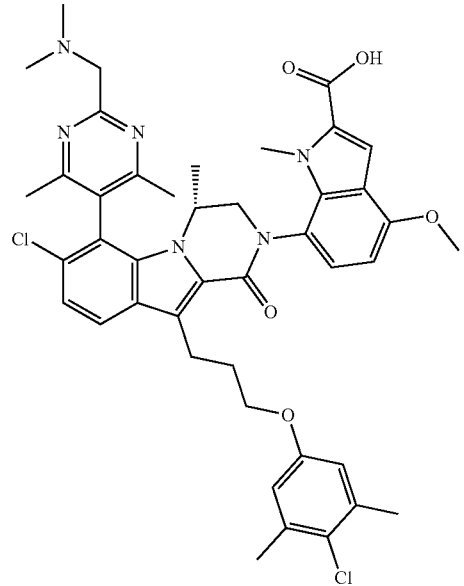
I-482
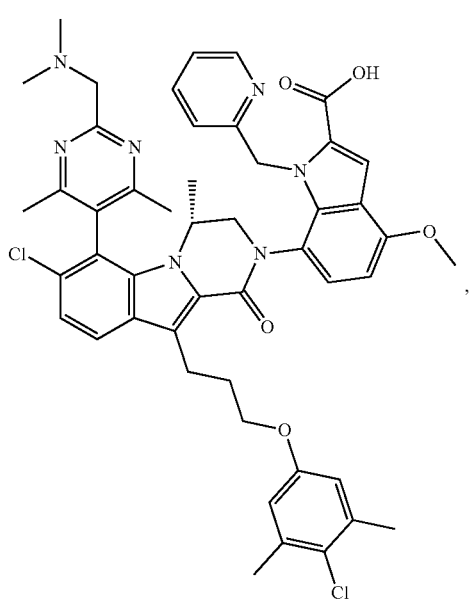
I-492
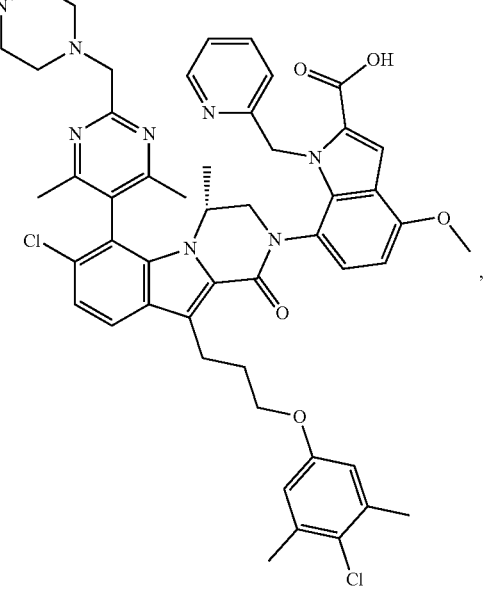

I-493
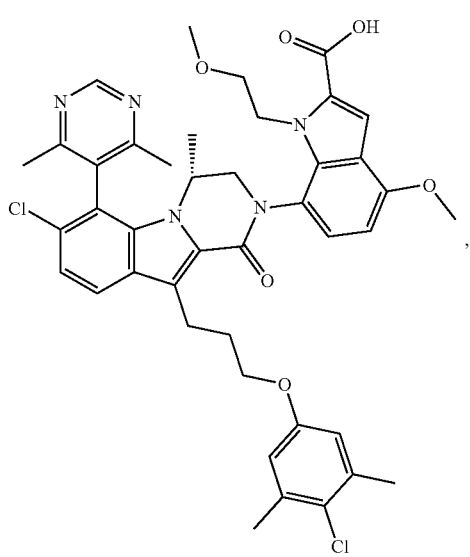
I-503
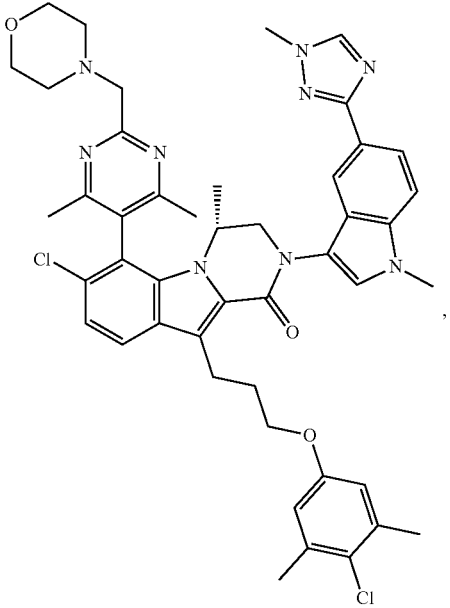
I-502
I-520

I-535
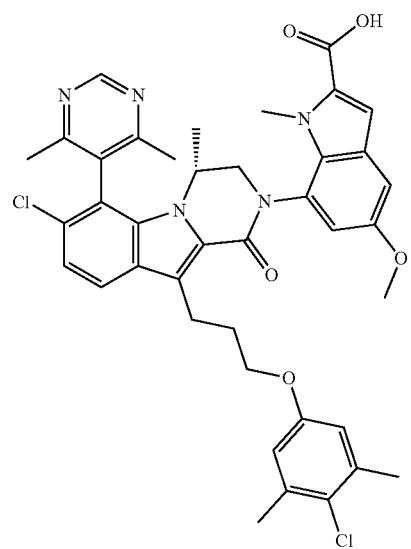
I-539
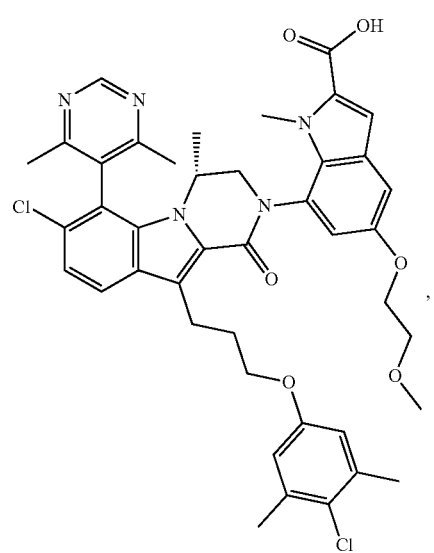
I-558
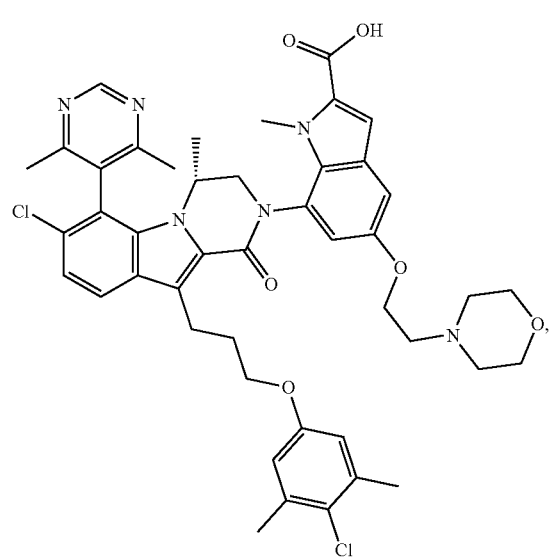
I-559
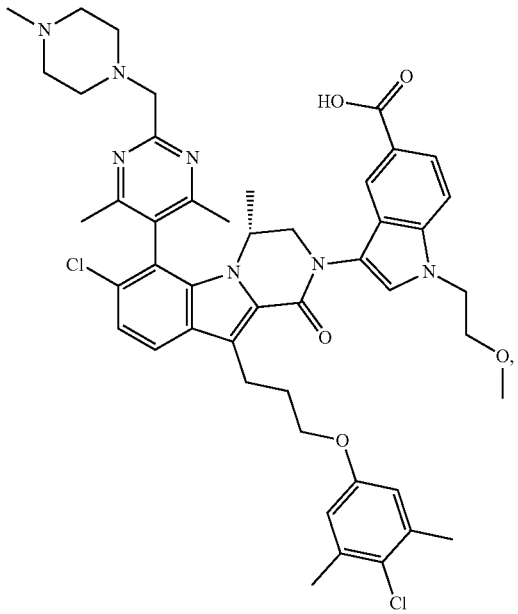
I-565
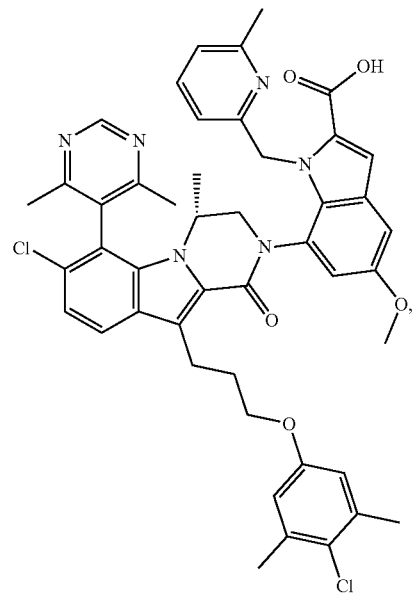

I-566
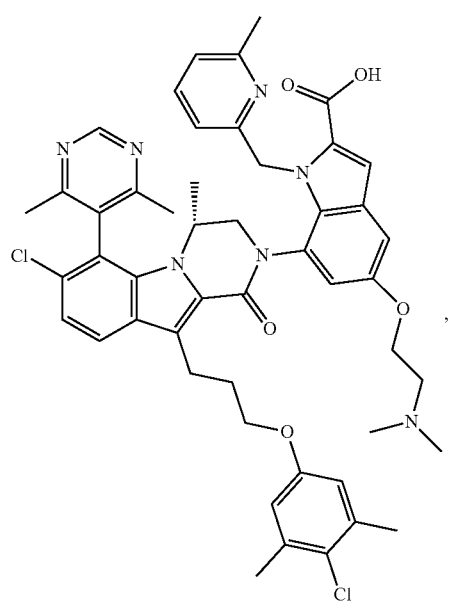
I-571
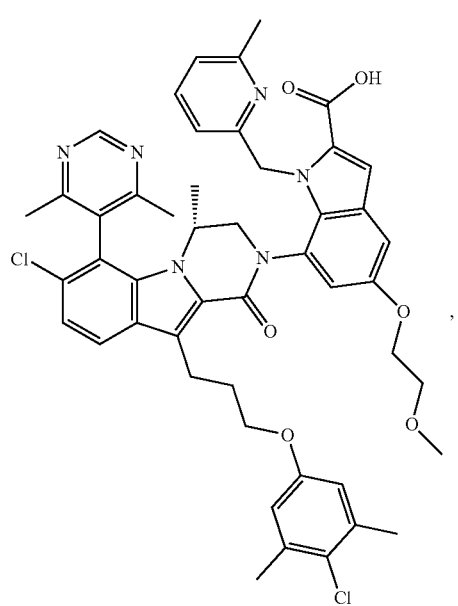
I-572
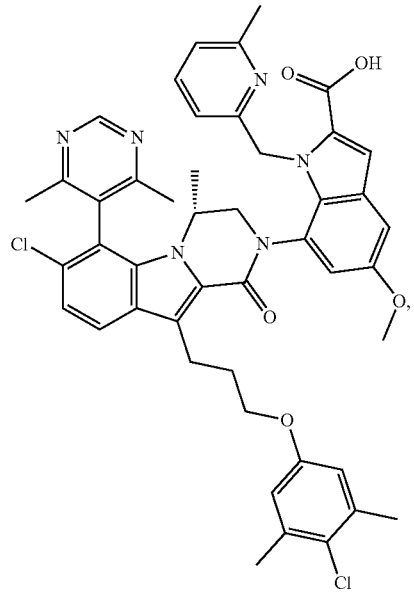
I-573
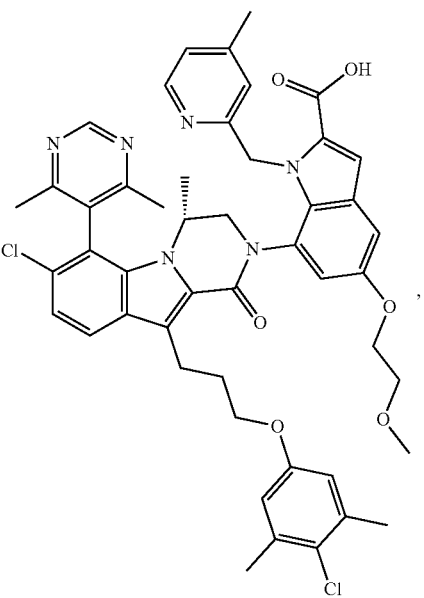

I-574
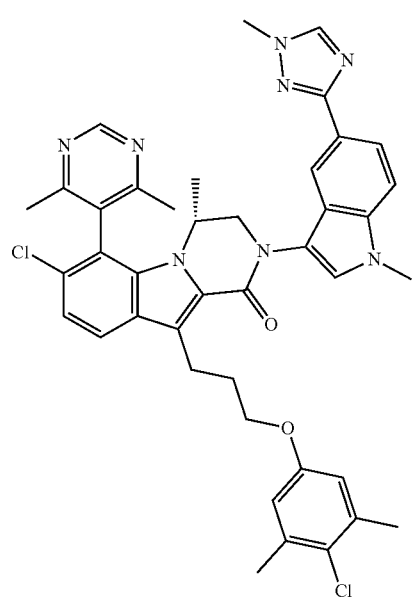
I-577
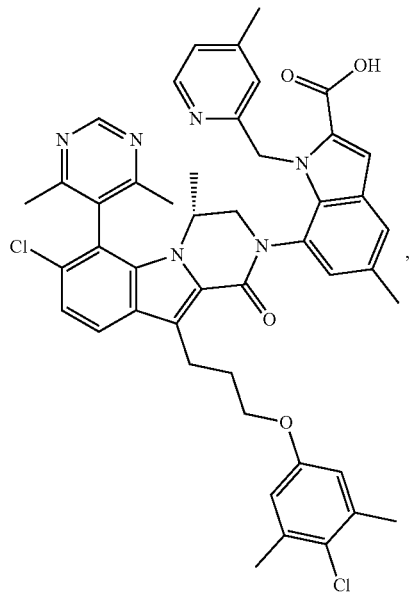
I-576
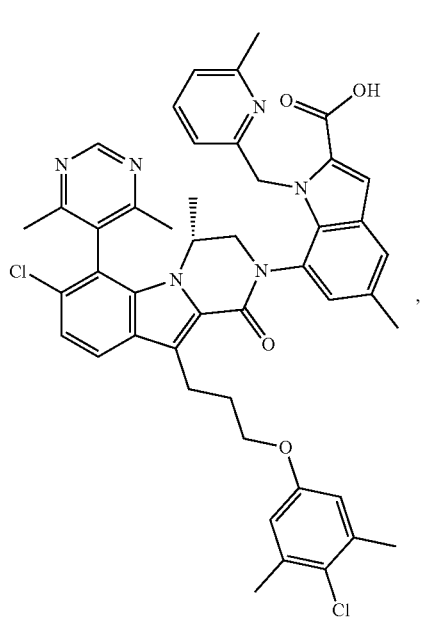
I-580
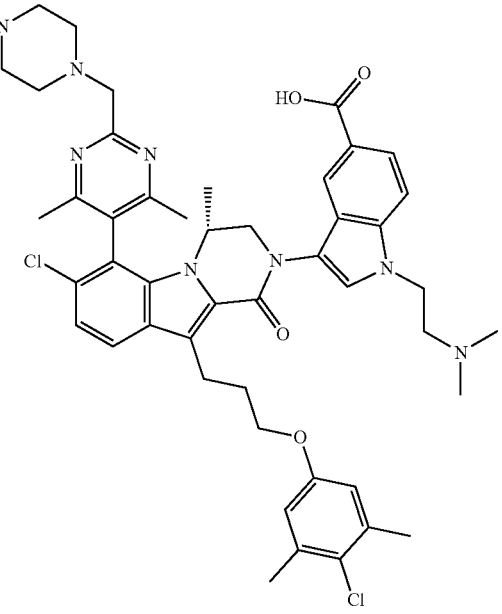

-continued
I-584
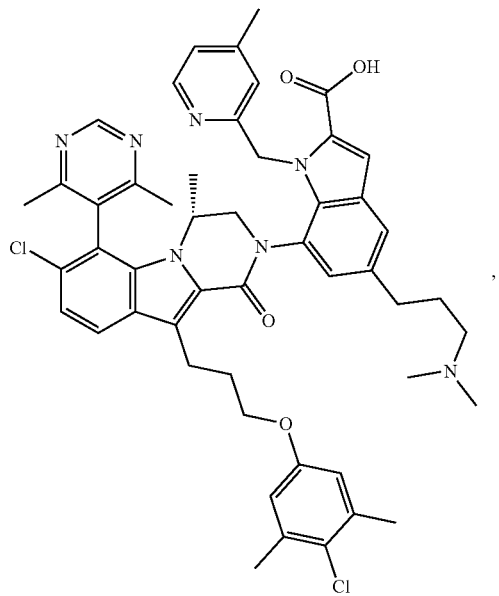
I-601
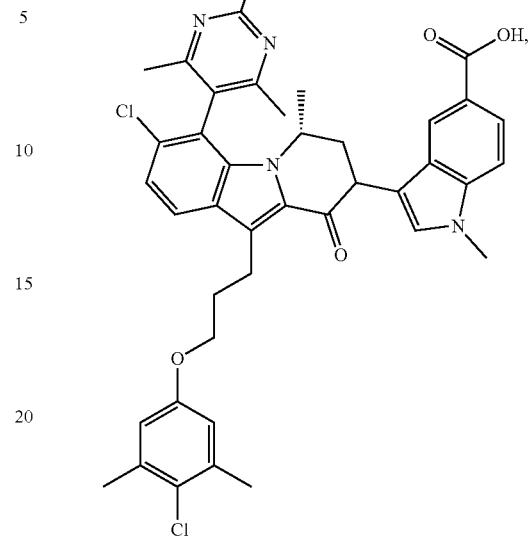
I-594
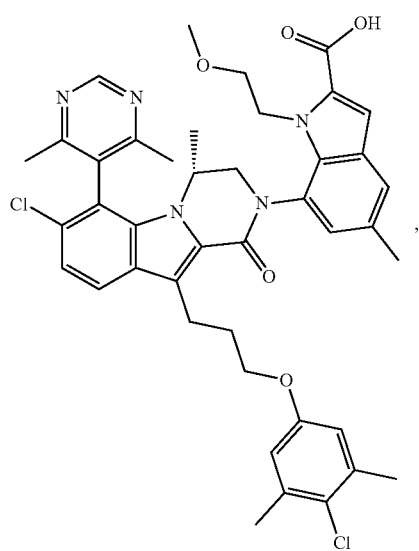
I-631
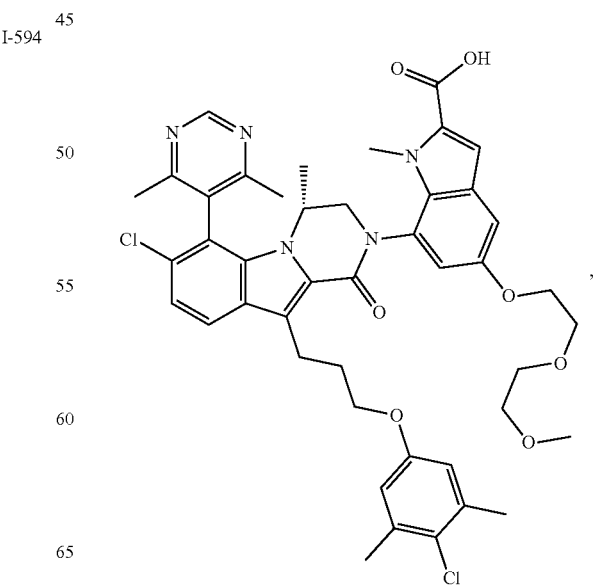

1151
-continued
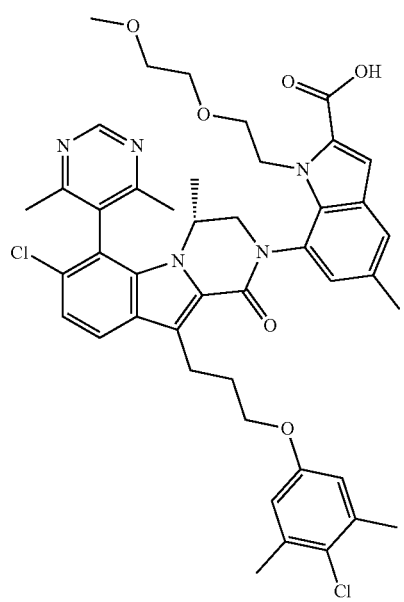
I-635
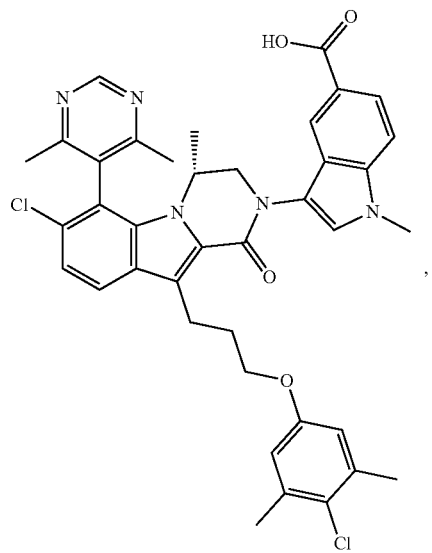
I-636
1152
-continued
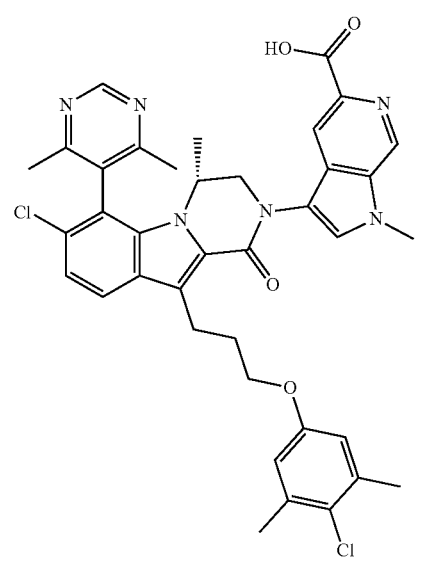
I-640
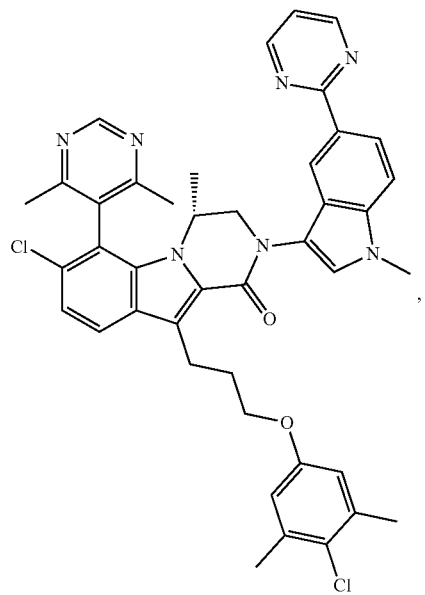
I-642

I-644
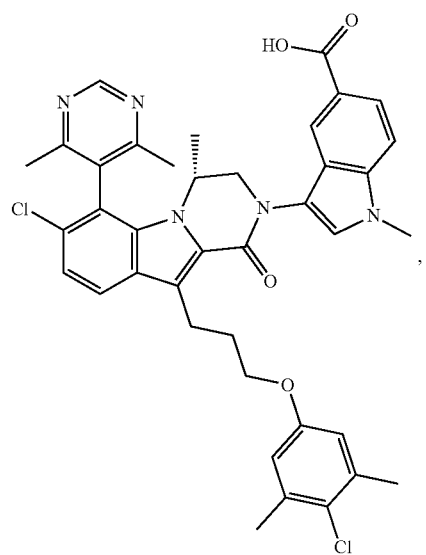
I-655
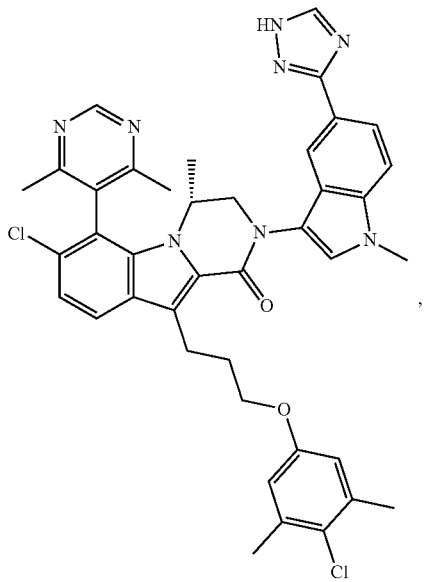
I-651
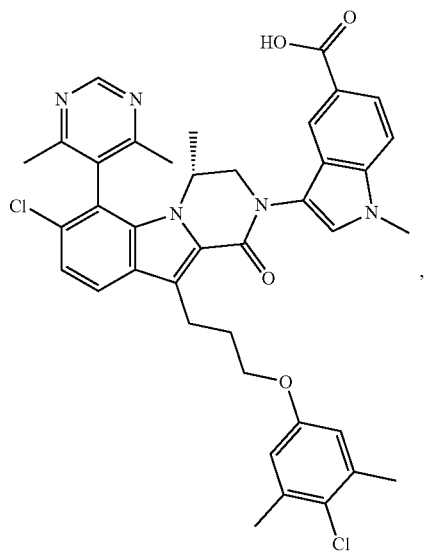
I-660
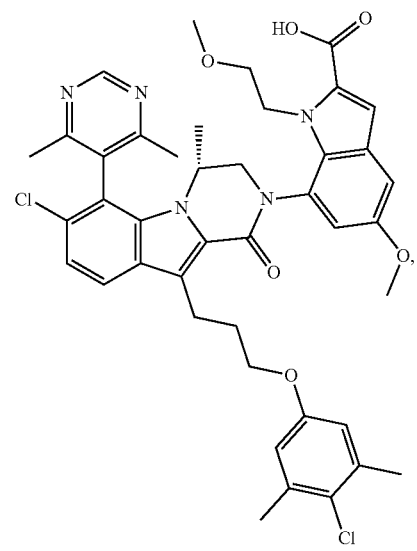

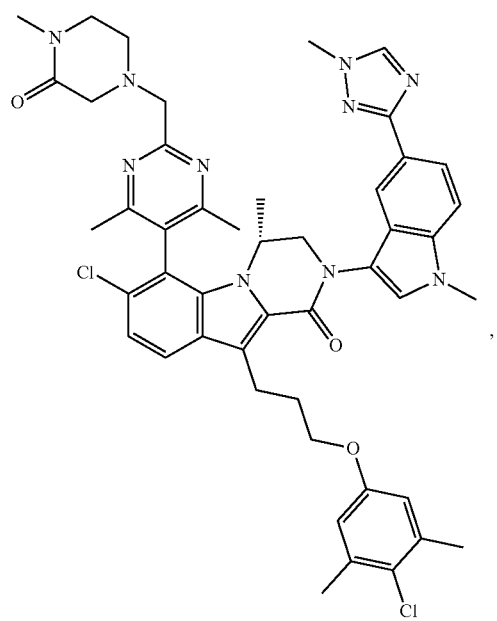
I-663
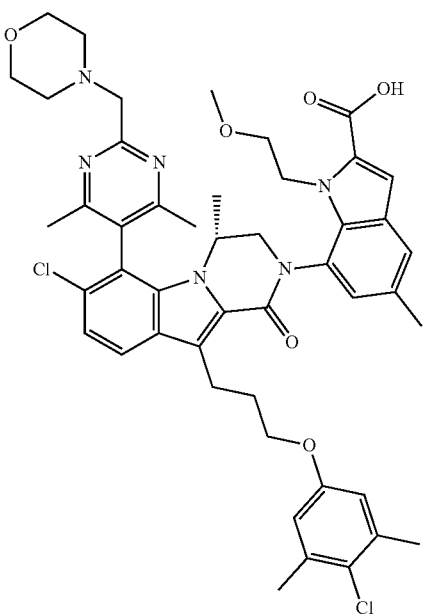
I-717
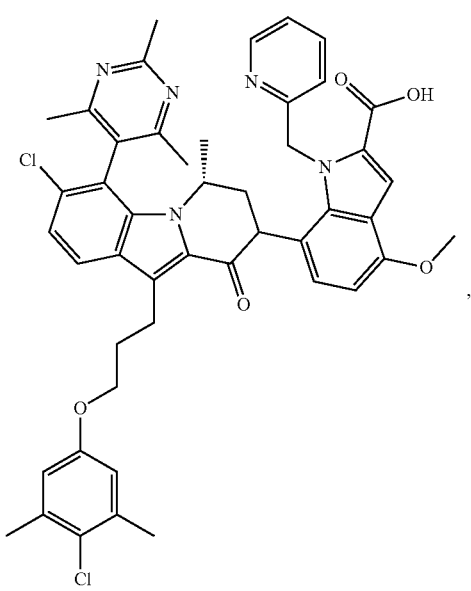
I-705
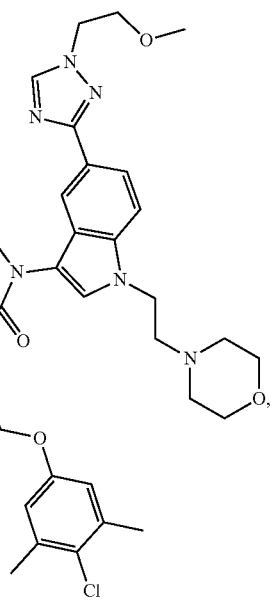
I-722 and

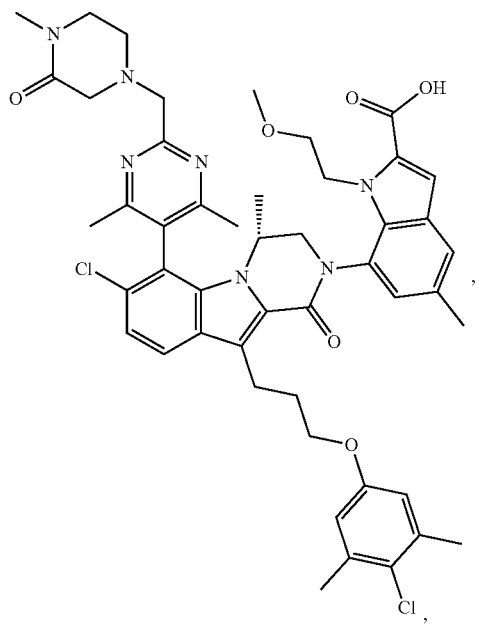

I-729 or a pharmaceutically acceptable salt thereof.

13. The compound of claim 1, or a pharmaceutically acceptable salt thereof, wherein the compound has a $K_i$ value less than about 1 μM for inhibition of Mcl-1.

14. A pharmaceutical composition comprised of a compound of claim 1, or a pharmaceutically acceptable salt thereof, and a pharmaceutically acceptable carrier.

15. The pharmaceutical composition of claim 14, further comprising one or more additional therapeutically active agents.

16. A method of inhibiting the activity of the Bcl-2 family of proteins comprising administering to a mammalian patient in need thereof a therapeutically effective amount of at least one compound of claim 1, or a pharmaceutically acceptable salt thereof, and, optionally, an additional therapeutic agent.

17. A method for treating a disease or disorder selected from the group consisting of leukemia and myeloma, comprising administering to a subject in need thereof, a therapeutically effective amount of a compound of claim 1, or a pharmaceutically acceptable salt thereof.

18. A method for treating a disease or disorder selected from the group consisting of leukemia and myeloma, comprising administering to a mammalian patient in need thereof a therapeutically effective amount of at least one compound of claim 1, or a pharmaceutically acceptable salt thereof, and, optionally, an additional therapeutic agent wherein:

the additional therapeutic agent is selected from the group of anti-cancer agents consisting of alkylating agents, angiogenesis inhibitors, antibodies, antimetabolites, antimitotics, antiproliferatives, aurora kinase inhibitors, Bcl-2 family protein inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, inhibitors of apoptosis proteins (lAPs), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids, deltoids, plant alkaloids, and topoisomerase inhibitors.

19. The method of claim 17, wherein the disease or disorder is selected from the group consisting of multiple myeloma, pediatric biphenotypic acute leukemia, and myelogenous leukemia.

20. The method of claim 18, wherein the disease or disorder is selected from the group consisting of multiple myeloma, pediatric biphenotypic acute leukemia, and myelogenous leukemia.

* * * * *

UNITED STATES PATENT AND TRADEMARK OFFICE
CERTIFICATE OF CORRECTION

PATENT NO. : 11,596,639 B2
APPLICATION NO. : 16/081709
DATED : March 7, 2023
INVENTOR(S) : Taekyu Lee et al.

Page 1 of 1

It is certified that error appears in the above-identified patent and that said Letters Patent is hereby corrected as shown below:

In the Specification

Column 1, Line 16:
Replace the following paragraph:
[[This invention was made with government support under Award DP1OD006933/DP1CA174419, awarded by the National Institutes of Health; under Contract No. HHSN261200800001E, awarded by the NCI Experimental Therapeutics (NExT) Program; and under Grant No. P50CA098131, awarded by the NCI SPORE grant in breast cancer. The government has certain rights in the invention.]]
With the paragraph:
--This invention was made with government support under grant numbers CA098131 and CA174419, awarded by the National Institutes of Health. The government has certain rights in the invention.--

Signed and Sealed this
Eighth Day of October, 2024

Katherine Kelly Vidal
*Director of the United States Patent and Trademark Office*